US012721037B2

(12) United States Patent
Uno

(10) Patent No.: US 12,721,037 B2
(45) Date of Patent: Aug. 25, 2026

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventor: Takuya Uno, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 273 days.

(21) Appl. No.: 17/194,949

(22) Filed: Mar. 8, 2021

(65) Prior Publication Data

US 2022/0416174 A1 Dec. 29, 2022

(30) Foreign Application Priority Data

May 11, 2020 (KR) ........................ 10-2020-0056177

(51) Int. Cl.

| | |
|---|---|
| ***H10K 50/15*** | (2023.01) |
| ***C07D 307/92*** | (2006.01) |
| ***C07D 333/74*** | (2006.01) |
| ***C07D 405/12*** | (2006.01) |
| ***C07D 407/12*** | (2006.01) |
| ***C07D 493/10*** | (2006.01) |
| ***C07F 7/08*** | (2006.01) |
| ***H10K 85/40*** | (2023.01) |
| ***H10K 85/60*** | (2023.01) |

(52) U.S. Cl.

CPC ....... *H10K 85/6572* (2023.02); *C07D 307/92* (2013.01); *C07D 333/74* (2013.01); *C07D 405/12* (2013.01); *C07D 407/12* (2013.01); *C07D 493/10* (2013.01); *C07F 7/0814* (2013.01); *H10K 85/40* (2023.02); *H10K 85/633* (2023.02); *H10K 85/636* (2023.02); *H10K 85/6574* (2023.02); *H10K 85/6576* (2023.02); *H10K 50/15* (2023.02)

(58) Field of Classification Search

None

See application file for complete search history.

(56) References Cited

U.S. PATENT DOCUMENTS

| | | | | |
|---|---|---|---|---|
| 8,614,010 | B2 | 12/2013 | Yabunouchi et al. | |
| 9,755,156 | B2 | 9/2017 | Ikeda et al. | |
| 10,270,040 | B2 | 4/2019 | Ikeda et al. | |
| 10,424,741 | B2 | 9/2019 | Lee et al. | |
| 10,586,927 | B2 | 3/2020 | Itoi | |
| 10,600,969 | B2 | 3/2020 | Mun et al. | |
| 2016/0351816 | A1 | 12/2016 | Kim et al. | |
| 2017/0092869 | A1 | 3/2017 | Mun et al. | |
| 2017/0125869 | A1 | 5/2017 | Ochi et al. | |
| 2017/0237013 | A1 | 8/2017 | Park et al. | |
| 2017/0288148 | A1 | 10/2017 | Park et al. | |
| 2017/0317290 | A1* | 11/2017 | Lee | C07D 409/14 |
| 2018/0083197 | A1 | 3/2018 | Park et al. | |
| 2018/0186764 | A1 | 7/2018 | Jung et al. | |
| 2019/0229271 | A1 | 7/2019 | Lee et al. | |
| 2019/0237668 | A1 | 8/2019 | Miyake et al. | |
| 2019/0296244 | A1 | 9/2019 | Mun et al. | |
| 2020/0136052 | A1 | 4/2020 | So et al. | |
| 2020/0203620 | A1 | 6/2020 | Park et al. | |
| 2020/0403157 | A1* | 12/2020 | Kim | H01L 51/0061 |
| 2022/0199911 | A1* | 6/2022 | Lee | H10K 85/615 |
| 2023/0320201 | A1* | 10/2023 | Lee | C07C 211/57 257/40 |

FOREIGN PATENT DOCUMENTS

| | | | |
|---|---|---|---|
| CN | 104650029 | A | 5/2015 |
| CN | 108341795 | A | 7/2018 |
| CN | 108658932 | A | 10/2018 |
| CN | 108689972 | A | 10/2018 |
| CN | 108947902 | A | 12/2018 |

(Continued)

OTHER PUBLICATIONS

Machine translation of KR-2019007789, translation generated Jan. 2023, 65 pages. (Year: 2023).*

Machine translation of CN-108341795-A, translation generated Jan. 2024, 13 pages. (Year: 2024).*

Machine translation of WO-2016175533-A2, translation generated Dec. 2024, 36 pages. (Year: 2024).*

Machine translation of KR-20170095602-A, translation generated Mar. 2025, 27 pages. (Year: 2025).*

(Continued)

*Primary Examiner* — Robert S Loewe

(74) *Attorney, Agent, or Firm* — Womble Bond Dickinson (US) LLP

(57) ABSTRACT

An organic electroluminescence device includes a first electrode, a hole transport region disposed on the first electrode, an emission layer disposed on the hole transport region, an electron transport region disposed on the emission layer, and a second electrode disposed on the electron transport region, wherein the hole transport region includes a polycyclic compound represented by Formula 1, and the device shows high emission efficiency:

[Formula 1]

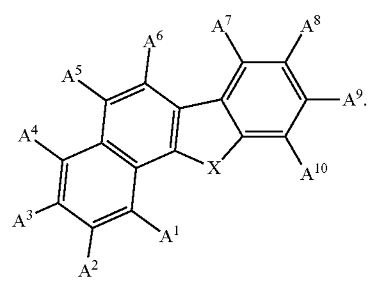

11 Claims, 2 Drawing Sheets

(56) References Cited

FOREIGN PATENT DOCUMENTS

| | | | | | |
|---|---|---|---|---|---|
| CN | 109195950 | A | | 1/2019 | |
| CN | 109233817 | A | | 1/2019 | |
| EP | 3466926 | A1 | | 4/2019 | |
| EP | 3 670 510 | A2 | | 6/2020 | |
| JP | WO2010/061824 | A1 | | 6/2010 | |
| JP | 5398397 | B2 | | 1/2014 | |
| JP | 6298769 | B2 | | 3/2018 | |
| JP | 6552802 | B2 | | 7/2019 | |
| KR | 10-1512058 | B1 | | 4/2015 | |
| KR | 10-2015-0098631 | A | | 8/2015 | |
| KR | 10-2015-0145033 | A | | 12/2015 | |
| KR | 10-2016-0047379 | A | | 5/2016 | |
| KR | 10-2016-0059602 | A | | 5/2016 | |
| KR | 10-2016-0059609 | A | | 5/2016 | |
| KR | 10-2017-0095602 | A | | 8/2017 | |
| KR | 10-2017-0096770 | A | | 8/2017 | |
| KR | 20170095602 | A | * | 8/2017 | ........... C07C 211/54 |
| KR | 10-2017-0126400 | A | | 11/2017 | |
| KR | 10-2018-0096458 | A | | 8/2018 | |
| KR | 10-1923171 | B1 | | 11/2018 | |
| KR | 2019007789 | A | * | 1/2019 | ......... H01L 51/0002 |
| KR | 10-2019-0019550 | A | | 2/2019 | |
| KR | 10-2019-0037772 | A | | 4/2019 | |
| KR | 10-1984244 | B1 | | 5/2019 | |
| KR | 10-2019-0130341 | A | | 11/2019 | |
| KR | 10-2019-0133617 | A | | 12/2019 | |
| KR | 10-2020-0004257 | A | | 1/2020 | |
| KR | 10-2076958 | B1 | | 2/2020 | |
| WO | WO 2014/104144 | A1 | | 7/2014 | |
| WO | WO 2015/194791 | A2 | | 12/2015 | |
| WO | WO 2016/072690 | A1 | | 5/2016 | |
| WO | WO 2016/122150 | A2 | | 8/2016 | |
| WO | WO-2016175533 | A2 | * | 11/2016 | ........... C07D 209/82 |
| WO | WO 2017/204556 | A1 | | 11/2017 | |
| WO | 2018016786 | A1 | | 1/2018 | |
| WO | 2018169261 | A1 | | 9/2018 | |
| WO | WO 2019/021146 | A1 | | 1/2019 | |
| WO | 2019124903 | A1 | | 6/2019 | |
| WO | 2019160335 | A1 | | 8/2019 | |
| WO | 2019190101 | A1 | | 10/2019 | |
| WO | 2020009398 | A1 | | 1/2020 | |

OTHER PUBLICATIONS

Machine translation of KR-20170096770-A, translation generated Oct. 2025, 26 pages. (Year: 2025).*

Machine translation of WO-2019021146-A1, translation generated Oct. 2025, 60 pages. (Year: 2025).*

Extended European Search dated Jan. 25, 2022, for corresponding European Patent Application No. 21169952.5 (17 pages).

* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

This application claims priority to and the benefit of Korean Patent Application No. 10-2020-0056177, filed on May 11, 2020, the entire content of which is hereby incorporated by reference.

BACKGROUND

1. Field

One or more aspects of embodiments of the present disclosure relate to an organic electroluminescence device and a polycyclic compound for an organic electroluminescence device.

2. Description of Related Art

Organic electroluminescence displays are being actively developed as image displays. An organic electroluminescence display differs from a liquid crystal display, and is a so-called self-luminescent display, in which holes and electrons respectively injected from a first electrode and a second electrode recombine in an emission layer, and a light-emitting material including an organic compound in the emission layer emits light to attain display.

In the application of organic electroluminescence devices (or organic electroluminescence display(s)) to a display device, a decreased driving voltage, and increased emission efficiency and/or lifespan of the organic electroluminescence devices are desired, and materials for an organic electroluminescence device stably attaining these characteristics are desired.

SUMMARY

One or more aspects of embodiments of the present disclosure are directed toward an organic electroluminescence device and a polycyclic compound for an organic electroluminescence device, and for example, an organic electroluminescence device with high efficiency and a polycyclic compound included in the hole transport region of the organic electroluminescence device.

One or more example embodiments of the present disclosure provide an organic electroluminescence device including: a first electrode; a hole transport region provided on the first electrode; an emission layer provided on the hole transport region; an electron transport region provided on the emission layer; and a second electrode provided on the electron transport region, wherein the hole transport region includes a polycyclic compound represented by Formula 1:

[Formula 1]

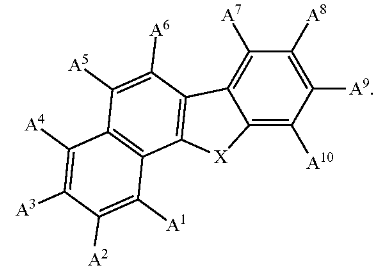

In Formula 1,

X may be O or S, any one among $A^1$ to $A^{10}$ may be represented by Formula 2-1, and the remainder may each independently be a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-1]

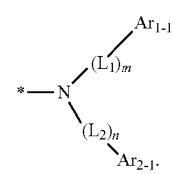

In Formula 2-1, $L_1$ and $L_2$ may each independently be a direct linkage, a substituted or unsubstituted arylene group of 6 to 30 carbon atoms for forming a ring or a substituted or unsubstituted heteroarylene group of 2 to 30 carbon atoms for forming a ring, "m" and "n" may each independently be an integer of 0 to 2, $Ar_{1-1}$ and $Ar_{2-1}$ may each independently be a substituted or unsubstituted aryl group of 10 to 40 carbon atoms for forming a ring or represented by Formula 3-1 or Formula 3-2, where at least one of $Ar_{1-1}$ and $Ar_{2-1}$ may be represented by Formula 3-1 or Formula 3-2. In a case where X is O, and any one of $A^2$, $A^3$, $A^8$ and $A^{10}$ is represented by Formula 2-1, $Ar_{1-1}$ and $Ar_{2-1}$ may each independently be represented by Formula 3-1 or Formula 3-2:

[Formula 3-1]

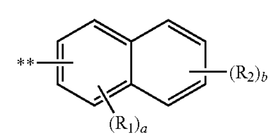

[Formula 3-2]

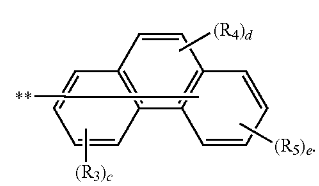

In Formula 3-1 and Formula 3-2, $R_1$ to $R_5$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, “a” may be an integer of 0 to 3, “b”, “c”, and “e” may each independently be an integer of 0 to 4, and “d” may be an integer of 0 to 2, where c+d+e is an integer of 9 or less.

In an embodiment, any one of $A^1$ to $A^{10}$ in Formula 1 may be represented by Formula 2-2, and the remainder may each independently be a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-2]

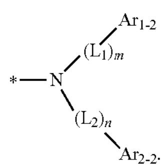

In Formula 2-2, $L_1$ and $L_2$ may each independently be a direct linkage, a substituted or unsubstituted arylene group of 6 to 30 carbon atoms for forming a ring, or a substituted or unsubstituted heteroarylene group of 2 to 30 carbon atoms for forming a ring, “m” and “n” may each independently be an integer of 0 to 2, and $Ar_{1-2}$ and $Ar_{2-2}$ may each independently be a substituted or unsubstituted aryl group of 10 to 40 carbon atoms for forming a ring or represented by Formula 3-3 or Formula 3-4, where at least one among $Ar_{1-2}$ and $Ar_{2-2}$ is represented by Formula 3-3 or Formula 3-4:

[Formula 3-3]

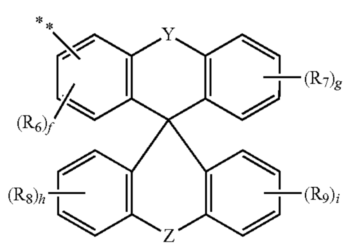

[Formula 3-4]

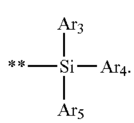

In Formula 3-3 and Formula 3-4, Y and Z may each independently be a direct linkage, O, or S, where a case in which both Y and Z are direct linkages is excluded (e.g., Y and Z are not simultaneously a direct linkage), $R_6$ to $R_9$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, “f” may be an integer of 0 to 3, “g” to “i” may each independently be an integer of 0 to 4, and $Ar_3$ to $Ar_5$ may each independently be a substituted or unsubstituted aryl group of 6 to 30 carbon atoms for forming a ring.

In an embodiment, any one among $A^1$ to $A^{10}$ in Formula 1 may be represented by Formula 2-3, and the remainder may each independently be a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-3]

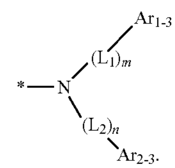

In Formula 2-3, $L_1$ and $L_2$ may each independently be a direct linkage, a substituted or unsubstituted arylene group of 6 to 30 carbon atoms for forming a ring or a substituted or unsubstituted heteroarylene group of 2 to 30 carbon atoms for forming a ring, “m” and “n” may each independently be an integer of 0 to 2, and $Ar_{1-3}$ and $Ar_{2-3}$ may each independently be a substituted or unsubstituted aryl group of 10 to 40 carbon atoms for forming a ring or represented by Formula 3-5 or Formula 3-6, where at least one among $Ar_{1-3}$ and $Ar_{2-3}$ is represented by Formula 3-5 or Formula 3-6:

[Formula 3-5]

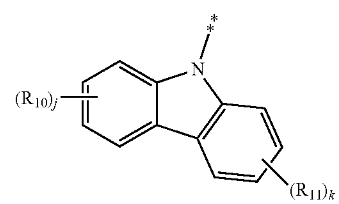

[Formula 3-6]

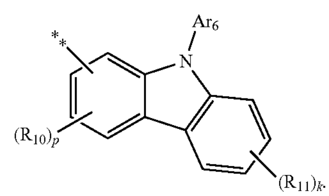

In Formula 3-5 and Formula 3-6, $R_{10}$ and $R_{11}$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring; $Ar_6$ may be a substituted or unsubstituted aryl group of 6 to 30 carbon atoms for forming a ring, “j” and “k” may each independently be an integer of 0 to 4, and “p” is an integer of 0 to 3.

In an embodiment, Formula 2-1 may be represented by Formula 4-1 or Formula 4-2:

[Formula 4-1]

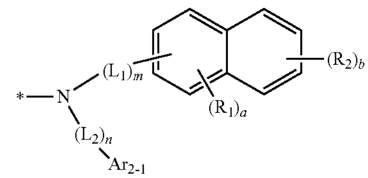

-continued

[Formula 4-2]

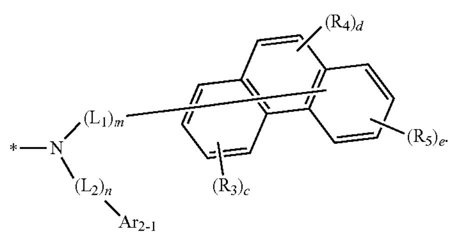

In Formula 4-1 and Formula 4-2, $Ar_{2-1}$ may be a substituted or unsubstituted aryl group of 10 to 40 carbon atoms for forming a ring, $L_1$, $L_2$, "m" and "n" may each independently be the same as defined in Formula 2-1, and $R_1$ to $R_5$, and "a" to "d" may each independently be the same as defined in Formula 3-1 and Formula 3-2.

In an embodiment, Formula 2-2 may be represented by Formula 5-1 or Formula 5-2:

[Formula 5-1]

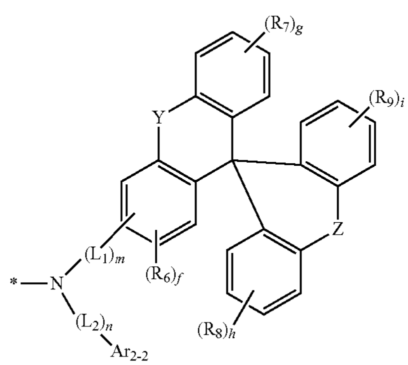

[Formula 5-2]

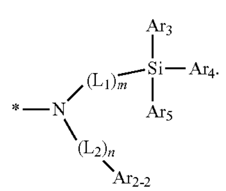

In Formula 5-1 and Formula 5-2, $Ar_{2-2}$ may be a substituted or unsubstituted aryl group of 10 to 40 carbon atoms for forming a ring; $L_1$, $L_2$, "m" and "n" may each independently be the same as defined in Formula 2-2; and Y, Z, $R_6$ to $R_9$, "f" to "i", and $Ar_3$ to $Ar_5$ may each independently be the same as defined in Formula 3-3 and Formula 3-4.

In an embodiment, Formula 2-3 may be represented by Formula 6-1 or Formula 6-2:

[Formula 6-1]

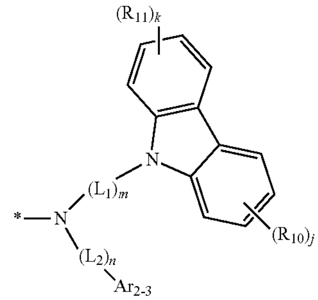

[Formula 6-2]

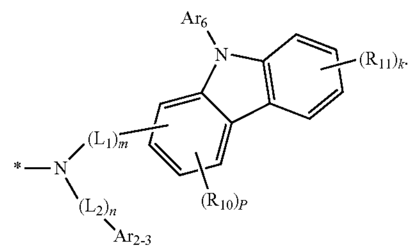

In Formula 6-1 and Formula 6-2, $Ar_{2-3}$ may be a substituted or unsubstituted aryl group of 10 to 40 carbon atoms for forming a ring; $L_1$, $L_2$, "m" and "n" may each independently be the same as defined in Formula 2-3; and $R_{10}$ and $R_{11}$, $Ar_6$, "j", "k", and "p" may each independently be the same as defined in Formula 3-5 and Formula 3-6.

In an embodiment, any one among $A^1$ to $A^6$ in Formula 1 may be represented by Formula 2-1.

In an embodiment, $A^7$ or $A^{10}$ in Formula 1 may be represented by Formula 2-1.

In an embodiment, any one among $A^1$ to $A^6$ in Formula 1 may be represented by Formula 2-2.

In an embodiment, any one among $A^7$ to $A^{10}$ in Formula 1 may be represented by Formula 2-2.

In an embodiment, any one among $A^1$ to $A^6$ in Formula 1 may be represented by Formula 2-3.

In an embodiment, any one among $A^7$ to $A^{10}$ in Formula 1 may be represented by Formula 2-3.

In an embodiment, the hole transport region may include a hole injection layer disposed on the first electrode, and a hole transport layer disposed on the hole injection layer, where the hole transport layer may include the polycyclic compound represented by Formula 1.

In an embodiment, $L_1$ and $L_2$ may each independently be a direct linkage, a substituted or unsubstituted phenylene group, or a substituted or unsubstituted naphthyl group.

In an embodiment, $L_2$ may be a direct linkage or a substituted or unsubstituted phenyl group, "n" may be 1, and $Ar_{2-1}$ to $Ar_{2-3}$ may each independently be a substituted or unsubstituted phenyl group, a substituted or unsubstituted biphenyl group, a substituted or unsubstituted terphenyl group, a substituted or unsubstituted phenanthrene group, a substituted or unsubstituted naphthyl group, or a substituted or unsubstituted fluorenyl group, where a case in which $L_2$ and any one among $Ar_{2-1}$ to $Ar_{2-3}$ (e.g., $L_2$ and $Ar_{2-1}$, $L_2$ and $Ar_{2-2}$, or $L_2$ and $Ar_{2-3}$) are simultaneously phenyl groups (e.g., at the same time) may be excluded.

In an embodiment, the polycyclic compound represented by Formula 1 may be at least one selected from the compounds represented in Compound Group 1 to Compound Group 6.

One or more example embodiments of the present disclosure provide a polycyclic compound represented by Formula 1.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
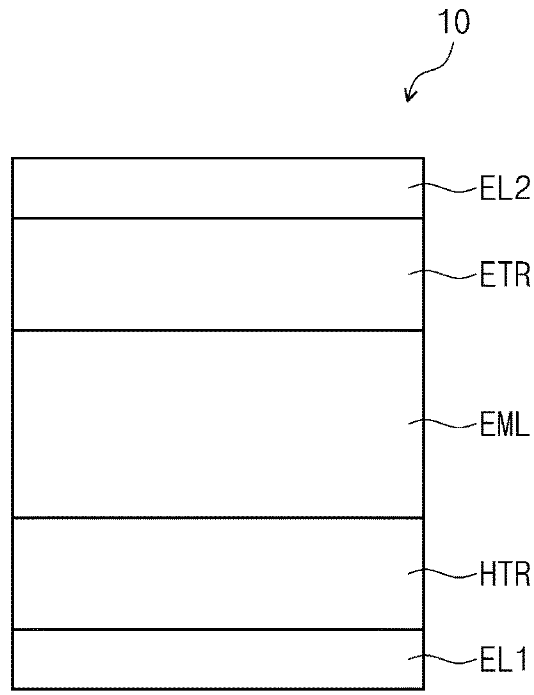
FIG. 1 is a cross-sectional view schematically illustrating an organic electroluminescence device according to an embodiment of the present disclosure.

The present disclosure may have various modifications and may be embodied in different forms, and example embodiments will be explained in more detail with reference to the accompanying drawings. The present disclosure may, however, be embodied in different forms and should not be construed as being limited to the embodiments set forth herein. Rather, all modifications, equivalents, and substituents that are within the spirit and technical scope of the present disclosure should be included in the present disclosure.

It will be understood that when an element (or region, layer, part, etc.) is referred to as being "on", "connected to" or "coupled to" another element, it can be directly on, connected or coupled to the other element, or one or more intervening elements may be present. When an element is referred to as being "directly on," "directly connected to," or "directly coupled to" another element, there are no intervening elements present.

Like reference numerals refer to like elements throughout, and duplicative descriptions thereof may not be provided. In the drawings, thicknesses, ratios, and dimensions of constituent elements may be exaggerated for effective explanation of technical contents.

As used herein, expressions such as "at least one of," "one of," and "selected from," when preceding a list of elements, modify the entire list of elements and do not modify the individual elements of the list. The term "and/or" includes any and all combinations of one or more of the associated listed items. Further, the use of "may" when describing embodiments of the present disclosure refers to "one or more embodiments of the present disclosure".

It will be understood that, although the terms first, second, etc. may be used herein to describe various elements, these elements should not be limited by these terms. These terms are only used to distinguish one element from another element. Thus, a first element could be alternatively termed a second element without departing from the teachings of the present disclosure. Similarly, a second element could be alternatively termed a first element. As used herein, the singular forms are intended to include the plural forms as well, unless the context clearly indicates otherwise.

In addition, the terms "below", "beneath", "on" and "above" are used for explaining spatial relationships between elements shown in the drawings. The terms are relative concepts, and are selected and to be interpreted based on the orientations shown in the drawing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

It will be further understood that the terms "includes," "including," "comprises," and/or "comprising," when used in this specification, specify the presence of stated features, numerals, steps, operations, elements, parts, or combinations thereof, but do not preclude the presence or addition of one or more other features, numerals, steps, operations, elements, parts, or combinations thereof.

Hereinafter, the organic electroluminescence device according to an embodiment of the present disclosure will be explained with reference to the attached drawings.

FIGS. 1 to 4 are cross-sectional views schematically showing organic electroluminescence devices according to example embodiments of the present disclosure. Referring to FIGS. 1 to 4, in an organic electroluminescence device 10 according to an embodiment, a first electrode EL1 and a second electrode EL2 are oppositely disposed, and between the first electrode EL1 and the second electrode EL2, an emission layer EML may be disposed.

In some embodiments, the organic electroluminescence device 10 of an embodiment further includes a plurality of functional layers between the first electrode EL1 and the second electrode EL2 in addition to the emission layer EML. The plurality of functional layers may include a hole transport region HTR and an electron transport region ETR. For example, the organic electroluminescence device 10 of an embodiment may include a first electrode EL1, a hole transport region HTR, an emission layer EML, an electron transport region ETR, and a second electrode, stacked one by one. In some embodiments, the organic electroluminescence device 10 of an embodiment may include a capping layer CPL disposed on the second electrode EL2.

The organic electroluminescence device 10 of an embodiment includes a polycyclic compound of an embodiment, which will be explained later, in the emission layer EML disposed between the first electrode EL1 and the second electrode EL2. However, embodiments of the present disclosure are not limited thereto, and the organic electroluminescence device 10 of an embodiment may include a polycyclic compound according to an embodiment in the hole transport region HTR or the electron transport region ETR (which are among the plurality of functional layers disposed between the first electrode EL1 and the second electrode EL2), or in the capping layer CPL disposed on the second electrode EL2 in addition to the emission layer EML.

Figure 2:
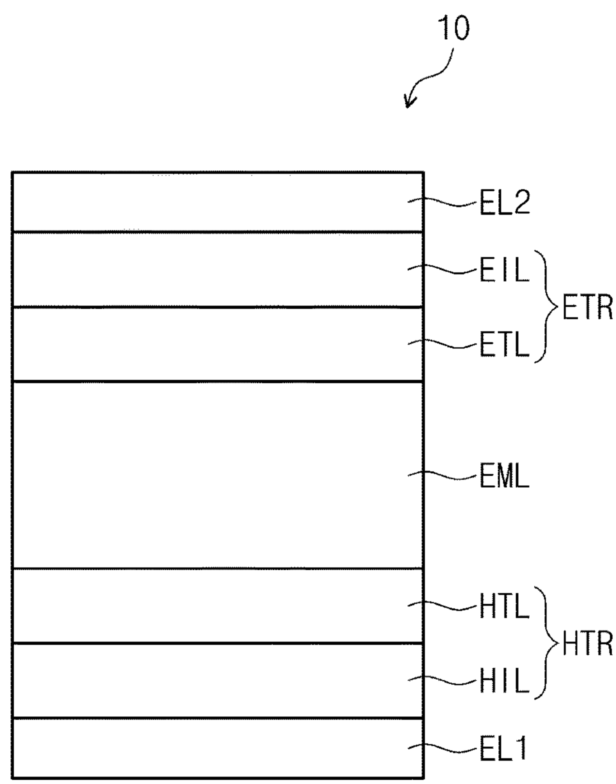
FIG. 2 is a cross-sectional view schematically illustrating an organic electroluminescence device according to an embodiment of the present disclosure.
Figure 3:
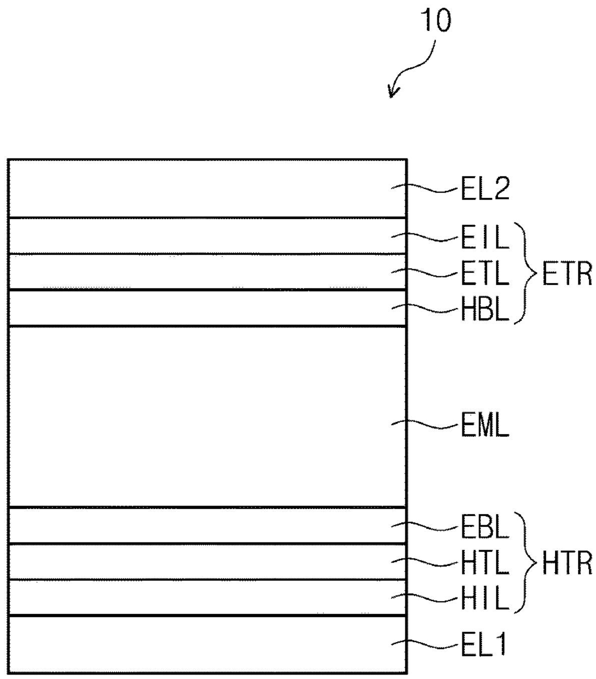
FIG. 3 is a cross-sectional view schematically illustrating an organic electroluminescence device according to an embodiment of the present disclosure.
Figure 4:
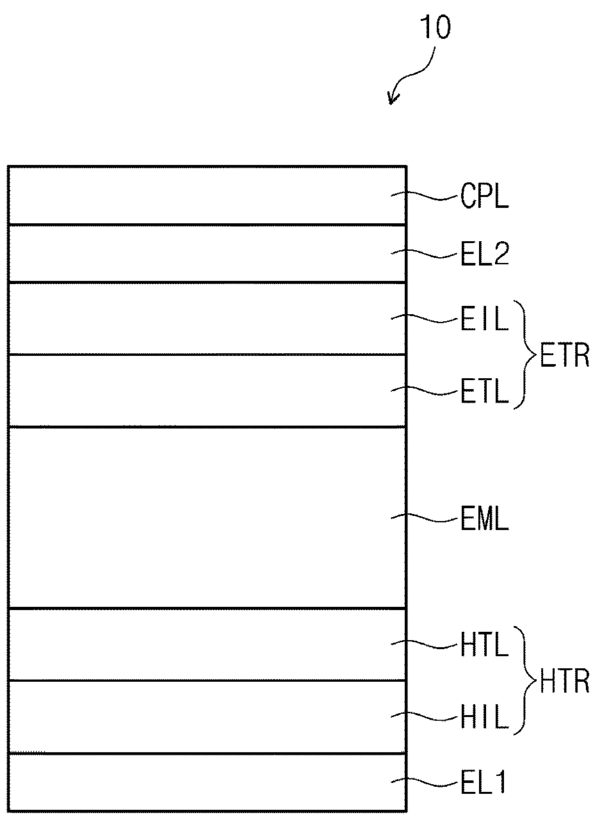
FIG. 4 is a cross-sectional view schematically illustrating an organic electroluminescence device according to an embodiment of the present disclosure.

Compared with FIG. 1, FIG. 2 shows the cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. Compared with FIG. 1, FIG. 3 shows the cross-sectional view of an organic electroluminescence device 10 of an embodiment, wherein the hole transport region HTR includes the hole injection layer HIL, the hole transport layer HTL, and an electron blocking layer EBL, and the electron transport region ETR includes the electron injection layer EIL, the electron transport layer ETL, and a hole blocking layer HBL. Compared with FIG. 2, FIG. 4 shows the cross-sectional view of an organic electroluminescence device 10 of an embodiment that includes a capping layer CPL disposed on the second electrode EL2.

The first electrode EL1 has conductivity (e.g., may be conductive). The first electrode EL1 may be formed using a metal alloy or a conductive compound. The first electrode EL1 may be a pixel electrode or an anode. The first electrode EL1 may be a transmissive electrode, a transflective electrode, or a reflective electrode. When the first electrode EL1 is a transmissive electrode, the first electrode EL1 may be formed using a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure including a plurality of layers, including a reflective layer or a transflective layer formed using the above materials, and a transmissive conductive layer formed using ITO, IZO, ZnO, and/or ITZO. For example, the first electrode EL1 may include a three-layer structure of ITO/Ag/ITO. However, embodiments of the present disclosure are not limited thereto. The thickness of the first electrode EL1 may be about 1,000 Å to about 10,000 Å, for example, about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer of a hole injection layer HIL or a hole transport layer HTL, or may have the structure of a single layer formed using a hole injection material and a hole transport material. In some embodiments, the hole transport region HTR may have the structure of a single layer formed using a plurality of different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR of the organic electroluminescence device 10 of an embodiment includes the polycyclic compound according to an embodiment of the present disclosure.

In the description, the term "substituted or unsubstituted" refers to a state of being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the exemplified substituents may be further substituted or unsubstituted. Further, a biphenyl group may be interpreted as a named aryl group, or as a phenyl group substituted with a phenyl group.

In the description, non-limiting examples of the halogen atom may include a fluorine atom, a chlorine atom, a bromine atom, and/or an iodine atom.

In the description, the term "alkyl group" may refer to a linear, branched or cyclic alkyl group. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the term "alkenyl group" may refer to a hydrocarbon group including one or more carbon-carbon double bonds in the middle or at the terminal end of an alkyl group of 2 or more carbon atoms. The alkenyl group may include a linear chain or a branched chain. The carbon number of the alkenyl group is not specifically limited, but may be 2 to 30, 2 to 20, or 2 to 10. Examples of the alkenyl group include a vinyl group, a 1-butenyl group, a 1-pentenyl group, a 1,3-butadienyl aryl group, a styrenyl group, a styrylvinyl group, etc., without limitation.

In the description, the term "alkynyl group" may refer to a hydrocarbon group including one or more carbon-carbon triple bonds in the middle or at the terminal end of an alkyl group of 2 or more carbon atoms. The alkynyl group may include a linear chain or a branched chain. The carbon number of the alkynyl group is not specifically limited, but may be 2 to 30, 2 to 20, or 2 to 10. Examples of the alkynyl group include an ethynyl group, a propynyl group, etc., without limitation.

In the description, the term "hydrocarbon ring group" may refer to an optional functional group or substituent derived from an aliphatic hydrocarbon ring, or an optional functional group or substituent derived from an aromatic hydrocarbon ring. The carbon number for forming a ring of the hydrocarbon ring group may be 5 to 60, 5 to 30, or 5 to 20.

In the description, the term "aryl group" may refer to an optional functional group or substituent derived from an aromatic hydrocarbon ring. The aryl group may be a monocyclic aryl group or a polycyclic aryl group. The carbon number for forming a ring of the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted, and two substituents (e.g., at the 9H position) may be combined with each other to form a spiro structure. Examples of a substituted fluorenyl group are as follows. However, embodiments of the present disclosure are not limited thereto:

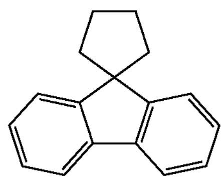

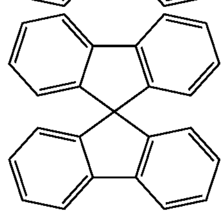

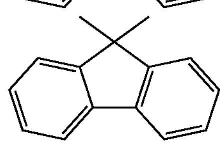

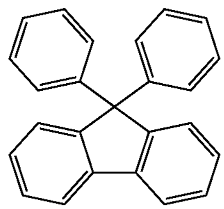

In the description, the term "heterocyclic group" may refer to an optional functional group or substituent derived from a ring including one or more among B, O, N, P, Si and S as heteroatoms. The heterocyclic group may include an aliphatic heterocyclic group and an aromatic heterocyclic group. The aromatic heterocyclic group may be a heteroaryl group. The aliphatic heterocyclic group and the aromatic heterocyclic group may be monocycles or polycycles.

In the description, the heterocyclic group may include one or more among B, O, N, P, Si and S as heteroatoms. When the heterocyclic group includes two or more heteroatoms, the two or more heteroatoms may be the same or different. The heterocyclic group may be a monocyclic heterocyclic group or a polycyclic heterocyclic group, and has a concept including a heteroaryl group. The carbon number for forming a ring of the heteroaryl group may be 2 to 30, 2 to 20, or 2 to 10.

In the description, the aliphatic heterocyclic group may include one or more among B, O, N, P, Si and S as heteroatoms. The carbon number for forming a ring of the aliphatic heterocyclic group may be 2 to 30, 2 to 20, or 2 to 10. Examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more among B, O, N, P, Si and S as heteroatoms. When the heteroaryl group includes two or more heteroatoms, the two or more heteroatoms may be the same or different. The heteroaryl group may be a monocyclic heteroaryl group or polycyclic heteroaryl group. The carbon number for forming a ring of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the description, the carbon number of the amine group is not specifically limited, but may be 1 to 30. The amine group may include an alkyl amine group, an aryl amine group, or a heteroaryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

In the description, the explanation on the aryl group is applied to an arylene group except that the arylene group is a divalent group.

In the description, the explanation on the heteroaryl group is applied to a heteroarylene group except that the arylene group is a divalent group.

In the description, "—*" and "┅ **" indicate positions of connection (e.g., to other groups, moieties, etc.).

The polycyclic compound according to an embodiment of the present disclosure is represented by Formula 1:

[Formula 1]

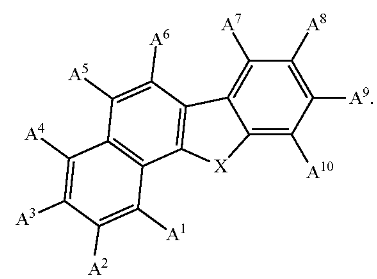

In Formula 1, X may be O or S.

In Formula 1, any one among $A^1$ to $A^{10}$ may be represented by Formula 2-1, and the remainder may each independently be a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-1]

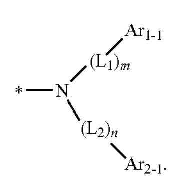

In Formula 2-1, $L_1$ and $L_2$ may each independently be a direct linkage, a substituted or unsubstituted arylene group of 6 to 30 carbon atoms for forming a ring, or a substituted or unsubstituted heteroarylene group of 2 to 30 carbon atoms for forming a ring.

In Formula 2-1, "m" and "n" are each independently an integer of 0 to 2, where when "m" is 2 or more, a plurality of $L_1$ groups may be the same or different from each other, and when "n" is 2 or more, a plurality of $L_2$ groups may be the same or different from each other.

In Formula 2-1, $Ar_{1-1}$ and $Ar_{2-1}$ may each independently be a substituted or unsubstituted aryl group of 10 to 40 carbon atoms for forming a ring, or may be represented by Formula 3-1 or Formula 3-2, where at least one among $Ar_{1-1}$ and $Ar_{2-1}$ is represented by Formula 3-1 or Formula 3-2.

When X is O in Formula 1, and any one among $A^2$, $A^3$, $A^8$ and $A^{10}$ is represented by Formula 2-1, $Ar_{1-1}$ and $Ar_{2-1}$ may each independently be represented by Formula 3-1 or Formula 3-2.

In Formula 2-1, "—*" indicates a position connected with Formula 1.

[Formula 3-1]

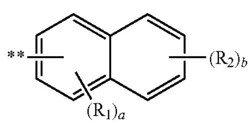

[Formula 3-2]

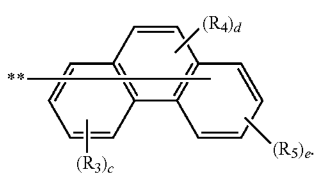

In Formula 3-1 and Formula 3-2, $R_1$ to $R_5$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 3-1, "a" may be an integer of 0 to 3, and when "a" is 2 or more, a plurality of $R_1$ groups may be the same or different from each other.

In Formula 3-1, "b" may be an integer of 0 to 4, and when "b" is 2 or more, a plurality of $R_2$ groups may be the same or different from each other.

In Formula 3-2, "c" and "e" may each independently be an integer of 0 to 4, and when "c" is 2 or more, a plurality of $R_3$ groups may be the same or different from each other, and when "e" is 2 or more, a plurality of $R_5$ groups may be the same or different from each other.

In Formula 3-2, "d" may be an integer of 0 to 2, and when "d" is 2, a plurality of $R_4$ groups may be the same or different from each other.

In Formula 3-2, c+d+e may be an integer of 9 or less.

In Formula 3-1 and Formula 3-2, "—**" indicates a position connected with Formula 2-1.

In an embodiment, $L_1$ and $L_2$ of Formula 2-1 may each independently be a direct linkage, a substituted or unsubstituted phenylene group, or a substituted or unsubstituted naphthyl group.

In an embodiment, $L_2$ of Formula 2-1 may be a direct linkage or a substituted or unsubstituted phenyl group, and when "n" is 1, each $Ar_{2-1}$ may independently be a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group. However, a case in which $L_2$ and $Ar_{2-1}$ are phenyl groups at the same time is excluded.

In an embodiment, any one among $A^1$ to $A^6$ in Formula 1 may be represented by Formula 2-1.

In an embodiment, $A^7$ or $A^{10}$ in Formula 1 may be represented by Formula 2-1.

In an embodiment, any one among $A^1$ to $A^{10}$ in the polycyclic compound represented by Formula 1 may be represented by Formula 2-2, and the remainder may each independently be a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-2]

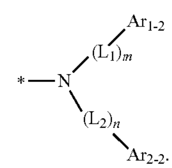

In Formula 2-2, $L_1$ and $L_2$ may each independently be a direct linkage, a substituted or unsubstituted arylene group of 6 to 30 carbon atoms for forming a ring, or a substituted or unsubstituted heteroarylene group of 2 to 30 carbon atoms for forming a ring.

In Formula 2-2, "m" and "n" may each independently be an integer of 0 to 2, and when "m" is 2 or more, a plurality of $L_1$ groups may be the same or different from each other, and when "n" is 2 or more, a plurality of $L_2$ groups may be the same or different from each other.

In Formula 2-2, $Ar_{1-2}$ and $Ar_{2-2}$ may each independently be a substituted or unsubstituted aryl group of 10 to 40 carbon atoms for forming a ring, or may be represented by Formula 3-3 or Formula 3-4, where at least one among $Ar_{1-2}$ and $Ar_{2-2}$ is represented by Formula 3-3 or Formula 3-4.

In Formula 2-2, "—*" indicates a position connected with Formula 1.

[Formula 3-3]

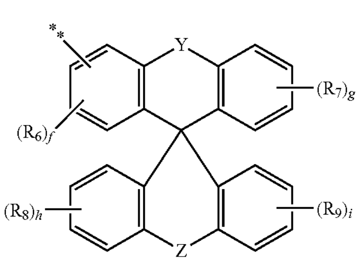

[Formula 3-4]

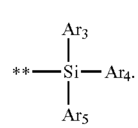

In Formula 3-3, Y and Z may each independently be a direct linkage, O, or S, where a case in which both Y and Z are direct linkages is excluded.

In Formula 3-3, $R_6$ to $R_9$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 3-3, “f” may be an integer of 0 to 3, and when “f” is 2 or more, a plurality of $R_6$ groups may be the same or different from each other.

In Formula 3-3, “g” to “i” may each independently be an integer of 0 to 4, and when “g” is 2 or more, a plurality of $R_7$ groups may be the same or different from each other, when “h” is 2 or more, a plurality of $R_8$ groups may be the same or different from each other, and when “i” is 2 or more, a plurality of $R_9$ groups may be the same or different from each other.

In Formula 3-4, $Ar_3$ to $Ar_5$ may each independently be a substituted or unsubstituted aryl group of 6 to 30 carbon atoms for forming a ring.

In Formula 3-3 and Formula 3-4, “ ------ **” indicates a position connected with Formula 2-2.

In an embodiment, $L_1$ and $L_2$ in Formula 2-2 may be a direct linkage, a substituted or unsubstituted phenylene group, or a substituted or unsubstituted naphthyl group.

In an embodiment, $L_2$ in Formula 2-2 is a direct linkage or a substituted or unsubstituted phenyl group, and when “n” is 1, each $Ar_{2-2}$ may independently be a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group. However, a case in which $L_2$ and $Ar_{2-2}$ are phenyl groups at the same time is excluded.

In an embodiment, any one among $A^1$ to $A^6$ in Formula 1 may be represented by Formula 2-2.

In an embodiment, any one among $A^7$ to $A^{10}$ in Formula 1 may be represented by Formula 2-2.

In an embodiment, any one among $A^1$ to $A^{10}$ in Formula 1 may be represented by Formula 2-3, and the remainder may each independently be a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-3]

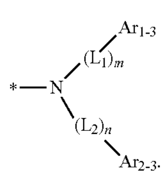

In Formula 2-3, $L_1$ and $L_2$ may each independently be a direct linkage, a substituted or unsubstituted arylene group of 6 to 30 carbon atoms for forming a ring, or a substituted or unsubstituted heteroarylene group of 2 to 30 carbon atoms for forming a ring.

In Formula 2-3, “m” and “n” may each independently be an integer of 0 to 2, and when “m” is 2 or more, a plurality of $L_1$ groups may be the same or different from each other, and when “n” is 2 or more, a plurality of $L_2$ may be the same or different from each other.

In Formula 2-3, $Ar_{1-3}$ and $Ar_{2-3}$ may each independently be a substituted or unsubstituted aryl group of 10 to 40 carbon atoms for forming a ring, or may be represented by Formula 3-5 or Formula 3-6 below, where at least one among $Ar_{1-3}$ and $Ar_{2-3}$ is represented by Formula 3-5 or Formula 3-6.

In Formula 2-3, “ —* ” indicates a position connected with Formula 1.

[Formula 3-5]

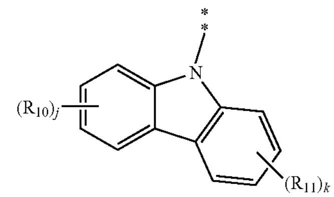

[Formula 3-6]

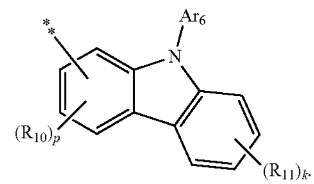

In Formula 3-5 and Formula 3-6, $R_{10}$ and $R_{11}$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 3-5 and Formula 3-6, “j” and “k” may each independently be an integer of 0 to 4, and when “j” is 2 or more, a plurality of $R_{10}$ groups may be the same or different from each other, and when “k” is 2 or more, a plurality of $R_1$ groups may be the same or different from each other.

In Formula 3-6, “p” may be an integer of 0 to 3, and when “p” is 2 or more, a plurality of $R_{10}$ groups may be the same or different from each other.

In Formula 3-6, $Ar_6$ may be a substituted or unsubstituted aryl group of 6 to 30 carbon atoms for forming a ring.

In Formula 3-5 and Formula 3-6, “ ------ ** ” indicates a position connected with Formula 2-3.

In an embodiment, $L_1$ and $L_2$ in Formula 2-3 may each independently be a direct linkage, a substituted or unsubstituted phenylene group, or a substituted or unsubstituted naphthyl group.

In an embodiment, $L_2$ of Formula 2-3 is a direct linkage or a substituted or unsubstituted phenyl group, and when “n” is 1, each $Ar_{2-3}$ may independently be a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group. However, a case in which $L_2$ and $Ar_{2-3}$ are phenyl groups at the same time is excluded.

In an embodiment, any one among $A^1$ to $A^6$ in Formula 1 may be represented by Formula 2-3.

In an embodiment, any one among $A^7$ to $A^{10}$ in Formula 1 may be represented by Formula 2-3.

In the polycyclic compound of the present disclosure, the polycyclic compound represented by Formula 1 makes a direct linkage (e.g., is directly linked) with the amine group represented by Formula 2-1 to Formula 2-3 without a linker therebetween.

In an embodiment, Formula 2-1 may be represented by Formula 4-1 or Formula 4-2:

[Formula 4-1]

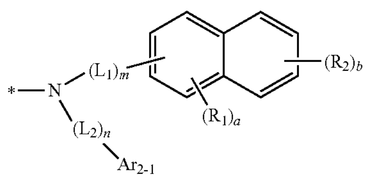

[Formula 4-2]

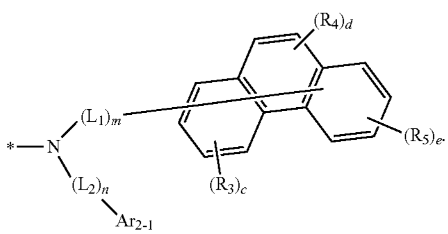

In Formula 4-1 and Formula 4-2, $Ar_{2-1}$ may be a substituted or unsubstituted aryl group of 10 to 40 carbon atoms for forming a ring.

In Formula 4-1 and Formula 4-2, $L_1$, $L_2$, "m" and "n" may be the same as defined in Formula 2-1, and $R_1$ to $R_5$, and "a" to "e" may be the same as defined in Formula 3-1 and Formula 3-2.

In Formula 4-1 and Formula 4-2, "—*" indicates a position connected with Formula 1.

In an embodiment, Formula 2-2 may be represented by Formula 5-1 or Formula 5-2:

[Formula 5-1]

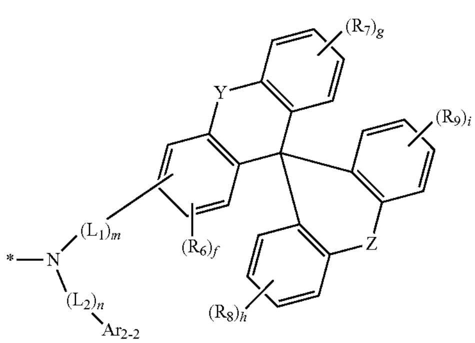

[Formula 5-2]

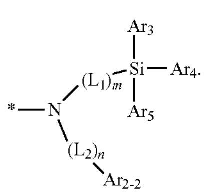

In Formula 5-1 and Formula 5-2, $Ar_{2-2}$ may be a substituted or unsubstituted aryl group of 10 to 40 carbon atoms for forming a ring.

In Formula 5-1 and Formula 5-2, $L_1$, $L_2$, "m" and "n" may each independently be the same as defined in Formula 2-2, and Y, Z, $R_6$ to $R_9$, "f" to "i", and $Ar_3$ to $Ar_5$ may each independently be the same as defined in Formula 3-3 and Formula 3-4.

In Formula 5-1 and Formula 5-2, "—*" indicates a position connected with Formula 1.

In an embodiment, Formula 2-3 may be represented by Formula 6-1 or Formula 6-2:

[Formula 6-1]

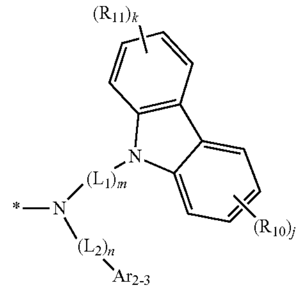

[Formula 6-2]

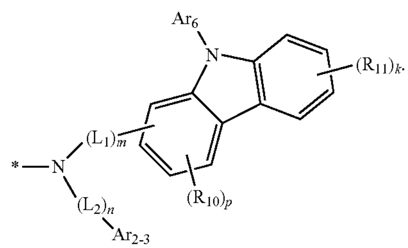

In Formula 6-1 and Formula 6-2, $Ar_{2-3}$ may be a substituted or unsubstituted aryl group of 10 to 40 carbon atoms for forming a ring.

In Formula 6-1 and Formula 6-2, $L_1$, $L_2$, "m" and "n" may each independently be the same as defined in Formula 2-3, and $R_{10}$ and $R_{11}$, $Ar_6$, "j", "k", and "p" may each independently be the same as defined in Formula 3-5 and Formula 3-6.

In Formula 6-1 and Formula 6-2, "—*" indicates a position connected with Formula 1.

The polycyclic compound represented by Formula 1 according to an embodiment of the present disclosure may be at least one selected from the compounds represented in Compound Group 1 to Compound Group 6:

[Compound Group 1]

A1

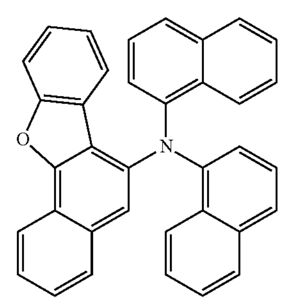

-continued
A2
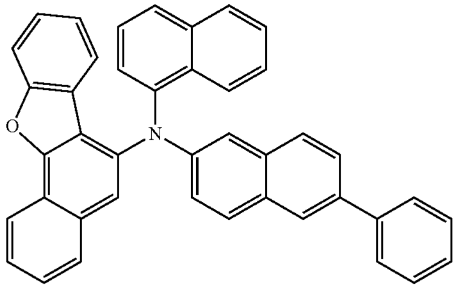
A3
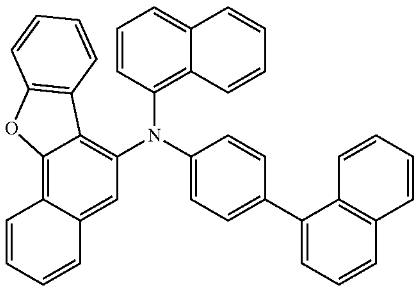
A4
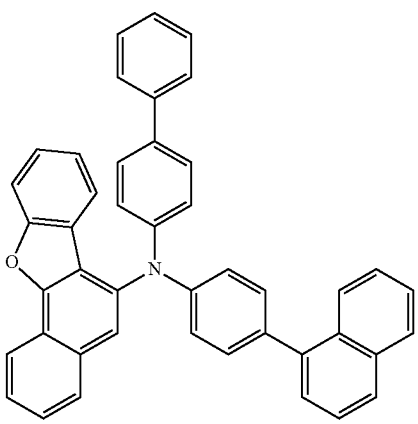
A5
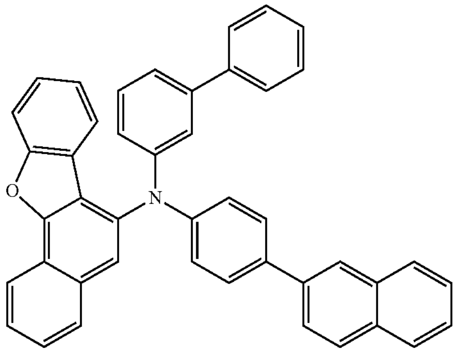
-continued
A6
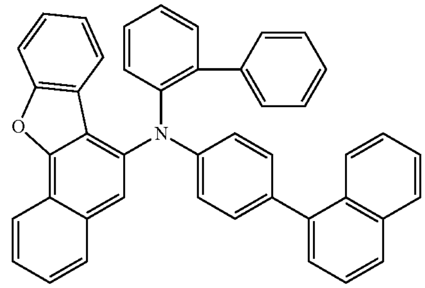
A7
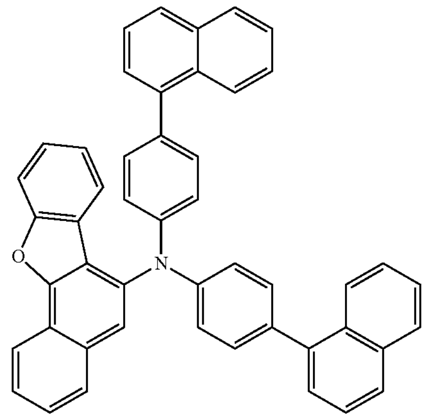
A8
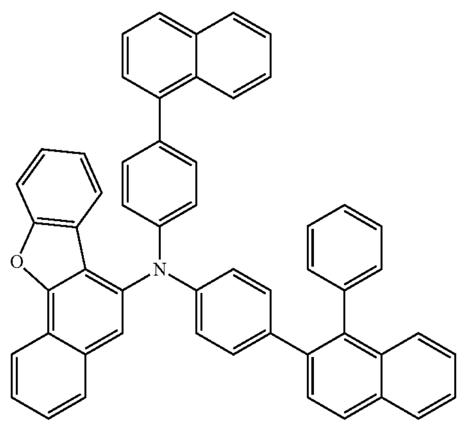
A9
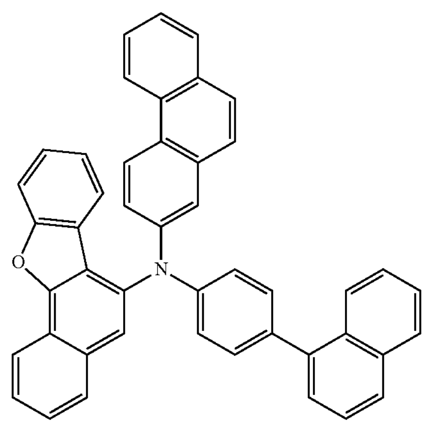

-continued
A10
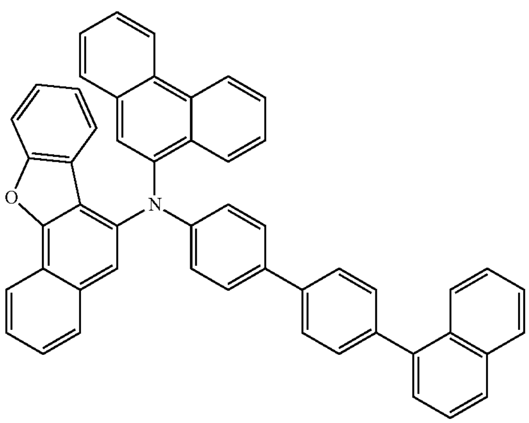
A11
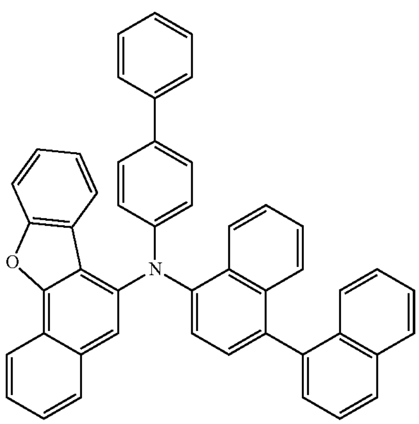
A12
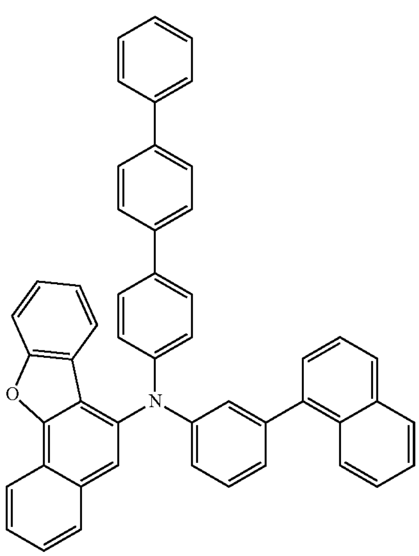
-continued
A13
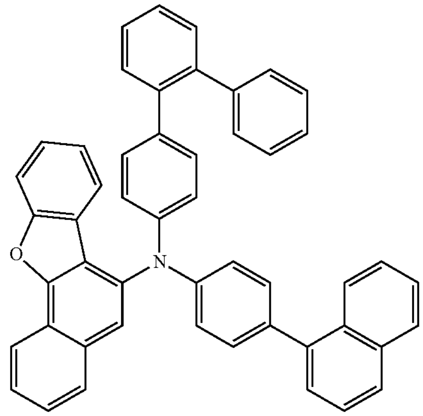
A14
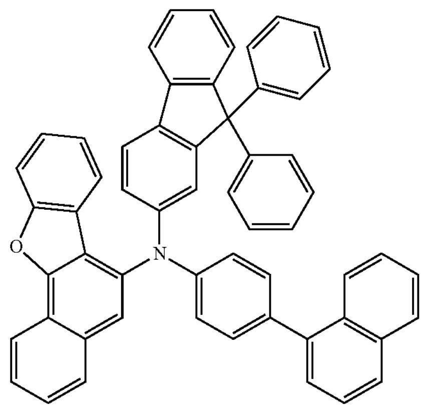
A15
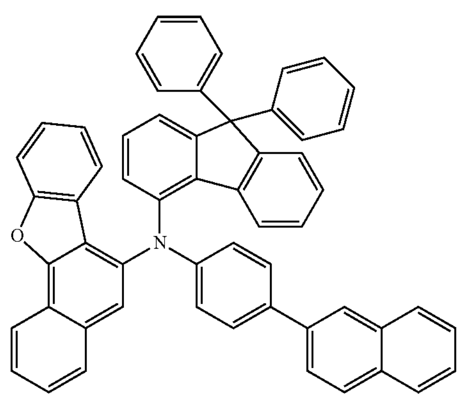

-continued
A16
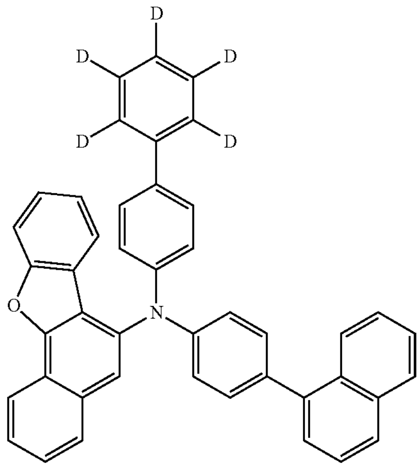
A17
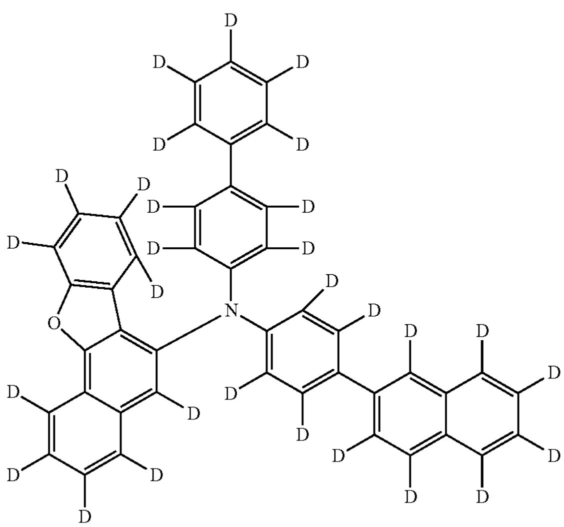
A18
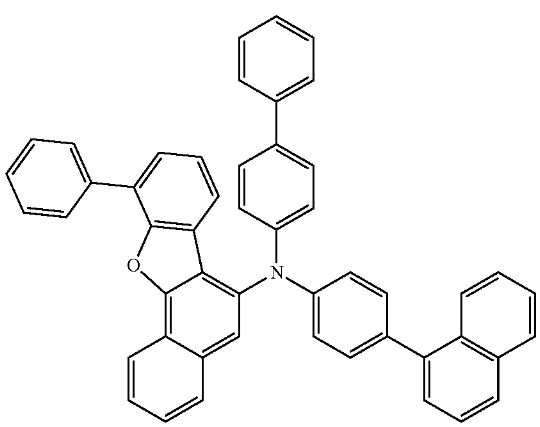
-continued
A19
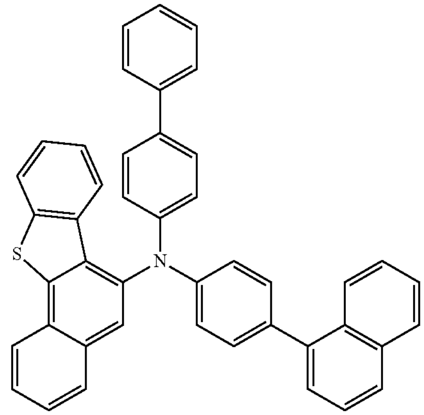
A20
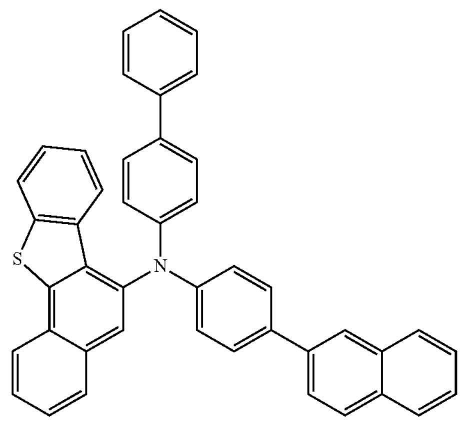
A21
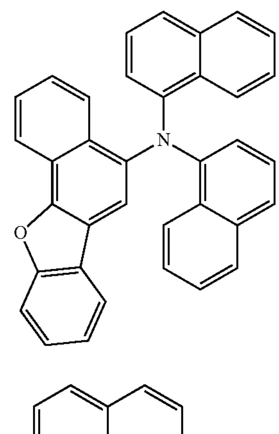
A22
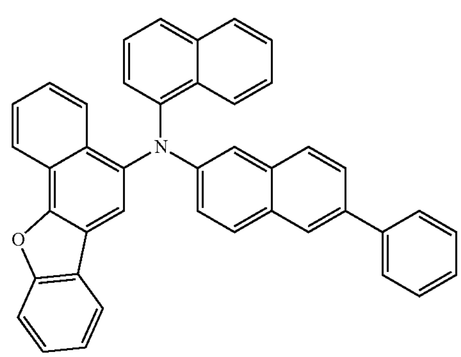

-continued
A23
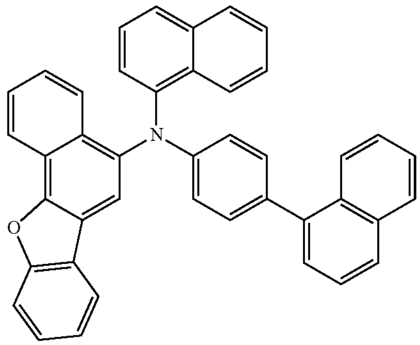
A24
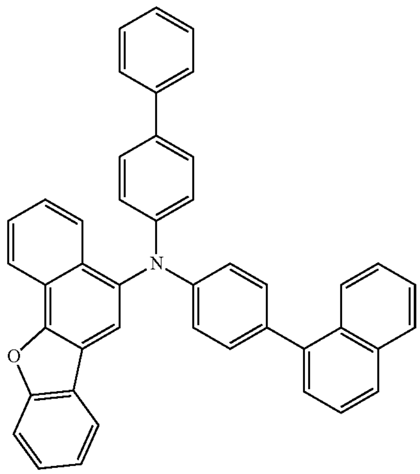
A25
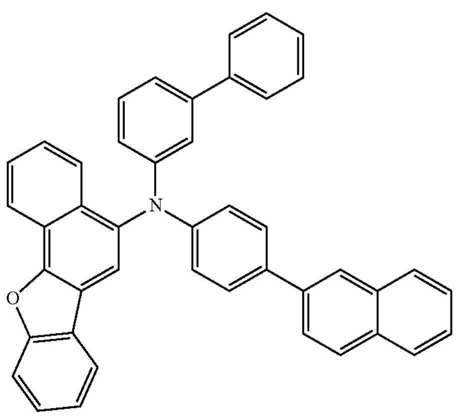
A26
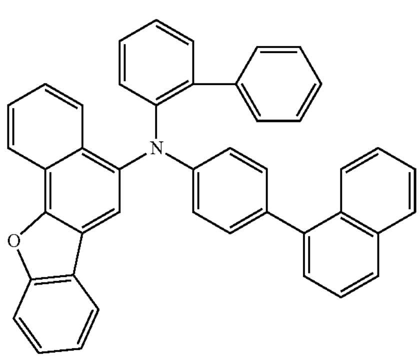
-continued
A27
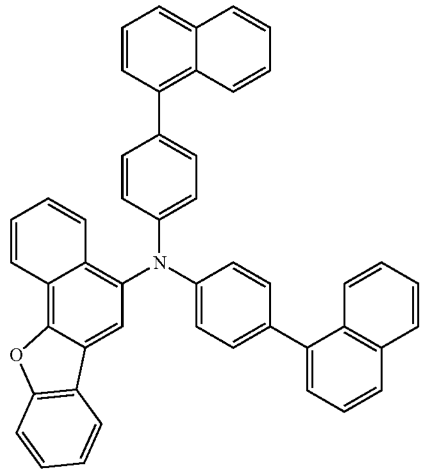
A28
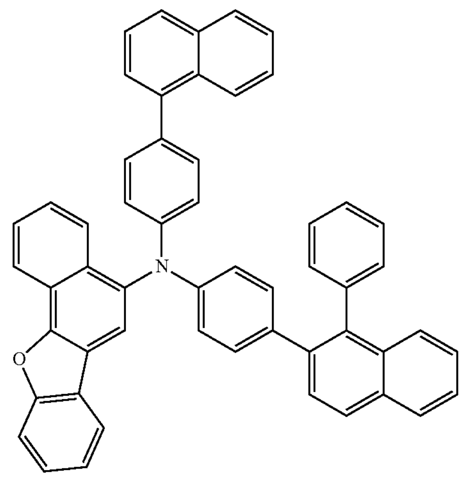
A29
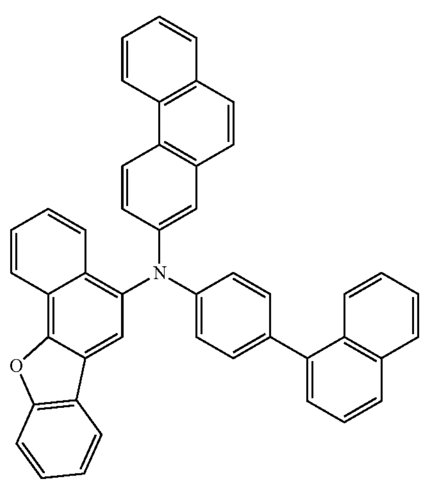

-continued
A30
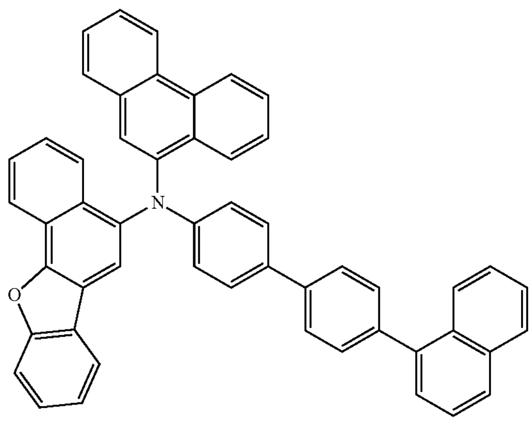
A31
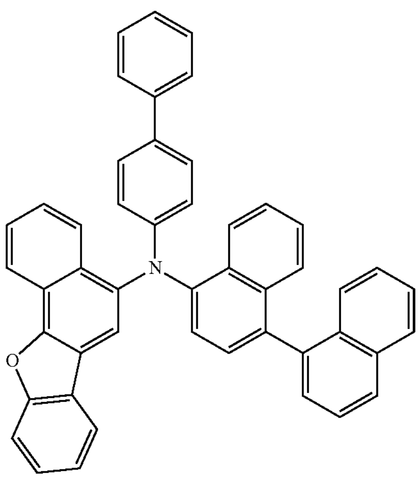
A32
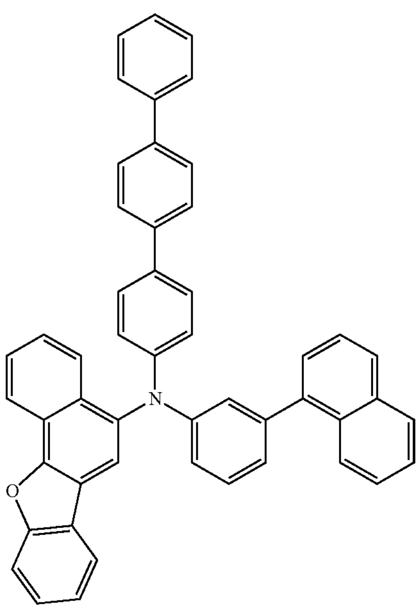
-continued
A33
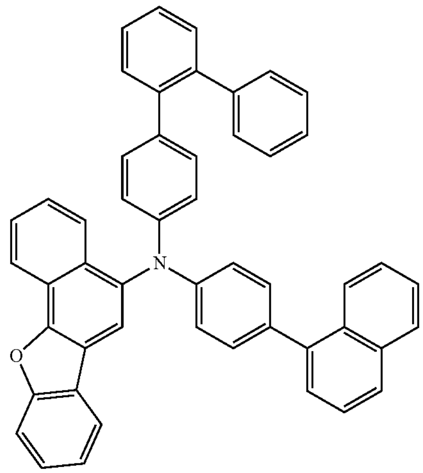
A34
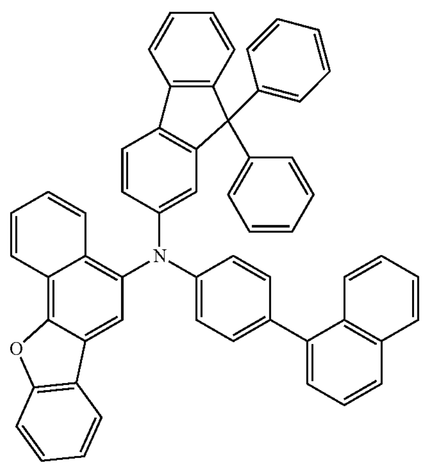
A35
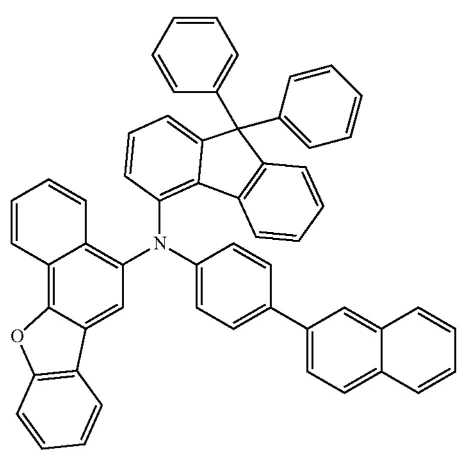

-continued
A36
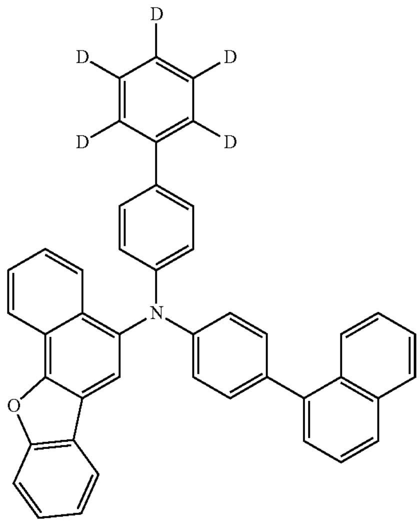
A37
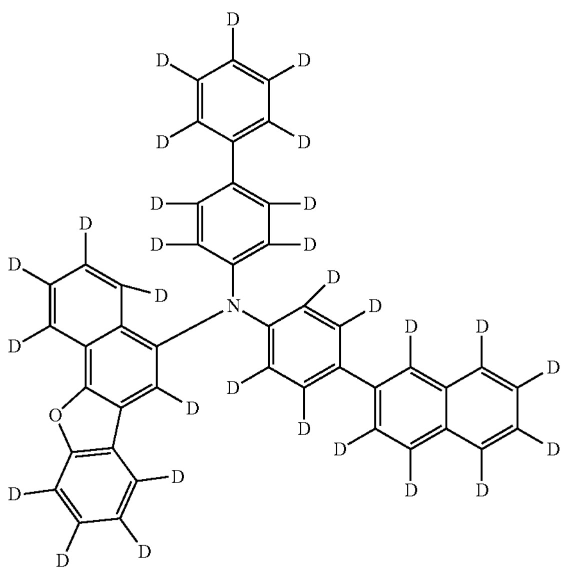
A38
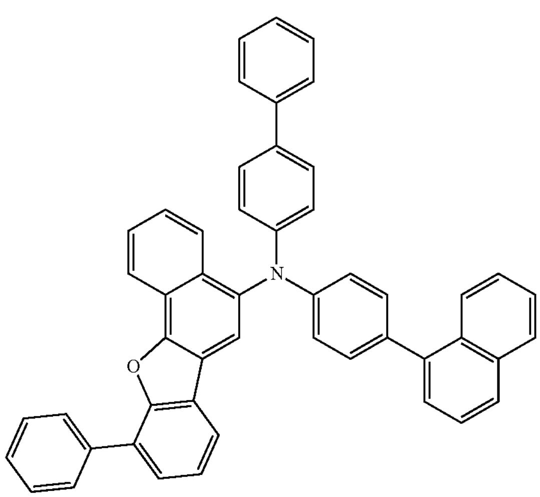
-continued
A39
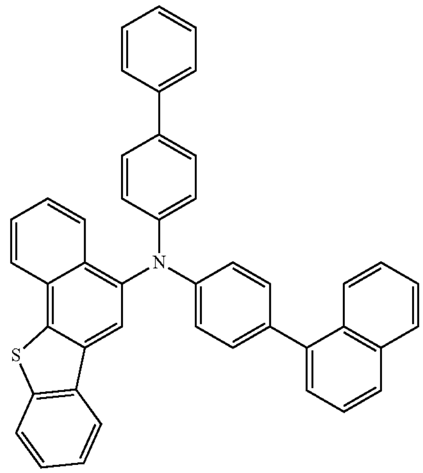
A40
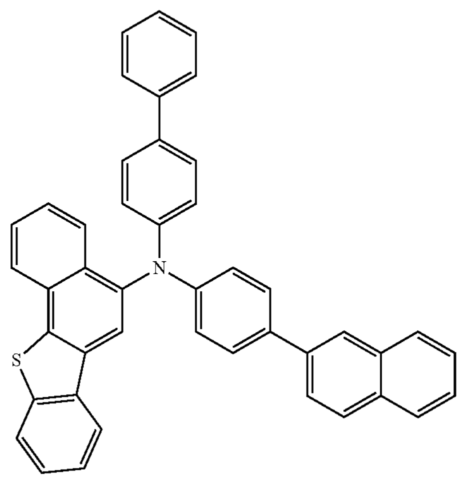
A41
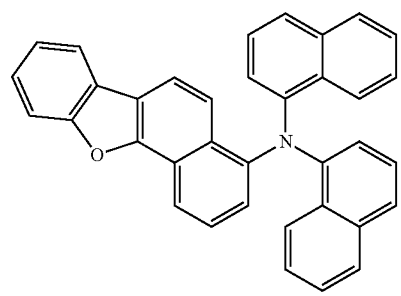
A42
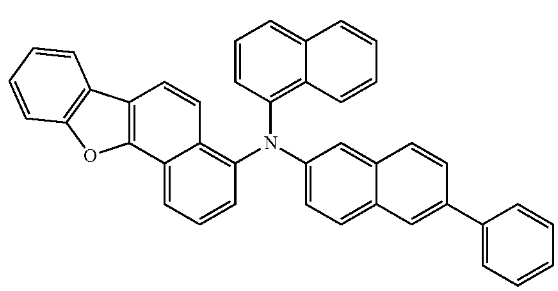

-continued
A43
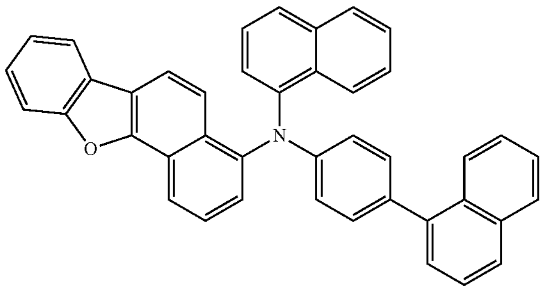
A44
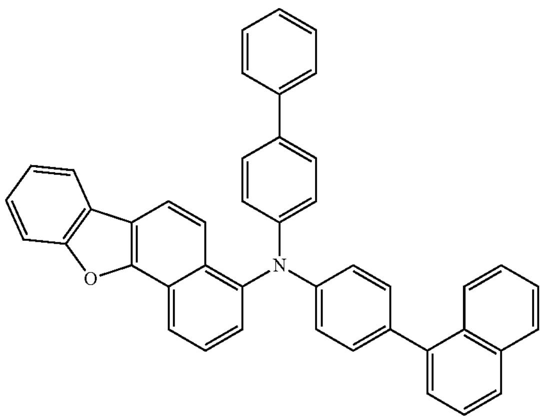
A45
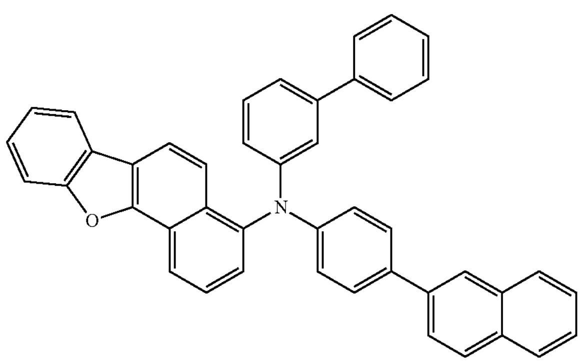
A46
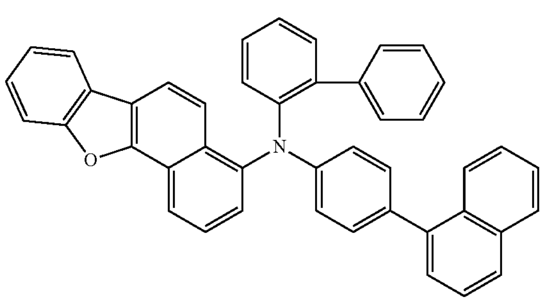
-continued
A47
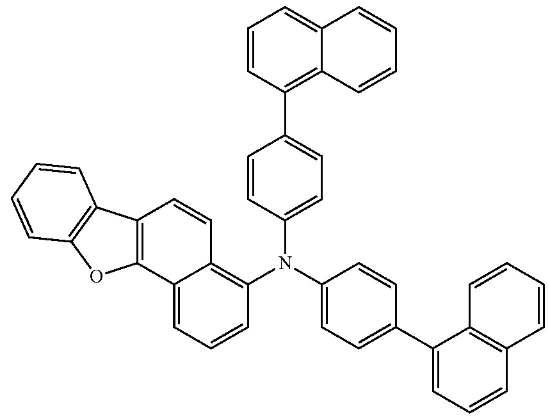
A48
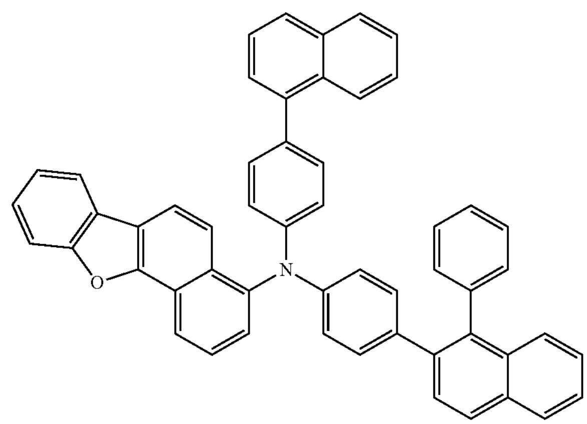
A49
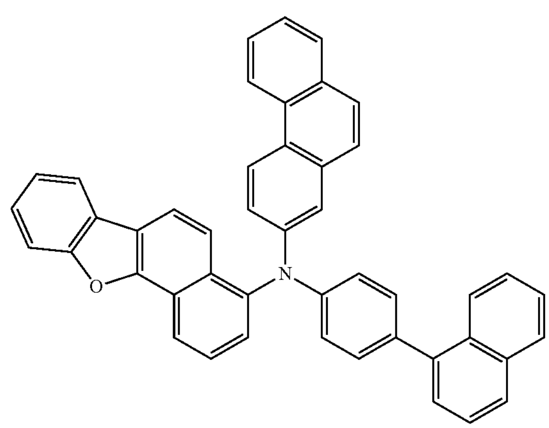

-continued
A50
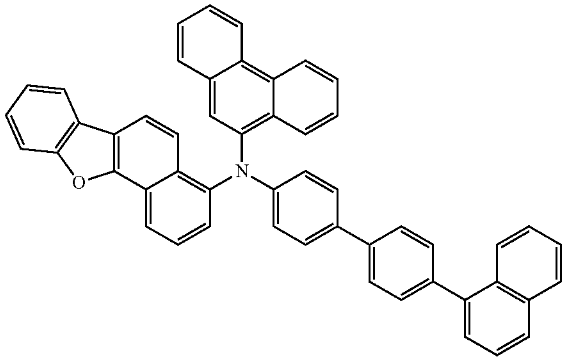
A51
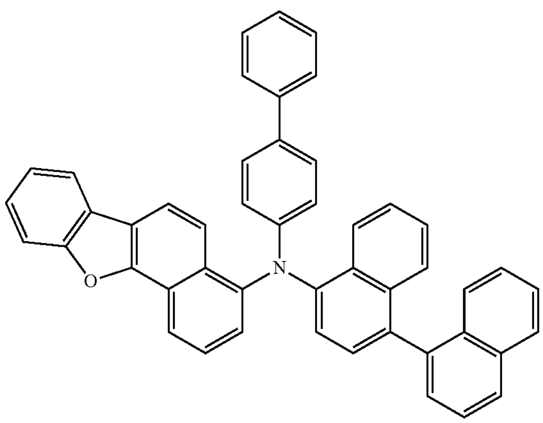
A52
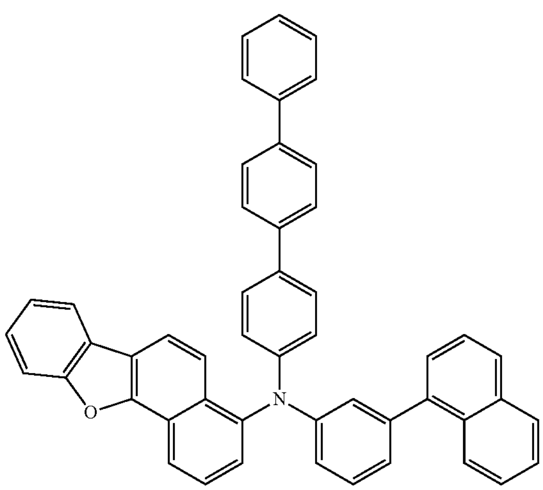
-continued
A53
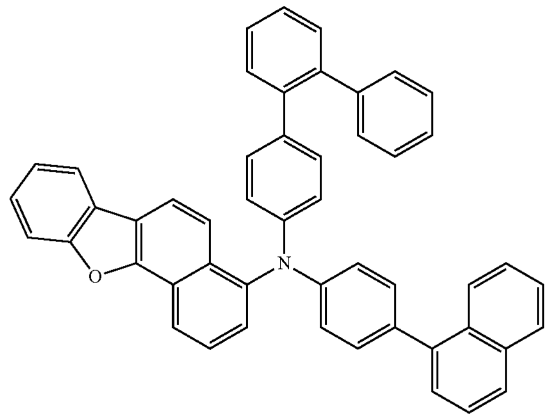
A54
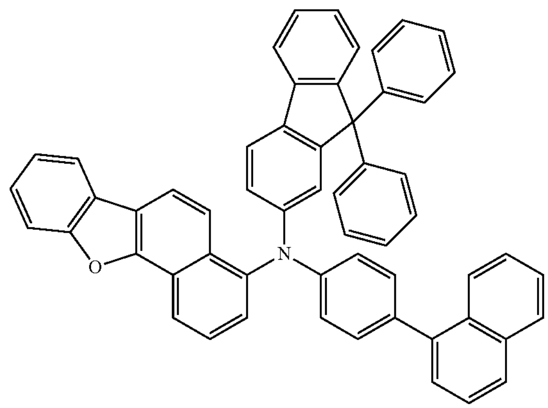
A55
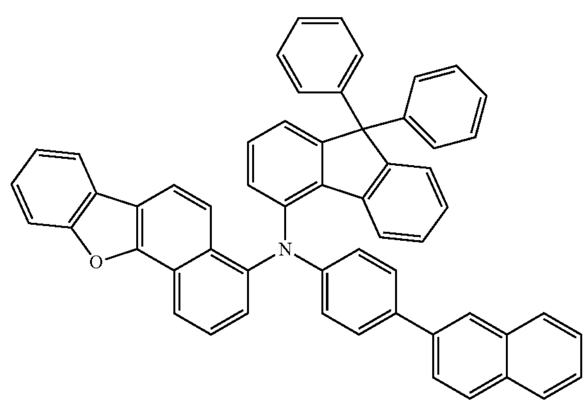

-continued
A56
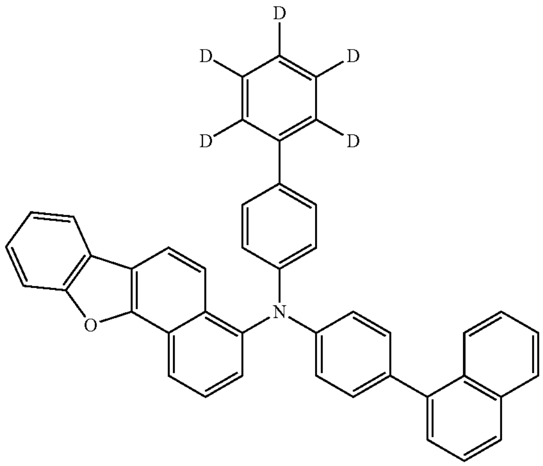
A57
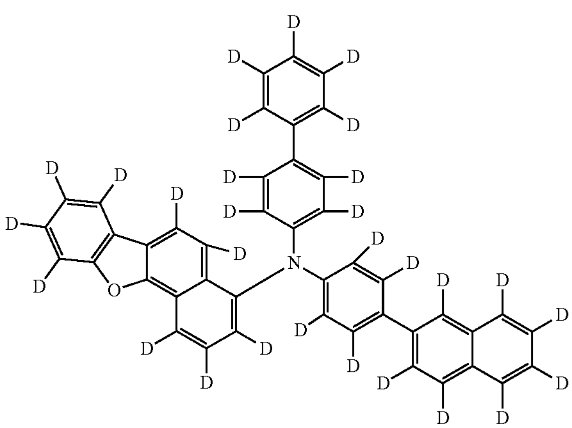
A58
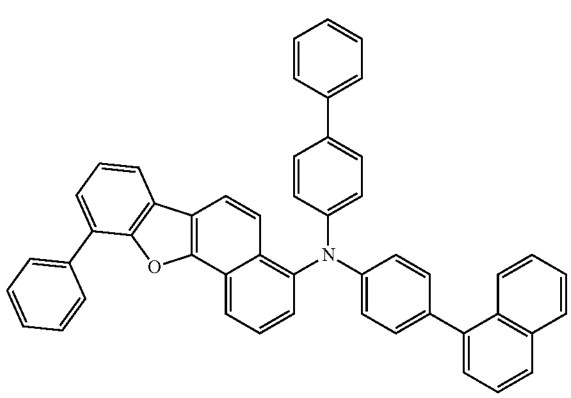
-continued
A59
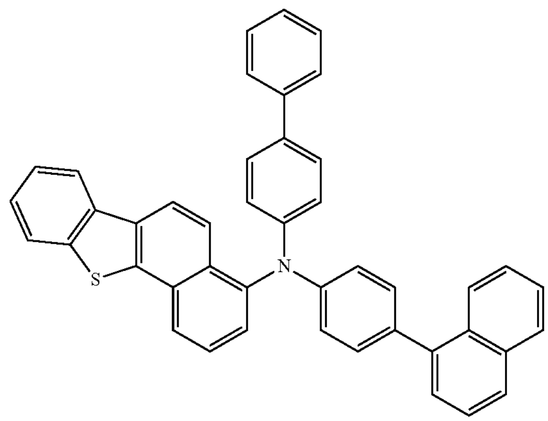
A60
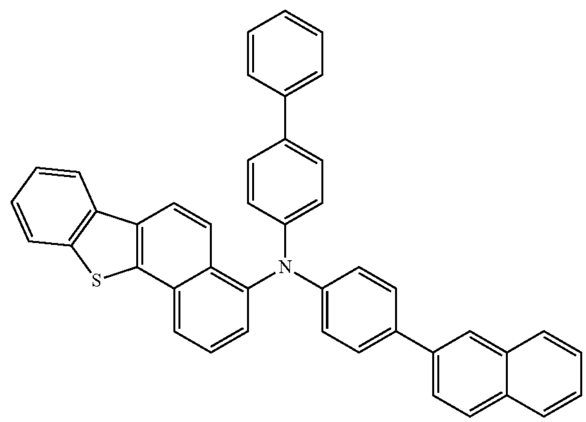
A61
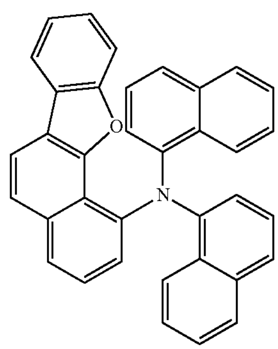
A62
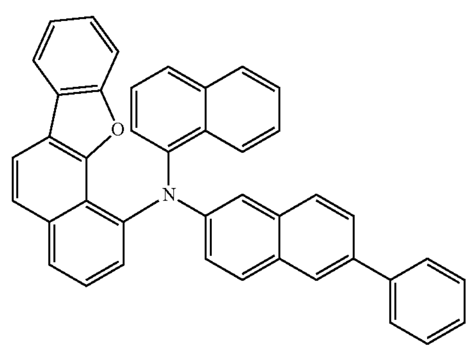

-continued
A63
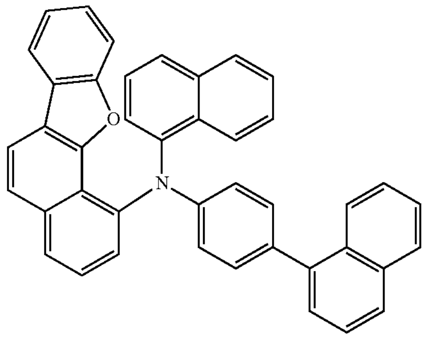
A64
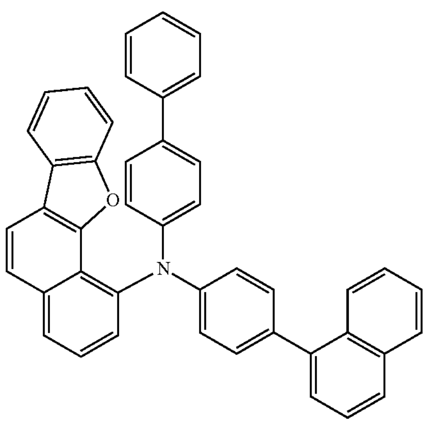
A65
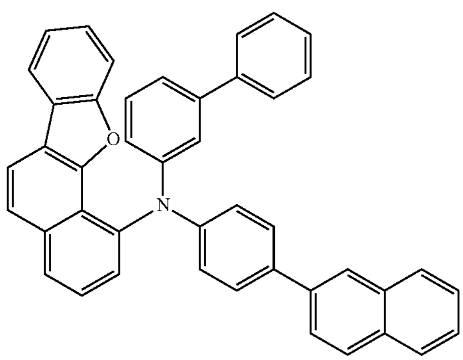
A66
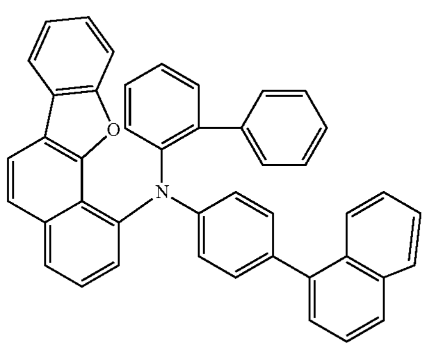
-continued
A67
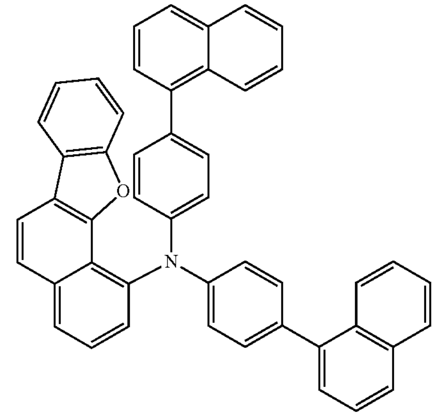
A68
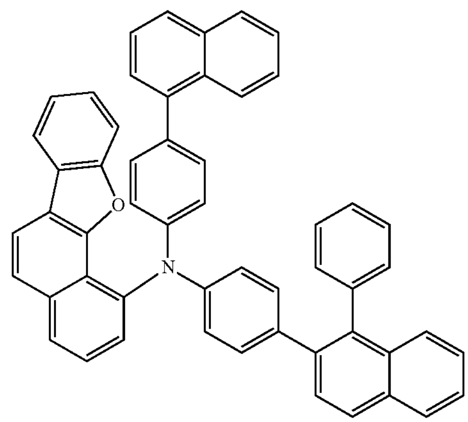
A69
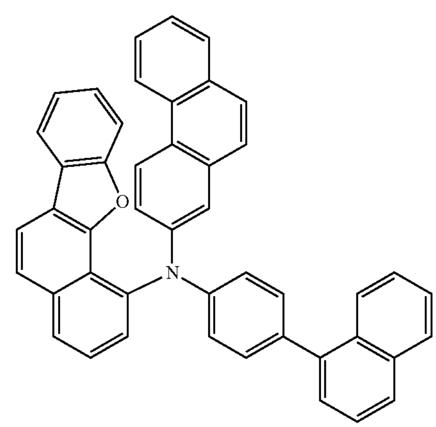

-continued
A70
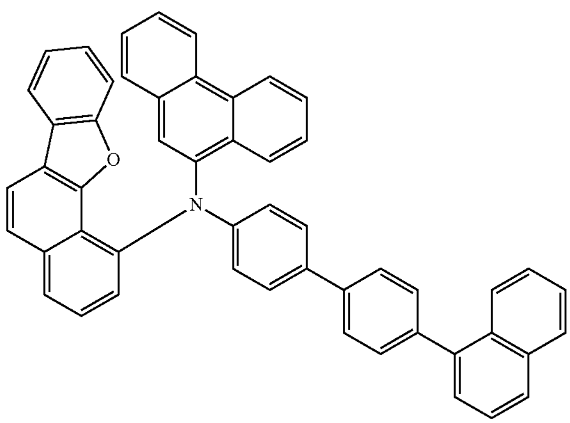
A71
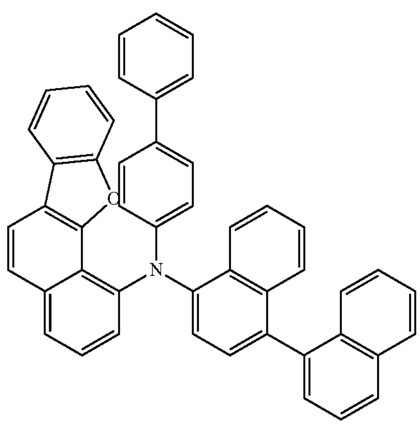
A72
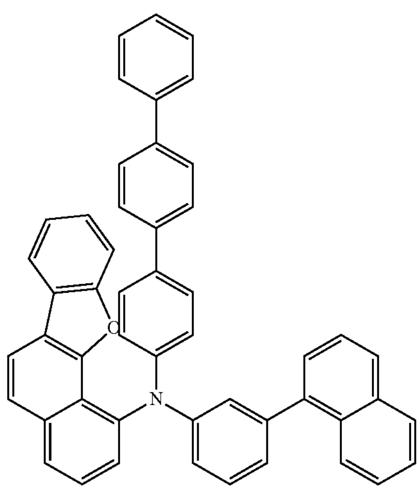
-continued
A73
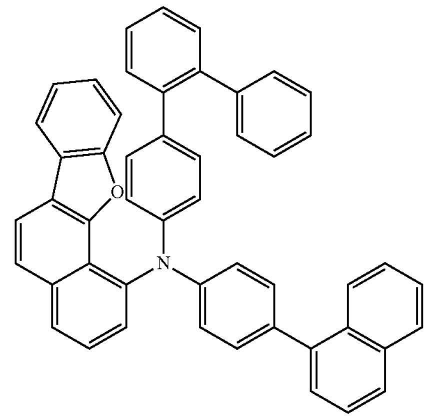
A74
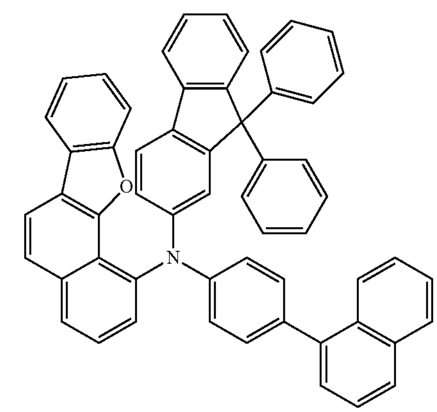
A75
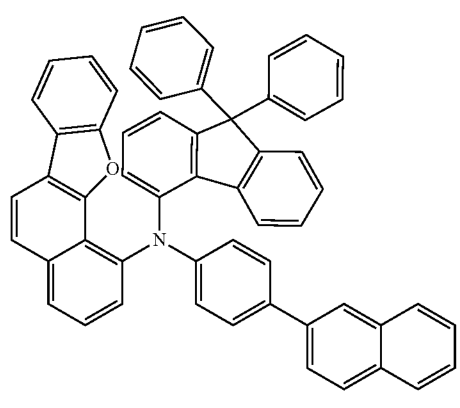

-continued
A76
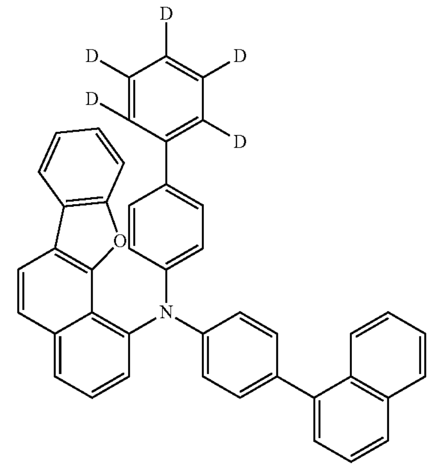
A77
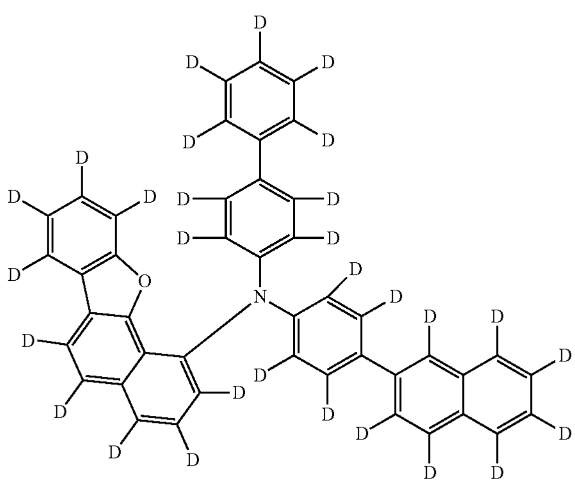
A78
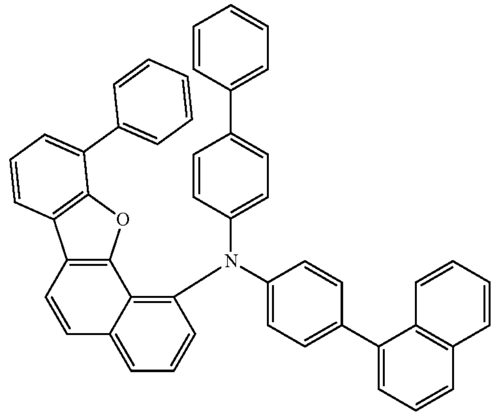
-continued
A79
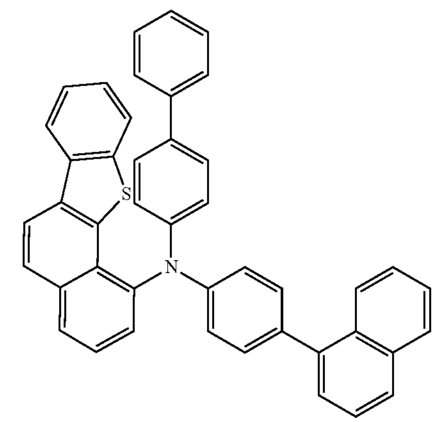
A80
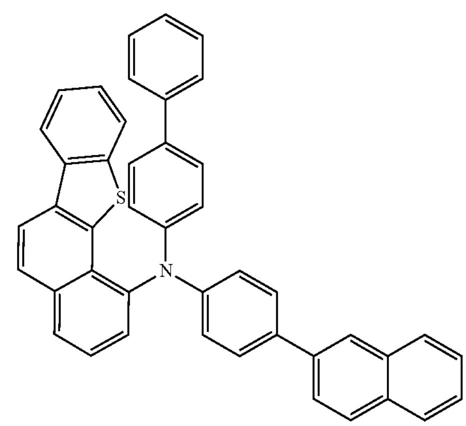
A81
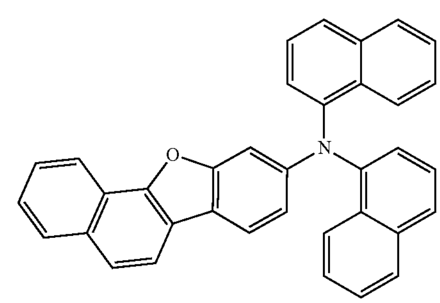
A82
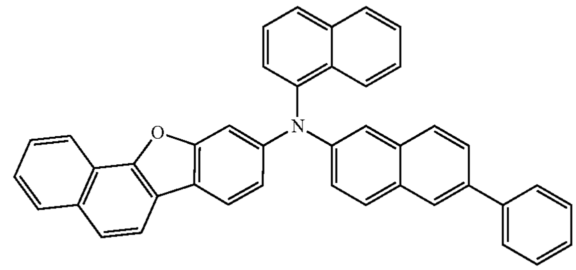

-continued
A83
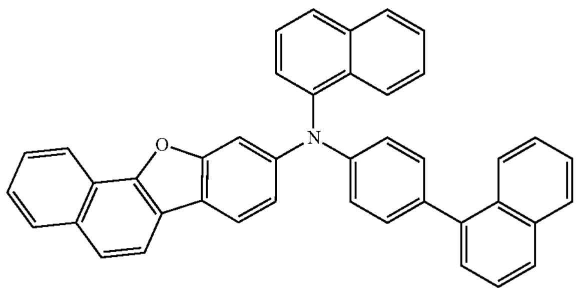
A84
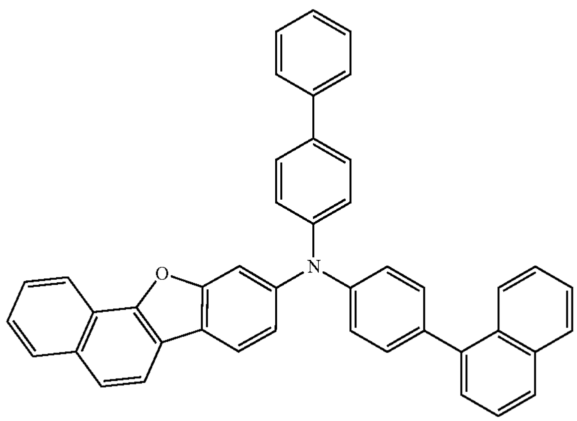
A85
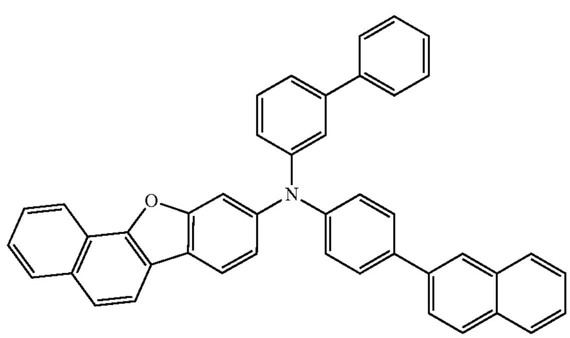
A86
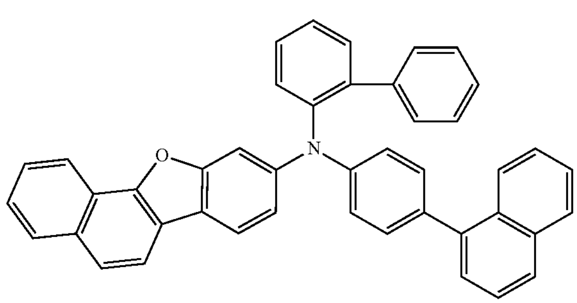
-continued
A87
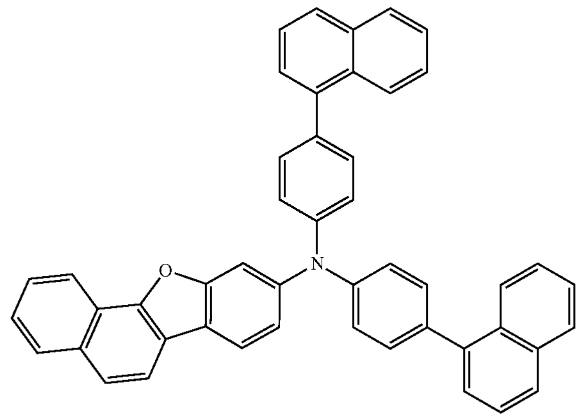
A88
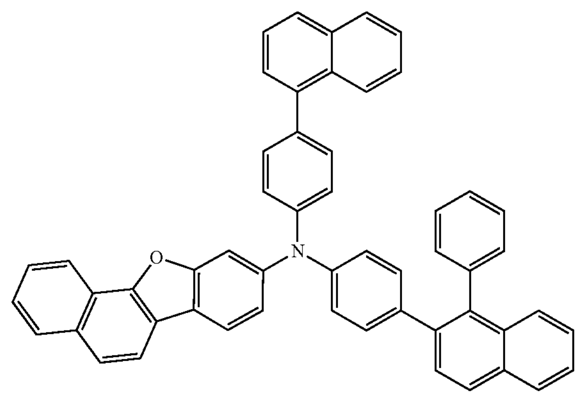
A89
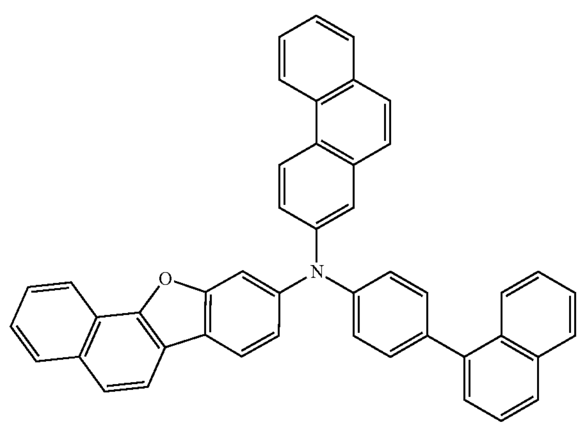
A90
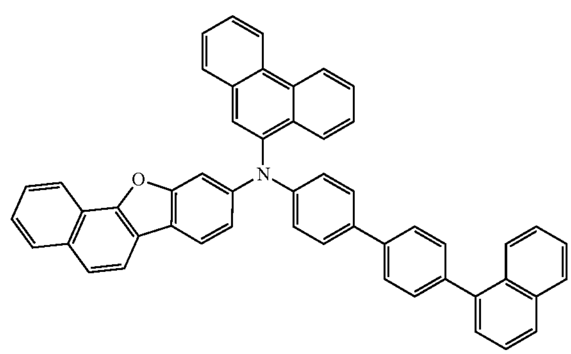

-continued
A91
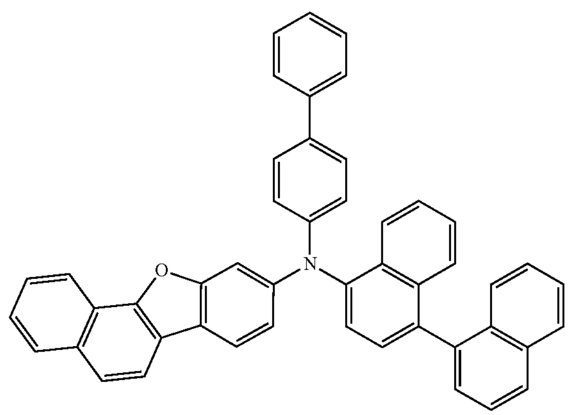
A92
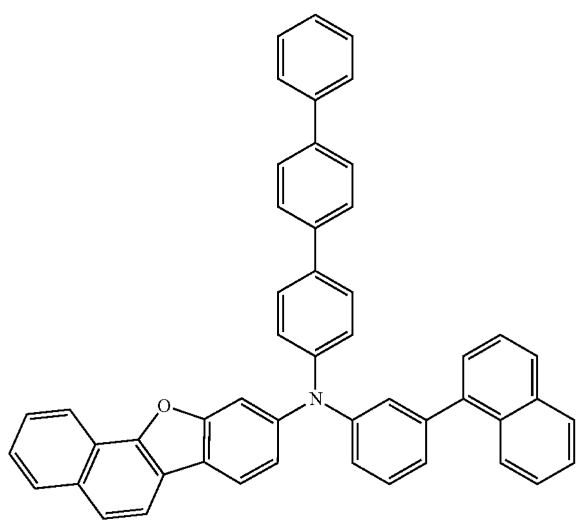
A93
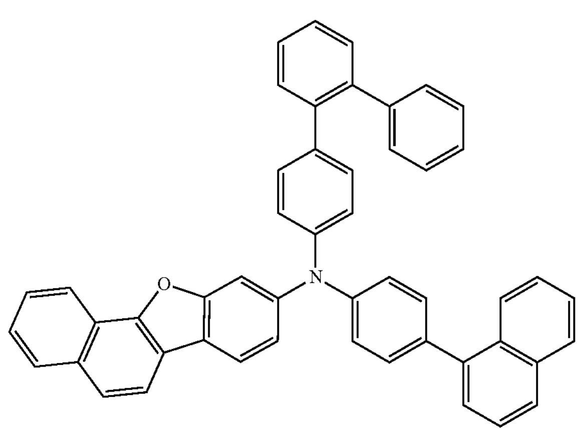
-continued
A94
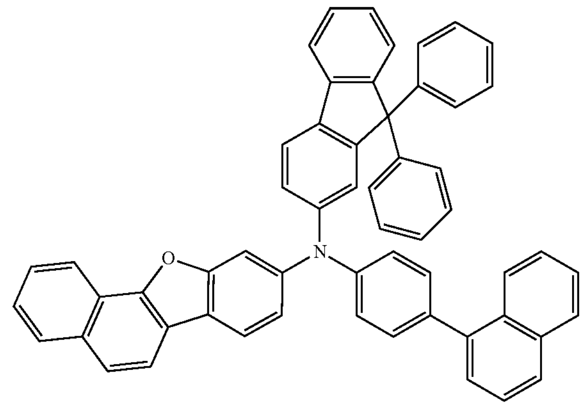
A95
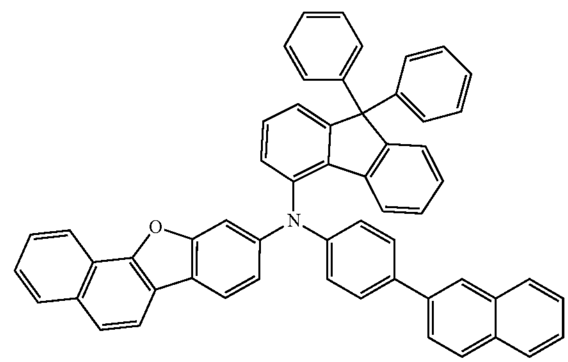
A96
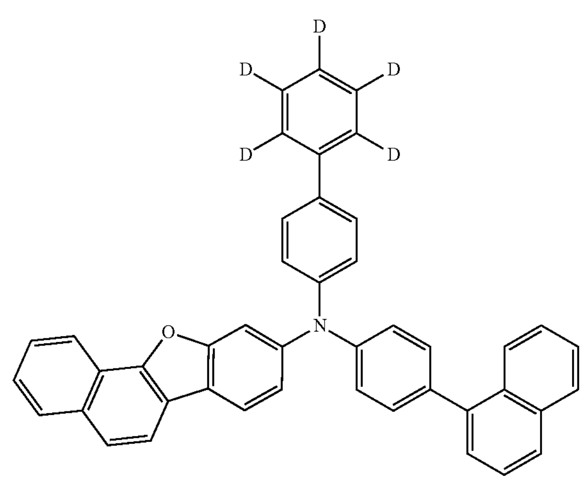

-continued
A97
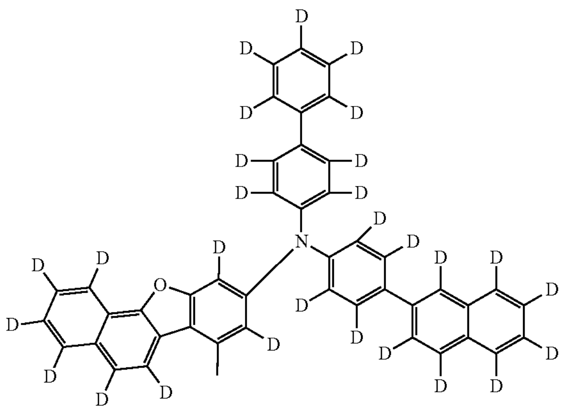
A98
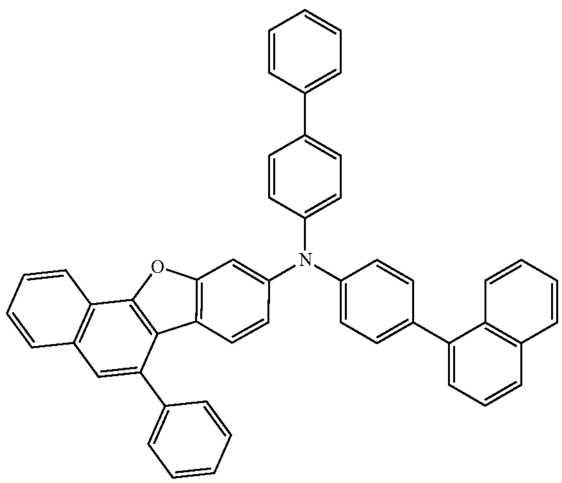
A99
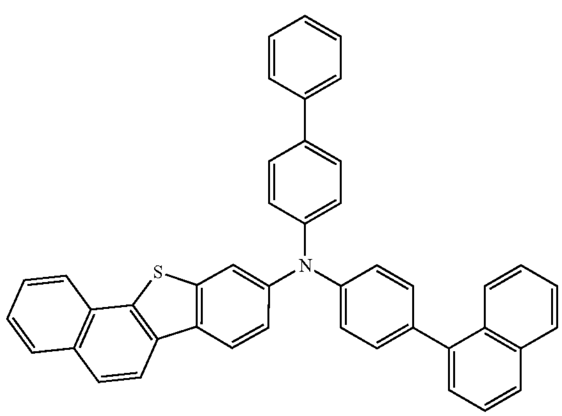
-continued
A100
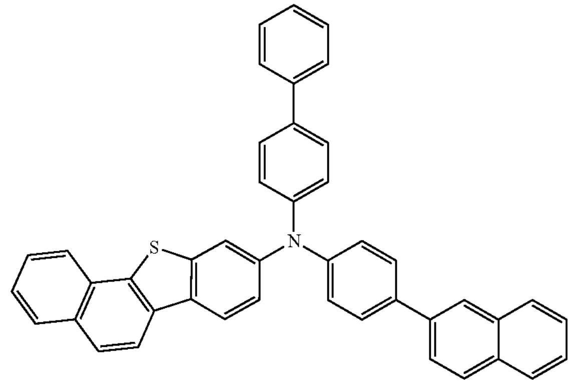
A101
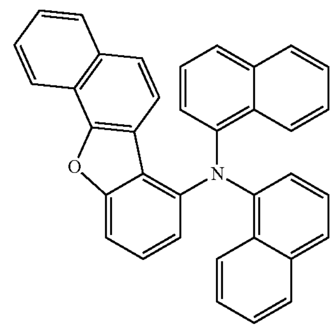
A102
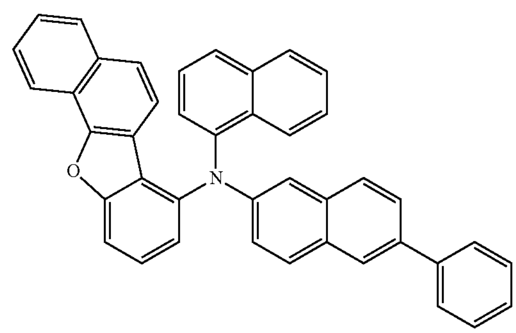
A103
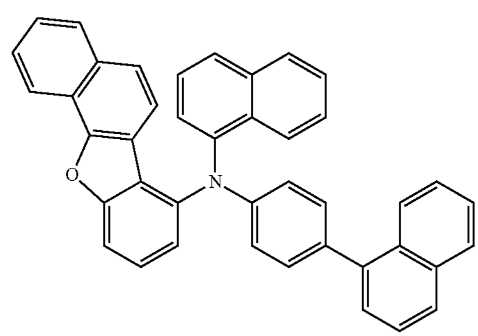

-continued
A104
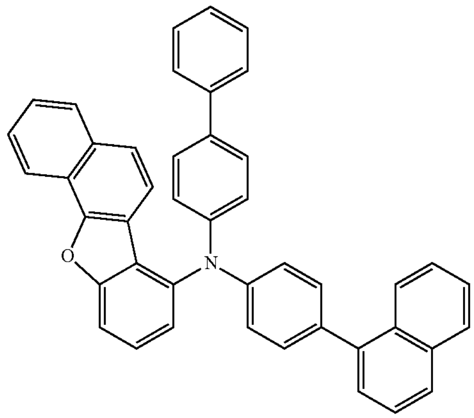
A105
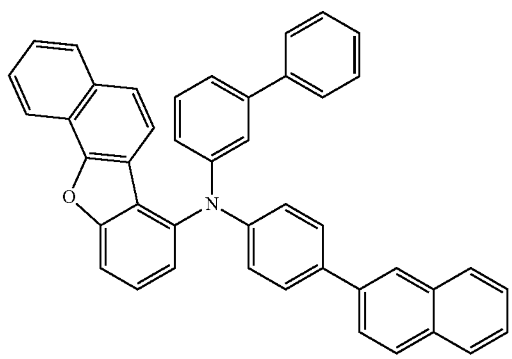
A106
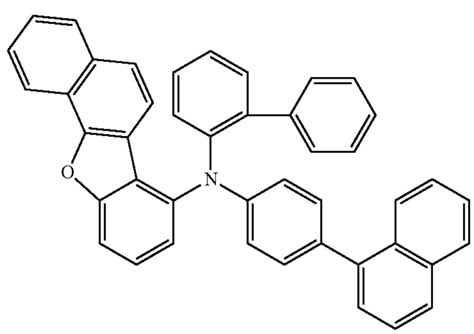
A107
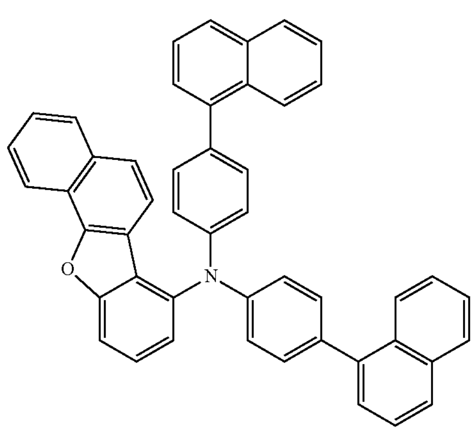
-continued
A108
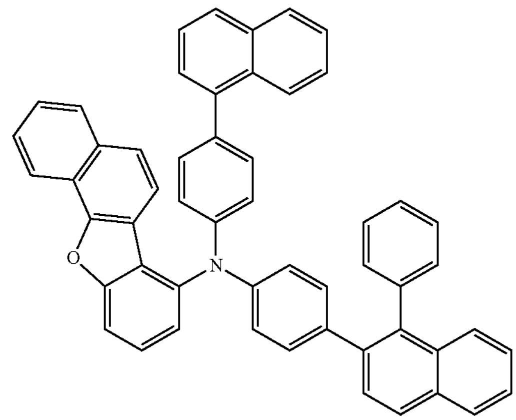
A109
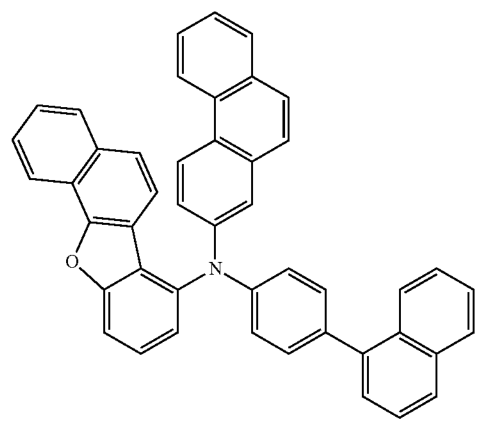
A110
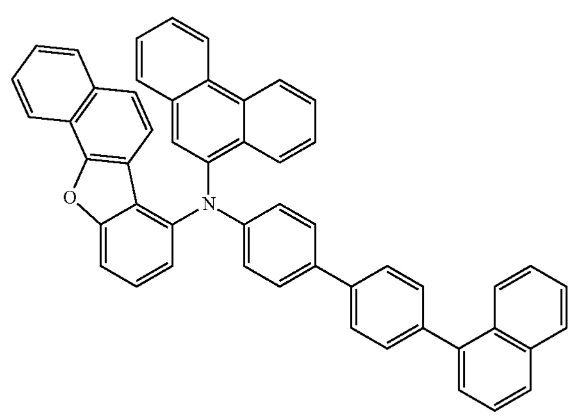

-continued
A111
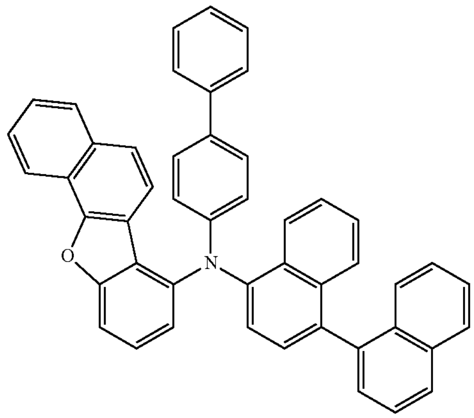
A112
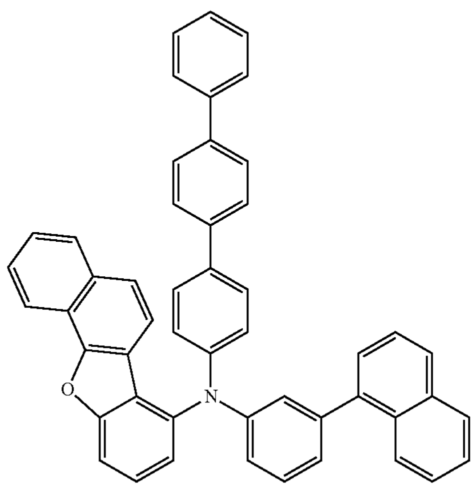
A113
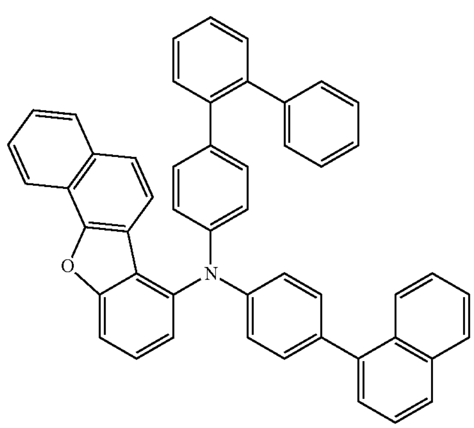
-continued
A114
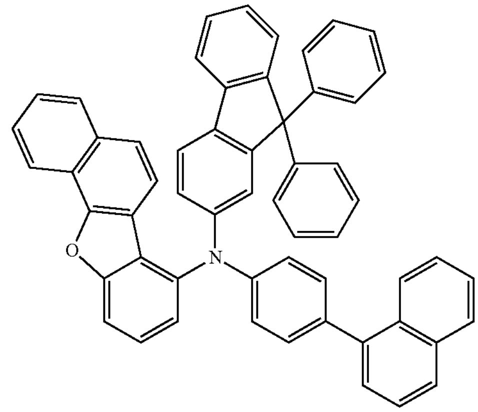
A115
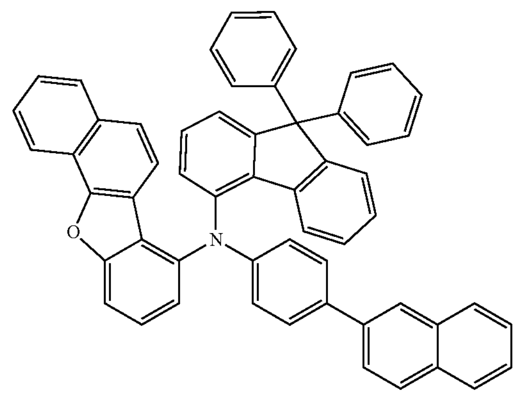
A116
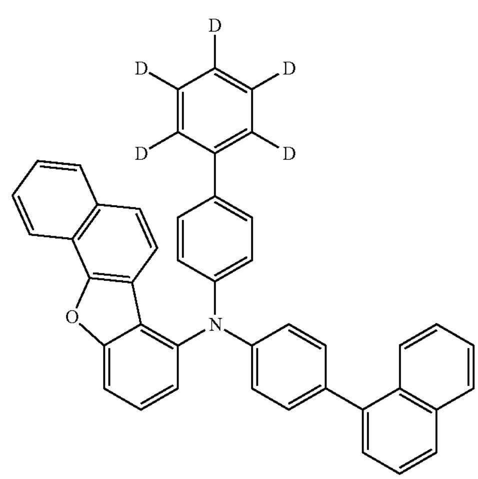

-continued
A117
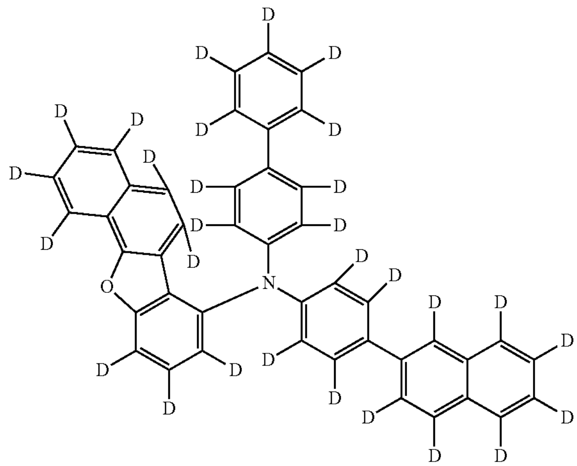
A118
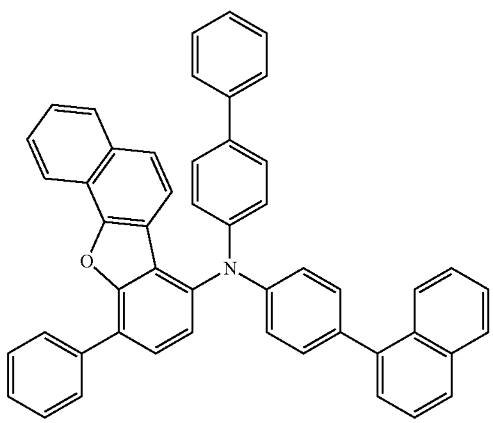
A119
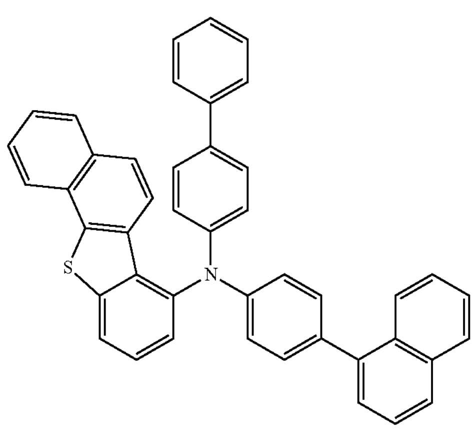
-continued
A120
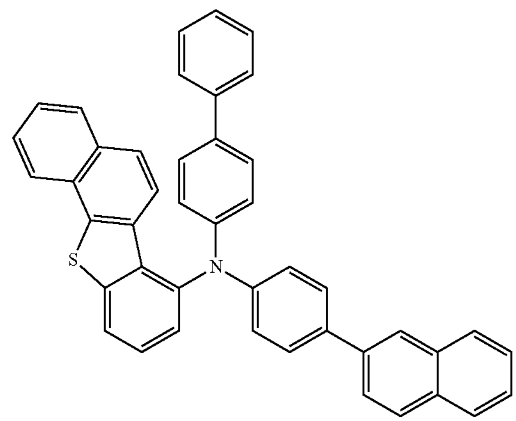
A121
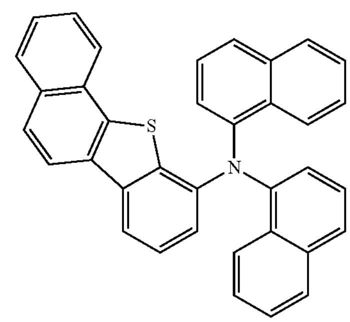
A122
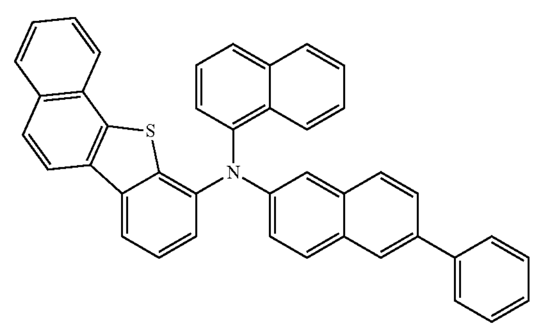
A123
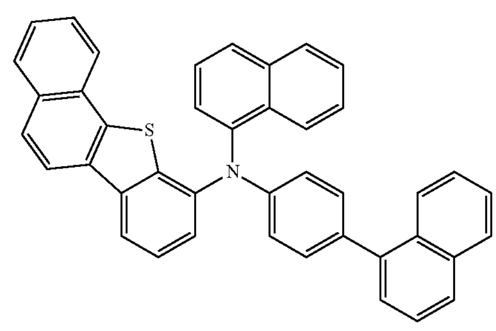

-continued
A124
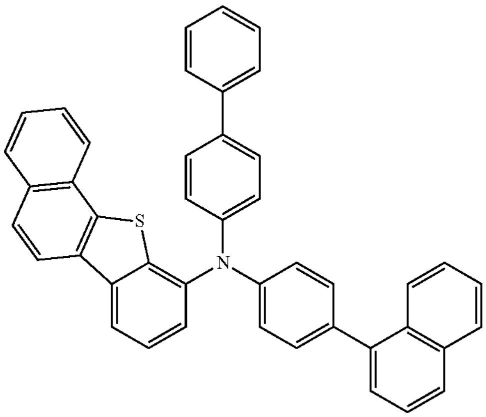
A125
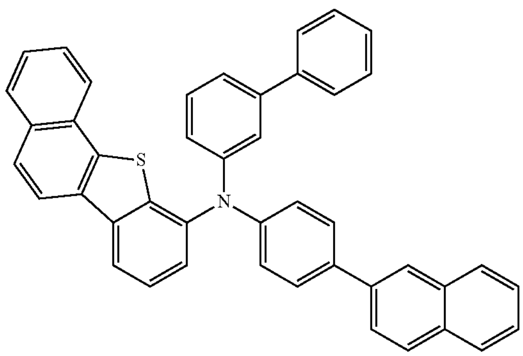
A136
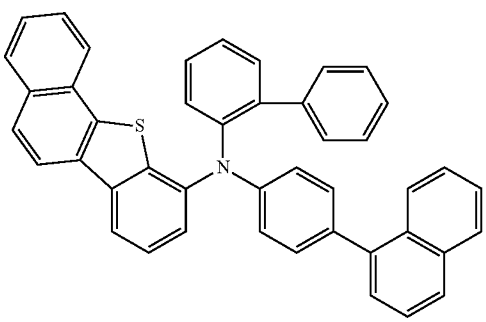
A127
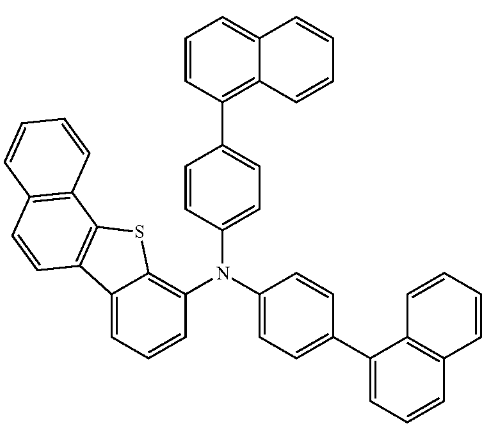
-continued
A128
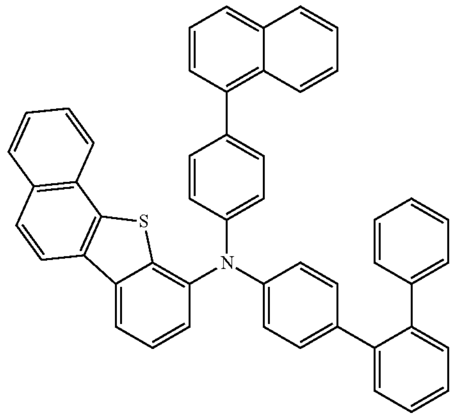
A129
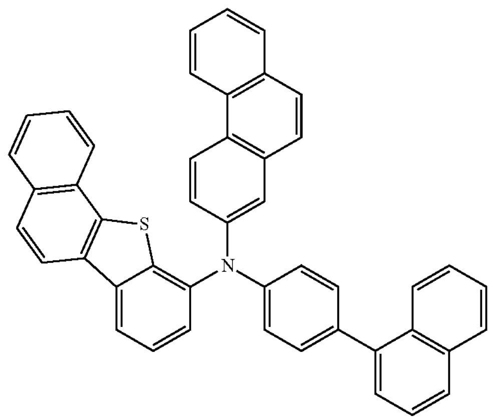
A130
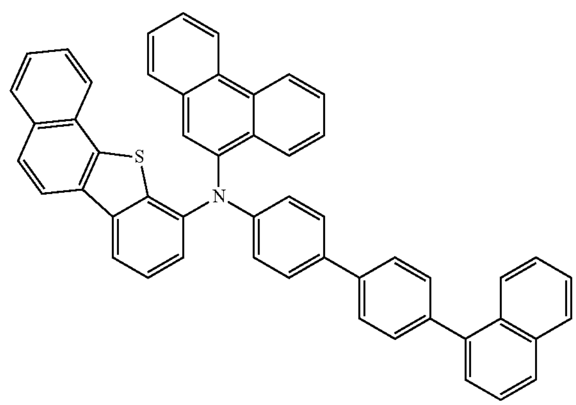
A131
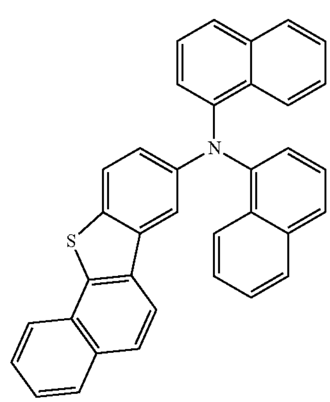

-continued
A132
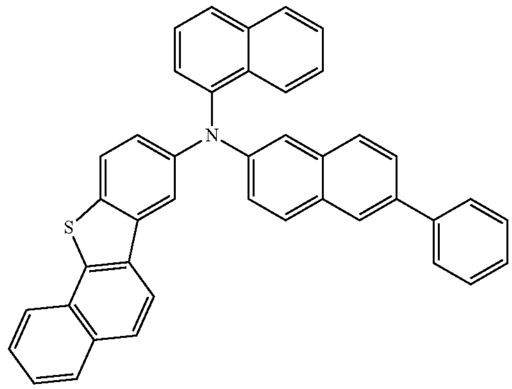
A133
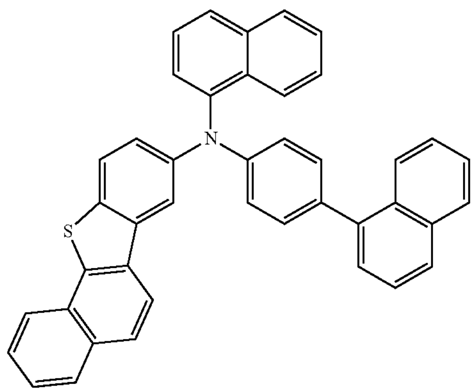
A134
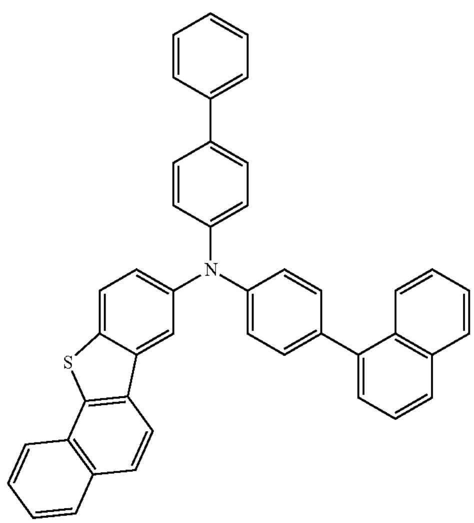
-continued
A135
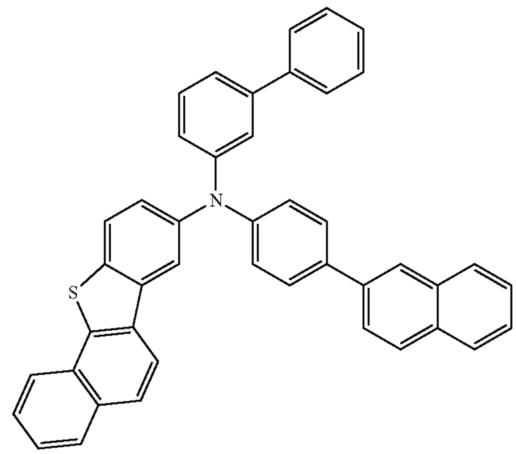
A136
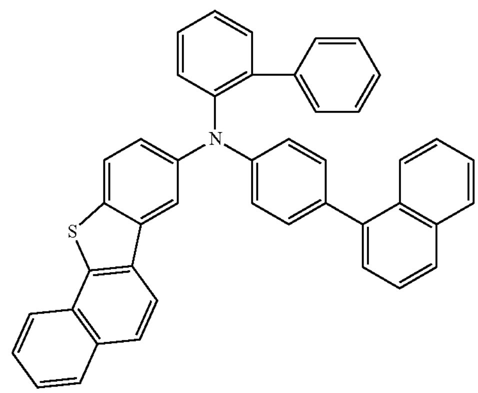
A137
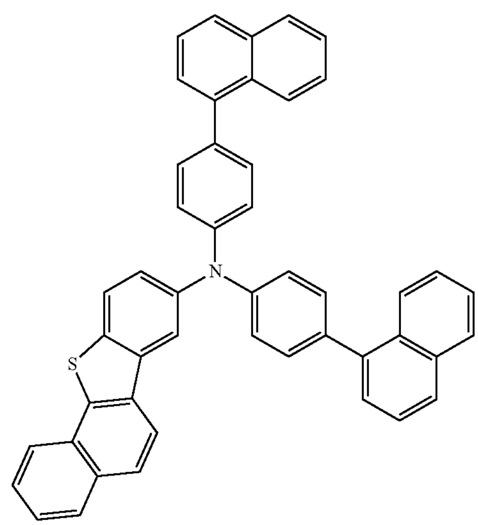

-continued
A138
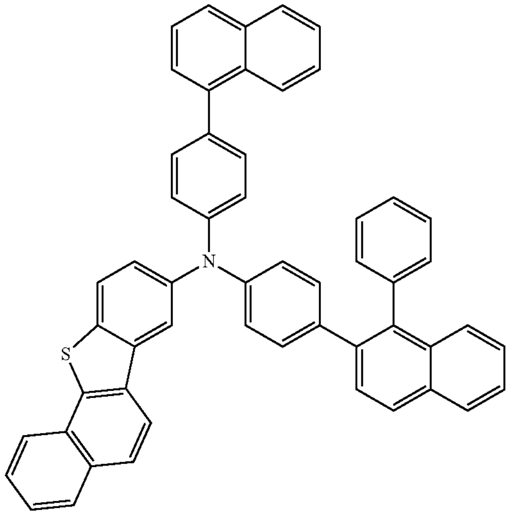
A139
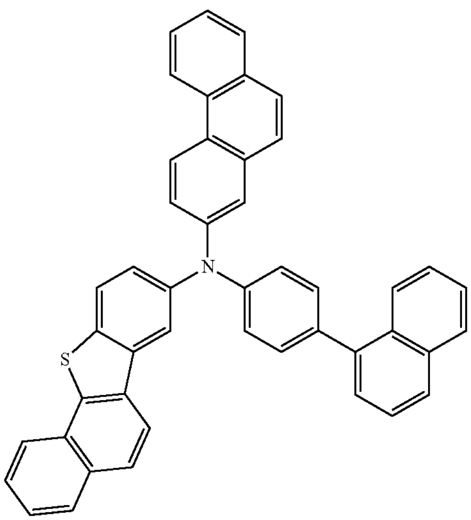
A140
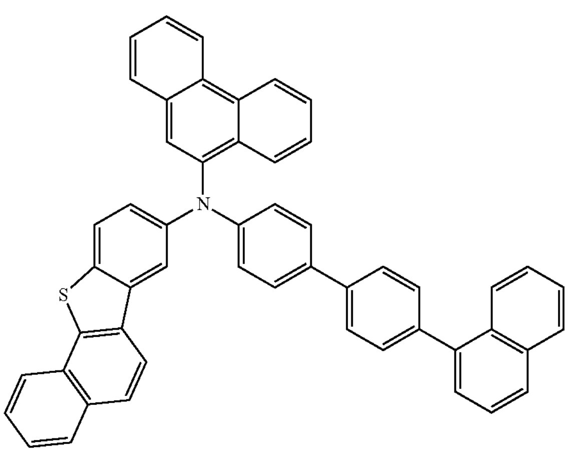
-continued
A141
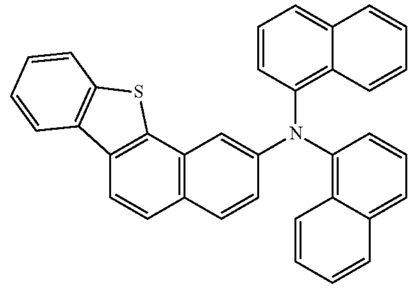
A142
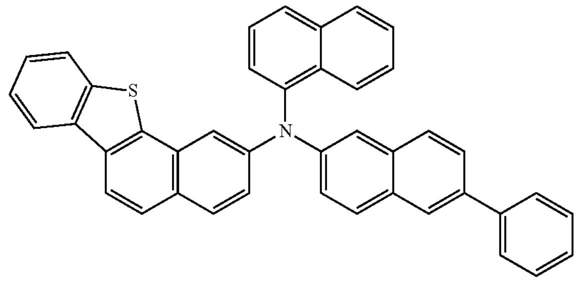
A143
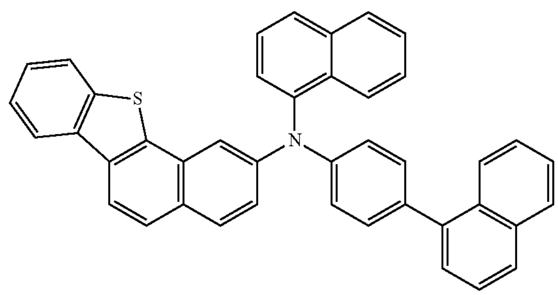
A144
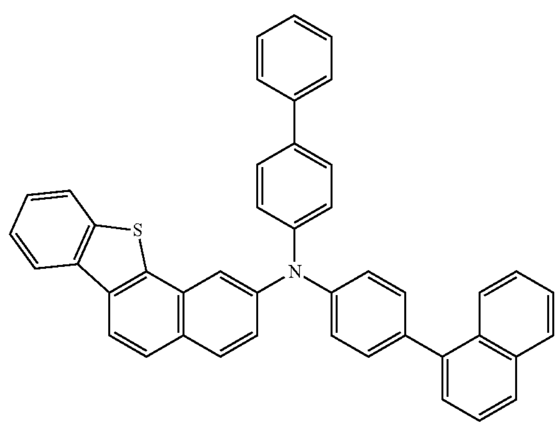

-continued
A145
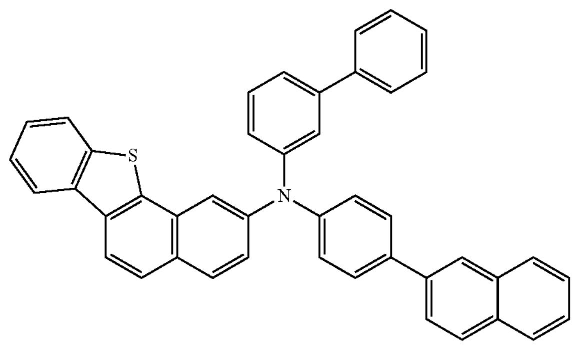
A146
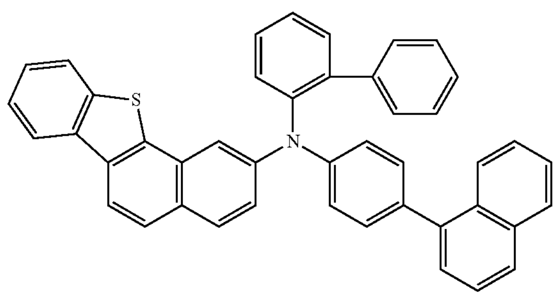
A147
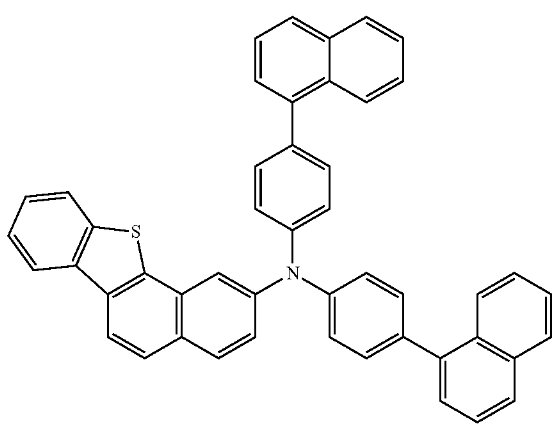
A148
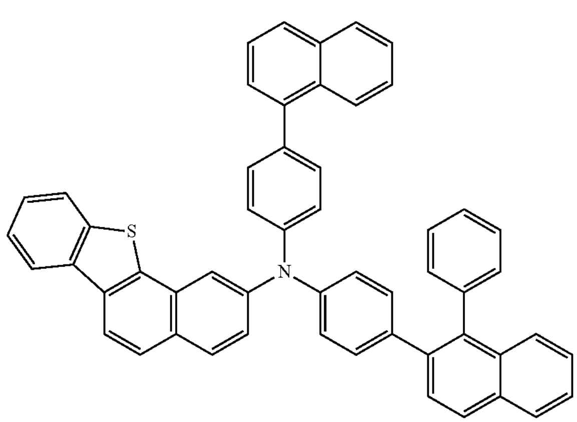
-continued
A149
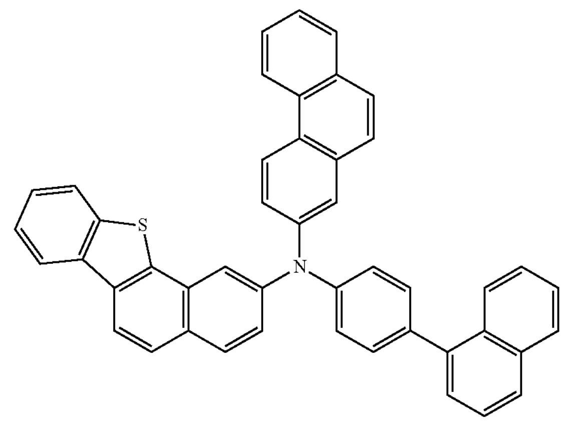
A150
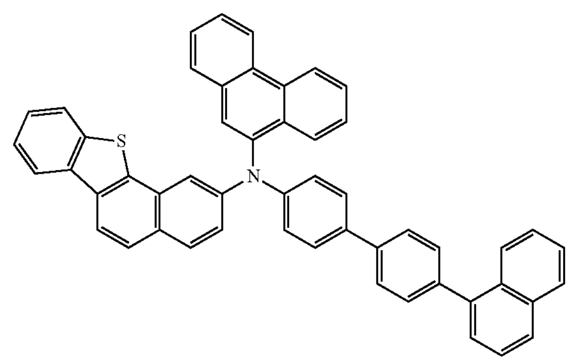
A151
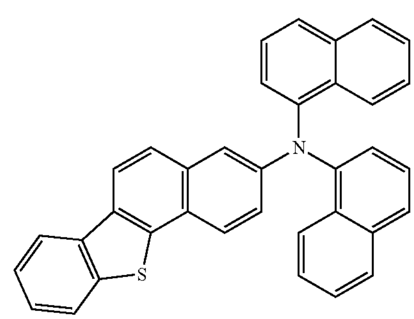
A152
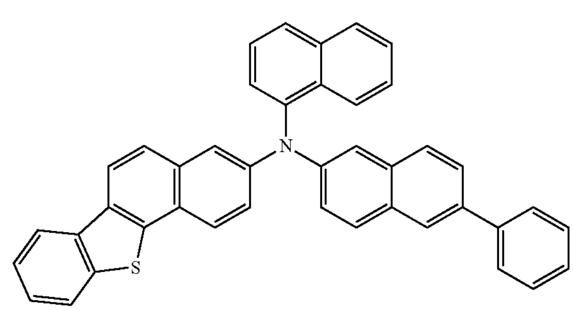

-continued
A153
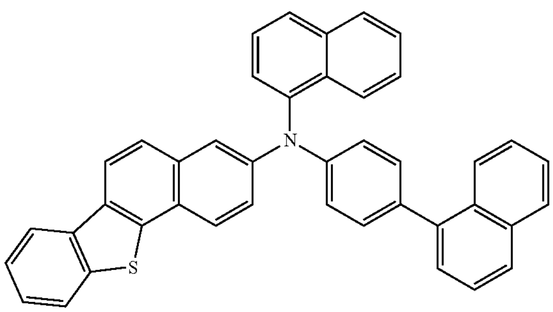
A154
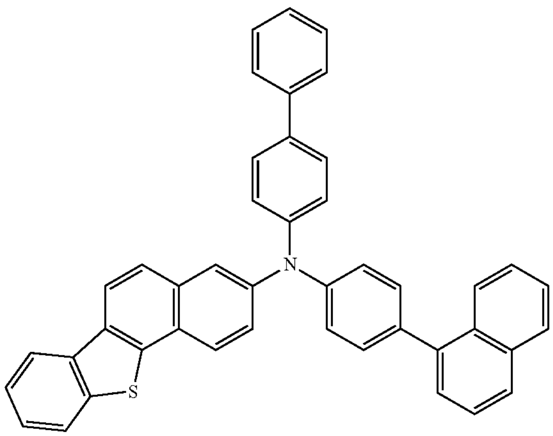
A155
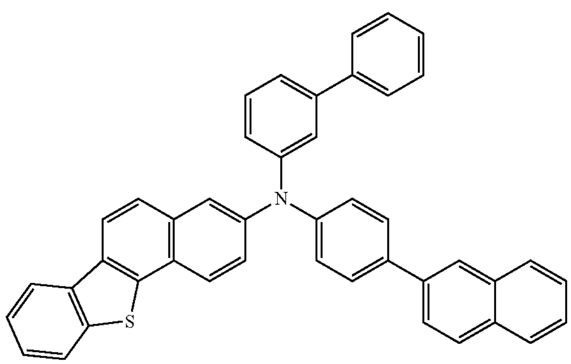
A156
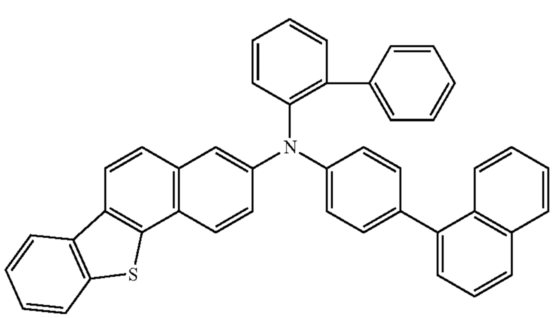
-continued
A157
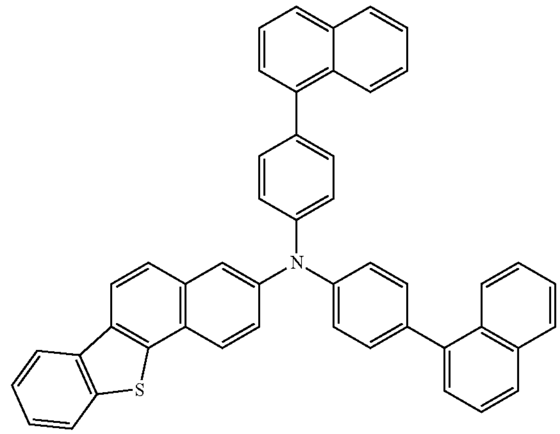
A158
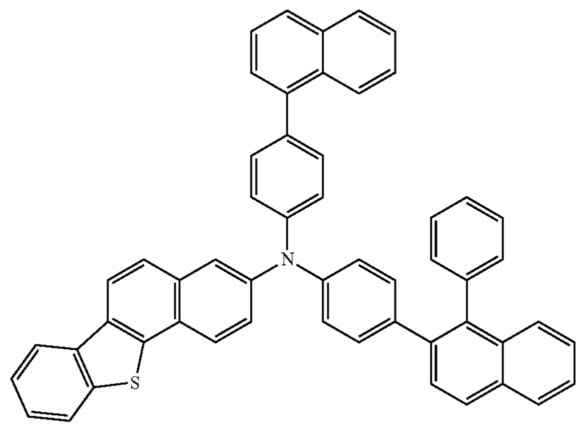
A159
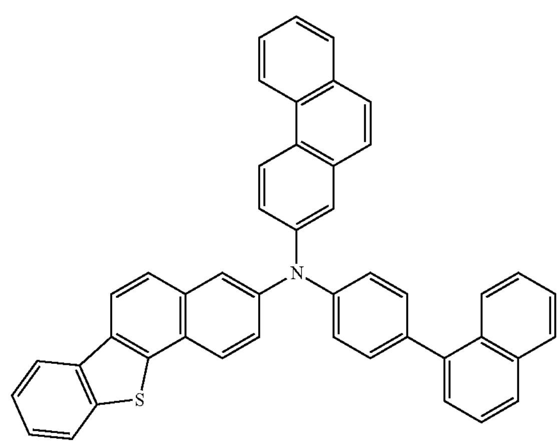

-continued
A160
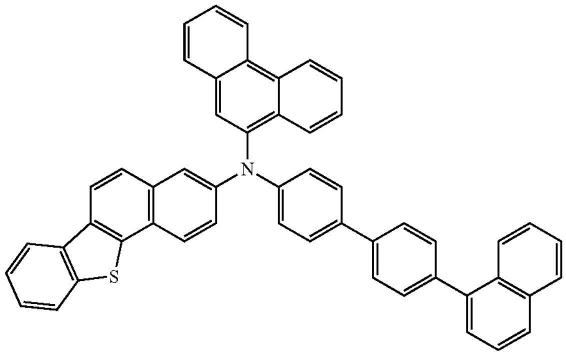
A161
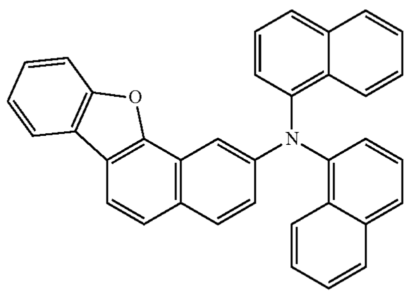
A162
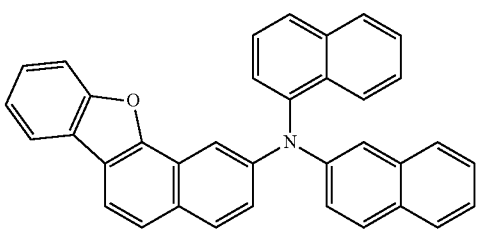
A163
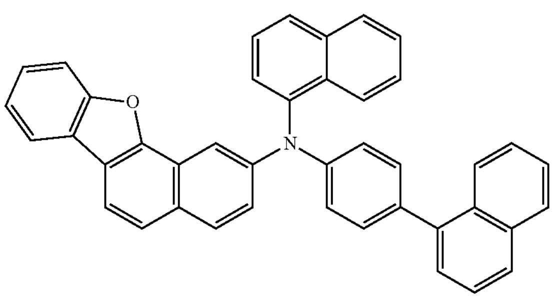
A164
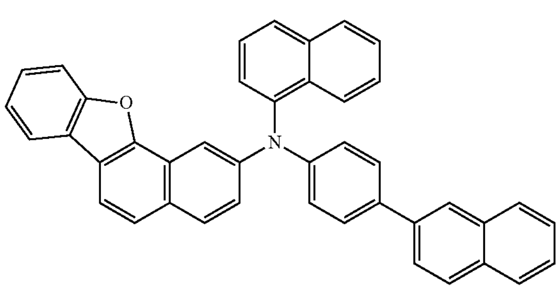
-continued
A165
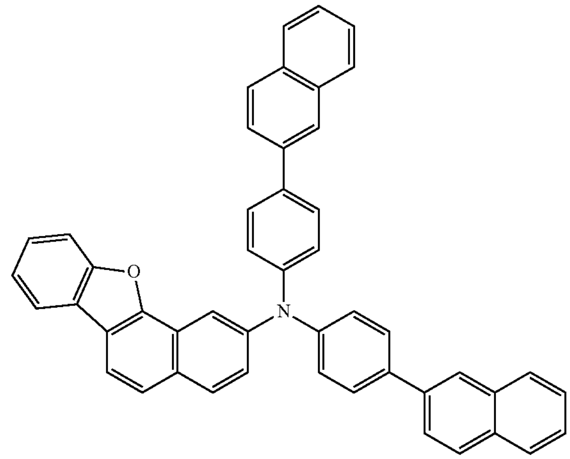
A166
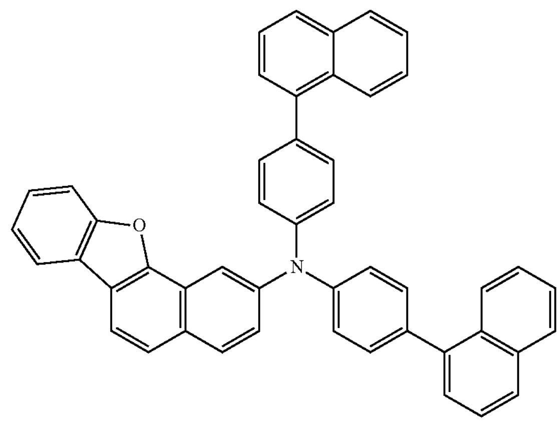
A167
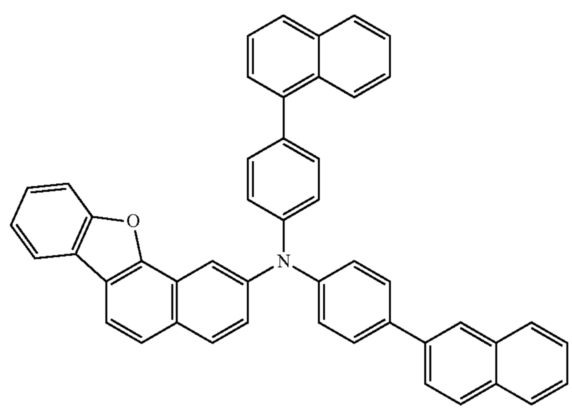

-continued
A168
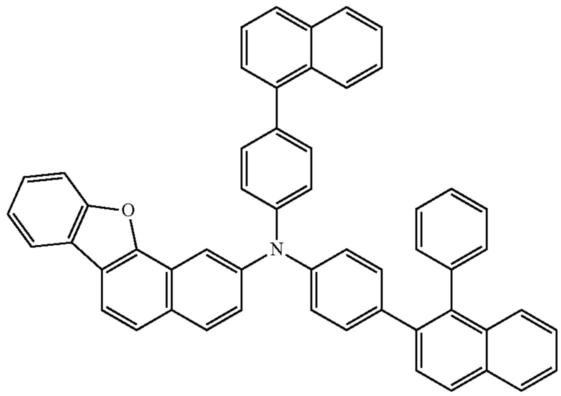
A169
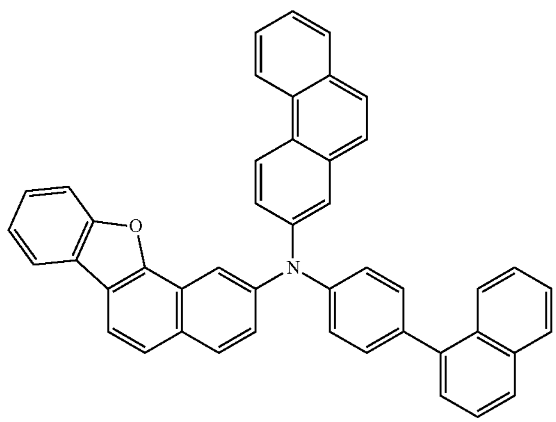
A170
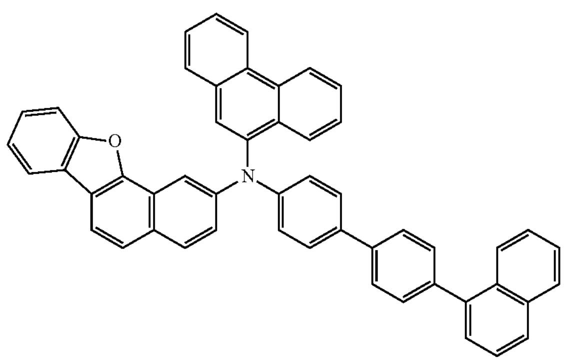
A171
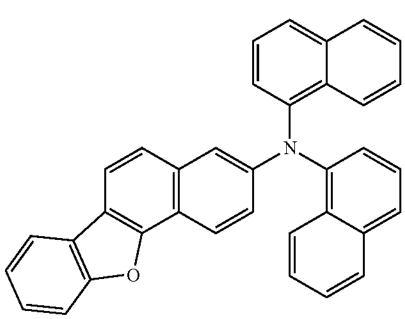
-continued
A172
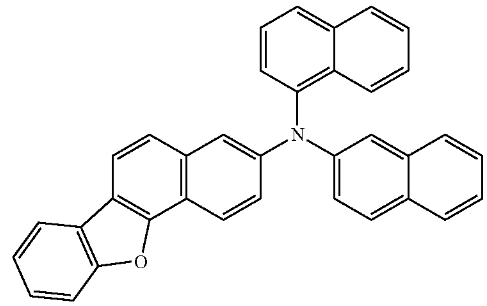
A173
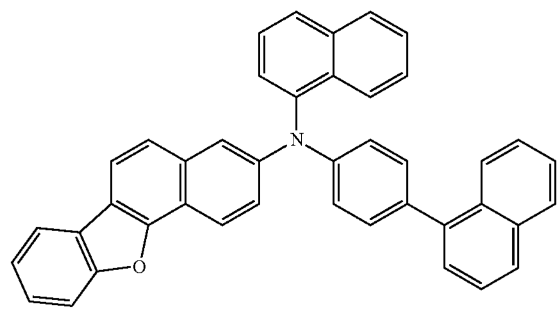
A174
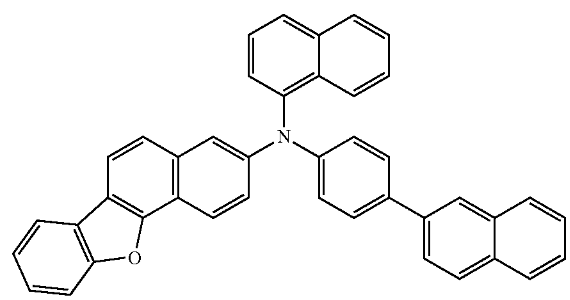
A175
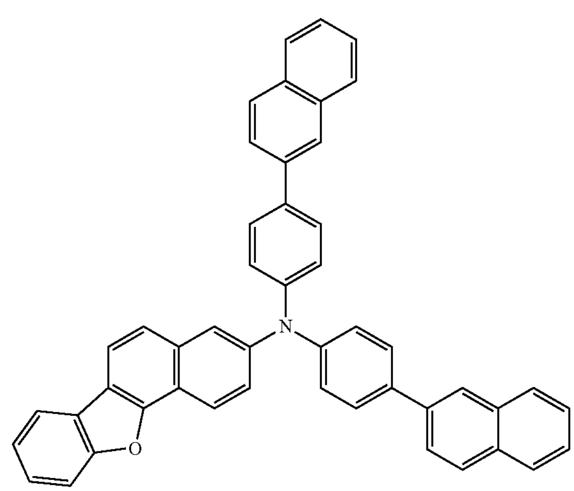

-continued
A176
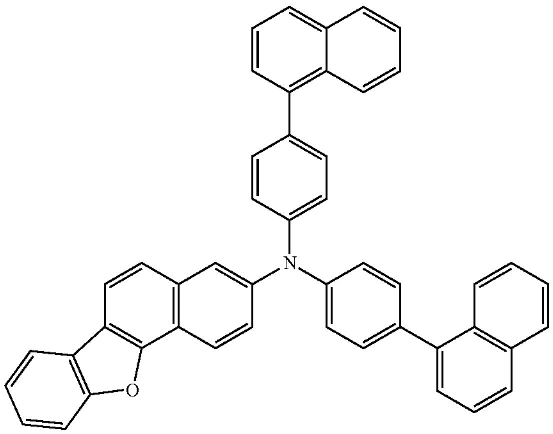
A177
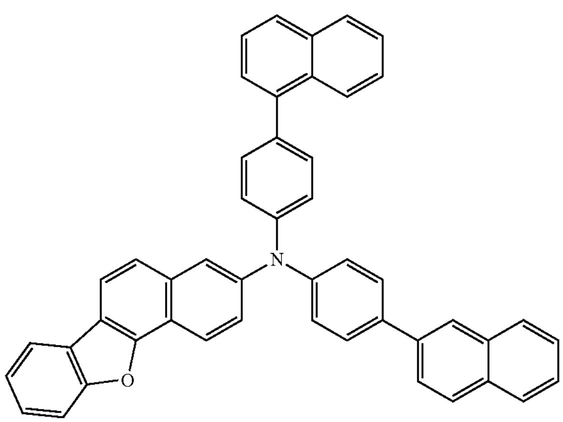
A178
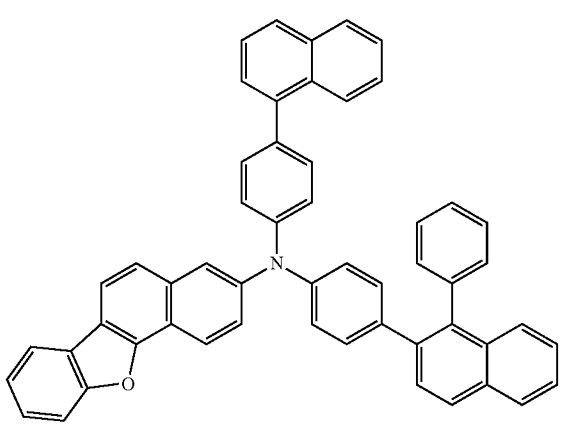
-continued
A179
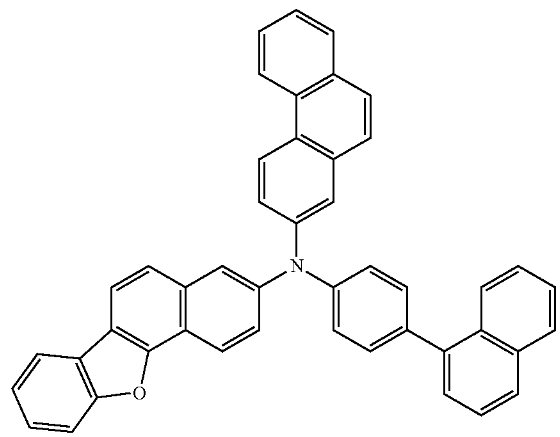
A180
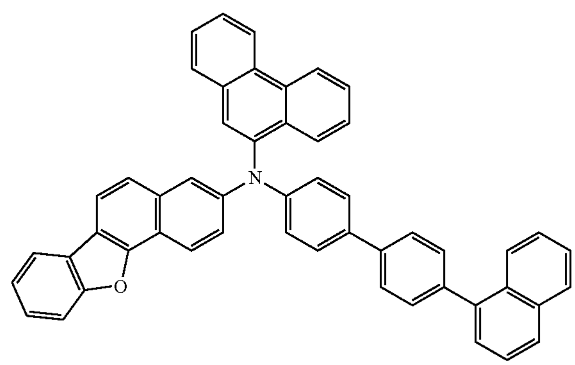
A181
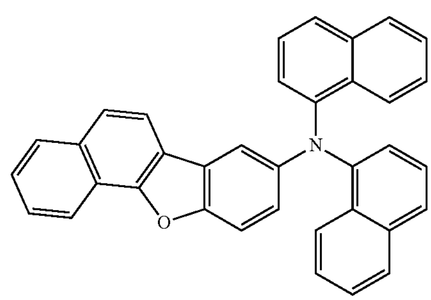
A182
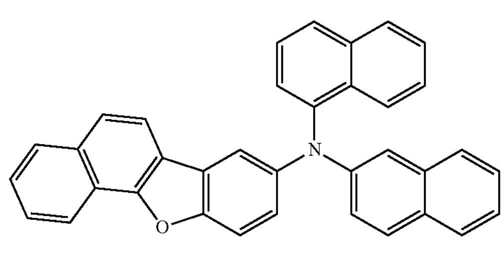

-continued
A183
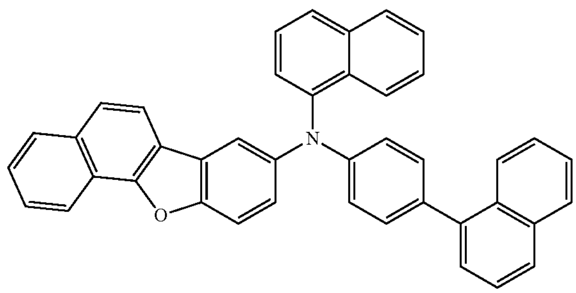
A184
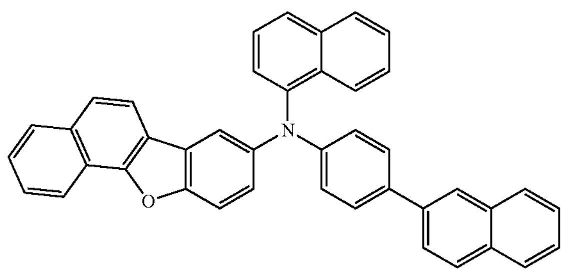
A185
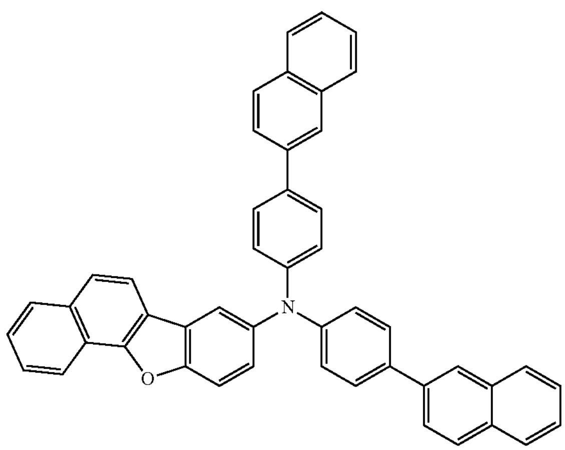
A186
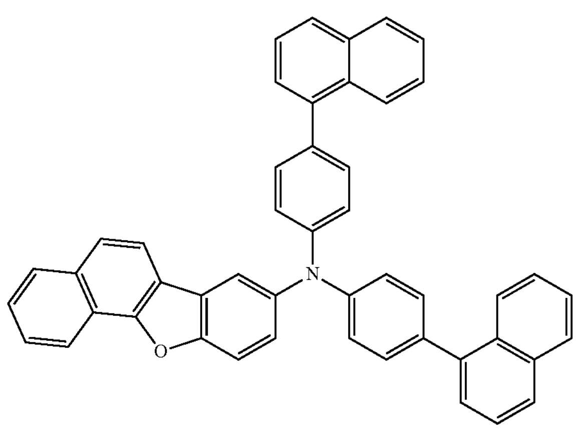
-continued
A187
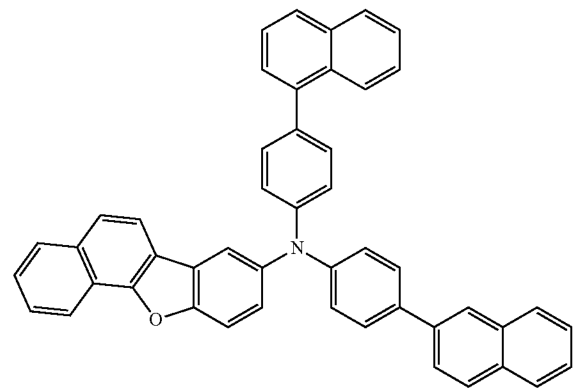
A188
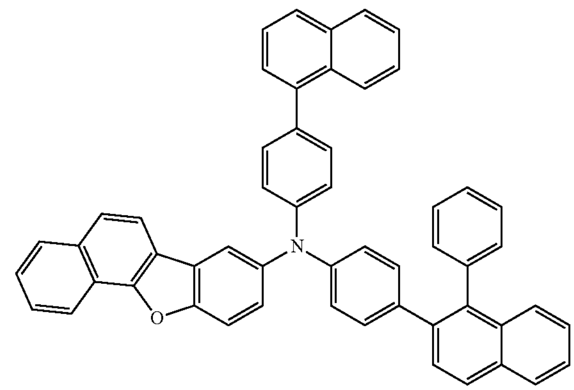
A189
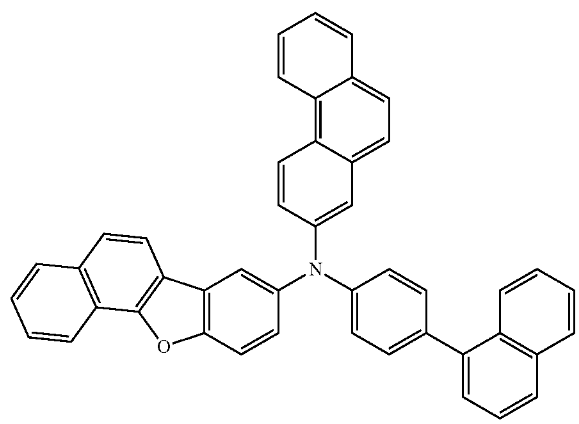
A190
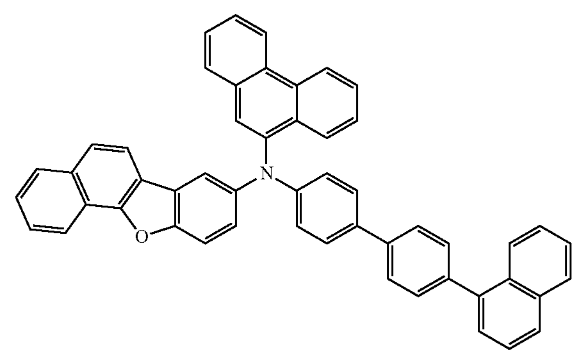

-continued
A191
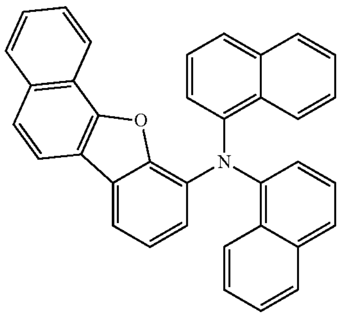
A192
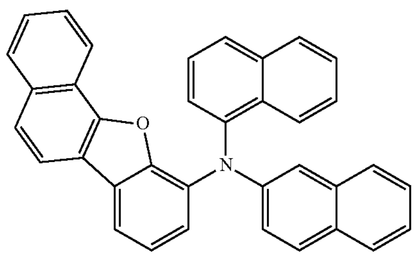
A193
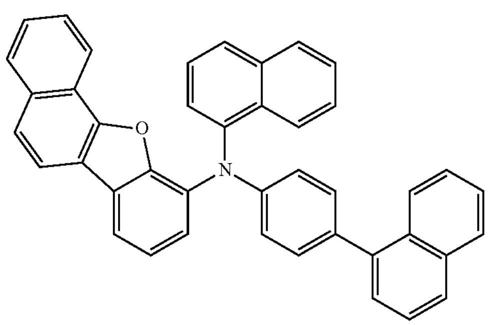
A194
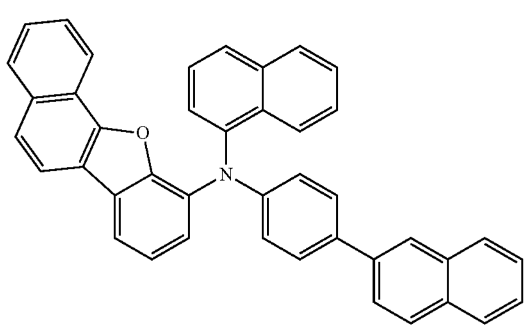
-continued
A195
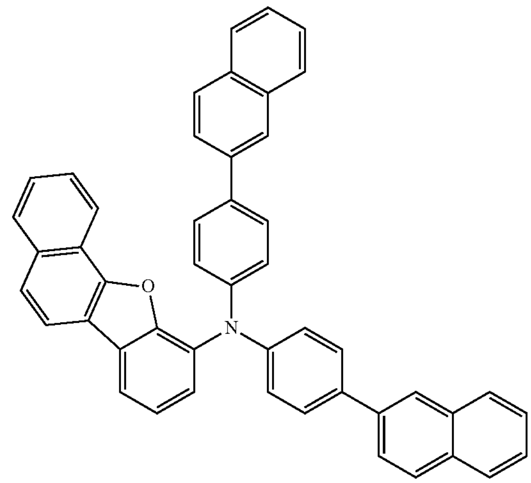
A196
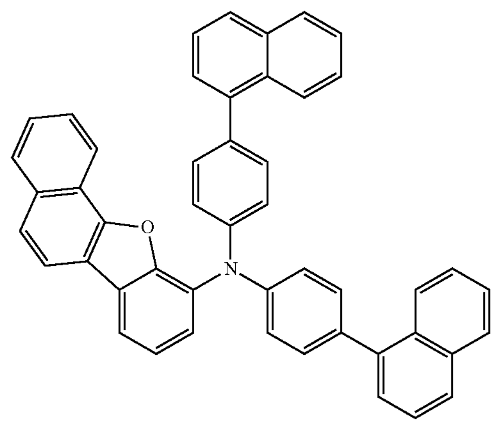
A197
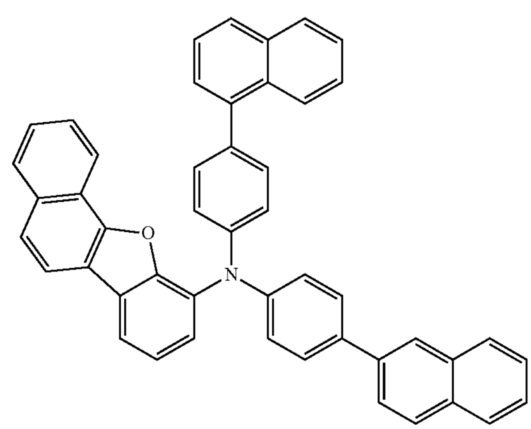

-continued
A198
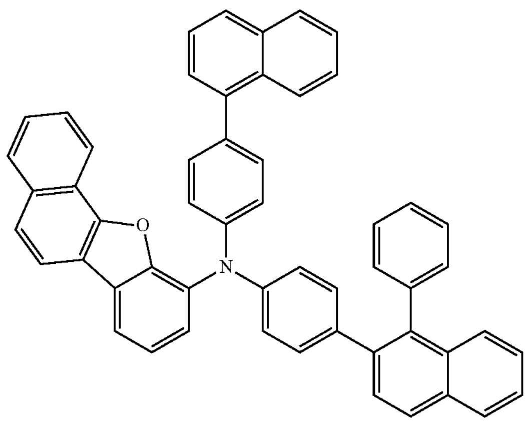
A199
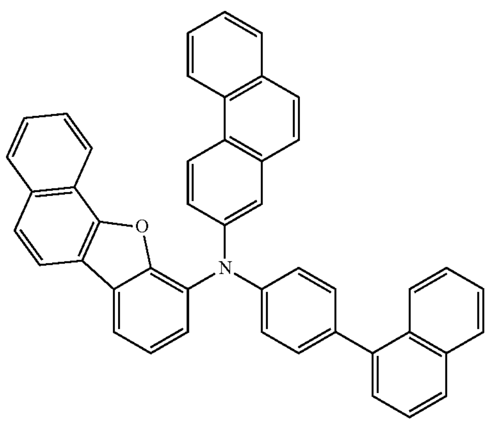
A200
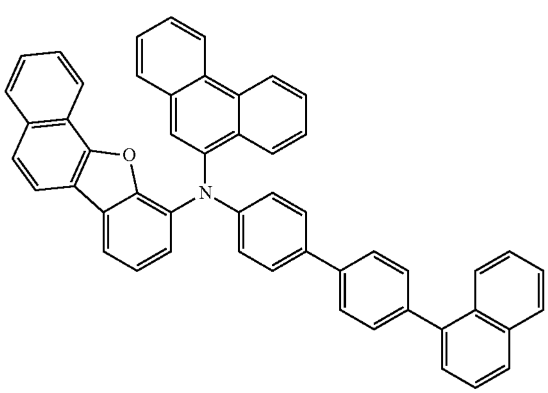
[Compound Group 2]
B1
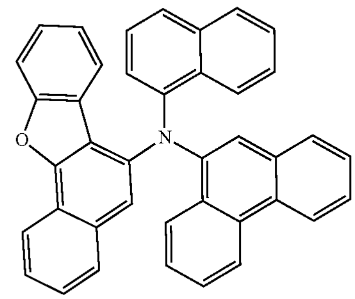
B2
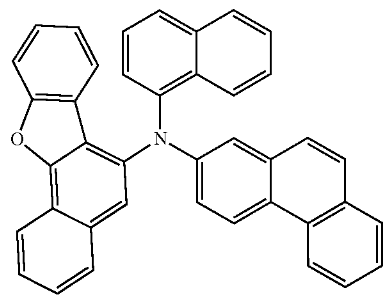
B3
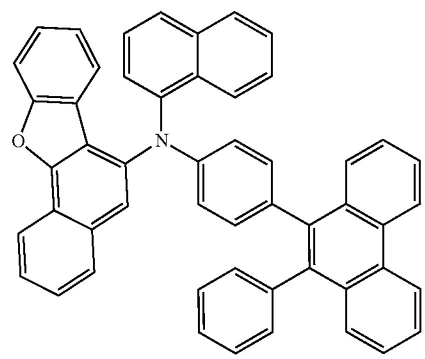
B4
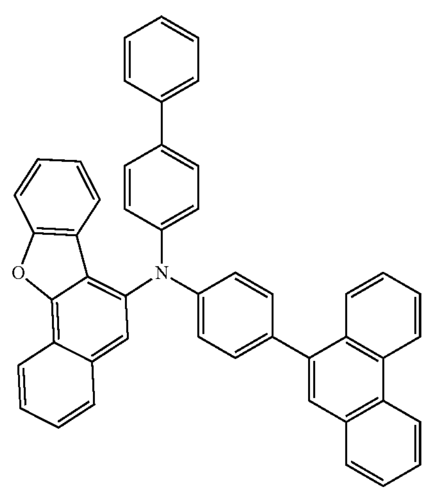

-continued
B5
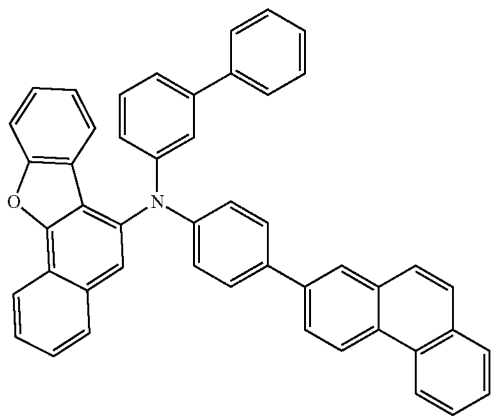
B6
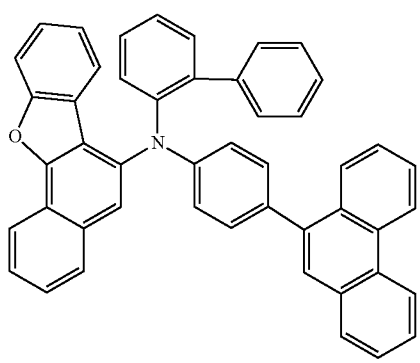
B7
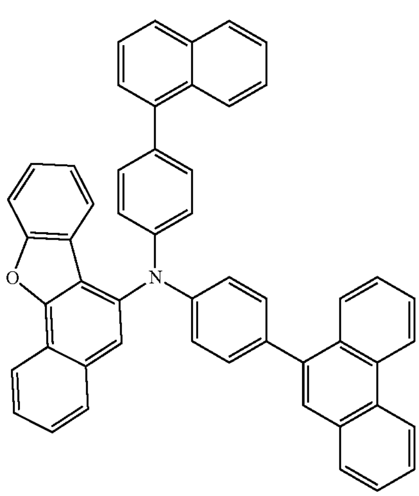
-continued
B8
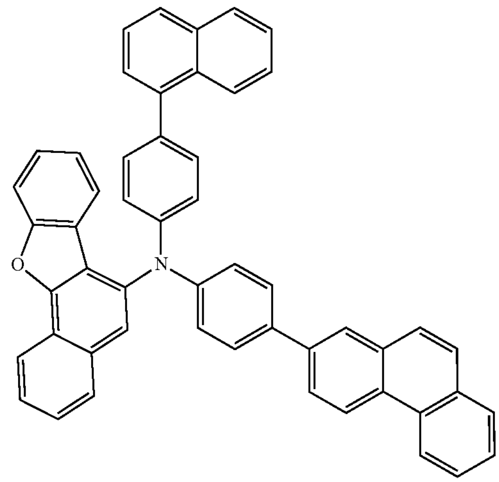
B9
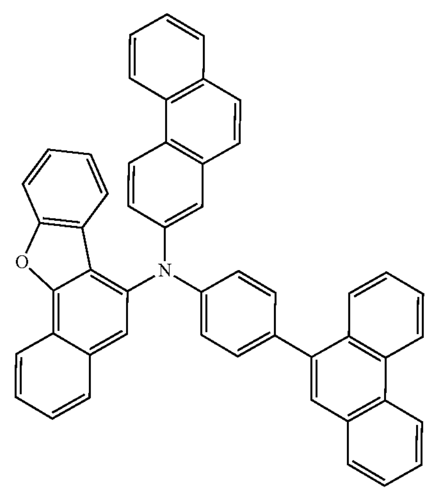
B10
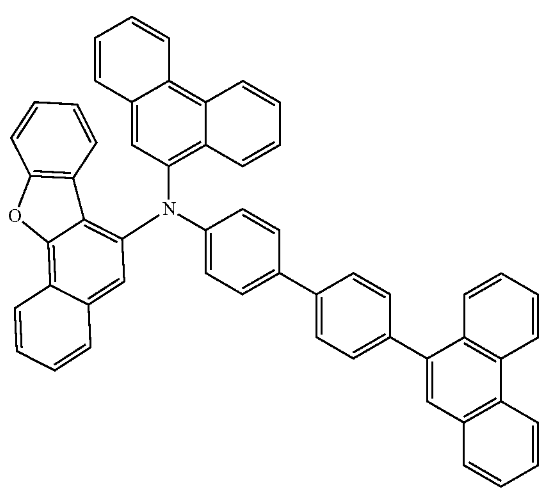

-continued
B11
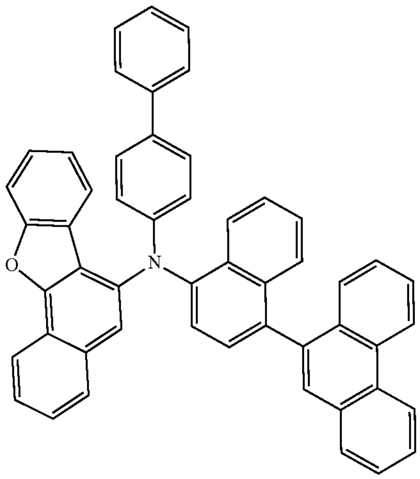
B12
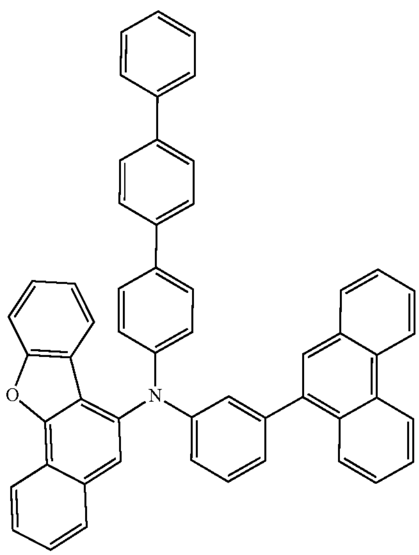
B13
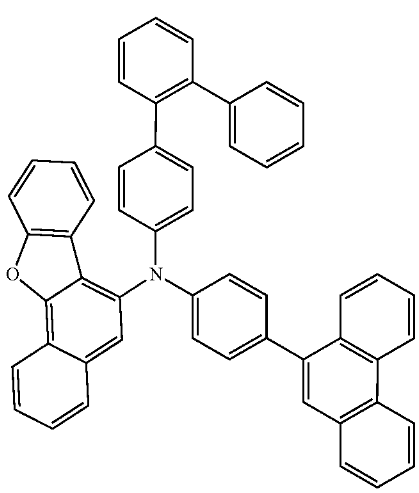
-continued
B14
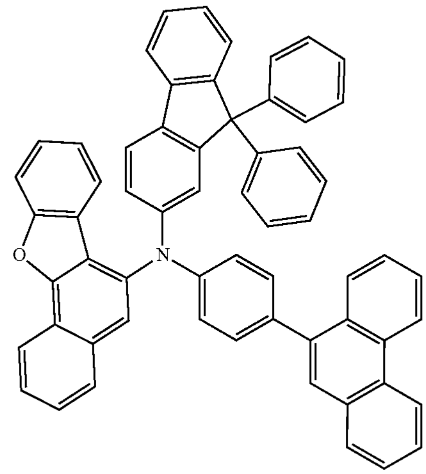
B15
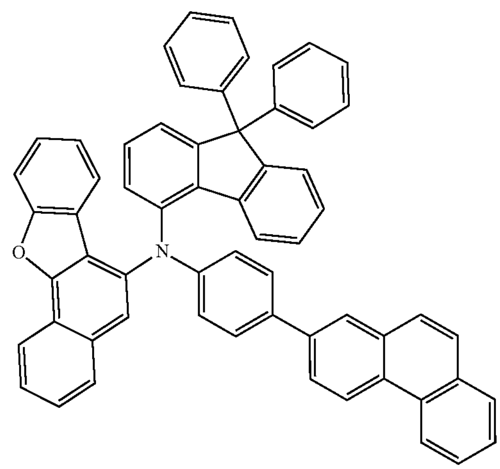
B16
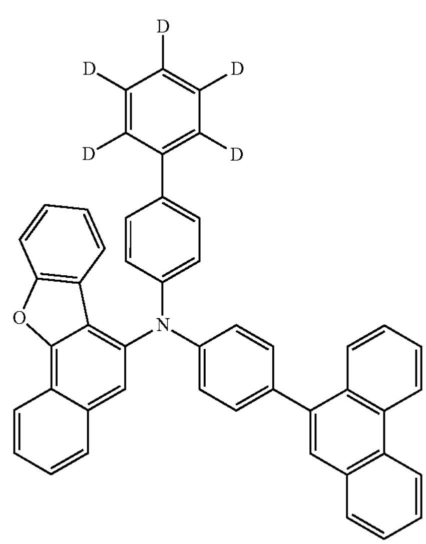

-continued
B17
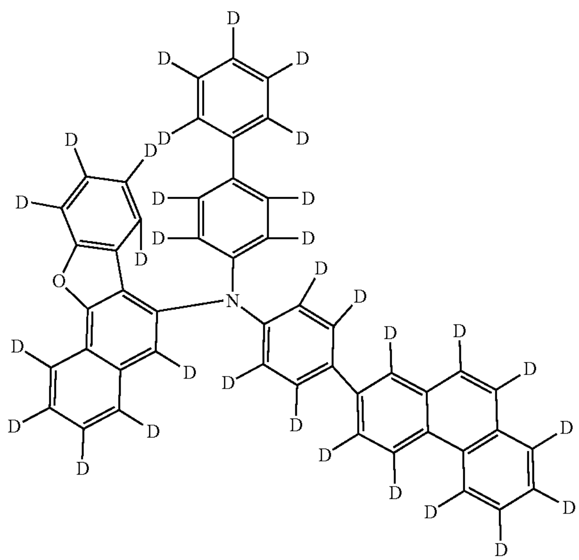
B18
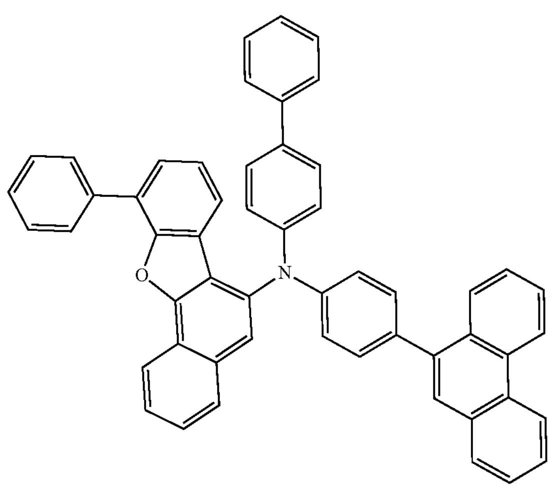
B19
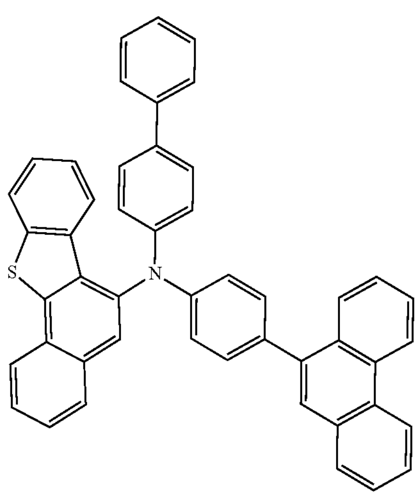
-continued
B20
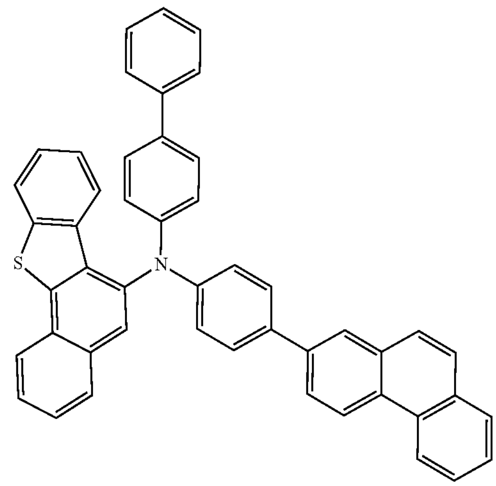
B21
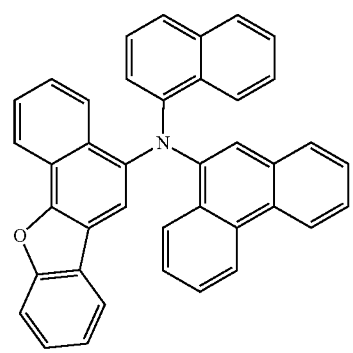
B22
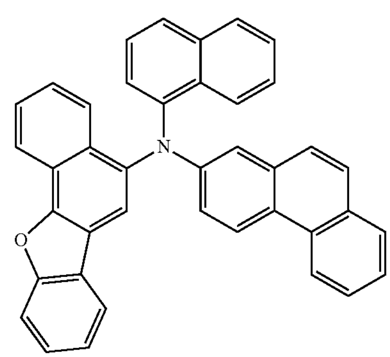
B23
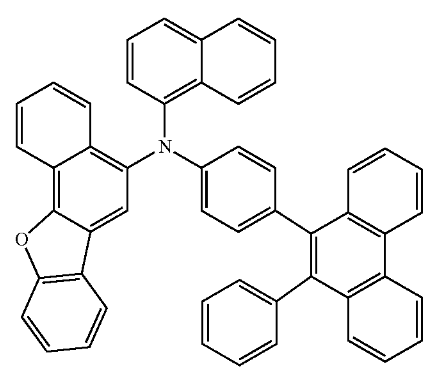

-continued
B24
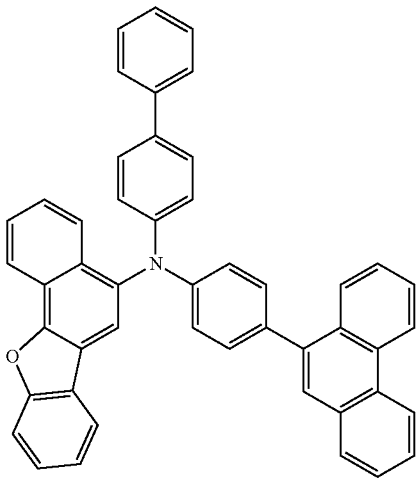
B25
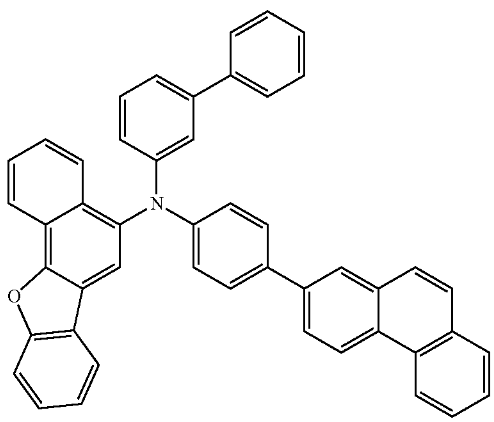
B26
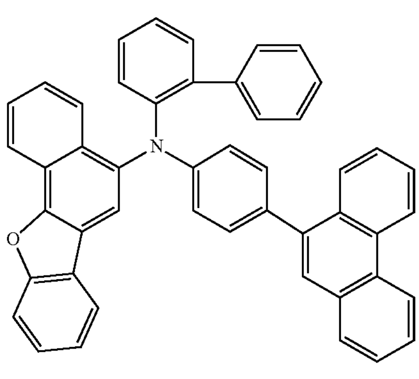
-continued
B27
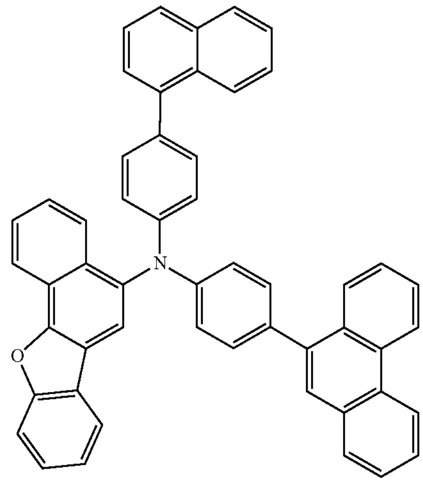
B28
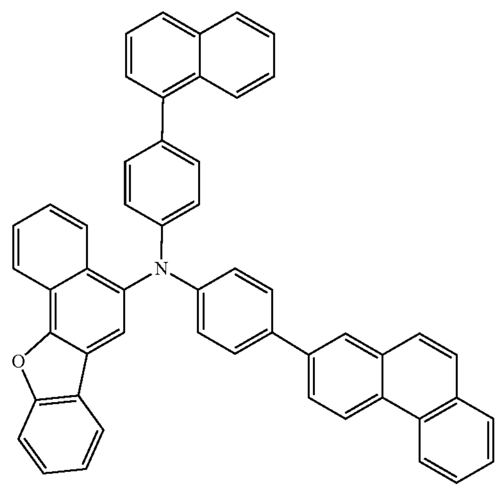
B29
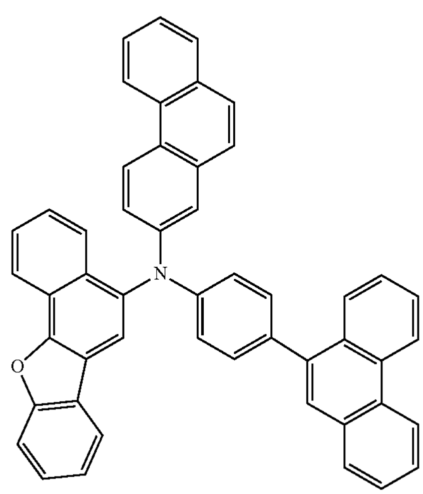

-continued
B30
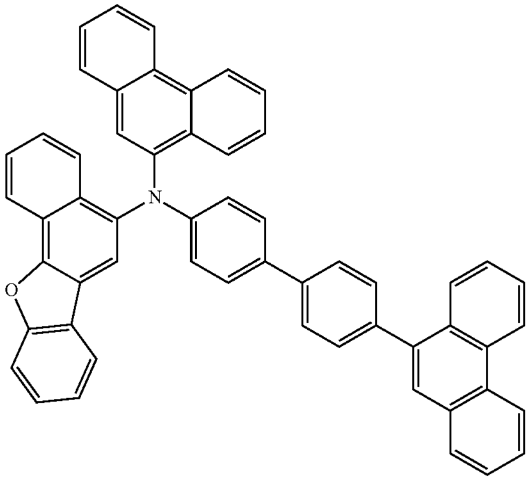
B31
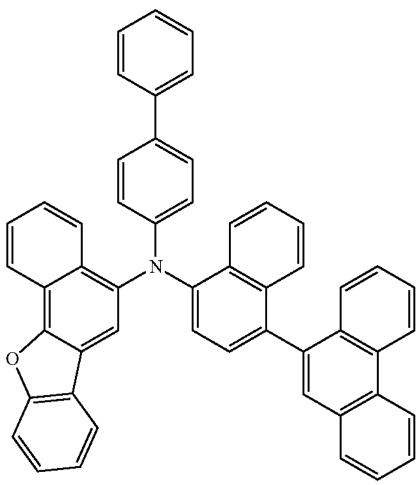
B32
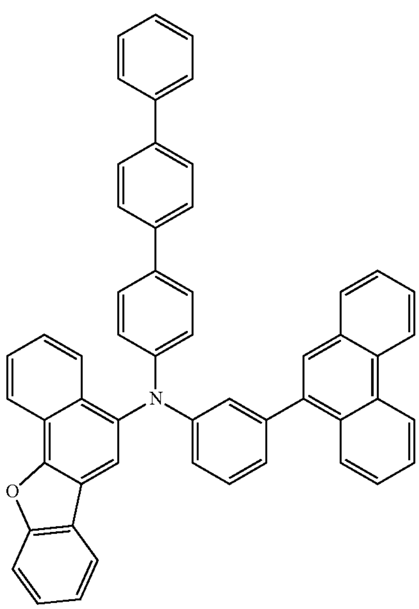
-continued
B33
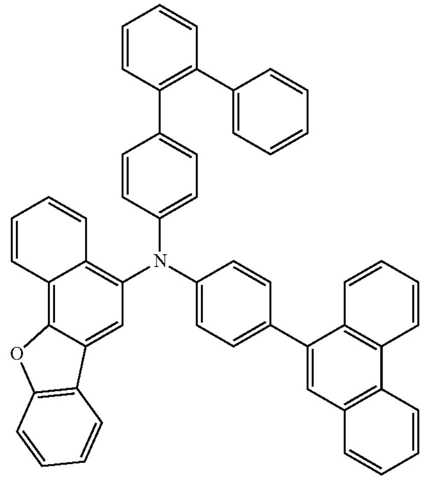
B34
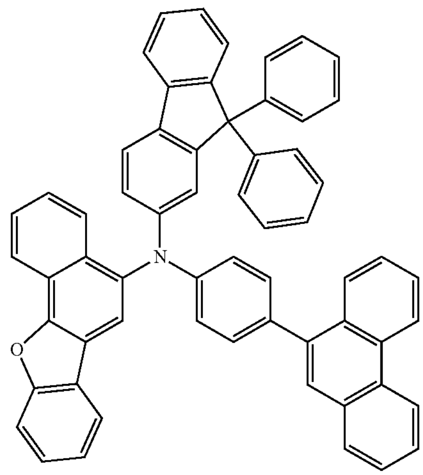
B35
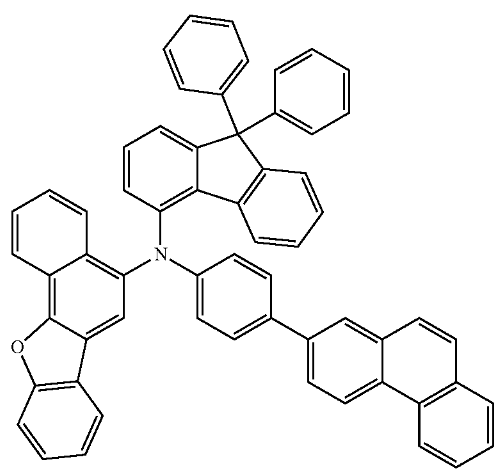

-continued
B36
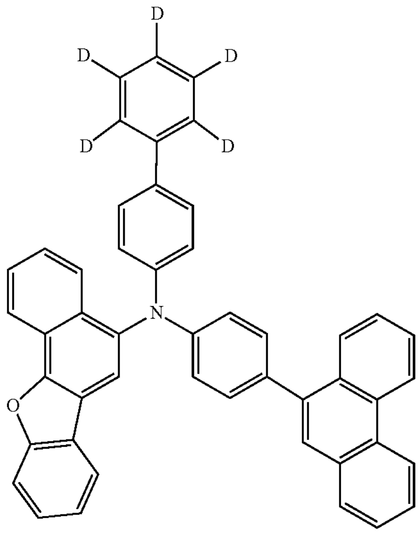
B37
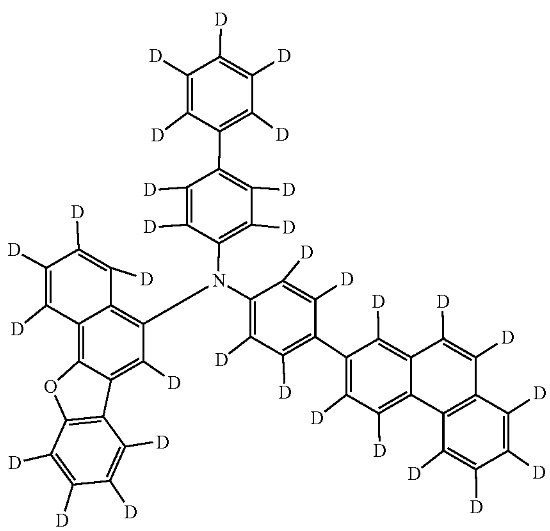
B38
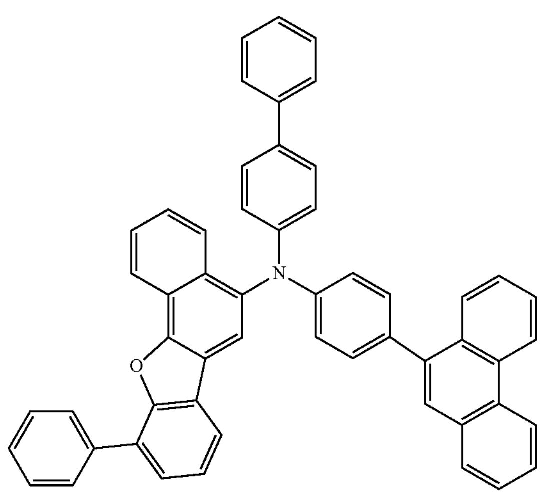
-continued
B39
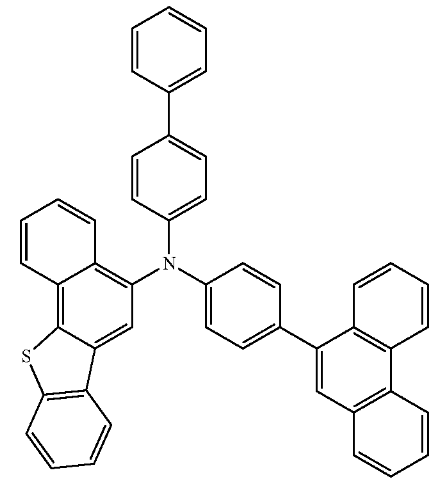
B40
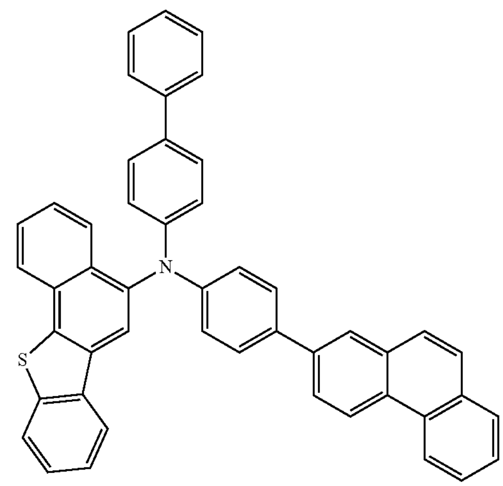
B41
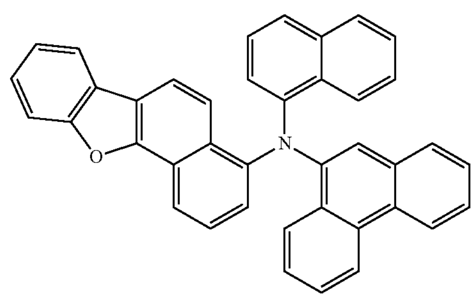
B42
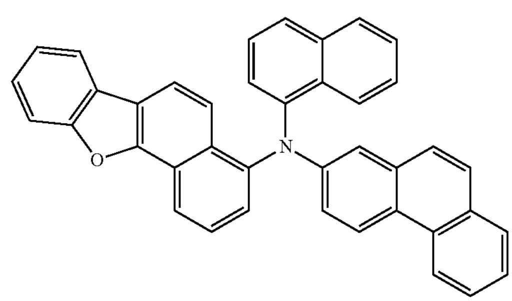

-continued
B43
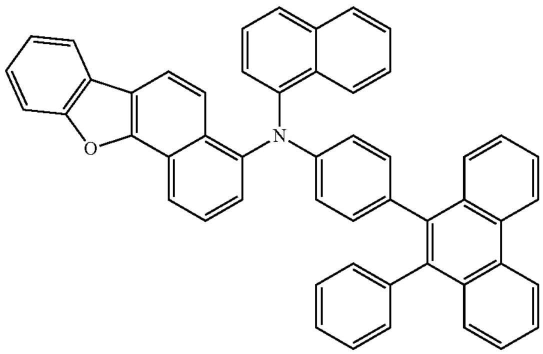
B44
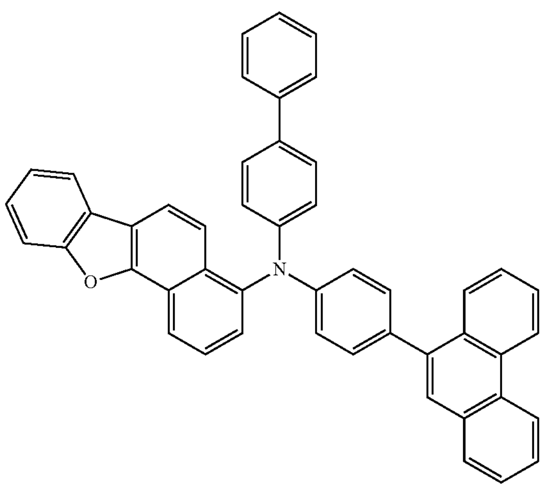
B45
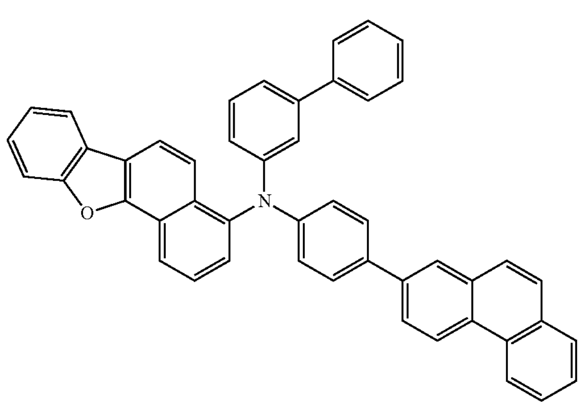
-continued
B46
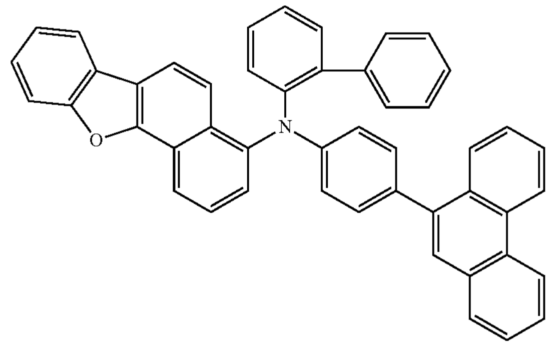
B47
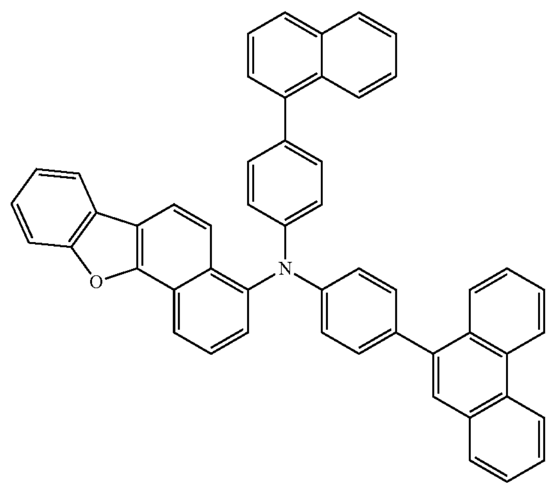
B48
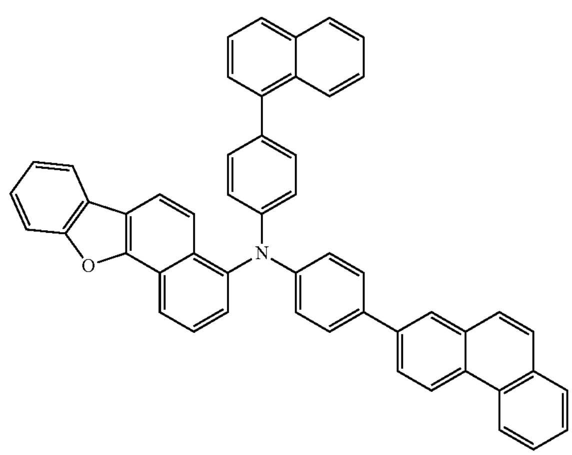

-continued
B49
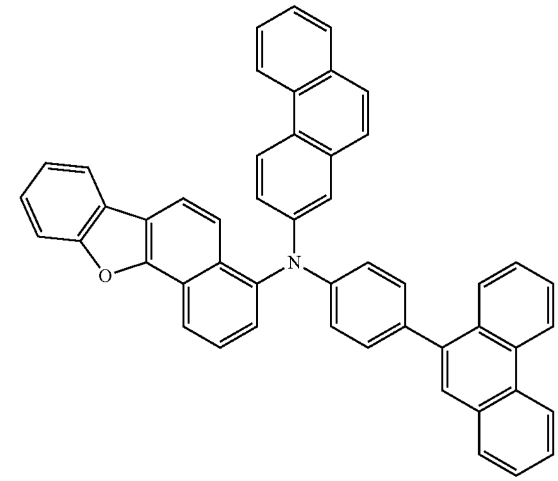
B50
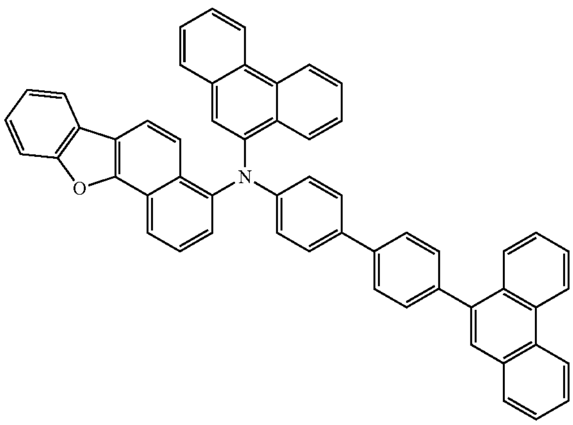
B51
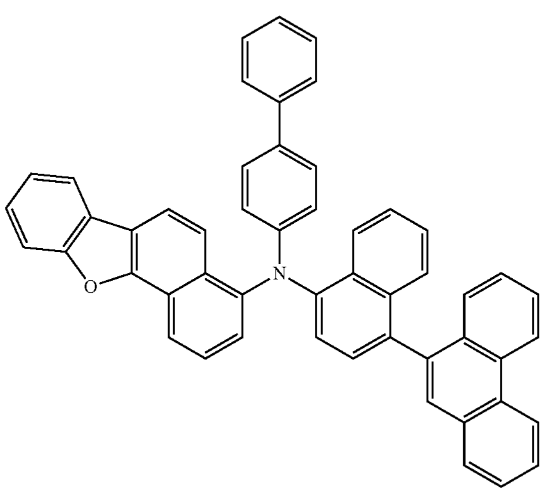
-continued
B52
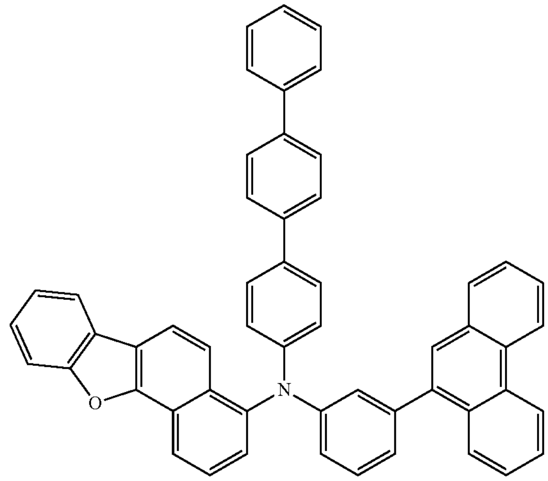
B53
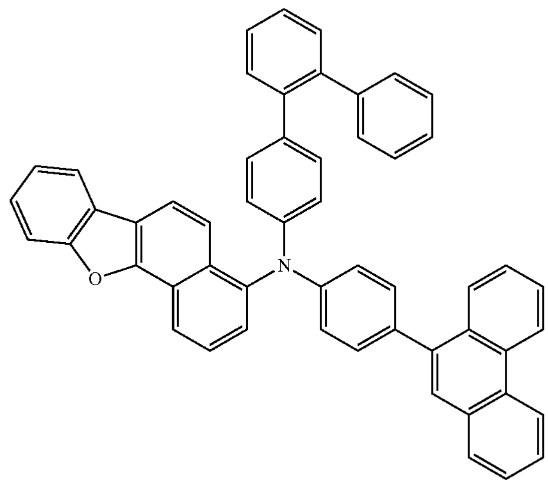
B54
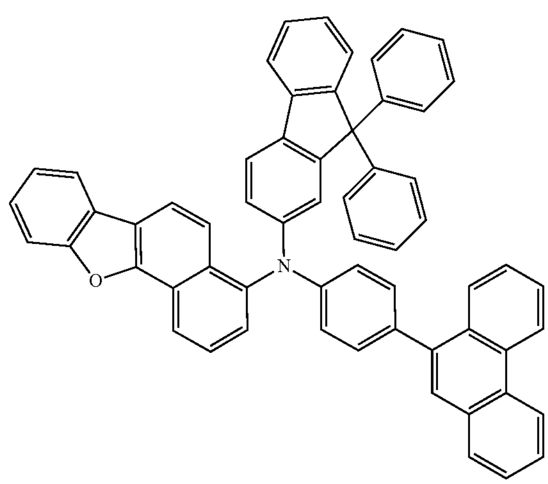

-continued
B55
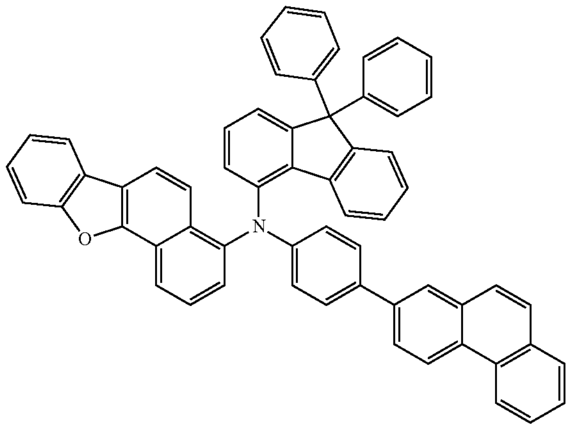
B56
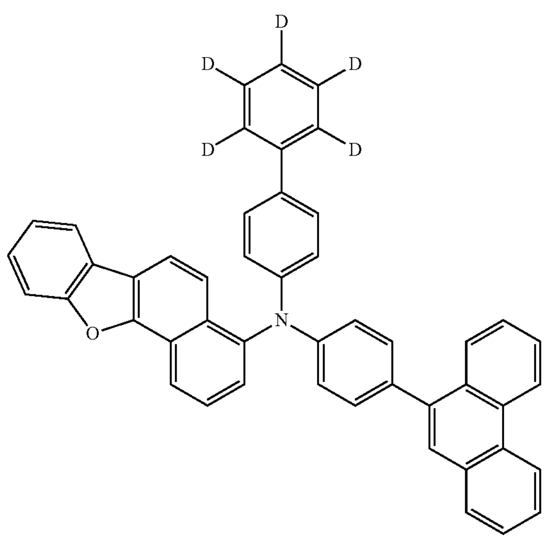
B57
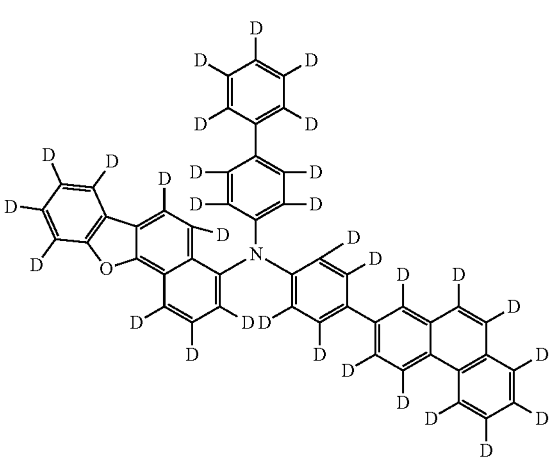
-continued
B58
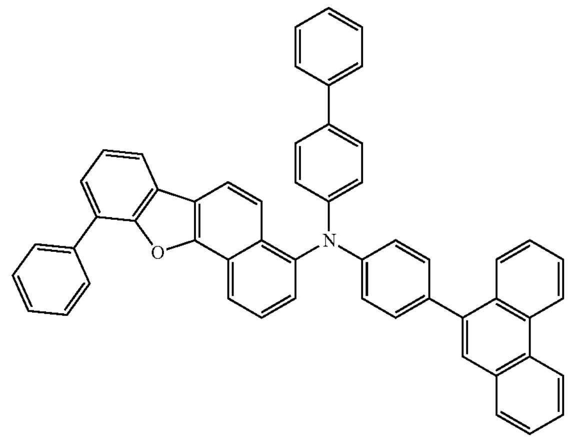
B59
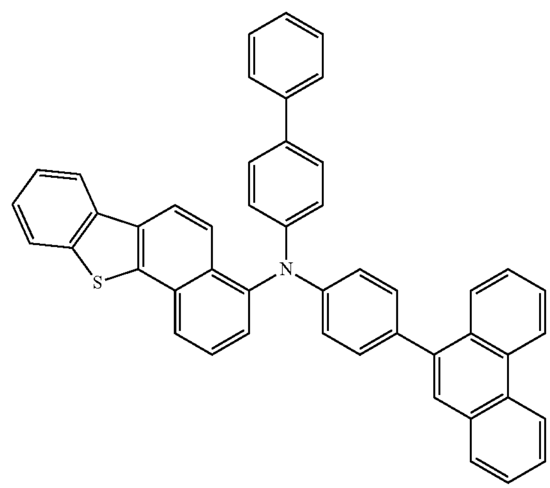
B60
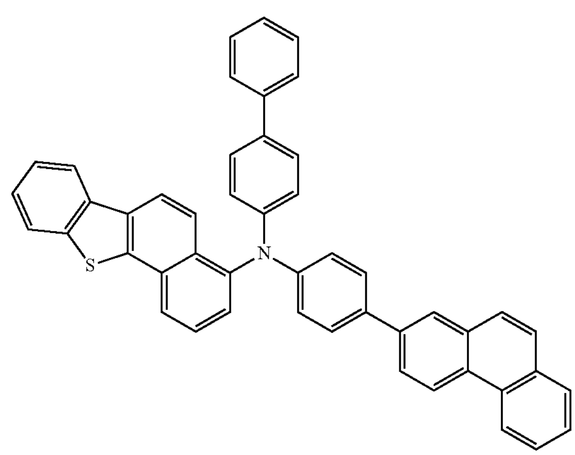

-continued
B61
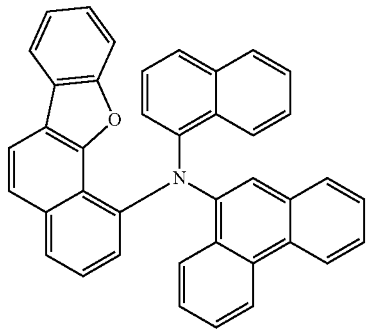
B62
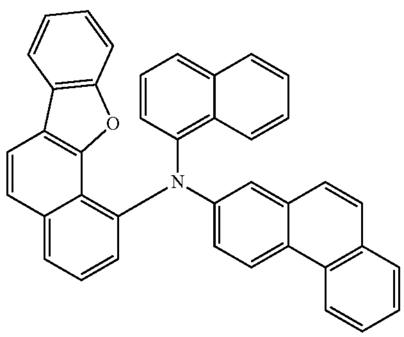
B63
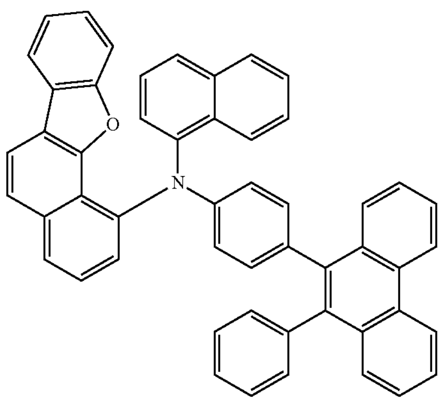
B64
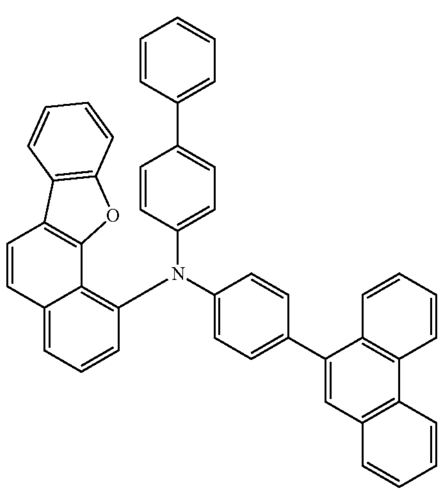
-continued
B65
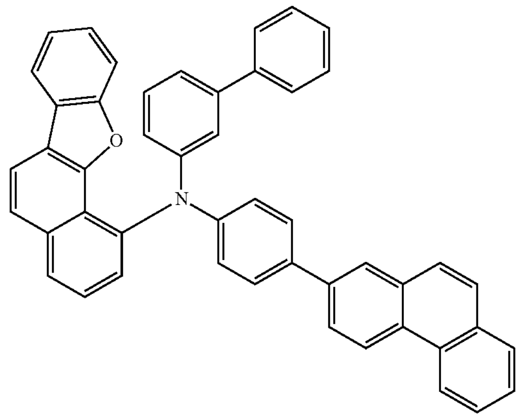
B66
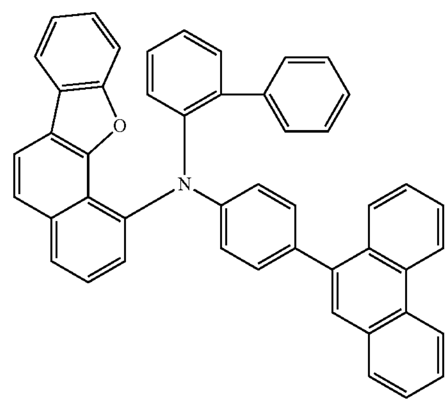
B67
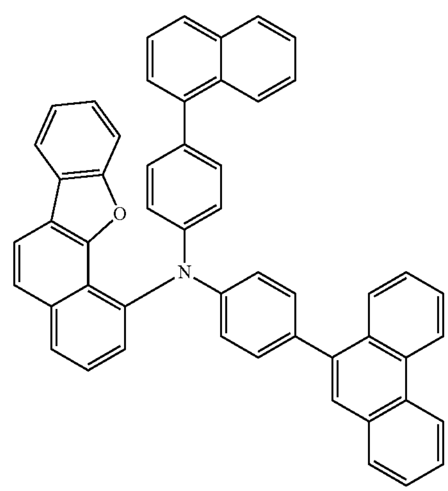

-continued
B68
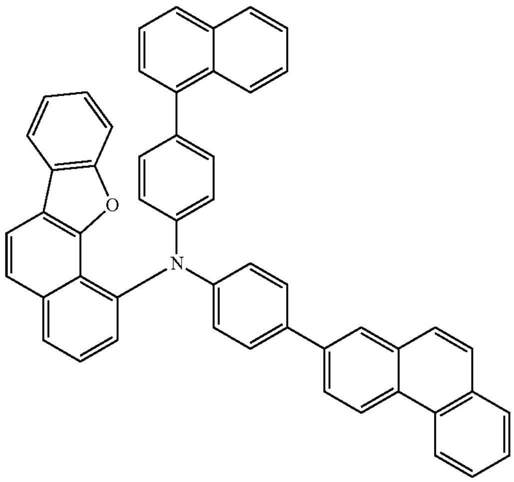
B69
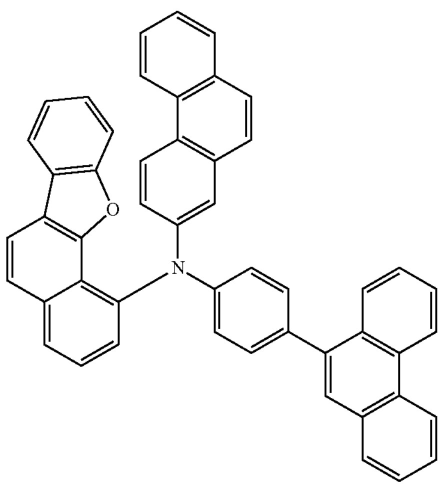
B70
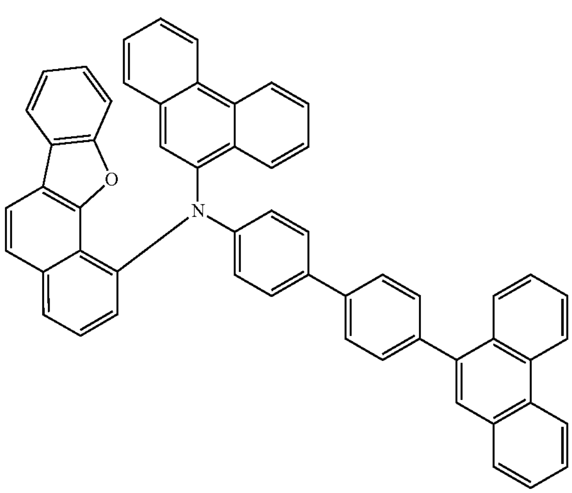
-continued
B71
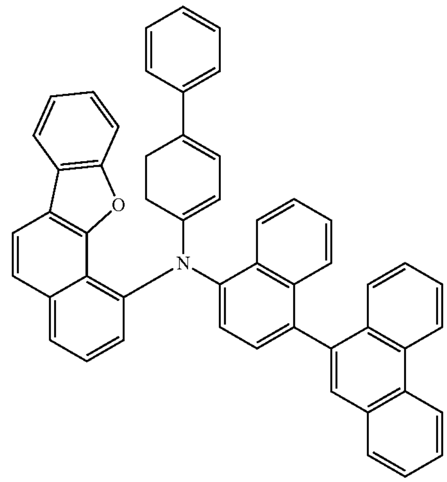
B72
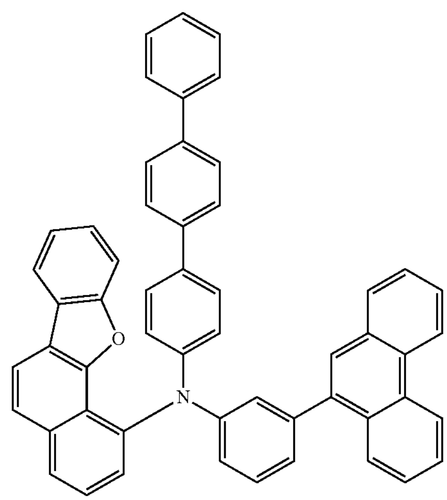
B73
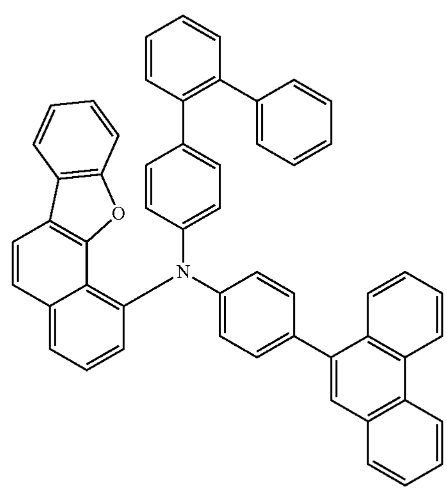

-continued
B74
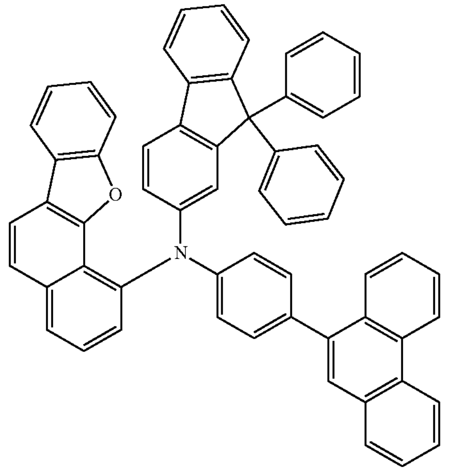
B75
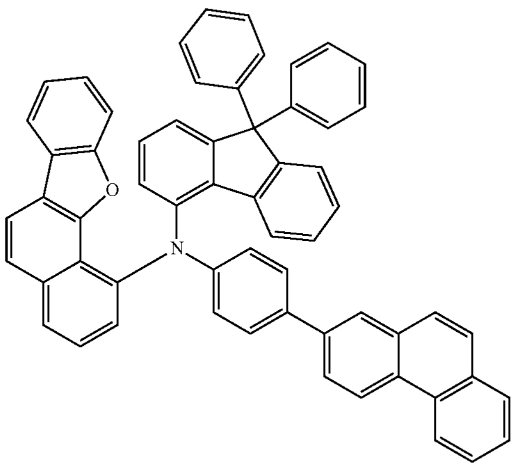
B76
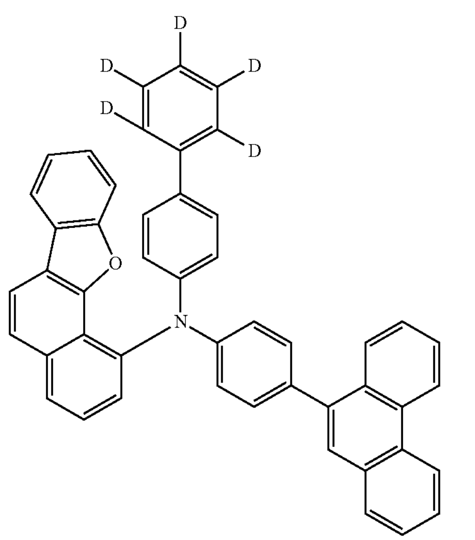
-continued
B77
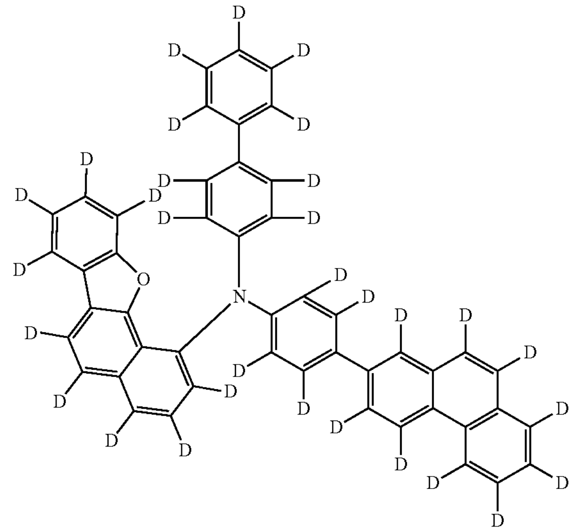
B78
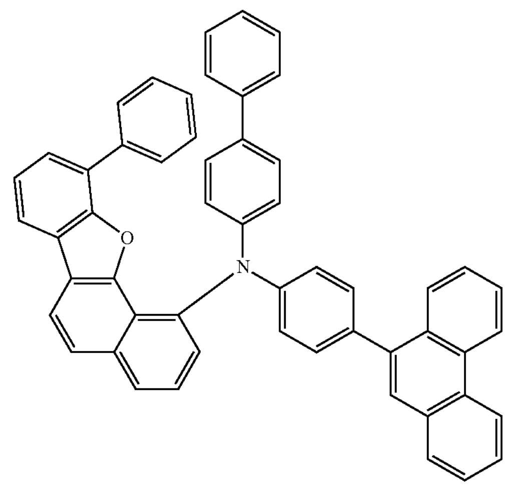
B79
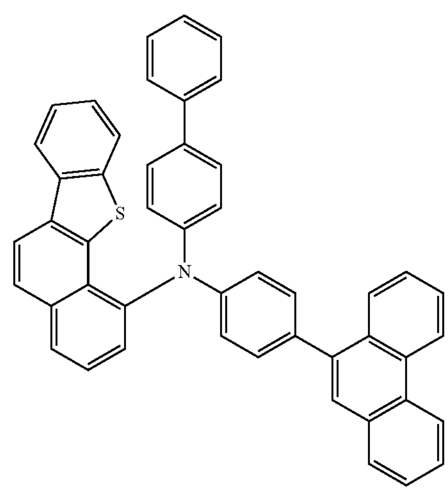

-continued
B80
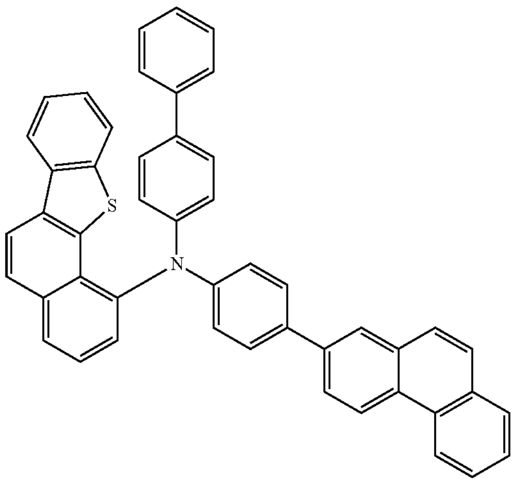
B81
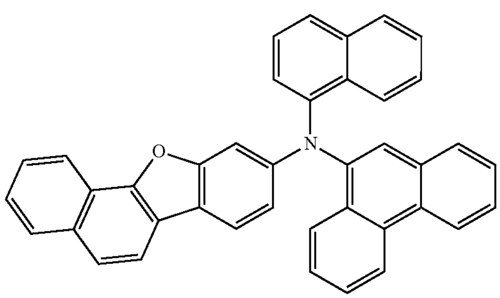
B82
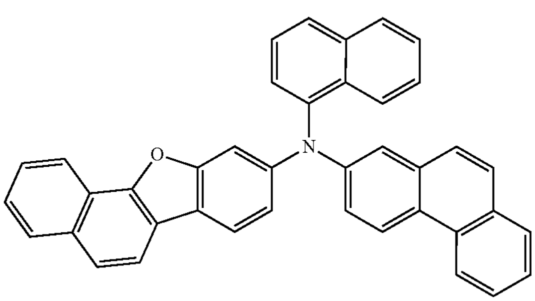
B83
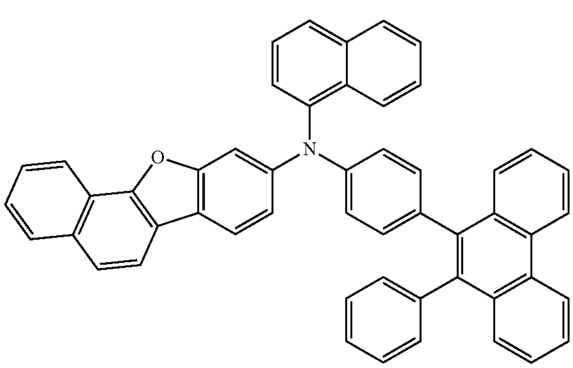
-continued
B84
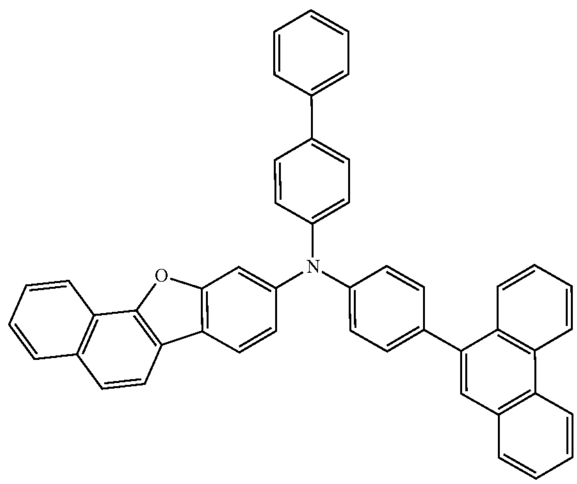
B85
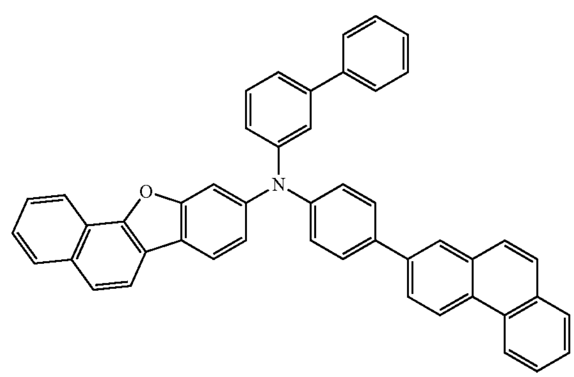
B86
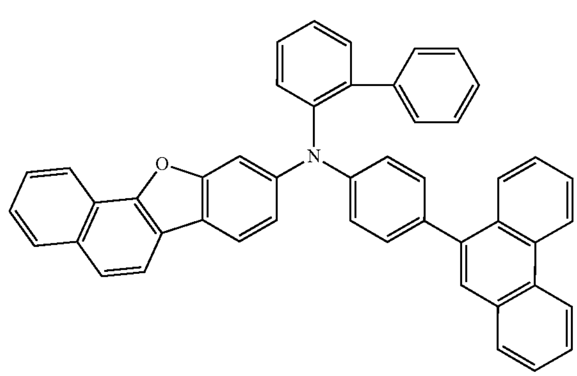

-continued
B87
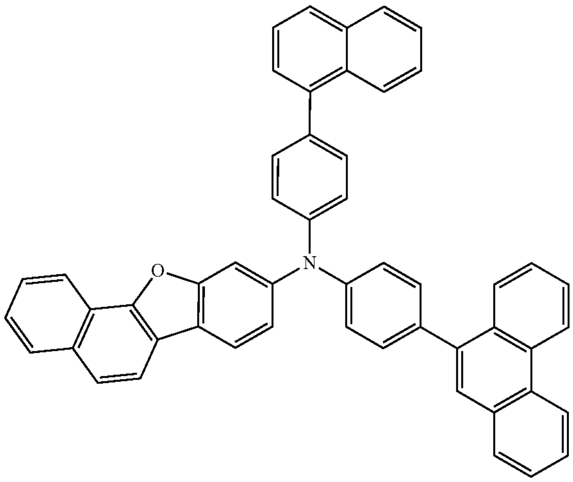
B88
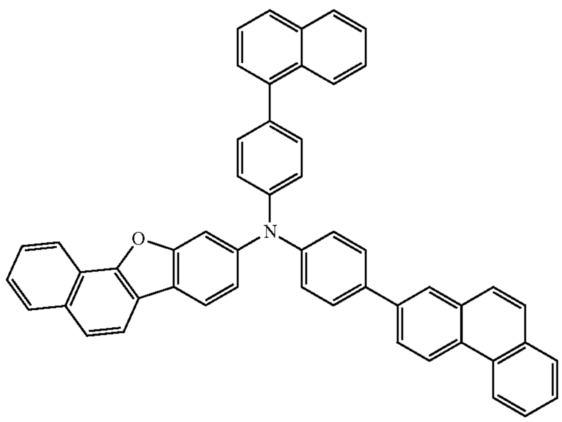
B89
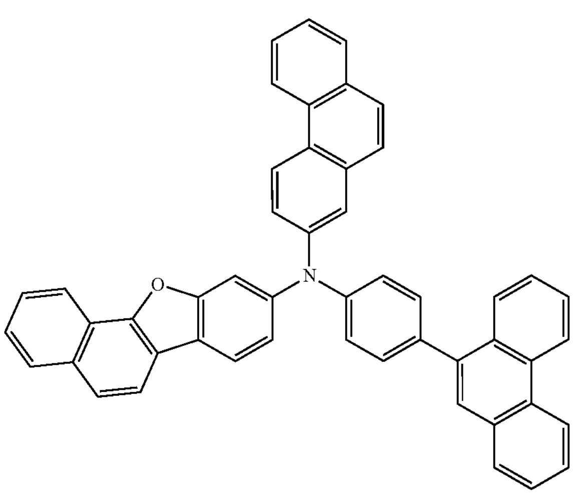
-continued
B90
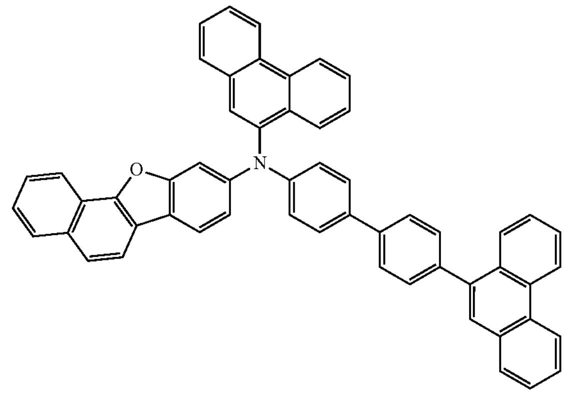
B91
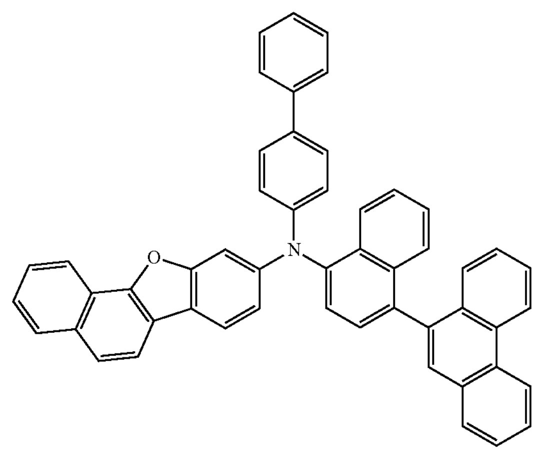
B92
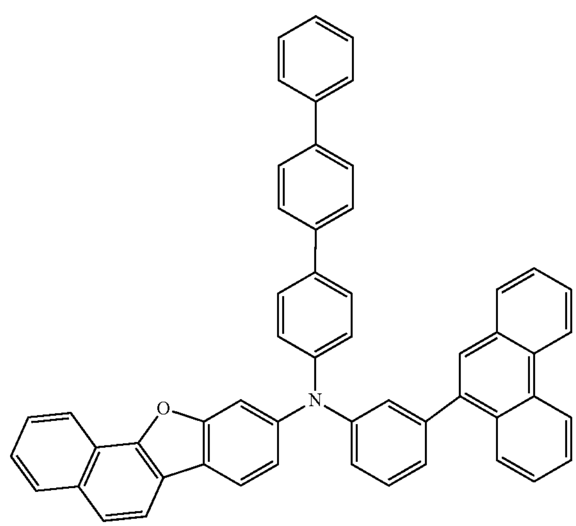

-continued
B93
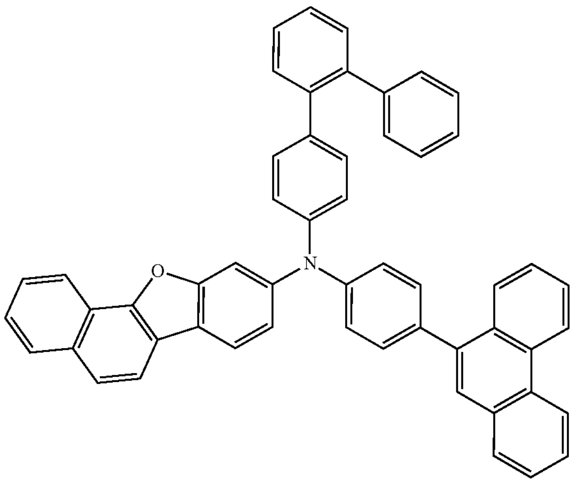
B94
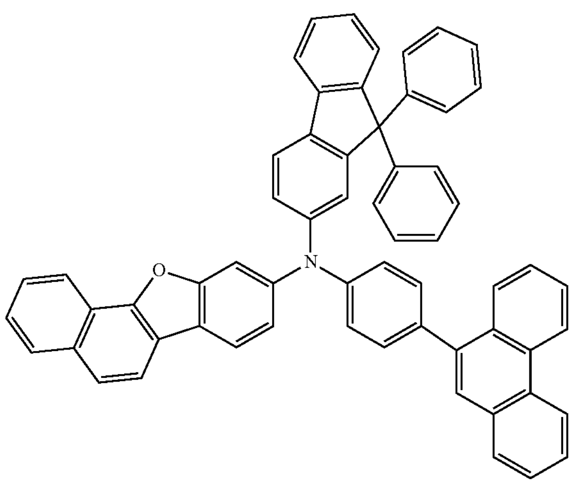
B95
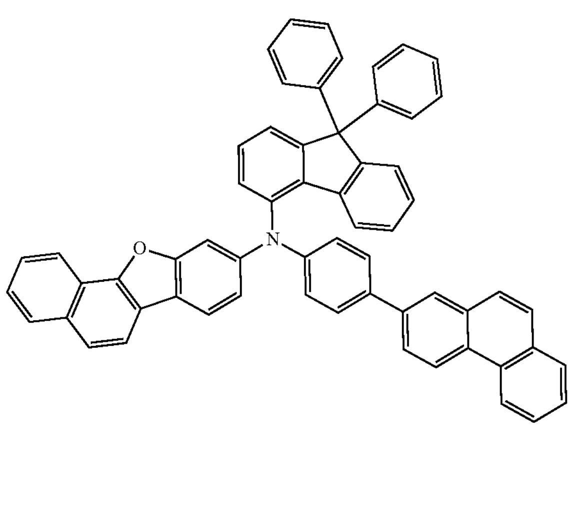
-continued
B96
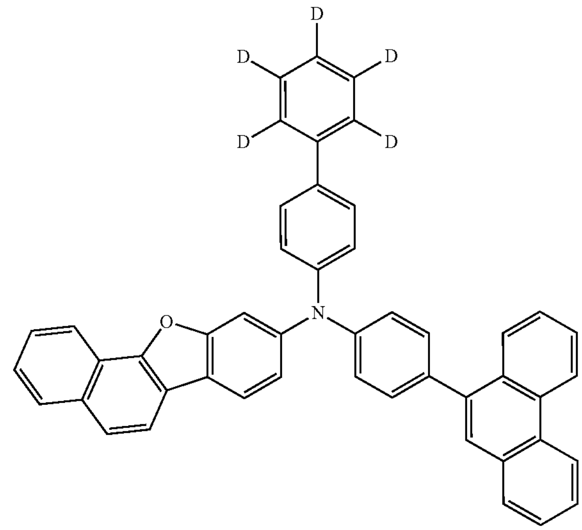
B97
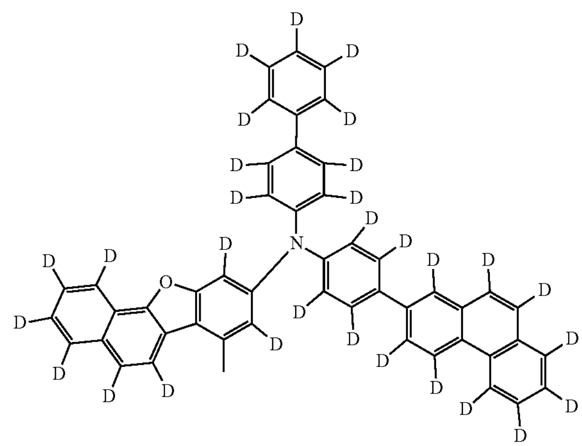
B98
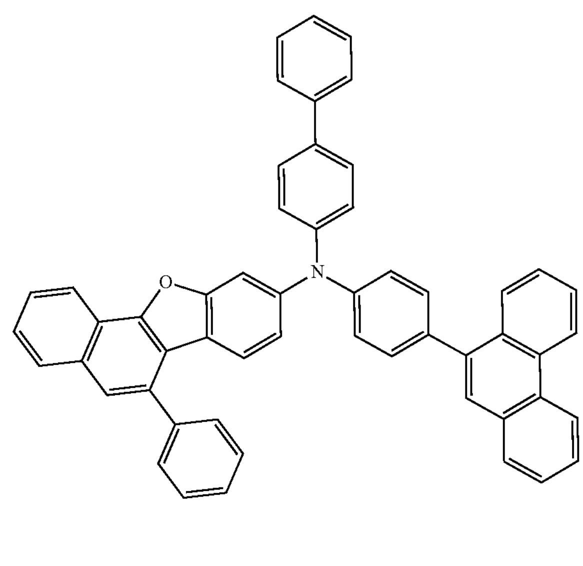

-continued
B99
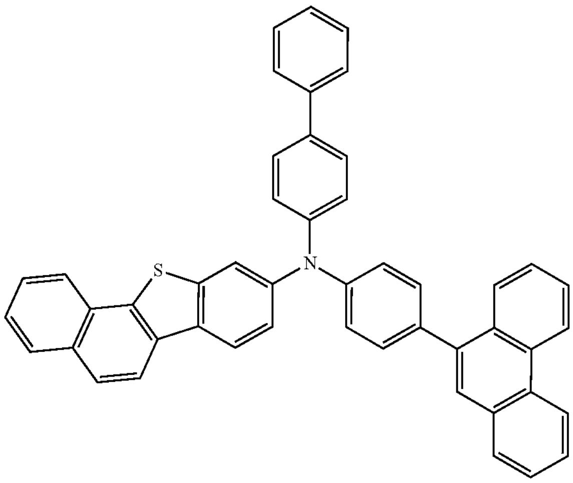
B100
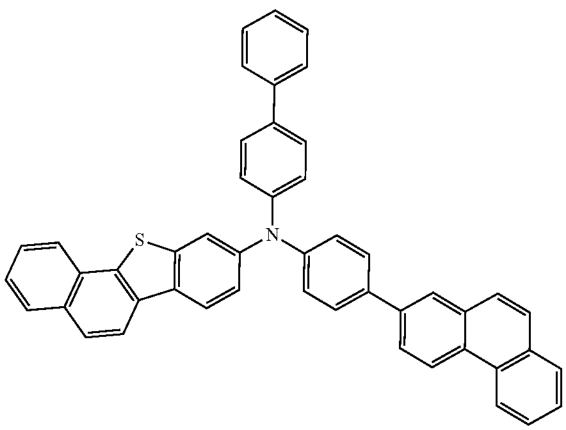
B101
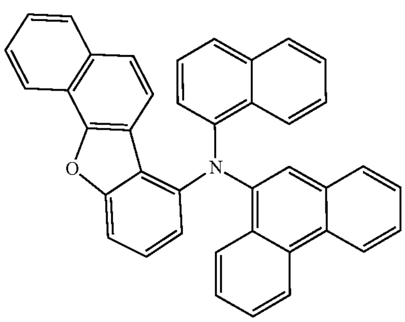
B102
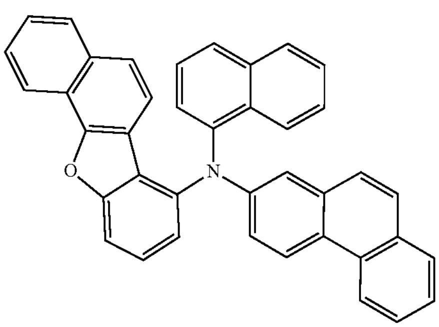
-continued
B103
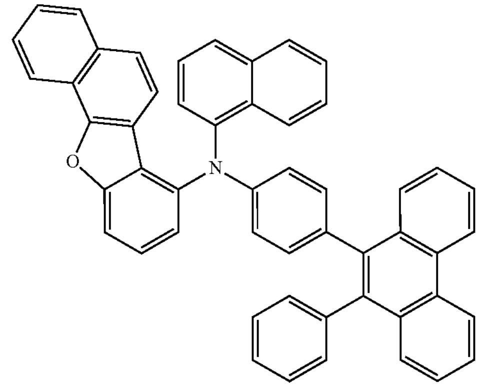
B104
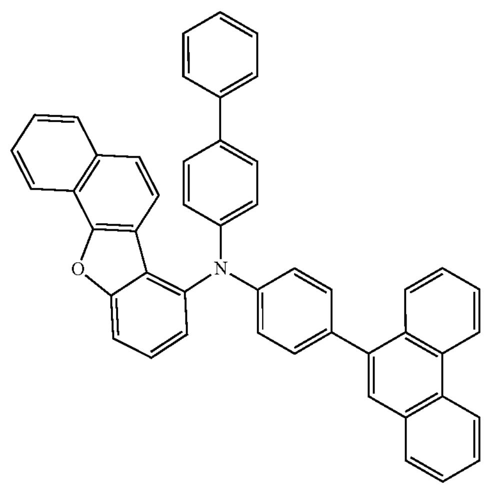
B105
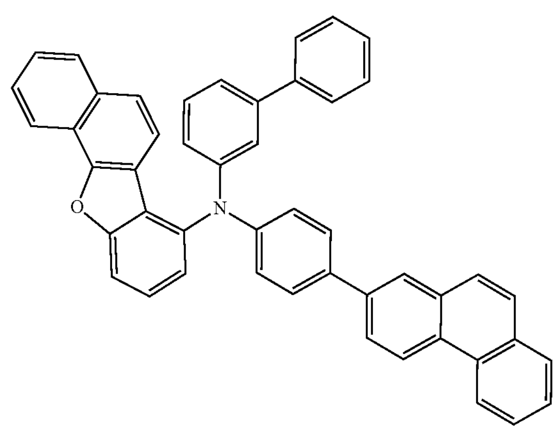

-continued
B106
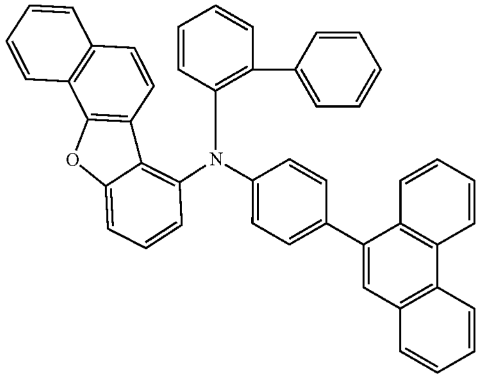
B107
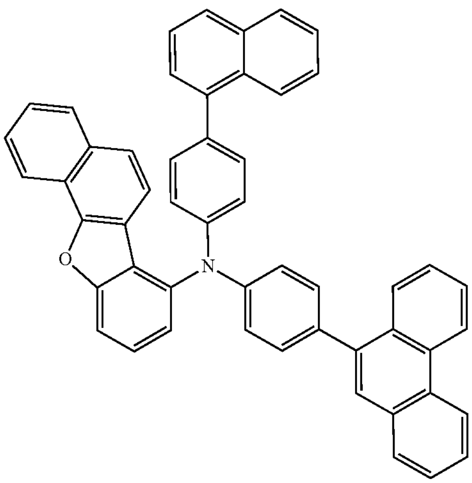
B108
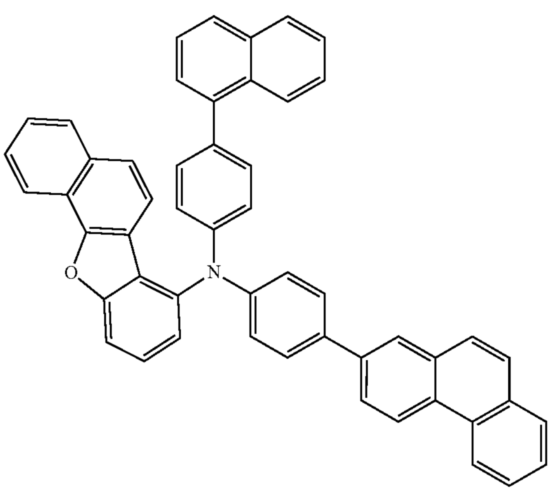
-continued
B109
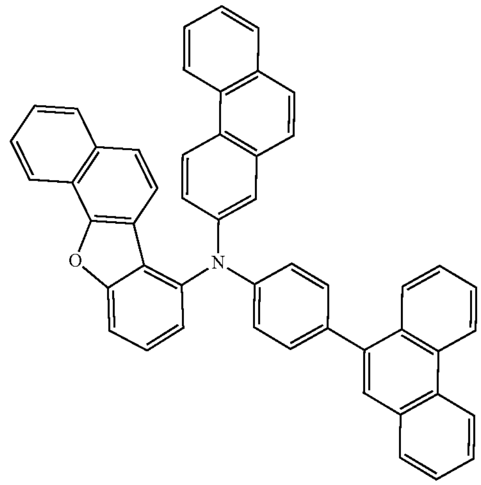
B110
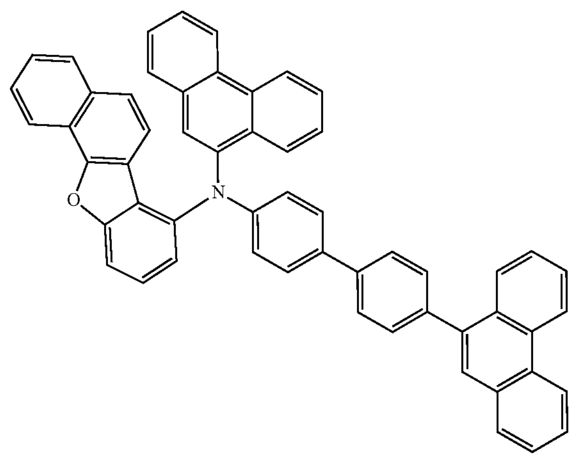
B111
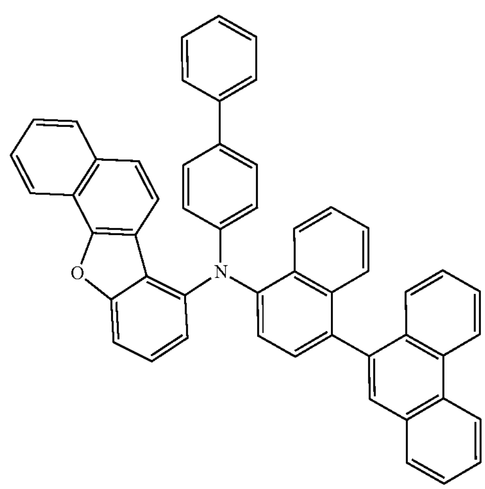

-continued
B112
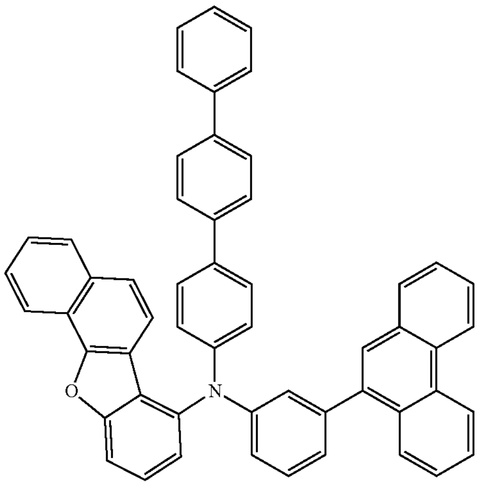
B113
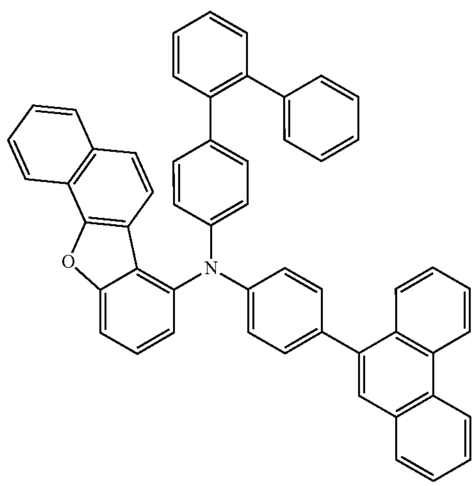
B114
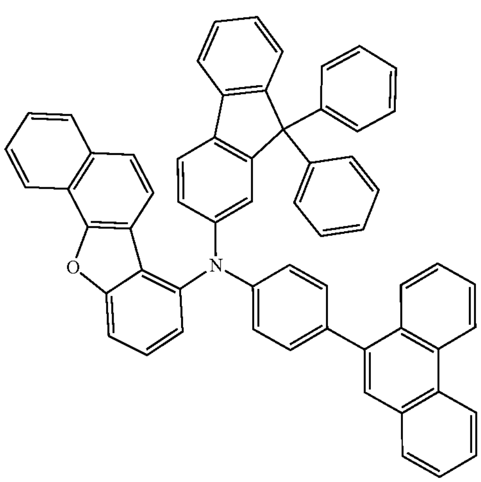
-continued
B115
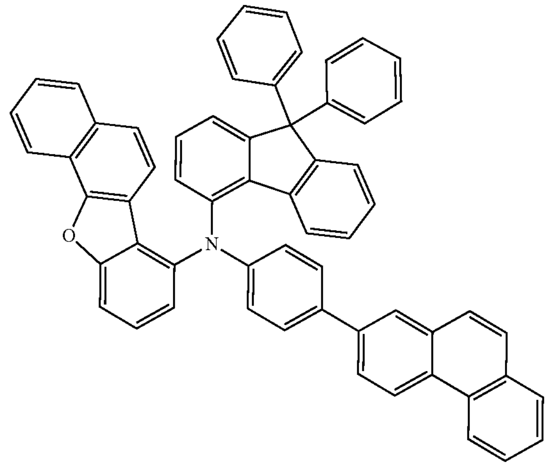
B116
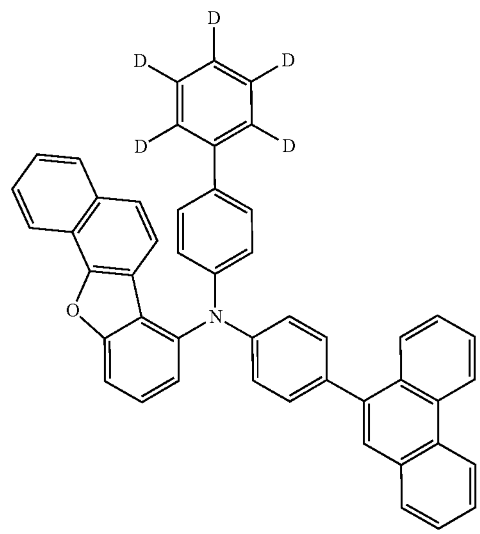
B117
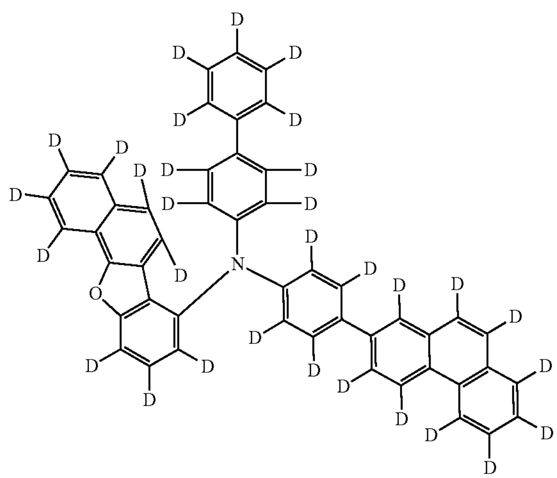

-continued
B118
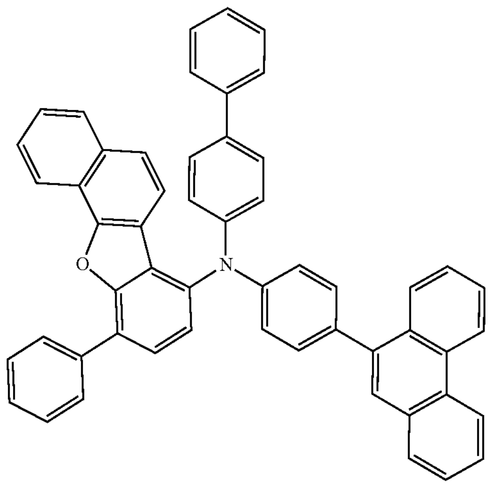
B119
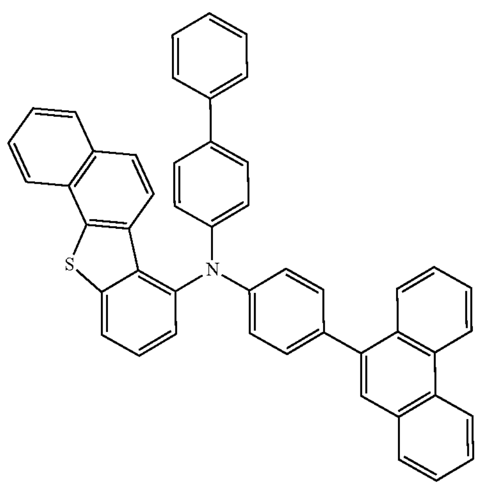
B120
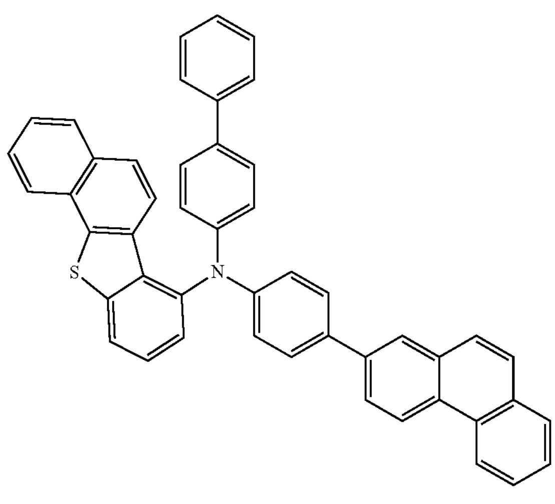
-continued
B121
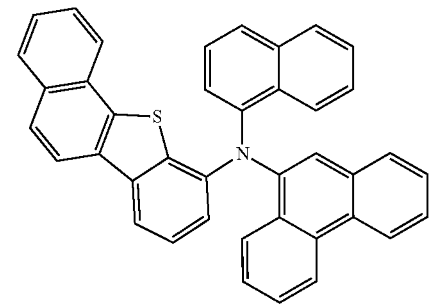
B122
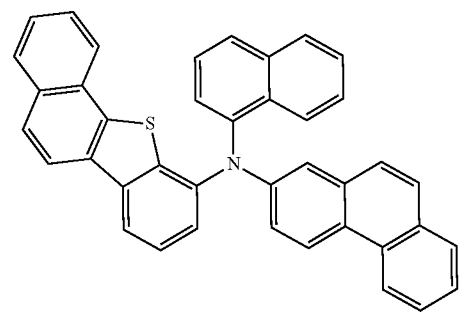
B123
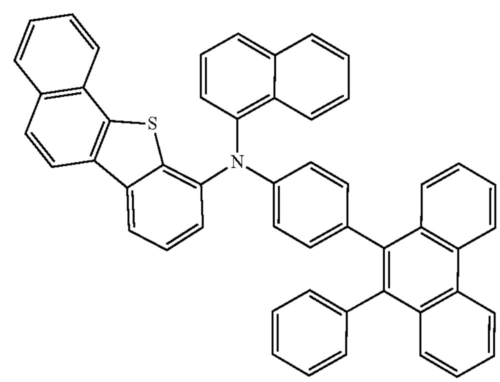
B124
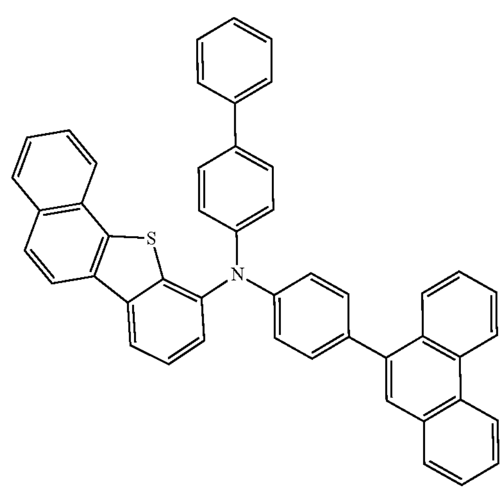

-continued
B125
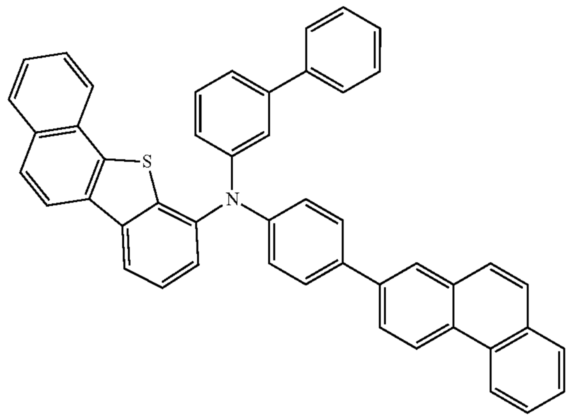
B126
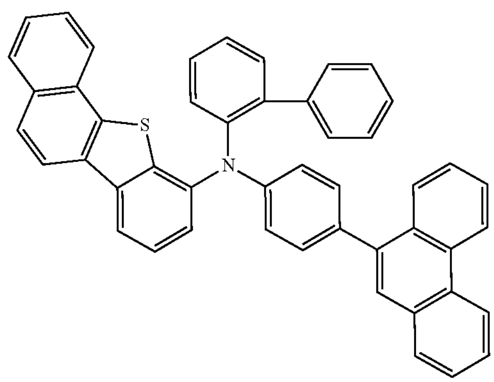
B127
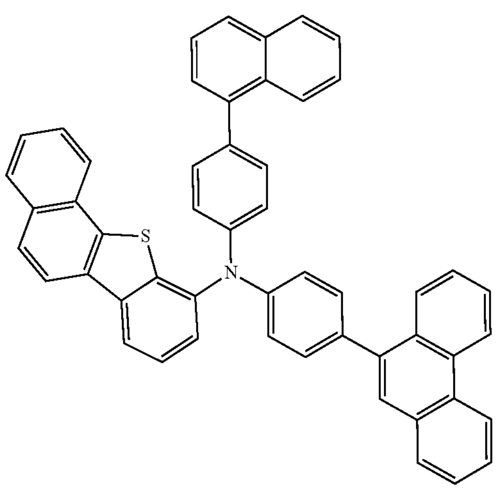
-continued
B128
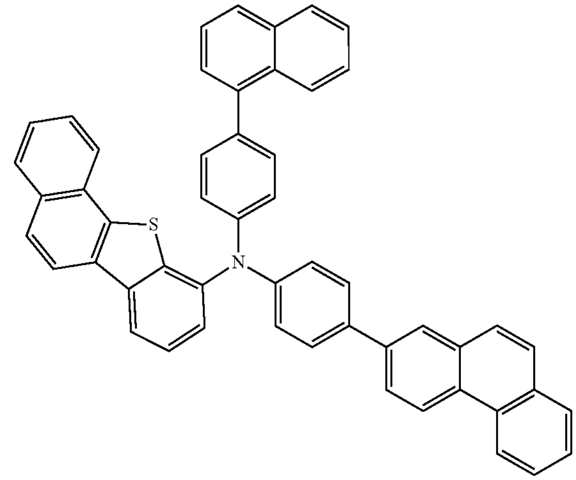
B129
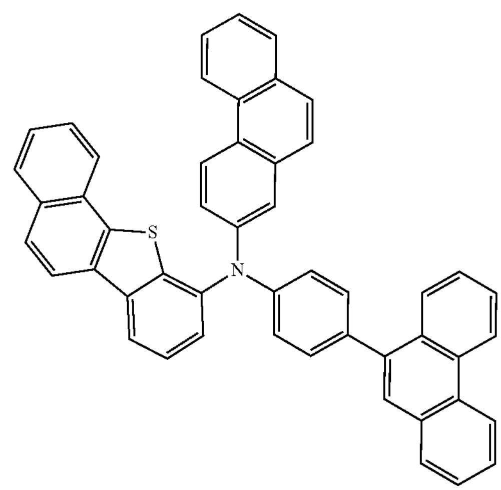
B130
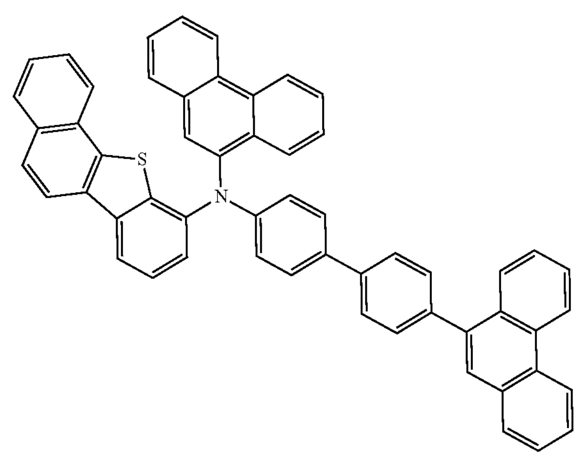

-continued
B131
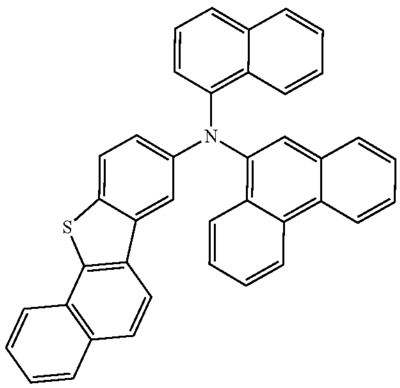
B132
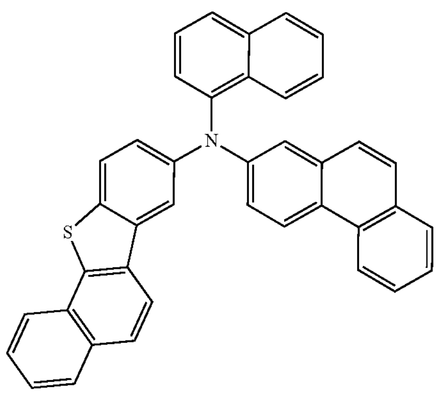
B133
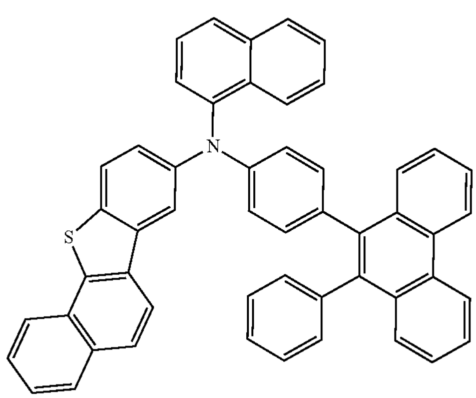
-continued
B134
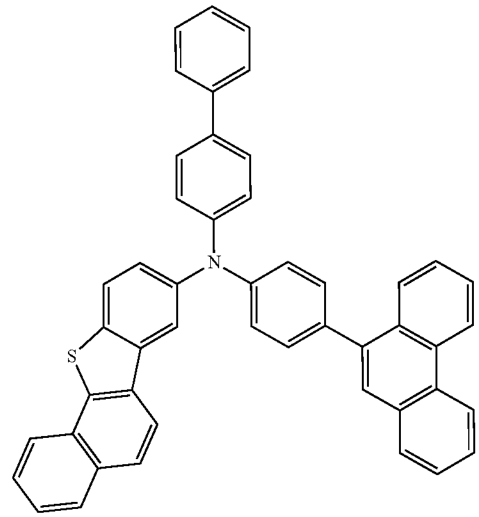
B135
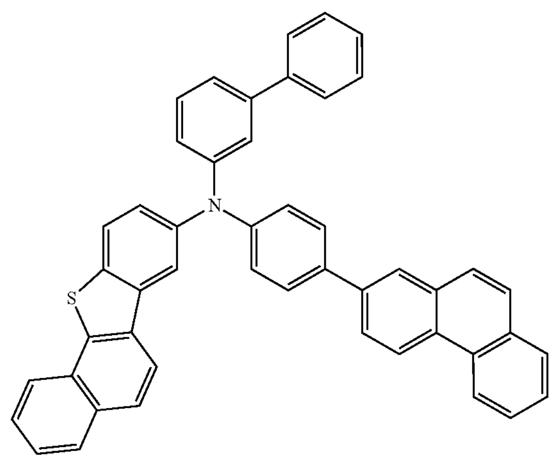
B136
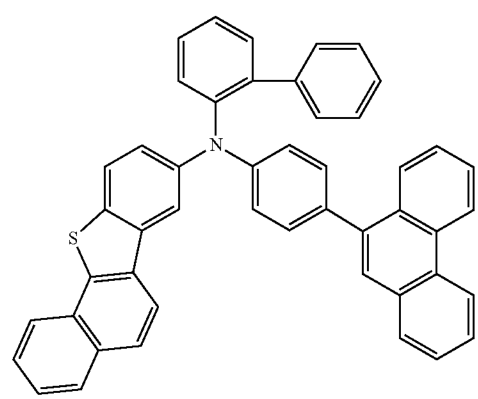

-continued
B137
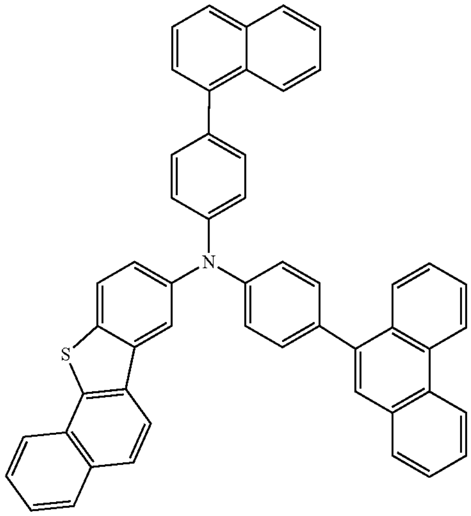
B138
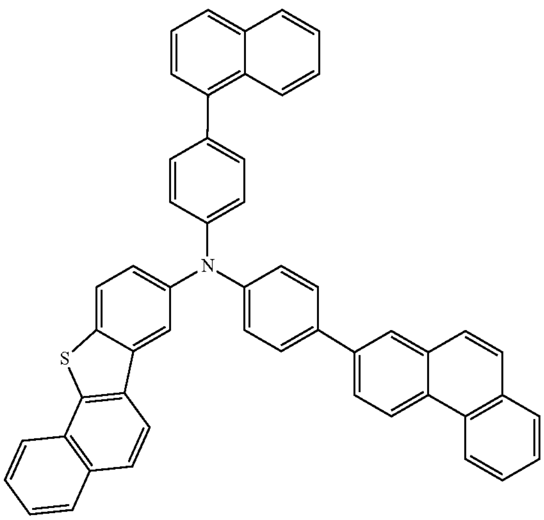
B139
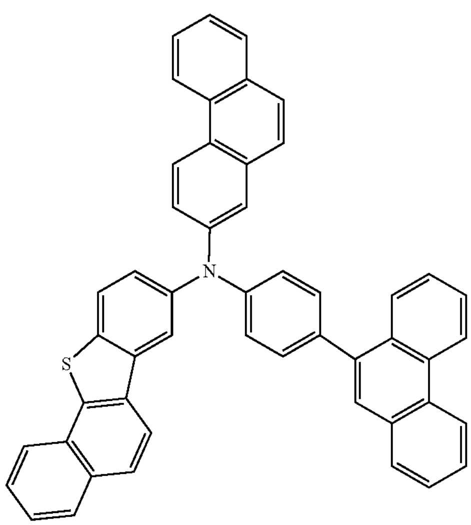
-continued
B140
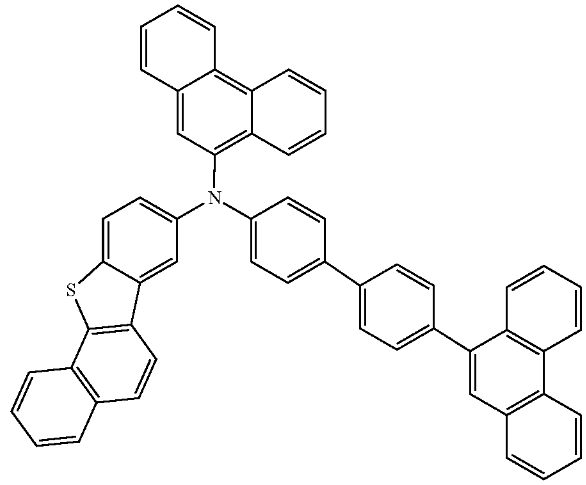
B141
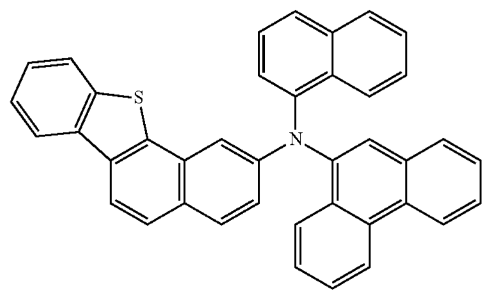
B142
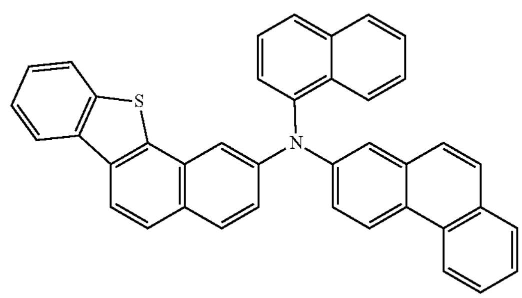
B143
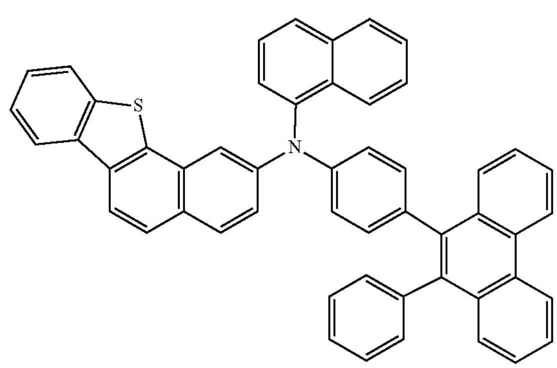

-continued
B144
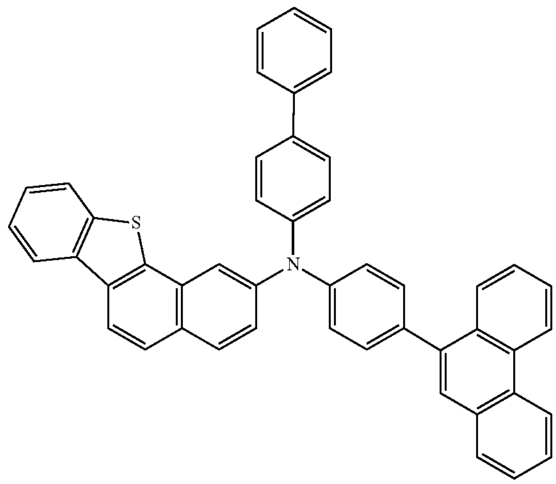
B145
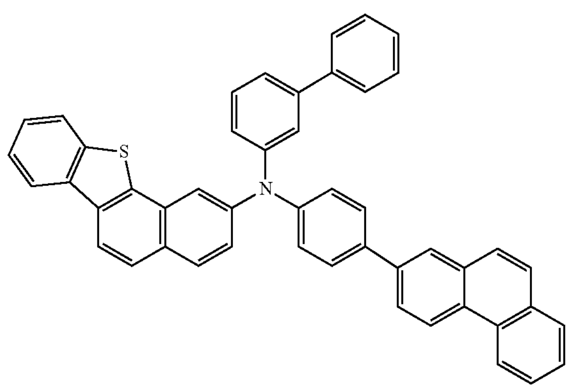
B146
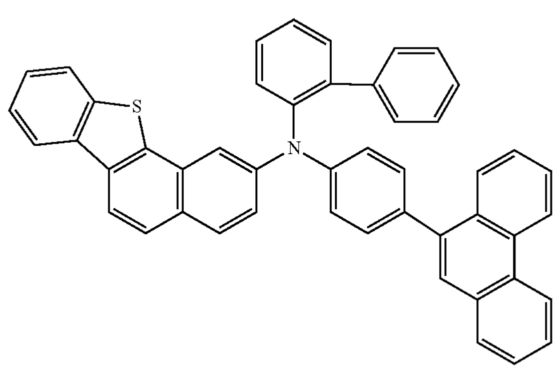
-continued
B147
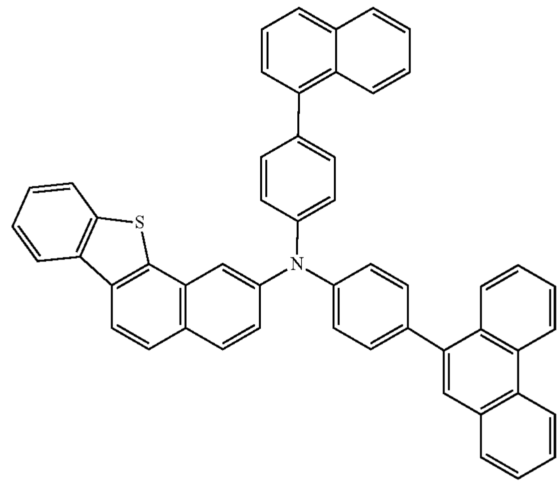
B148
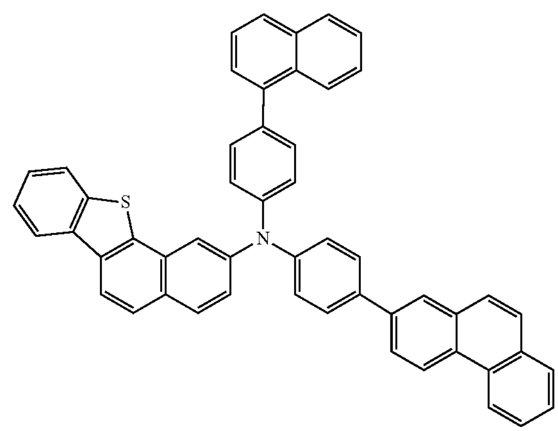
B149
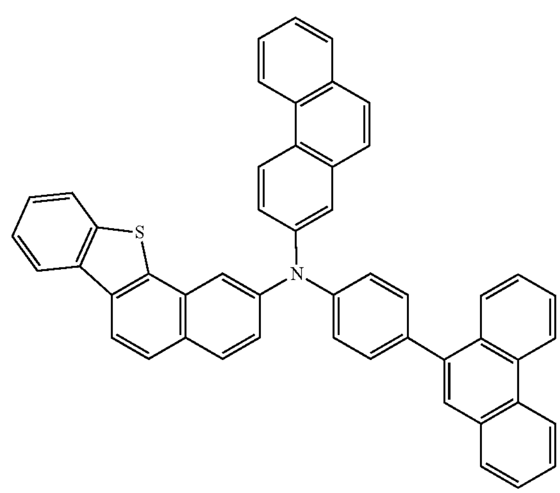

-continued
B150
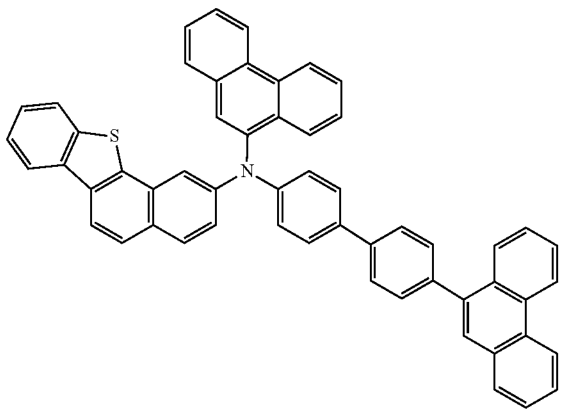
B151
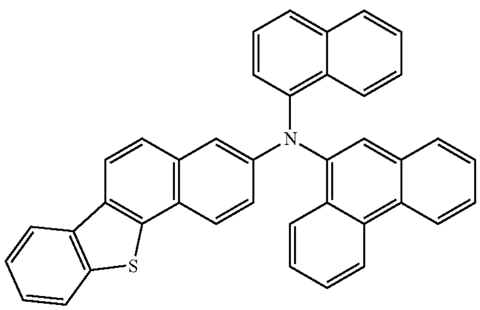
B152
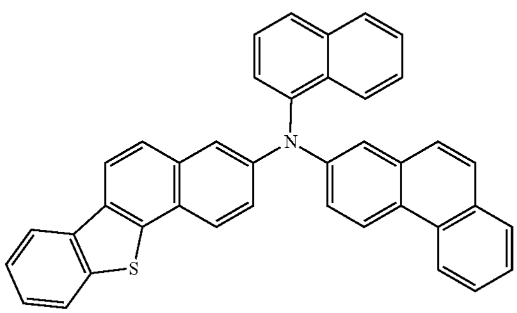
B153
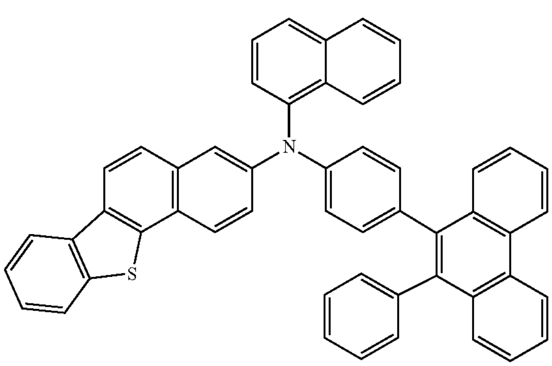
-continued
B154
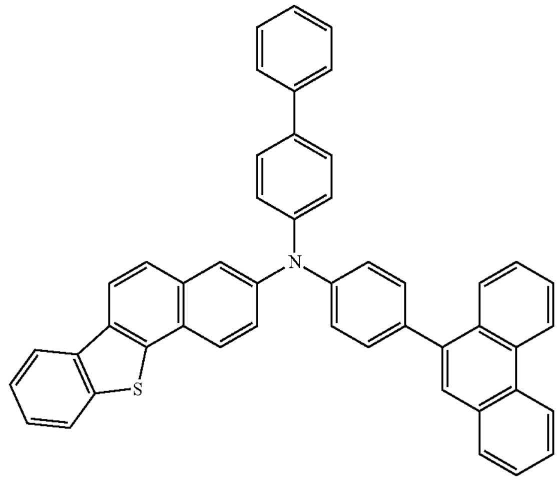
B155
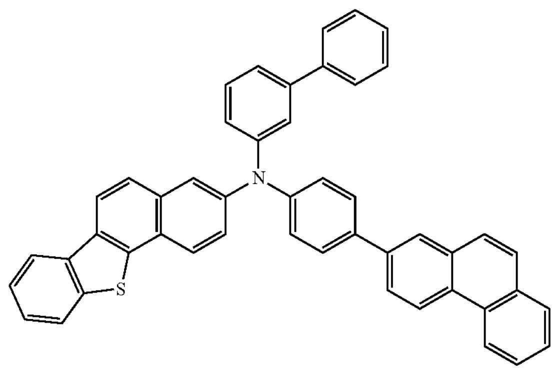
B156
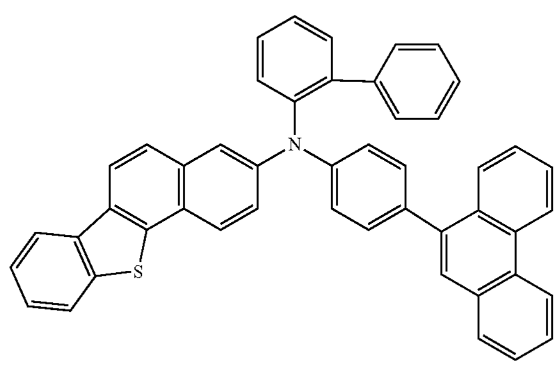

-continued
B157
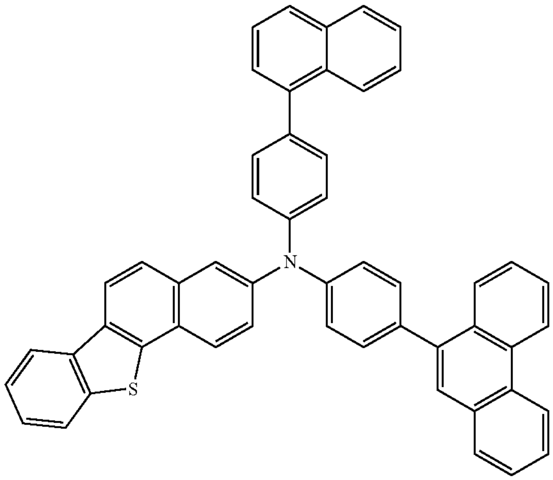
B158
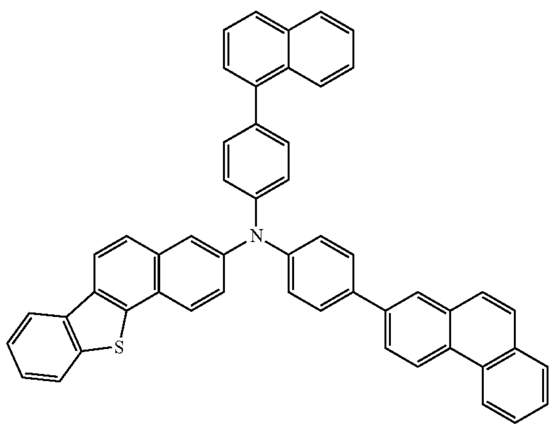
B159
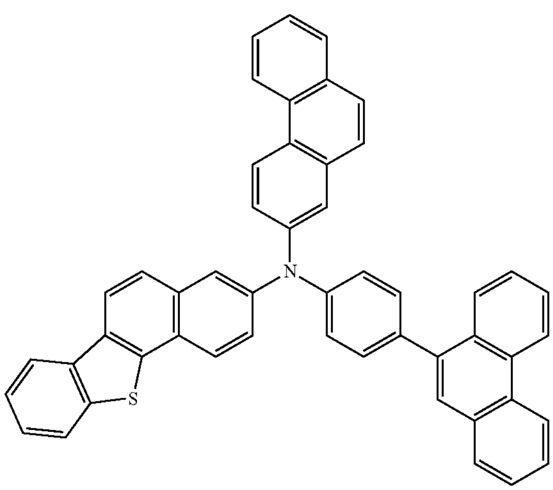
-continued
B160
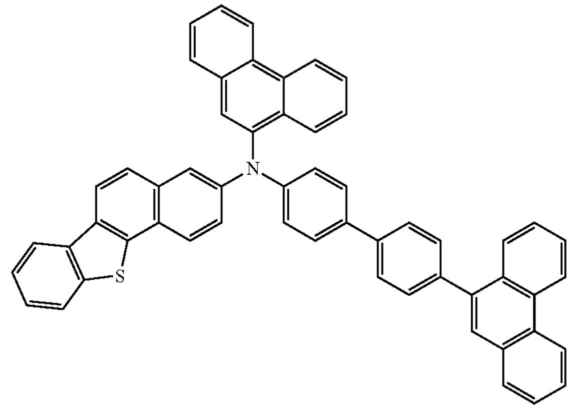
B161
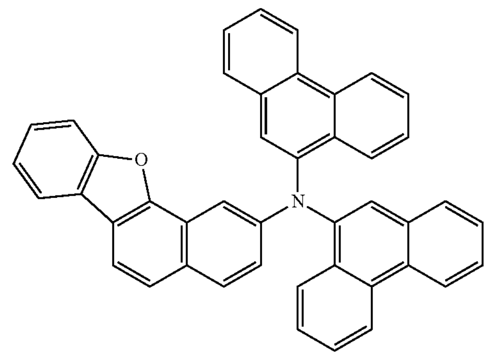
B162
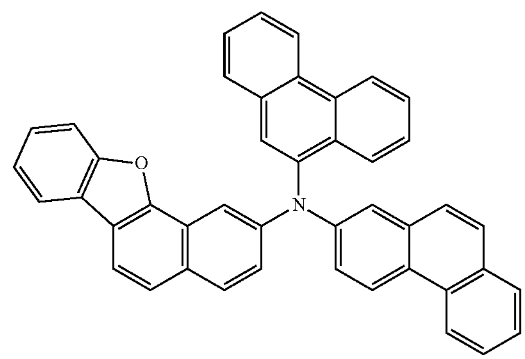
B163
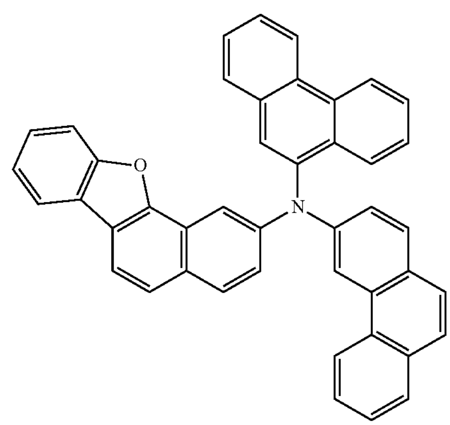

-continued
B164
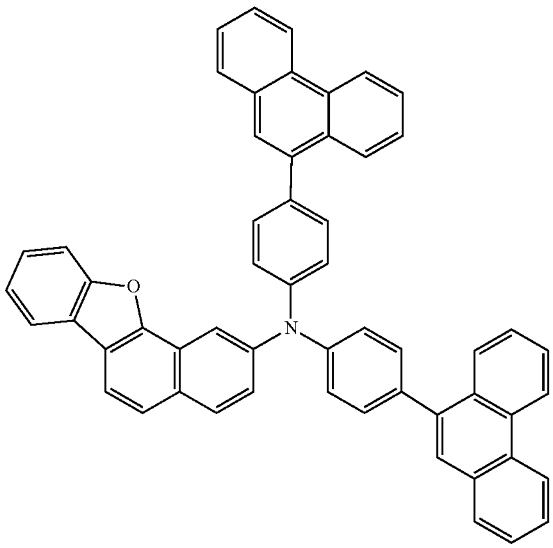
B165
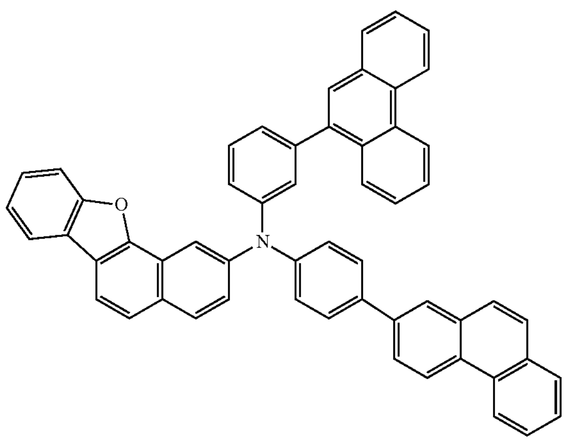
B166
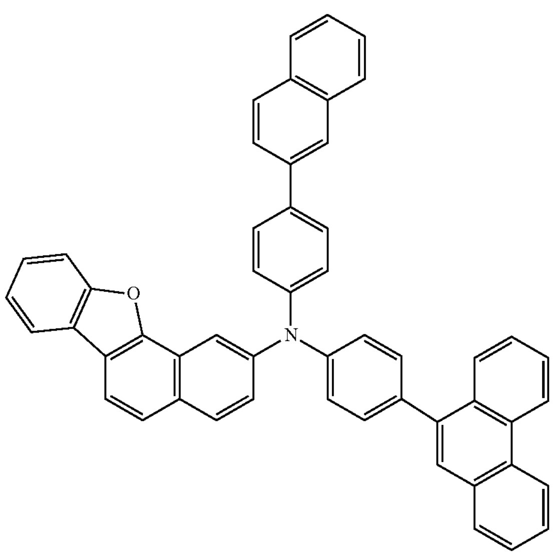
-continued
B167
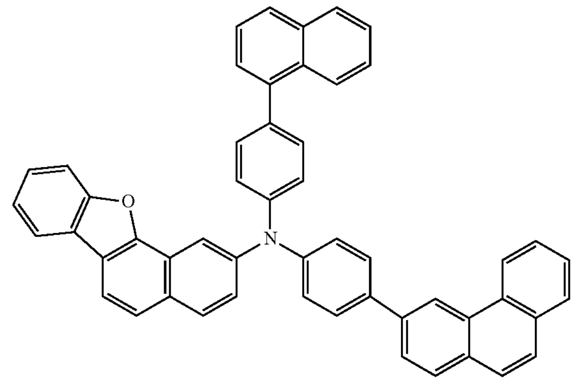
B168
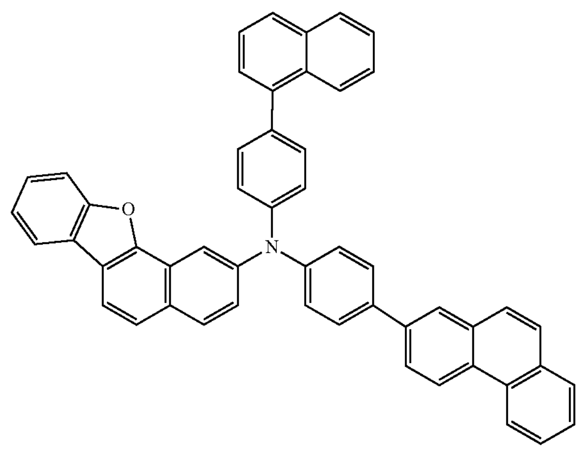
B169
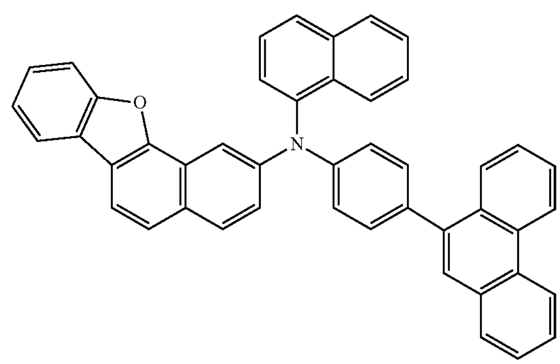
B170
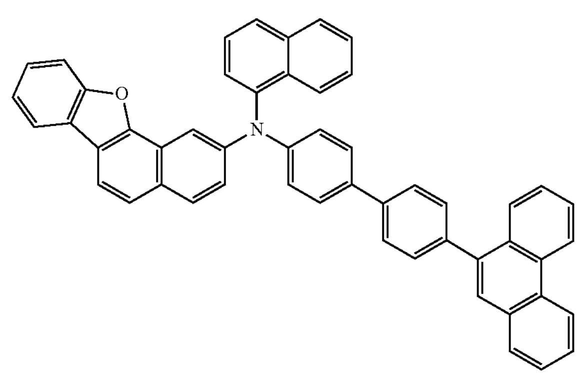

-continued
B171
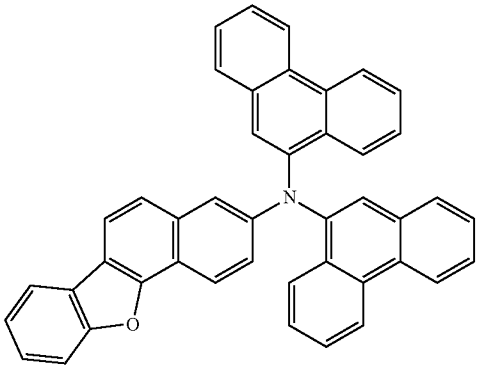
B172
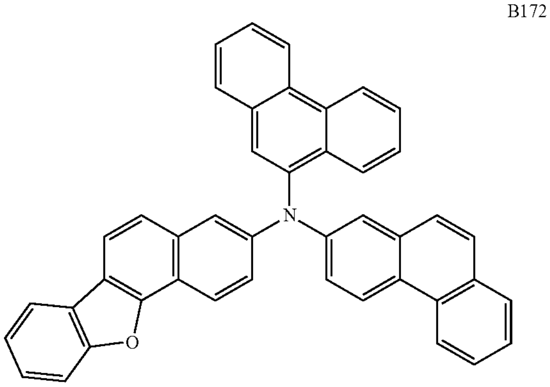
B173
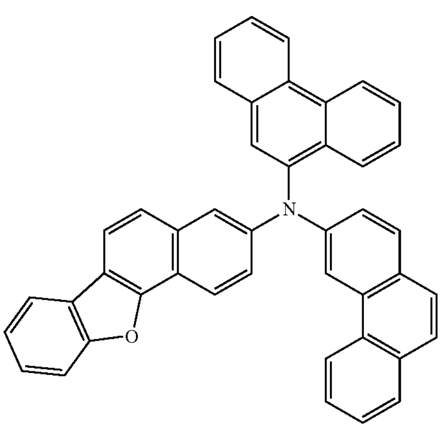
-continued
B174
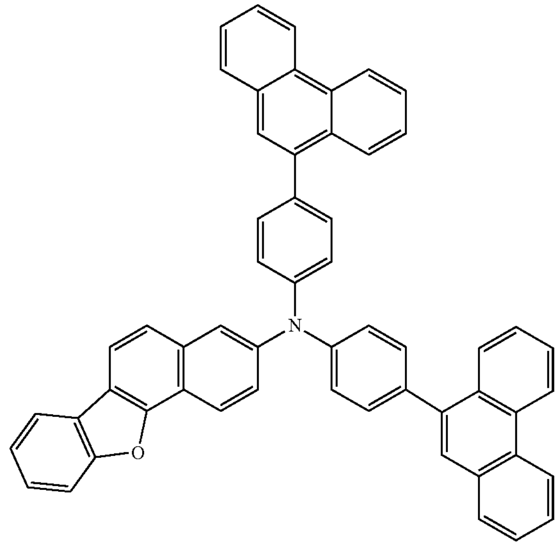
B175
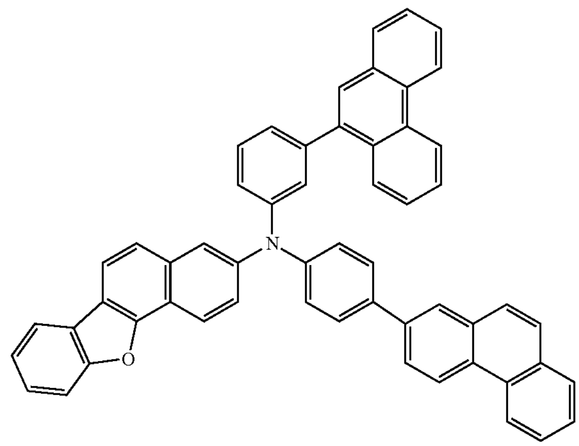
B176
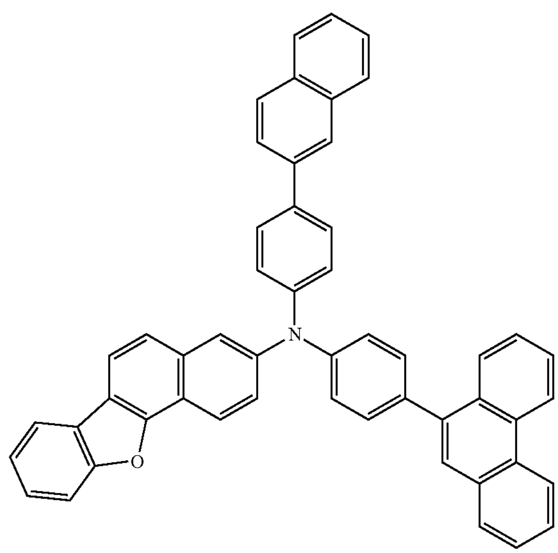

B177
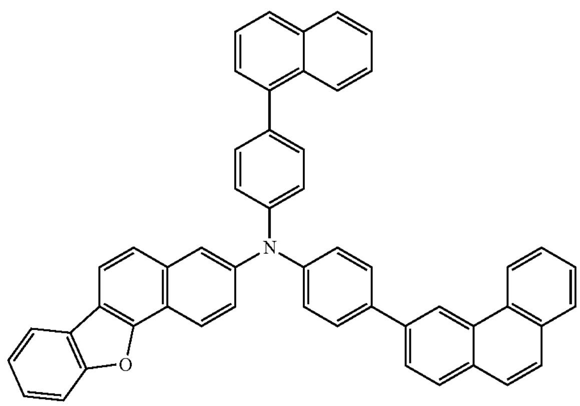
B178
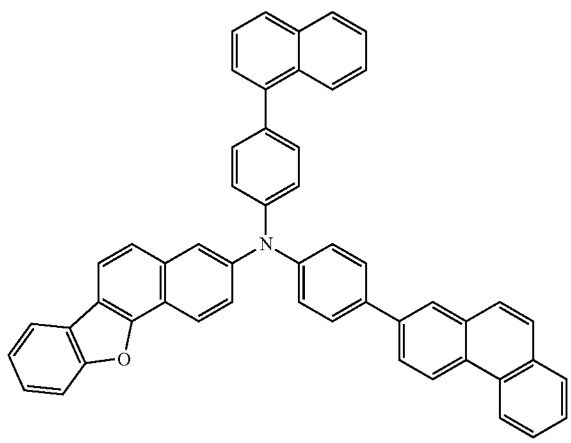
B179
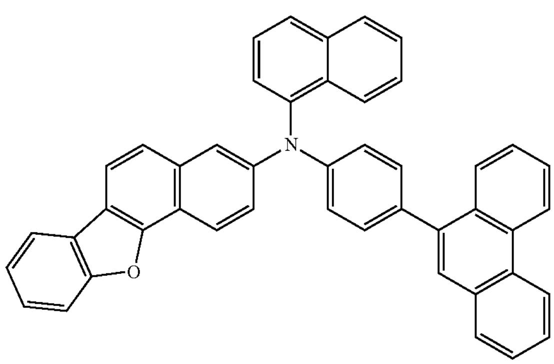
B180
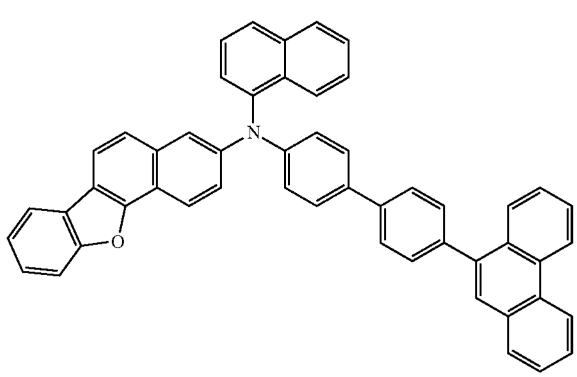
B181
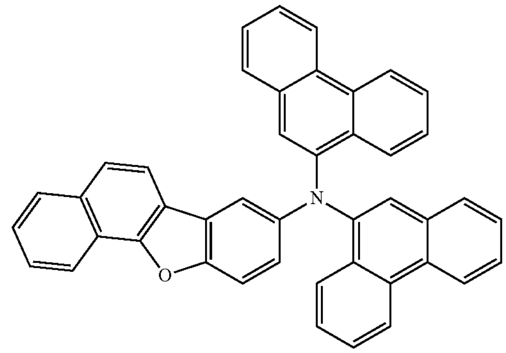
B182
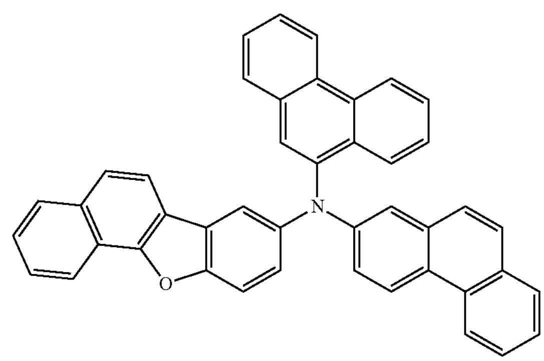
B183
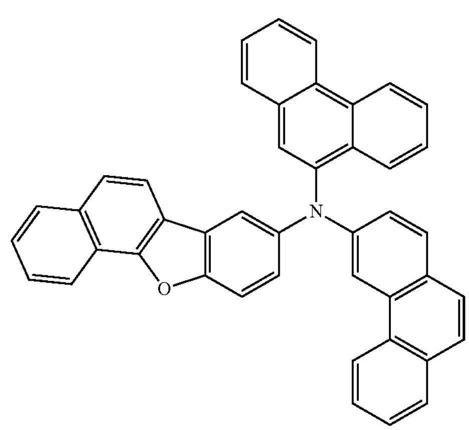

-continued
B184
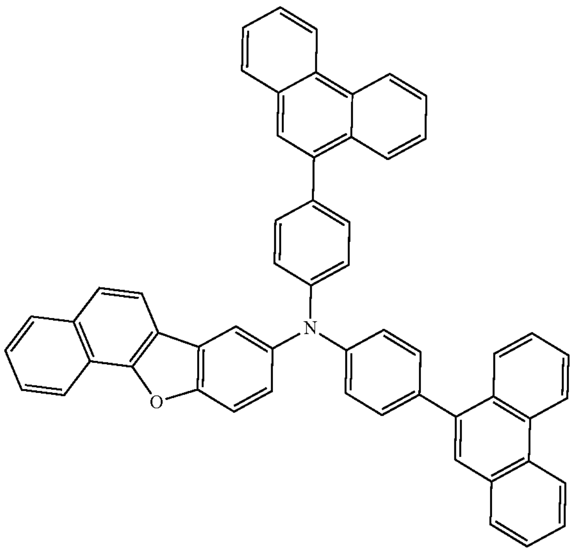
B185
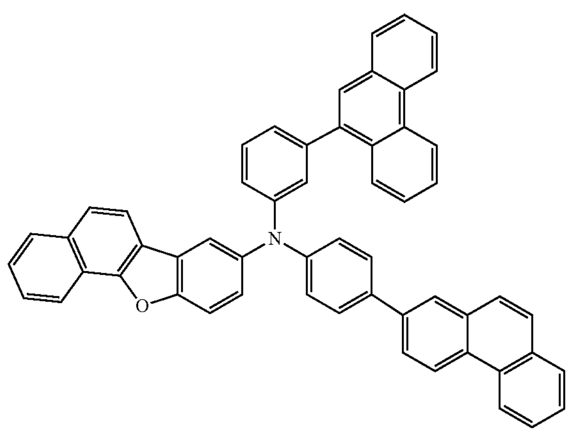
B186
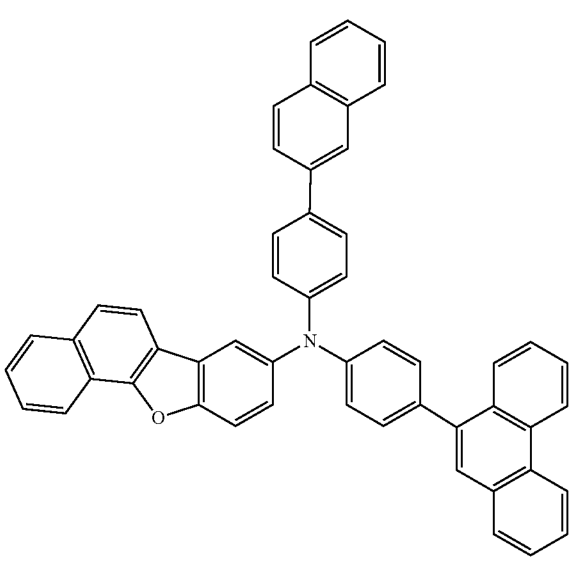
-continued
B187
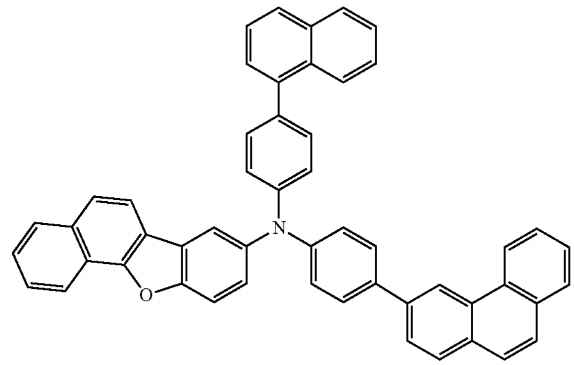
B188
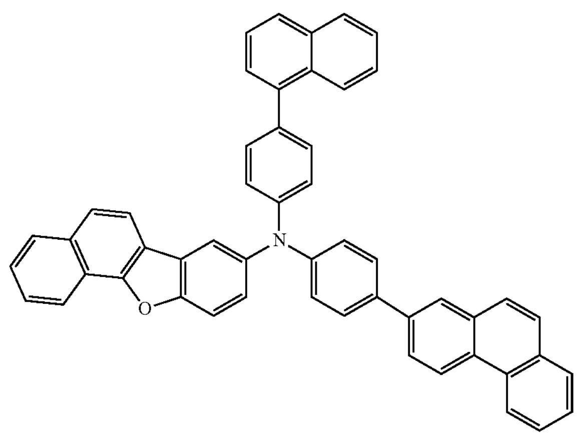
B189
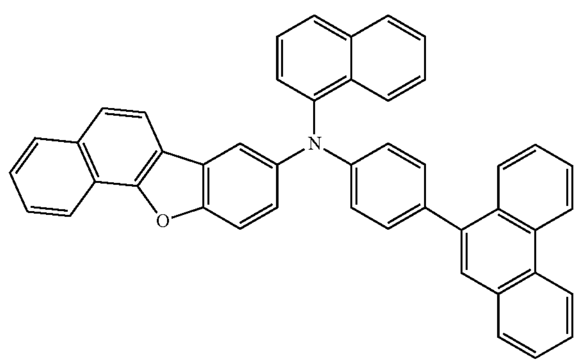
B190
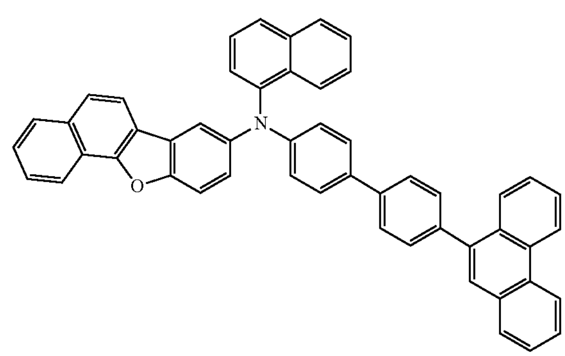

-continued
B191
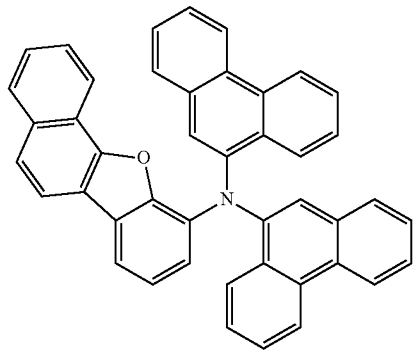
B192
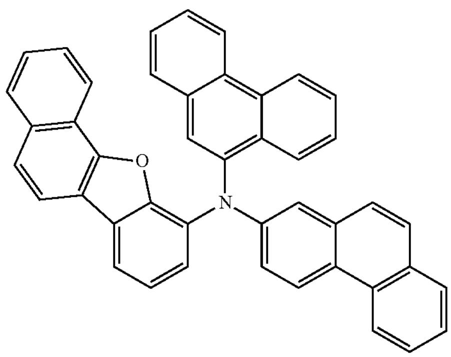
B193
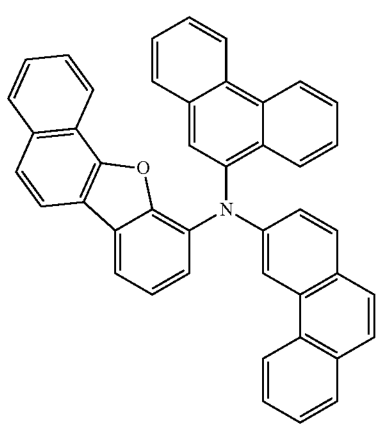
-continued
B194
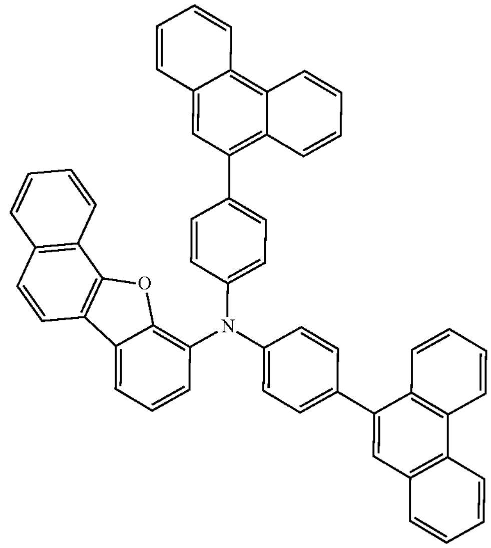
B195
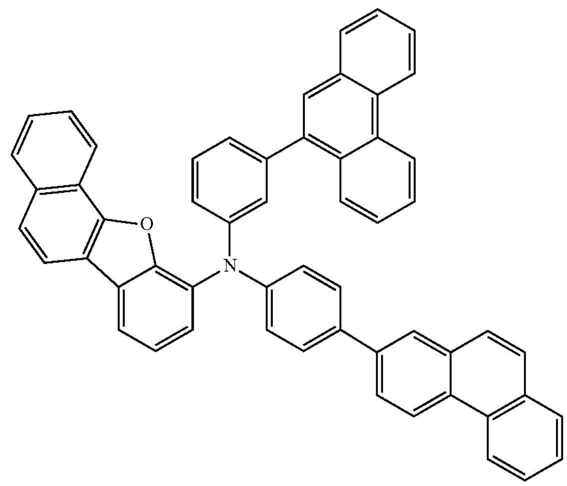
B196
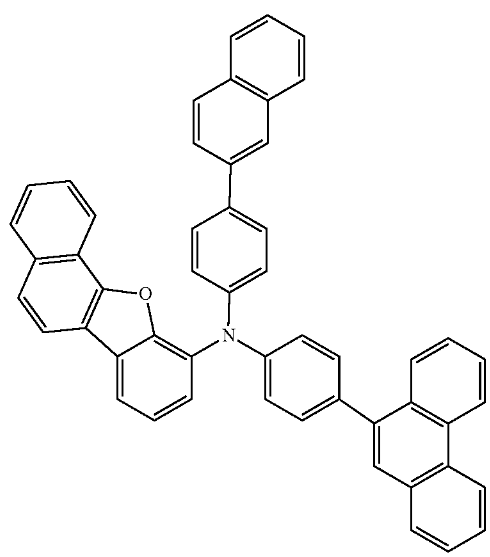

-continued
B197
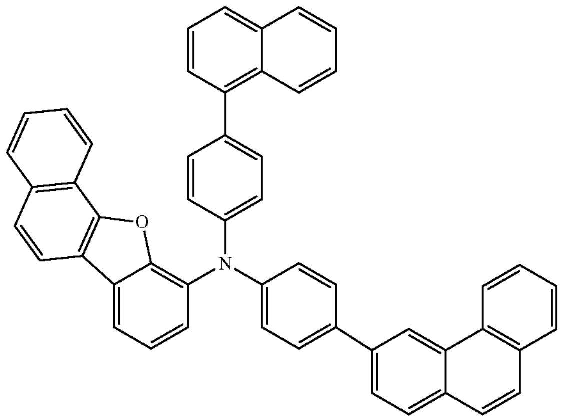
B198
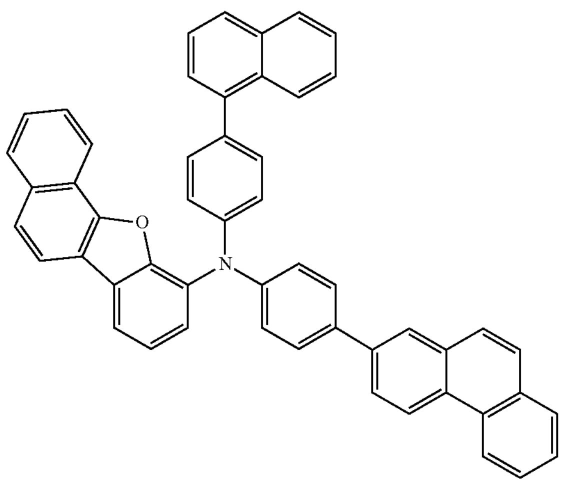
-continued
B199
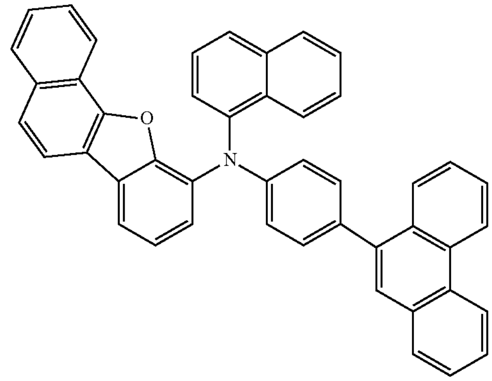
B200
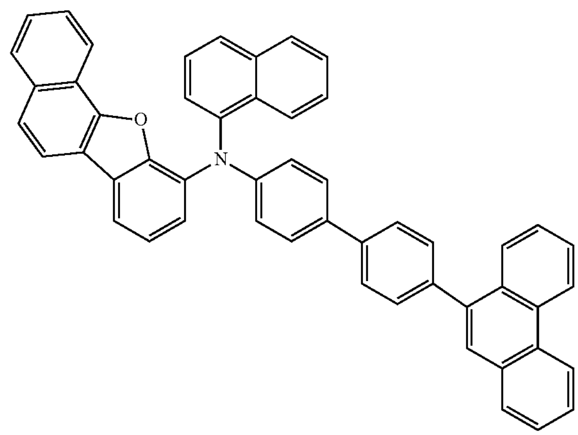
[Compound Group 3]
C1
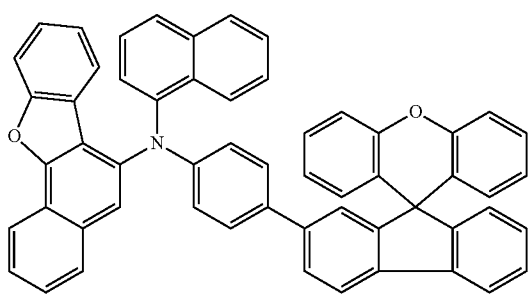

-continued
C2
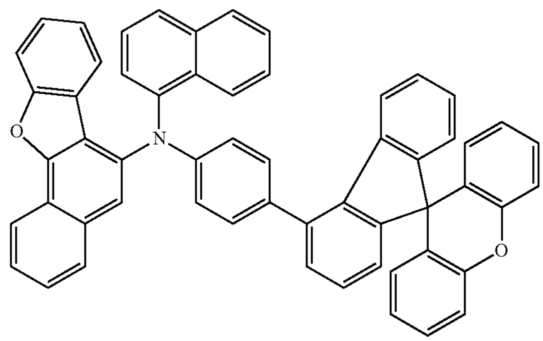
C3
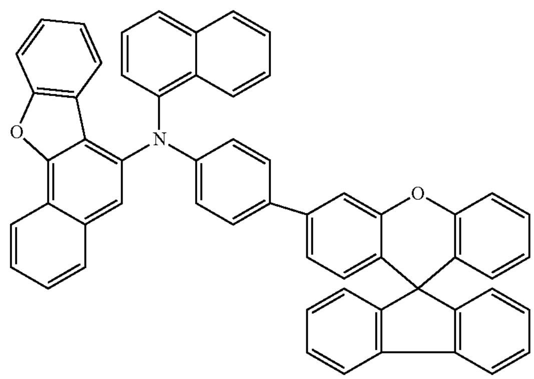
C4
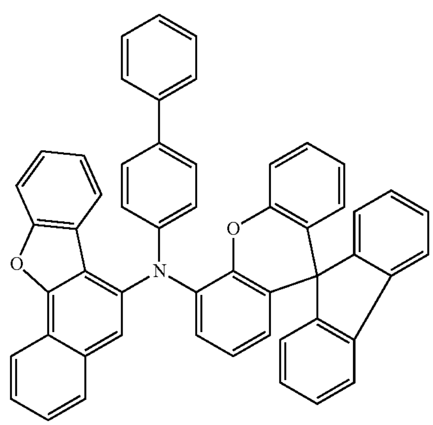
C5
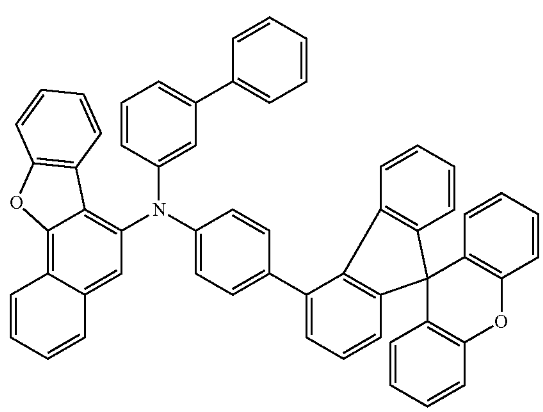

-continued
C6
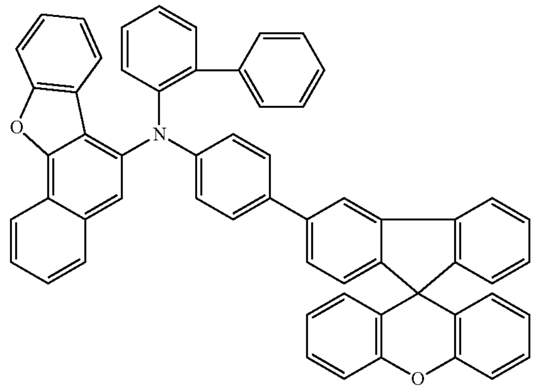
C7
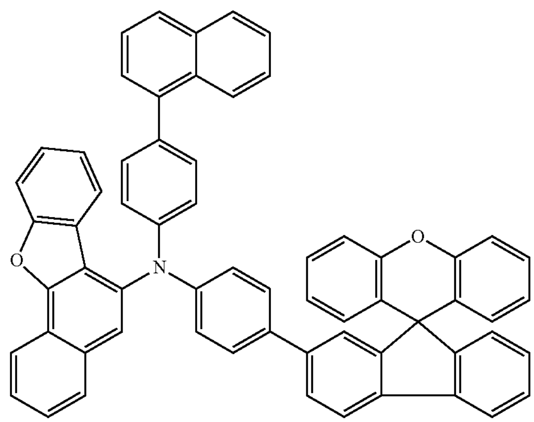
C8
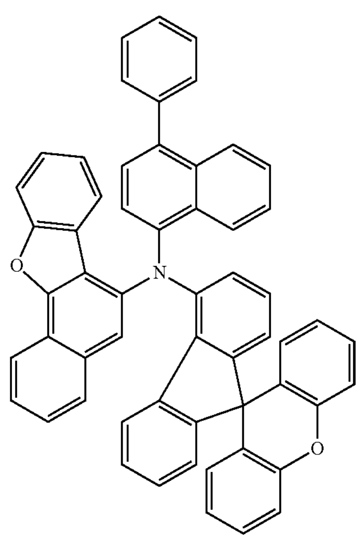

-continued
C9
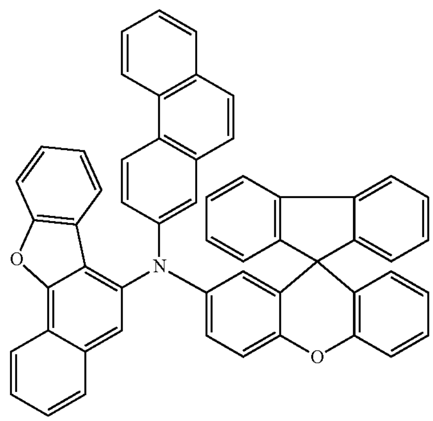
C10
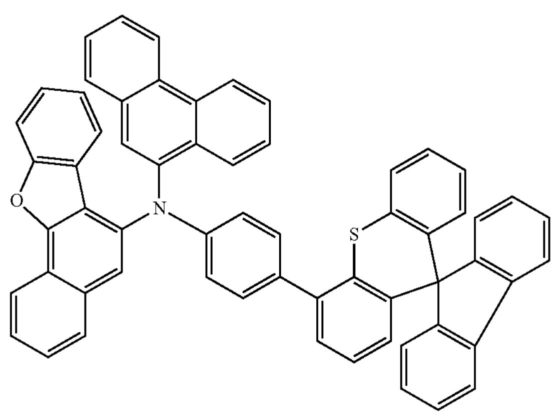
C11
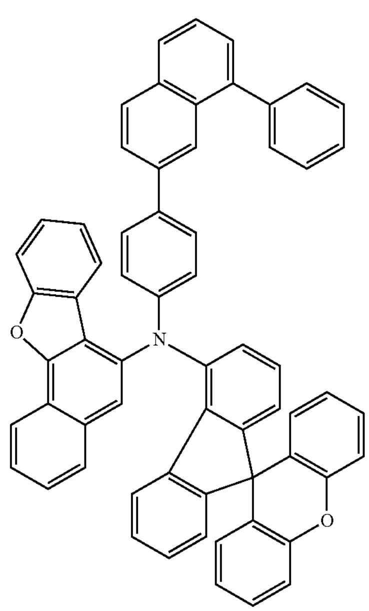

-continued
C12
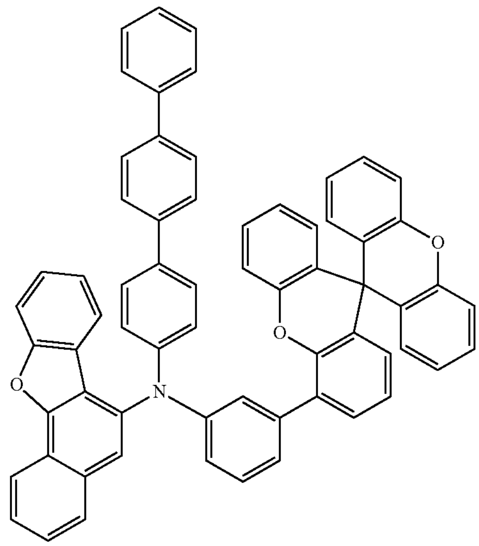
C13
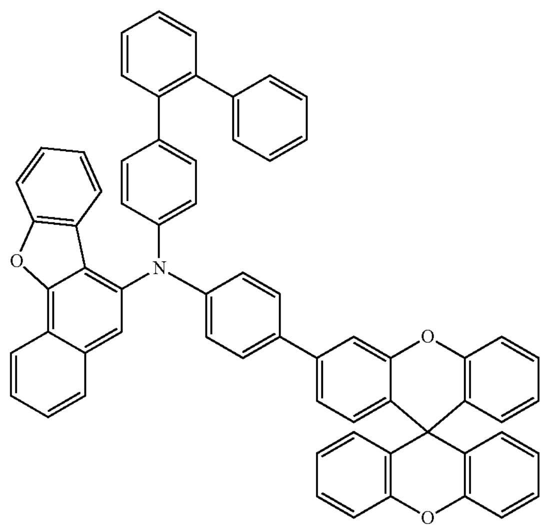
C124
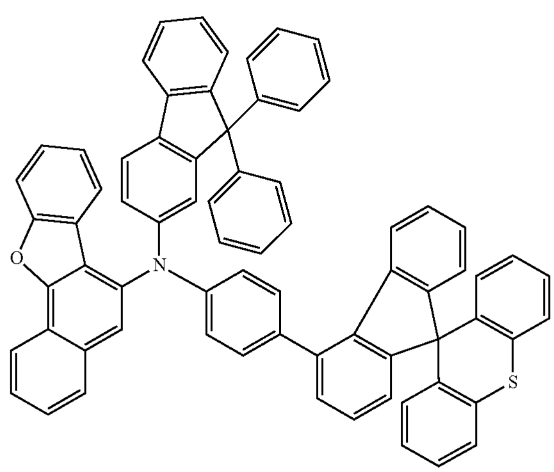

-continued
C15
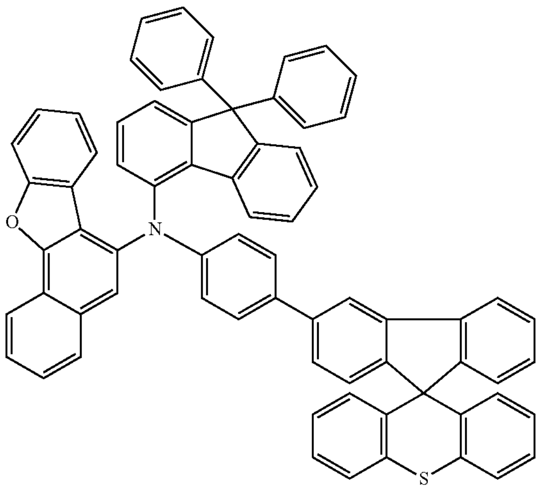
C16
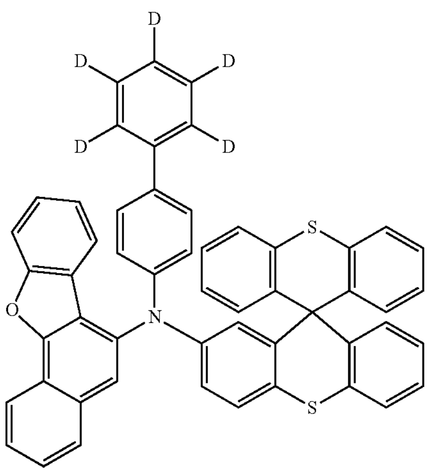
C17
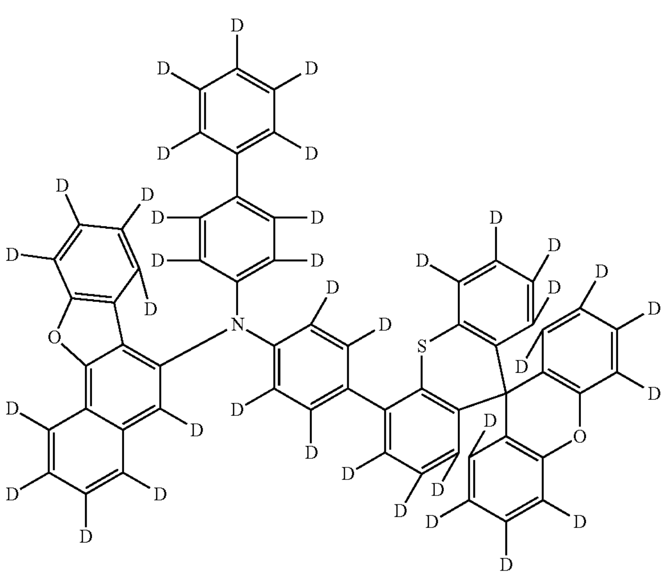

-continued
C18
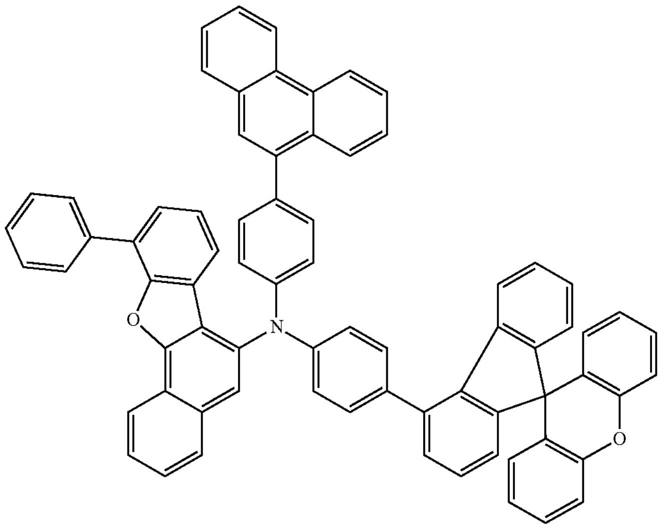
C19
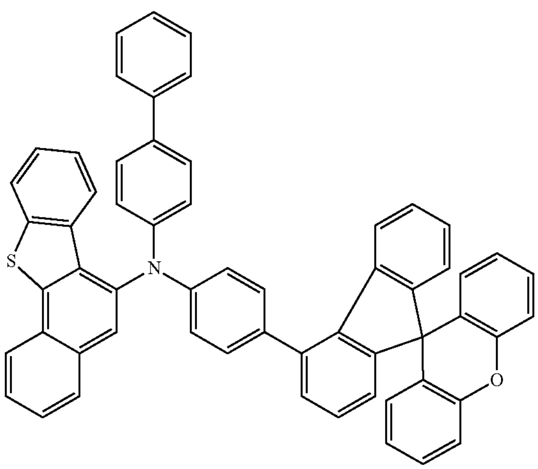
C20
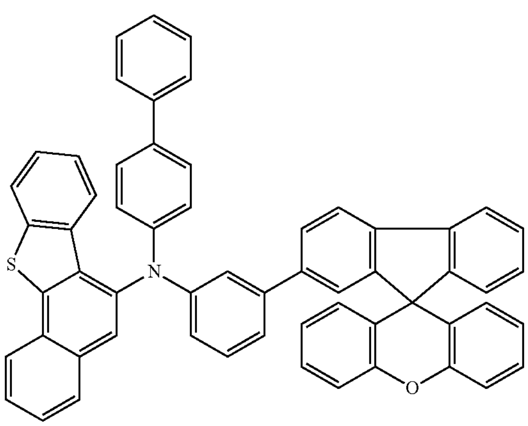

-continued
C21
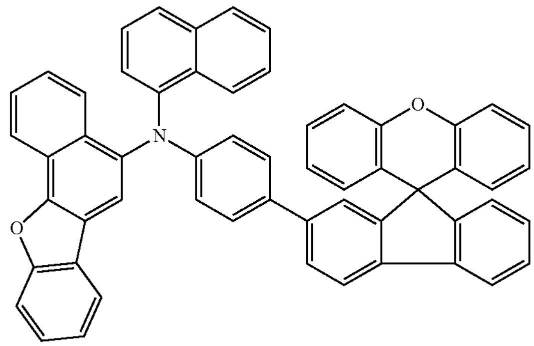
C22
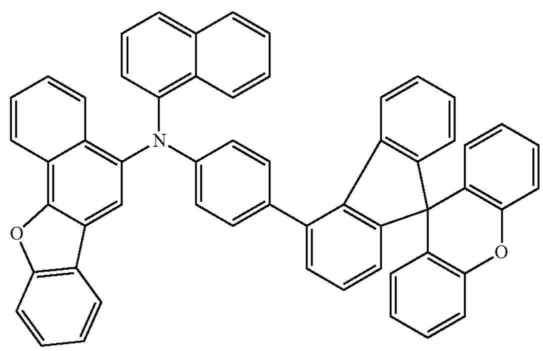
C23
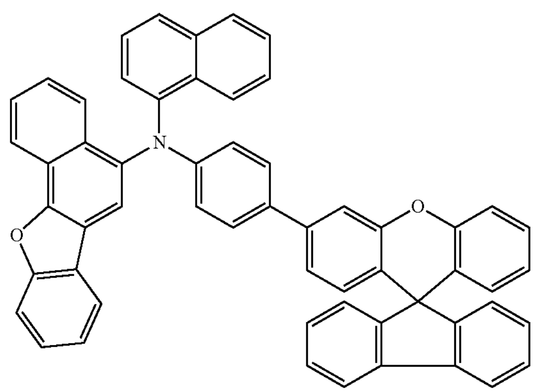
C24
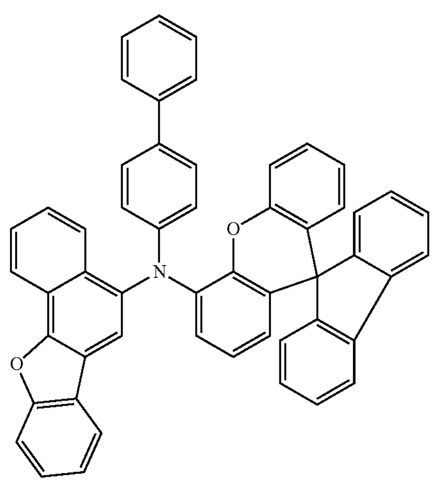

-continued
C25
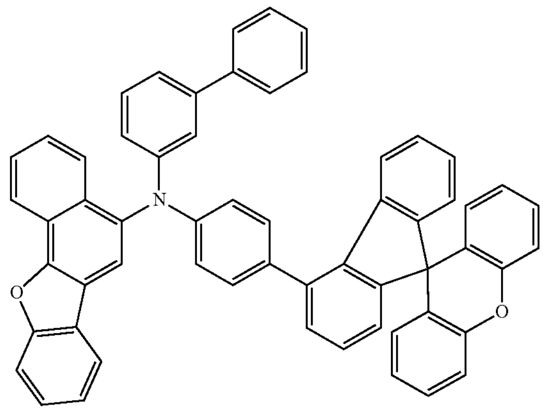
C26
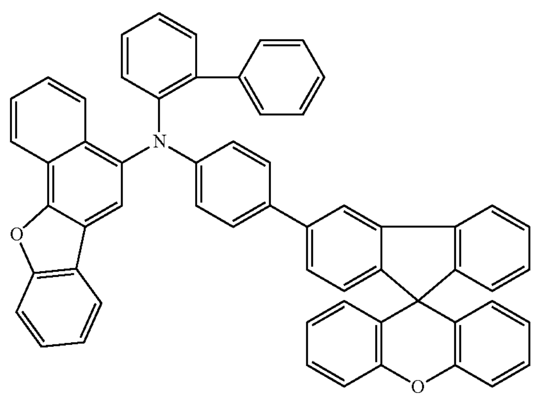
C27
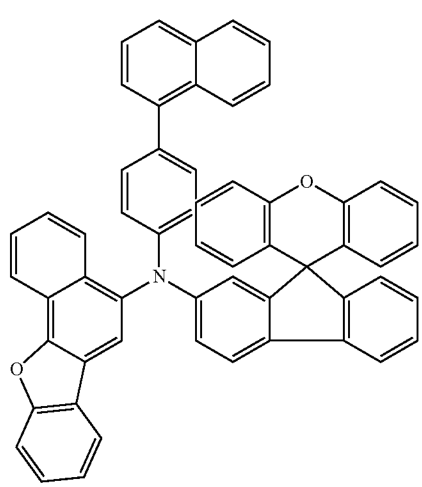

-continued
C28
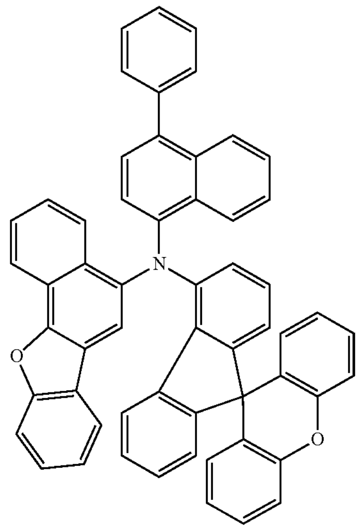
C29
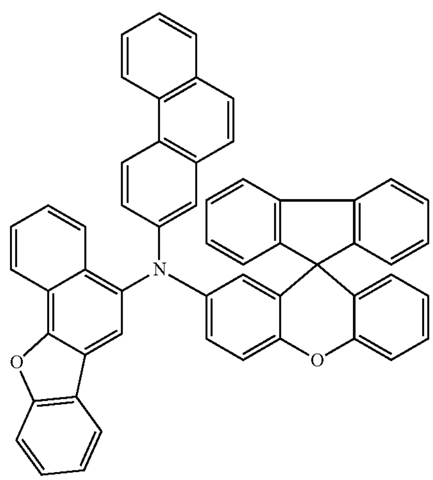
C30
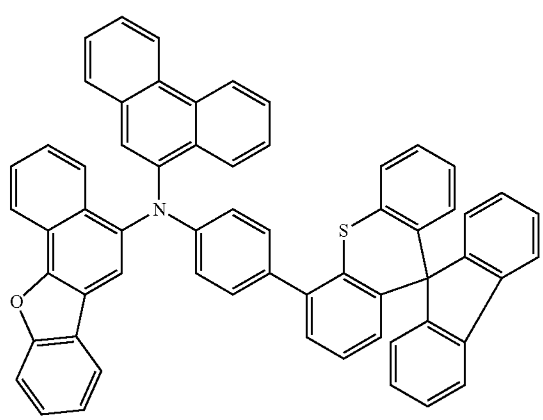

-continued
C31
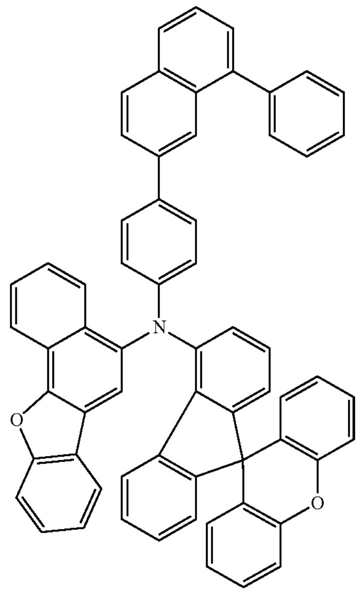
C32
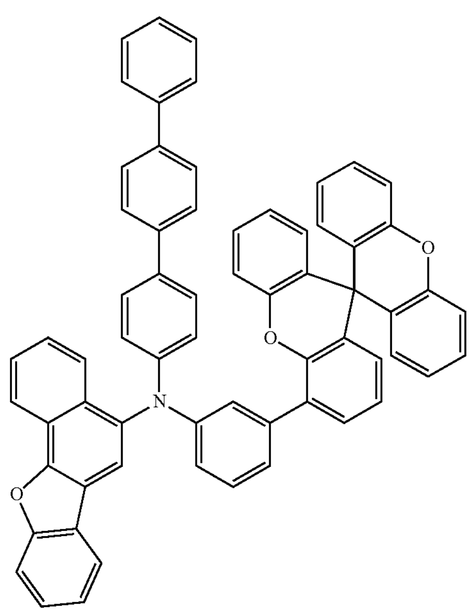

-continued
C33
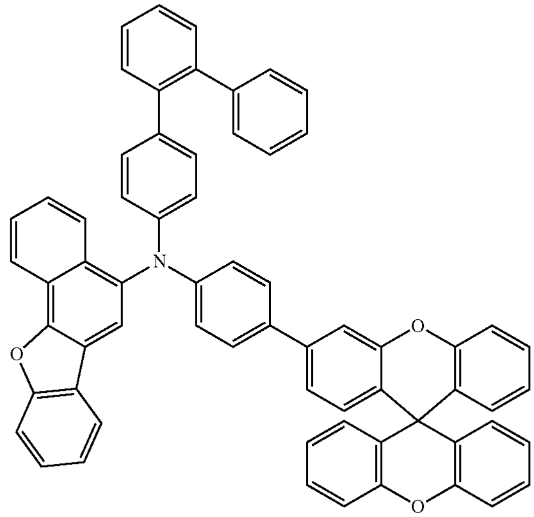
C34
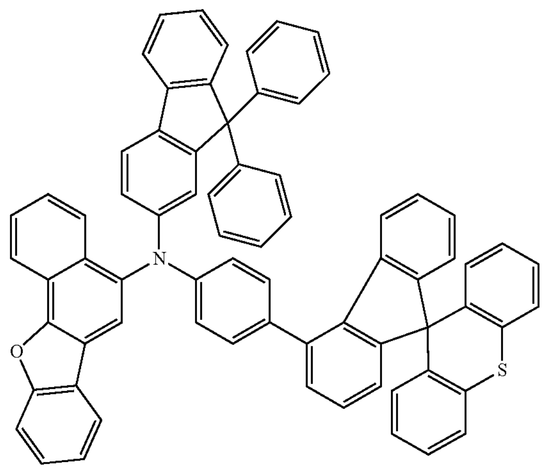
C35
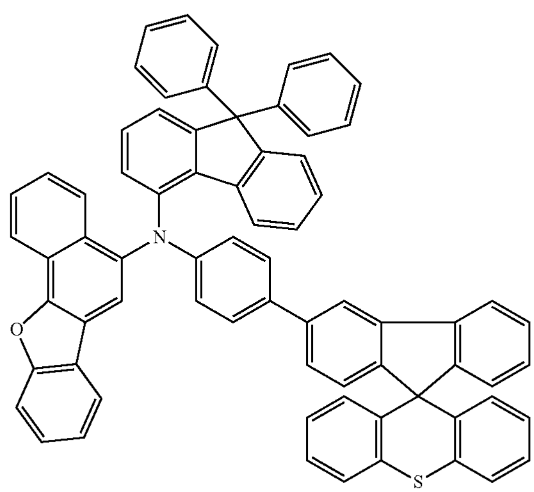

-continued
C36
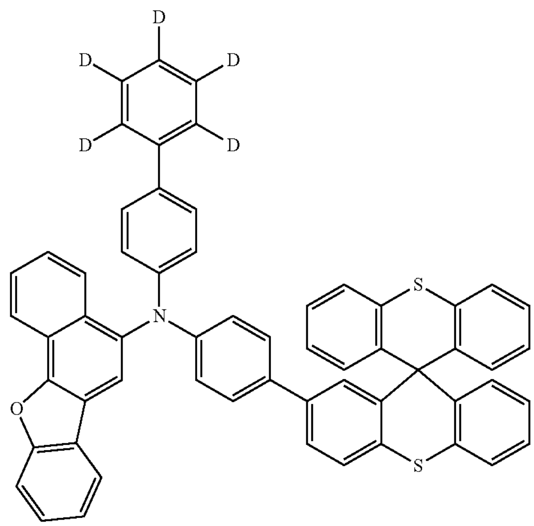
C37
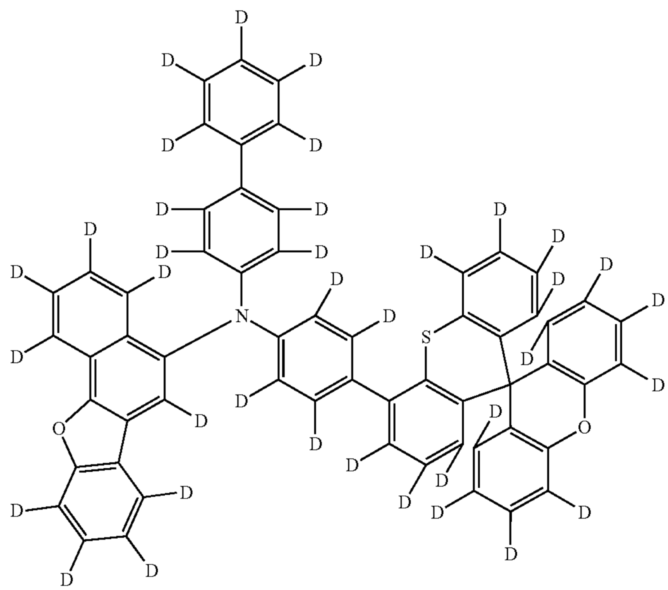
C38
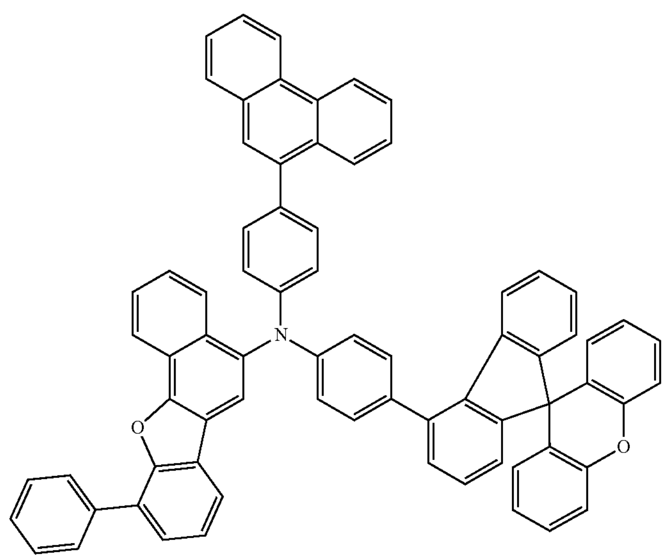

-continued
C39
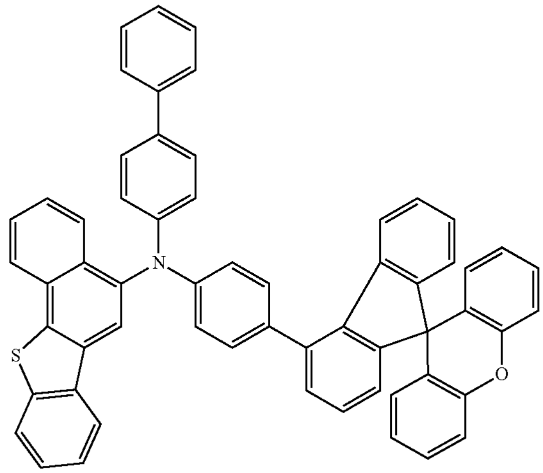
C40
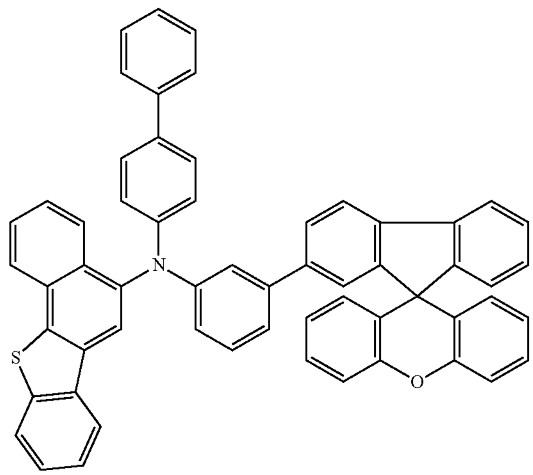
C41
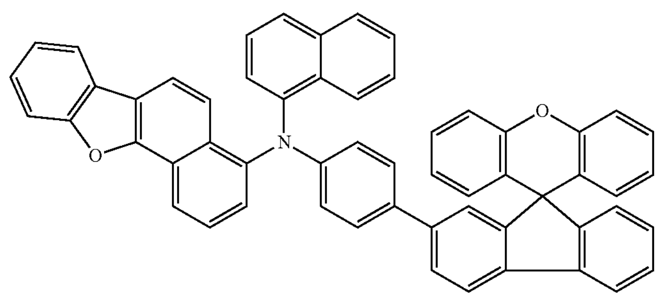
C42
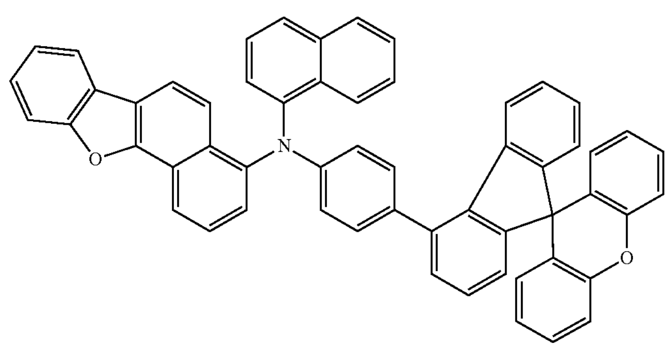

-continued
C43
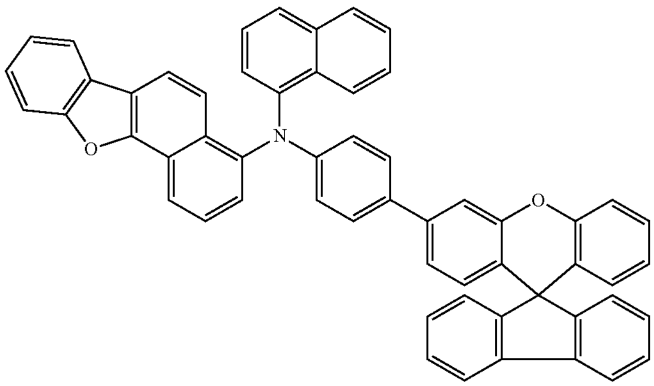
C44
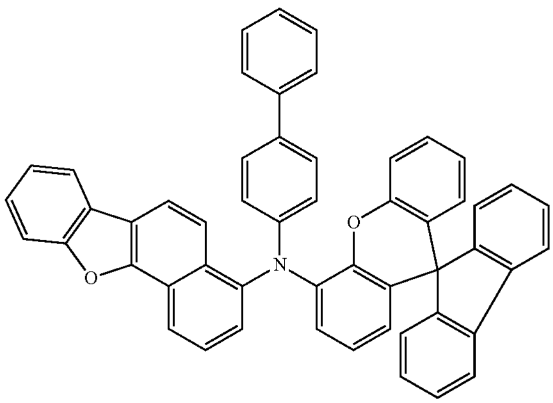
C45
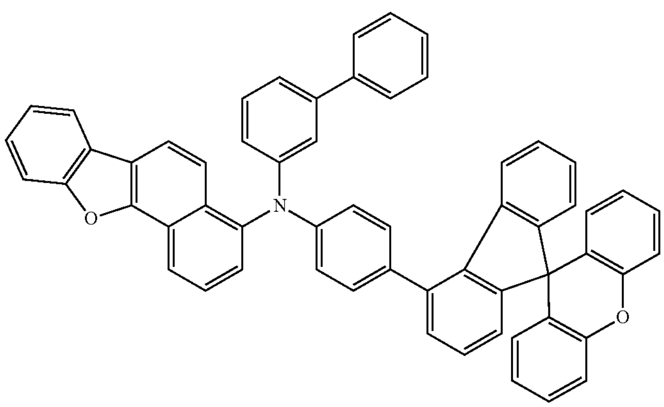
C46
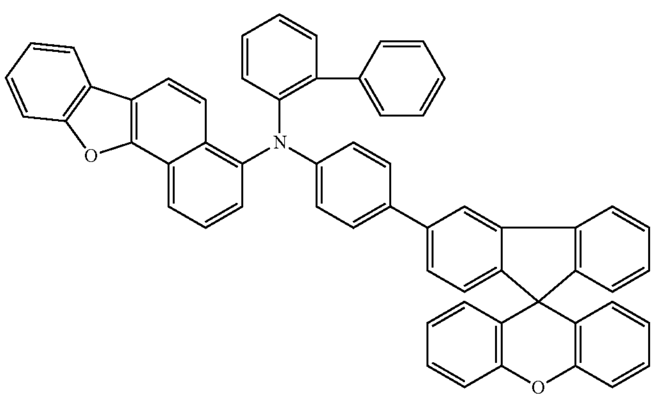

-continued
C47
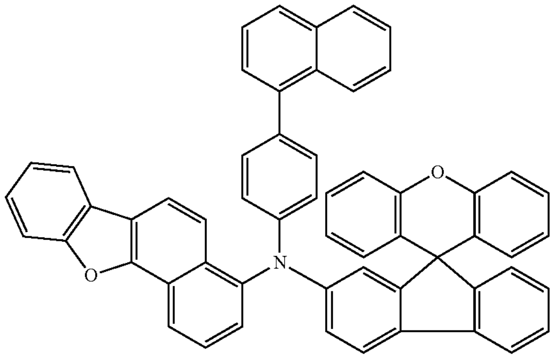
C48
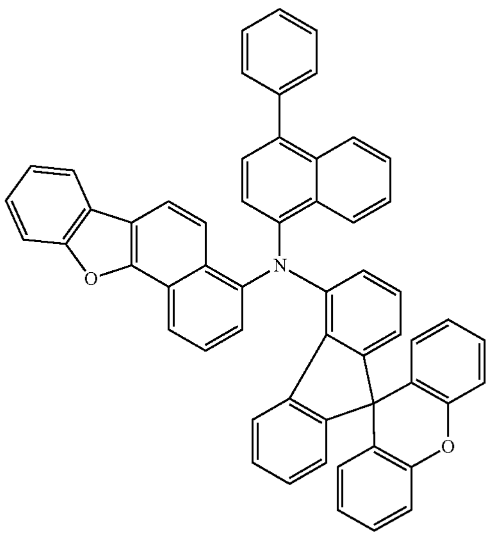
C49
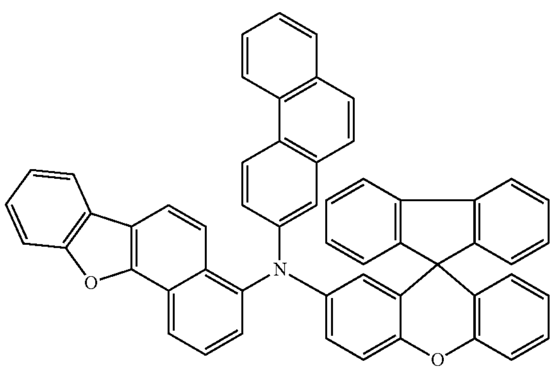
C50
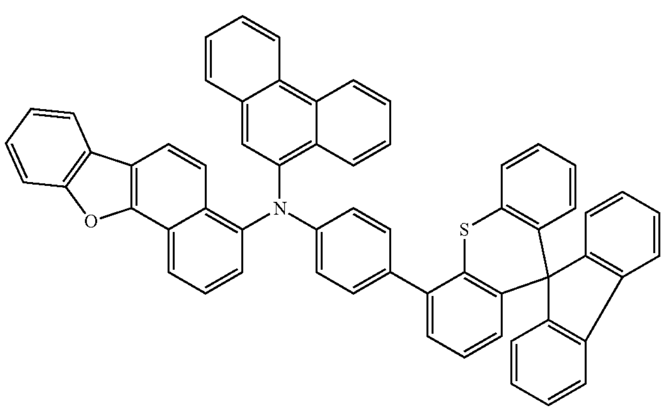

-continued
C51
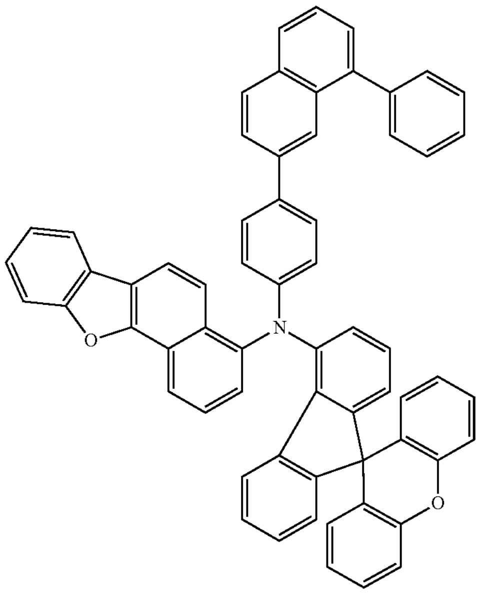
C52
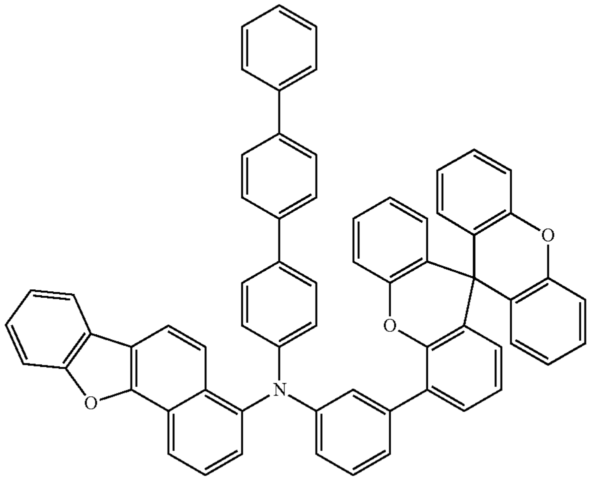
C53
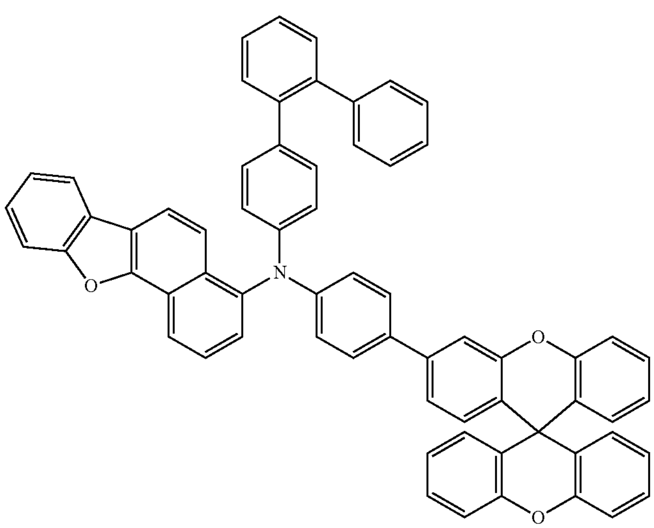

-continued
C54
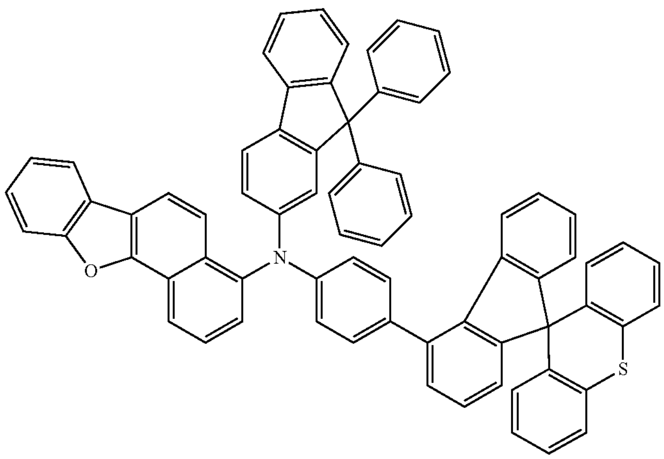
C55
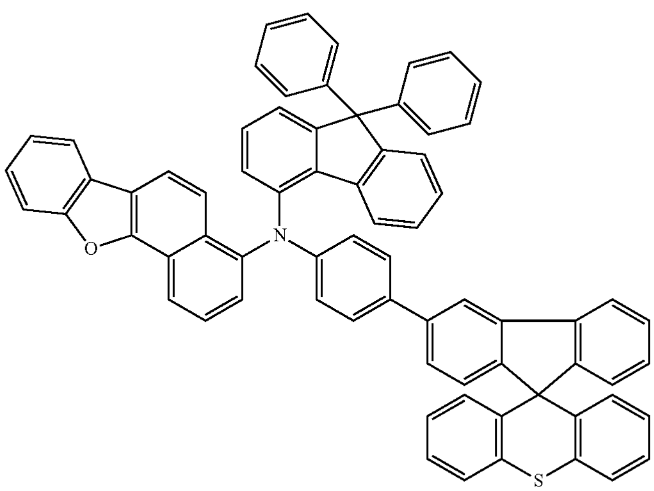
C56
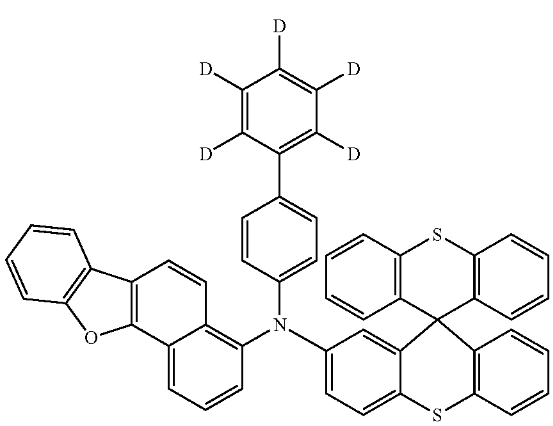

-continued
C57
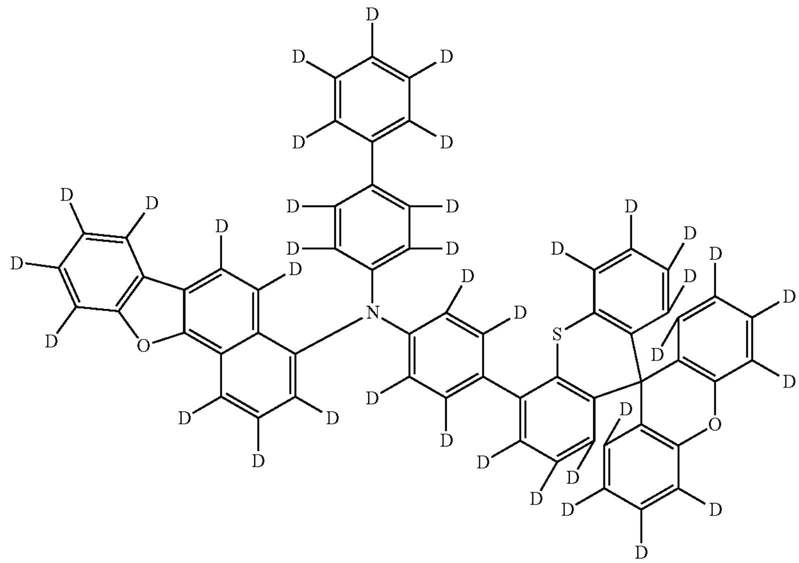
C58
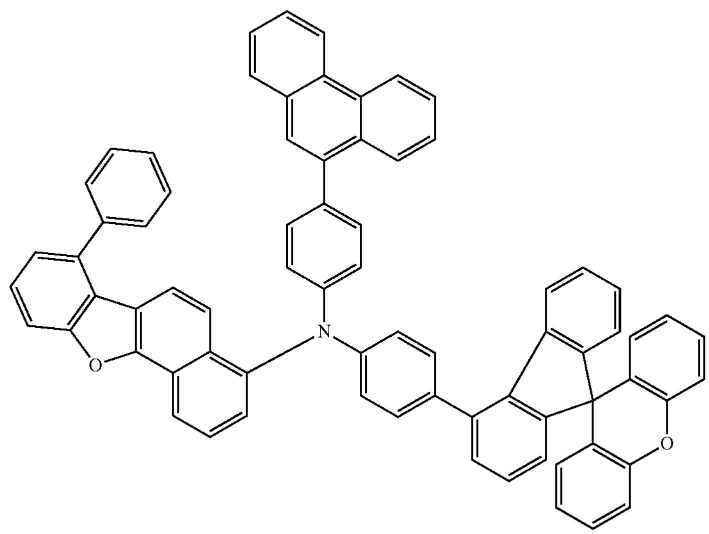
C59
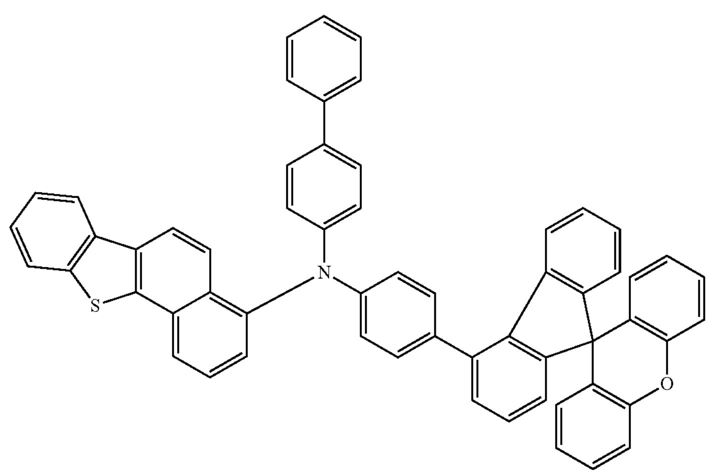

-continued
C60
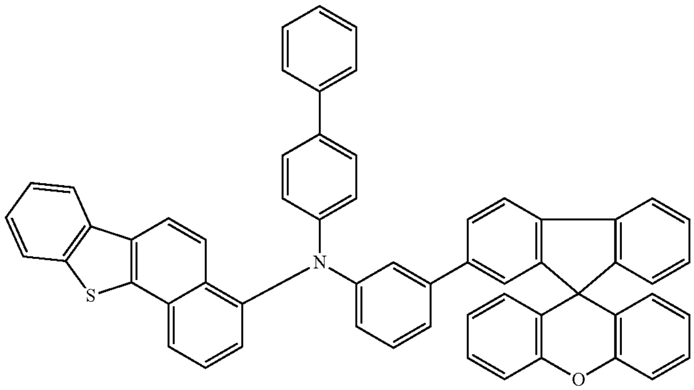
C61
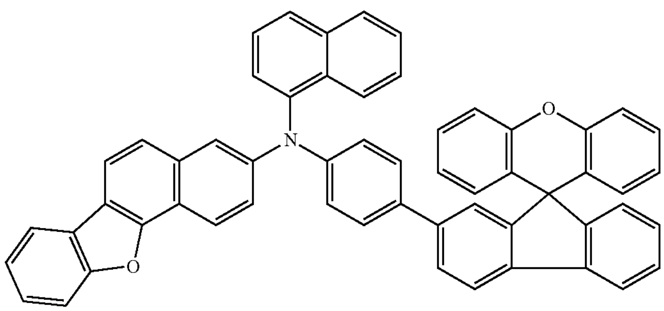
C62
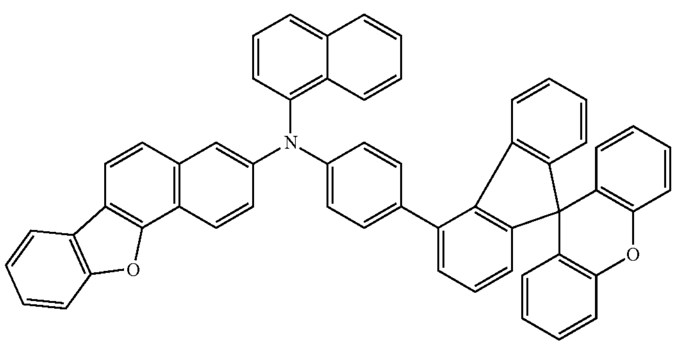
C63
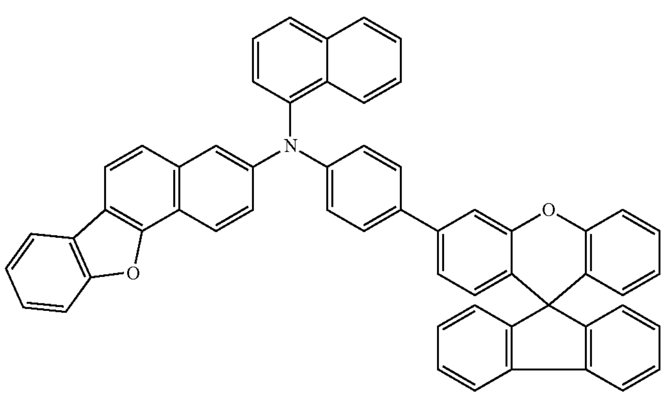

-continued
C64
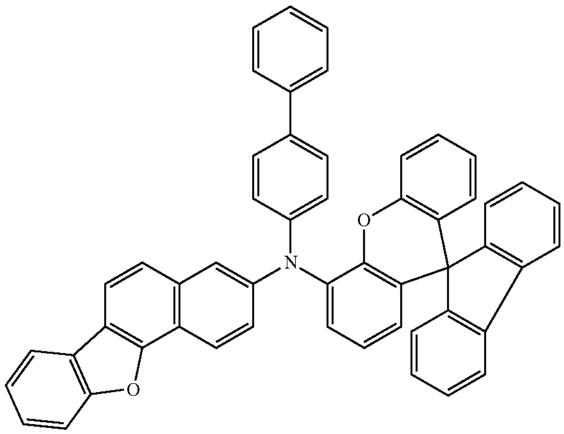
C65
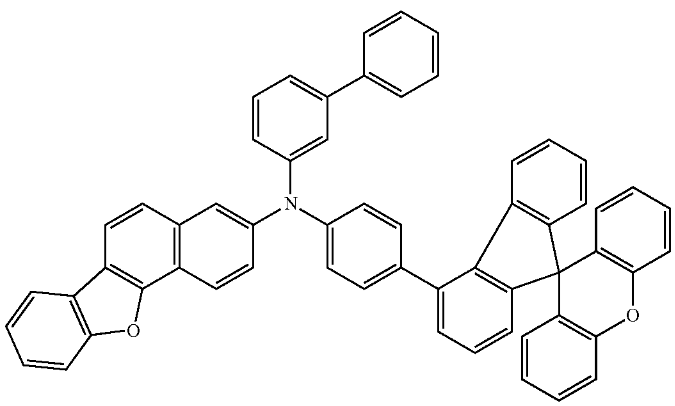
C66
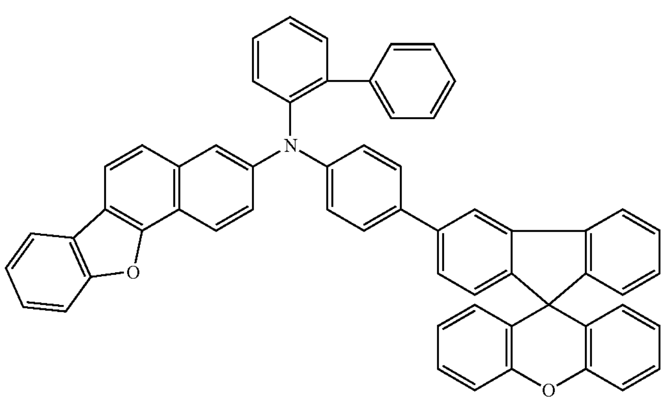

-continued
C67
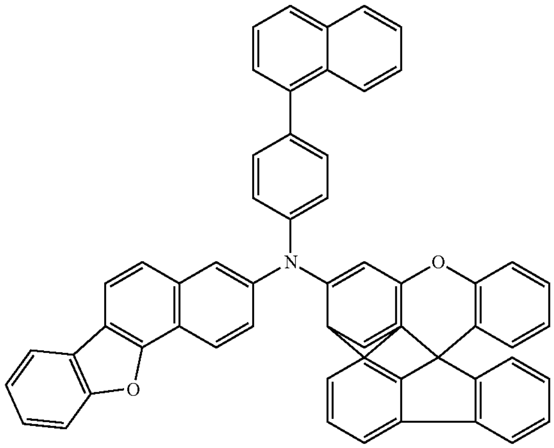
C68
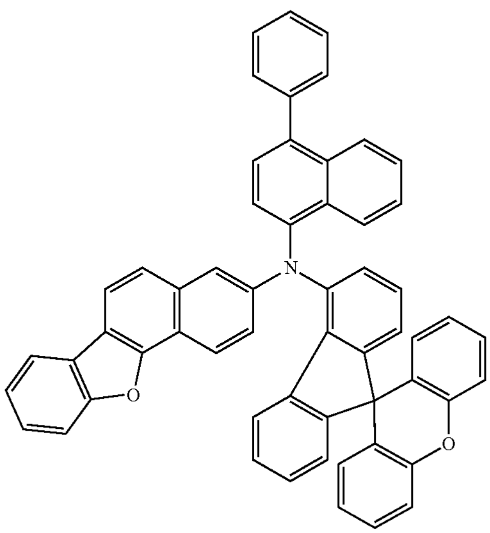
C69
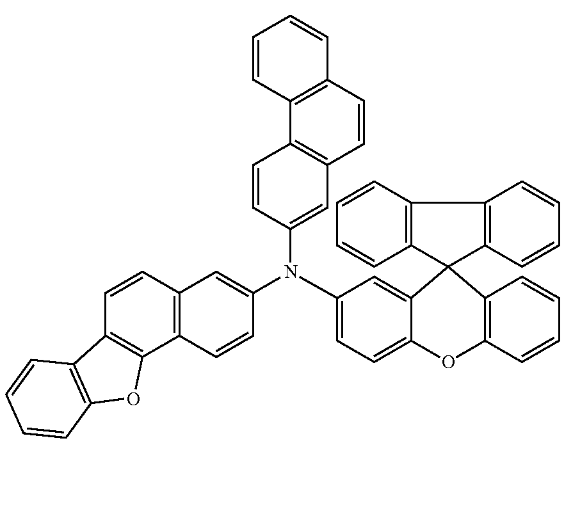

-continued
C70
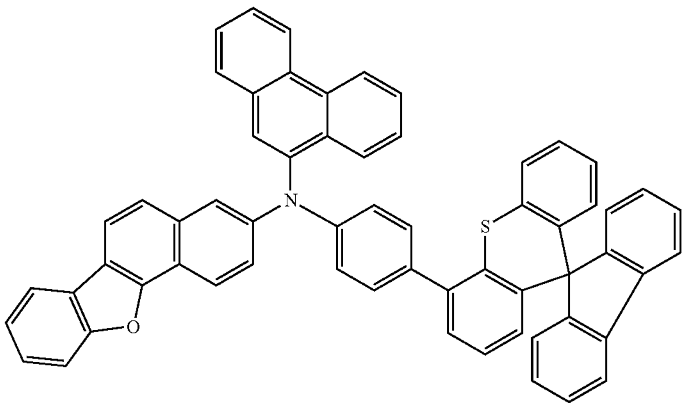
C71
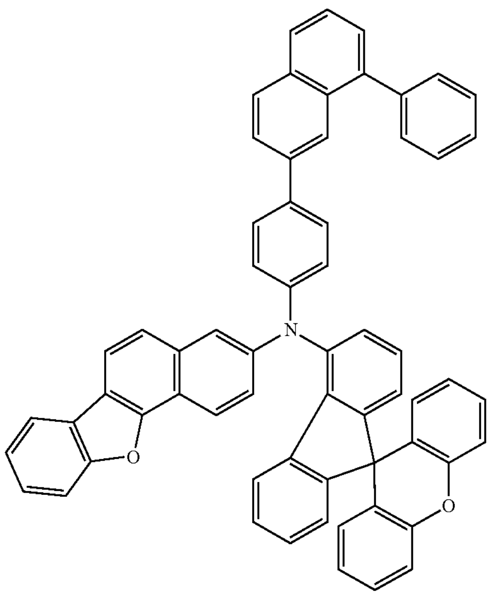
C72
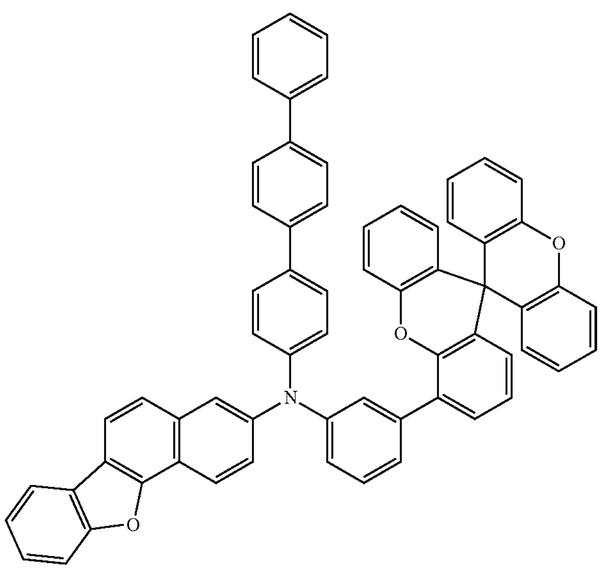

-continued
C73
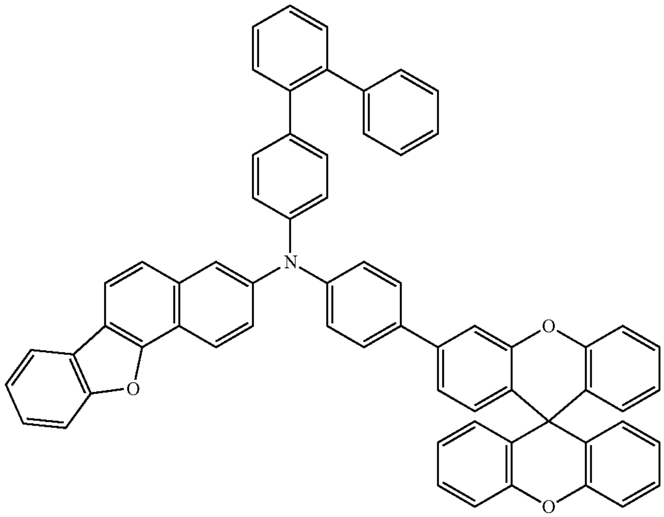
C74
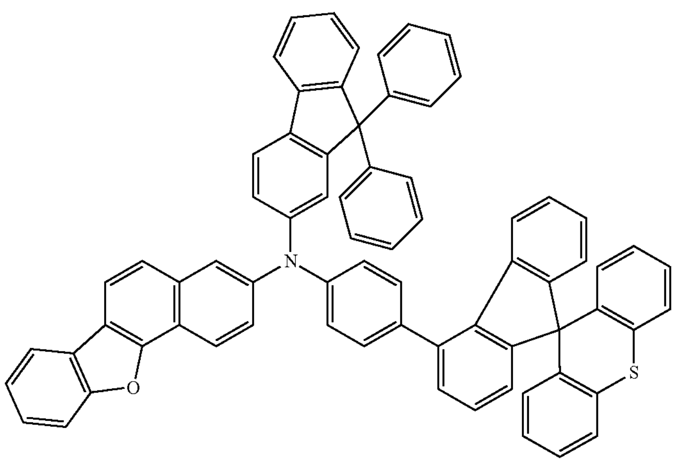
C75
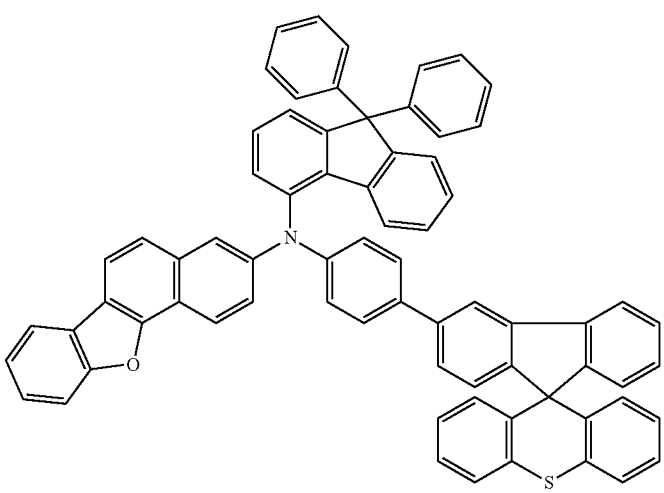

-continued
C76
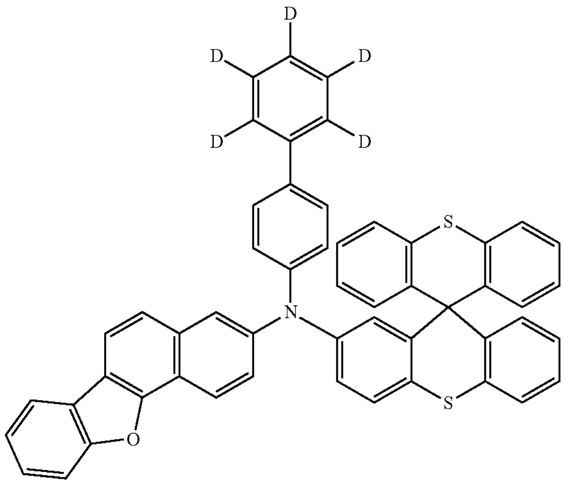
C77
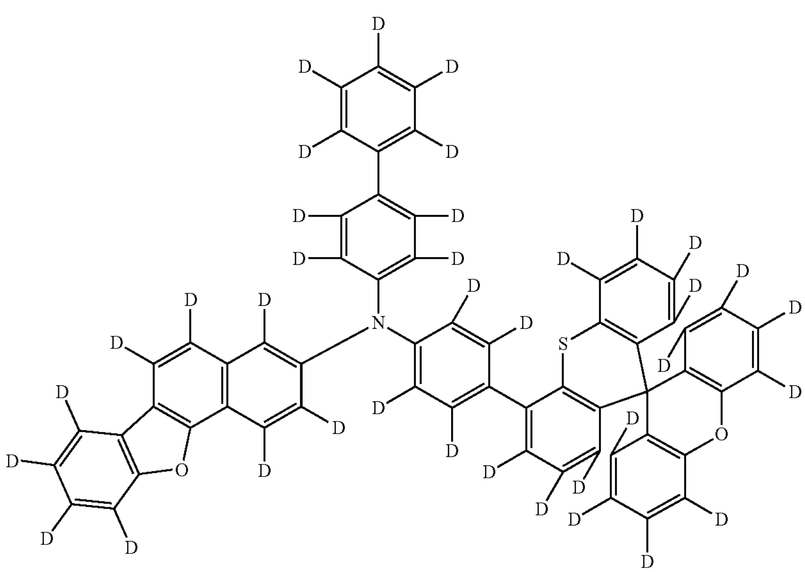

-continued
C78
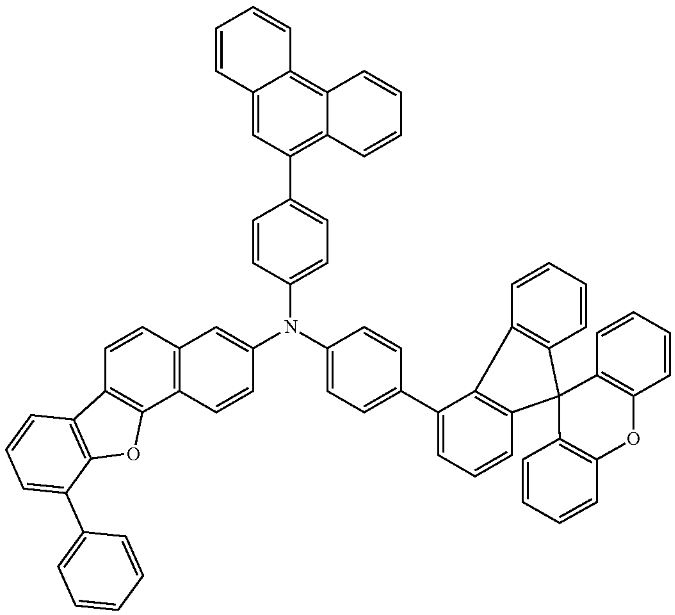
C79
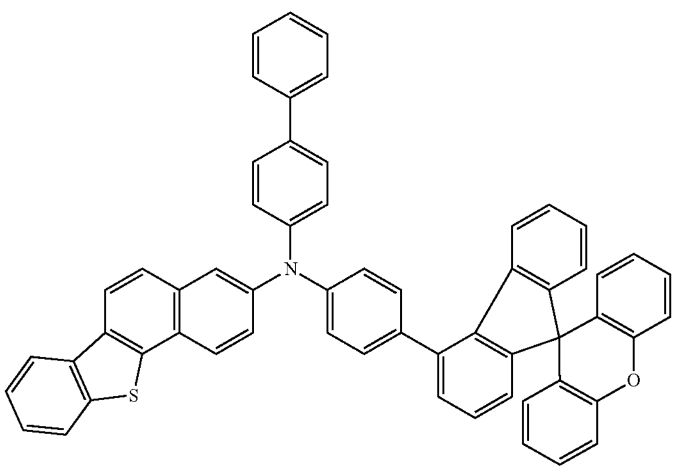
C80
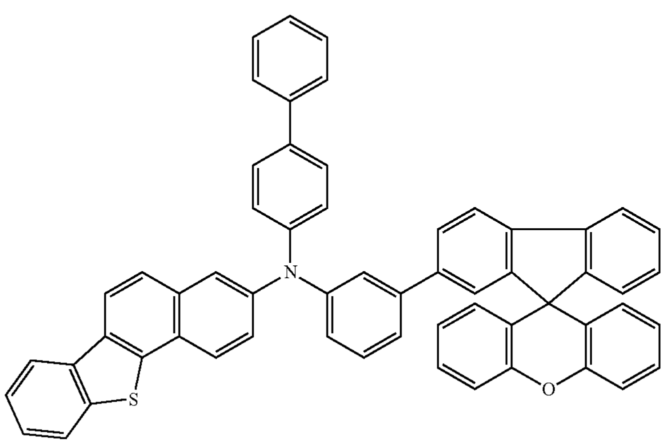

-continued
C81
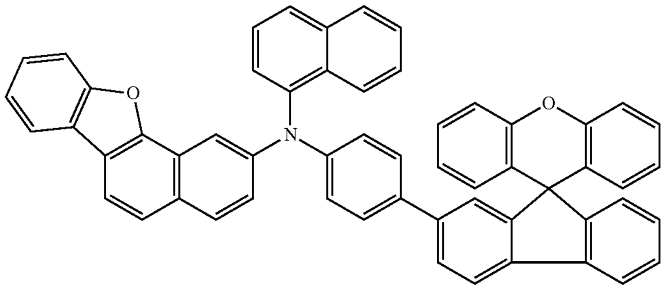
C82
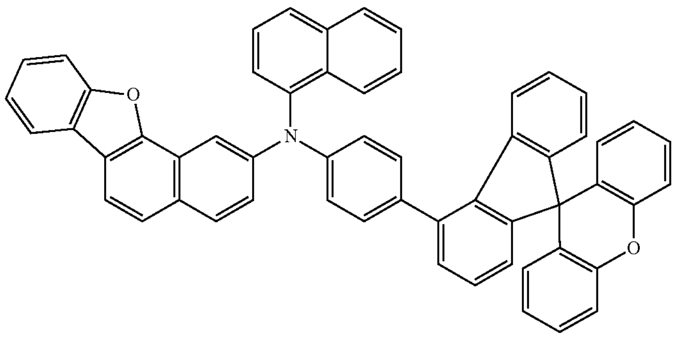
C83
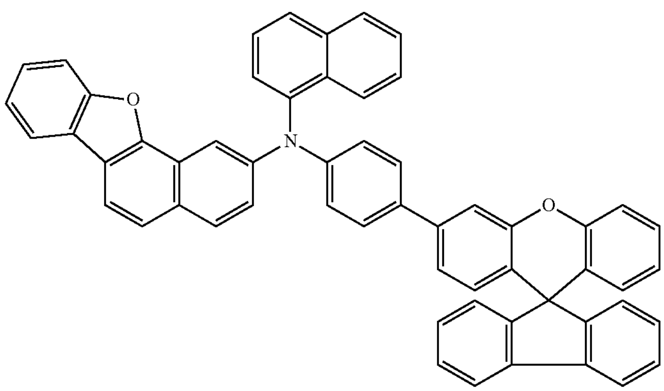
C84
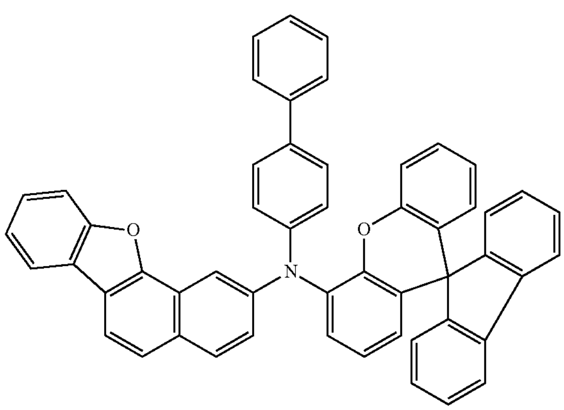

-continued
C85
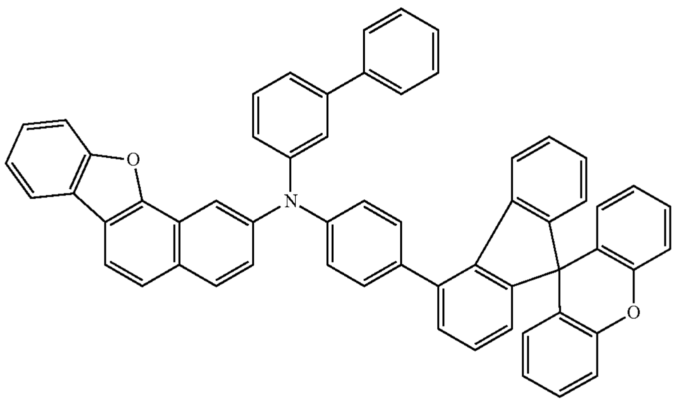
C86
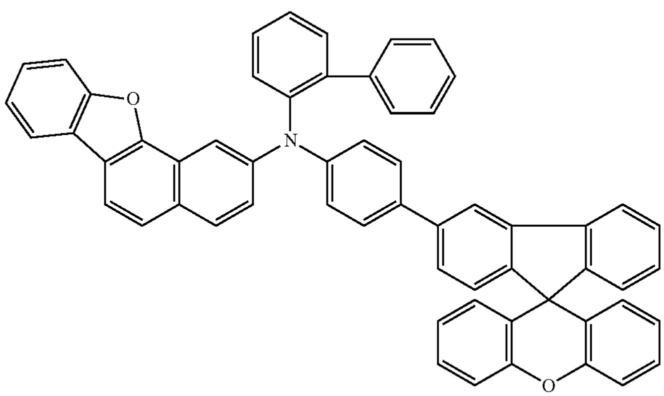
C87
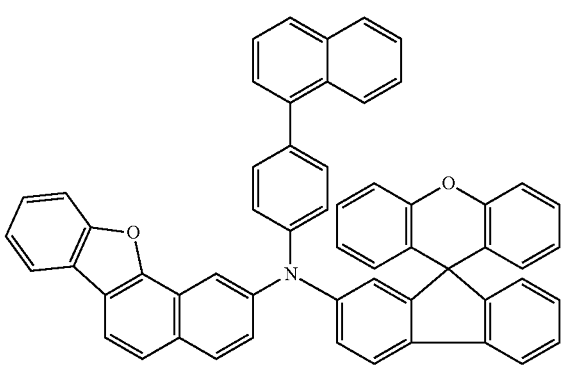

-continued
C88
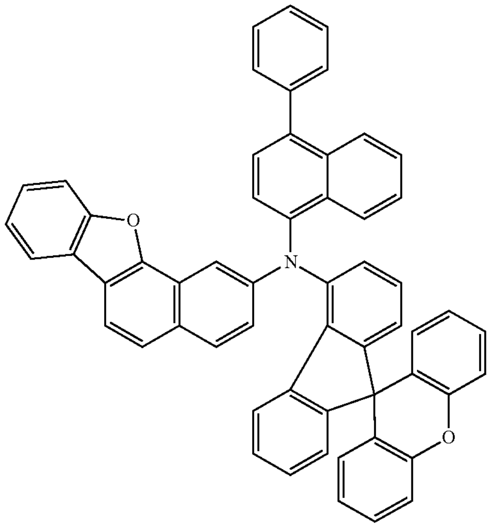
C89
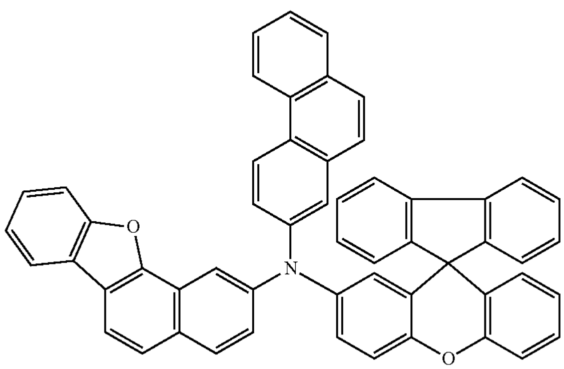
C90
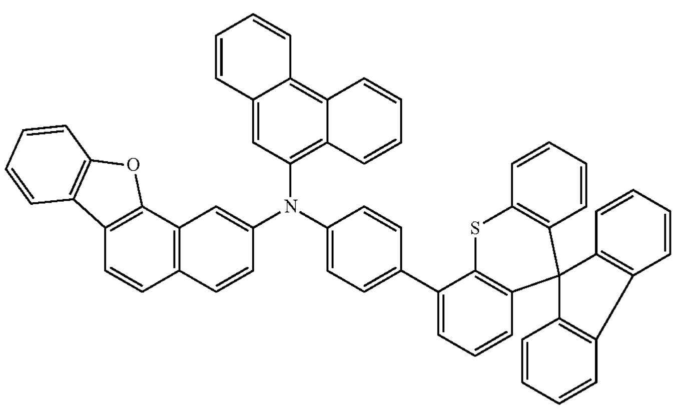

-continued
C91
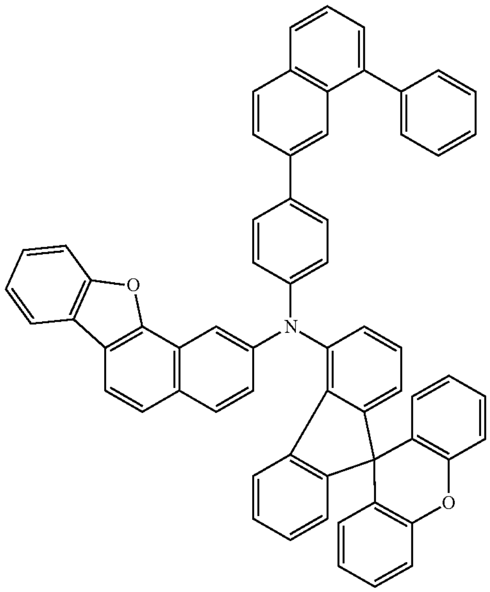
C92
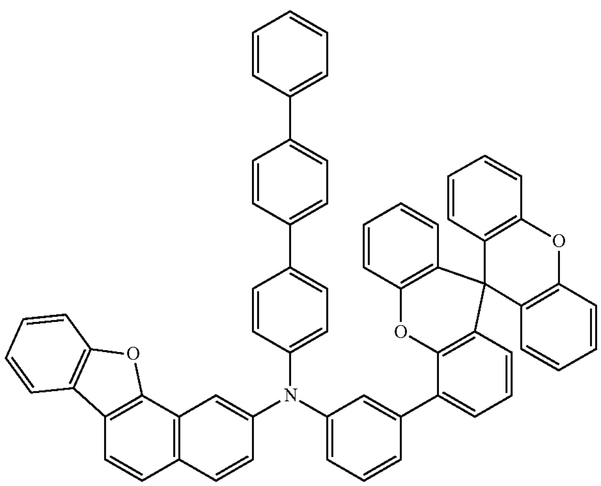
C93
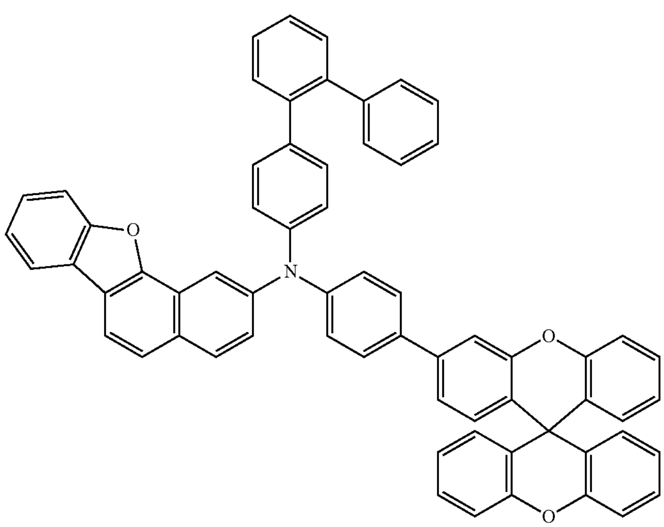

-continued
C94
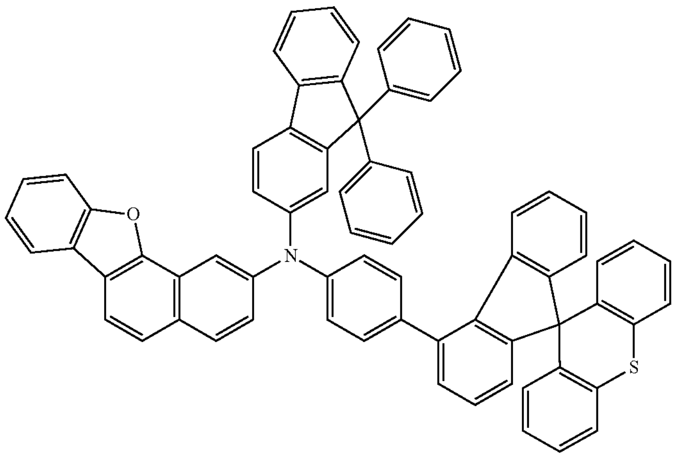
C95
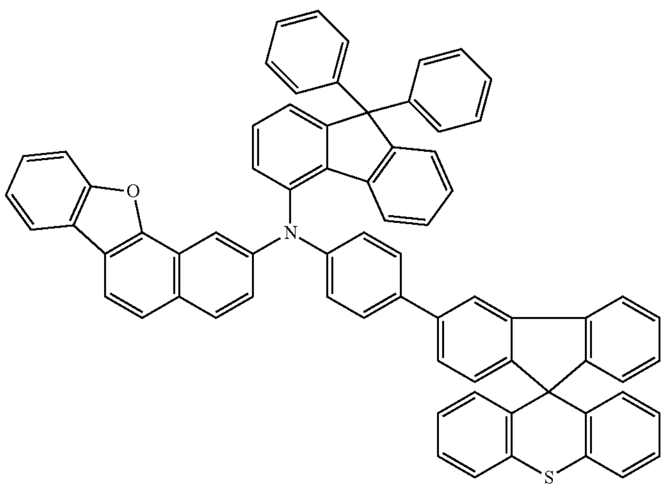
C96
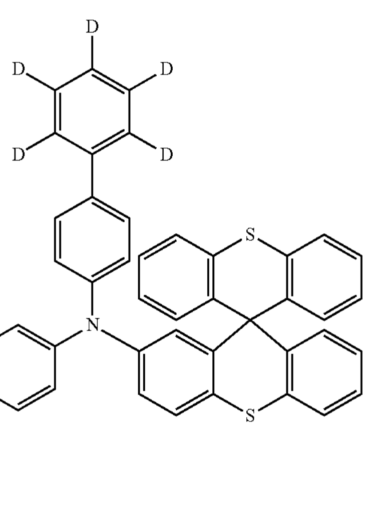

-continued
C97
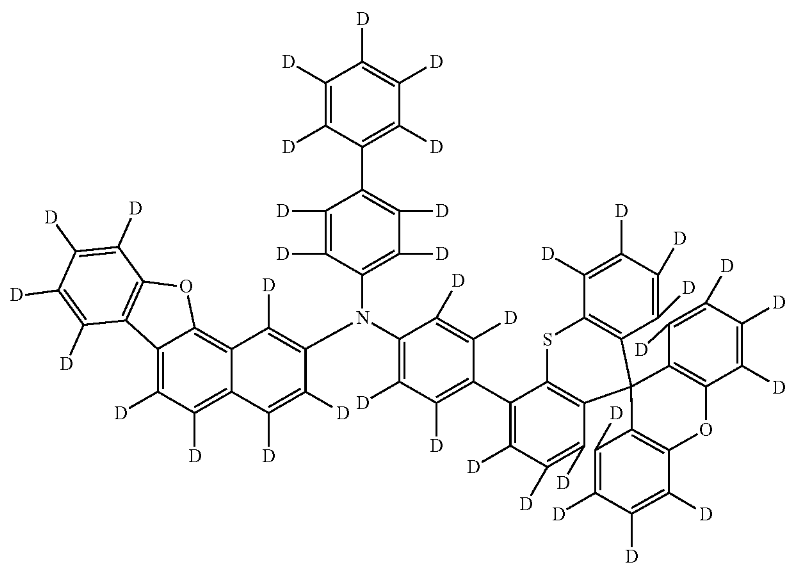
C98
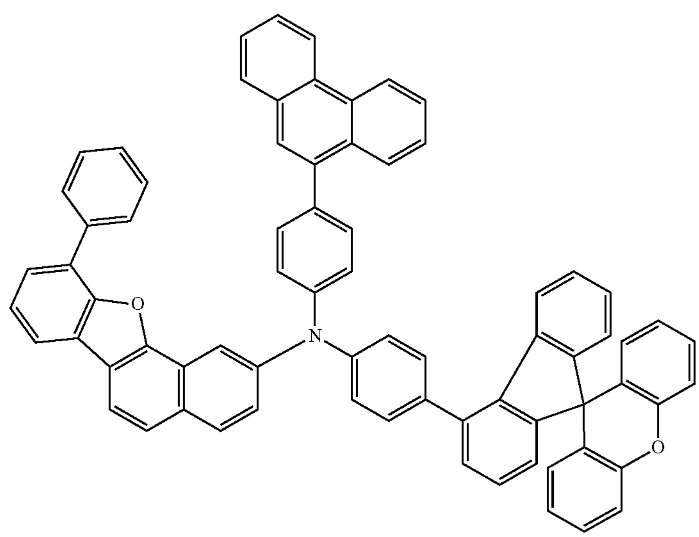
C99
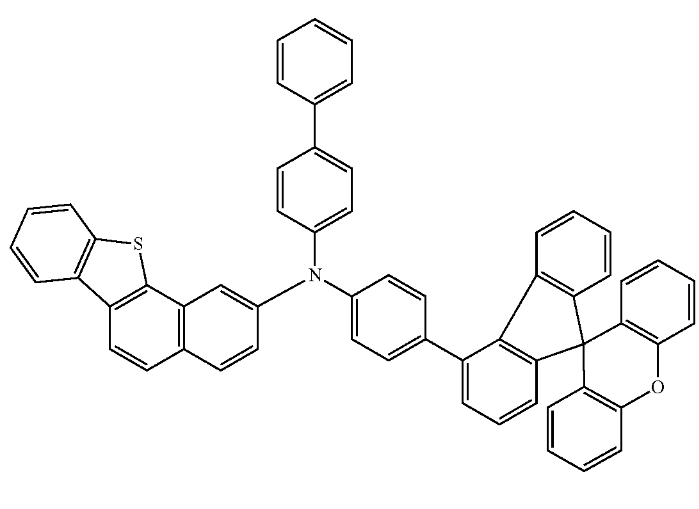

-continued
C100
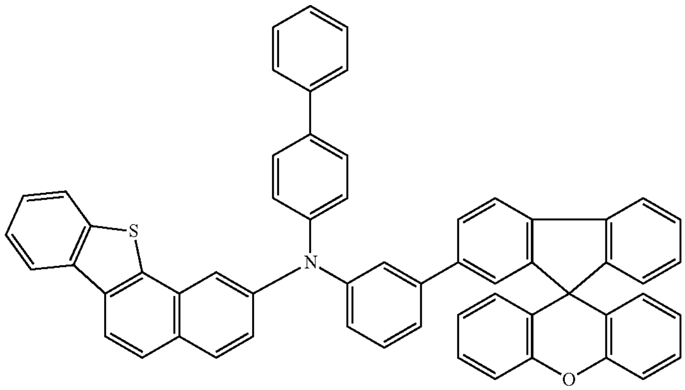
C101
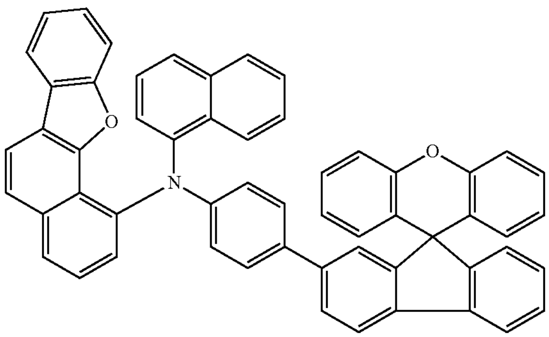
C102
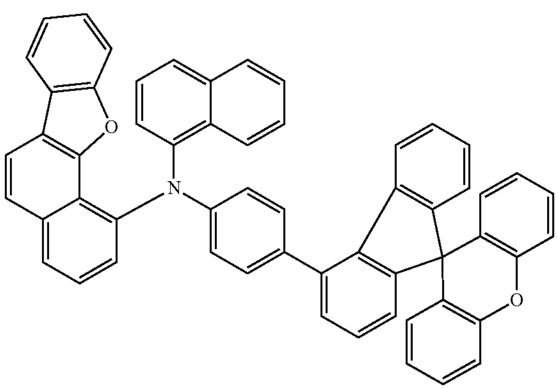
C103
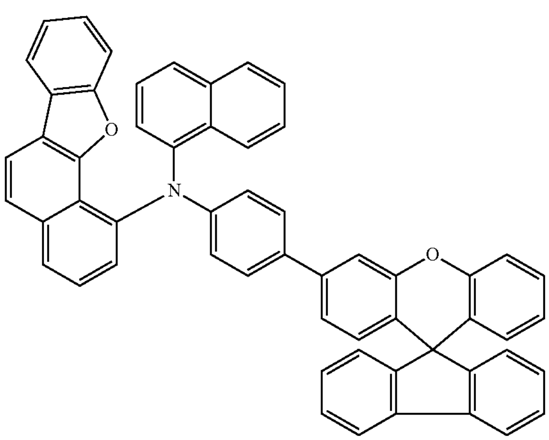

-continued
C104
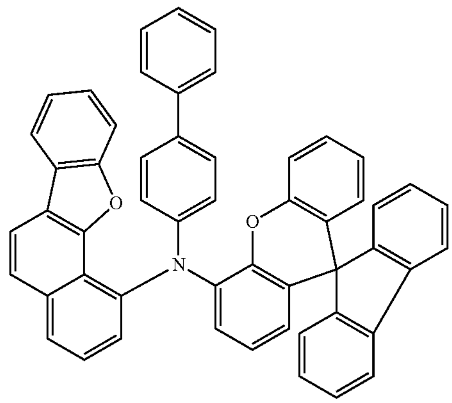
C105
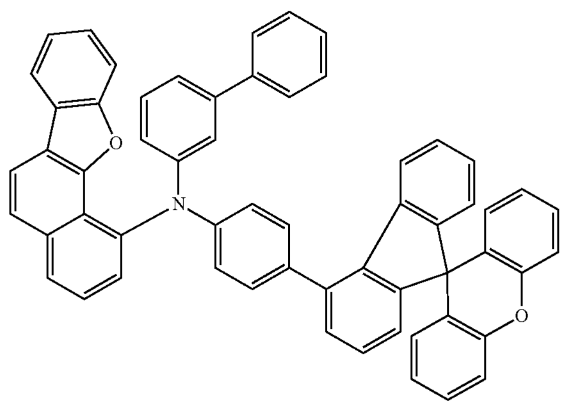
C106
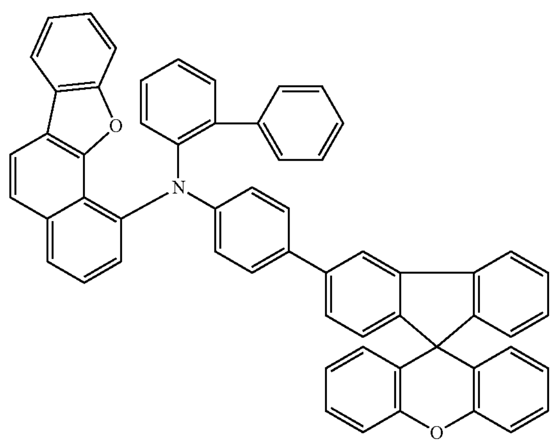
C107
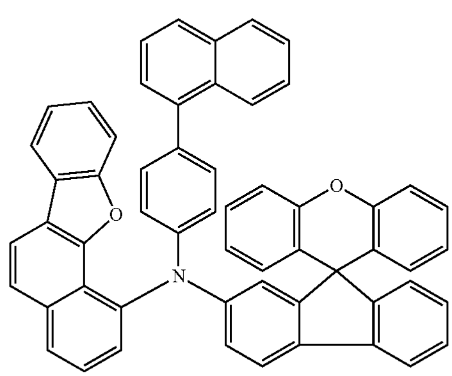

-continued
C108
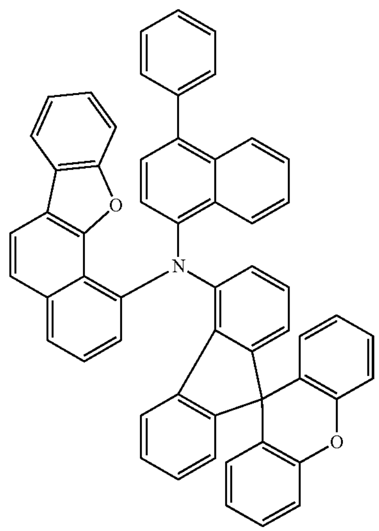
C109
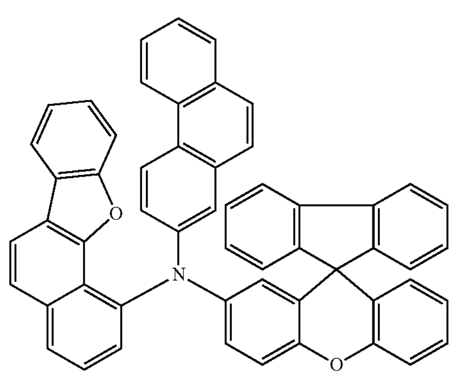
C110
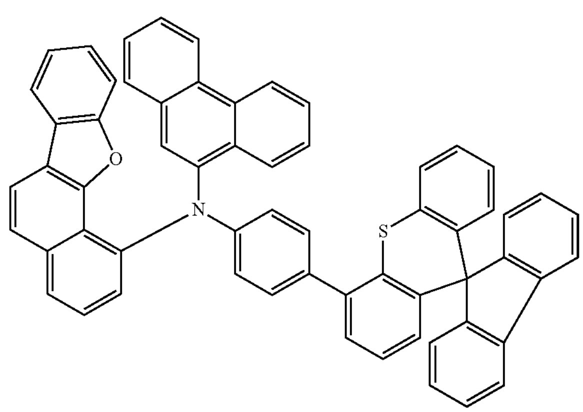

-continued
C111
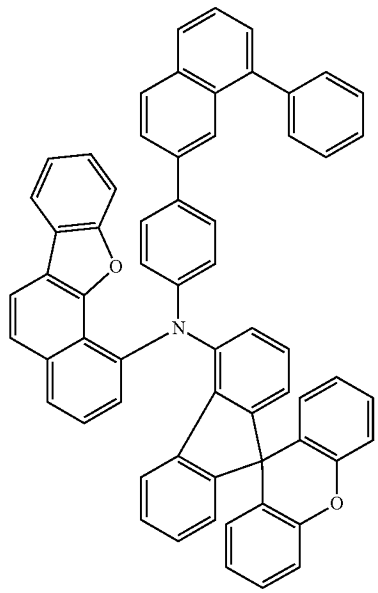
C112
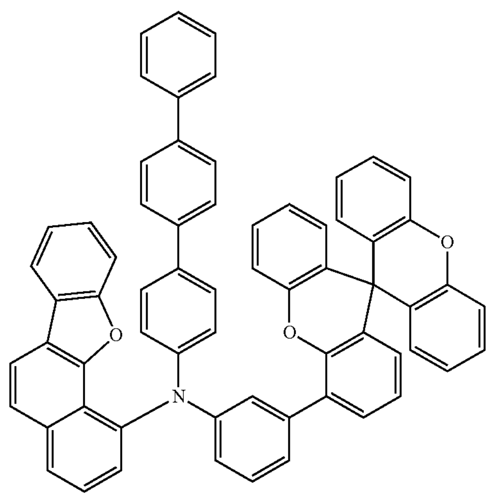
C113
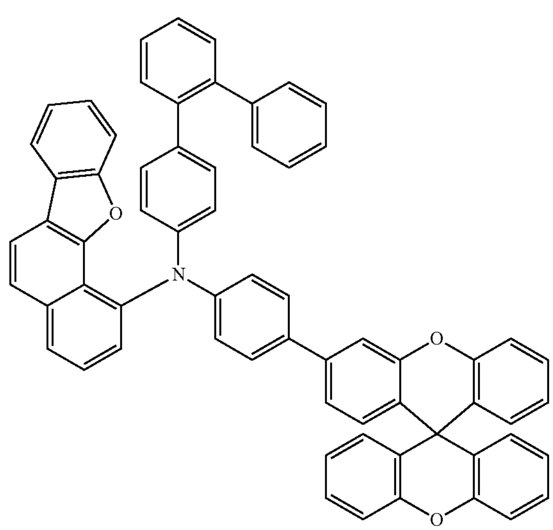

-continued
C114
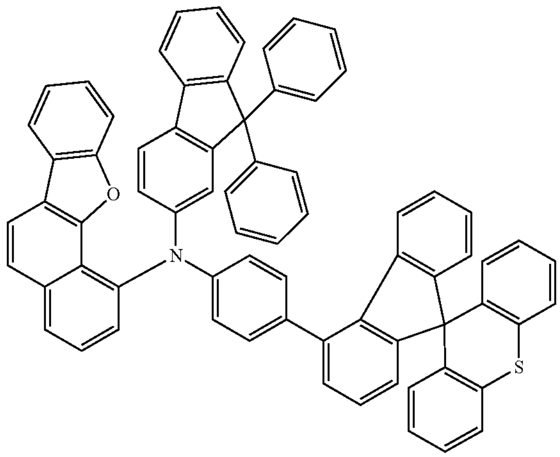
C115
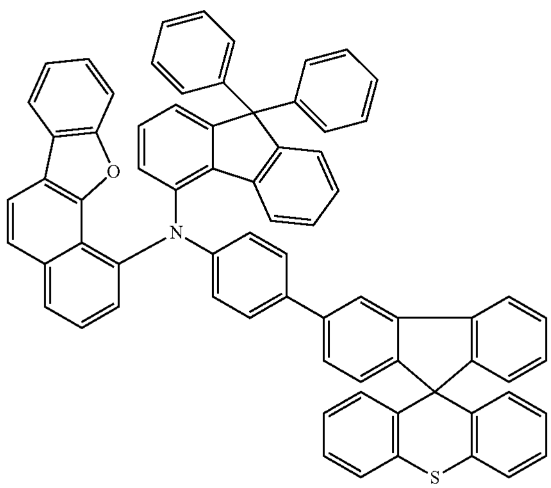
C116
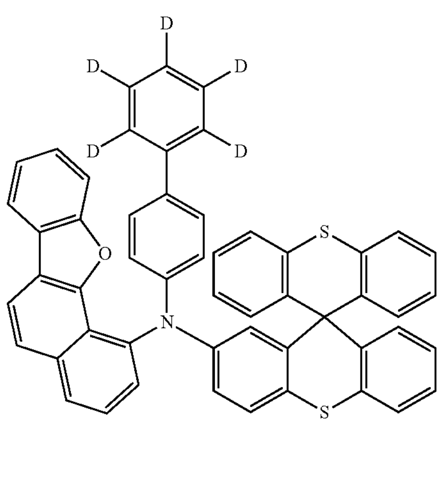

-continued
C117
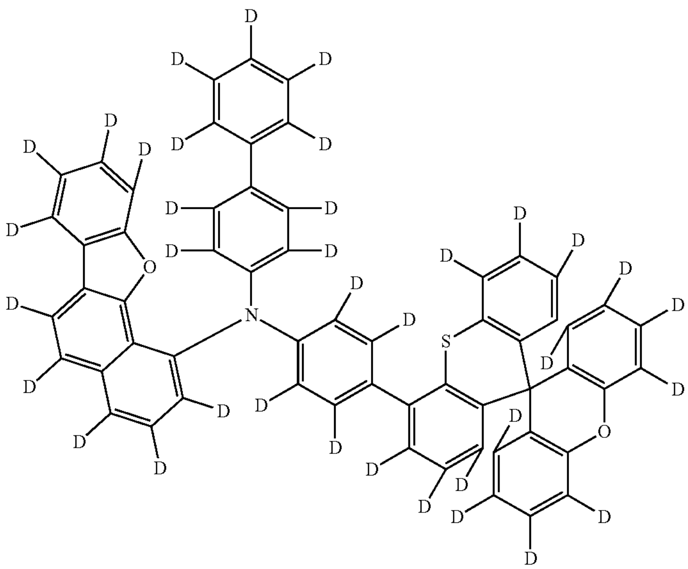
C118
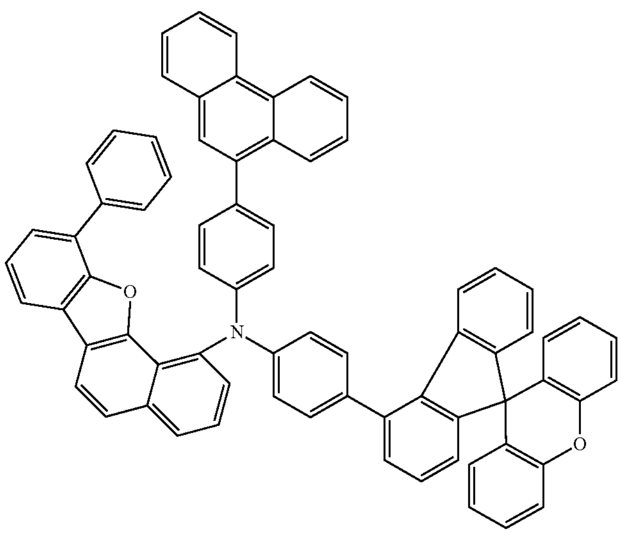
C119
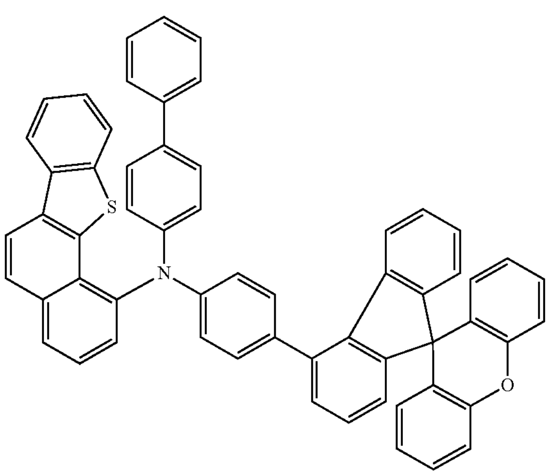

-continued
C120
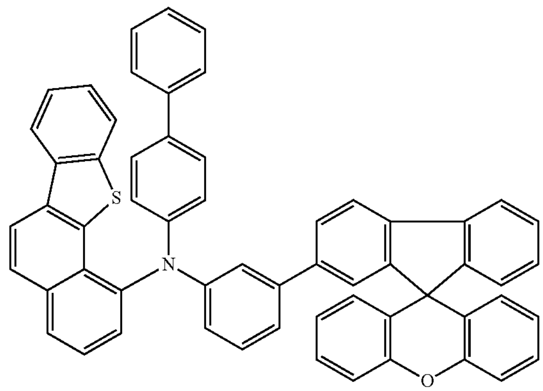
C121
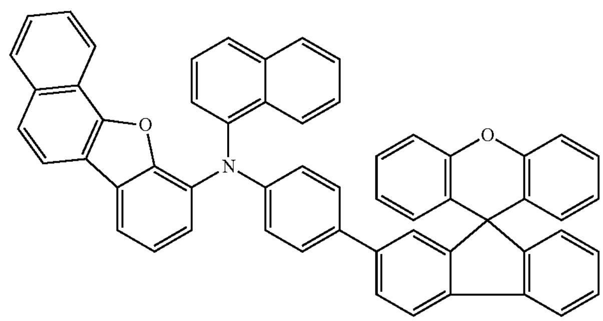
C122
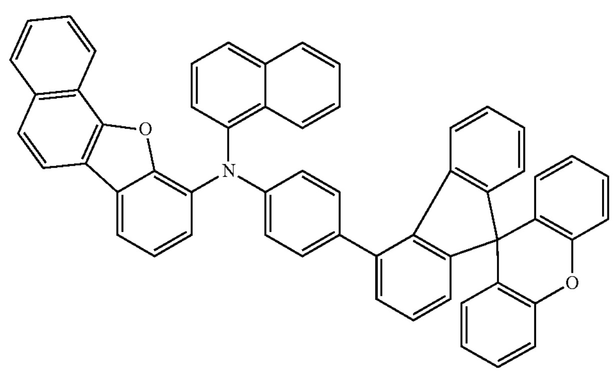
C123
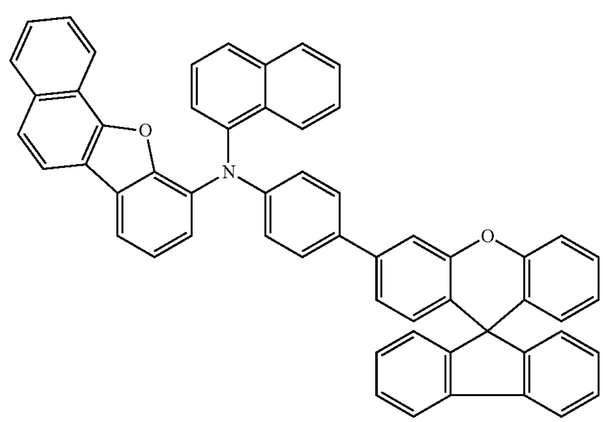

-continued
C124
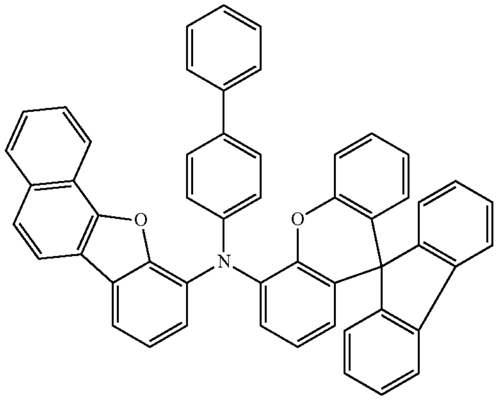
C125
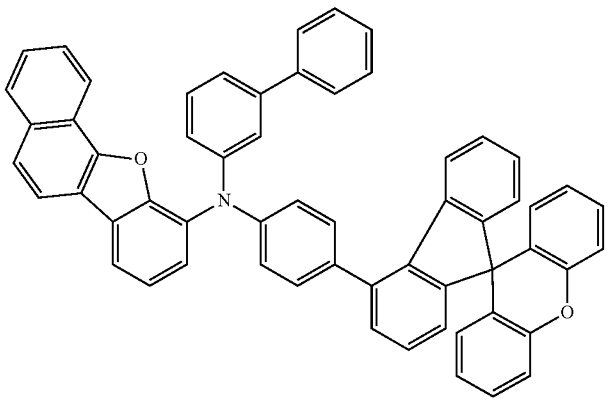
C126
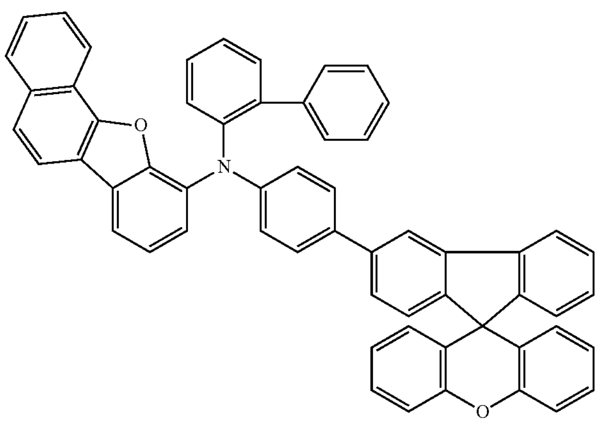
C127
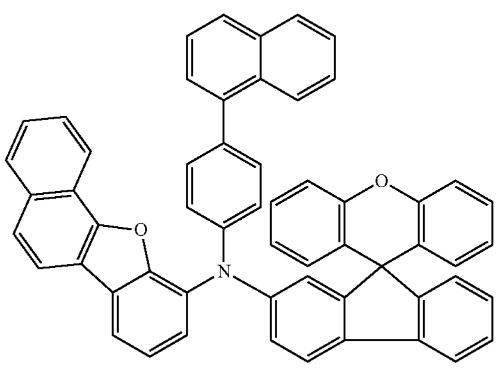

-continued
C128
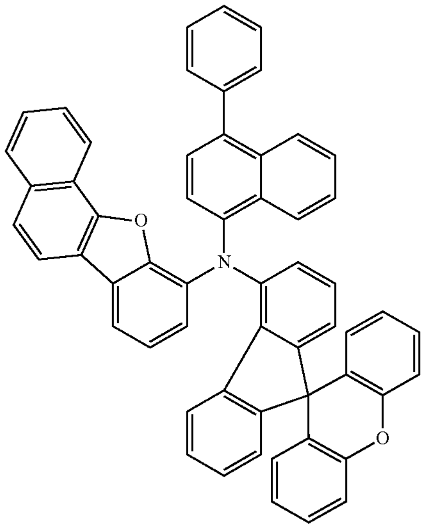
C129
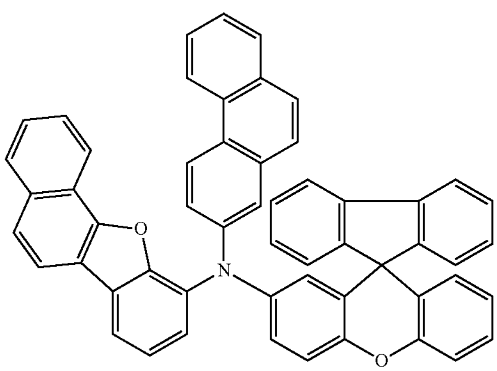
C130
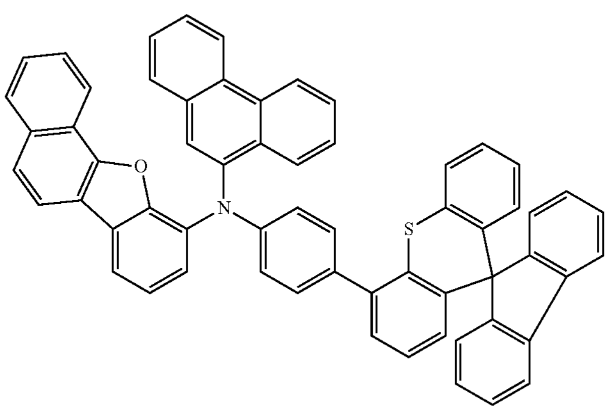

-continued
C131
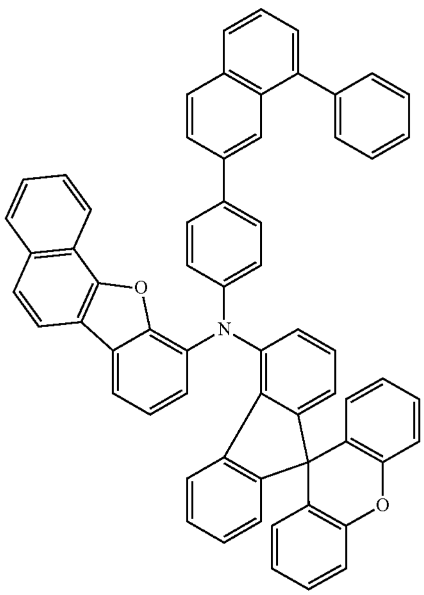
C132
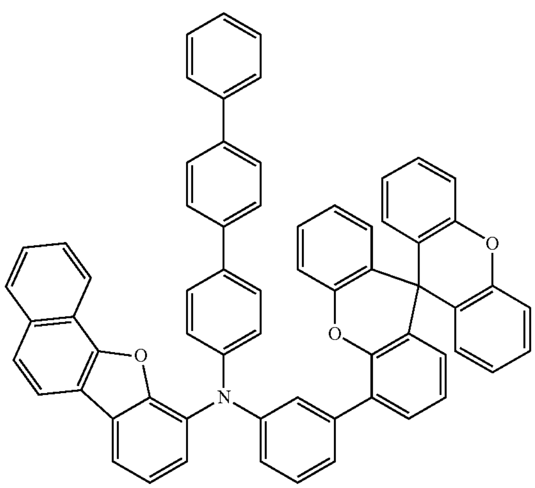
C133
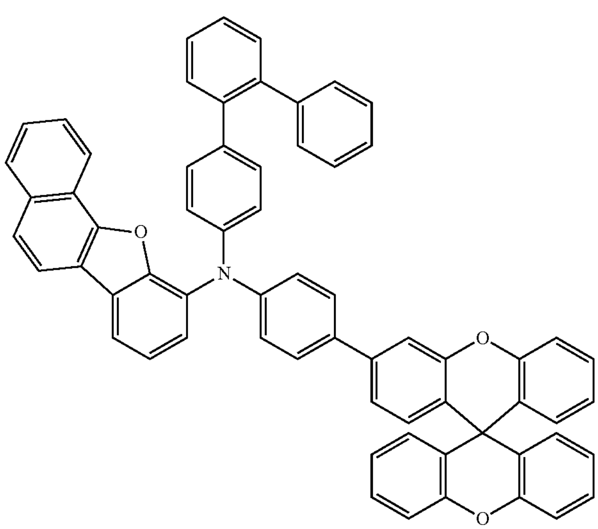

-continued
C134
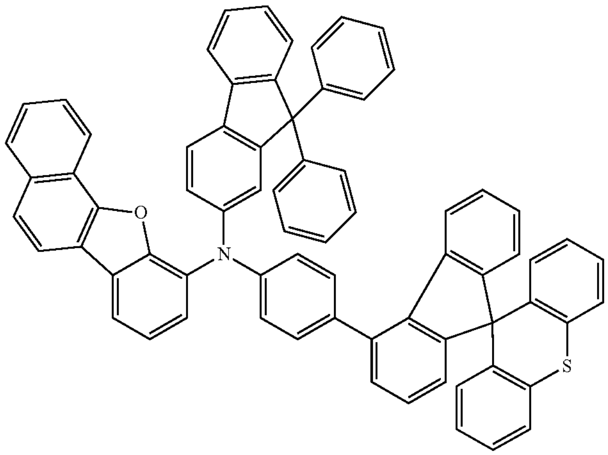
C135
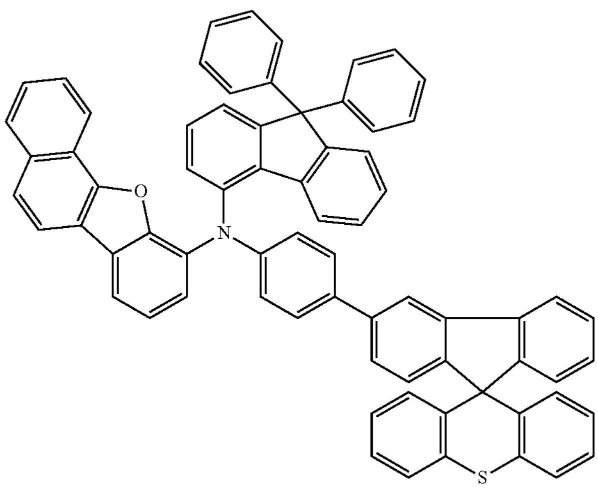
C136
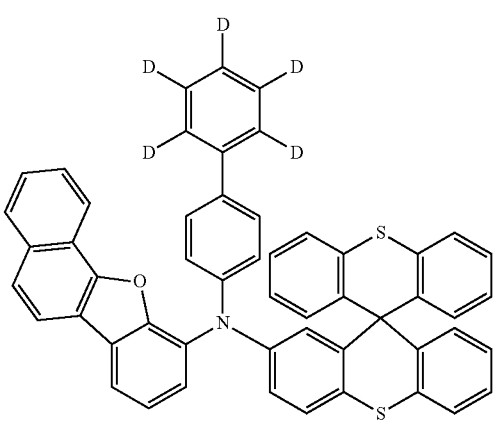

-continued
C137
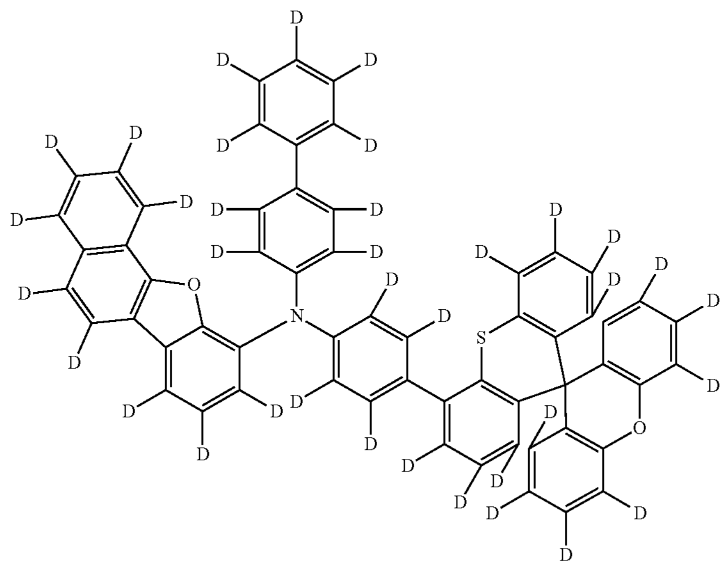
C138
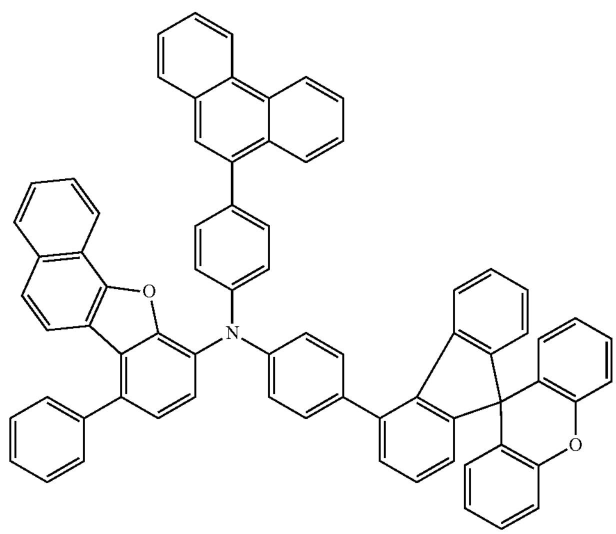
C139
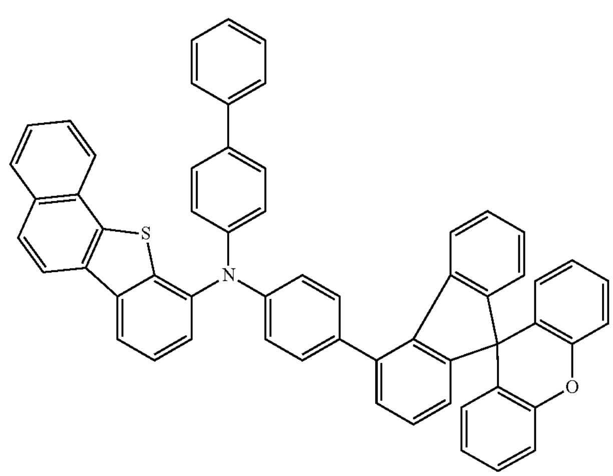

-continued
C140
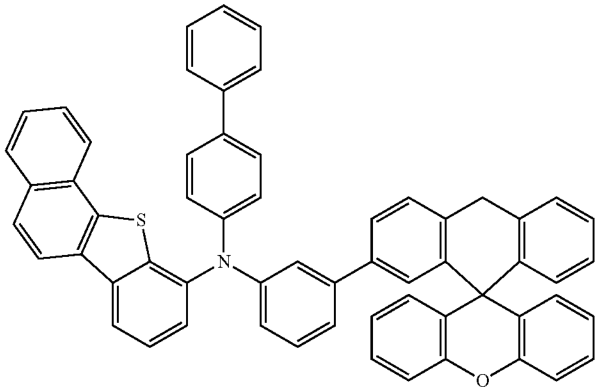
C141
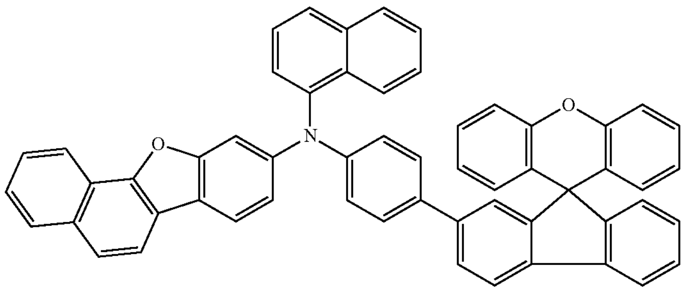
C142
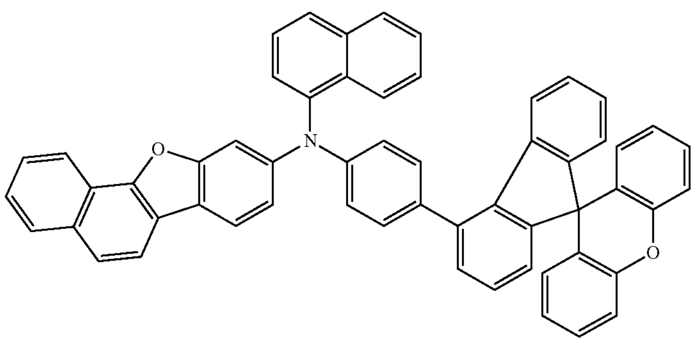
C143
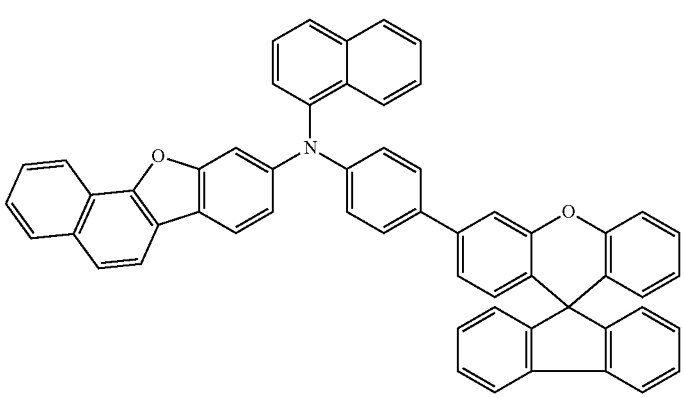

-continued
C144
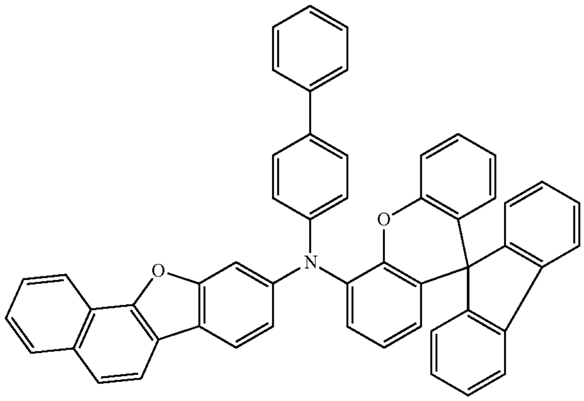
C145
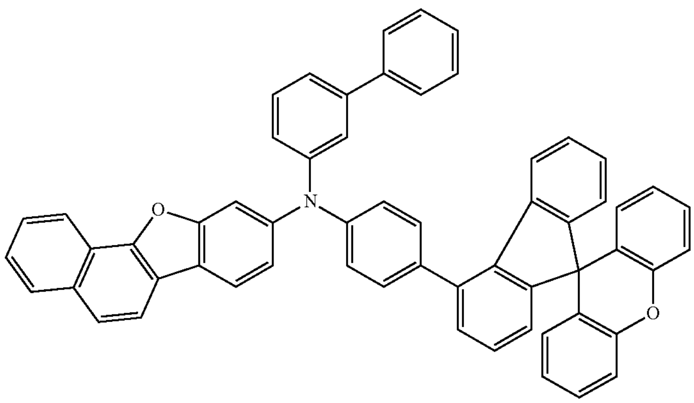
C146
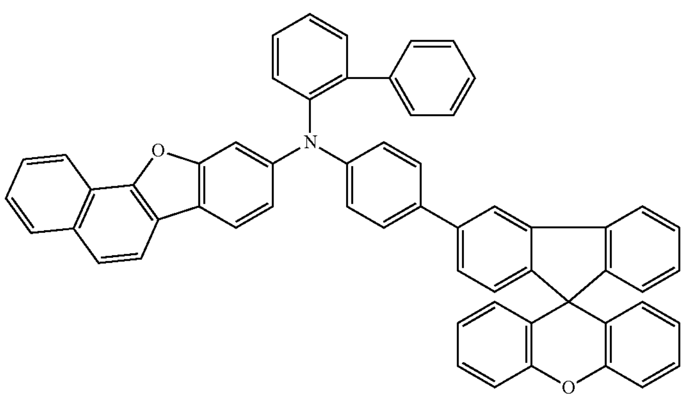
C147
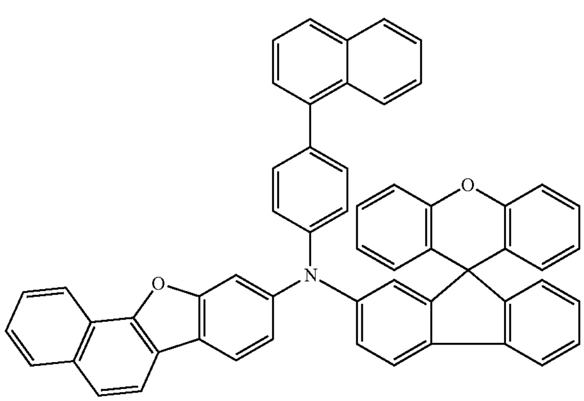

-continued
C148
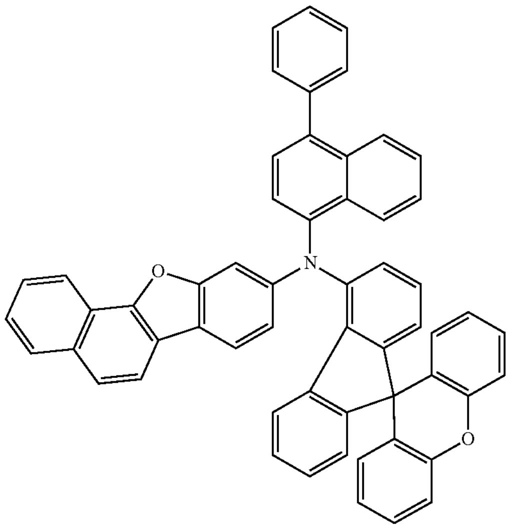
C149
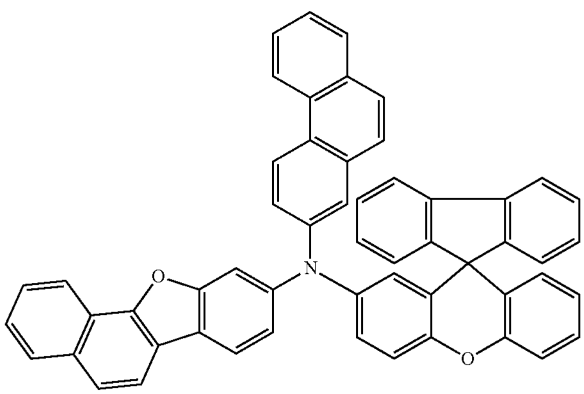
C150
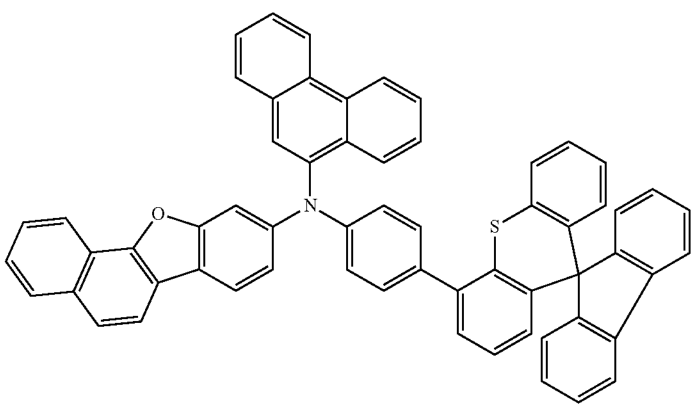

-continued
C151
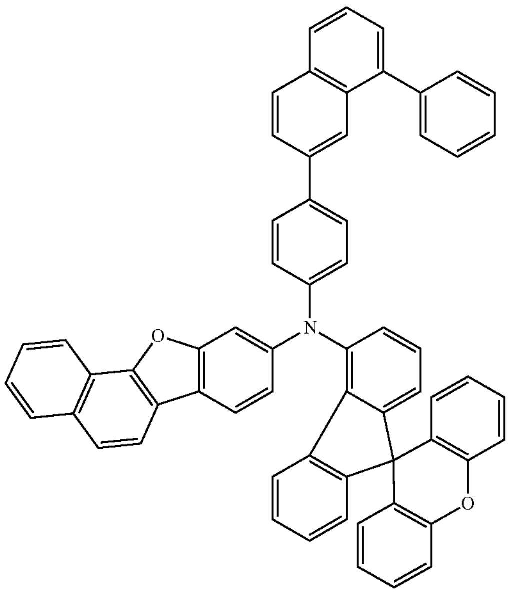
C152
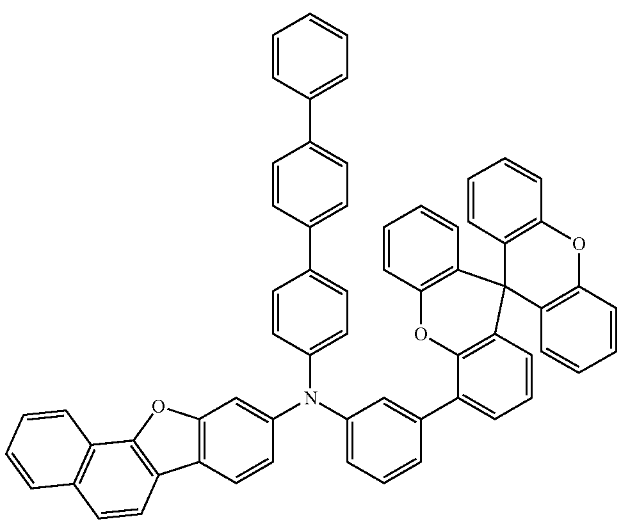
C153
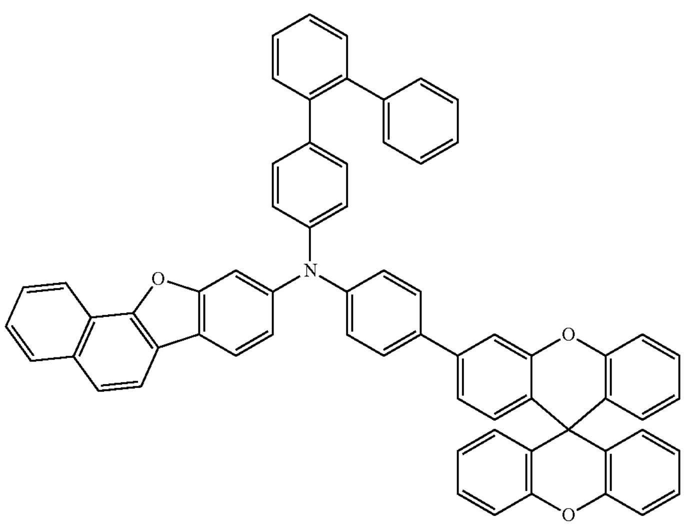

-continued
C154
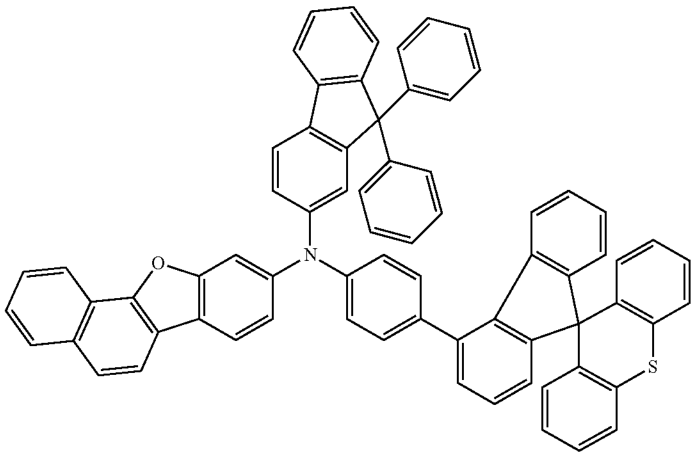
C155
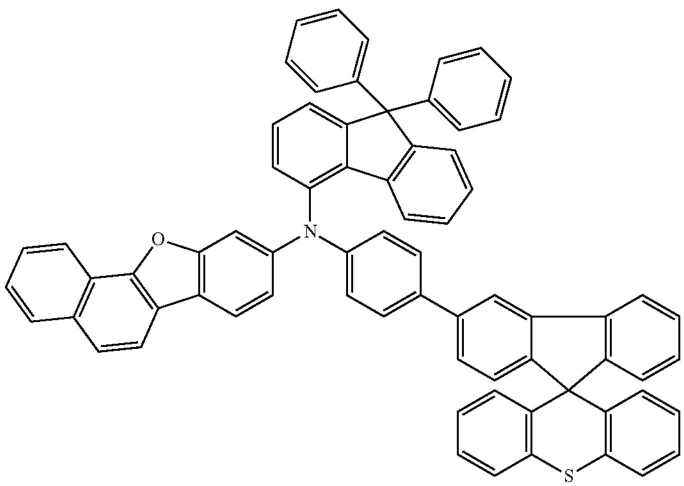
C156
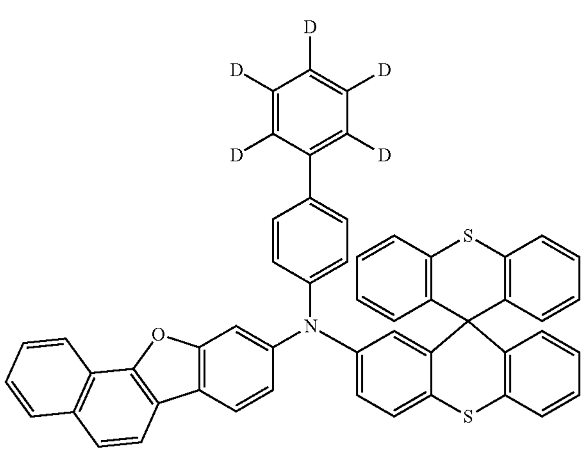

-continued
C157
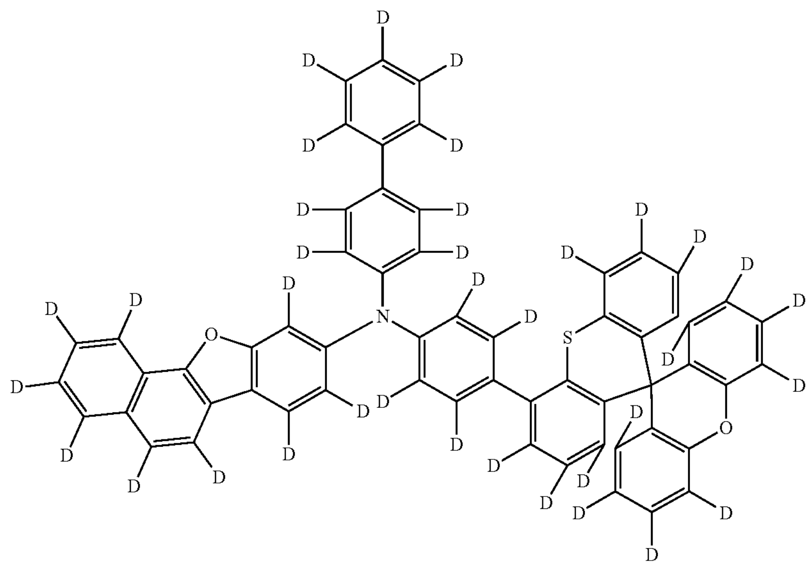
C158
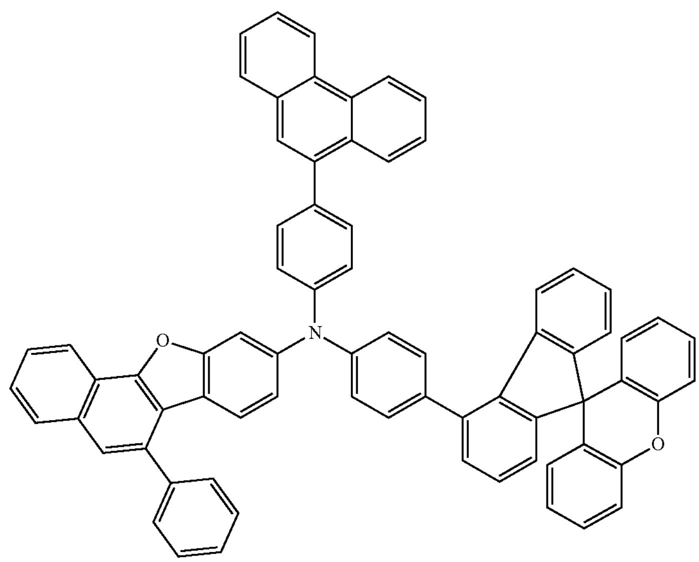
C159
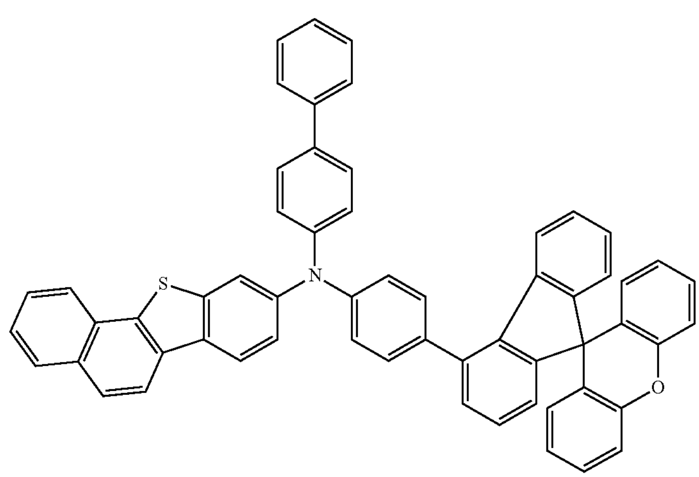

-continued
C160
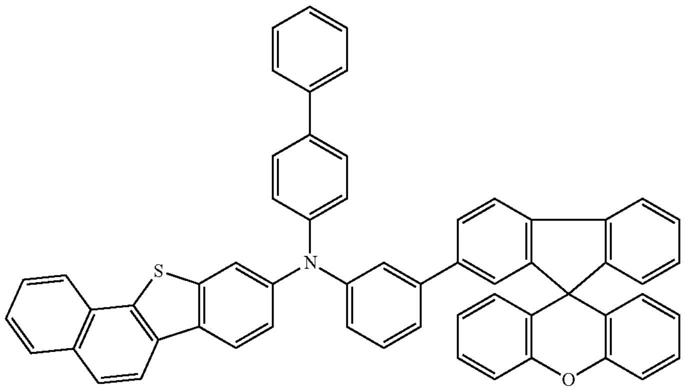
C161
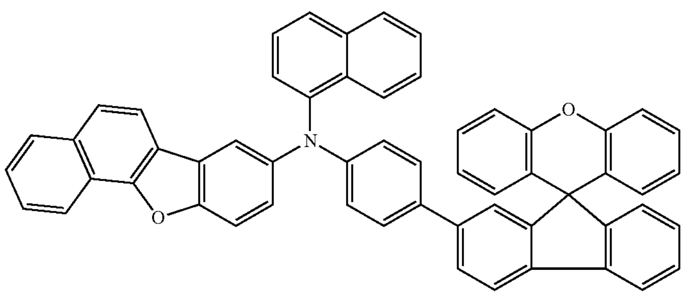
C162
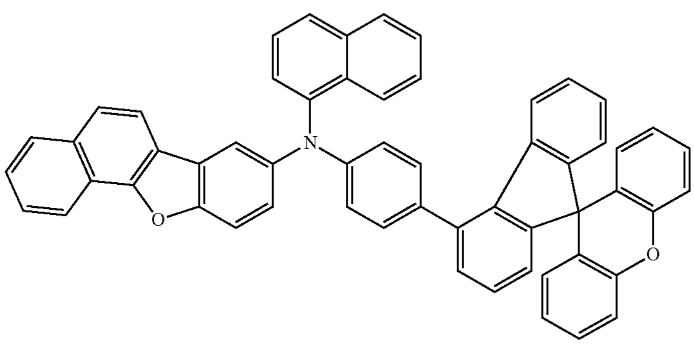
C163
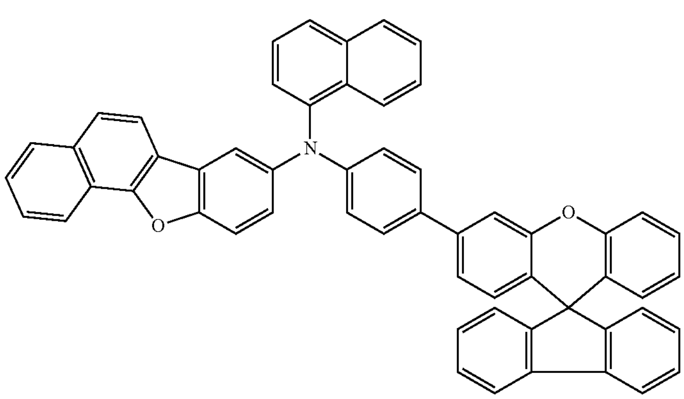

-continued
C164
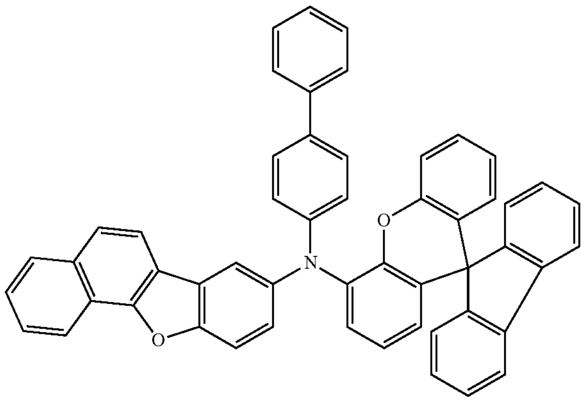
C165
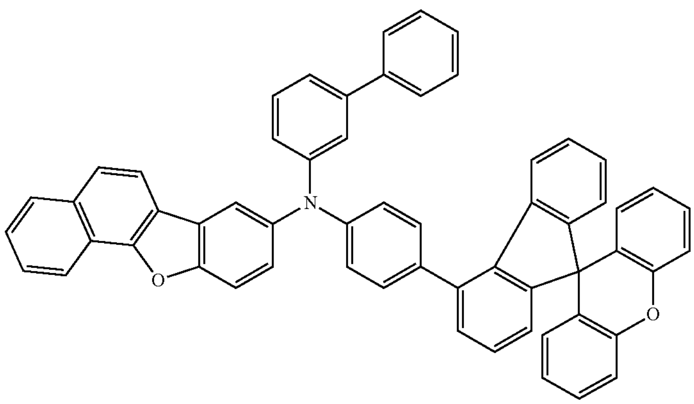
C166
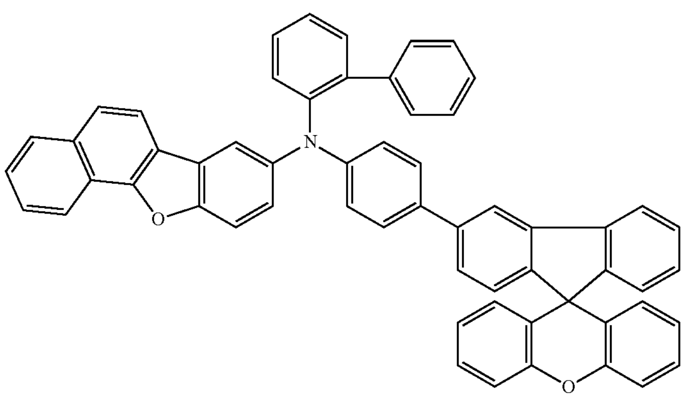
C167
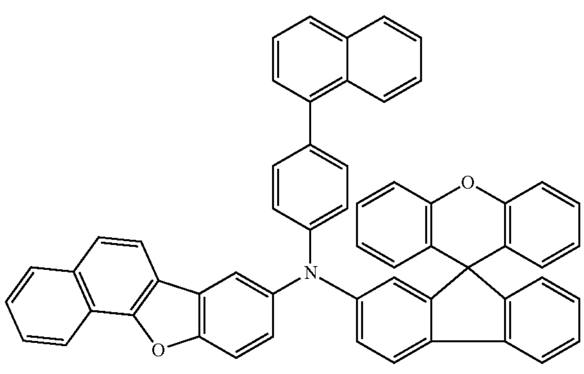

-continued
C168
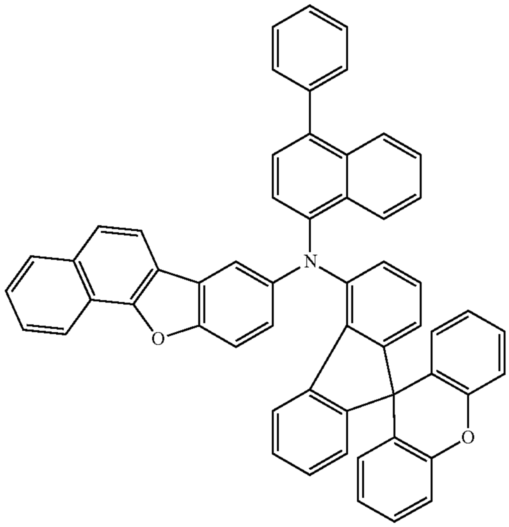
C169
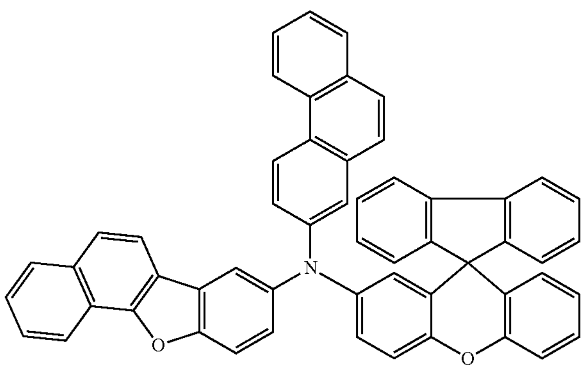
C170
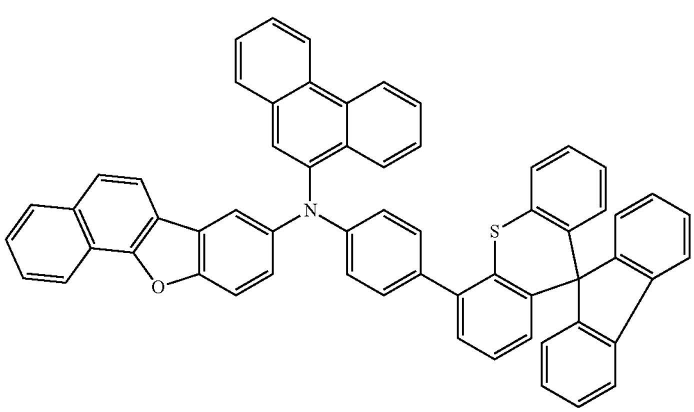

-continued
C171
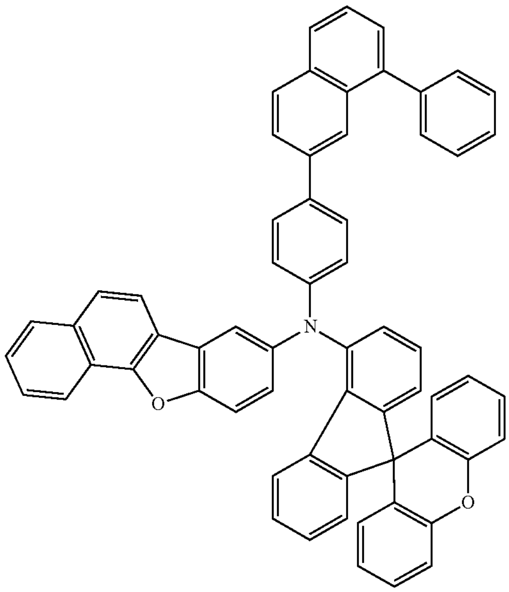
C172
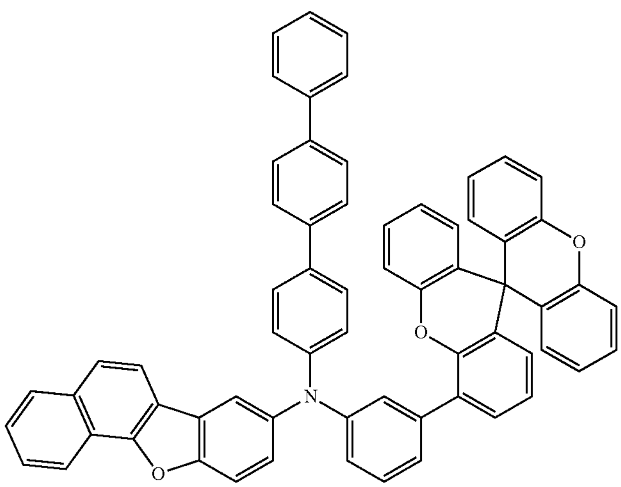
C173
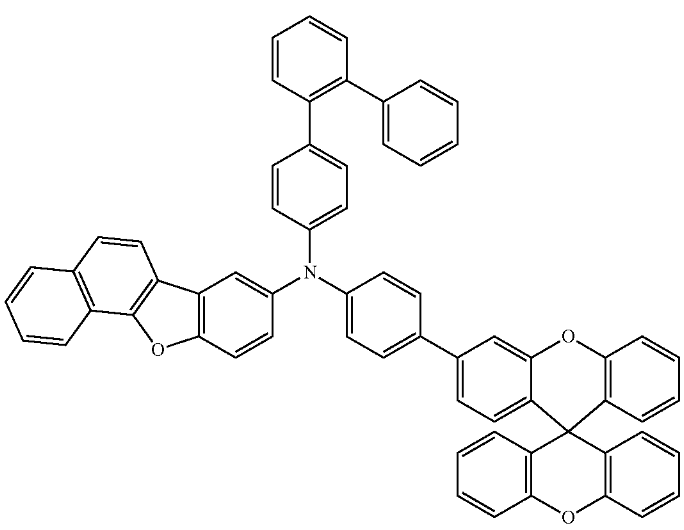

-continued
C174
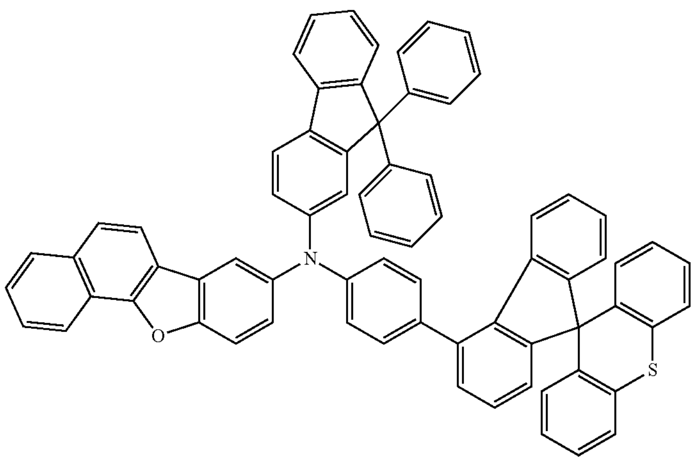
C175
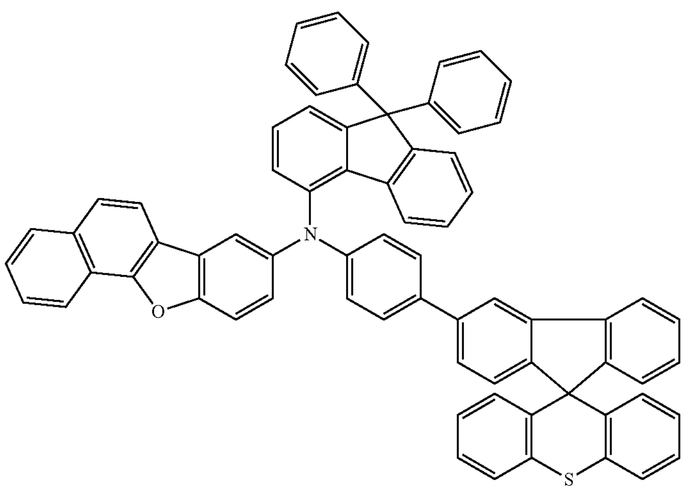
C176
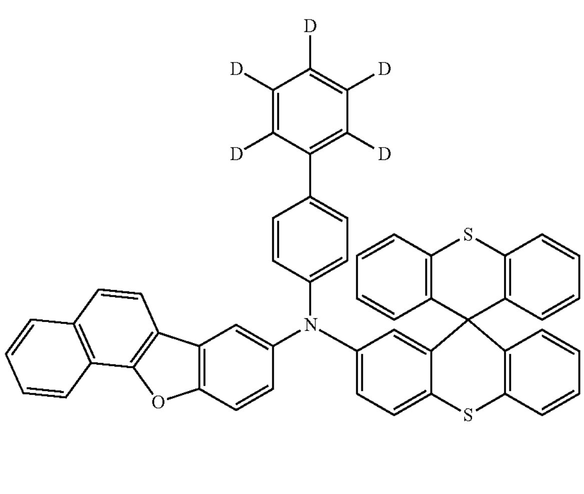

-continued
C177
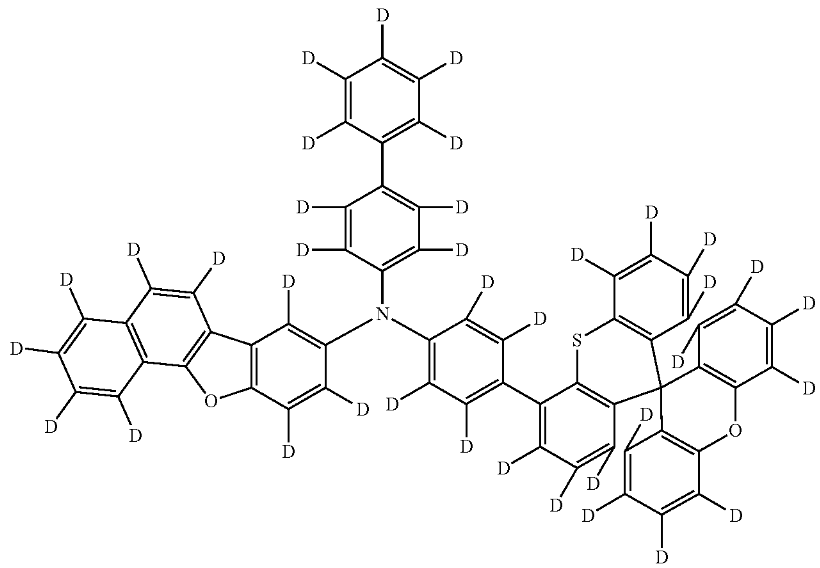
C178
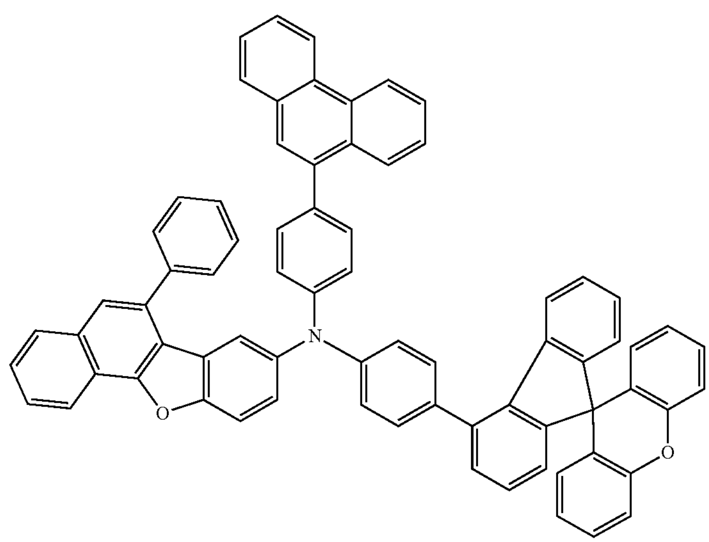
C179
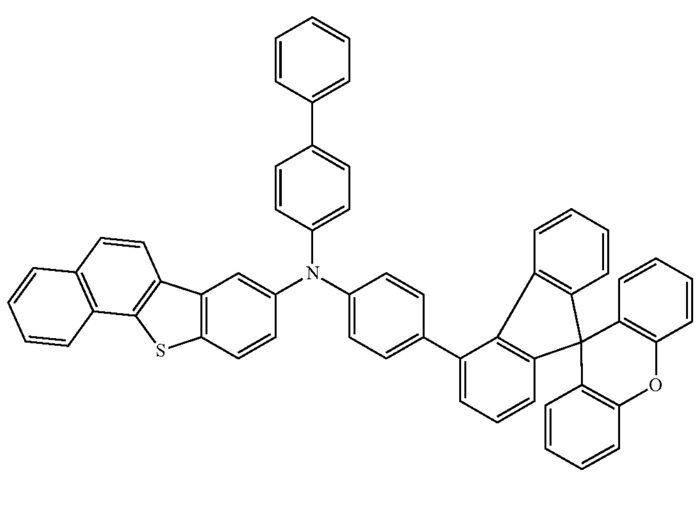

-continued
C180
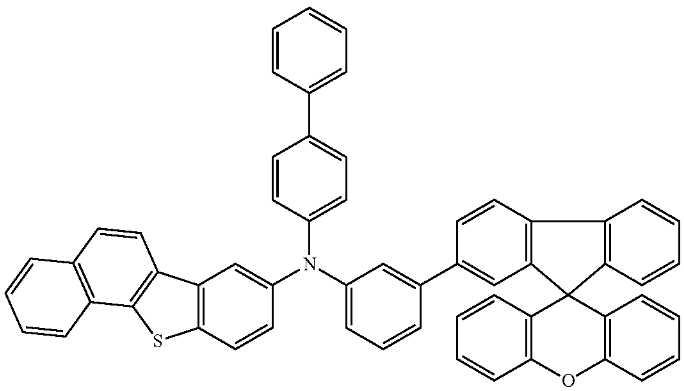
C181
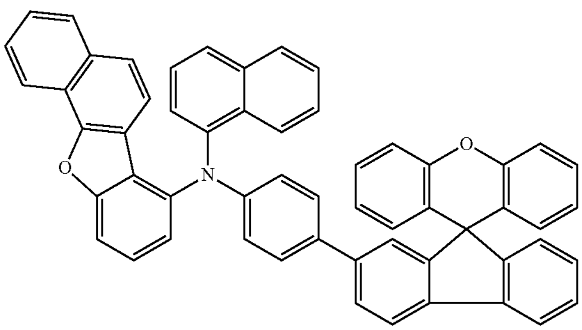
C182
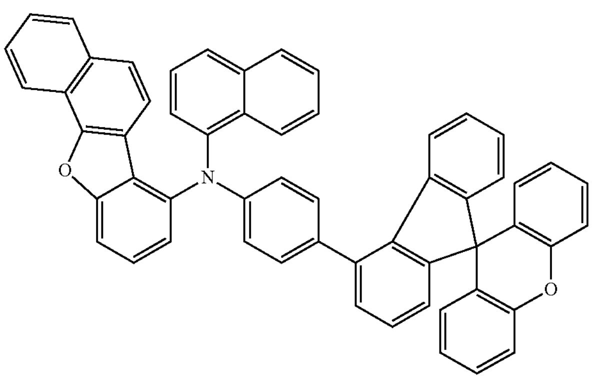
C183
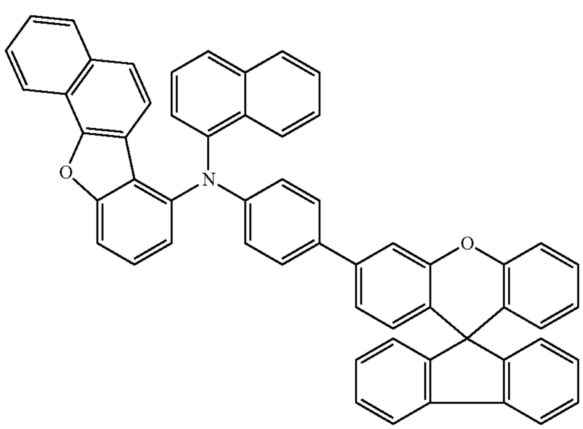

-continued
C184
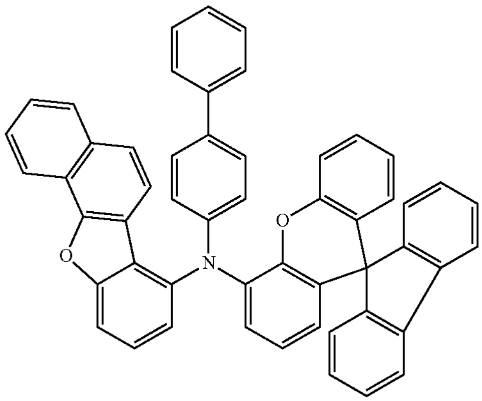
C185
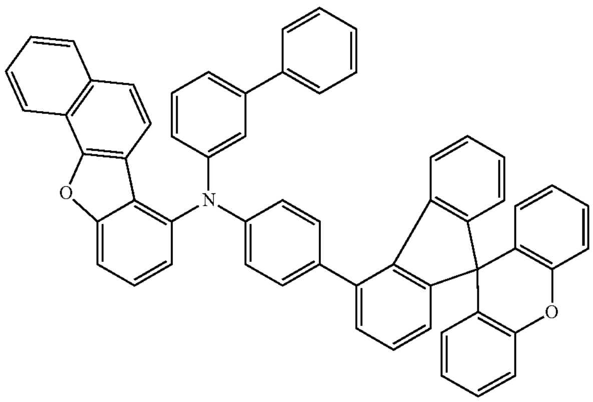
C186
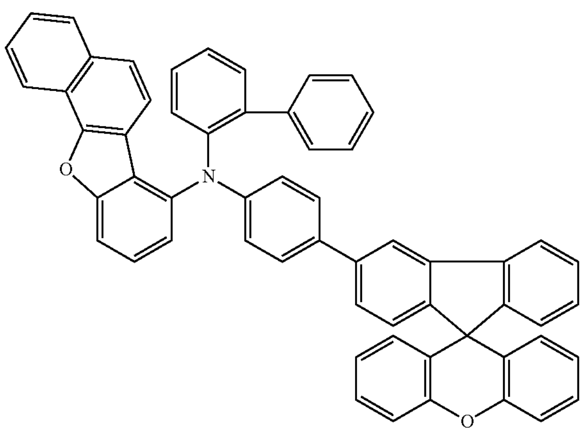
C187
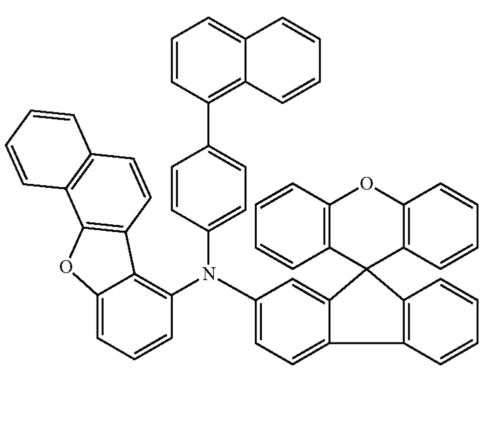

-continued
C188
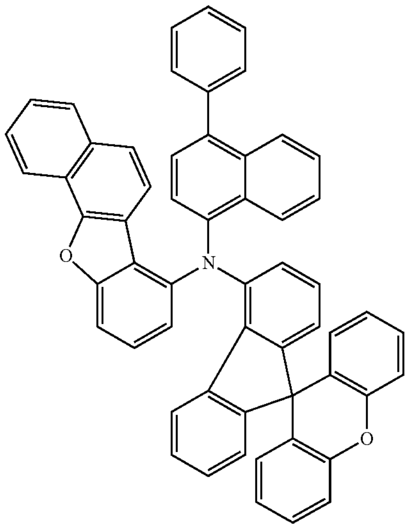
C189
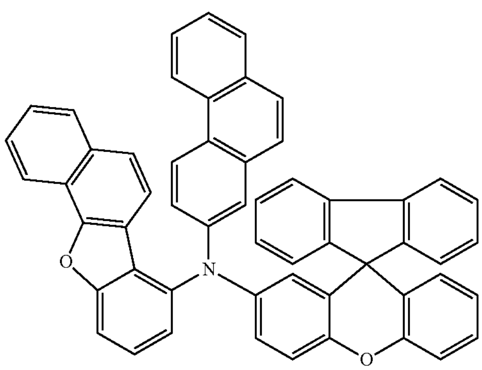
C190
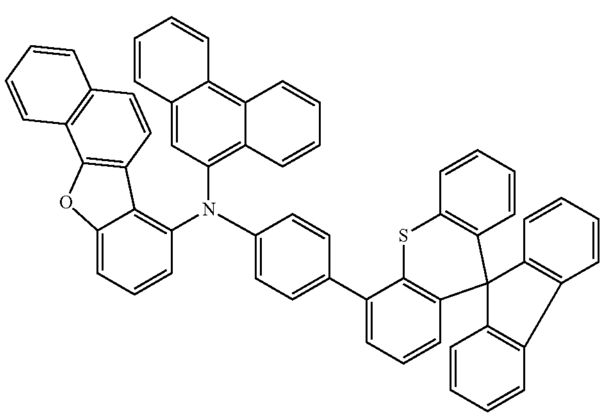

-continued
C191
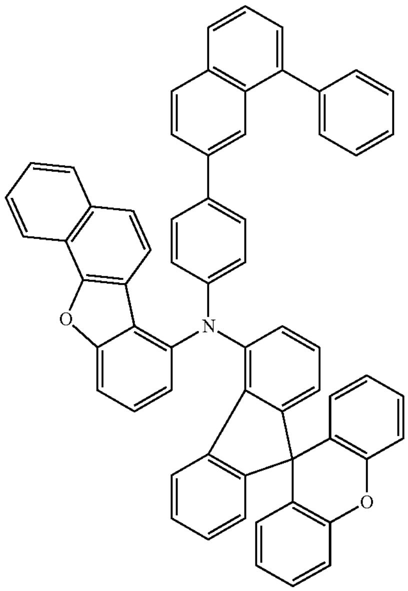
C192
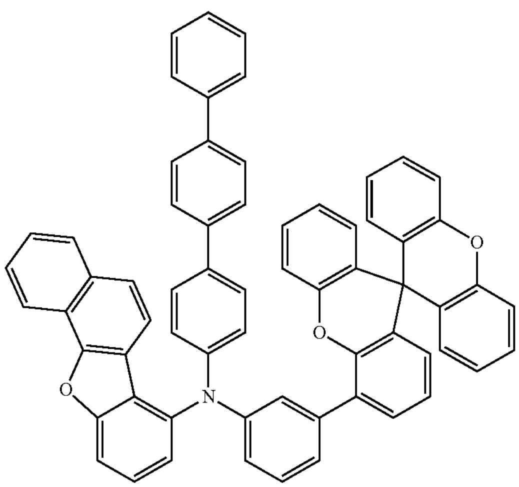
C193
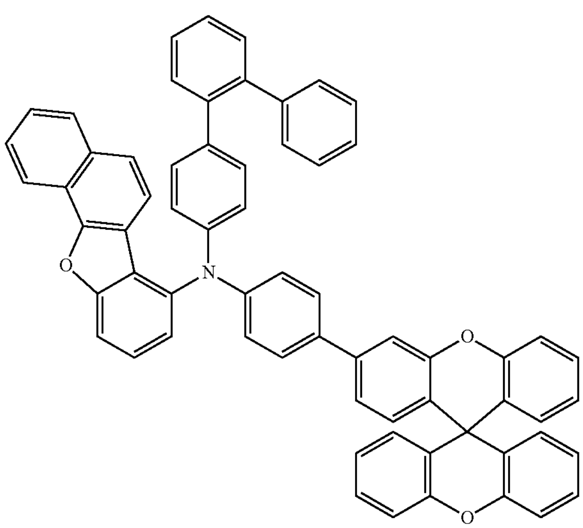

-continued
C194
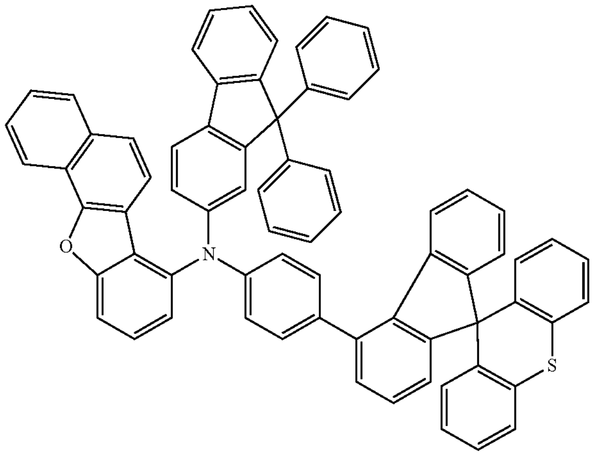
C195
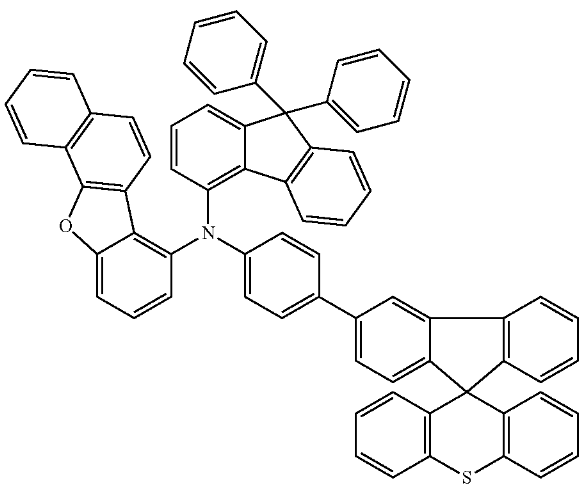
C196
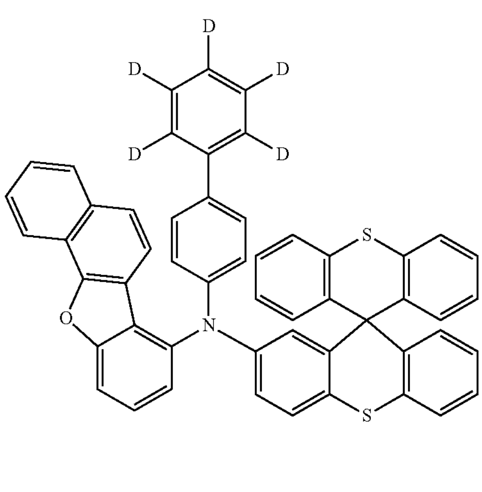

-continued
C197
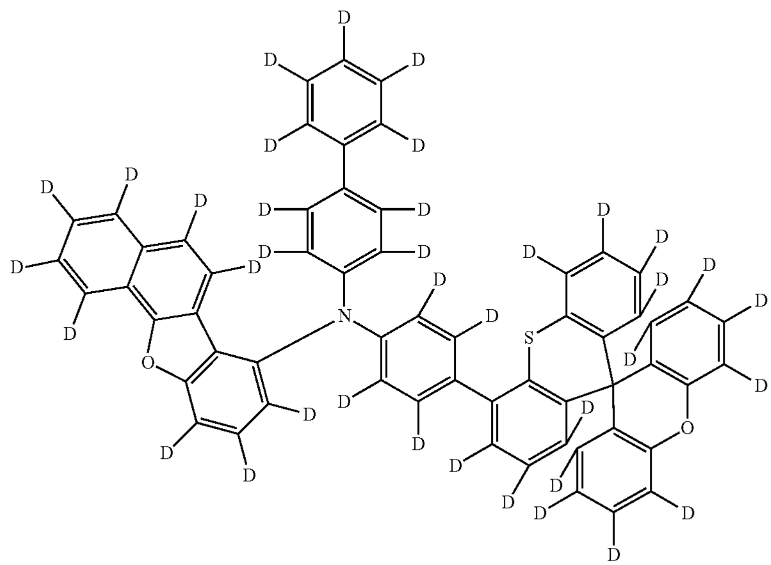
C198
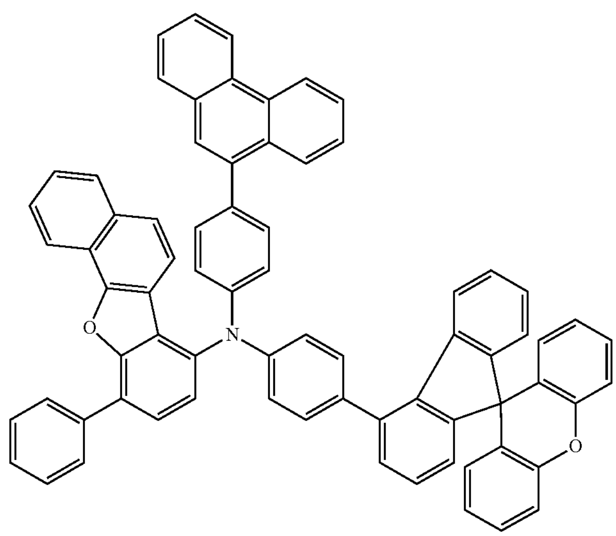
C199
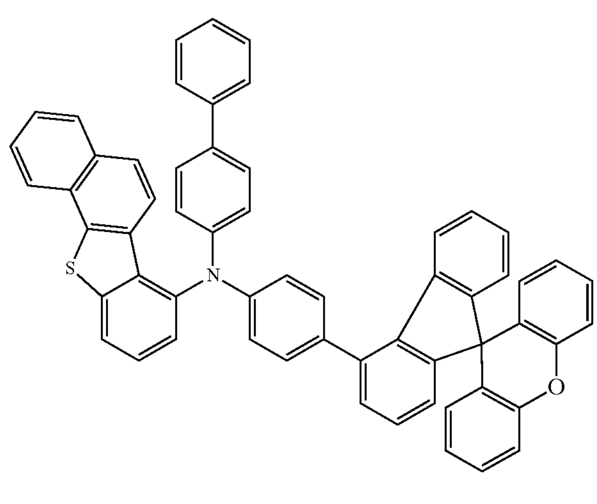

-continued
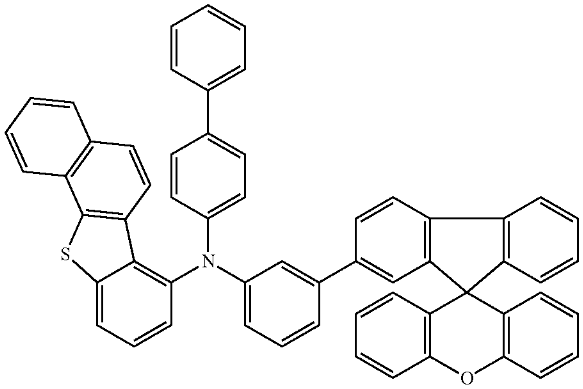
C200
[Compounded Group 4]
D1
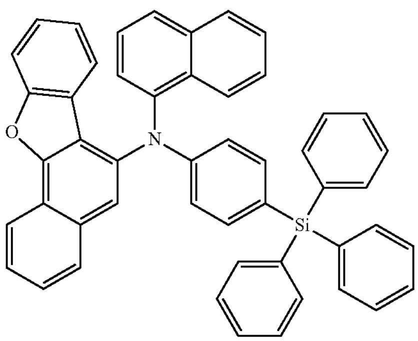
-continued
D3
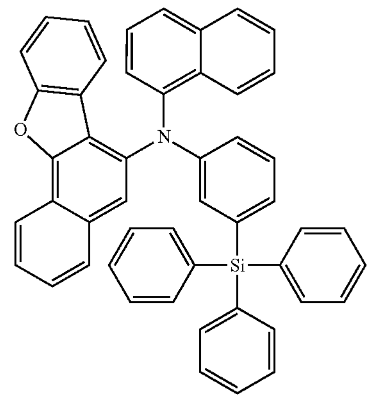
D2
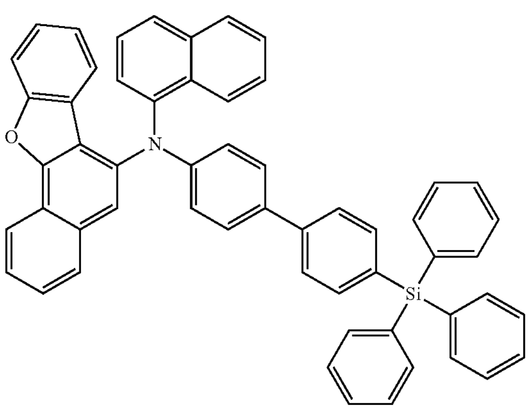
D4
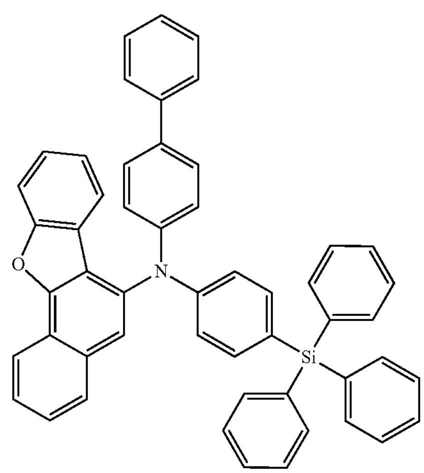

-continued
D5
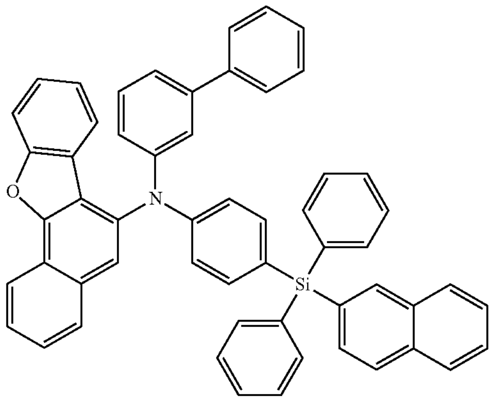
D6
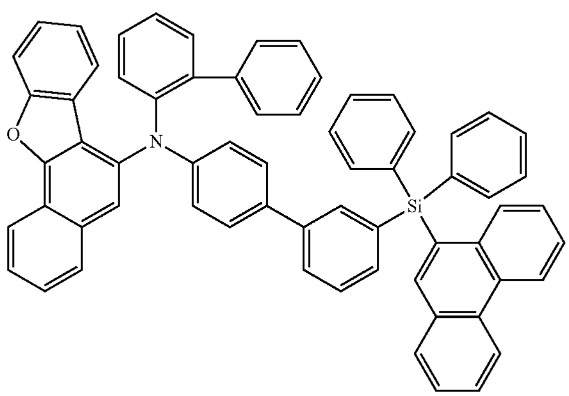
D7
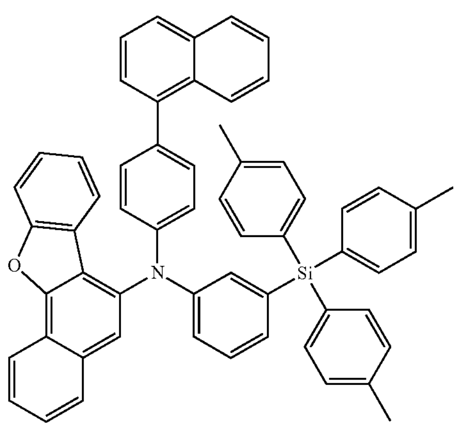
-continued
D8
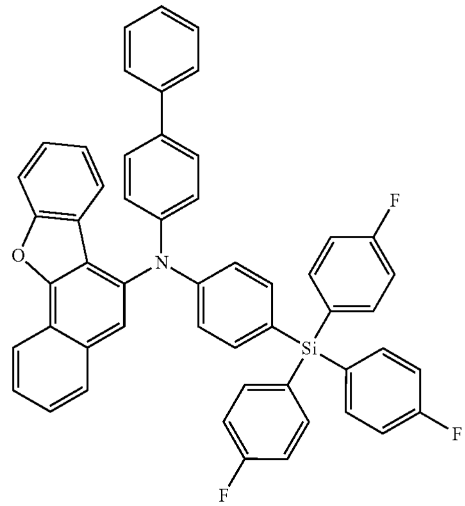
D9
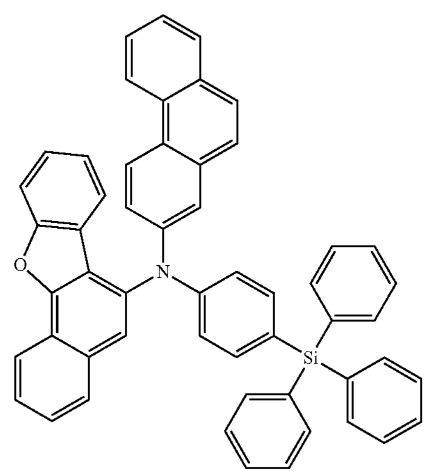
D10
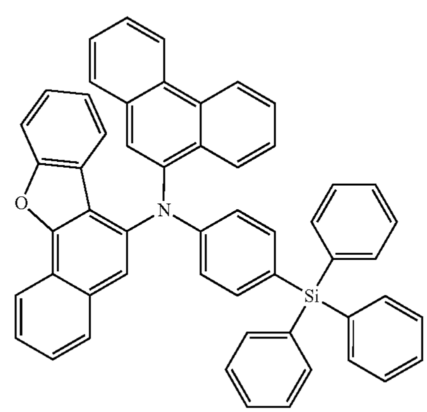

-continued
D11
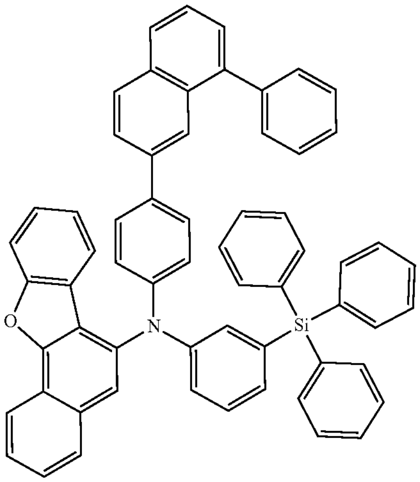
D12
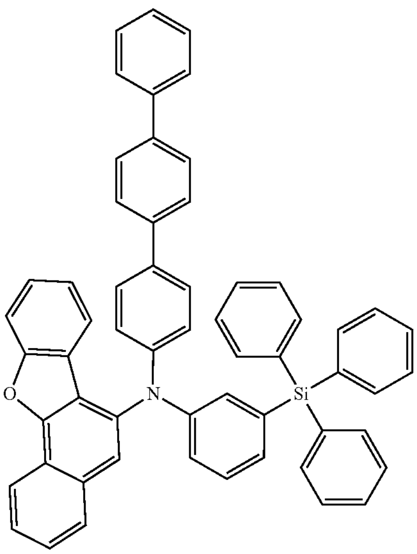
D13
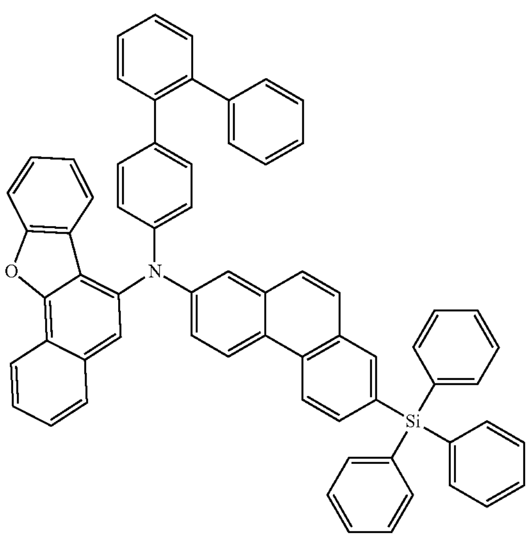
-continued
D14
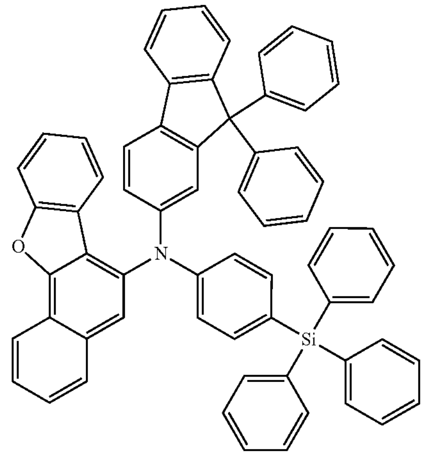
D15
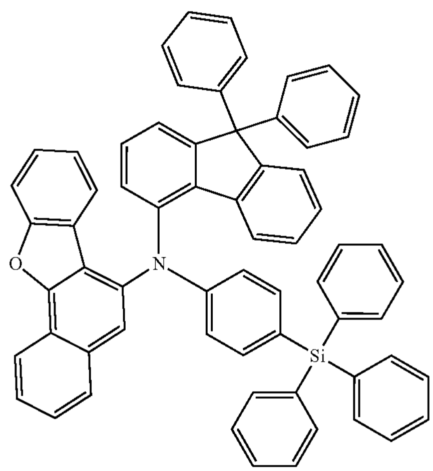
D16
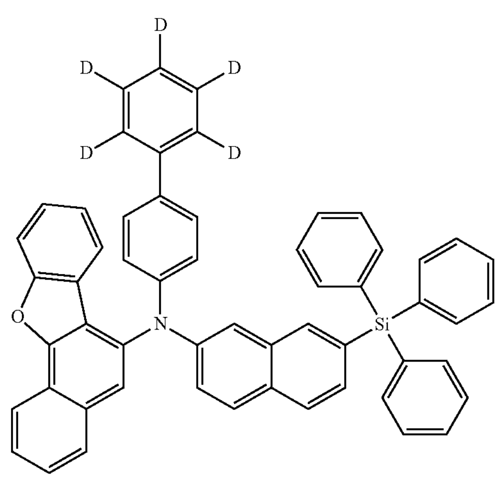

-continued
D17
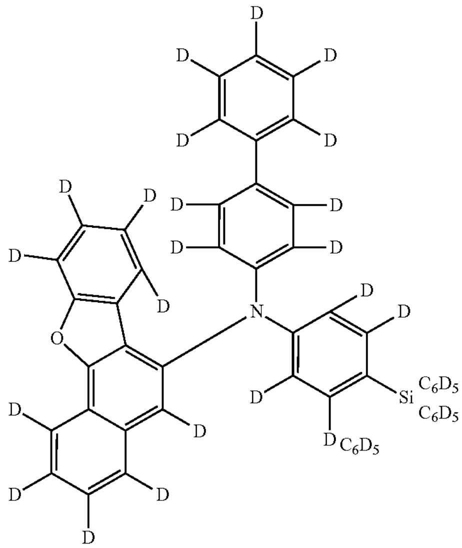
D18
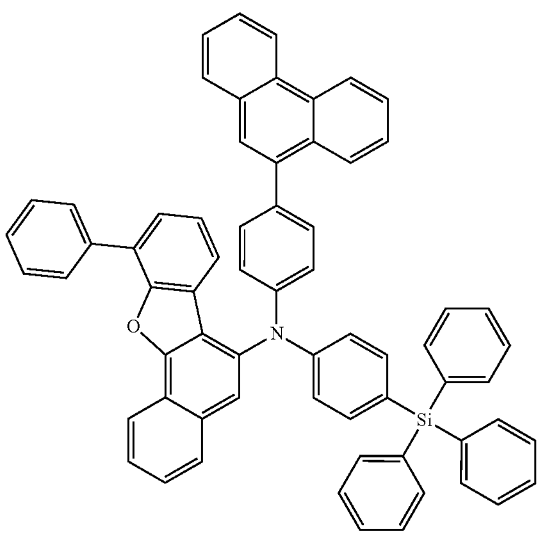
D19
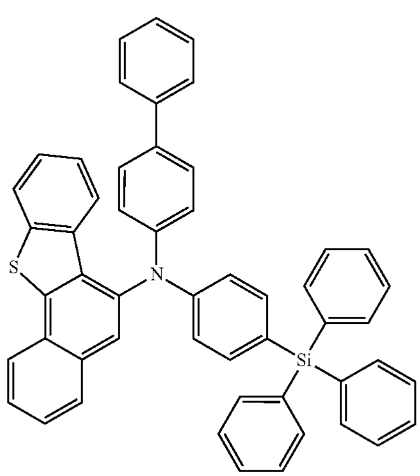
-continued
D20
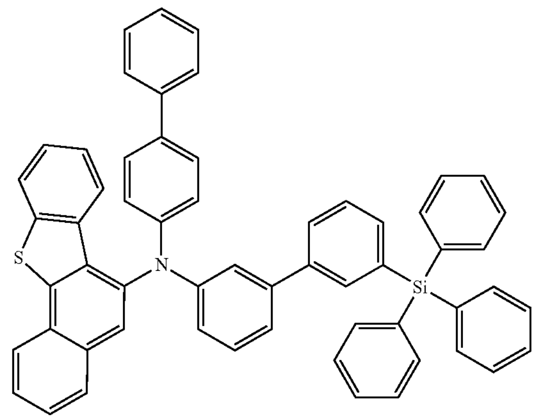
D21
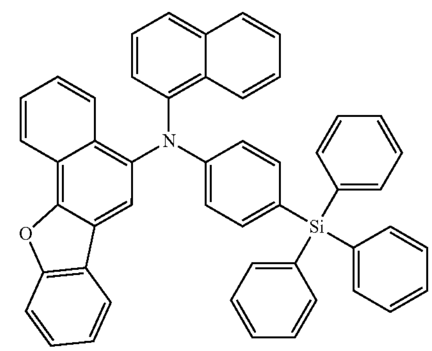
D22
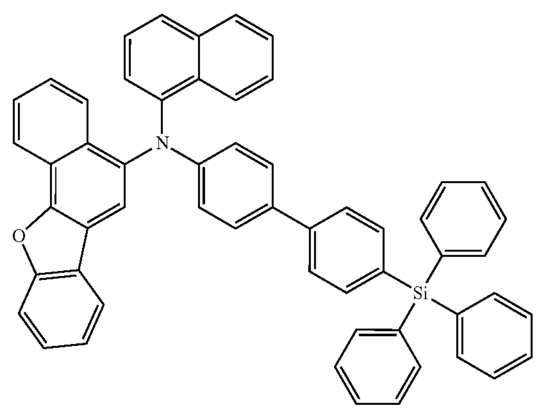
D23
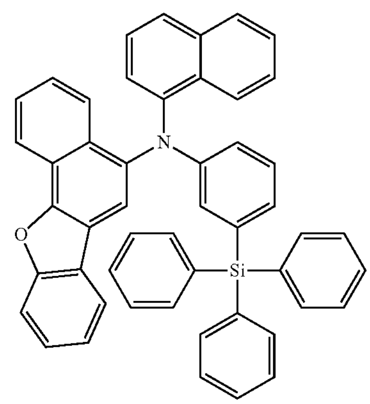

-continued
D24
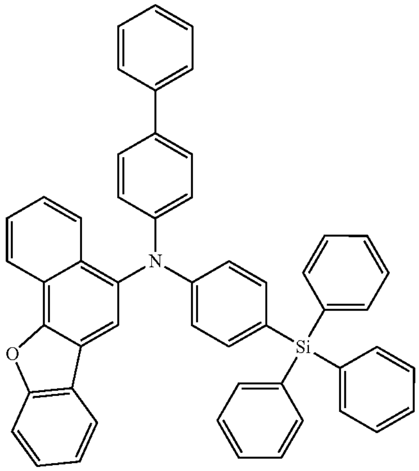
D25
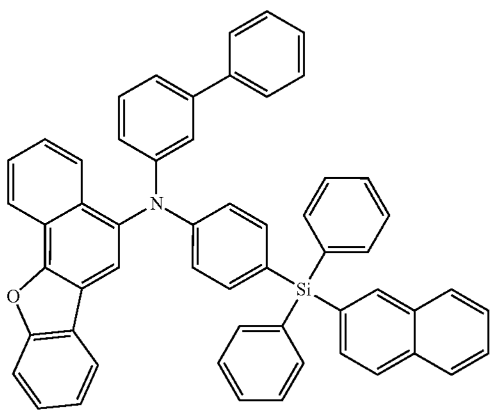
D26
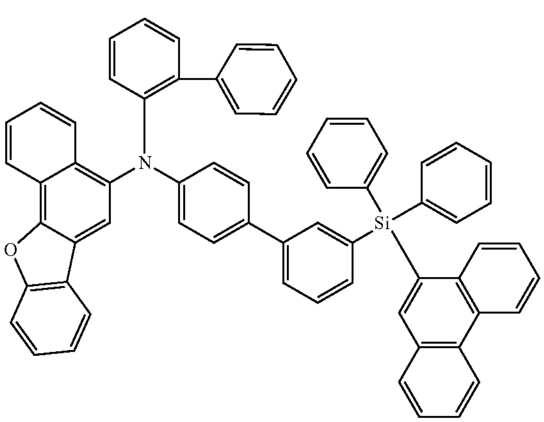
-continued
D27
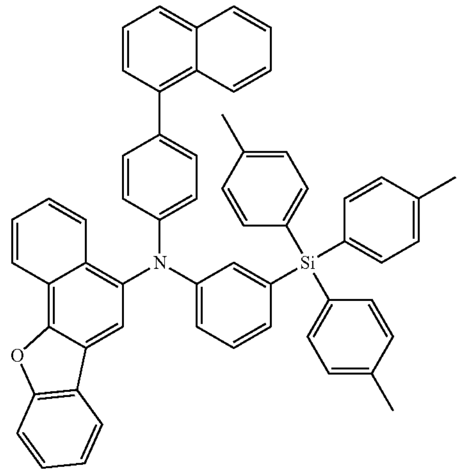
D28
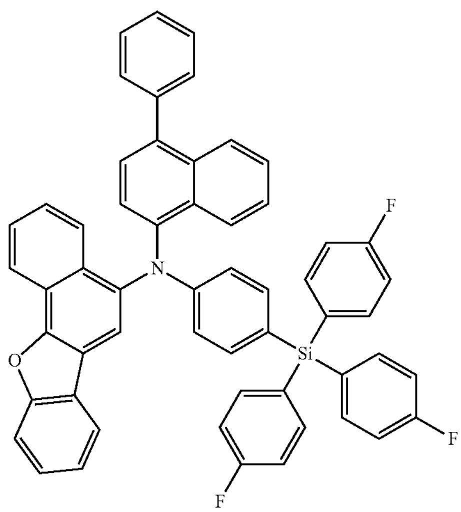
D29
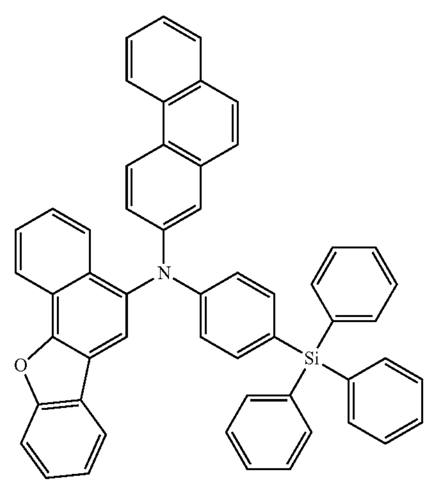

-continued
D30
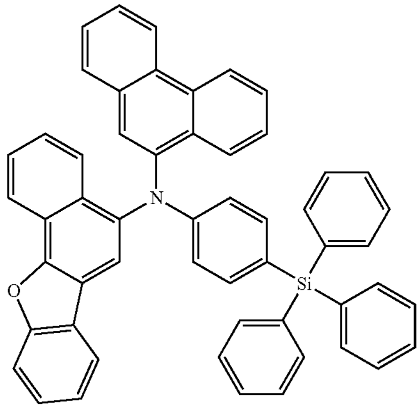
D31
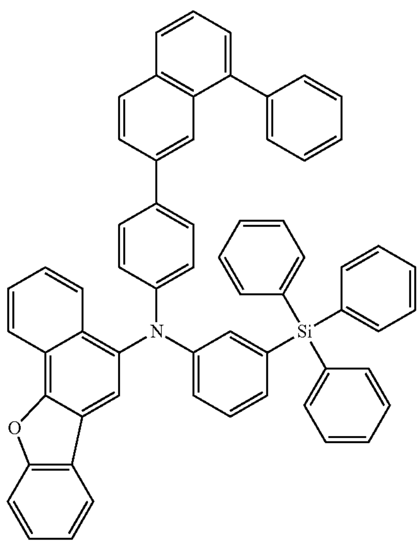
D32
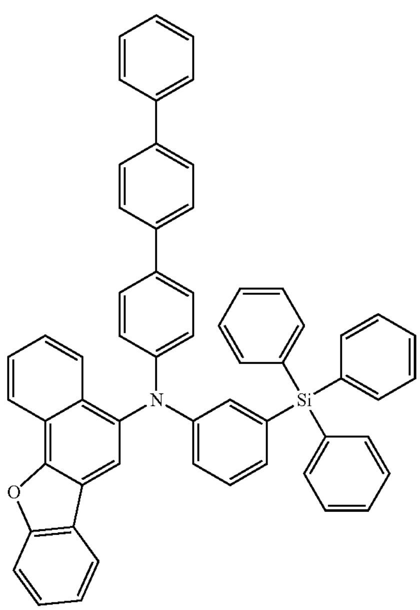
-continued
D33
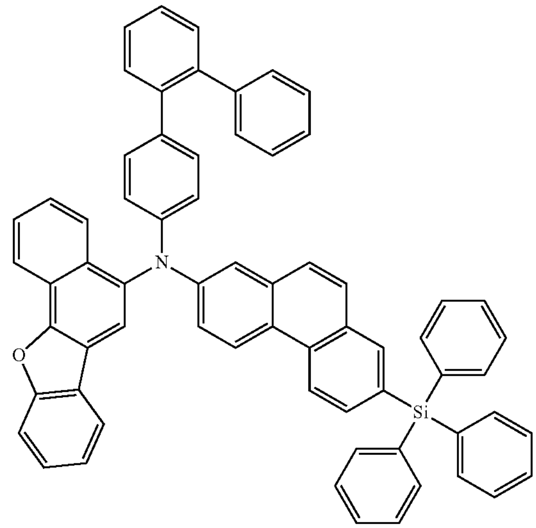
D34
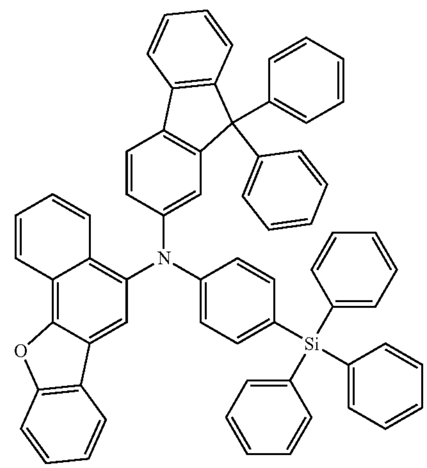
D35
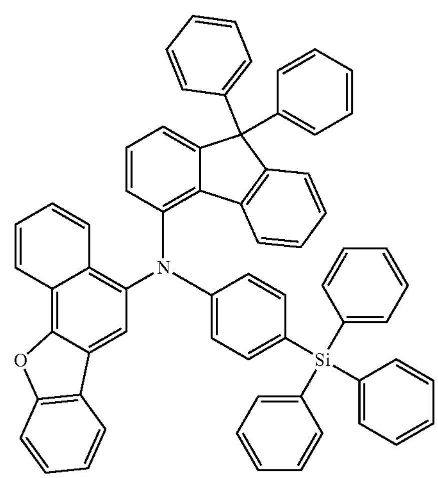

-continued
D36
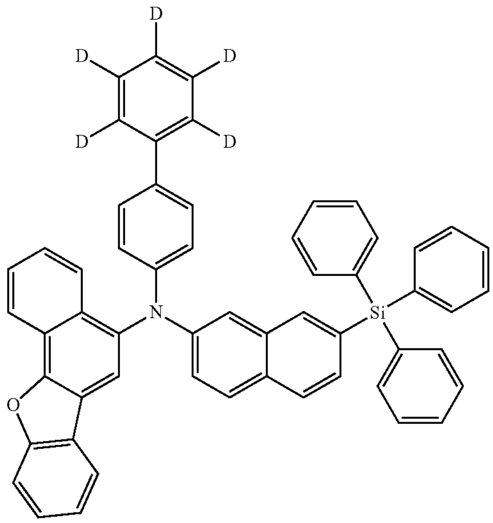
D37
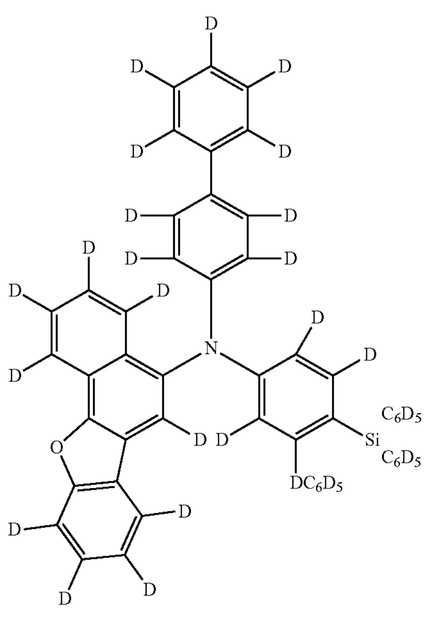
-continued
D38
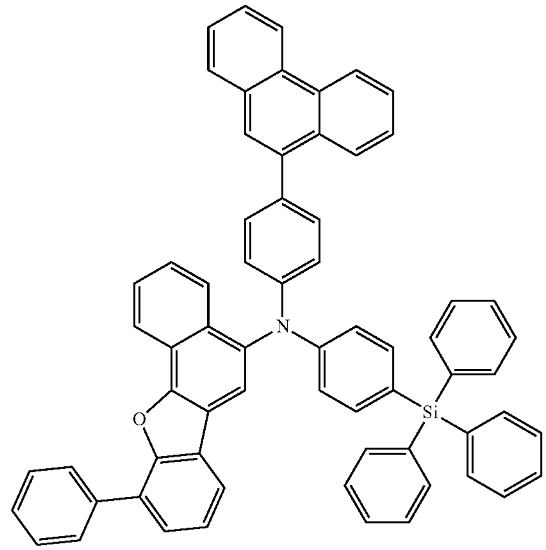
D39
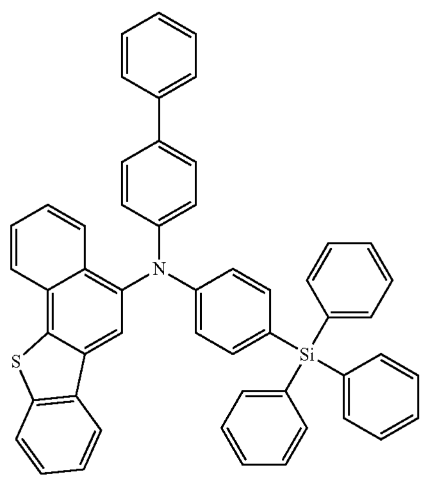
D40
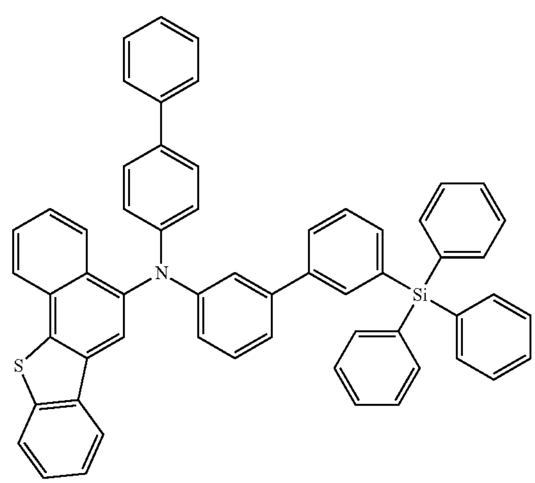

-continued
D41
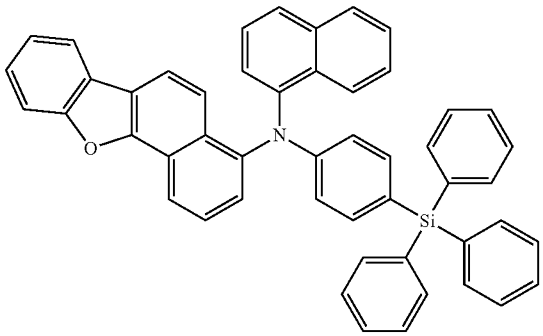
D42
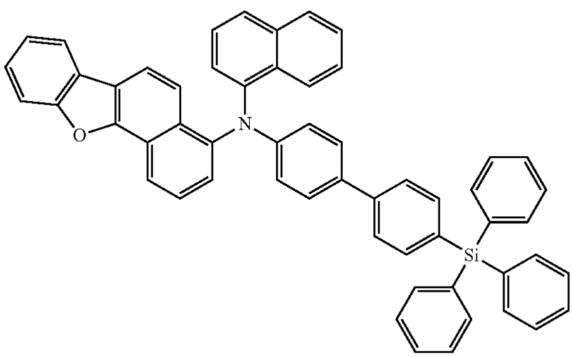
D43
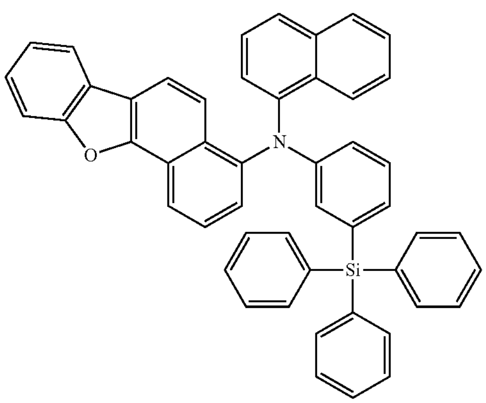
D44
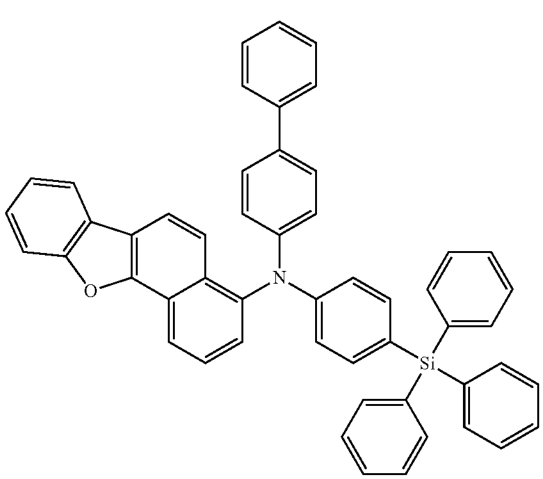
-continued
D45
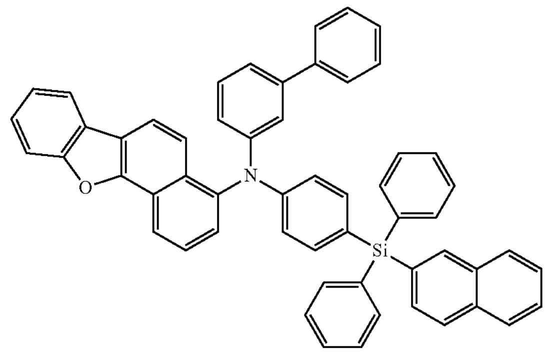
D46
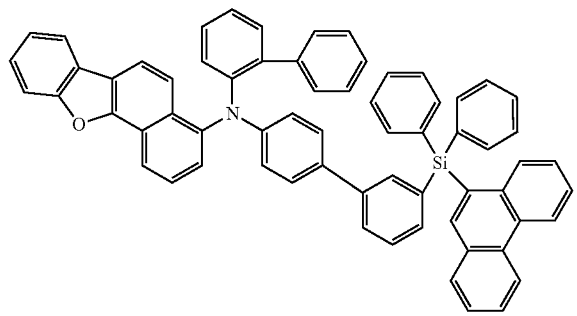
D47
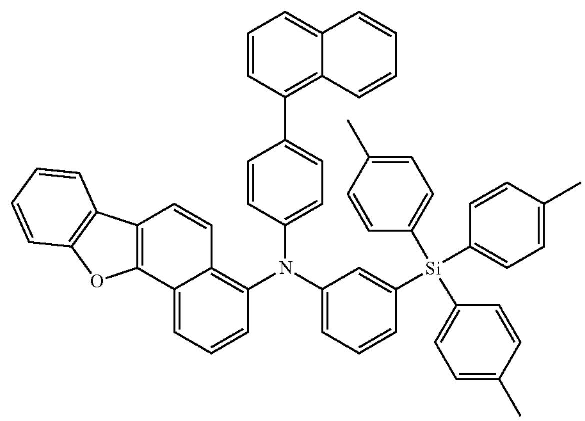
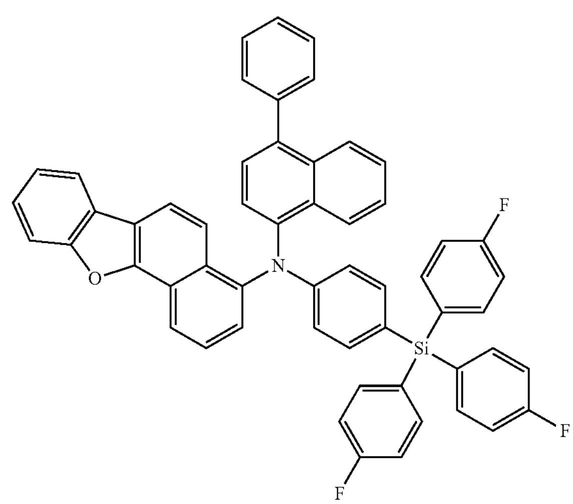

-continued
D49
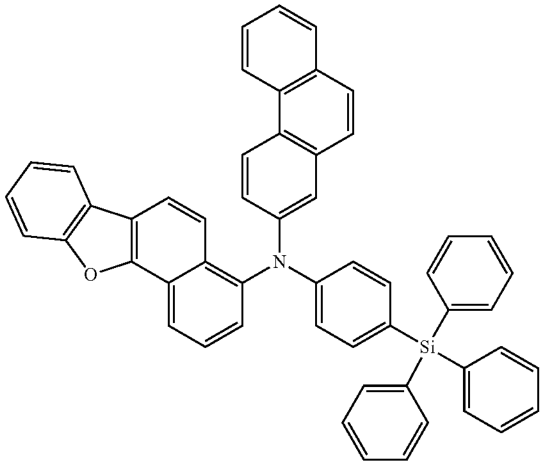
D50
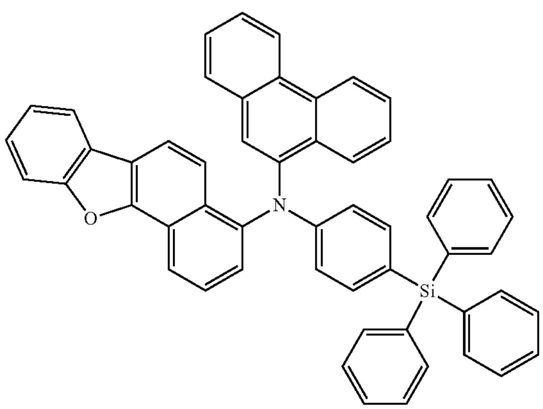
D51
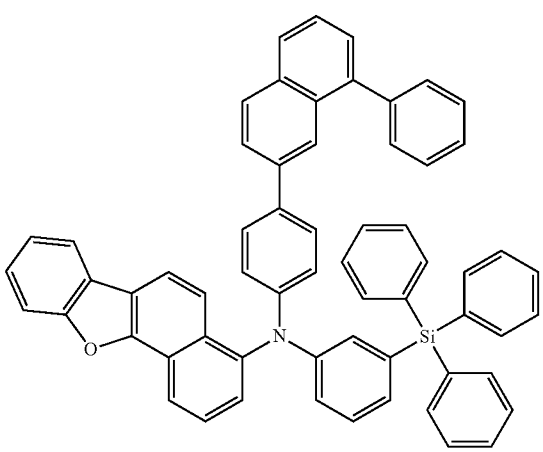
-continued
D52
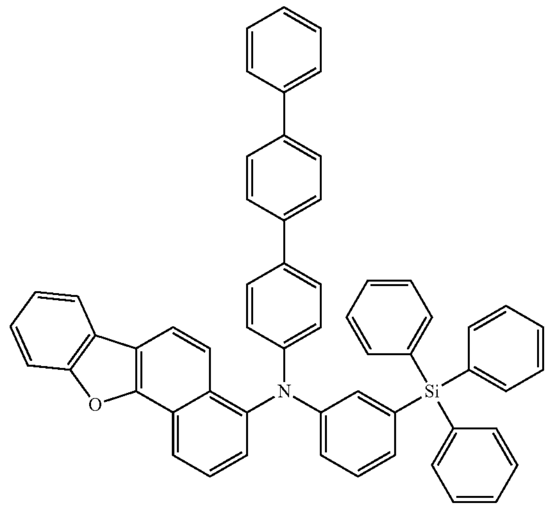
D53
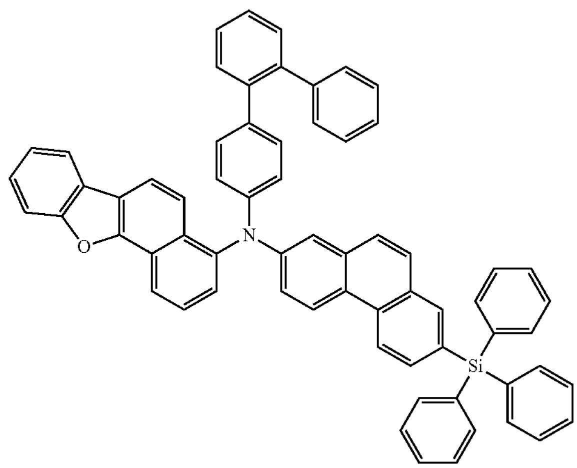
D54
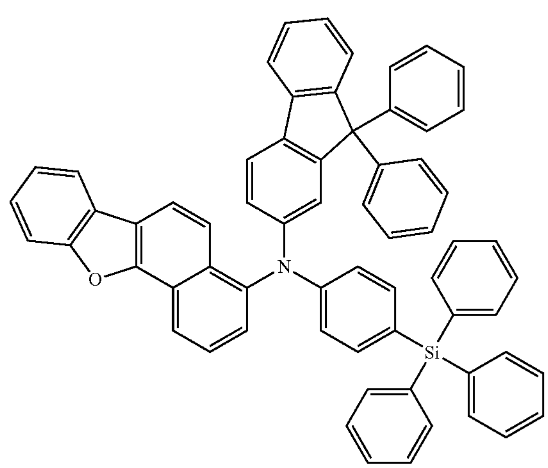

D55
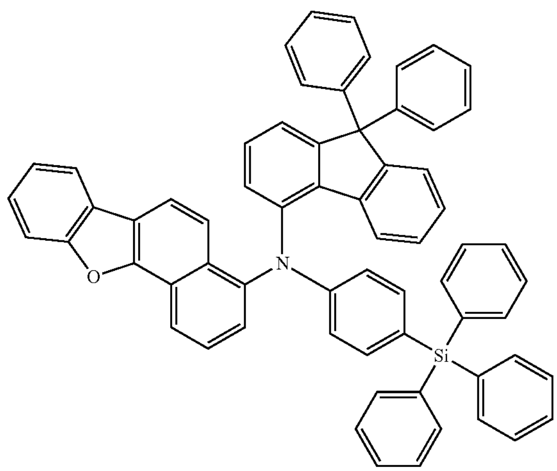
D56
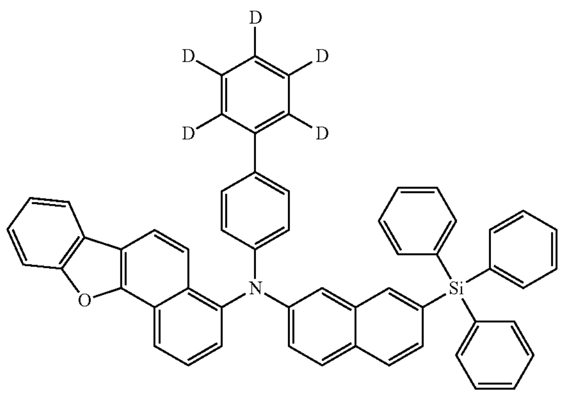
D58
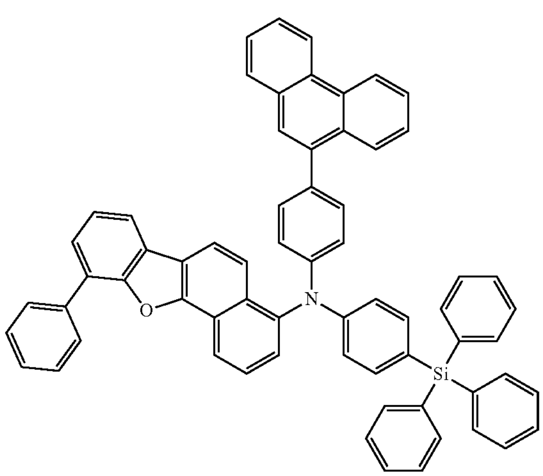
D59
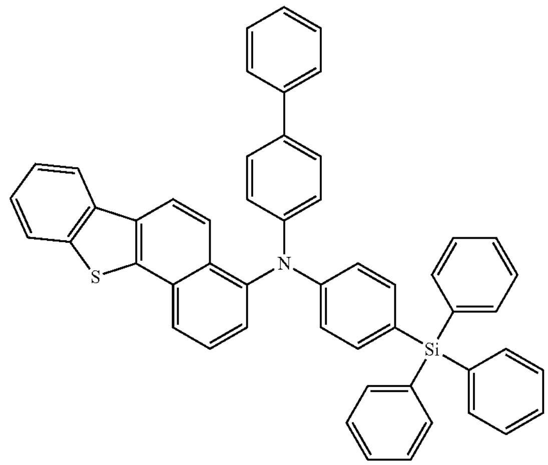
D60
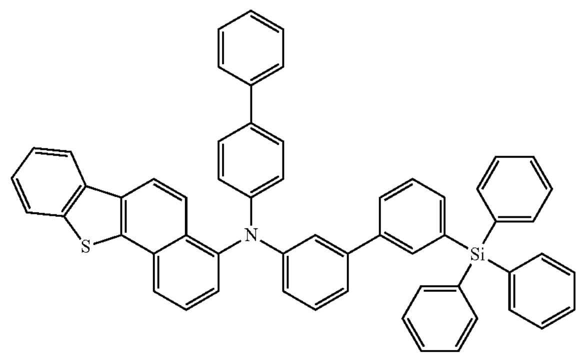
D61
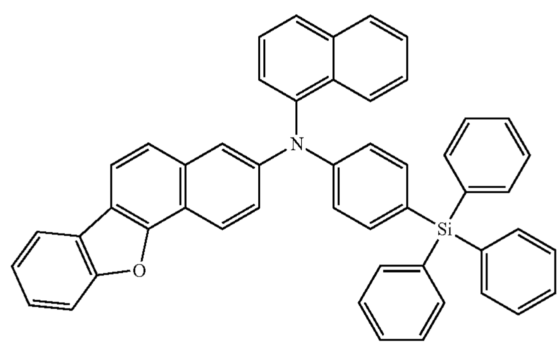
D62
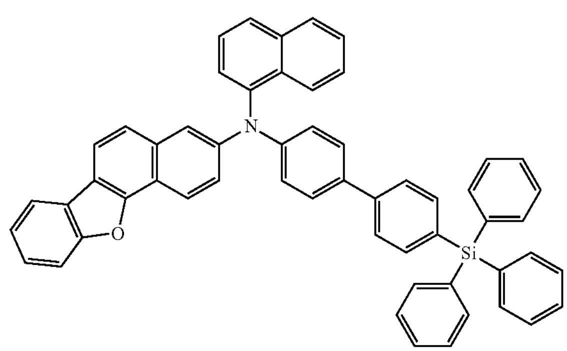

-continued
D63
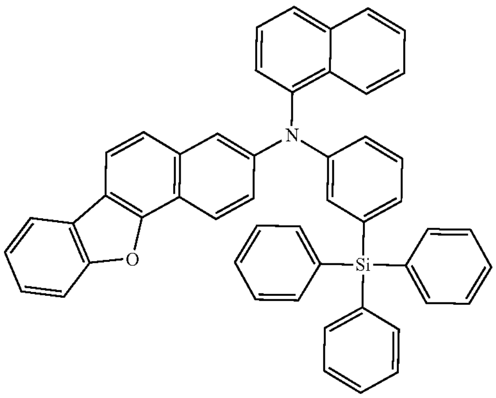
D64
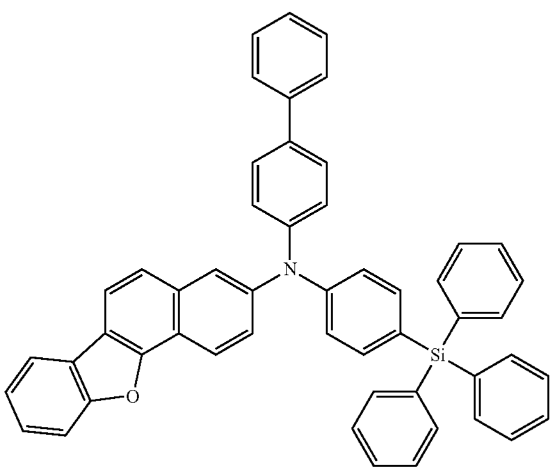
D65
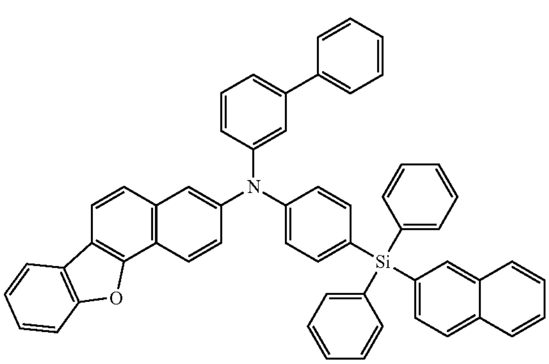
D66
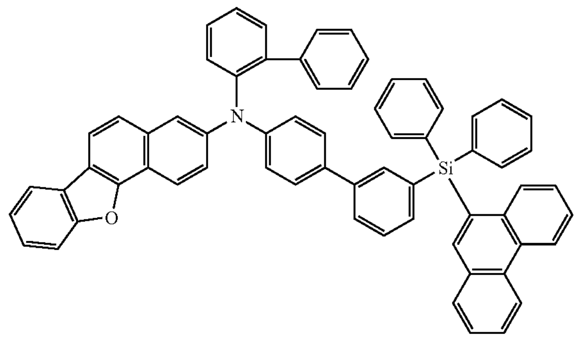
D67
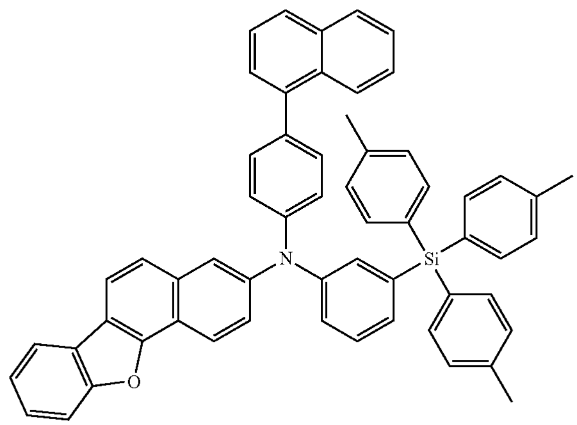
D68
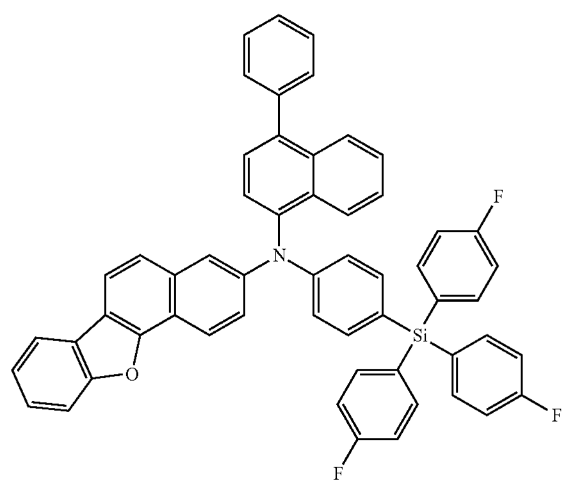

-continued
D69
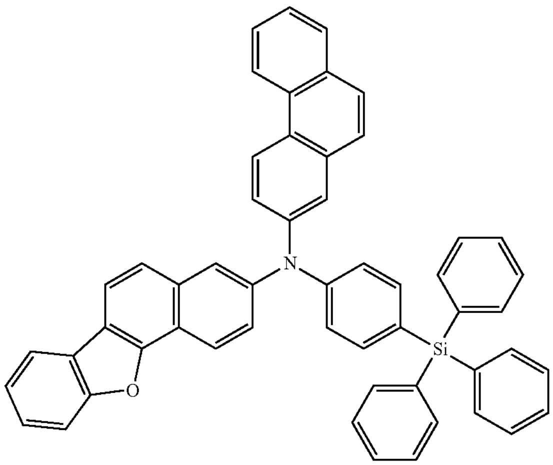
D70
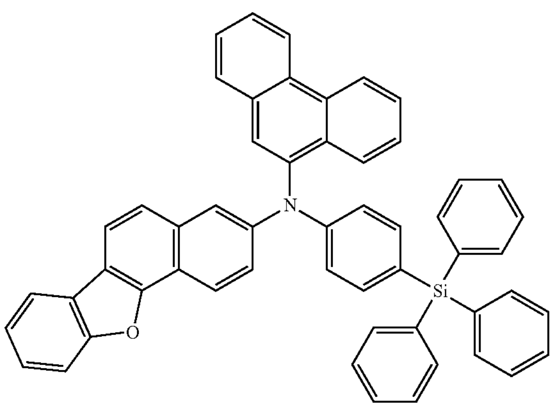
D71
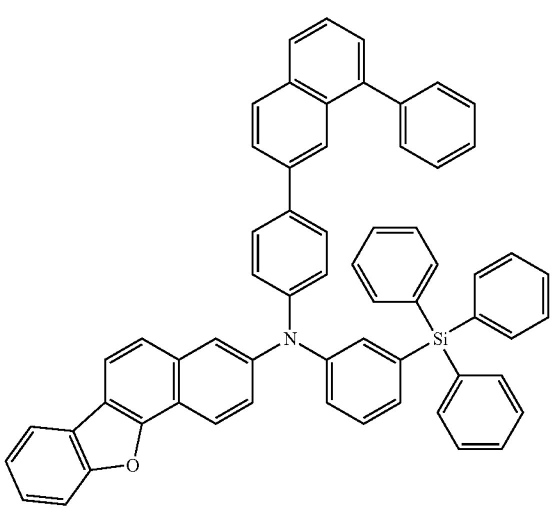
-continued
D72
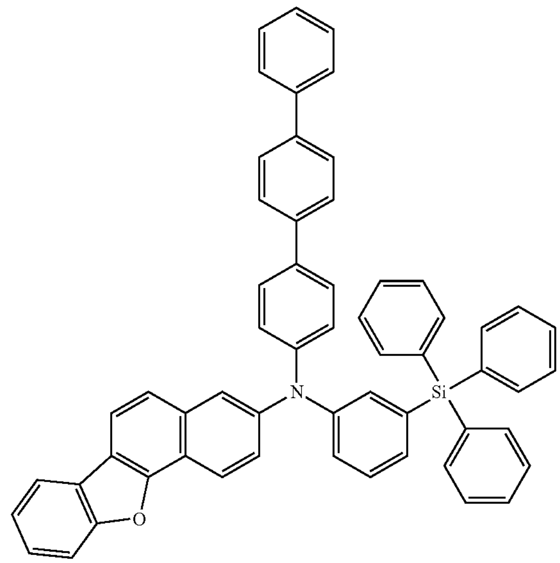
D73
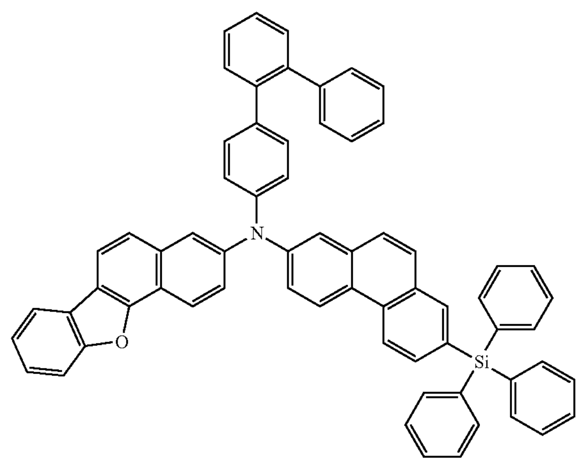
D74
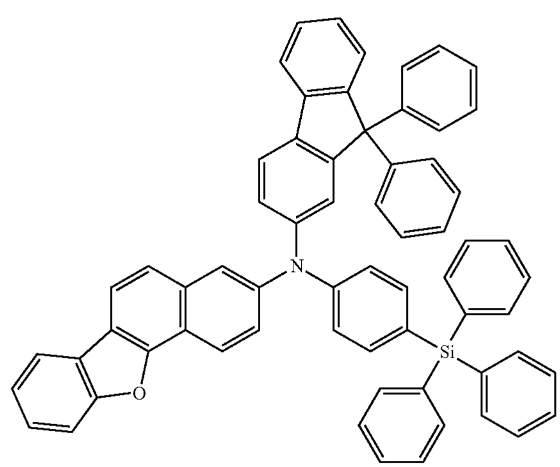

-continued
D75
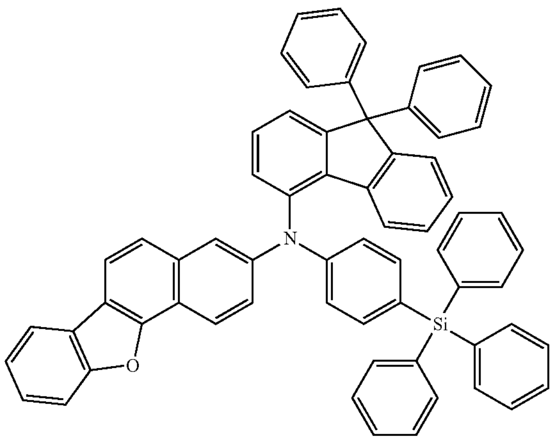
D76
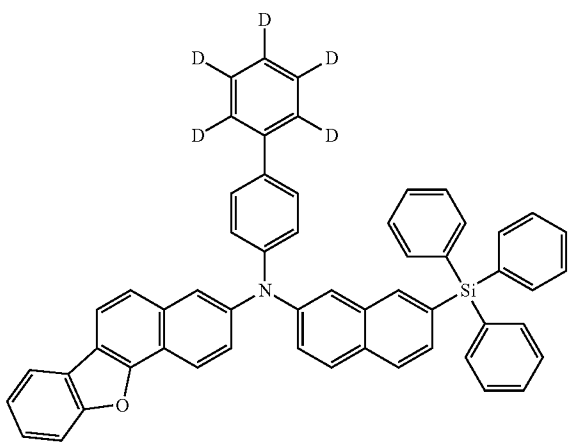
D78
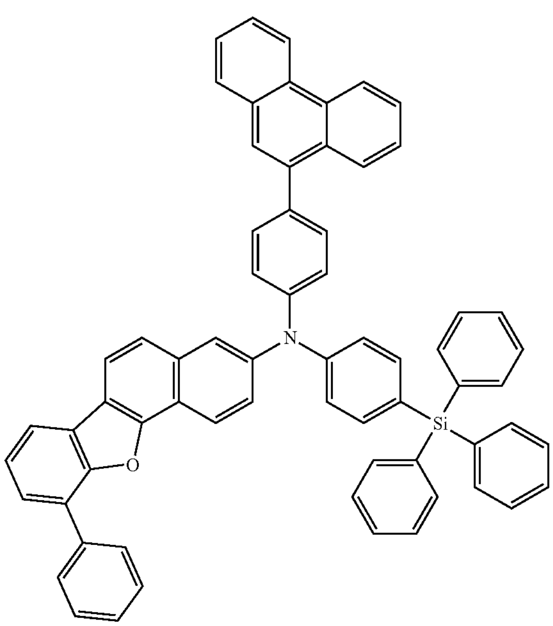
-continued
D79
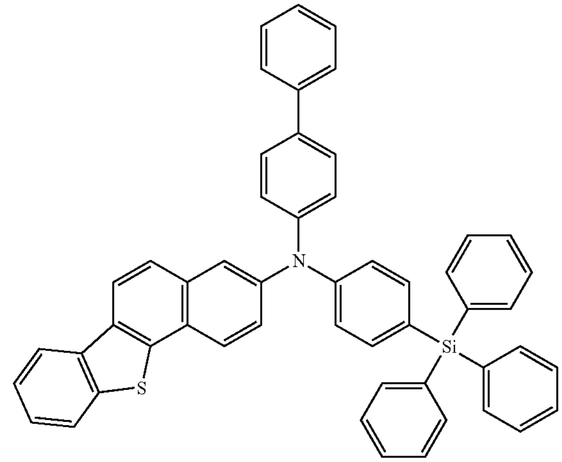
D80
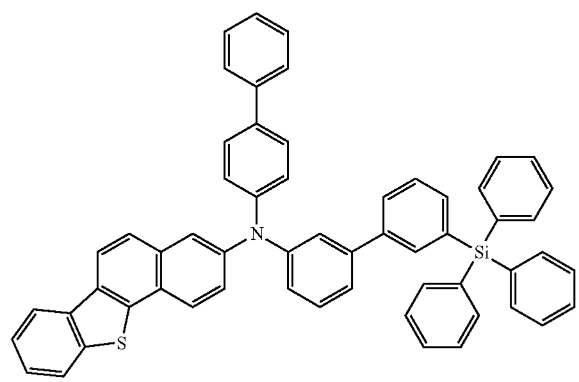
D81
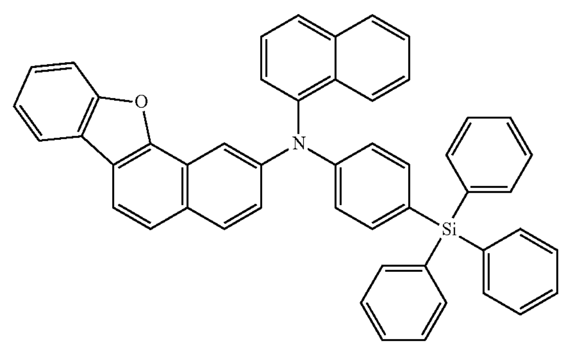
D82
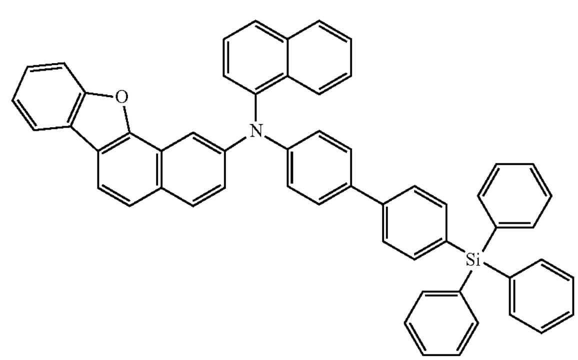

-continued
D83
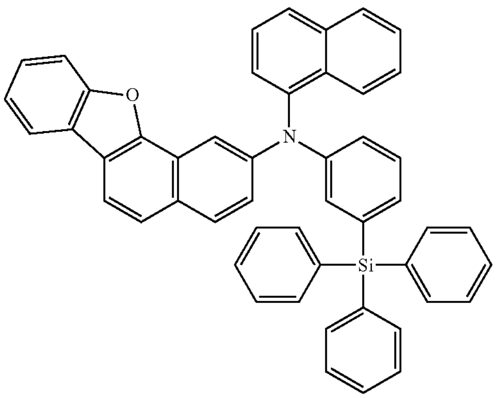
D84
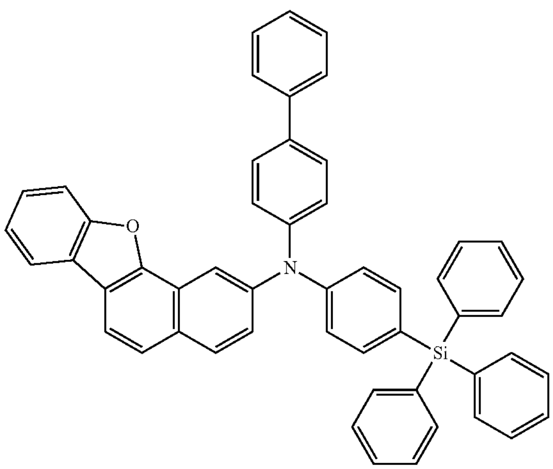
D85
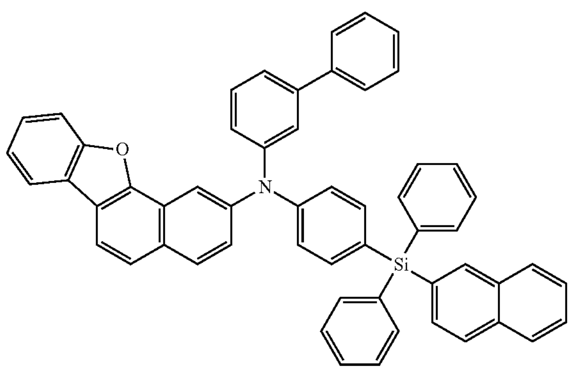
D86
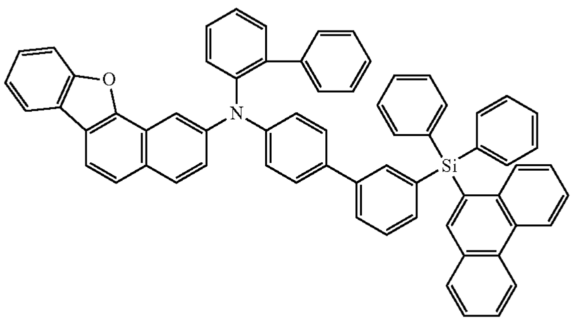
-continued
D87
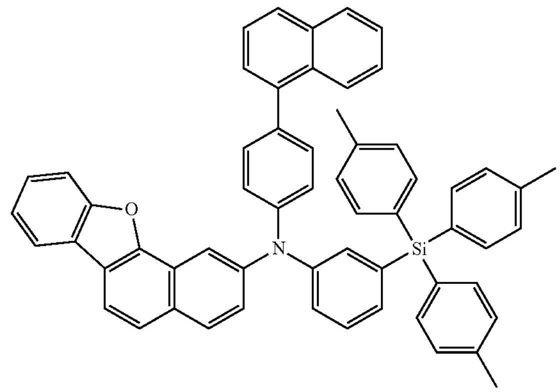
D88
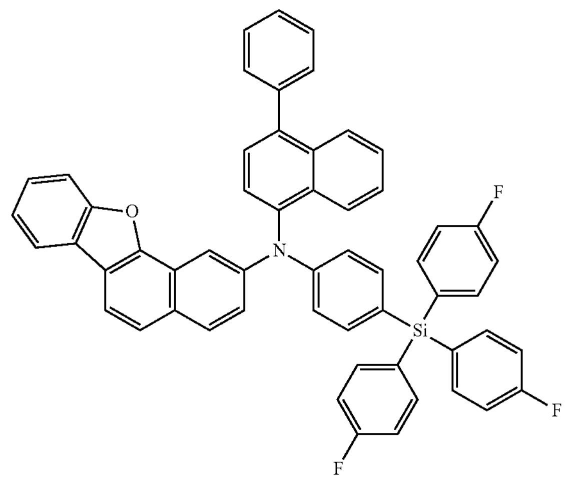
D89
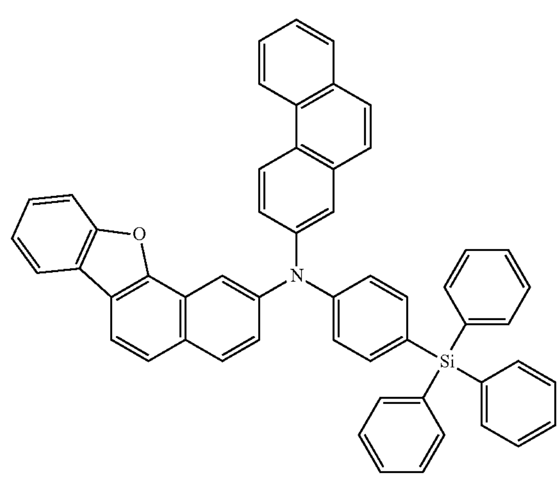

-continued
D90
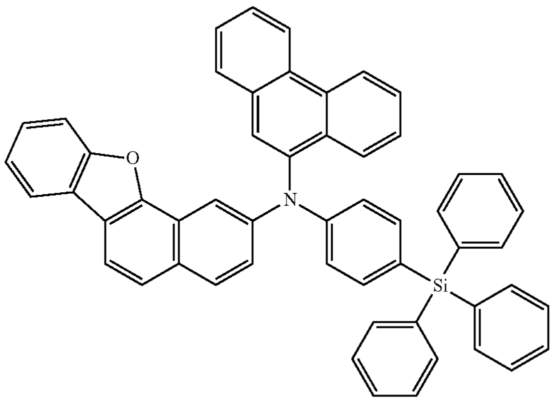
D91
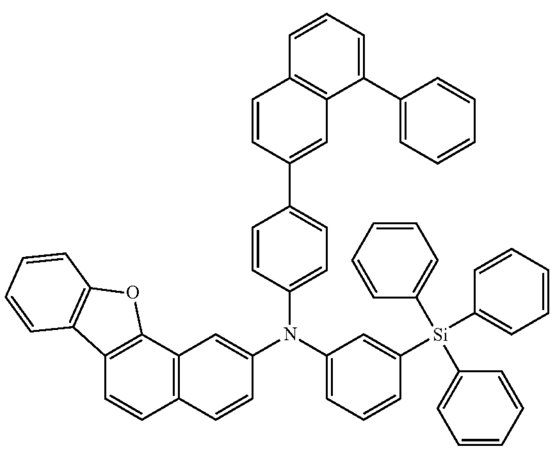
D92
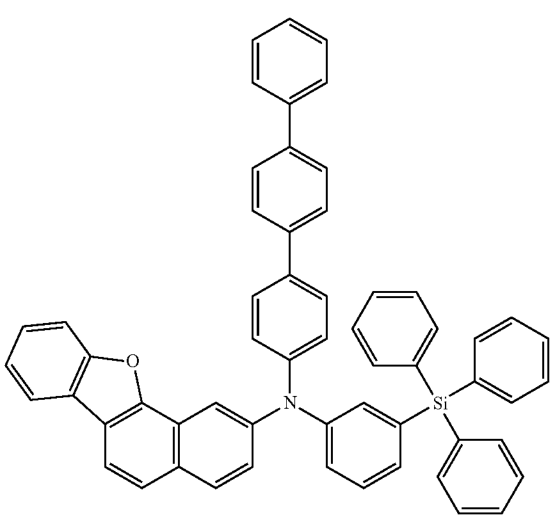
-continued
D93
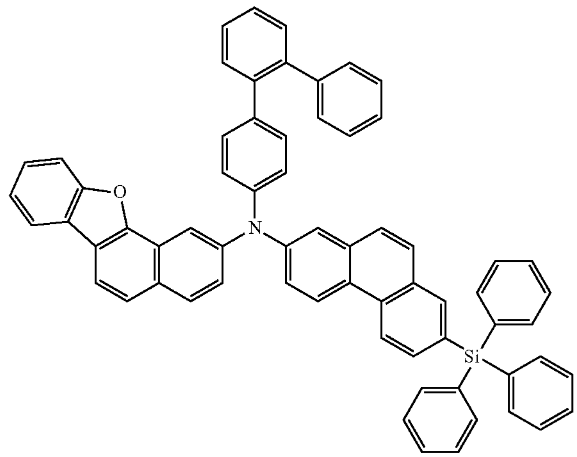
D94
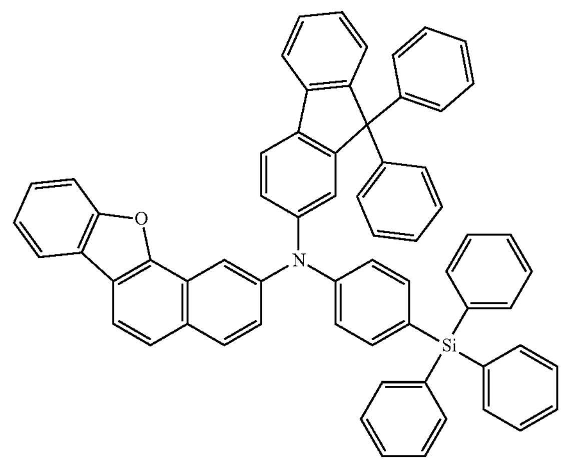
D95
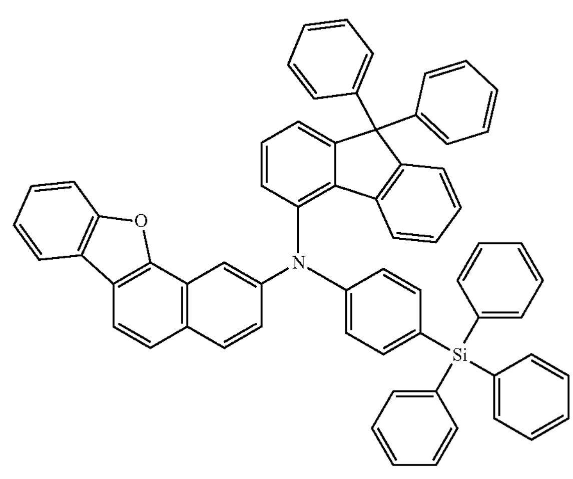

D96
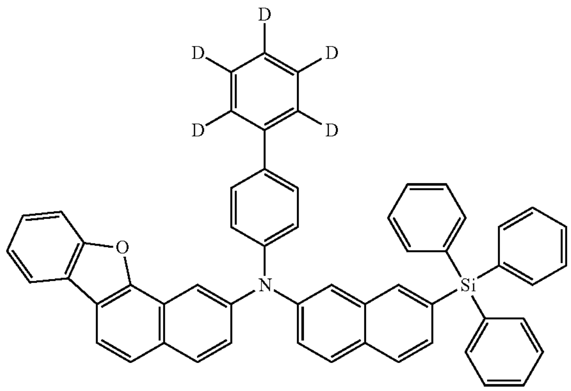
D98
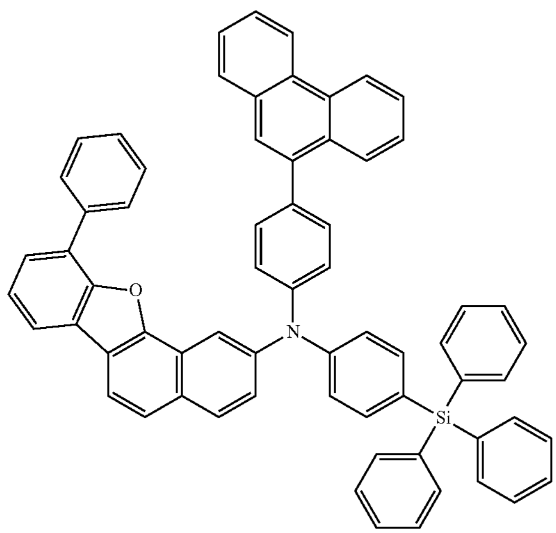
D99
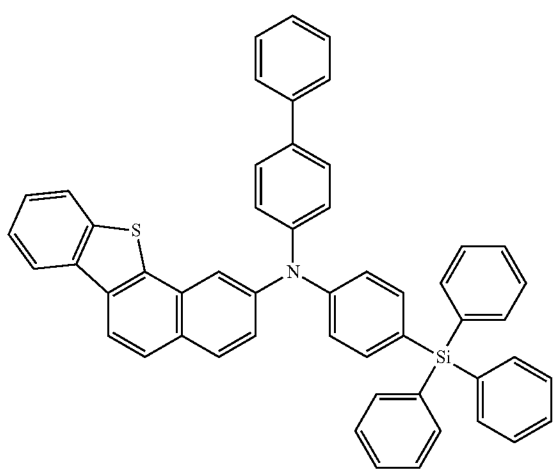
D100
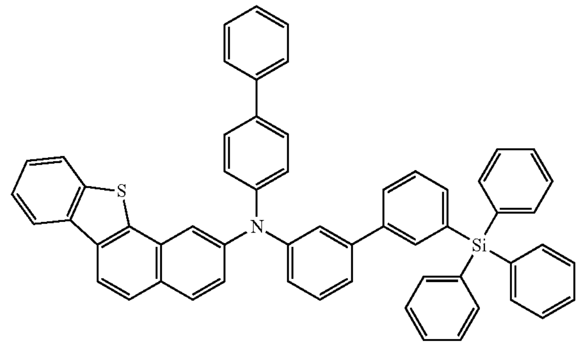
D101
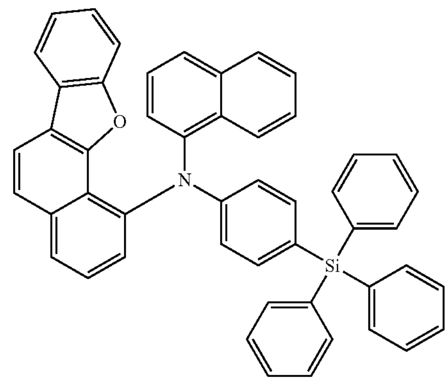
D102
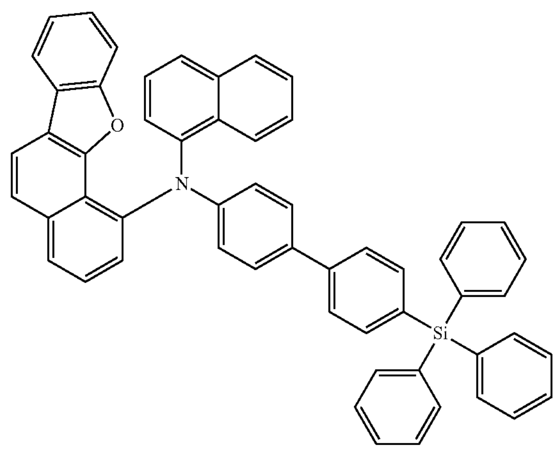
D103
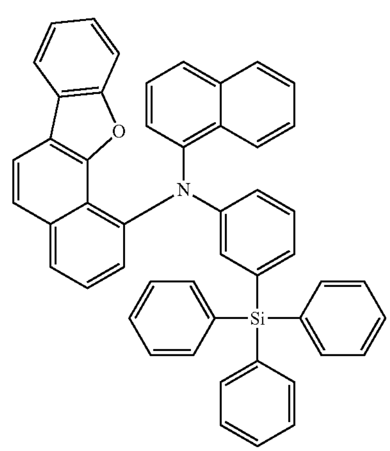

-continued
D104
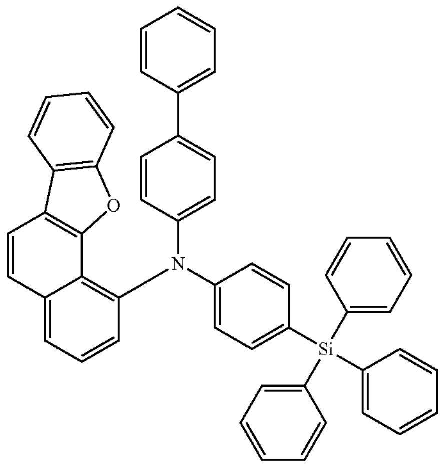
D105
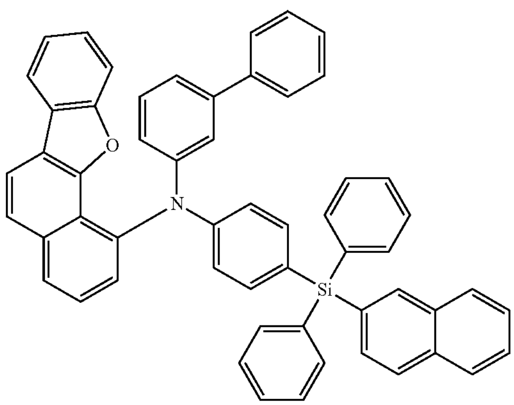
D106
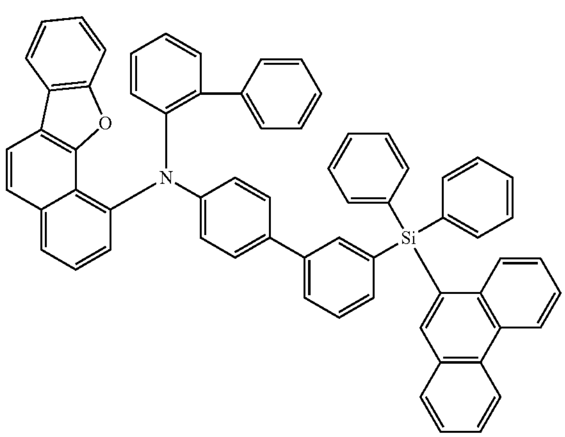
-continued
D107
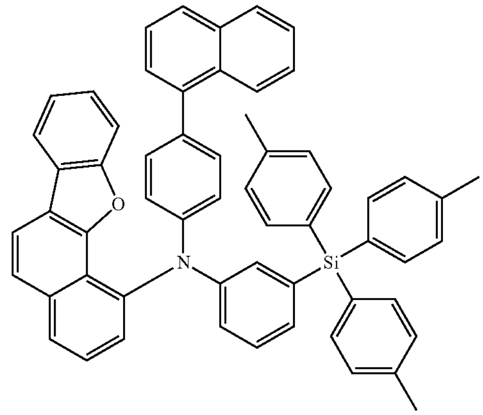
D108
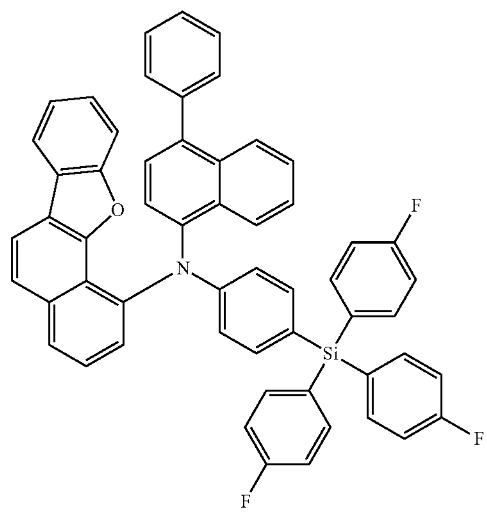
D109
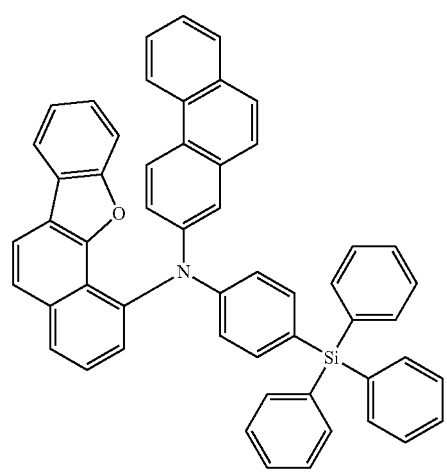

-continued
D110
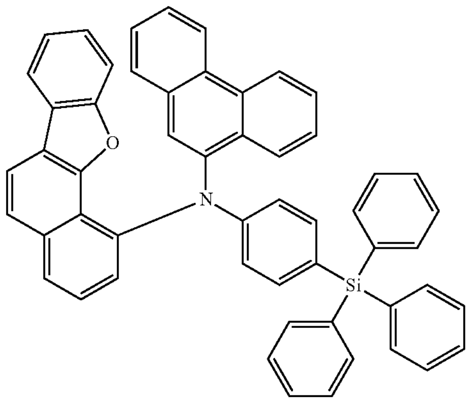
D111
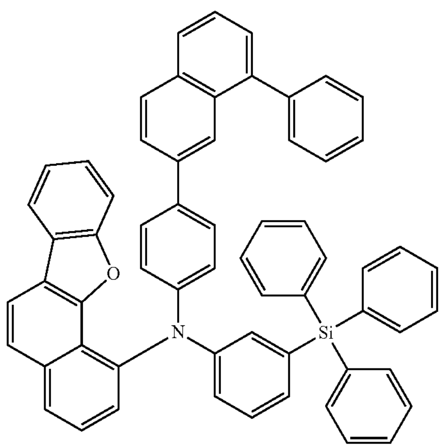
D112
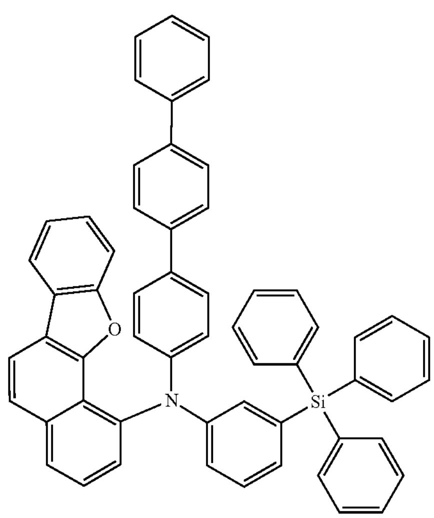
-continued
D113
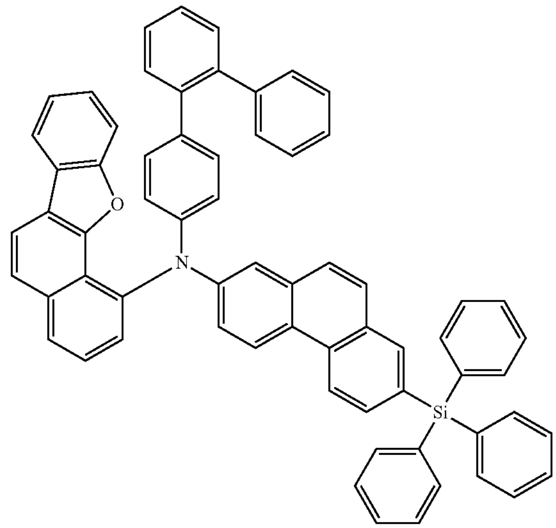
D114
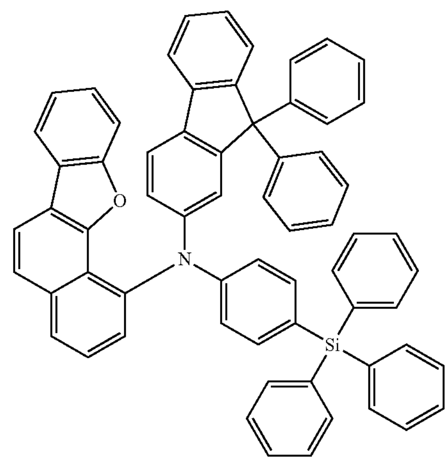
D115
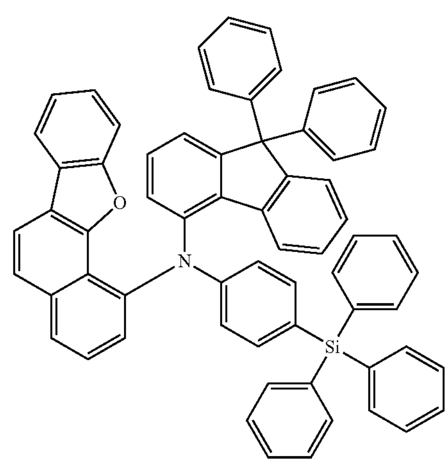

-continued
D116
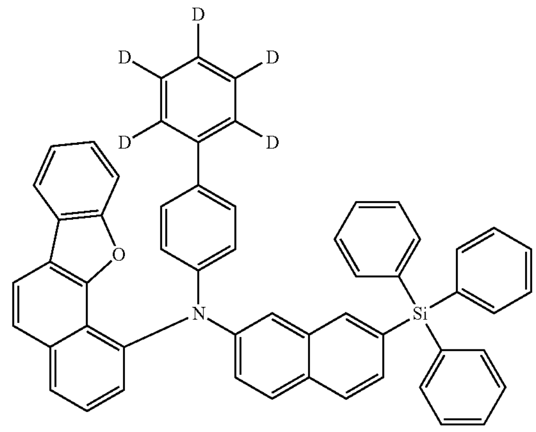
D117
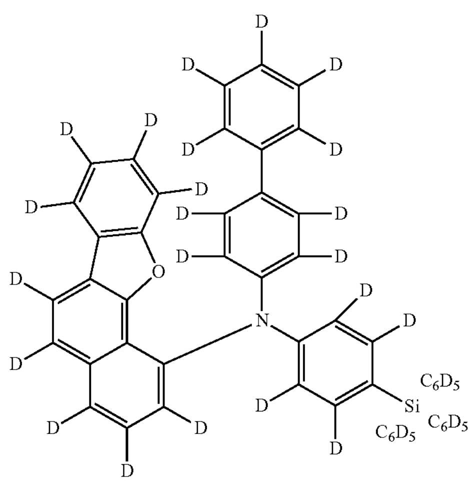
D118
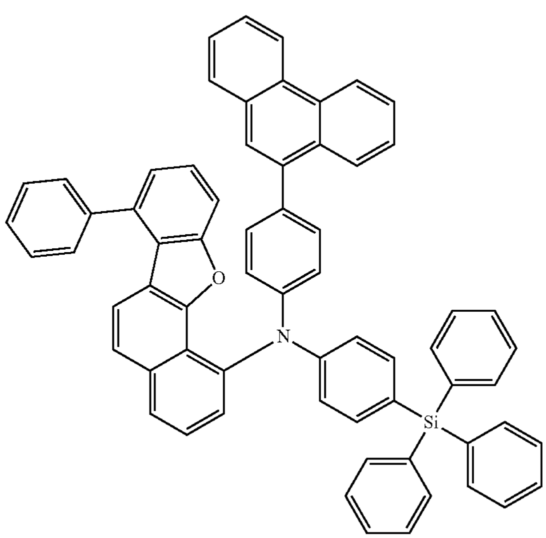
-continued
D119
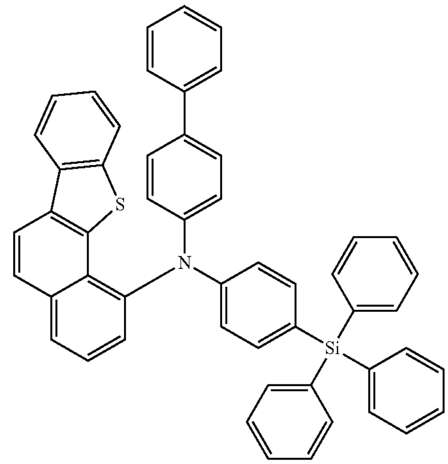
D120
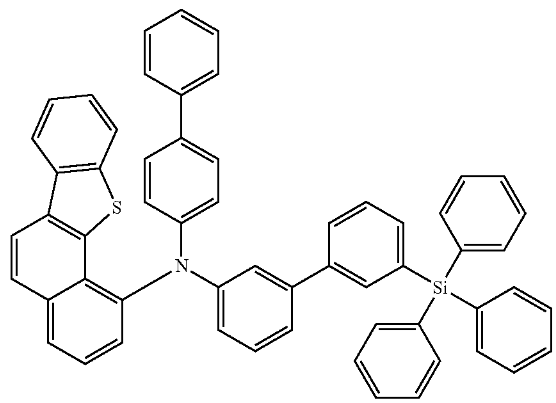
D121
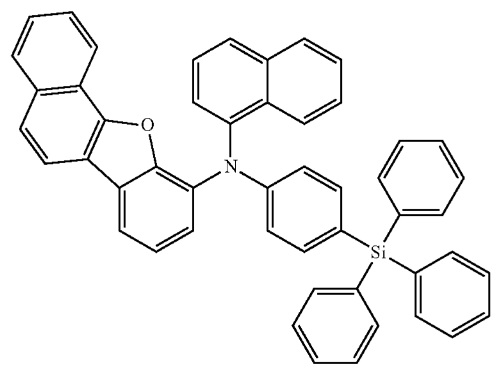

-continued
D122
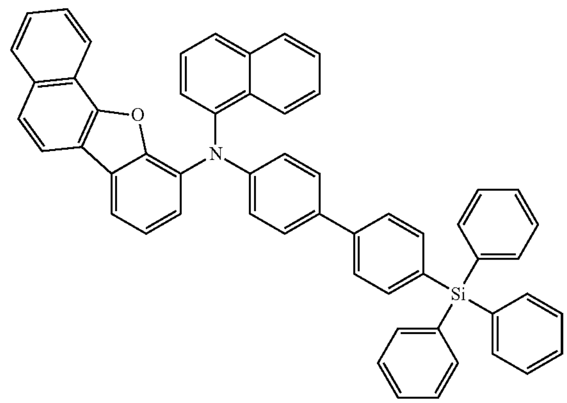
D123
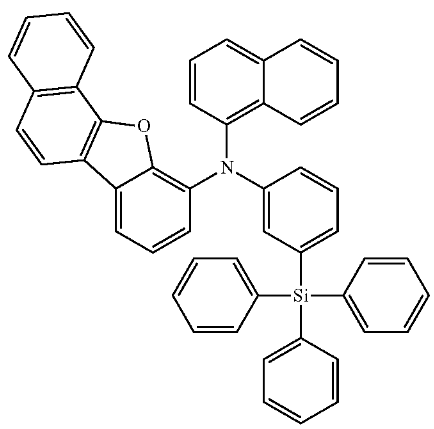
D124
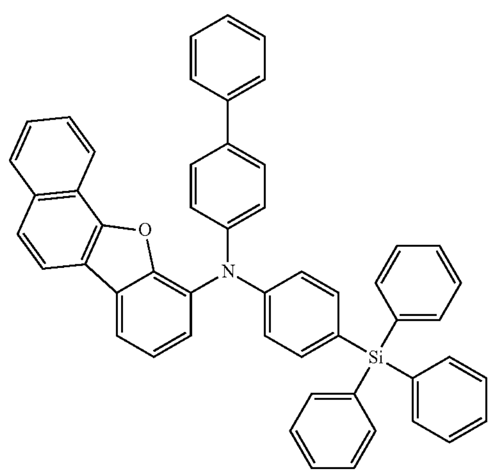
-continued
D125
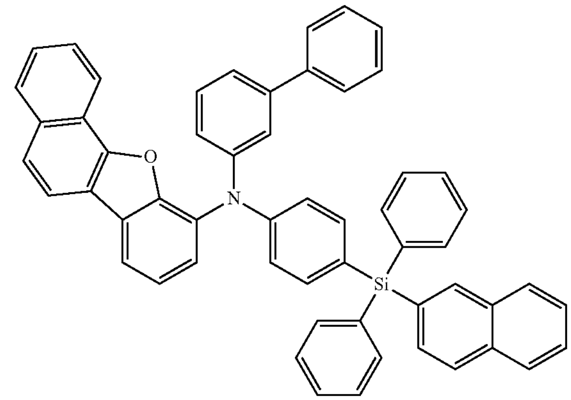
D126
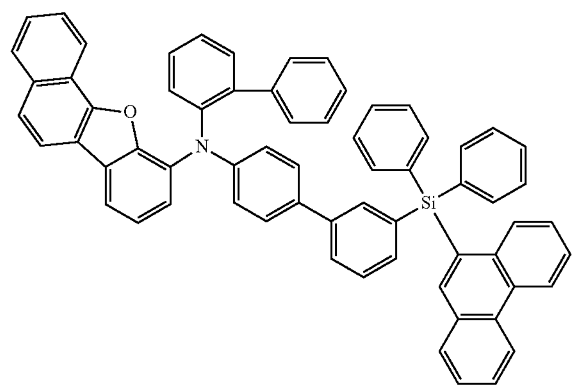
D127
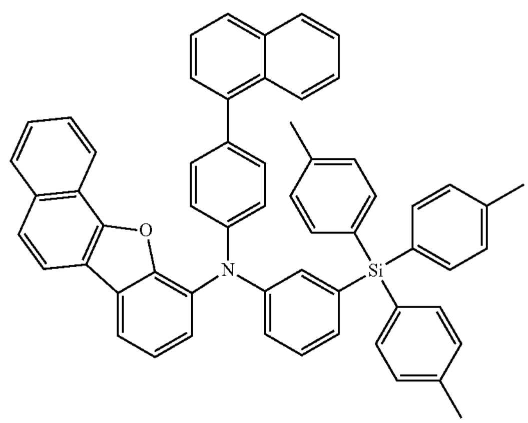

-continued
D128
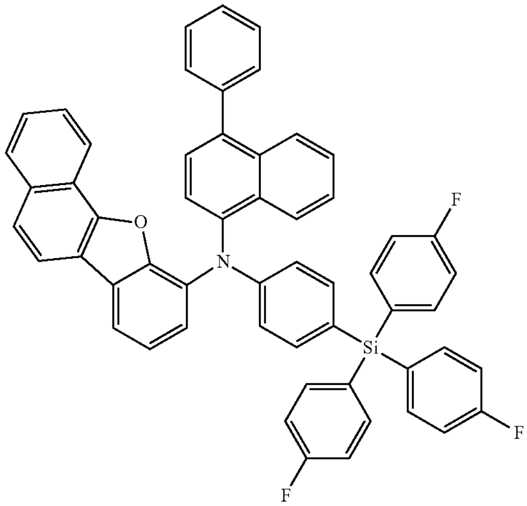
D129
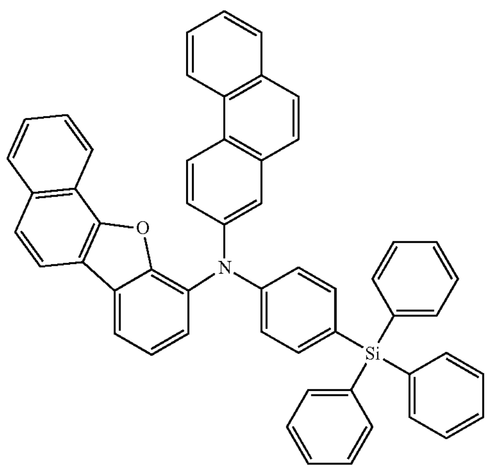
D130
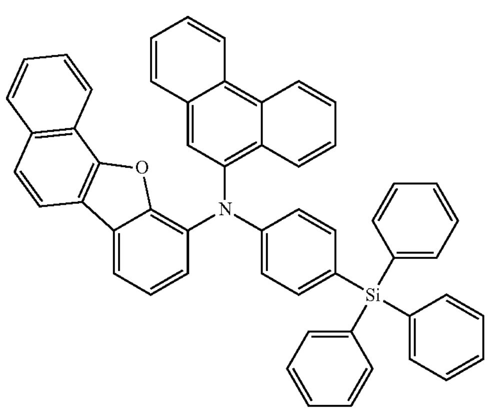
-continued
D131
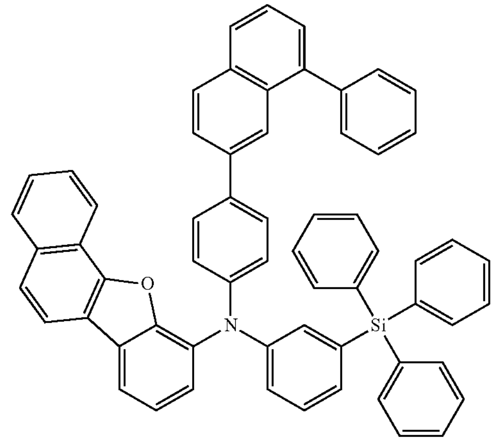
D132
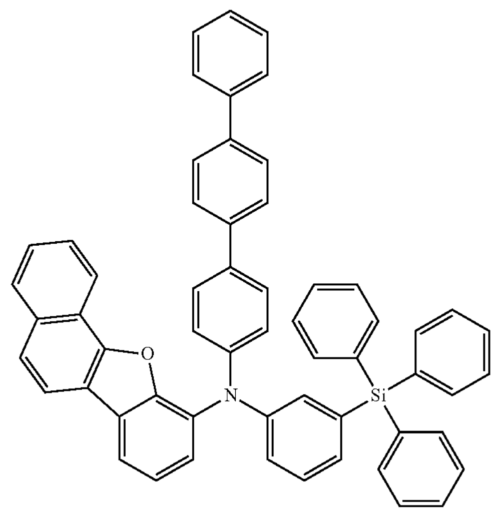
D133
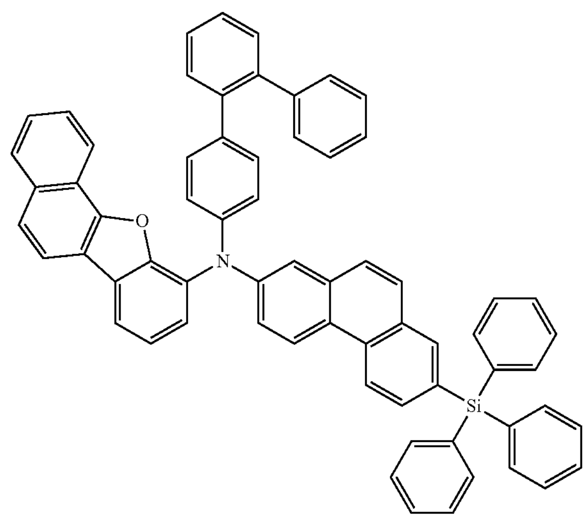

-continued
D134
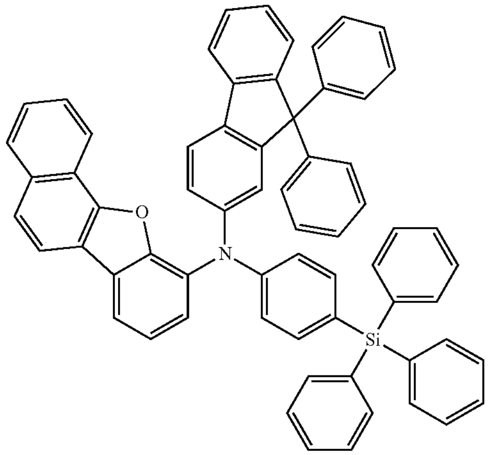
D135
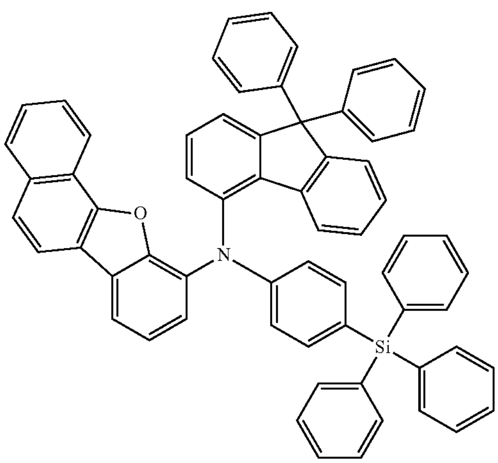
D136
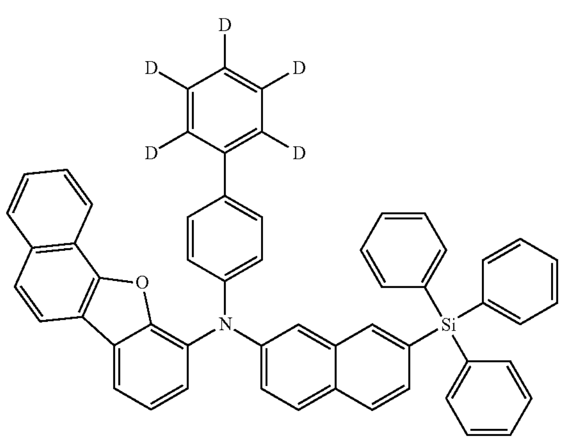
-continued
D137
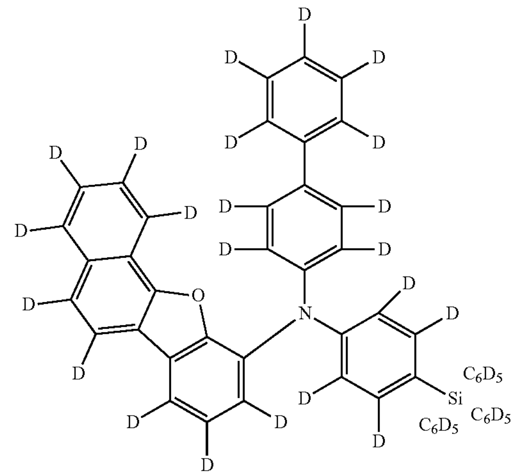
D138
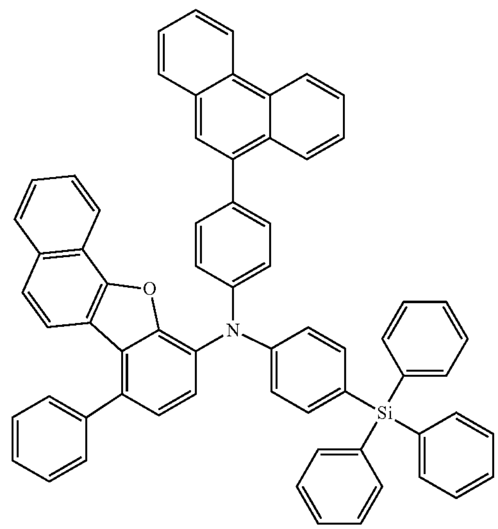
D139
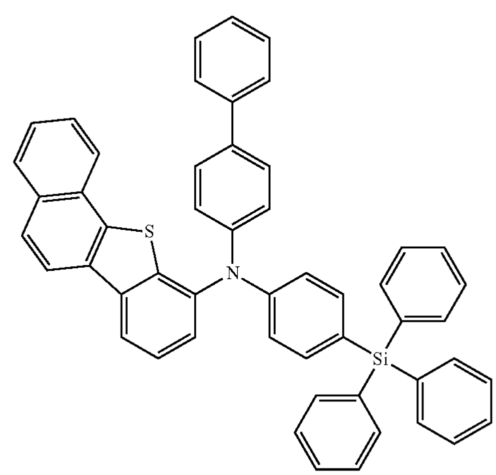

-continued
D140
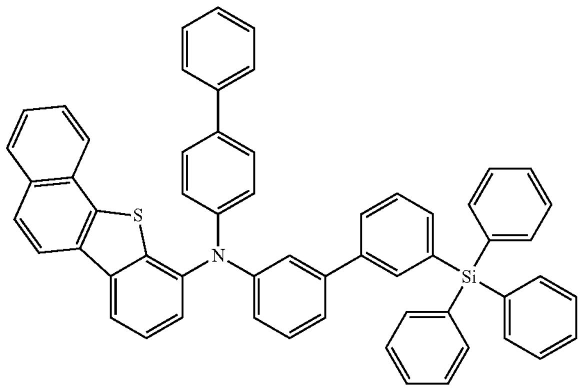
D141
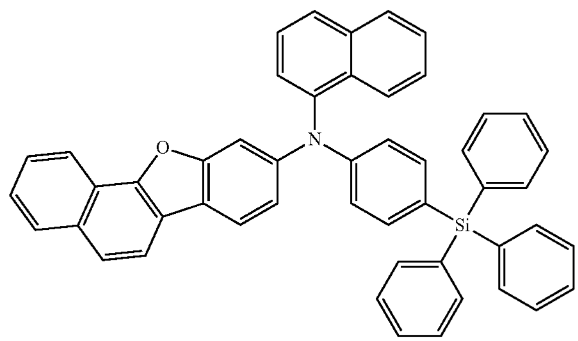
D142
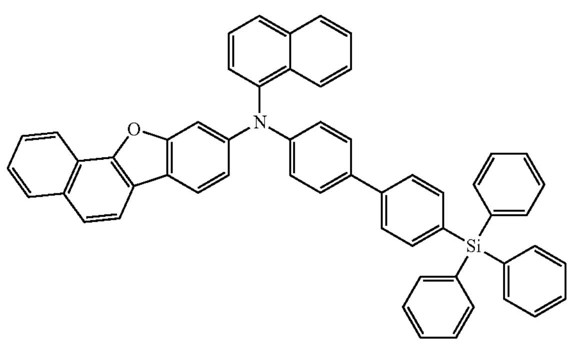
D143
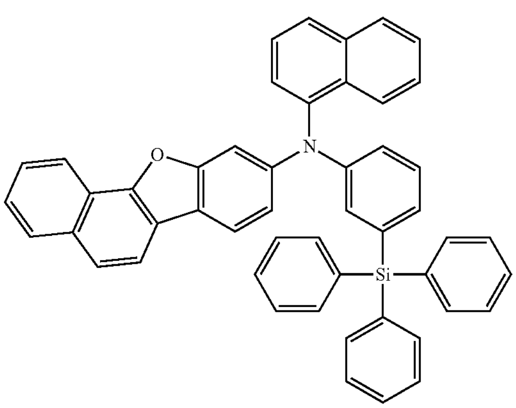
-continued
D144
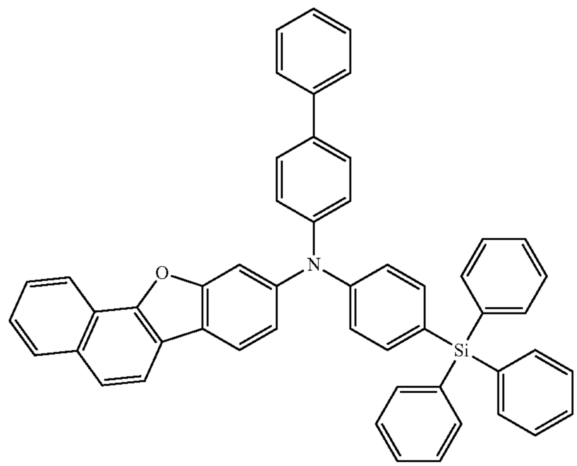
D145
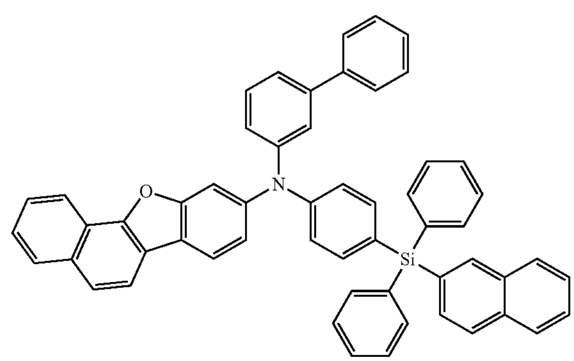
D146
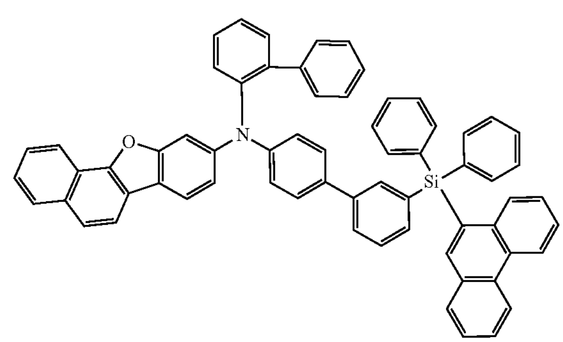

-continued
D147
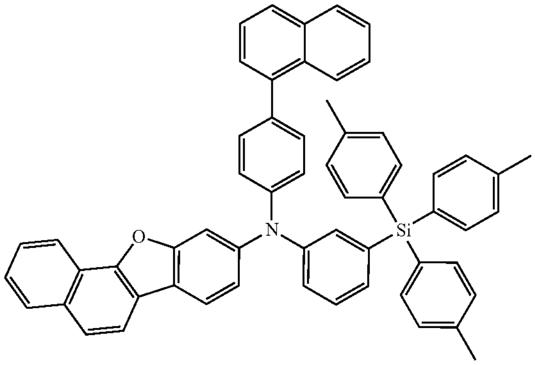
D148
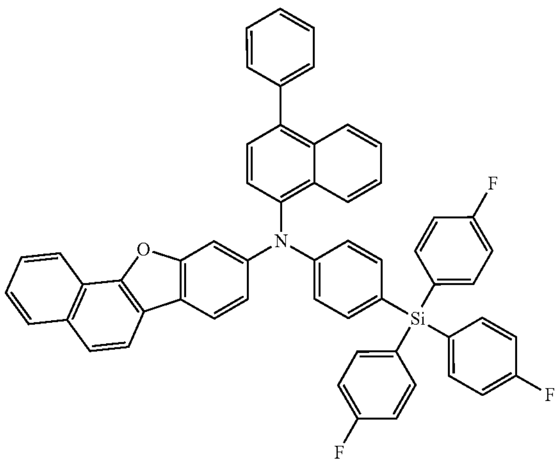
D149
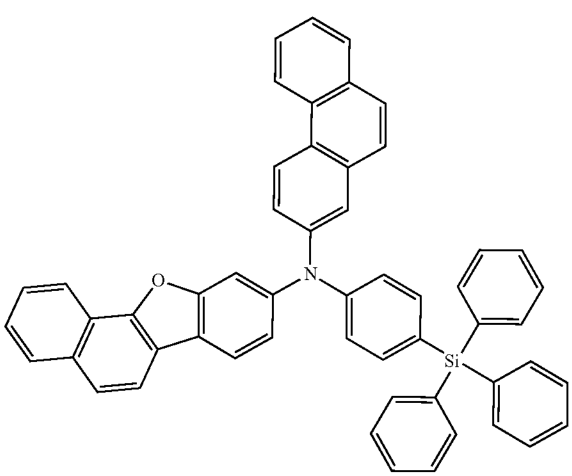
-continued
D150
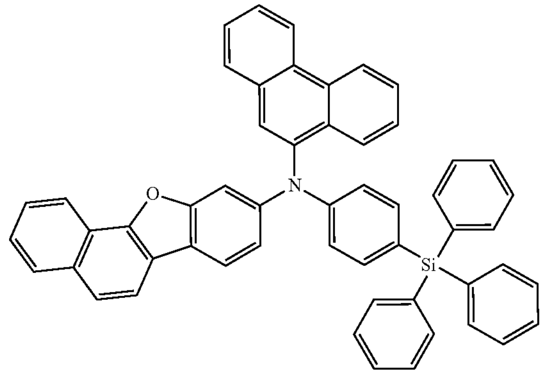
D151
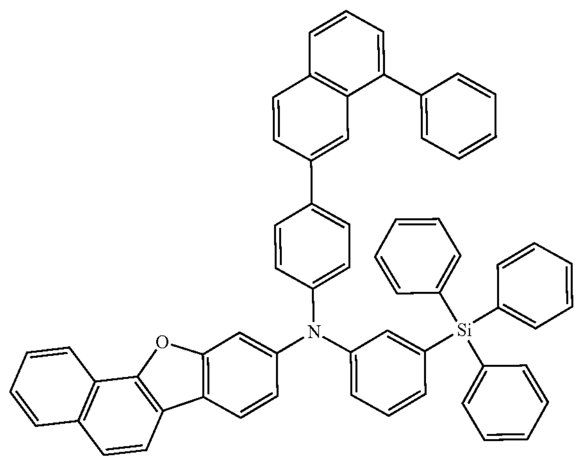
D152
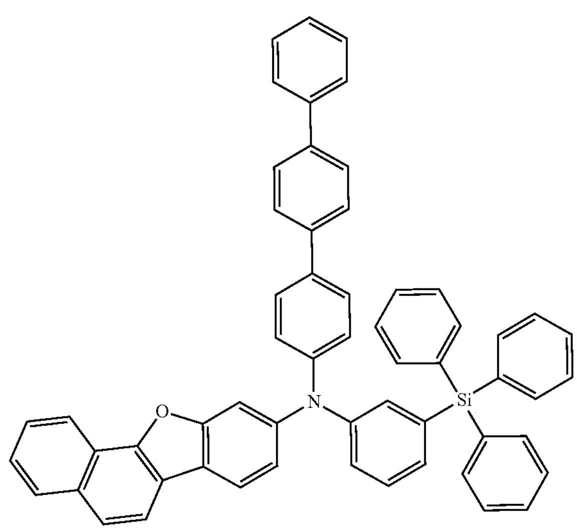

-continued
D153
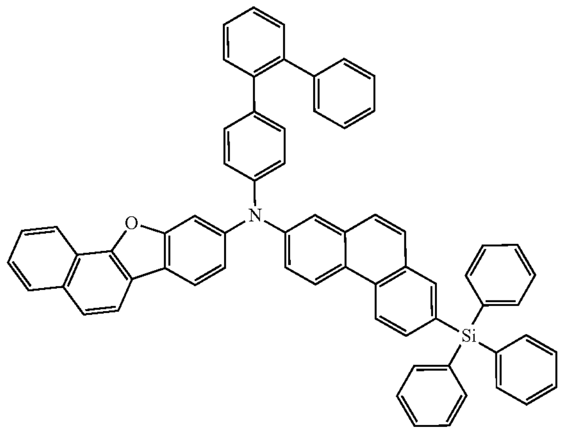
D154
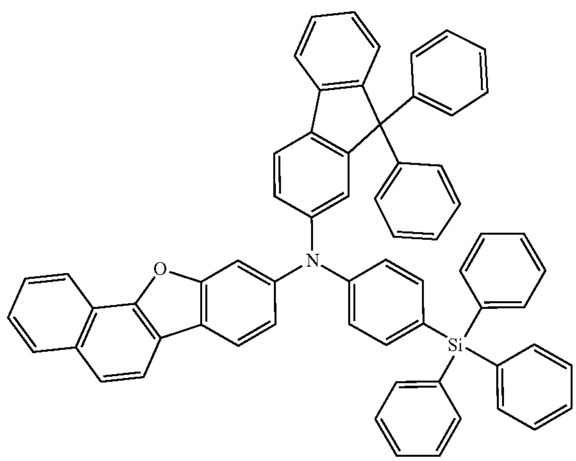
D155
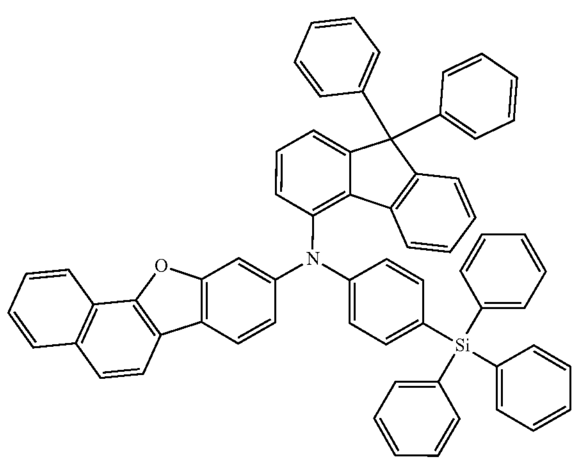
-continued
D156
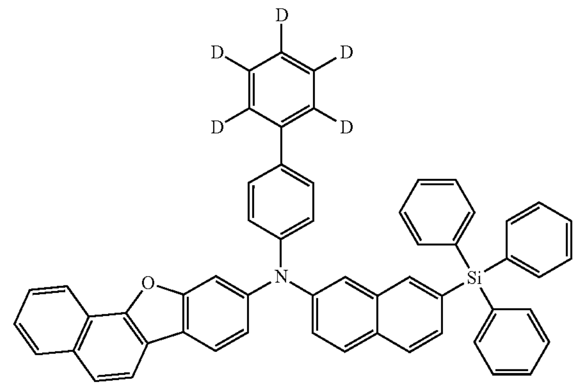
D158
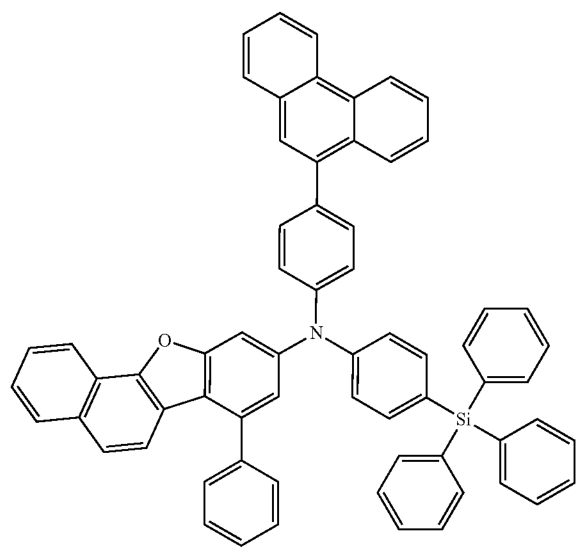
D159
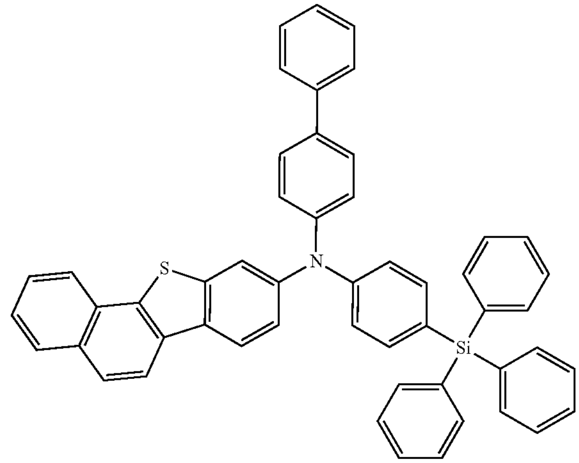

-continued
D160
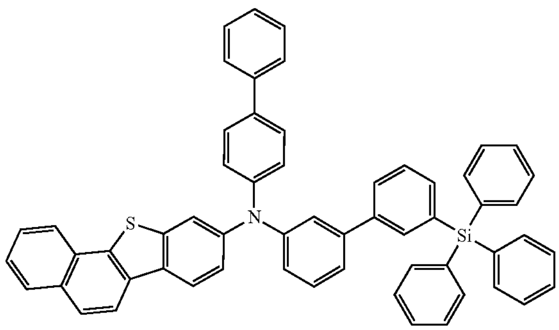
D161
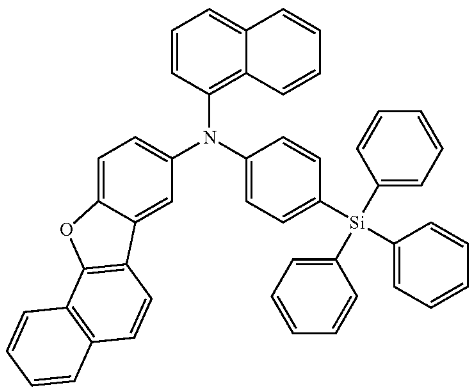
D162
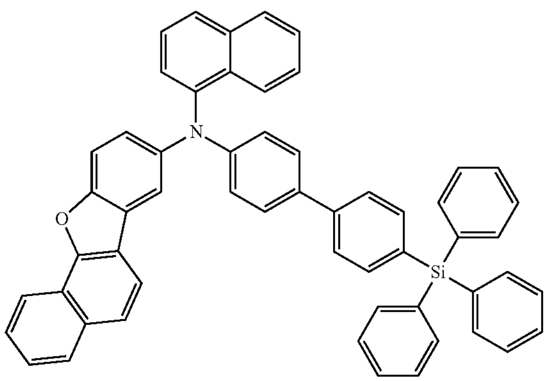
D163
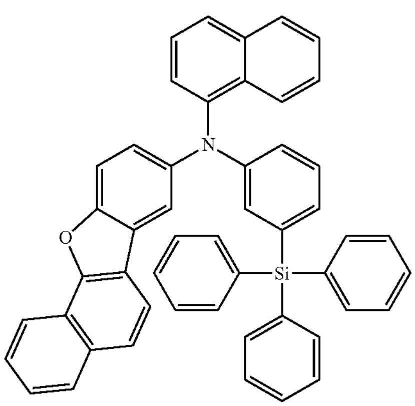
-continued
D164
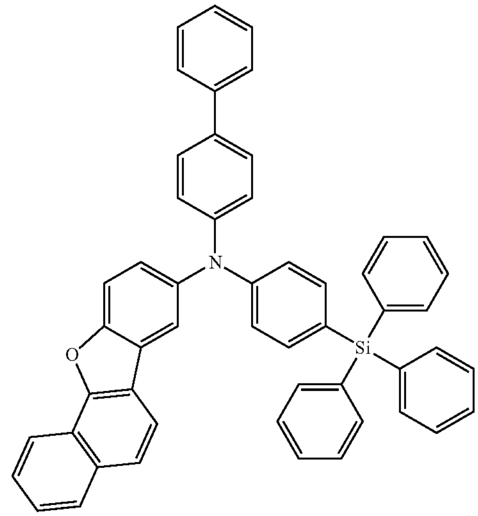
D165
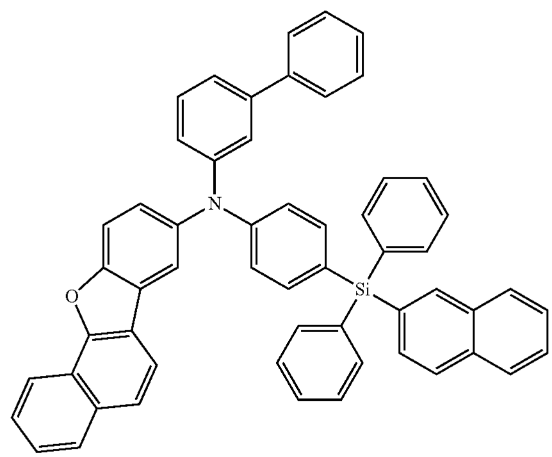
D166
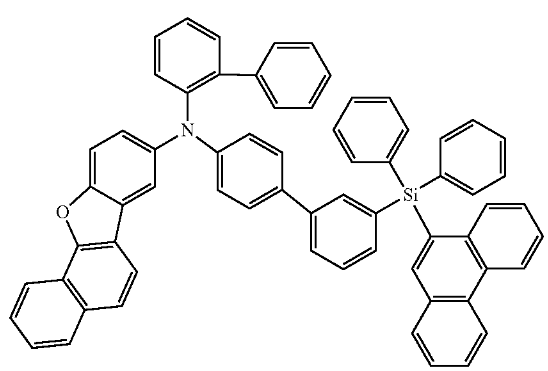

-continued
D167
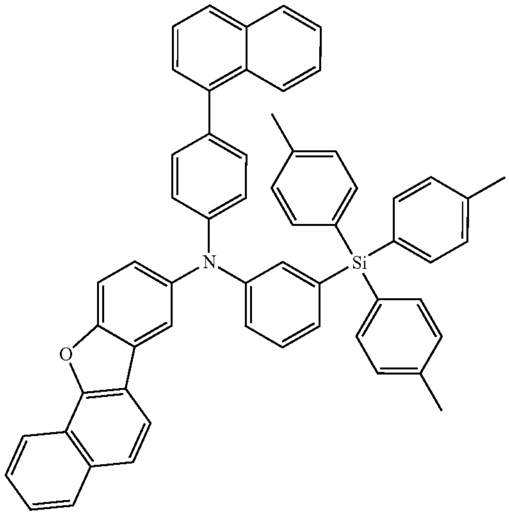
D168
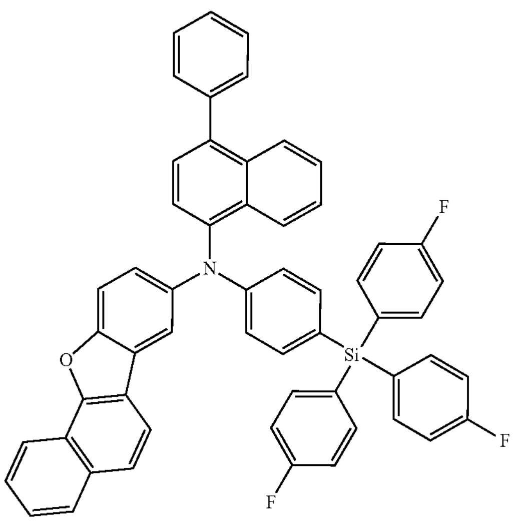
D169
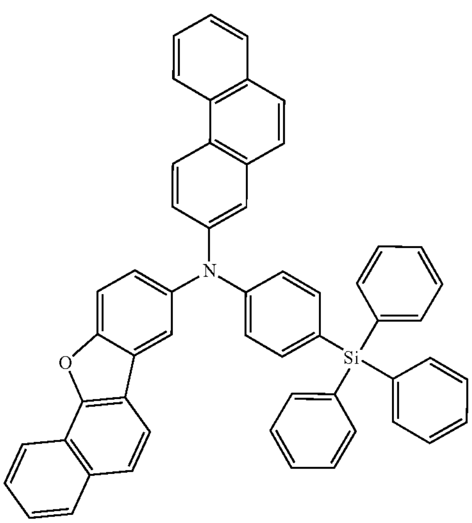
-continued
D170
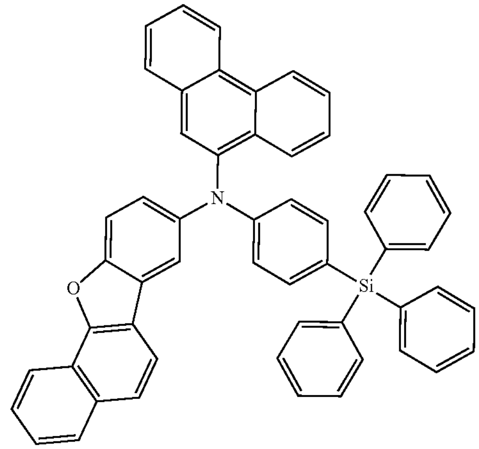
D171
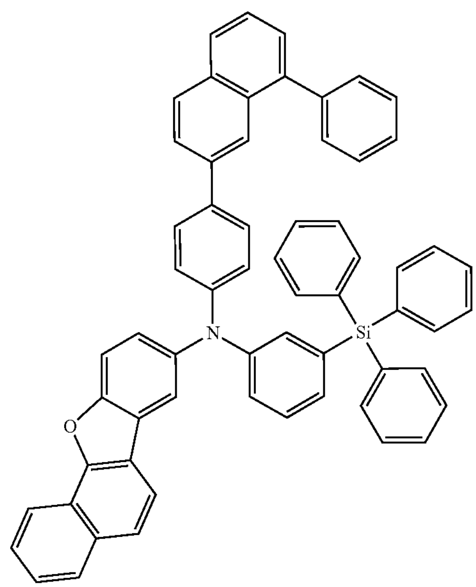

-continued
D172
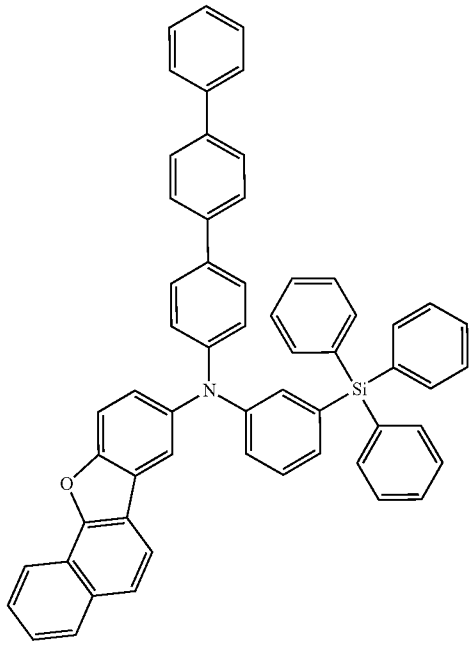
D173
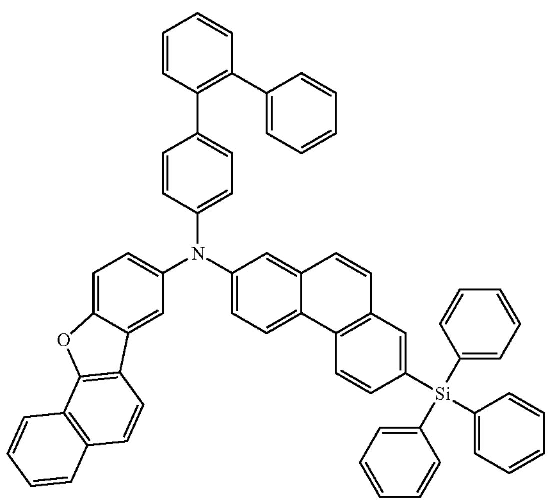
D174
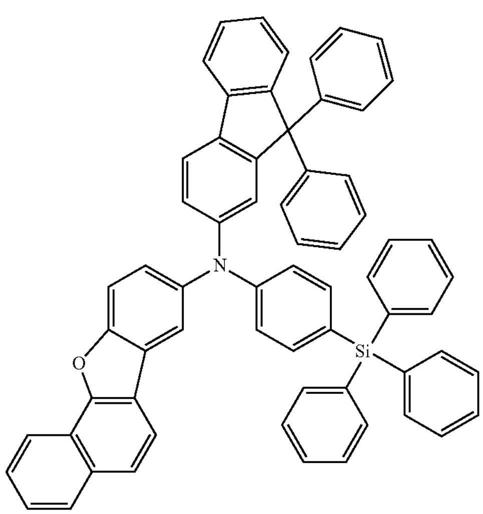
-continued
D175
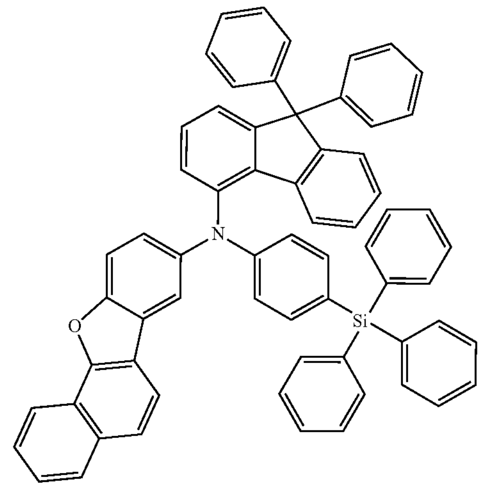
D176
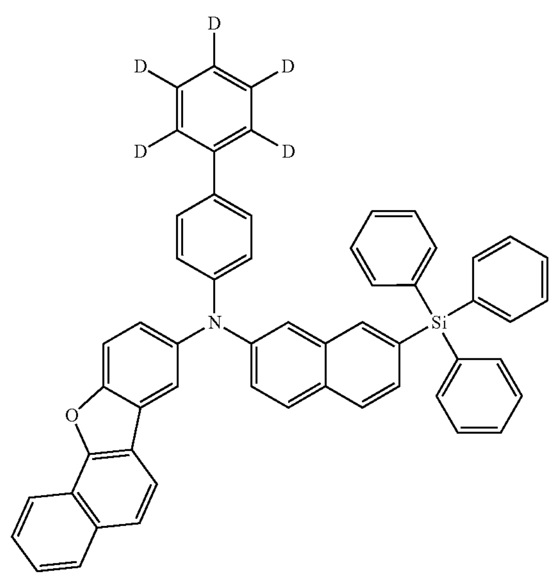

-continued
D177
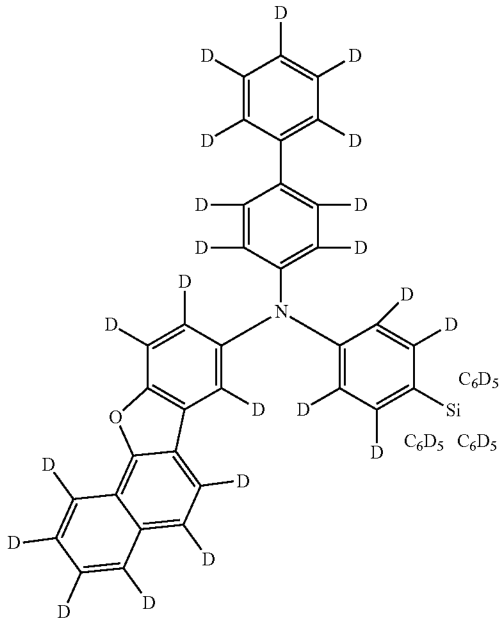
D178
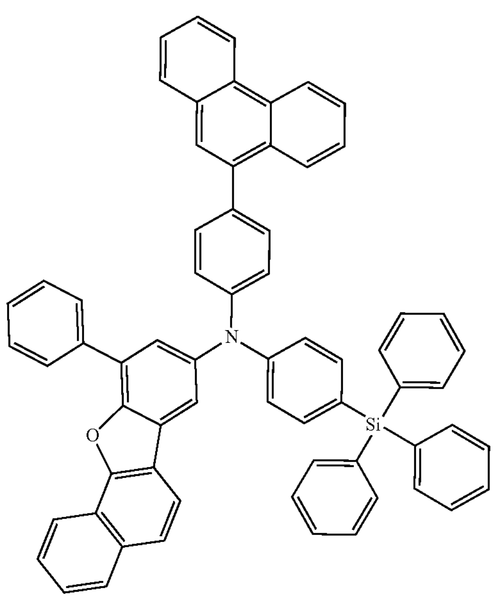
-continued
D179
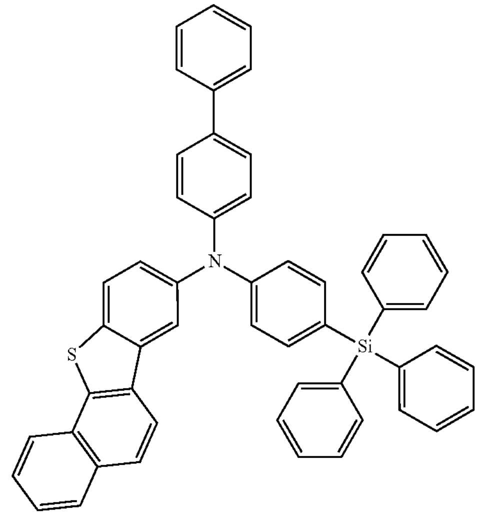
D180
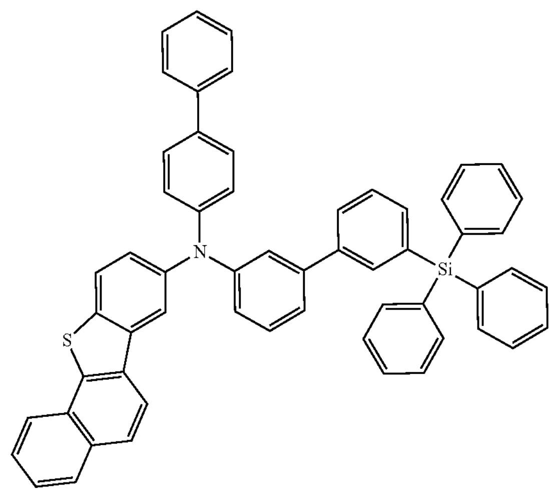
D181
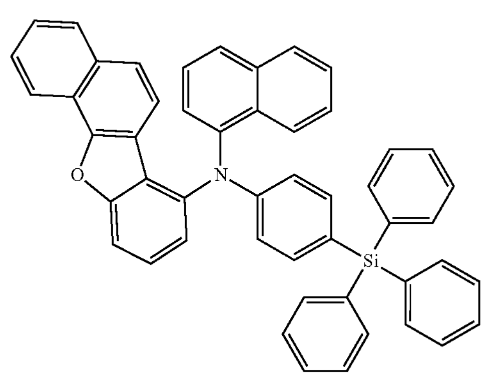

-continued
D182
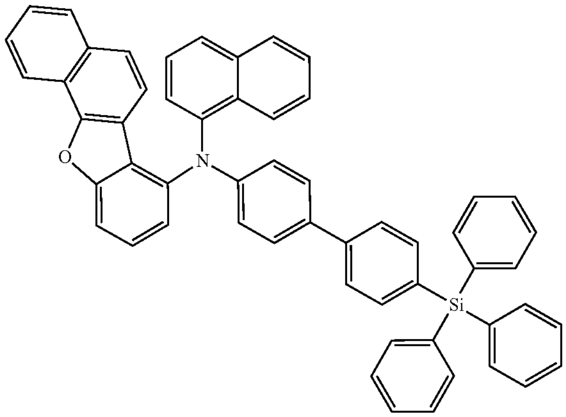
D183
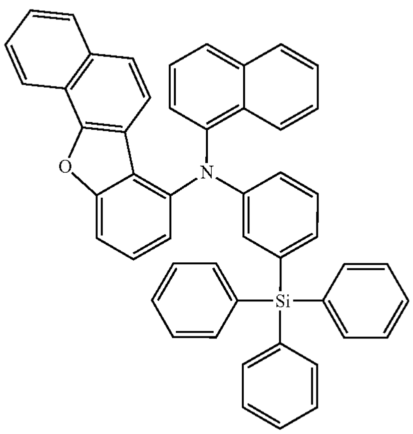
D184
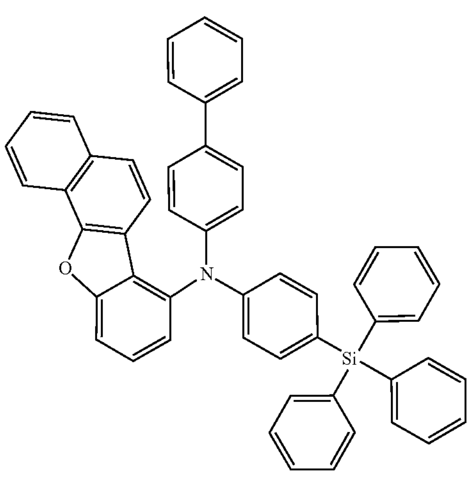
-continued
D185
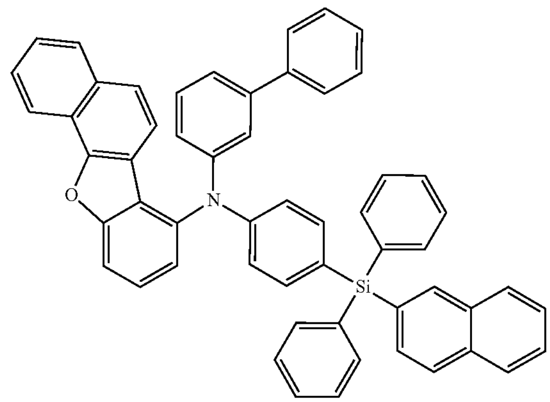
D186
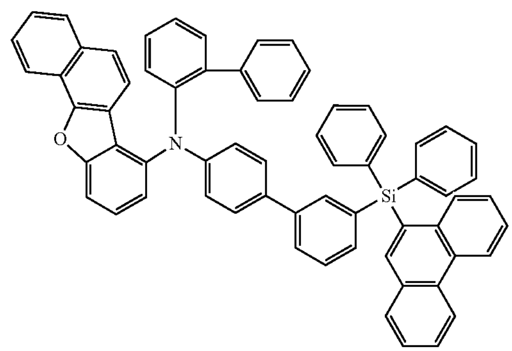
D187
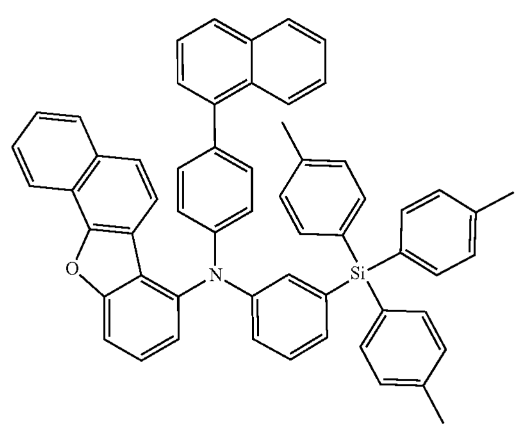

-continued
D188
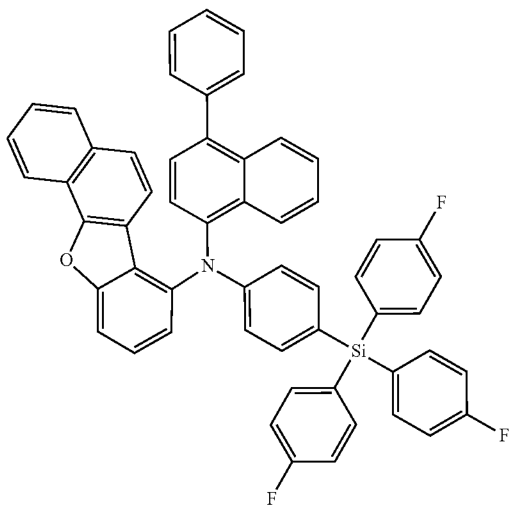
D189
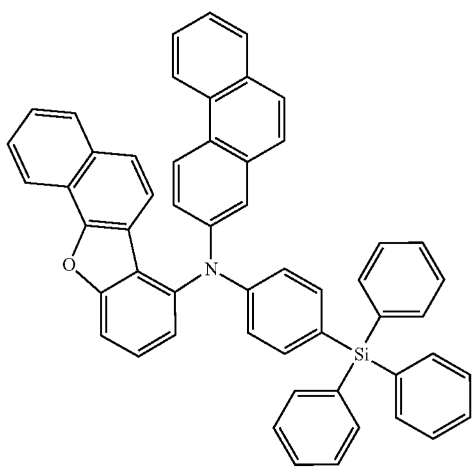
D190
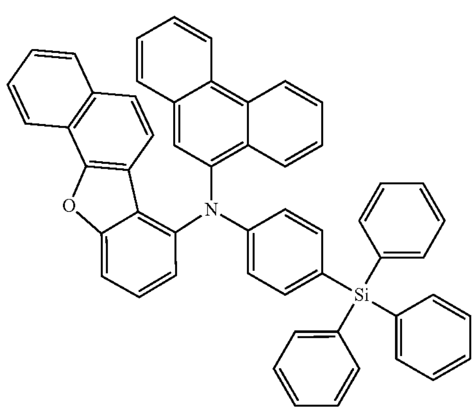
-continued
D191
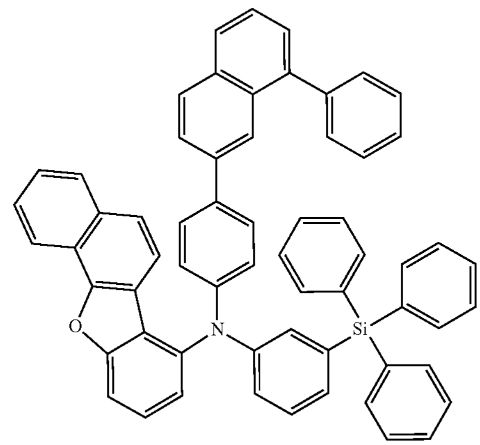
D192
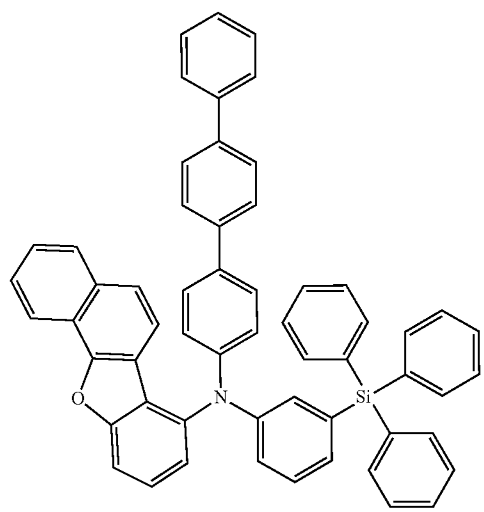
D193
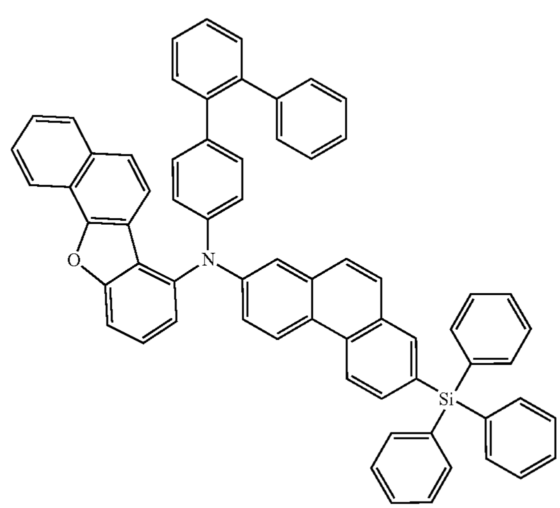

-continued
D194
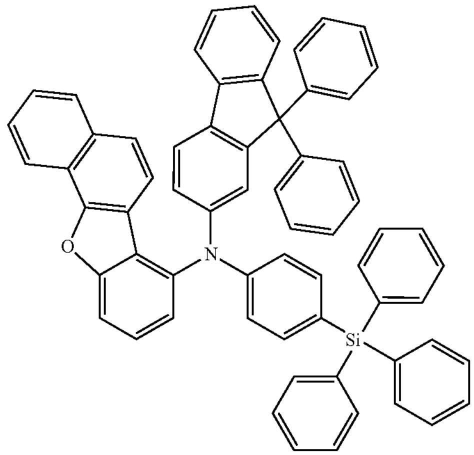
D195
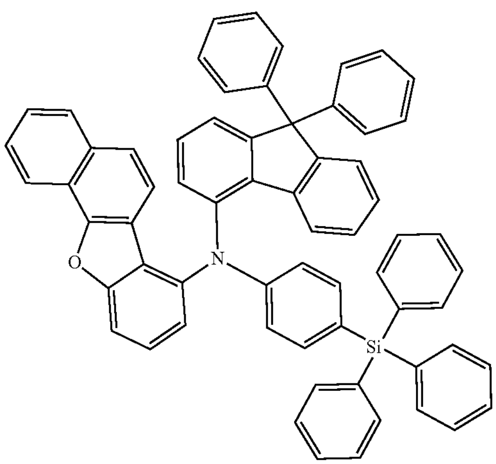
D196
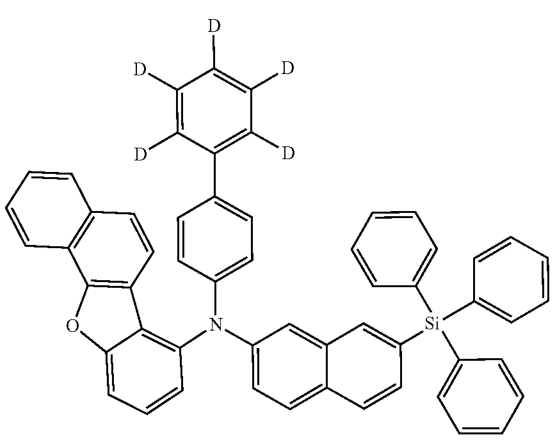
-continued
D197
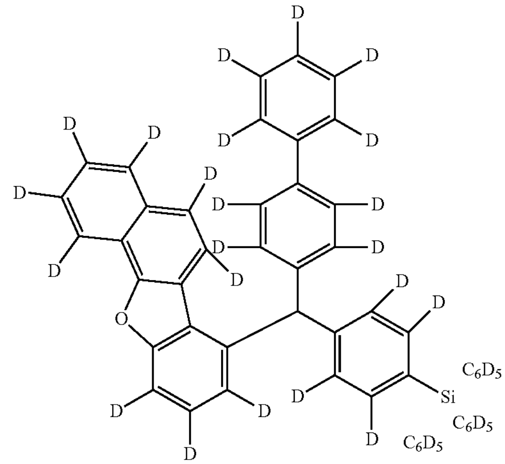
D198
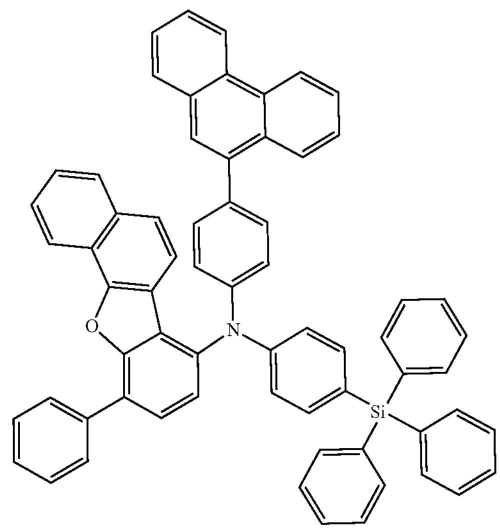
D199
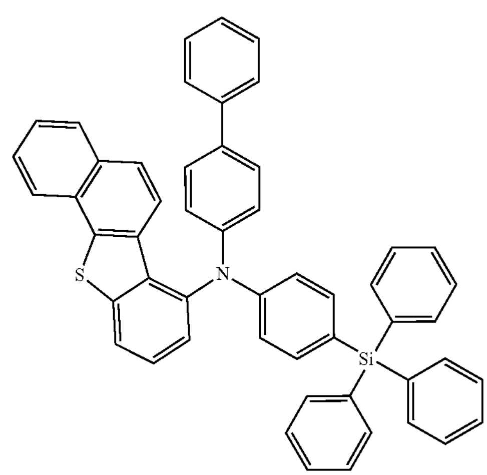

-continued
D200
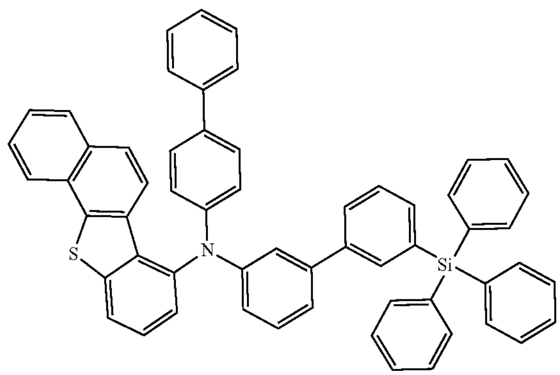
D57
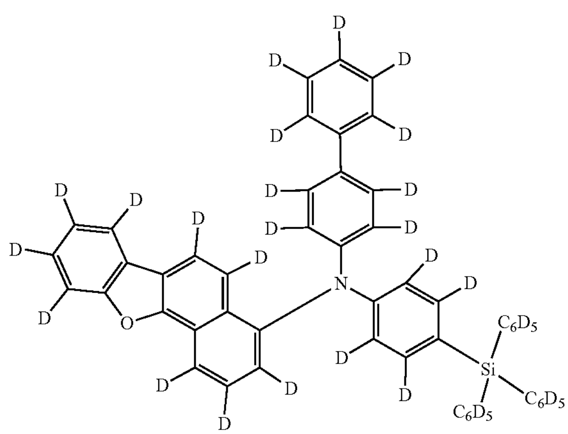
D77
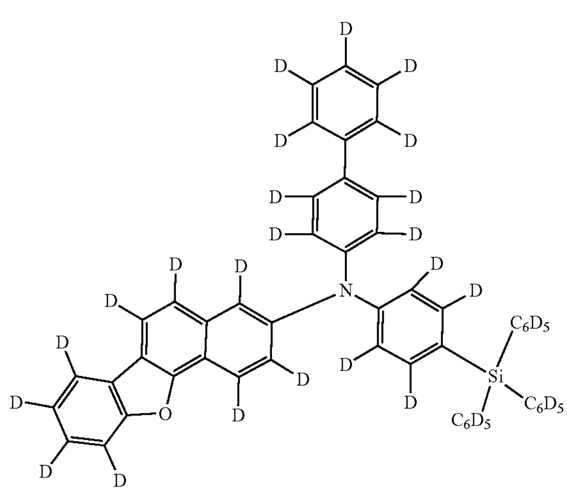
-continued
D97
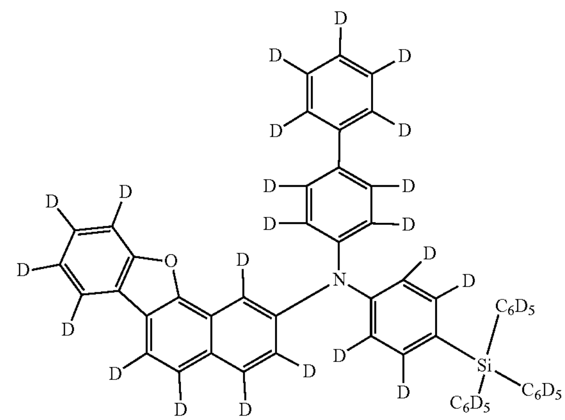
D157
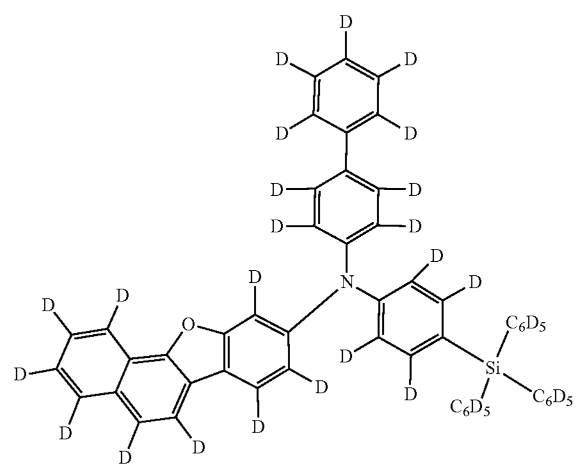
[Compound Group 5]
E1
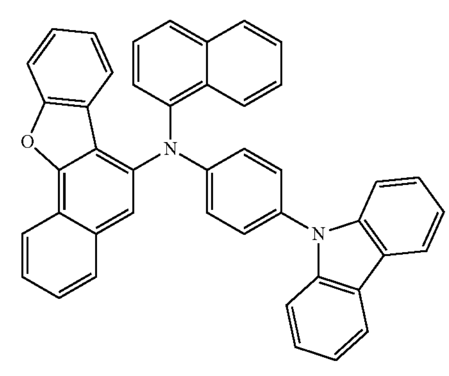

-continued
E2
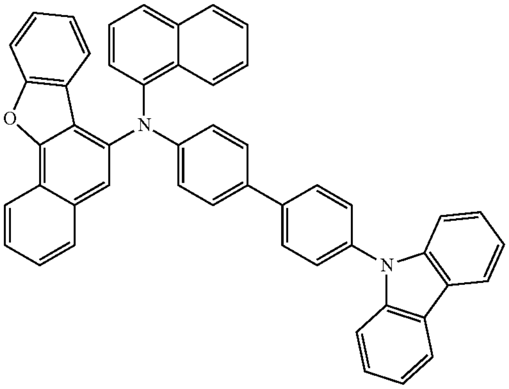
E3
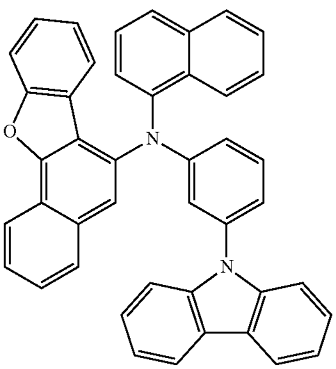
E4
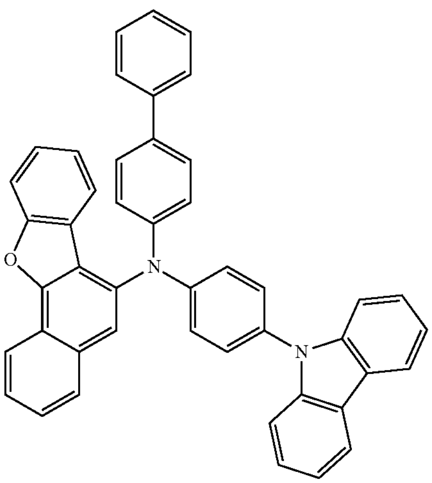
5
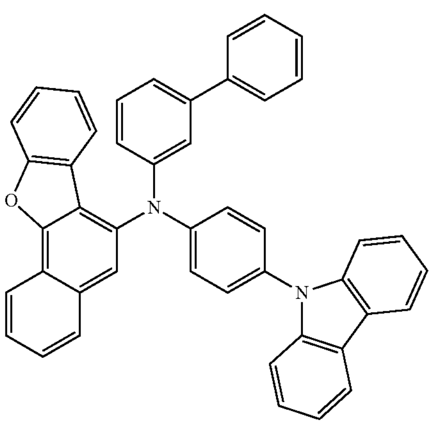
-continued
E6
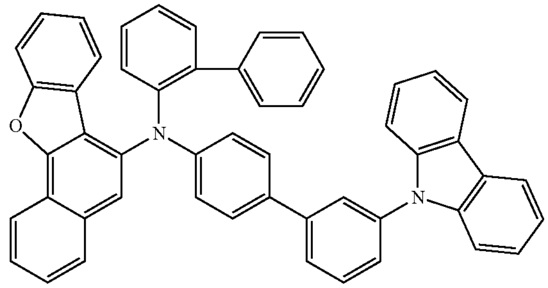
E7
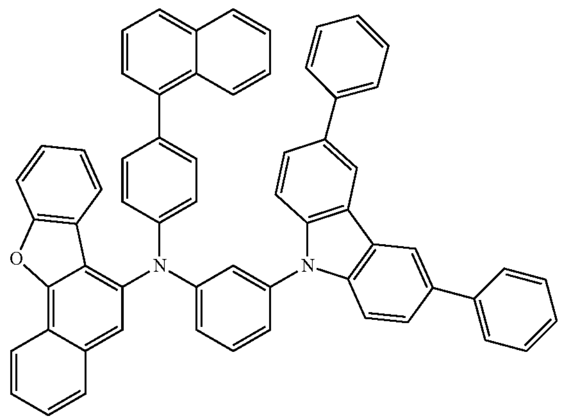
E8
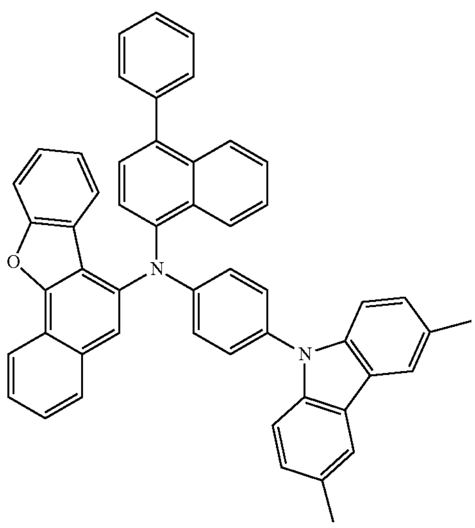

-continued
E9
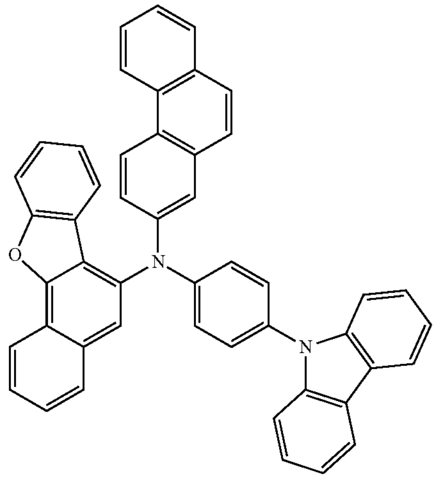
E10
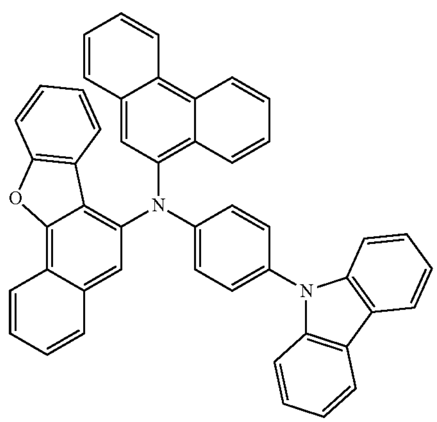
E11
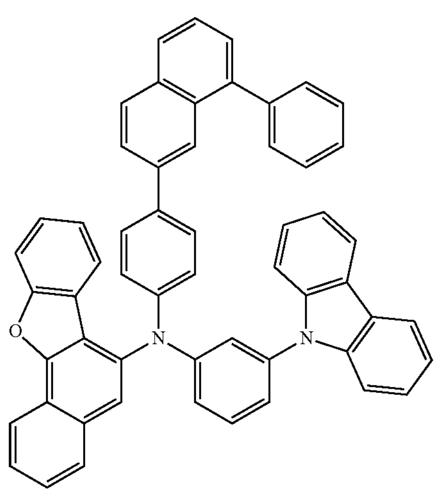
-continued
E12
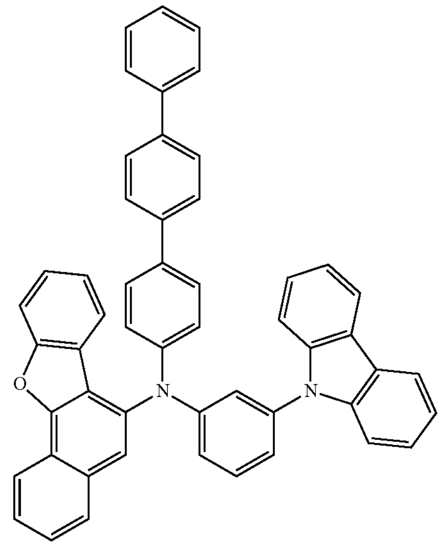
E13
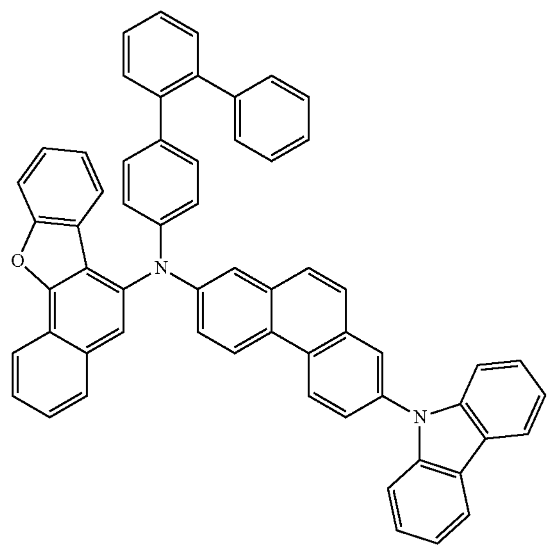
E14
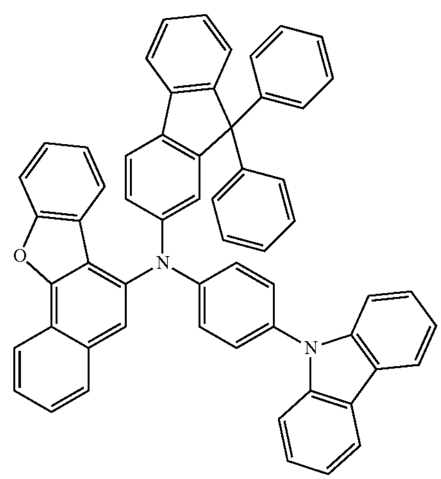

-continued
E15
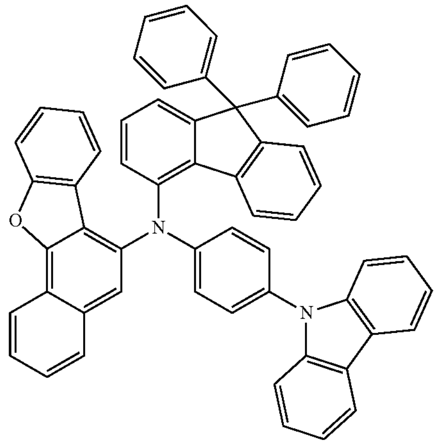
E16
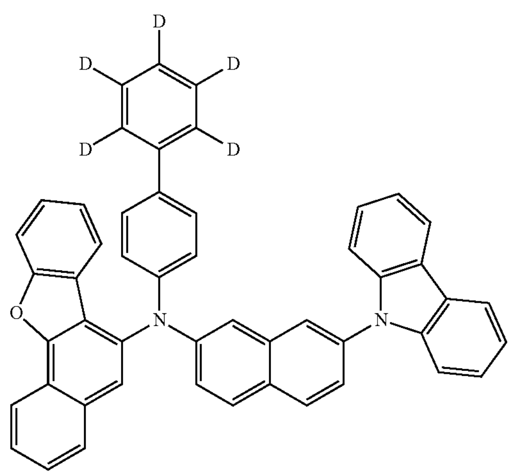
E17
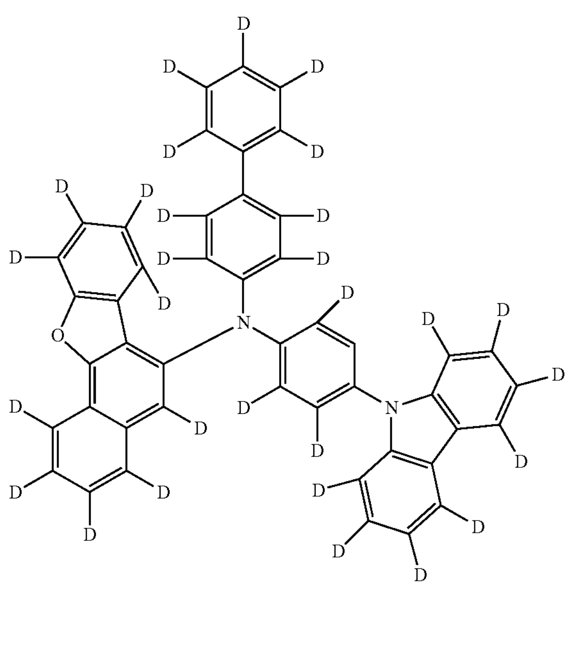
-continued
E18
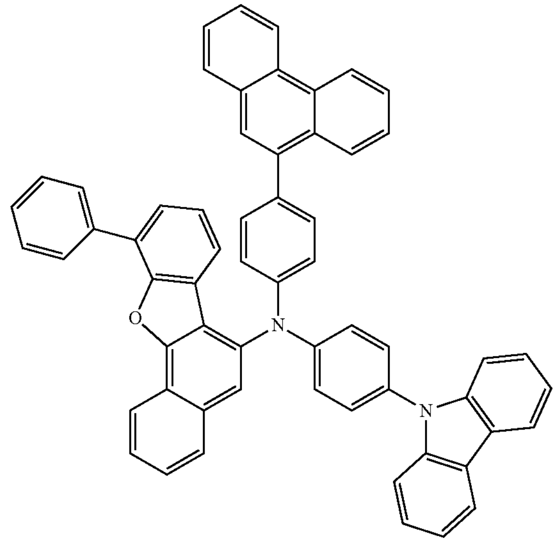
E19
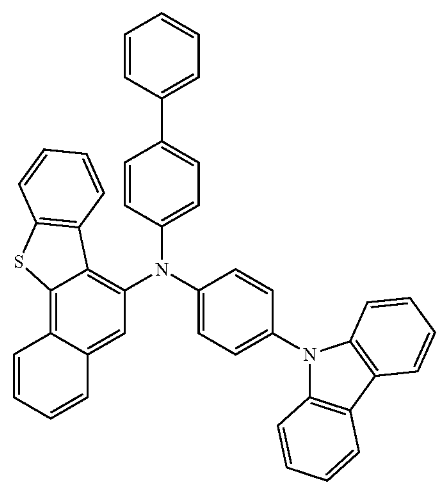
E20
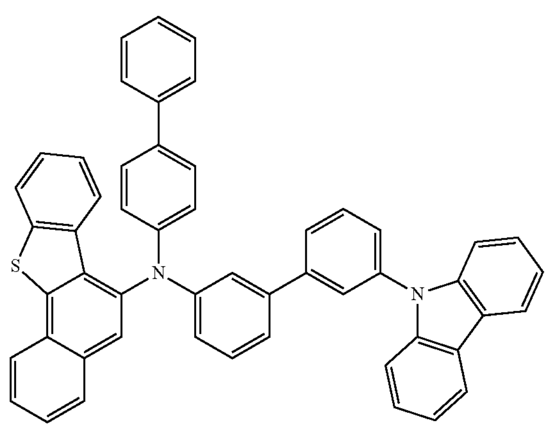

-continued
E21
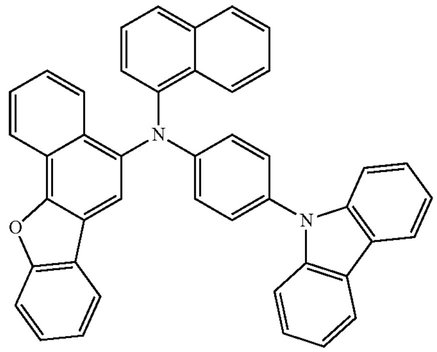
E22
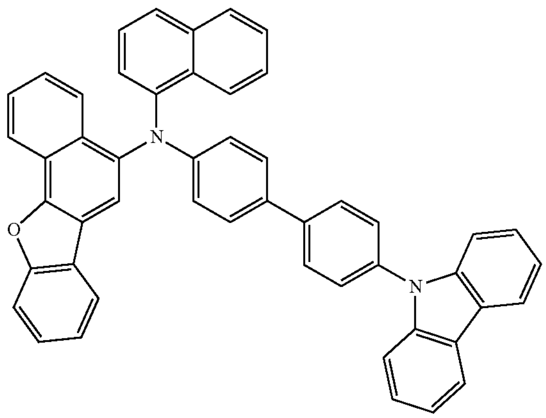
E23
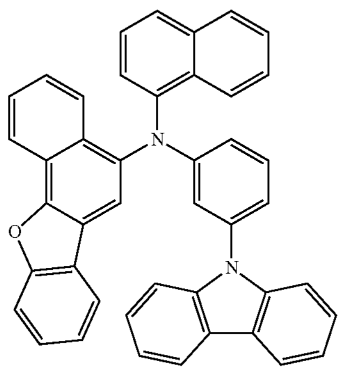
E24
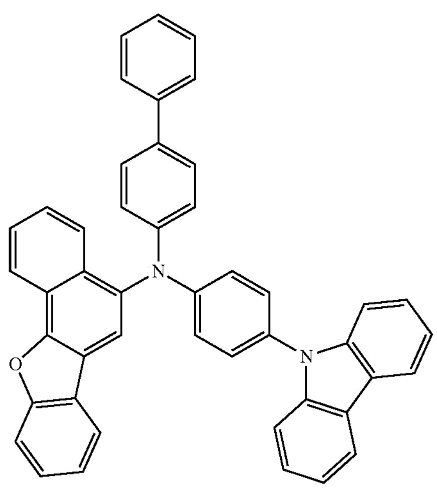
-continued
E25
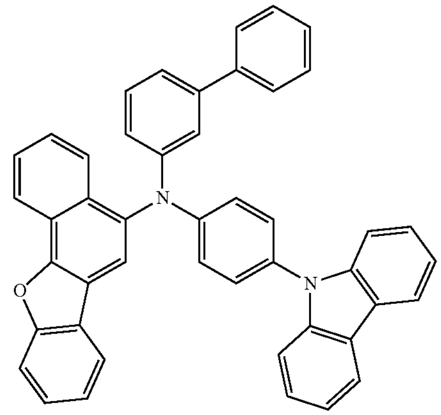
E26
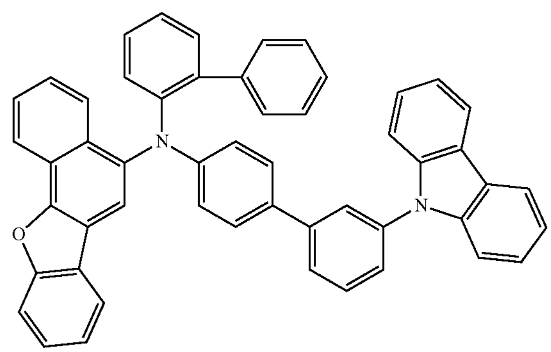
27
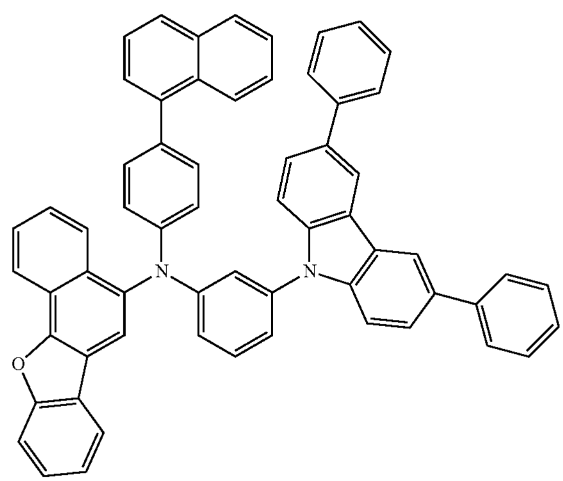

-continued
E28
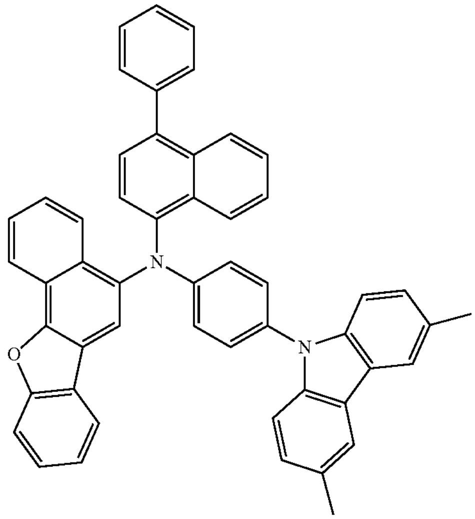
E29
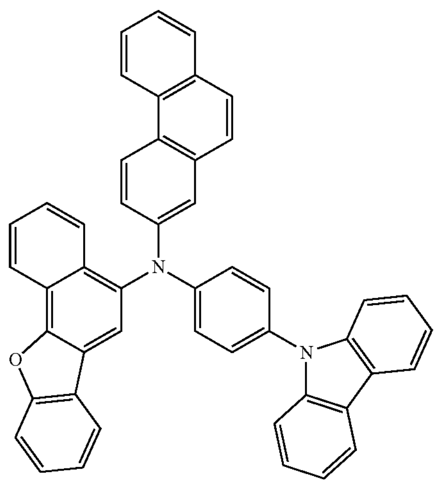
E30
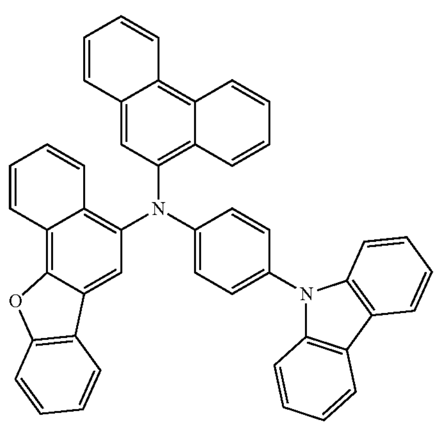
-continued
E31
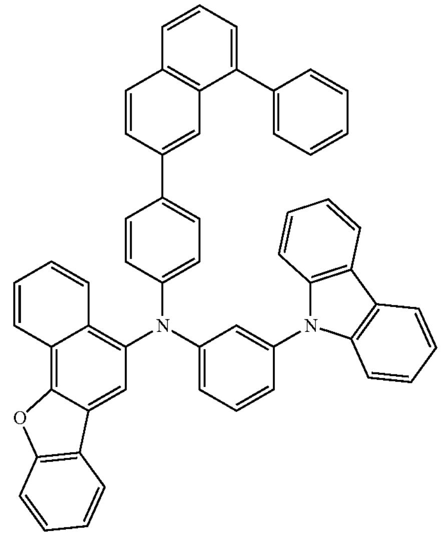
E32
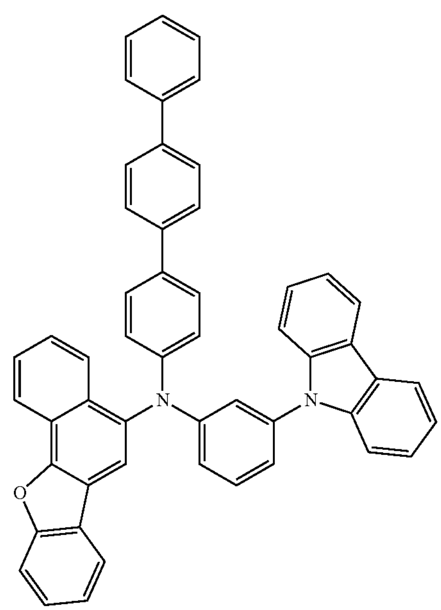

-continued
E33
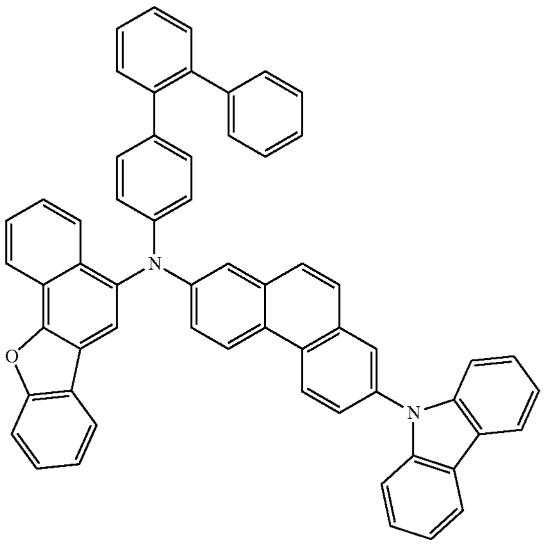
E34
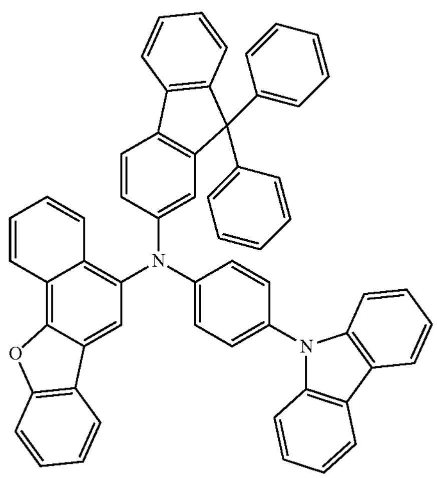
E35
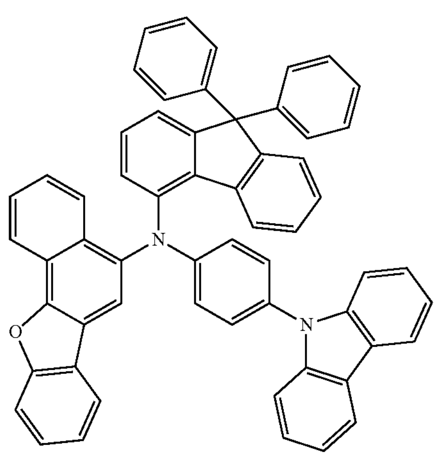
-continued
E36
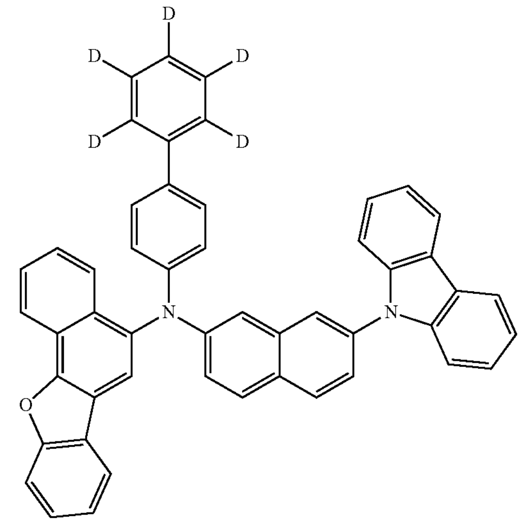
E37
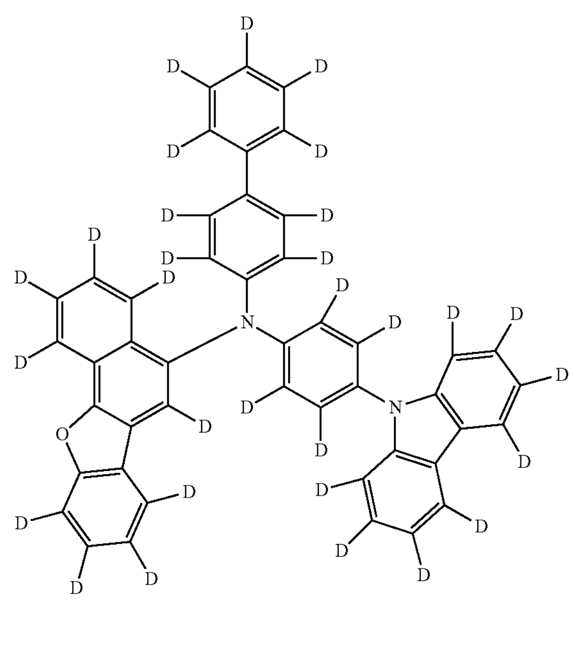

-continued
E38
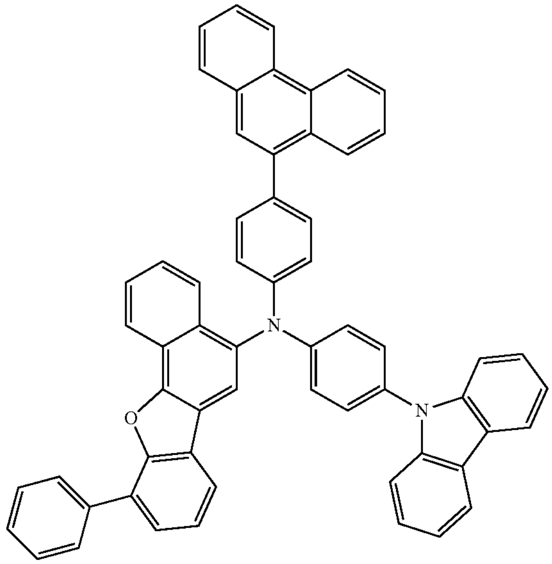
E39
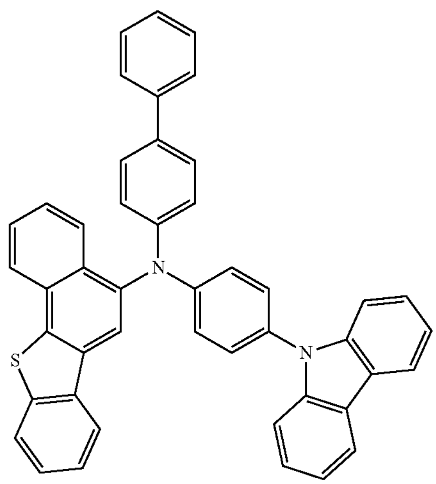
E40
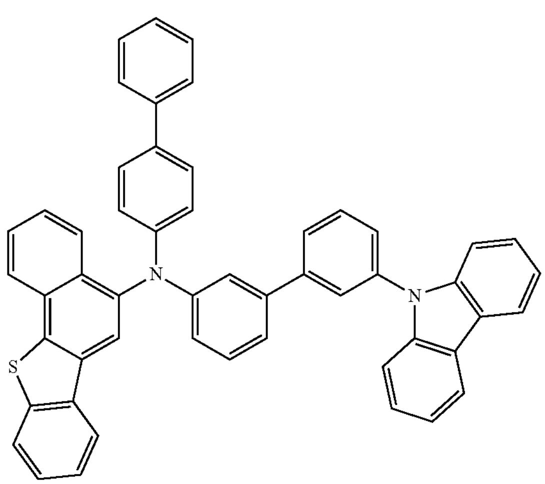
-continued
E41
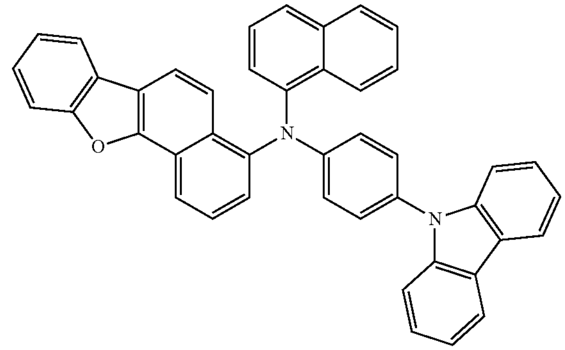
E42
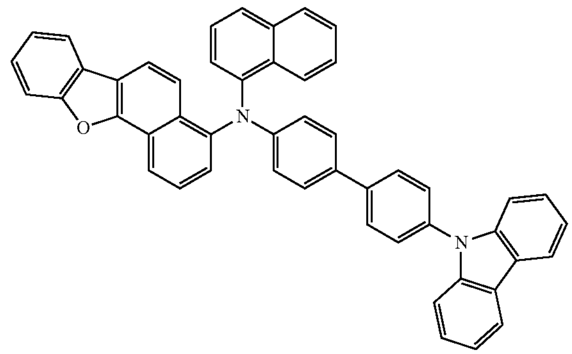
E43
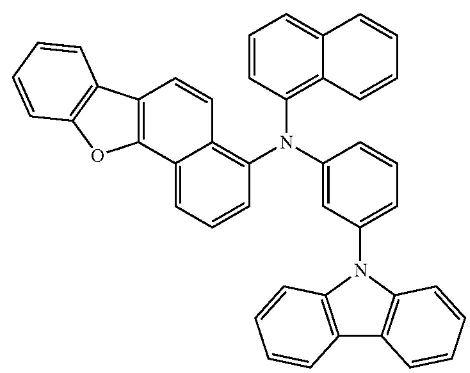
E44
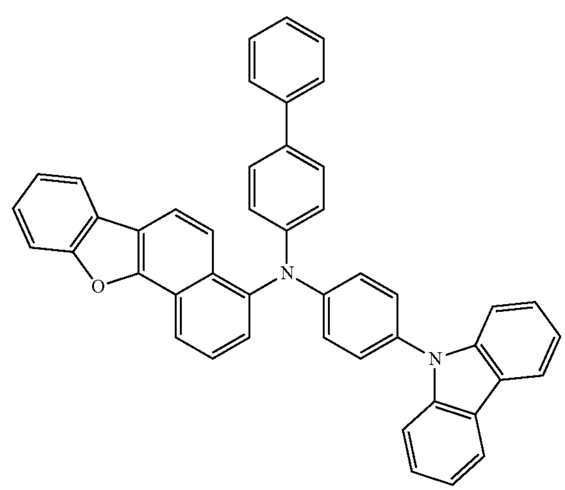

-continued
E45
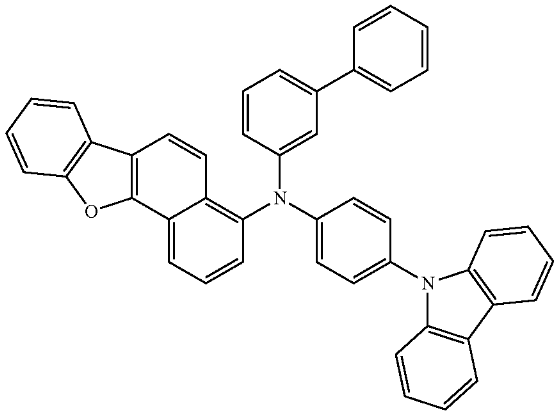
E46
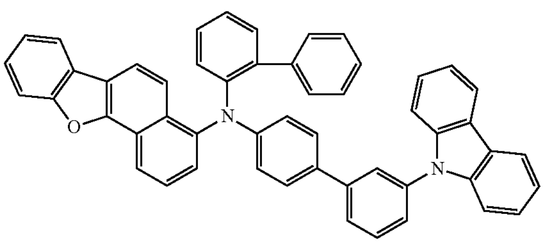
E47
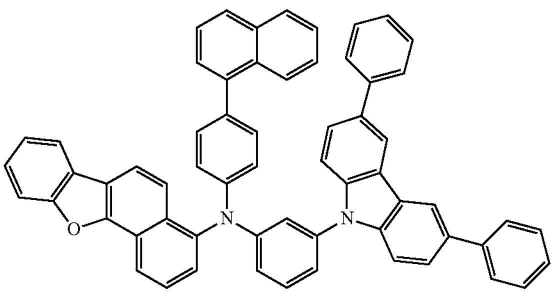
E48
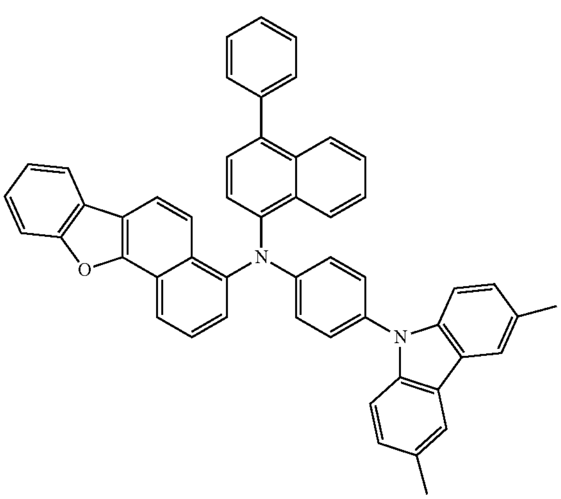
-continued
E49
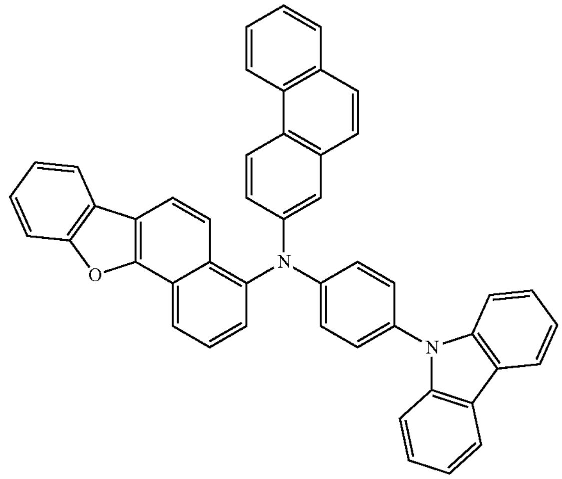
E50
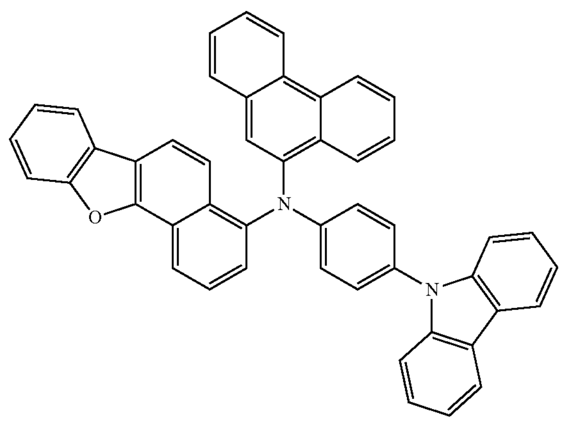
E51
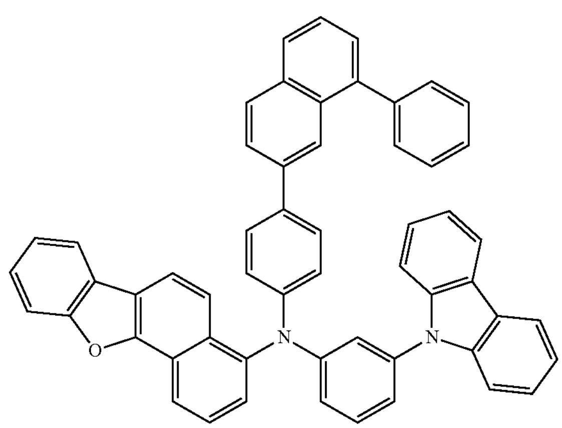

-continued
E52
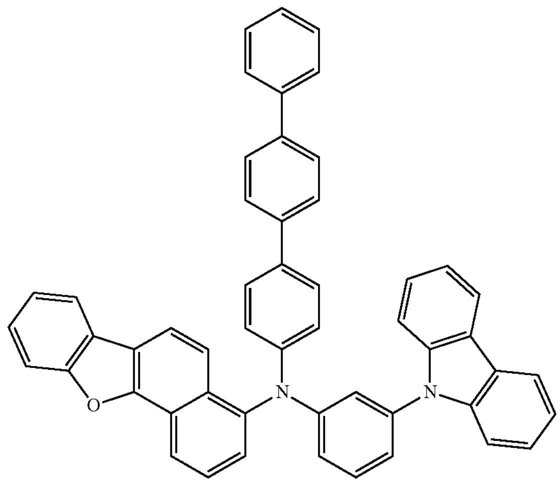
E53
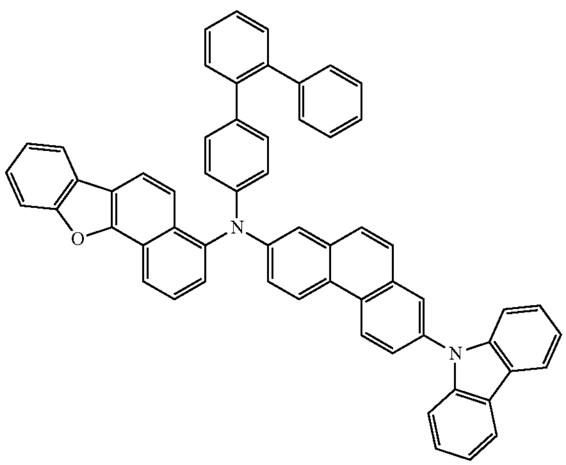
E54
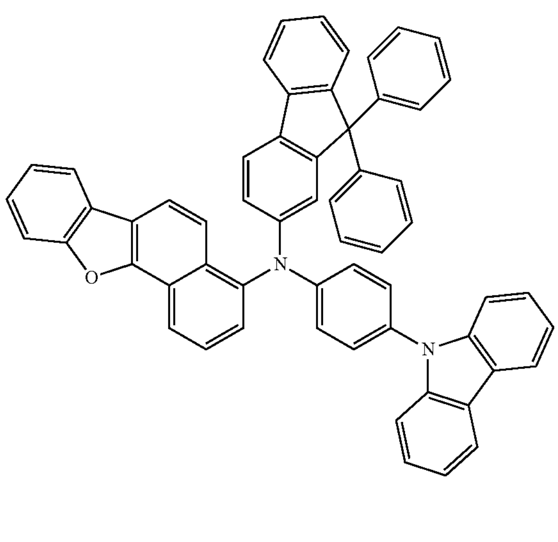
-continued
E55
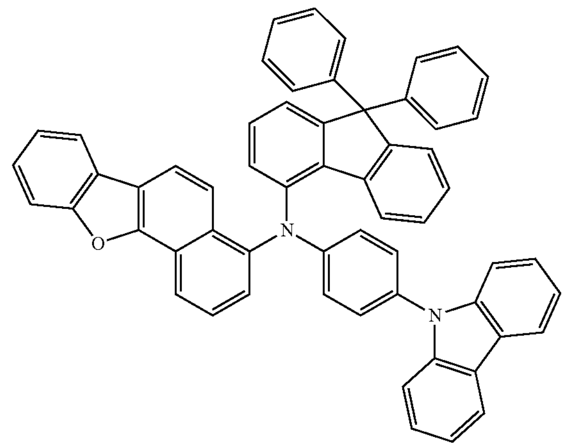
E56
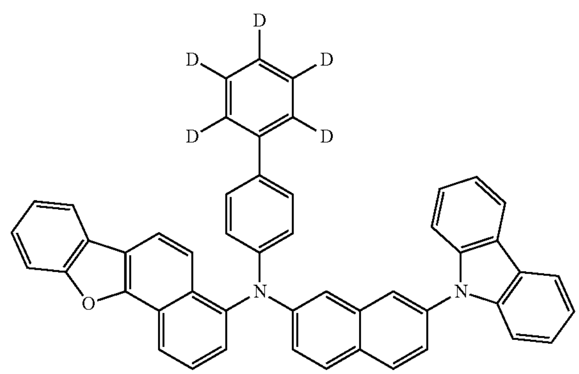
E57
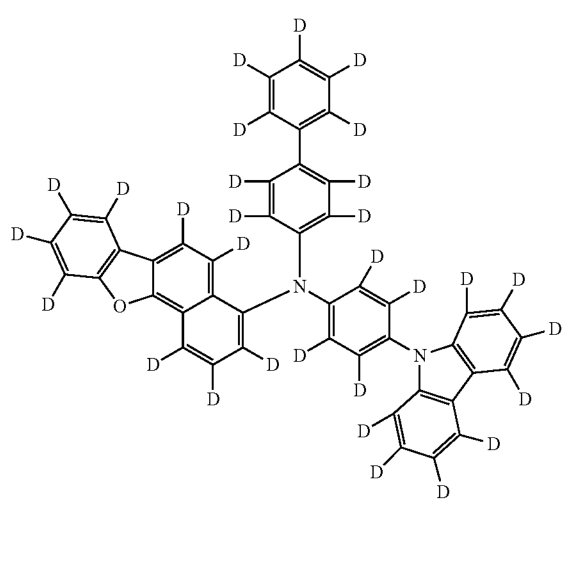

-continued
E58
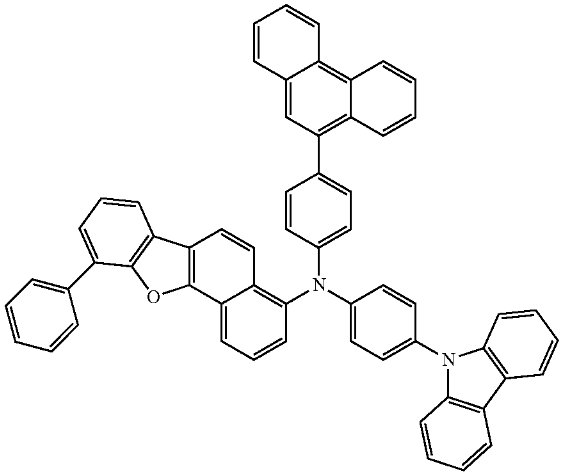
E59
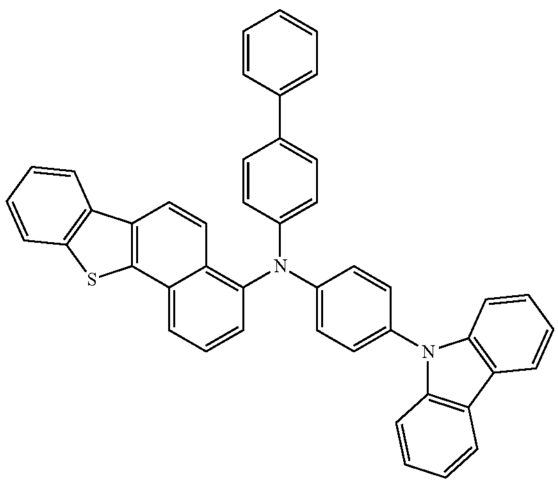
E60
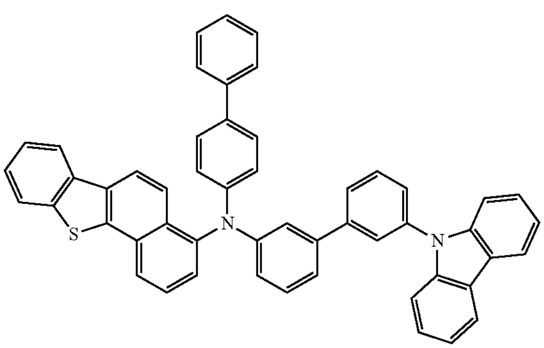
-continued
E61
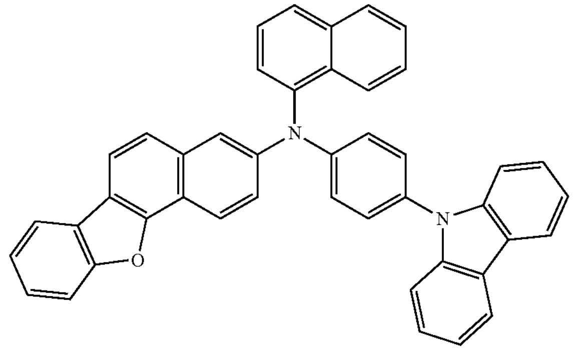
E62
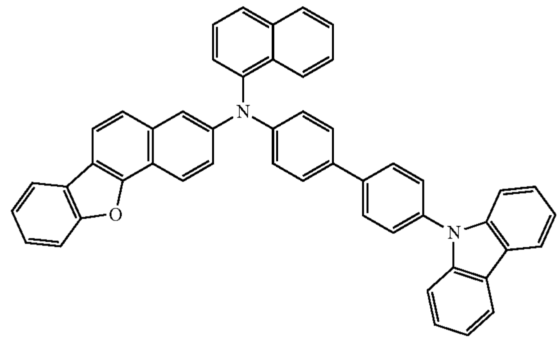
E63
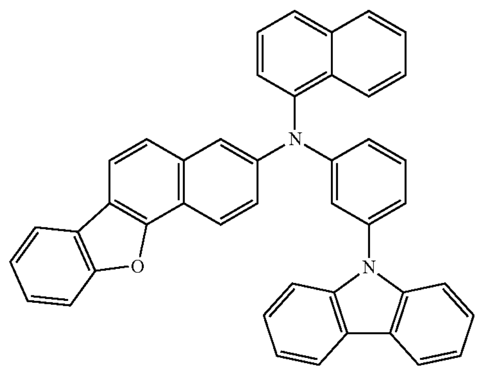
E64
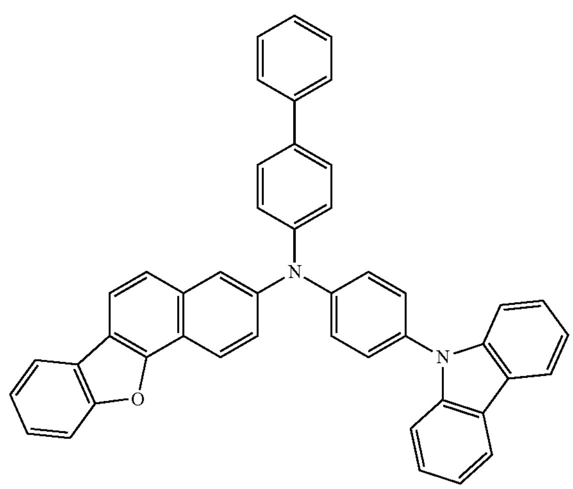

-continued
E65
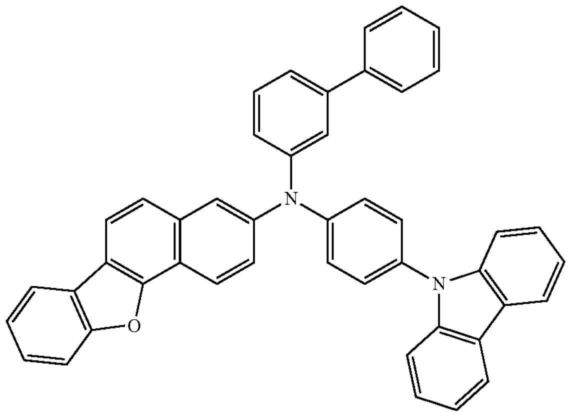
E66
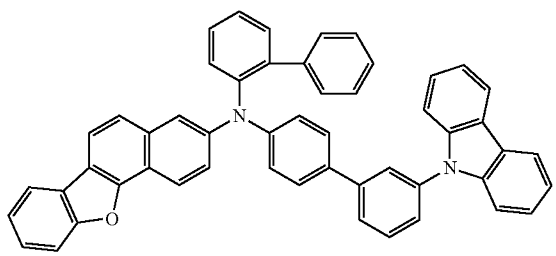
E67
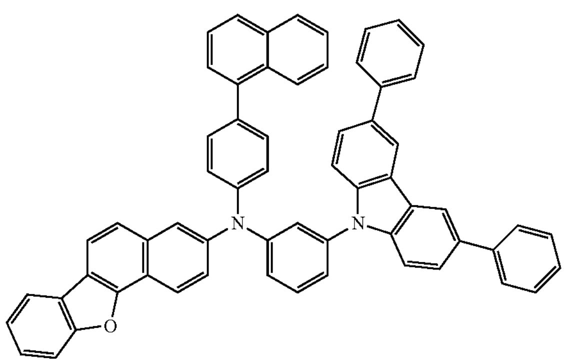
E68
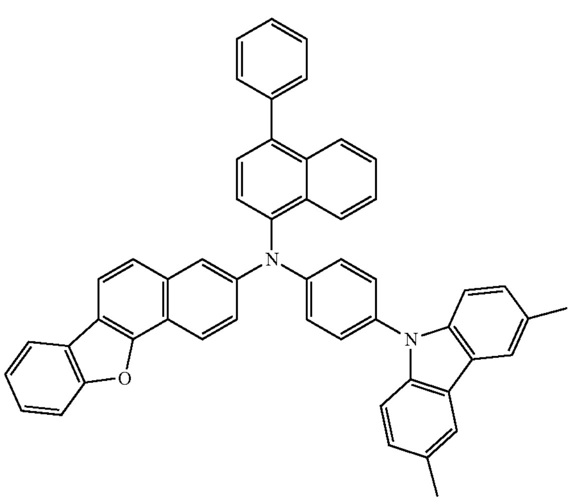
-continued
E69
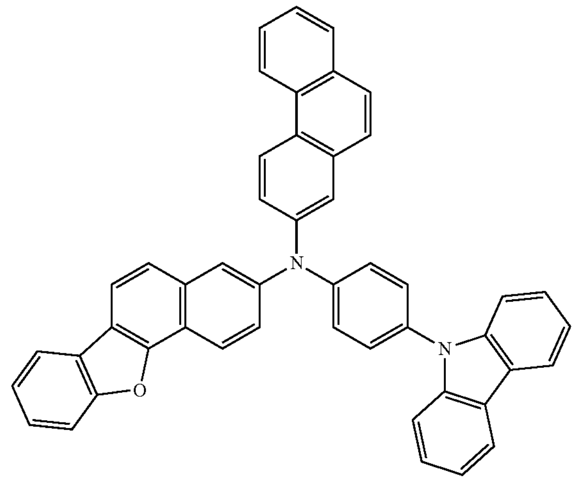
E70
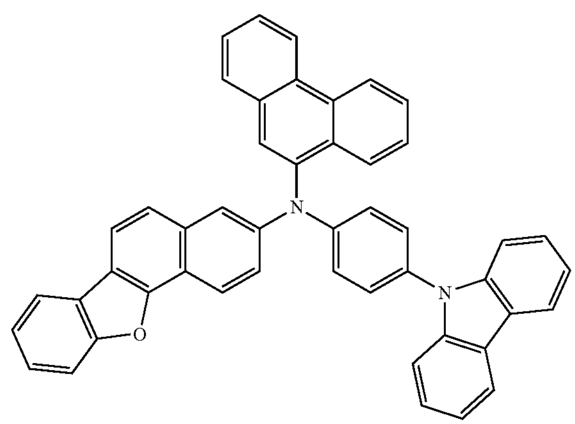
E71
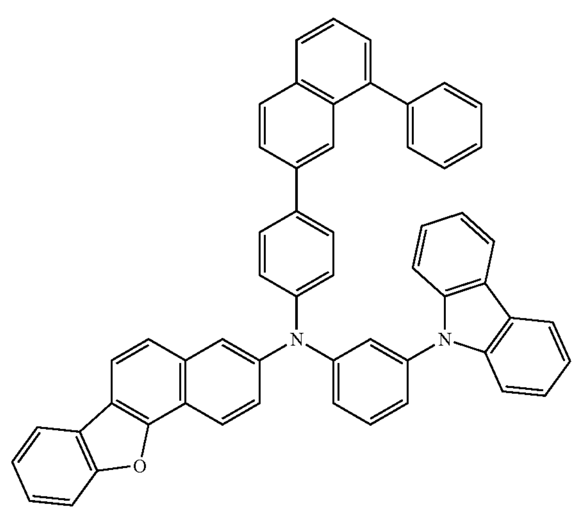

-continued
E72
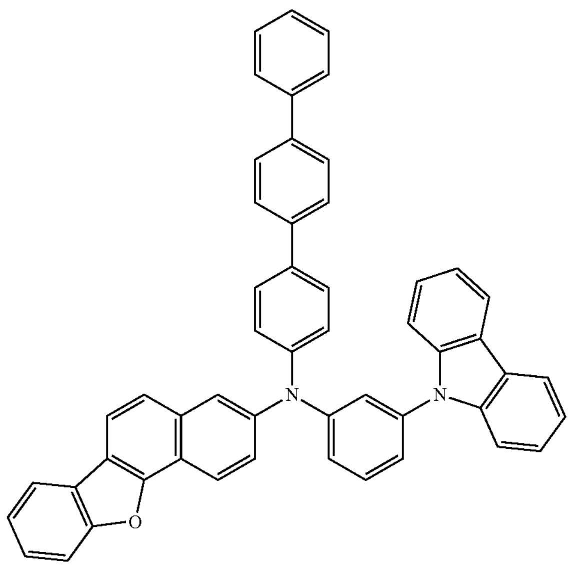
E73
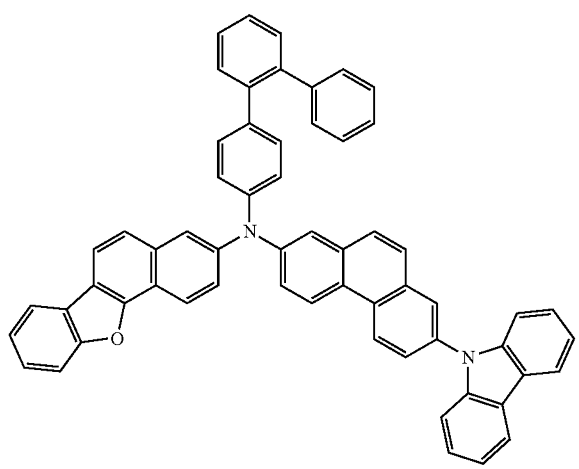
E74
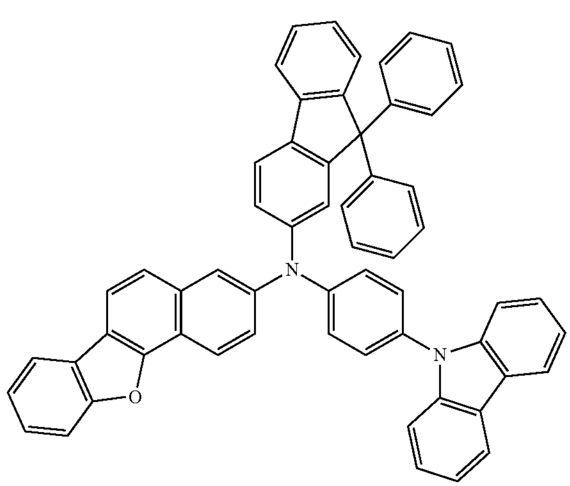
-continued
E75
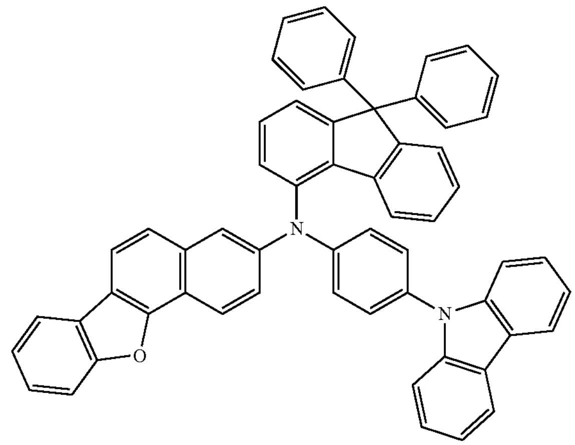
F76
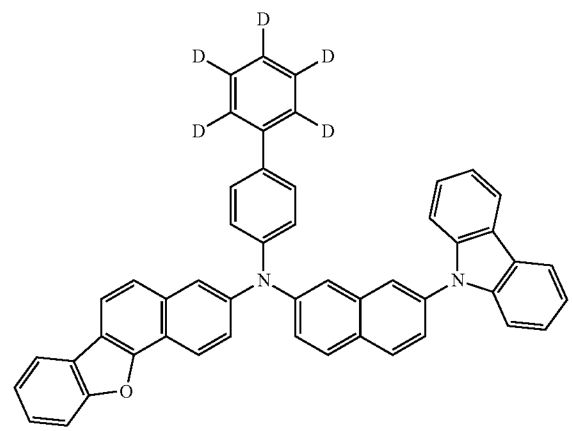
F77
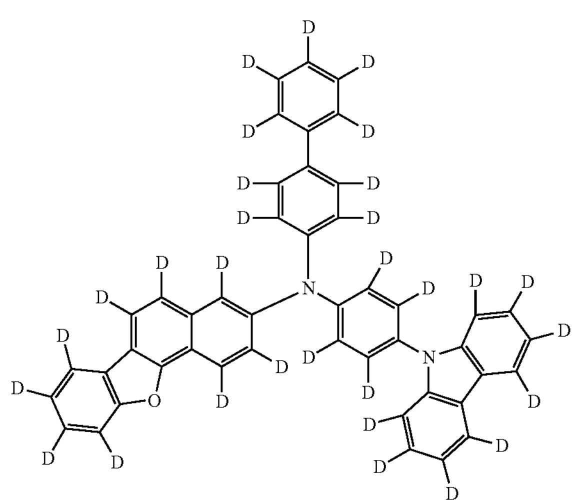

-continued
F78
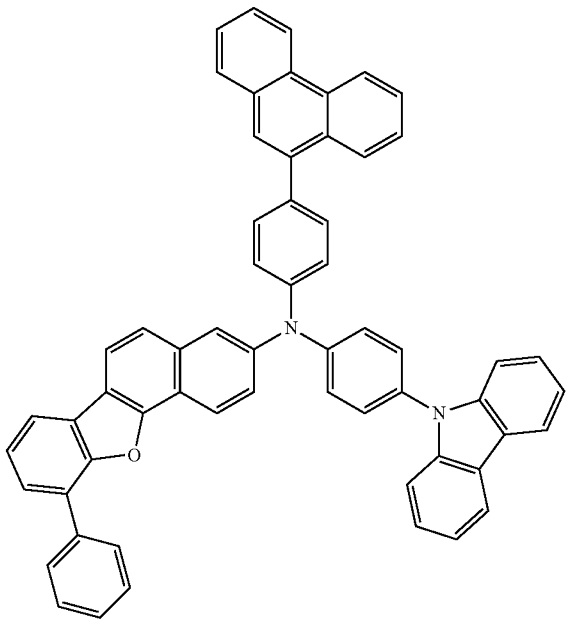
E79
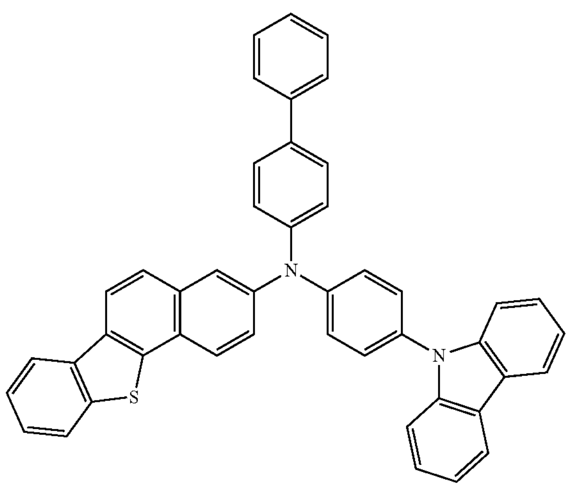
E80
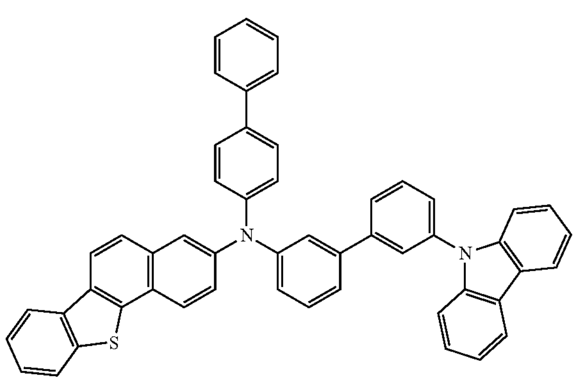
-continued
E81
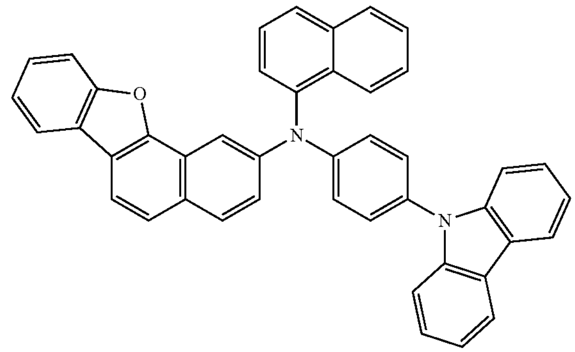
E82
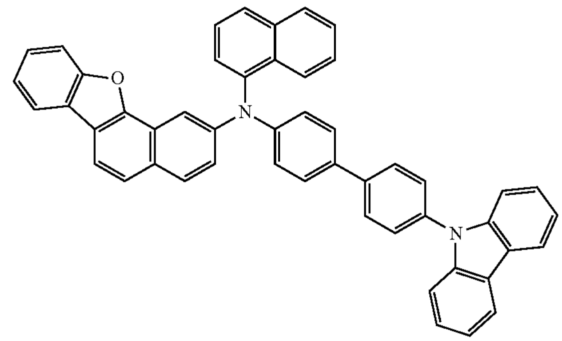
E83
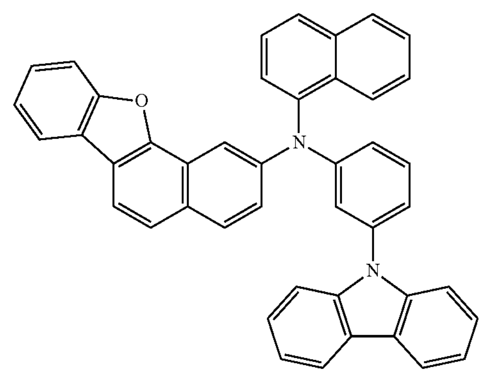
E84
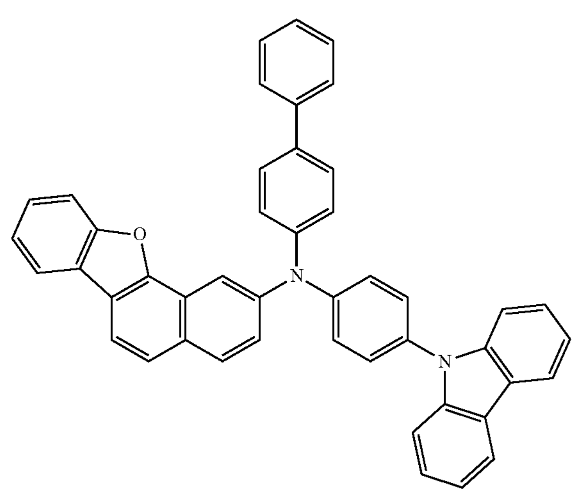

-continued
E85
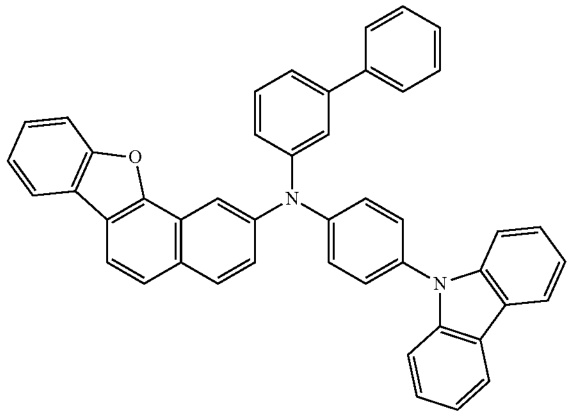
E86
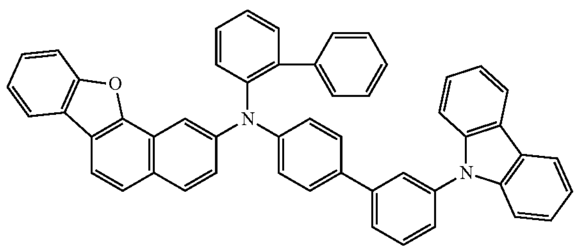
E87
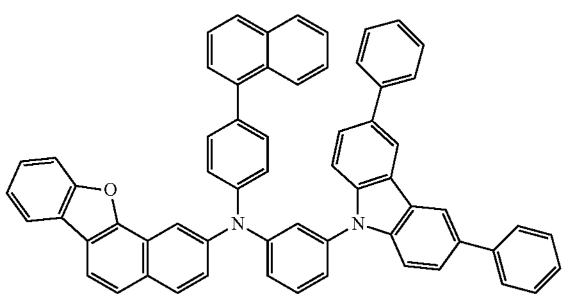
E88
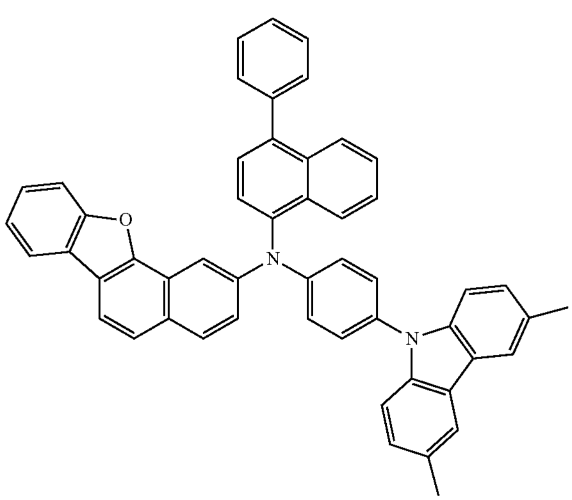
-continued
E89
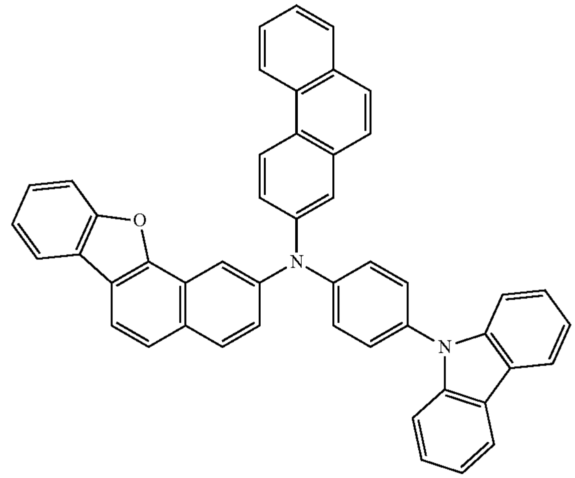
E90
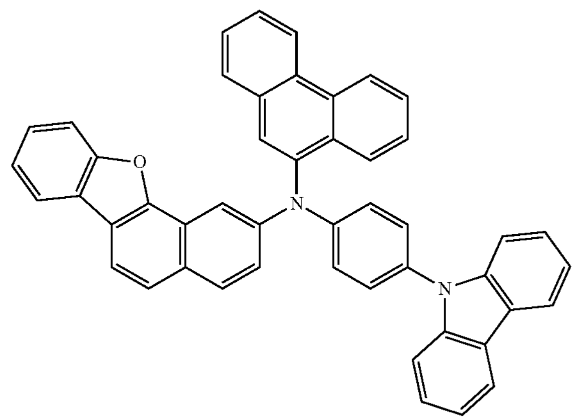
E91
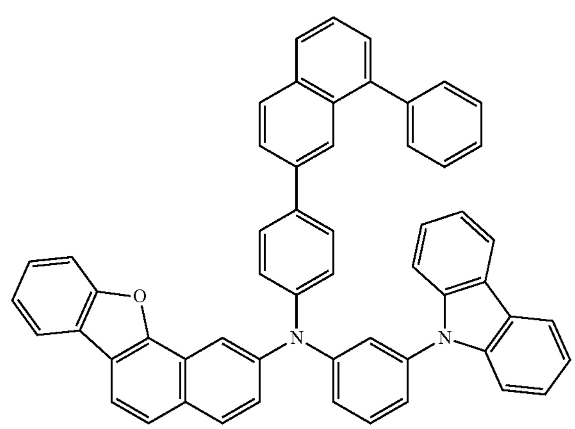

-continued
E92
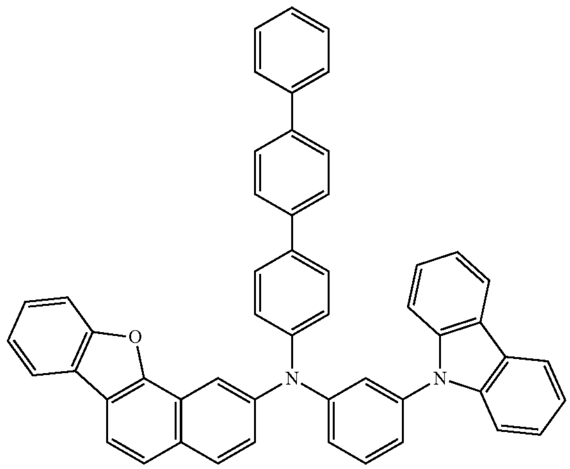
E93
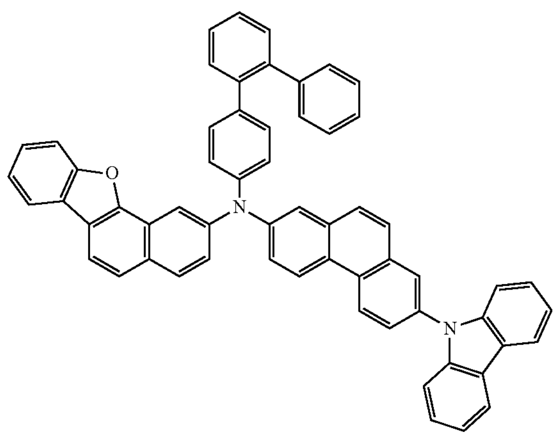
E94
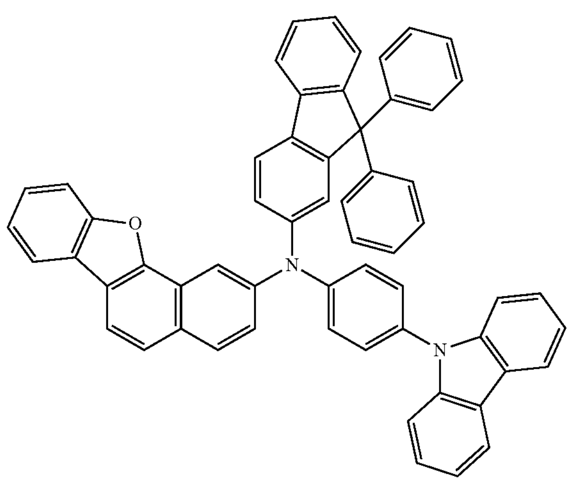
-continued
E95
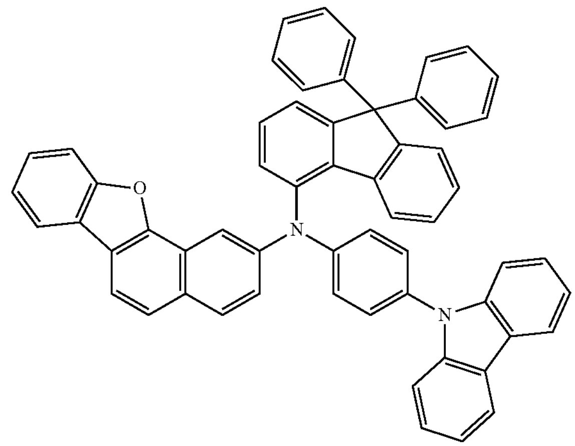
E96
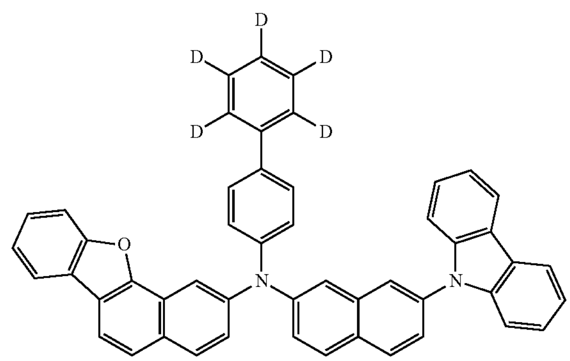
E97
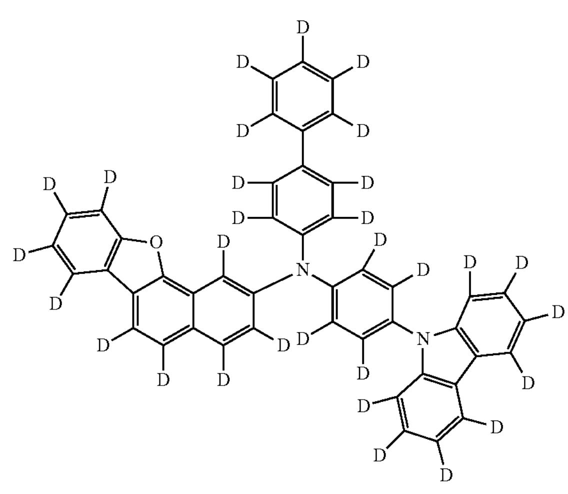

-continued
E98
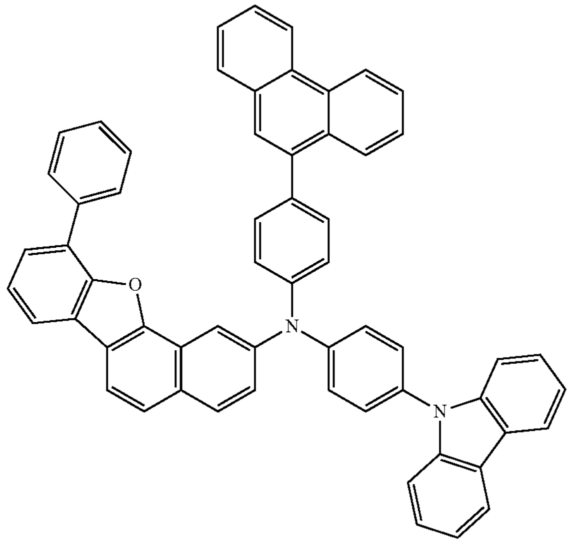
E99
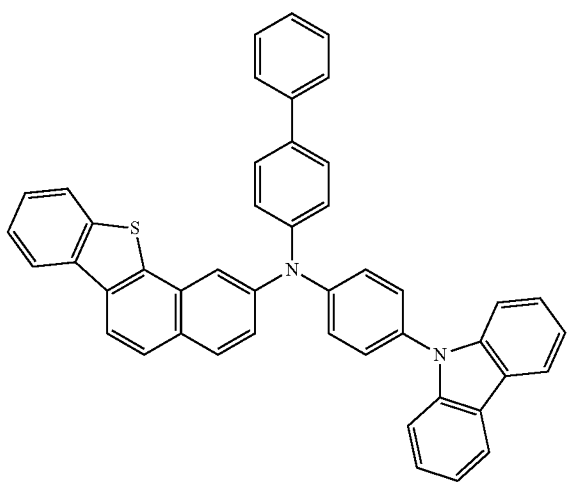
E100
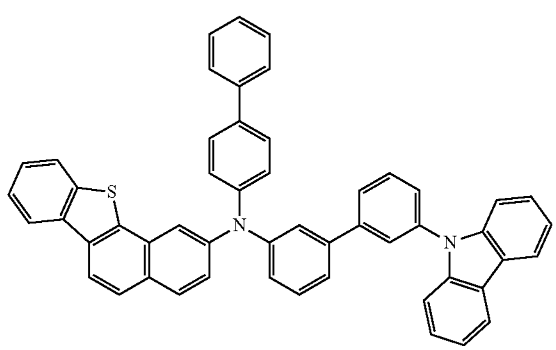
-continued
E101
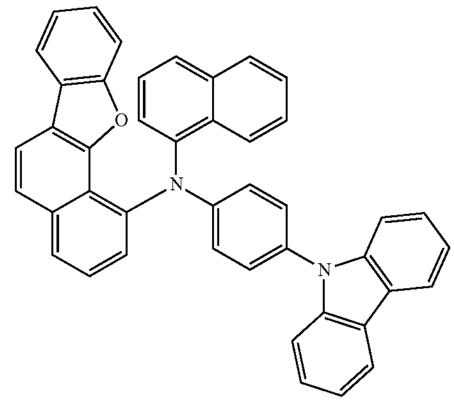
E102
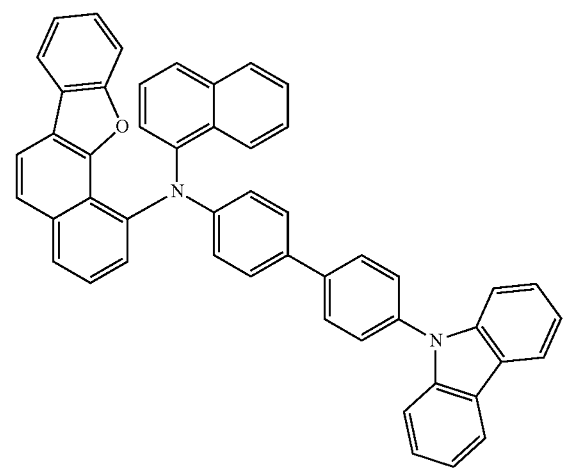
E103
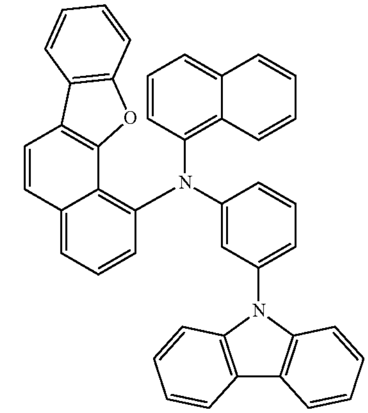

-continued
E104
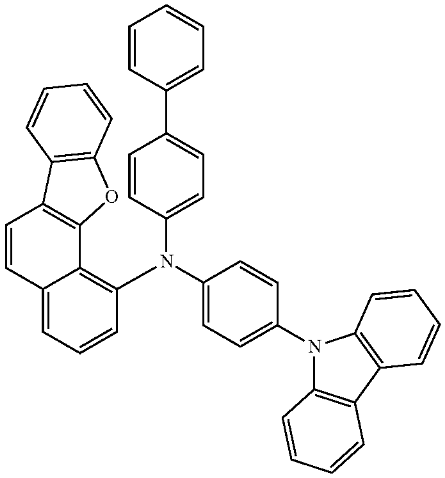
E105
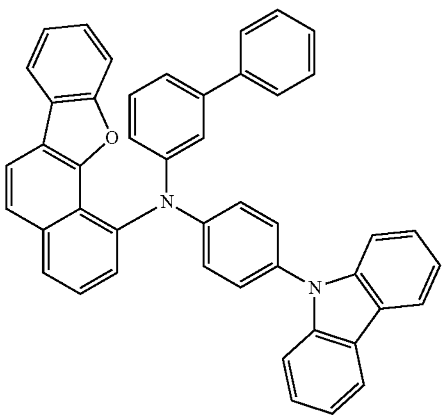
E106
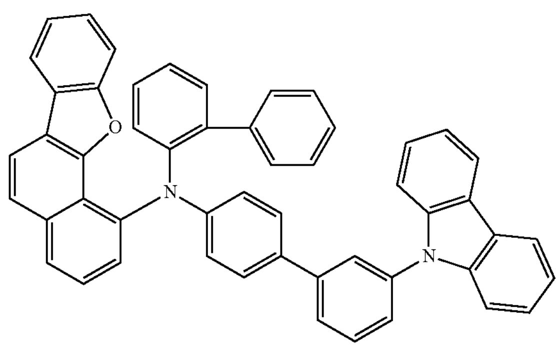
E107
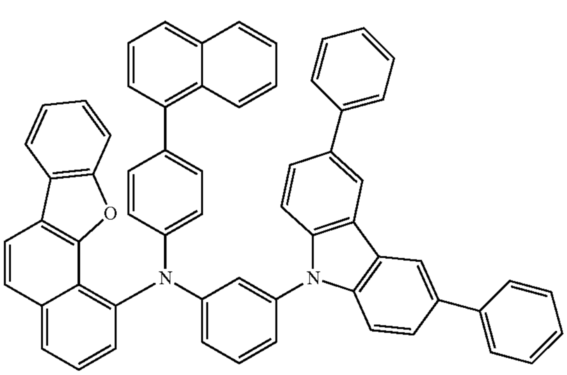
-continued
E108
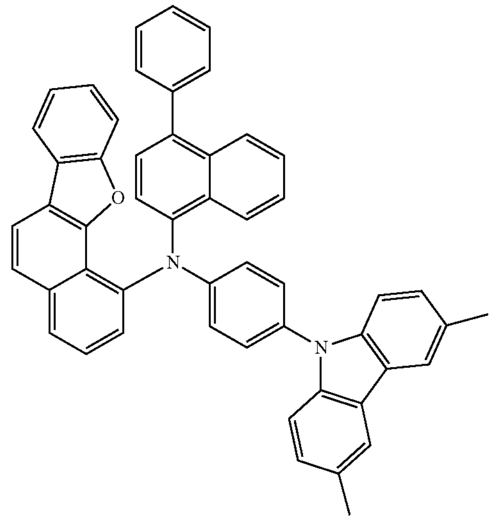
E109
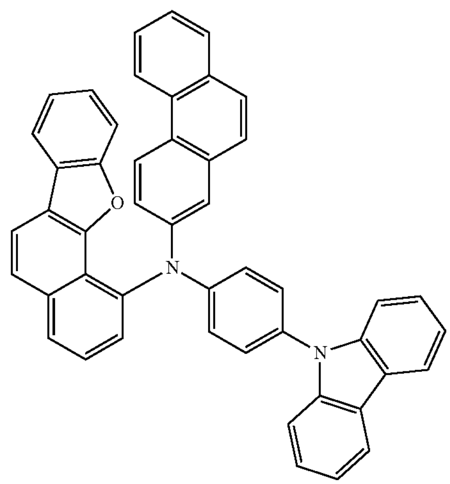
E110
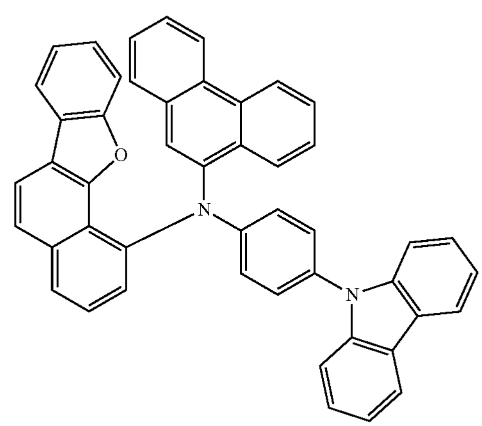

-continued
E111
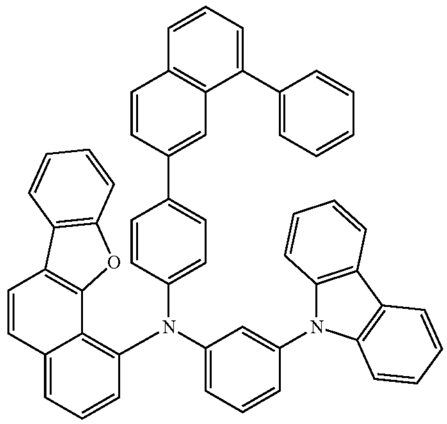
E112
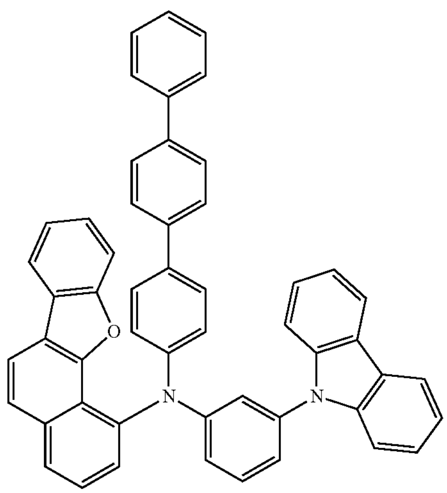
E113
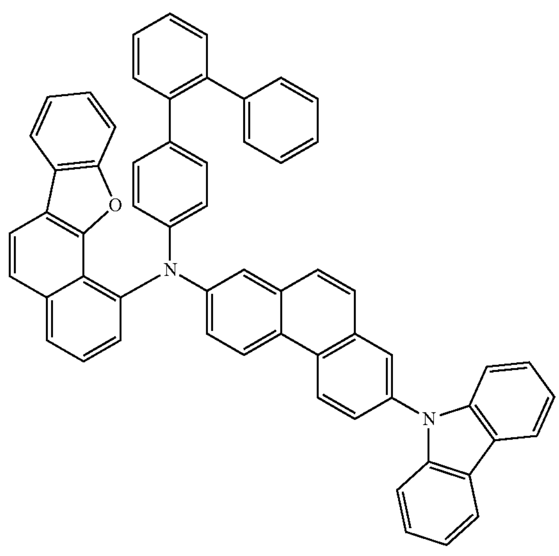
-continued
E114
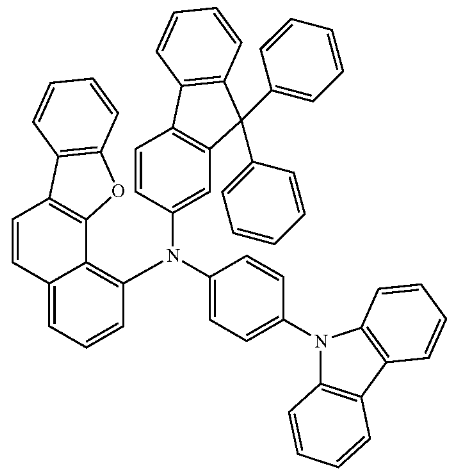
E115
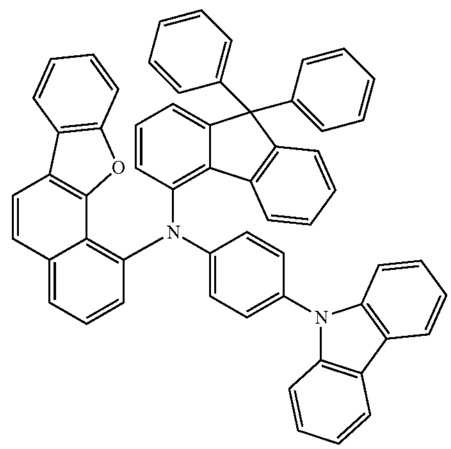
E116
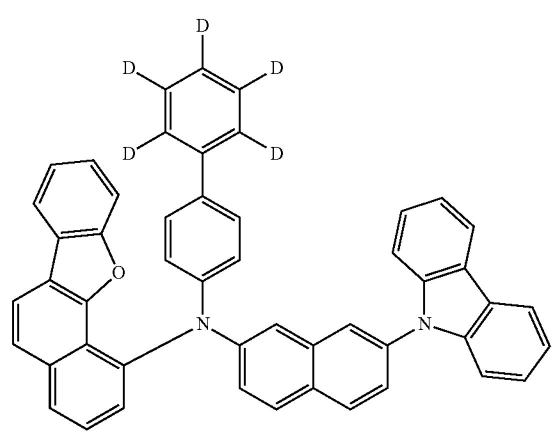

-continued
E1147
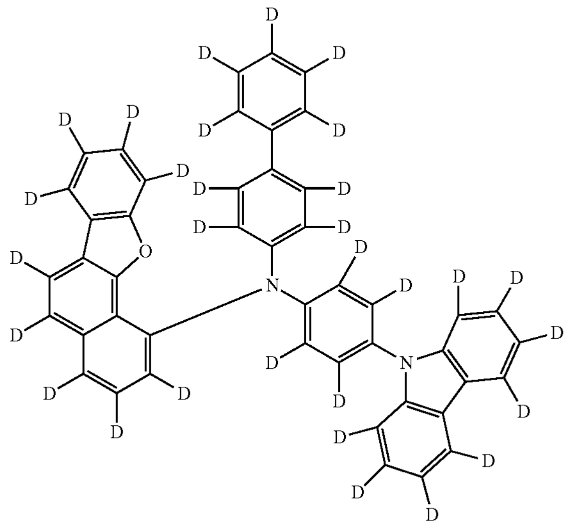
E118
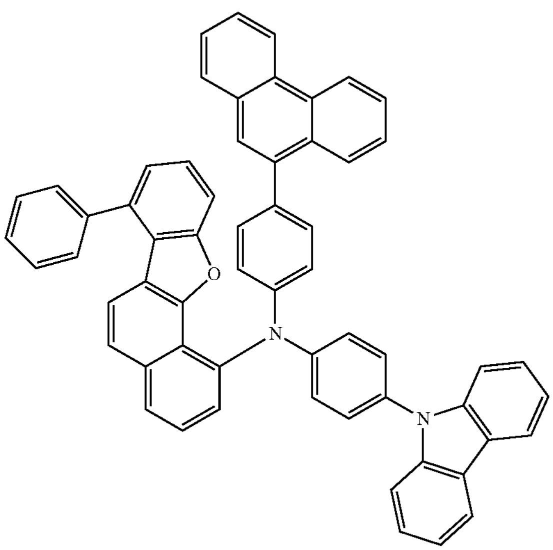
E119
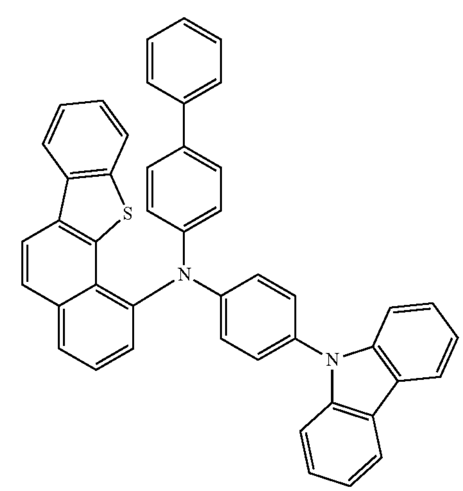
-continued
E120
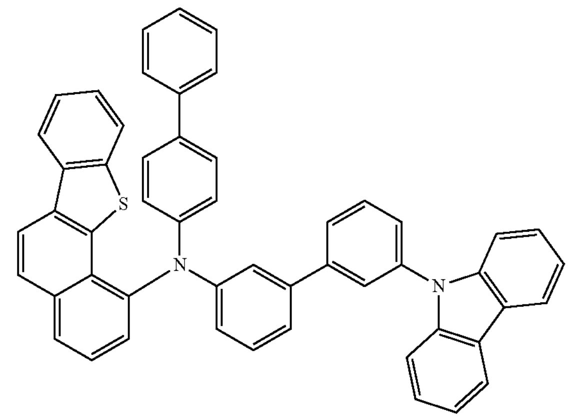
E121
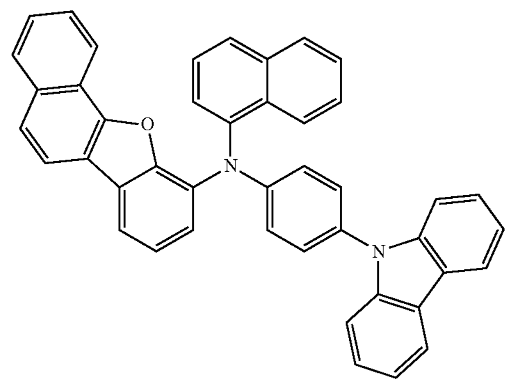
E122
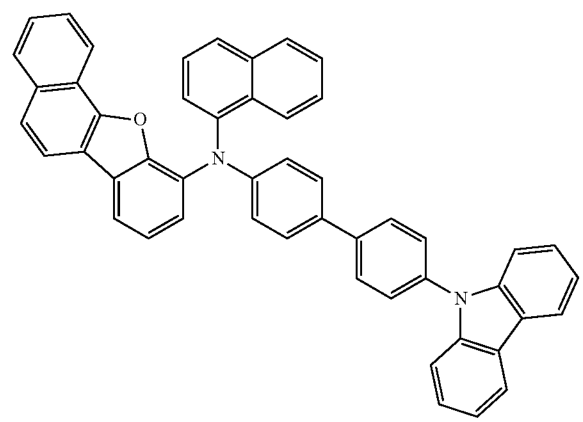
E123
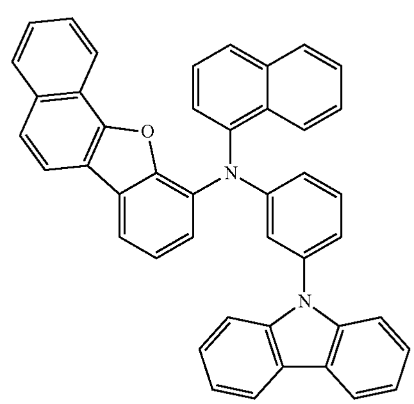

-continued
E124
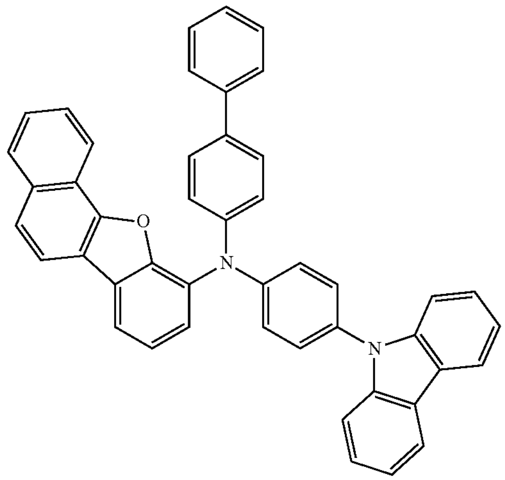
E125
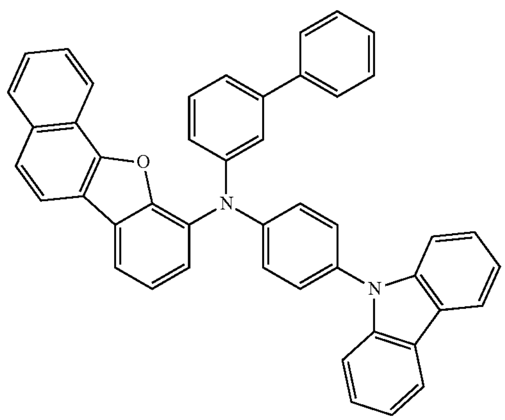
E126
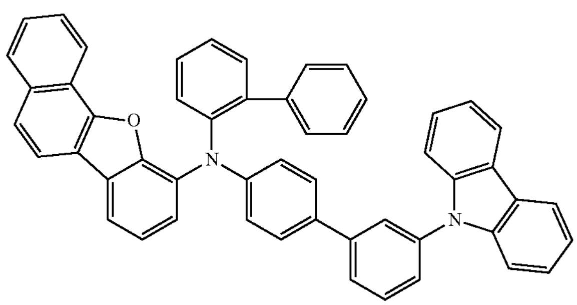
E127
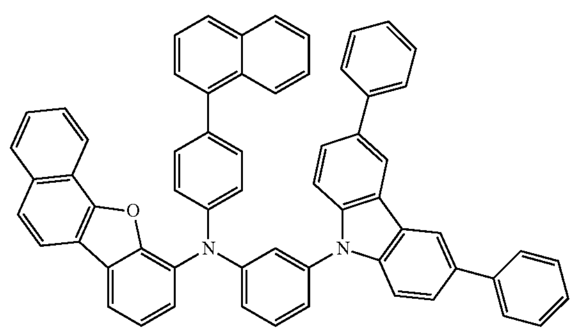
-continued
E128
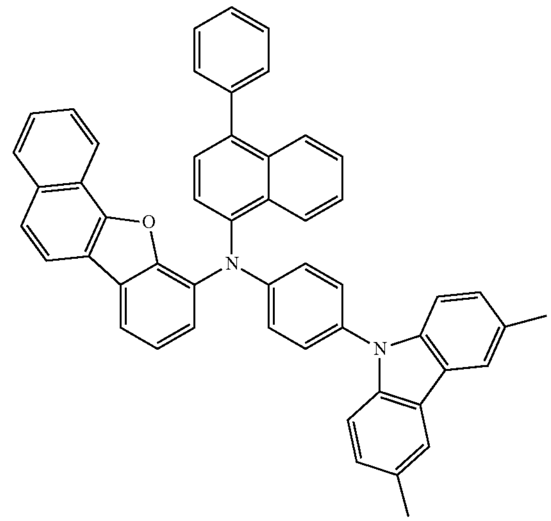
E129
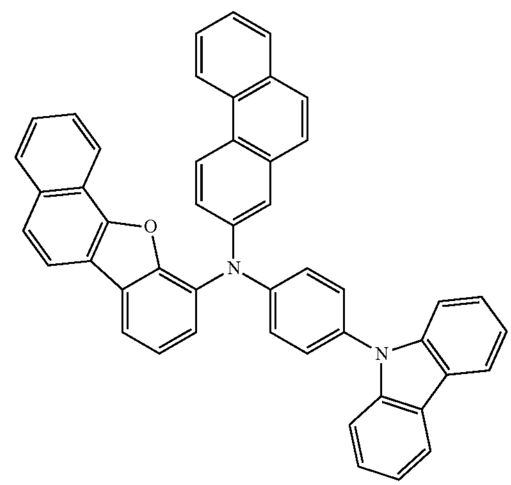
E130
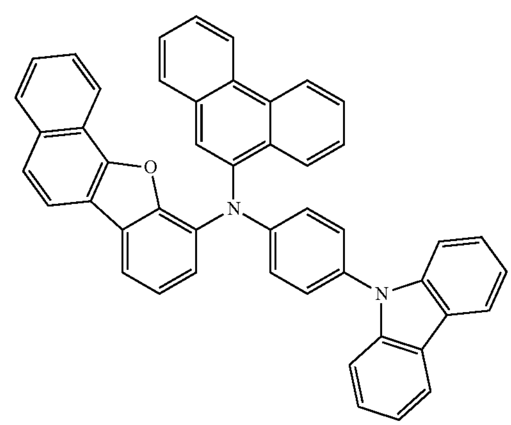

-continued
E131
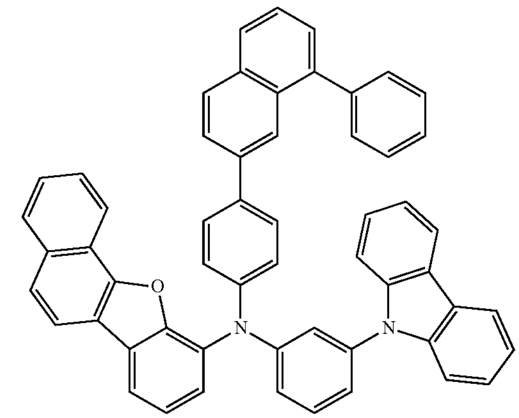
E132
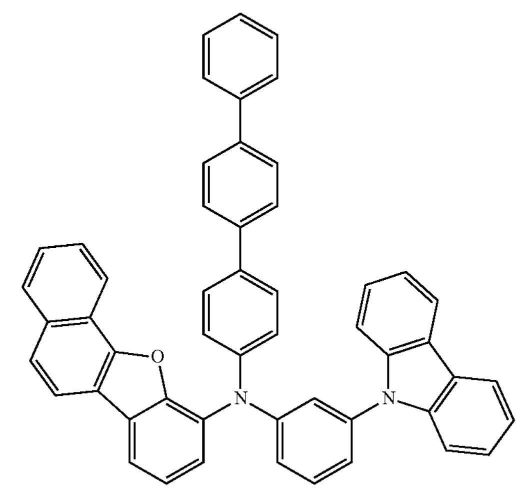
E133
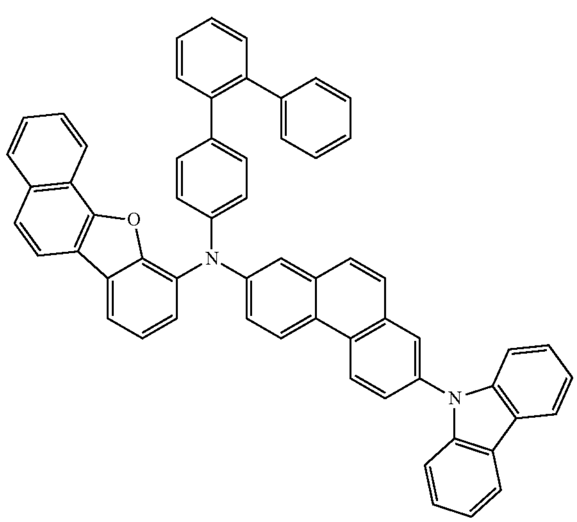
-continued
E134
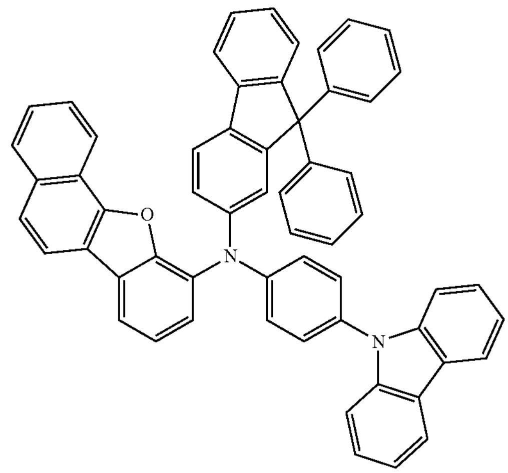
E135
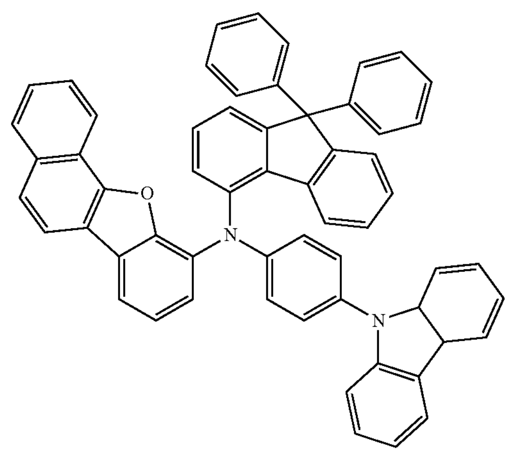
E136
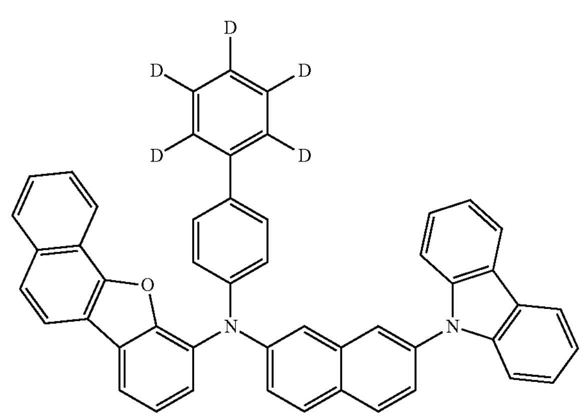

-continued
E137
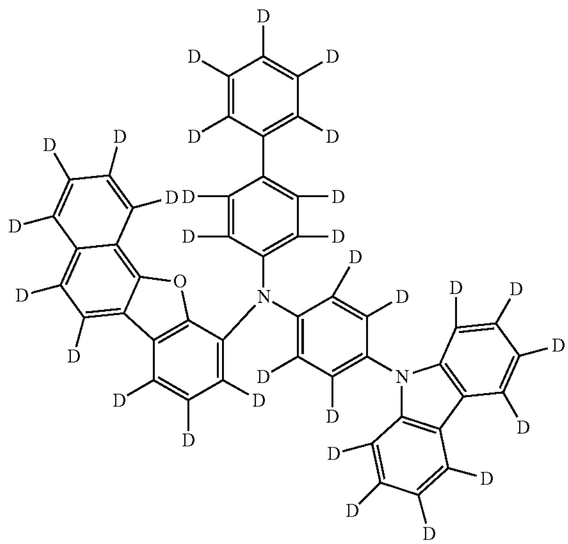
E138
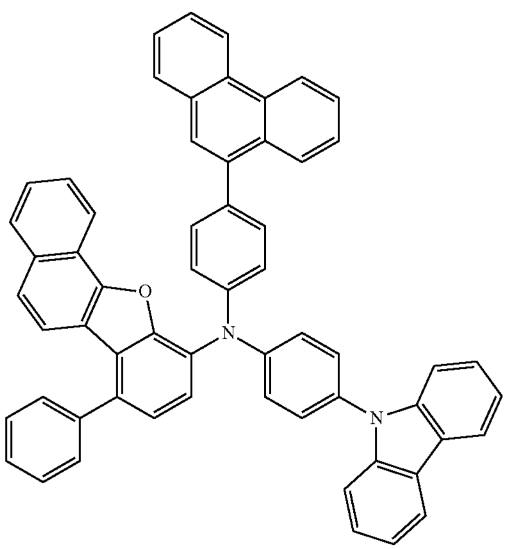
E139
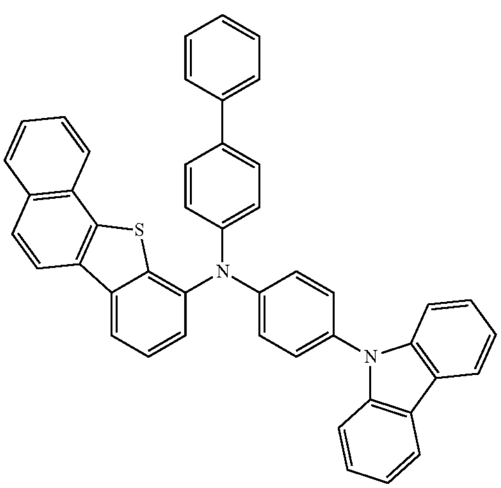
-continued
E140
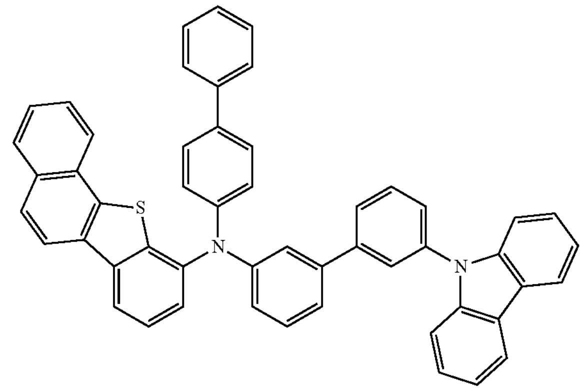
E141
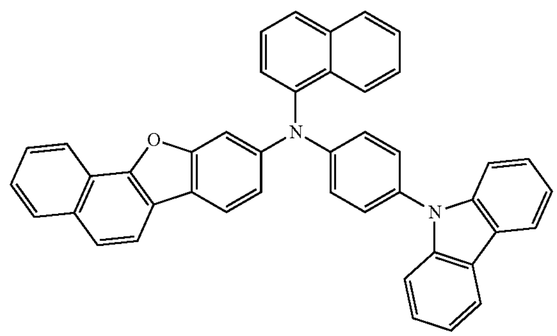
E142
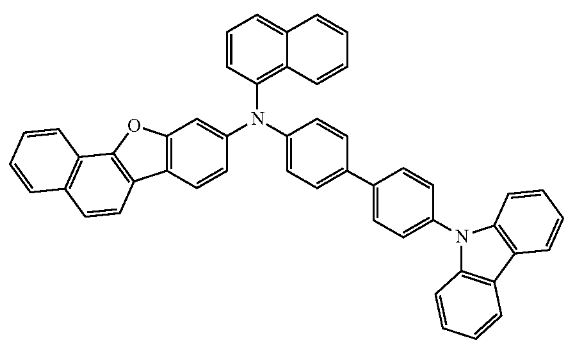
E143
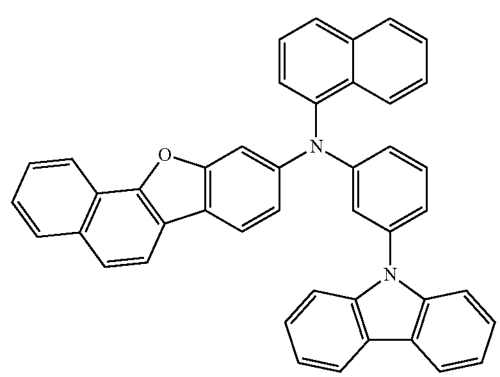

-continued
E144
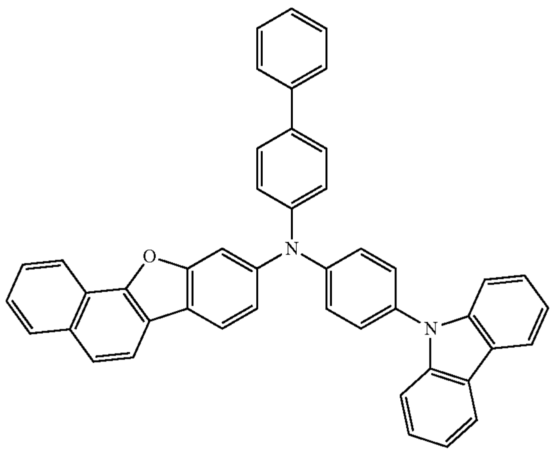
E145
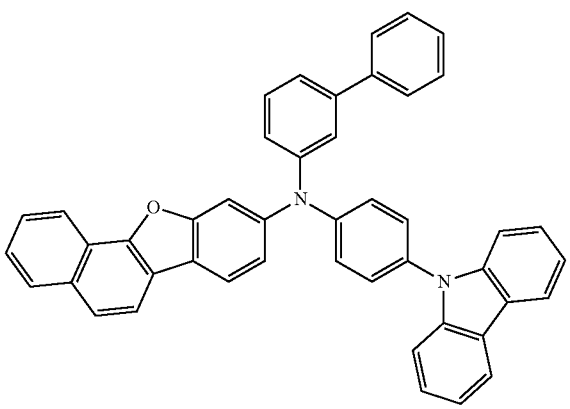
E146
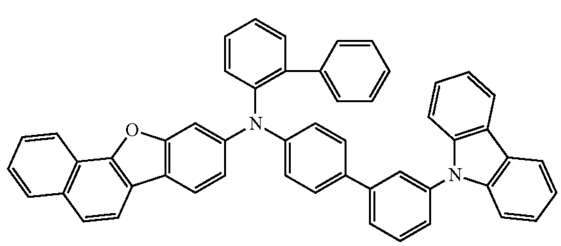
E147
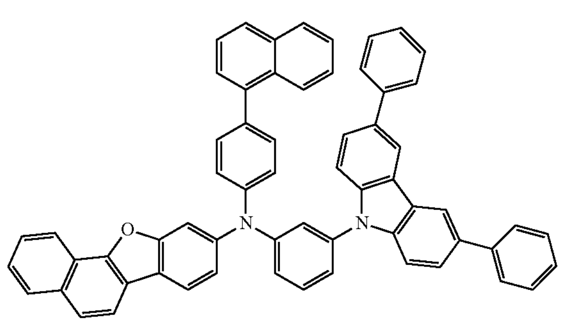
-continued
E148
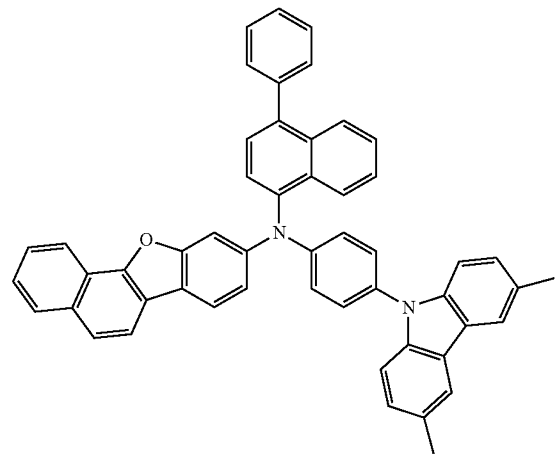
E149
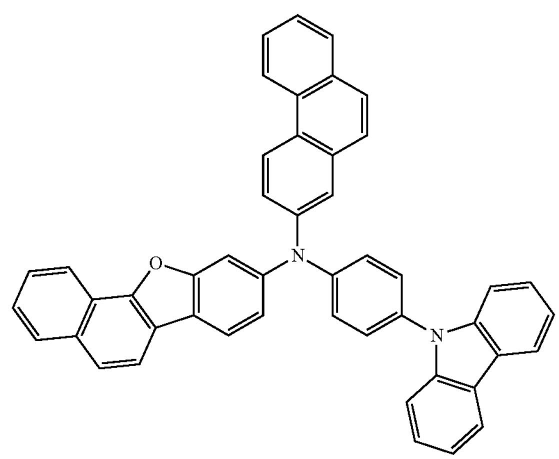
E150
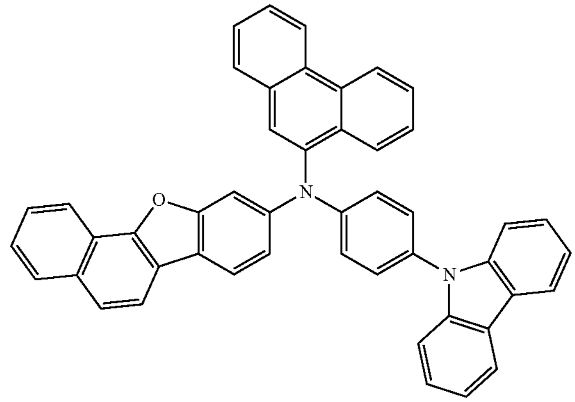

E151
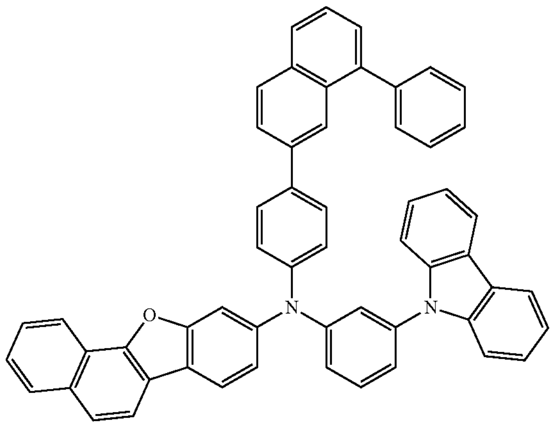
E152
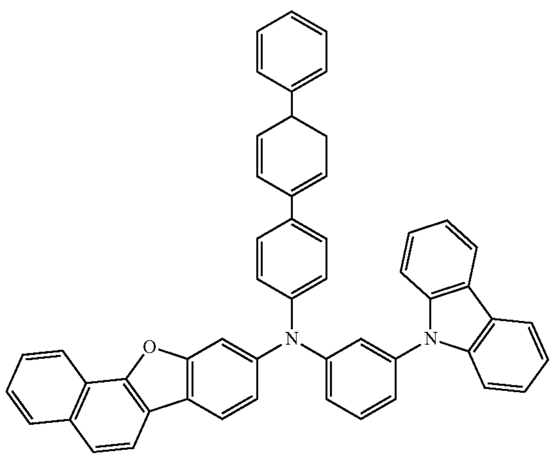
E153
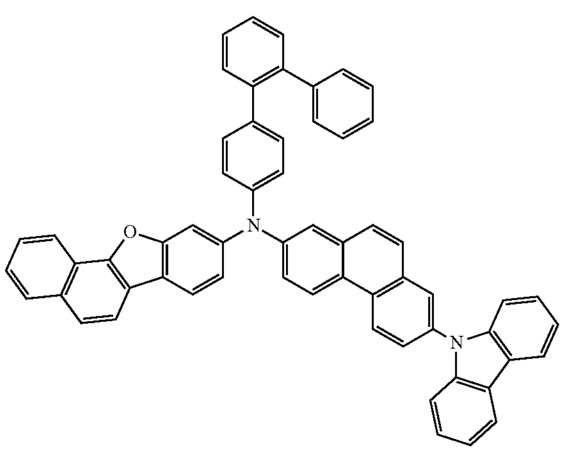
E154
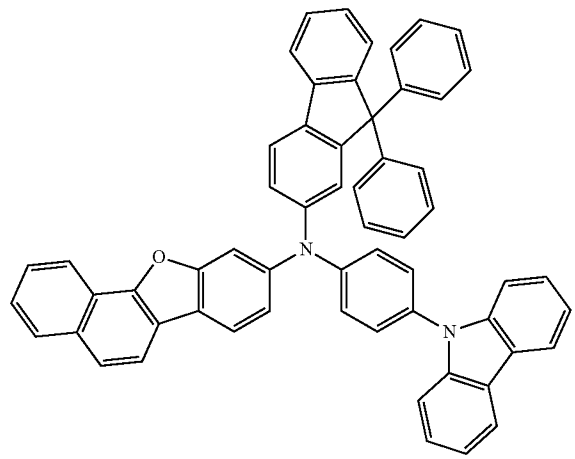
E155
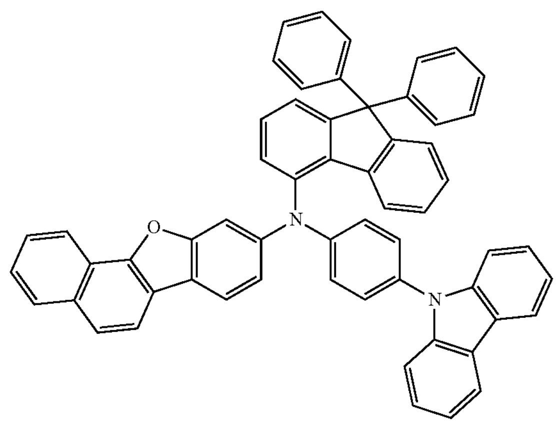
E156
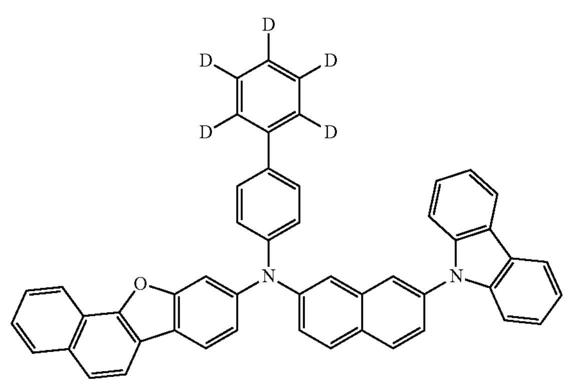

-continued
E157
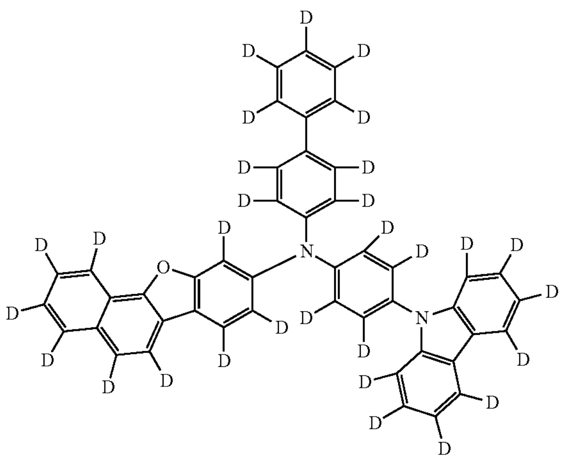
E158
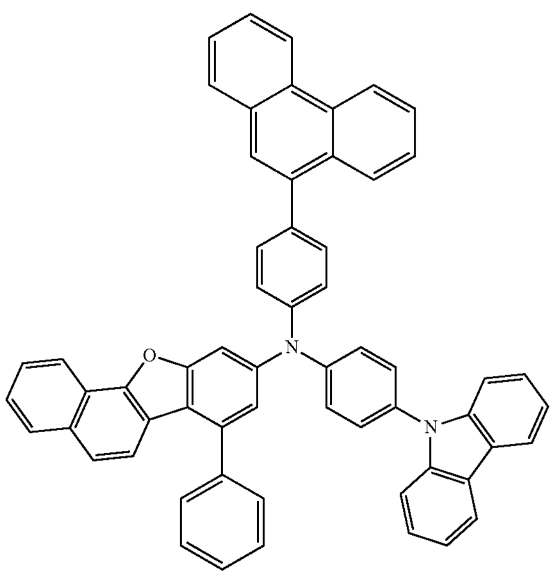
E159
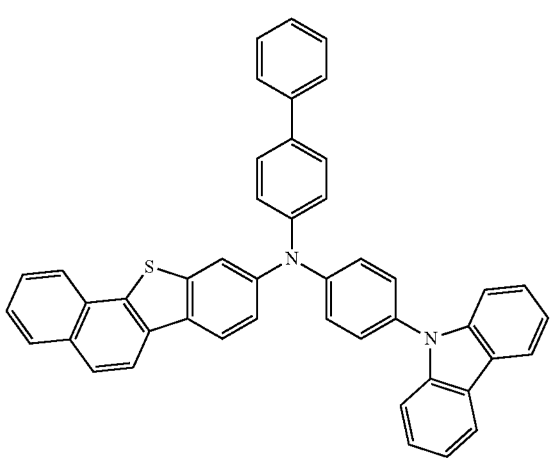
-continued
E160
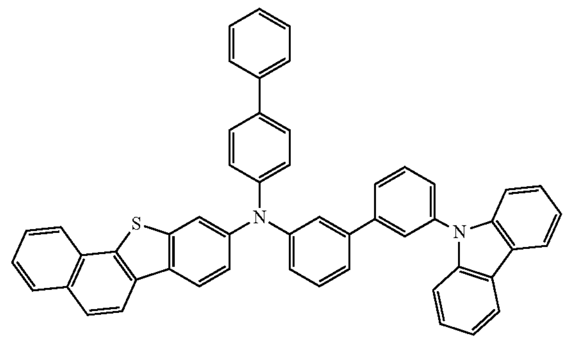
E161
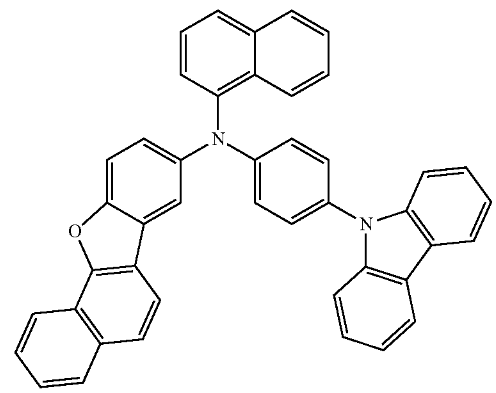
E162
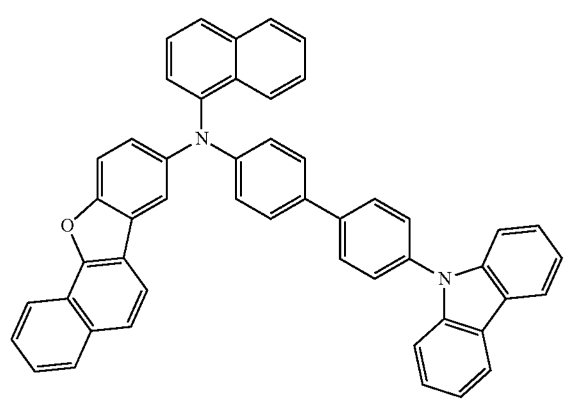
E163
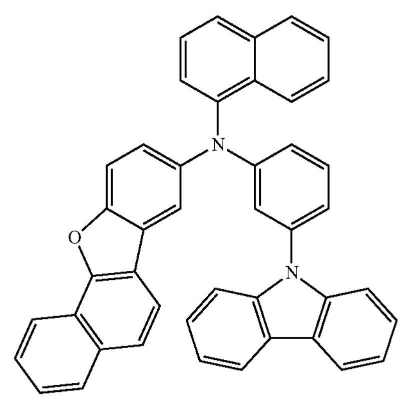

-continued
E164
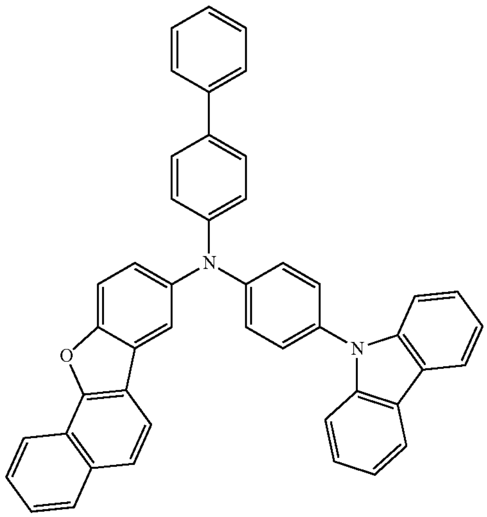
E165
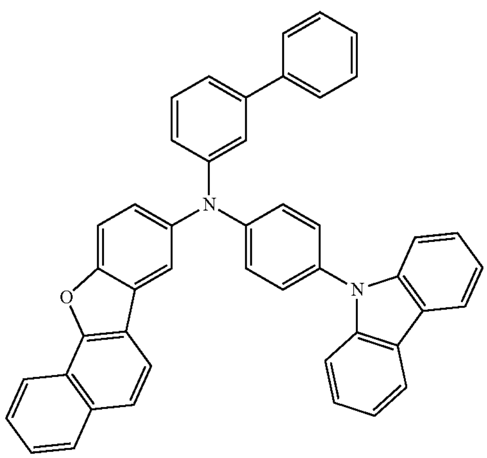
E166
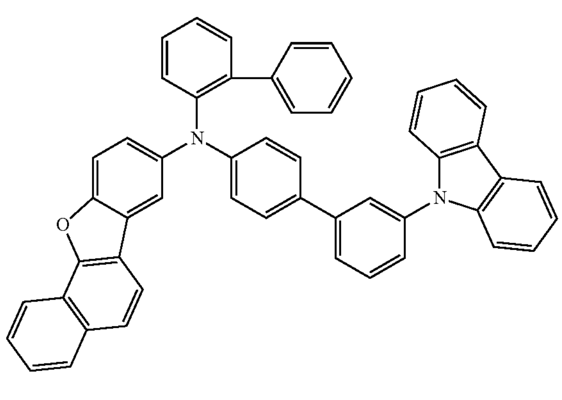
-continued
E167
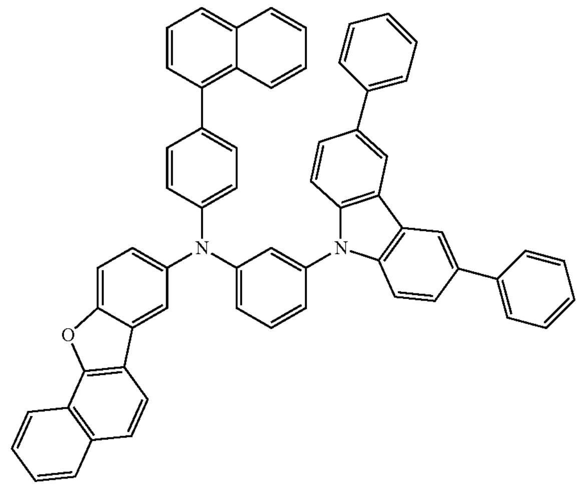
E168
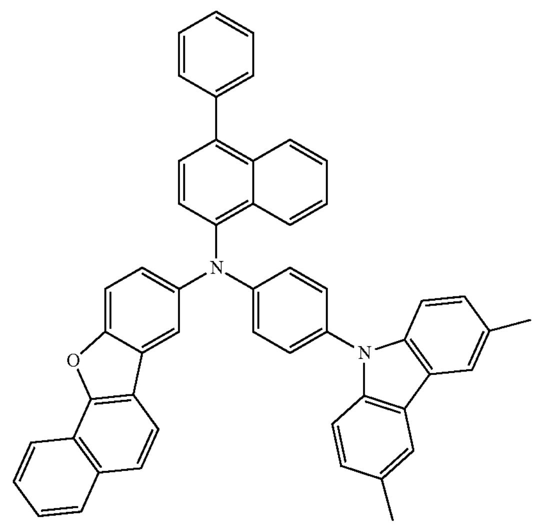
E169
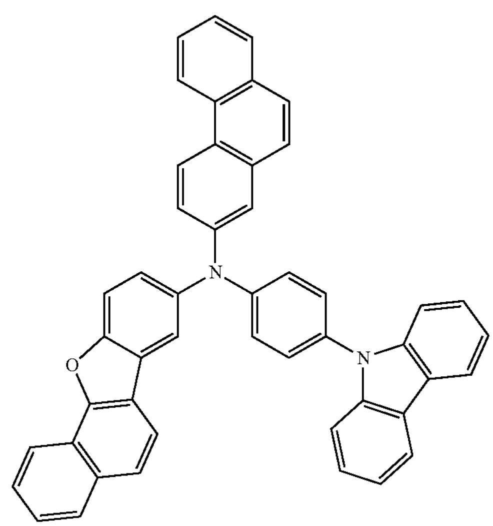

-continued
E170
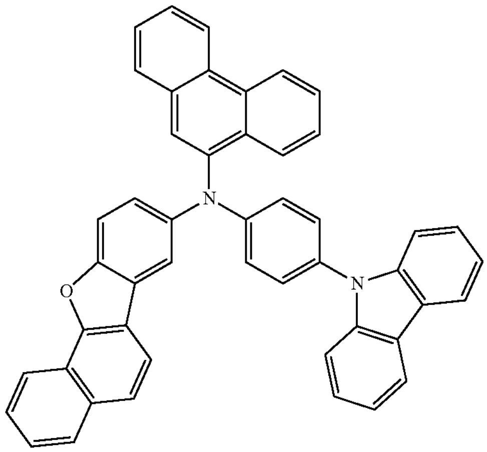
E171
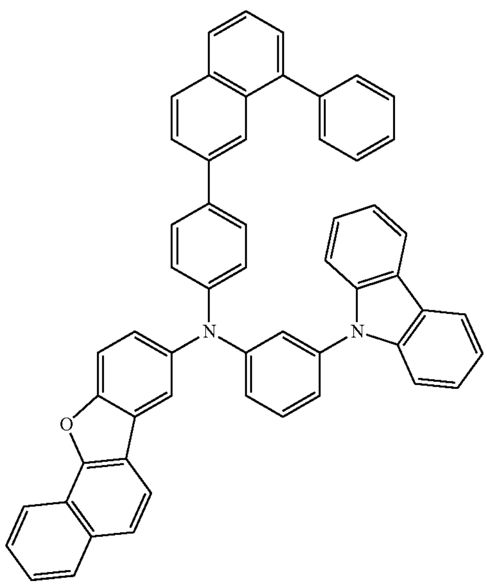
E172
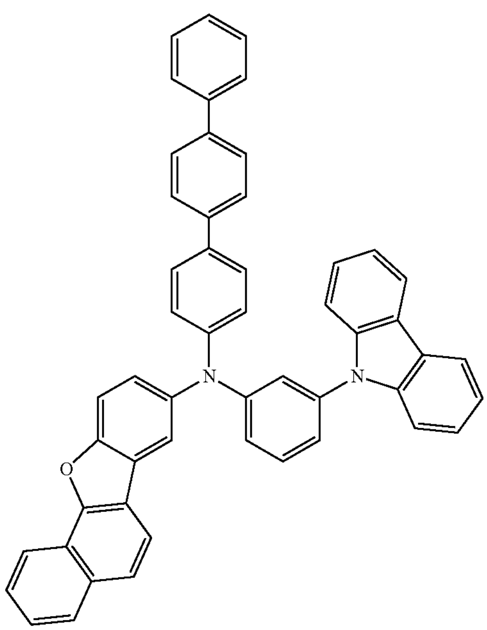
-continued
E173
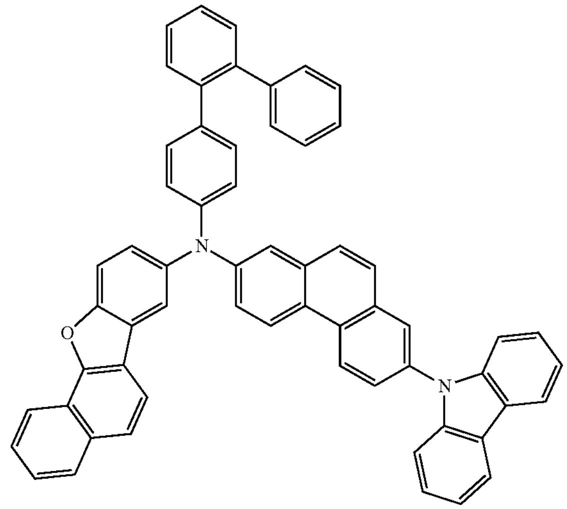
E174
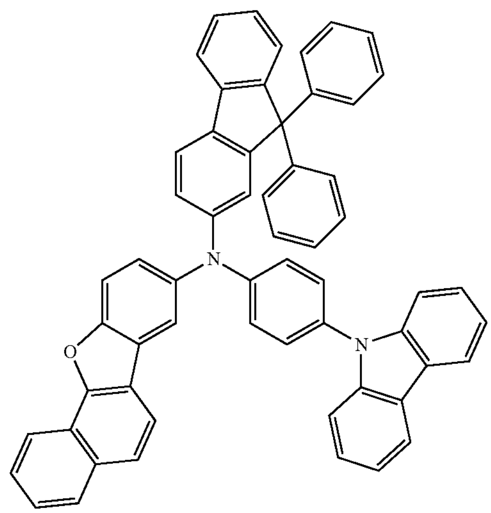
E175
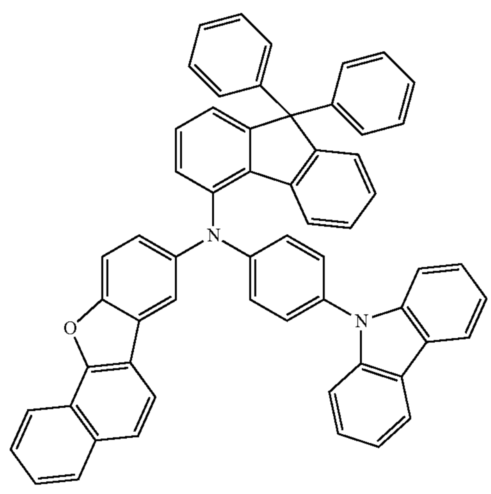

-continued
E176
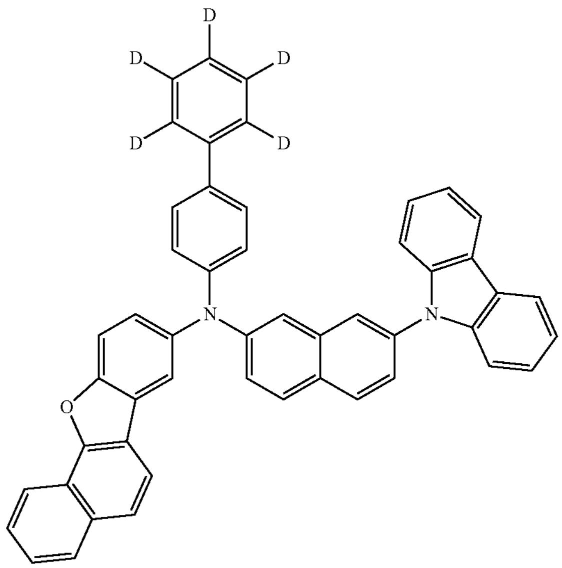
E177
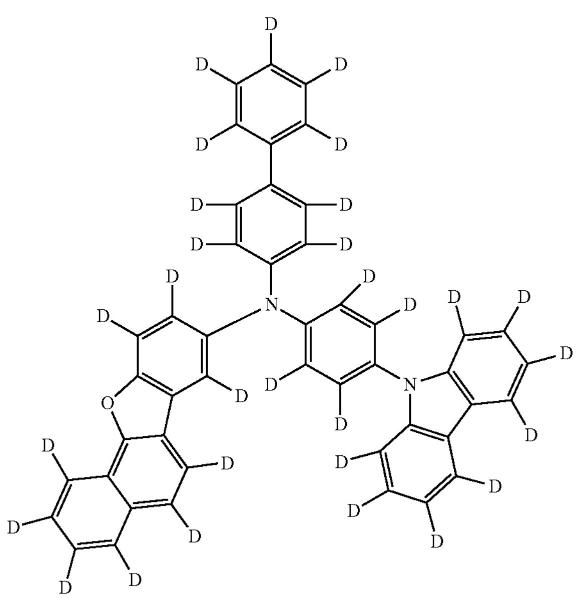
-continued
E178
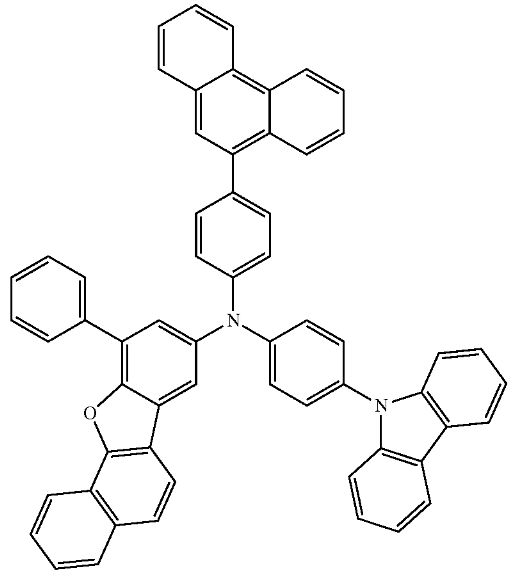
E179
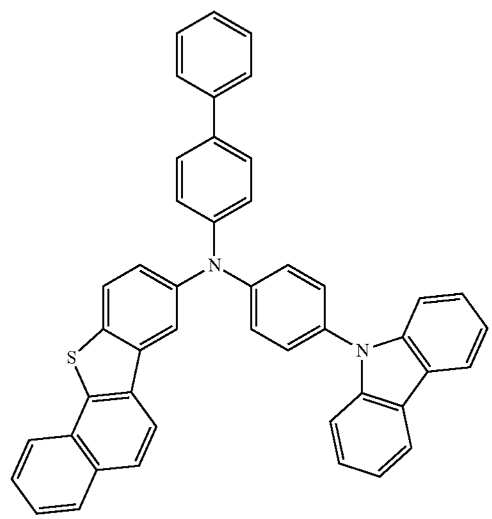
E180
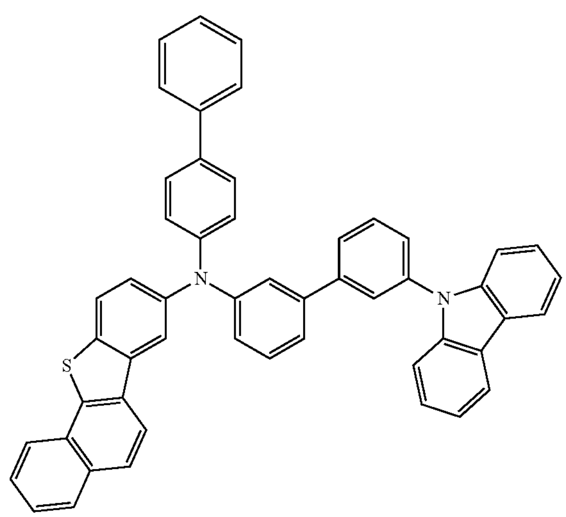

E181
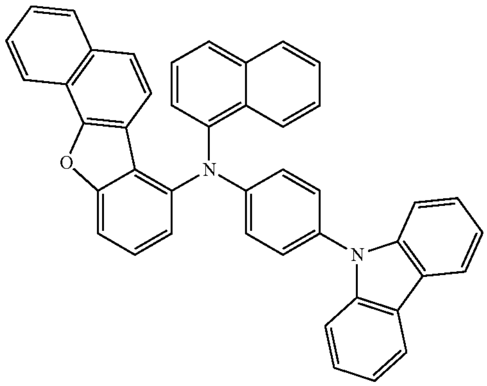
E182
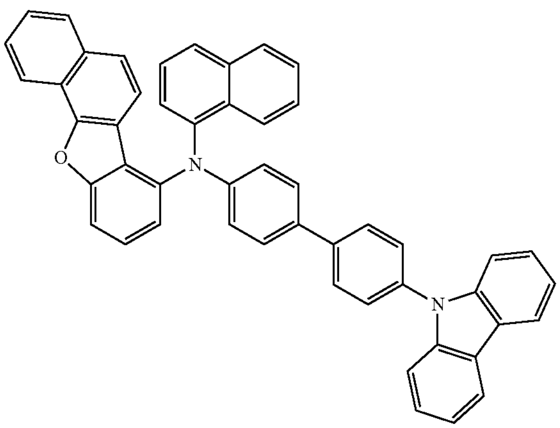
E183
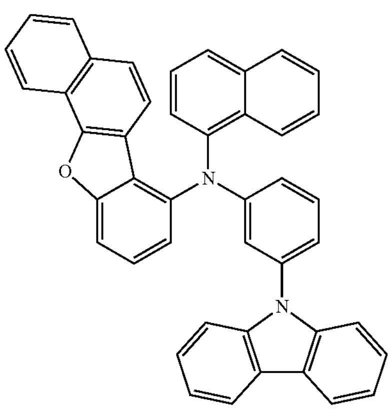
E184
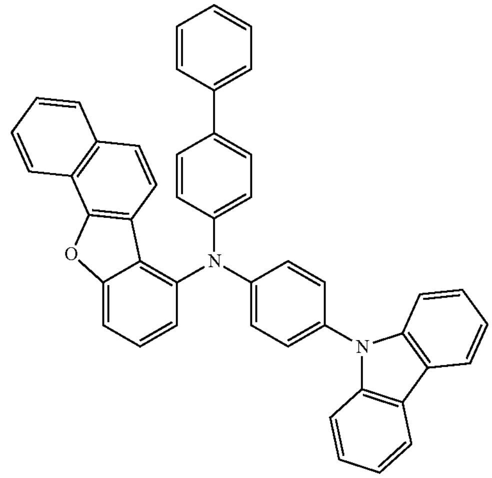
E185
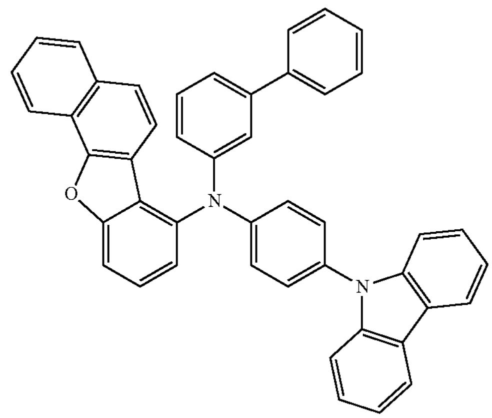
E186
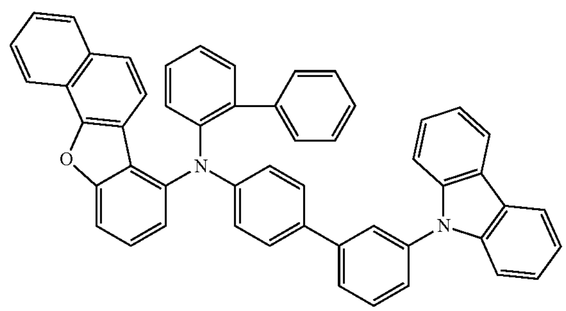
E187
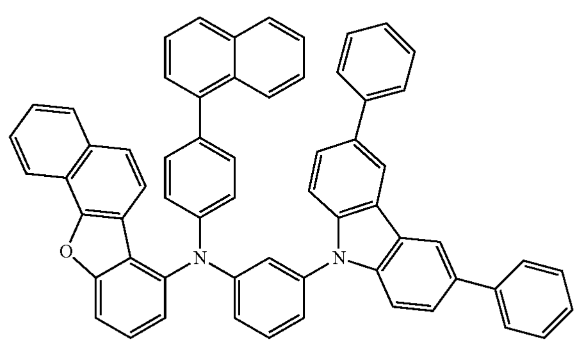

-continued
E188
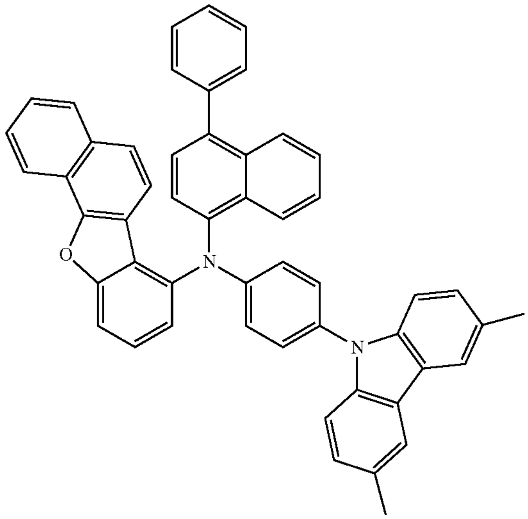
E189
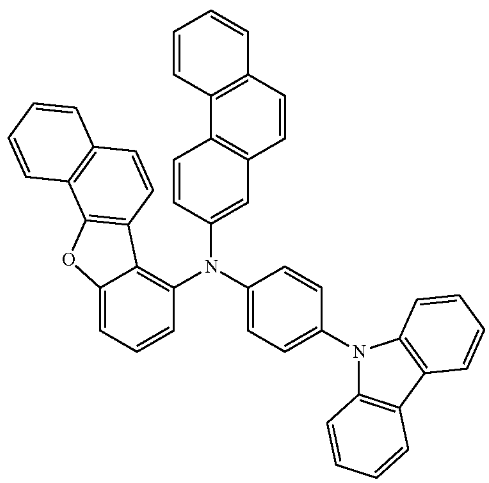
E190
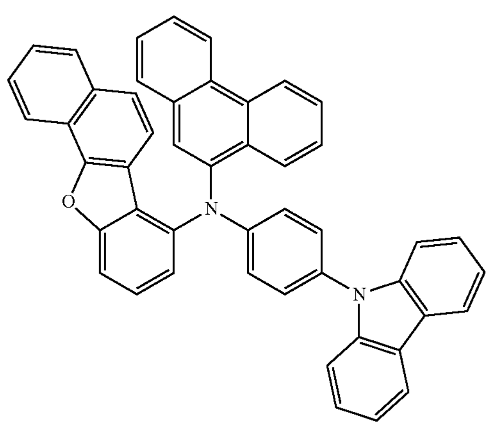
-continued
E191
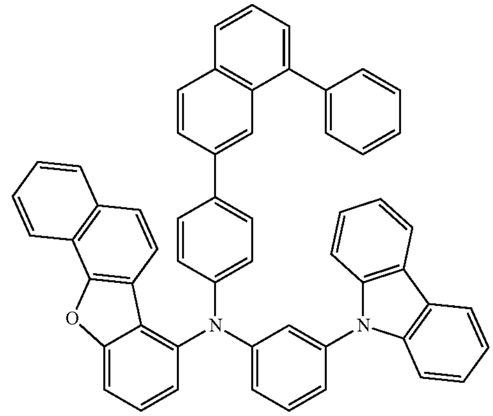
E192
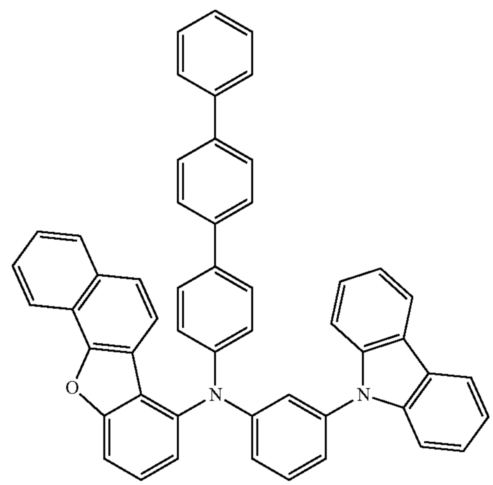
E193
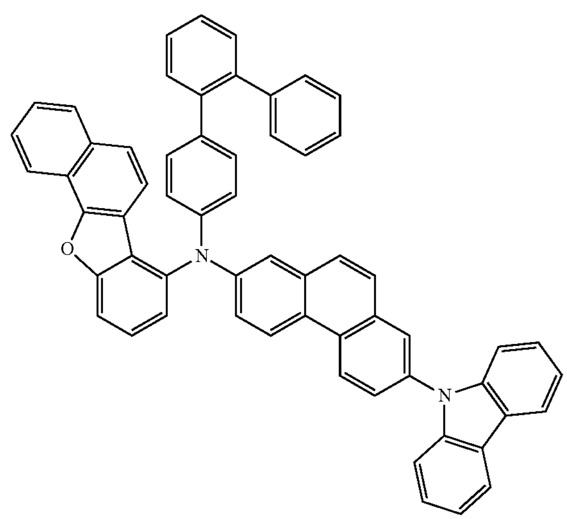

-continued
E194
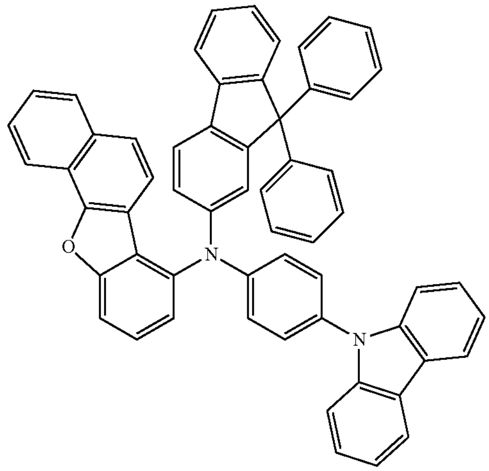
E195
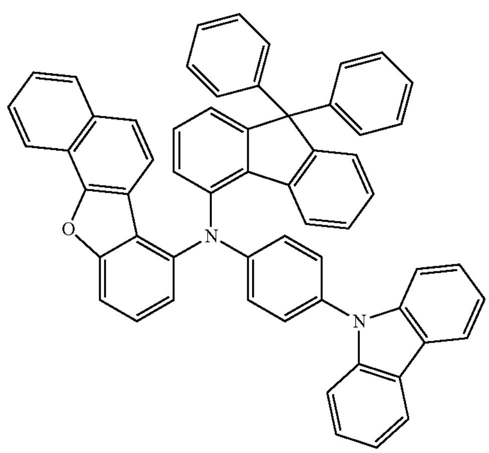
E196
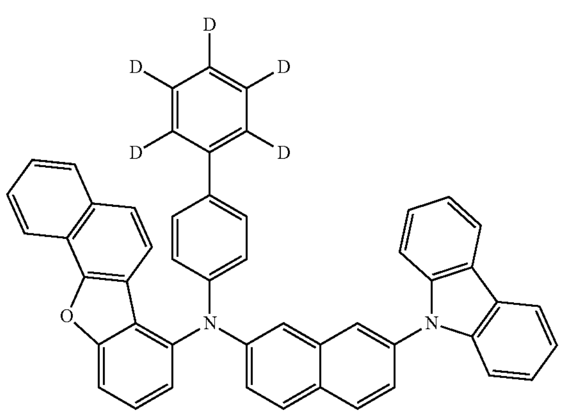
-continued
E197
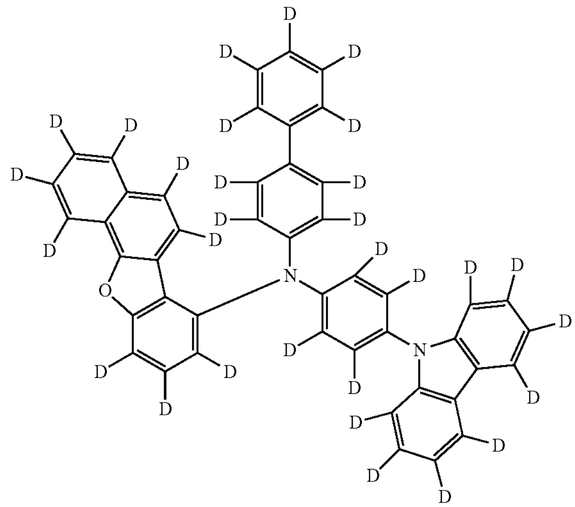
E198
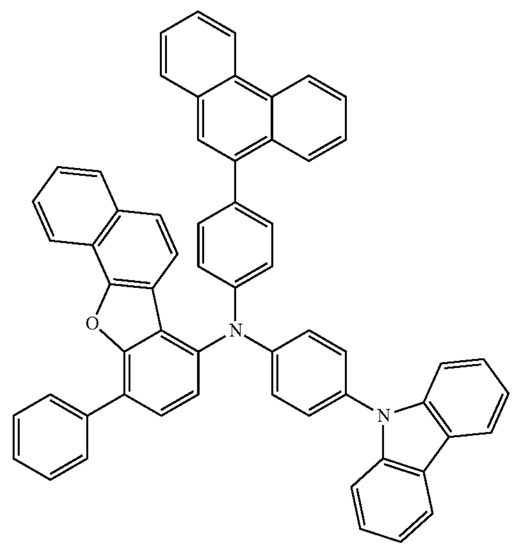
E199
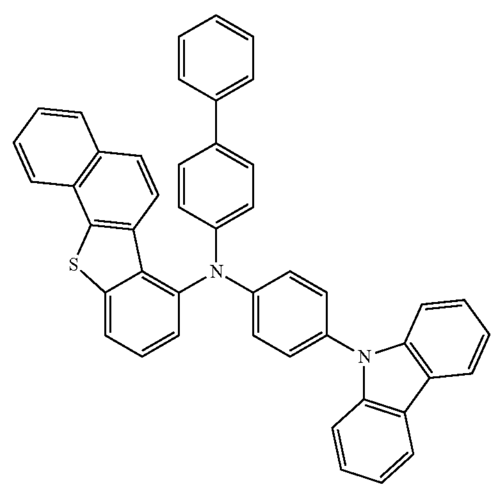

-continued
E200
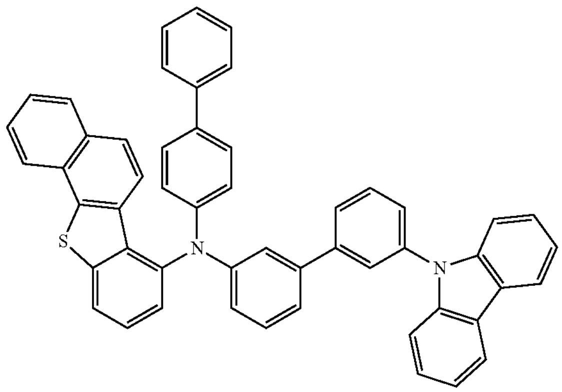
[Compound Group 6]
F1
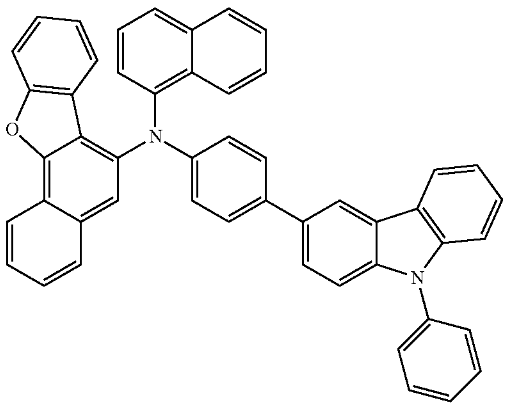
F2
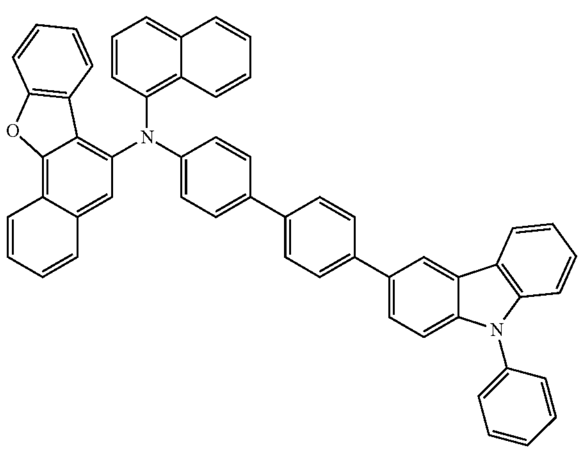
-continued
F3
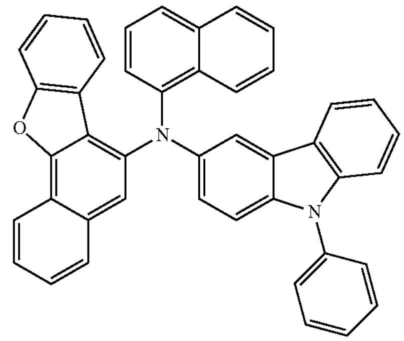
F4
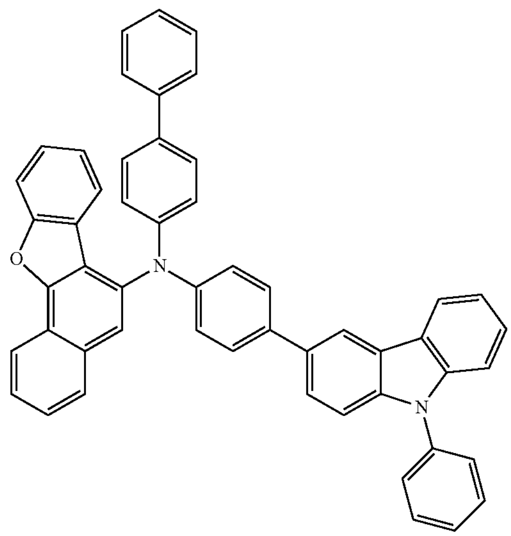
F5
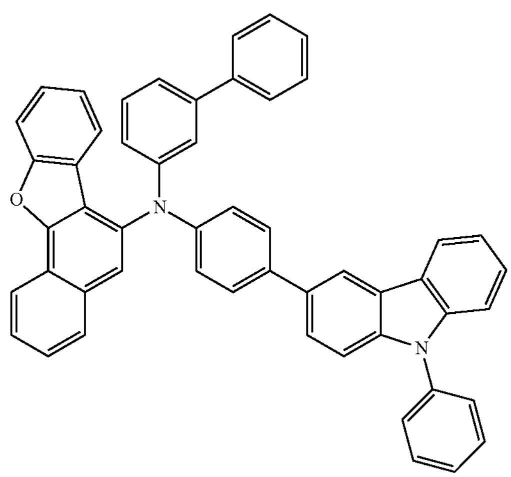
F6
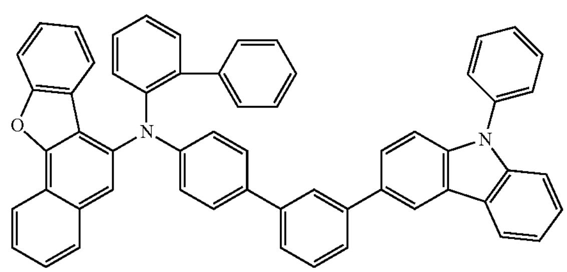

-continued
F7
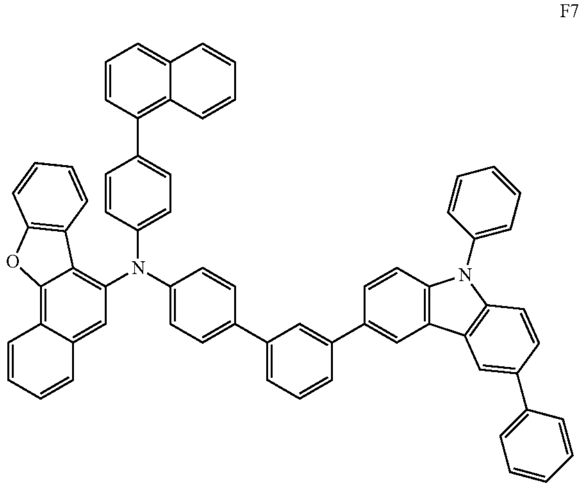
F8
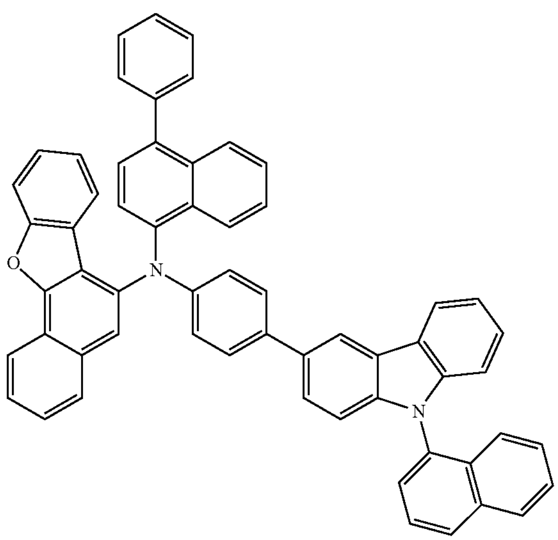
F9
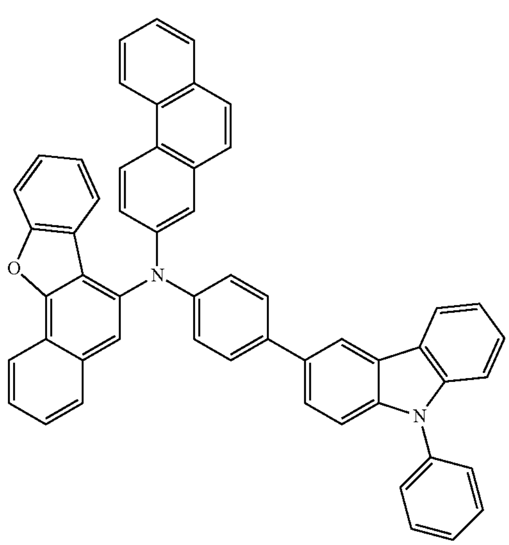
-continued
F10
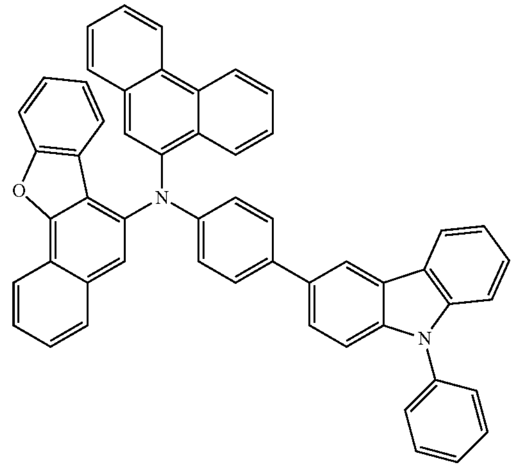
F11
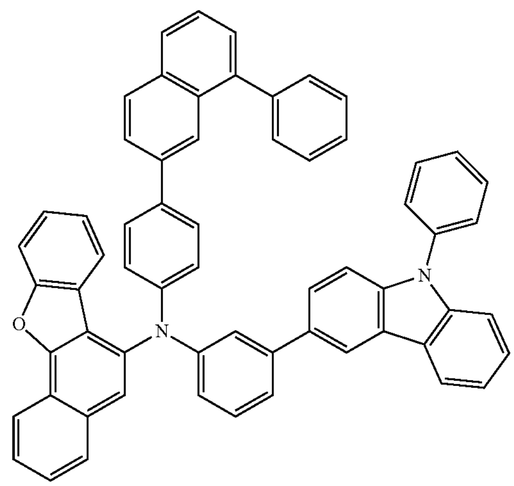
F12
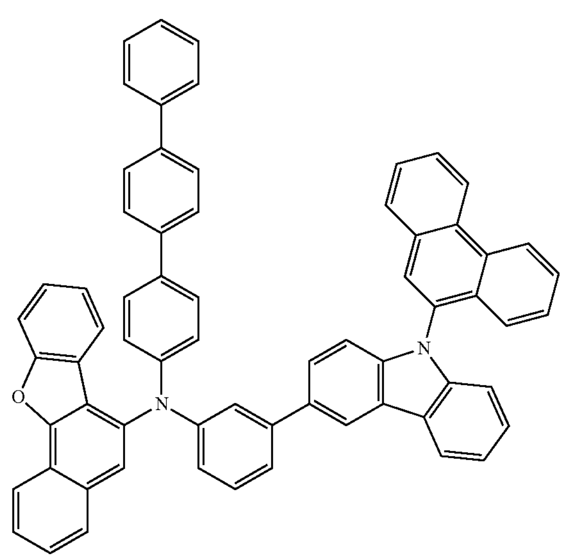

-continued
F13
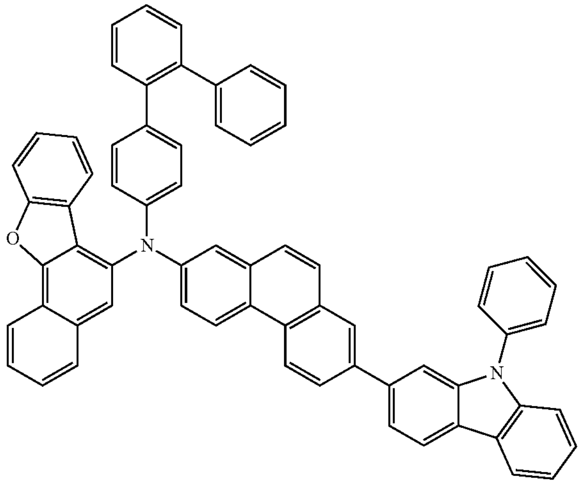
F14
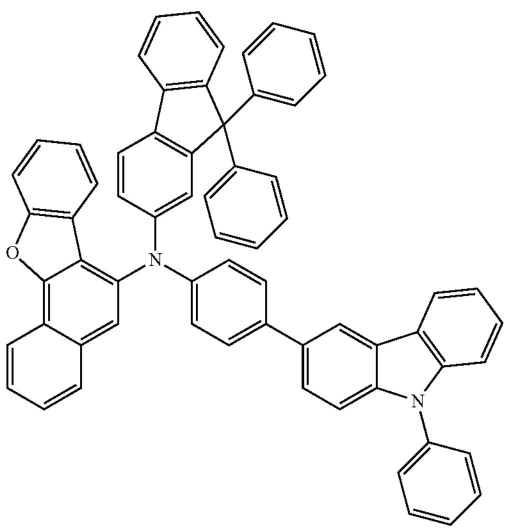
F15
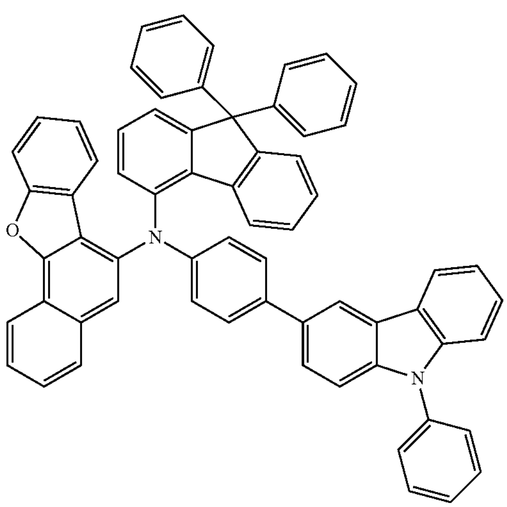
-continued
F16
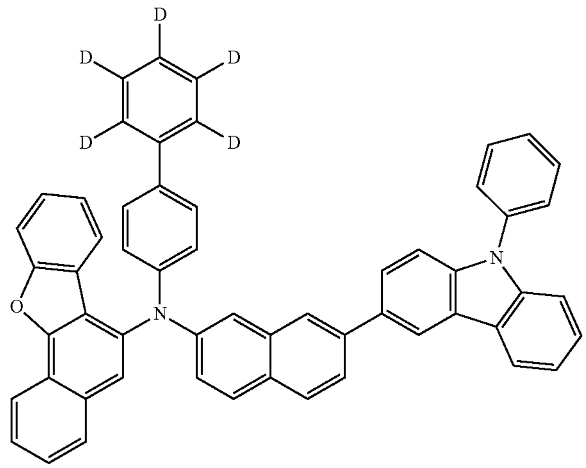
F17
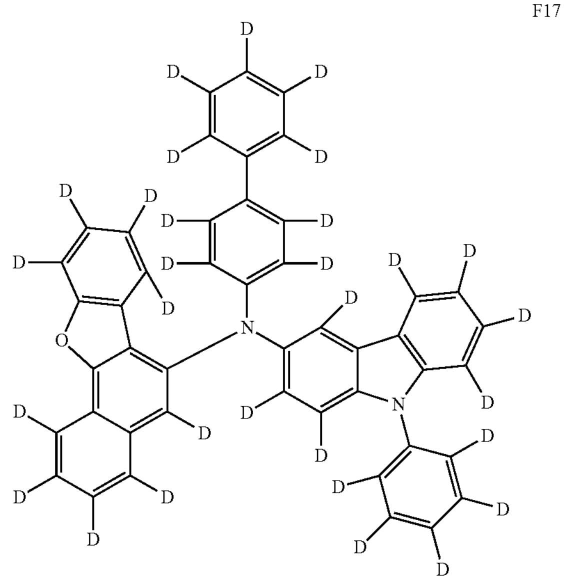
F18
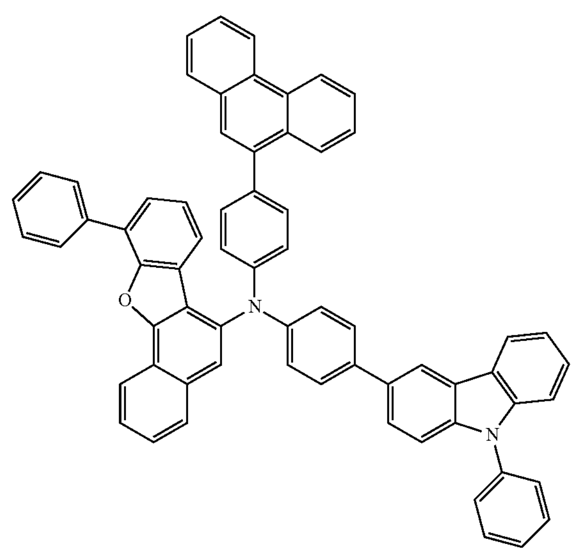

F19
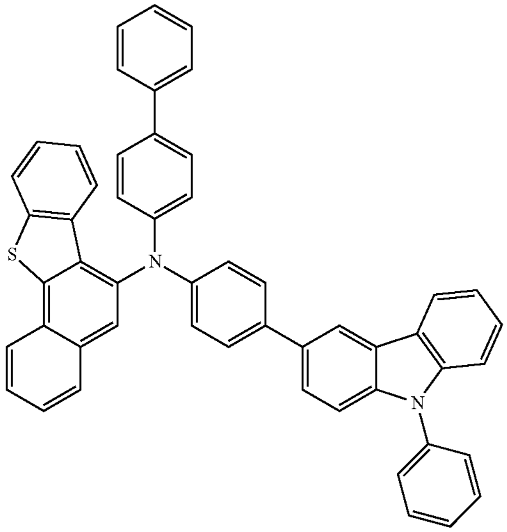
F20
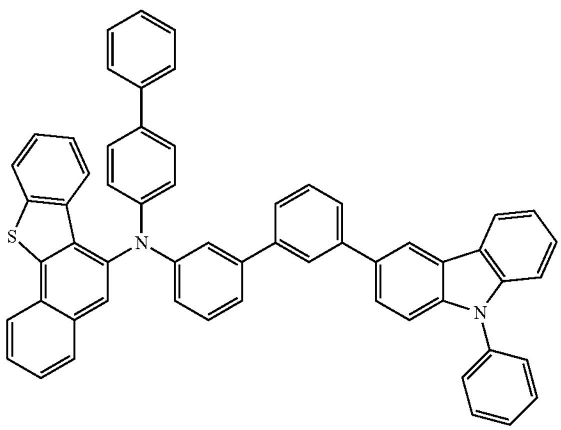
F21
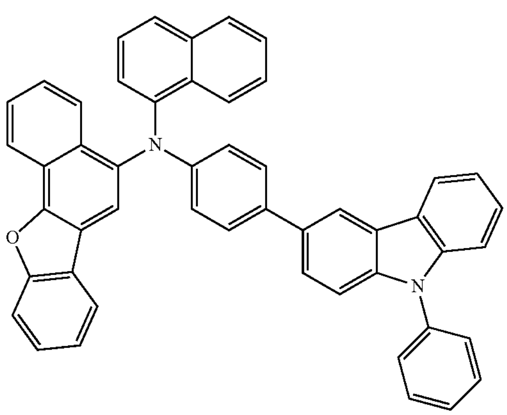
F22
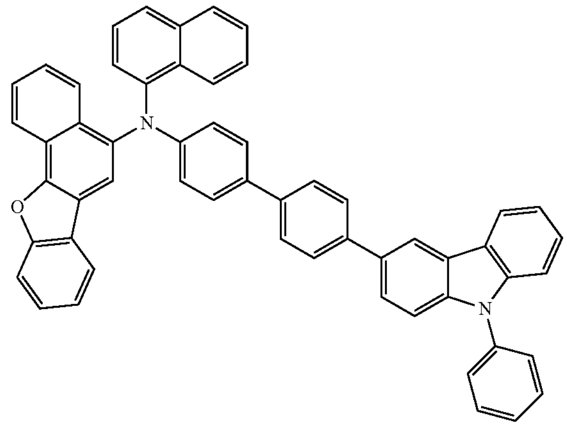
F23
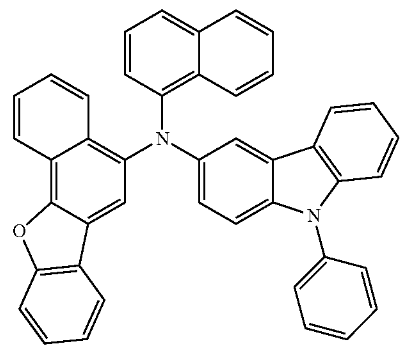
F24
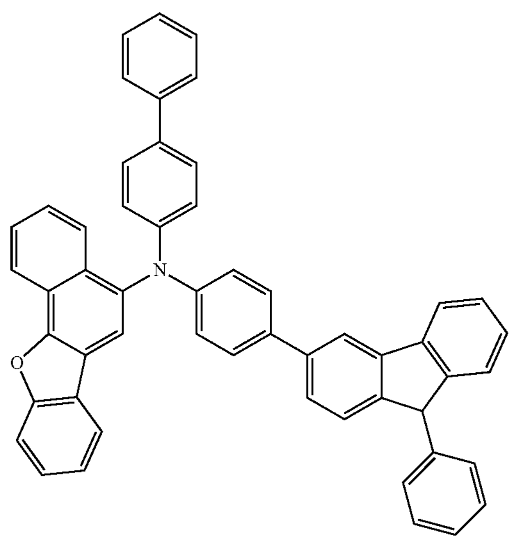

F25
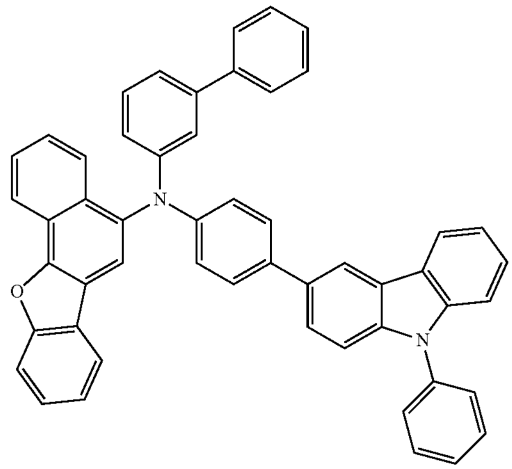
F26
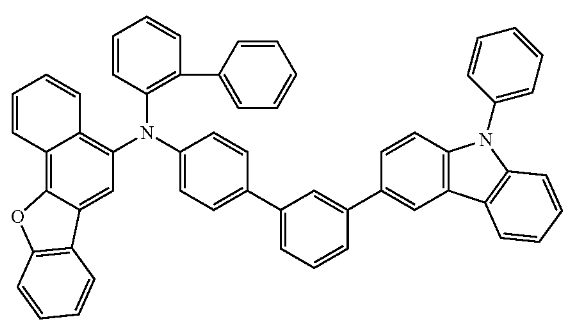
F27
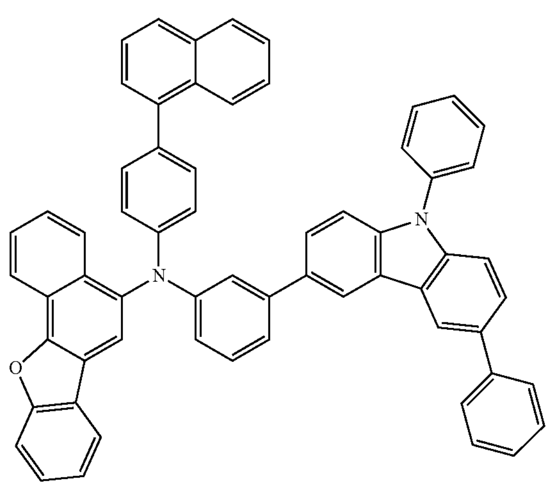
F28
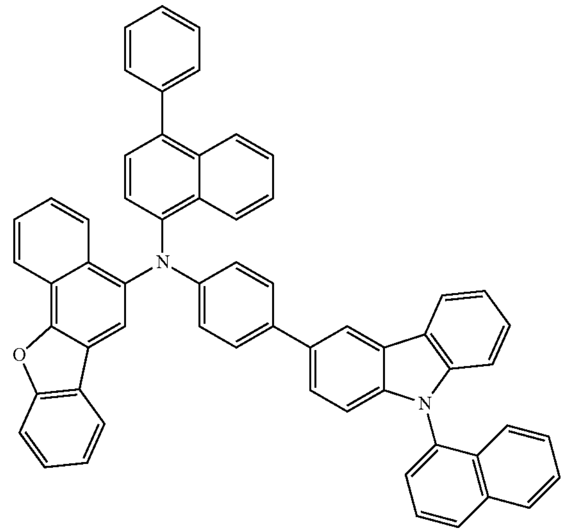
F29
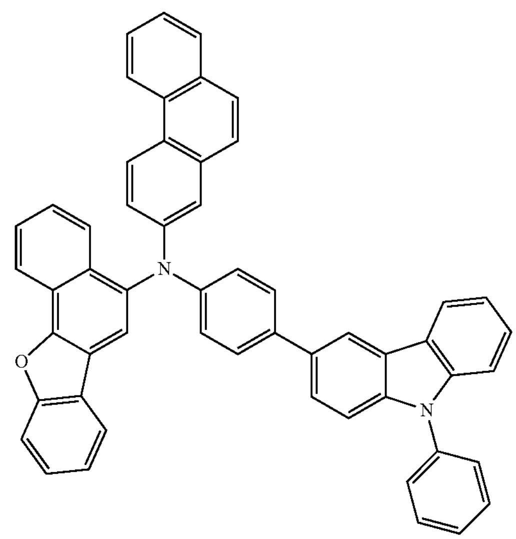
F30
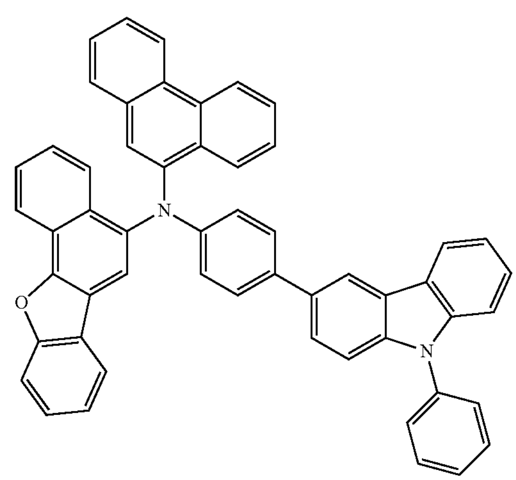

F31
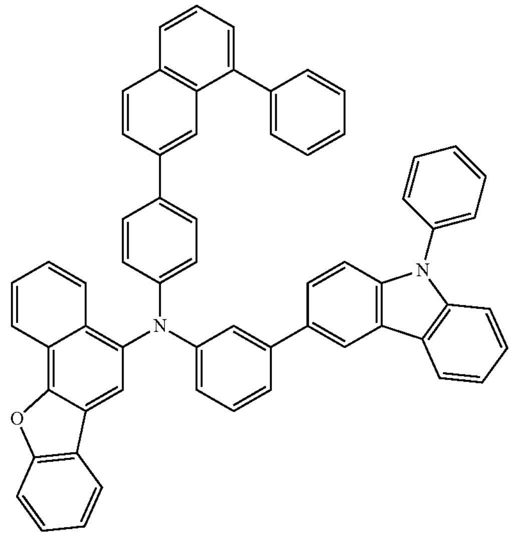
F32
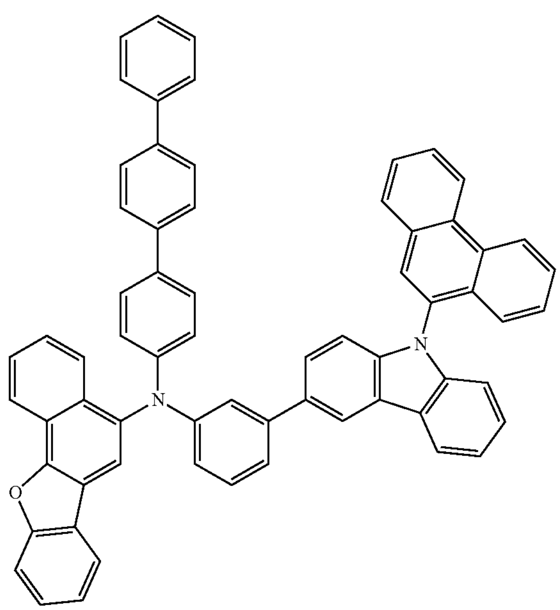
F33
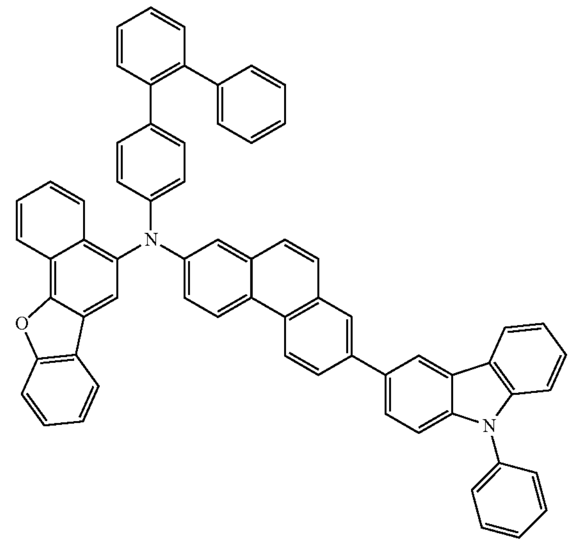
F34
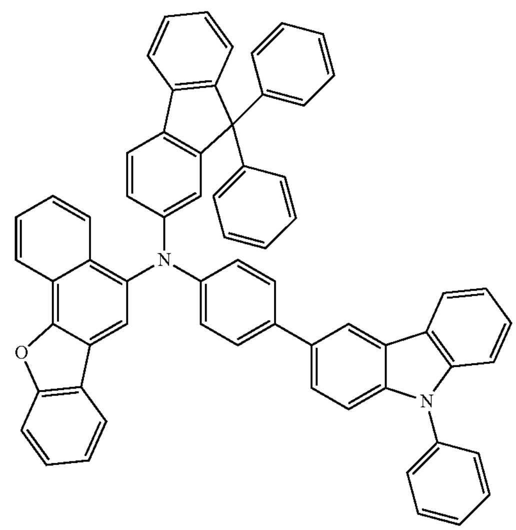
F35
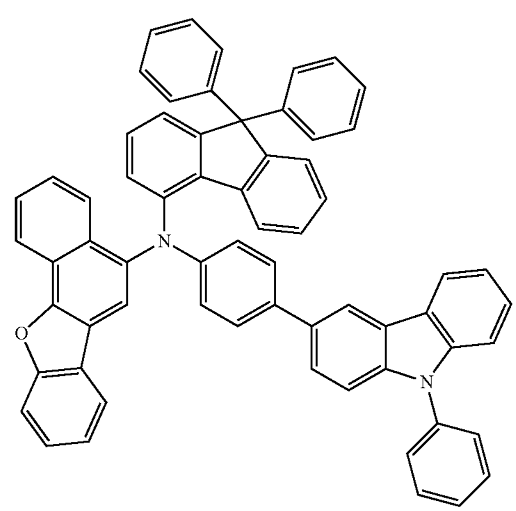

-continued
36
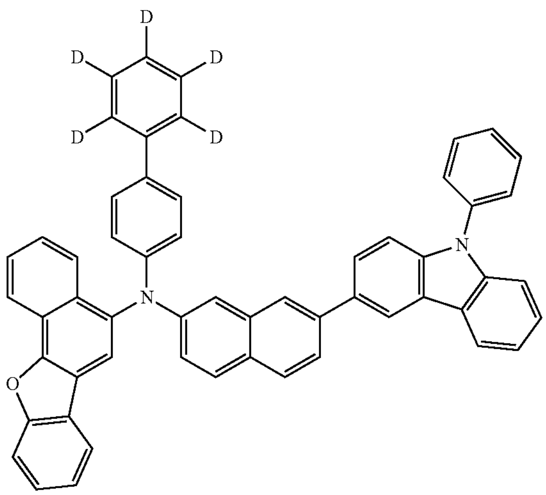
F37
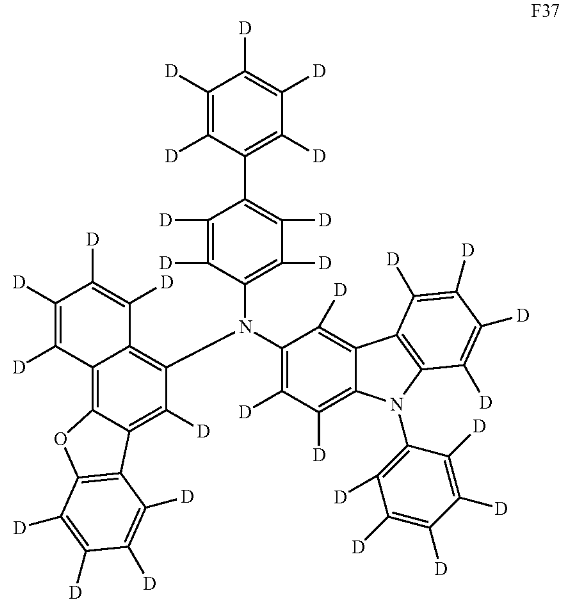
F38
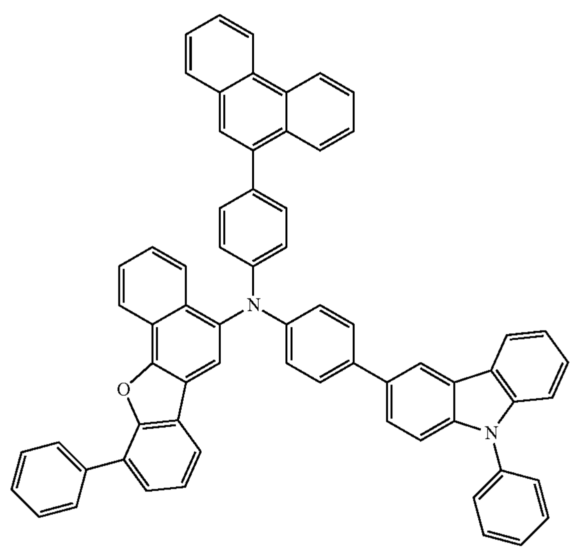
-continued
F39
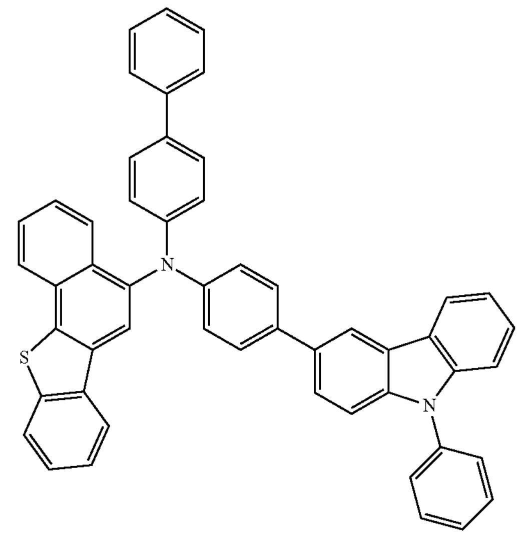
F40
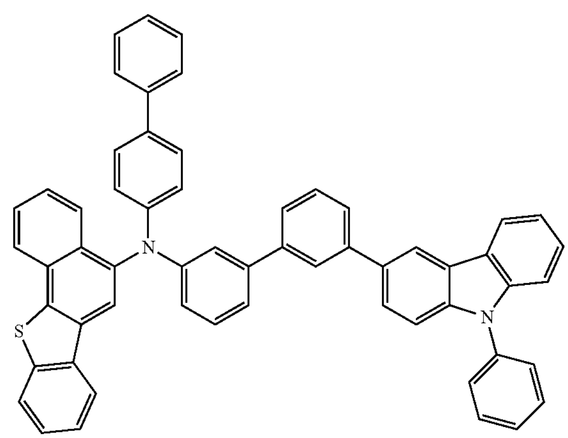
F41
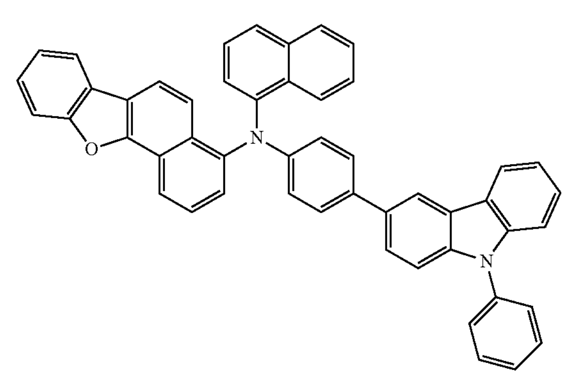

-continued
F42
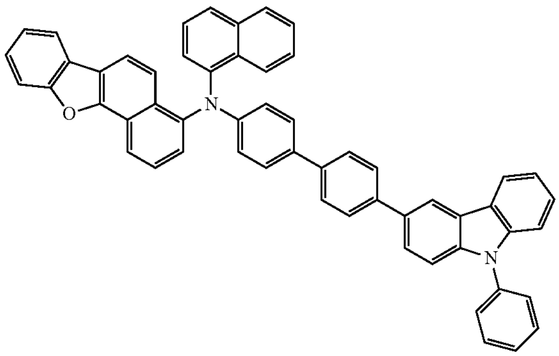
F43
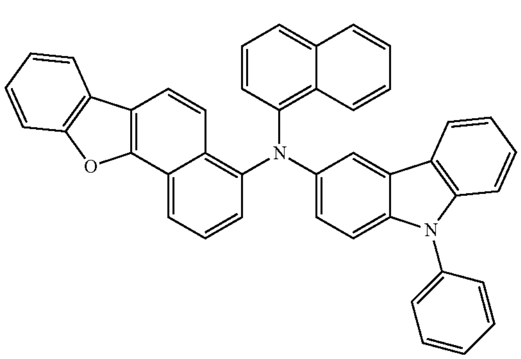
F44
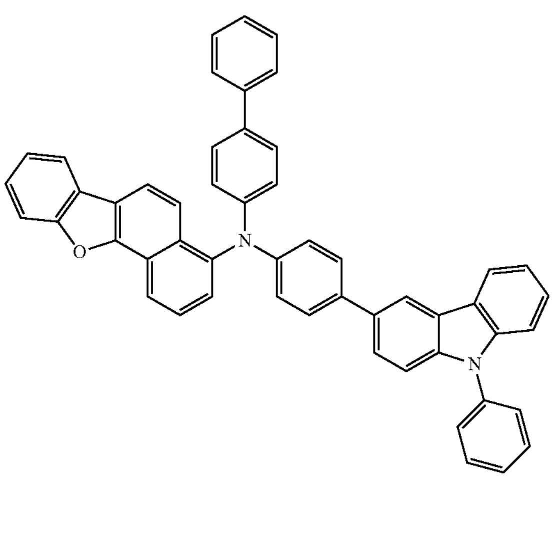
-continued
F45
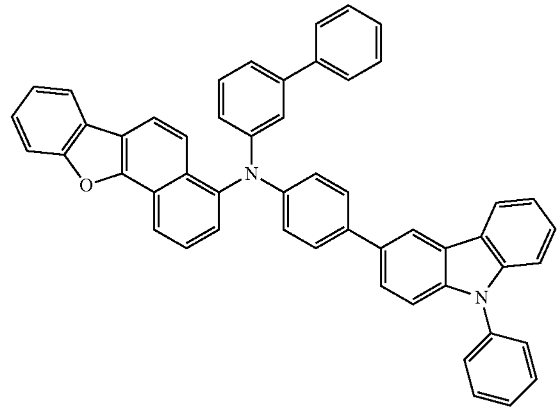
F46
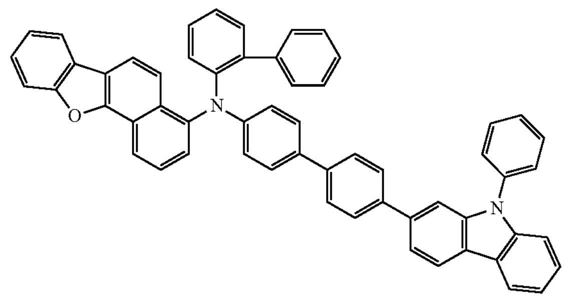
F47
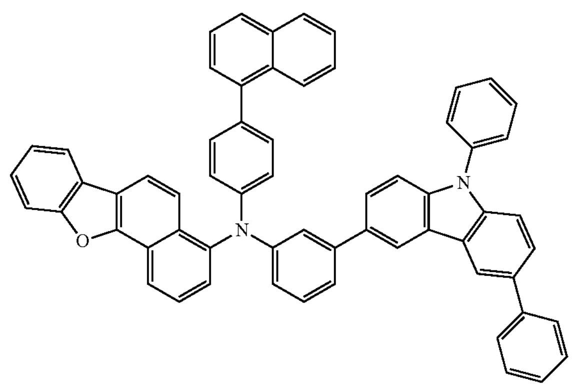
F48
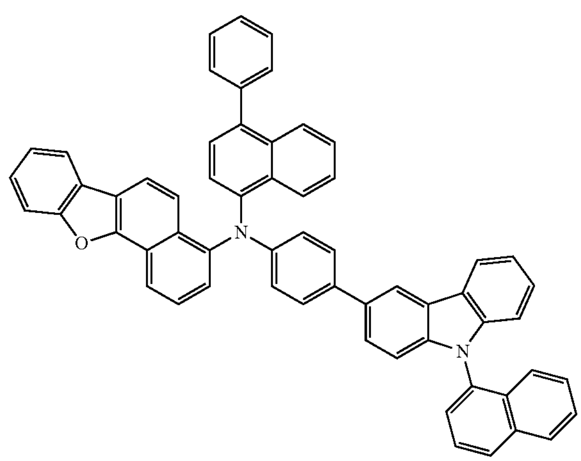

-continued
F49
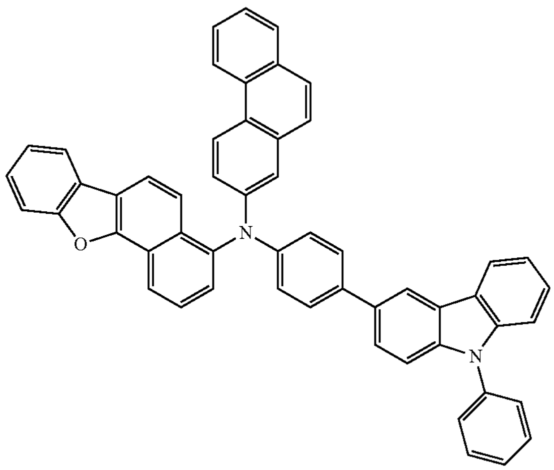
F50
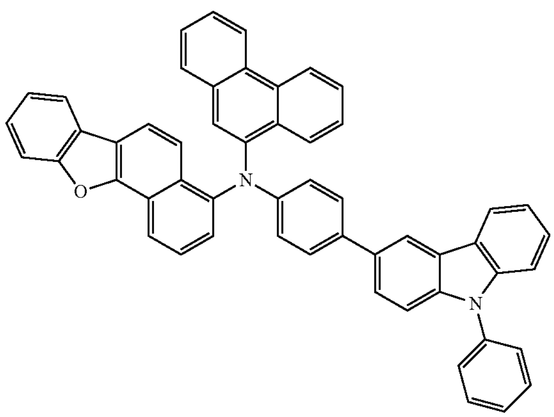
F51
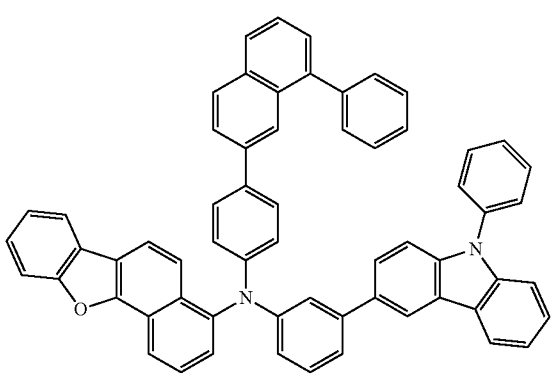
-continued
F52
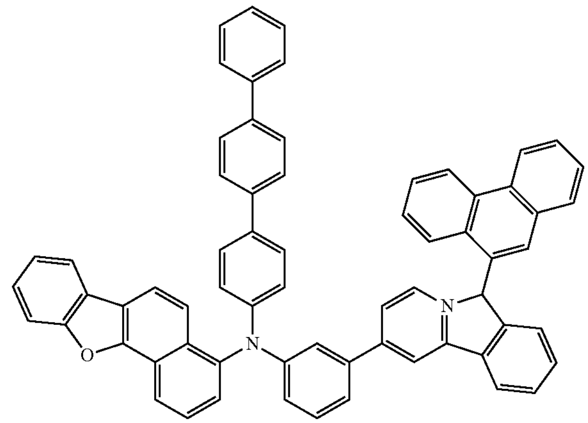
F53
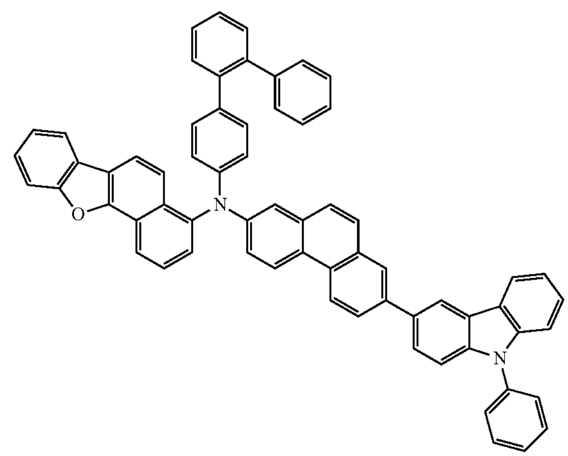
F54
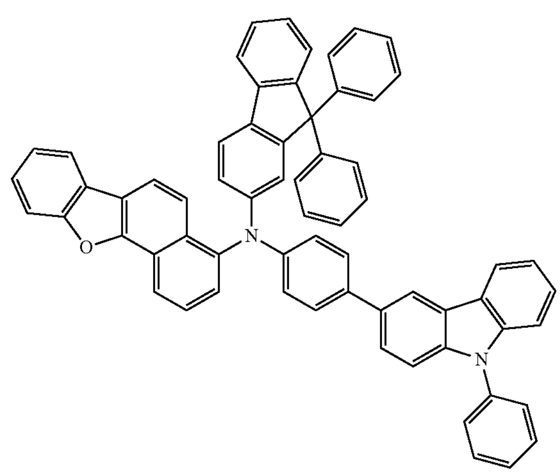

-continued
F55
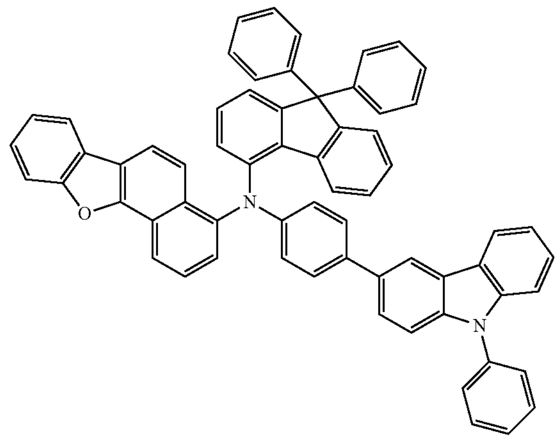
F56
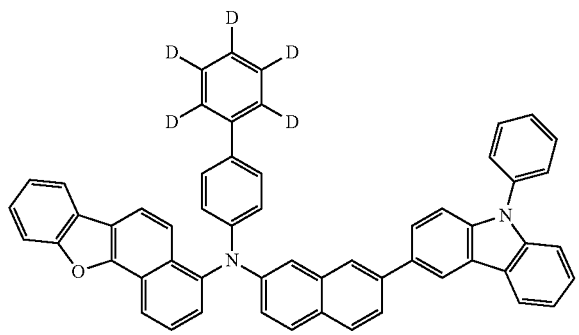
F57
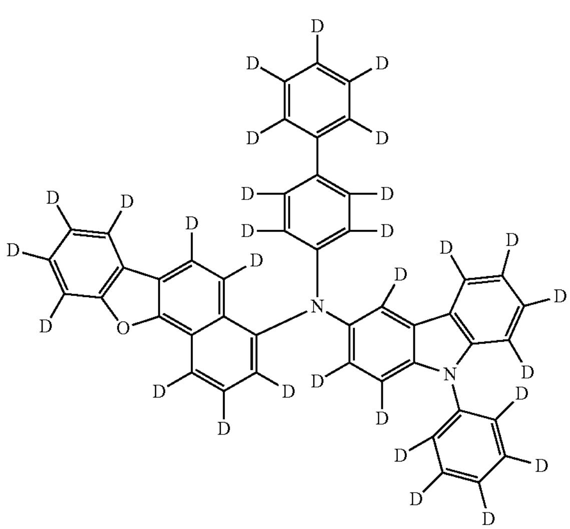
-continued
F58
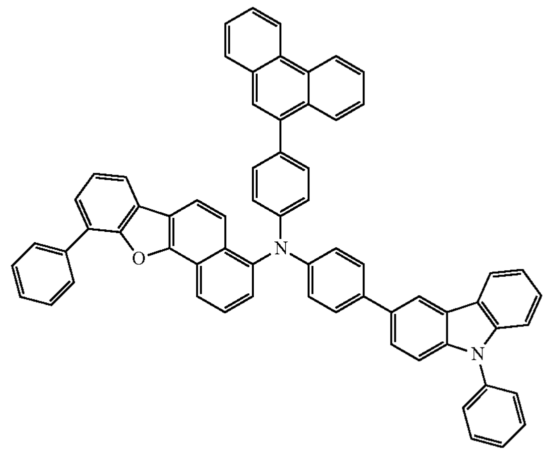
F59
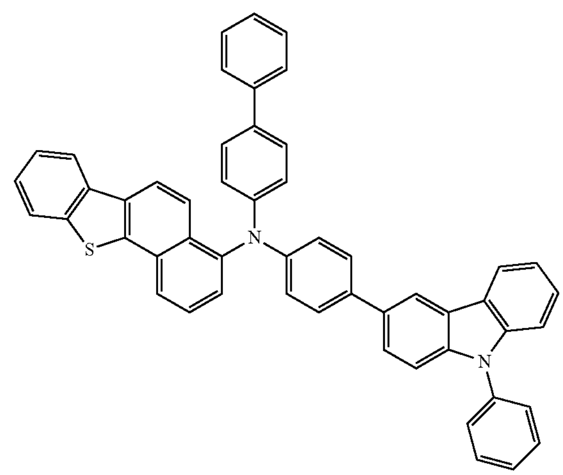
F60
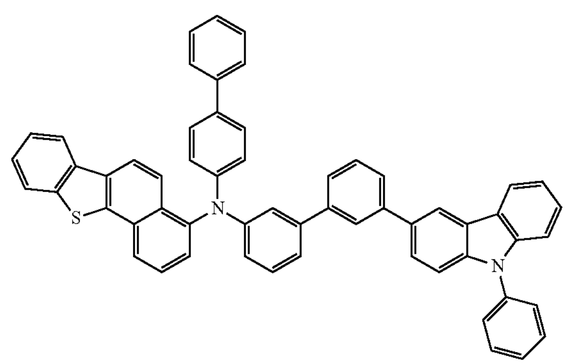

-continued
F61
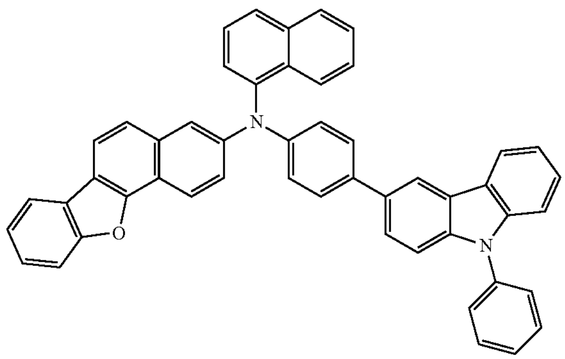
F62
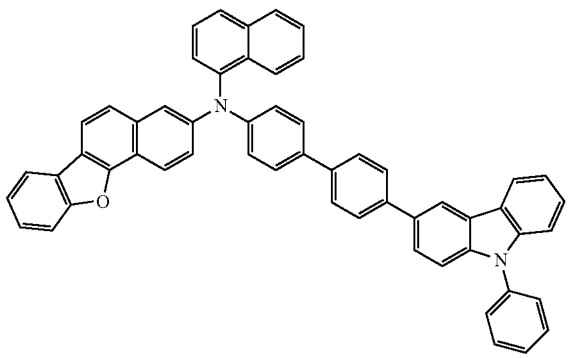
F63
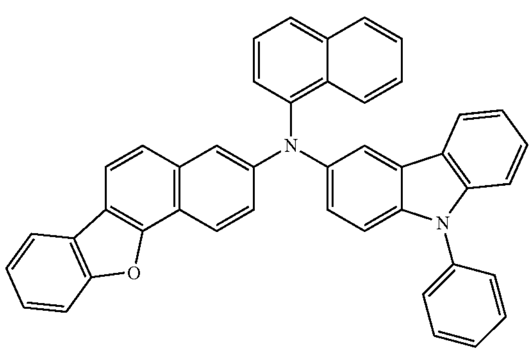
F64
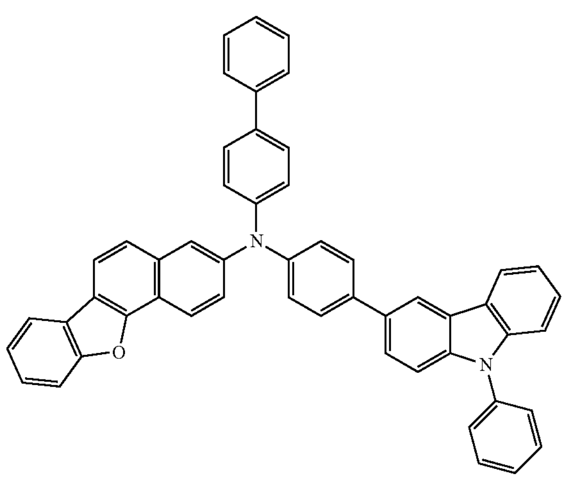
-continued
F65
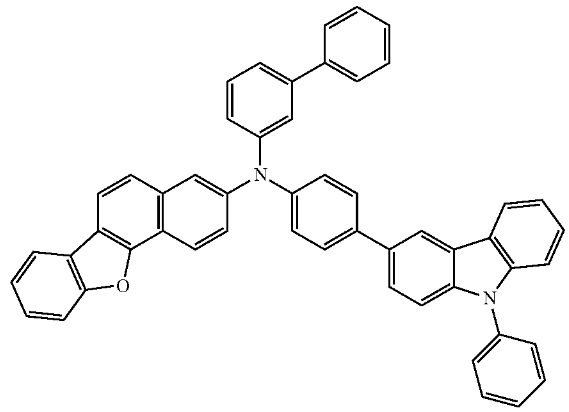
F66
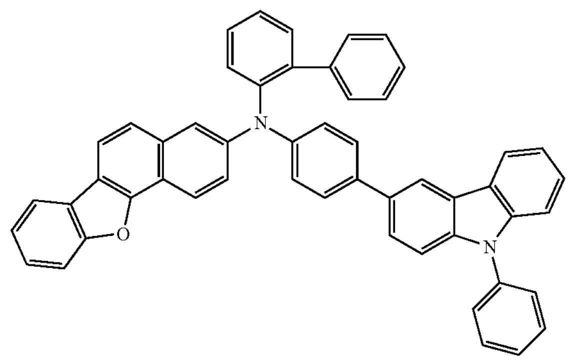
F67
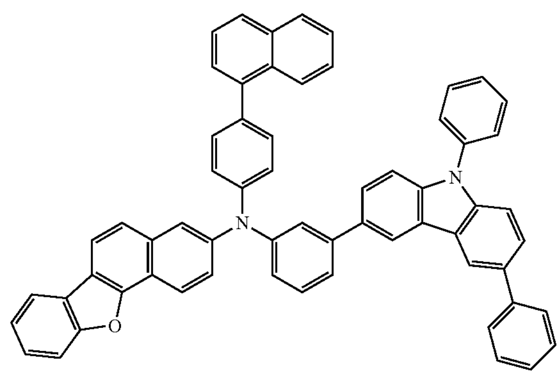
F68
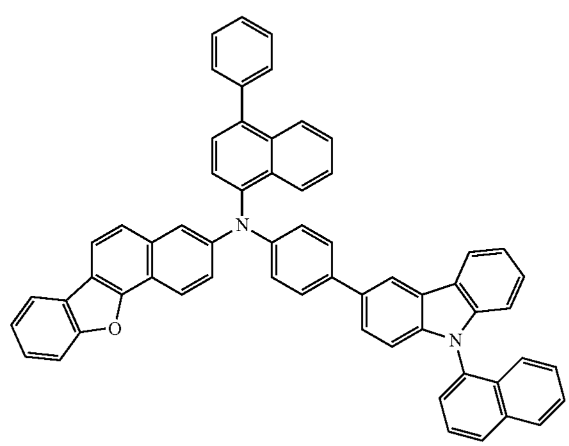

-continued
F69
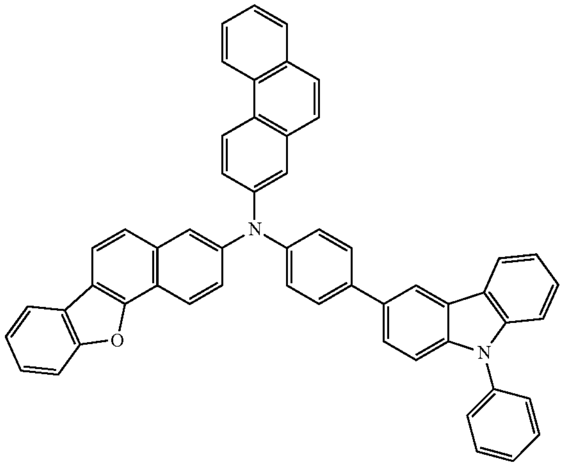
F70
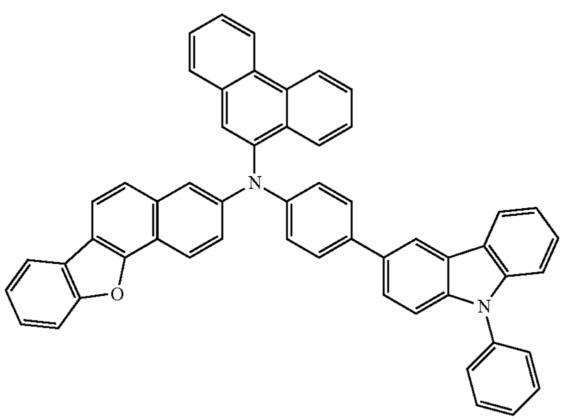
F71
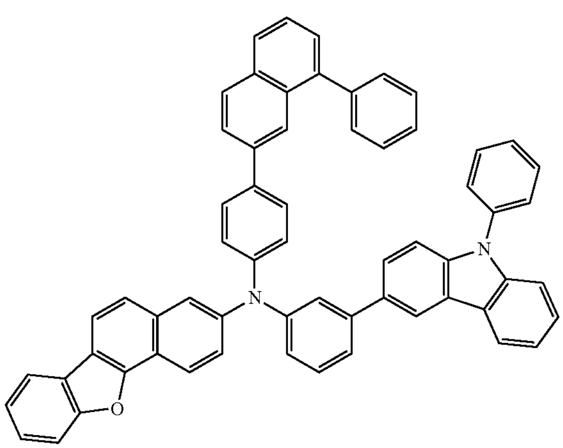
-continued
F72
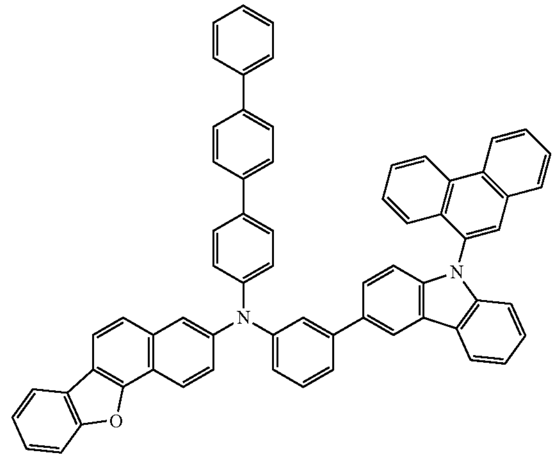
F73
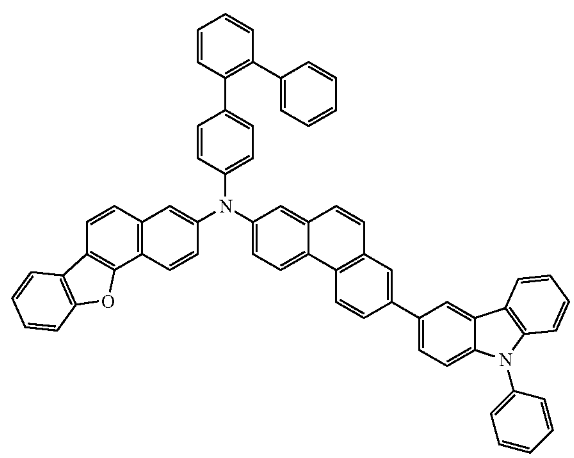
F74
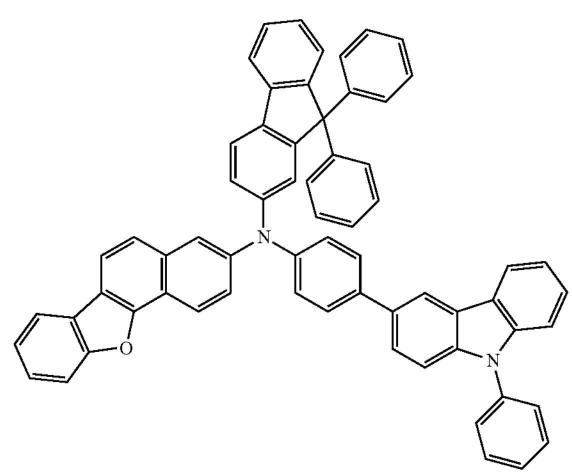

-continued
F75
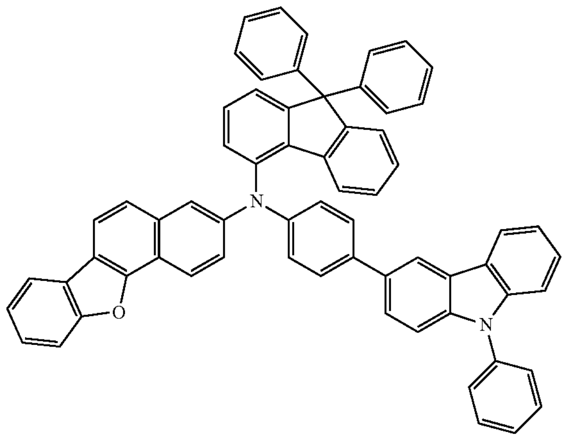
F76
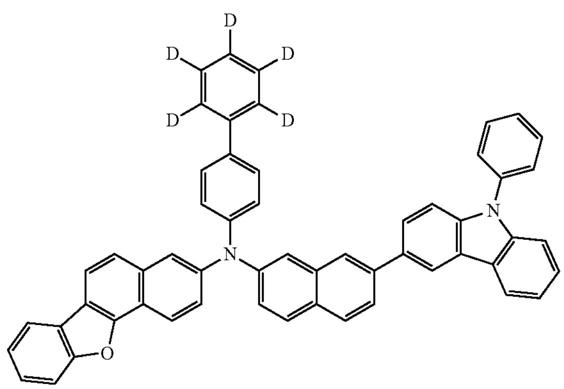
F77
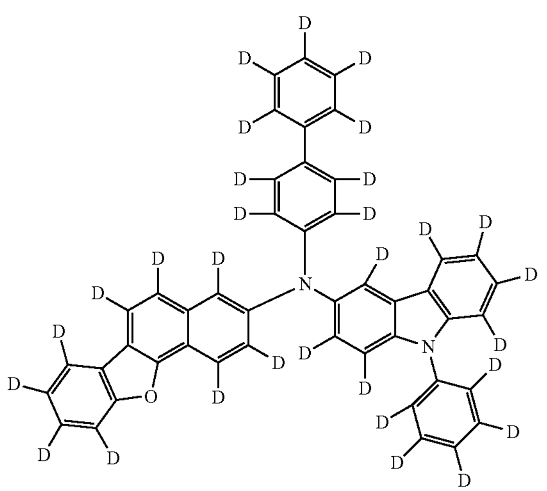
-continued
F78
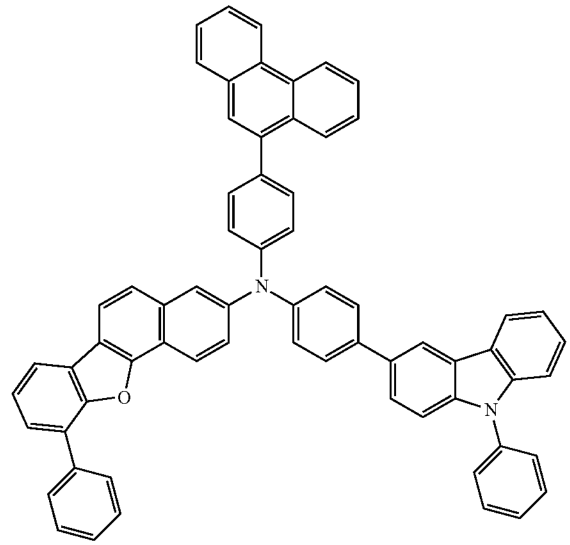
F79
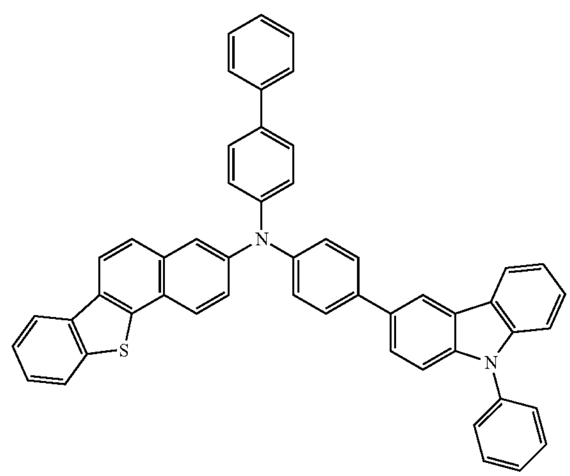
F80
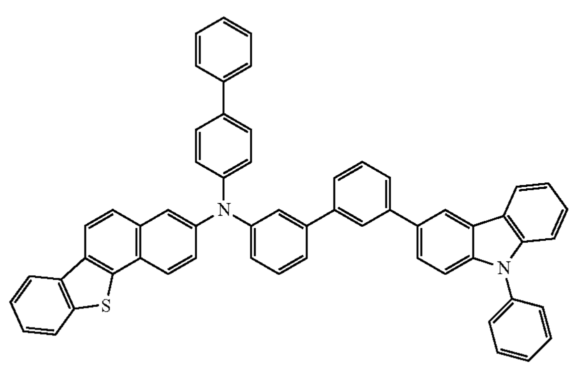

-continued
F81
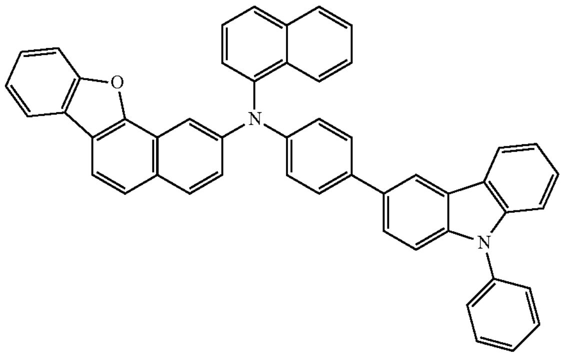
F82
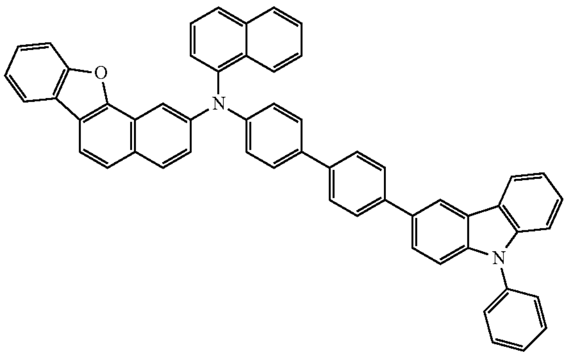
F83
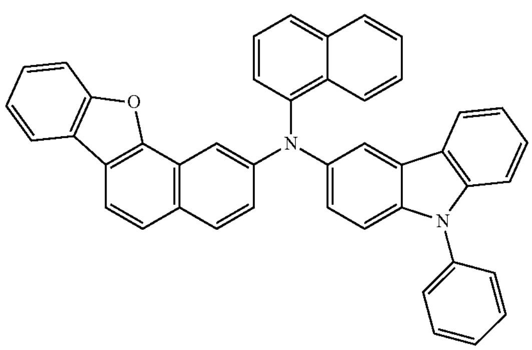
F84
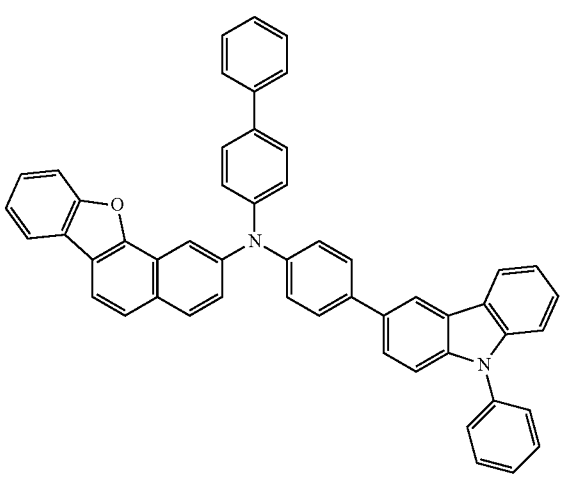
-continued
F85
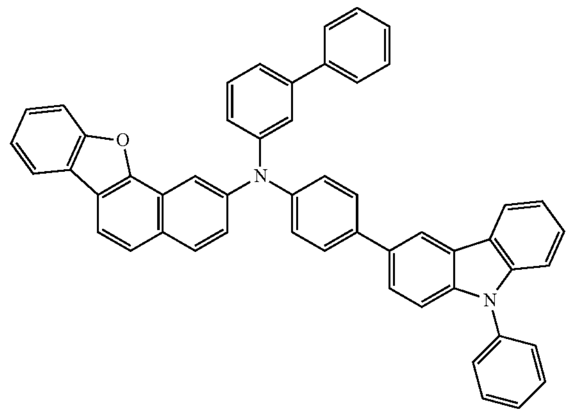
F86
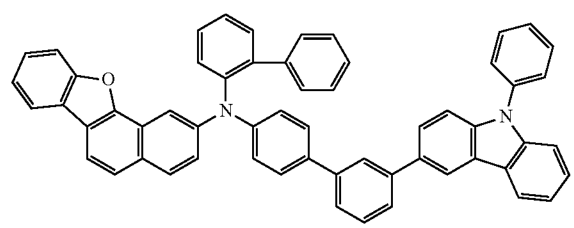
F87
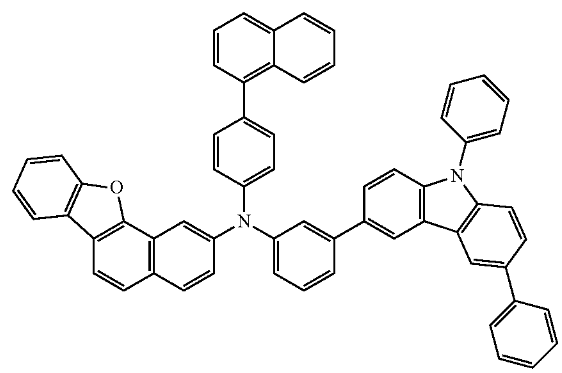
F88
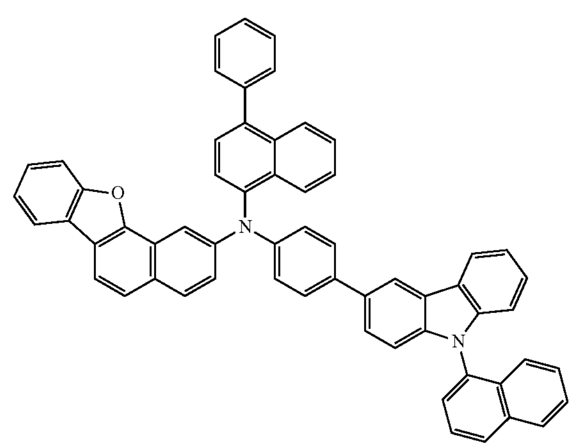

-continued
F89
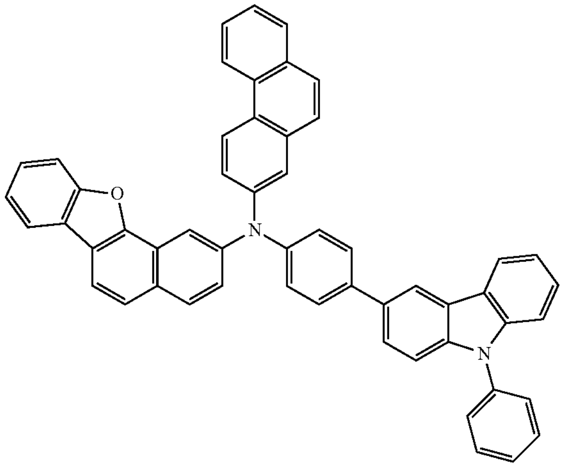
F90
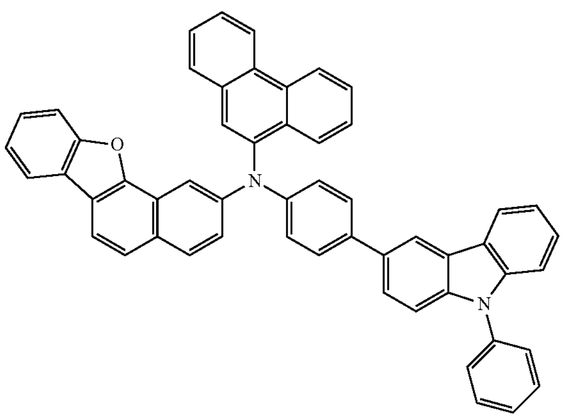
F91
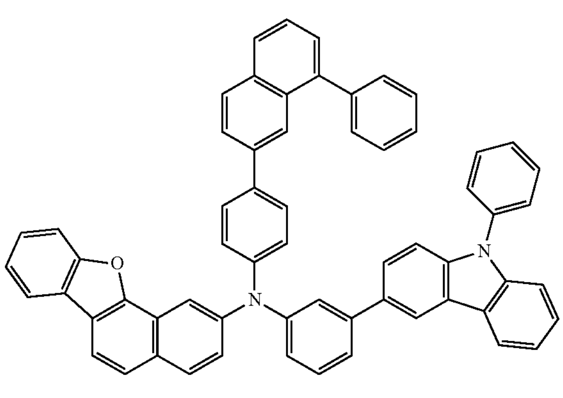
-continued
F92
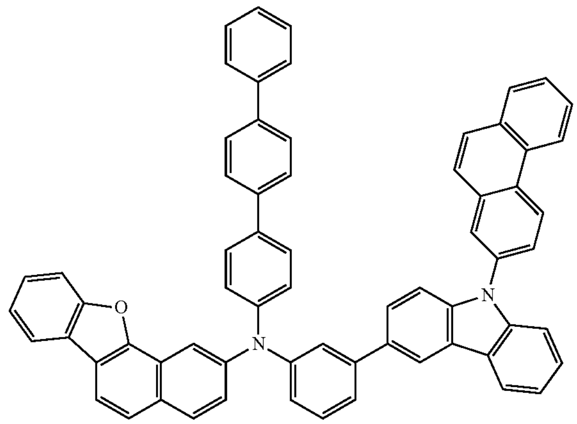
F93
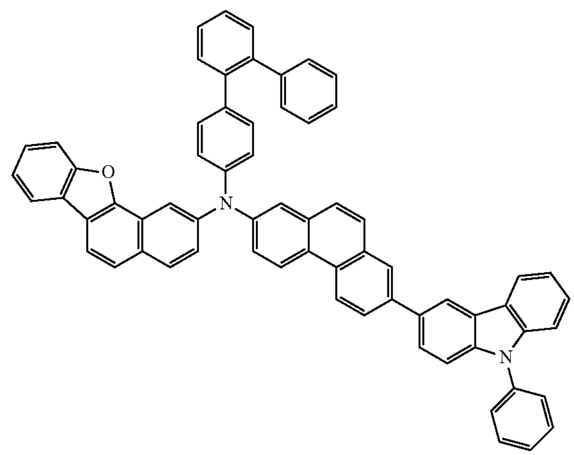
F94
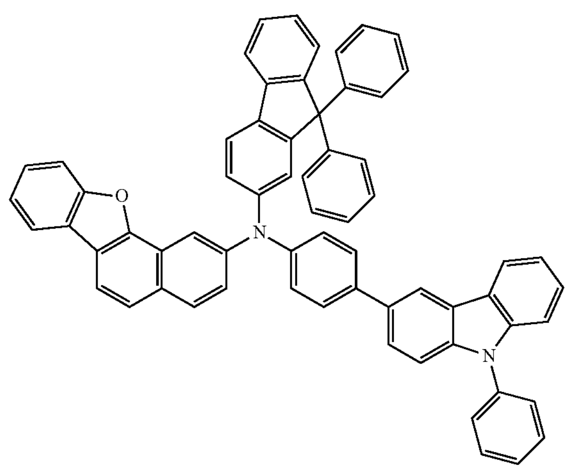

-continued
F95
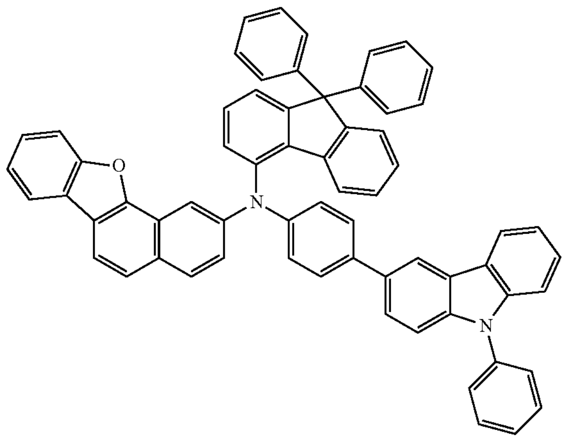
F96
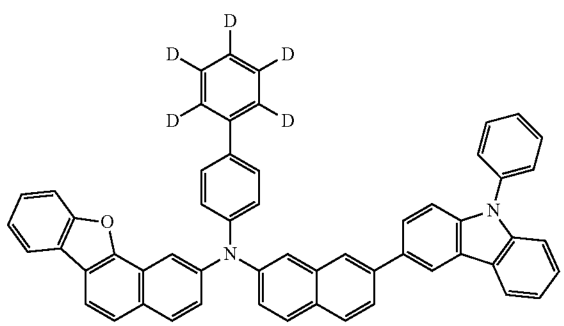
F97
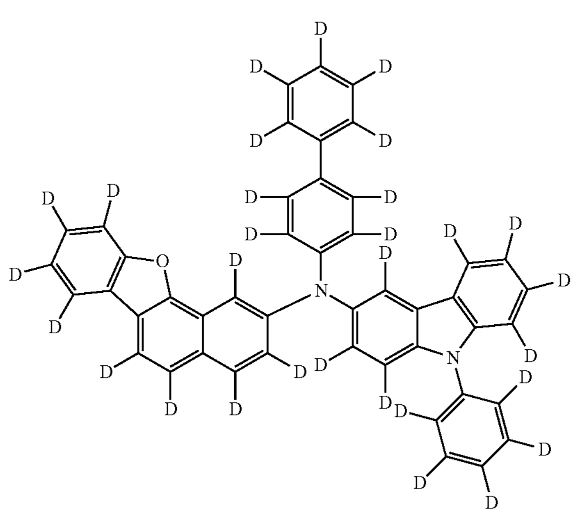
-continued
F98
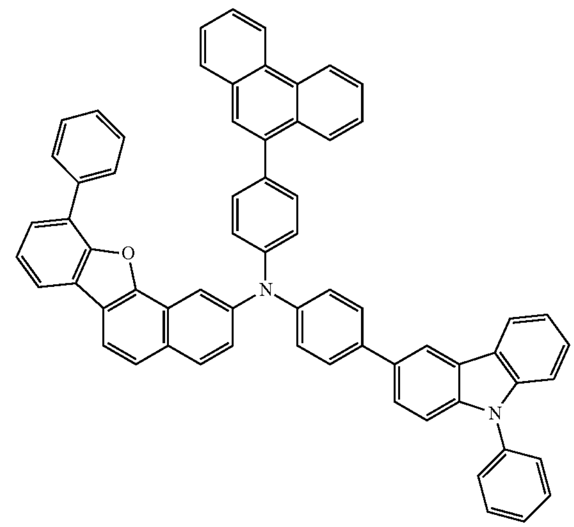
F999
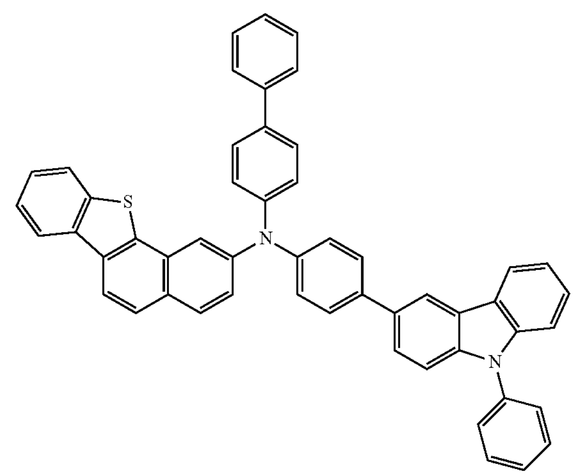
F100
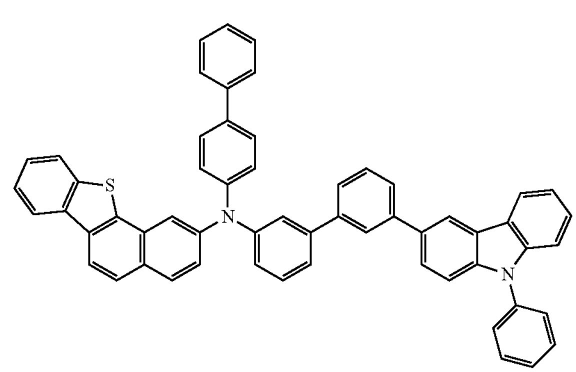

F101
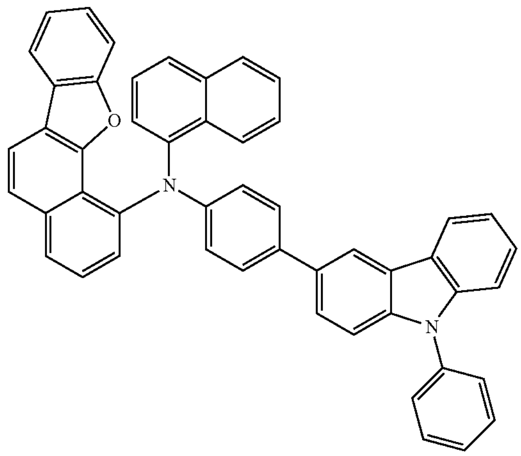
F102
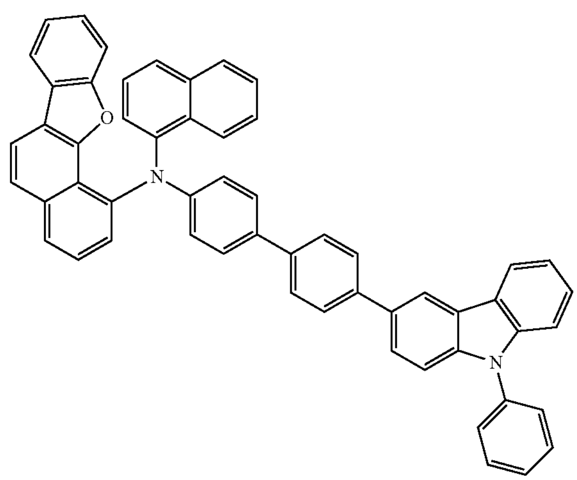
F103
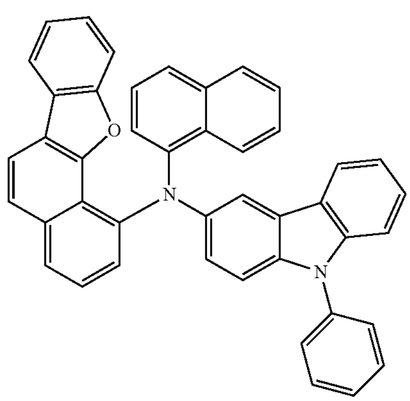
F104
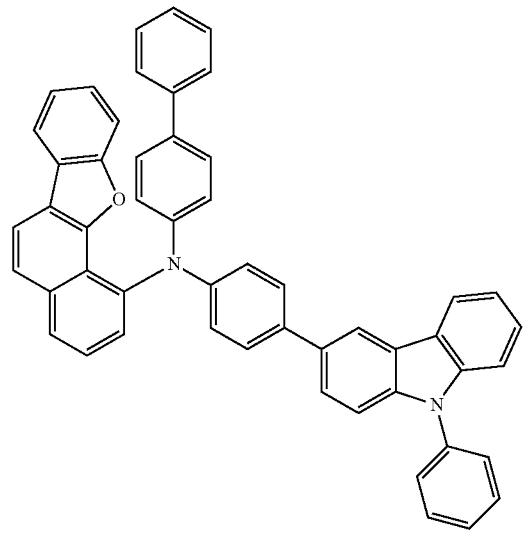
F105
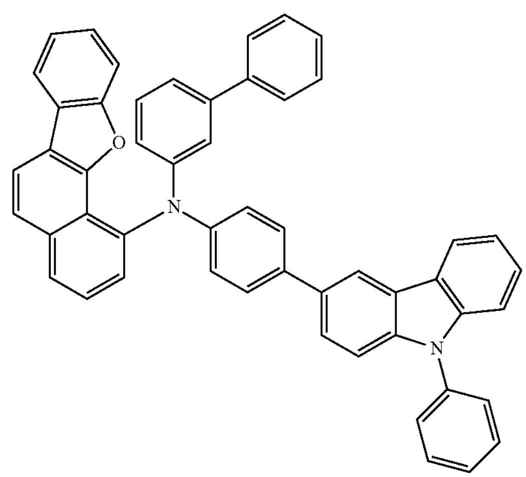
F106
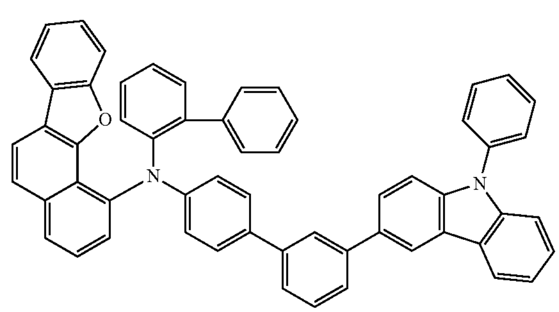

-continued
F107
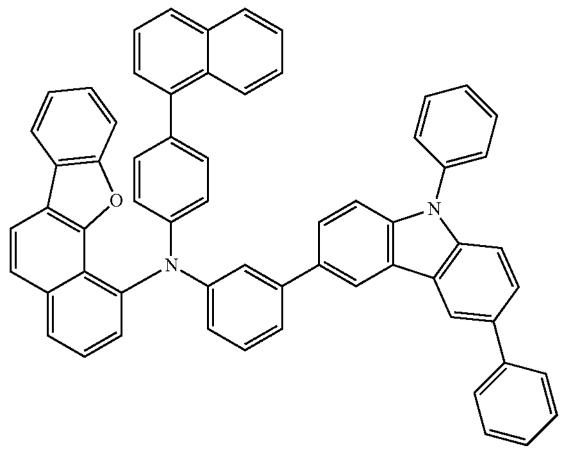
F108
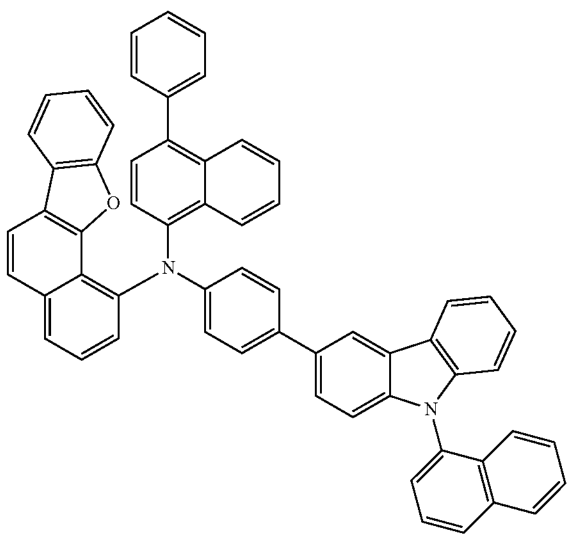
F109
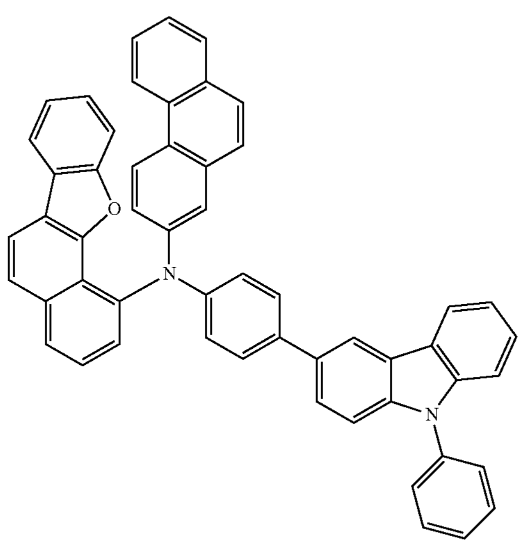
-continued
F110
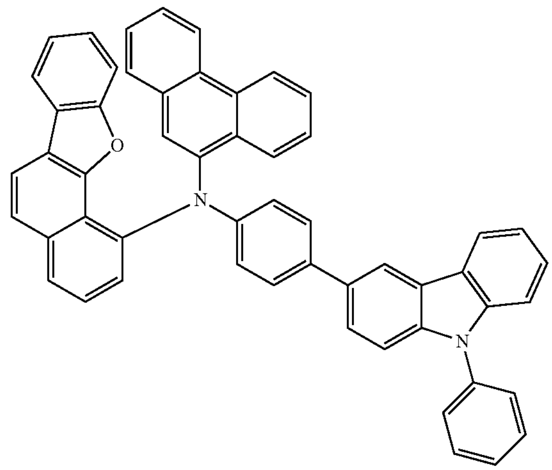
F111
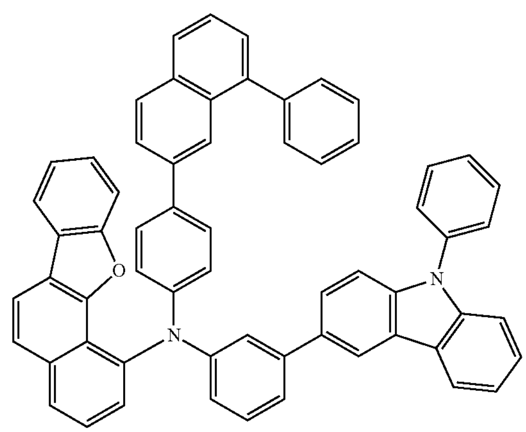
F112
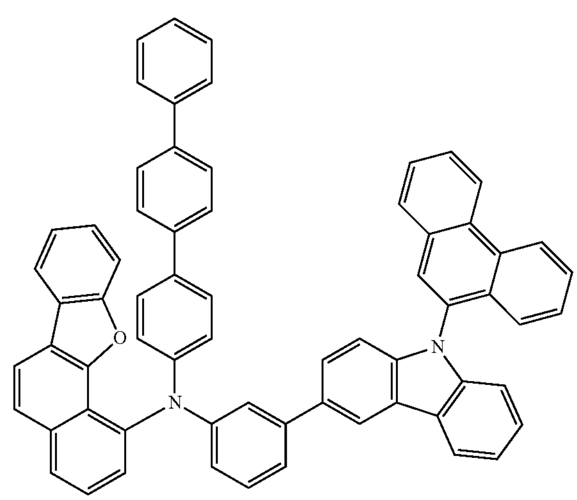

-continued
F113
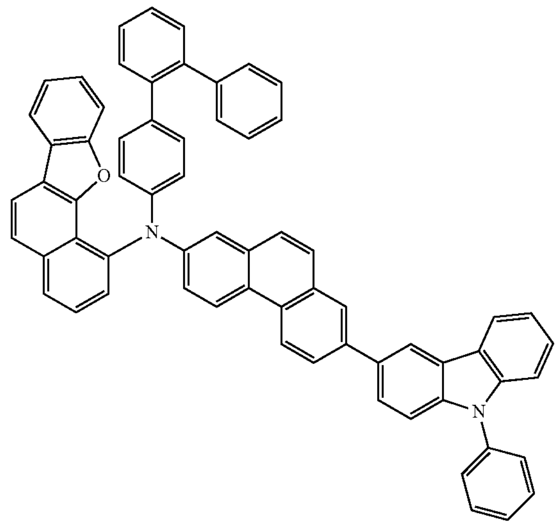
F114
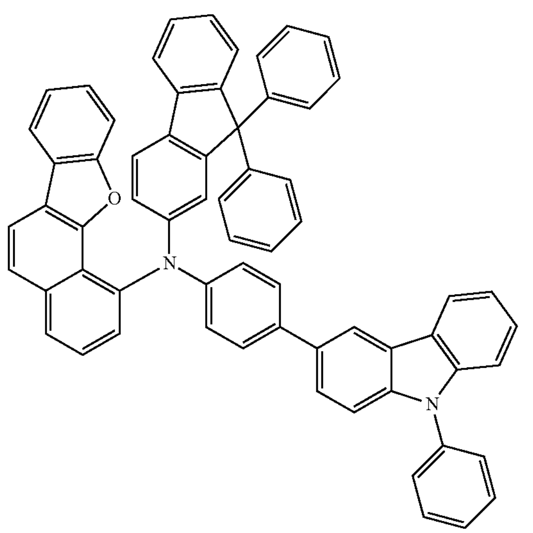
F115
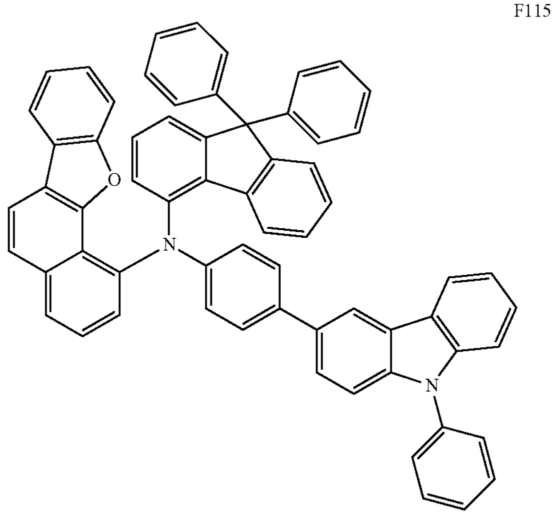
-continued
F116
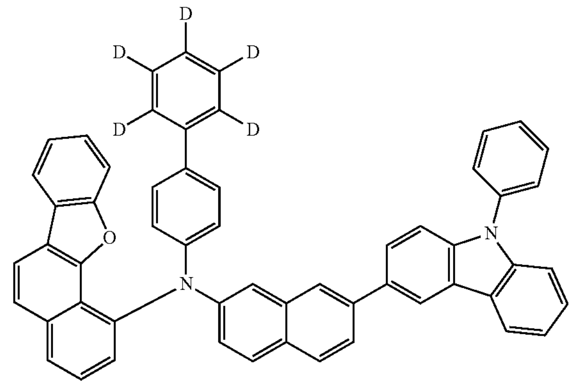
F117
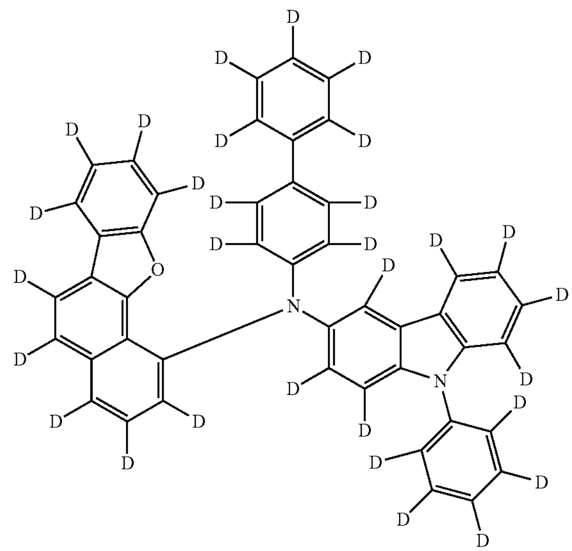
F118
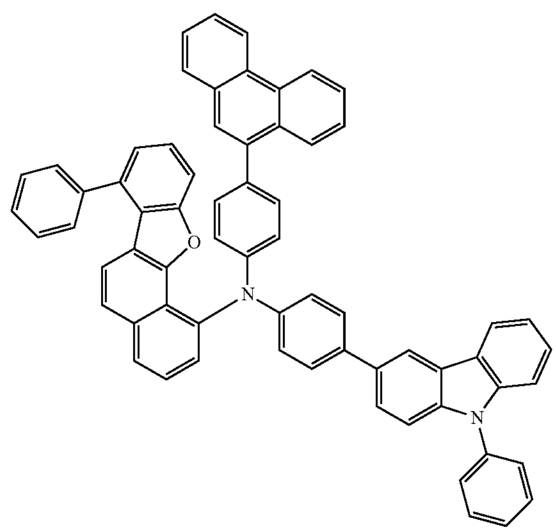

-continued
F119
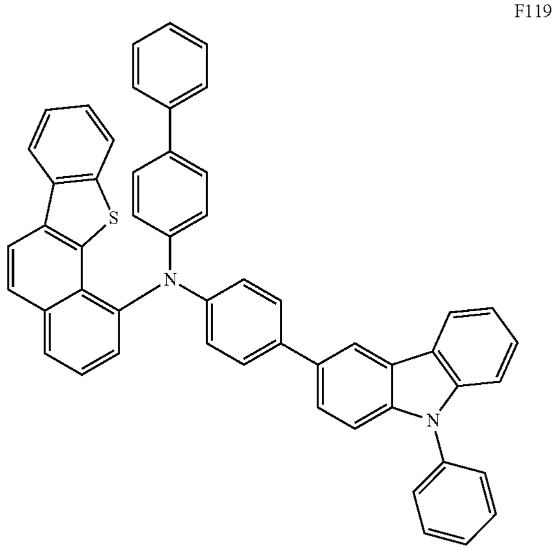
F120
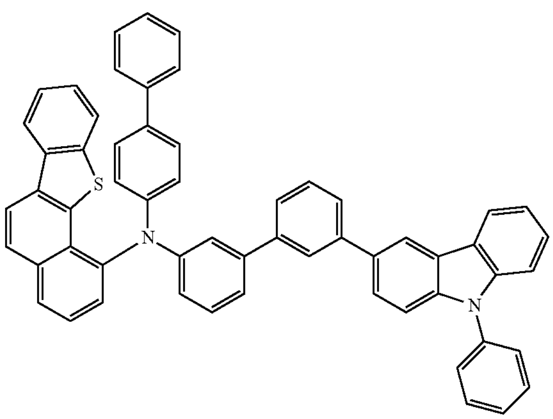
F121
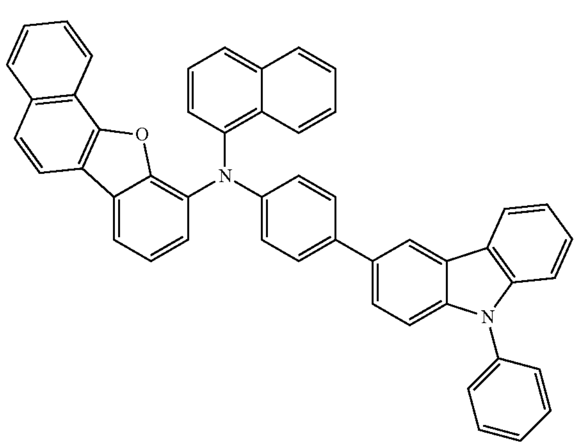
-continued
F122
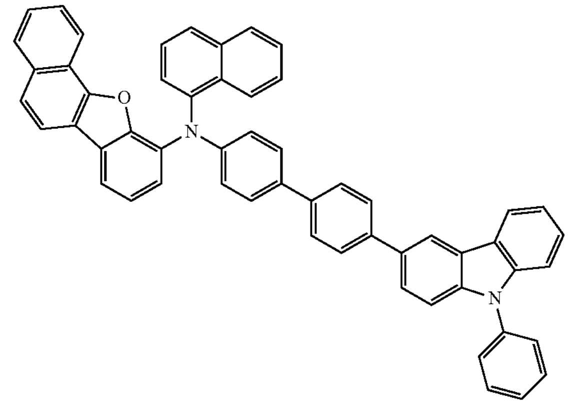
F123
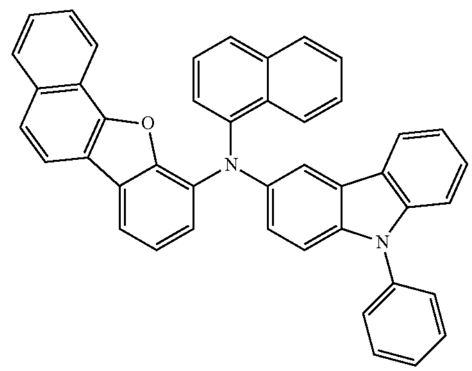
F124
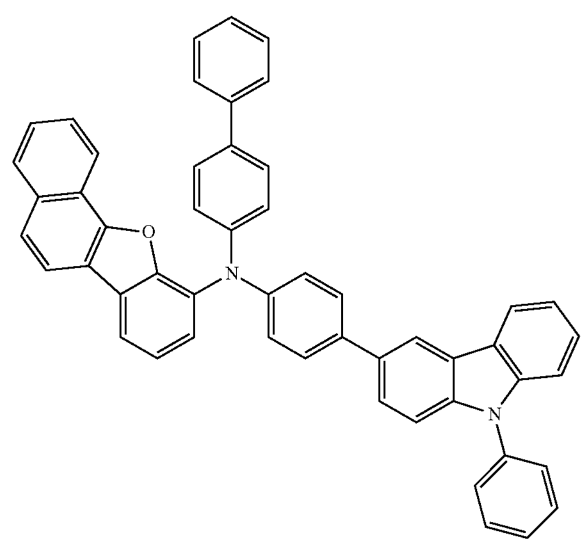

-continued
F125
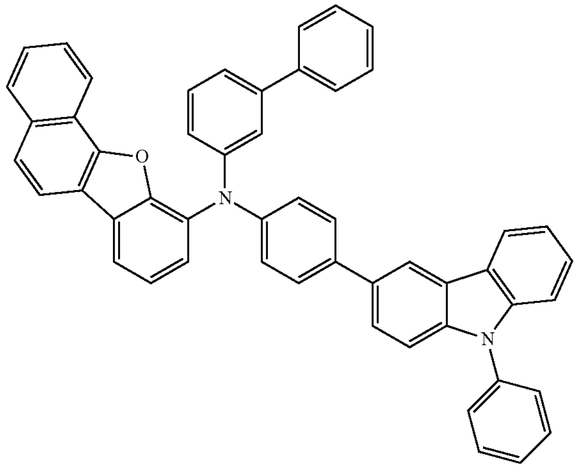
F126
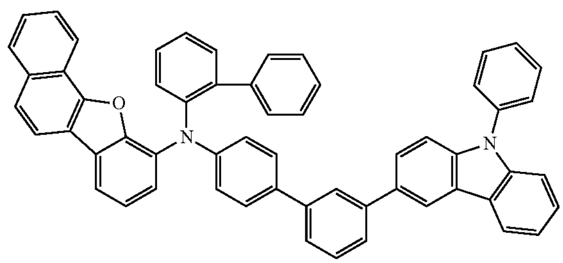
F127
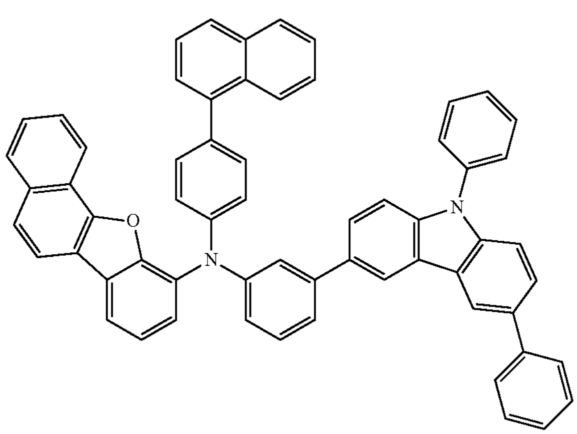
-continued
F128
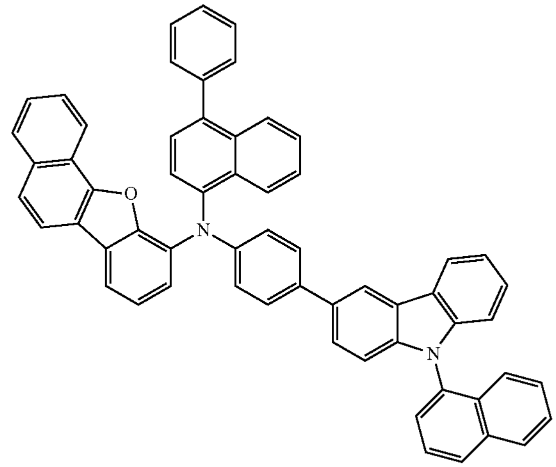
F129
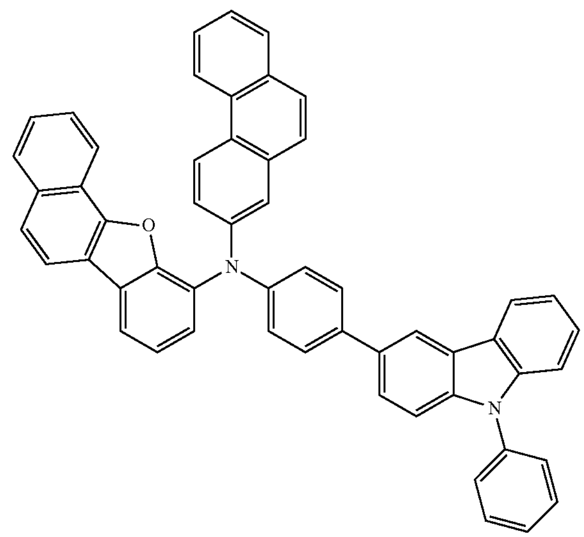
F130
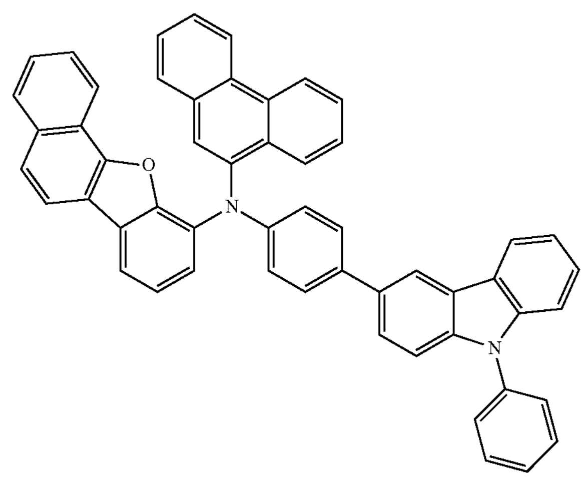

F131
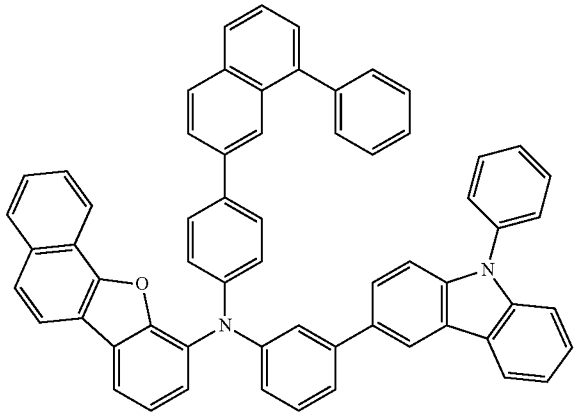
F132
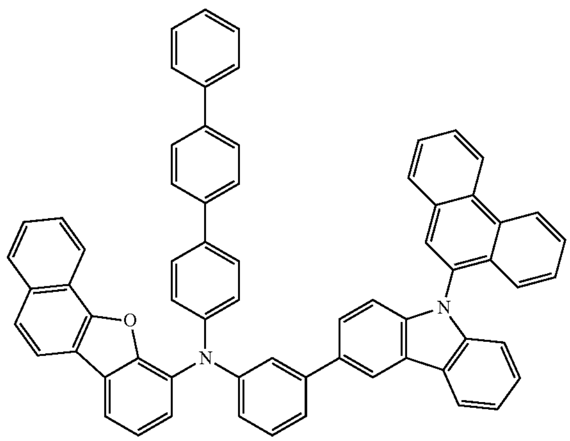
F133
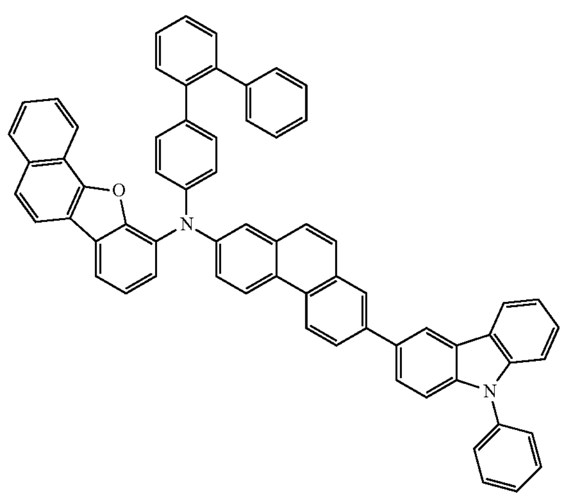
F134
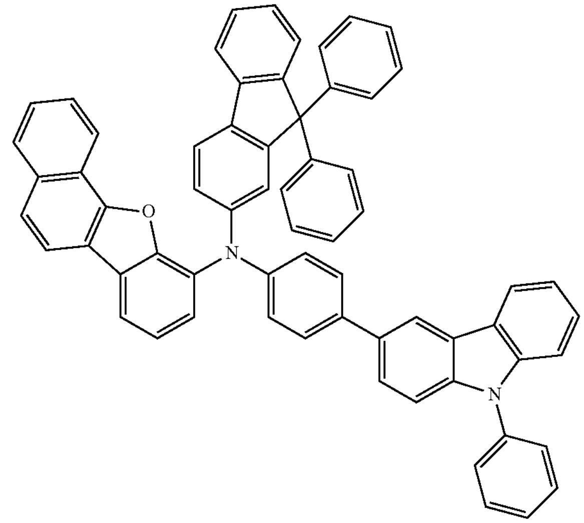
F135
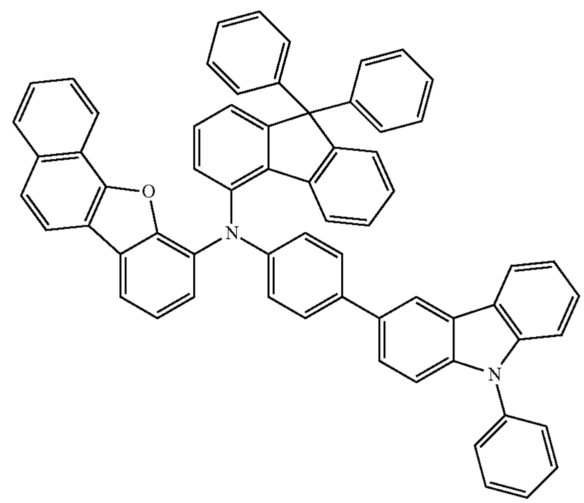
F136
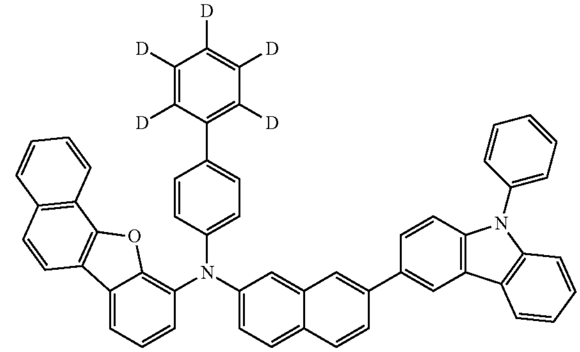

-continued
F137
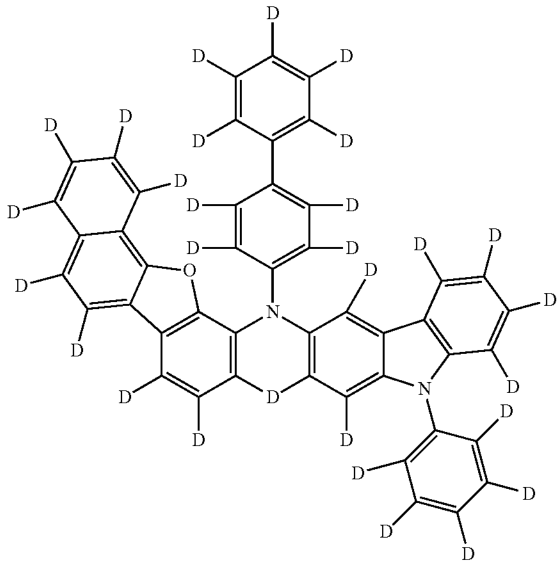
F138
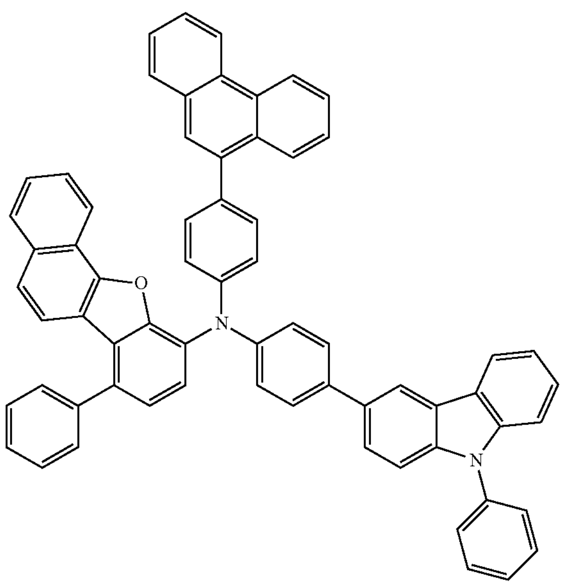
-continued
F139
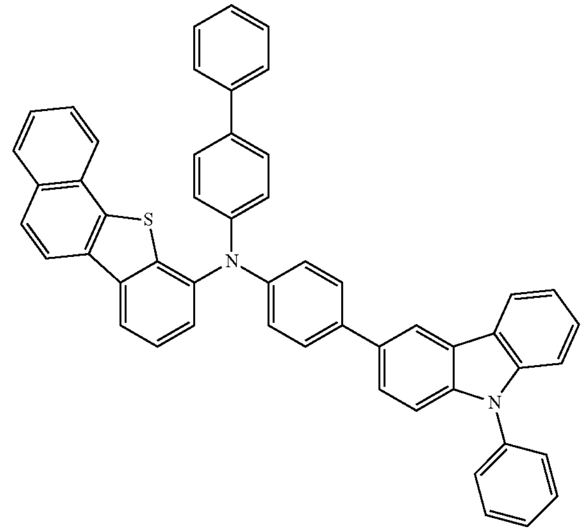
F140
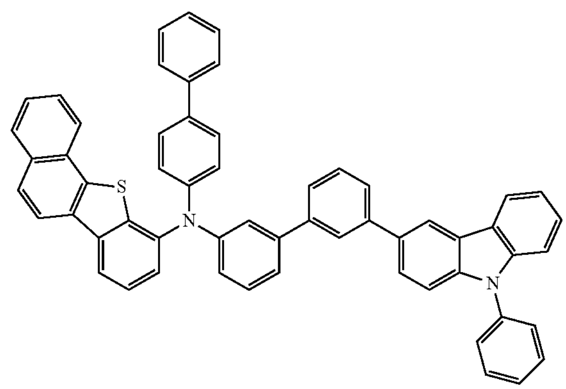
F141
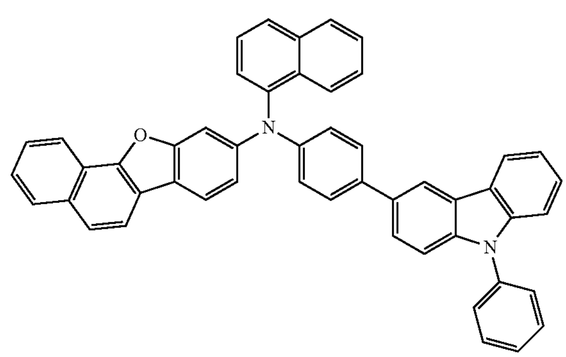

-continued
F142
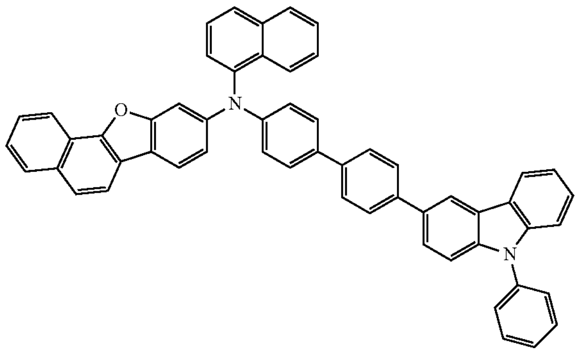
F143
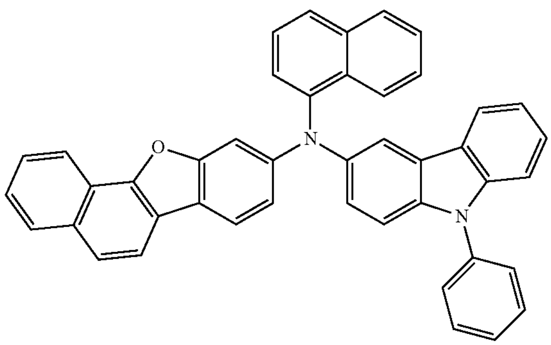
F144
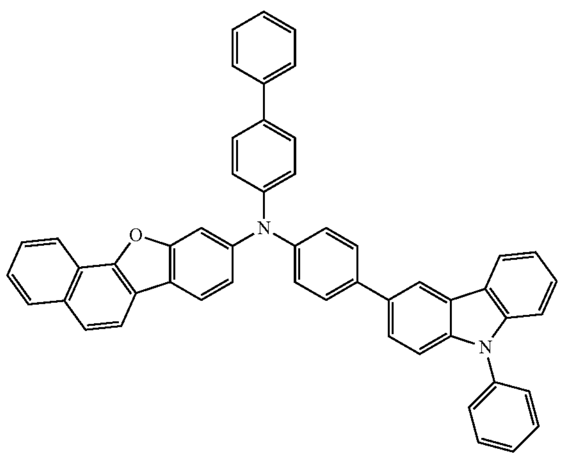
F145
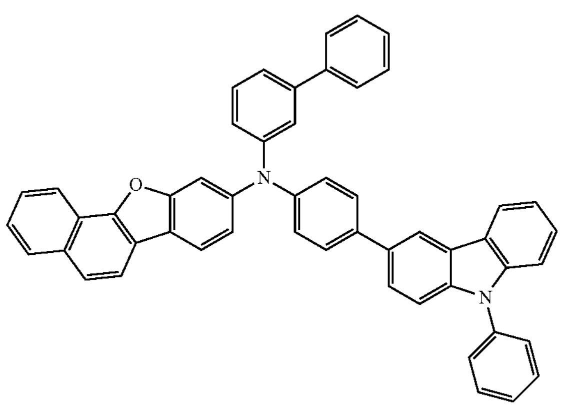
-continued
F146
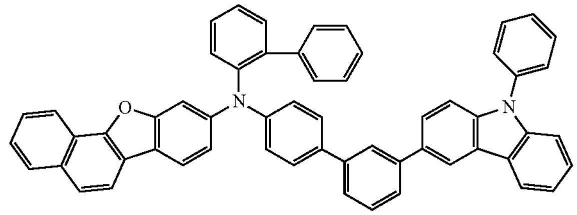
F147
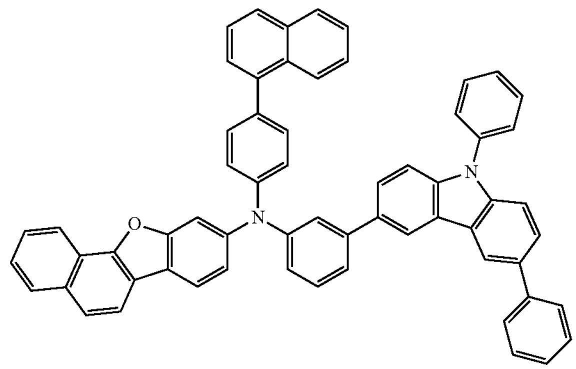
F148
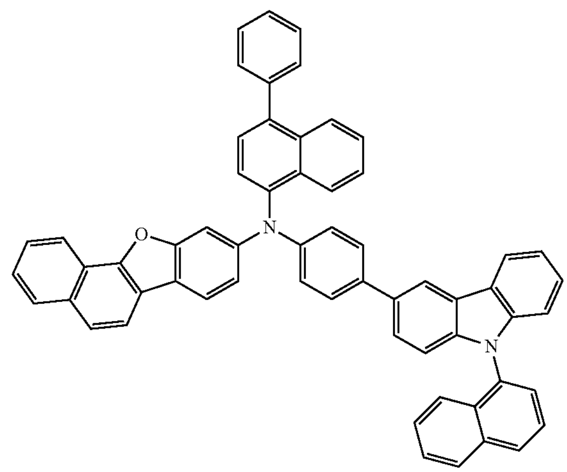
F149
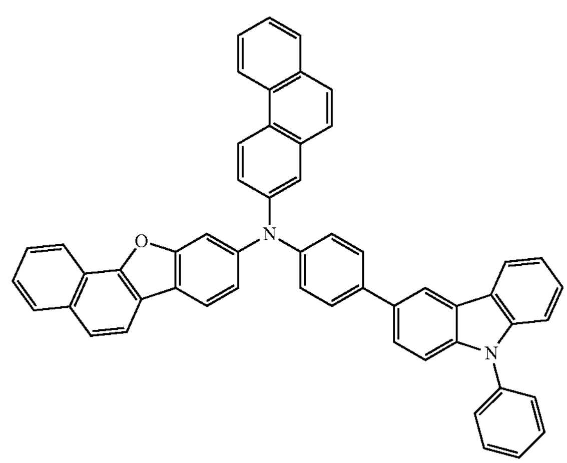

-continued
F150
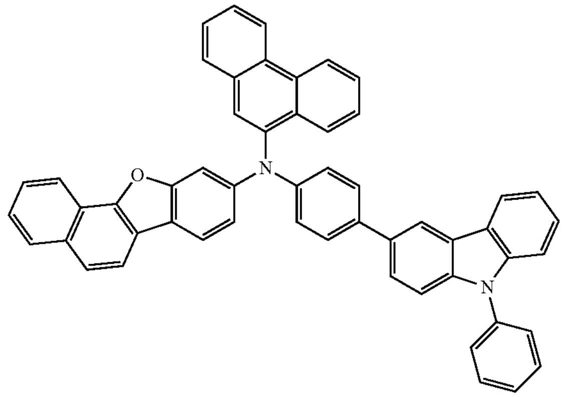
F151
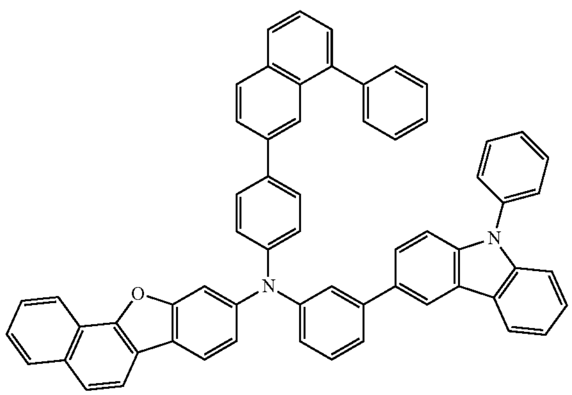
F152
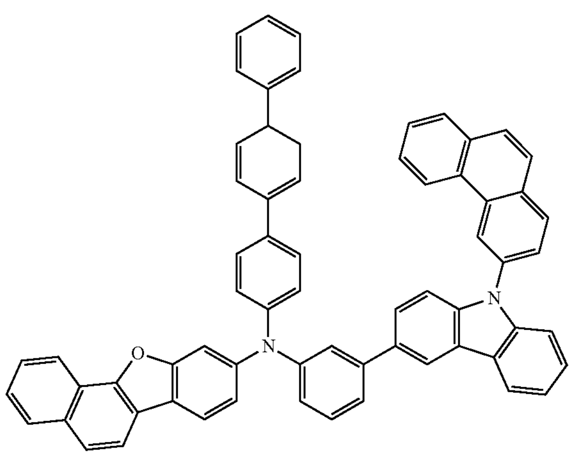
-continued
F153
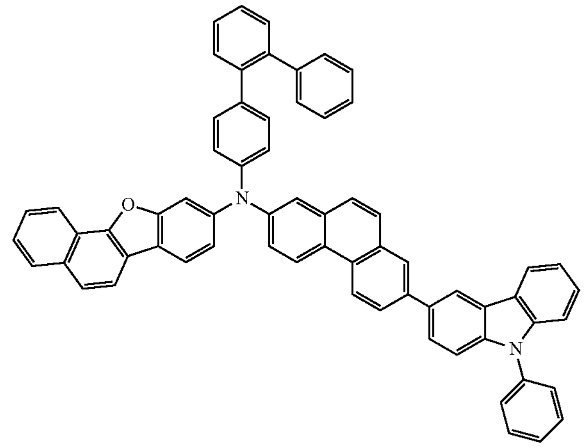
F154
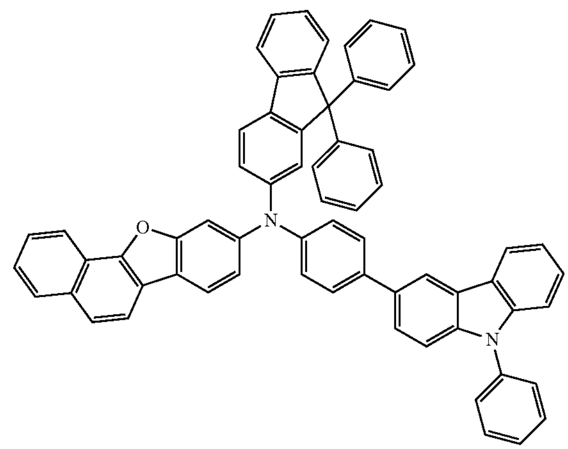
F155
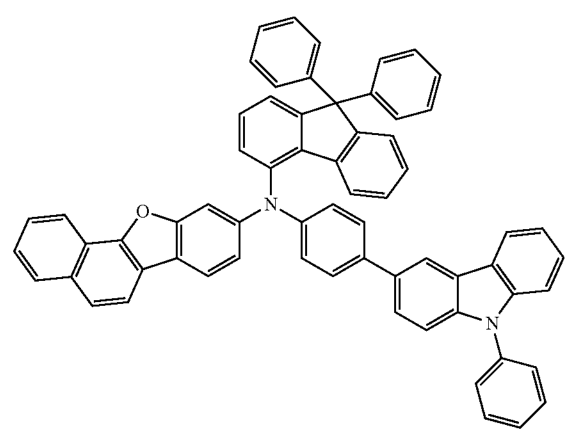

F156
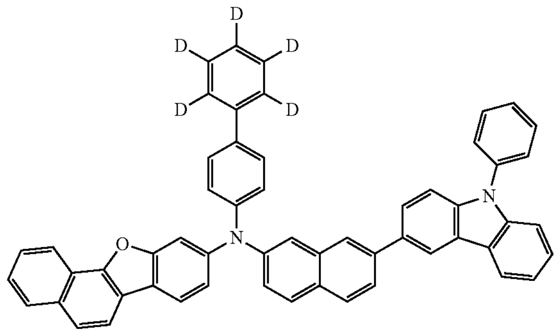
F157
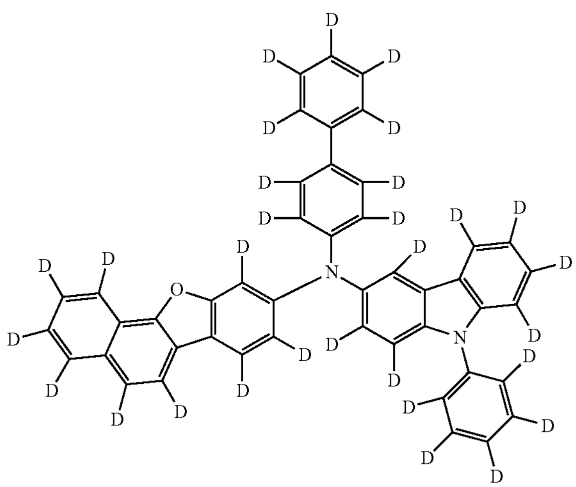
F158
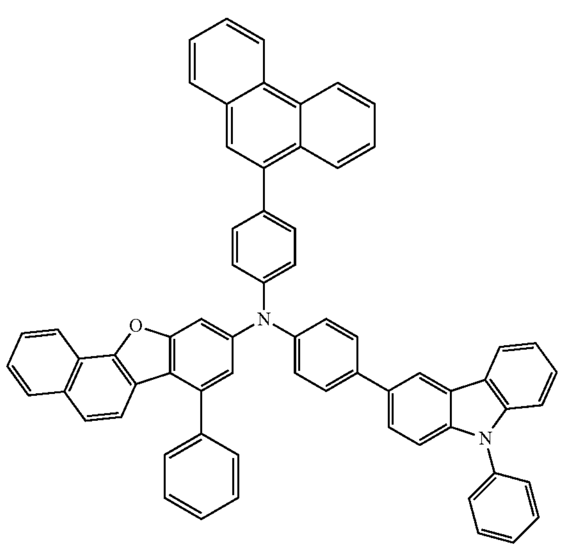
F159
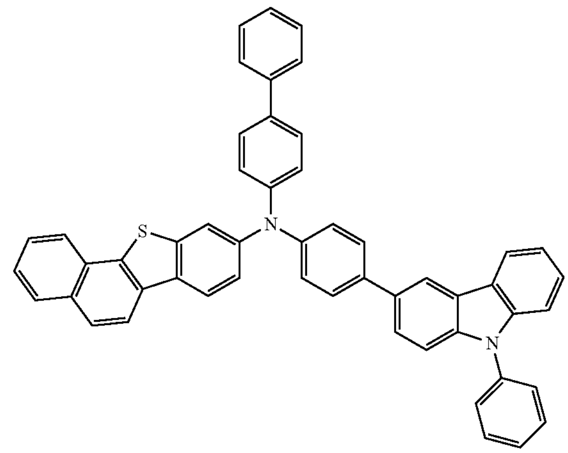
F160
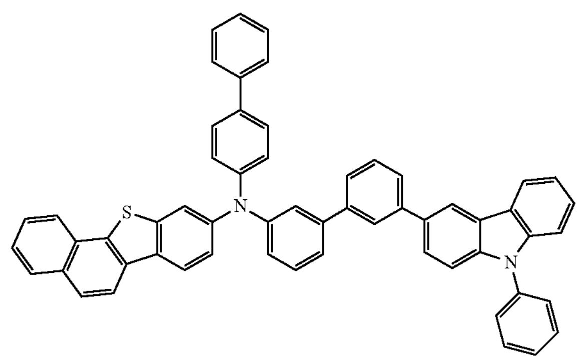
F161
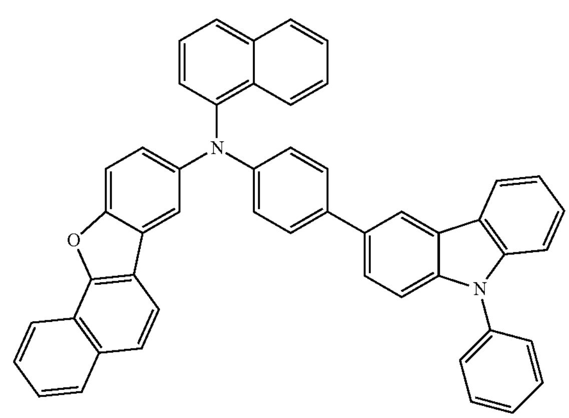

-continued
F162
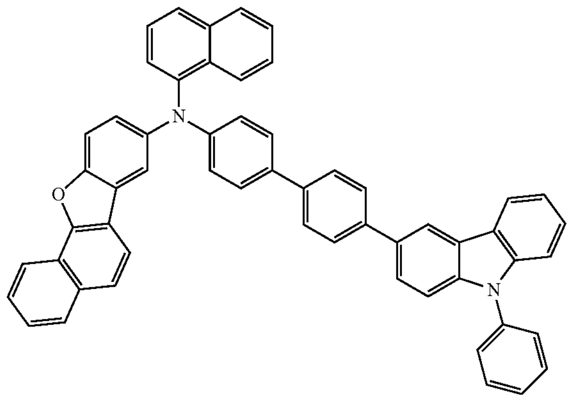
F163
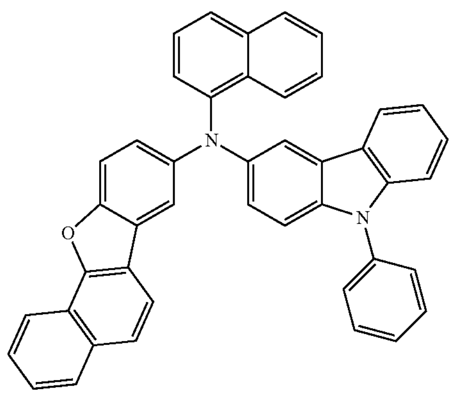
F164
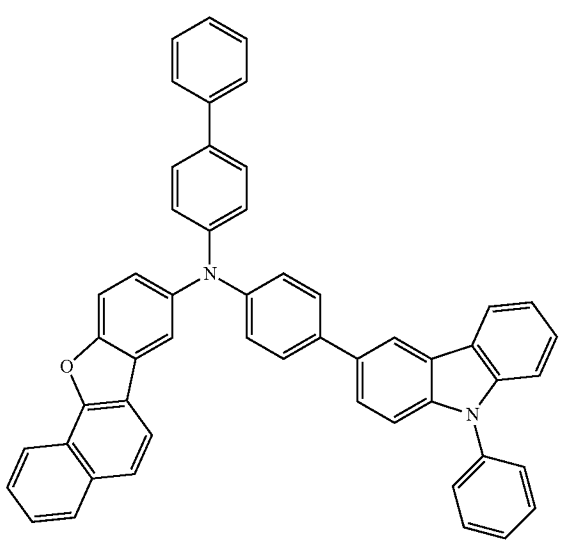
-continued
F165
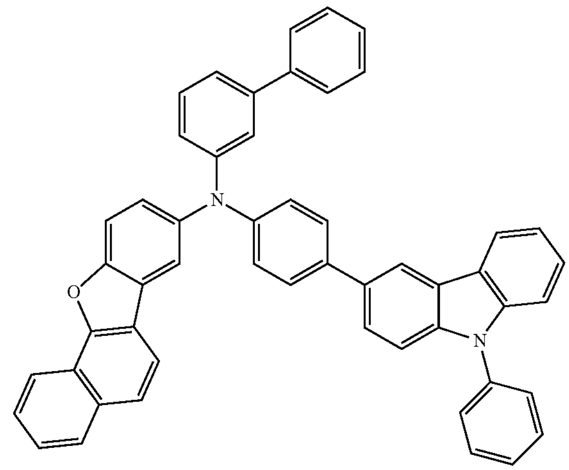
F166
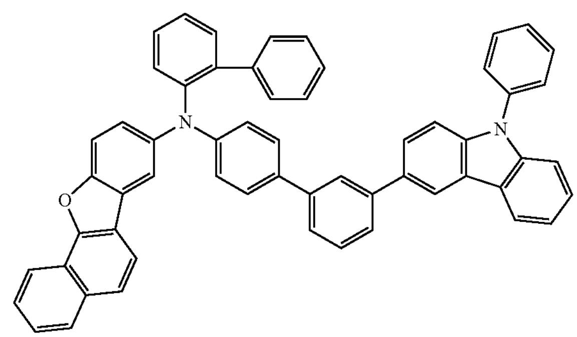
F167
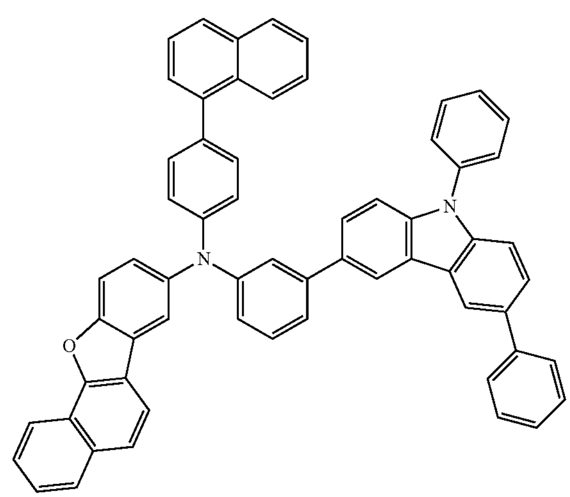

-continued
F168
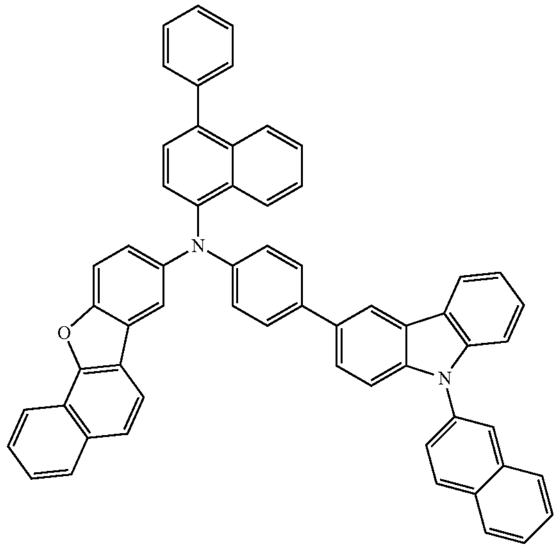
F169
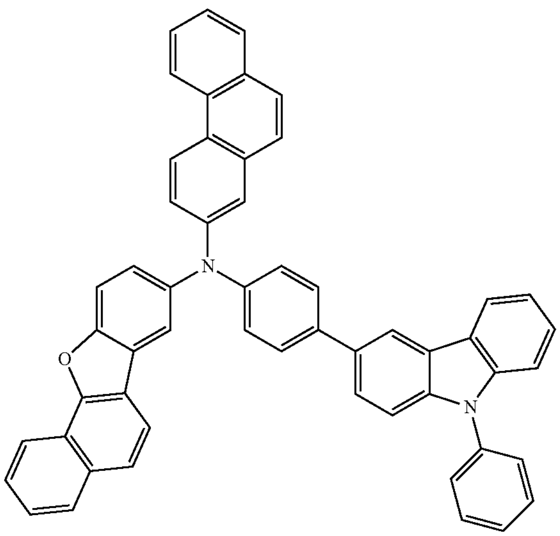
F170
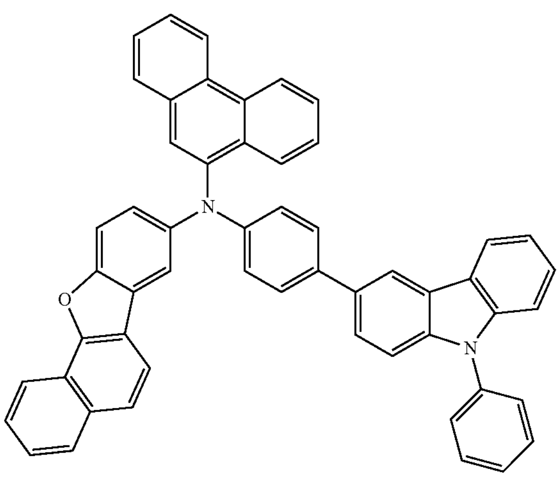
-continued
F171
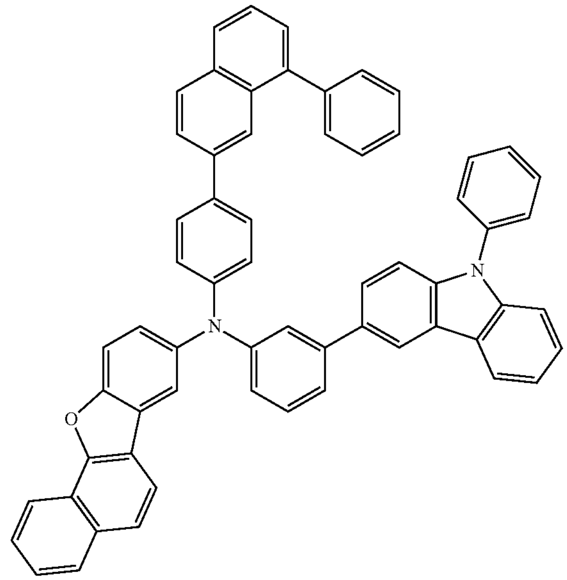
F172
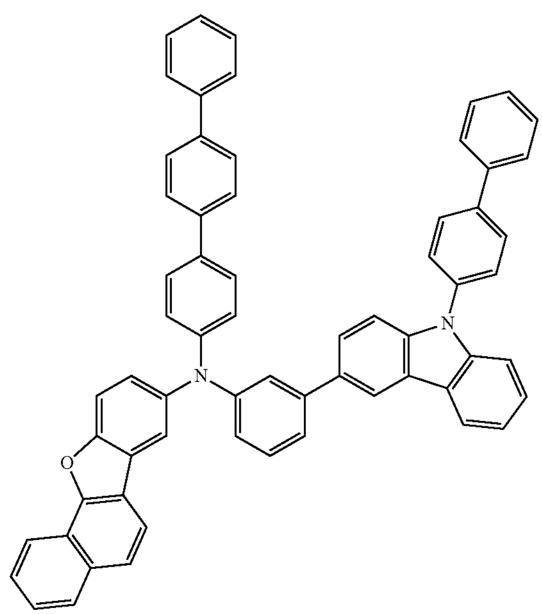

-continued
F173
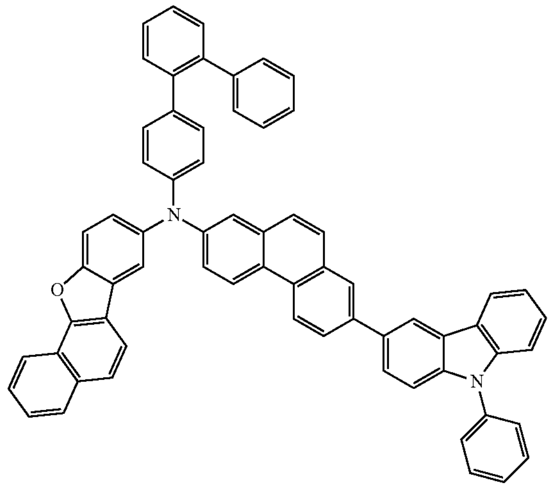
F174
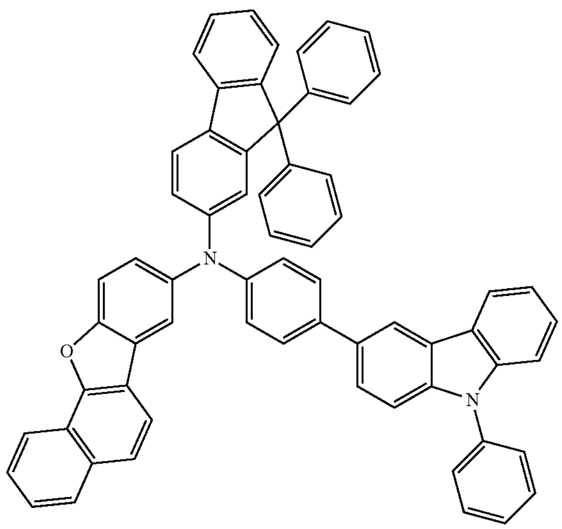
F175
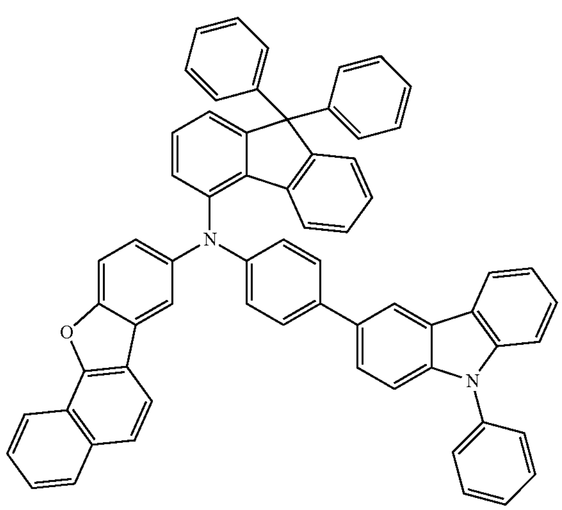
-continued
F176
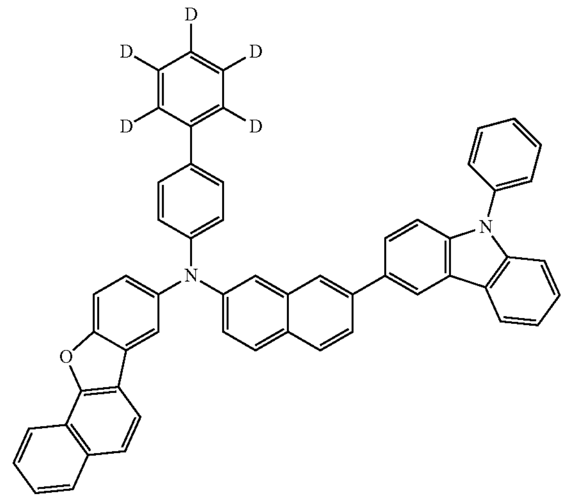
F177
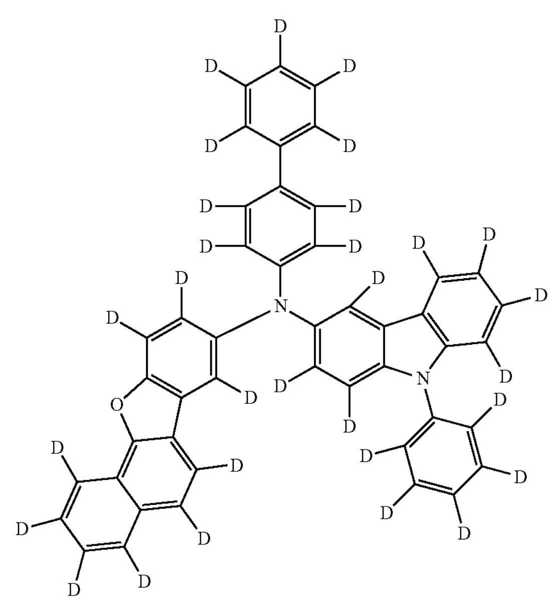

F178
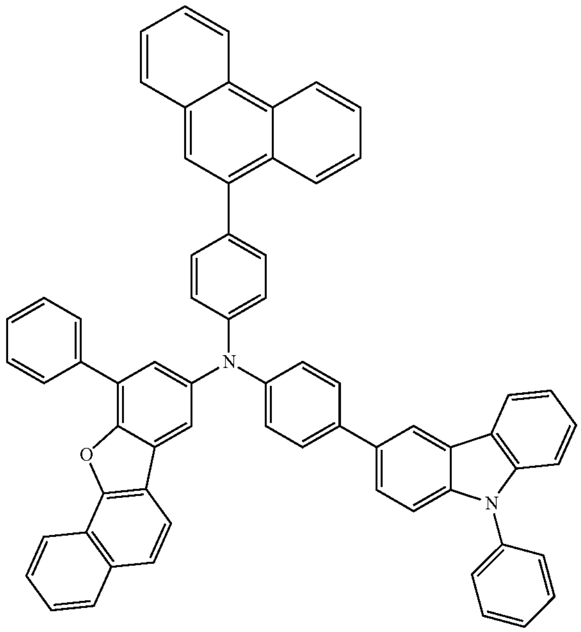
F179
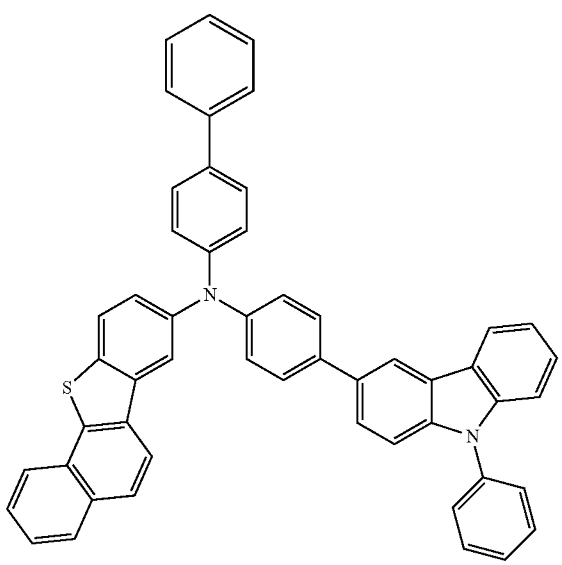
F180
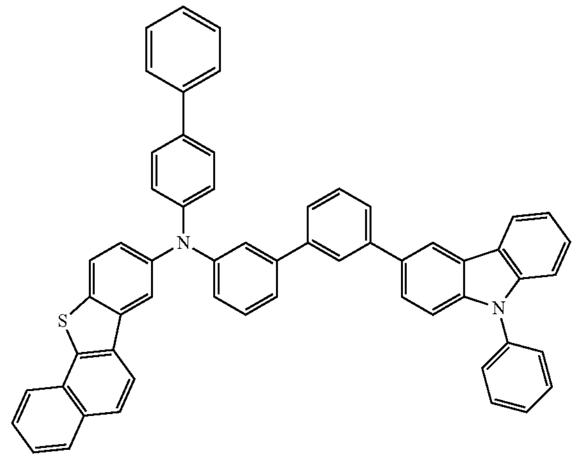
F181
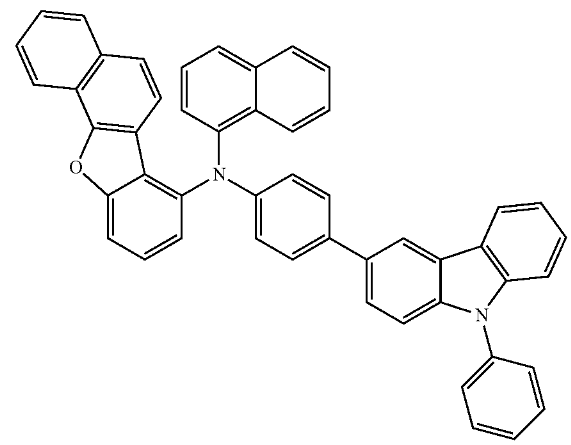
F182
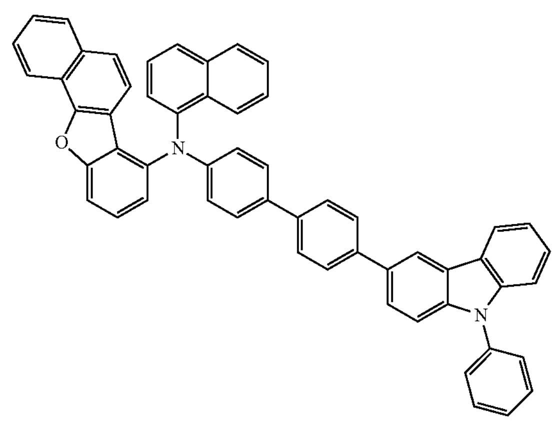

-continued
F183
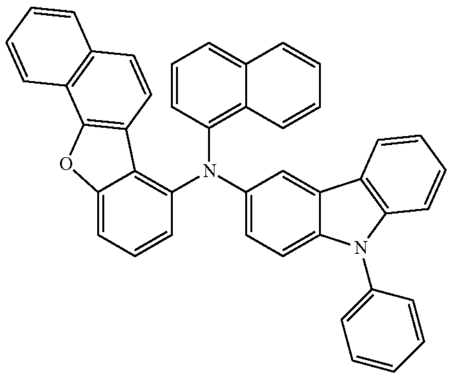
F184
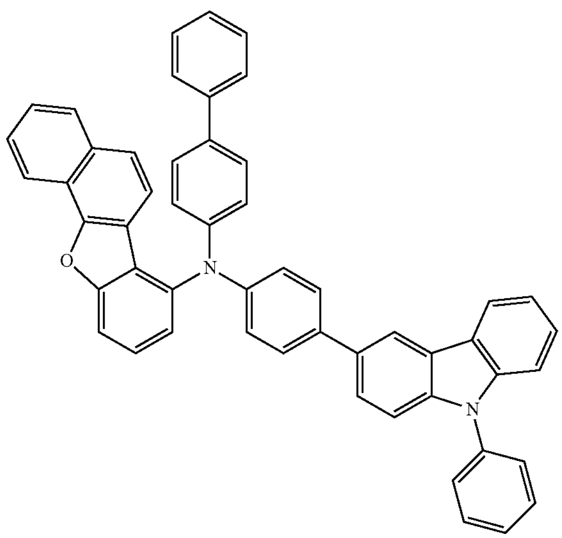
F185
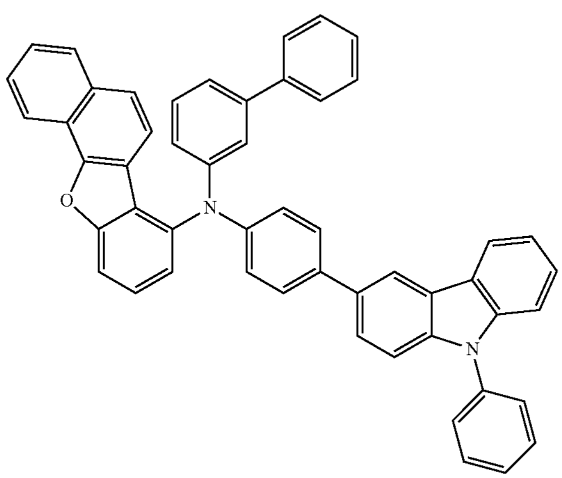
-continued
F186
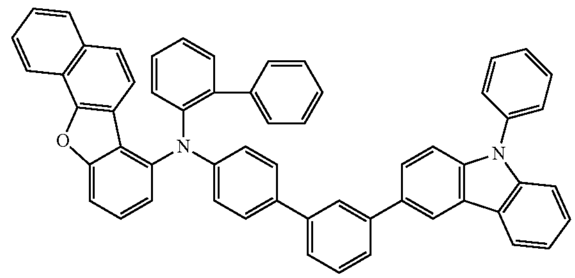
F187
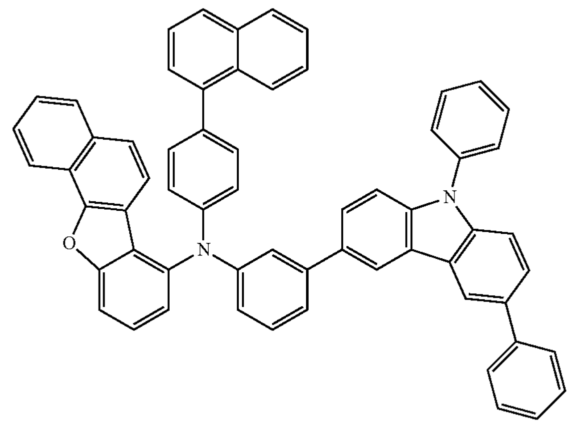
F188
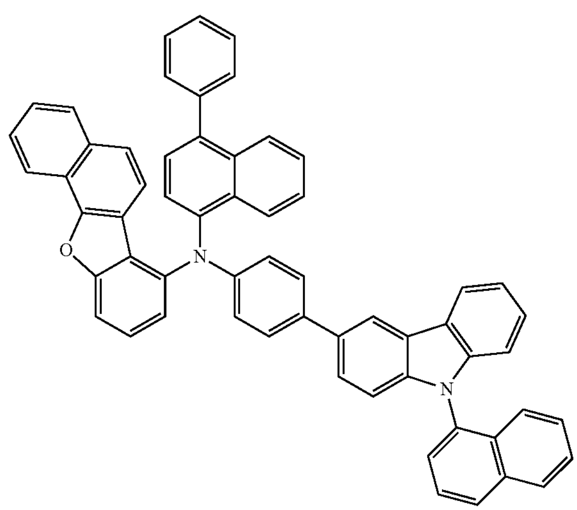

-continued
F189
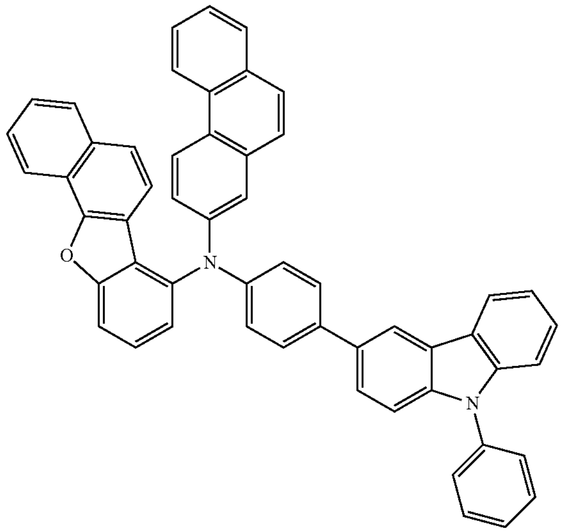
F190
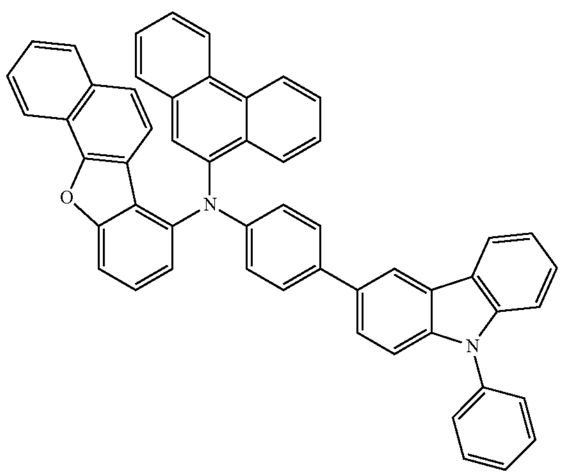
F191
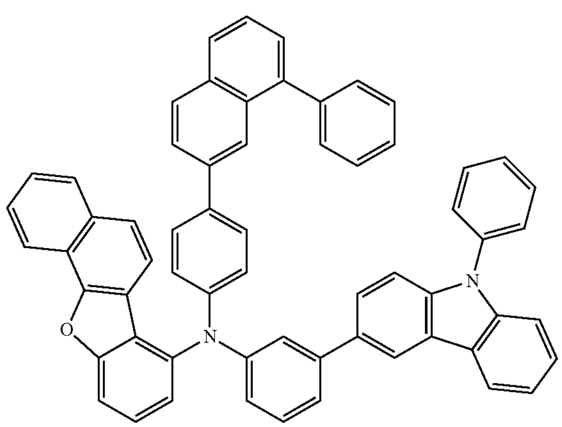
-continued
F192
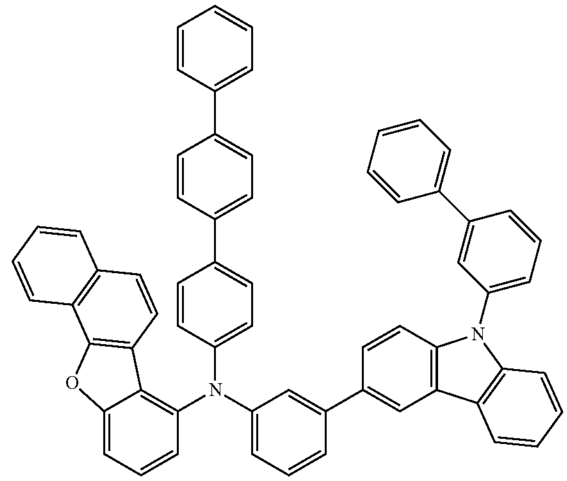
F193
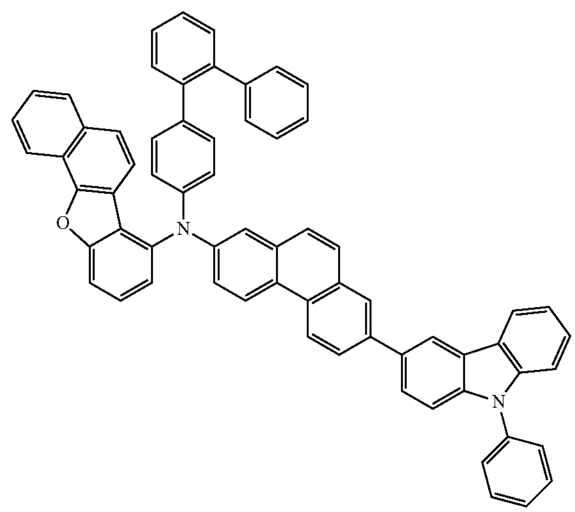
F194
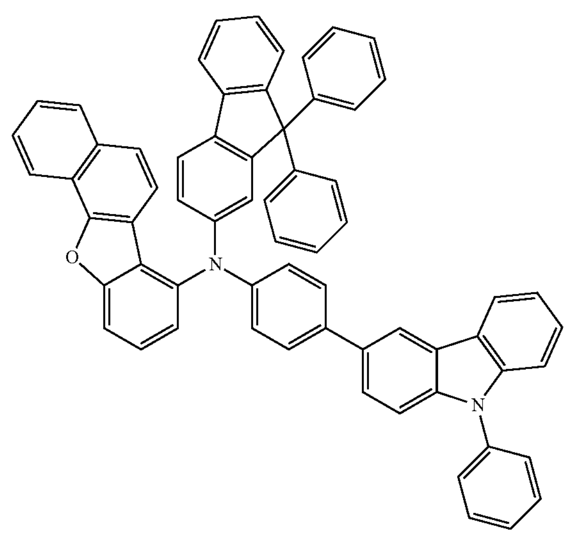

-continued
F195
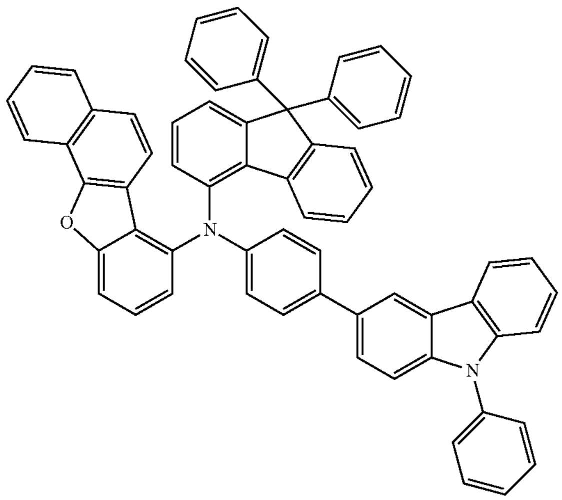
F196
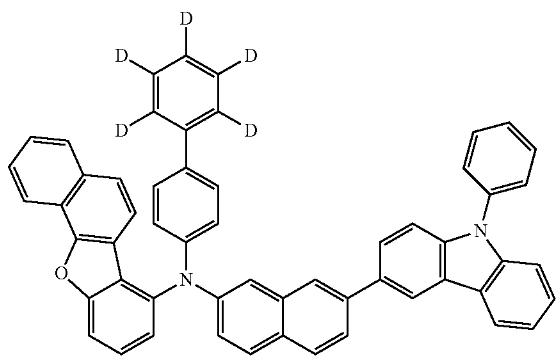
F197
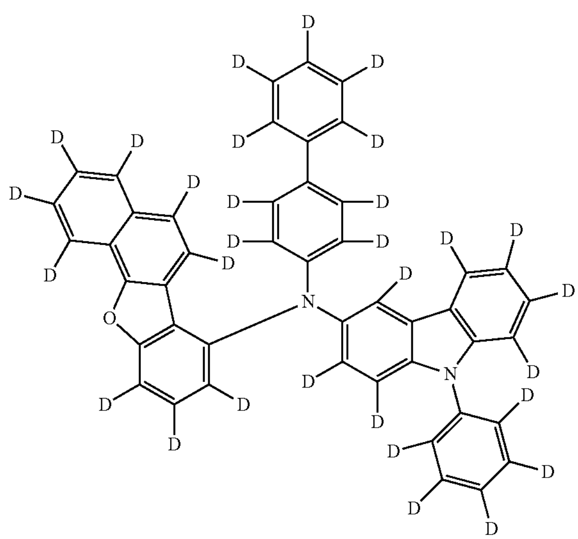
-continued
F198
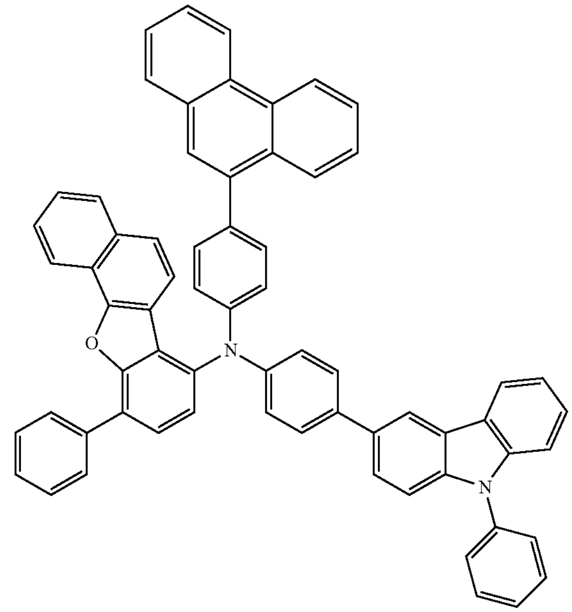
F199
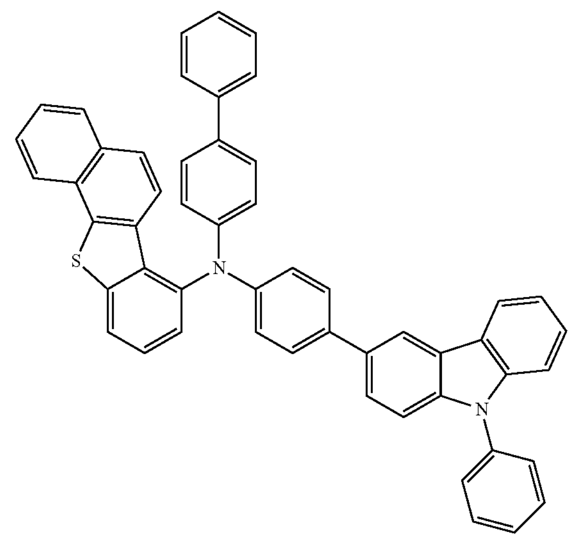
F200
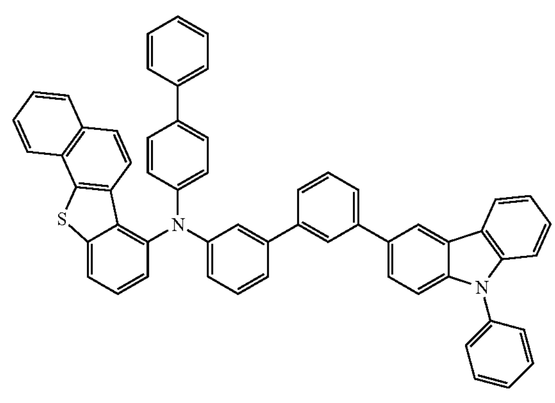
.

Referring to FIG. 1 to FIG. 3, the organic electroluminescence device according to an embodiment of the present disclosure will be explained.

As described above, the hole transport region HTR includes the polycyclic compound according to an embodiment of the present disclosure. For example, the hole transport region HTR includes the polycyclic compound represented by Formula 1.

When the hole transport region HTR has a multilayer structure having a plurality of layers, any one layer among the plurality of layers may include the polycyclic compound represented by Formula 1. For example, the hole transport region HTR may include a hole injection layer HIL disposed on the first electrode EL1 and a hole transport layer HTL disposed on the hole injection layer HIL, and the hole transport layer HTL may include the polycyclic compound represented by Formula 1. However, embodiments of the present disclosure are not limited thereto, and for example, the hole injection layer HIL may include the polycyclic compound represented by Formula 1.

The hole transport region HTR may include at least one structure of the polycyclic compound represented by Formula 1. For example, the hole transport region HTR may include at least one selected among the compounds represented in the Compound Group 1 to Compound Group 6 above.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

However, the hole transport region may further include the materials below in each layer.

The hole injection layer HIL may include, for example, a phthalocyanine compound (such as copper phthalocyanine), N,N'-diphenyl-N,N'-bis-[4-(phenyl-m-tolyl-amino)-phenyl]-phenyl-4,4'-diamine (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N,-2-naphthyl)-N-phenylamino}-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(1-naphthalene-1-yl)-N,N'-diphenyl-benzidine (NPD), triphenylamine-containing polyether ketone (TPAPEK), 4-isopropyl-4'-methyldiphenyliodonium [tetrakis(pentafluorophenyl)borate], and dipyrazino[2,3-f:2',3'-h]quinoxaline-2,3,6,7,10,11-hexacarbonitrile (HAT-CN).

The hole transport layer HTL may include any suitable hole transport material available in the art, for example, carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPD), 4,4'-cyclohexylidene bis[N,N-bis(4-methylphenyl)benzenamine (TAPC), 4,4'-bis[N,N'-(3-tolyl)amino]-3,3'-dimethylbiphenyl (HMTPD), 1,3-bis(N-carbazolyl)benzene (mCP), etc.

The electron blocking layer EBL may include, for example, carbazole derivatives (such as N-phenyl carbazole and/or polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(1-naphthalene-1-yl)-N,N'-diphenyl-benzidine (NPD), 4,4'-cyclohexylidene bis[N,N-bis(4-methylphenyl)benzenamine (TAPC), 4,4'-bis[N,N'-(3-tolyl)amino]-3,3'-dimethylbiphenyl (HMTPD), mCP, etc.

The thickness of the hole transport region HTR may be about 50 Å to about 15,000 Å, for example, about 100 Å to about 5,000 Å. The thickness of the hole injection region HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives (such as tetracyanoquinodimethane (TCNQ) and/or 2,3,5,6-tetrafluoro-7,7',8,8'-tetracyanoquinodimethane (F4-TCNQ)), metal halides (such as $MgF_2$, CuI, and/or RbI), metal oxides (such as tungsten oxide and/or molybdenum oxide), without limitation.

As described above, the hole transport region HTR may further include at least one of a hole butter layer or an electron blocking layer EBL. The hole buffer layer may compensate for an optical resonance distance of light emitted from an emission layer EML, and may increase the light emission efficiency of the device. Materials that may be included in a hole transport region HTR may also be used as materials in a hole buffer layer. The electron blocking layer EBL may prevent or reduce electron injection from the electron transport region ETR to the hole transport region HTR.

The emission layer EML is provided on the hole transport region HTR. The emission layer EML may have a thickness of, for example, about 100 Å to about 1,000 Å or about 100 Å to about 600 Å. The emission layer EML may have a single layer formed using a single material, a single layer formed using a plurality of different materials, or a multilayer structure having a plurality of layers formed using a plurality of different materials.

As the material of the emission layer EML, any suitable luminescent materials may be used, for example, fluoranthene derivatives, pyrene derivatives, arylacetylene derivatives, anthracene derivatives, fluorene derivatives, perylene derivatives, and chrysene derivatives. In some embodiments, pyrene derivatives, perylene derivatives, and anthracene derivatives may be included. For example, as the host material of the emission layer EML, anthracene derivatives represented by Formula 10 below may be used.

[Formula 10]

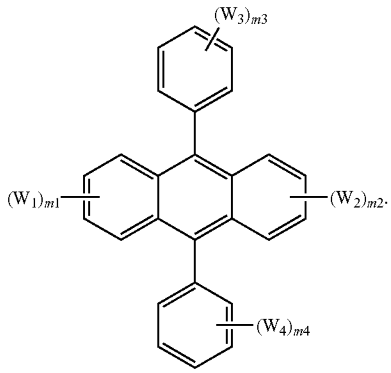

In Formula 10, $W_1$ to $W_4$ may each independently be a hydrogen atom, a deuterium atom, a halogen atom, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, and/or may be combined with an adjacent group to form a ring. m1 and m2 may each independently be an integer of 0 to 4, and m3 and m4 may each independently be an integer of 0 to 5.

When m1 is 1, $W_1$ may not be a hydrogen atom; when m2 is 1, $W_2$ may not be a hydrogen atom; when m3 is 1, $W_3$ may not be a hydrogen atom; and when m4 is 1, $W_4$ may not be a hydrogen atom.

When m1 is 2 or more, a plurality of $W_1$ groups are the same or different; when m2 is 2 or more, a plurality of $W_2$ groups are the same or different; when m3 is 2 or more, a plurality of $W_4$ groups are the same or different; and when m4 is 2 or more, a plurality of $W_4$ groups are the same or different.

The compound represented by Formula 10 may include, for example, the compounds represented by the structures below. However, the compound represented by Formula 10 is not limited thereto:

a-1

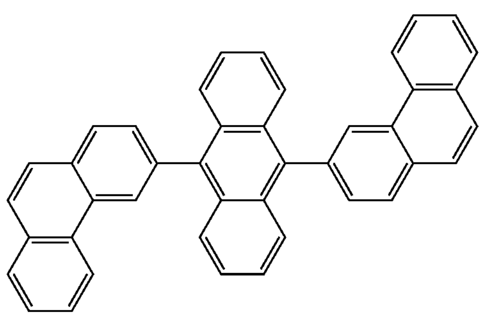

a-2

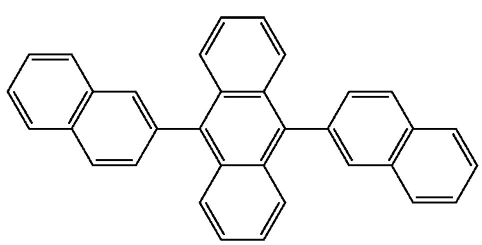

-continued a-3

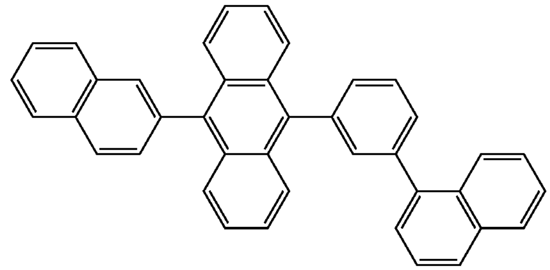

a-4

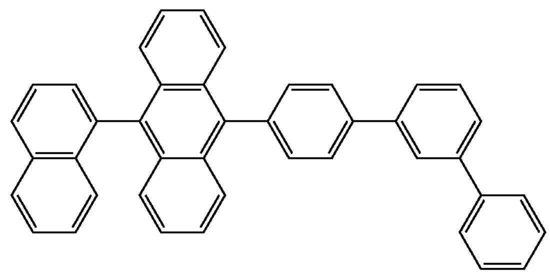

a-5

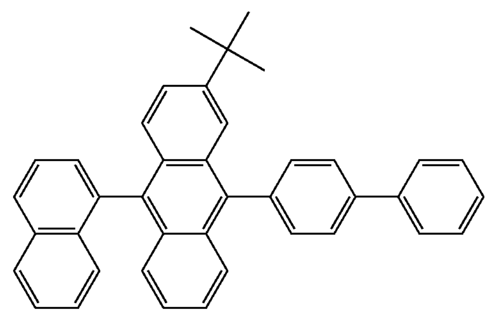

a-6

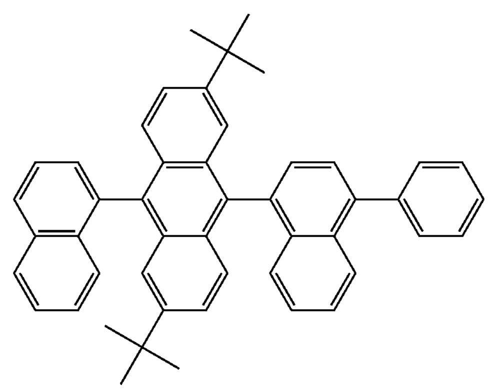

a-7

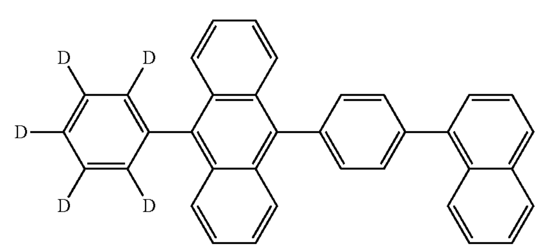

-continued a-8

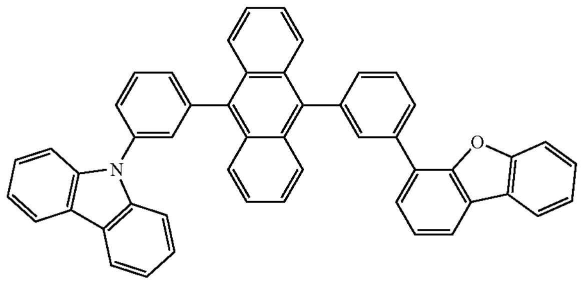

a-9

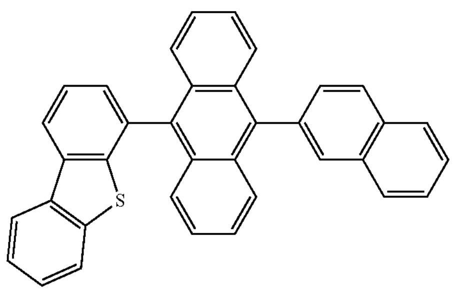

a-10

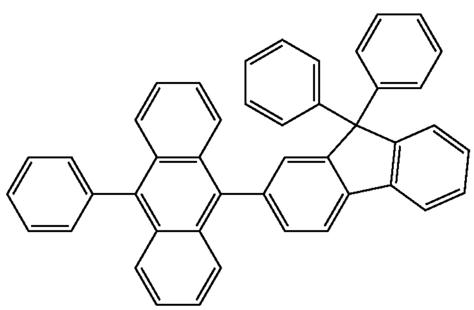

a-11

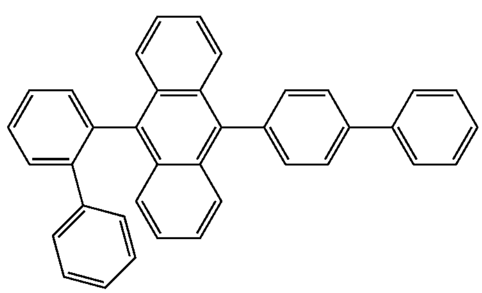

a-12

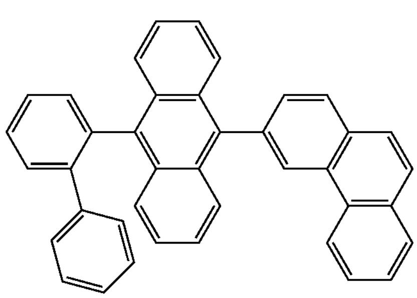

-continued a-13

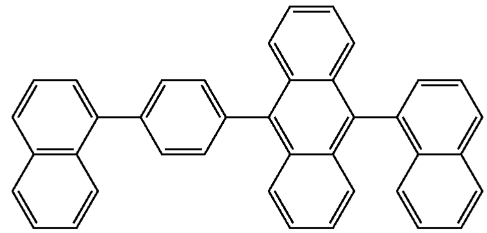

a-14

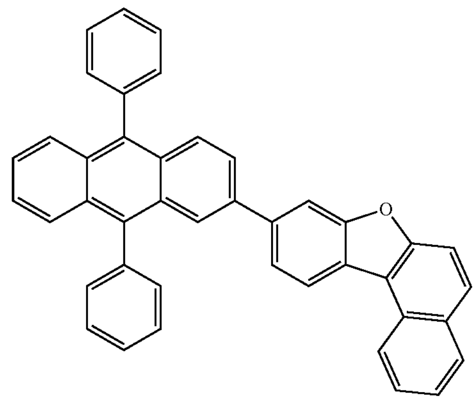

a-15

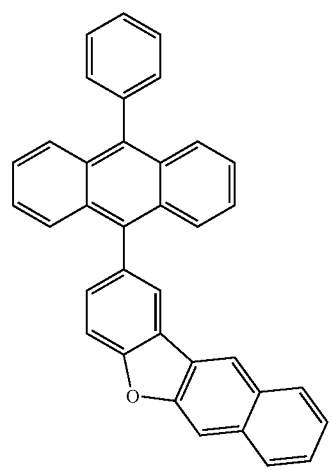

a-16

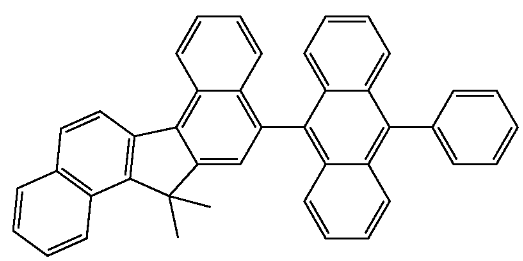

.

The emission layer EML may include a dopant, and the dopant may include any suitable dopant material. For example, the dopant may include at least one among styryl derivatives (for example, 1,4-bis[2-(3-N-ethylcarbazolyl)vinyl]benzene (BCzVB), 4-(di-p-tolylamino)-4"-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBP)), and pyrene and derivatives thereof (for example, 1,1-dipyrene, 1,4-dipyrenylbenzene, 1,4-bis(N,N-diphenylamino)pyrene), 1,6-bis(N,N-diphenylamino) pyrene), 2,5,8,11-tetra-t-butylperylene (TBP), and 1,3,5-tris (1-phenyl-1H-benz[d]imidazole-2-yl)benzene)), without limitation.

The emission layer EML may include a host material. For example, the emission layer EML may include as a host material, at least one among tris(8-hydroxyquinolino)aluminum ($Alq_3$), bis[2-(diphenylphosphino)phenyl]ether oxide (DPEPO), 4,4'-bis(N-carbazol-9-yl)biphenyl (CBP), 1,3-bis (carbazol-9-yl)benzene (mCP), 2,8-bis(diphenylphosphoryl) dibenzo[b,d]furan (PPF), 4,4',4"-tris(carbazol-9-yl)-triphenylamine (TCTA), poly(N-vinylcarbazole) (PVK), 9,10-di (naphthalene-2-yl)anthracene (ADN), 3-tert-butyl-9,10-di (naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH-2), hexaphenylcyclotrisiloxane (DPSiO3), octaphenylcyclotetrasiloxane (DPSiO4), 2,8-bis(diphenylphosphoryl)dibenzofuran (PPF), and 1,3,5-tris(1-phenyl-1H-benz[d]imidazol-2-yl)benzene (TPBi), without limitation.

When the emission layer EML is to emit red light, the emission layer EML may further include, for example, a fluorescence material including tris(dibenzoylmethanato) phenanthroline europium (PBD:Eu$(DBM)_3$(Phen)) or perylene. When the emission layer EML is to emit red light, the dopant included in the emission layer EML may be selected from, for example, a metal complex or an organometallic complex (such as bis(1-phenylisoquinoline)acetylacetonate iridium (PIQIr(acac)), bis(1-phenylquinoline) acetylacetonate iridium (PQIr(acac)), tris(1-phenylquinoline)iridium (PQIr), and/or octaethylporphyrin platinum (PtOEP)), rubrene and derivatives thereof, and 4-dicyanomethylene-2-(p-dimethylaminostyryl)-6-methyl-4H-pyran (DCM) and derivatives thereof.

When the emission layer EML is to emit green light, the emission layer EML may further include, for example, a fluorescence material including tris(8-hydroxyquinolino) aluminum ($Alq_3$). When the emission layer EML is to emit green light, the dopant included in the emission layer EML may be selected from, for example, a metal complex or an organometallic complex (such as fac-tris(2-phenylpyridine) iridium ($Ir(ppy)_3$)), and coumarin and derivatives thereof.

When the emission layer EML is to emit blue light, the emission layer EML may further include a fluorescence material including any one selected from the group consisting of spiro-DPVBi, spiro-6P, distyryl-benzene (DSB), distyryl-arylene (DSA), a polyfluorene (PFO)-based polymer, and a poly(p-phenylene vinylene (PPV)-based polymer. When the emission layer EML is to emit blue light, the dopant included in the emission layer EML may be selected from, for example, a metal complex or an organometallic complex (such as $(4,6\text{-}F_2ppy)_2Irpic$), and perylene and derivatives thereof.

The electron transport region ETR is provided on the emission layer EML. The electron transport region ETR may include at least one of a hole blocking layer HBL, an electron transport layer ETL, or an electron injection layer EIL, but embodiments of the present disclosure are not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, about 100 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include an anthracene-based compound. The electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzimidazolyl-1-ylphenyl)-9,10-dinaphthylanthracene, 1,3,5-tri(1-phenyl-1H-benz [d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate ($Bebq_2$), 9,10-di(naphthalene-2-yl)anthracene (ADN), or mixtures thereof, without limitation. The thickness of the electron transport layer ETL may be about 100 Å to about 1,000 Å and may be, for example, about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include, a metal halide (such as LiF, NaCl, CsF, RbCl, and/or RbI), a lanthanide metal (such as Yb), a metal oxide (such as $Li_2O$ and/or BaO), or lithium quinolate (LiQ). However, an embodiment of the present disclosure is not limited thereto. In some embodiments, the electron injection layer EIL may be formed using a mixture material of an electron transport material and an insulating organo metal salt. The organo metal salt may be a material having an energy band gap of about 4 eV or more. The organo metal salt may include, for example, metal acetates, metal benzoates, metal acetoacetates, metal acetylacetonates, and/or metal stearates. The thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing a substantial increase in driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), bis[2-

(diphenylphosphino)phenyl]ether oxide (DPEPO), or 4,7-diphenyl-1,10-phenanthroline (Bphen). However, embodiments of the present disclosure are not limited thereto.

The second electrode EL2 is provided on the electron transport region ETR. The second electrode EL2 may be a common electrode or a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, compounds thereof, or mixtures thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

Referring to FIG. 4, on the second electrode EL2 of the organic electroluminescence device 10 of an embodiment, a capping layer (CPL) may be further disposed. The capping layer CPL may have a single layer or multilayer.

In an embodiment, the capping layer CPL may be an organic layer or an inorganic layer. For example, when the capping layer CPL includes an inorganic material, the inorganic material may include an alkali metal compound (such as LiF), and/or an alkaline earth compound (such as $MgF_2$, SiON, $SiN_x$, $SiO_y$, etc.)

For example, when the capping layer (CPL) includes an organic material, the organic material may include α-NPD, NPB, TPD, m-MTDATA, $Alq_3$, CuPc, N4,N4,N4',N4'-tetra (biphenyl-4-yl) biphenyl-4,4'-diamine (TPD15), 4,4',4"-tris (carbazol-9-yl) triphenylamine (TCTA), etc., or may include an epoxy resin, or acrylate such as methacrylate. However, an embodiment of the present disclosure is not limited thereto, and the capping layer CPL may include an amine compound. For example, the capping layer CPL may include any one among Compounds P1 to P5.

P1

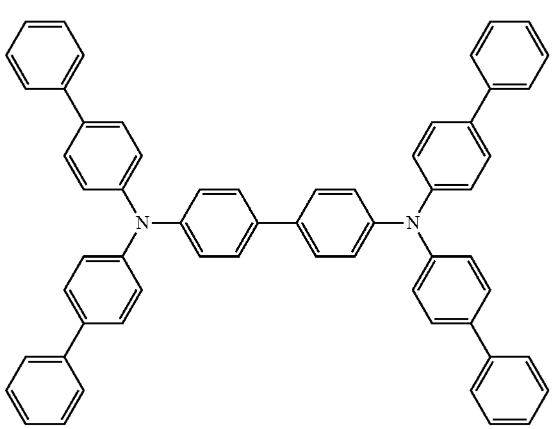

-continued

P2

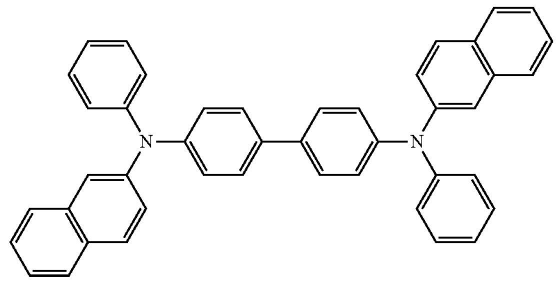

P3

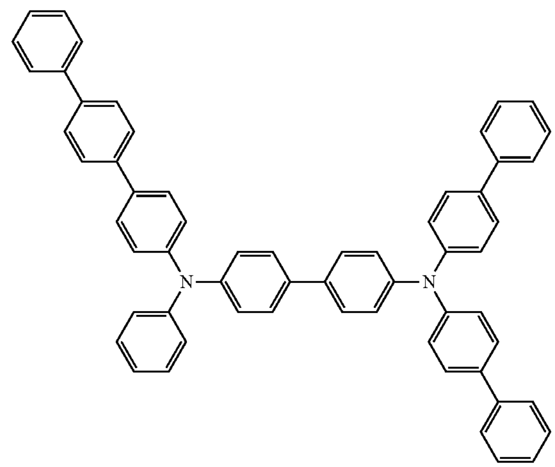

P4

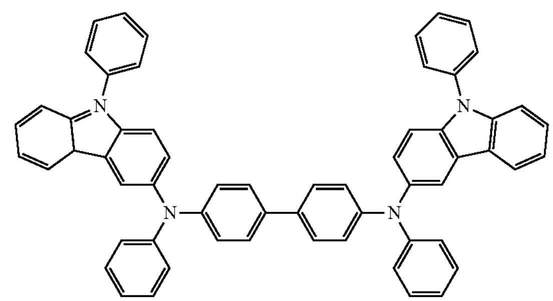

P5

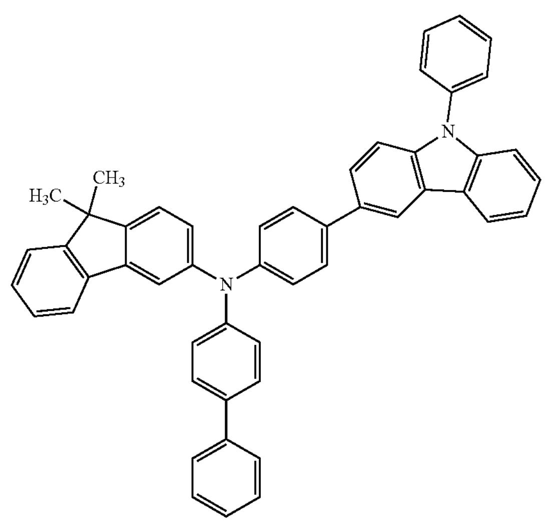

.

The refractive index of the capping layer CPL may be 1.6 or more. For example, the refractive index of the capping layer CPL may be 1.6 or more with respect to light having a wavelength of about 550 nm to about 660 nm.

In the organic electroluminescence device 10, according to the application of voltages to the first electrode EL1 and the second electrode EL2, respectively, holes injected from the first electrode EL1 move through the hole transport region HTR to the emission layer EML, and electrons injected from the second electrode EL2 move through the electron transport region ETR to the emission layer EML. The electrons and holes may recombine in the emission layer EML to produce excitons, and light may be emitted via transition of the excitons from an excited state to the ground state.

When the organic electroluminescence device 10 is a top emission type, the first electrode EL1 may be a reflective electrode, and the second electrode EL2 may be a transmissive or a transflective electrode. When the organic electroluminescence device 10 is a bottom emission type, the first electrode EL1 may be a transmissive or transflective electrode, and the second electrode EL2 may be a reflective electrode.

The organic electroluminescence device 10 according to an embodiment of the present disclosure includes the polycyclic compound represented by Formula 1, and accordingly, high efficiency and/or long lifespan may be achieved. In addition, a decreased driving voltage may be achieved.

Hereinafter, the present disclosure will be explained referring to embodiments and comparative embodiments. The following example embodiments are only illustrations to assist the understanding of the present disclosure, and the scope of the present disclosure is not limited thereto.

Synthetic Examples

The polycyclic compound according to an embodiment of the present disclosure may be synthesized, for example, as follows. However, the synthetic method of the polycyclic compound according to an embodiment of the present disclosure is not limited thereto.

1. Synthesis of Compound A1

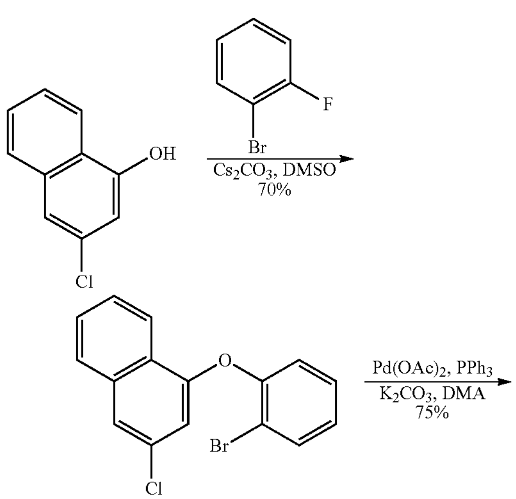

IM-1

-continued

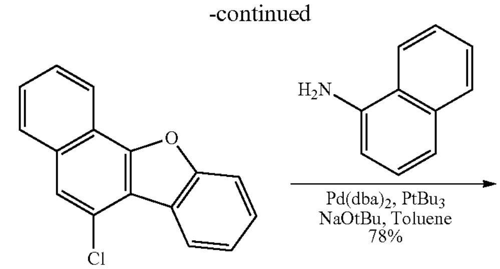

IM-2

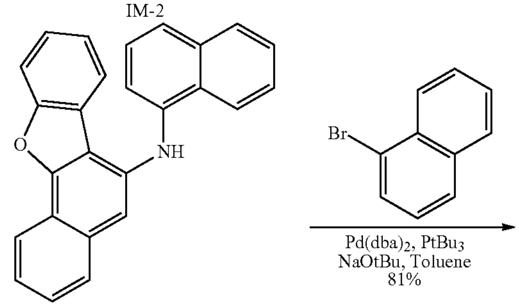

IM-3

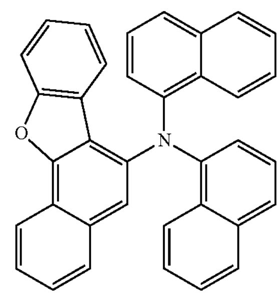

A1

(Synthesis of Intermediate IM-1)

Under an Ar atmosphere, to a 500 mL, three neck flask, 25.00 g (140.0 mmol) of 3-chloronaphthalen-1-ol, 29.39 g (1.2 eq, 168.0 mmol) of 1-bromo-2-fluorobenzene, 91.20 g (2.0 eq, 280.0 mmol) of $Cs_2CO_3$, and 280 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-1 (32.68 g, yield 70%).

By FAB-MS measurement, mass number m/z=333 was observed as the molecular ion peak, and Intermediate IM-1 was identified.

(Synthesis of Intermediate IM-2)

Under an Ar atmosphere, to a 500 mL, three neck flask, 25.00 g (74.9 mmol) of IM-1, 0.84 g (0.05 eq, 3.7 mmol) of $Pd(OAc)_2$, 15.54 g (1.5 eq, 112.4 mmol) of $K_2CO_3$, 1.97 g (0.10 eq, 7.5 mmol) of $PPh_3$, and 300 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-2 (14.20 g, yield 75%).

By FAB-MS measurement, mass number m/z=252 was observed as the molecular ion peak, and Intermediate IM-2 was identified.

(Synthesis of Intermediate IM-3)

Under an Ar atmosphere, to a 500 mL, three neck flask, 12.00 g (47.5 mmol) of IM-2, 0.82 g (0.03 eq, 1.4 mmol) of $Pd(dba)_2$, 4.56 g (2.0 eq, 47.5 mmol) of NaOtBu, 237 mL of toluene, 7.48 g (1.1 eq, 45.2 mmol) of naphthalene-1-amine, and 0.96 g (0.1 eq, 4.7 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-3 (13.31 g, yield 78%).

By FAB-MS measurement, mass number m/z=359 was observed as the molecular ion peak, and Intermediate IM-3 was identified.

(Synthesis of Compound A1)

Under an Ar atmosphere, to a 300 mL, three neck flask, 10.00 g (27.8 mmol) of IM-3, 0.48 g (0.03 eq, 0.8 mmol) of $Pd(dba)_2$, 5.35 g (2.0 eq, 55.6 mmol) of NaOtBu, 139 mL of toluene, 6.34 g (1.1 eq, 30.6 mmol) of 1-bromonaphthalene, and 0.56 g (0.1 eq, 2.8 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound A1 (10.94 g, yield 81%) as a solid.

By FAB-MS measurement, mass number m/z=485 was observed as the molecular ion peak, and Compound A1 was identified.

2. Synthesis of Compound A19

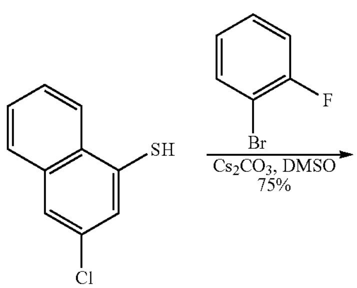

-continued

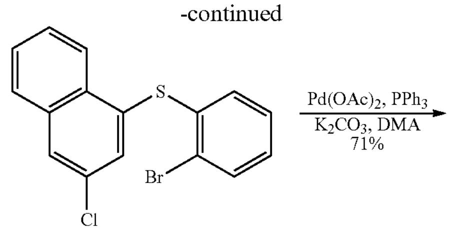

IM-4

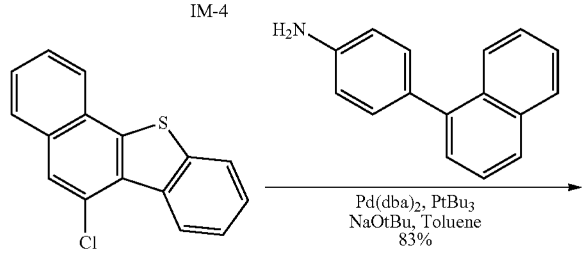

IM-5

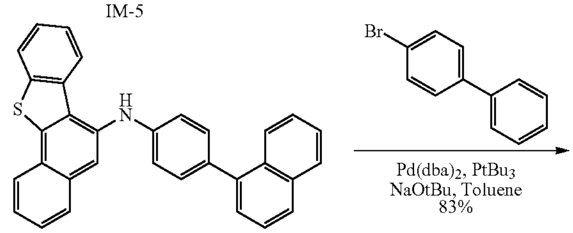

IM-6

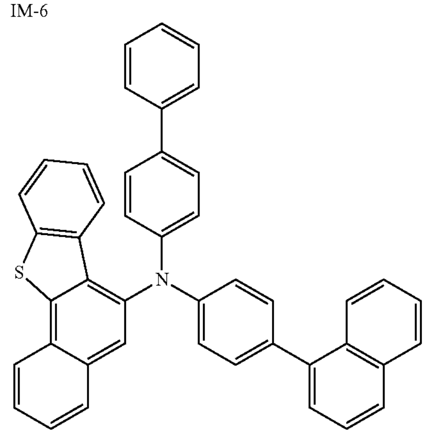

A19

(Synthesis of Intermediate IM-4)

Under an Ar atmosphere, to a 500 mL, three neck flask, 25.00 g (128.4 mmol) of 3-chloronaphthalen-1-thiol, 26.97 g (1.2 eq, 154.1 mmol) of 1-bromo-2-fluorobenzene, 83.68 g (2.0 eq, 256.8 mmol) of $Cs_2CO_3$, and 257 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-4 (33.68 g, yield 75%).

By FAB-MS measurement, mass number m/z=349 was observed as the molecular ion peak, and Intermediate IM-4 was identified.

(Synthesis of Intermediate IM-5)

Under an Ar atmosphere, to a 500 mL, three neck flask, 25.00 g (71.5 mmol) of IM-4, 0.80 g (0.05 eq, 3.6 mmol) of $Pd(OAc)_2$, 14.52 g (1.5 eq, 107.2 mmol) of $K_2CO_3$, 1.88 g (0.10 eq, 7.1 mmol) of $PPh_3$, and 286 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-5 (13.64 g, yield 71%).

By FAB-MS measurement, mass number m/z=268 was observed as the molecular ion peak, and Intermediate IM-5 was identified.

(Synthesis of Intermediate IM-6)

Under an Ar atmosphere, to a 500 mL, three neck flask, 12.00 g (44.7 mmol) of IM-6, 0.77 g (0.03 eq, 1.3 mmol) of $Pd(dba)_2$, 4.29 g (2.0 eq, 44.7 mmol) of NaOtBu, 224 mL of toluene, 10.77 g (1.1 eq, 49.1 mmol) of 4-(naphthalene-1-yl)aniline, and 0.90 g (0.1 eq, 4.5 mmol) of $tBu_3P$ were added in order, followed by heating, refluxing and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-6 (16.74 g, yield 83%).

By FAB-MS measurement, mass number m/z=451 was observed as the molecular ion peak, and Intermediate IM-6 was identified.

(Synthesis of Compound A19)

Under an Ar atmosphere, to a 300 mL, three neck flask, 10.00 g (22.1 mmol) of IM-6, 0.38 g (0.03 eq, 0.7 mmol) of $Pd(dba)_2$, 4.26 g (2.0 eq, 44.3 mmol) of NaOtBu, 111 mL of toluene, 5.68 g (1.1 eq, 24.4 mmol) of 4-bromobiphenyl, and 0.45 g (0.1 eq, 2.2 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound A19 (11.10 g, yield 83%) as a solid.

By FAB-MS measurement, mass number m/z=603 was observed as the molecular ion peak, and Compound A19 was identified.

3. Synthesis of Compound A65

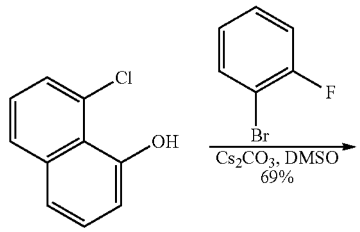

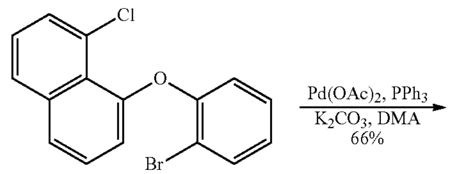

IM-7

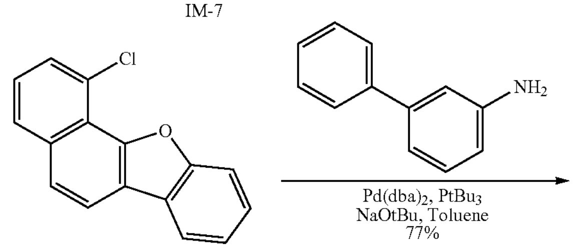

IM-8

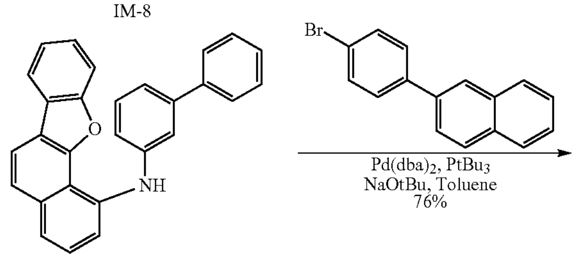

IM-9

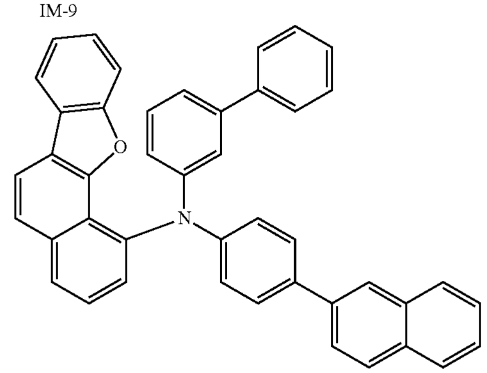

A65

(Synthesis of Intermediate IM-7)

Under an Ar atmosphere, to a 500 mL, three neck flask, 25.00 g (140.0 mmol) of 8-chloronaphthalen-1-ol, 29.39 g (1.2 eq, 168.0 mmol) of 1-bromo-2-fluorobenzene, 91.20 g (2.0 eq, 280.0 mmol) of $Cs_2CO_3$, and 280 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-7 (32.22 g, yield 69%).

By FAB-MS measurement, mass number m/z=333 was observed as the molecular ion peak, and Intermediate IM-7 was identified.

(Synthesis of Intermediate IM-8)

Under an Ar atmosphere, to a 500 mL, three neck flask, 25.00 g (74.9 mmol) of IM-7, 0.84 g (0.05 eq, 3.7 mmol) of $Pd(OAc)_2$, 15.54 g (1.5 eq, 112.4 mmol) of $K_2CO_3$, 1.97 g (0.10 eq, 7.5 mmol) of $PPh_3$, and 300 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-8 (12.50 g, yield 66%).

By FAB-MS measurement, mass number m/z=252 was observed as the molecular ion peak, and Intermediate IM-8 was identified.

(Synthesis of Intermediate IM-9)

Under an Ar atmosphere, to a 300 mL, three neck flask, 10.00 g (39.6 mmol) of IM-8, 0.68 g (0.03 eq, 1.2 mmol) of $Pd(dba)_2$, 3.80 g (1.0 eq, 39.6 mmol) of NaOtBu, 198 mL of toluene, 7.37 g (1.1 eq, 43.5 mmol) of [1,1'-biphenyl]-3-amine, and 0.80 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-9 (11.75 g, yield 77%).

By FAB-MS measurement, mass number m/z=385 was observed as the molecular ion peak, and Intermediate IM-9 was identified.

(Synthesis of Compound A65)

Under an Ar atmosphere, to a 300 mL, three neck flask, 10.00 g (25.9 mmol) of IM-9, 0.45 g (0.03 eq, 0.8 mmol) of $Pd(dba)_2$, 4.99 g (2.0 eq, 51.9 mmol) of NaOtBu, 130 mL of toluene, 8.08 g (1.1 eq, 28.5 mmol) of 2-(4-bromophenyl) naphthalene, and 0.52 g (0.1 eq, 2.6 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound A65 (11.59 g, yield 76%) as a solid.

By FAB-MS measurement, mass number m/z=587 was observed as the molecular ion peak, and Compound A65 was identified.

4. Synthesis of Compound B49

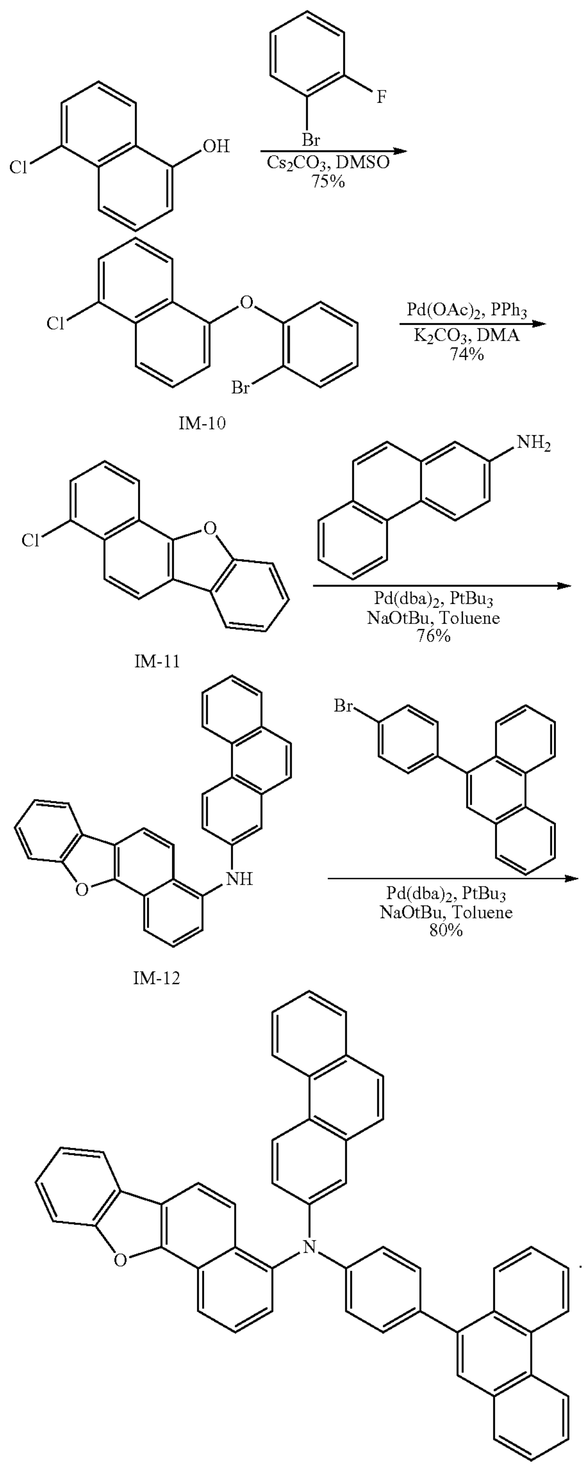

IM-10
IM-11
IM-12
B49

(Synthesis of Intermediate IM-10)

Under an Ar atmosphere, to a 500 mL, three neck flask, 25.00 g (140.0 mmol) of 5-chloronaphthalen-1-ol, 29.39 g (1.2 eq, 168.0 mmol) of 1-bromo-2-fluorobenzene, 91.20 g (2.0 eq, 280.0 mmol) of $Cs_2CO_3$, and 280 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-10 (35.02 g, yield 75%).

By FAB-MS measurement, mass number m/z=333 was observed as the molecular ion peak, and Intermediate IM-10 was identified.

(Synthesis of Intermediate IM-11)

Under an Ar atmosphere, to a 500 mL, three neck flask, 25.00 g (74.9 mmol) of IM-10, 0.84 g (0.05 eq, 3.7 mmol) of $Pd(OAc)_2$, 15.54 g (1.5 eq, 112.4 mmol) of $K_2CO_3$, 1.97 g (0.10 eq, 7.5 mmol) of $PPh_3$, and 300 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-11 (14.01 g, yield 74%).

By FAB-MS measurement, mass number m/z=252 was observed as the molecular ion peak, and Intermediate IM-11 was identified.

(Synthesis of Intermediate IM-12)

Under an Ar atmosphere, to a 500 mL, three neck flask, 12.00 g (47.5 mmol) of IM-11, 0.82 g (0.03 eq, 1.4 mmol) of $Pd(dba)_2$, 4.57 g (1.0 eq, 47.5 mmol) of NaOtBu, 237 mL of toluene, 10.09 g (1.1 eq, 52.2 mmol) of phenanthren-2-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-12 (14.78 g, yield 76%).

By FAB-MS measurement, mass number m/z=409 was observed as the molecular ion peak, and Intermediate IM-12 was identified.

(Synthesis of Compound B49)

Under an Ar atmosphere, to a 300 mL, three neck flask, 10.00 g (24.4 mmol) of IM-12, 0.42 g (0.03 eq, 0.7 mmol) of $Pd(dba)_2$, 4.69 g (2.0 eq, 48.8 mmol) of NaOtBu, 122 mL of toluene, 8.95 g (1.1 eq, 26.9 mmol) of 9-(4-bromophenyl) naphthalene, and 0.49 g (0.1 eq, 2.4 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound B49 (12.93 g, yield 80%) as a solid.

By FAB-MS measurement, mass number m/z=661 was observed as the molecular ion peak, and Compound B49 was identified.

5. Synthesis of Compound B94

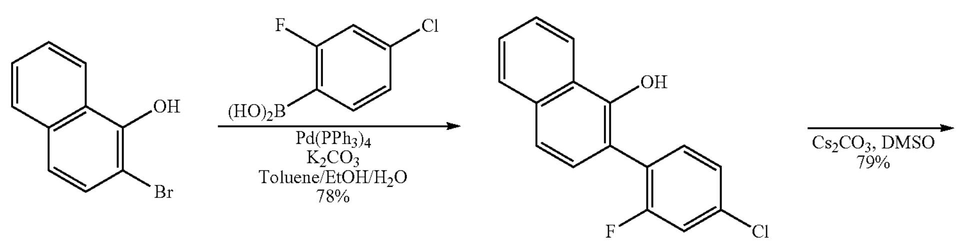

IM-13

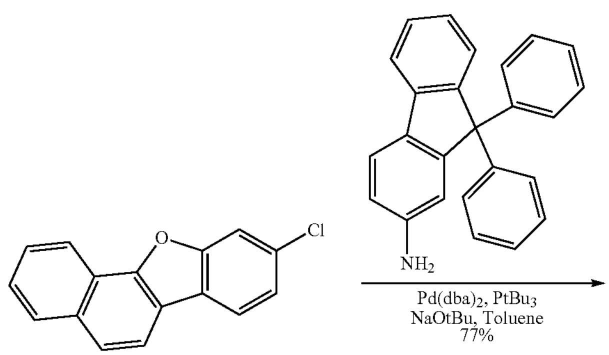

IM-14

-continued

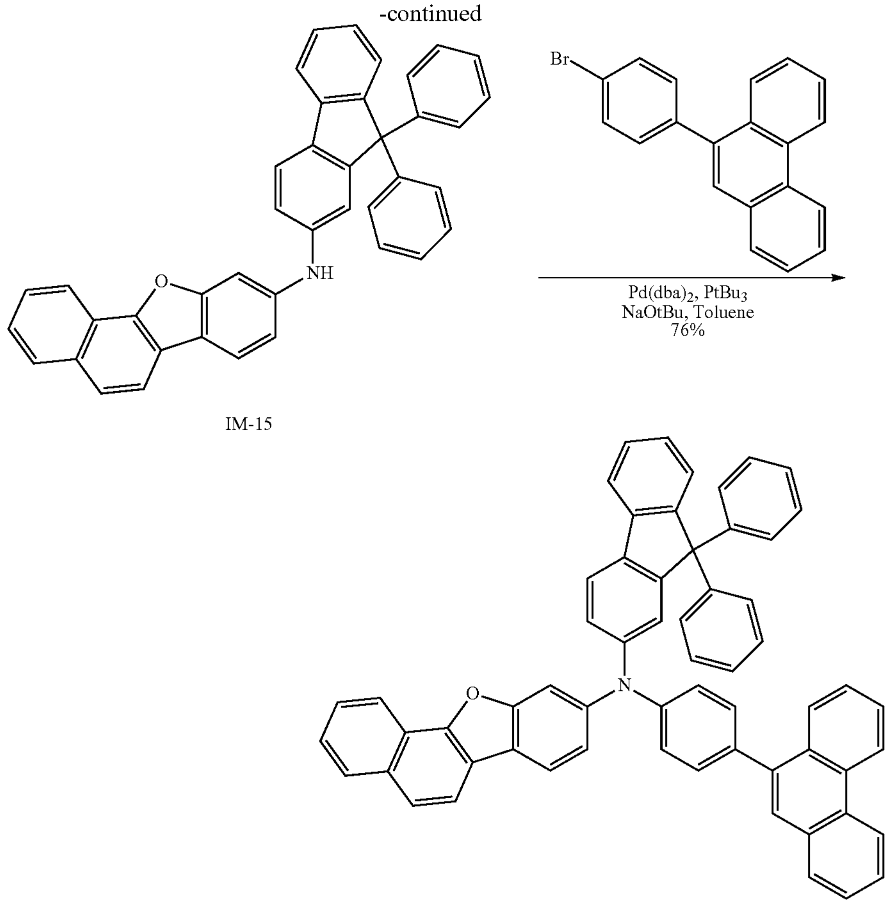

IM-15

B94

(Synthesis of Intermediate IM-13)

Under an Ar atmosphere, to a 2,000 mL, three neck flask, 30.00 g (134.5 mmol) of 2-bromo-1-naphthol, 25.79 g (1.1 eq, 147.9 mmol) of (4-chloro-2-fluorophenyl)boronic acid, 55.76 g (3.0 eq, 403.5 mmol) of $K_2CO_3$, 7.77 g (0.05 eq, 6.7 mmol) of $Pd(PPh_3)_4$, and 941 mL of a mixture solution of toluene/EtOH/$H_2O$ (4/2/1) were added in order, followed by heating and stirring at about 80° C. After cooling to room temperature, the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-13 (28.61 g, yield 78%).

By FAB-MS measurement, mass number m/z=272 was observed as the molecular ion peak, and Intermediate IM-13 was identified.

(Synthesis of Intermediate IM-14)

Under an Ar atmosphere, to a 300 mL, three neck flask, 25.00 g (91.7 mmol) of IM-13, 59.74 g (2.0 eq, 183.4 mmol) of $Cs_2CO_3$, and 184 mL of DMSO were added in order, followed by heating to about 110° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-14 (18.30 g, yield 79%).

By FAB-MS measurement, mass number m/z=252 was observed as the molecular ion peak, and Intermediate IM-14 was identified.

(Synthesis of Intermediate IM-15)

Under an Ar atmosphere, to a 500 mL, three neck flask, 12.00 g (47.5 mmol) of IM-14, 0.82 g (0.03 eq, 1.4 mmol) of Pd(dba)$_2$, 4.57 g (1.0 eq, 47.5 mmol) of NaOtBu, 237 mL of toluene, 17.42 g (1.1 eq, 52.2 mmol) of 9,9-diphenyl-9H-fluoren-2-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-15 (20.10 g, yield 77%).

By FAB-MS measurement, mass number m/z=549 was observed as the molecular ion peak, and Intermediate IM-15 was identified.11

(Synthesis of Compound B94)

Under an Ar atmosphere, to a 300 mL, three neck flask, 10.00 g (18.2 mmol) of IM-15, 0.31 g (0.03 eq, 0.5 mmol) of $Pd(dba)_2$, 3.50 g (2.0 eq, 36.4 mmol) of NaOtBu, 91 mL of toluene, 6.67 g (1.1 eq, 20.0 mmol) of 9-(4-bromophenyl) phenanthrene, and 0.37 g (0.1 eq, 1.8 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound B94 (11.09 g, yield 76%) as a solid.

By FAB-MS measurement, mass number m/z=801 was observed as the molecular ion peak, and Compound B94 was identified.

6. Synthesis of Compound C67

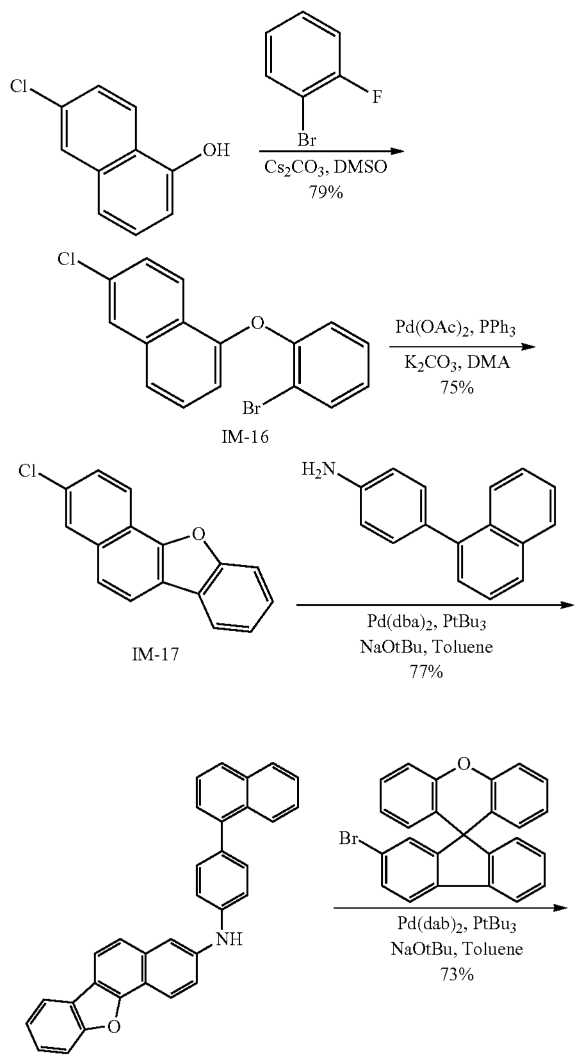

-continued

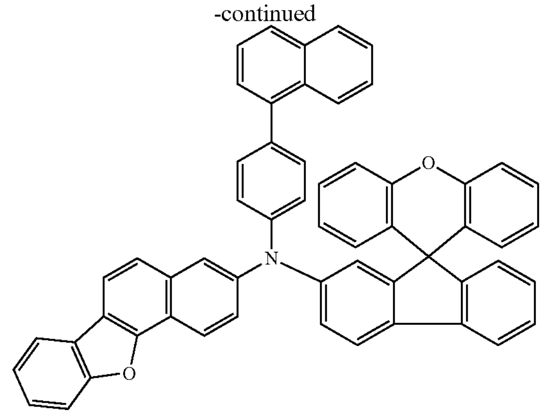

C67

(Synthesis of Intermediate IM-16)

Under an Ar atmosphere, to a 500 mL, three neck flask, 25.00 g (140.0 mmol) of 6-chloronaphthalen-1-ol, 29.39 g (1.2 eq, 168.0 mmol) of 1-bromo-2-fluorobenzene, 91.20 g (2.0 eq, 280.0 mmol) of $Cs_2CO_3$, and 280 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-16 (36.89 g, yield 79%).

By FAB-MS measurement, mass number m/z=333 was observed as the molecular ion peak, and Intermediate IM-16 was identified.

(Synthesis of Intermediate IM-17)

Under an Ar atmosphere, to a 500 mL, three neck flask, 25.00 g (74.9 mmol) of IM-16, 0.84 g (0.05 eq, 3.7 mmol) of $Pd(OAc)_2$, 15.54 g (1.5 eq, 112.4 mmol) of $K_2CO_3$, 1.97 g (0.10 eq, 7.5 mmol) of $PPh_3$, and 300 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-17 (14.20 g, yield 75%).

By FAB-MS measurement, mass number m/z=252 was observed as the molecular ion peak, and Intermediate IM-17 was identified.

(Synthesis of Intermediate IM-18)

Under an Ar atmosphere, to a 500 mL, three neck flask, 12.00 g (47.5 mmol) of IM-17, 0.82 g (0.03 eq, 1.4 mmol) of $Pd(dba)_2$, 4.57 g (1.0 eq, 47.5 mmol) of NaOtBu, 237 mL of toluene, 11.45 g (1.1 eq, 52.2 mmol) of 4-(naphthalene-1-yl)aniline, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-18 (15.93 g, yield 77%).

By FAB-MS measurement, mass number m/z=435 was observed as the molecular ion peak, and Intermediate IM-18 was identified.

(Synthesis of Compound C67)

Under an Ar atmosphere, to a 300 mL, three neck flask, 10.00 g (23.0 mmol) of IM-18, 0.40 g (0.03 eq, 0.7 mmol) of $Pd(dba)_2$, 4.41 g (2.0 eq, 45.9 mmol) of NaOtBu, 115 mL of toluene, 10.39 g (1.1 eq, 25.3 mmol) of 2-bromo-spiro[fluorene-9,9'-xanthene], and 0.47 g (0.1 eq, 2.3 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound C67 (12.84 g, yield 73%) as a solid.

By FAB-MS measurement, mass number m/z=765 was observed as the molecular ion peak, and Compound C67 was identified.

7. Synthesis of Compound C124

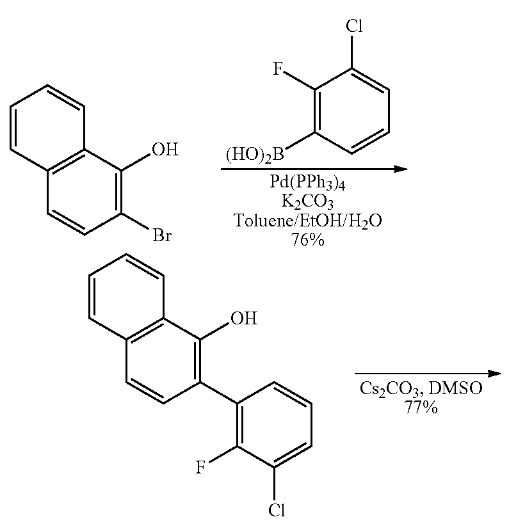

IM-19

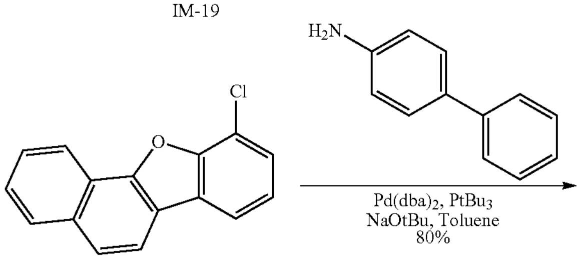

IM-20

-continued

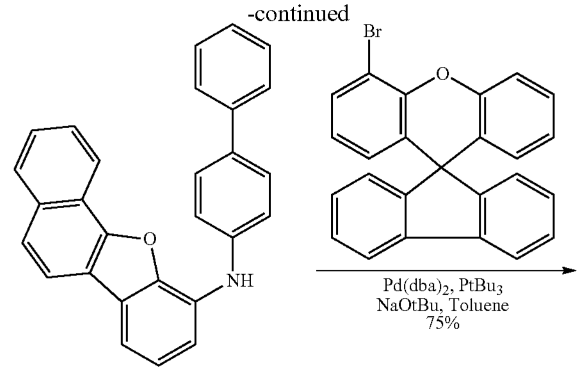

IM-21

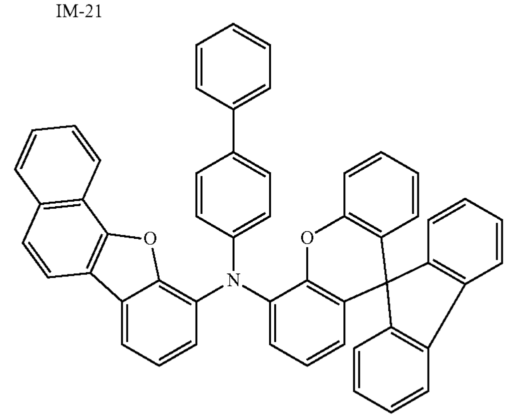

C124

(Synthesis of Intermediate IM-19)

Under an Ar atmosphere, to a 2,000 mL, three neck flask, 30.00 g (134.5 mmol) of 2-bromo-1-naphthol, 25.79 g (1.1 eq, 147.9 mmol) of (3-chloro-2-fluorophenyl)boronic acid, 55.76 g (3.0 eq, 403.5 mmol) of $K_2CO_3$, 7.77 g (0.05 eq, 6.7 mmol) of $Pd(PPh_3)_4$, and 941 mL of a mixture solution of toluene/EtOH/$H_2O$ (4/2/1) were added in order, followed by heating and stirring at about 80° C. After cooling to room temperature, the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-19 (27.87 g, yield 76%).

By FAB-MS measurement, mass number m/z=272 was observed as the molecular ion peak, and Intermediate IM-19 was identified.

(Synthesis of Intermediate IM-20)

Under an Ar atmosphere, to a 300 mL, three neck flask, 25.00 g (91.7 mmol) of IM-19, 59.74 g (2.0 eq, 183.4 mmol) of $Cs_2CO_3$, and 184 mL of DMSO were added in order, followed by heating to about 110° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-20 (17.84 g, yield 77%).

By FAB-MS measurement, mass number m/z=252 was observed as the molecular ion peak, and Intermediate IM-20 was identified.

(Synthesis of Intermediate IM-21)

Under an Ar atmosphere, to a 500 mL, three neck flask, 12.00 g (47.5 mmol) of IM-20, 0.82 g (0.03 eq, 1.4 mmol) of $Pd(dba)_2$, 4.57 g (1.0 eq, 47.5 mmol) of NaOtBu, 237 mL of toluene, 8.84 g (1.1 eq, 52.2 mmol) of 4-aminobiphenyl, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-21 (14.64 g, yield 80%).

By FAB-MS measurement, mass number m/z=385 was observed as the molecular ion peak, and Intermediate IM-21 was identified.

(Synthesis of Compound C124)

Under an Ar atmosphere, to a 300 mL, three neck flask, 10.00 g (25.9 mmol) of IM-21, 0.45 g (0.03 eq, 0.8 mmol) of $Pd(dba)_2$, 4.99 g (2.0 eq, 51.9 mmol) of NaOtBu, 130 mL of toluene, 11.74 g (1.1 eq, 28.5 mmol) of 4'-bromospiro[fluorene-9,9'-xanthene], and 0.52 g (0.1 eq, 2.6 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound C124 (13.93 g, yield 75%) as a solid.

By FAB-MS measurement, mass number m/z=715 was observed as the molecular ion peak, and Compound C124 was identified.

8. Synthesis of Compound C153

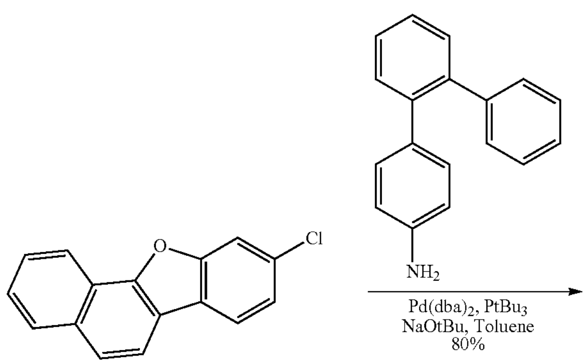

IM-14

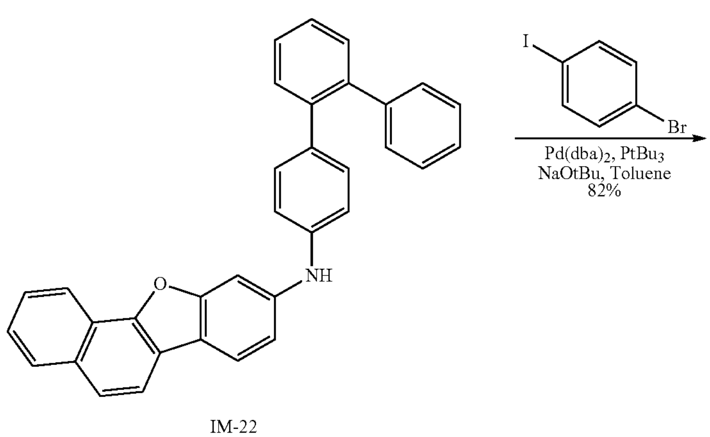

IM-22

-continued

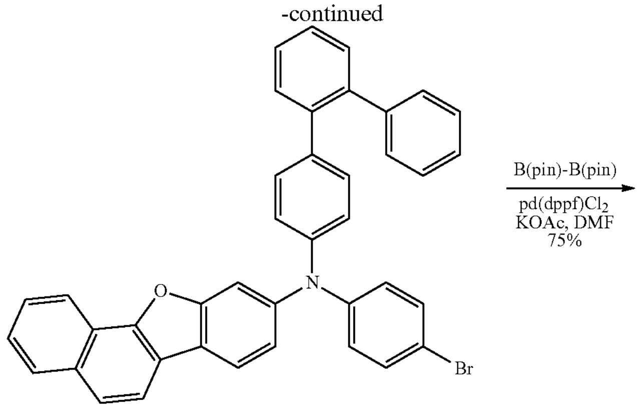

IM-23

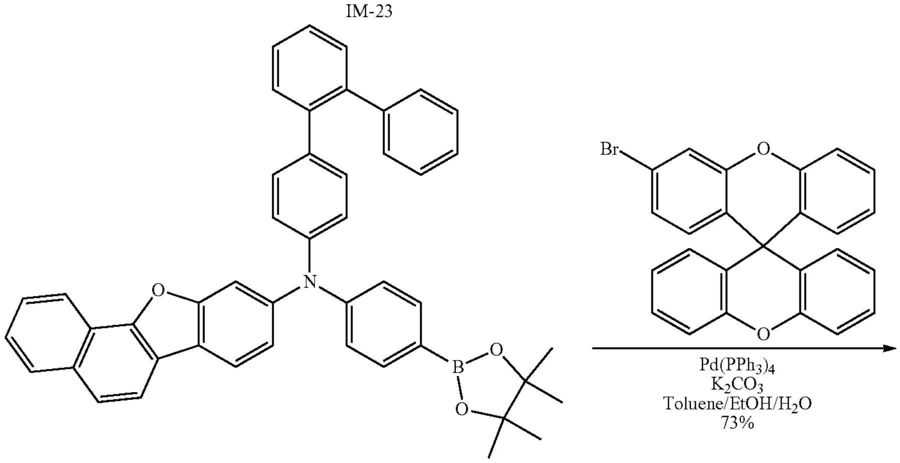

IM-24

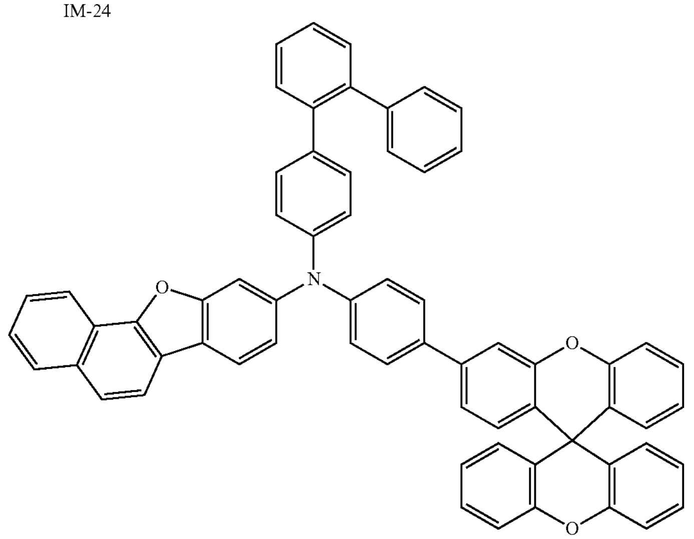

C153

(Synthesis of Intermediate IM-22)

Under an Ar atmosphere, to a 500 mL, three neck flask, 12.00 g (47.5 mmol) of IM-14, 0.82 g (0.03 eq, 1.4 mmol) of Pd(dba)$_2$, 4.57 g (1.0 eq, 47.5 mmol) of NaOtBu, 237 mL of toluene, 12.81 g (1.1 eq, 52.2 mmol) of [1,1':2',1"-terphenyl]-4-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to an aqueous layer, and further organic layers were extracted. The organic layers were collected, washed with a saturated saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-22 (17.53 g, yield 80%).

By FAB-MS measurement, mass number m/z=461 was observed as the molecular ion peak, and Intermediate IM-22 was identified.

(Synthesis of Intermediate IM-23)

Under an Ar atmosphere, to a 500 mL, three neck flask, 15.00 g (32.5 mmol) of IM-22, 0.56 g (0.03 eq, 1.0 mmol) of $Pd(dba)_2$, 6.25 g (1.0 eq, 65.0 mmol) of NaOtBu, 162 mL of toluene, 10.11 g (1.1 eq, 35.7 mmol) of 1-bromo-4-iodobenzene, and 0.66 g (0.1 eq, 3.2 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-23 (16.43 g, yield 82%).

By FAB-MS measurement, mass number m/z=616 was observed as the molecular ion peak, and Intermediate IM-23 was identified.

(Synthesis of Intermediate IM-24)

Under an Ar atmosphere, to a 300 mL, three neck flask, 15.00 g (24.3 mmol) of IM-23, 1.99 g (0.10 eq, 2.4 mmol) of $Pd(dppf)Cl_2$, 4.77 g (2.0 eq, 48.7 mmol) of KOAc, 122 mL of DMF, and 7.41 g (1.2 eq, 29.2 mmol) of bis(pinacolato)diboron were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-24 (12.11 g, yield 75%).

By FAB-MS measurement, mass number m/z=663 was observed as the molecular ion peak, and Intermediate IM-24 was identified.

(Synthesis of Compound C153)

Under an Ar atmosphere, to a 300 mL, three neck flask, 10.00 g (31.8 mmol) of IM-24, 7.08 g (1.1 eq, 16.6 mmol) of 3-bromo-9,9'-spirobi[xanthene], 6.25 g (3.0 eq, 45.2 mmol) of $K_2CO_3$, 0.87 g (0.05 eq, 0.8 mmol) of $Pd(PPh_3)_4$, and 105 mL of a mixture solution of toluene/EtOH/$H_2O$ (4/2/1) were added in order, followed by heating to about 80° C. and stirring. After cooling to room temperature, the reaction solution was extracted with toluene. An aqueous layer was removed, and an organic layer was washed with a saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound C153 (9.72 g, yield 73%) as a solid.

By FAB-MS measurement, mass number m/z=884 was observed as the molecular ion peak, and Compound C153 was identified.

9. Synthesis of Compound D32

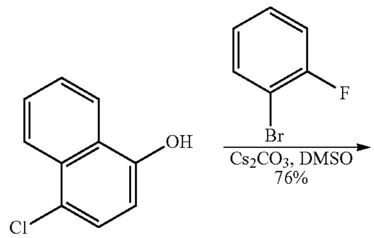

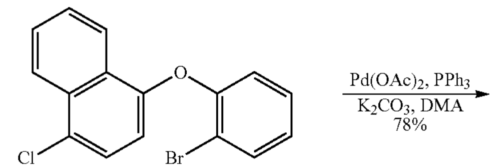

IM-25

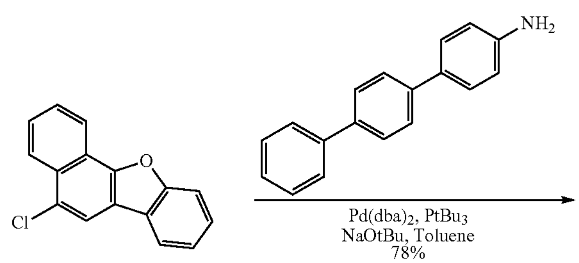

IM-26

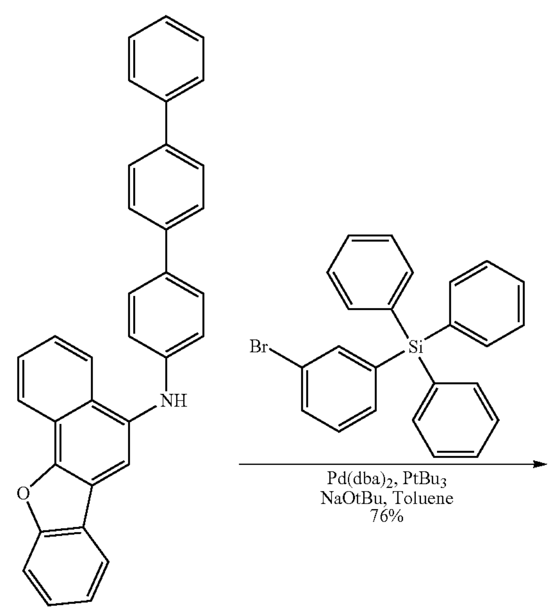

IM-27

-continued

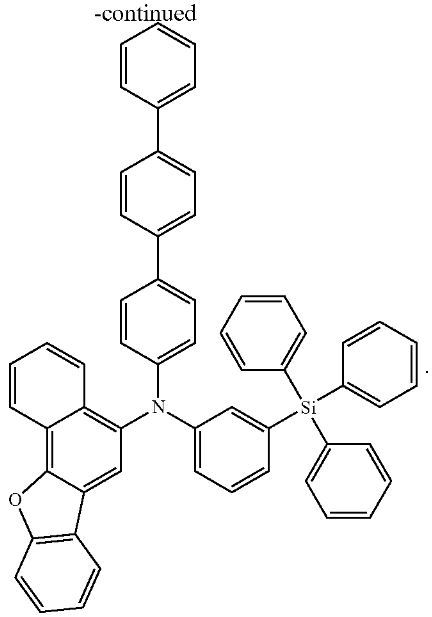

D32

(Synthesis of Intermediate IM-25)

Under an Ar atmosphere, to a 500 mL, three neck flask, 25.00 g (140.0 mmol) of 4-chloronaphthalen-1-ol, 29.39 g (1.2 eq, 168.0 mmol) of 1-bromo-2-fluorobenzene, 91.20 g (2.0 eq, 280.0 mmol) of $Cs_2CO_3$, and 280 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-25 (35.49 g, yield 76%).

By FAB-MS measurement, mass number m/z=333 was observed as the molecular ion peak, and Intermediate IM-25 was identified.

(Synthesis of Intermediate IM-26)

Under an Ar atmosphere, to a 500 mL, three neck flask, 25.00 g (74.9 mmol) of IM-25, 0.84 g (0.05 eq, 3.7 mmol) of $Pd(OAc)_2$, 15.54 g (1.5 eq, 112.4 mmol) of $K_2CO_3$, 1.97 g (0.10 eq, 7.5 mmol) of $PPh_3$, and 300 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-26 (14.77 g, yield 78%).

By FAB-MS measurement, mass number m/z=252 was observed as the molecular ion peak, and Intermediate IM-26 was identified.

(Synthesis of Intermediate IM-27)

Under an Ar atmosphere, to a 500 mL, three neck flask, 12.00 g (47.5 mmol) of IM-26, 0.82 g (0.03 eq, 1.4 mmol) of $Pd(dba)_2$, 4.57 g (1.0 eq, 47.5 mmol) of NaOtBu, 237 mL of toluene, 12.81 g (1.1 eq, 52.2 mmol) of [1,1':4',1"-terphenyl]-4-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-27 (17.10 g, yield 78%).

By FAB-MS measurement, mass number m/z=461 was observed as the molecular ion peak, and Intermediate IM-27 was identified.

(Synthesis of Compound D32)

Under an Ar atmosphere, to a 300 mL, three neck flask, 10.00 g (21.7 mmol) of IM-27, 0.37 g (0.03 eq, 0.6 mmol) of $Pd(dba)_2$, 4.16 g (2.0 eq, 43.3 mmol) of NaOtBu, 108 mL of toluene, 9.90 g (1.1 eq, 23.8 mmol) of 3-bromotetraphenylsilane, and 0.44 g (0.1 eq, 2.2 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound D32 (13.11 g, yield 76%) as a solid.

By FAB-MS measurement, mass number m/z=796 was observed as the molecular ion peak, and Compound D32 was identified.

10. Synthesis of Compound D162

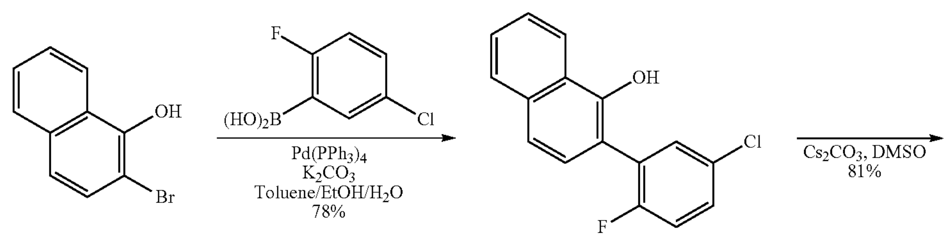

IM-28

-continued

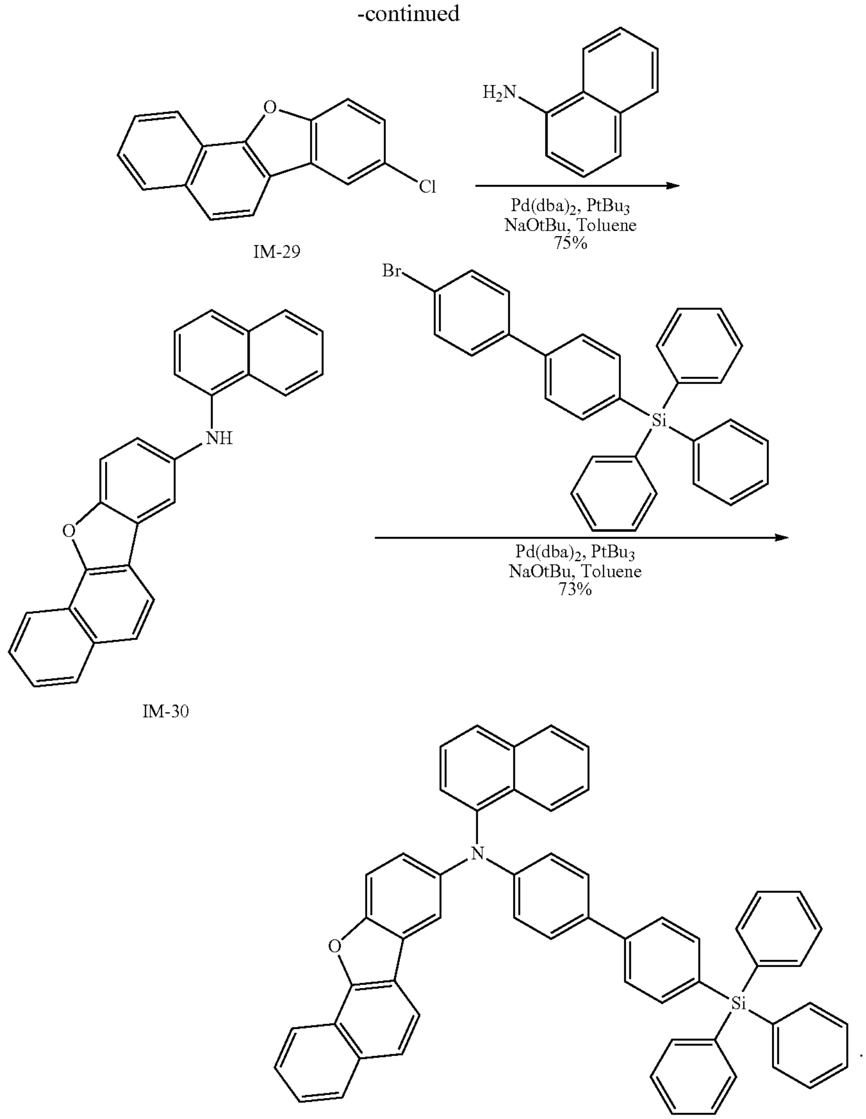

IM-29

IM-30

D162

(Synthesis of Intermediate IM-28)

Under an Ar atmosphere, to a 2,000 mL, three neck flask, 30.00 g (134.5 mmol) of 2-bromo-1-naphthol, 25.79 g (1.1 eq, 147.9 mmol) of (5-chloro-2-fluorophenyl)boronic acid, 55.76 g (3.0 eq, 403.5 mmol) of $K_2CO_3$, 7.77 g (0.05 eq, 6.7 mmol) of $Pd(PPh_3)_4$, and 941 mL of a mixture solution of toluene/EtOH/$H_2O$ (4/2/1) were added in order, followed by heating and stirring at about 80° C. After cooling to room temperature, the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-28 (13.83 g, yield 78%).

By FAB-MS measurement, mass number m/z=272 was observed as the molecular ion peak, and Intermediate IM-28 was identified.

(Synthesis of Intermediate IM-29)

Under an Ar atmosphere, to a 300 mL, three neck flask, 25.00 g (91.7 mmol) of IM-28, 59.74 g (2.0 eq, 183.4 mmol) of $Cs_2CO_3$, and 184 mL of DMSO were added in order, followed by heating to about 110° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-29 (18.76 g, yield 81%).

By FAB-MS measurement, mass number m/z=252 was observed as the molecular ion peak, and Intermediate IM-29 was identified.

(Synthesis of Intermediate IM-30)

Under an Ar atmosphere, to a 500 mL, three neck flask, 12.00 g (47.5 mmol) of IM-29, 0.82 g (0.03 eq, 1.4 mmol) of $Pd(dba)_2$, 4.57 g (1.0 eq, 47.5 mmol) of NaOtBu, 237 mL of toluene, 7.48 g (1.1 eq, 52.2 mmol) of naphthalene-1-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-30 (12.80 g, yield 75%).

By FAB-MS measurement, mass number m/z=359 was observed as the molecular ion peak, and Intermediate IM-30 was identified.

(Synthesis of Compound D162)

Under an Ar atmosphere, to a 300 mL, three neck flask, 10.00 g (27.8 mmol) of IM-30, 0.48 g (0.03 eq, 0.8 mmol) of $Pd(dba)_2$, 5.35 g (2.0 eq, 55.6 mmol) of NaOtBu, 139 mL of toluene, 15.04 g (1.1 eq, 30.6 mmol) of [4'-bromo-(1,1'-biphenyl)-4-yl]triphenylsilane, and 0.56 g (0.1 eq, 2.8 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound D162 (15.64 g, yield 73%) as a solid.

By FAB-MS measurement, mass number m/z=770 was observed as the molecular ion peak, and Compound D162 was identified.

11. Synthesis of Compound E87

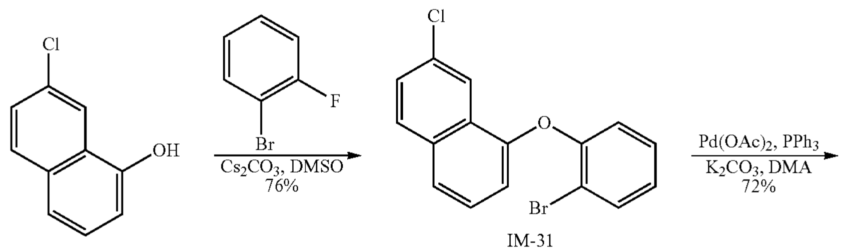

IM-31

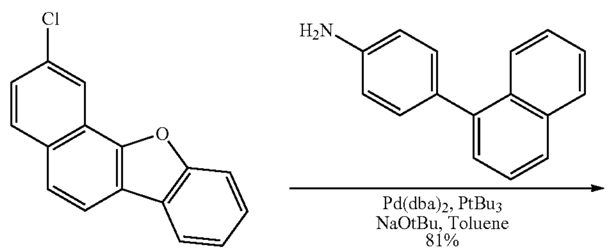

IM-32

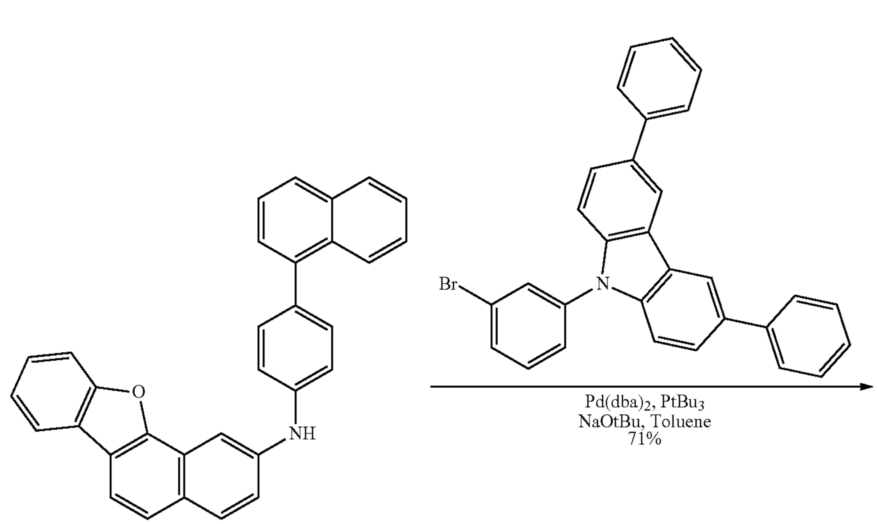

IM-33

-continued

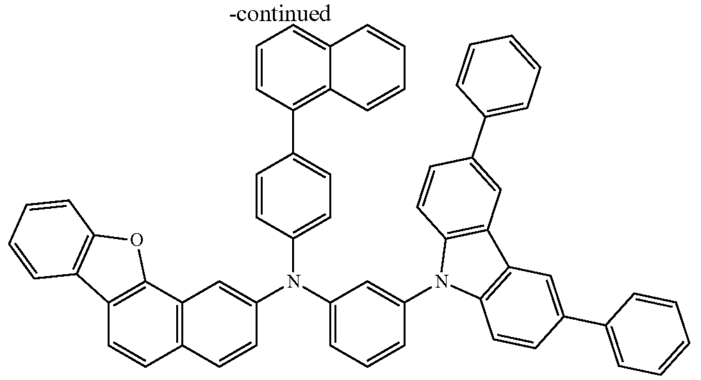

E87

(Synthesis of Intermediate IM-31)

Under an Ar atmosphere, to a 500 mL, three neck flask, 25.00 g (140.0 mmol) of 7-chloronaphthalen-1-ol, 29.39 g (1.2 eq, 168.0 mmol) of 1-bromo-2-fluorobenzene, 91.20 g (2.0 eq, 280.0 mmol) of $Cs_2CO_3$, and 280 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-31 (35.49 g, yield 76%).

By FAB-MS measurement, mass number m/z=333 was observed as the molecular ion peak, and Intermediate IM-31 was identified.

(Synthesis of Intermediate IM-32)

Under an Ar atmosphere, to a 500 mL, three neck flask, 25.00 g (74.9 mmol) of IM-31, 0.84 g (0.05 eq, 3.7 mmol) of $Pd(OAc)_2$, 15.54 g (1.5 eq, 112.4 mmol) of $K_2CO_3$, 1.97 g (0.10 eq, 7.5 mmol) of $PPh_3$, and 300 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-32 (13.63 g, yield 72%).

By FAB-MS measurement, mass number m/z=252 was observed as the molecular ion peak, and Intermediate IM-32 was identified.

(Synthesis of Intermediate IM-33)

Under an Ar atmosphere, to a 500 mL, three neck flask, 12.00 g (47.5 mmol) of IM-32, 0.82 g (0.03 eq, 1.4 mmol) of $Pd(dba)_2$, 4.57 g (1.0 eq, 47.5 mmol) of NaOtBu, 237 mL of toluene, 11.45 g (1.1 eq, 52.2 mmol) of 4-(naphthalen-1-yl)aniline, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-33 (16.75 g, yield 81%).

By FAB-MS measurement, mass number m/z=435 was observed as the molecular ion peak, and Intermediate IM-33 was identified.

(Synthesis of Compound E87)

Under an Ar atmosphere, to a 300 mL, three neck flask, 10.00 g (23.0 mmol) of IM-33, 0.40 g (0.03 eq, 0.7 mmol) of $Pd(dba)_2$, 4.41 g (2.0 eq, 45.9 mmol) of NaOtBu, 115 mL of toluene, 11.98 g (1.1 eq, 25.3 mmol) of 9-(3-bromotetraphenyl)-3,6-diphenyl-9H-carbazole, and 0.46 g (0.1 eq, 2.3 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound E87 (13.51 g, yield 71%) as a solid.

By FAB-MS measurement, mass number m/z=829 was observed as the molecular ion peak, and Compound E87 was identified.

12. Synthesis of Compound E190

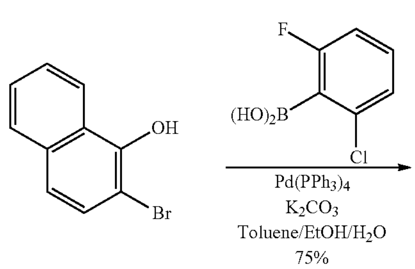

-continued

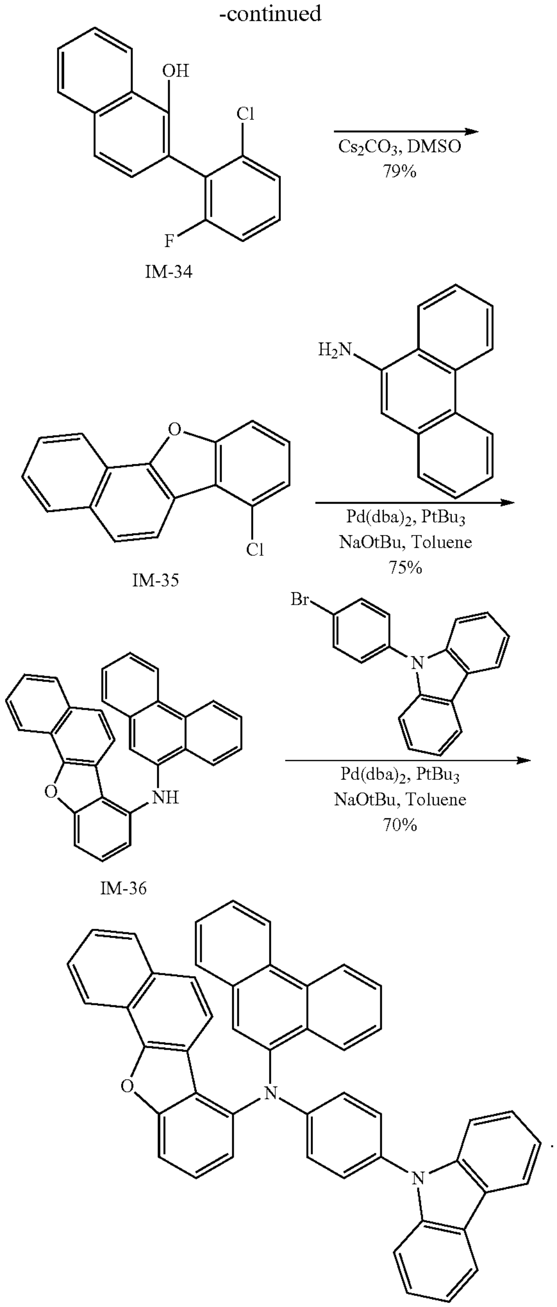

E190

(Synthesis of Intermediate IM-34)

Under an Ar atmosphere, to a 2,000 mL, three neck flask, 30.00 g (134.5 mmol) of 2-bromo-1-naphthol, 25.79 g (1.1 eq, 147.9 mmol) of (2-chloro-6-fluorophenyl)boronic acid, 55.76 g (3.0 eq, 403.5 mmol) of $K_2CO_3$, 7.77 g (0.05 eq, 6.7 mmol) of $Pd(PPh_3)_4$, and 941 mL of a mixture solution of toluene/EtOH/$H_2O$ (4/2/1) were added in order, followed by heating and stirring at about 80° C. After cooling to room temperature, the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-34 (27.51 g, yield 75%).

By FAB-MS measurement, mass number m/z=272 was observed as the molecular ion peak, and Intermediate IM-34 was identified.

(Synthesis of Intermediate IM-35)

Under an Ar atmosphere, to a 300 mL, three neck flask, 25.00 g (91.7 mmol) of IM-34, 59.74 g (2.0 eq, 183.4 mmol) of $Cs_2CO_3$, and 184 mL of DMSO were added in order, followed by heating to about 110° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-35 (18.30 g, yield 79%).

By FAB-MS measurement, mass number m/z=252 was observed as the molecular ion peak, and Intermediate IM-35 was identified.

(Synthesis of Intermediate IM-36)

Under an Ar atmosphere, to a 500 mL, three neck flask, 12.00 g (47.5 mmol) of IM-35, 0.82 g (0.03 eq, 1.4 mmol) of Pd(dba)$_2$, 4.57 g (1.0 eq, 47.5 mmol) of NaOtBu, 237 mL of toluene, 10.09 g (1.1 eq, 52.2 mmol) of 9-aminophenanthrene, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-36 (14.58 g, yield 75%).

By FAB-MS measurement, mass number m/z=650 was observed as the molecular ion peak, and Intermediate IM-36 was identified.

(Synthesis of Compound E190)

Under an Ar atmosphere, to a 300 mL, three neck flask, 10.00 g (24.4 mmol) of IM-36, 0.42 g (0.03 eq, 0.7 mmol) of Pd(dba)$_2$, 4.69 g (2.0 eq, 48.8 mmol) of NaOtBu, 122 mL of toluene, 8.66 g (1.1 eq, 26.9 mmol) of 9-(4-bromophenyl)-9H-carbazole, and 0.49 g (0.1 eq, 2.4 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound E190 (11.12 g, yield 70%) as a solid.

By FAB-MS measurement, mass number m/z=650 was observed as the molecular ion peak, and Compound E190 was identified.

13. Synthesis of Compound F15

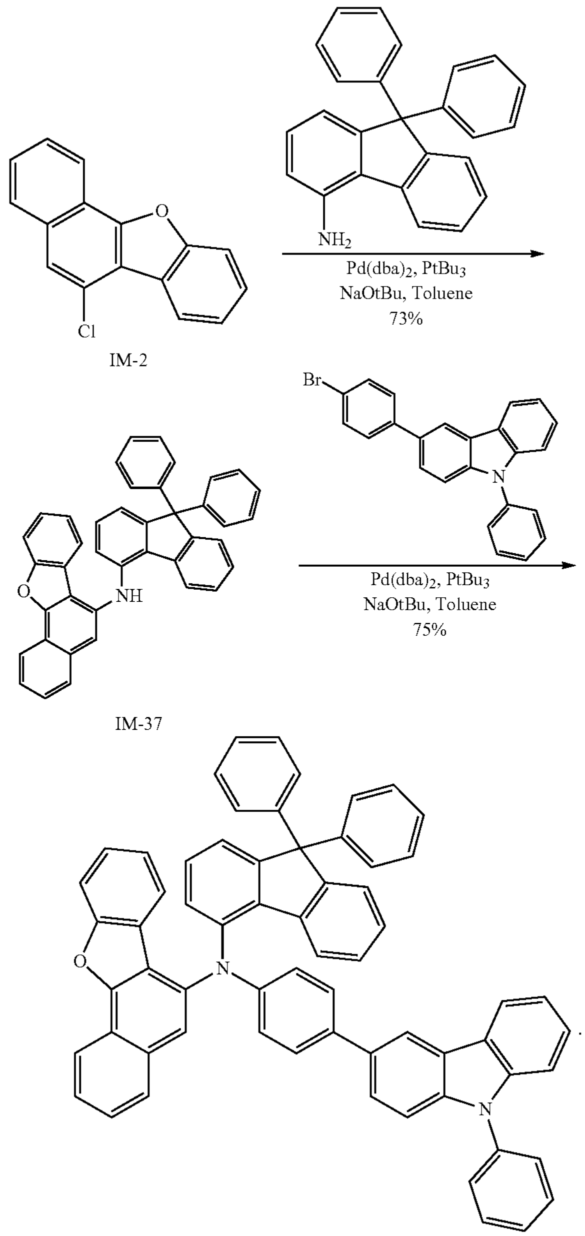

IM-2

IM-37

F15

(Synthesis of Intermediate IM-37)

Under an Ar atmosphere, to a 500 mL, three neck flask, 12.00 g (47.5 mmol) of IM-2, 0.82 g (0.03 eq, 1.4 mmol) of $Pd(dba)_2$, 4.57 g (1.0 eq, 47.5 mmol) of NaOtBu, 237 mL of toluene, 17.42 g (1.1 eq, 52.2 mmol) of 9,9-diphenyl-9H-fluoren-4-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-37 (19.05 g, yield 73%).

By FAB-MS measurement, mass number m/z=549 was observed as the molecular ion peak, and Intermediate IM-37 was identified.

(Synthesis of Compound F15)

Under an Ar atmosphere, to a 300 mL, three neck flask, 10.00 g (18.2 mmol) of IM-37, 0.31 g (0.03 eq, 0.5 mmol) of $Pd(dba)_2$, 3.50 g (2.0 eq, 36.4 mmol) of NaOtBu, 91 mL of toluene, 7.97 g (1.1 eq, 20.0 mmol) of 3-(4-bromophenyl)-9-phenyl-9H-carbazole, and 0.37 g (0.1 eq, 1.8 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound F15 (11.83 g, yield 75%) as a solid.

By FAB-MS measurement, mass number m/z=867 was observed as the molecular ion peak, and Compound F15 was identified.

14. Synthesis of Compound F146

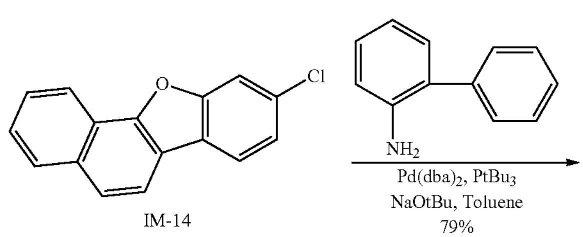

IM-14

-continued

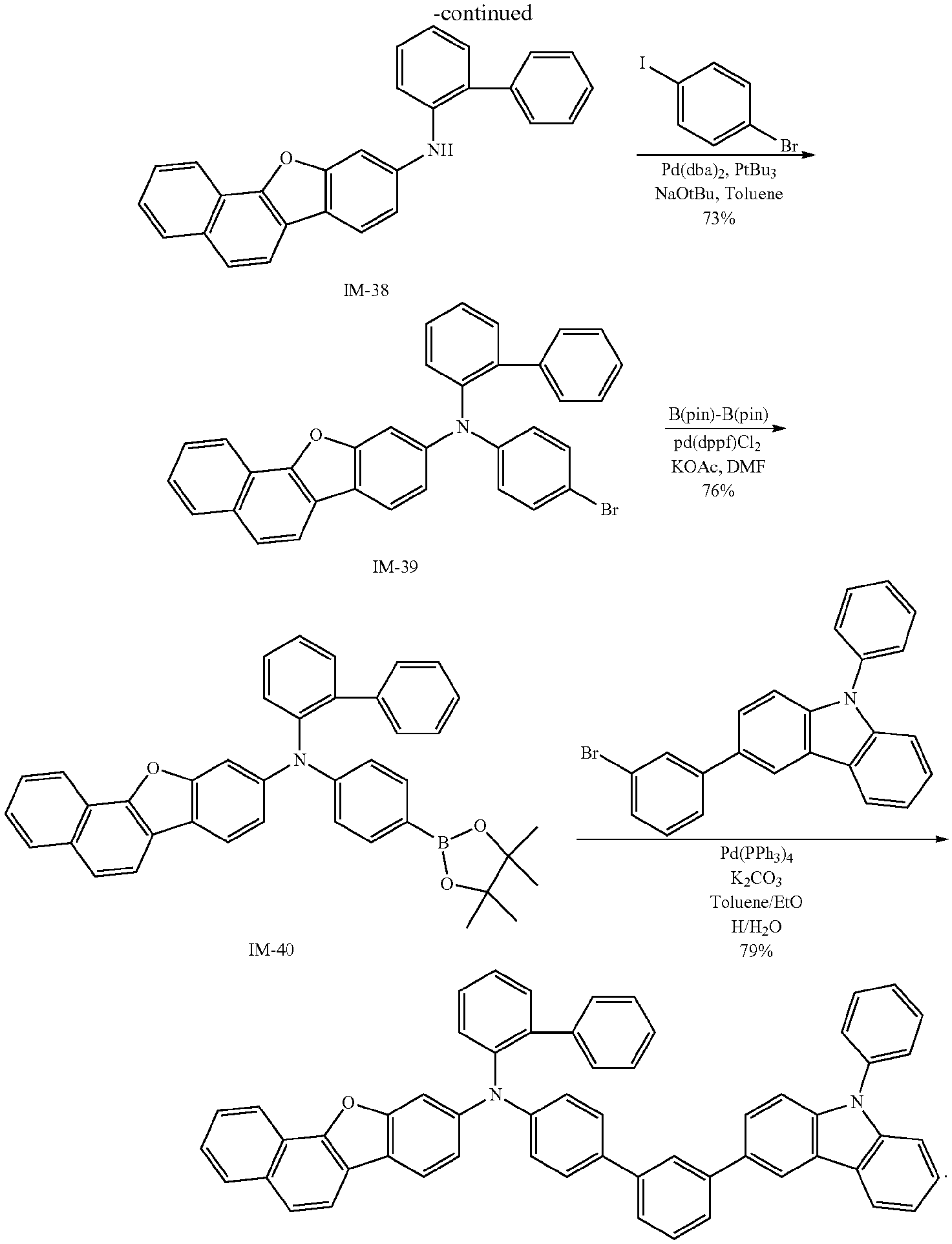

IM-38

IM-39

IM-40

F146

(Synthesis of Intermediate IM-38)

Under an Ar atmosphere, to a 500 mL, three neck flask, 12.00 g (47.5 mmol) of IM-14, 0.82 g (0.03 eq, 1.4 mmol) of $Pd(dba)_2$, 4.57 g (1.0 eq, 47.5 mmol) of NaOtBu, 237 mL of toluene, 8.84 g (1.1 eq, 52.2 mmol) of [1,1'-biphenyl]-2-amine, and 0.96 g (0.1 eq, 4.0 mmol) of $tBu_3P$ were added in order, followed by heating, refluxing, and stirring. After cooling to room temperature, water was added to the reaction solution, and an organic layer was separated. Toluene was added to an aqueous layer, and further organic layers were extracted. The organic layers were collected, washed with a saturated saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-38 (14.46 g, yield 79%).

By FAB-MS measurement, mass number m/z=385 was observed as the molecular ion peak, and Intermediate IM-38 was identified.

(Synthesis of Intermediate IM-39)

Under an Ar atmosphere, to a 500 mL, three neck flask, 14.00 g (36.3 mmol) of IM-38, 0.63 g (0.03 eq, 1.1 mmol) of $Pd(dba)_2$, 6.98 g (1.0 eq, 72.6 mmol) of NaOtBu, 182 mL of toluene, 11.30 g (1.1 eq, 40.0 mmol) of 1-bromo-4-iodobenzene, and 0.73 g (0.1 eq, 3.6 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-39 (14.33 g, yield 73%).

By FAB-MS measurement, mass number m/z=540 was observed as the molecular ion peak, and Intermediate IM-39 was identified.

(Synthesis of Intermediate IM-40)

Under an Ar atmosphere, to a 300 mL, three neck flask, 13.00 g (24.1 mmol) of IM-39, 1.96 g (0.10 eq, 2.4 mmol) of $Pd(dppf)Cl_2$, 4.72 g (2.0 eq, 48.1 mmol) of KOAc, 120 mL of DMF, and 7.33 g (1.2 eq, 28.9 mmol) of bis(pinacolato)diboron were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-40 (10.74 g, yield 76%).

By FAB-MS measurement, mass number m/z=587 was observed as the molecular ion peak, and Intermediate IM-40 was identified.

(Synthesis of Compound F146)

Under an Ar atmosphere, to a 300 mL, three neck flask, 10.00 g (17.0 mmol) of IM-40, 7.46 g (1.1 eq, 18.7 mmol) of 3-(3-bromophenyl)-9-phenyl-9H-carbazole, 7.05 g (3.0 eq, 51.1 mmol) of $K_2CO_3$, 0.98 g (0.05 eq, 0.9 mmol) of $Pd(PPh_3)_4$, and 119 mL of a mixture solution of toluene/$EtOH/H_2O$ (4/2/1) were added in order, followed by heating to about 80° C. and stirring. After cooling to room temperature, the reaction solution was extracted with toluene. An aqueous layer was removed, and an organic layer was washed with a saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound F146 (10.47 g, yield 79%) as a solid.

By FAB-MS measurement, mass number m/z=778 was observed as the molecular ion peak, and Compound F146 was identified.

15. Synthesis of Compound F198

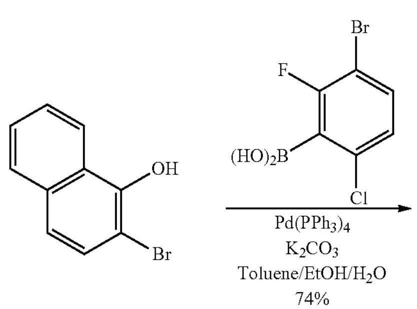

-continued

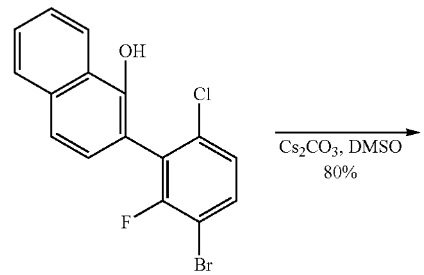

IM-41

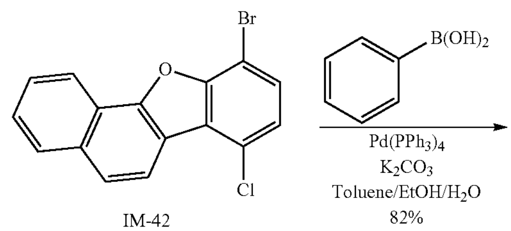

IM-42

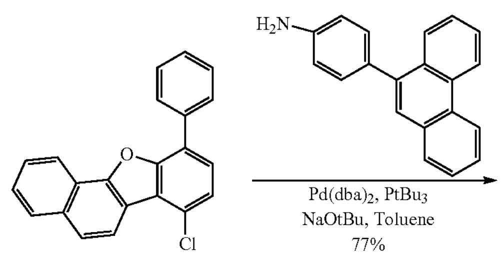

IM-43

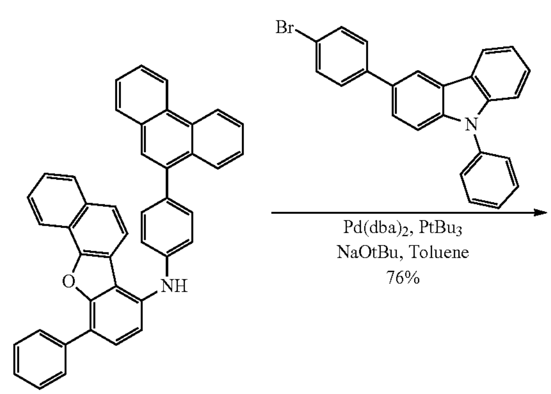

IM-44

-continued

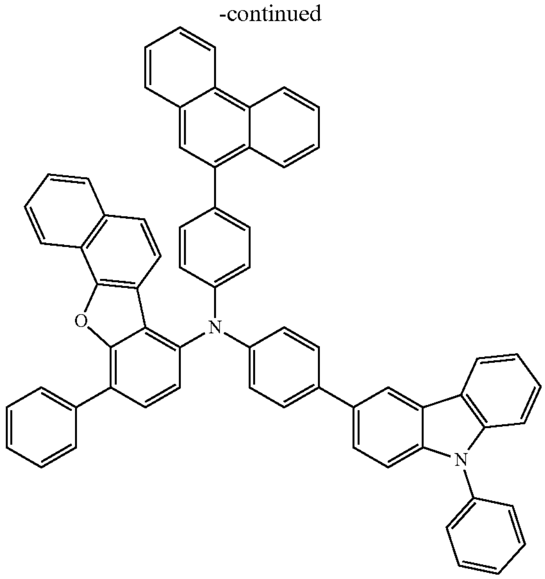

F198

(Synthesis of Intermediate IM-41)

Under an Ar atmosphere, to a 2,000 mL, three neck flask, 30.00 g (134.5 mmol) of 2-bromo-1-naphthol, 37.47 g (1.1 eq, 147.9 mmol) of (3-bromo-6-chloro-2-fluorophenyl)boronic acid, 55.76 g (3.0 eq, 403.5 mmol) of $K_2CO_3$, 7.77 g (0.05 eq, 6.7 mmol) of $Pd(PPh_3)_4$, and 941 mL of a mixture solution of toluene/EtOH/$H_2O$ (4/2/1) were added in order, followed by heating and stirring at about 80° C. After cooling to room temperature, the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-41 (35.00 g, yield 74%).

By FAB-MS measurement, mass number m/z=351 was observed as the molecular ion peak, and Intermediate IM-41 was identified.

(Synthesis of Intermediate IM-42)

Under an Ar atmosphere, to a 300 mL, three neck flask, 30.00 g (85.3 mmol) of IM-41, 55.60 g (2.0 eq, 170.6 mmol) of $Cs_2CO_3$, and 170 mL of DMSO were added in order, followed by heating to about 110° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-42 (22.63 g, yield 80%).

By FAB-MS measurement, mass number m/z=331 was observed as the molecular ion peak, and Intermediate IM-42 was identified.

(Synthesis of Intermediate IM-43)

Under an Ar atmosphere, to a 1,000 mL, three neck flask, 20.00 g (60.3 mmol) of IM-42, 8.09 g (1.1 eq, 66.3 mmol) of phenylboronic acid, 25.01 g (3.0 eq, 180.9 mmol) of $K_2CO_3$, 3.48 g (0.05 eq, 3.0 mmol) of $Pd(PPh_3)_4$, and 422 mL of a mixture solution of toluene/EtOH/$H_2O$ (4/2/1) were added in order, followed by heating and stirring at about 80° C. After cooling to room temperature, the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-43 (16.26 g, yield 82%).

By FAB-MS measurement, mass number m/z=328 was observed as the molecular ion peak, and Intermediate IM-43 was identified.

(Synthesis of Intermediate IM-44)

Under an Ar atmosphere, to a 500 mL, three neck flask, 12.00 g (36.5 mmol) of IM-43, 0.63 g (0.03 eq, 1.1 mmol) of $Pd(dba)_2$, 3.51 g (1.0 eq, 36.5 mmol) of NaOtBu, 182 mL of toluene, 10.81 g (1.1 eq, 40.1 mmol) of 4-(phenanthren-9-yl)aniline, and 0.74 g (0.1 eq, 3.6 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-44 (15.78 g, yield 77%).

By FAB-MS measurement, mass number m/z=561 was observed as the molecular ion peak, and Intermediate IM-44 was identified.

(Synthesis of Compound F198)

Under an Ar atmosphere, to a 300 mL, three neck flask, 10.00 g (17.8 mmol) of IM-44, 0.31 g (0.03 eq, 0.5 mmol) of $Pd(dba)_2$, 3.42 g (2.0 eq, 35.6 mmol) of NaOtBu, 89 mL of toluene, 7.80 g (1.1 eq, 19.6 mmol) of 3-(4-bromophenyl)-9-phenyl-9H-carbazole, and 0.36 g (0.1 eq, 1.8 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound F198 (11.89 g, yield 76%) as a solid.

By FAB-MS measurement, mass number m/z=879 was observed as the molecular ion peak, and Compound F198 was identified.

16. Synthesis of Compound A127

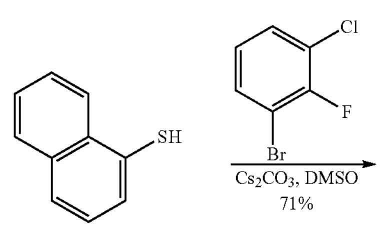

-continued

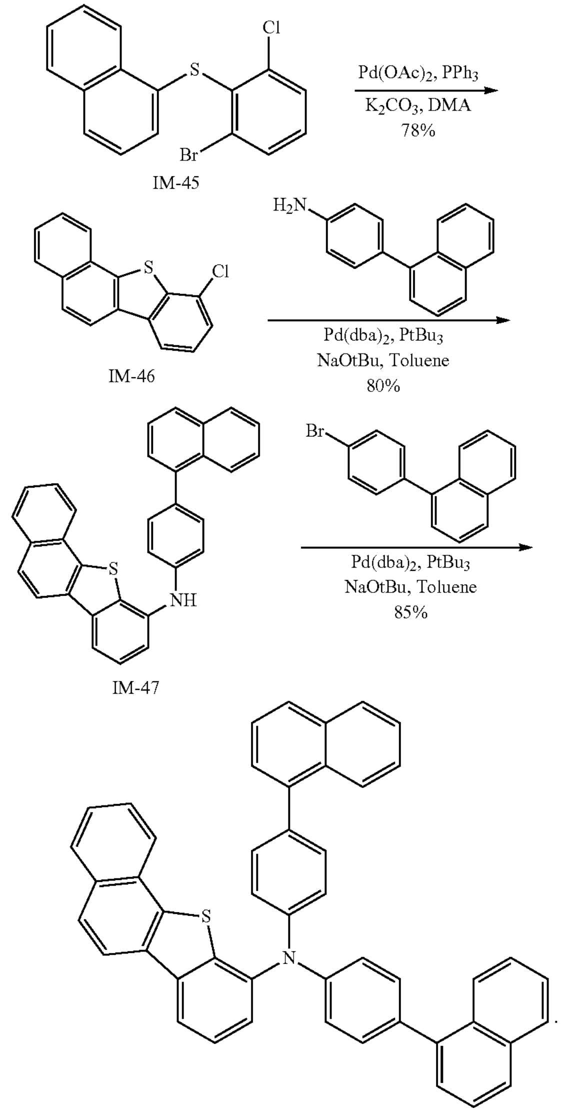

IM-45

IM-46

IM-47

A127

(Synthesis of Intermediate IM-45)

Under an Ar atmosphere, to a 500 mL, three neck flask, 25.00 g (156.0 mmol) of naphthalene-1-thiol, 39.21 g (1.2 eq, 187.2 mmol) of 1-bromo-3-chloro-2-fluorobenzene, 101.67 g (2.0 eq, 312.1 mmol) of $Cs_2CO_3$, and 312 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-45 (38.74 g, yield 71%).

By FAB-MS measurement, mass number m/z=349 was observed as the molecular ion peak, and Intermediate IM-45 was identified.

(Synthesis of Intermediate IM-46)

Under an Ar atmosphere, to a 500 mL, three neck flask, 25.00 g (71.5 mmol) of IM-45, 0.80 g (0.05 eq, 3.6 mmol) of $Pd(OAc)_2$, 14.52 g (1.5 eq, 107.2 mmol) of $K_2CO_3$, 1.88 g (0.10 eq, 7.1 mmol) of $PPh_3$, and 286 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-46 (14.99 g, yield 71%).

By FAB-MS measurement, mass number m/z=268 was observed as the molecular ion peak, and Intermediate IM-46 was identified.

(Synthesis of Intermediate IM-47)

Under an Ar atmosphere, to a 500 mL, three neck flask, 12.00 g (44.7 mmol) of IM-46, 0.77 g (0.03 eq, 1.3 mmol) of $Pd(dba)_2$, 4.29 g (2.0 eq, 44.7 mmol) of NaOtBu, 224 mL of toluene, 10.77 g (1.1 eq, 49.1 mmol) of 4-(naphthalen-1-yl)aniline, and 0.90 g (0.1 eq, 4.5 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-47 (16.13 g, yield 80%).

By FAB-MS measurement, mass number m/z=451 was observed as the molecular ion peak, and Intermediate IM-47 was identified.

(Synthesis of Compound A127)

Under an Ar atmosphere, to a 300 mL, three neck flask, 10.00 g (22.1 mmol) of IM-47, 0.38 g (0.03 eq, 0.7 mmol) of $Pd(dba)_2$, 4.26 g (2.0 eq, 44.3 mmol) of NaOtBu, 111 mL of toluene, 6.90 g (1.1 eq, 24.4 mmol) of 1-(4-bromophenyl) naphthalene, and 0.45 g (0.1 eq, 2.2 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound A127 (12.31 g, yield 85%) as a solid.

By FAB-MS measurement, mass number m/z=653 was observed as the molecular ion peak, and Compound A127 was identified.

17. Synthesis of Compound B138

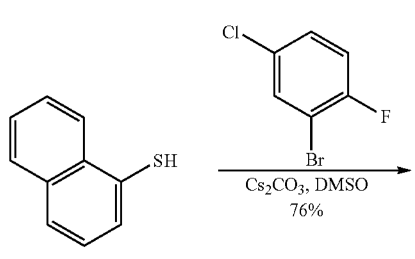

-continued

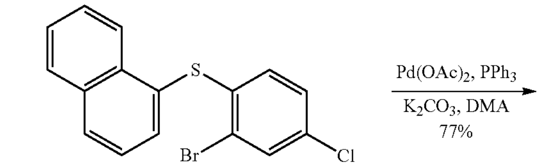

IM-48

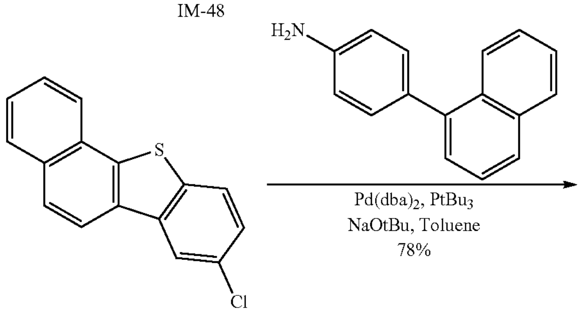

IM-49

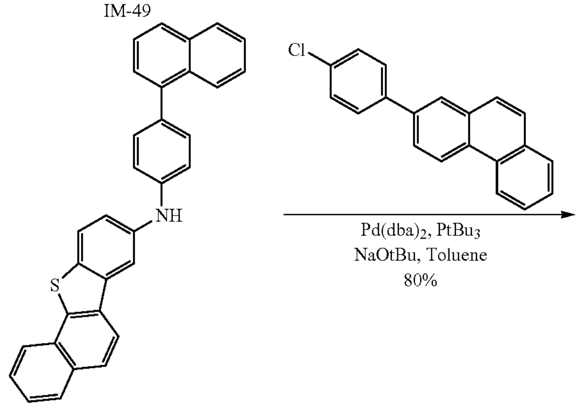

IM-50

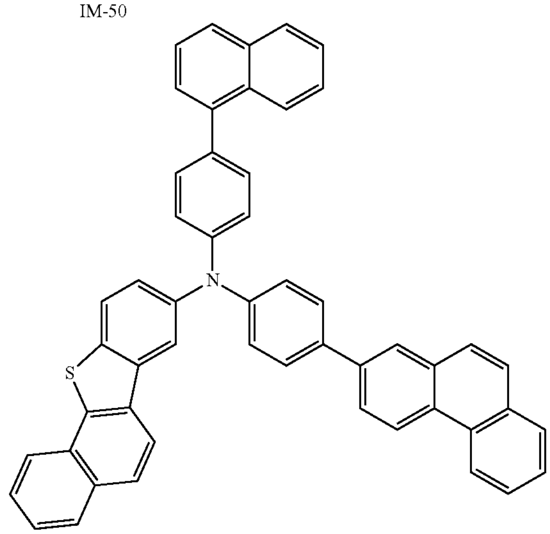

B138

(Synthesis of Intermediate IM-48)

Under an Ar atmosphere, to a 500 mL, three neck flask, 25.00 g (156.0 mmol) of naphthalen-1-thiol, 39.21 g (1.2 eq, 187.2 mmol) of 1-bromo-3-chloro-fluorobenzene, 101.67 g (2.0 eq, 312.1 mmol) of $Cs_2CO_3$, and 312 mL of DMSO were added in order, followed by heating and stirring at about 110° C. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-48 (41.46 g, yield 76%).

By FAB-MS measurement, mass number m/z=349 was observed as the molecular ion peak, and Intermediate IM-48 was identified.

(Synthesis of Intermediate IM-49)

Under an Ar atmosphere, to a 500 mL, three neck flask, 25.00 g (71.5 mmol) of IM-48, 0.80 g (0.05 eq, 3.6 mmol) of $Pd(OAc)_2$, 14.52 g (1.5 eq, 107.2 mmol) of $K_2CO_3$, 1.88 g (0.10 eq, 7.1 mmol) of $PPh_3$, and 286 mL of DMA were added in order, followed by heating to about 140° C. and stirring. After cooling to room temperature, water was added to the reaction solution, and the reaction solution was extracted with toluene. An aqueous layer was removed, and an organic layer was washed with a saturated saline solution and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-49 (12.68 g, yield 77%).

By FAB-MS measurement, mass number m/z=268 was observed as the molecular ion peak, and Intermediate IM-49 was identified.

(Synthesis of Intermediate IM-50)

Under an Ar atmosphere, to a 500 mL, three neck flask, 12.00 g (44.7 mmol) of IM-49, 0.77 g (0.03 eq, 1.3 mmol) of $Pd(dba)_2$, 4.29 g (2.0 eq, 44.7 mmol) of NaOtBu, 224 mL of toluene, 10.77 g (1.1 eq, 49.1 mmol) of 4-(naphthalen-1-yl)aniline, and 0.90 g (0.1 eq, 4.5 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Intermediate IM-50 (16.08 g, yield 78%).

By FAB-MS measurement, mass number m/z=451 was observed as the molecular ion peak, and Intermediate IM-50 was identified.

(Synthesis of Compound B138)

Under an Ar atmosphere, to a 300 mL, three neck flask, 10.00 g (22.1 mmol) of IM-50, 0.38 g (0.03 eq, 0.7 mmol) of $Pd(dba)_2$, 4.26 g (2.0 eq, 44.3 mmol) of NaOtBu, 111 mL of toluene, 6.88 g (1.1 eq, 24.4 mmol) of 2-(4-chlorophenyl)phenanthrene, and 0.45 g (0.1 eq, 2.2 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound B138 (12.20 g, yield 80%) as a solid.

By FAB-MS measurement, mass number m/z=703 was observed as the molecular ion peak, and Compound B138 was identified.

18. Synthesis of Compound A178

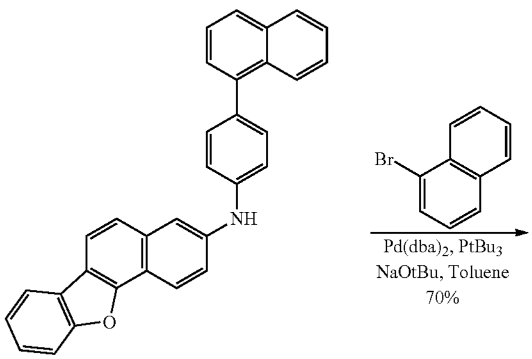

IM-18

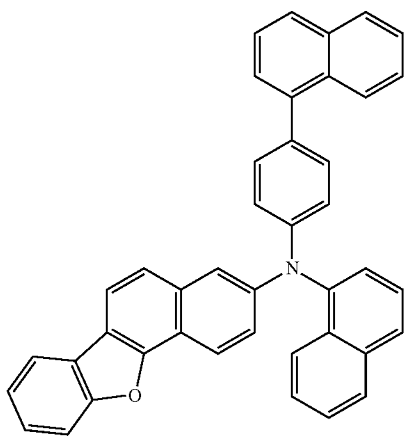

A173

Under an Ar atmosphere, to a 300 mL, three neck flask, 10.00 g (23.0 mmol) of IM-18, 0.40 g (0.03 eq, 0.7 mmol) of Pd(dba)$_2$, 4.41 g (2.0 eq, 45.9 mmol) of NaOtBu, 115 mL of toluene, 5.23 g (1.1 eq, 25.3 mmol) of 1-bromonaphthalene, and 0.46 g (0.1 eq, 2.3 mmol) of tBu$_3$P were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with MgSO$_4$. MgSO$_4$ was separated by filtering, an organic layer was concentrated, and the crude product thus obtained was separated by silica gel column chromatography (a mixture solvent of hexane and toluene was used as an eluent) to obtain Compound A173 (9.03 g, yield 70%) as a solid.

By FAB-MS measurement, mass number m/z=561 was observed as the molecular ion peak, and Compound A173 was identified. 19. Synthesis of Compound A195 bis(4-(naphthalen-2-yl)phenyl)amine

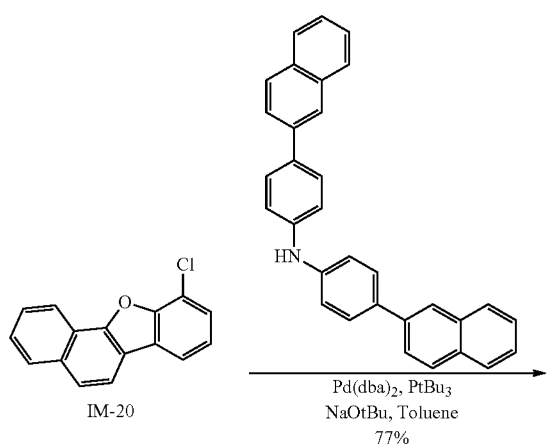

IM-20

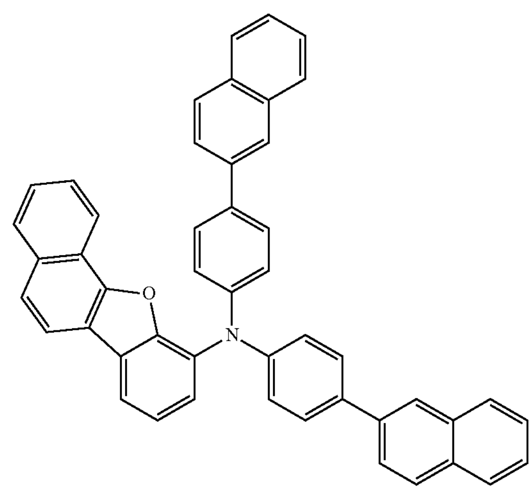

A195

Under an Ar atmosphere, to a 300 mL, three neck flask, 10.00 g (39.6 mmol) of IM-20, 0.68 g (0.03 eq, 1.2 mmol) of Pd(dba)$_2$, 7.61 g (2.0 eq, 79.1 mmol) of NaOtBu, 198 mL of toluene, 18.35 g (1.1 eq, 43.5 mmol) of bis[4-(naphthalen-2-yl)phenyl]amine, and 0.80 g (0.1 eq, 4.0 mmol) of tBu$_3$P were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with MgSO$_4$. MgSO$_4$ was separated by filtering, an organic layer was concentrated, and the crude product thus obtained was separated by silica gel column chromatography (a mixture solvent of hexane and toluene was used as an eluent) to obtain Compound A195 (19.43 g, yield 77%) as a solid.

By FAB-MS measurement, mass number m/z=637 was observed as the molecular ion peak, and Compound A195 was identified.

20. Synthesis of Compound B189

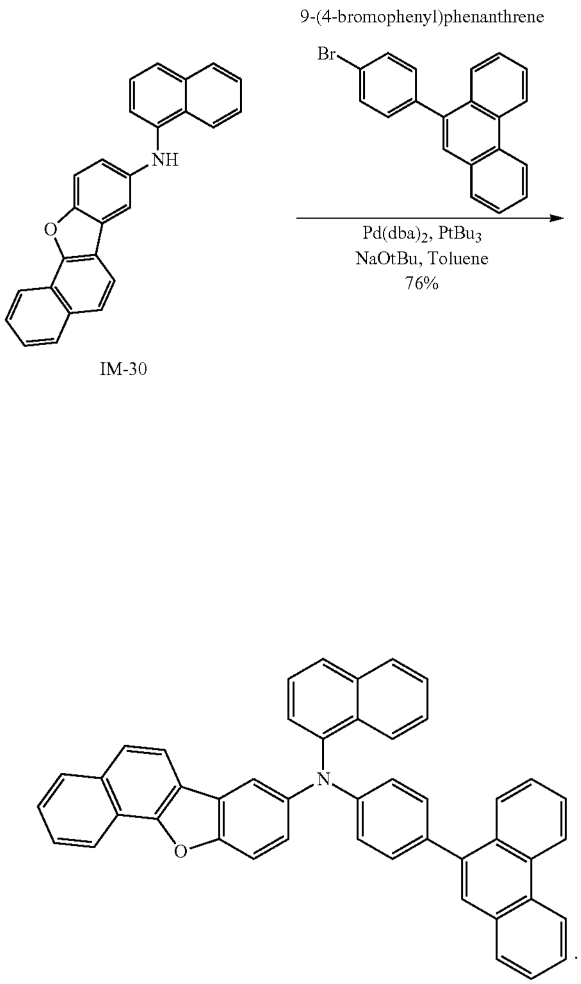

IM-30

B189

Under an Ar atmosphere, to a 300 mL, three neck flask, 10.00 g (27.8 mmol) of IM-30, 0.48 g (0.03 eq, 0.8 mmol) of $Pd(dba)_2$, 5.35 g (2.0 eq, 55.6 mmol) of NaOtBu, 139 mL of toluene, 10.20 g (1.1 eq, 30.6 mmol) of 9-(4-bromophenyl)phenanthrene, and 0.56 g (0.1 eq, 2.8 mmol) of $tBu_3P$ were added in order, followed by heating, refluxing, and stirring. After cooling to room temperature, water was added to the reaction solution, and an organic layer was separated. Toluene was added to the aqueous layer, and further organic layers were extracted. The organic layers were collected, washed with a saline solution, and dried with $MgSO_4$. $MgSO_4$ was separated by filtering, an organic layer was concentrated, and the crude product thus obtained was separated by silica gel column chromatography (a mixture solvent of hexane and toluene was used as an eluent) to obtain Compound B189 (12.93 g, yield 76%) as a solid.

By FAB-MS measurement, mass number m/z=611 was observed as the molecular ion peak, and Compound B189 was identified.

(Device Manufacturing Examples)

Organic electroluminescence devices were manufactured using Example Compounds and Comparative Compounds as materials for a hole transport region:

[Example Compounds]

A1

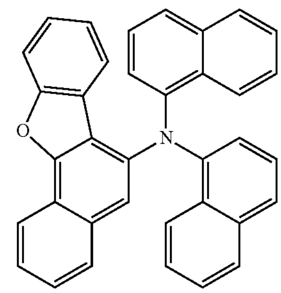

A19

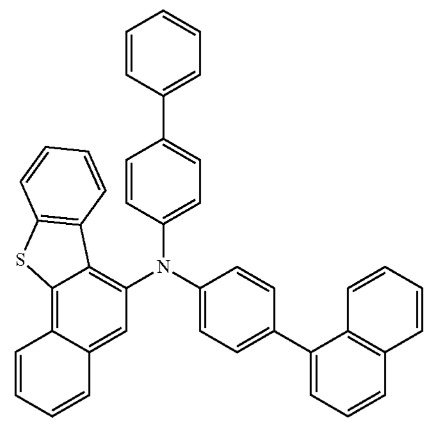

A65

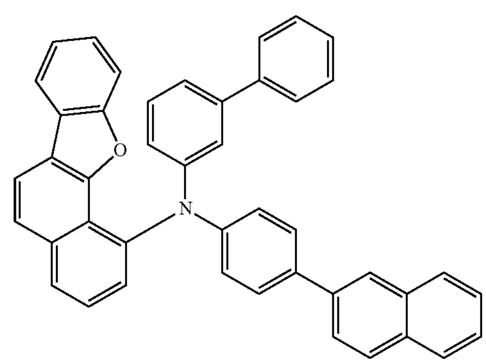

B49

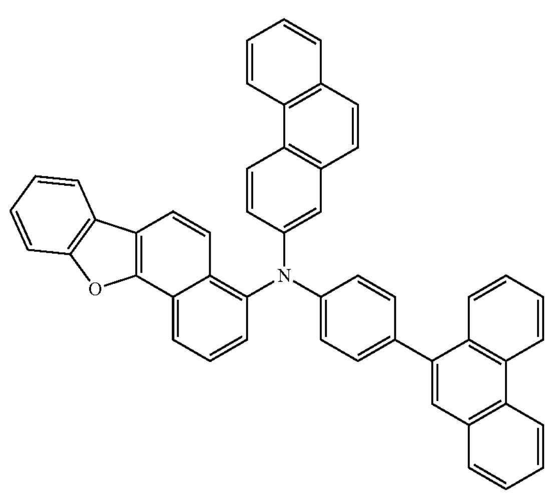

B94
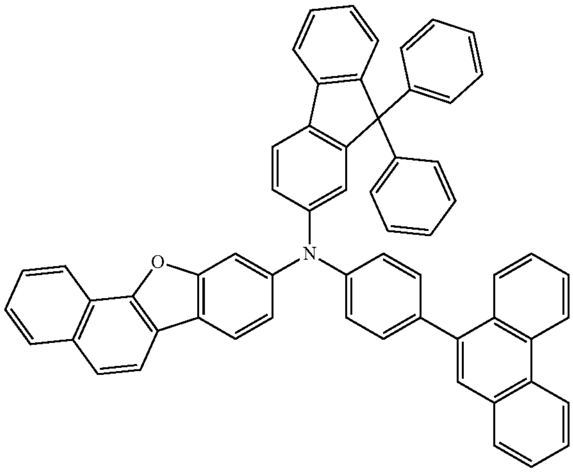
C67
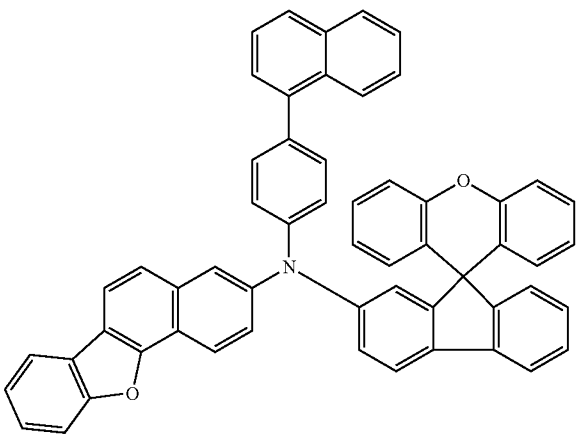
C124
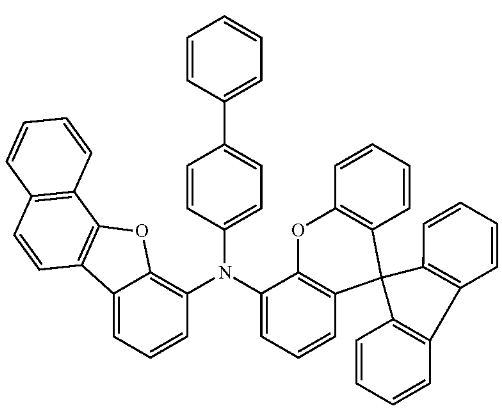
C163
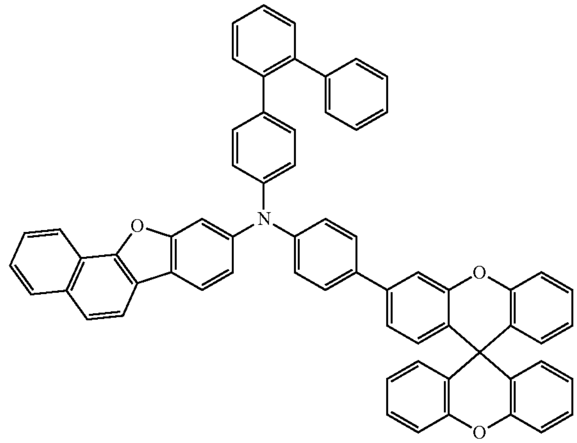
D32
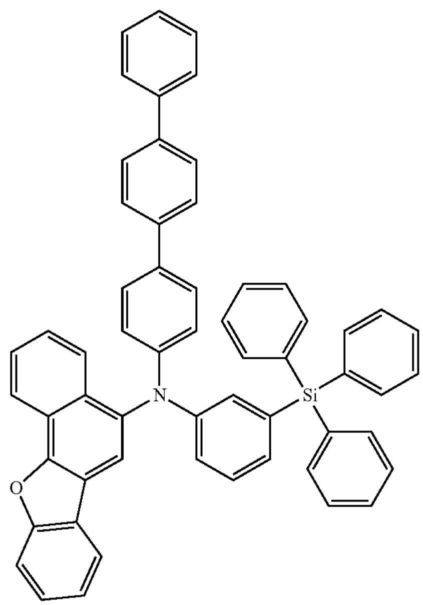
D162
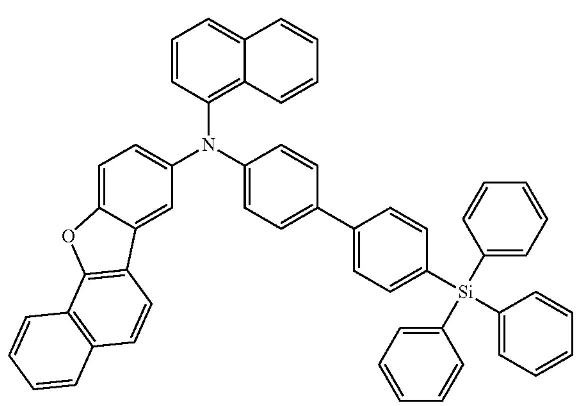

E87
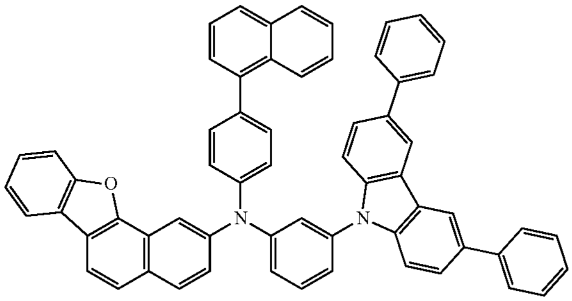
E190
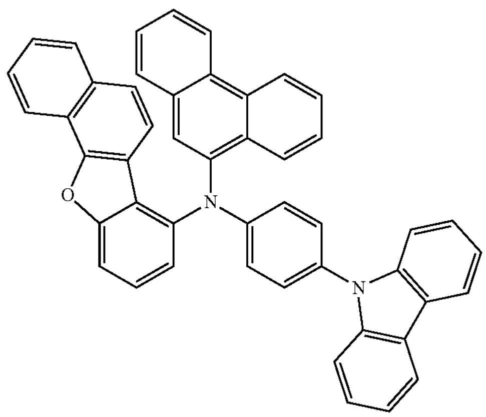
F15
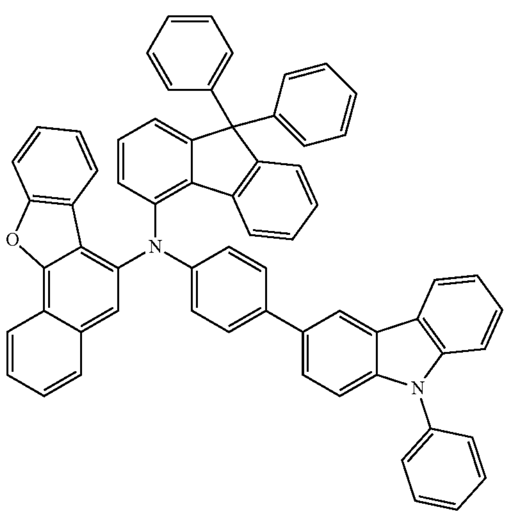
F146
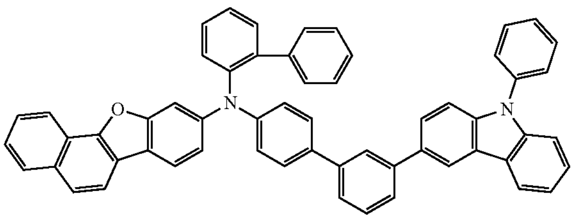
F198
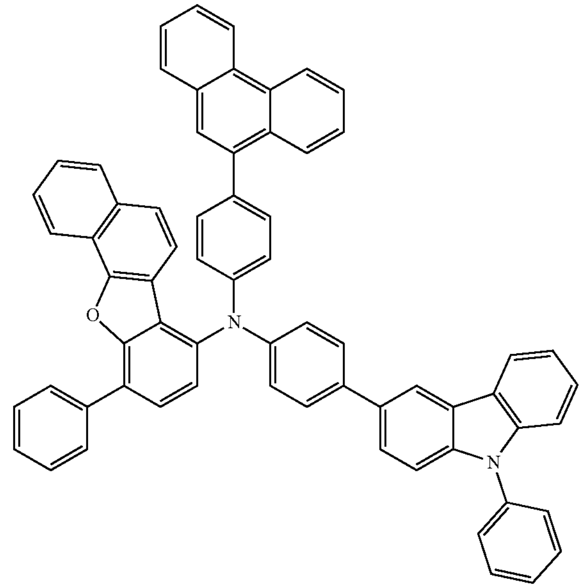
A127
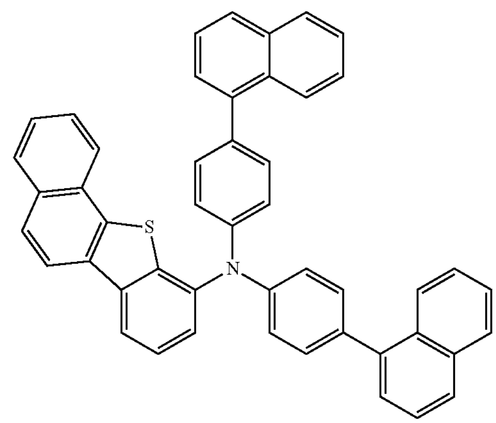
B138
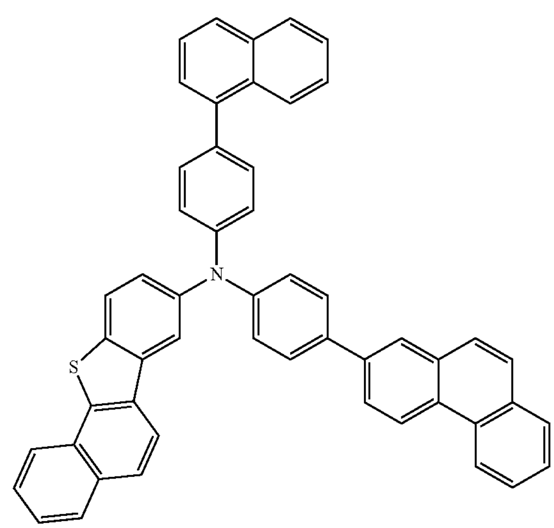

-continued
A173
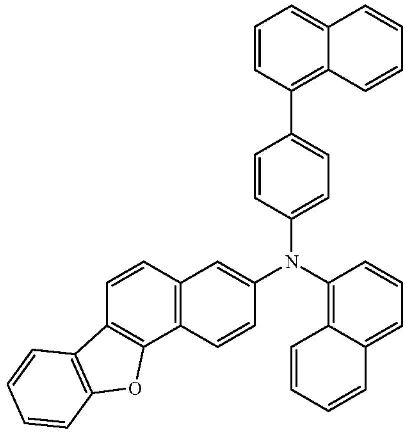
A195
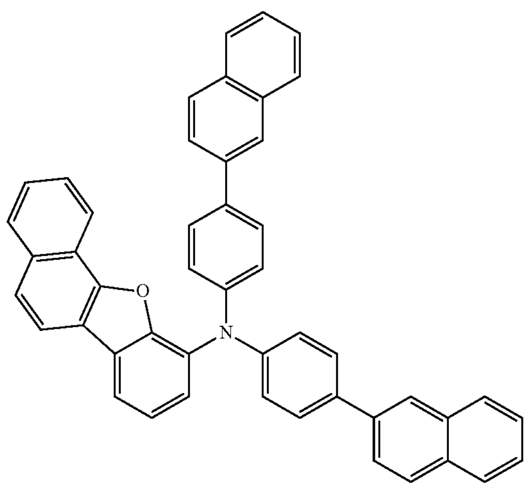
B189
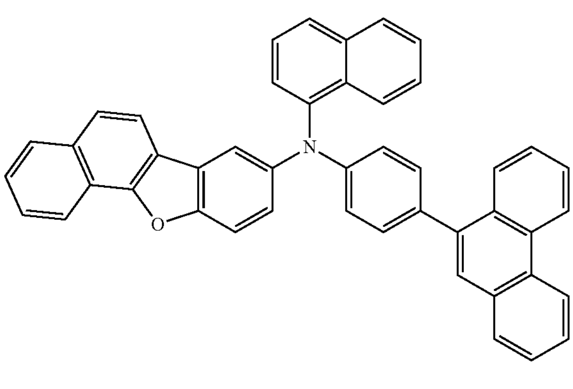
[Comparative Compounds]
R1
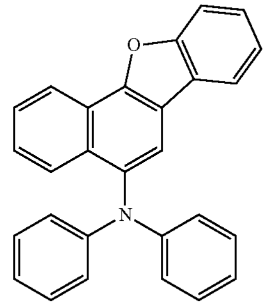
R2
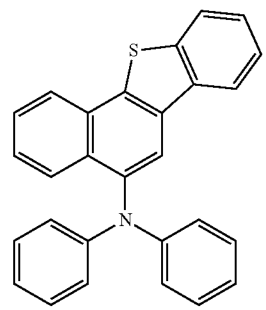
R3
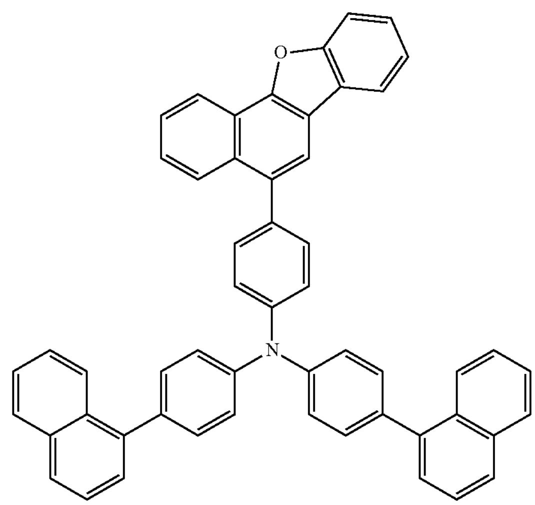
R4
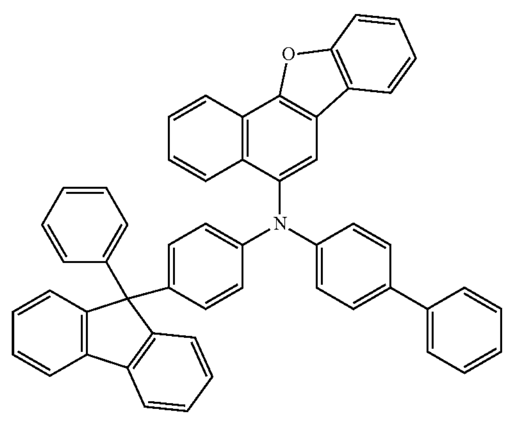

-continued
R5
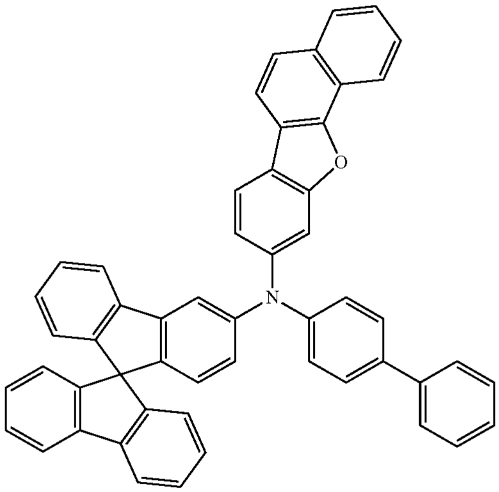
R6
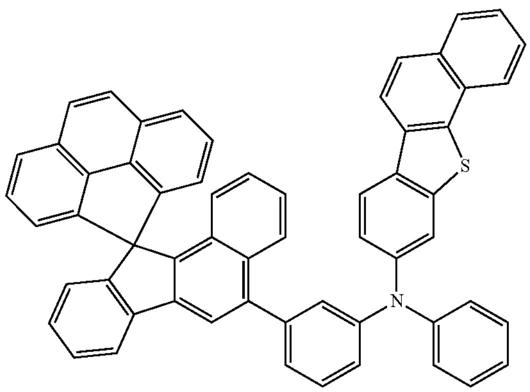
R7
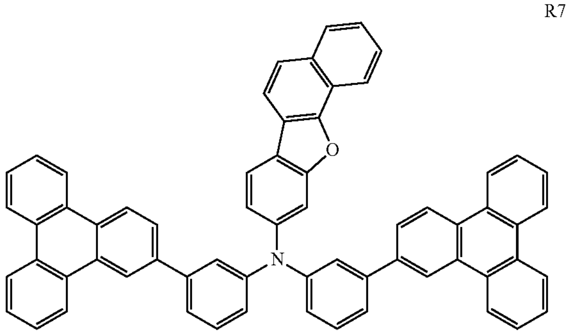
R8
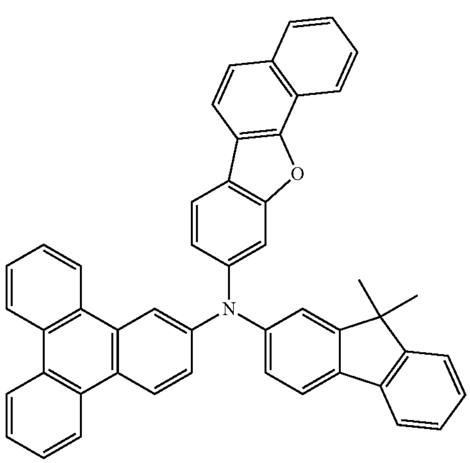
-continued
R9
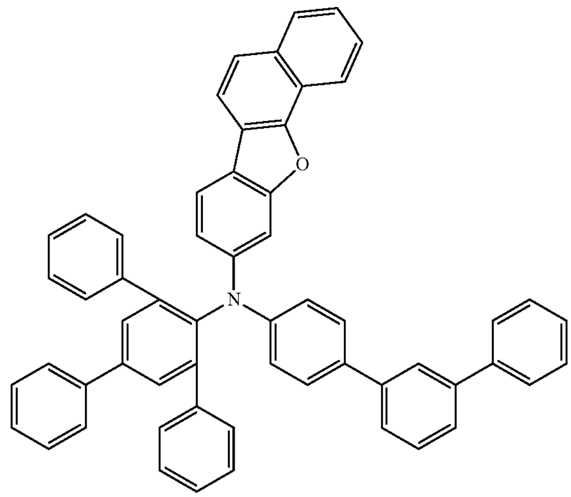
R10
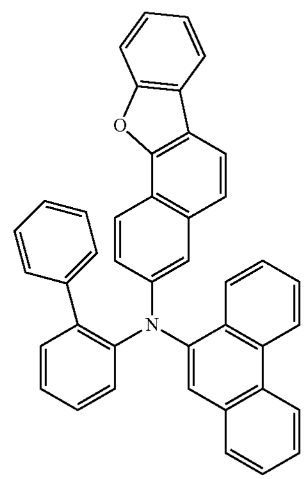
R11
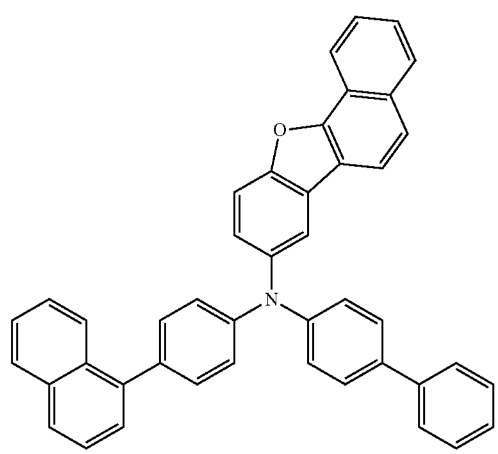

-continued
R12
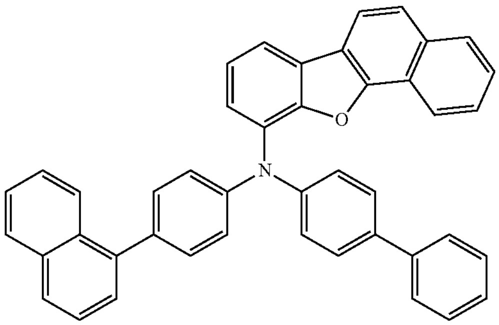
R13
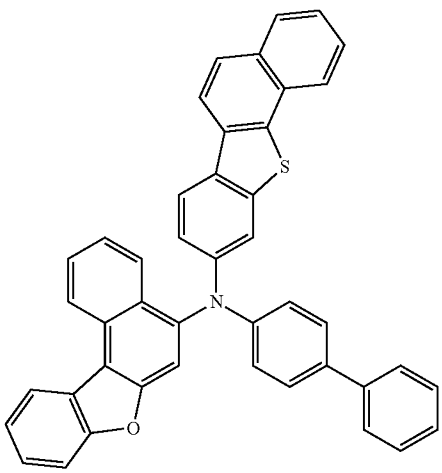
R14
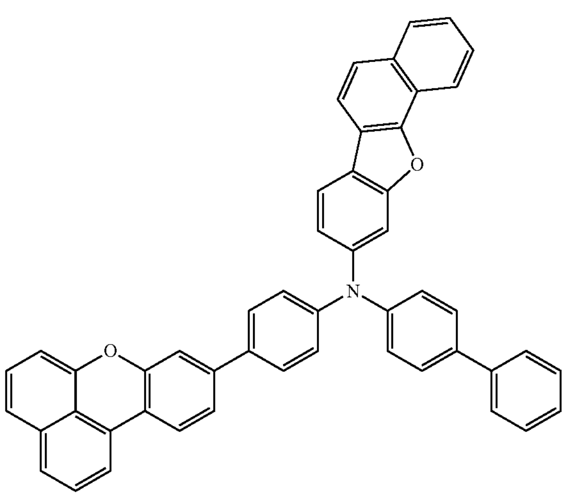
-continued
R15
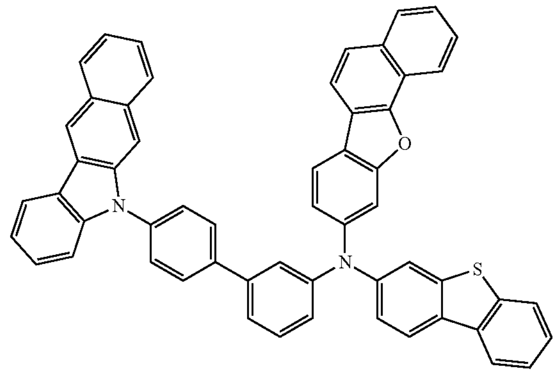
R16
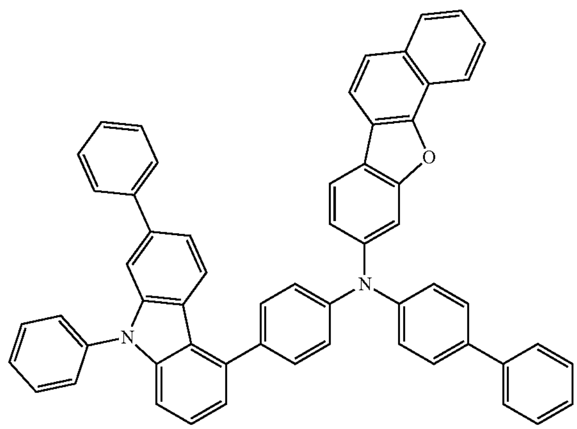
R17
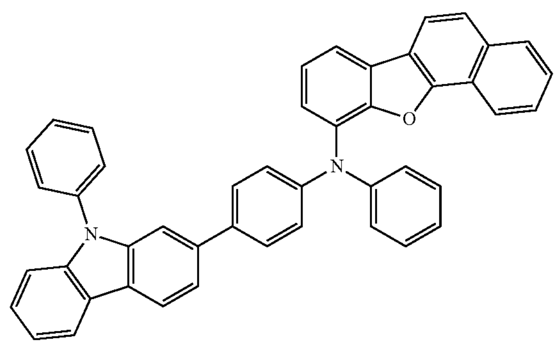
R18
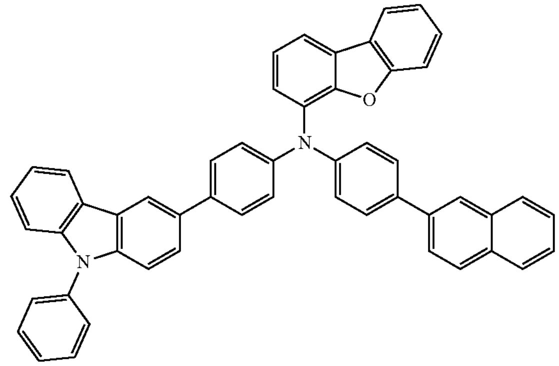
Each of the organic electroluminescence devices of the Examples and Comparative Examples was manufactured using the method below. ITO with a thickness of about 150 nm was patterned on a glass substrate, washed with ultra-pure water, and treated with UV-ozone for about 10 minutes to form a first electrode. Then, 1-TNATA was deposited to a thickness of about 60 nm, and a hole transport layer with a thickness of about 30 nm was formed using each of the Example Compounds or the Comparative Compounds. Then, an emission layer with a thickness of about 25 nm was formed using ADN doped with 3% TBP, and on the emission layer, a layer with a thickness of about 25 nm was formed using $Alq_3$, and a layer with a thickness of about 1 nm was formed using LiF to form an electron transport region. After that, a second electrode with a thickness of about 100 nm was formed using aluminum (Al). Then, Compound P4 was deposited to a thickness of about 70 nm to form a capping layer. Each layer was formed by a vacuum deposition method.

The emission efficiencies of the organic electroluminescence devices according to Examples to 20 and Comparative Examples 1 to 18 are shown in Table 1. The efficiency was measured at a current density of about 10 mA/cm$^2$, and the half life $LT_{50}$ is the time elapsed for the luminance to fall from an initial value of about 1,000 cd/m$^2$ to half.

TABLE 1

| | Hole transport layer | Voltage (V) | Efficiency (cd/A) | Life ($LT_{50}$ (h)) |
|---|---|---|---|---|
| Example 1 | Example Compound A1 | 5.6 | 7.7 | 2100 |
| Example 2 | Example Compound A19 | 5.5 | 7.6 | 2150 |
| Example 3 | Example Compound A65 | 5.5 | 7.5 | 2150 |
| Example 4 | Example Compound B49 | 5.5 | 7.6 | 2100 |
| Example 5 | Example Compound B94 | 5.4 | 7.7 | 2050 |
| Example 6 | Example Compound C67 | 5.5 | 7.6 | 2200 |
| Example 7 | Example Compound C124 | 5.6 | 7.8 | 2000 |
| Example 8 | Example Compound C153 | 5.5 | 7.8 | 2050 |
| Example 9 | Example Compound D32 | 5.6 | 7.5 | 2100 |
| Example 10 | Example Compound D162 | 5.6 | 7.8 | 2050 |
| Example 11 | Example Compound E87 | 5.4 | 7.6 | 2100 |
| Example 12 | Example Compound E190 | 5.4 | 7.9 | 1950 |
| Example 13 | Example Compound F15 | 5.4 | 7.7 | 2150 |
| Example 14 | Example Compound F146 | 5.5 | 7.9 | 2000 |
| Example 15 | Example Compound F198 | 5.5 | 7.8 | 2050 |
| Example 16 | Example Compound A127 | 5.4 | 7.9 | 2000 |
| Example 17 | Example Compound B138 | 5.5 | 7.8 | 2100 |
| Example 18 | Example Compound A173 | 5.5 | 7.5 | 2150 |
| Example 19 | Example Compound A195 | 5.6 | 7.8 | 2100 |
| Example 20 | Example Compound B189 | 5.5 | 7.6 | 2050 |
| Comparative Example 1 | Comparative Compound R1 | 6.4 | 5.7 | 1500 |
| Comparative Example 2 | Comparative Compound R2 | 6.5 | 5.8 | 1450 |
| Comparative Example 3 | Comparative Compound R3 | 6.3 | 6.0 | 1650 |

TABLE 1-continued

| | Hole transport layer | Voltage (V) | Efficiency (cd/A) | Life ($LT_{50}$ (h)) |
|---|---|---|---|---|
| Comparative Example 4 | Comparative Compound R4 | 6.3 | 6.2 | 1550 |
| Comparative Example 5 | Comparative Compound R5 | 6.5 | 6.4 | 1600 |
| Comparative Example 6 | Comparative Compound R6 | 6.4 | 6.0 | 1550 |
| Comparative Example 7 | Comparative Compound R7 | 6.5 | 6.2 | 1550 |
| Comparative Example 8 | Comparative Compound R8 | 6.3 | 6.1 | 1450 |
| Comparative Example 9 | Comparative Compound R9 | 6.5 | 6.4 | 1500 |
| Comparative Example 10 | Comparative Compound R10 | 6.5 | 6.6 | 1550 |
| Comparative Example 11 | Comparative Compound R11 | 6.5 | 6.7 | 1700 |
| Comparative Example 12 | Comparative Compound R12 | 6.5 | 6.8 | 1650 |
| Comparative Example 13 | Comparative Compound R13 | 6.5 | 6.5 | 1650 |
| Comparative Example 14 | Comparative Compound R14 | 6.5 | 6.1 | 1550 |
| Comparative Example 15 | Comparative Compound R15 | 6.5 | 6.6 | 1650 |
| Comparative Example 16 | Comparative Compound R16 | 6.5 | 6.5 | 1650 |
| Comparative Example 17 | Comparative Compound R17 | 6.5 | 6.8 | 1600 |
| Comparative Example 18 | Comparative Compound R18 | 6.5 | 6.8 | 1700 |

Referring to Table 1, it could be confirmed that each of Examples 1 to 20 exhibited a lower voltage, a longer life and a higher efficiency than each of Comparative Examples 1 to 18.

The polycyclic compound according to the present disclosure has a core structure including benzonaphthofuran or benzonaphthothiophene combined with an amine group having a particular substituent, and without being bound by the correctness of any theory or explanation, this structure supports a decreased driving voltage, and increased lifespan and efficiency in an organic electroluminescence device. It is thought that the heteroatom (e.g., O or S) included in the core structure of benzonaphthofuran or benzonaphthothiophene improves hole transport capacity, such that the recombination probability of holes and electrons in an emission layer is improved, and the emission efficiency is improved.

Examples 1 to 4, 6, 9, 11, 13 and 18 each include a compound in which the amine group is bound to the naphthalene ring in the core structure of benzonaphthofuran or benzonaphthothiophene, and exhibit improved device life. Without being bound by the correctness of any theory or explanation, it is believed that because rr electrons around the amine were widely expanded in the naphthalene ring, stability of radical states was enhanced.

Examples 5, 7, 8, 10, 12, 14 to 17, 19 and 20 each include a compound in which the amine group is bound to the benzene ring in the core structure of benzonaphthofuran or benzonaphthothiophene, and exhibit improved emission efficiency. Without being bound by the correctness of any theory or explanation, it is believed that because the heteroatom included in the benzonaphthofuran or benzonaphthothiophene skeleton and the nitrogen atom of an amine group are substituted on the same ring, hole transport effects due to the heteroatom were enhanced.

Comparative Examples 1 and 2 each showed reduced emission efficiency and lifespan when compared with the Examples. Comparative Examples 1 and 2 are compounds in which an amine group is combined with the core structure of benzonaphthofuran or benzonaphthothiophene, but an unsubstituted phenyl group is combined with a nitrogen atom (e.g., the amine group includes only unsubstituted phenyl groups). Without being bound by the correctness of any theory or explanation, it is believed that the glass transition temperature (Tg) of the material was insufficient such that the charge tolerance of the unsubstituted phenyl group was low, and the materials were deteriorated during continuous driving.

Comparative Example 3 showed reduced device efficiency and life when compared with the Examples. Comparative Example 3 is a compound in which benzonaphthofuran and an amine group are combined via a linker (e.g., an intervening phenyl ring), such that the planarity of a molecule was increased, and decomposition occurred during deposition for forming a hole transport layer.

Comparative Example 4 showed reduced device efficiency and life when compared with the Examples. In the compound of Comparative Example 4, a phenyl substituent on the amine is substituted with a fluorenyl group, and without being bound by the correctness of any theory or explanation, it is believed that instability of the $sp^3$ carbon in the fluorenyl group resulted in decomposition under a radical state and high temperature conditions.

In contrast, the polycyclic compounds of Examples 6 to 8 including a spirocyclic structure with a heteroatom showed improved stability, and provided excellent device properties. In Example 5, because a nitrogen atom was combined on (e.g., directly bonded to) a fluorene ring, the stability of a material was improved due to multi-resonance effects. Accordingly, improved emission efficiency and life were exhibited compared with Comparative Example 4.

Comparative Examples 5 and 6 showed particularly reduced emission efficiencies when compared with Examples 6 to 8. Without being bound by the correctness of any theory or explanation, it is believed that because a heteroatom was not included in the spirocycle of the compounds of Comparative Examples 5 and 6, hole transport properties were degraded, and the recombination probability of holes and electrons in an emission layer was decreased.

Comparative Examples 7 and 8 are amine compounds including a triphenylene substituent, and without being bound by the correctness of any theory or explanation, it is believed that because the planarity of the molecule was increased, the molecule was decomposed during hole transport layer formation, and device efficiency and lifespan were both (e.g., simultaneously) degraded.

Comparative Example 9 is an amine compound including a (2,4,6-triphenyl)phenyl group. Without being bound by the correctness of any theory or explanation, it is thought that because the volume around the nitrogen atom is excessively large, the molecule was decomposed during hole transport layer formation, and device efficiency and lifespan were both degraded.

In addition, though an amine group having a phenanthrene group may be combined with the core structure of benzonaphthofuran similar to the present disclosure, the effect on device efficiency and lifespan may depend on the type (e.g., position) of substituent. For example, if the amine group is at position 2 of Chemical Formula 1 or at position 3 of Chemical Formula 1 as in Comparative Example 10, device efficiency and lifespan are both degraded. Without being bound by the correctness of any theory or explanation, it is thought that in this case, the planarity of the molecule as a whole was increased, intermolecular stacking was enhanced, and hole transport properties were deteriorated.

[Chemical Formula 1]

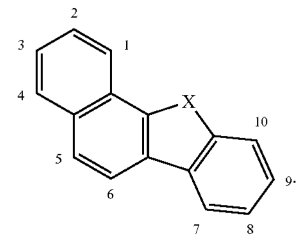

In contrast, as confirmed in Examples 6 and 11, when $Ar_1$ and $Ar_2$ are substituents including a heteroatom, hole transport properties are improved due to the influence of the heteroatom in $Ar_1$ and $Ar_2$, and excellent device properties may be shown observed regardless of the position at which the amine group is bound to the core structure. In addition, as shown in Example 18, when $Ar_1$ and $Ar_2$ are substituents having polycyclic aromatic rings, interactions between the polycyclic aromatic rings of $Ar_1$ and $Ar_2$ and the emission layer host material may be enhanced, hole transport properties may be improved, and excellent device properties may be shown.

Comparative Examples 11 and 12 have a structure in which an amine group having a naphthyl substituent is combined with a benzonaphthofuran core structure, similar to the polycyclic compound of the present disclosure. However, compared with the polycyclic compound of the present disclosure, the position of the amine group is different. In the compounds of Comparative Examples 11 and 12, the oxygen atom and the nitrogen atom are ortho- or para- to each other on the benzene ring, which induces electronic instability, and device efficiency and lifespan were both degraded when compared with the Examples.

By comparison to Example 9, however, when the oxygen atom and the nitrogen atom in the benzonaphthofuran ring are para to each other on the naphthalene ring, electrons may be expanded (e.g., due to resonance) so that the molecular structure may be stabilized, and excellent device properties may be shown.

Further, as confirmed in Examples 7 and 10, when the amine has a substituent having a heteroatom, the electronic instability issue may be solved due to the effects of the heteroatom, and excellent device properties may be shown regardless of the combination position of the amine group. For example, it could be confirmed that if an amine group does not have a substituent including a heteroatom, the bonding position of the nitrogen atom with benzonaphthofuran or benzonaphthothiophene significantly influences device properties, and only a case where the amine group is combined at a specific position showed improved efficiency and life.

In addition, as confirmed in Examples 16 and 17, in a compound having a benzonaphthothiophene core, even when a sulfur atom and a nitrogen atom are combined at ortho or para position, excellent device properties are shown. Compared with an oxygen atom, a sulfur atom has smaller electronegativity (e.g., is less electronegative), and electrons may be more delocalized around the ring. Accordingly, even when the nitrogen atom is bound ortho or para to the sulfur atom, the electronic instability issue may be solved, and efficiency and lifespan may be improved.

Comparative Examples 13 and 15 each include a dibenzoheterole substituent on the amine, but carrier balance is collapsed, and device efficiency and lifespan were both degraded compared with the Examples. Comparative Example 14 includes a benzoxanthene substituent on the amine, but the heat resistance of the benzoxanthene skeleton is insufficient, and device efficiency and lifespan were both degraded when compared with the Examples.

Comparative Examples 16 and 17 are amine compounds having a carbazole group substituents, but the binding positions of the carbazole groups are different from the materials of the Examples, and the device efficiency and lifespan were both degraded when compared with the Examples. In contrast, in the polycyclic compound according to the present disclosure, the amine moiety is bound to position 3 or position 9 of the carbazole ring, which are the most electron-rich positions, such that hole transport properties were improved, and emission efficiency was improved.

Comparative Example 18 is an amine compound having a dibenzofuran substituent, and thermal and charge tolerance were degraded, and device efficiency and lifespan were both degraded compared with the Examples.

The polycyclic compound according to an embodiment of the present disclosure may be included in a hole transport region to contribute to the decrease of the driving voltage and the increase of the efficiency and lifespan of an organic electroluminescence device.

The organic electroluminescence device according to an embodiment of the present disclosure may have excellent efficiency.

The polycyclic compound according to an embodiment of the present disclosure may be used as a material for the hole transport region of an organic electroluminescence device, and the efficiency of the organic electroluminescence device may be improved by the compound.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although example embodiments of the present disclosure have been described, it is understood that the present disclosure is not limited to these example embodiments, and that various changes and modifications can be made by one of ordinary skill in the art that would be within the spirit and scope of the present disclosure, as set forth in the following claims and equivalents thereof.

What is claimed is:

1. An organic electroluminescence device, comprising:

a first electrode;

a hole transport region on the first electrode;

an emission layer on the hole transport region;

an electron transport region on the emission layer; and a second electrode on the electron transport region, wherein the hole transport region comprises a polycyclic compound represented by Formula 1:

[Formula 1]

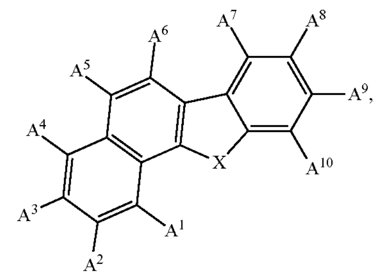

wherein in Formula 1,

X is O or S, any one among $A^1$ to $A^{10}$ is represented by Formula 2-2, and the remainder of $A^1$ to $A^{10}$ are each independently a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-2]

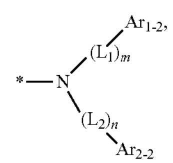

wherein in Formula 2-2, $L_1$ and $L_2$, are each independently a direct linkage, a substituted or unsubstituted arylene group of 6 to 30 carbon atoms for forming a ring, or a substituted or unsubstituted heteroarylene group of 2 to 30 carbon atoms for forming a ring, "m" and "n" are each independently an integer of 0 to 2, and $Ar_{1-2}$ and $Ar_{2-2}$ are each independently a substituted or unsubstituted aryl group of 10 to 40 carbon atoms for forming a ring or are represented by Formula 3-3 or Formula 3-4, where at least one among $Ar_{1-2}$ and $Ar_{2-2}$ is represented by Formula 3-3 or Formula 3-4:

[Formula 3-3]

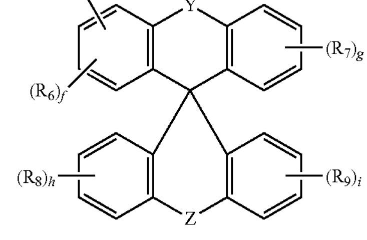

-continued

[Formula 3-4]

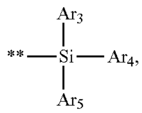

and wherein in Formula 3-3 and Formula 3-4,

Y and Z are each independently a direct linkage, O, or S, where a case in which both Y and Z are direct linkages is excluded, $R_6$ to $R_9$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "f" is an integer of 0 to 3, "g" to "i" are each independently an integer of 0 to 4, and $Ar_3$ to $Ar_5$ are each independently a substituted or unsubstituted aryl group of 6 to 30 carbon atoms for forming a ring.

2. The organic electroluminescence device of claim 1, wherein Formula 2-2 is represented by Formula 5-1 or Formula 5-2:

[Formula 5-1]

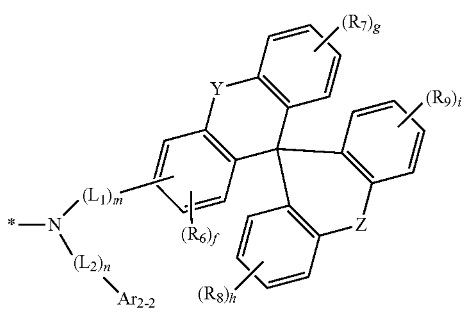

[Formula 5-2]

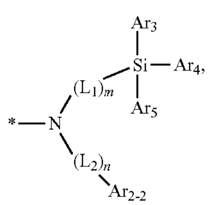

and wherein in Formula 5-1 and Formula 5-2, $Ar_{2-2}$ is a substituted or unsubstituted aryl group of 10 to 40 carbon atoms for forming a ring, $L_1$, $L_2$, "m" and "n" are each independently the same as defined in Formula 2-2, and Y, Z, $R_6$ to $R_9$, "f" to "i", and $Ar_3$ to $Ar_5$ are each independently the same as defined in Formula 3-3 and Formula 3-4.

3. The organic electroluminescence device of claim 1, wherein any one among $A^1$ to $A^6$ in Formula 1 is represented by Formula 2-2.

4. The organic electroluminescence device of claim 1, wherein any one among $A^7$ to $A^{10}$ in Formula 1 is represented by Formula 2-2.

5. The organic electroluminescence device according to claim 1, wherein the hole transport region comprises:

a hole injection layer on the first electrode; and a hole transport layer on the hole injection layer, and the hole transport layer comprises the polycyclic compound represented by Formula 1.

6. The organic electroluminescence device according to claim 1, wherein $L_1$ and $L_2$ are each independently a direct linkage, a substituted or unsubstituted phenylene group, or a substituted or unsubstituted naphthyl group.

7. The organic electroluminescence device according to claim 1, wherein:

$L_2$ is a direct linkage or a substituted or unsubstituted phenyl group, and $Ar_{2-2}$ is a substituted or unsubstituted biphenyl group, a substituted or unsubstituted terphenyl group, a substituted or unsubstituted phenanthrene group, a substituted or unsubstituted naphthyl group, or a substituted or unsubstituted fluorenyl group.

8. The organic electroluminescence device of claim 1, wherein the polycyclic compound represented by Formula 1 is at least one selected from compounds represented in Compound Group 3 and Compound Group 4:

[Compound Group 3]

C1

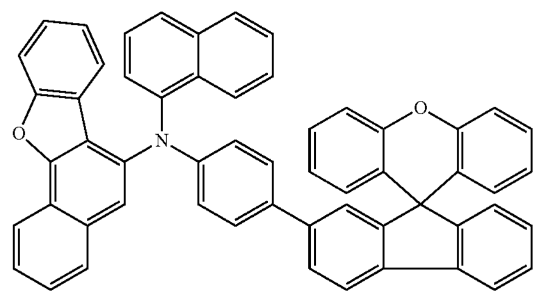

C2

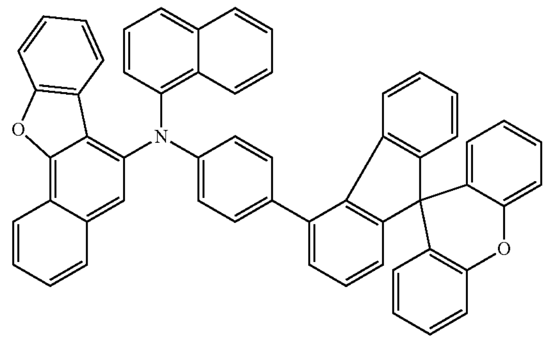

-continued
C3
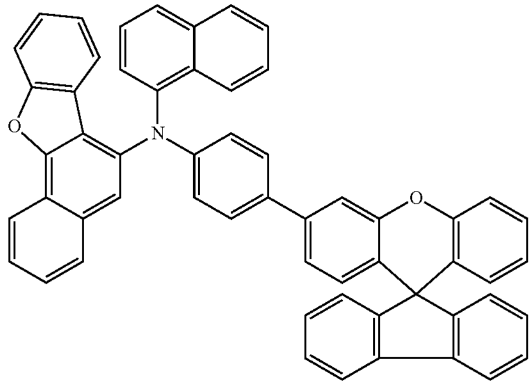
C4
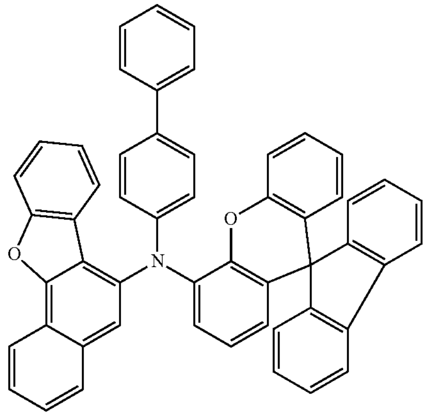
C5
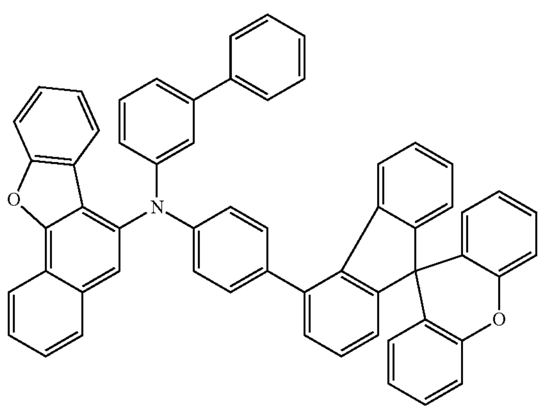
C6
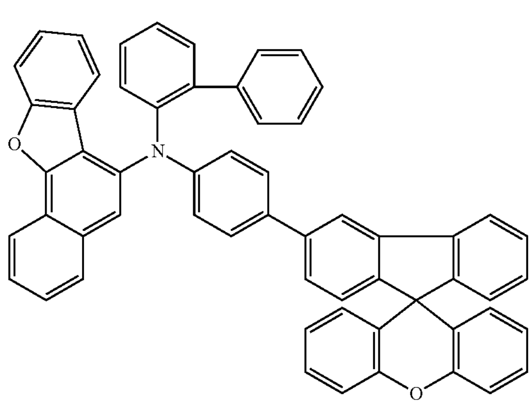
-continued
C7
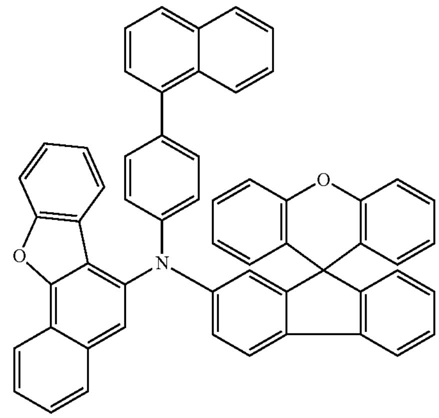
C8
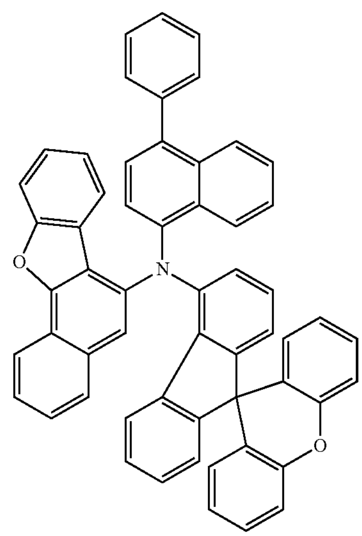
C9
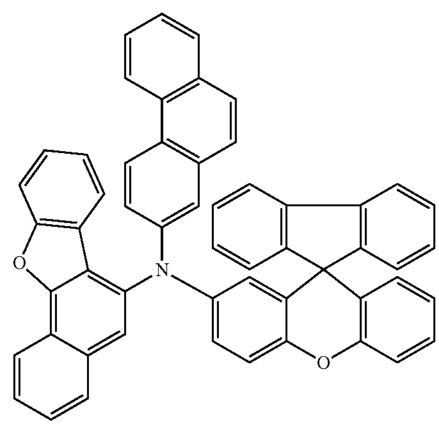

C10
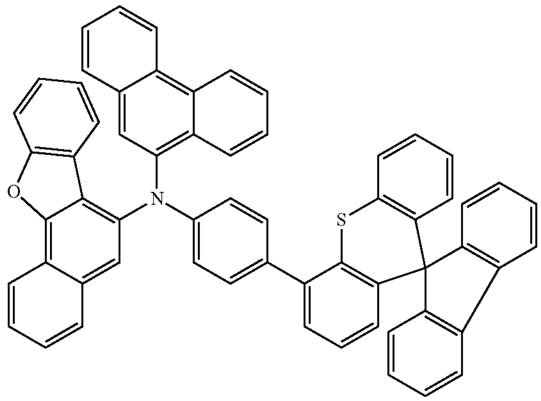
C11
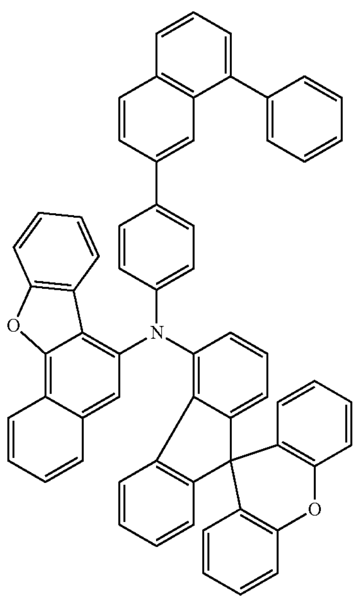
C12
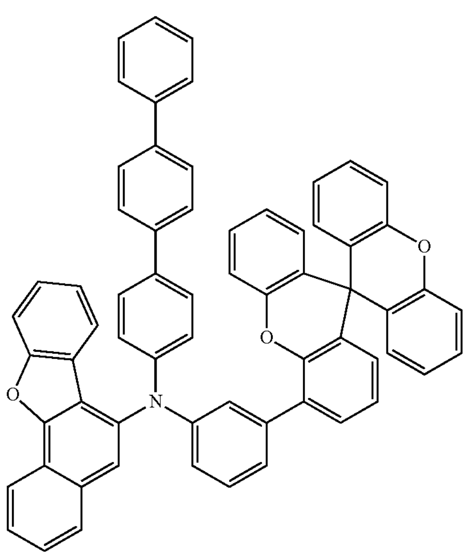
C13
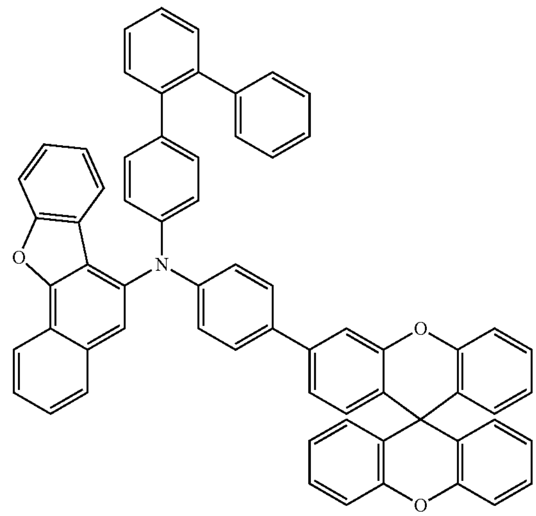
C14
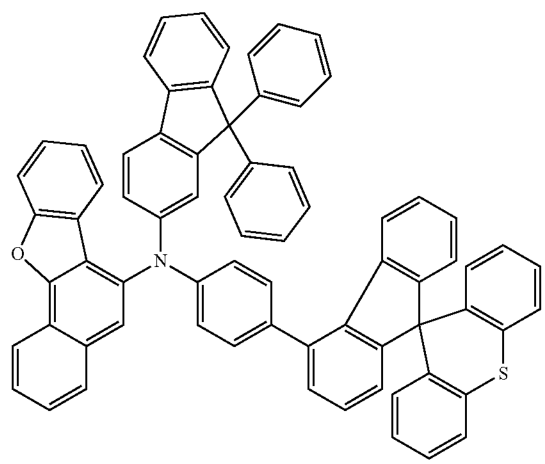
C15
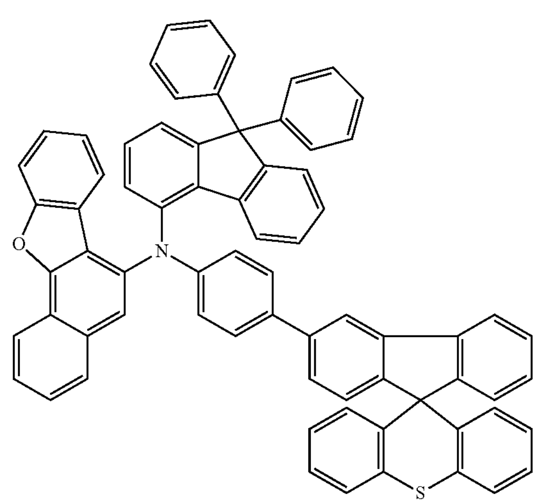

-continued
C16
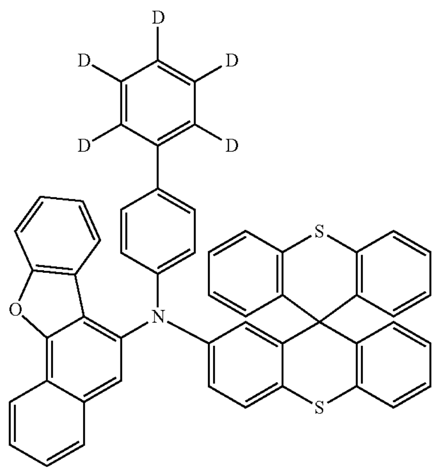
C17
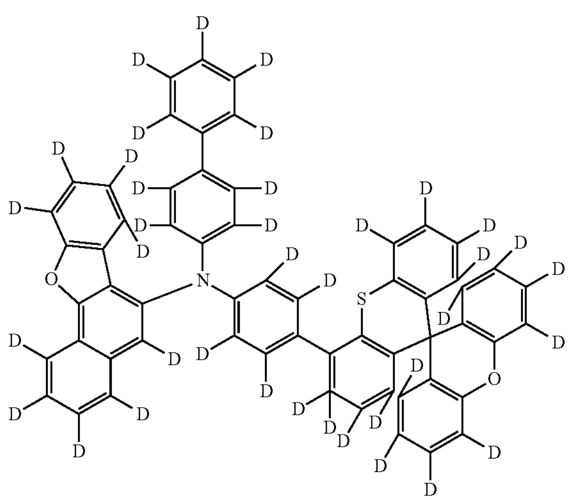
C18
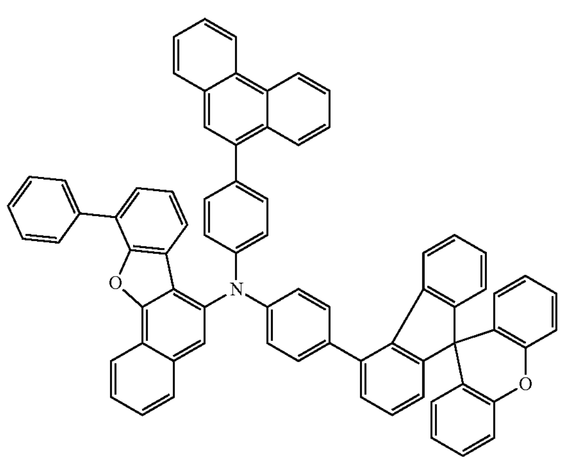
-continued
C19
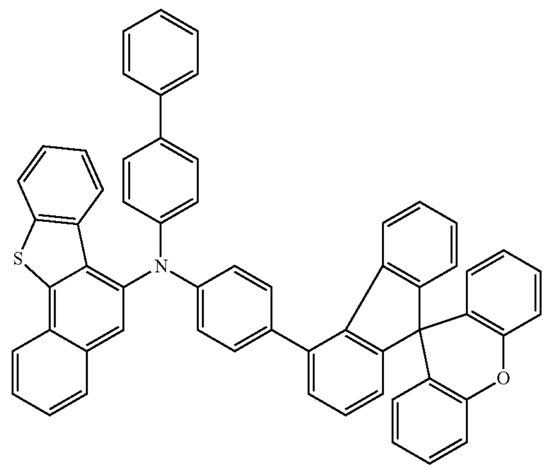
C20
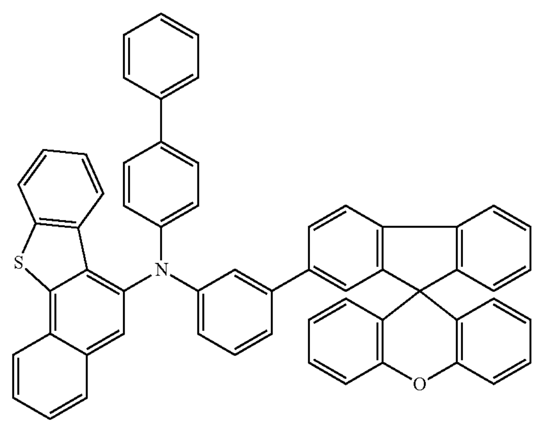
C21
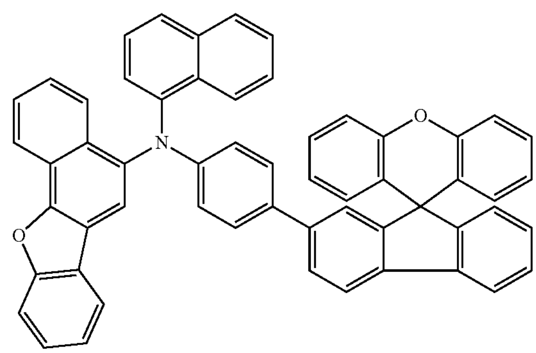
C22
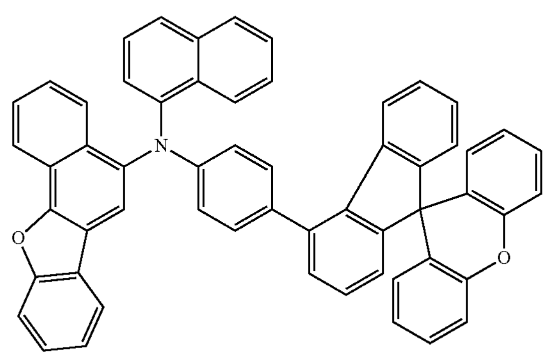

-continued
C23
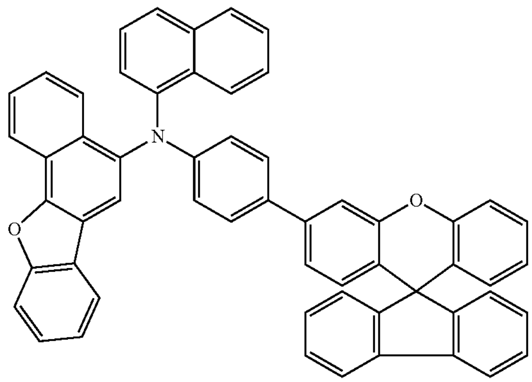
C24
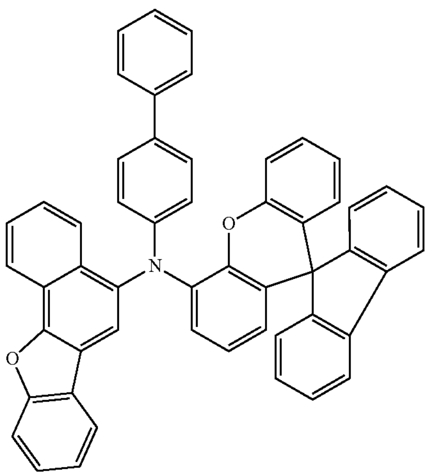
C25
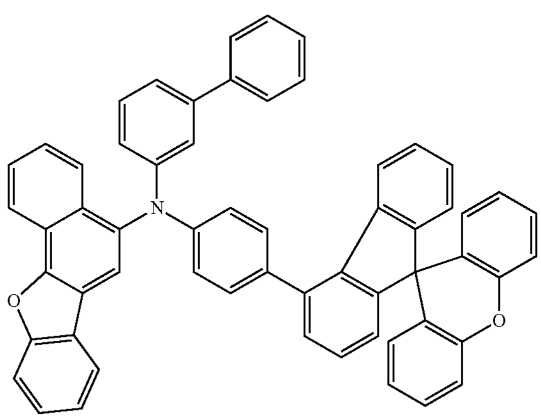
C26
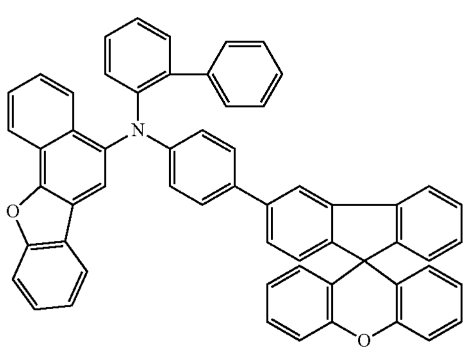
-continued
C27
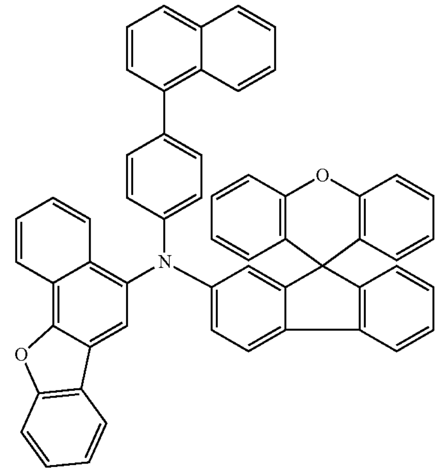
C28
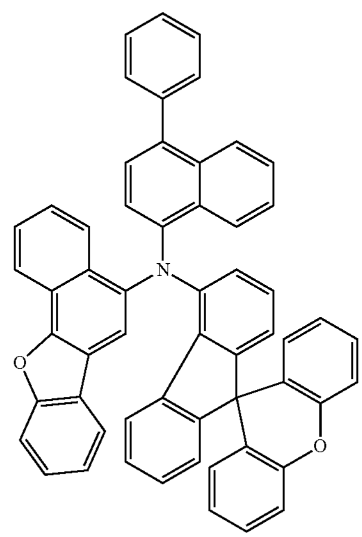
C29
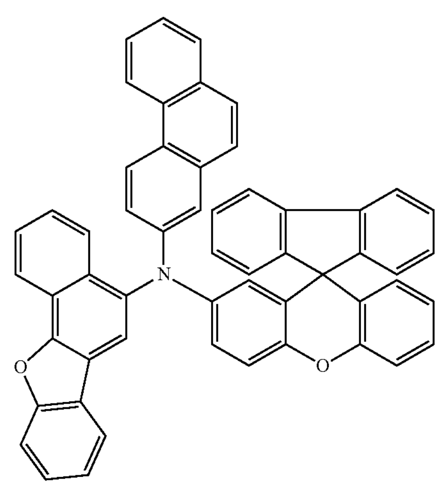

-continued
C30
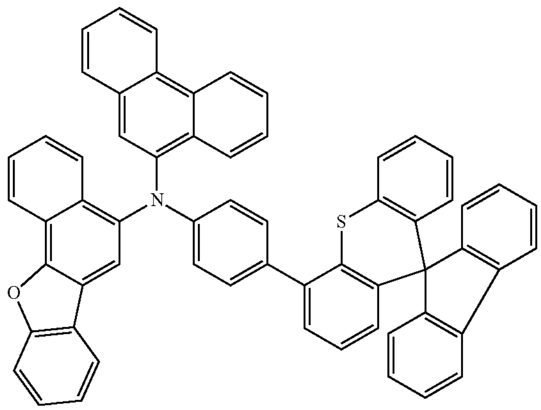
C31
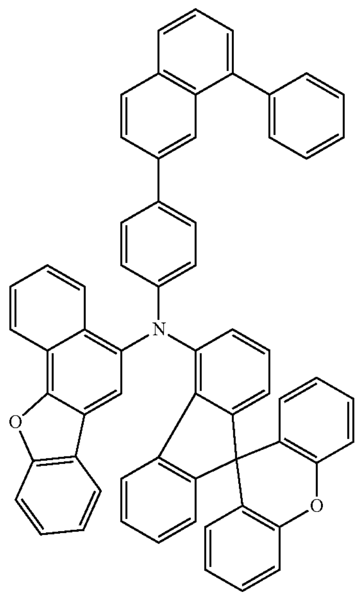
C32
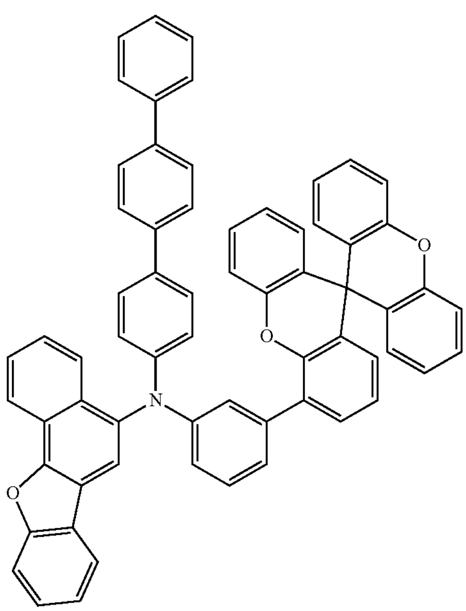
-continued
C33
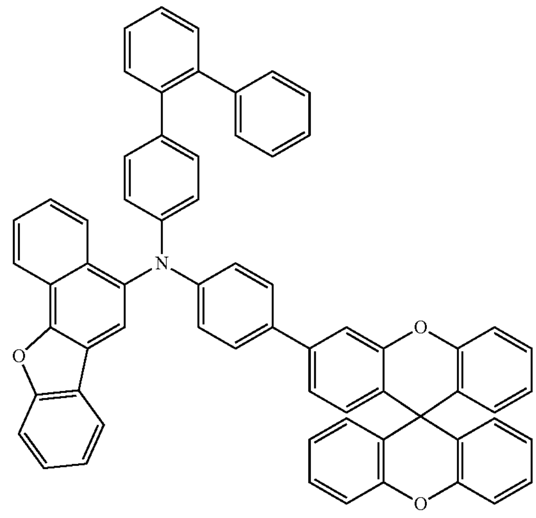
C34
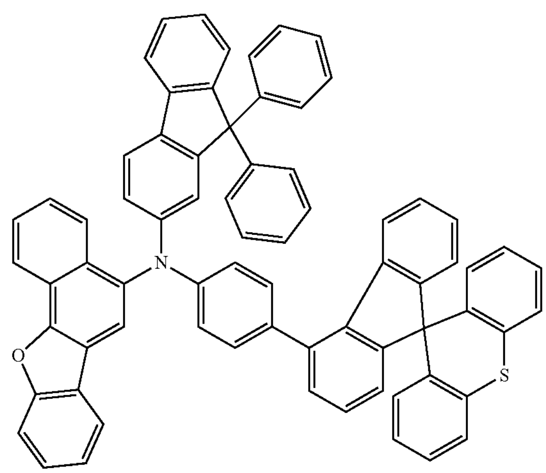
C35
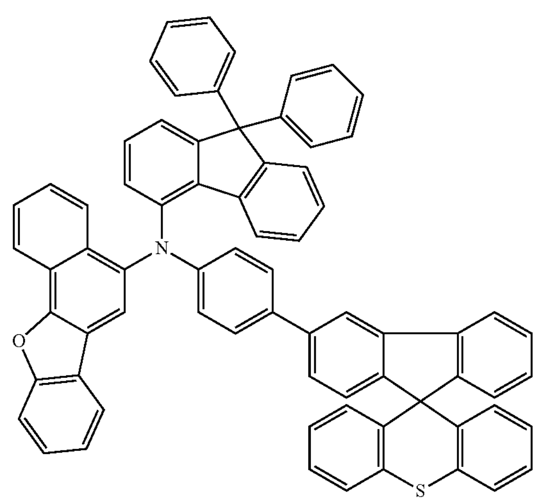

-continued
C36
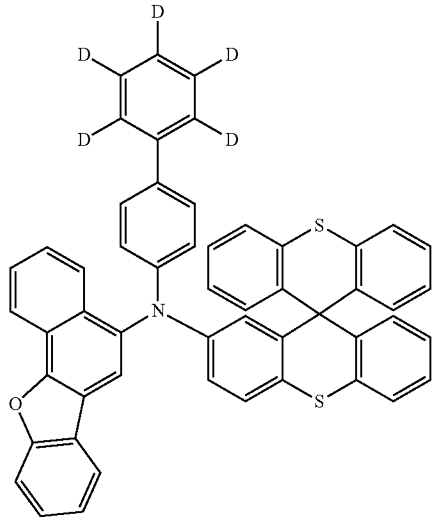
C37
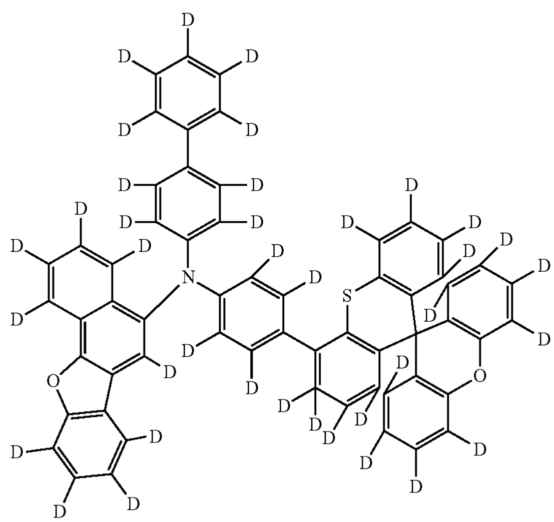
C38
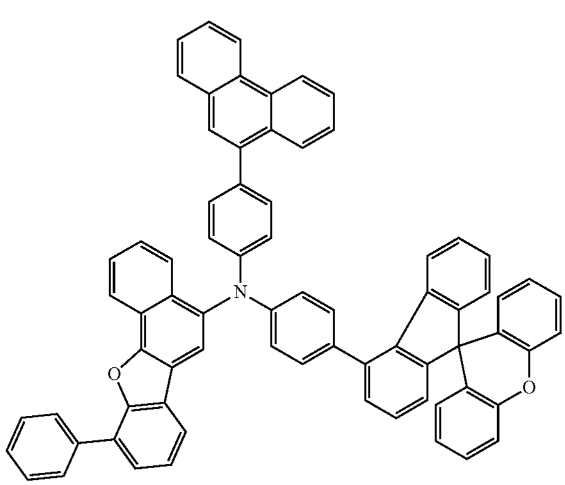
-continued
C39
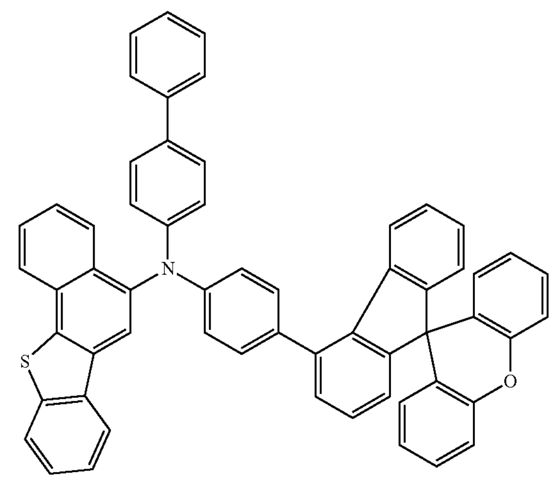
C40
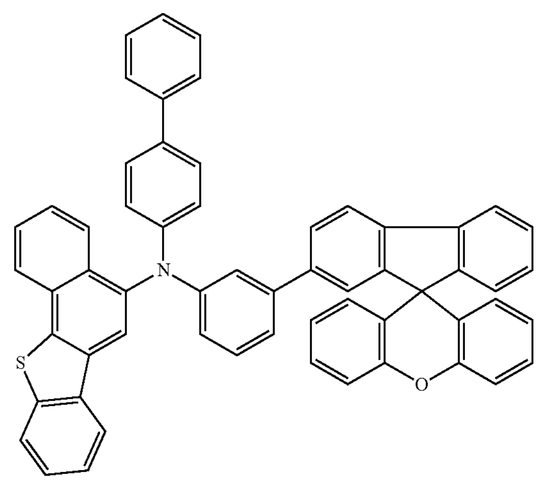
C41
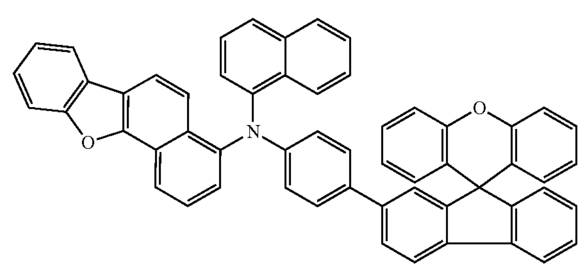
C42
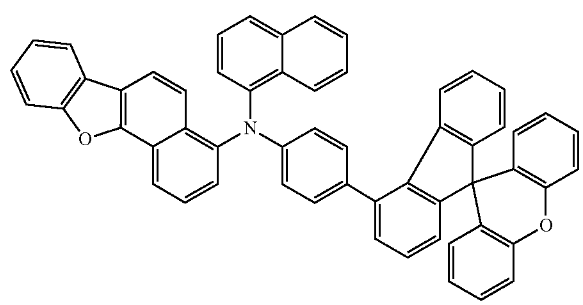

-continued
C43
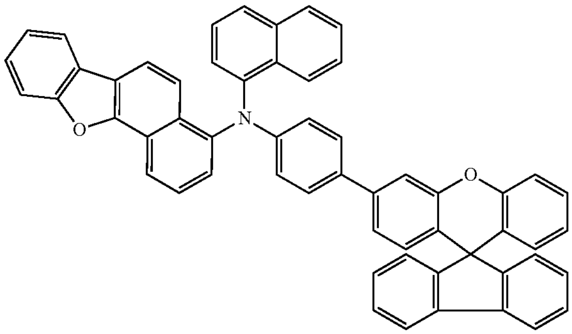
C44
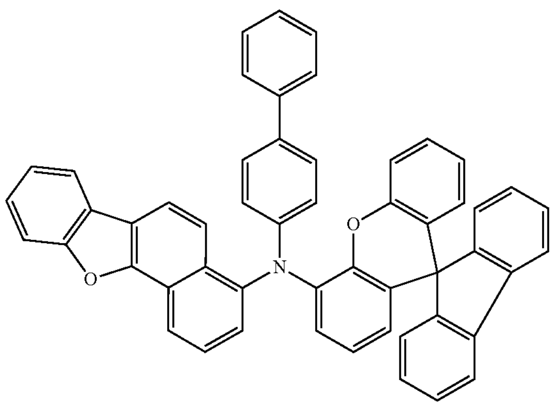
C45
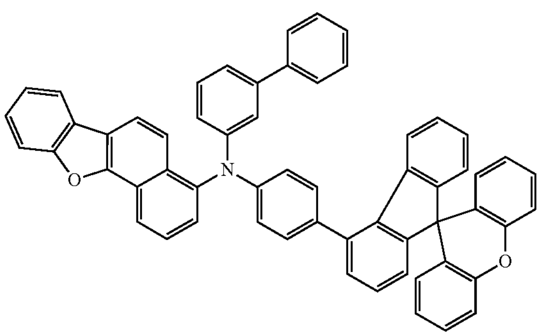
C46
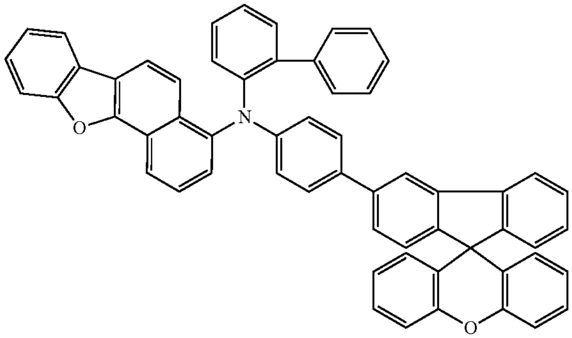
-continued
C47
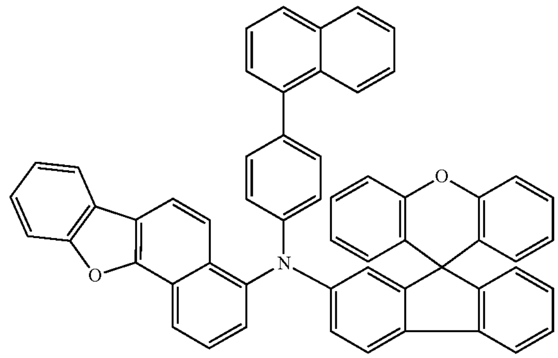
C48
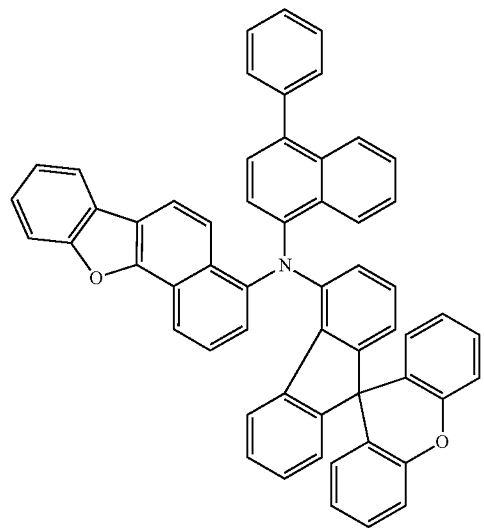
C49
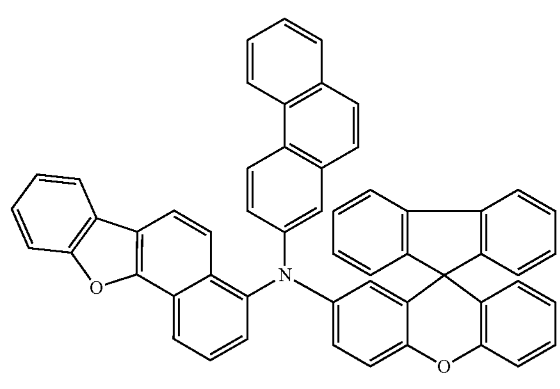

-continued
C50
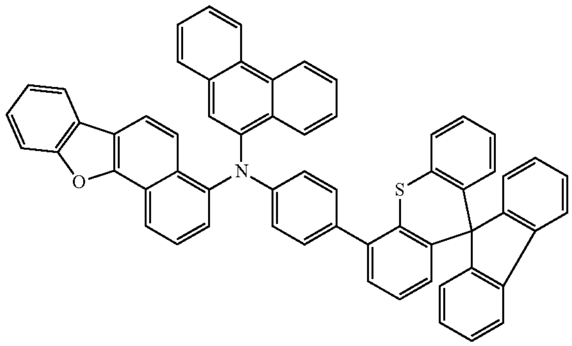
C51
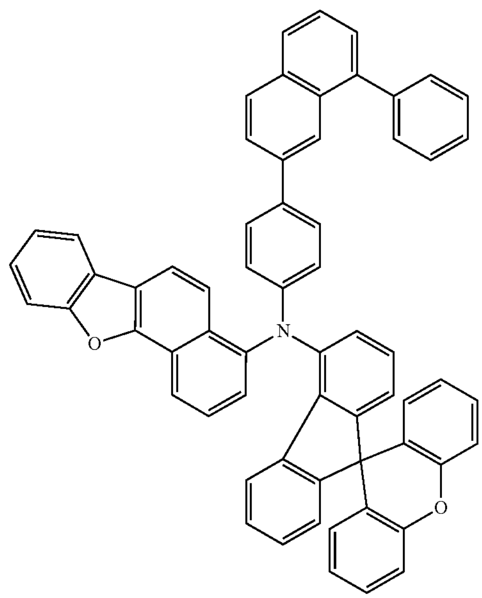
C52
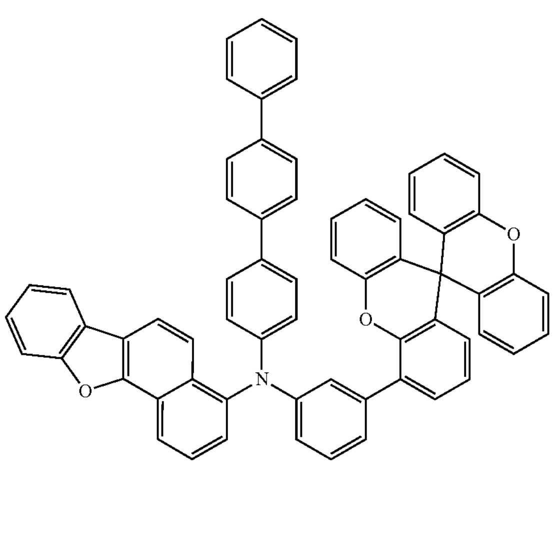
-continued
C53
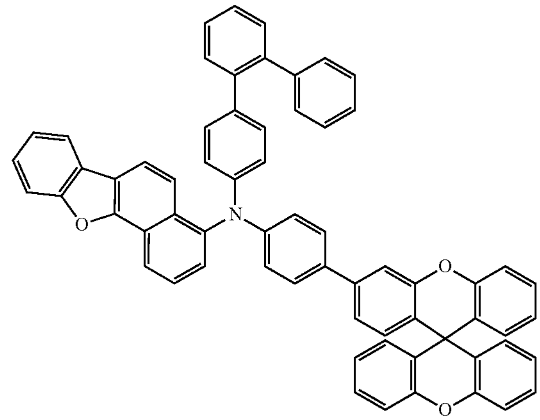
C54
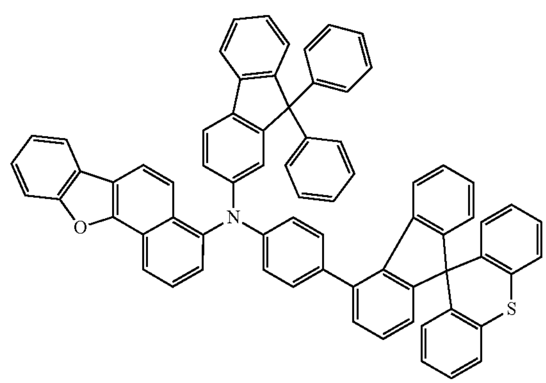
C55
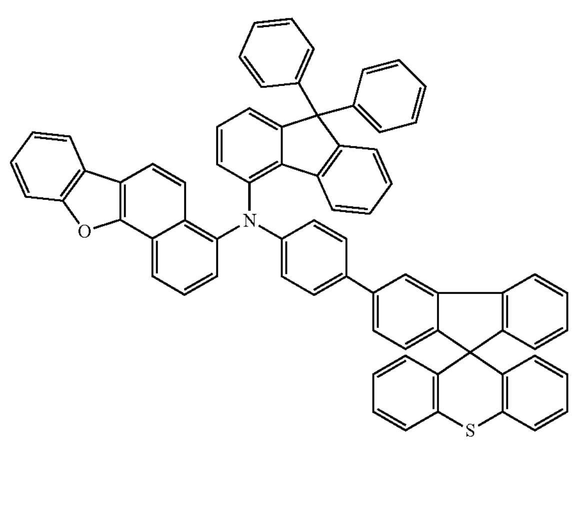

-continued
C56
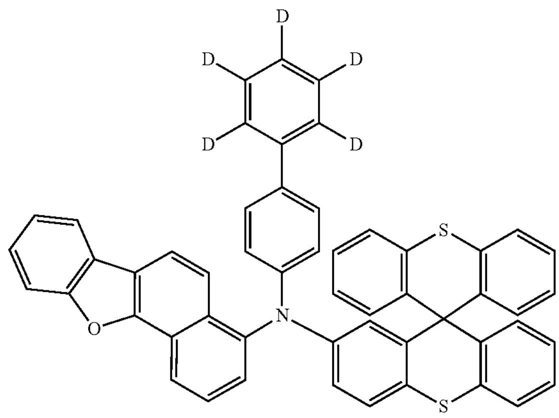
C57
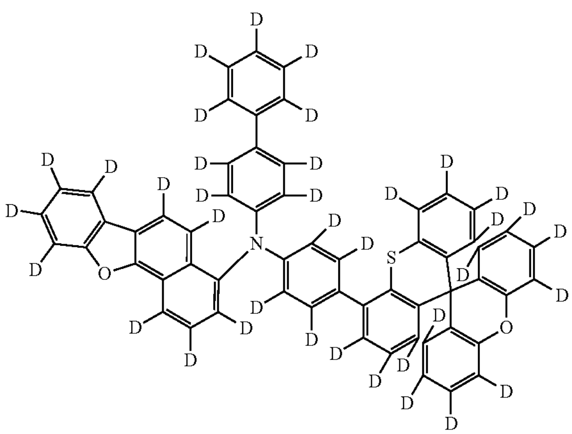
C58
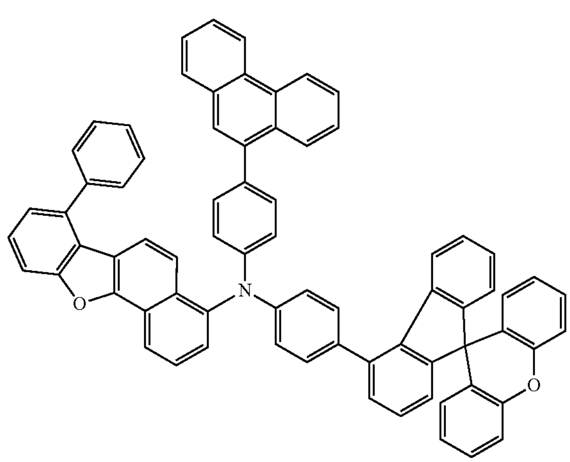
-continued
C59
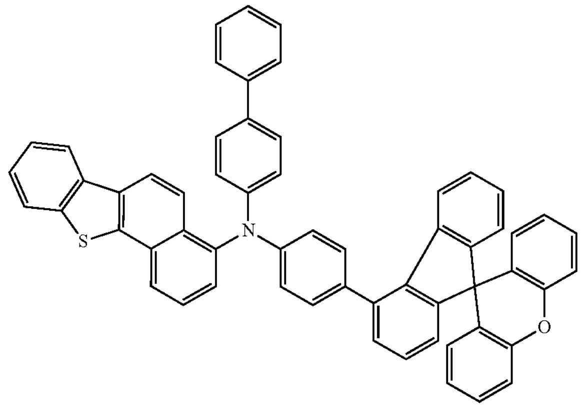
C60
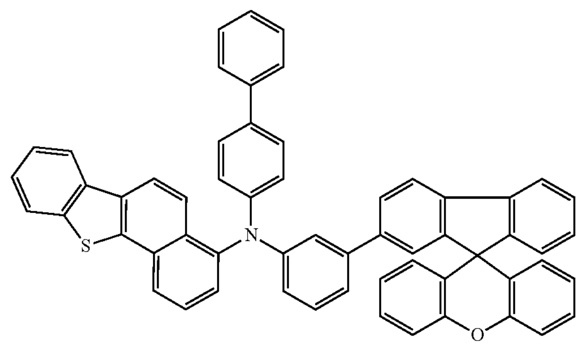
C61
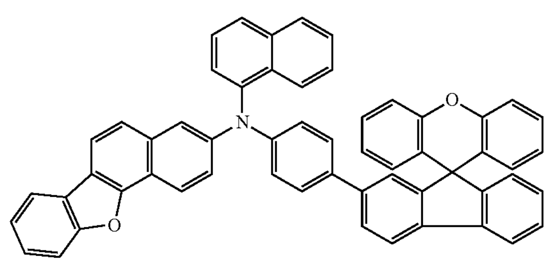
C62
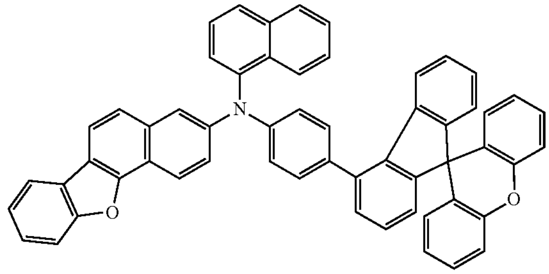

-continued
C63
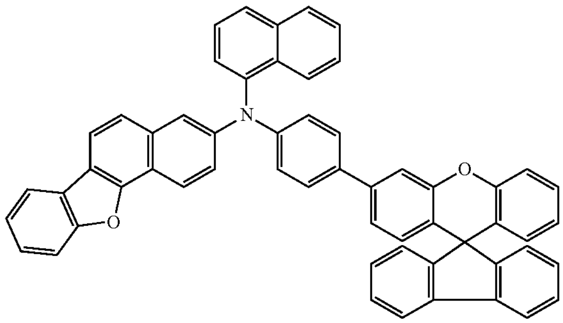
C64
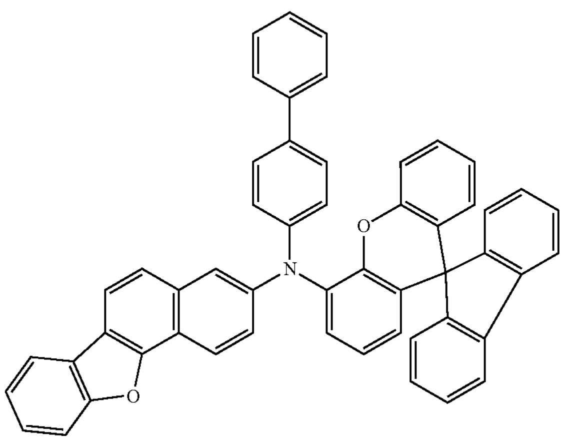
C65
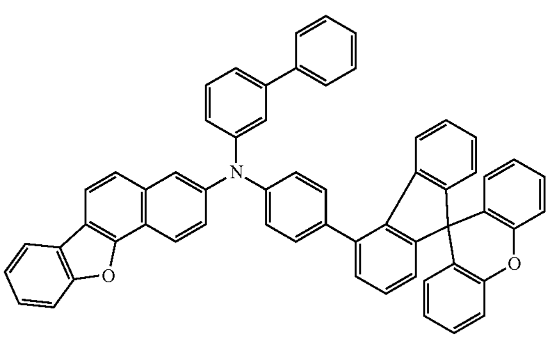
C66
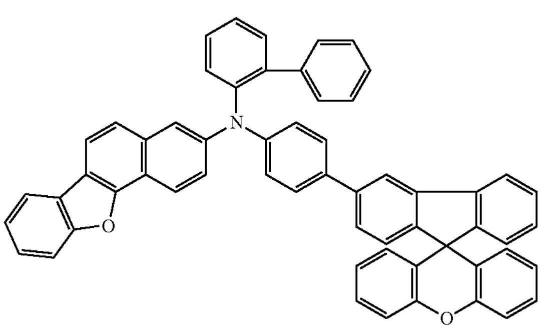
-continued
C67
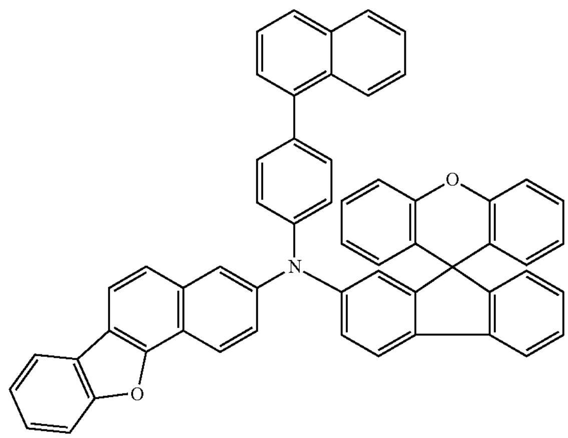
C68
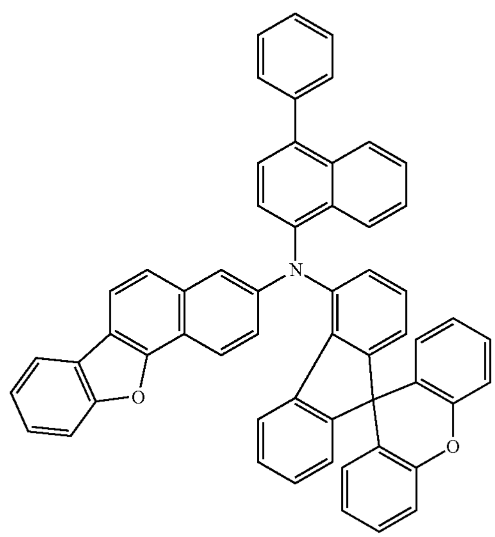
C69
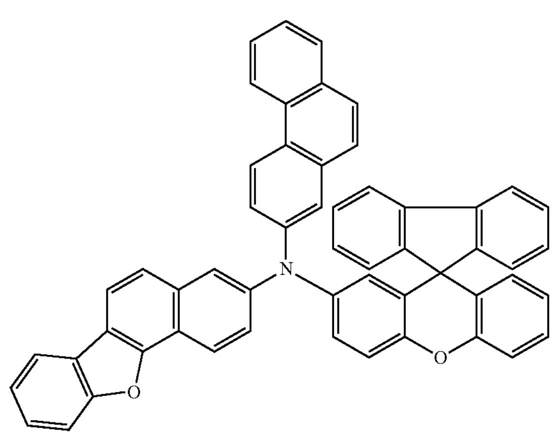

-continued
C70
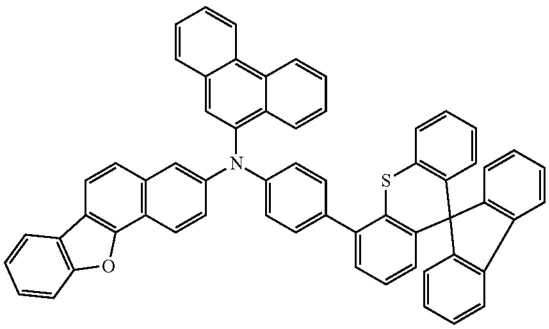
C71
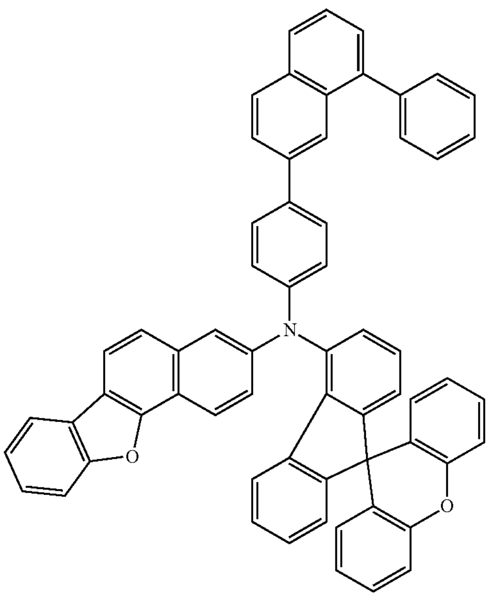
C72
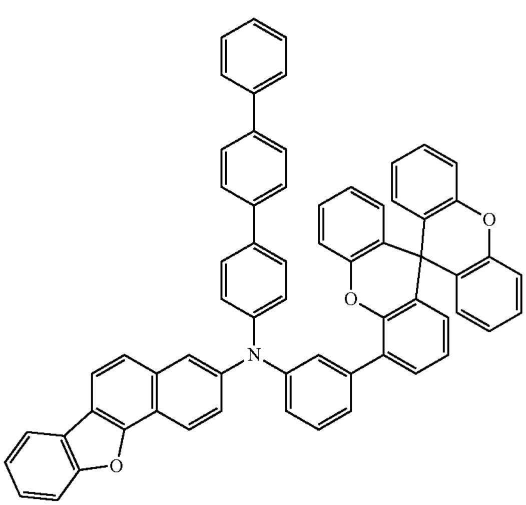
-continued
C73
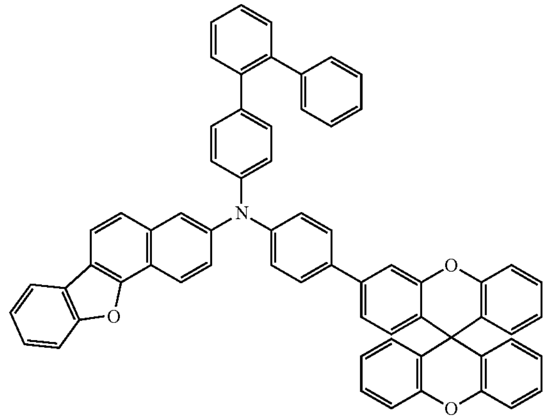
C74
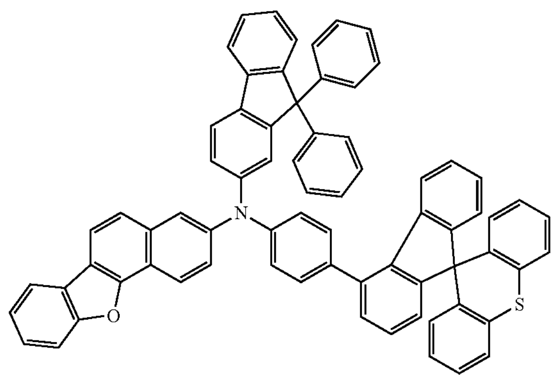
C75
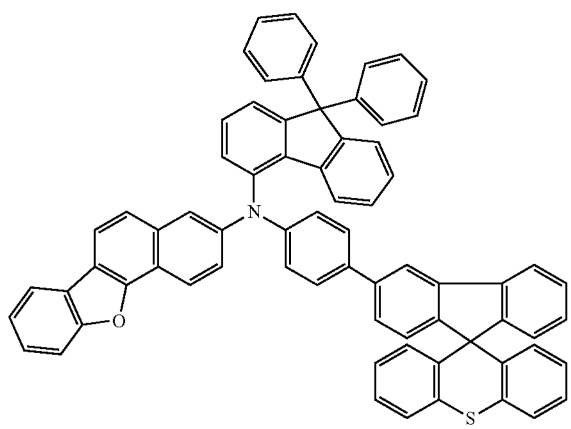

-continued
C76
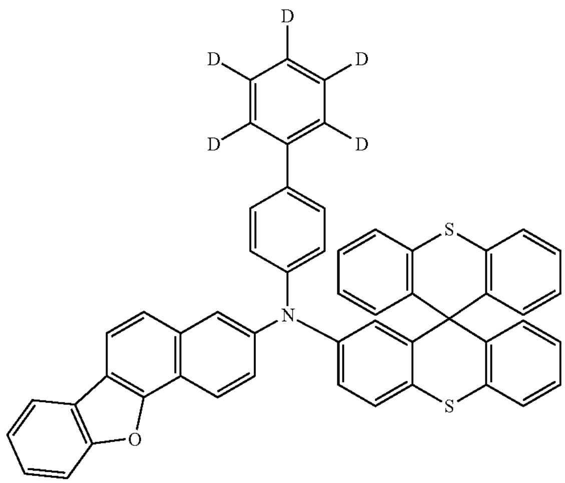
C77
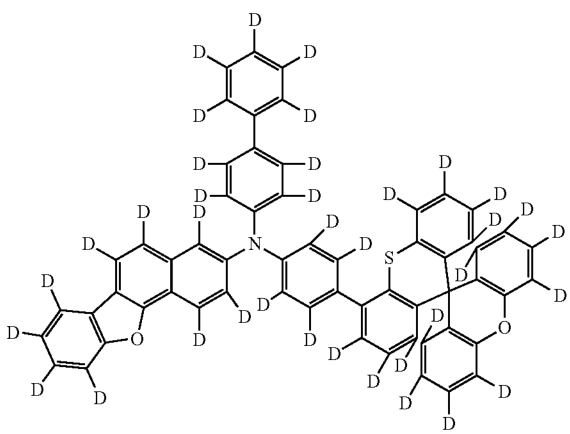
C78
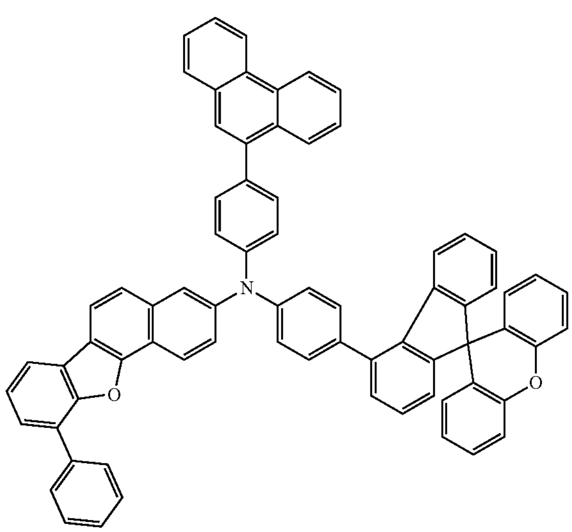
-continued
C79
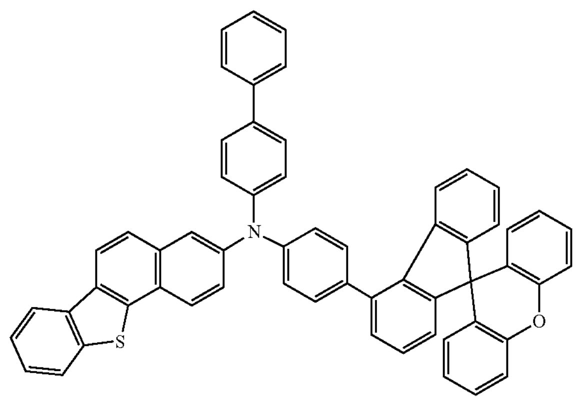
C80
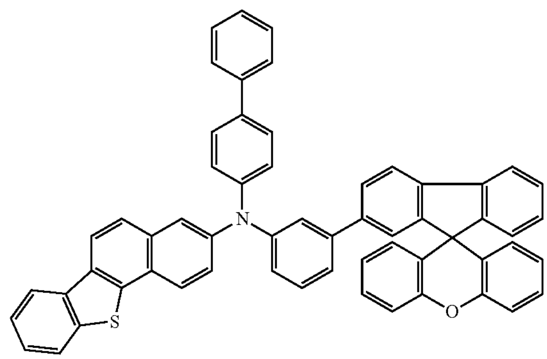
C81
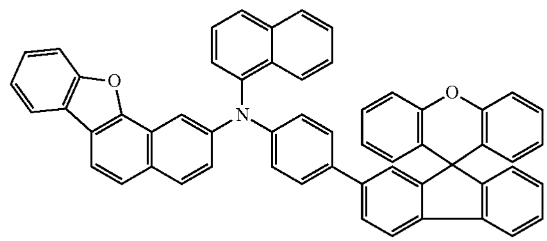
C82
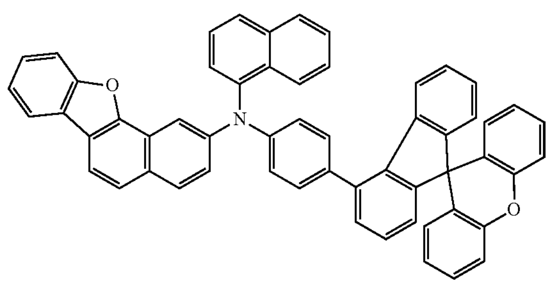

-continued
C83
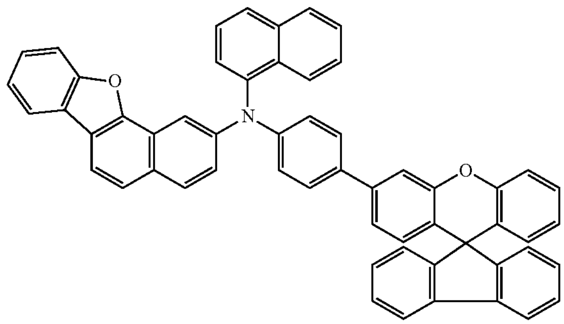
C84
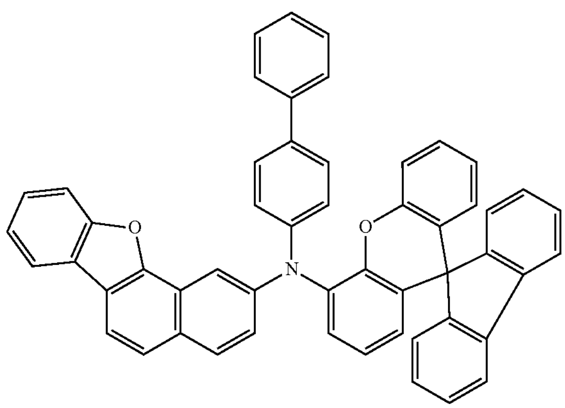
C85
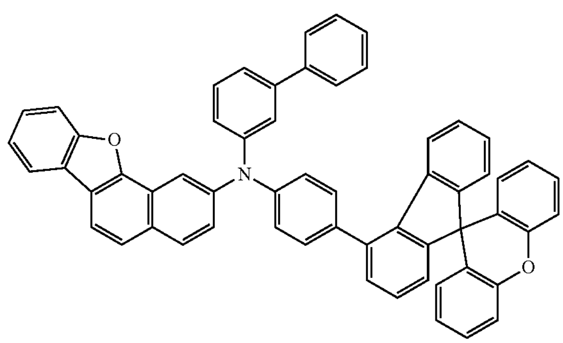
C86
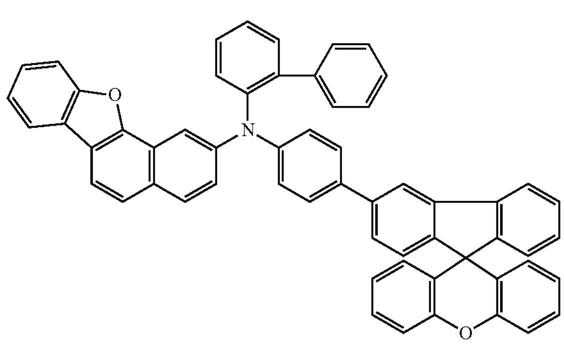
-continued
C87
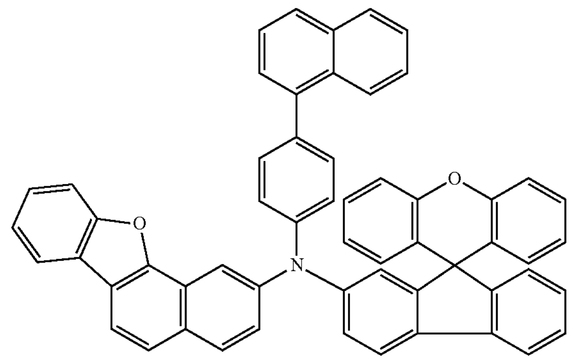
C88
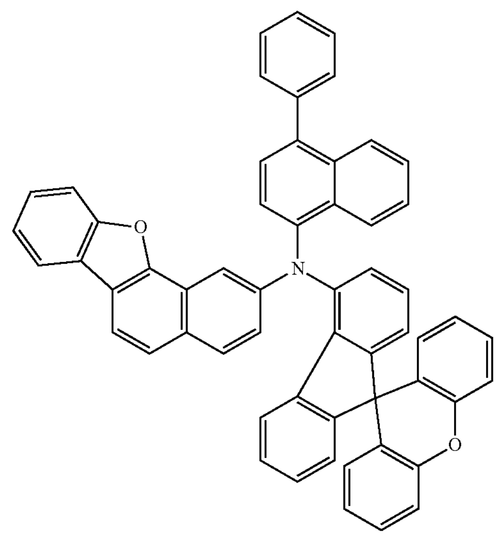
C89
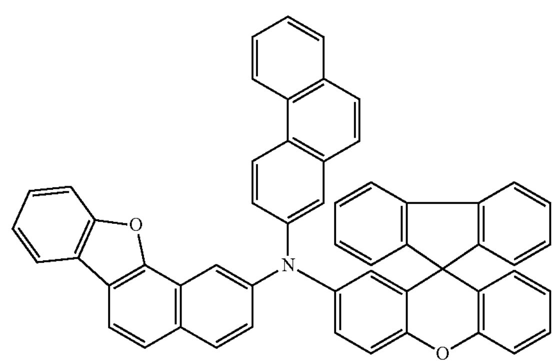
C90
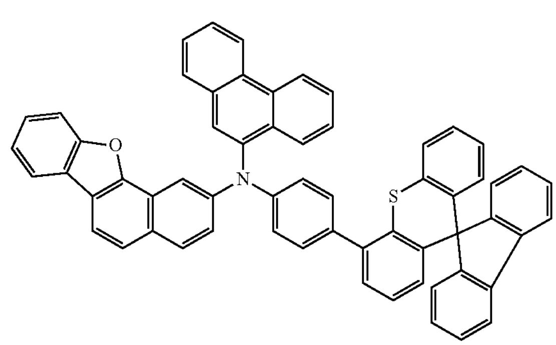

-continued
C91
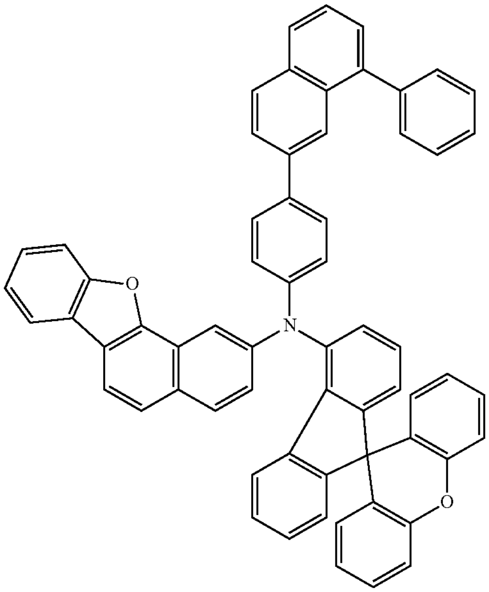
C92
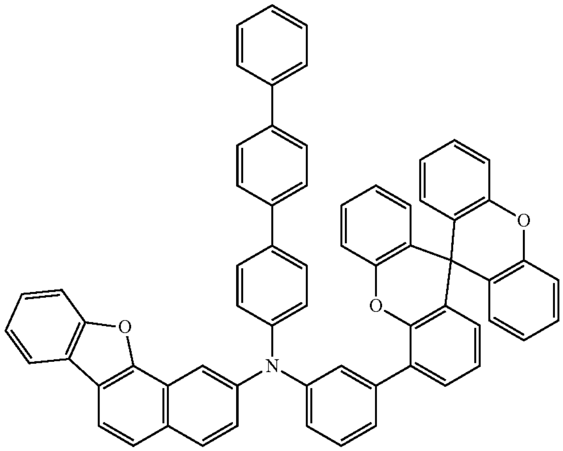
C93
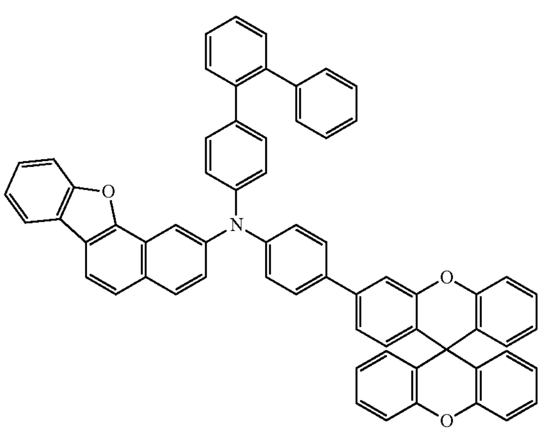
-continued
C94
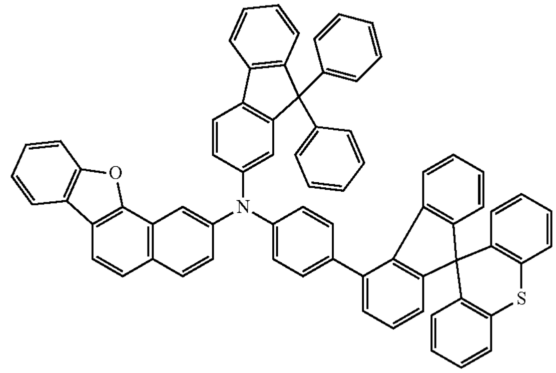
C95
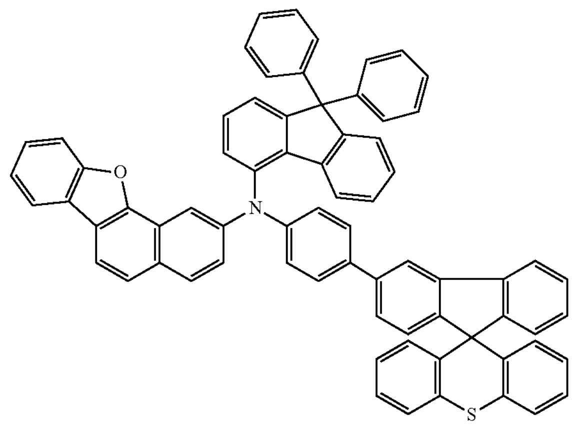
C96
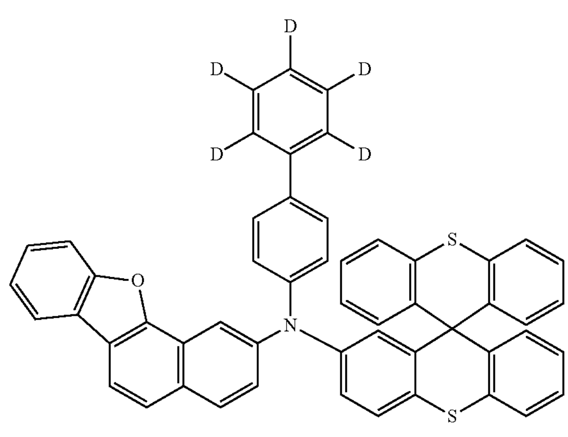

-continued
C97
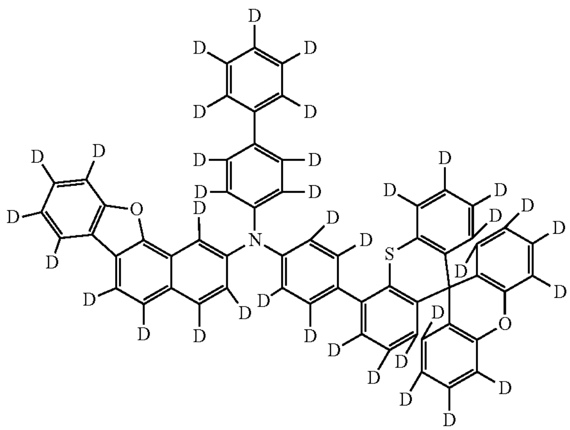
C98
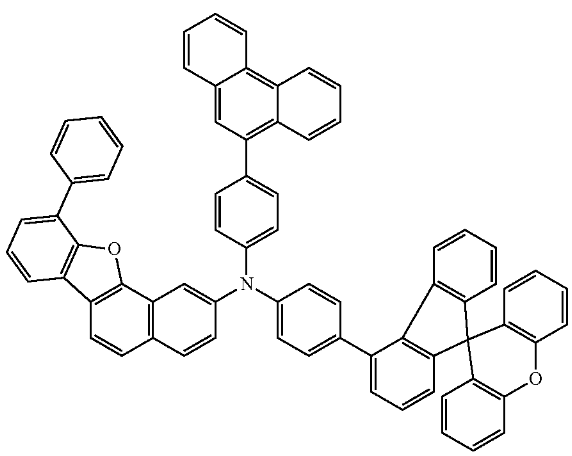
C99
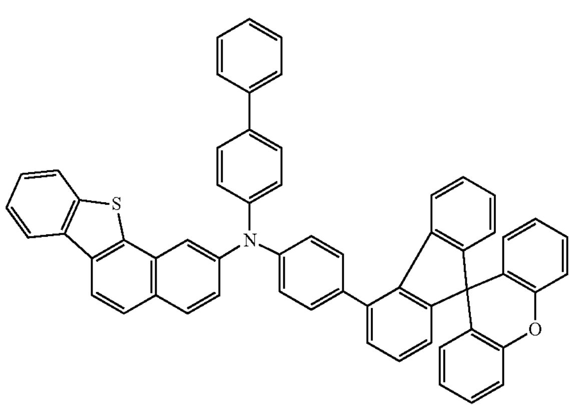
-continued
C100
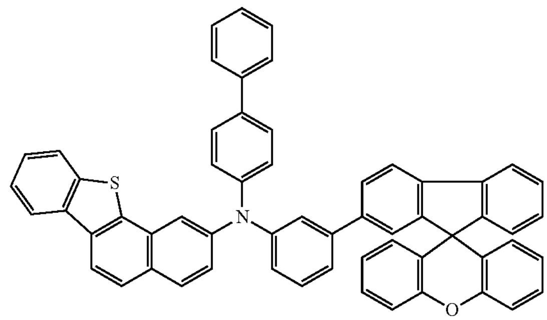
C101
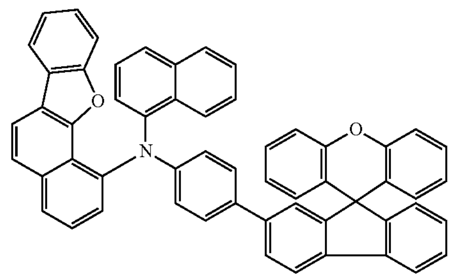
C102
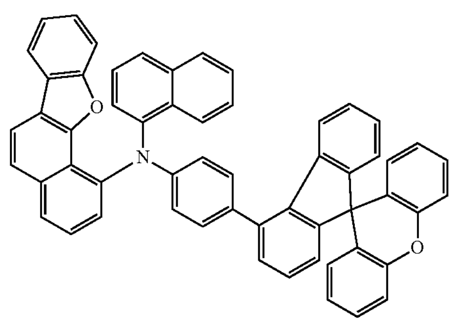
C103
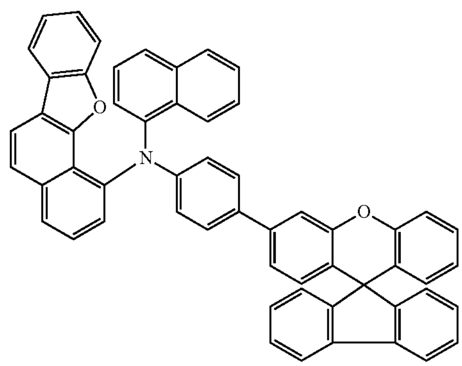

-continued
C104
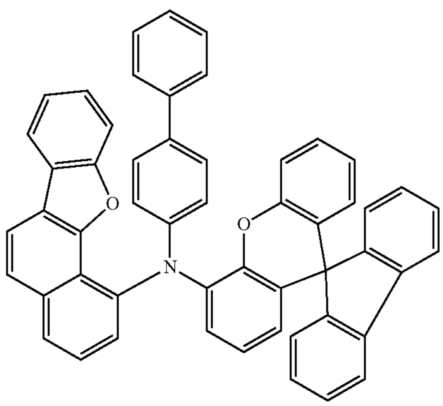
C105
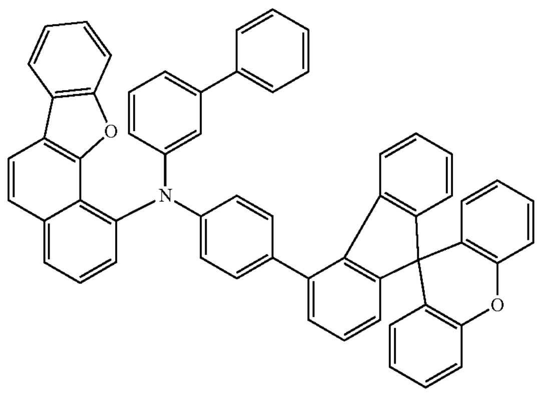
C106
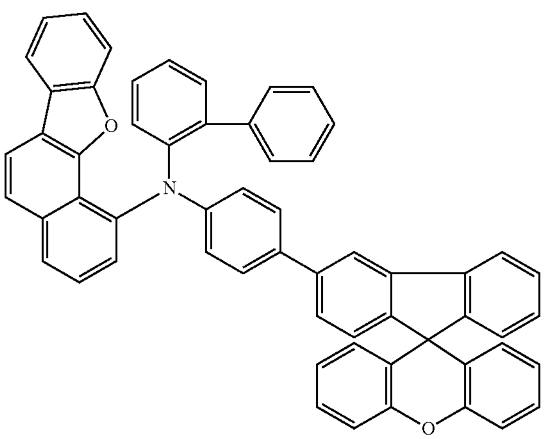
C107
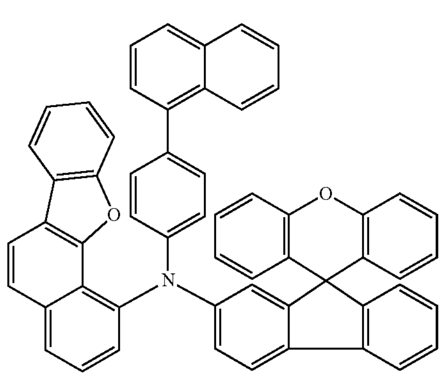
-continued
C108
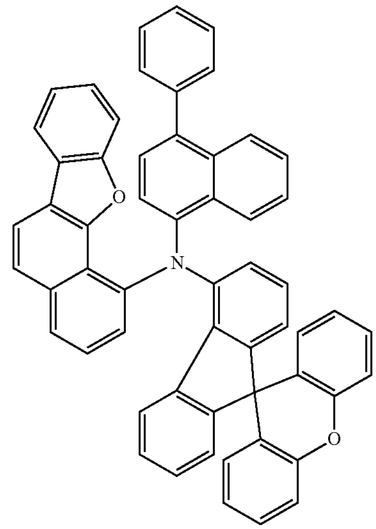
C109
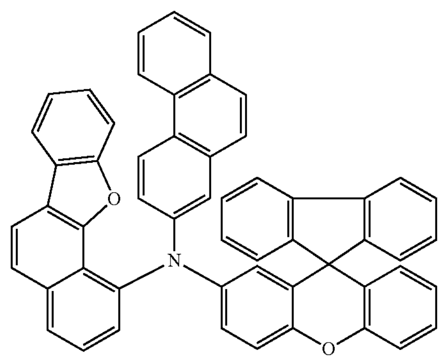
C110
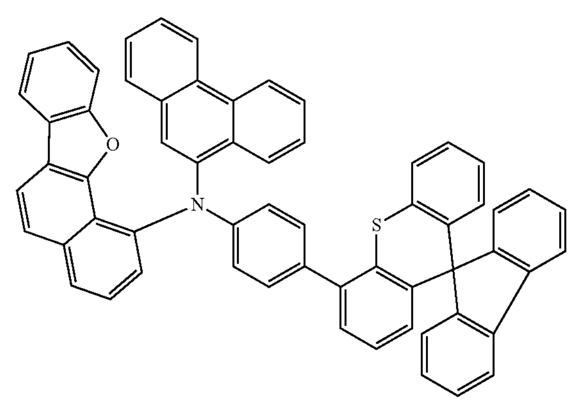

-continued
C111
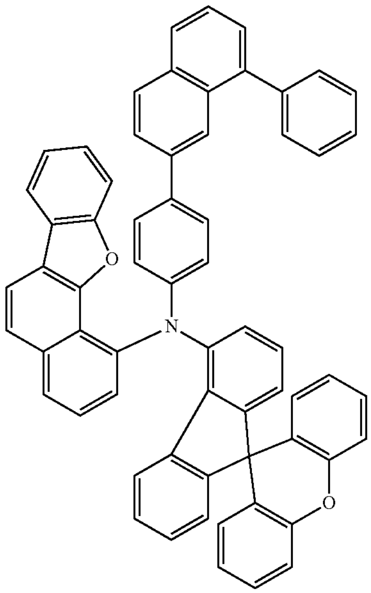
C112
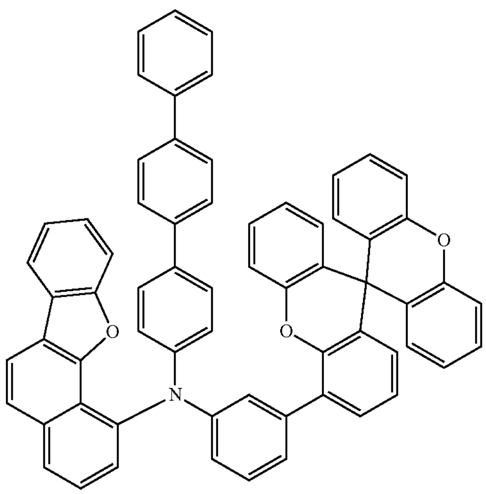
C113
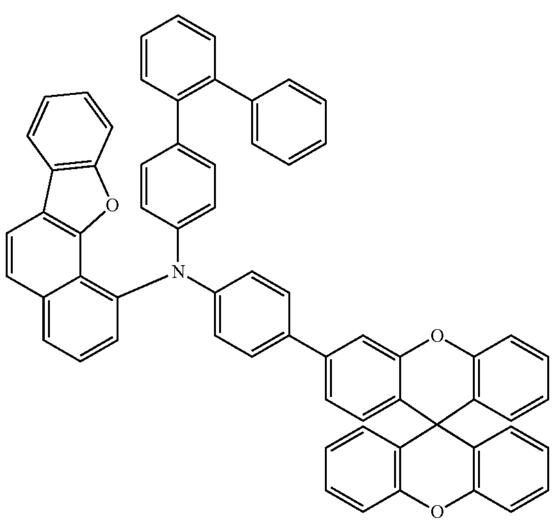
-continued
C114
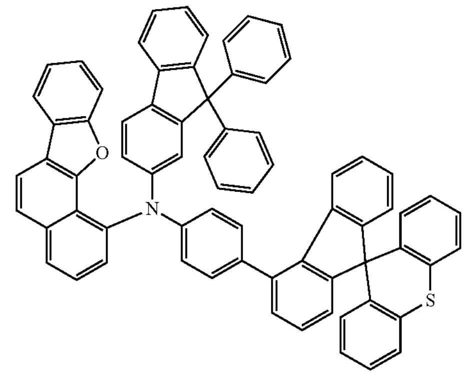
C115
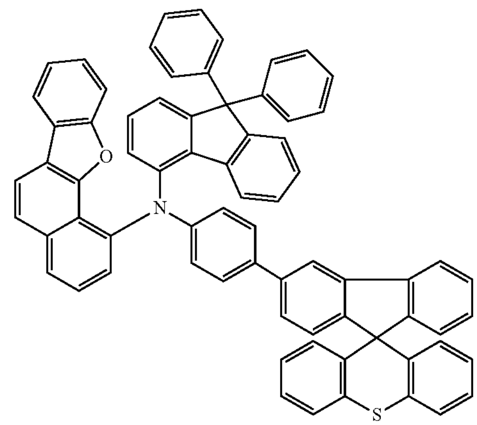
C116
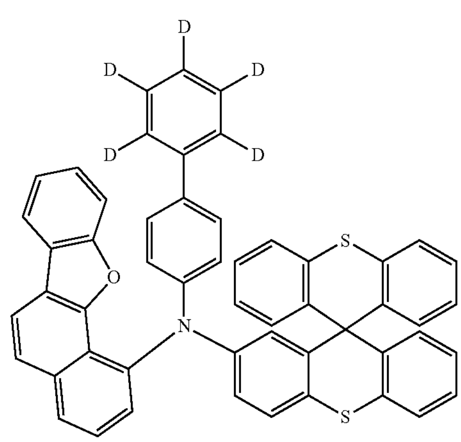

-continued
C117
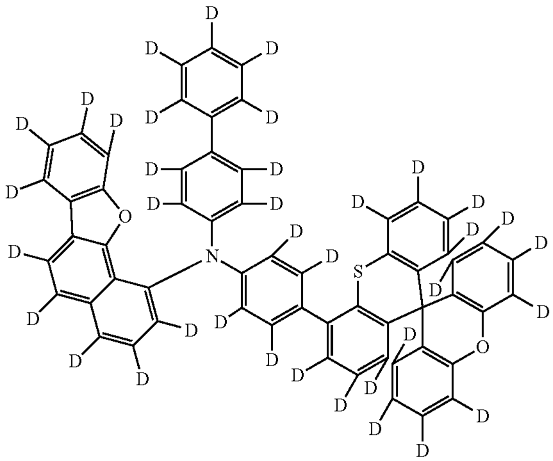
C118
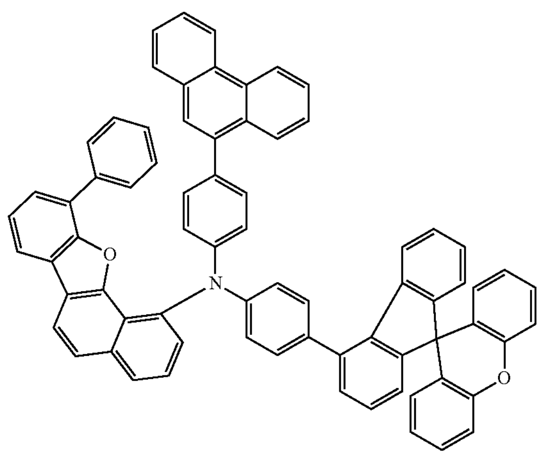
C119
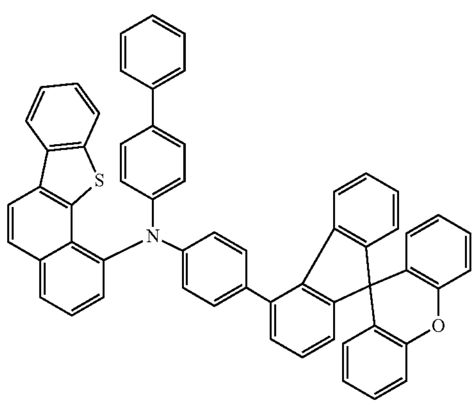
-continued
C120
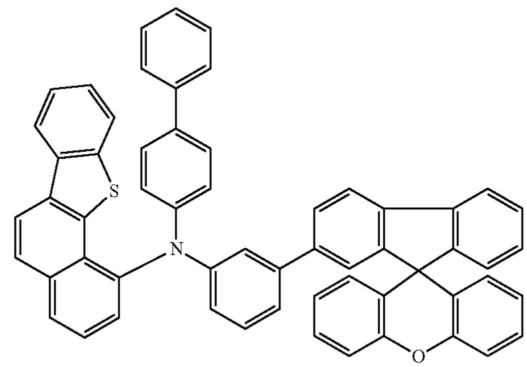
C121
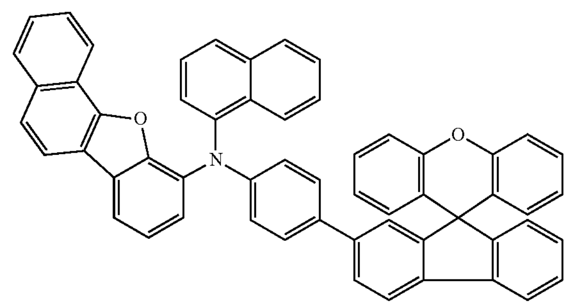
C122
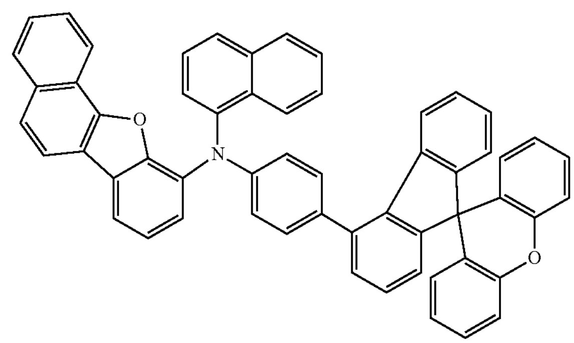
C123
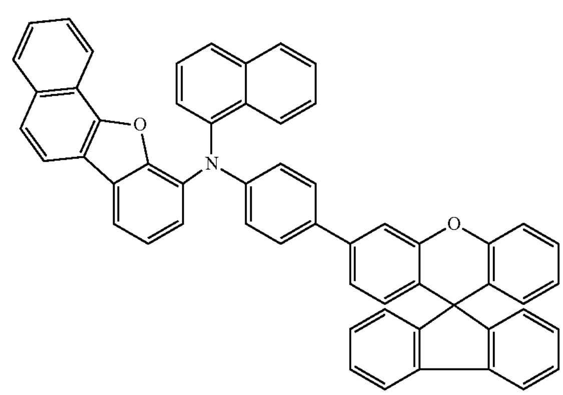

-continued
C124
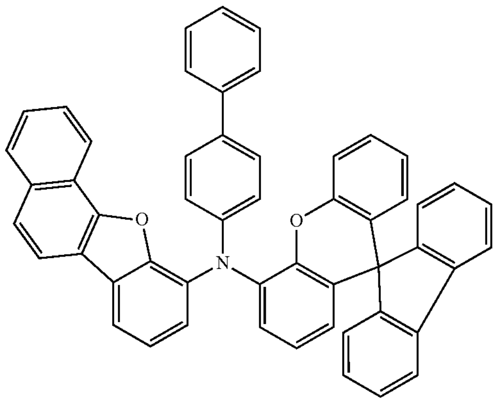
C125
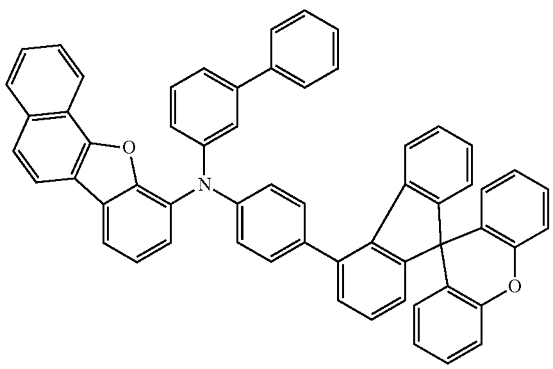
C126
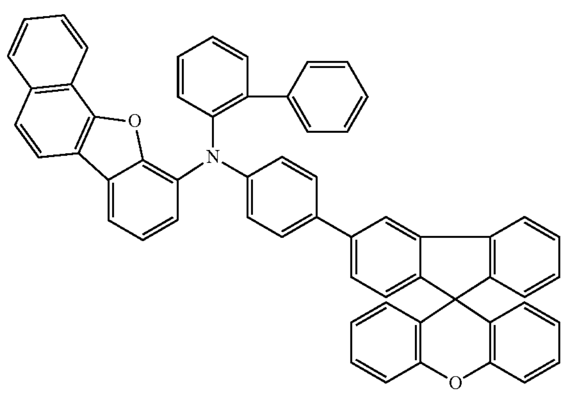
C127
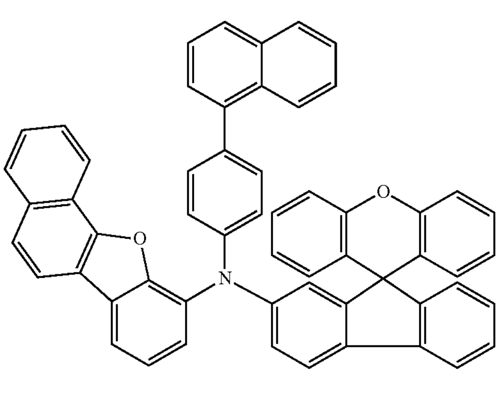
-continued
C128
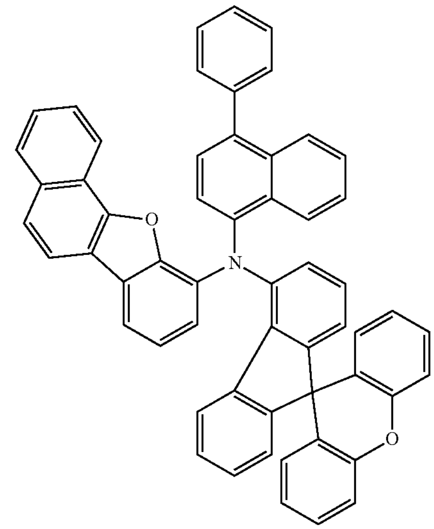
C129
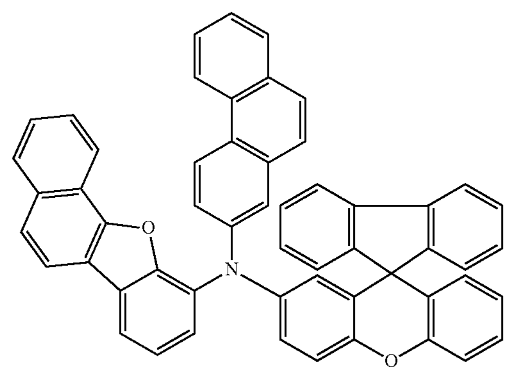
C130
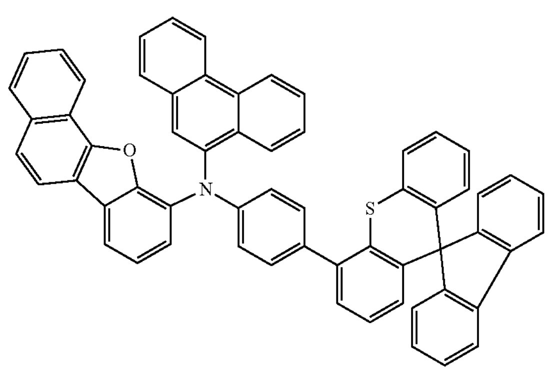

-continued
C131
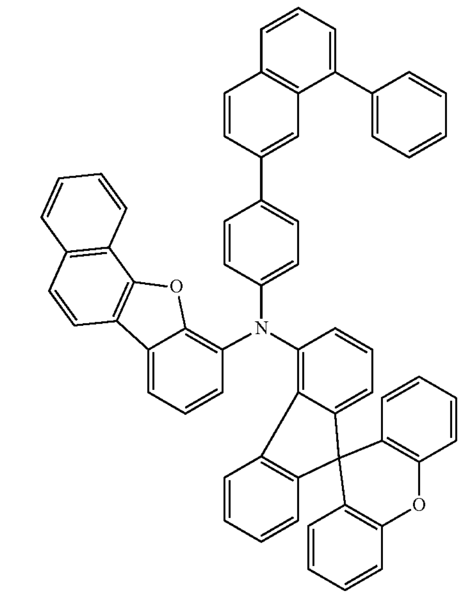
C132
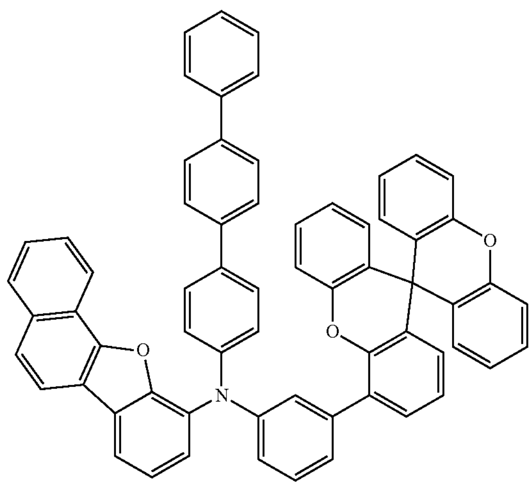
C133
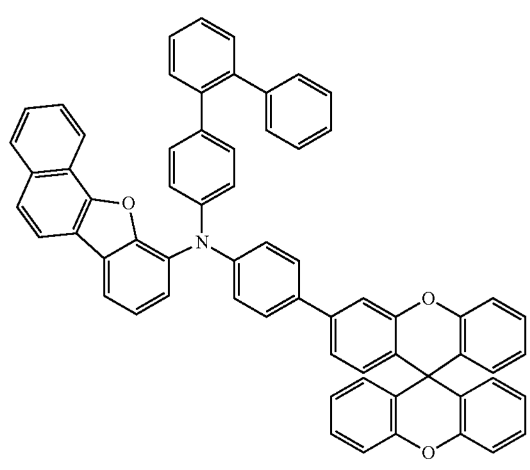
-continued
C134
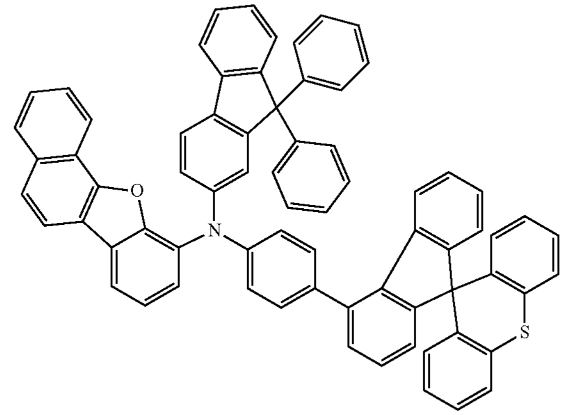
C135
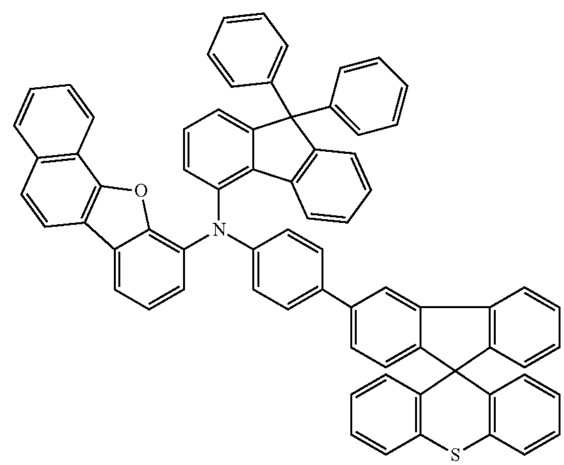
C136
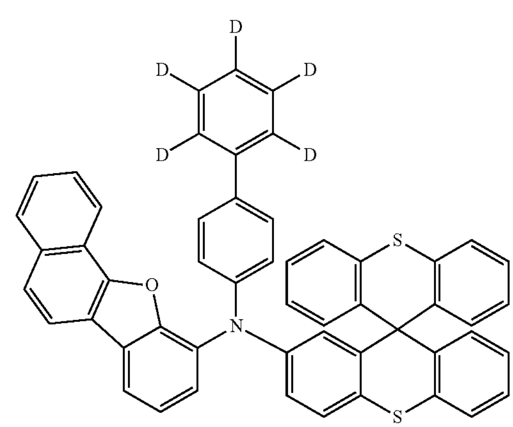

-continued
C137
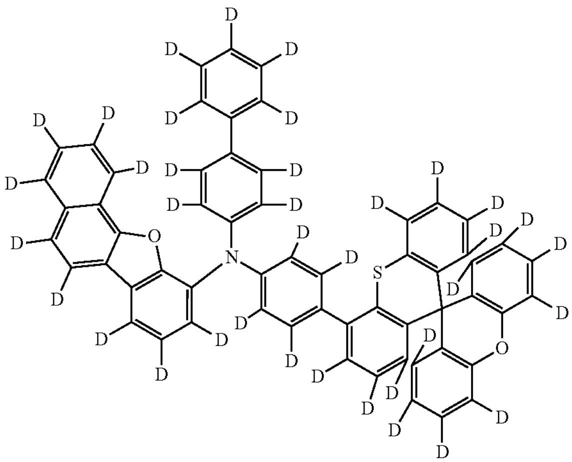
C138
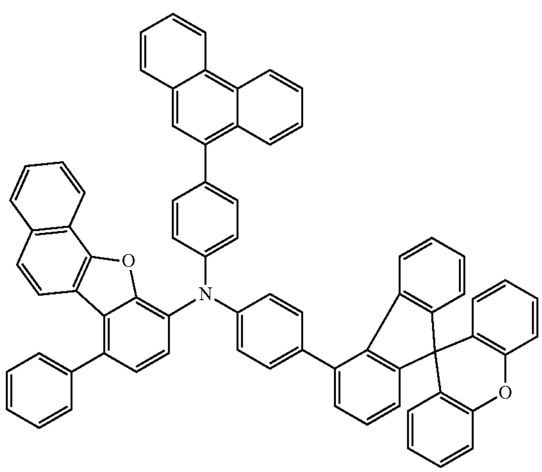
C139
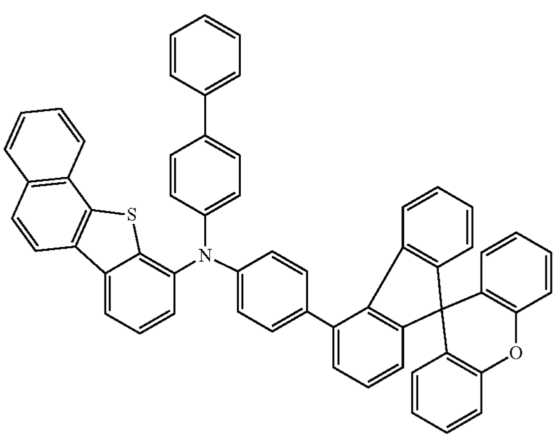
-continued
C140
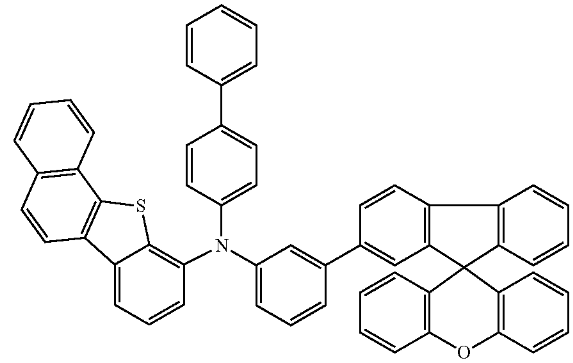
C141
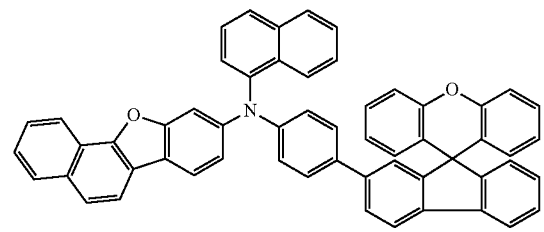
C142
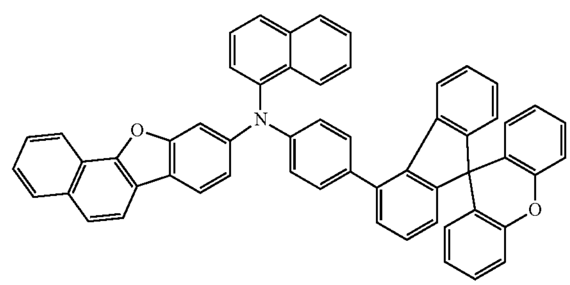
C143
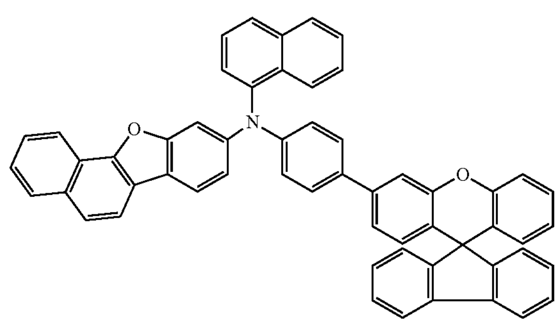

-continued
C144
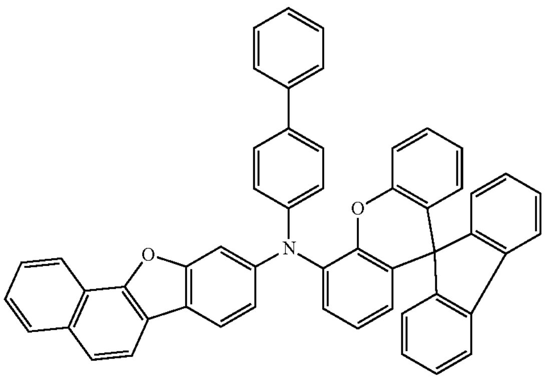
C145
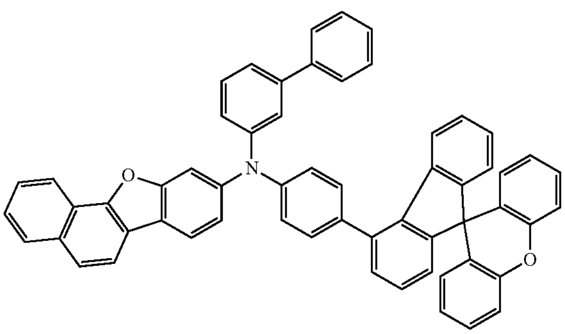
C146
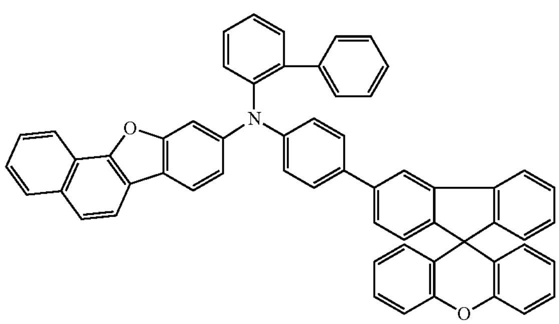
C147
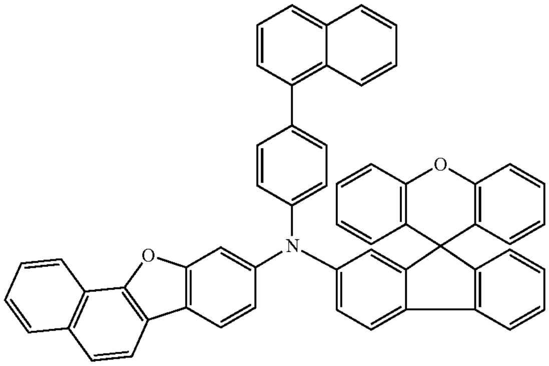
-continued
C148
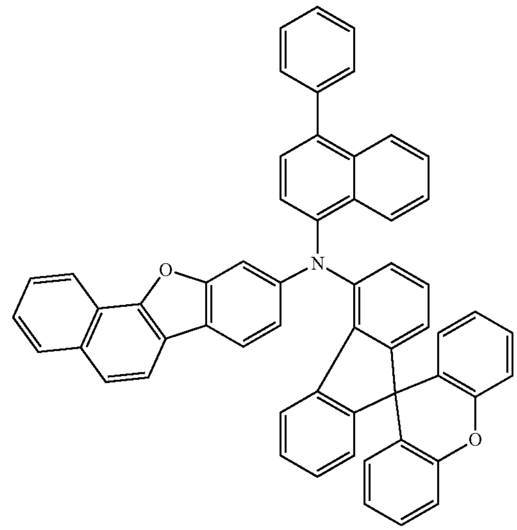
C149
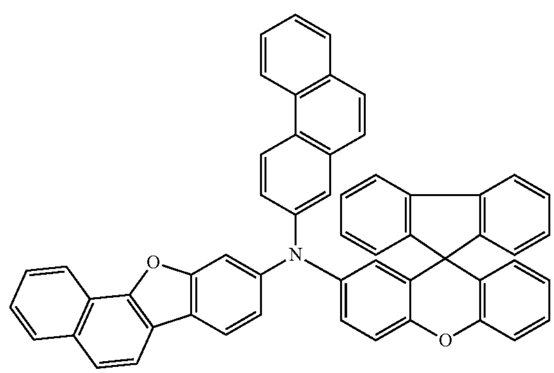
C150
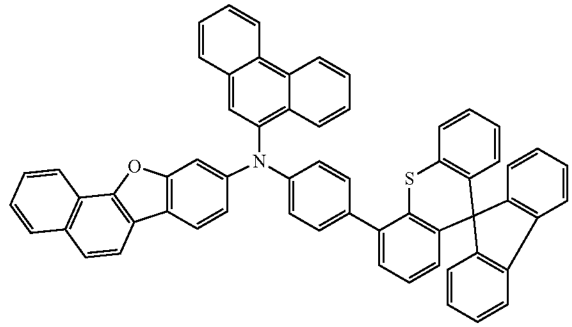

-continued
C151
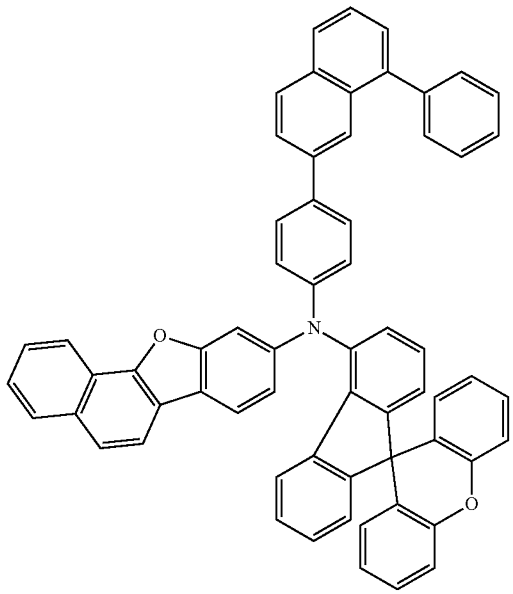
C152
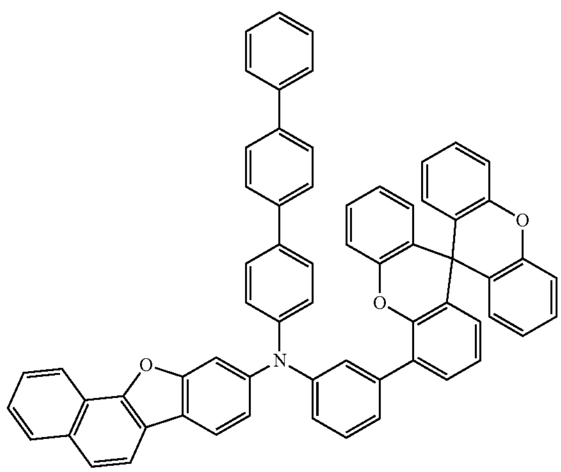
C153
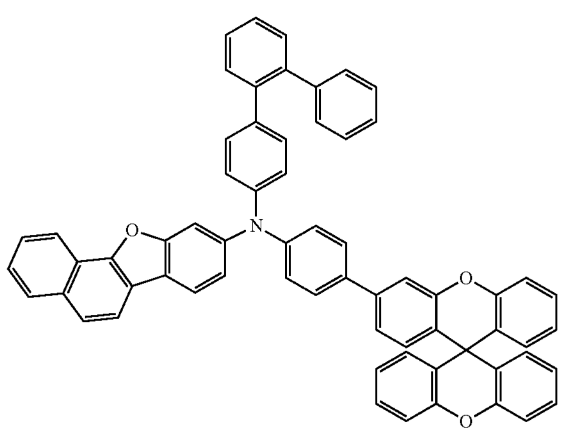
-continued
C154
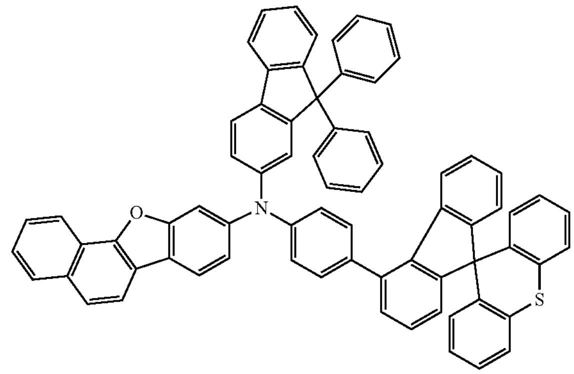
C155
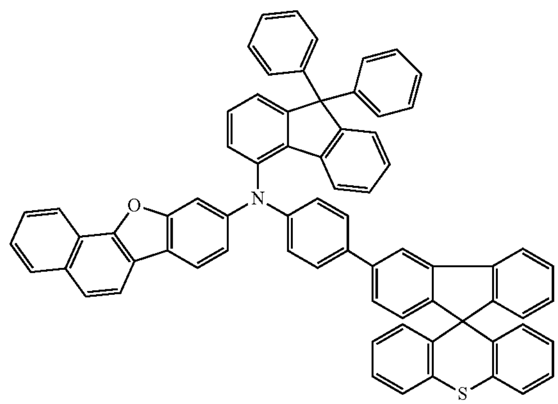
C156
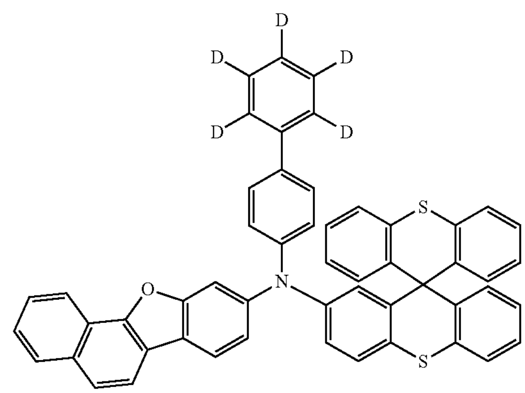
C157
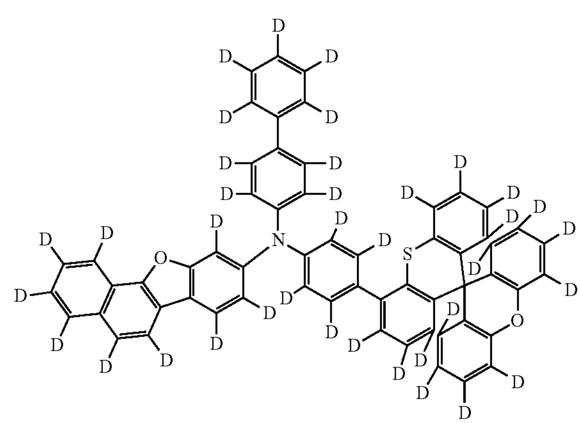

-continued
C158
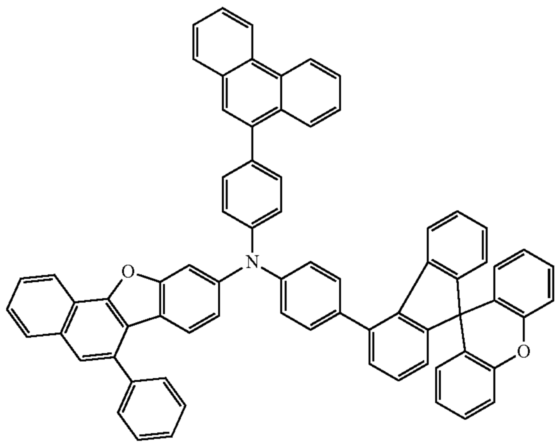
C159
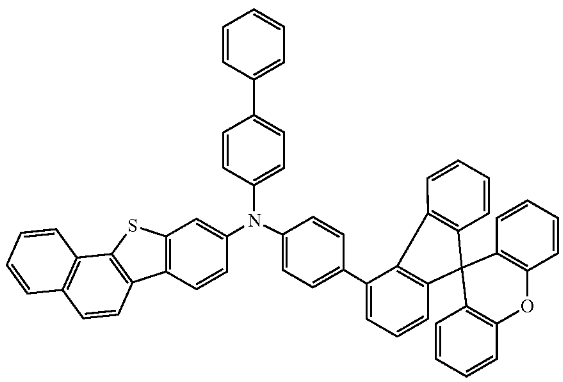
C160
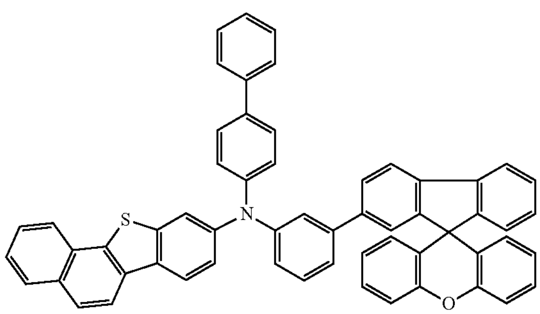
C161
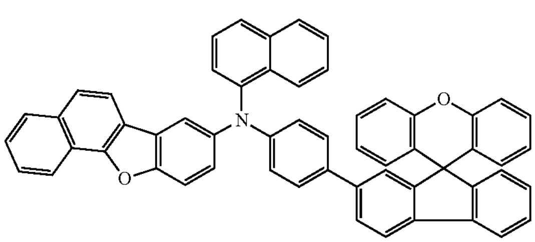
-continued
C162
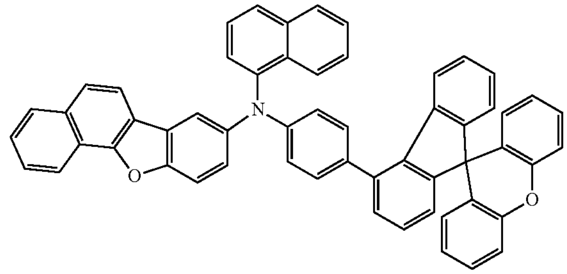
C163
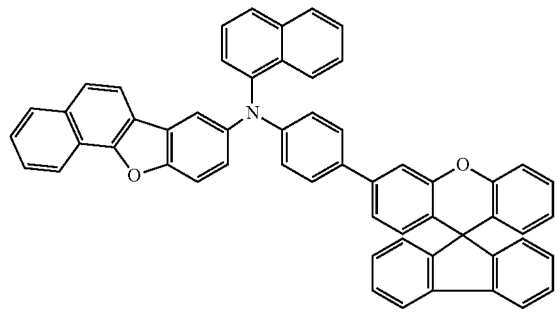
C164
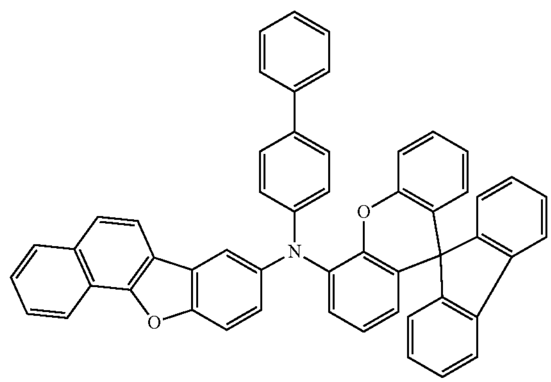
C165
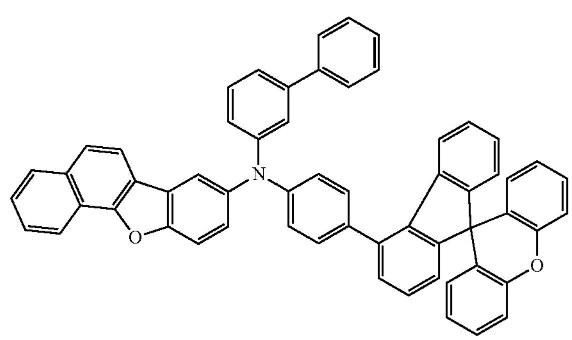

-continued
C166
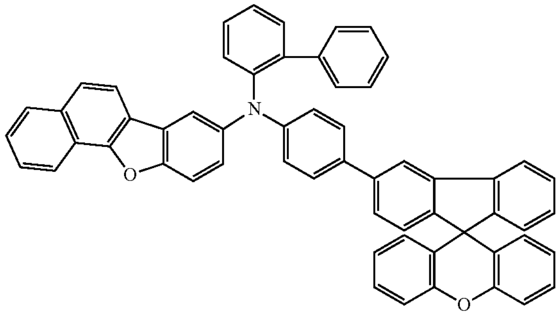
C167
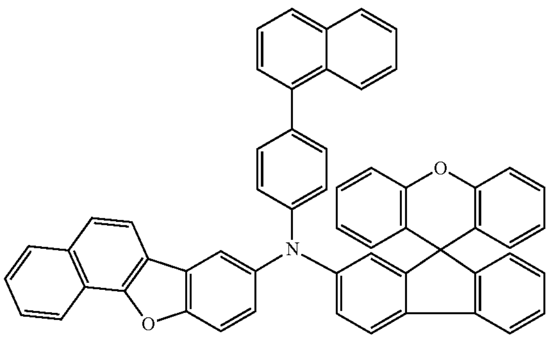
C168
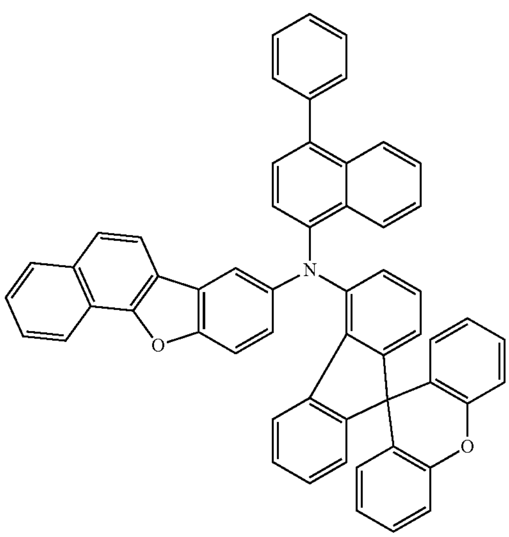
C169
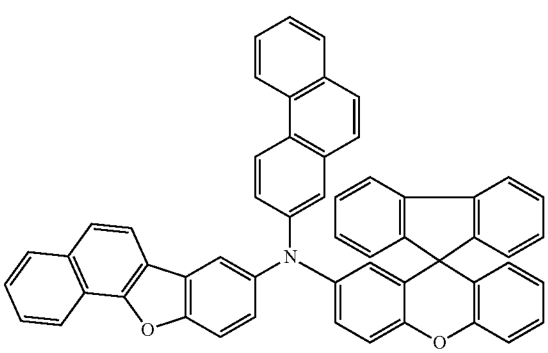
-continued
C170
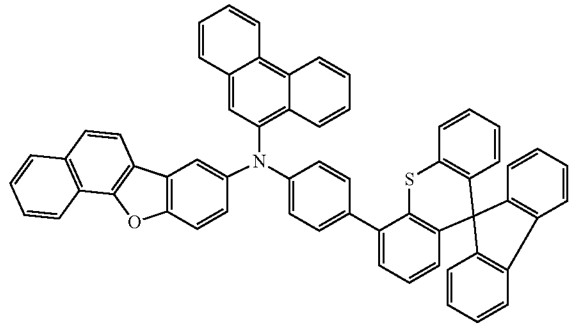
C171
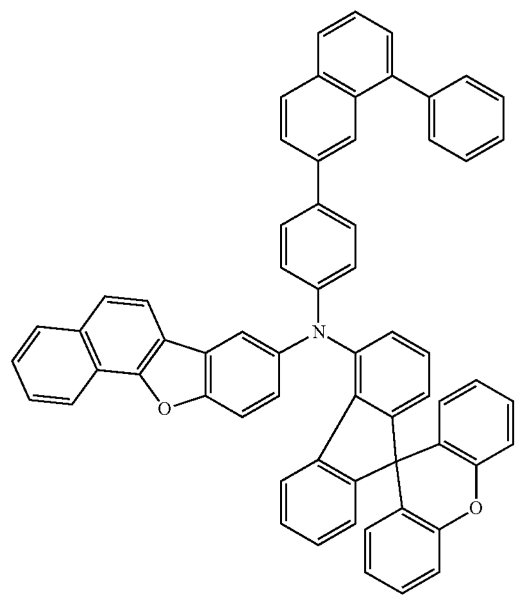
C172
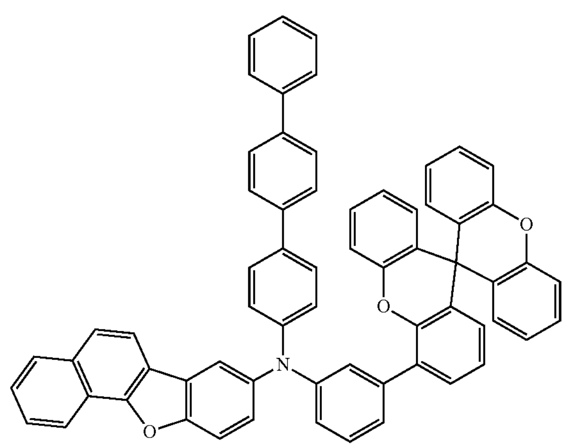

-continued
C173
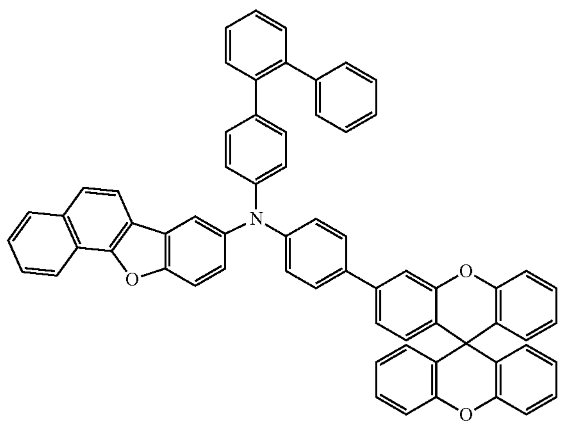
C174
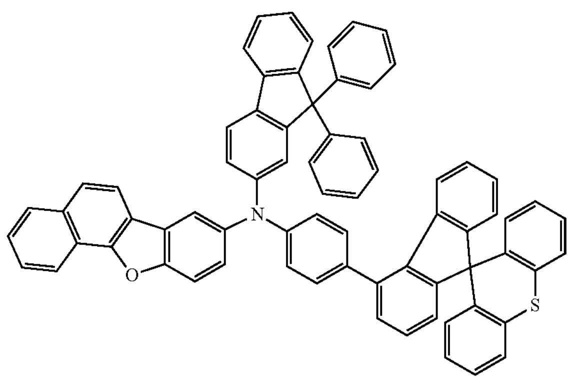
C175
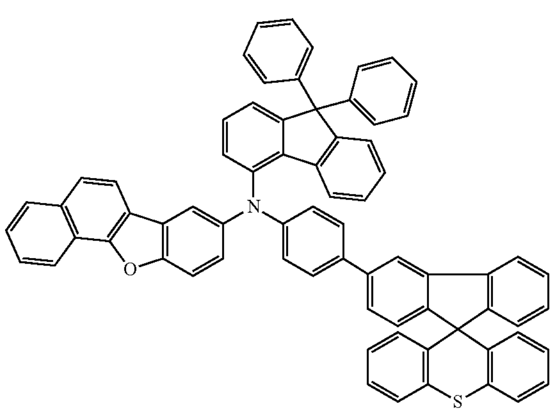
-continued
C176
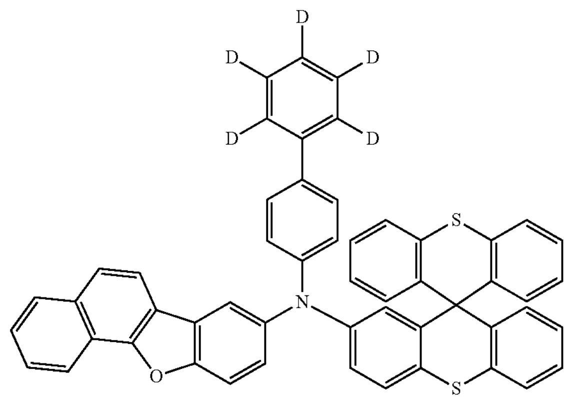
C177
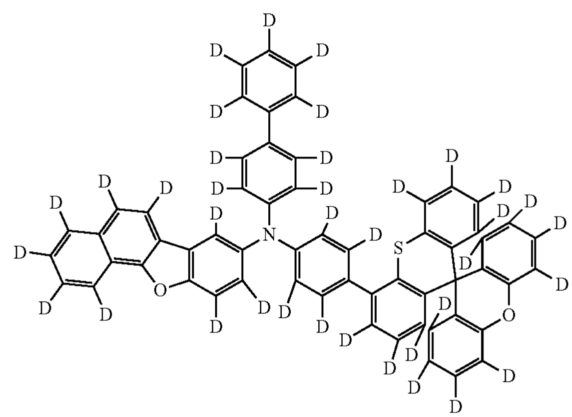
C178
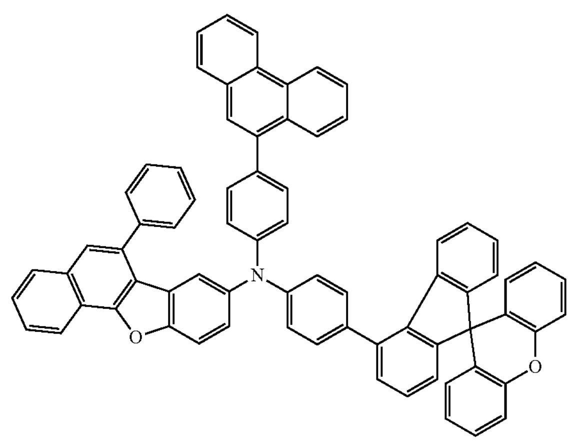

-continued
C179
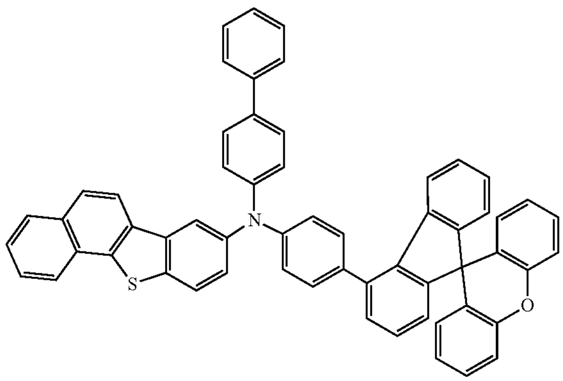
C180
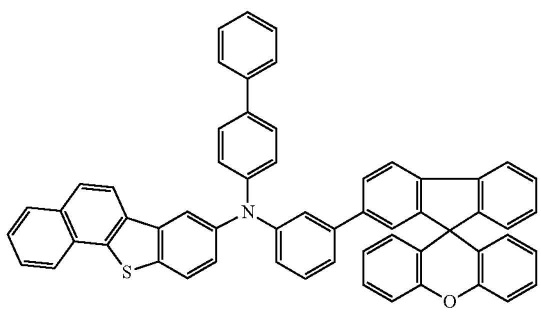
C181
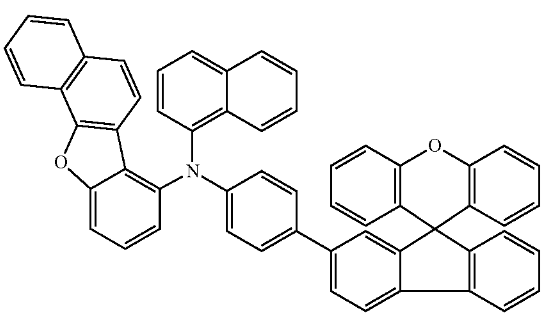
C182
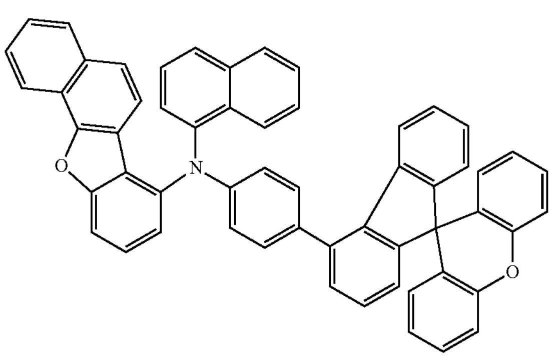
-continued
C183
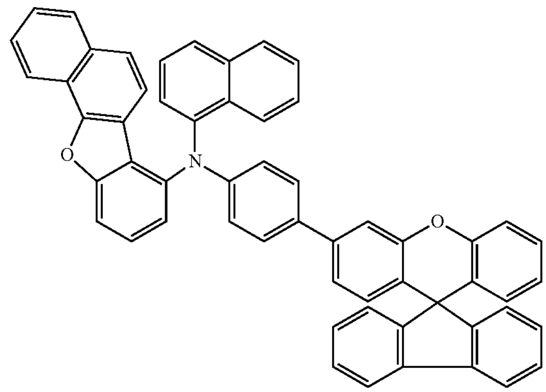
C184
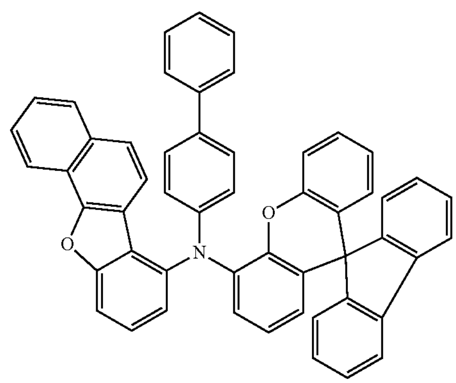
C185
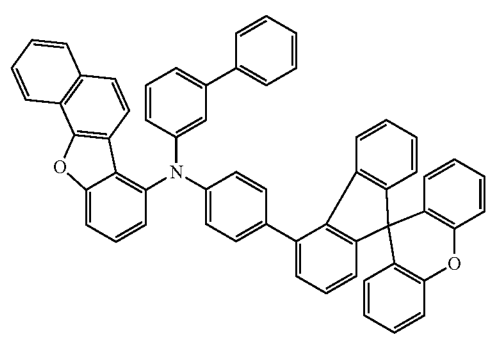
C186
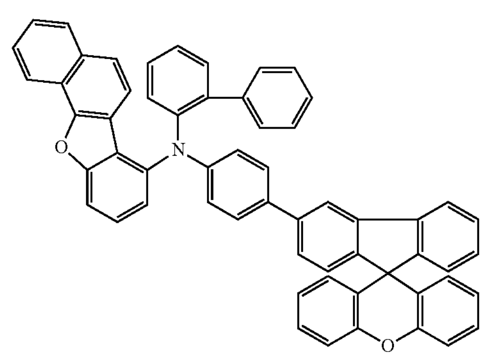

-continued
C187
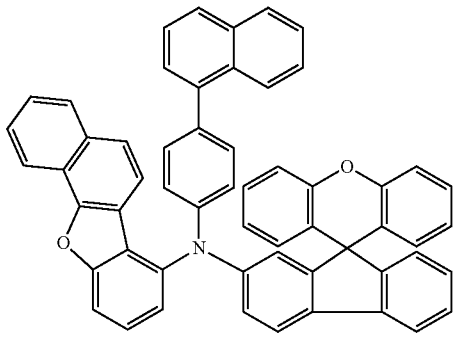
C188
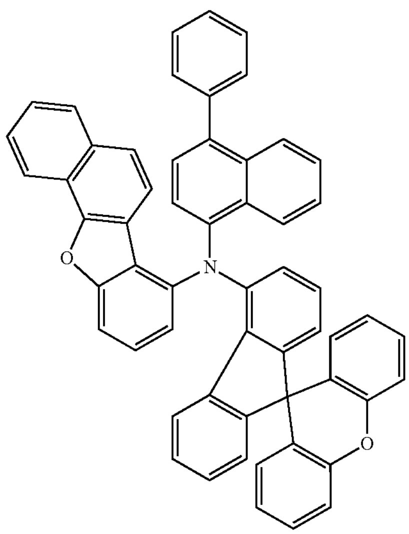
C189
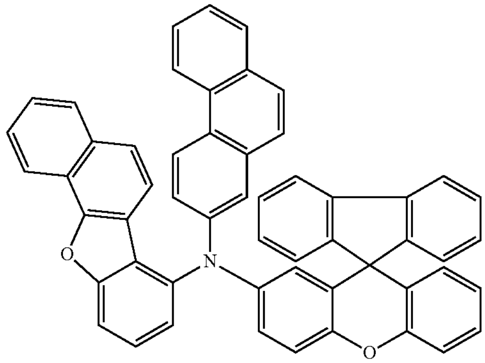
-continued
C190
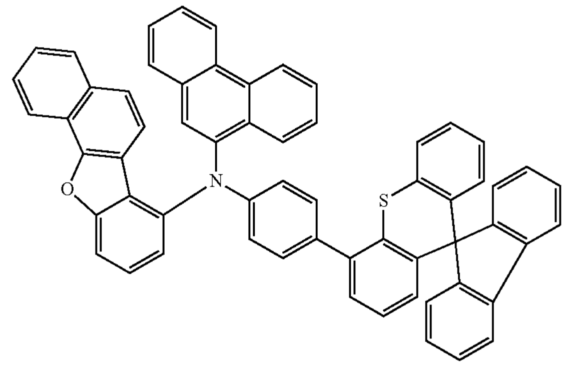
C191
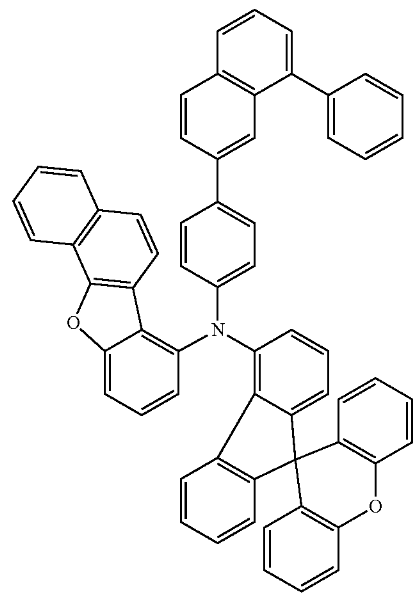
C192
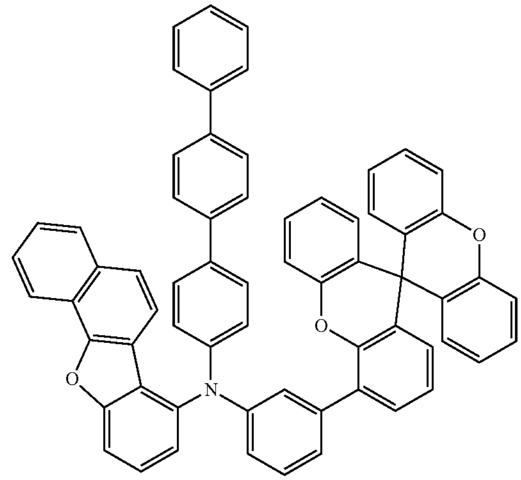

-continued
C193
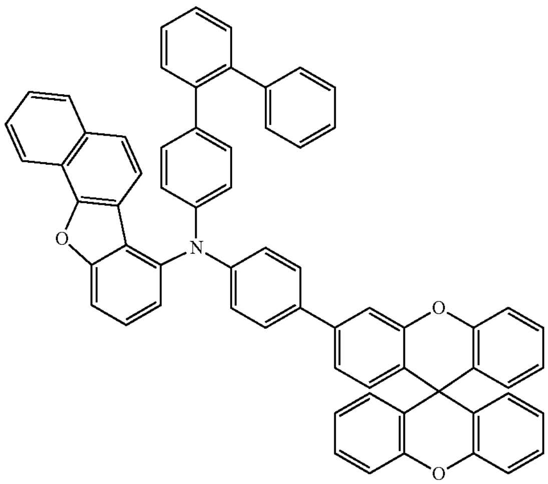
C194
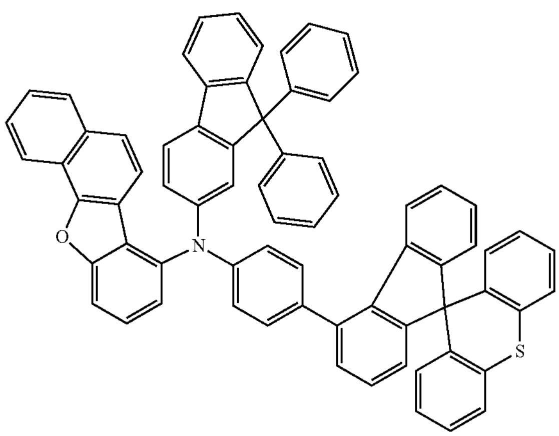
C195
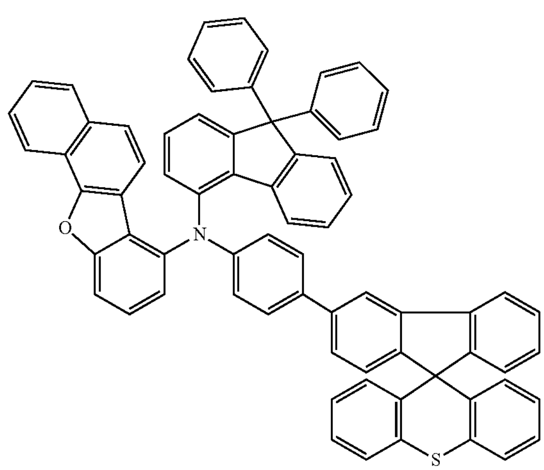
-continued
C196
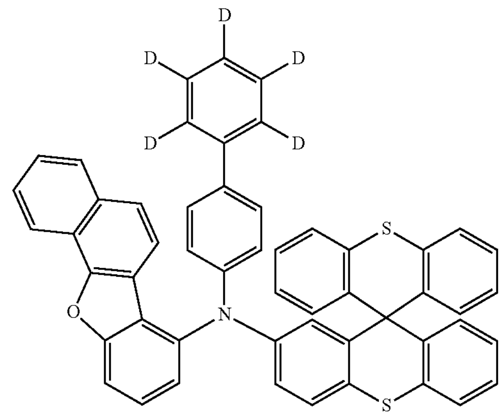
C197
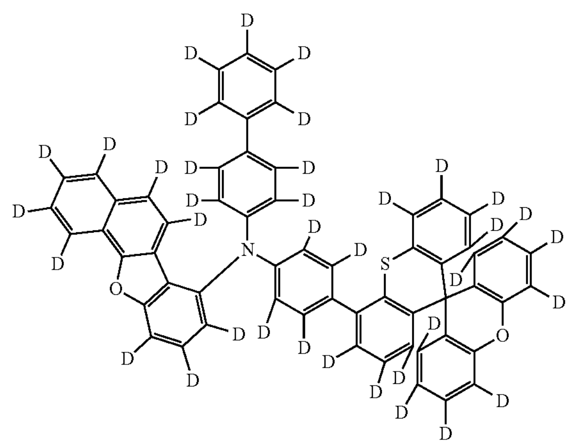
C198
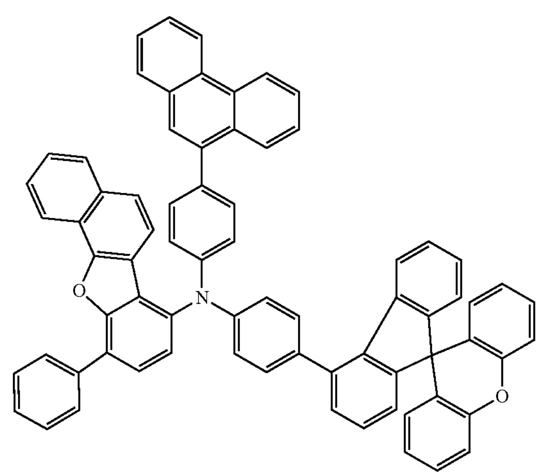

-continued
C199
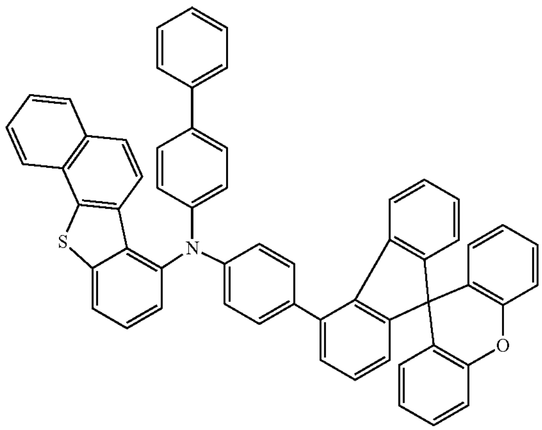
C200
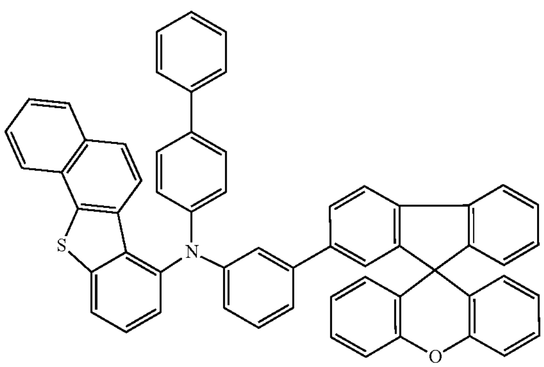
[Compound Group 4]
D1
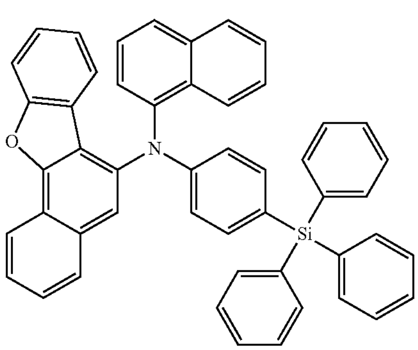
-continued
D2
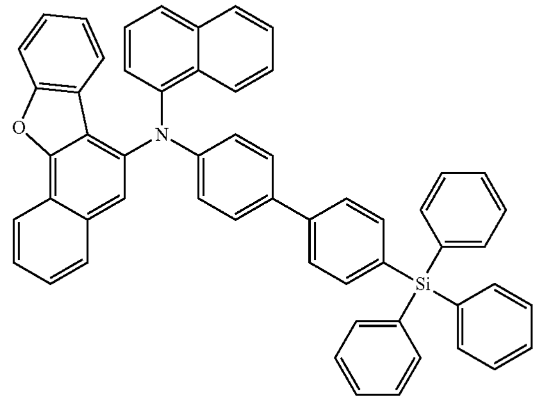
D3
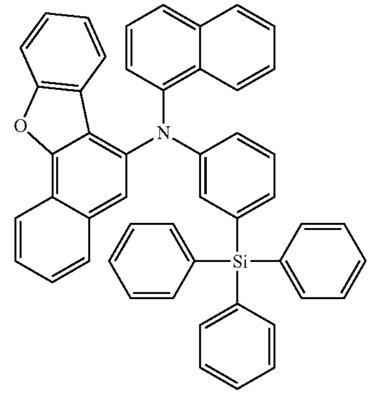
D4
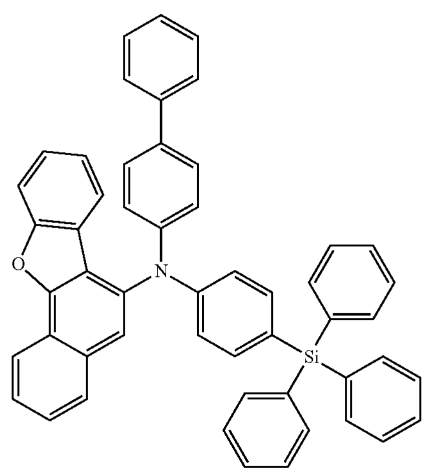

-continued
D5
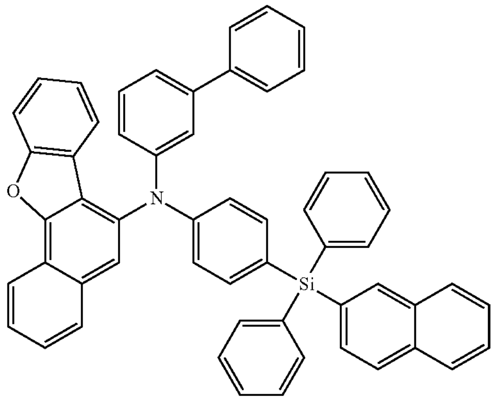
D6
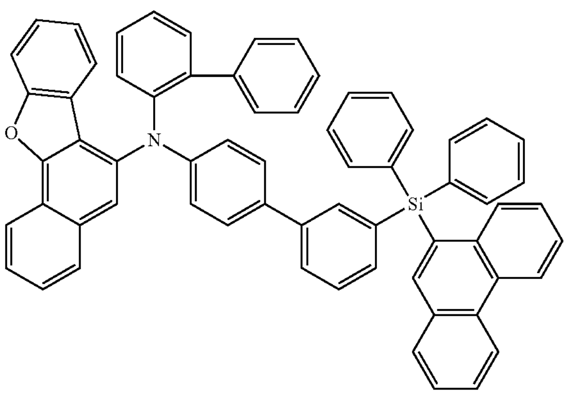
D7
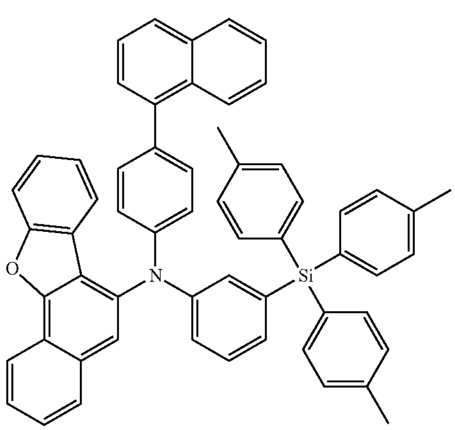
-continued
D8
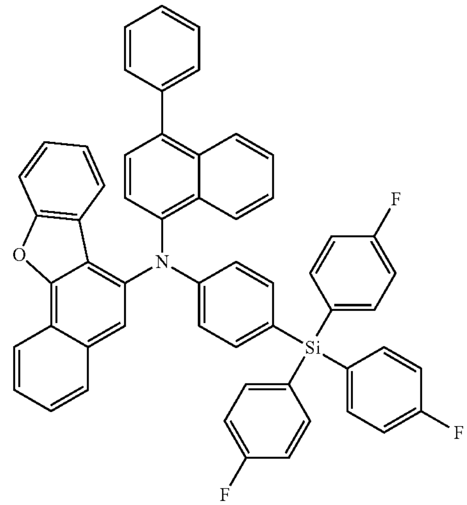
D9
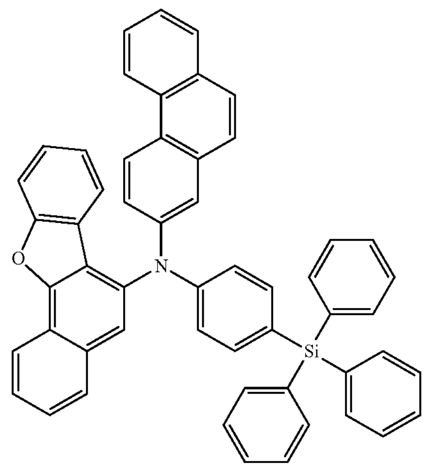
D10
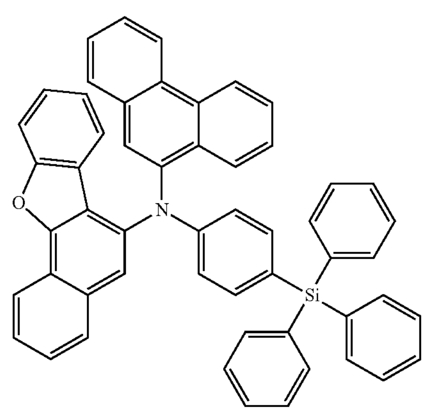

-continued
D11
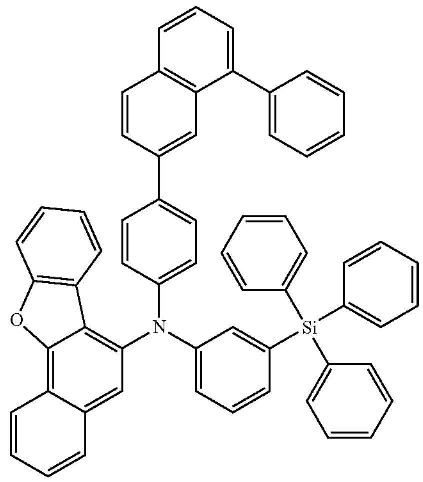
D12
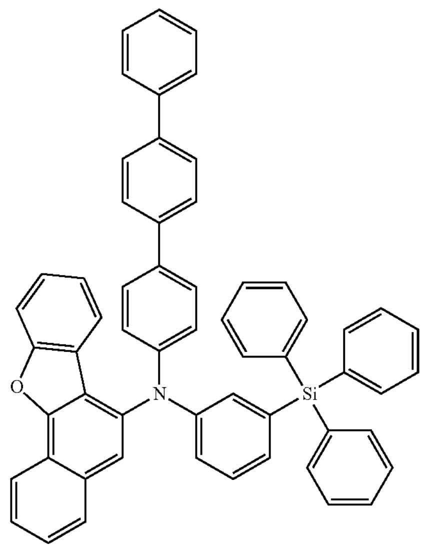
D13
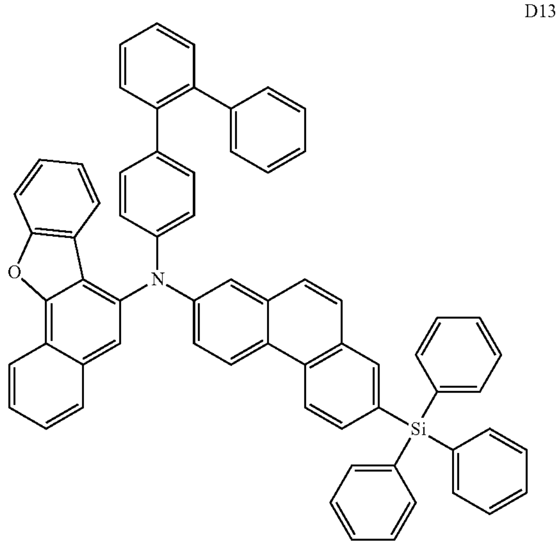
-continued
D14
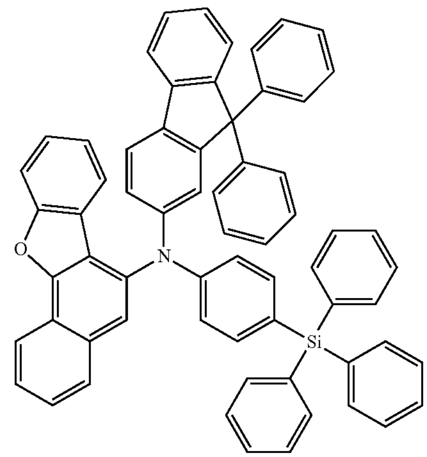
D15
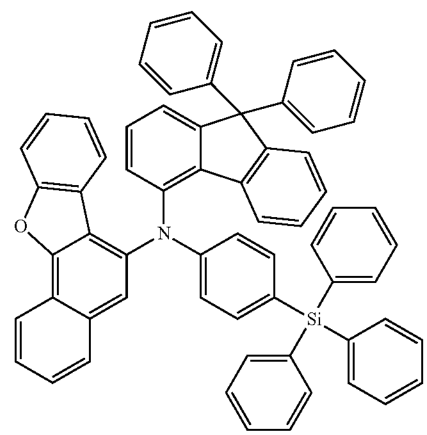
D16
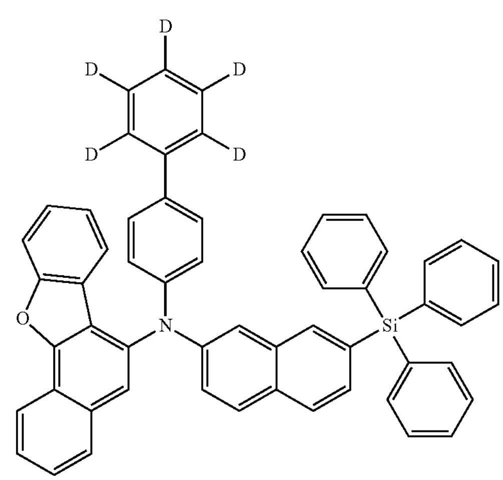

-continued
D18
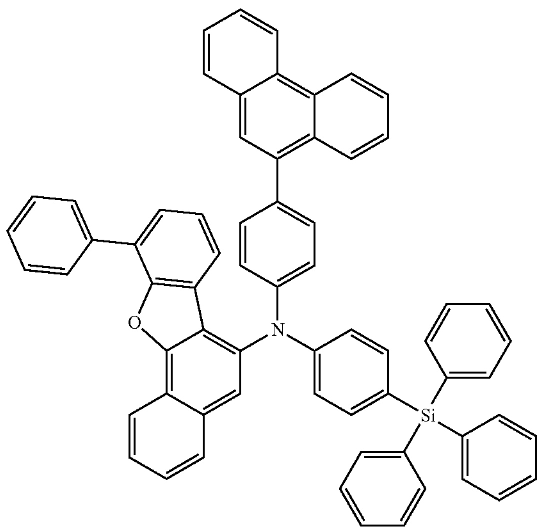
D19
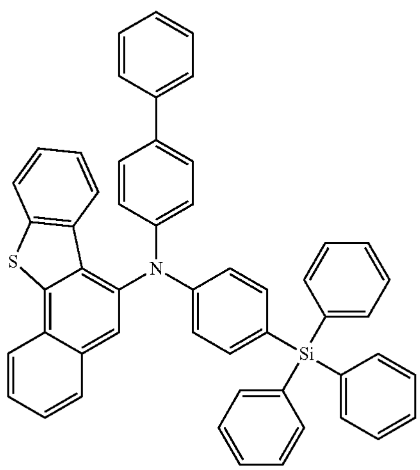
D20
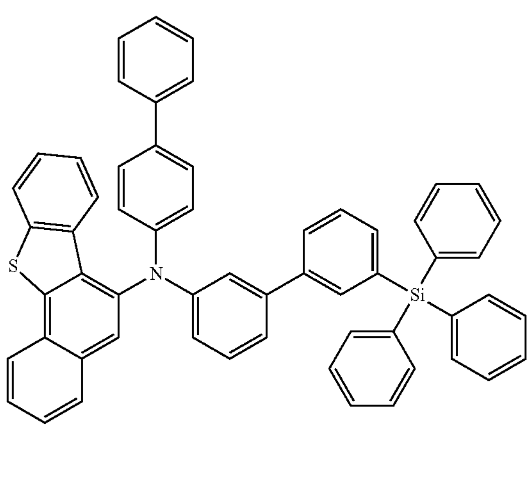
-continued
D21
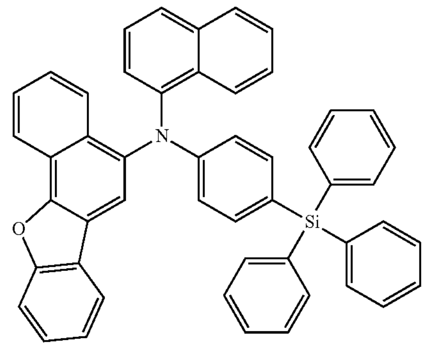
D22
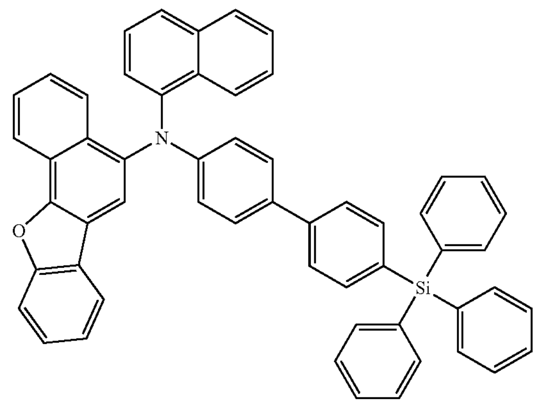
D23
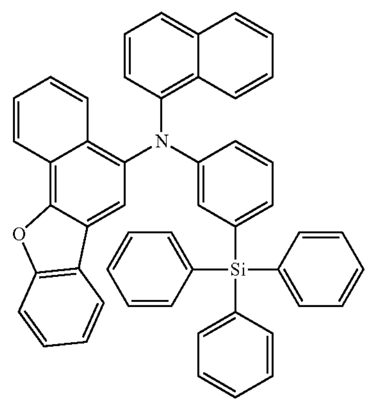
D24
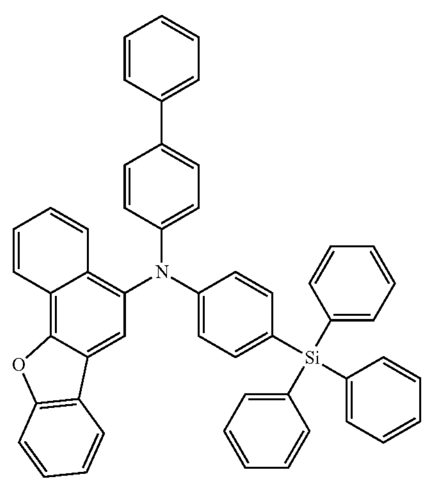

-continued
D25
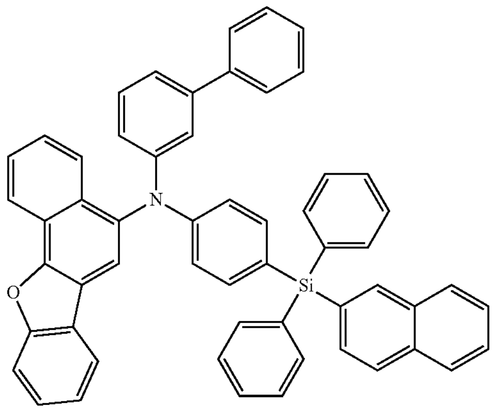
D26
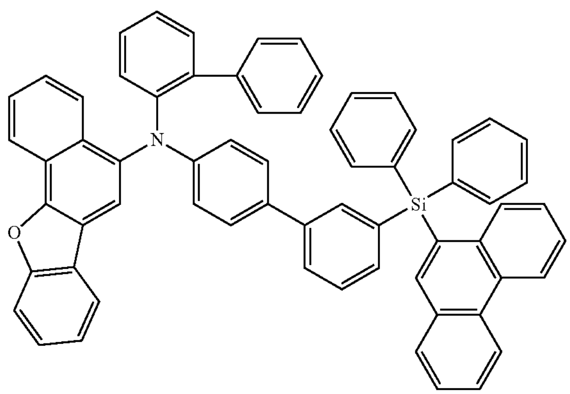
D27
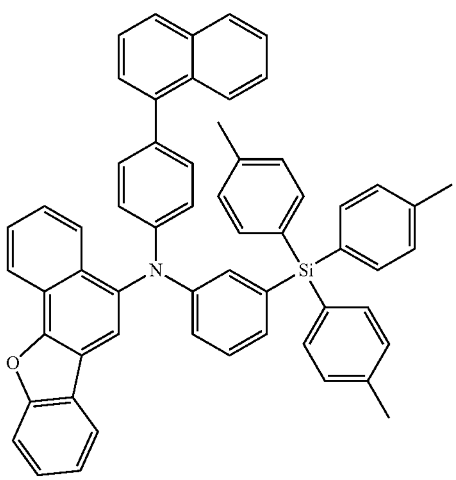
-continued
D28
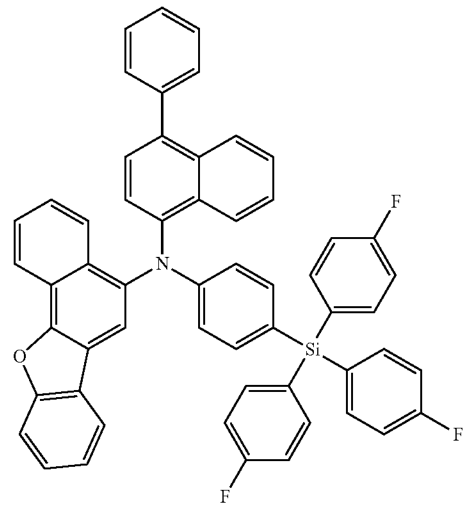
D29
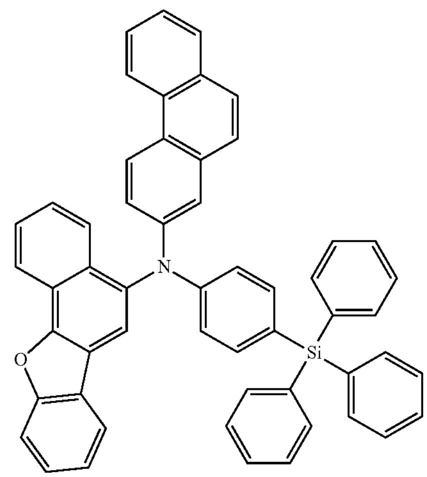
D30
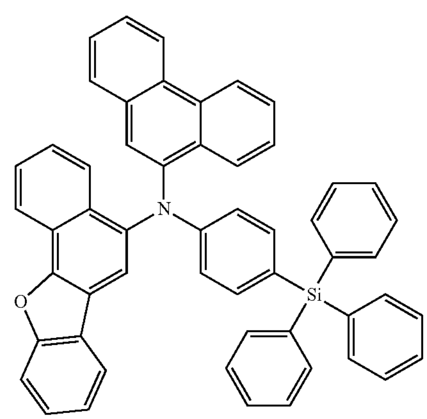

-continued
D31
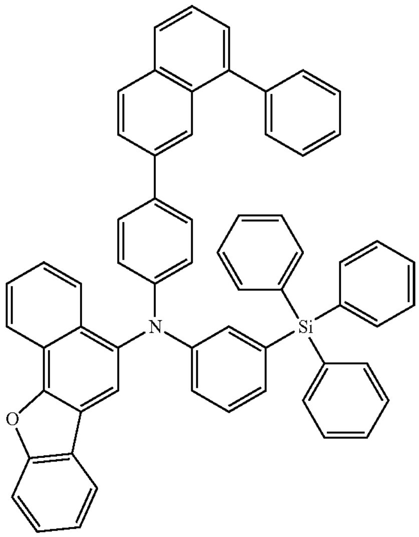
D32
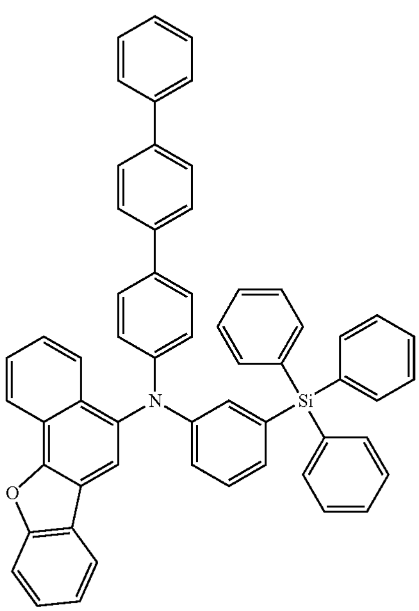
-continued
D33
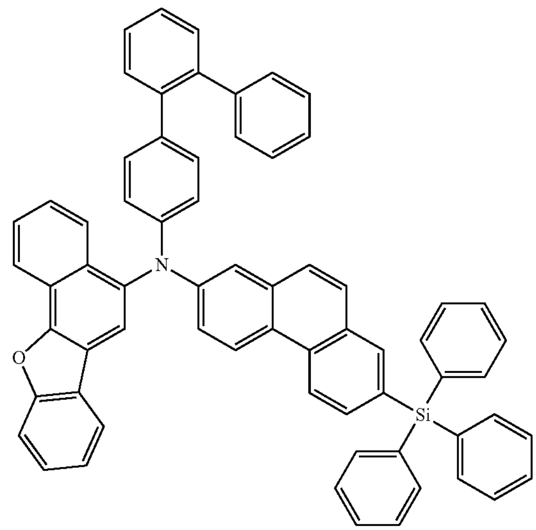
D34
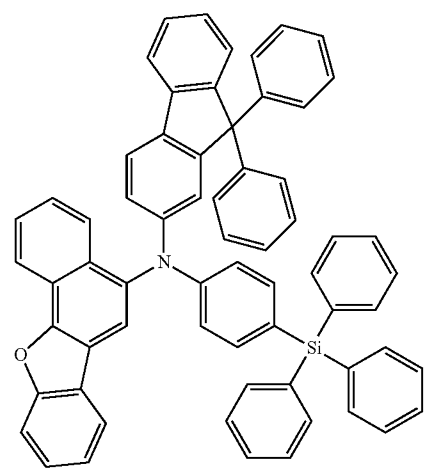
D35
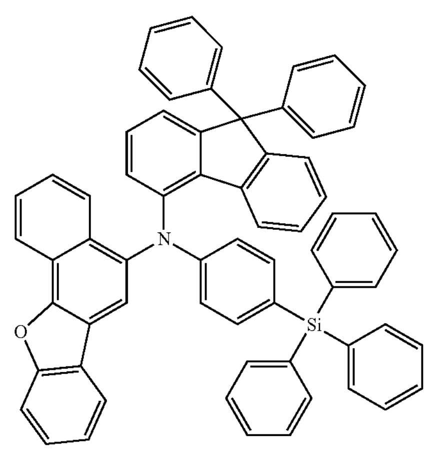

D36
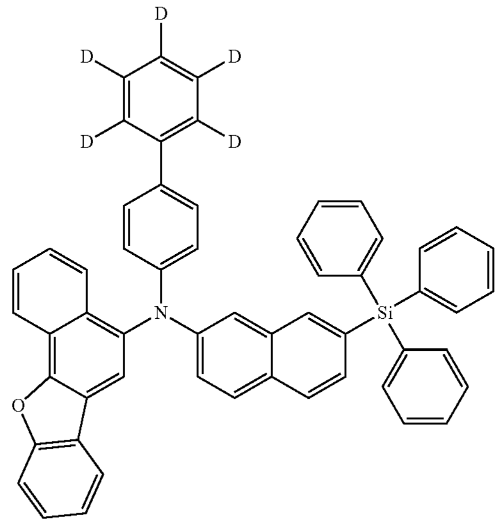
D38
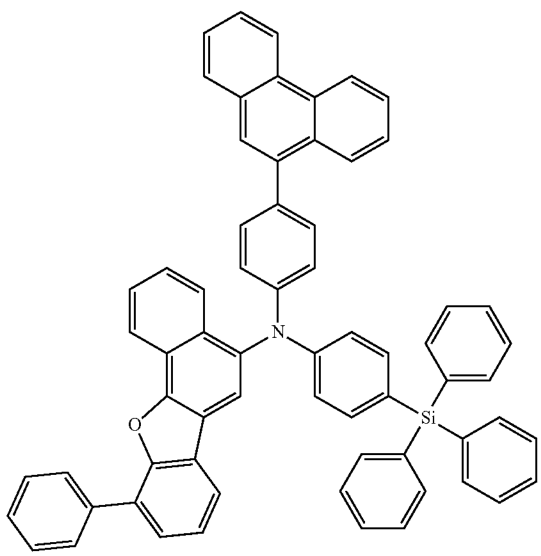
D39
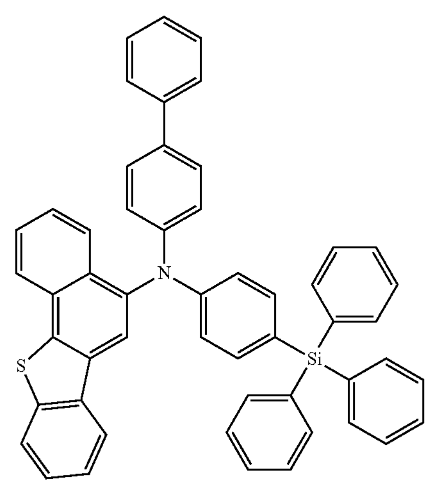
D40
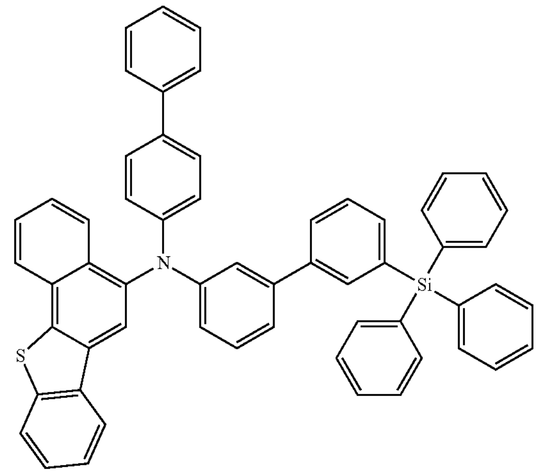
D41
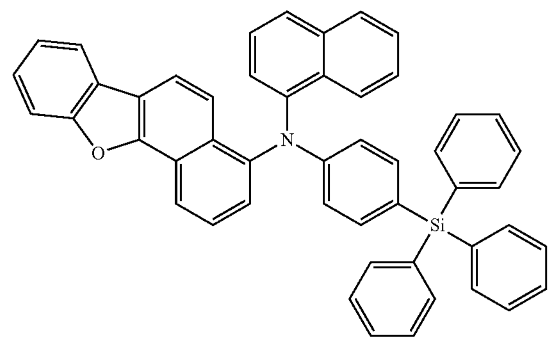
D42
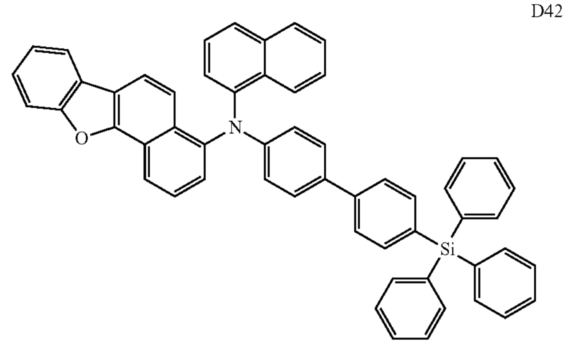
D43
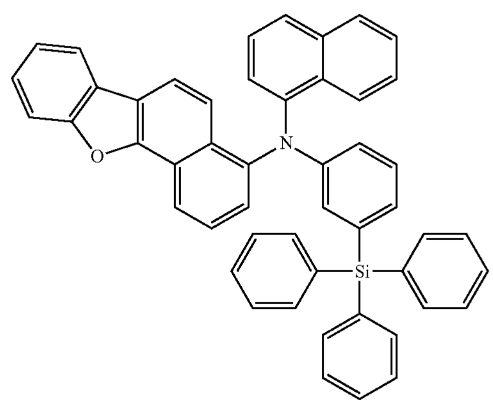

-continued
D44
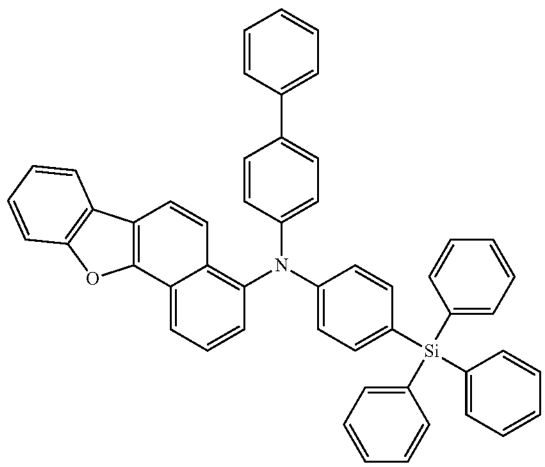
D45
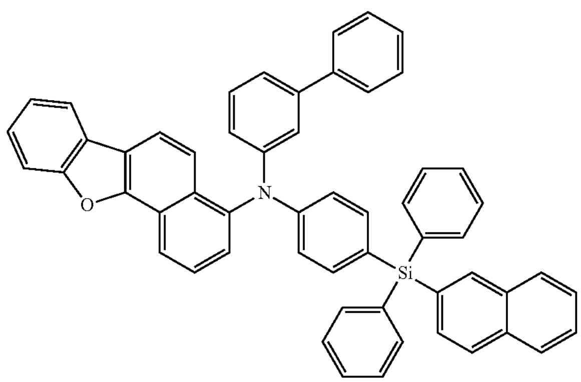
D46
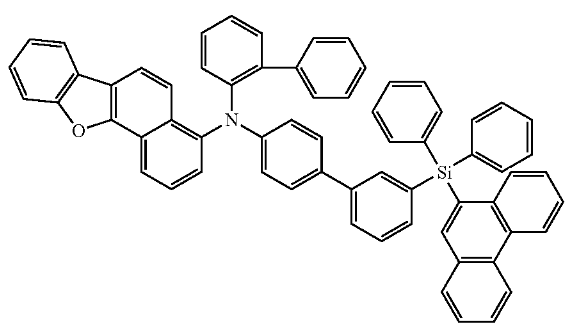
D47
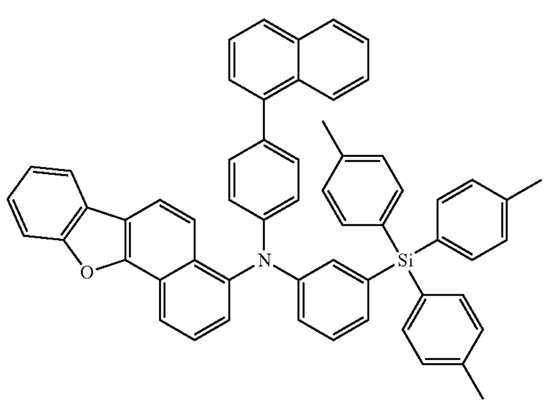
-continued
D48
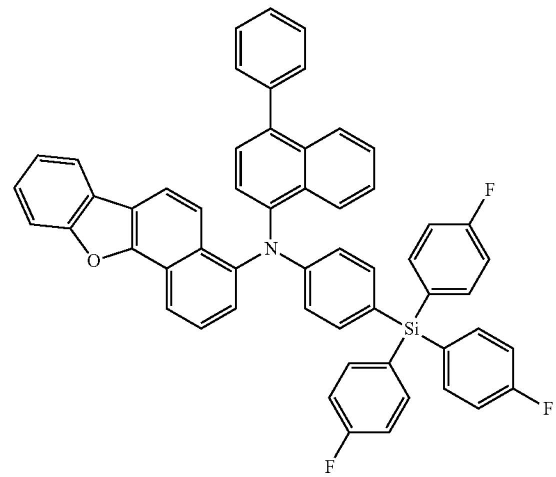
D49
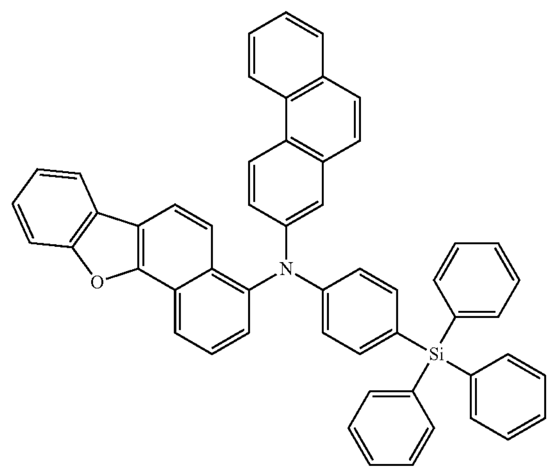
D50
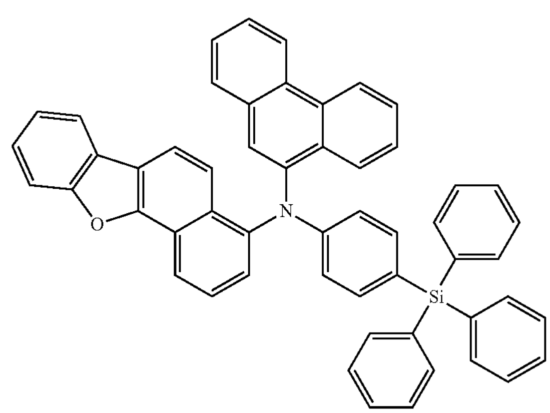

-continued
D51
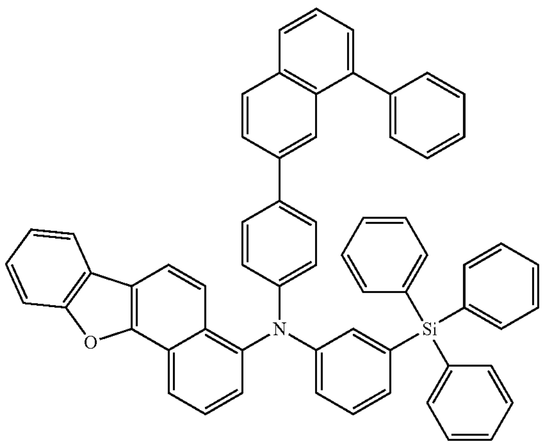
D52
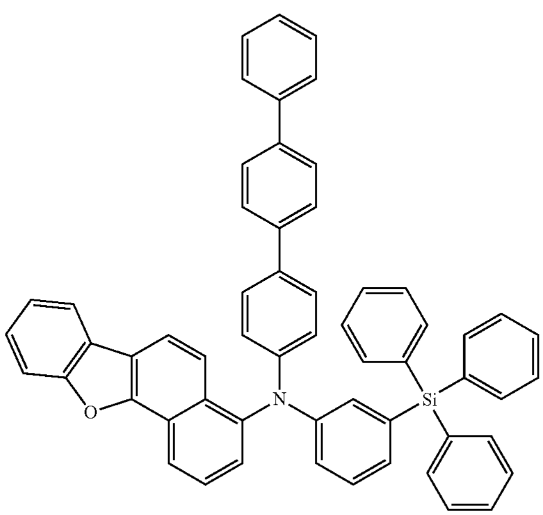
D53
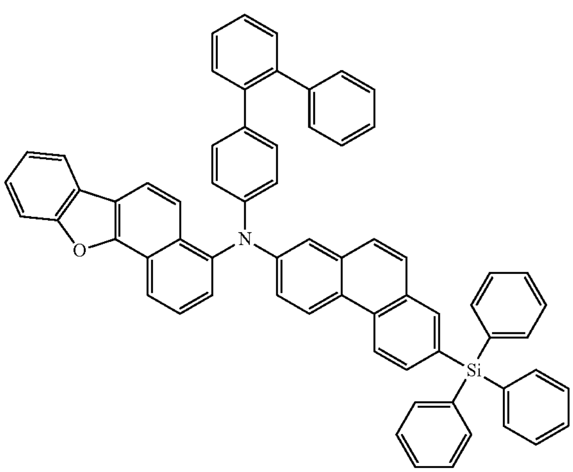
-continued
D54
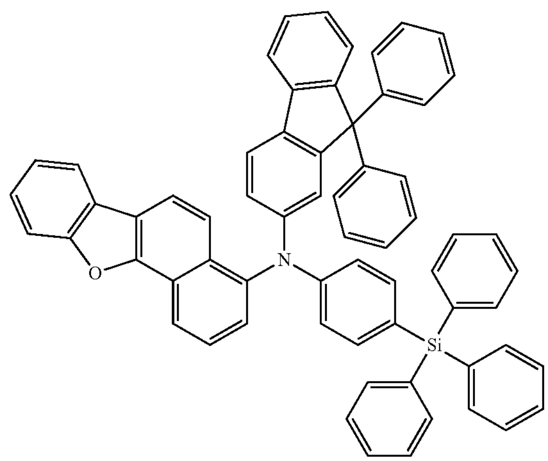
D55
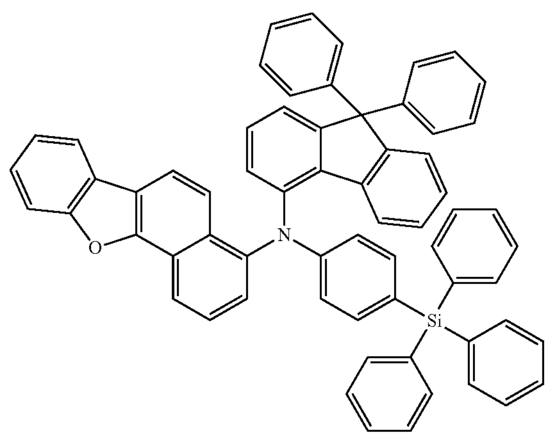
D56
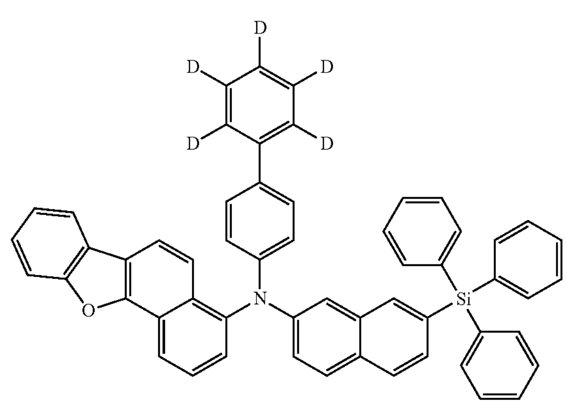

-continued
D58
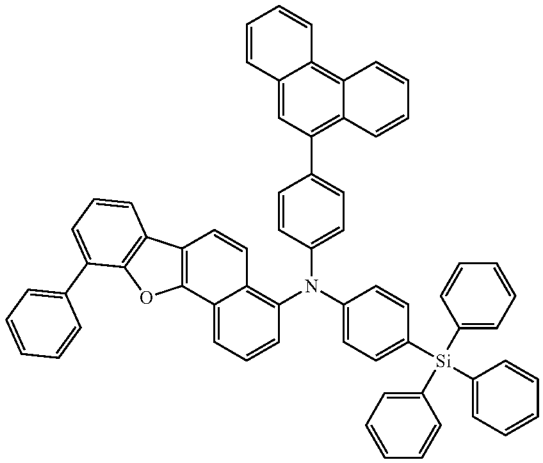
D59
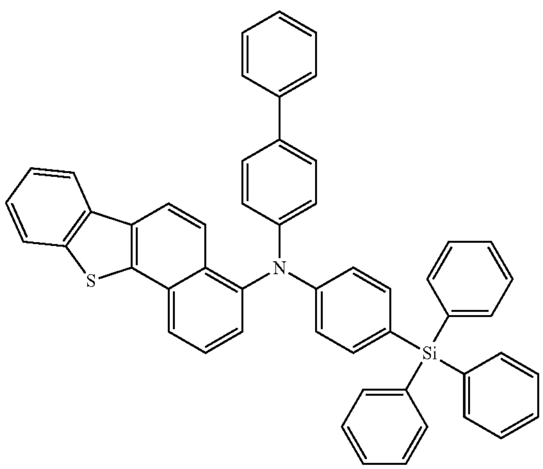
D60
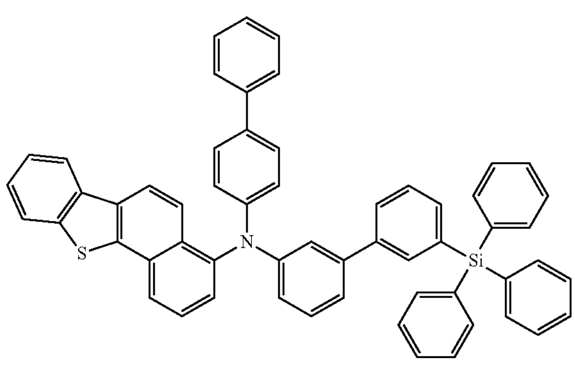
-continued
D61
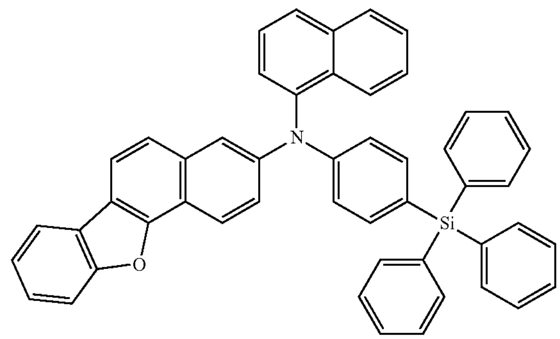
D62
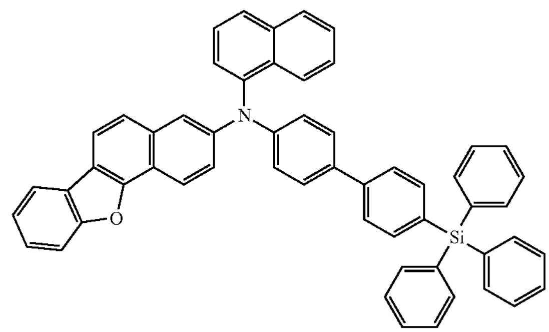
D63
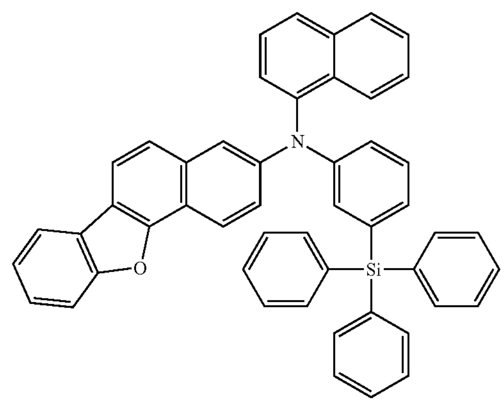
D64
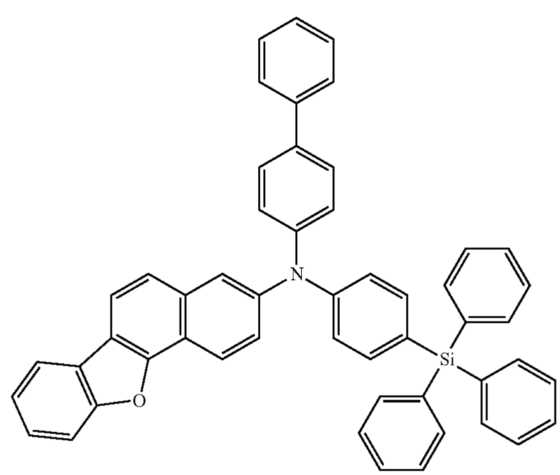

-continued
D65
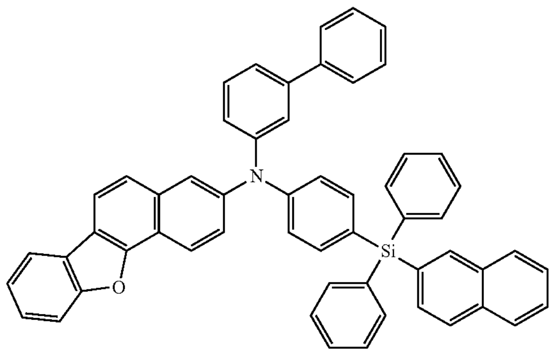
D66
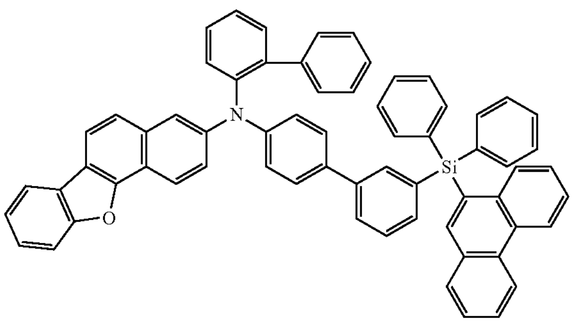
D67
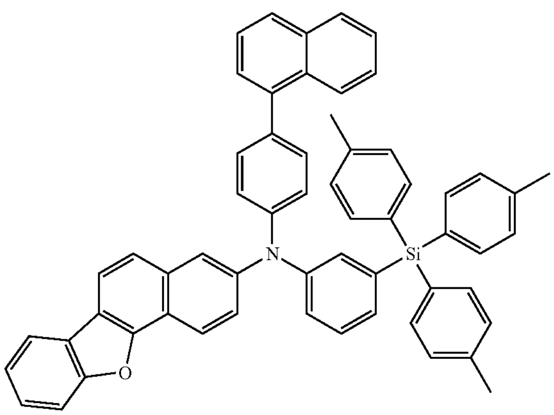
D68
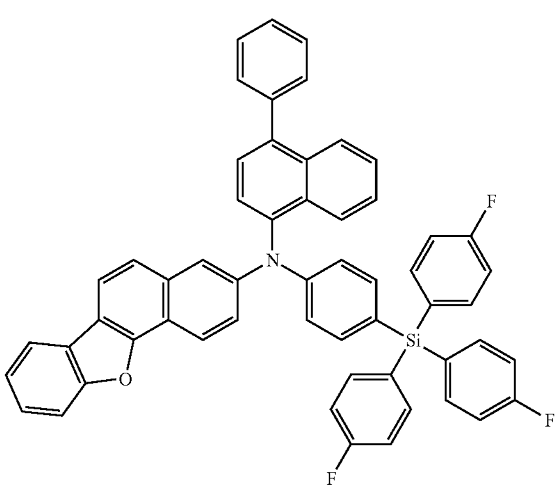
-continued
D69
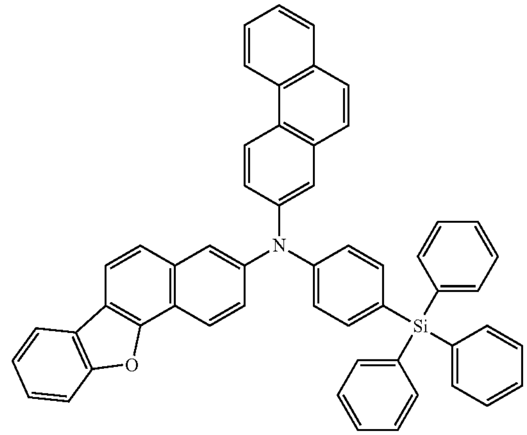
D70
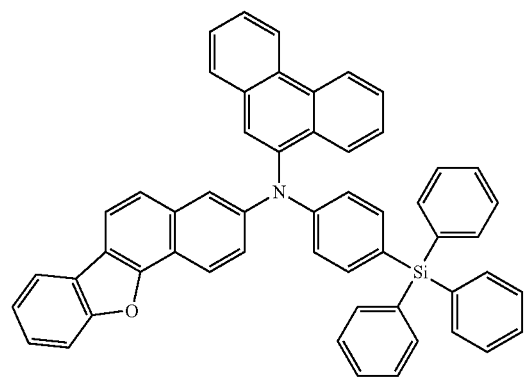
D71
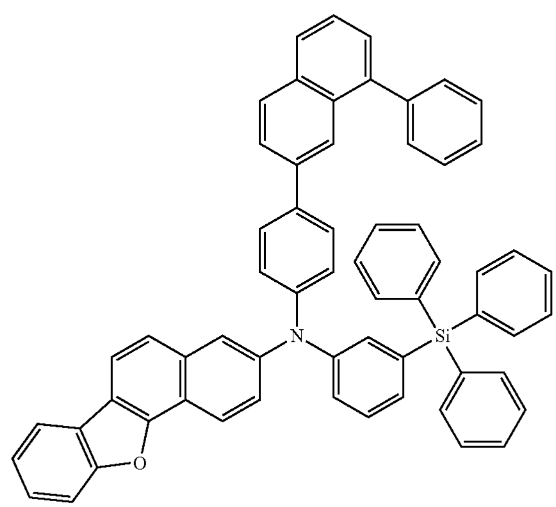

-continued
D72
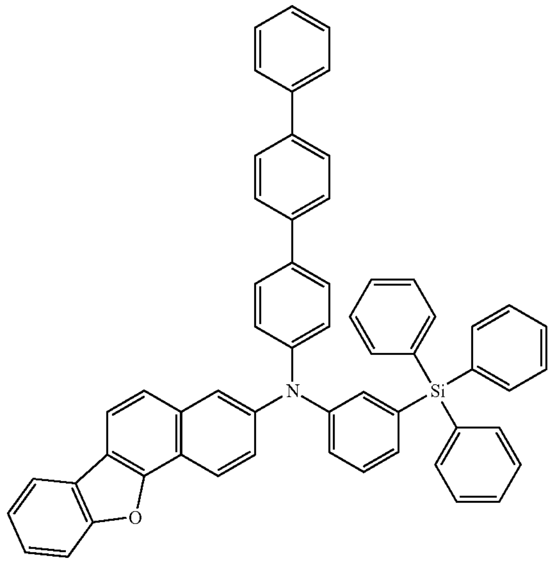
D73
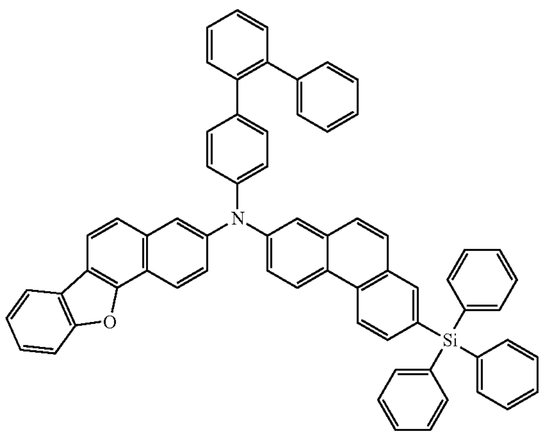
D74
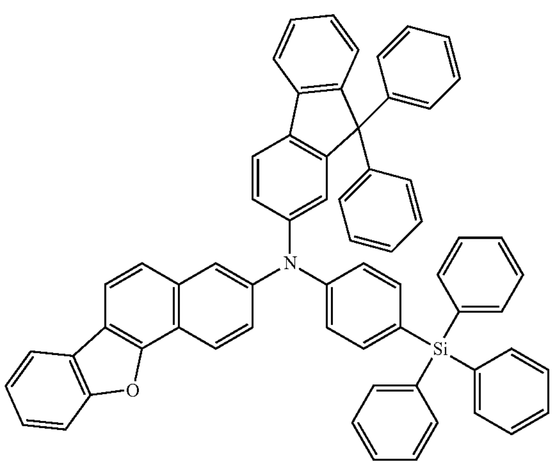
-continued
D75
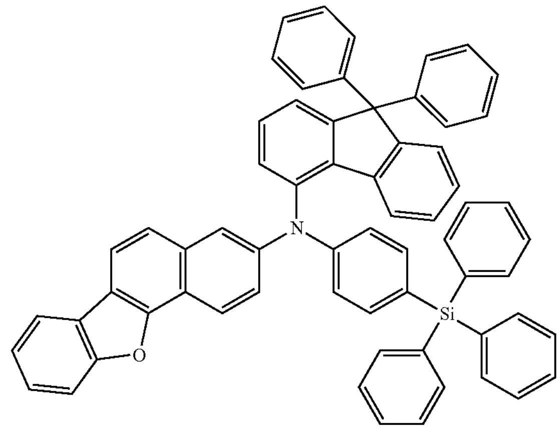
D76
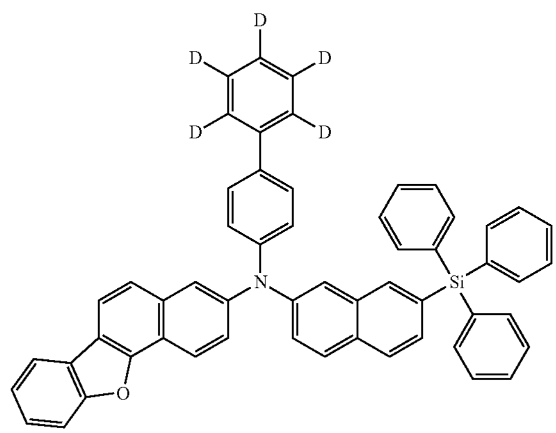
D78
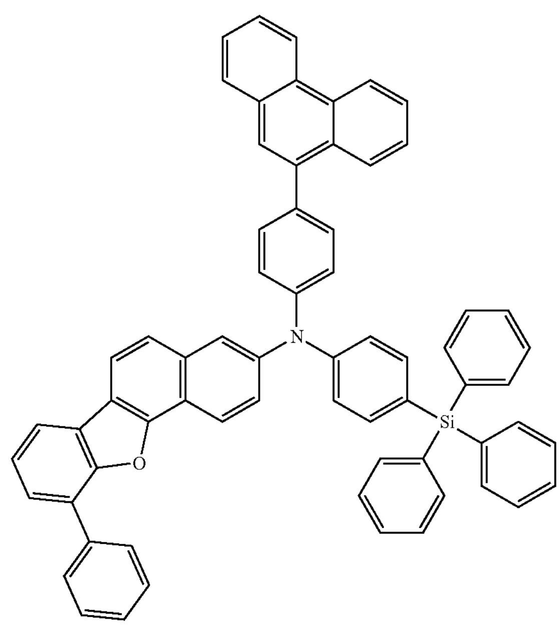

-continued
D79
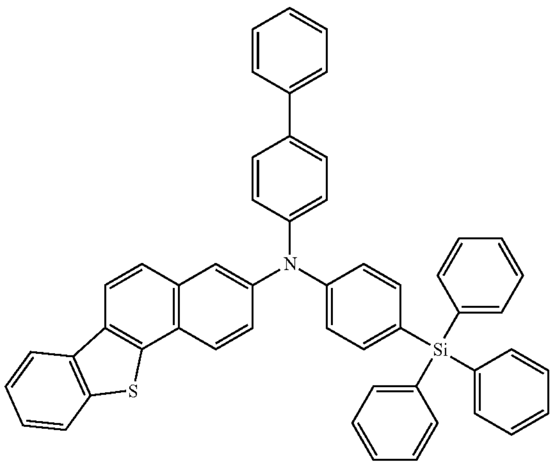
D80
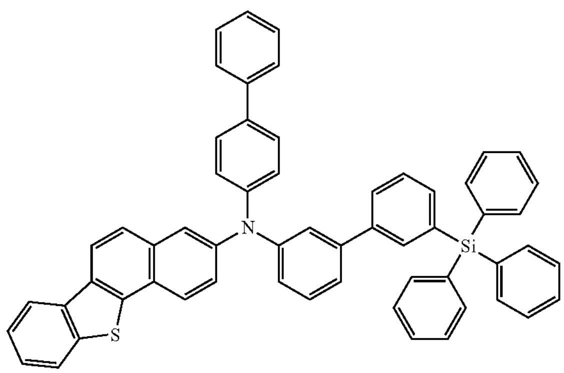
D81
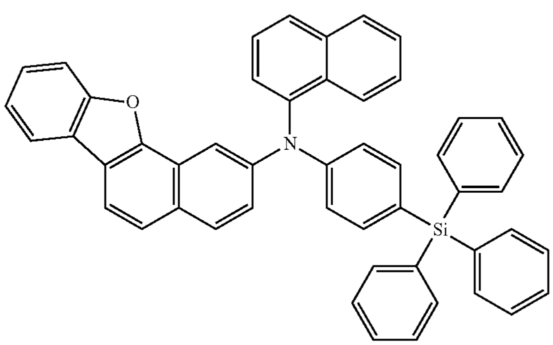
D82
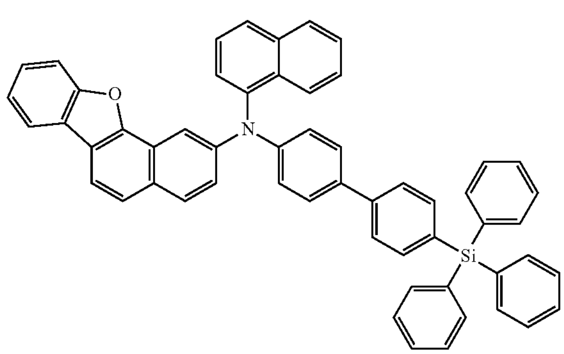
-continued
D83
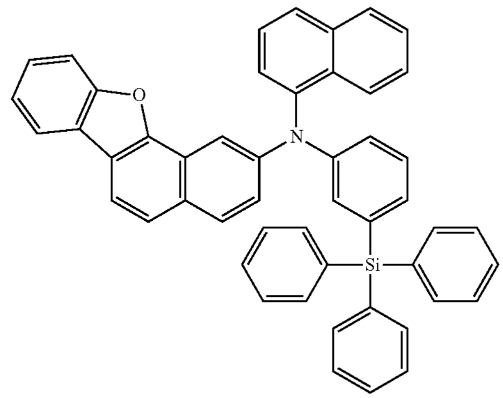
D84
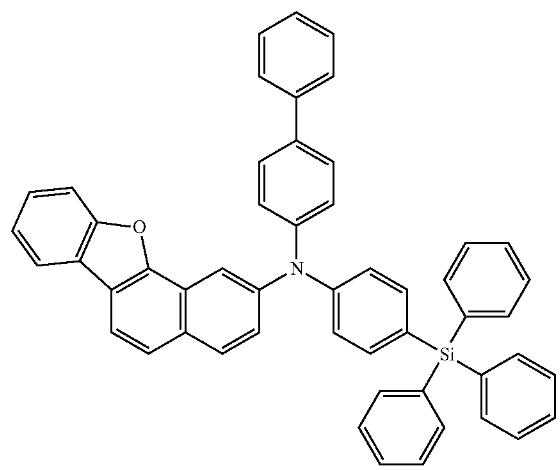
D85
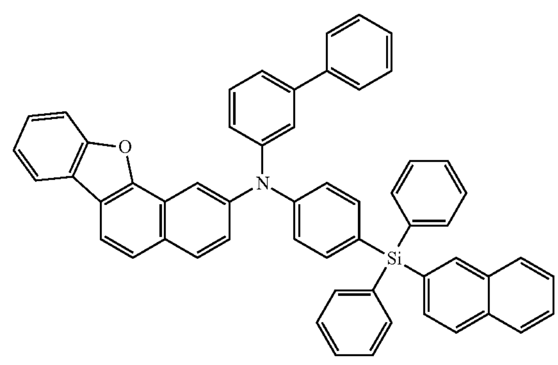
D86
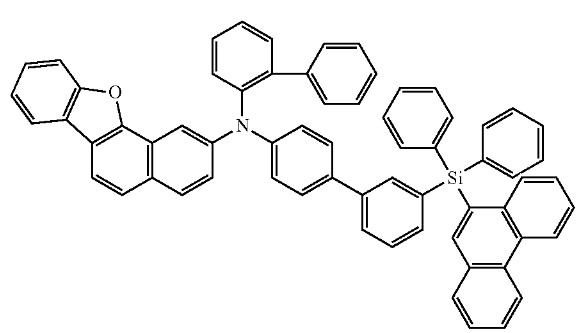

-continued
D87
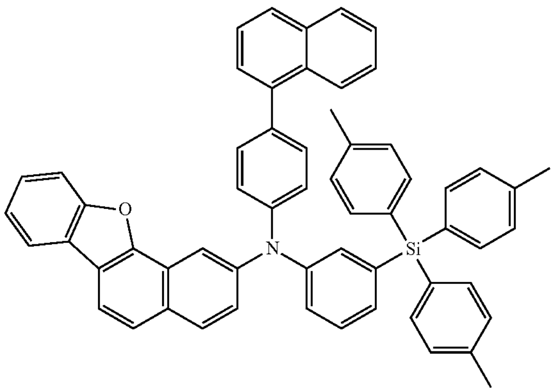
D88
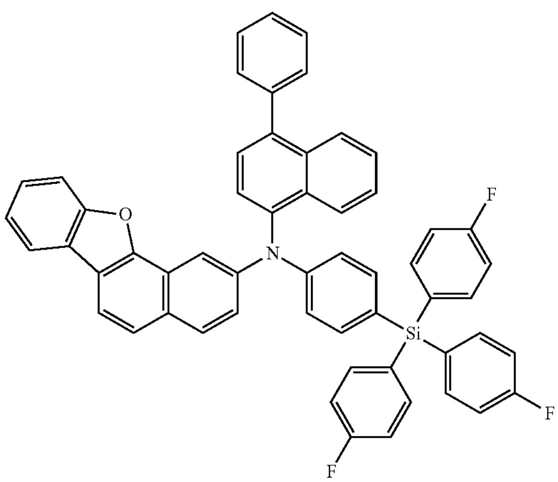
D89
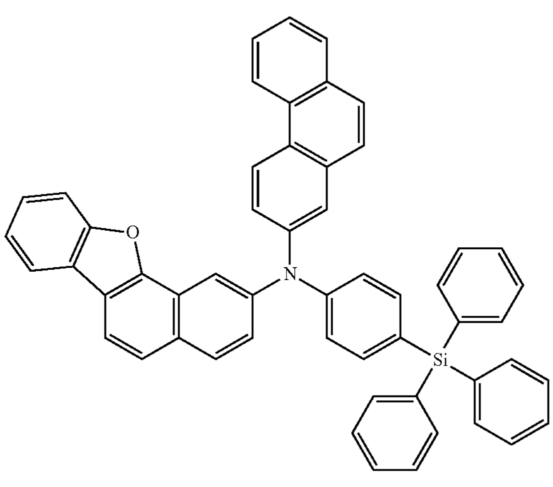
-continued
D90
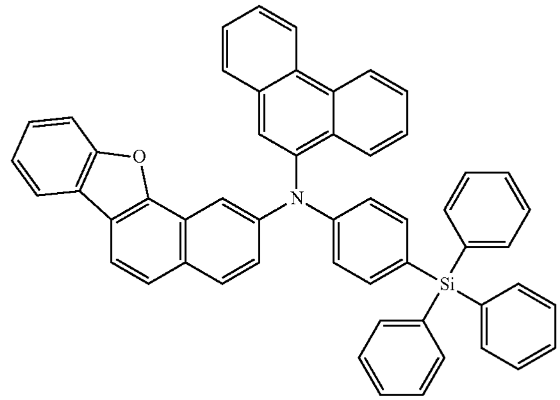
D91
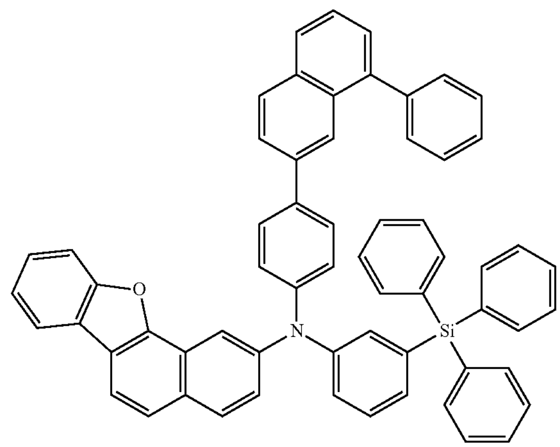
D92
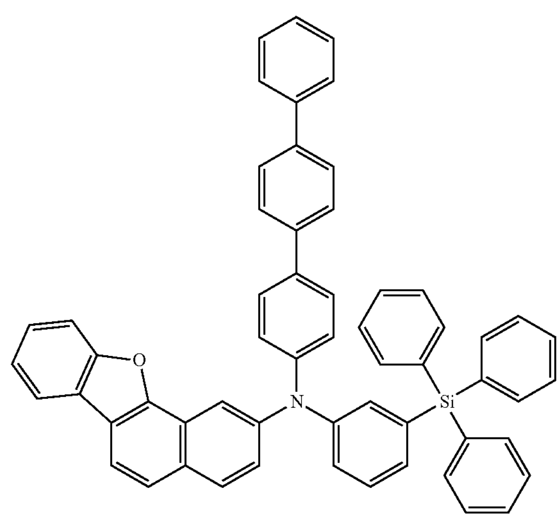

-continued
D93
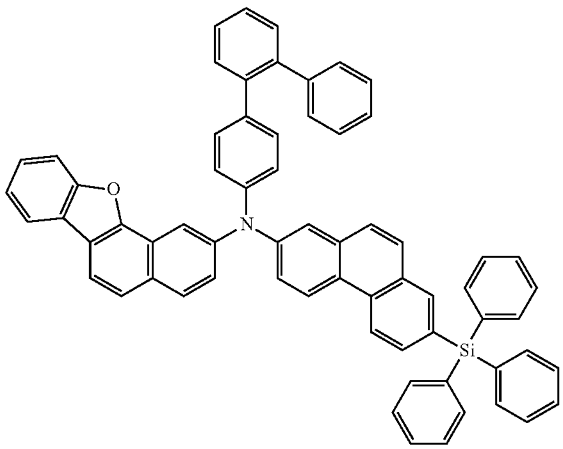
D94
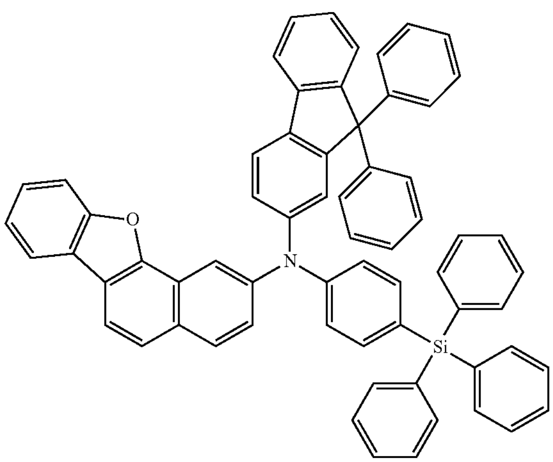
D95
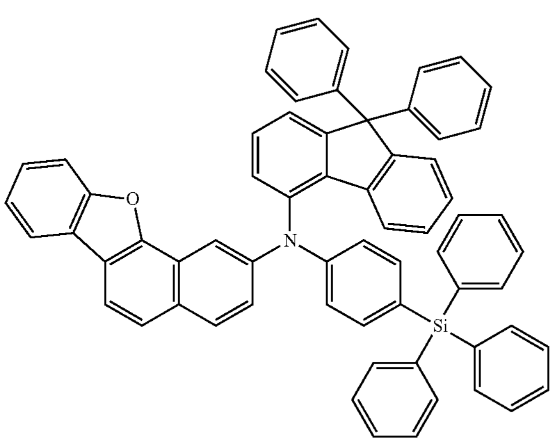
-continued
D96
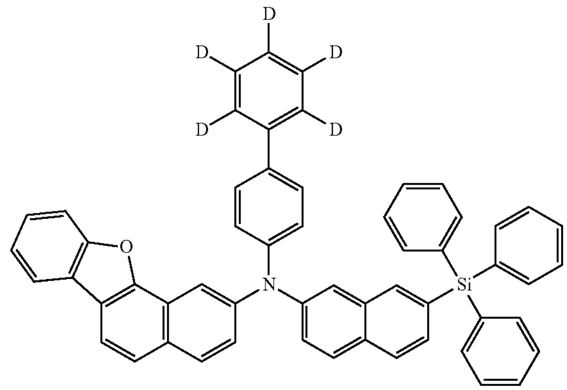
D98
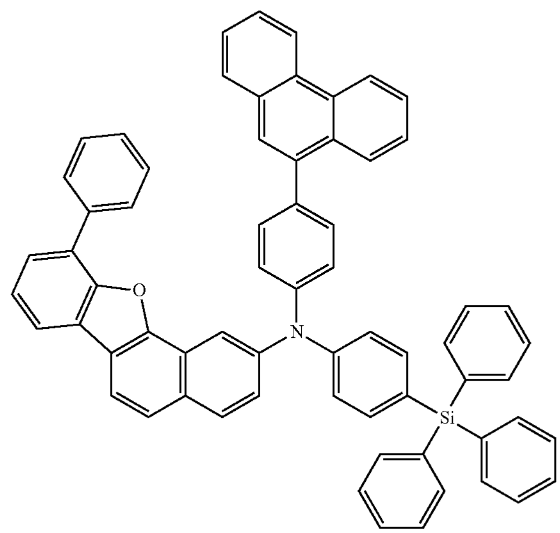
D99
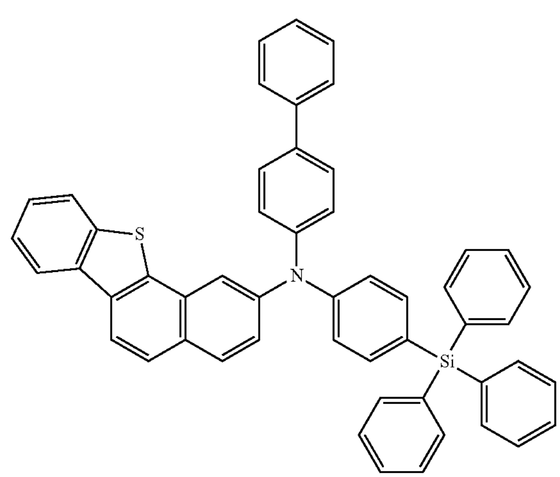

-continued
D100
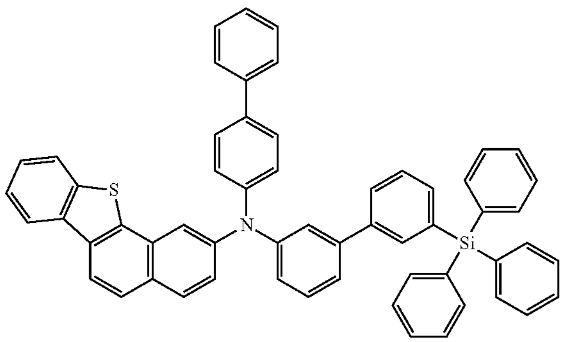
D101
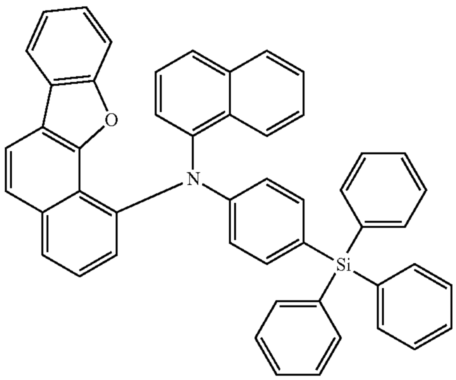
D102
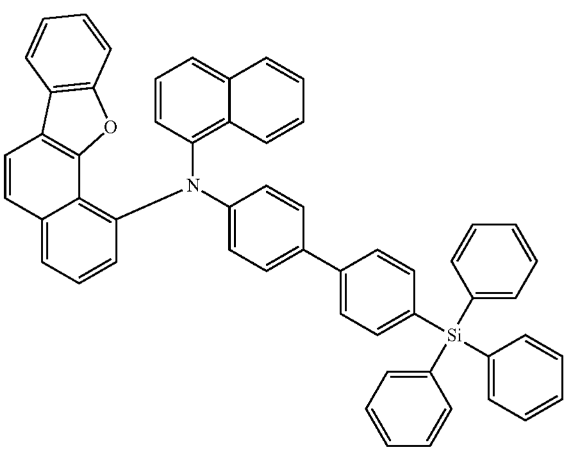
D103
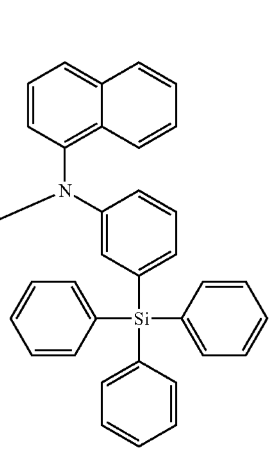
-continued
D104
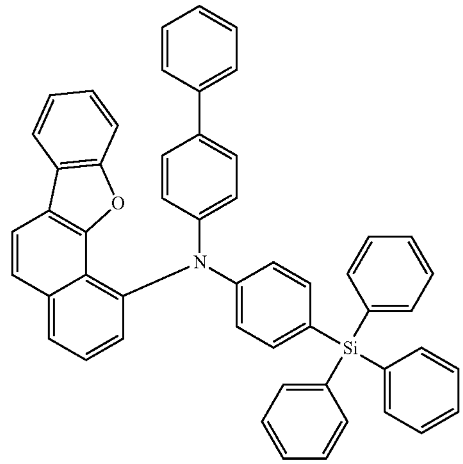
D105
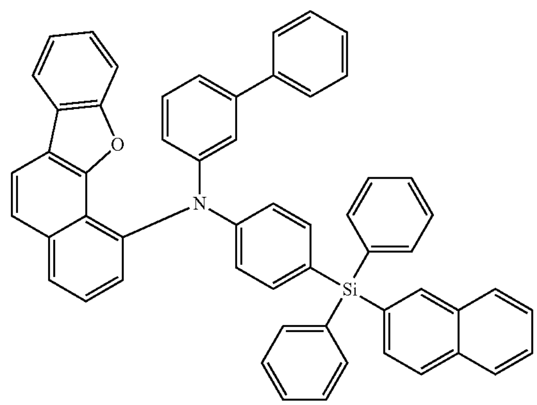
D106
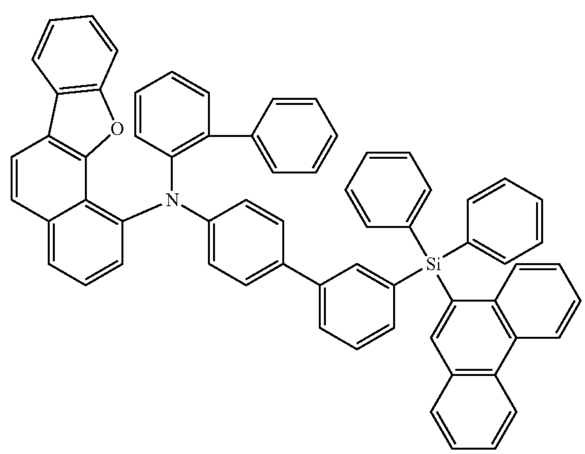

-continued
D107
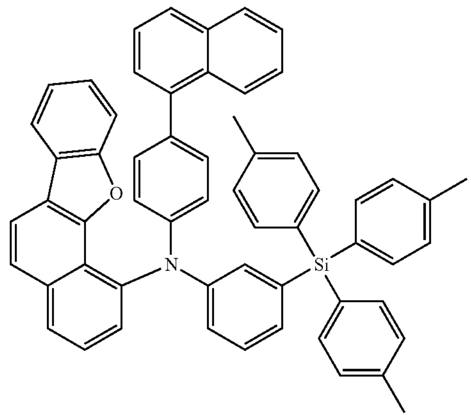
D108
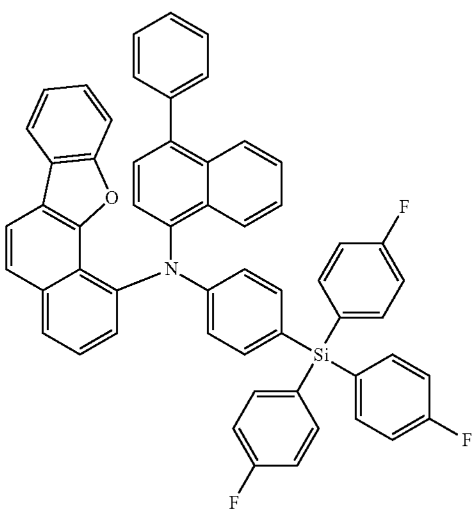
D109
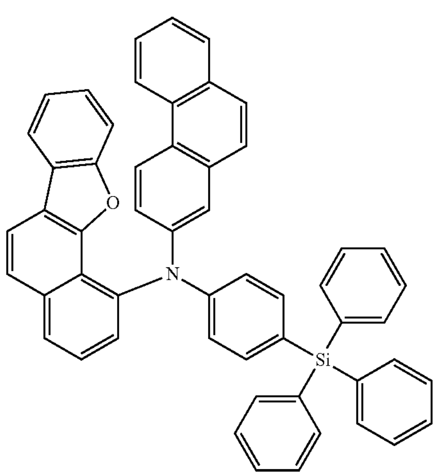
-continued
D110
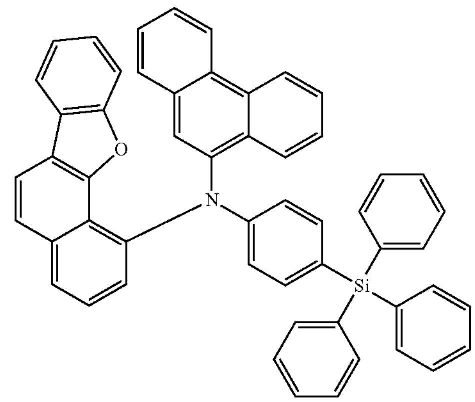
D111
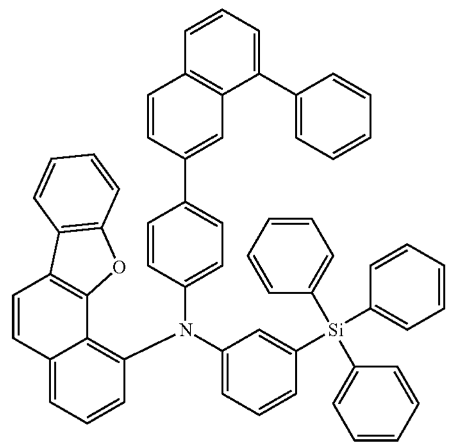
D112
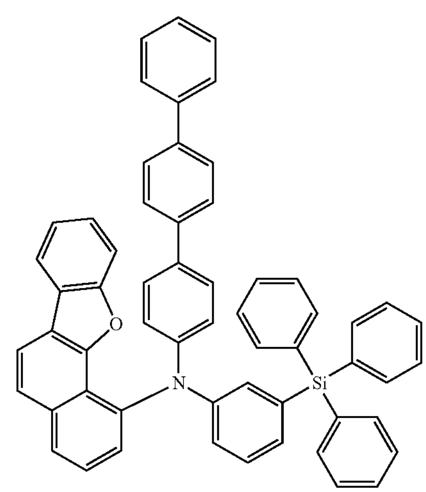

-continued
D113
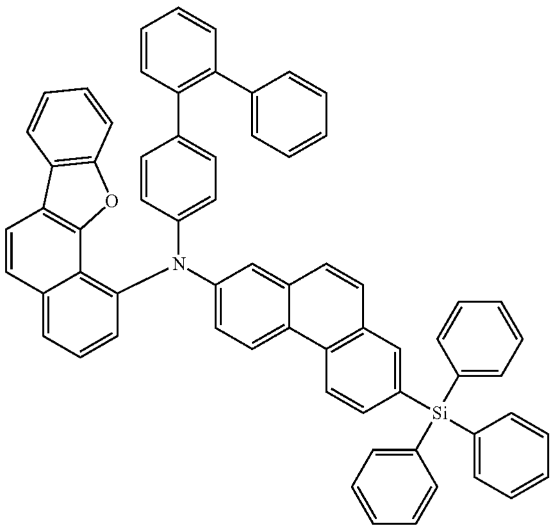
D114
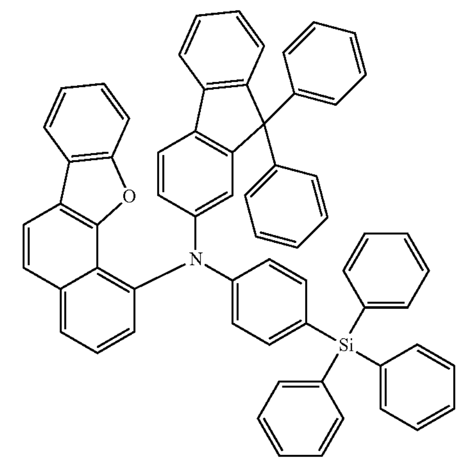
D115
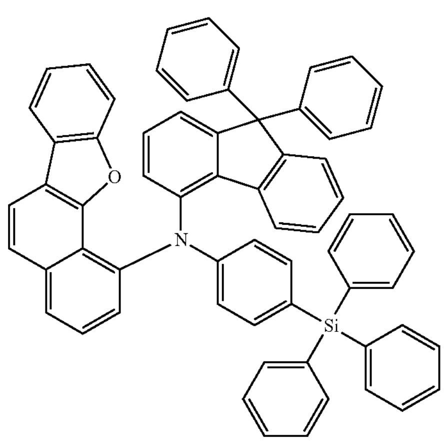
-continued
D116
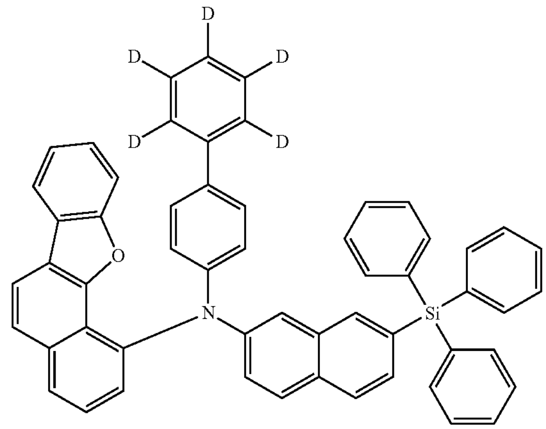
D118
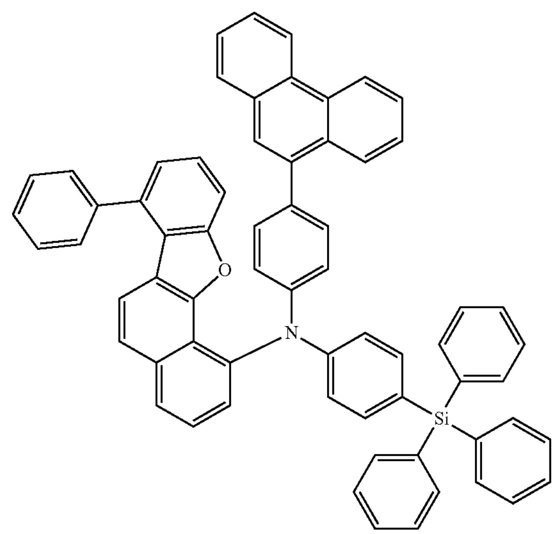
D119
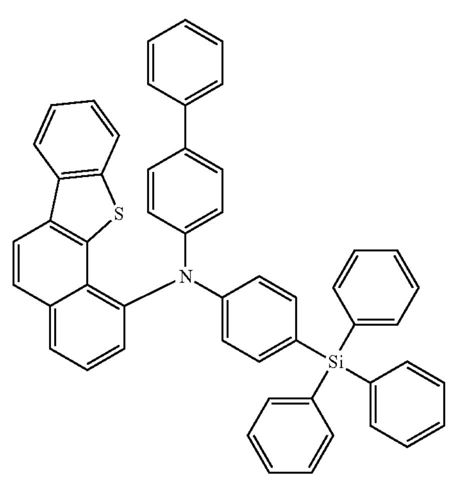

-continued
D120
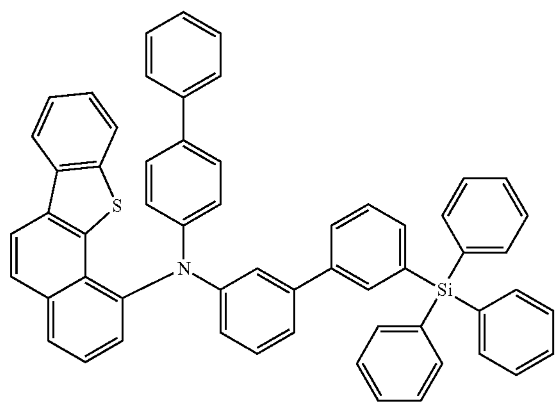
D121
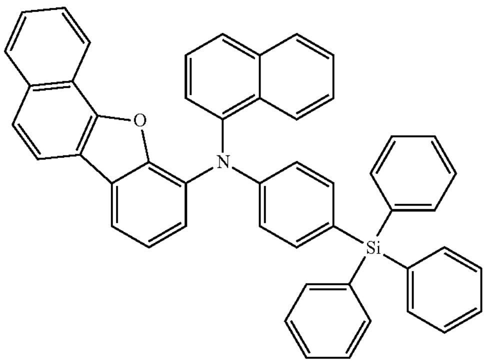
D122
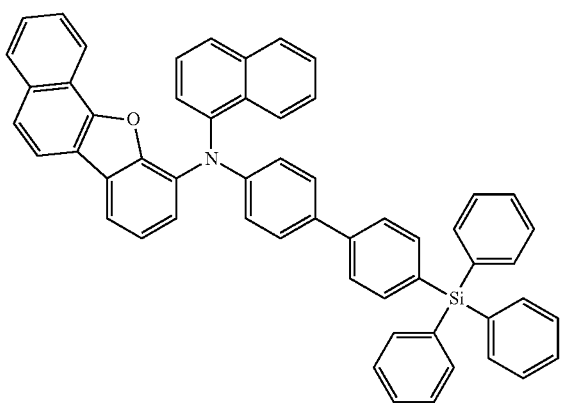
D123
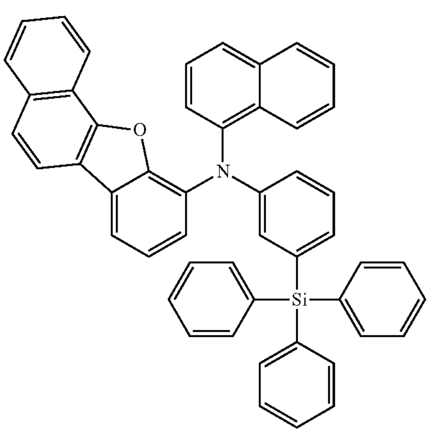
-continued
D124
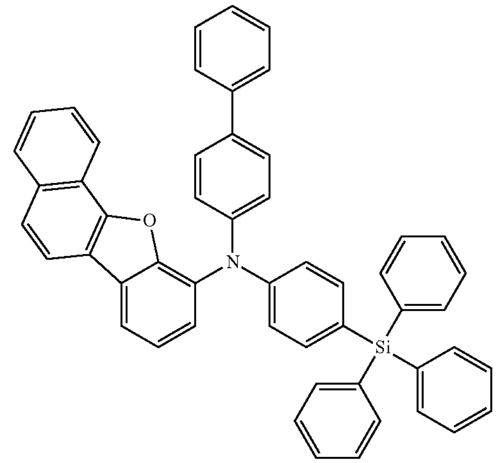
D125
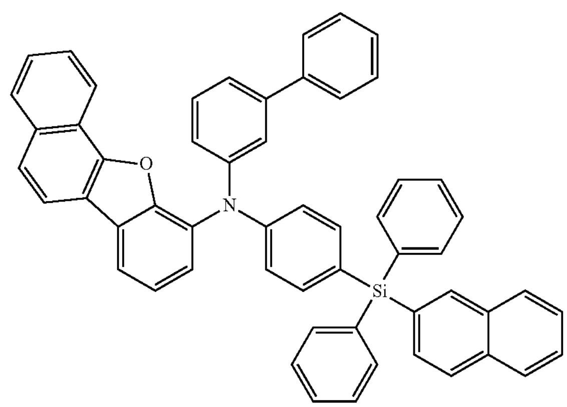
D126
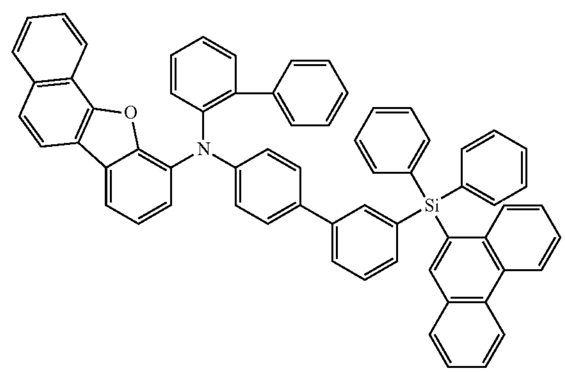

-continued
D127
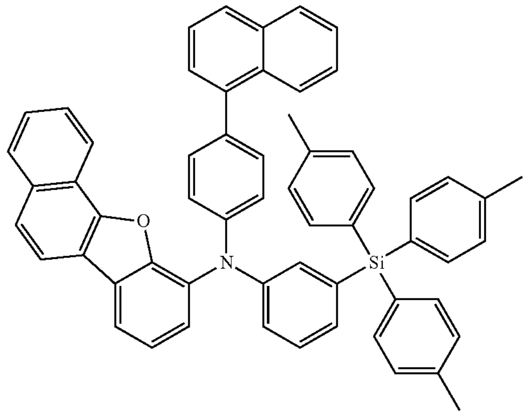
D128
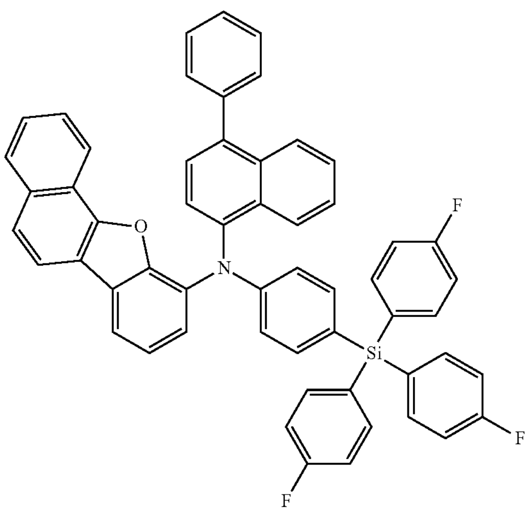
D129
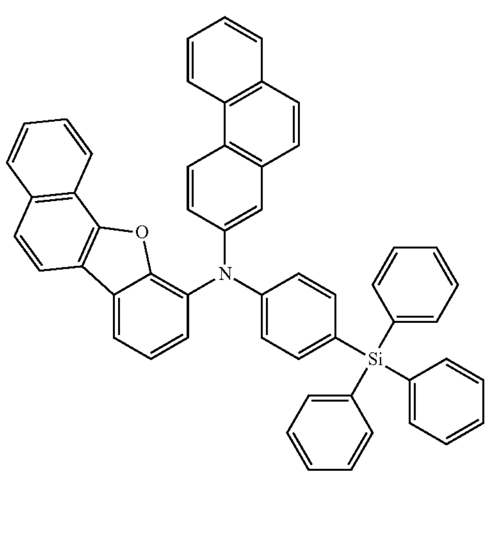
-continued
D130
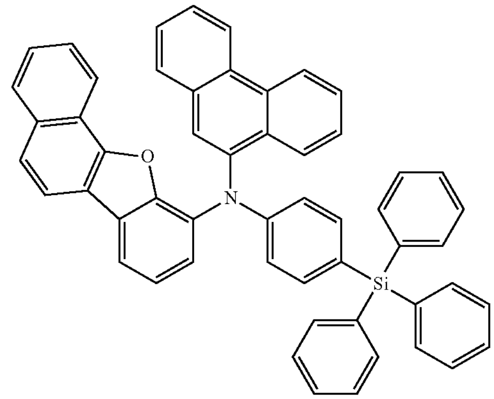
D131
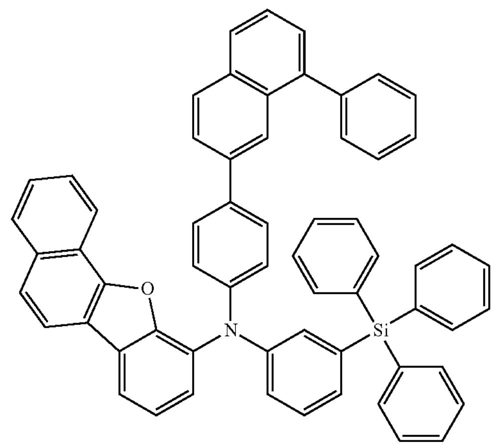
D132
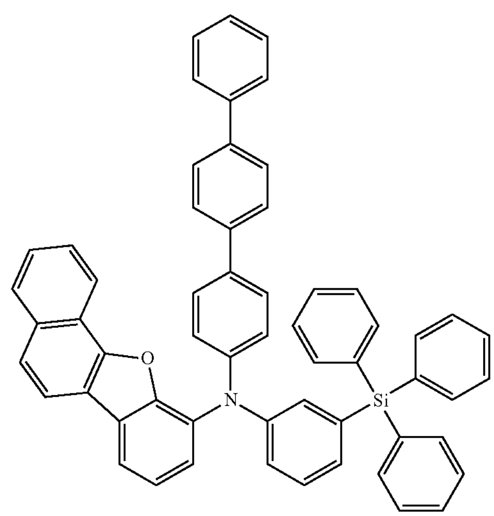

-continued
D133
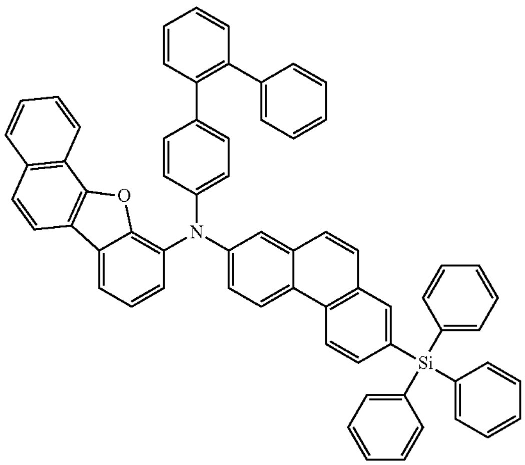
D134
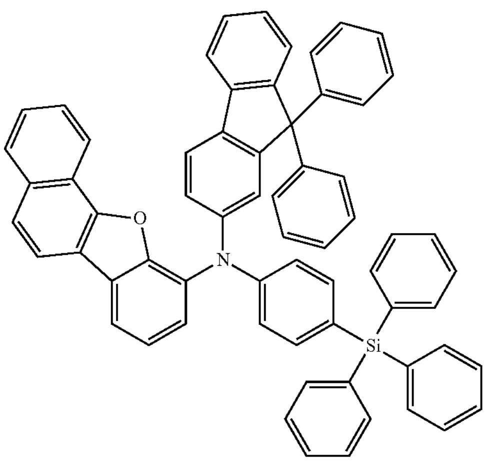
D135
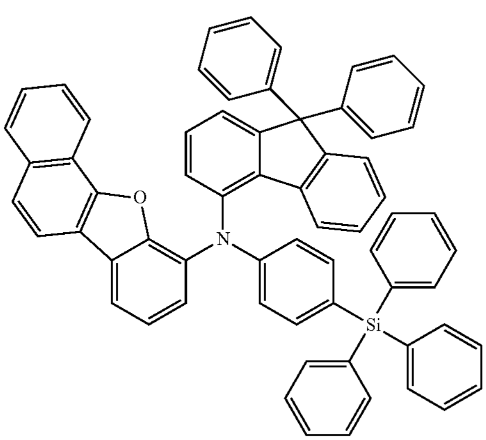
-continued
D136
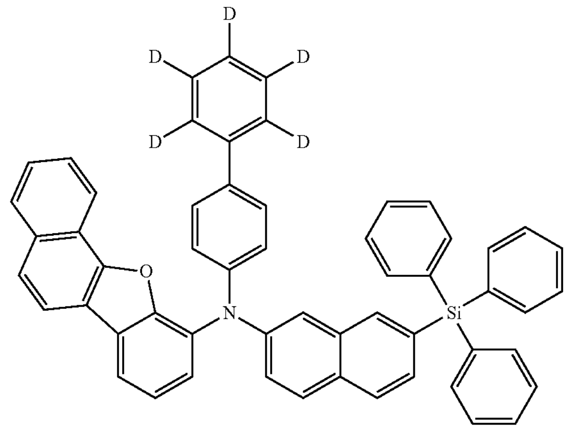
D138
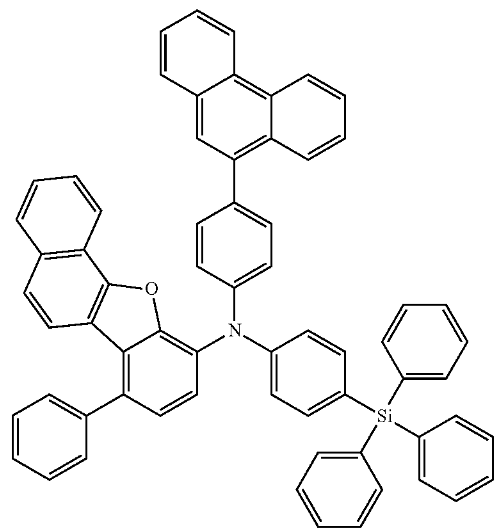
D139
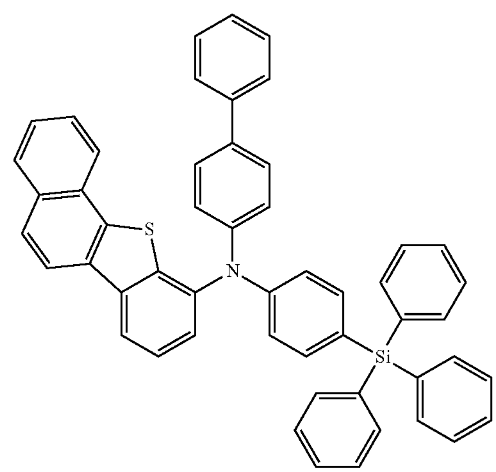

-continued
D140
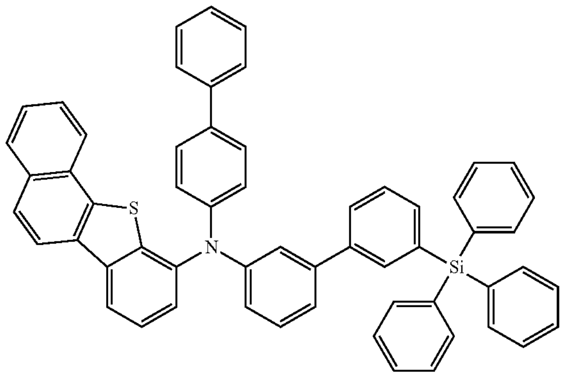
D141
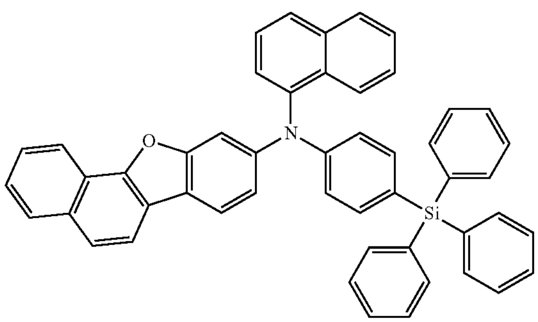
D142
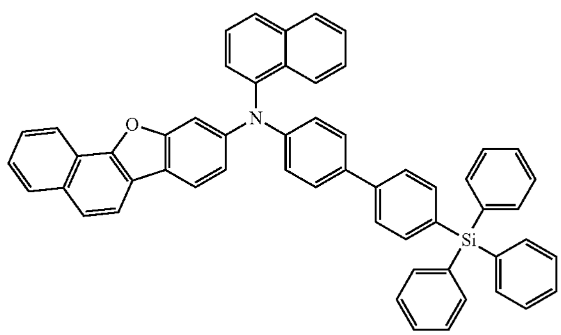
D143
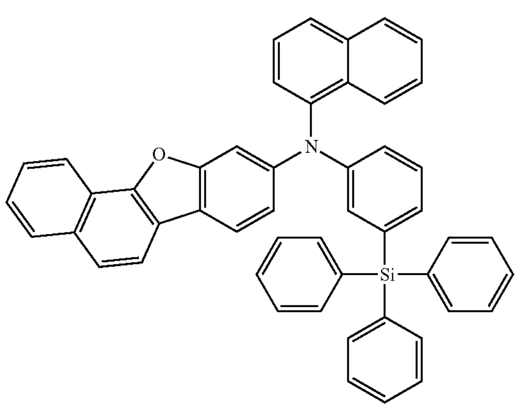
-continued
D144
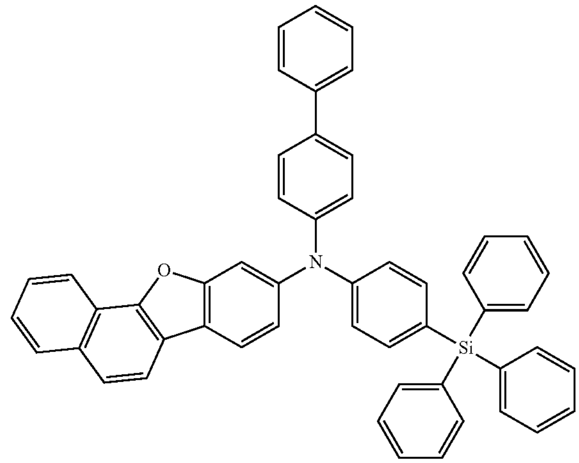
D145
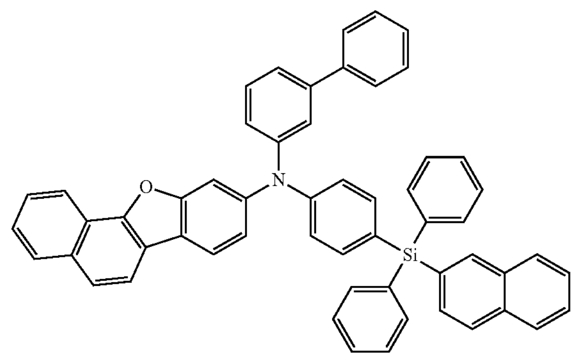
D146
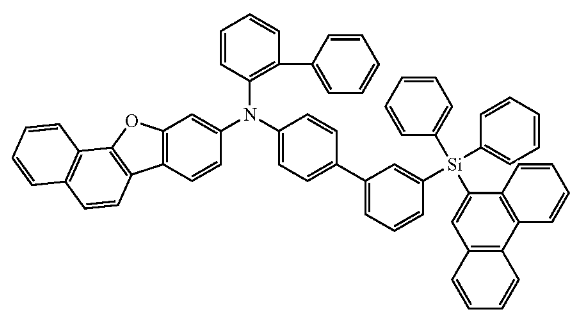
D147
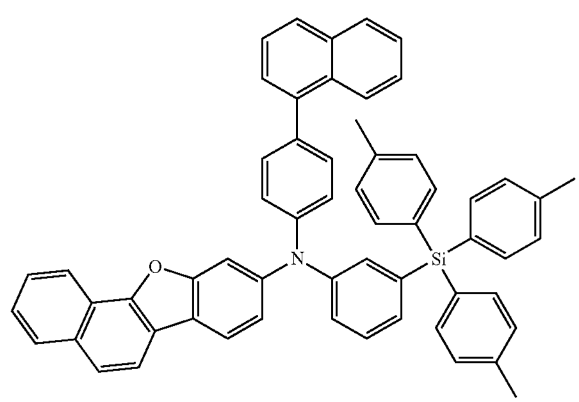

-continued
D148
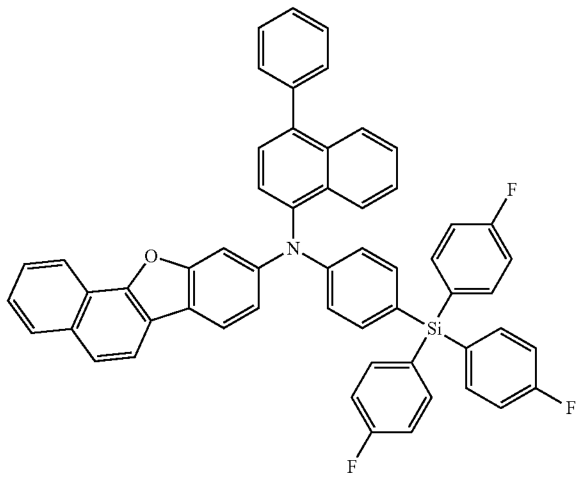
D149
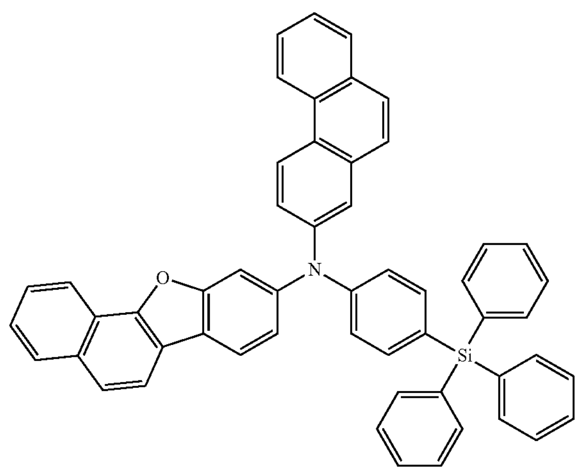
D150
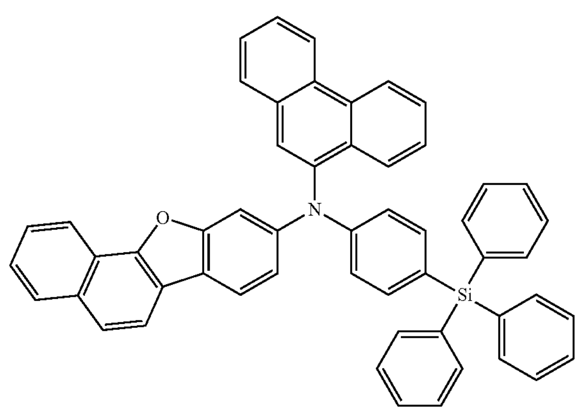
-continued
D151
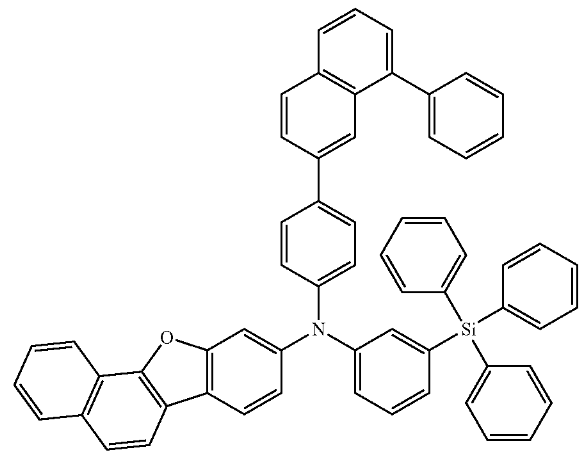
D152
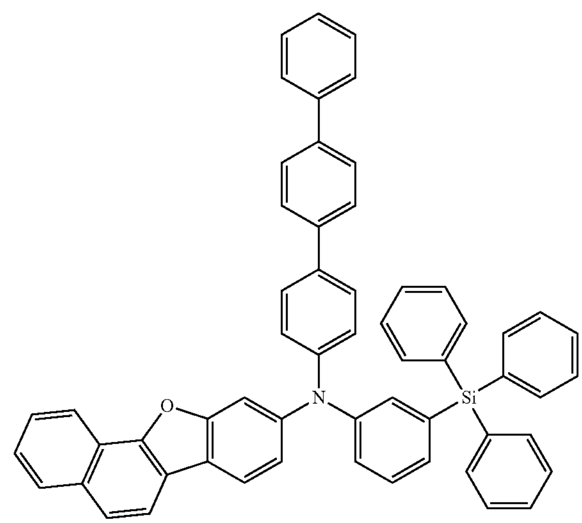
D153
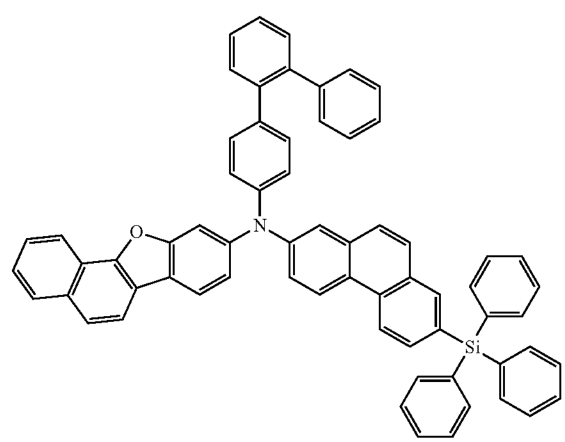

-continued
D154
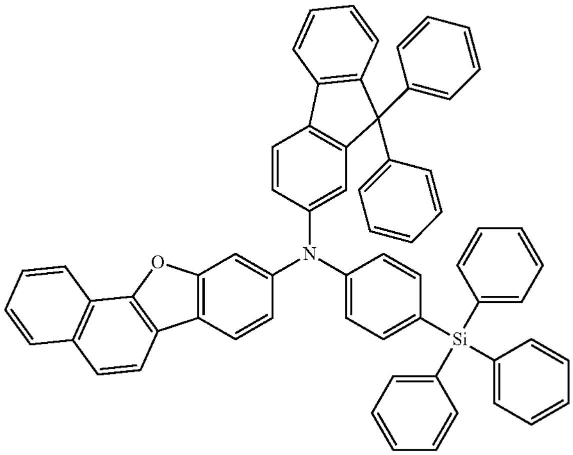
D155
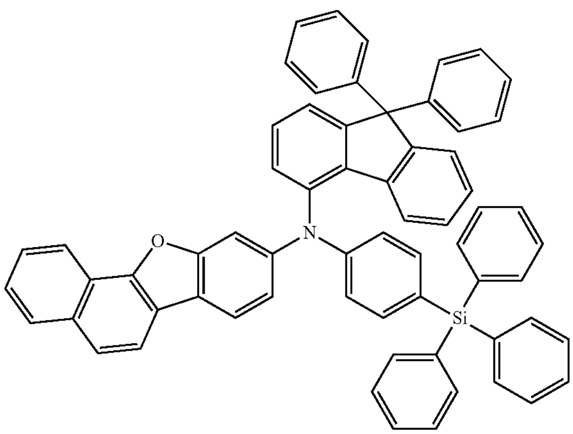
D156
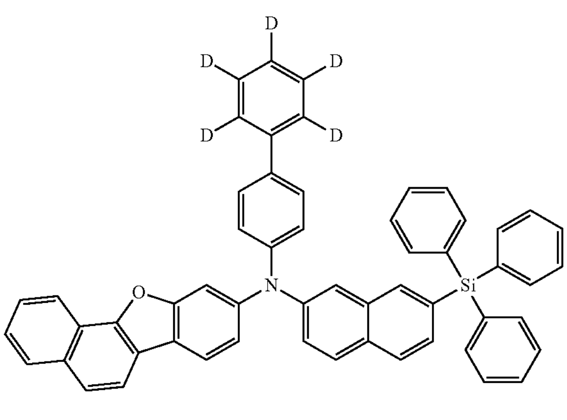
-continued
D158
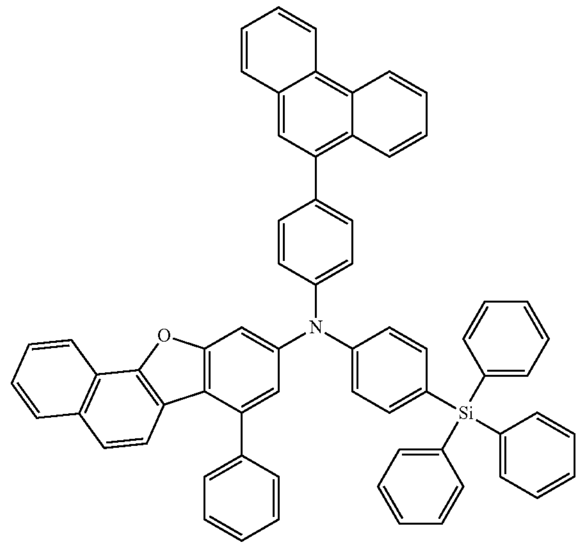
D159
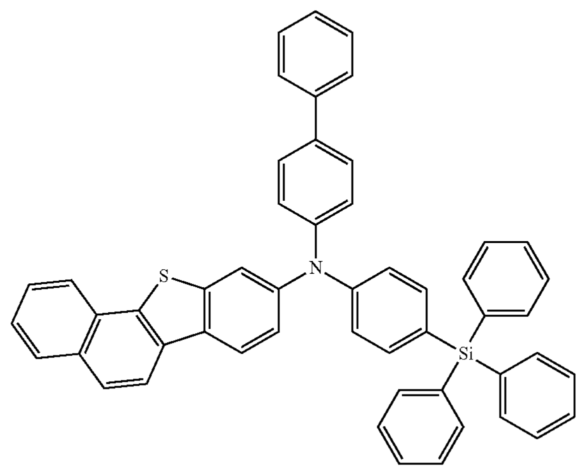
D160
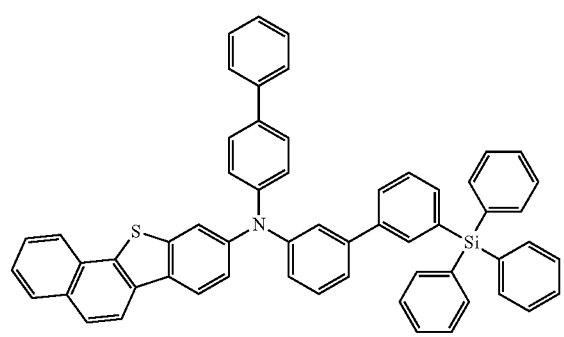

-continued
D161
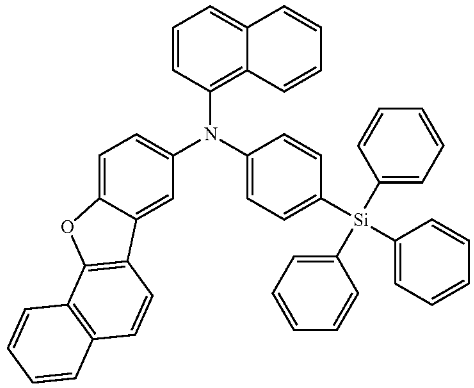
D162
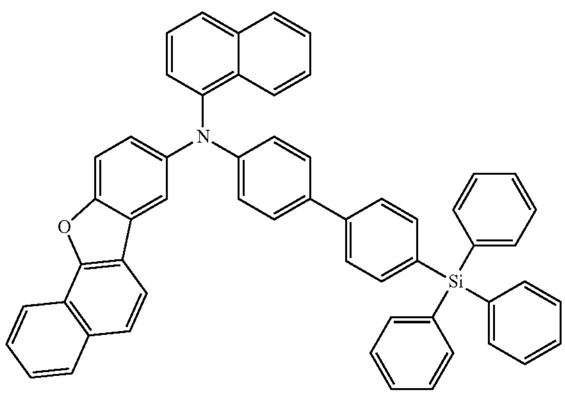
D163
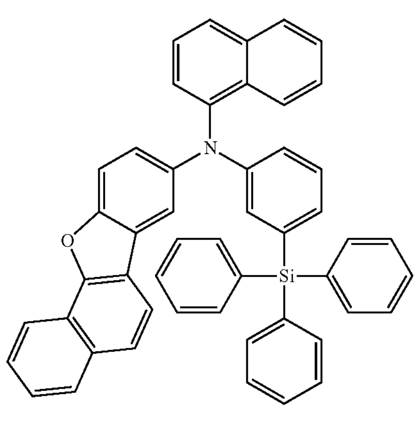
-continued
D164
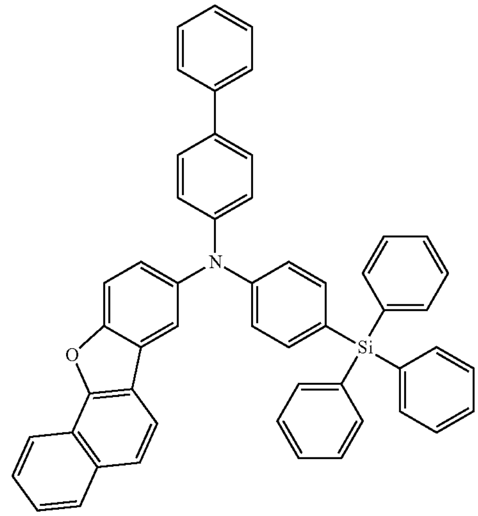
D165
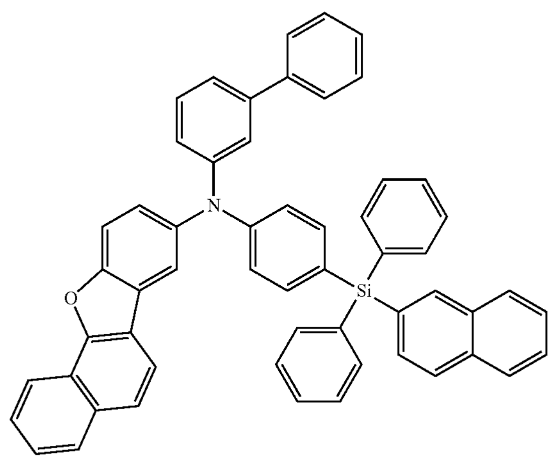
D166
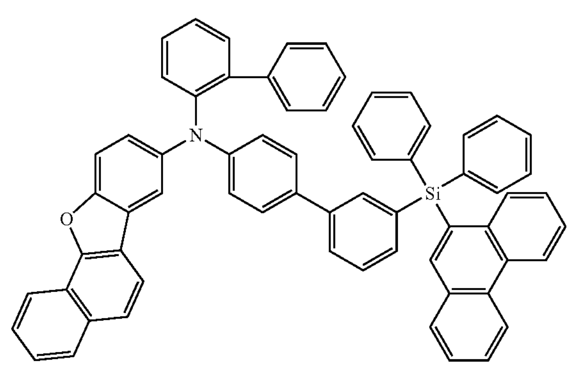

-continued
D167
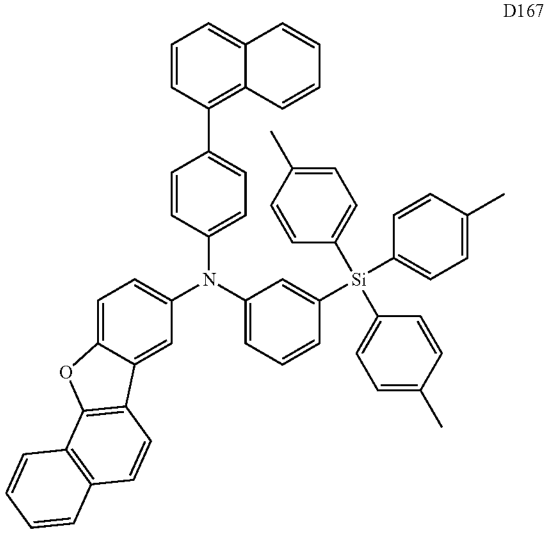
D168
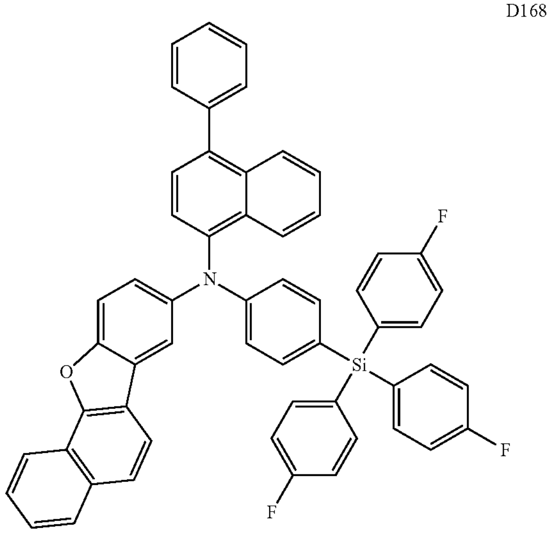
D169
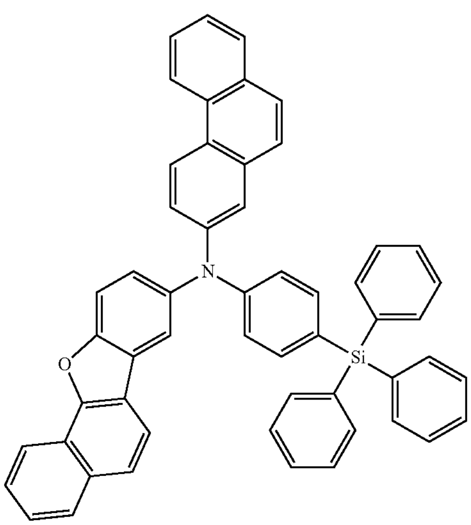
-continued
D170
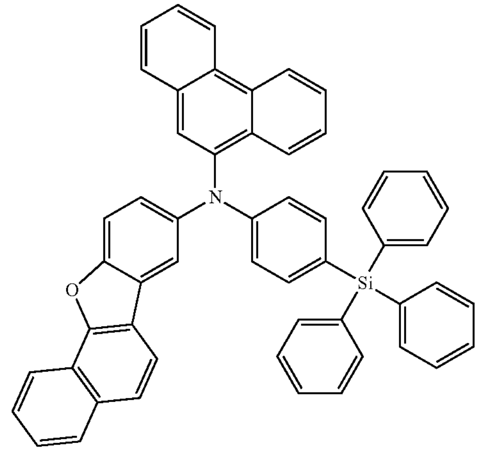
D171
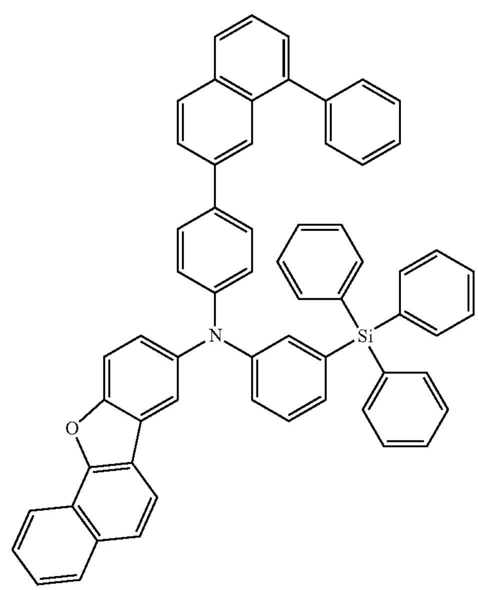

-continued
D172
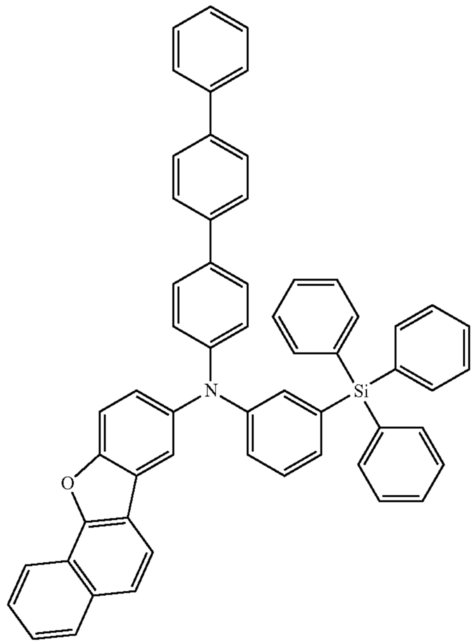
D173
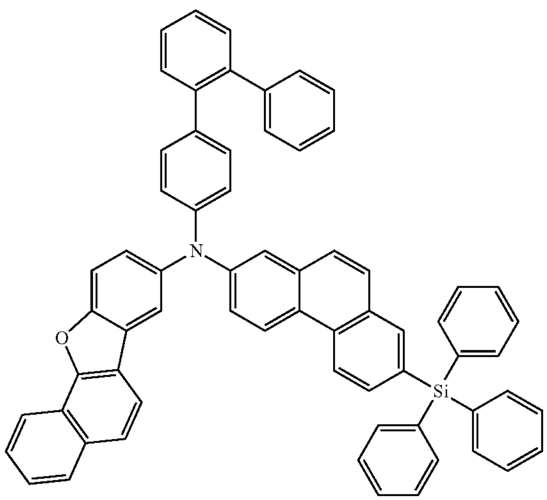
D174
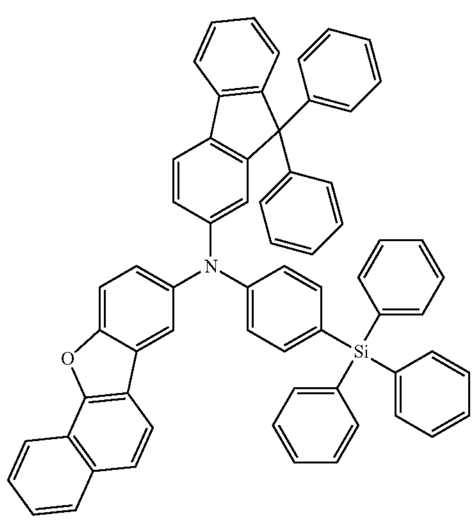
-continued
D175
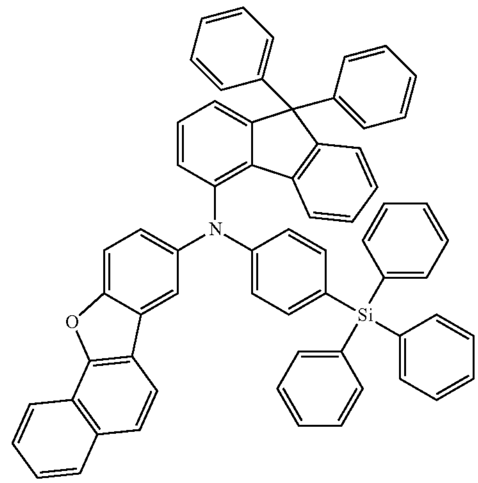
D176
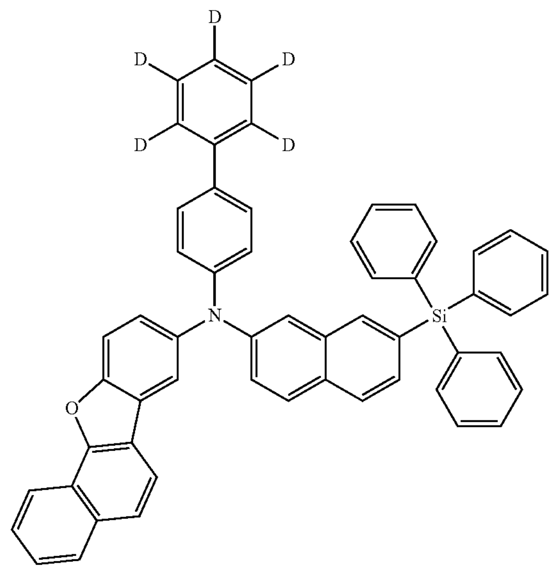
D178
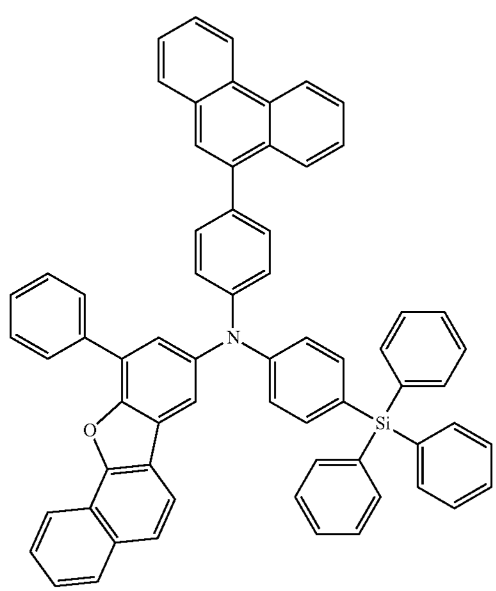

-continued
D179
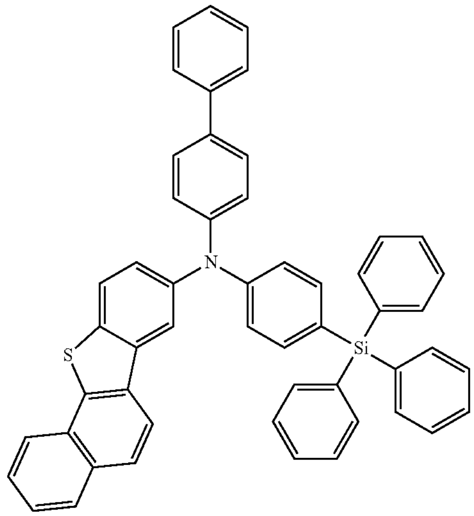
D180
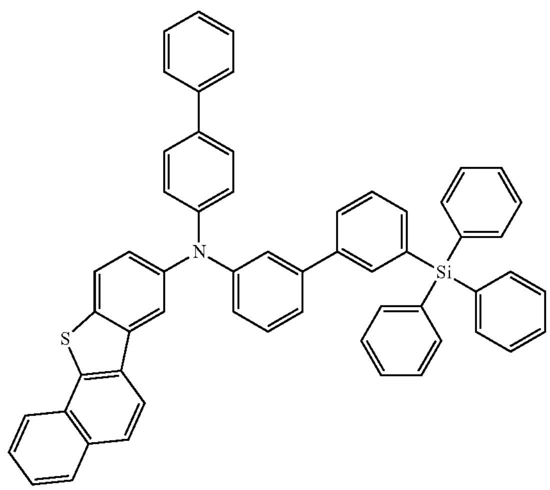
D181
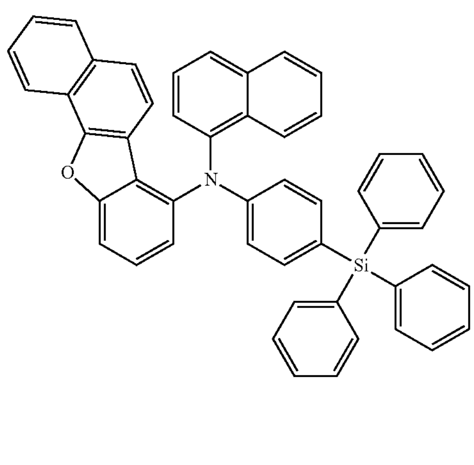
-continued
D182
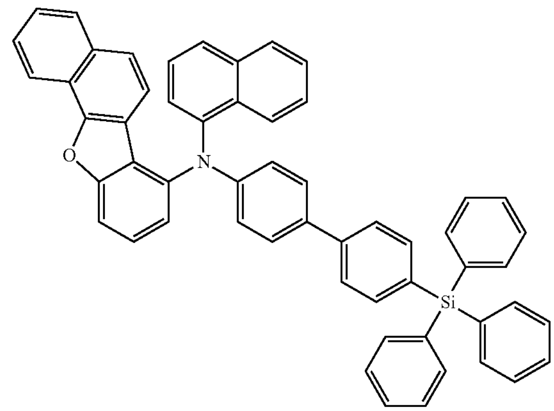
D183
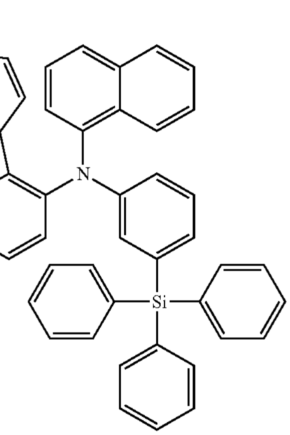
D184
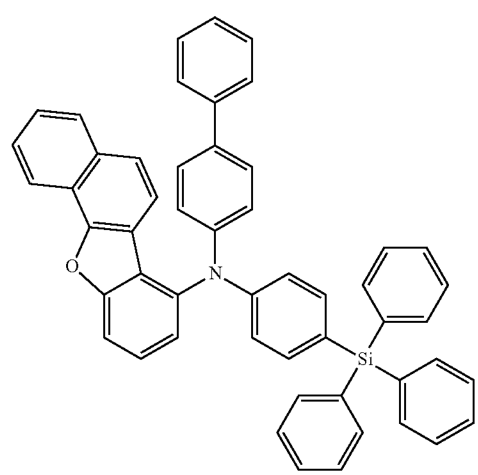

-continued
D185
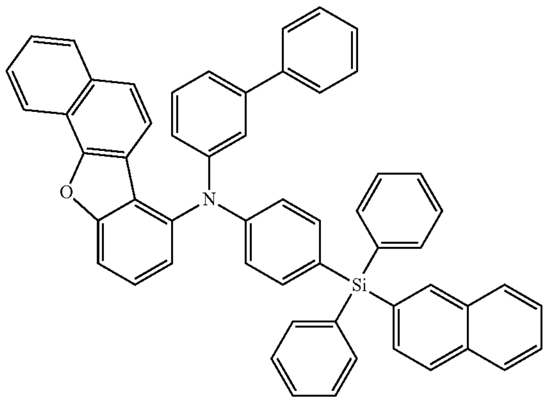
D186
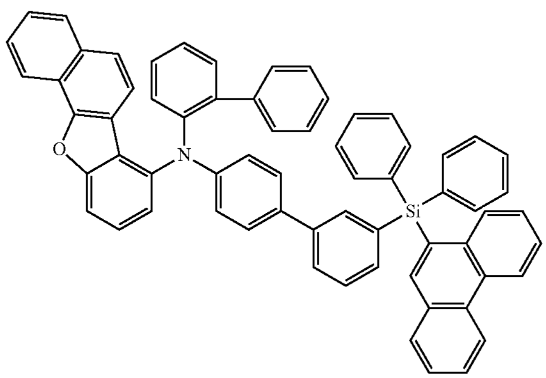
D187
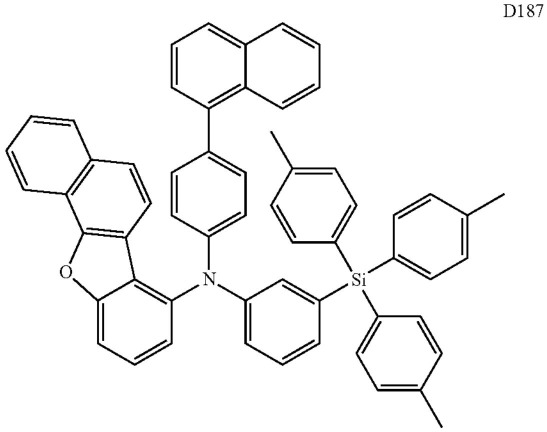
-continued
D188
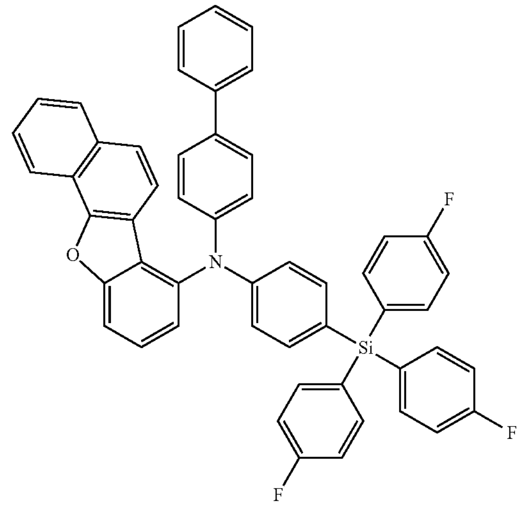
D189
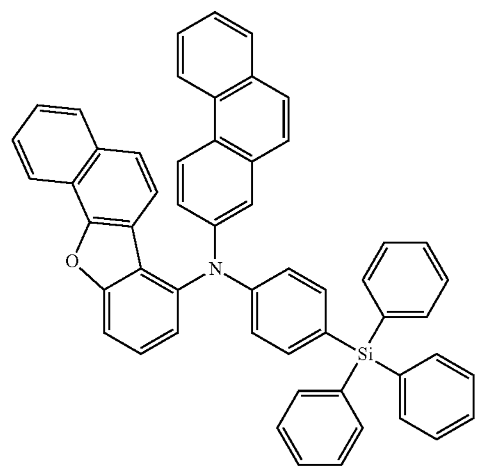
D190
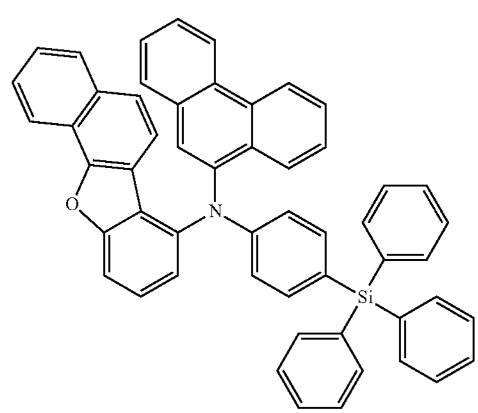

-continued
D191
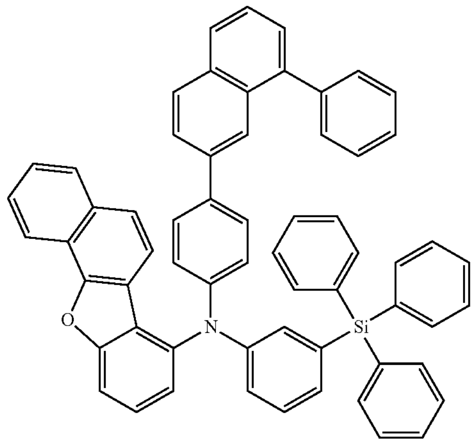
D192
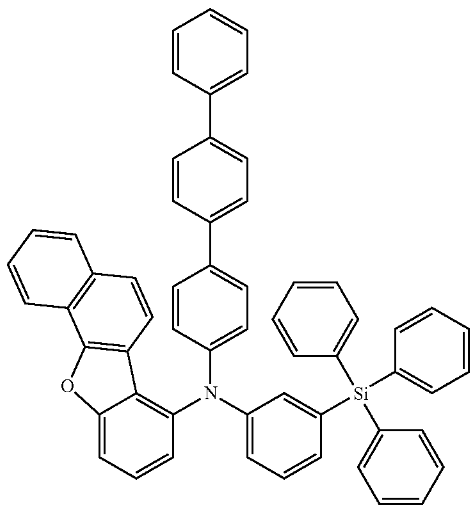
D193
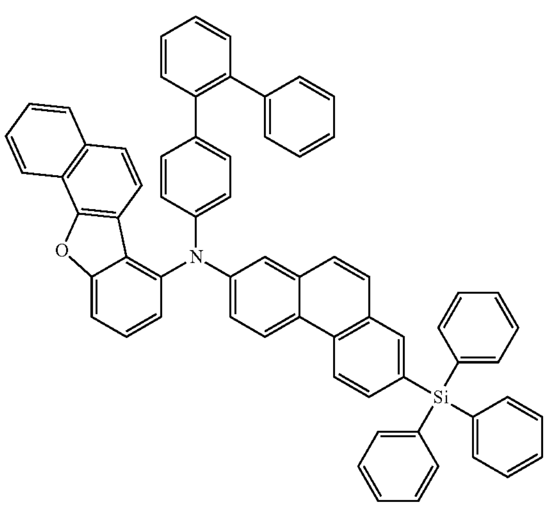
-continued
D194
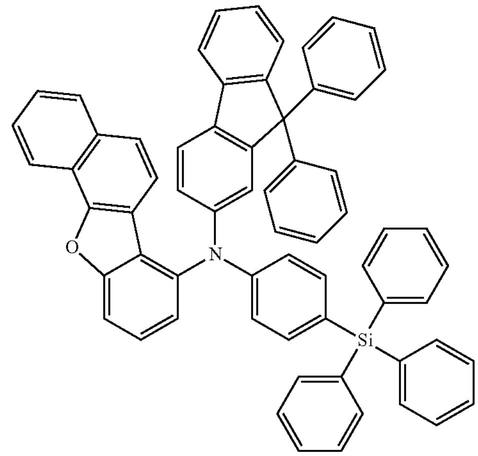
D195
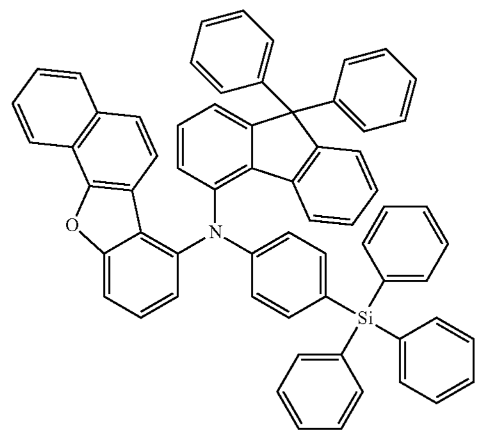
D196
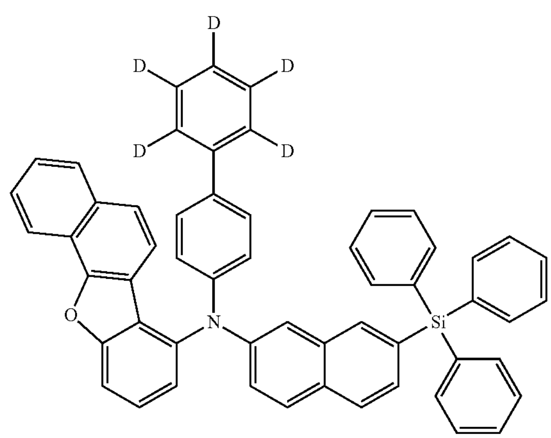

-continued
D198
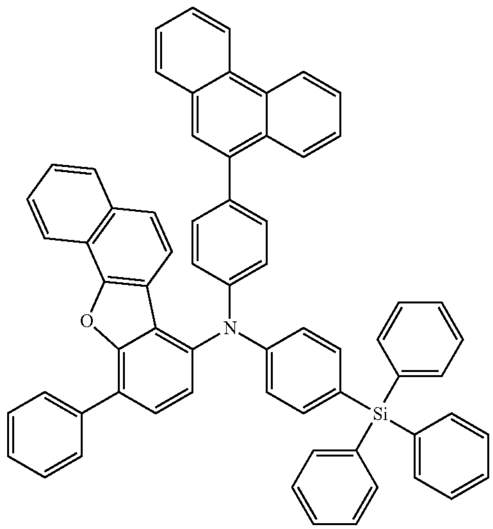
D199
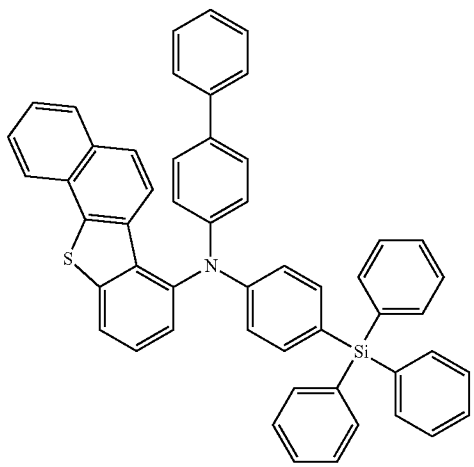
D200
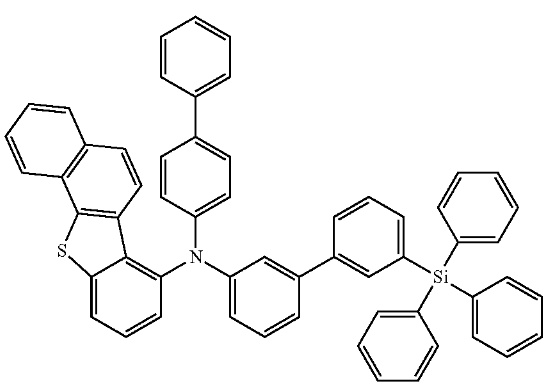
D17
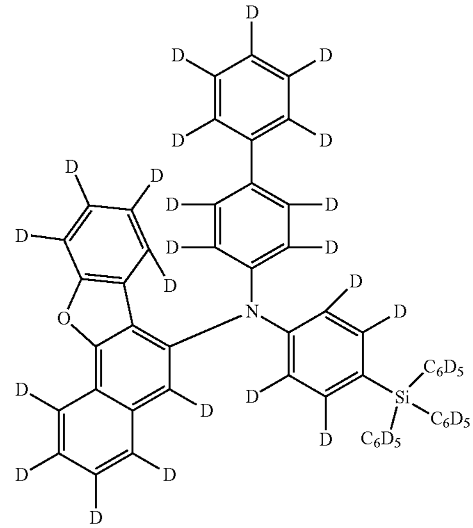
D37
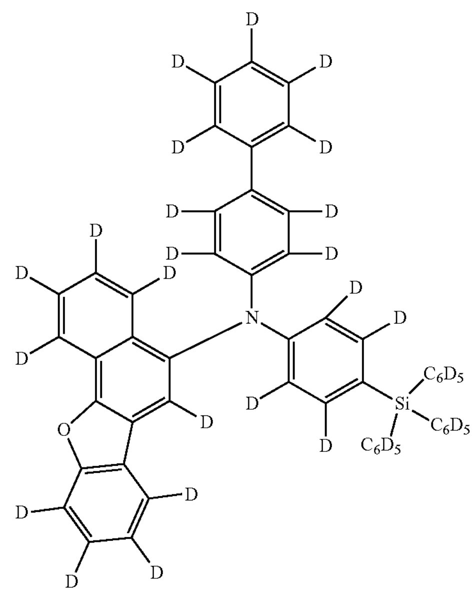
D117
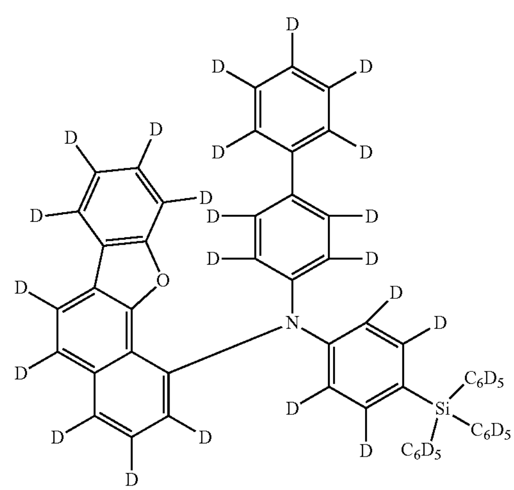

-continued
D137
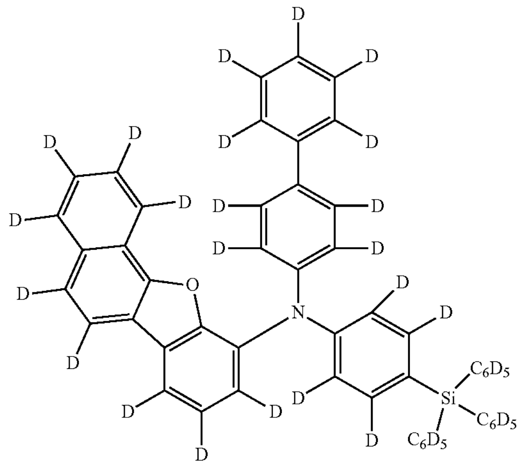
D177
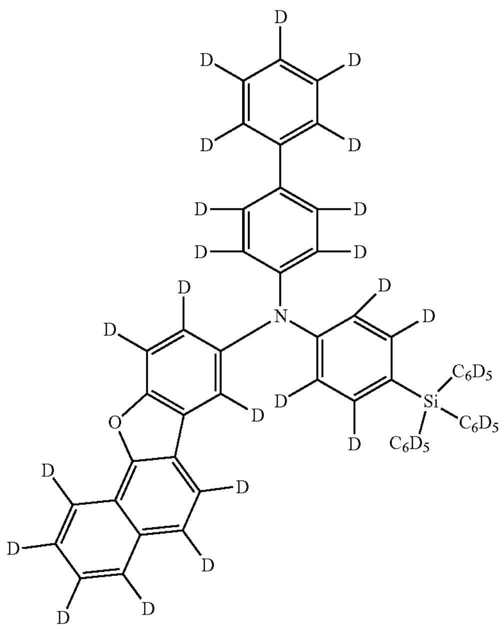
D197
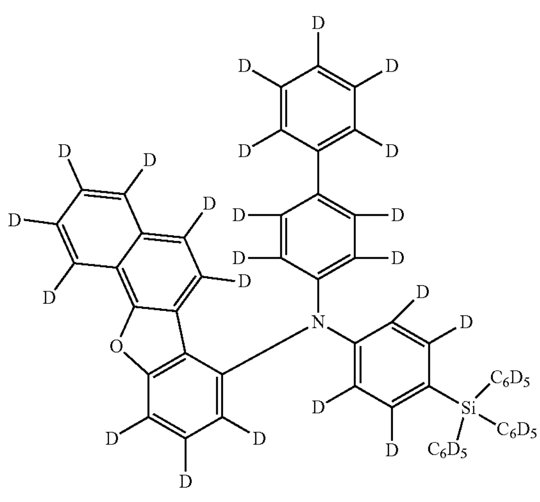
-continued
D57
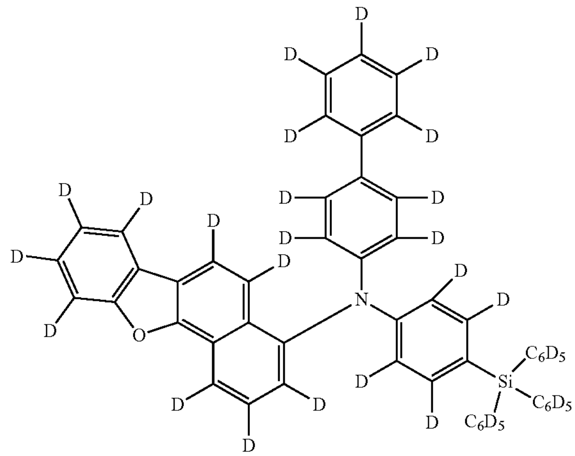
D77
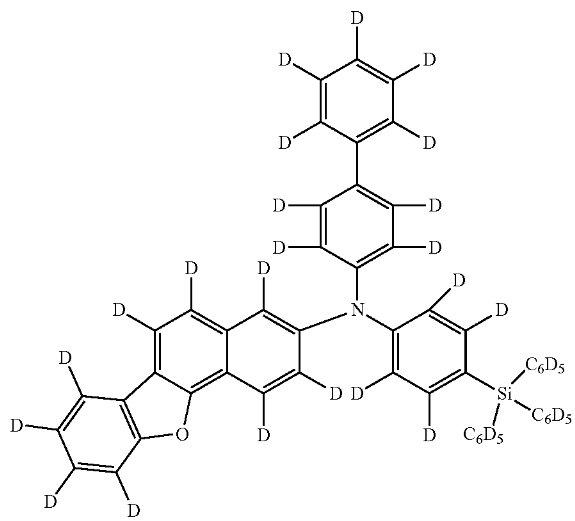
D97
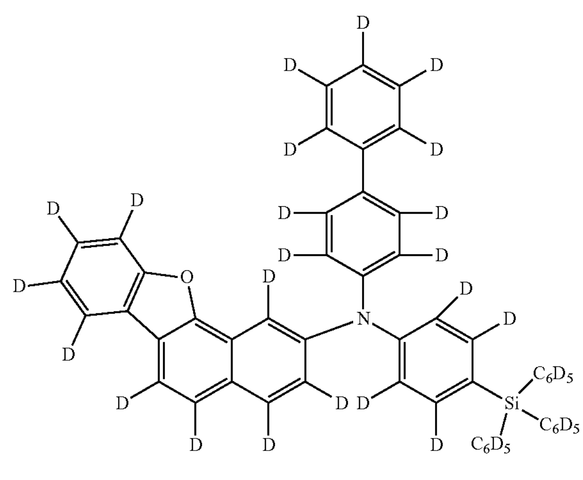

-continued

D157

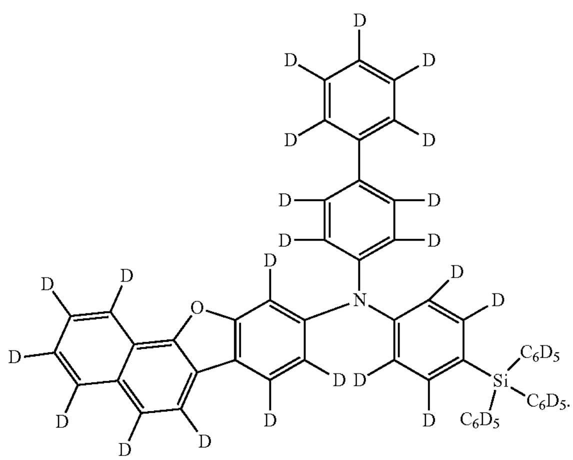

9. A polycyclic compound represented by Formula 1:

[Formula 1]

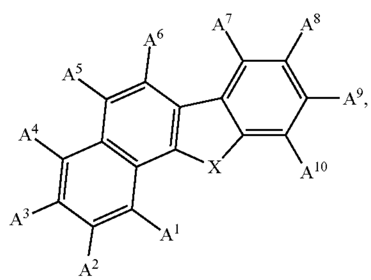

wherein in Formula 1,

X is O or S, any one among $A^1$ to $A^{10}$ is represented by Formula 2-2, and the remainder of $A^1$ to $A^{10}$ are each independently a hydrogen atom, a deuterium atom, a halogen atom, a substituted or unsubstituted alkyl group of 1 to 20 carbon atoms, or a substituted or unsubstituted aryl group of 6 to 30 carbon atoms for forming a ring:

[Formula 2-2]

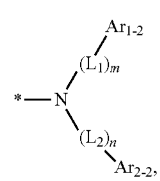

wherein in Formula 2-2, $L_1$ and $L_2$, are each independently a direct linkage, a substituted or unsubstituted arylene group of 6 to 30 carbon atoms for forming a ring, or a substituted or unsubstituted heteroarylene group of 2 to 30 carbon atoms for forming a ring, "m" and "n" are each independently an integer of 0 to 2, and $Ar_{1-2}$ and $Ar_{2-2}$ are each independently a substituted or unsubstituted aryl group of 10 to 40 carbon atoms for forming a ring or are represented by Formula 3-3 or Formula 3-4, where at least one among $Ar_{1-2}$ and $Ar_{2-2}$ is represented by Formula 3-3 or Formula 3-4:

[Formula 3-3]

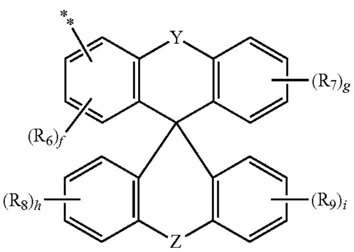

[Formula 3-4]

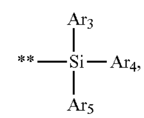

wherein in Formula 3-3 and Formula 3-4,

Y and Z are each independently a direct linkage, O, or S, where a case in which both Y and Z are direct linkages is excluded, $R_6$ to $R_9$ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "f" is an integer of 0 to 3, "g" to "i" are each independently an integer of 0 to 4, and $Ar_3$ to $Ar_5$ are each independently a substituted or unsubstituted aryl group of 6 to 30 carbon atoms for forming a ring.

10. The polycyclic compound of claim 9, wherein Formula 2-2 is represented by Formula 5-1 or Formula 5-2:

[Formula 5-1]

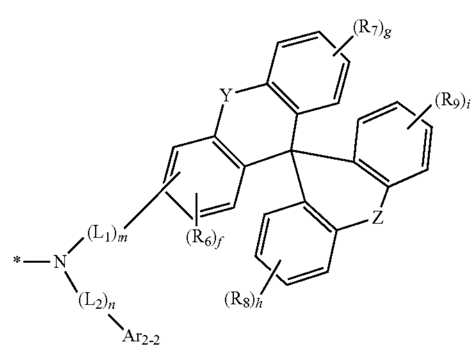

[Formula 5-2]

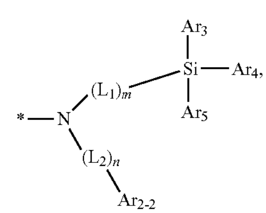

and wherein in Formula 5-1 and Formula 5-2, $Ar_{2-2}$ is a substituted or unsubstituted aryl group of 10 to 40 carbon atoms for forming a ring, $L_1$, $L_2$, "m" and "n" are each independently the same as defined in Formula 2-2, and Y, Z, $R_6$ to $R_9$, "f" to "i", and $Ar_3$ to $Ar_5$ are each independently the same as defined in Formula 3-3 and Formula 3-4.

11. The polycyclic compound of claim 9, wherein the polycyclic compound represented by Formula 1 is at least one selected from compounds represented in Compound Group 3 and Compound Group 4:

[Compound Group 3]

C1

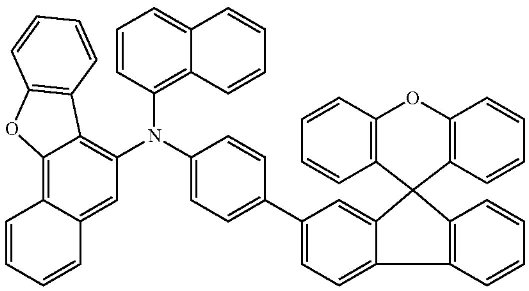

C2

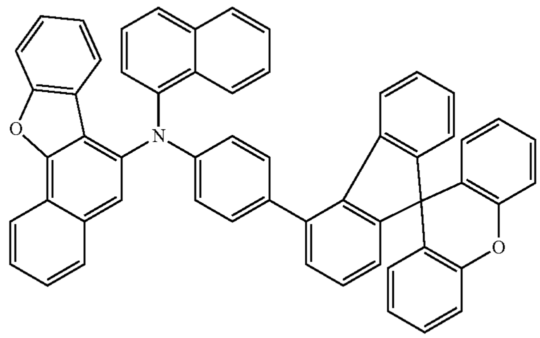

C3

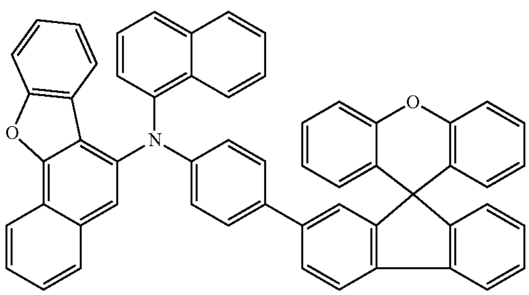

C4

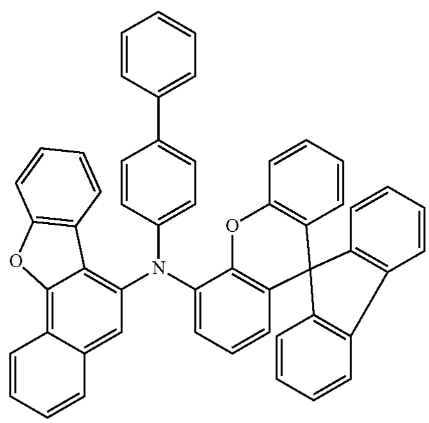

C5

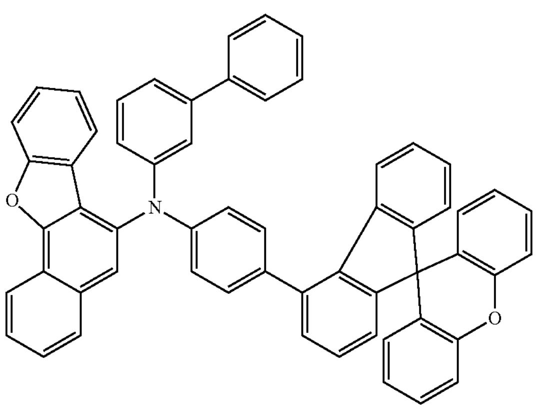

C6

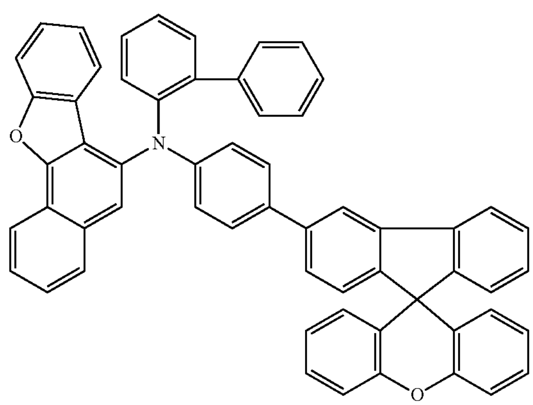

-continued
C7
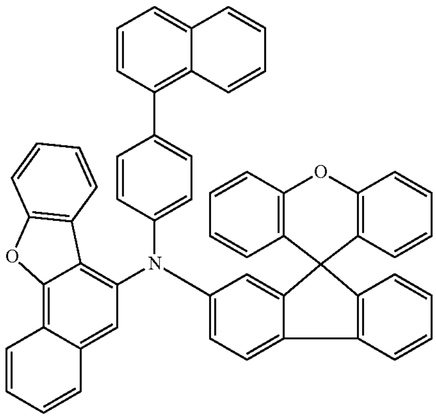
C8
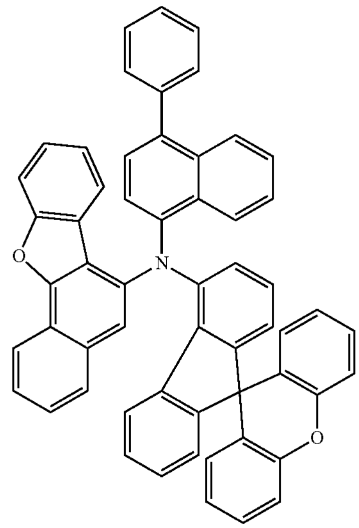
C9
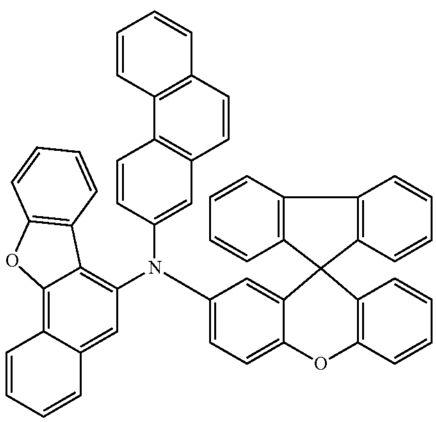
C10
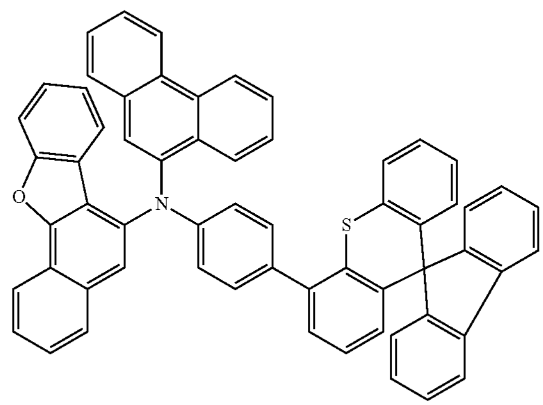
C11
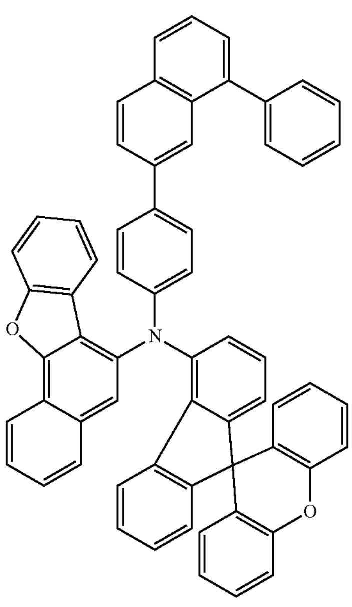
C12
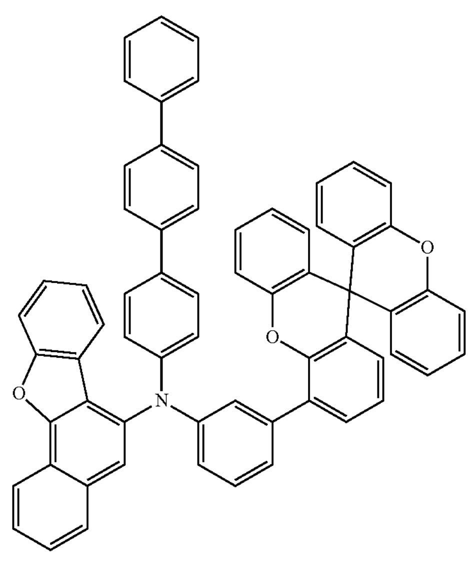

-continued
C13
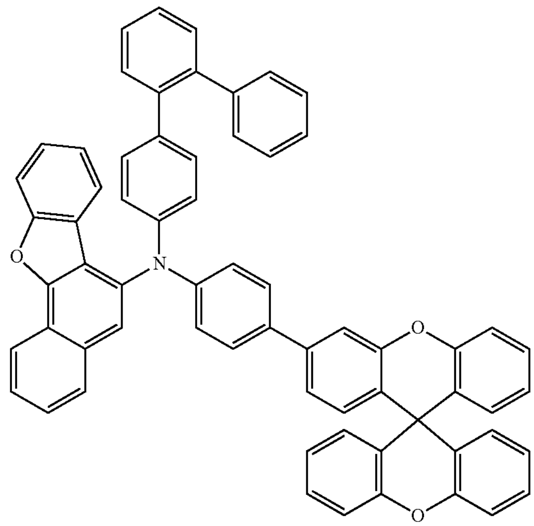
C14
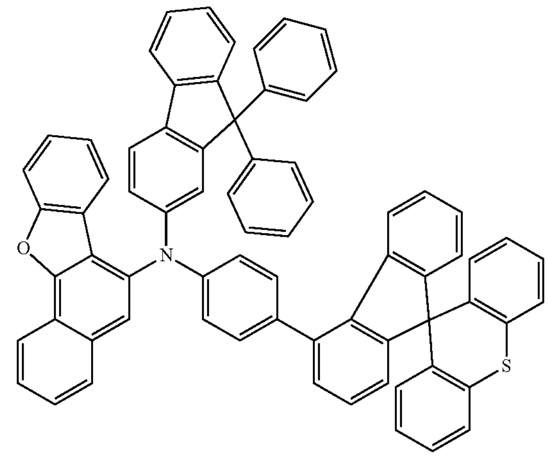
C15
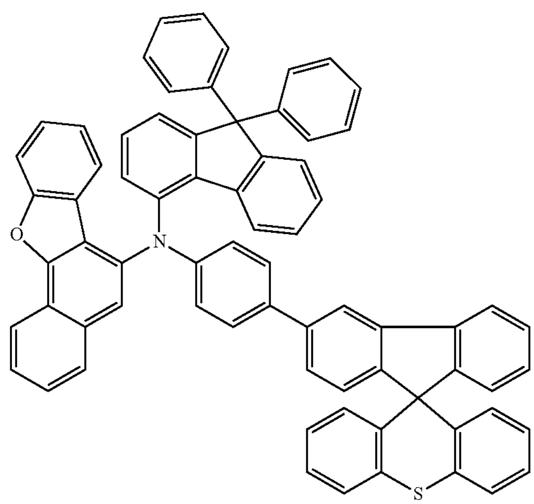
C16
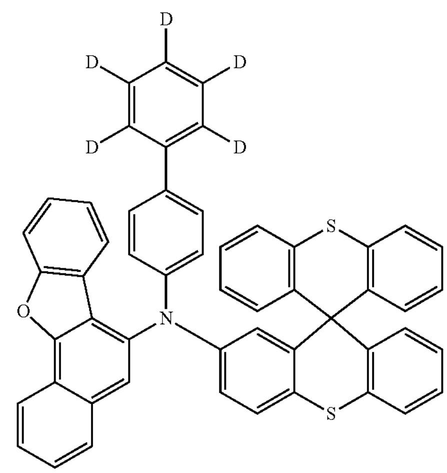
C17
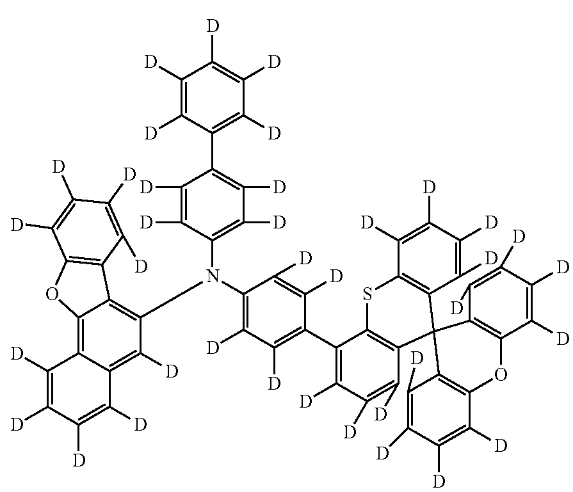
C18
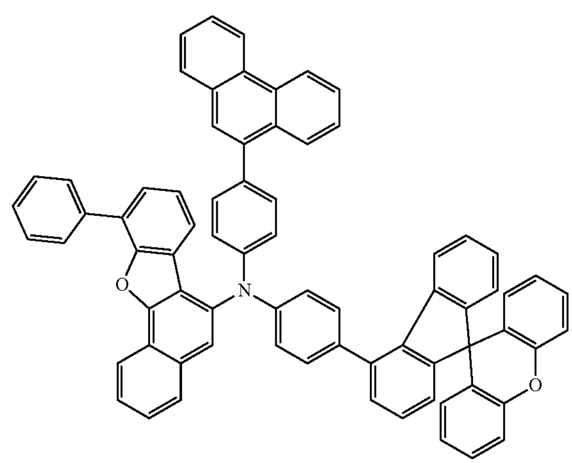

-continued
C19
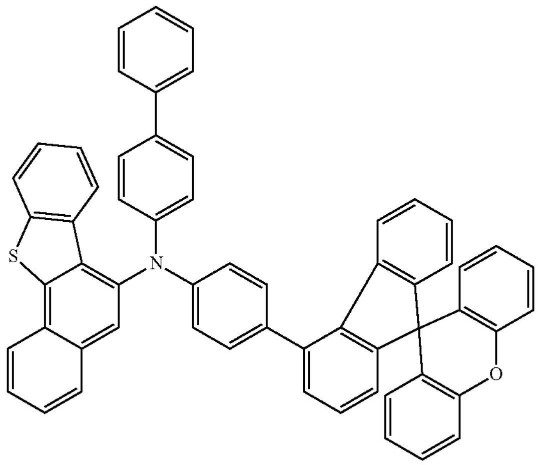
C20
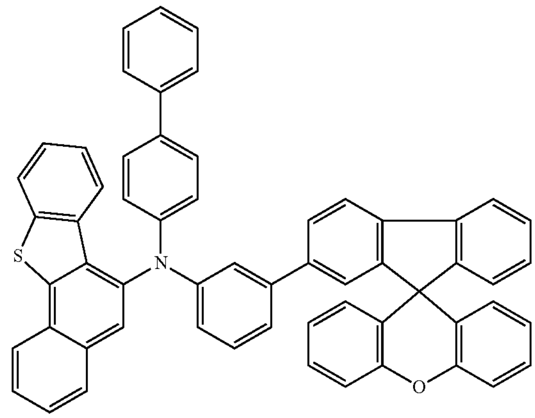
C21
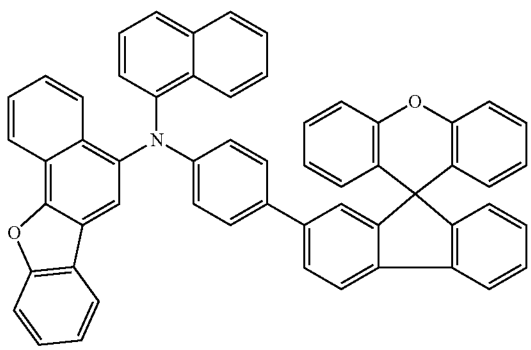
C22
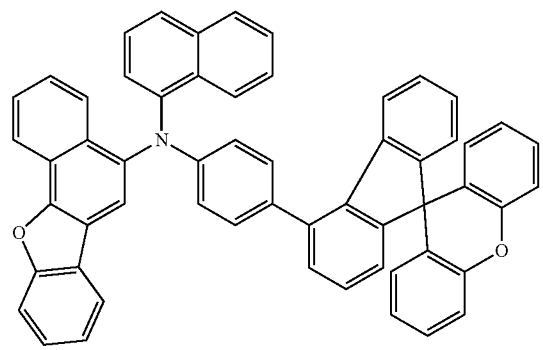
C23
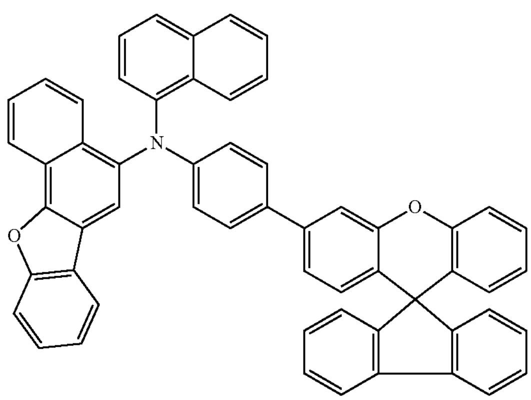
C24
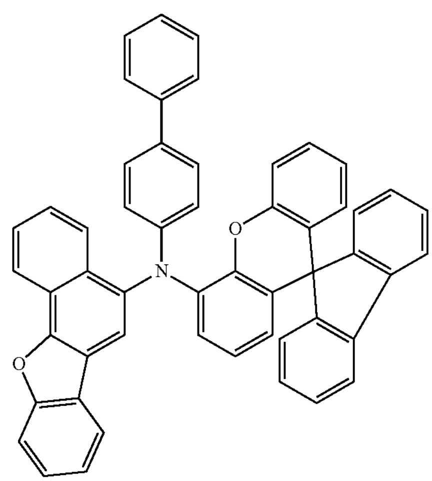

-continued
C25
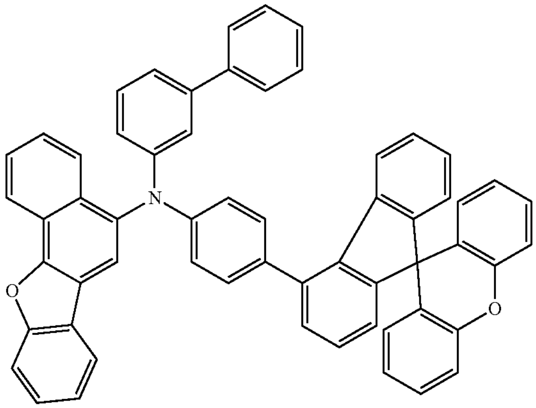
C26
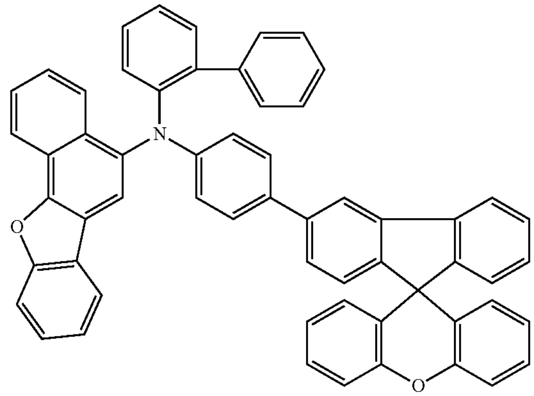
C27
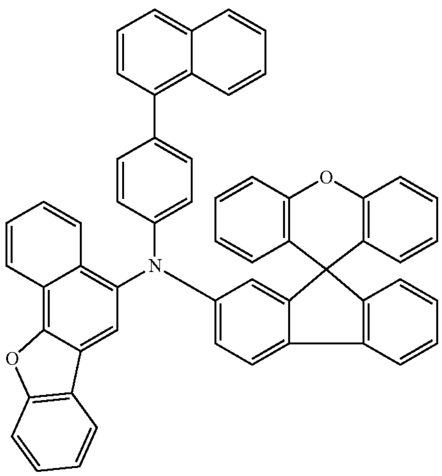
C28
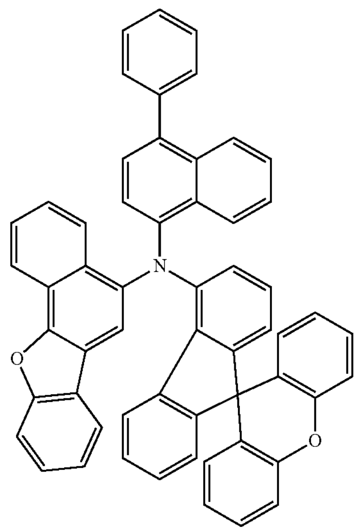
C29
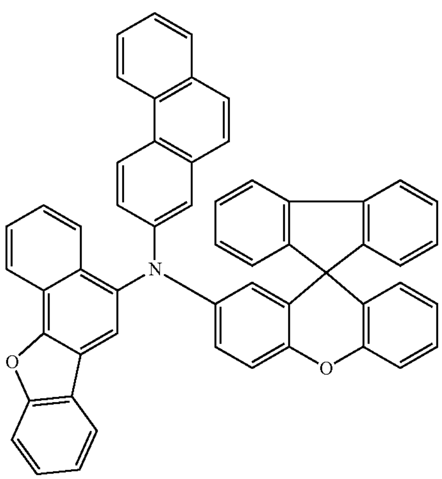
C30
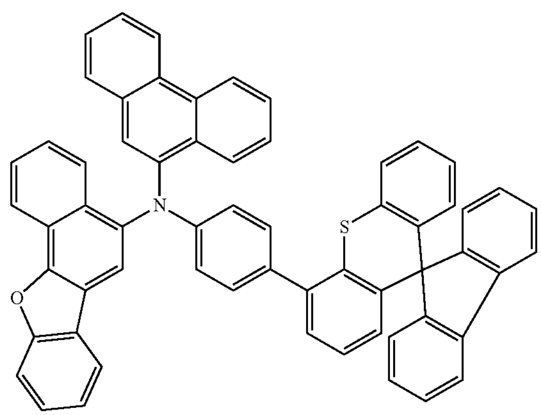

-continued
C31
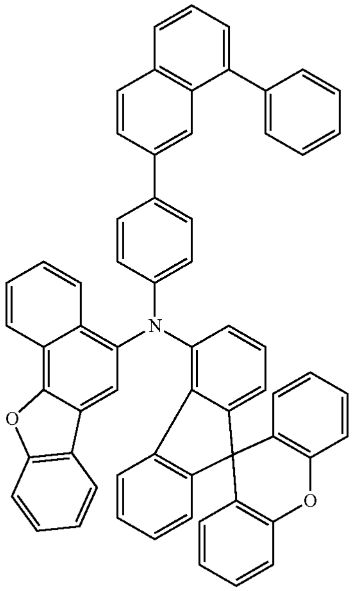
C32
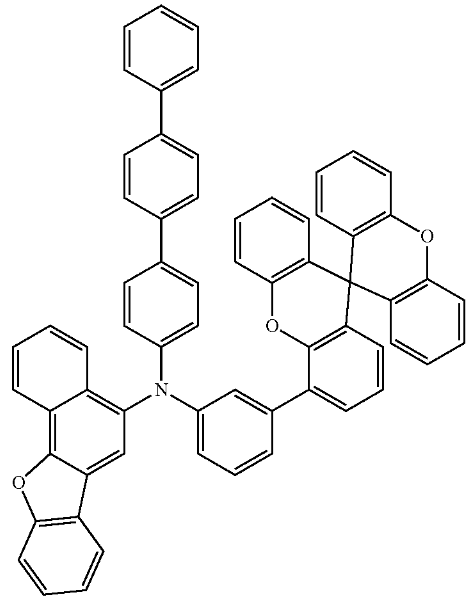
C33
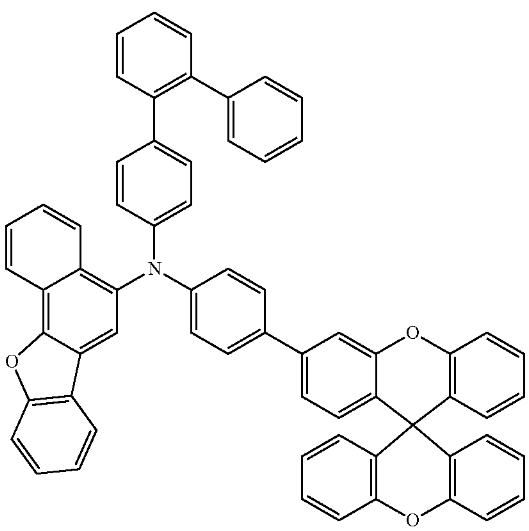
C34
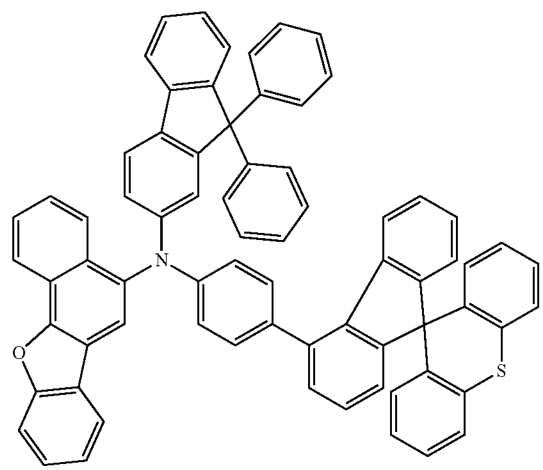
C35
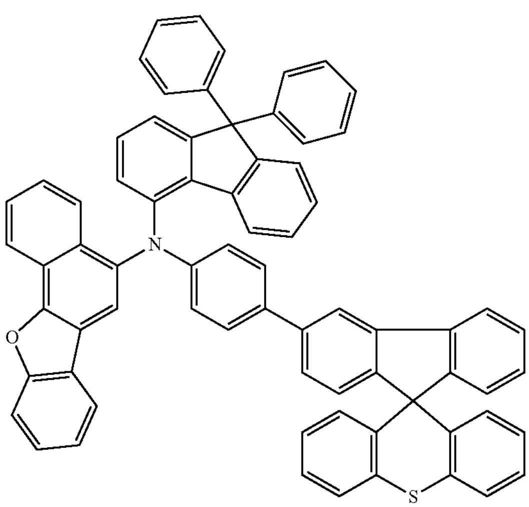
C36
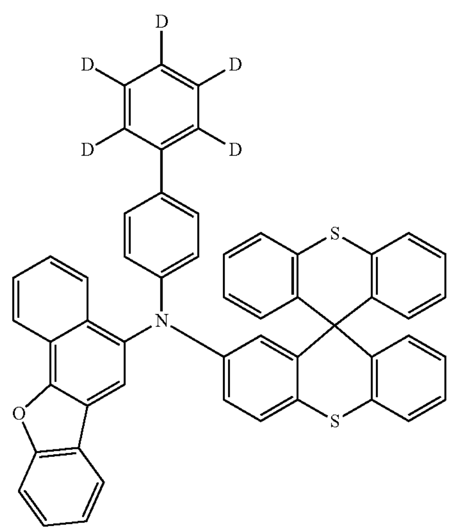

-continued
C37
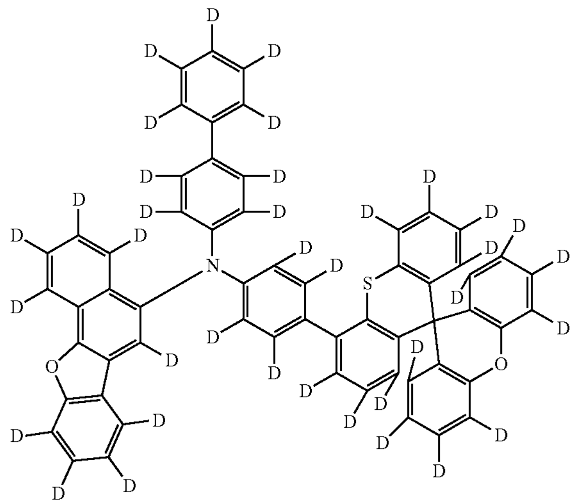
C38
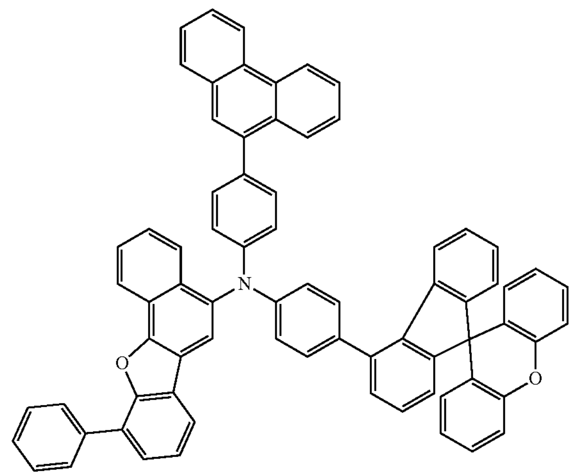
C39
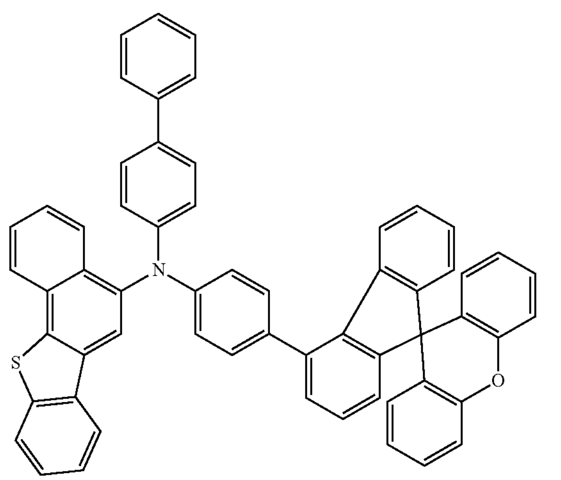
C40
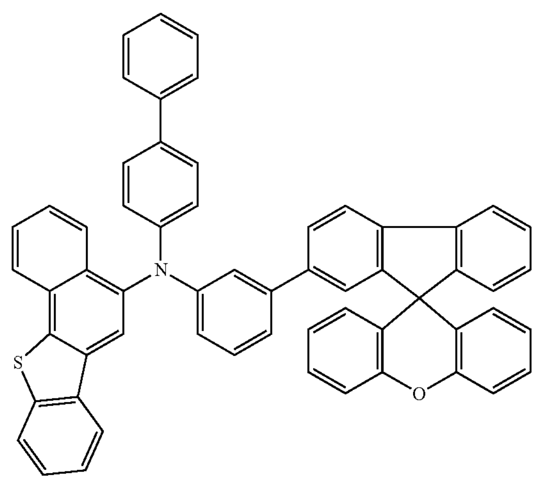
C41
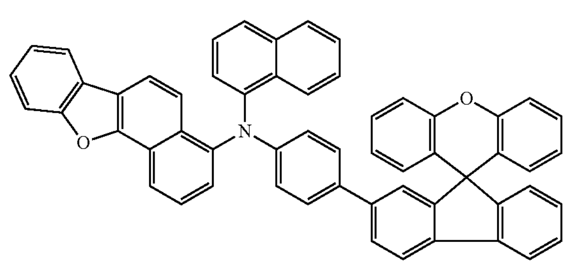
C42
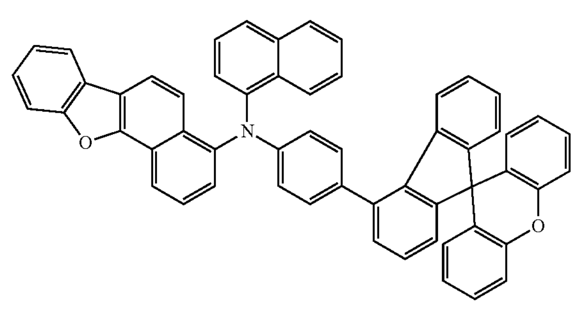

-continued
C43
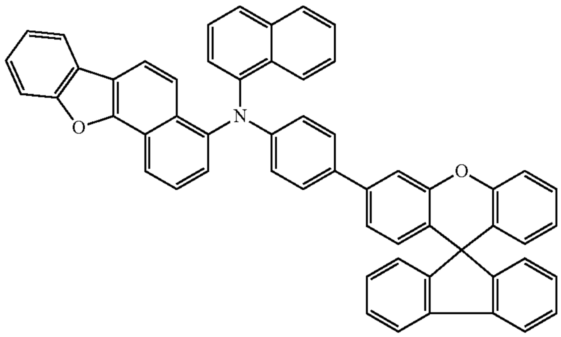
C44
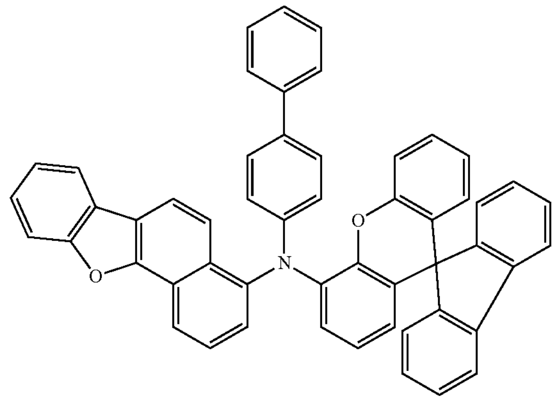
C45
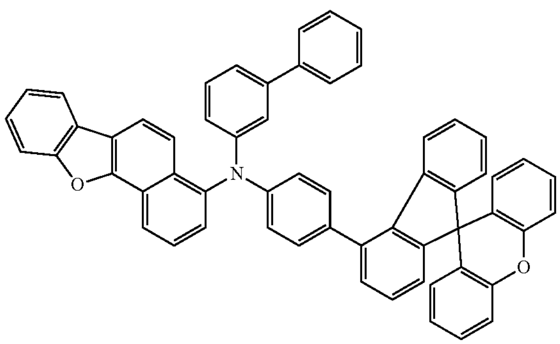
C46
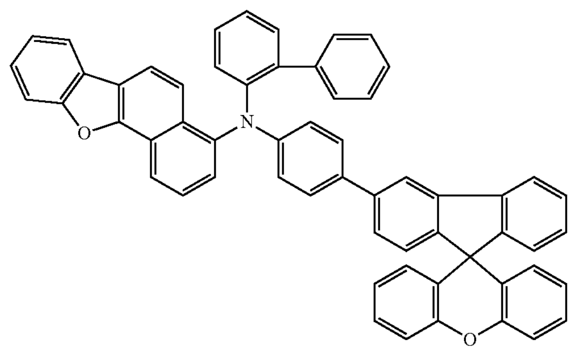
C47
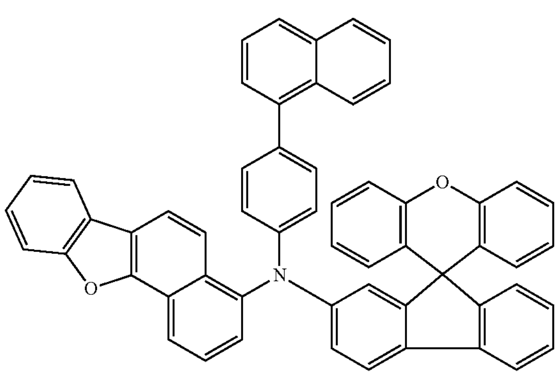
C48
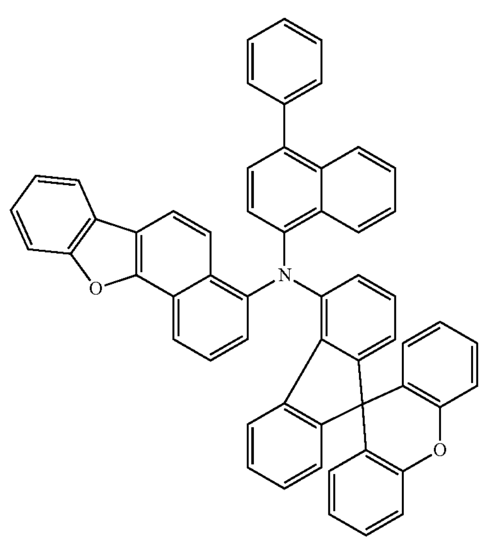

-continued
C49
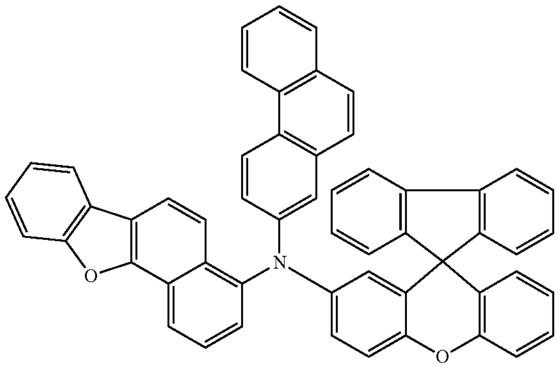
C50
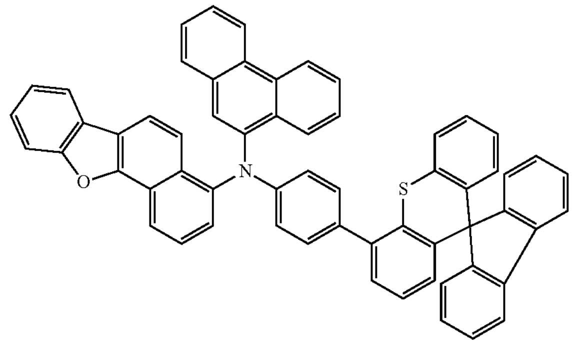
C51
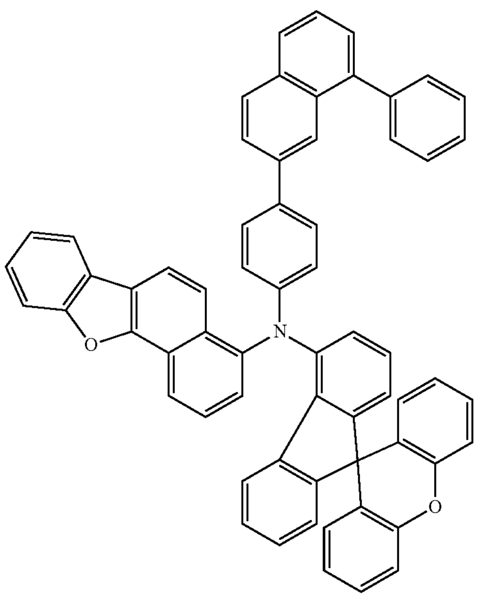
C52
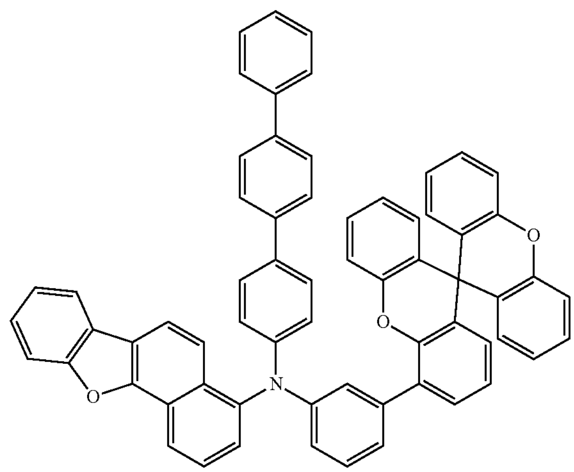
C53
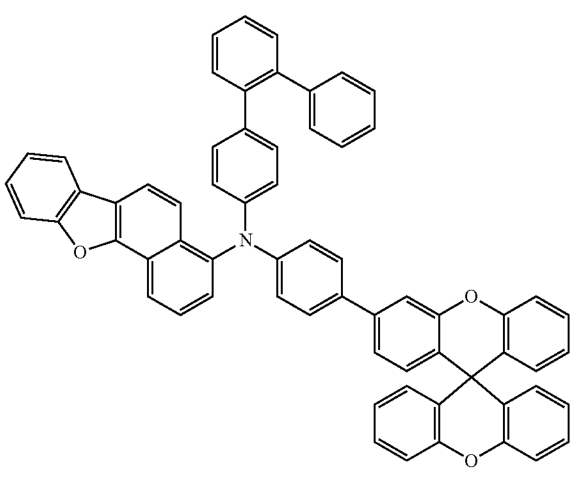
C54
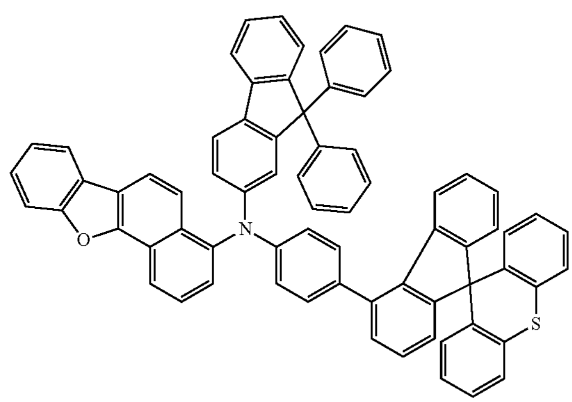

-continued
C55
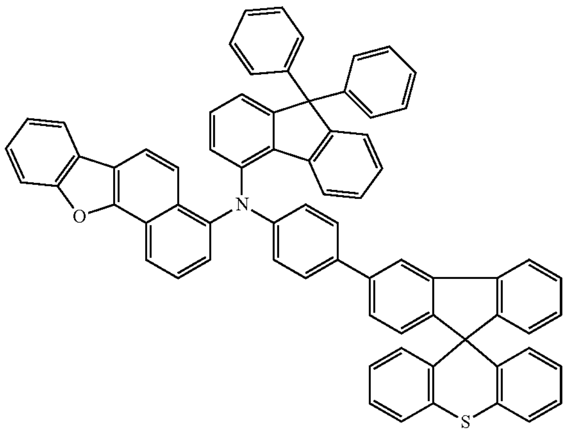
C56
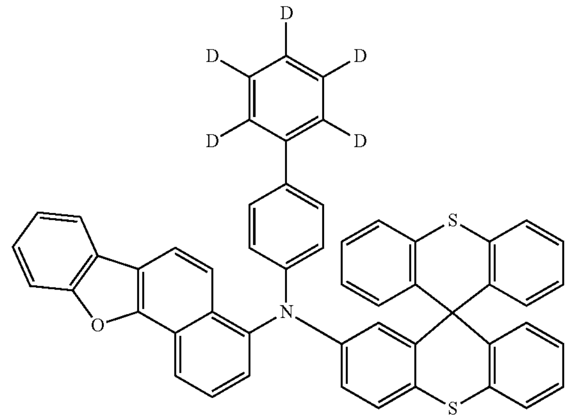
C57
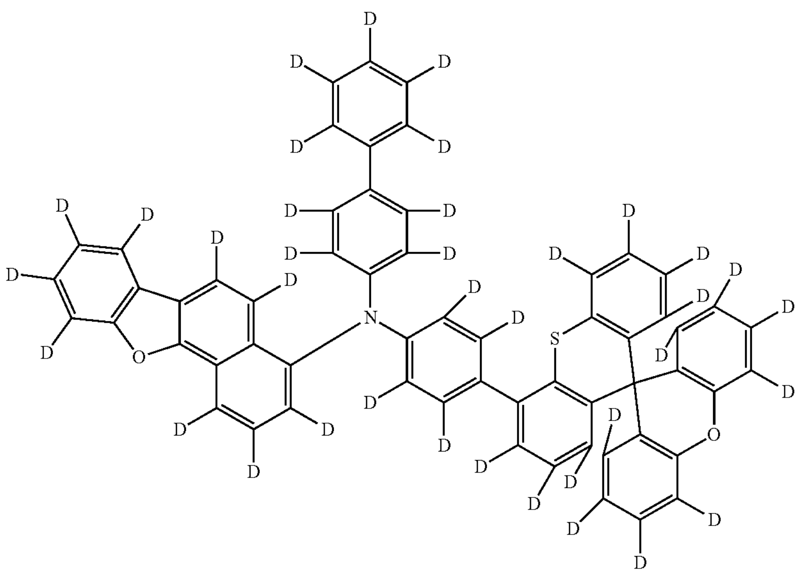
C58
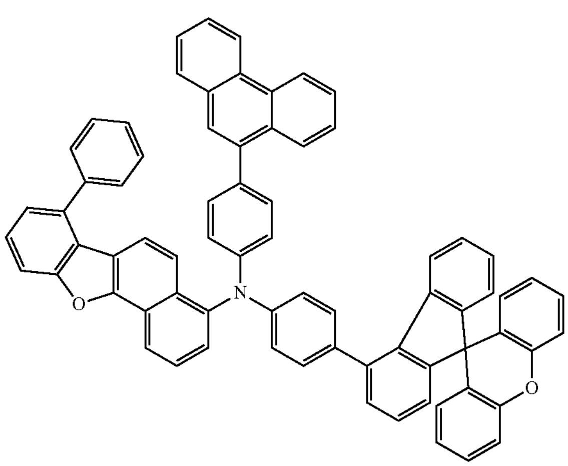
C59
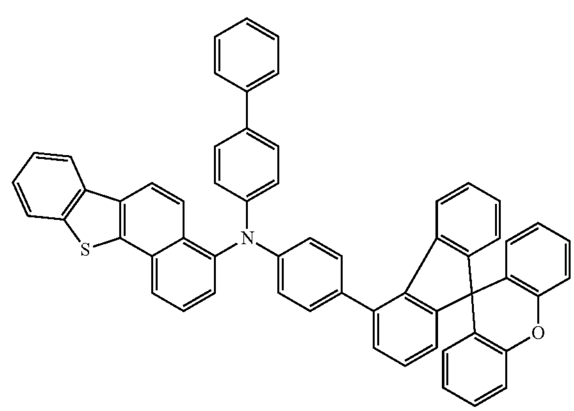

-continued
C60
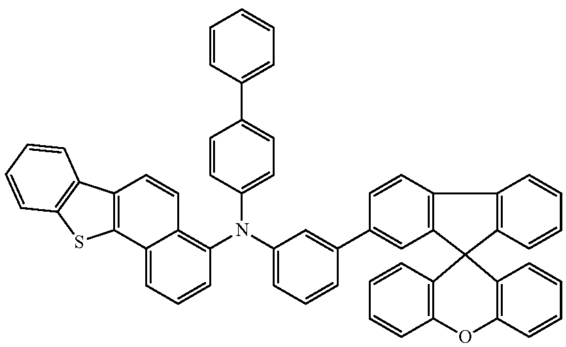
C61
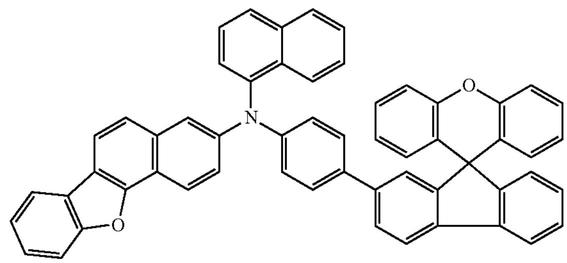
C62
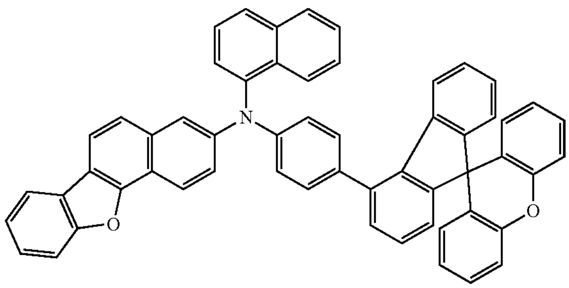
C63
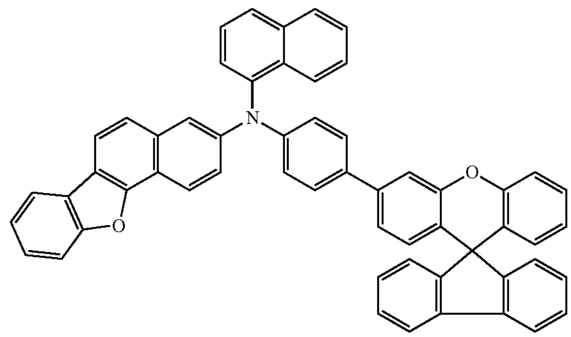
C64
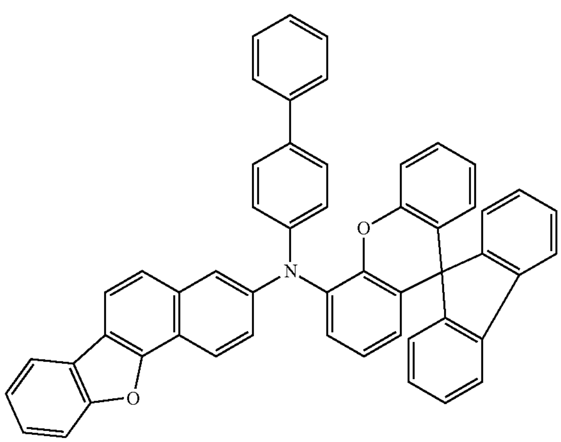
C65
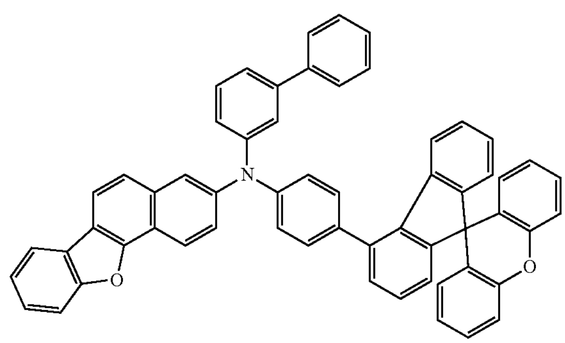
C66
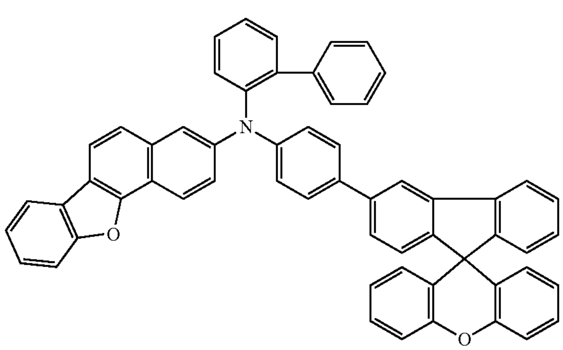
C67
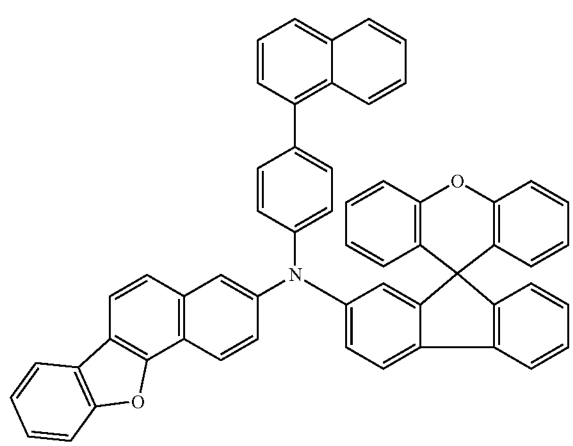

-continued
C68
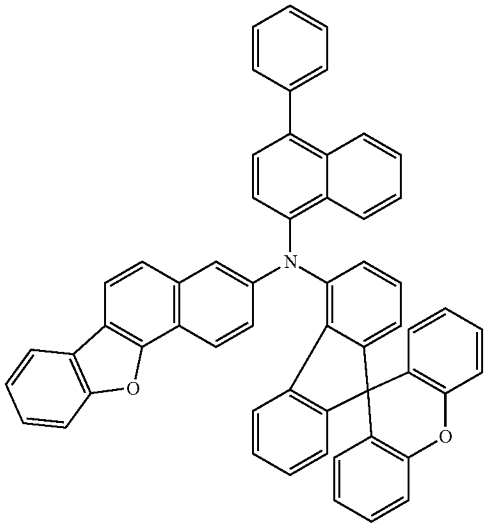
C69
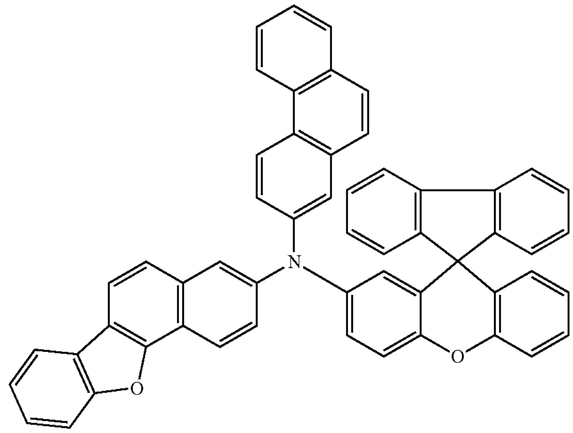
C70
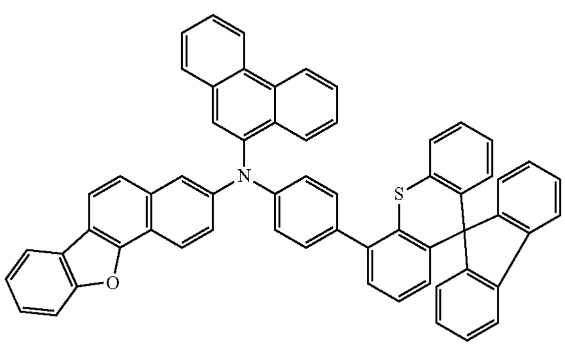
C71
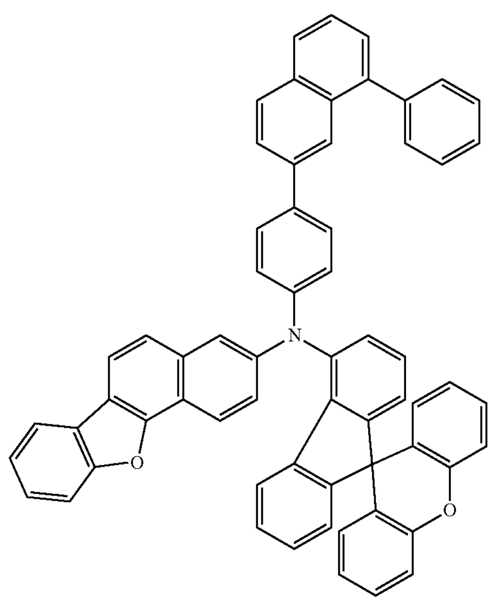

-continued
C72
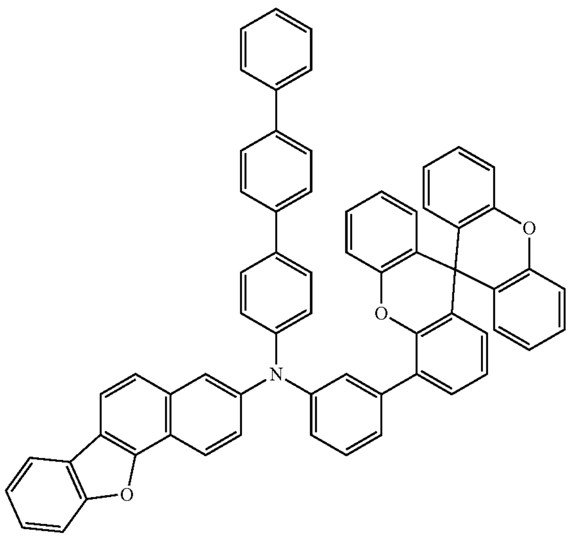
C73
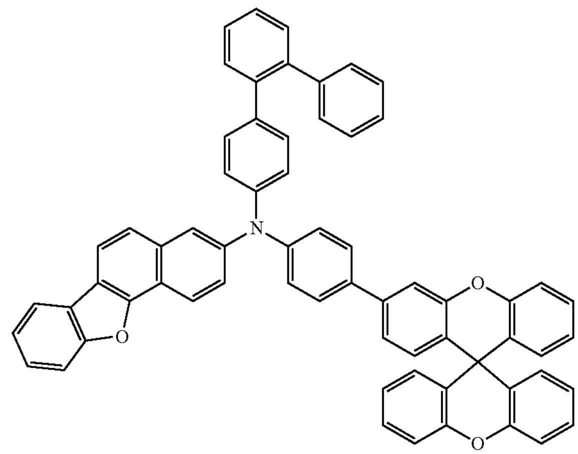
C74
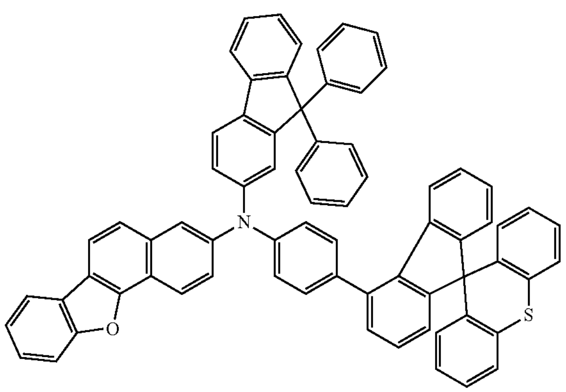
C75
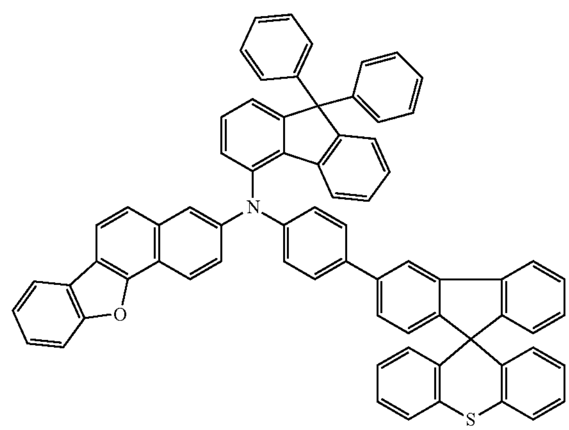
C76
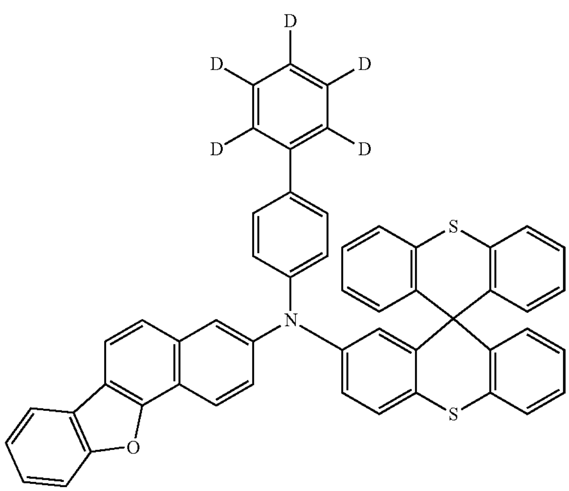

-continued
C77
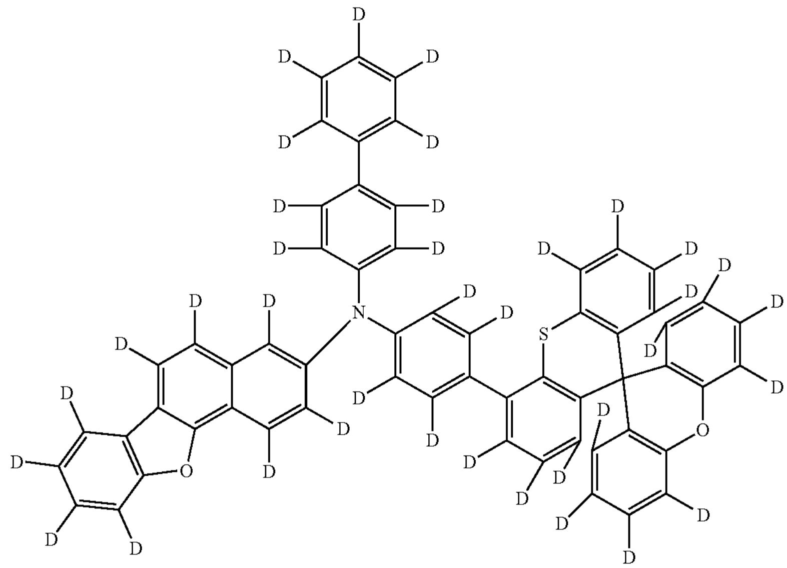
C78
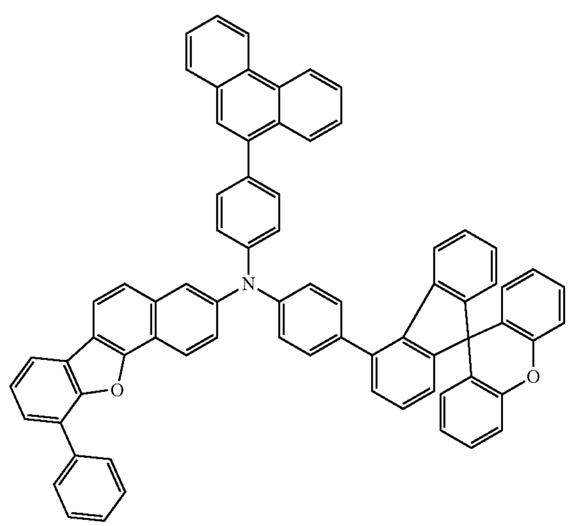
C79
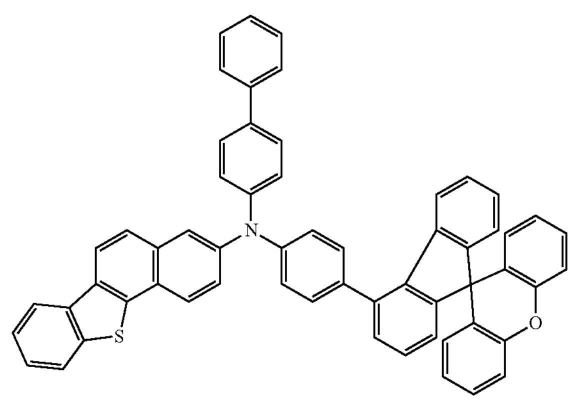
C80
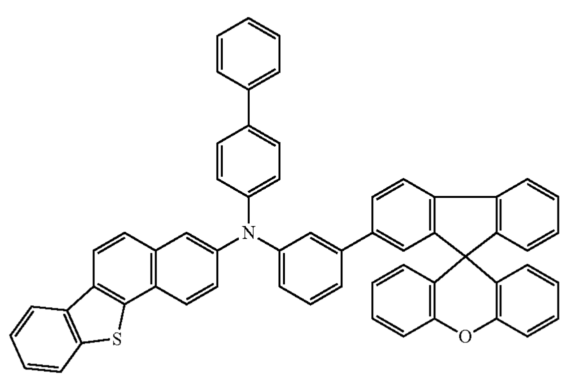
C81
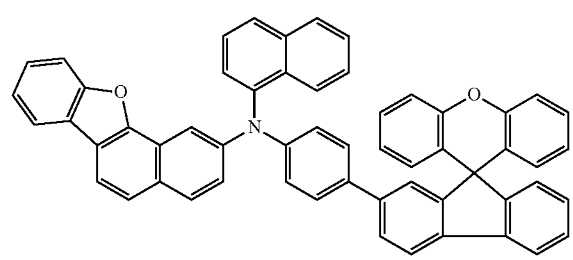

-continued
C82
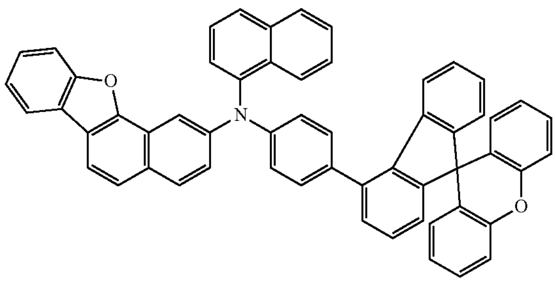
C83
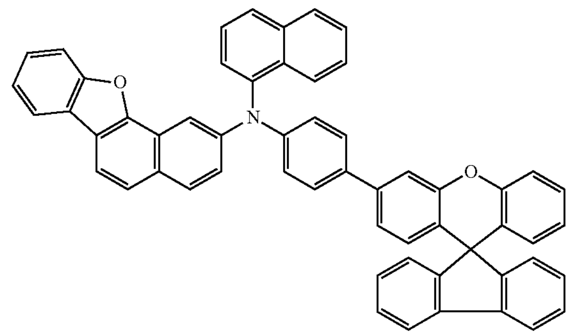
C84
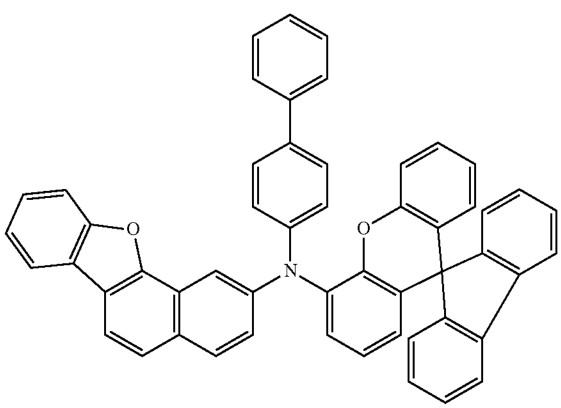
C85
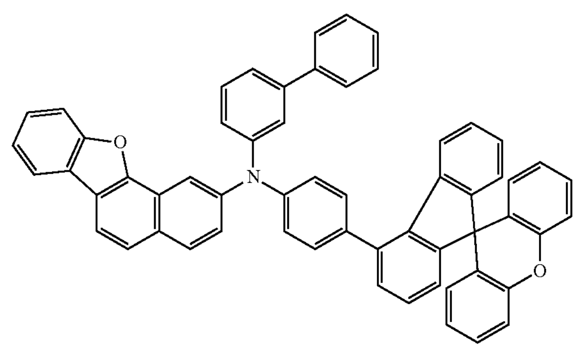
C86
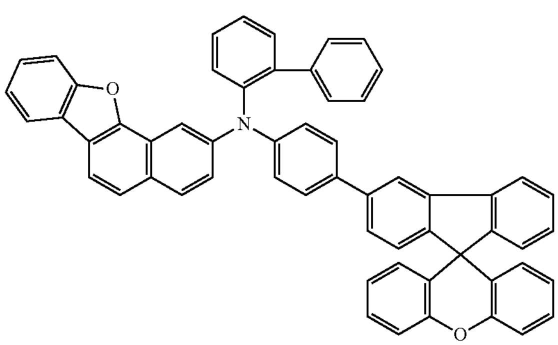
C87
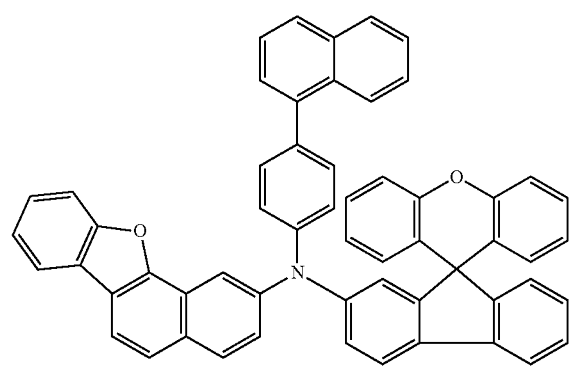

-continued
C88
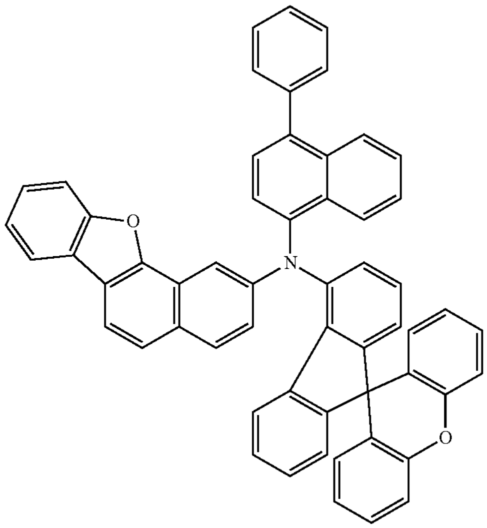
C89
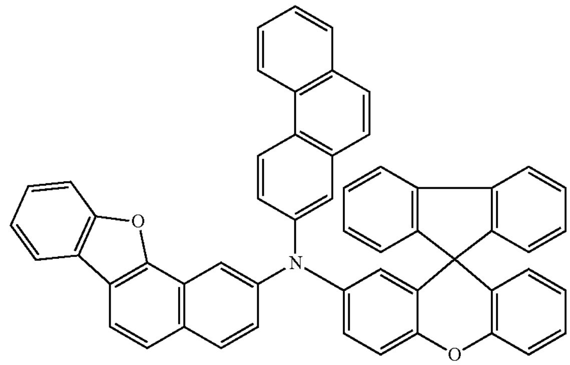
C90
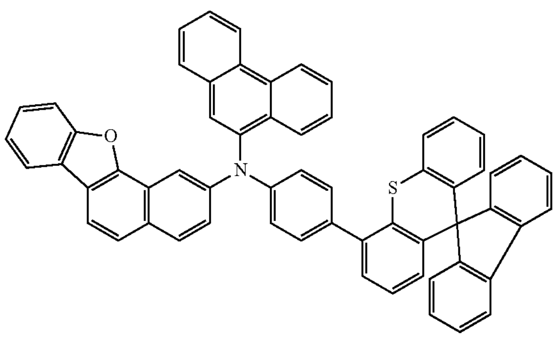
C91
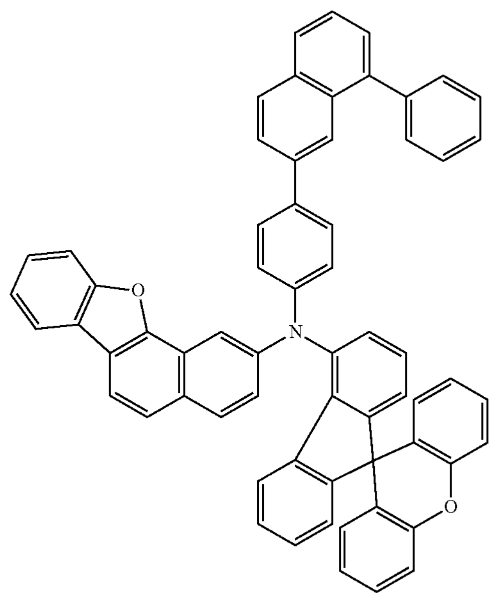
C92
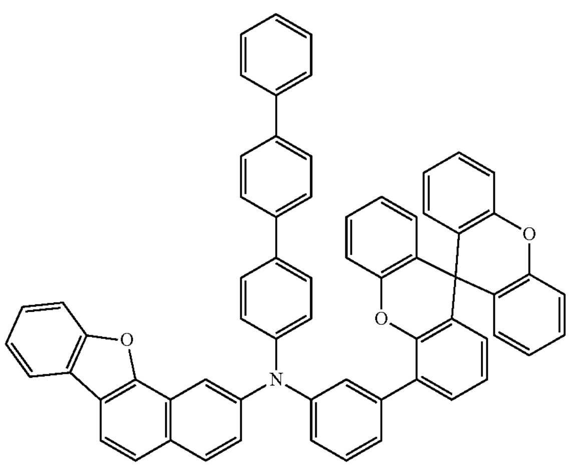
C93
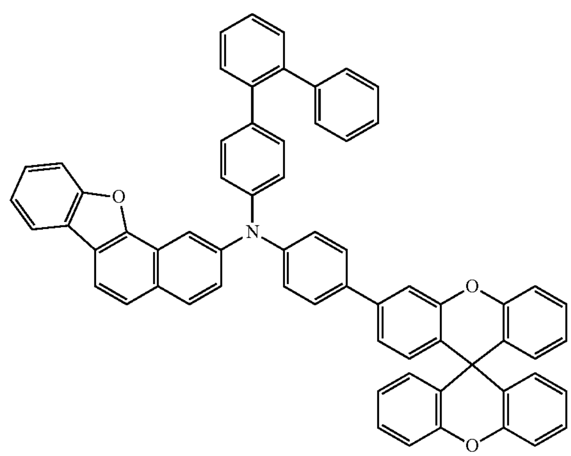

-continued
C94
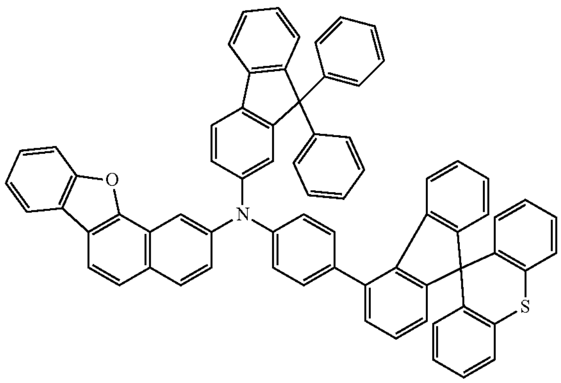
C95
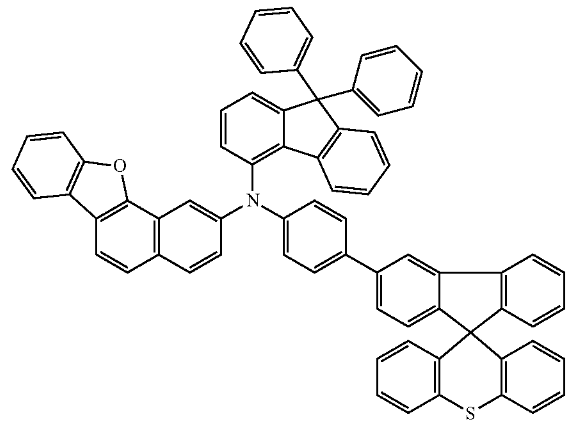
C96
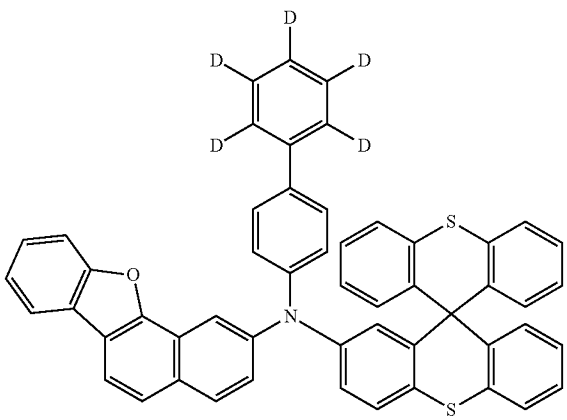
C97
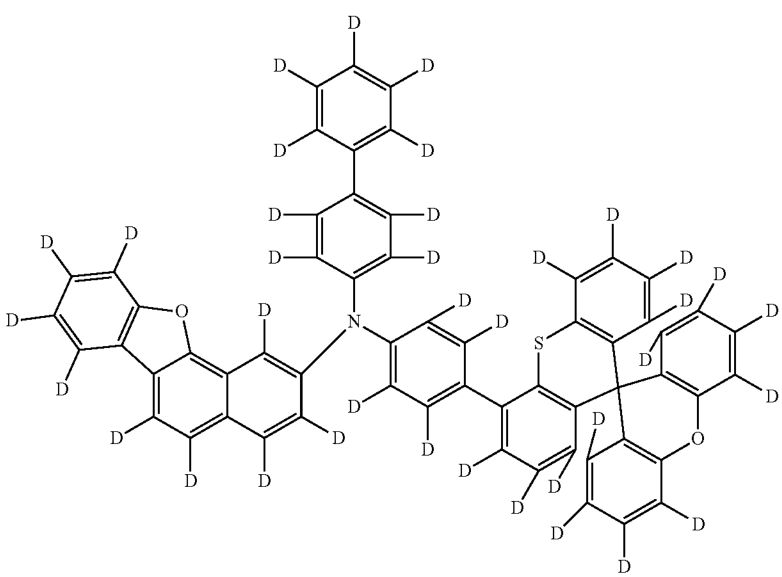

-continued
C98
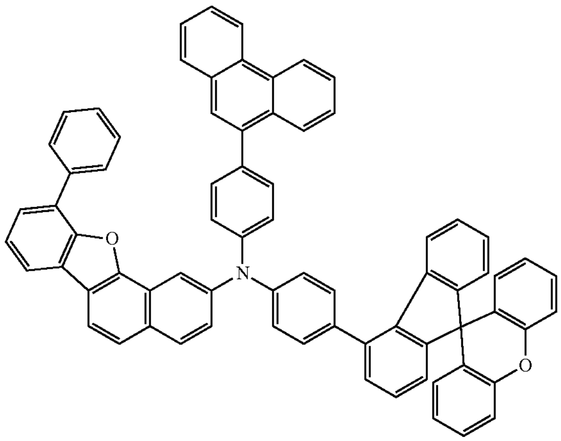
C99
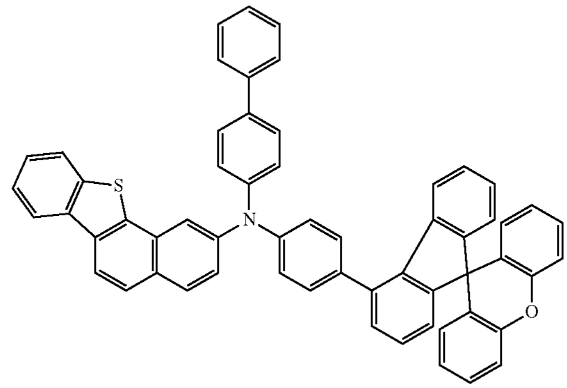
C100
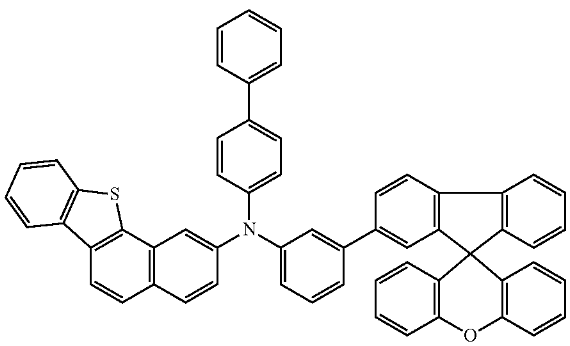
C101
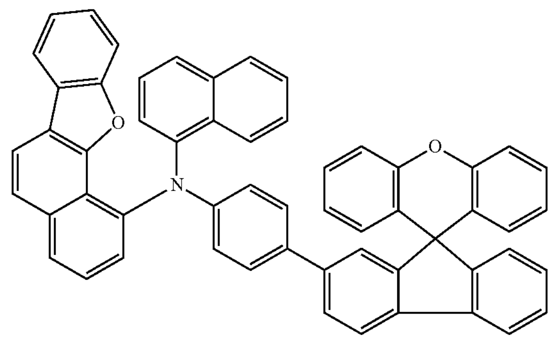
C102
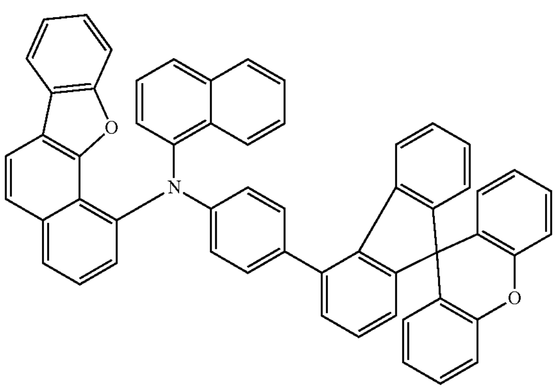
C103
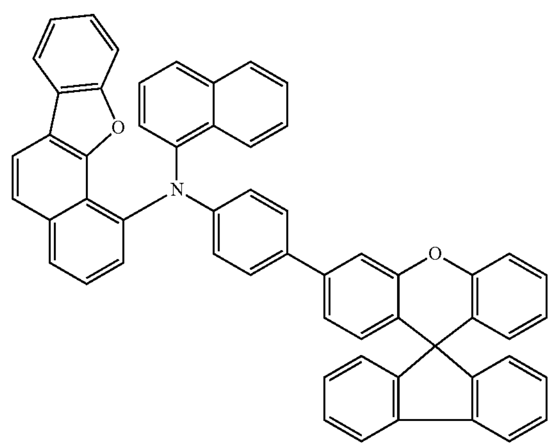

-continued
C104
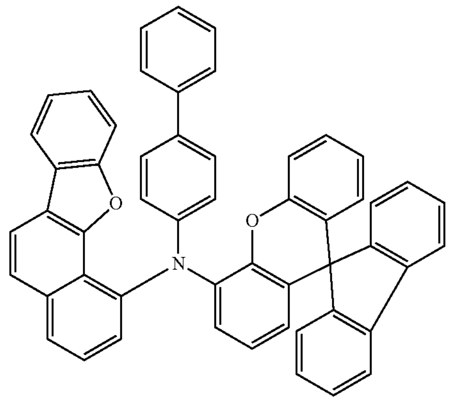
C105
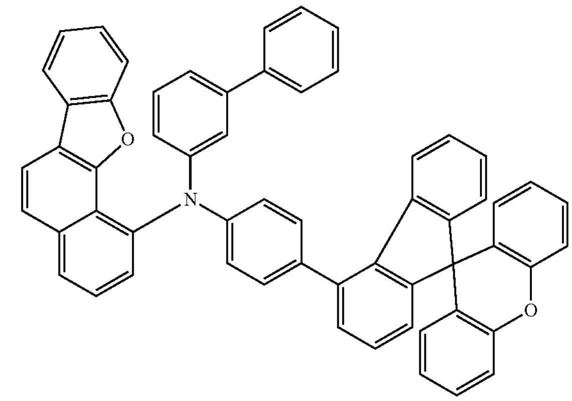
C106
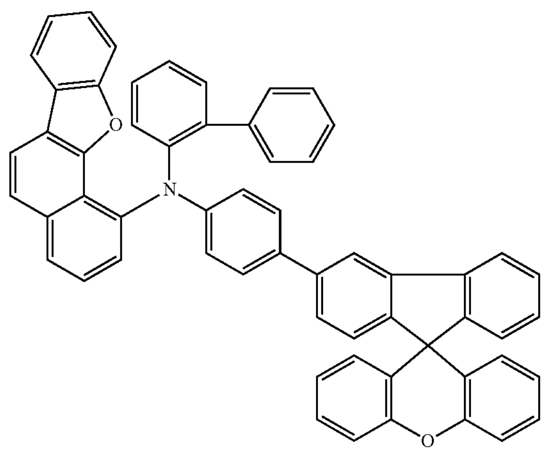
C107
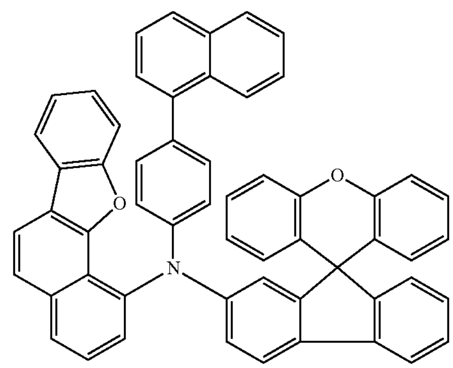
C108
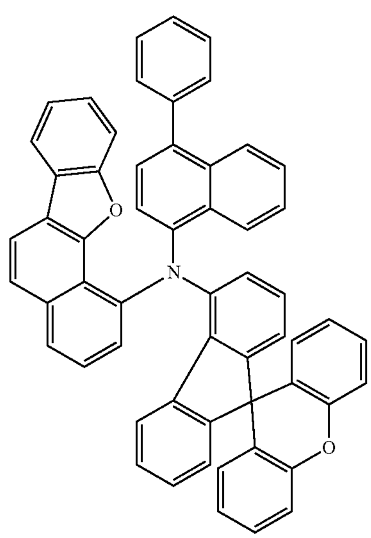
C109
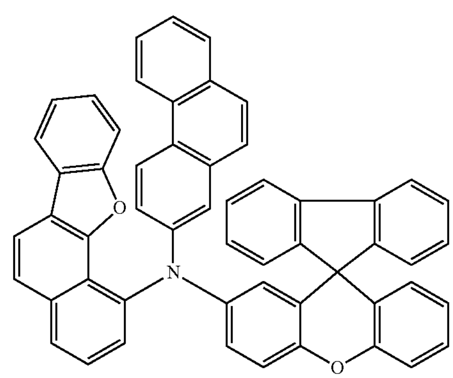

-continued
C110
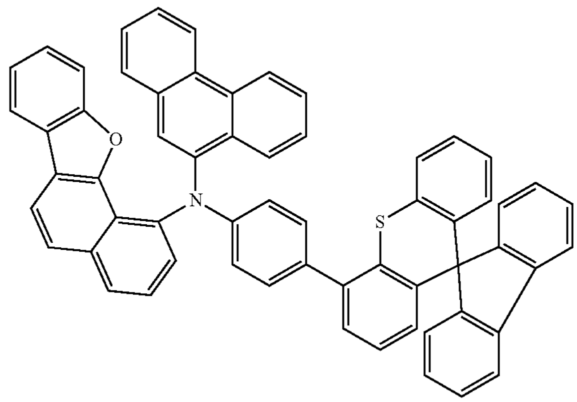
C111
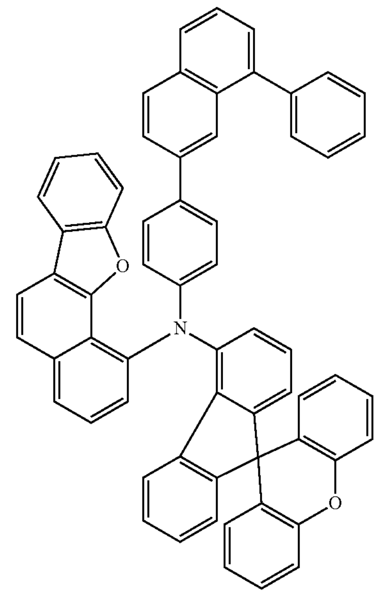
C112
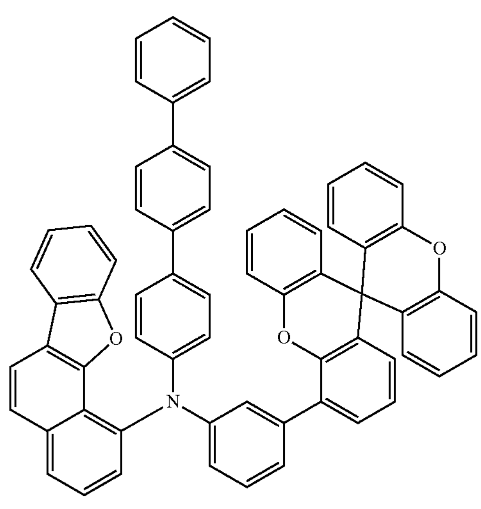
C113
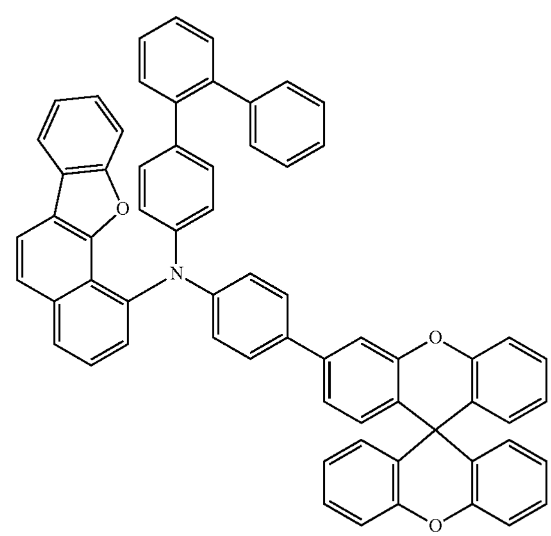

-continued
C114
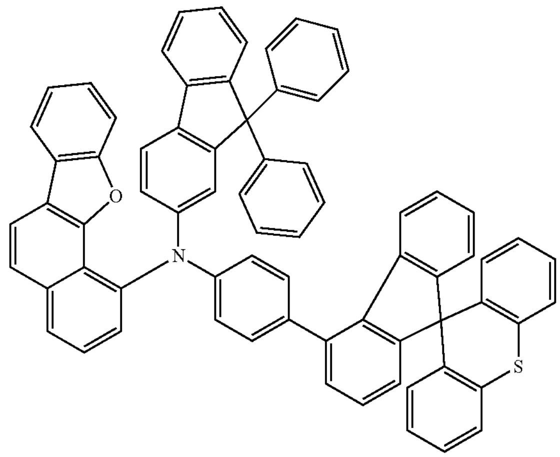
C115
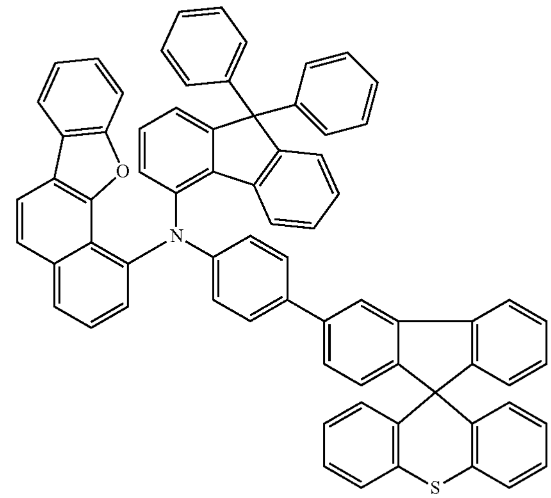
C116
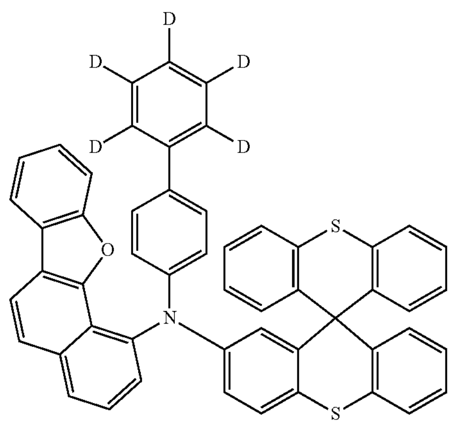
C117
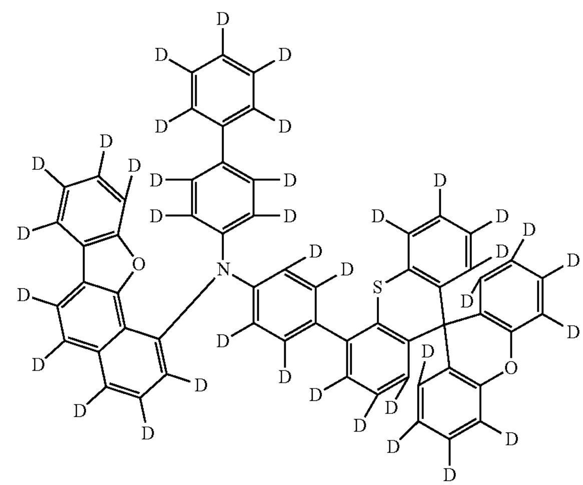
C118
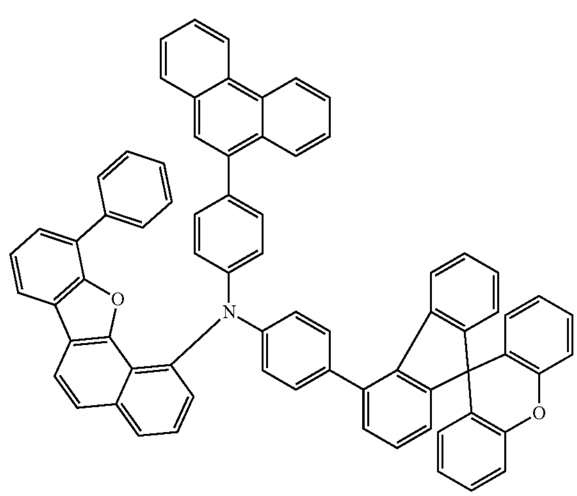
C119
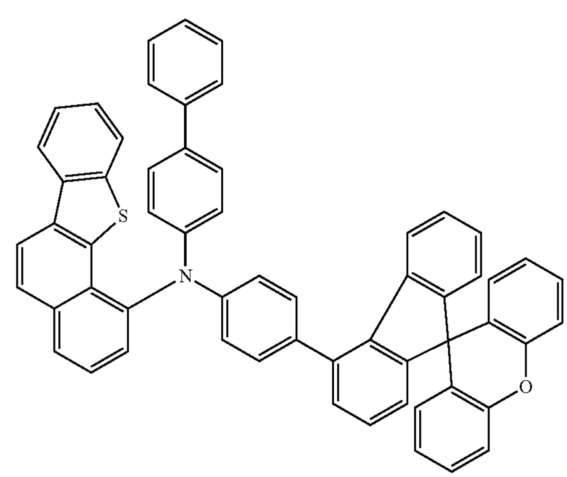

-continued
C120
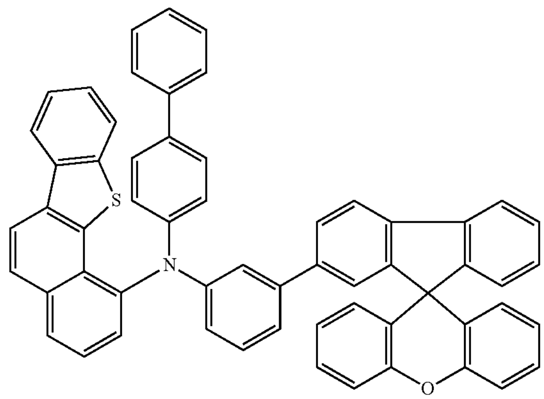
C121
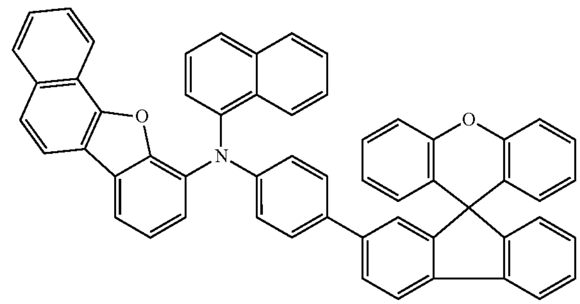
C122
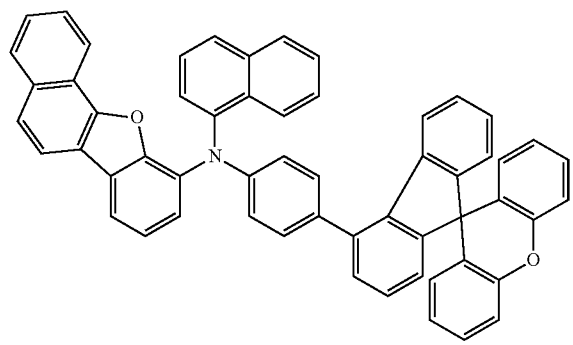
C123
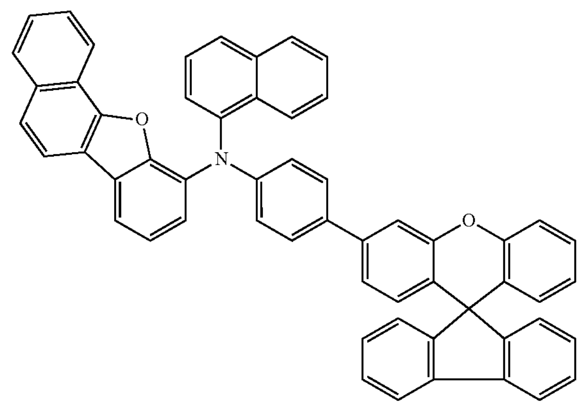
C124
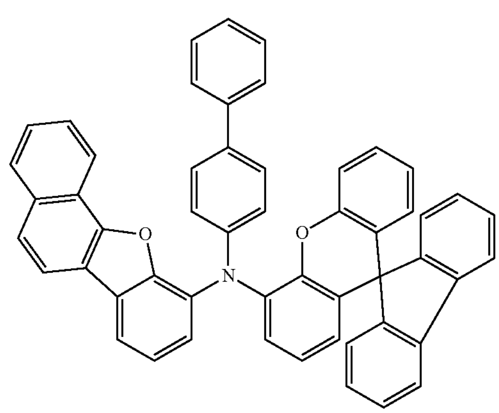
C125
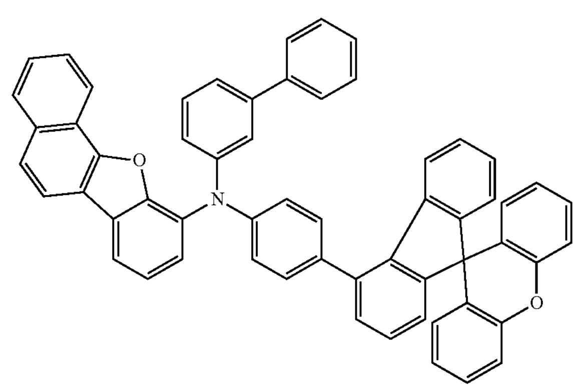

-continued
C126
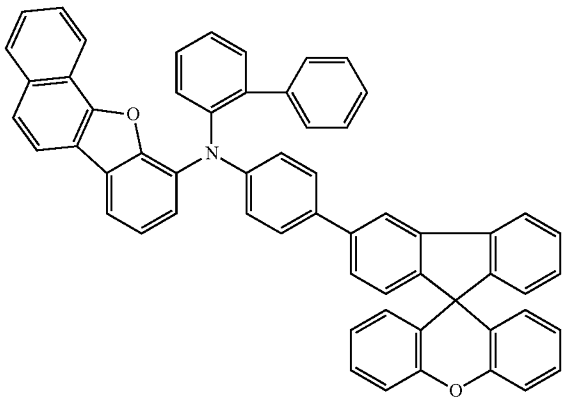
C127
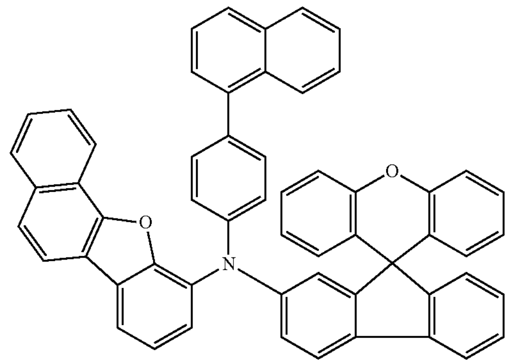
C128
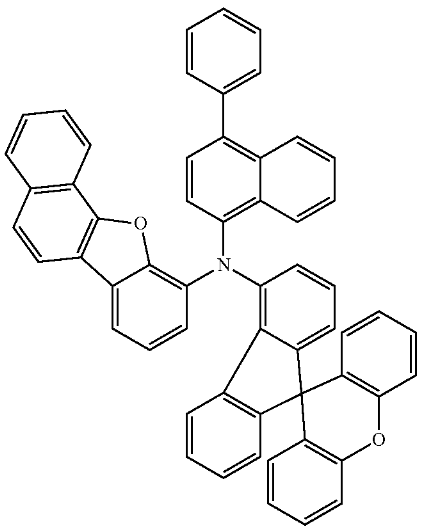
C129
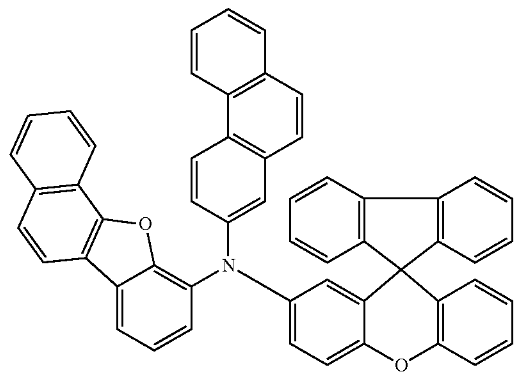
C130
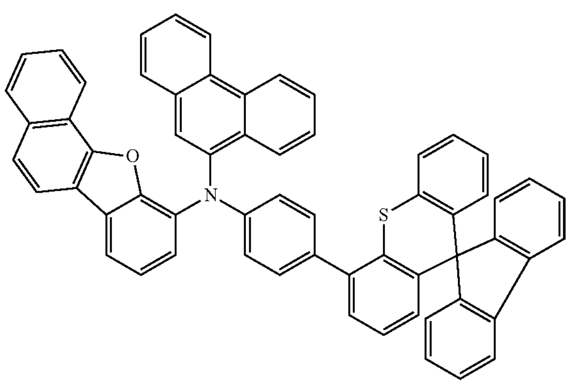
C131
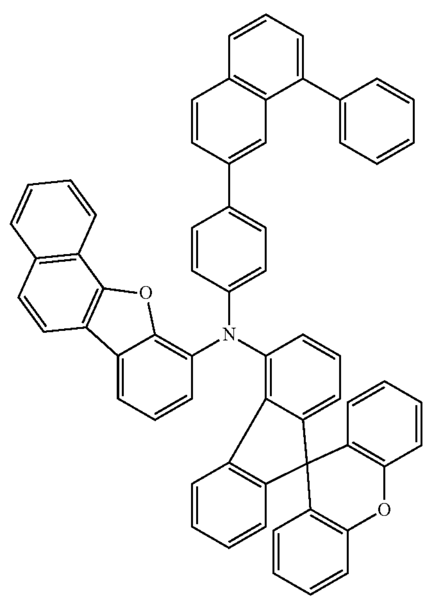

-continued
C132
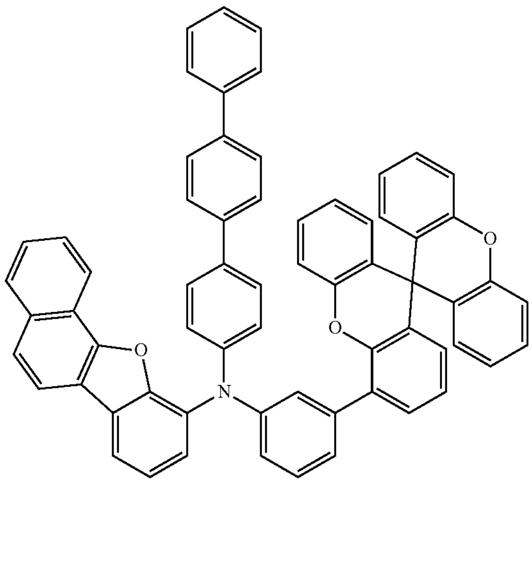
C133
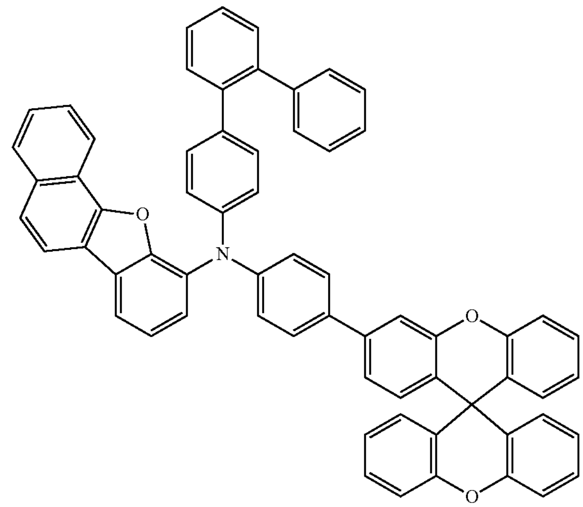
C134
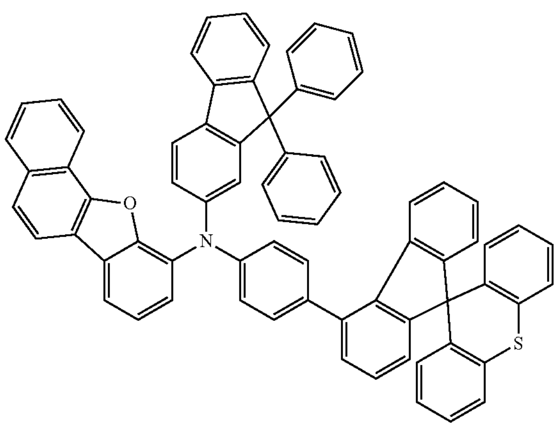
C135
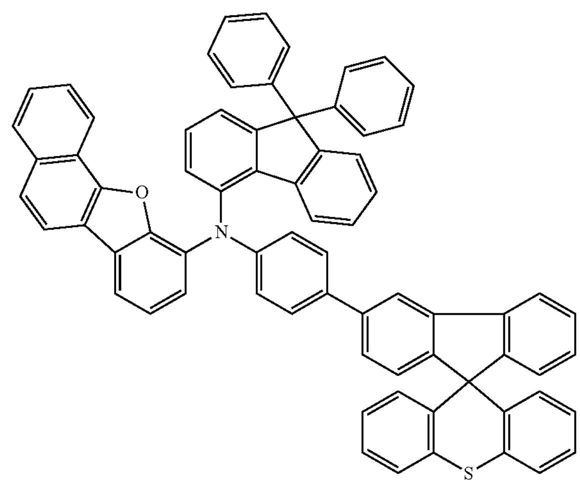
C136
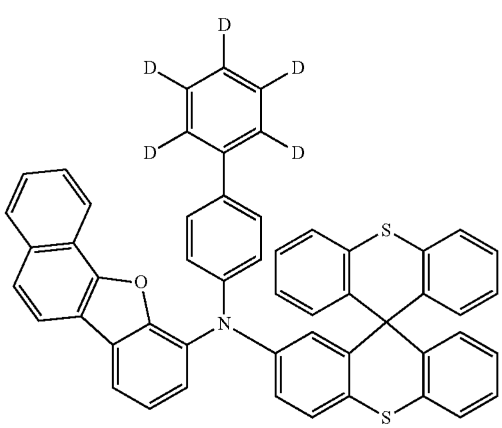
C137
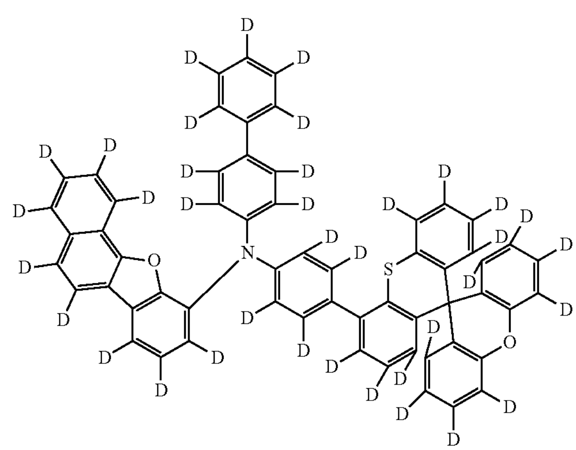

-continued
C138
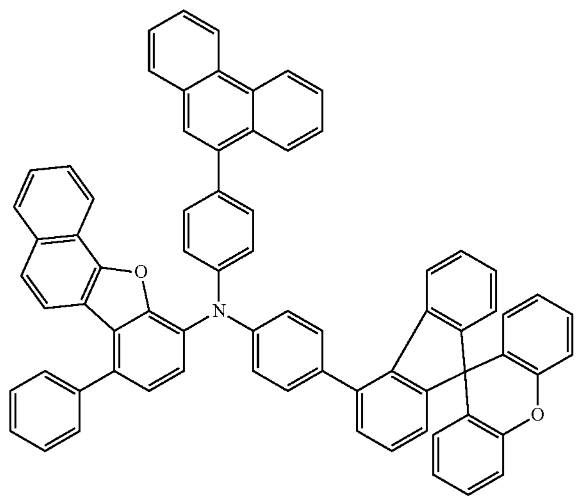
C139
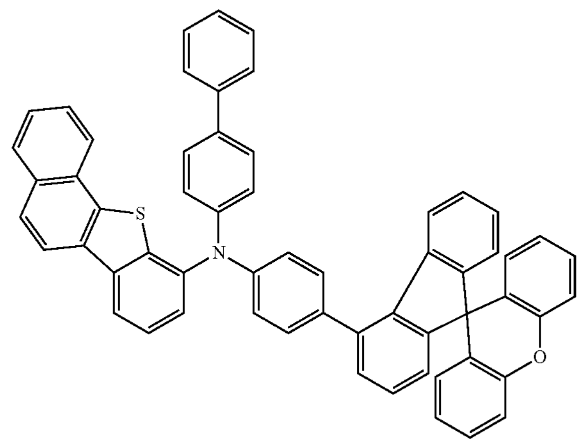
C140
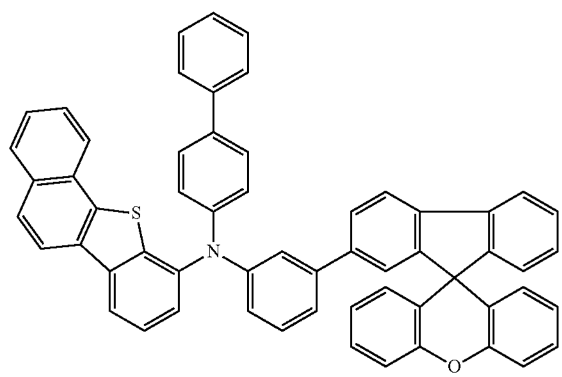
C141
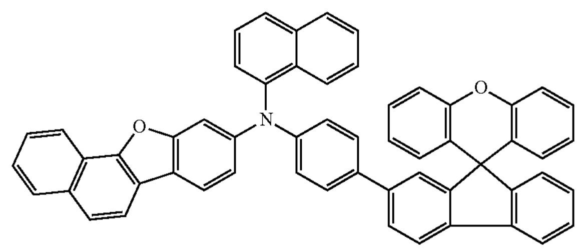
C142
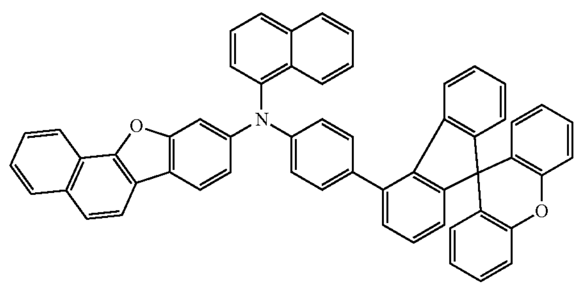
C143
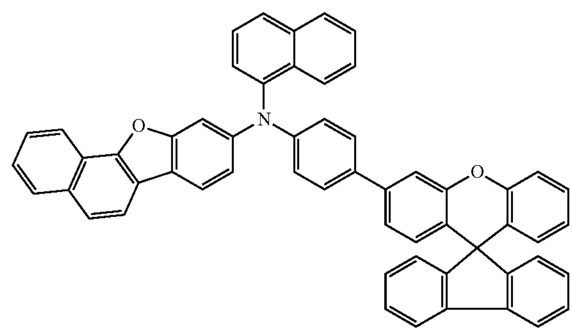

-continued
C144
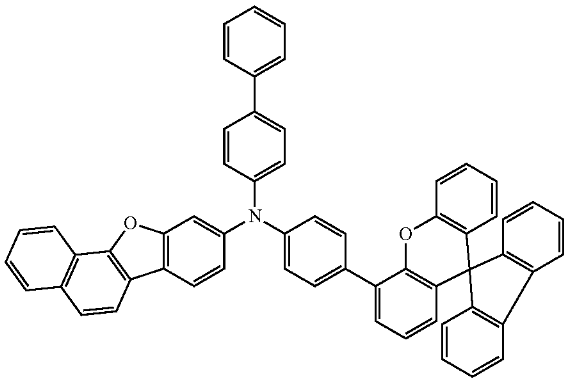
C145
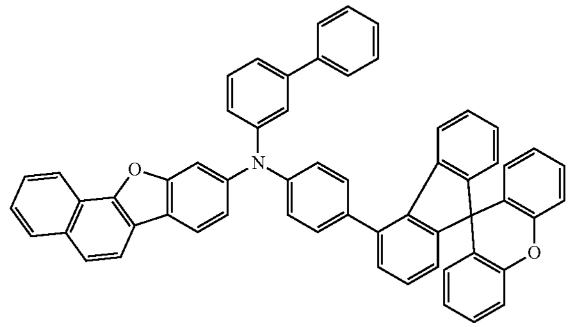
C146
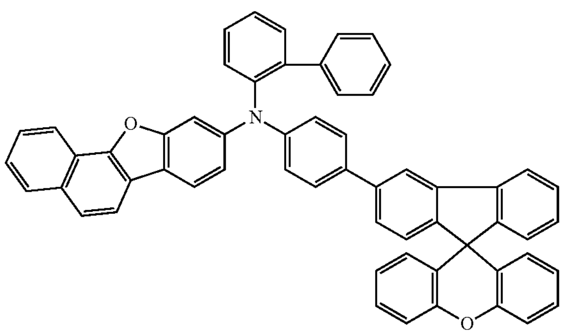
C147
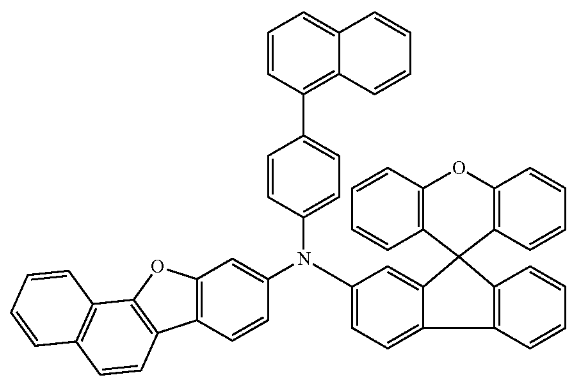
C148
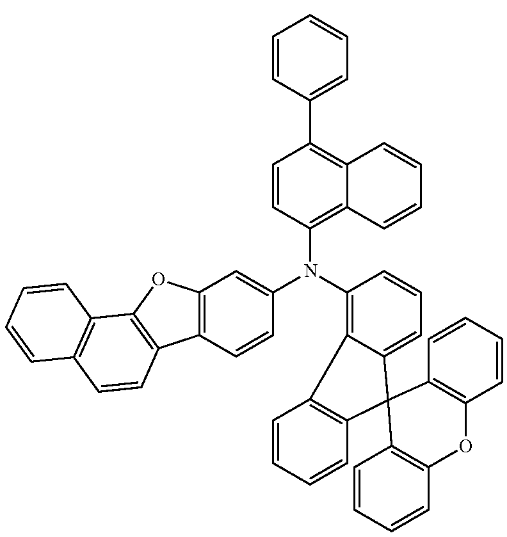
C149
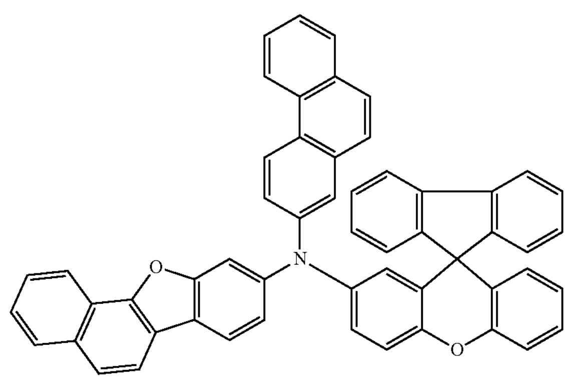

-continued
C150
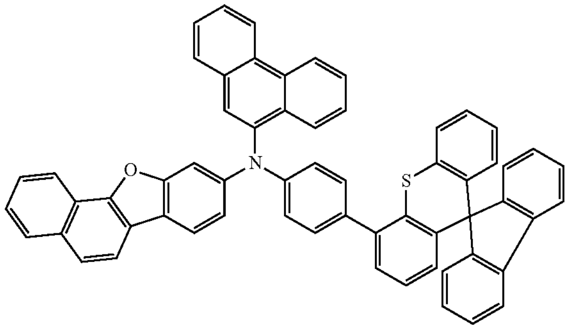
C151
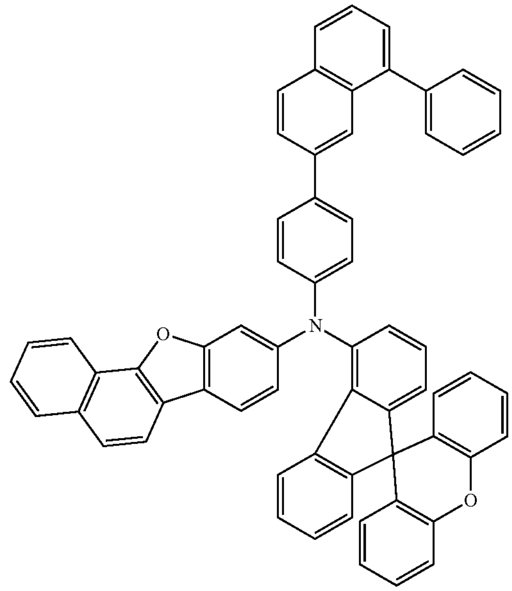
C152
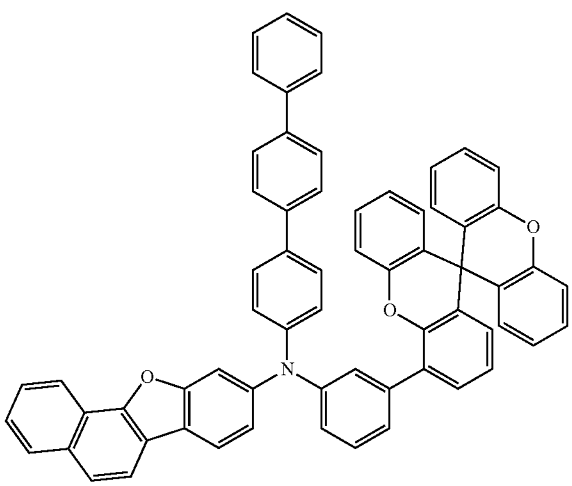
C153
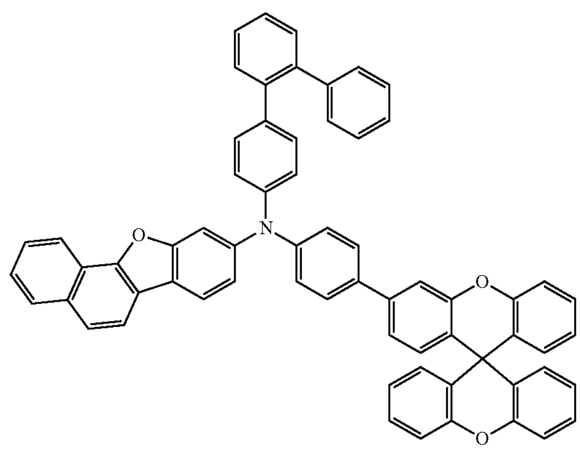
C154
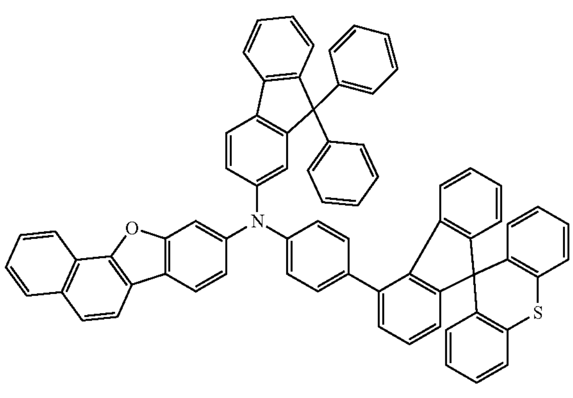
C155
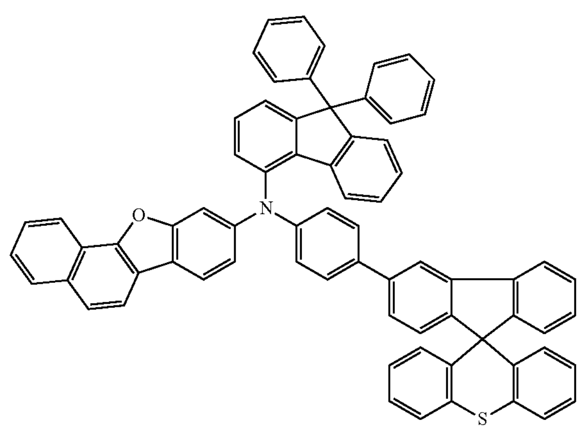

-continued
C156
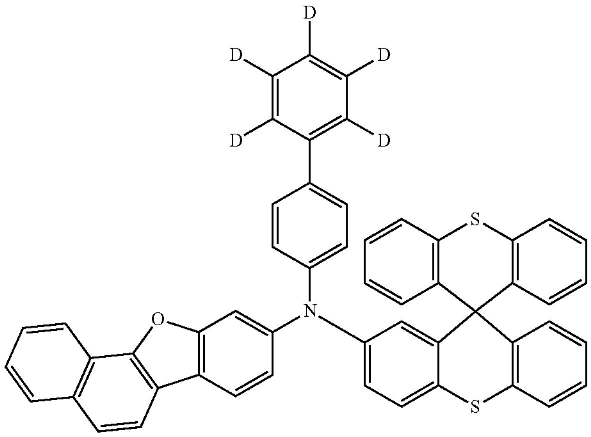
C157
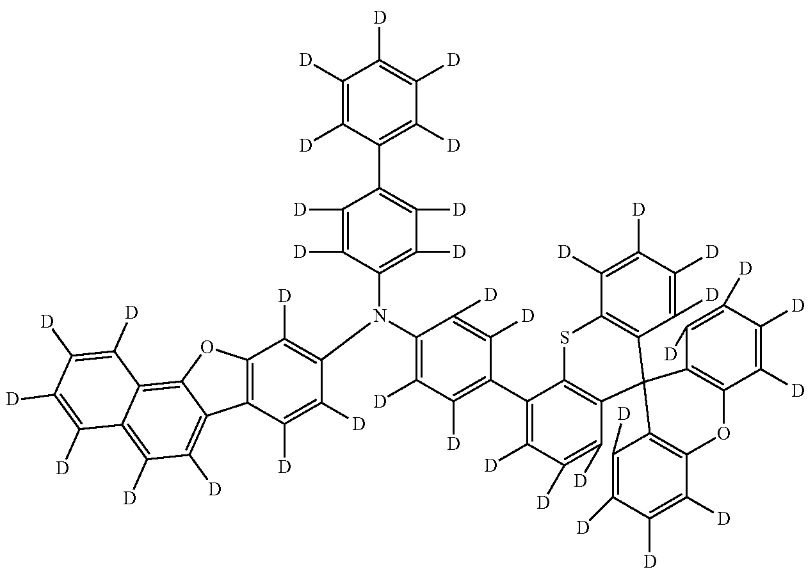
C158
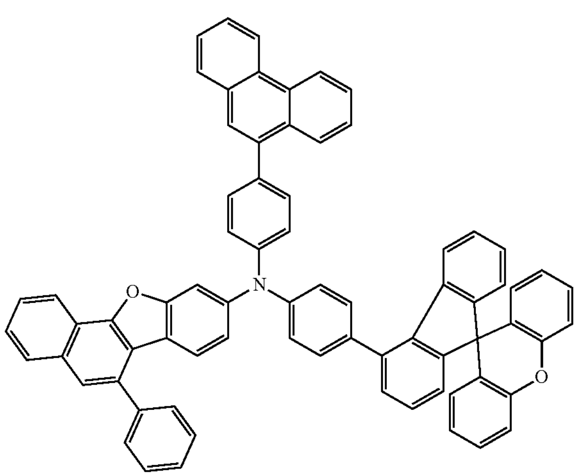
C159
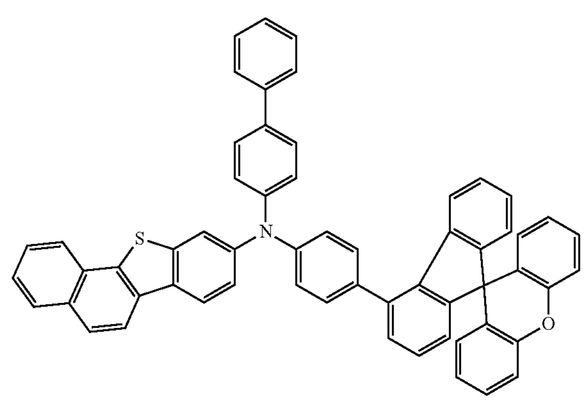

-continued
C160
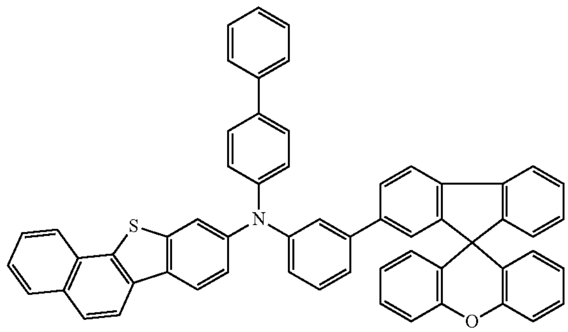
C161
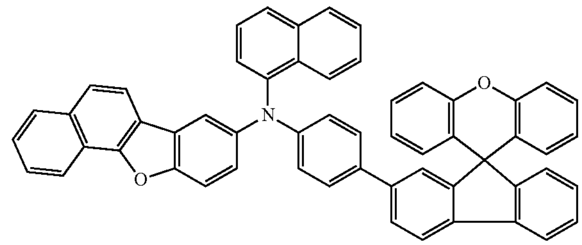
C162
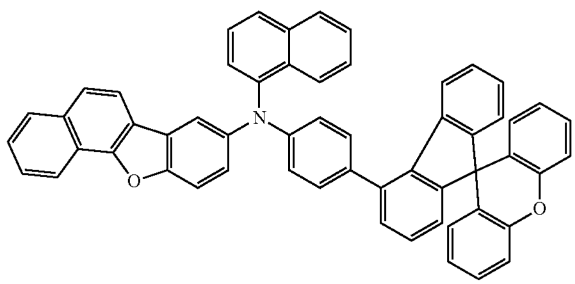
C163
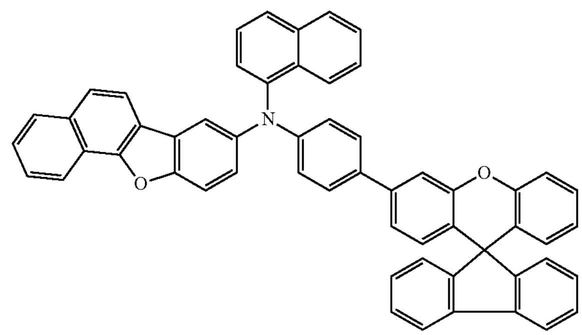
C164
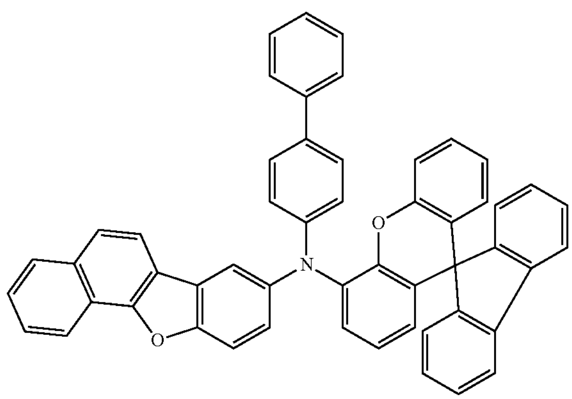
C165
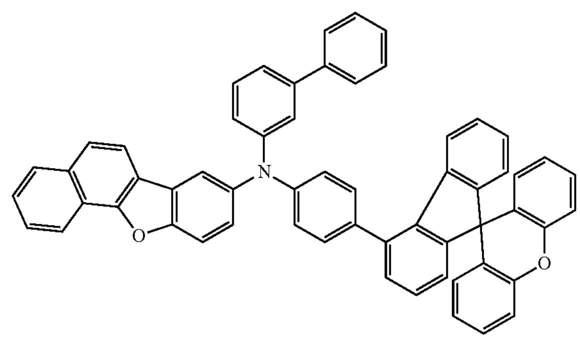
C166
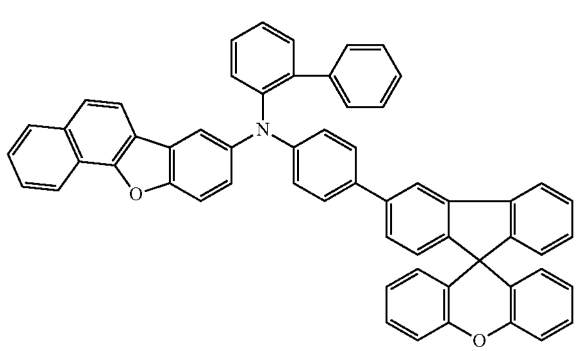
C167
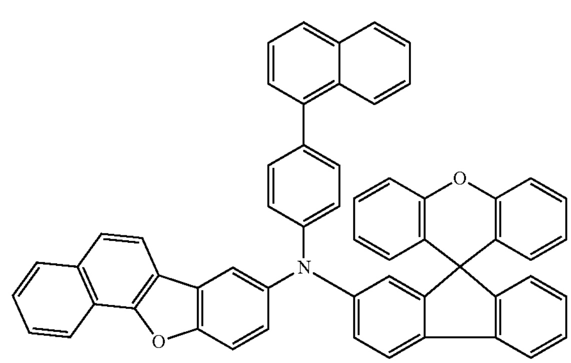

-continued
C168
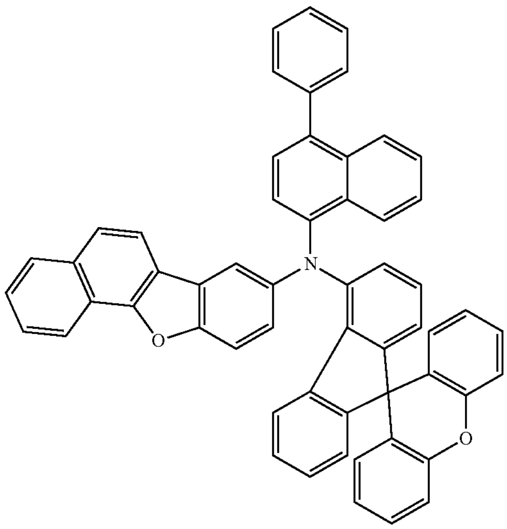
C169
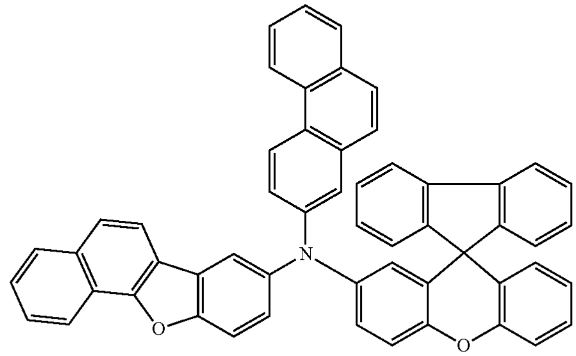
C170
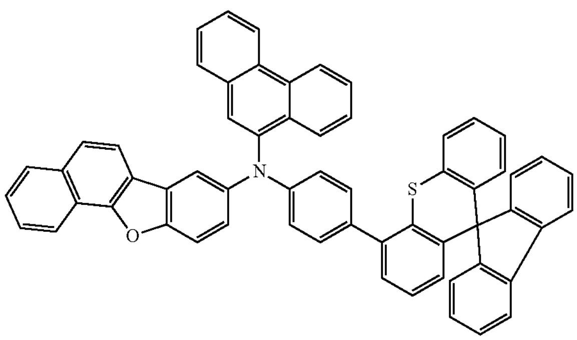
C171
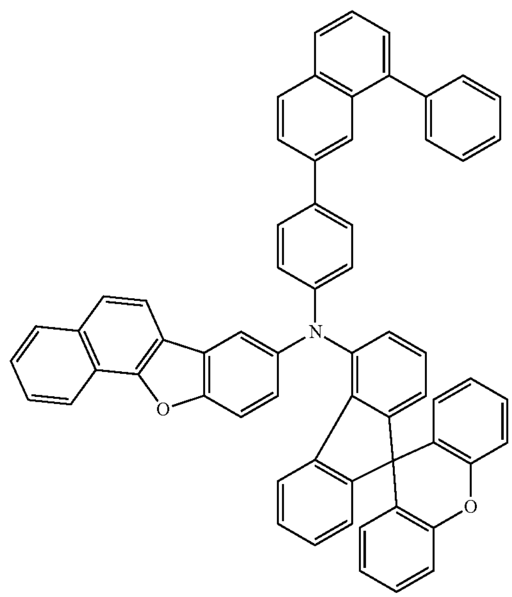
C172
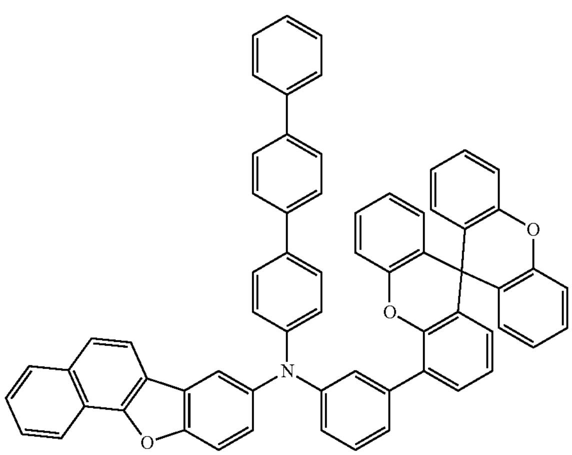
C173
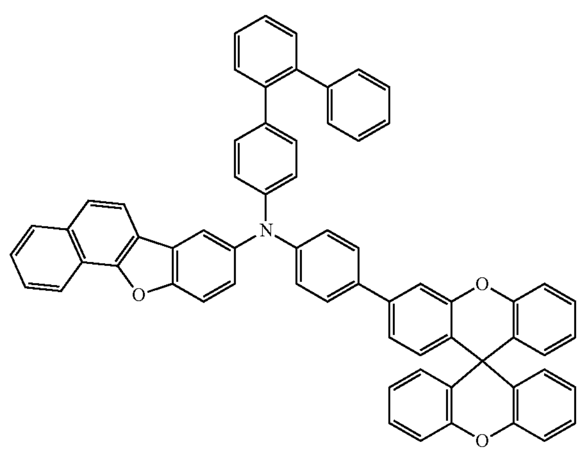

-continued
C174
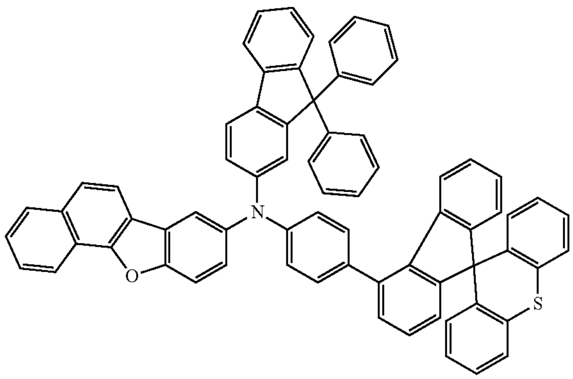
C175
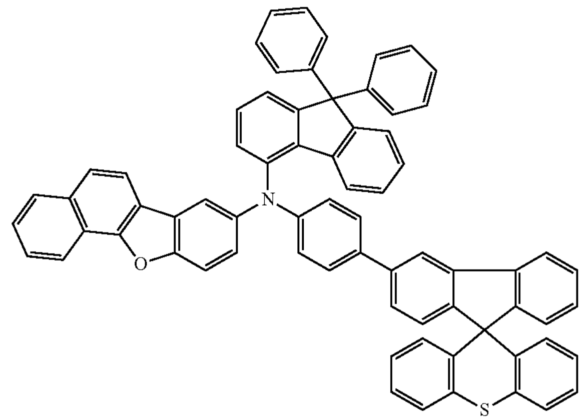
C176
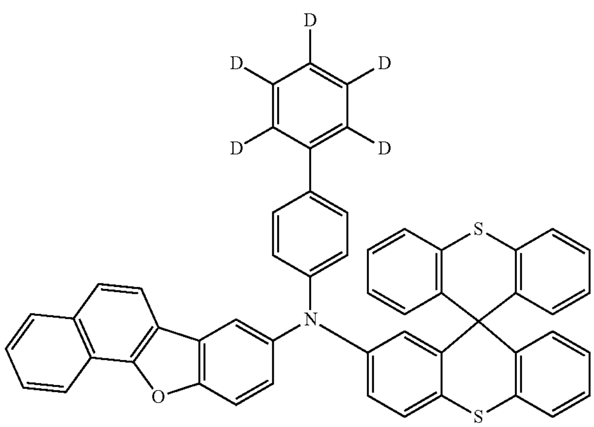
C177
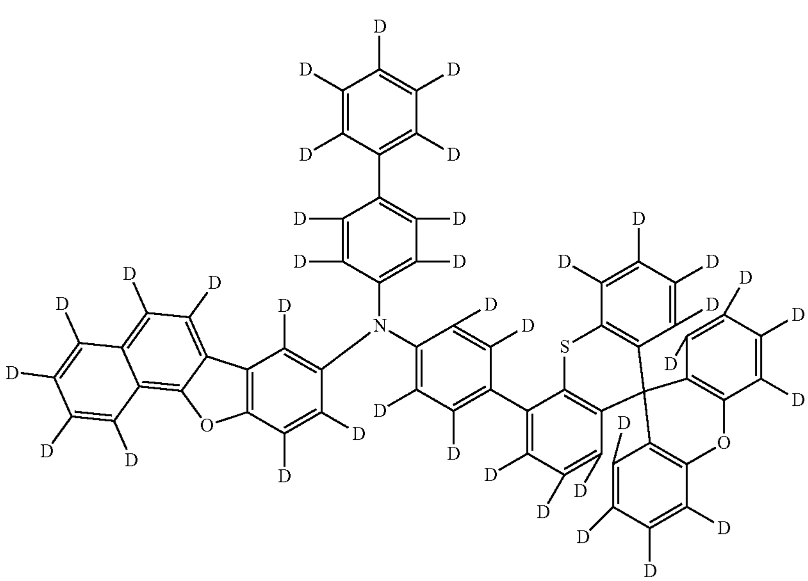

-continued
C178
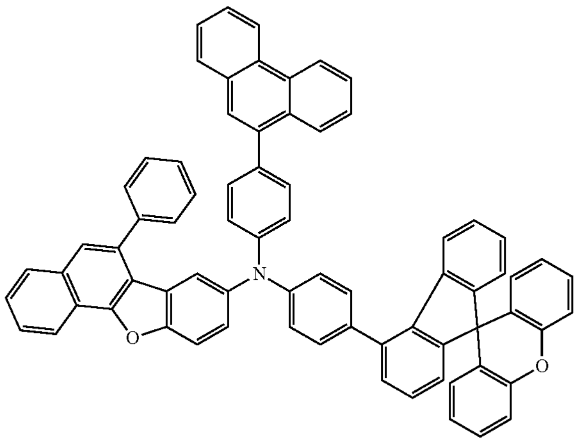
C179
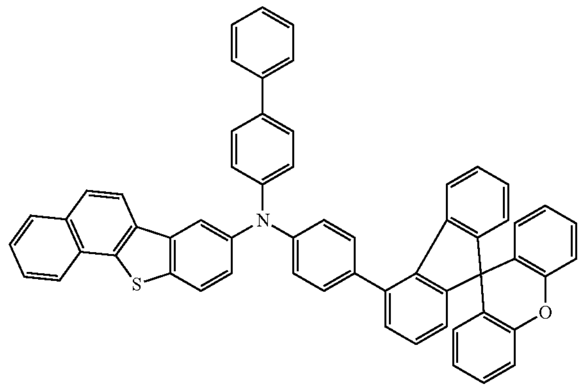
C180
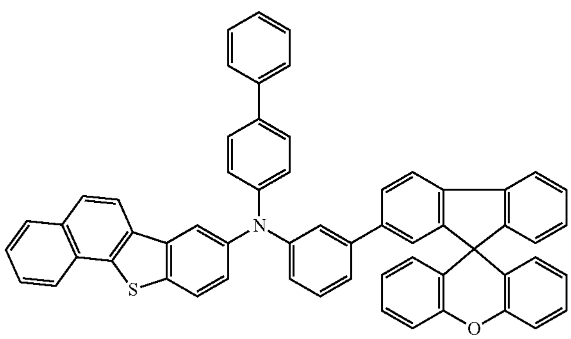
C181
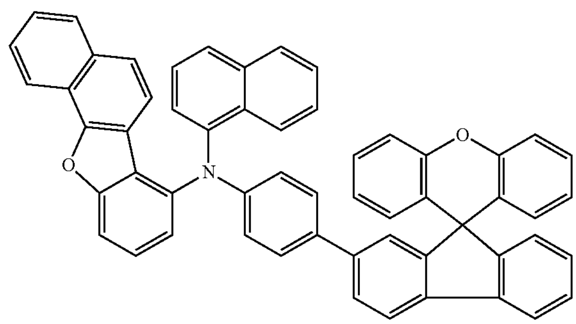
C182
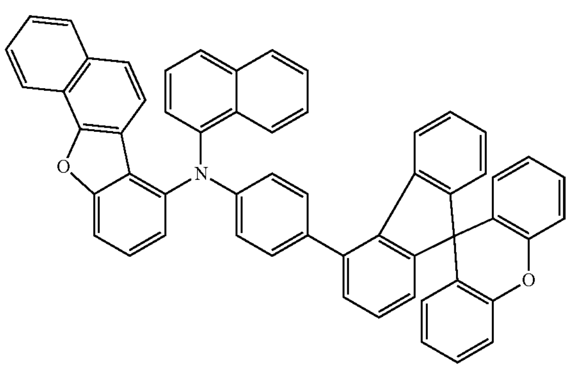
C183
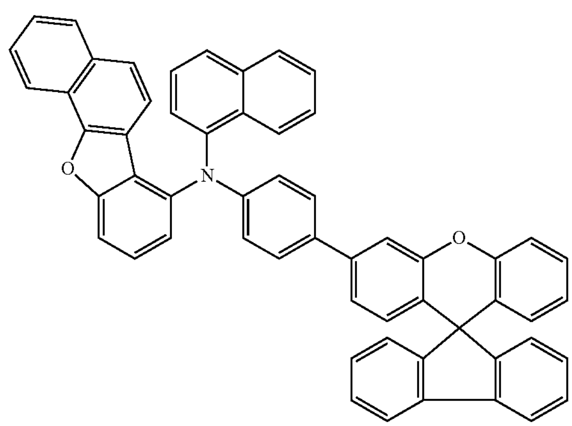

-continued
C184
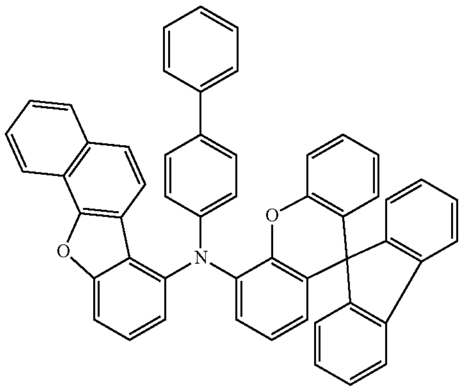
C185
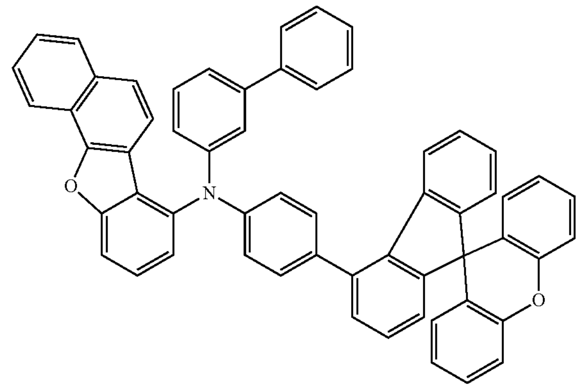
C186
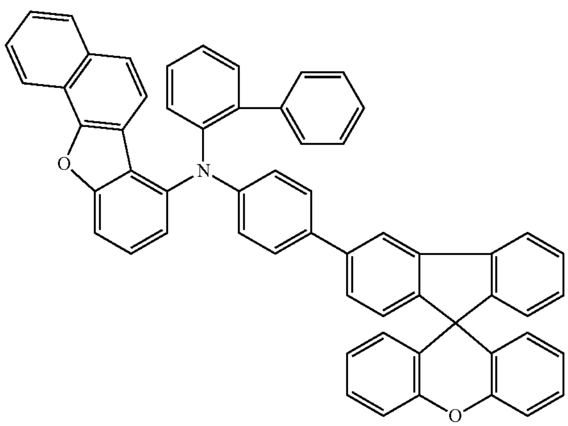
C187
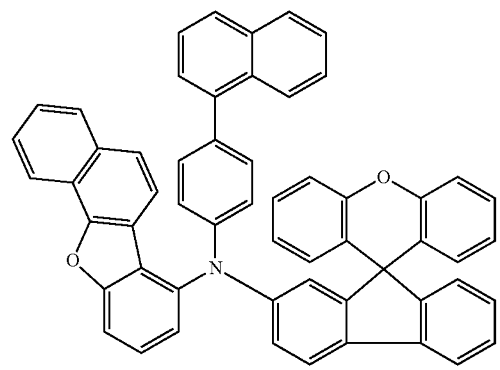
C188
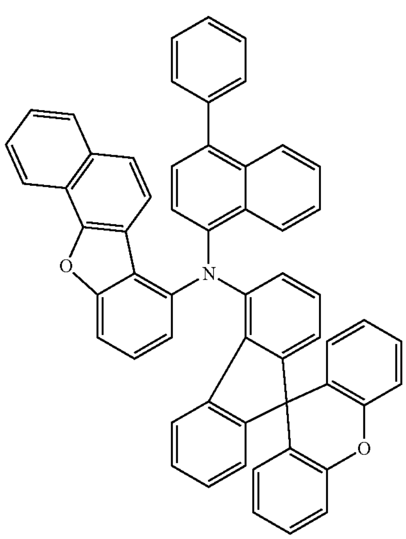
C189
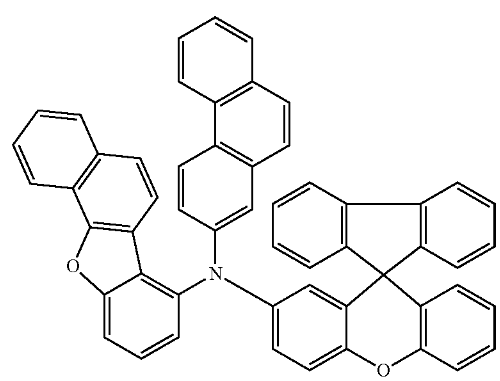

-continued
C190
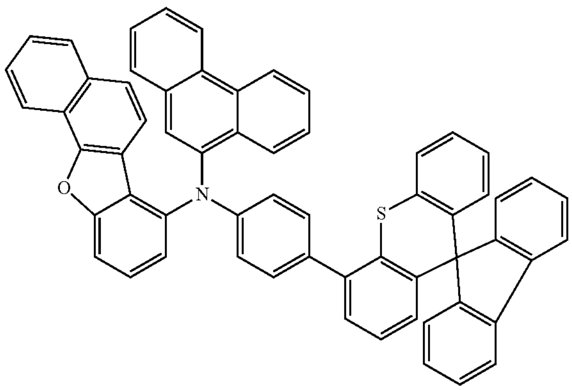
C191
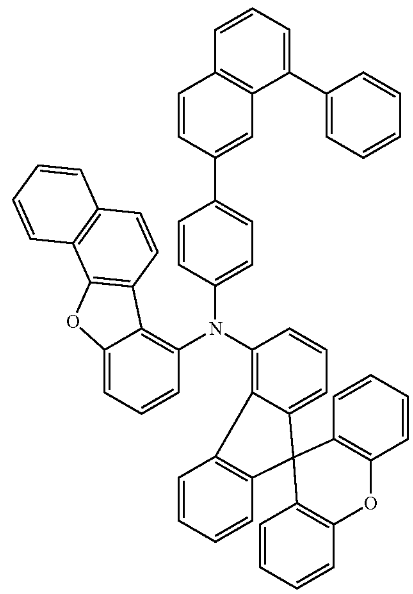
C192
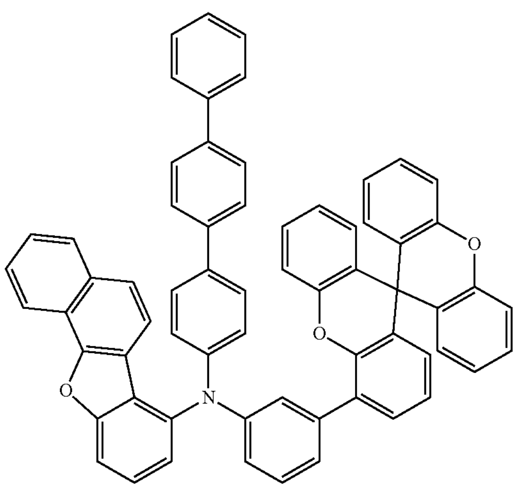
C193
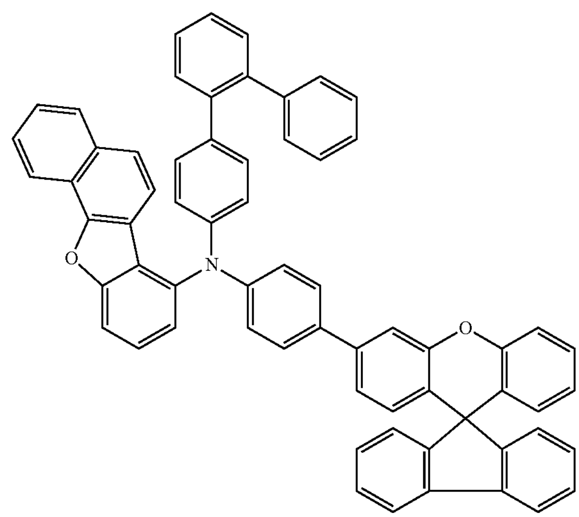
C194
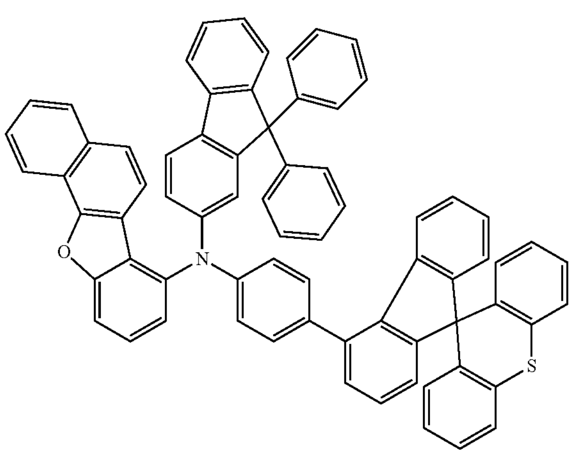
C195
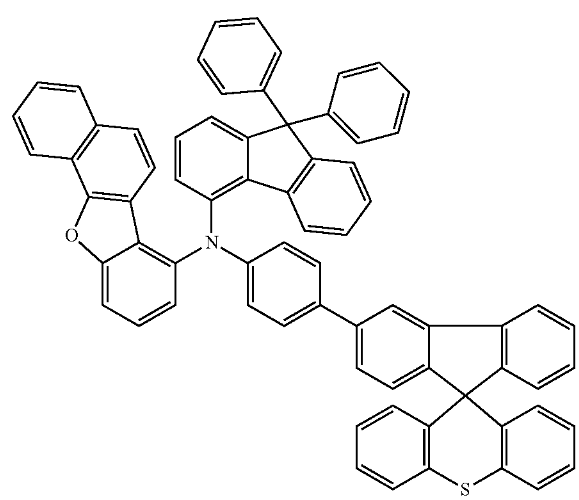

-continued
C196
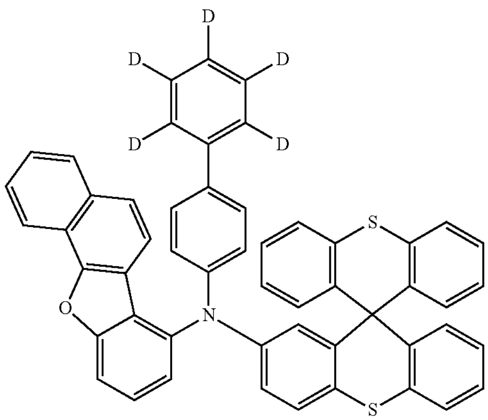
C197
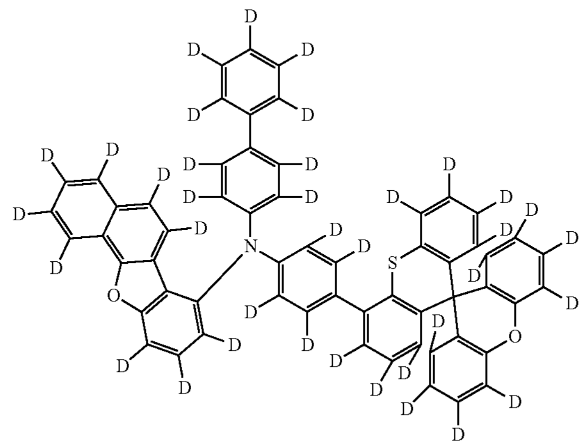
C198
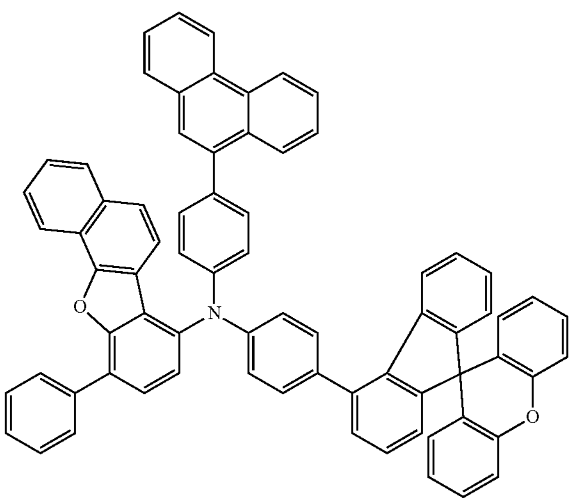
C199
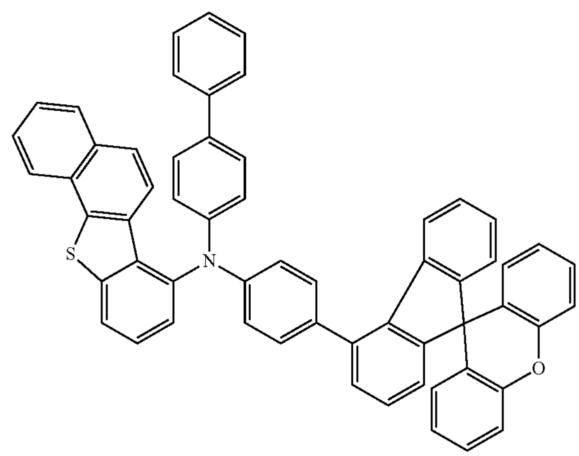
C200
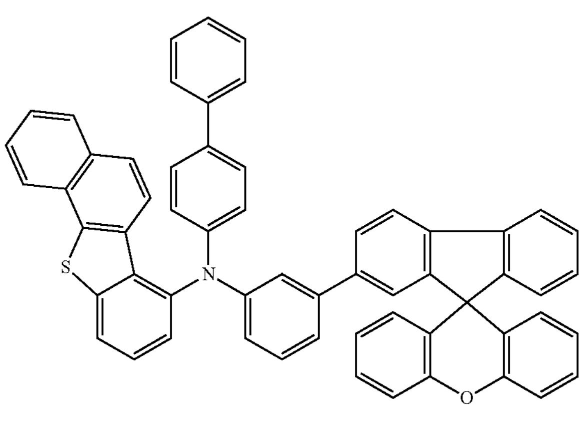

[Compound Group 4]
D1
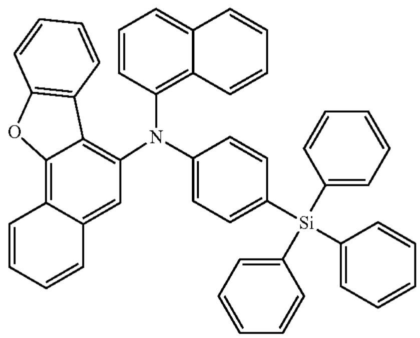
D2
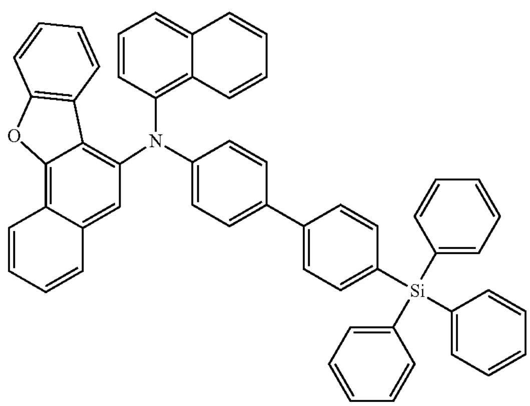
D3
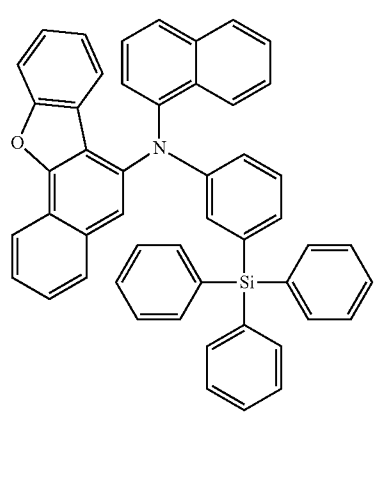
-continued
D4
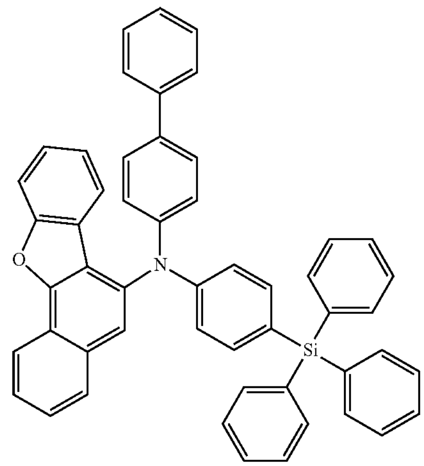
D5
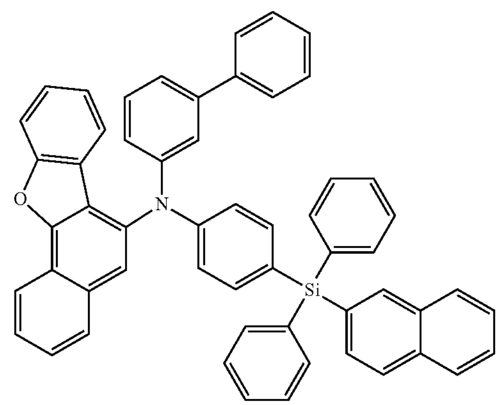
D6
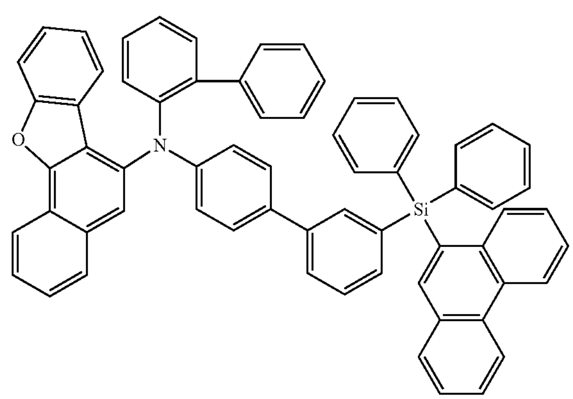

-continued
D7
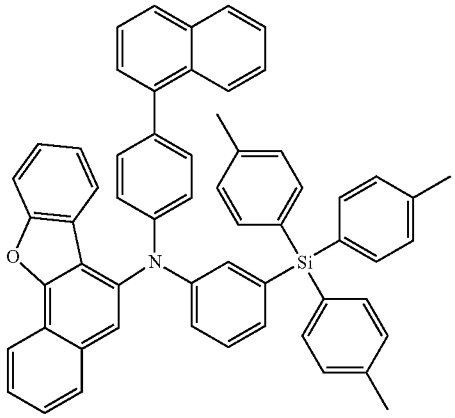
D8
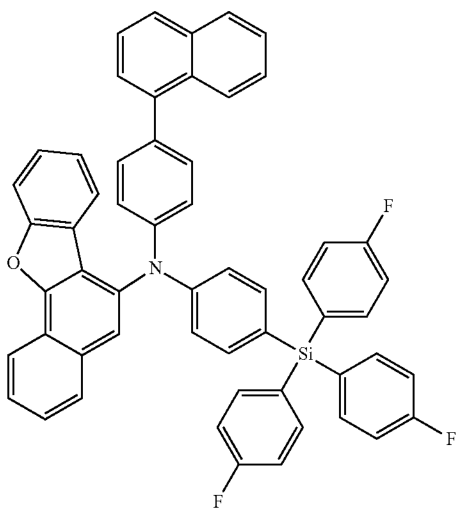
D9
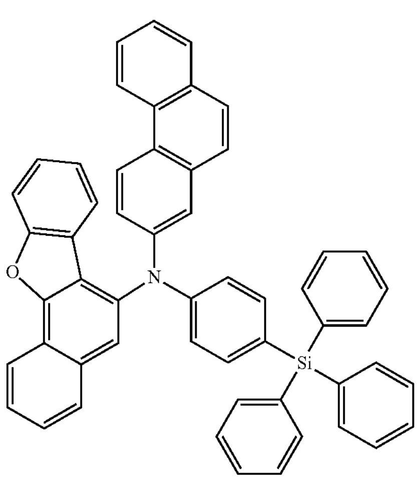
-continued
D10
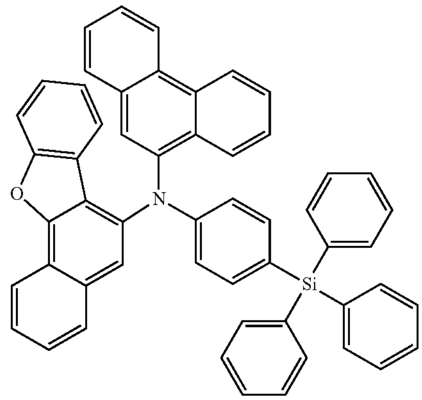
D11
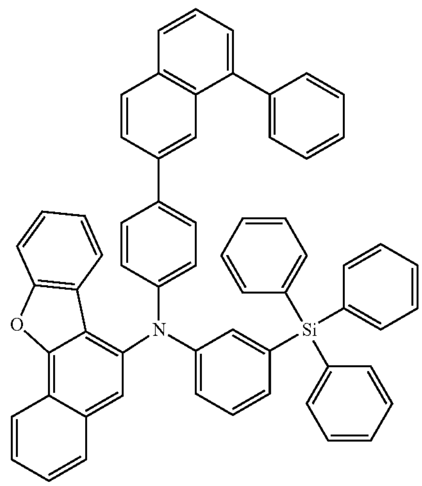
D12
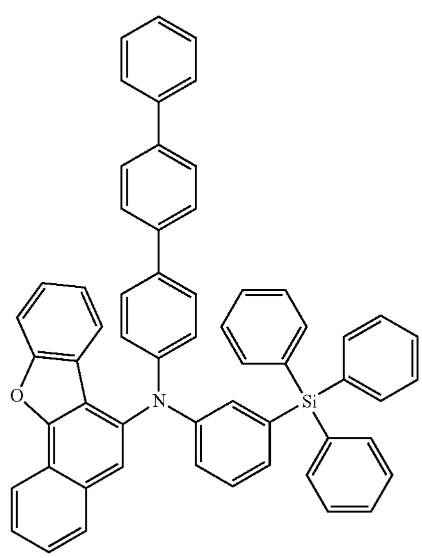

-continued
D13
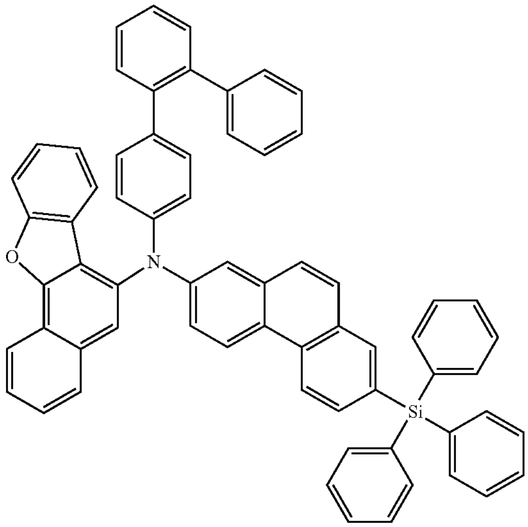
D14
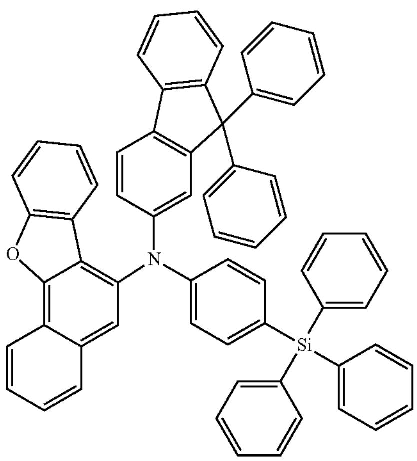
D15
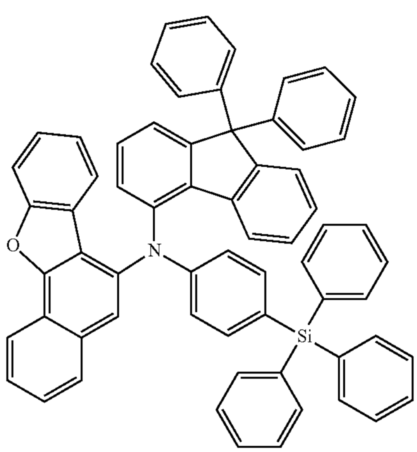
-continued
D16
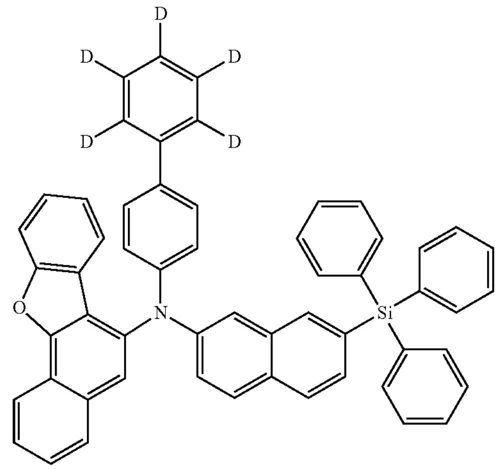
D18
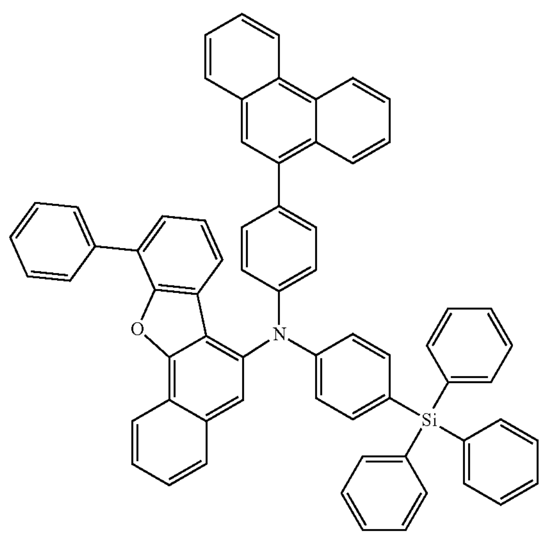
D19
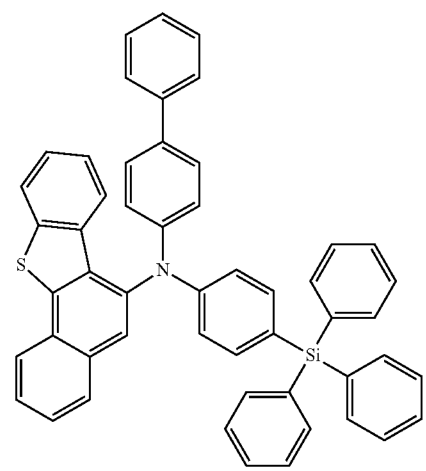

-continued
D20
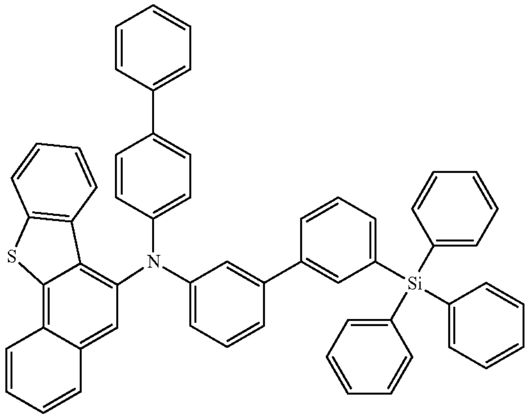
D21
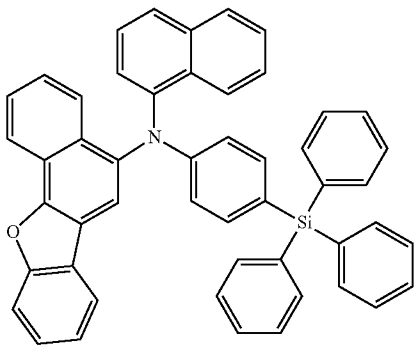
D22
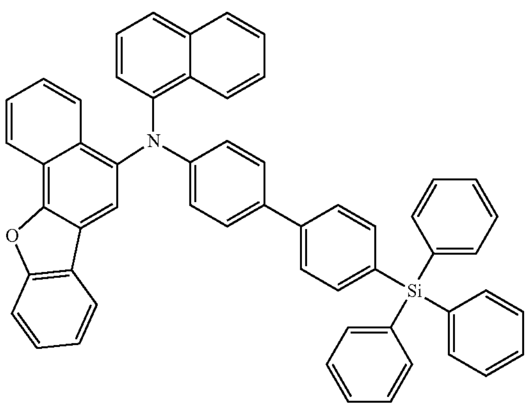
D23
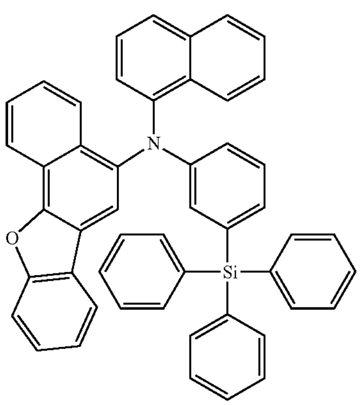
-continued
D24
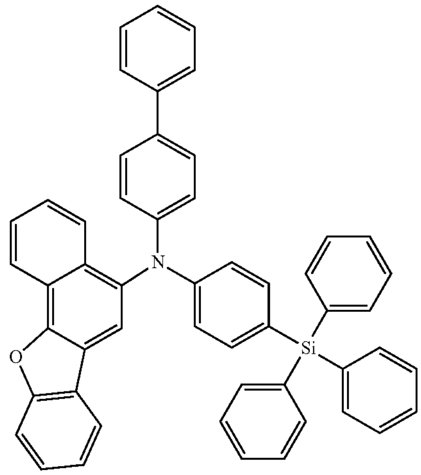
D25
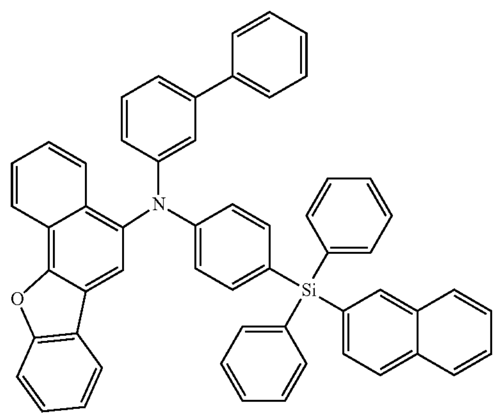
D26
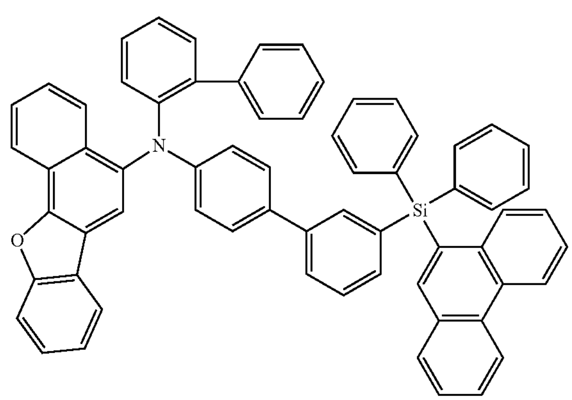

-continued
D27
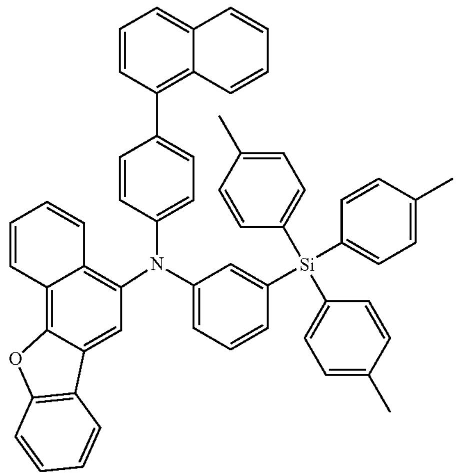
D28
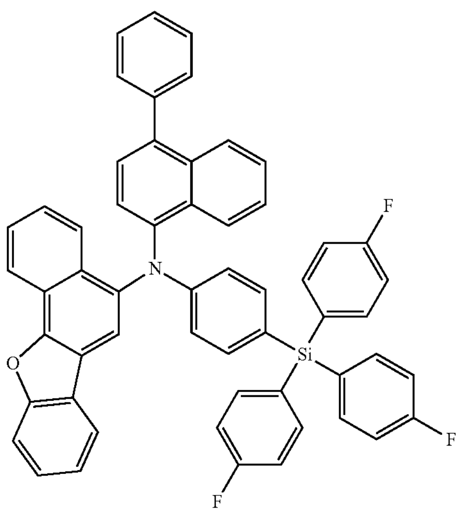
D29
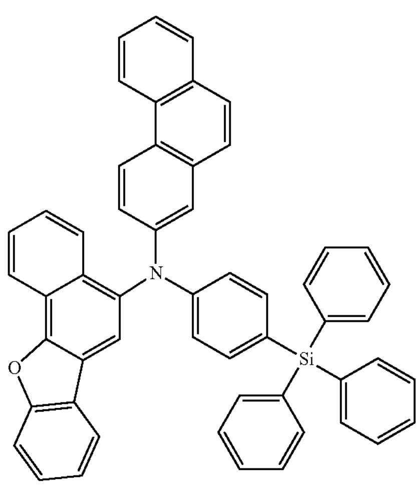
-continued
D30
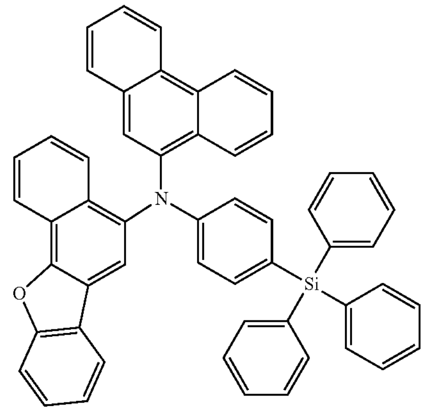
D31
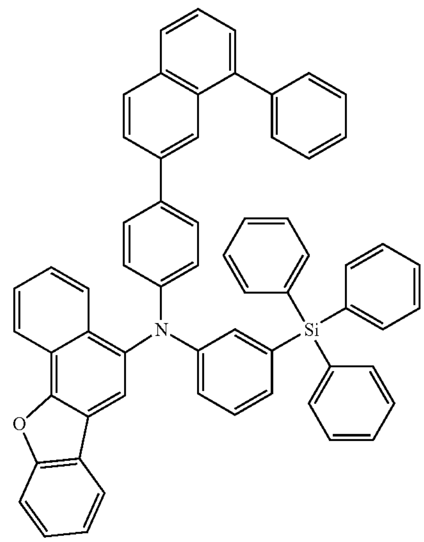
D32
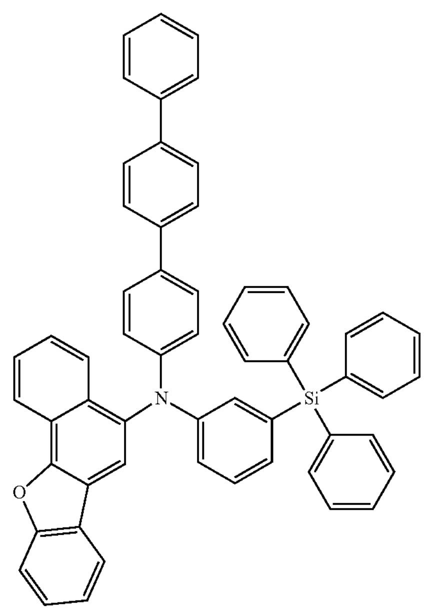

-continued
D33
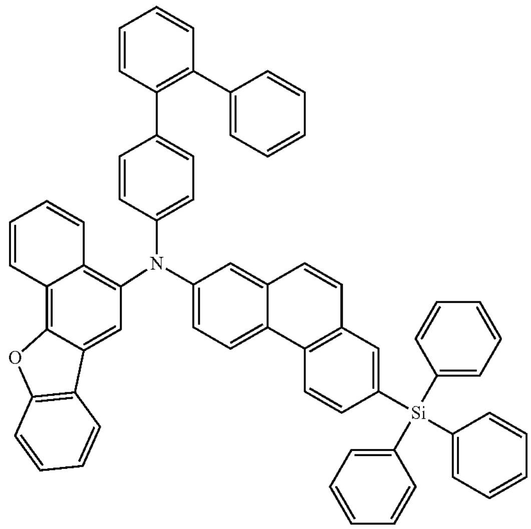
D34
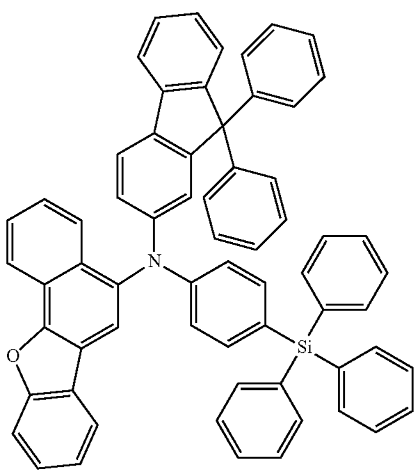
D35
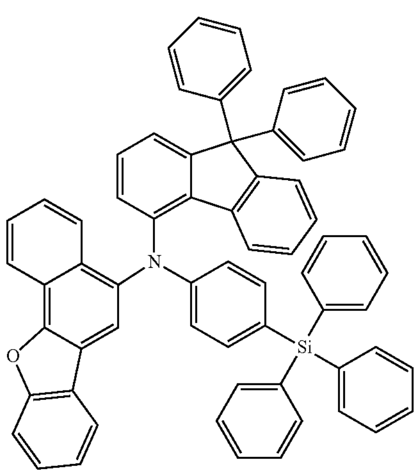
-continued
D36
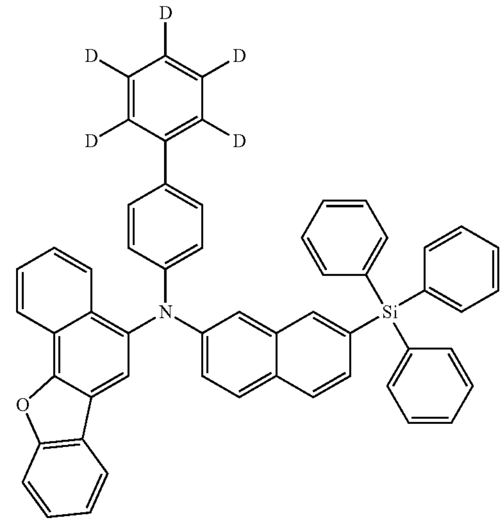
D38
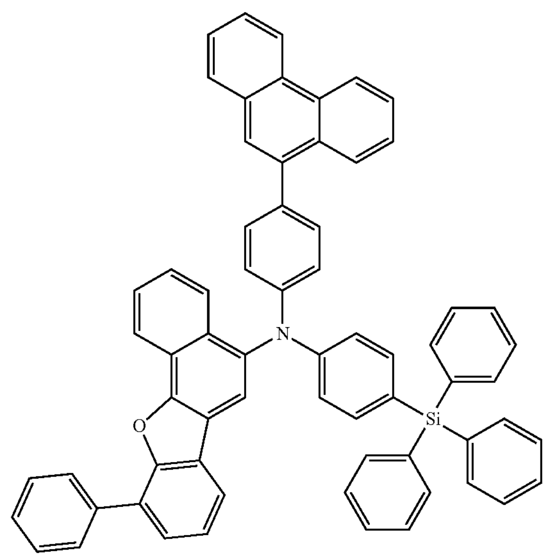
D39
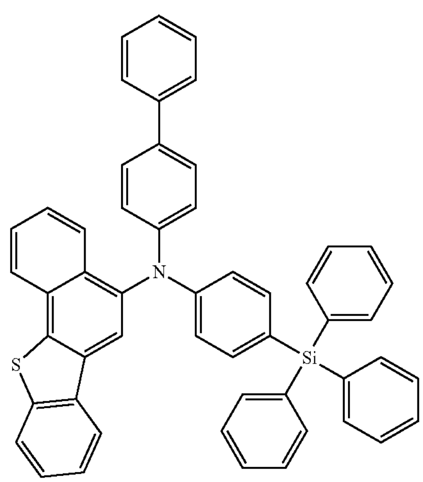

-continued
D40
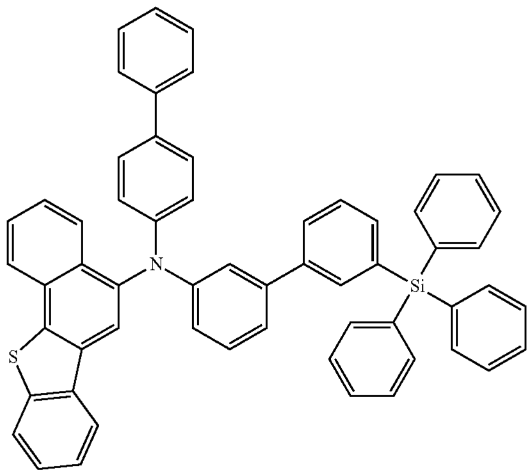
D41
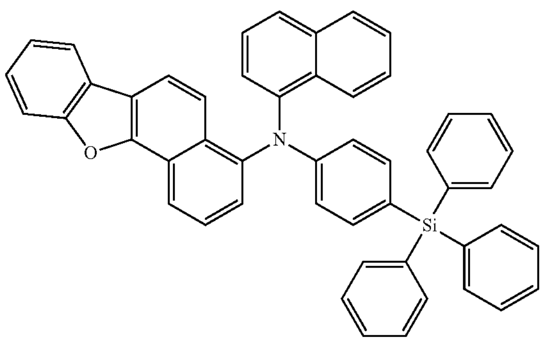
D42
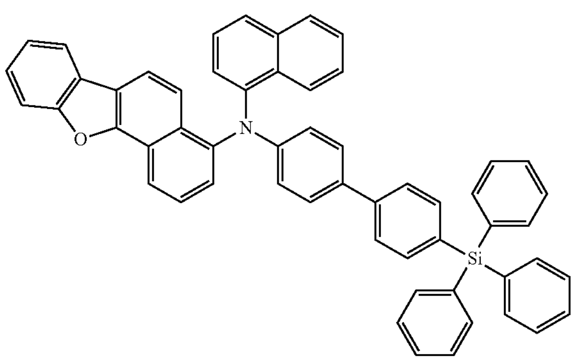
D43
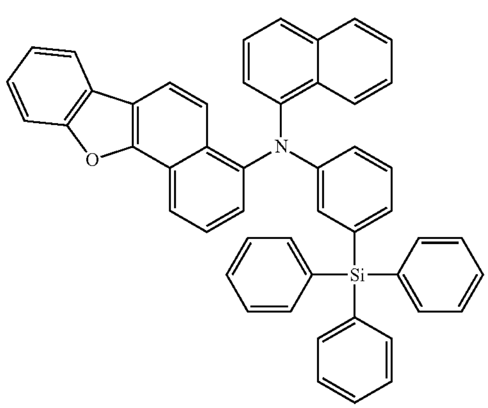
-continued
D44
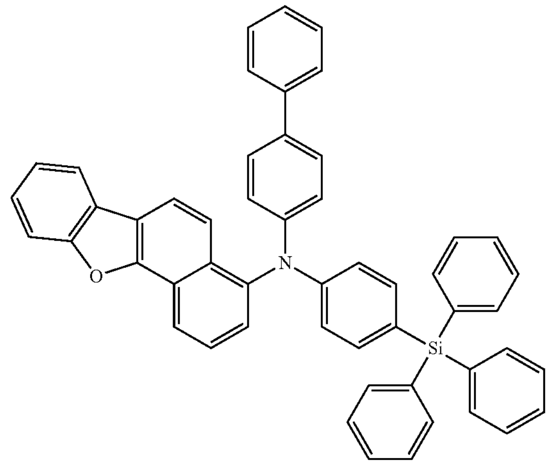
D45
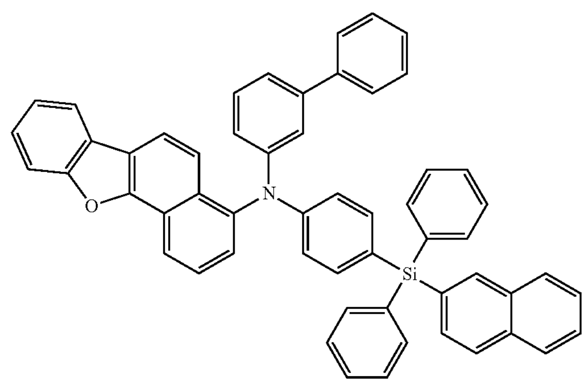
D46
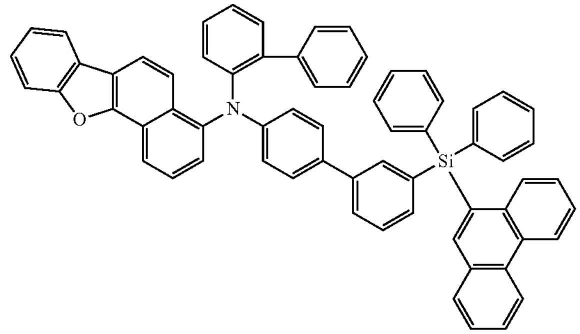

-continued
D47
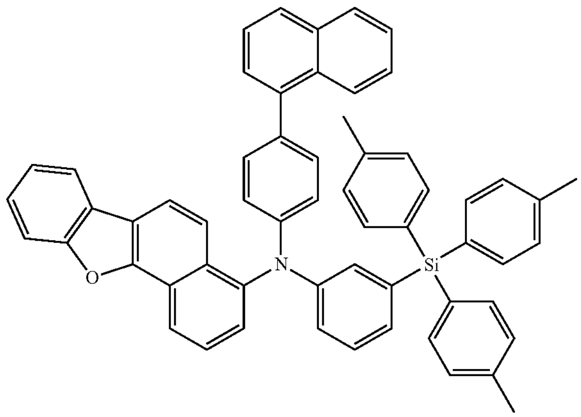
D48
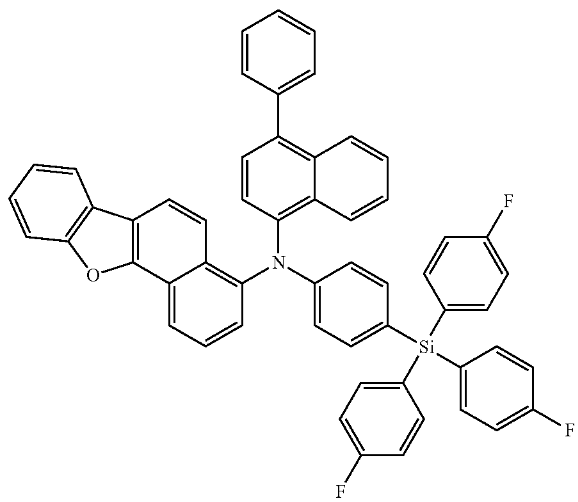
D49
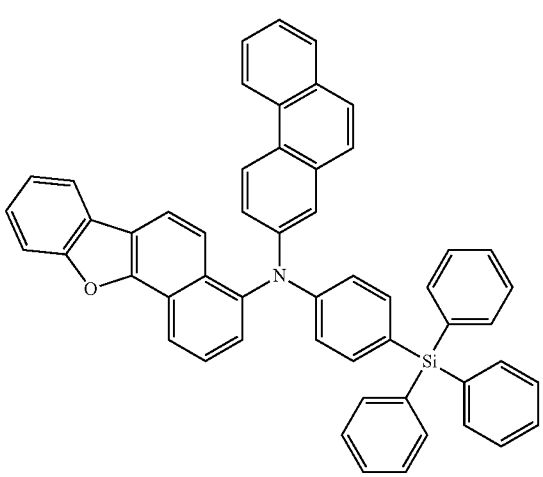
-continued
D50
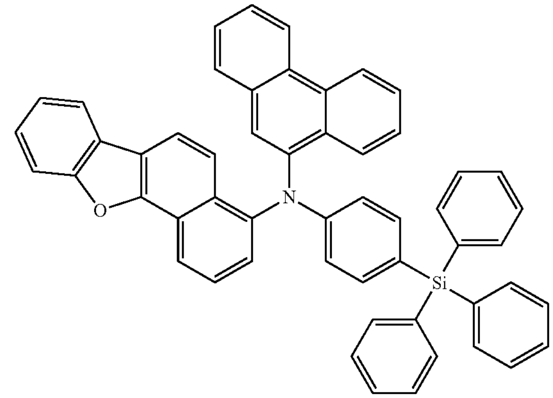
D51
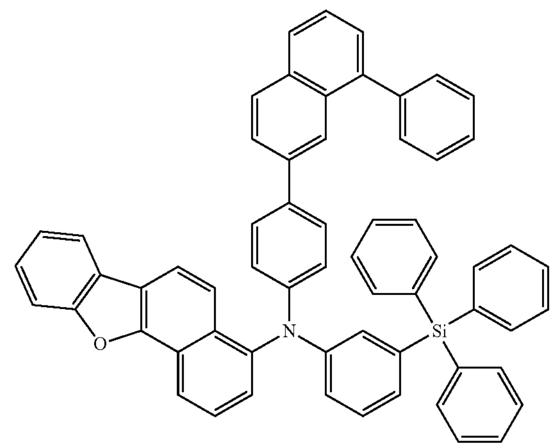
D52
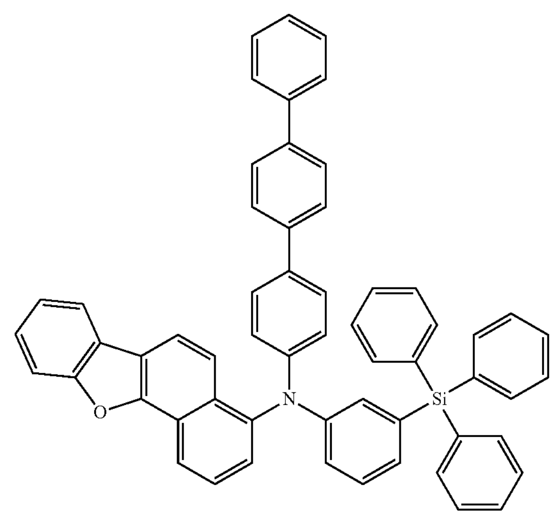

-continued
D53
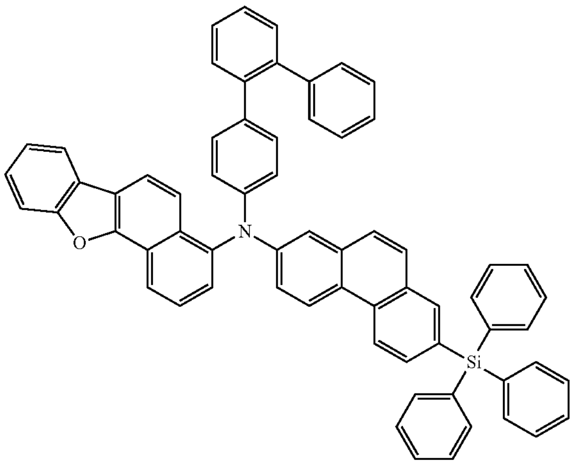
D54
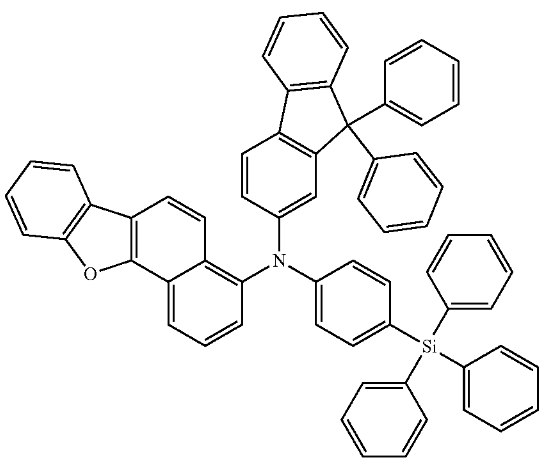
D55
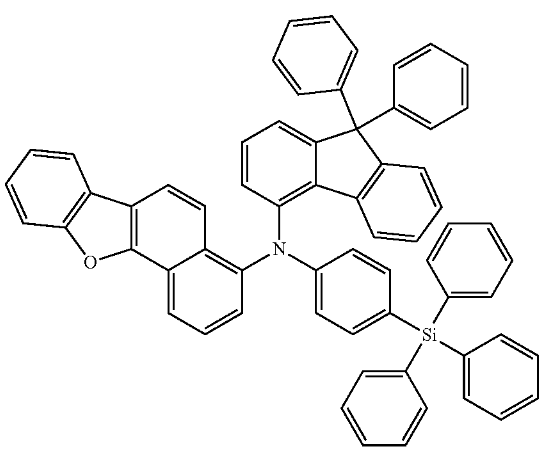
-continued
D56
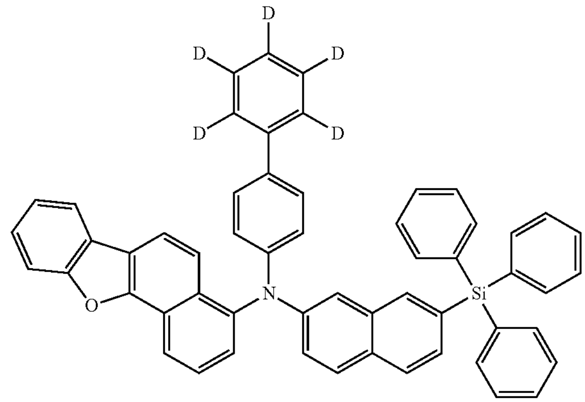
D58
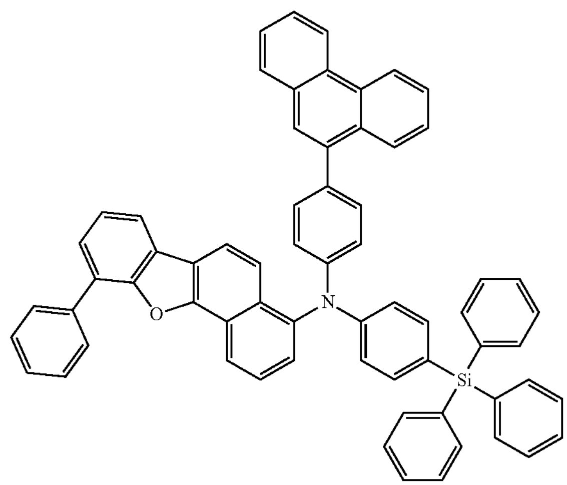
D59
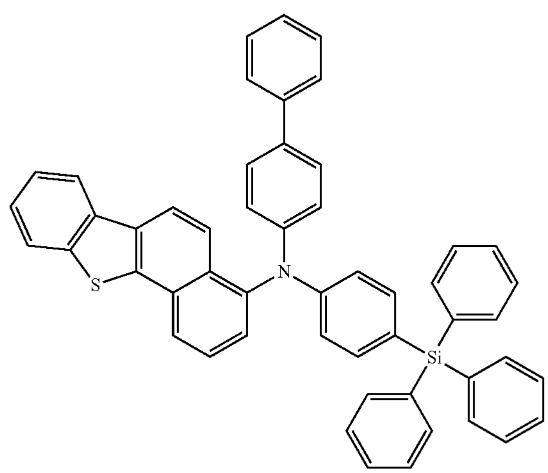

-continued
D60
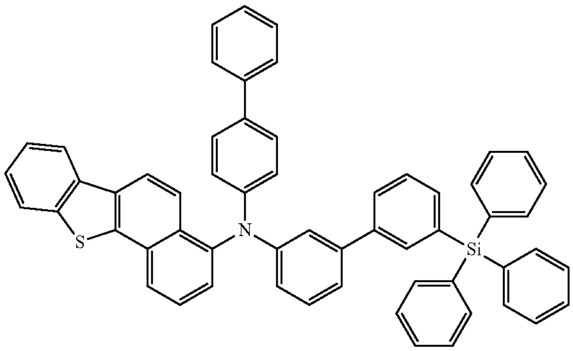
D61
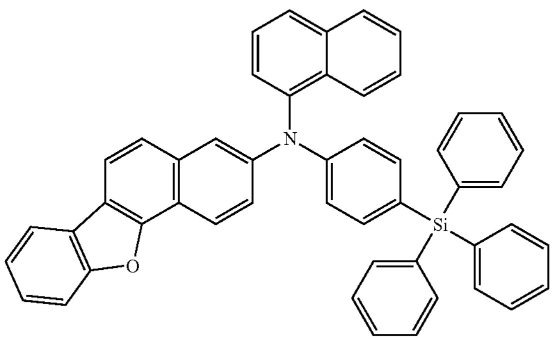
D62
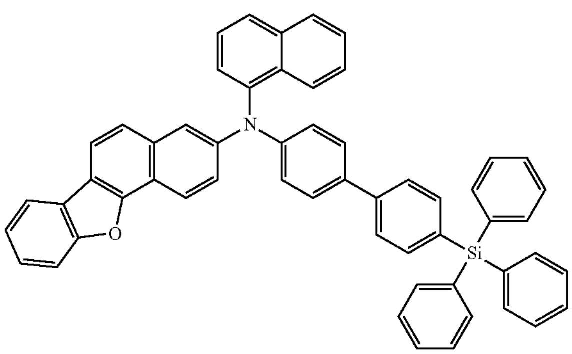
D63
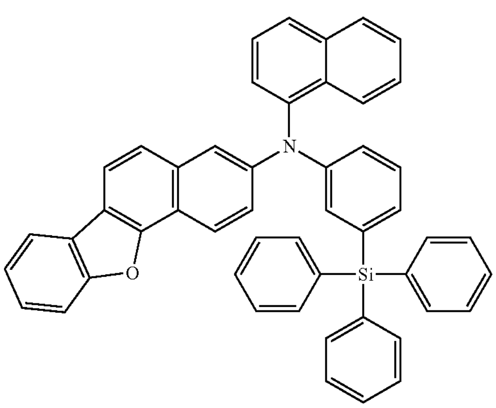
-continued
D64
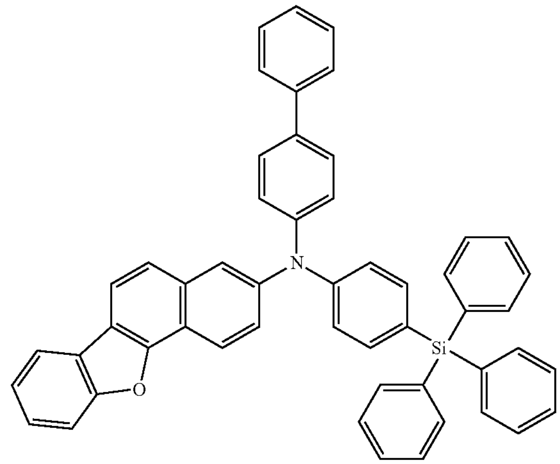
D65
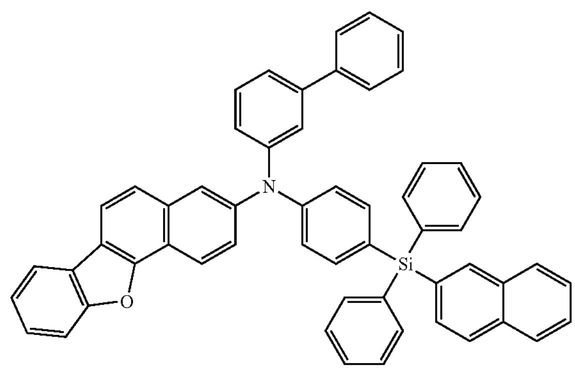
D66
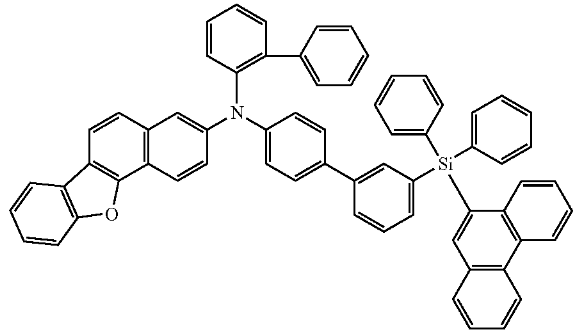

-continued
D67
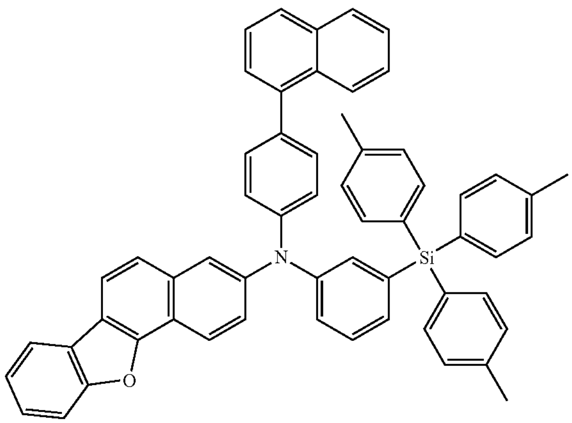
D68
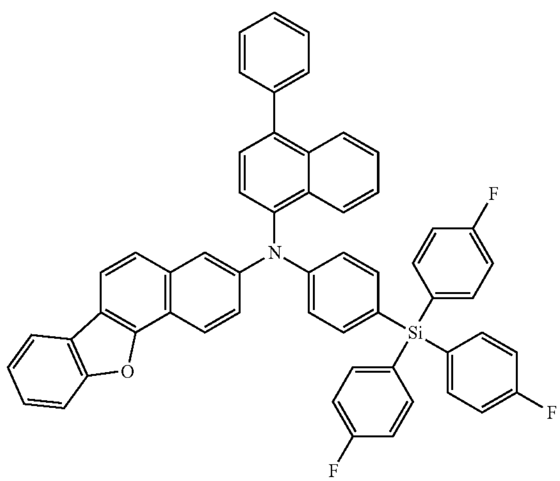
D69
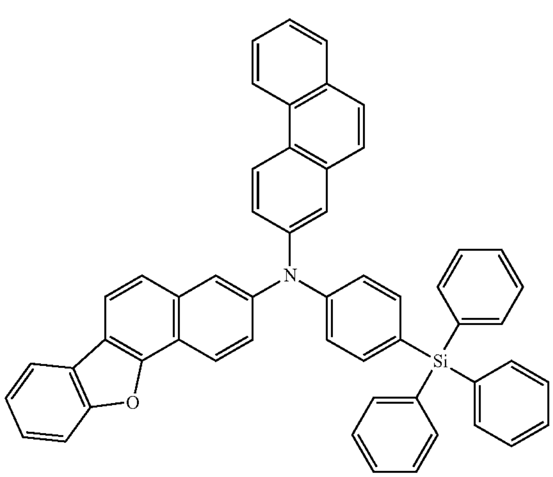
-continued
D70
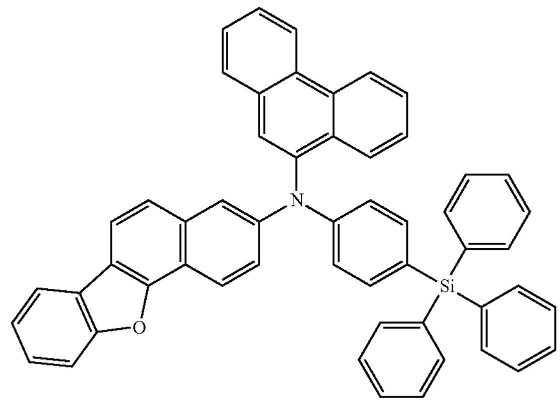
D71
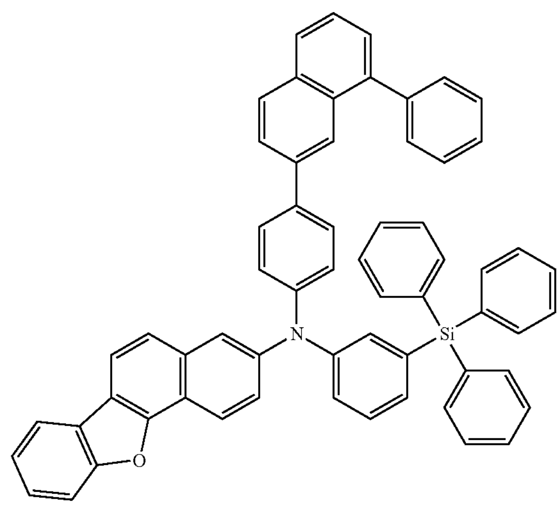
D72
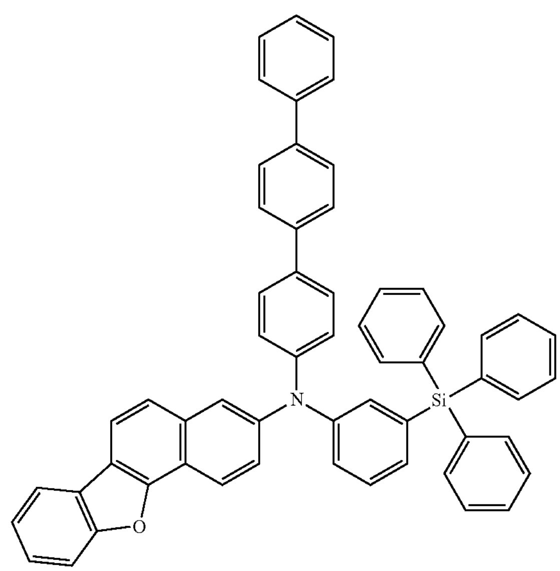

D73
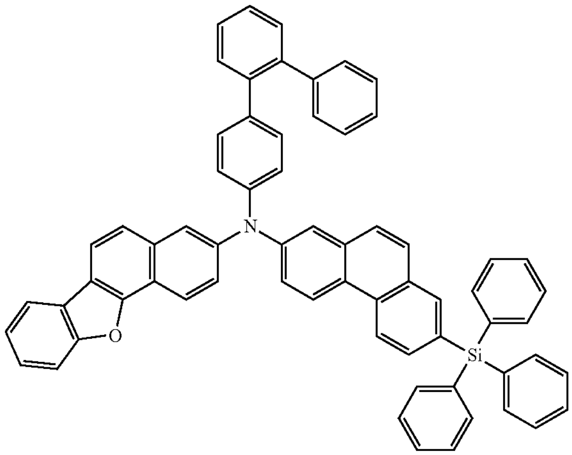
D74
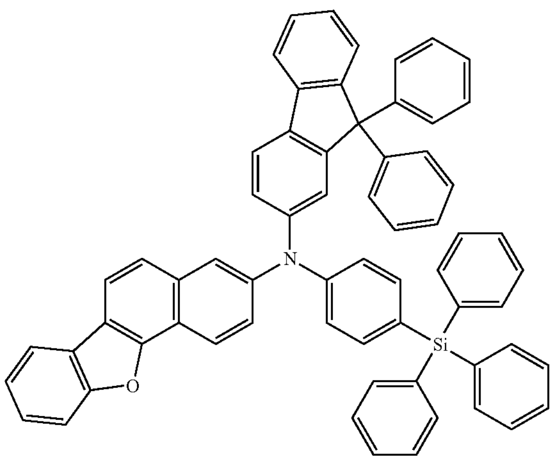
D75
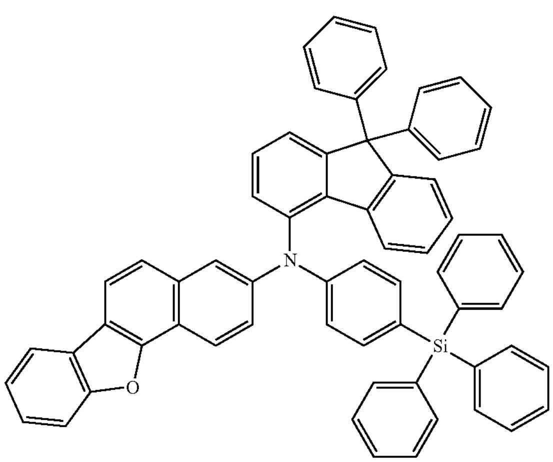
D76
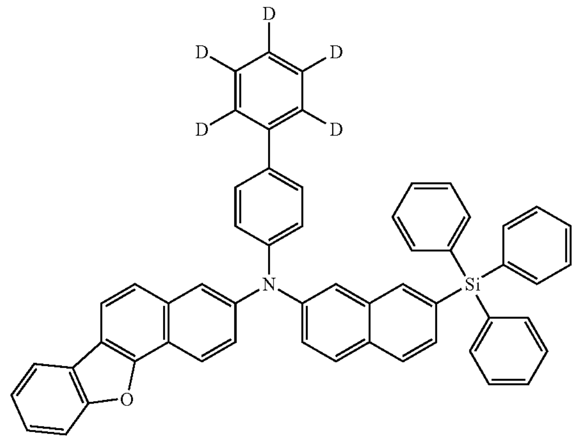
D78
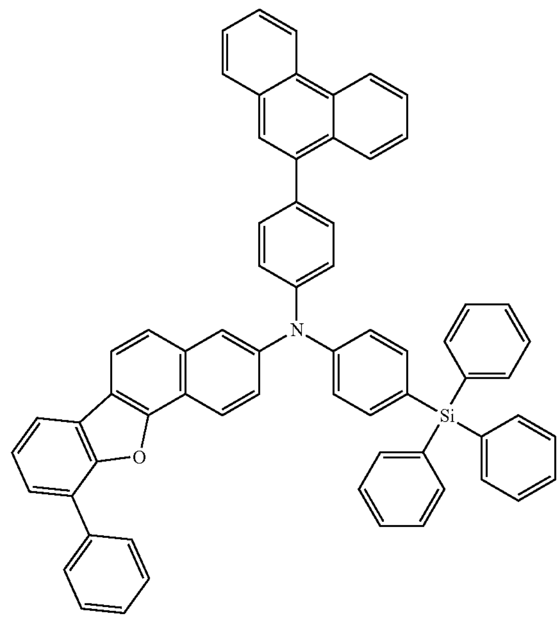
D79
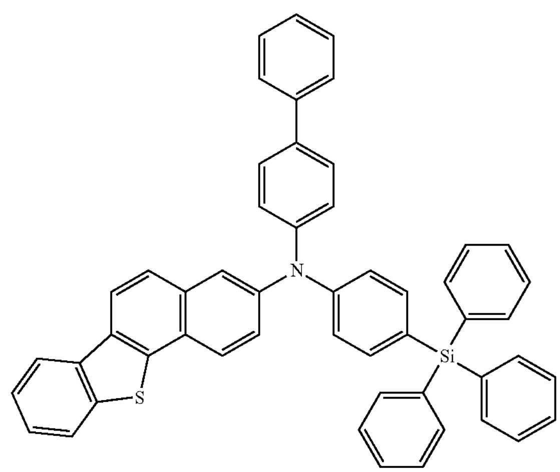

-continued
D80
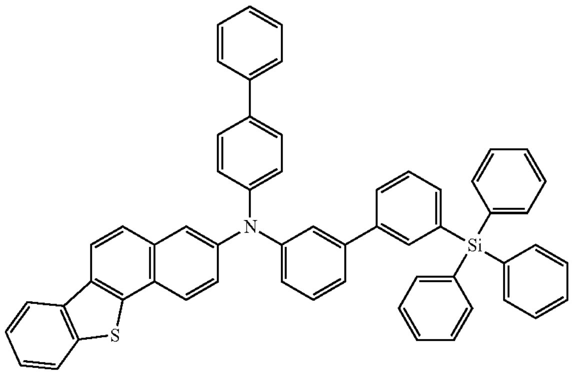
D81
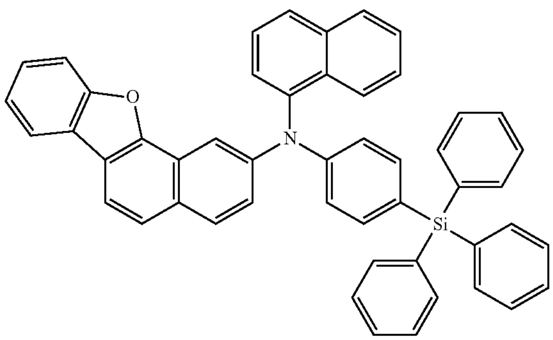
D82
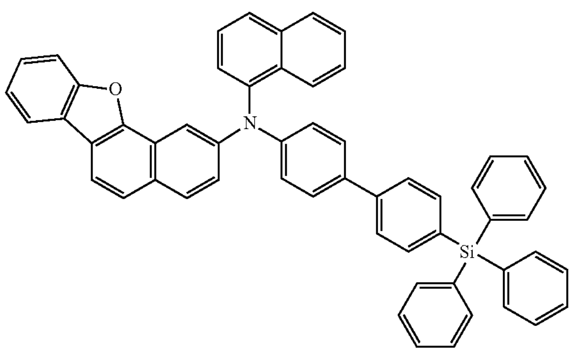
D83
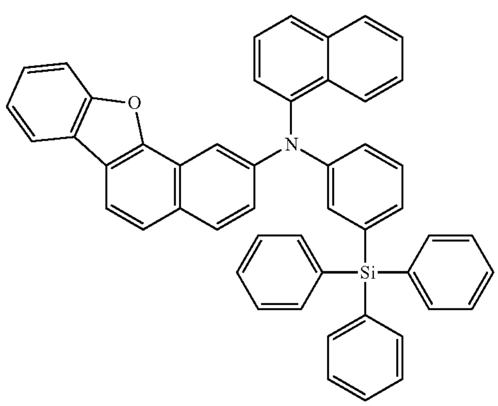
-continued
D84
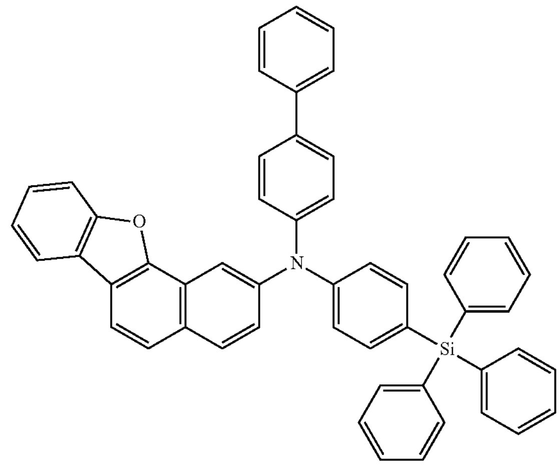
D85
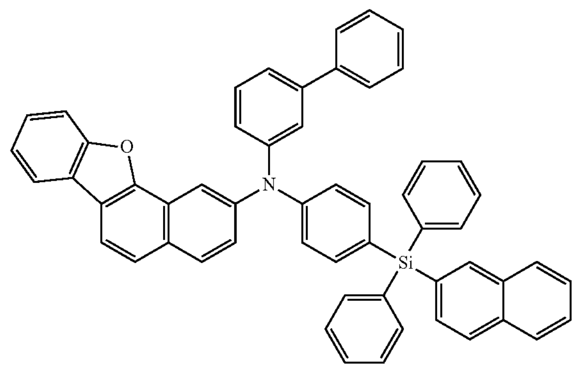
D86
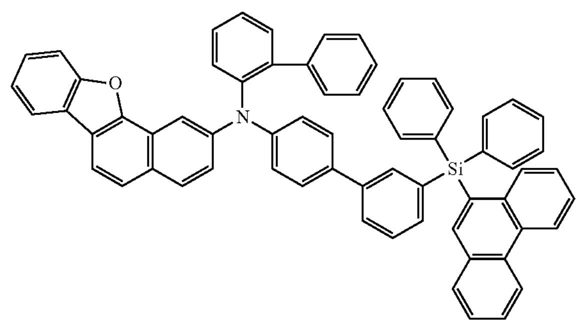
D87
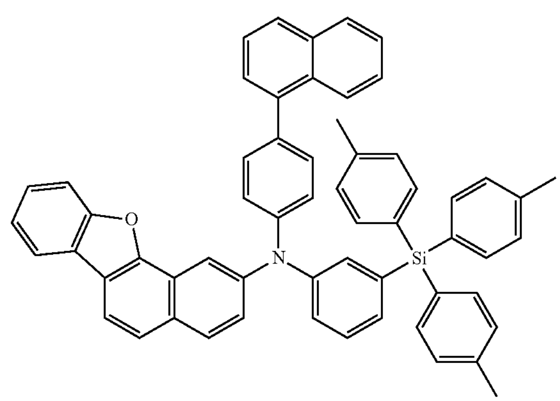

-continued
D88
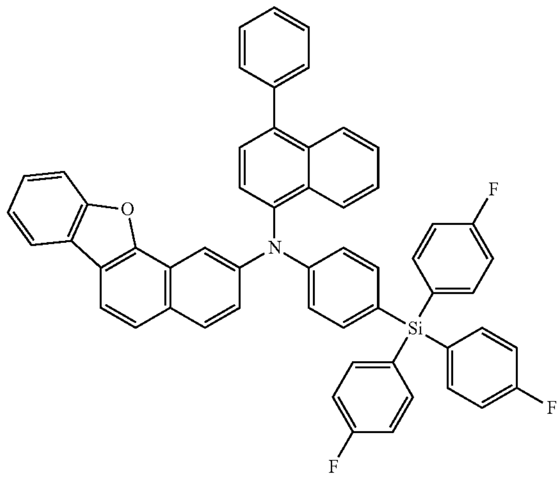
D89
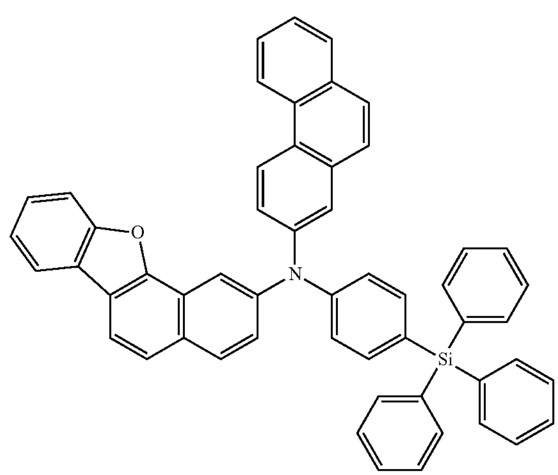
D90
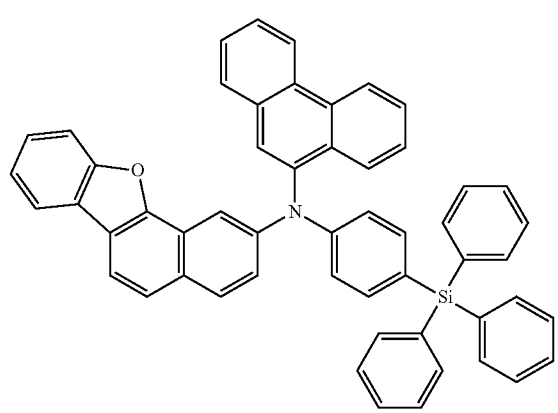
-continued
D91
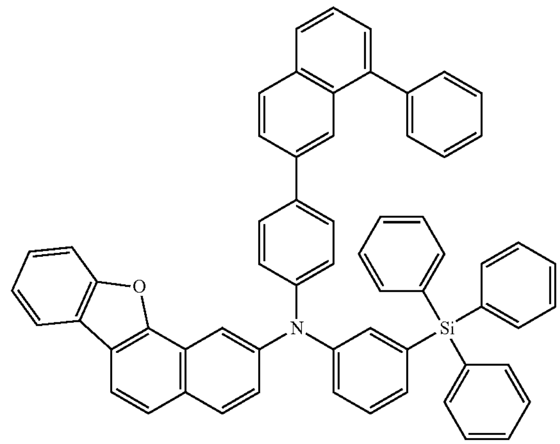
D92
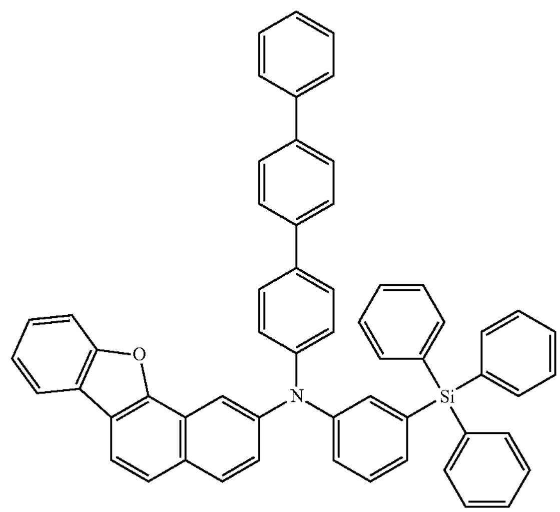
D93
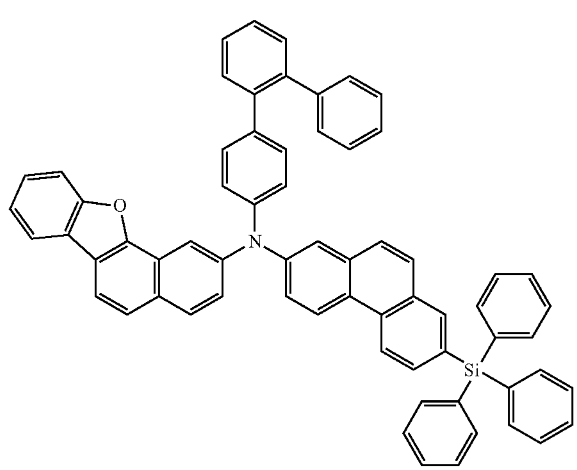

-continued
D94
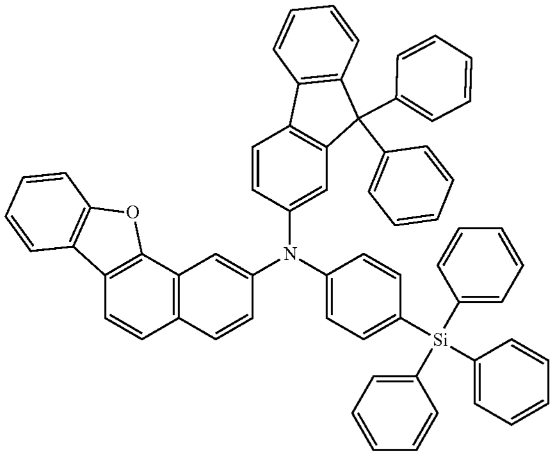
D95
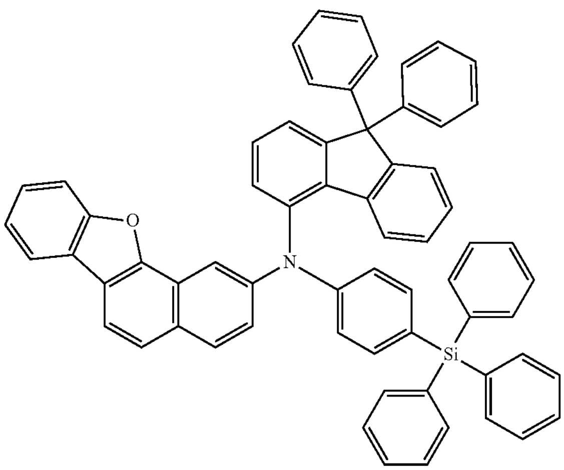
D96
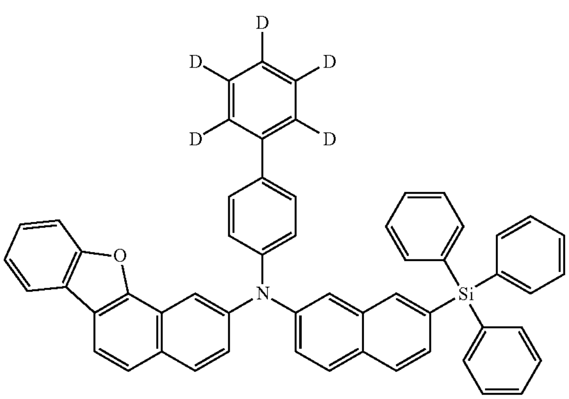
-continued
D98
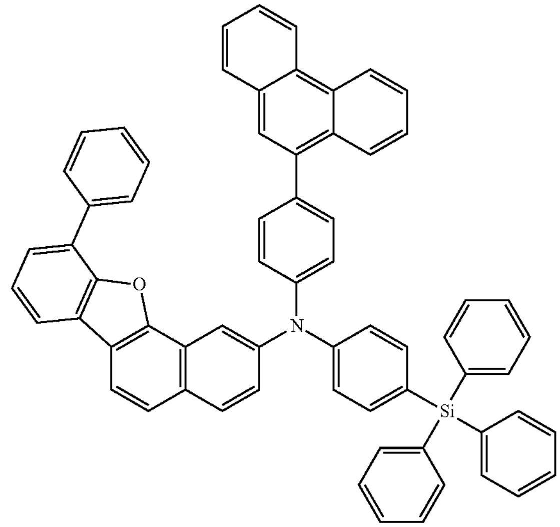
D99
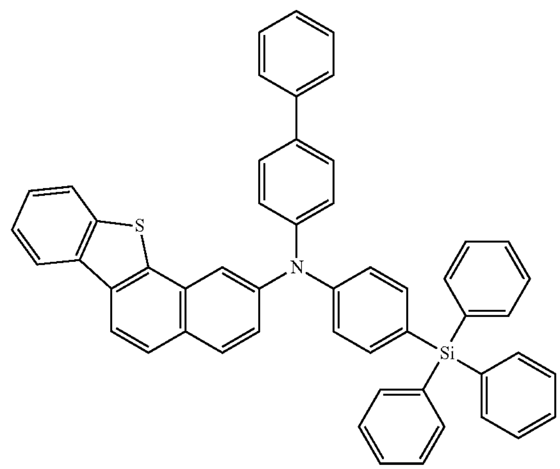
D100
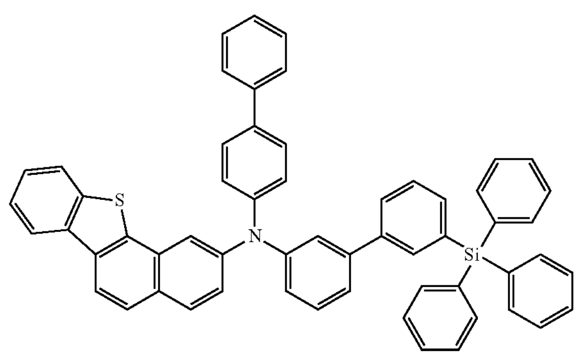

D101
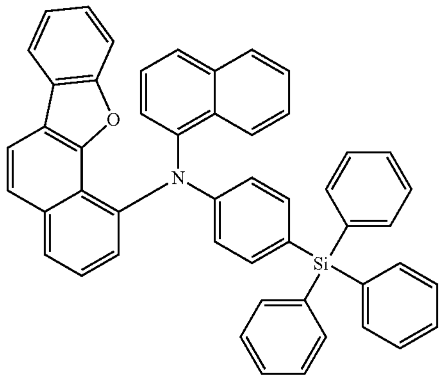
D102
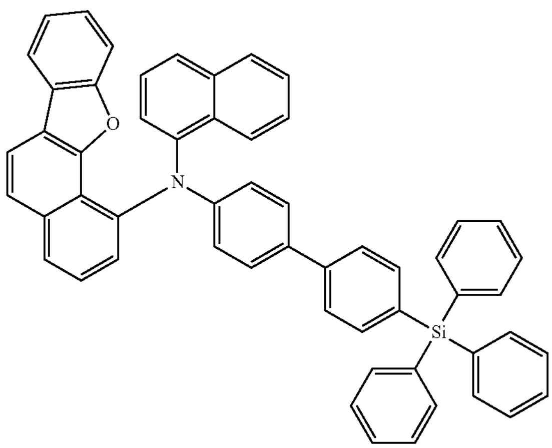
D103
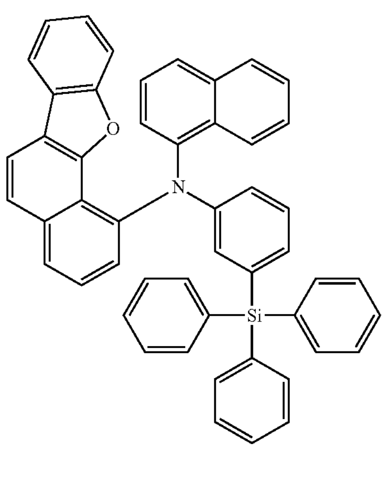
D104
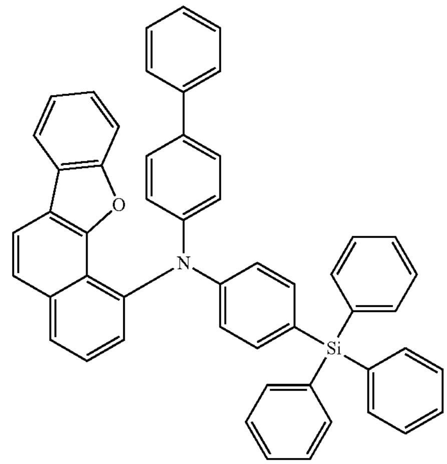
D105
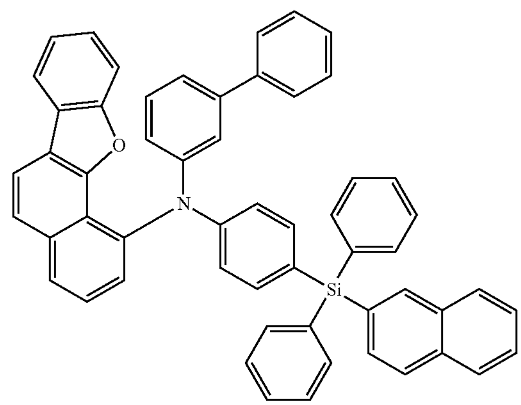
D106
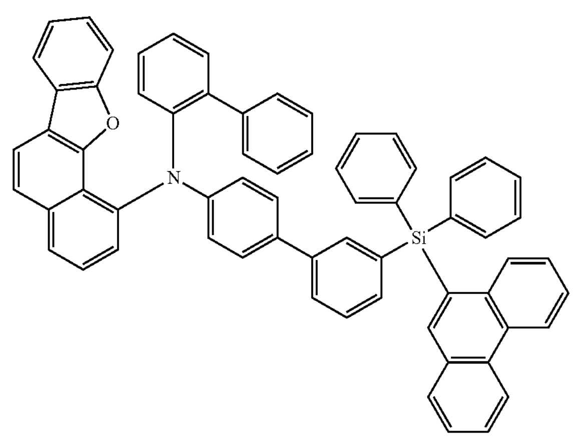

D107
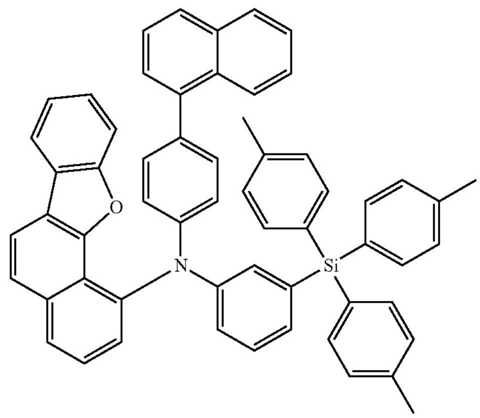
D108
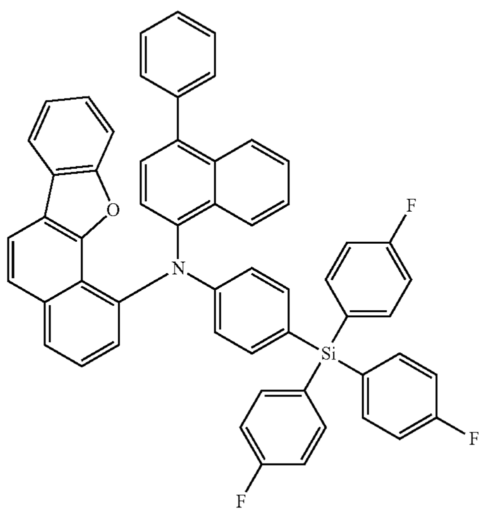
D109
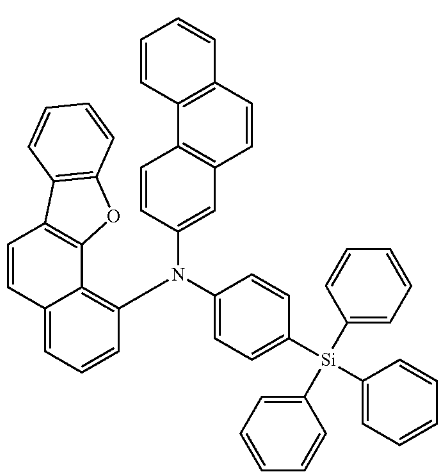
D110
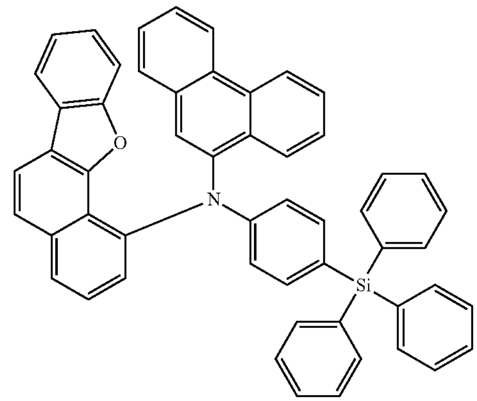
D111
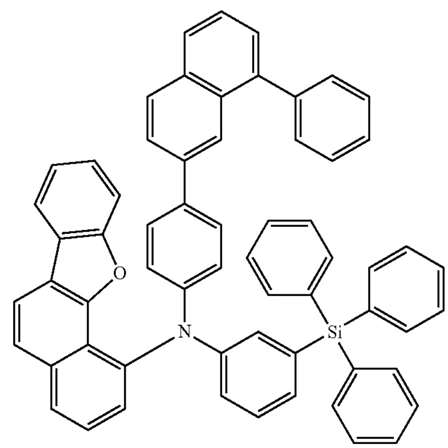
D112
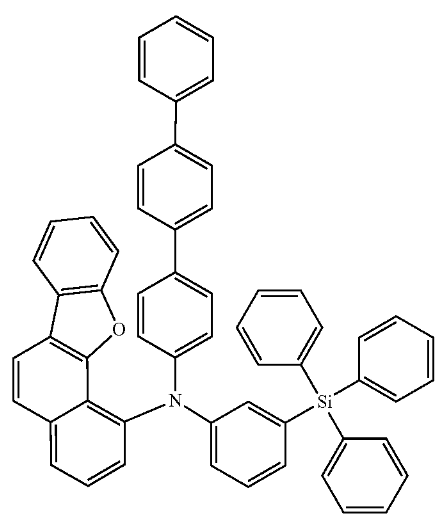

-continued
D113
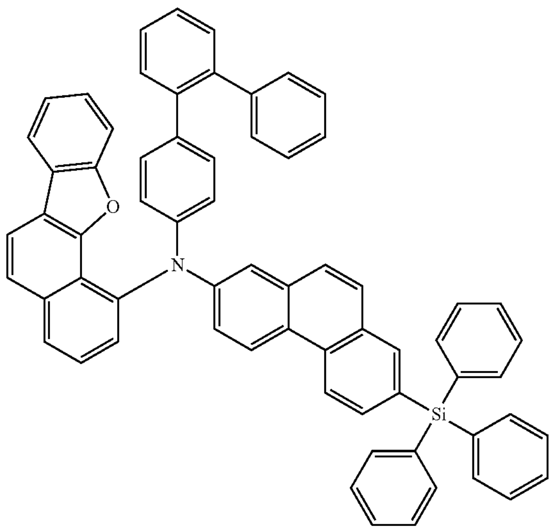
D114
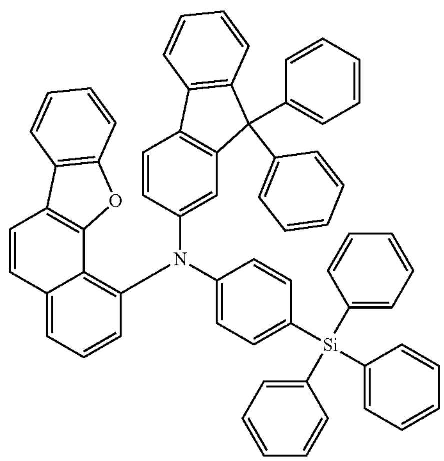
D115
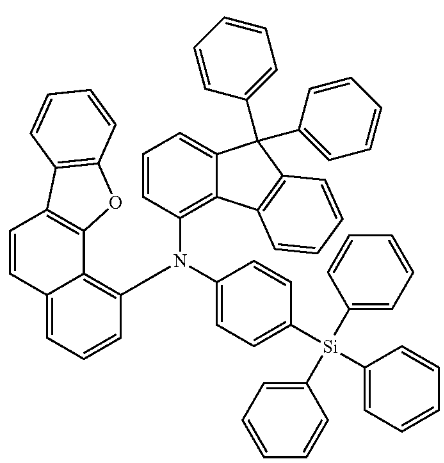
-continued
D116
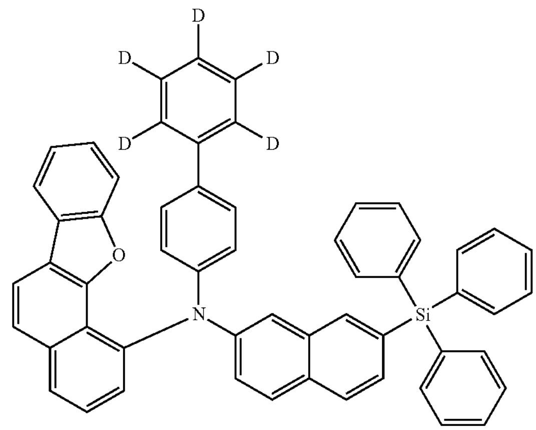
D118
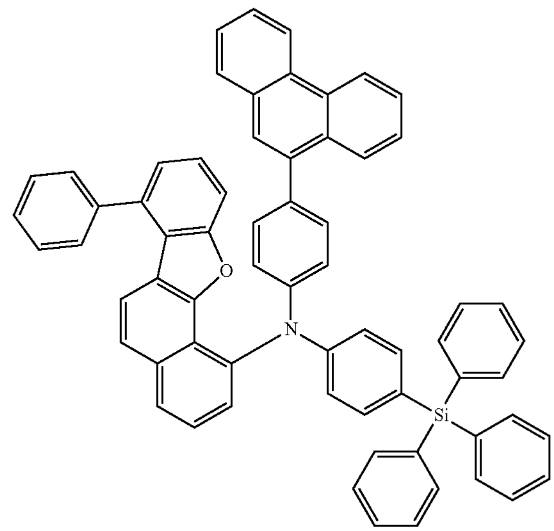
D119
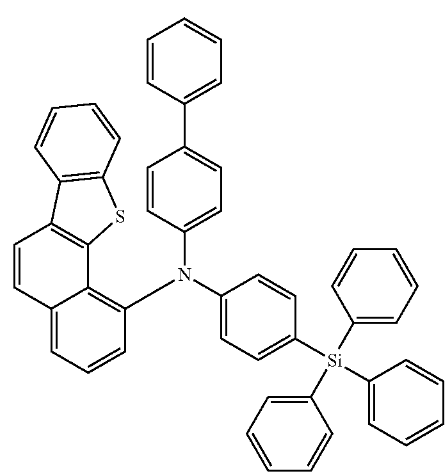

-continued
D120
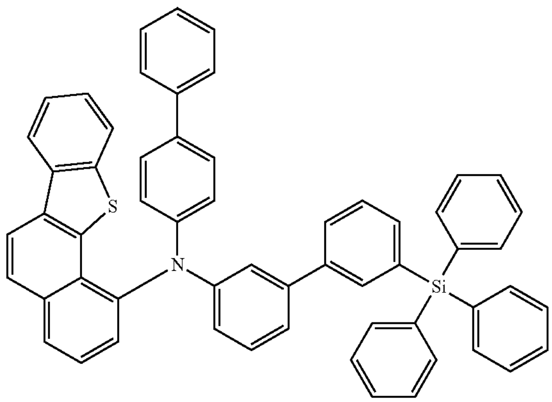
D121
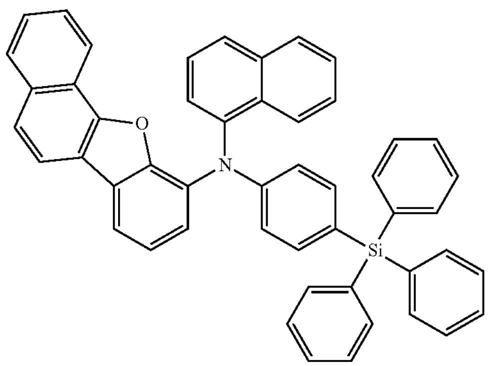
D122
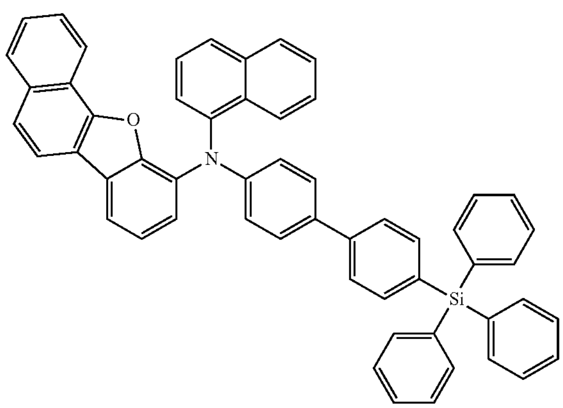
D123
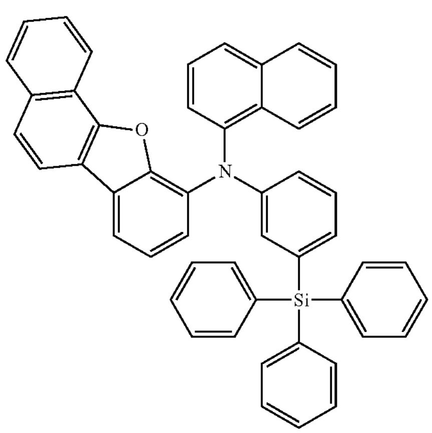
-continued
D124
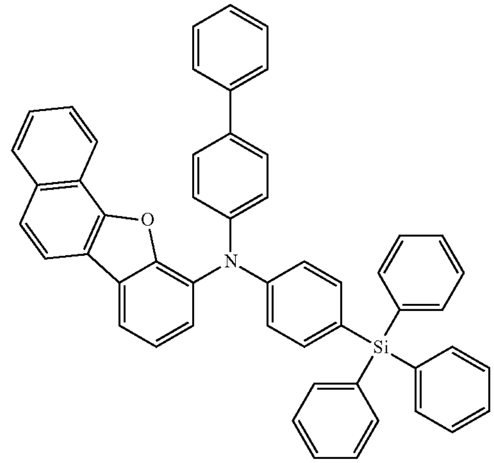
D125
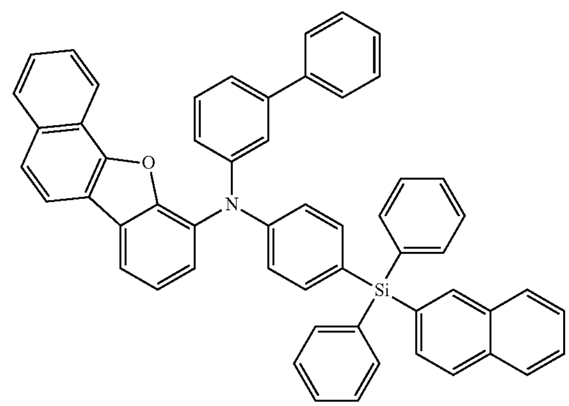
D126
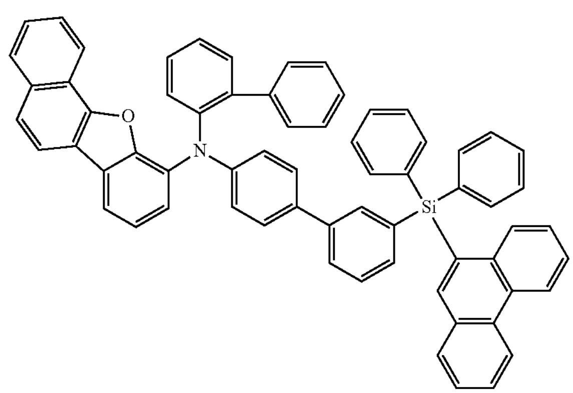

-continued
D127
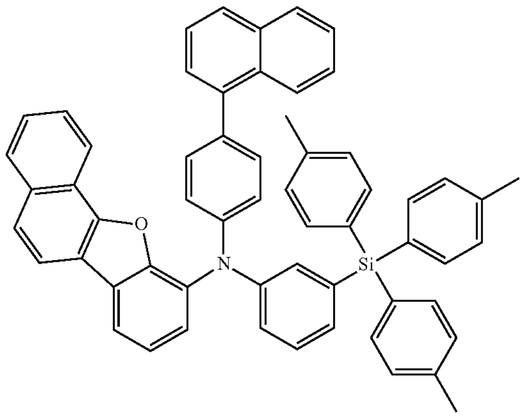
D128
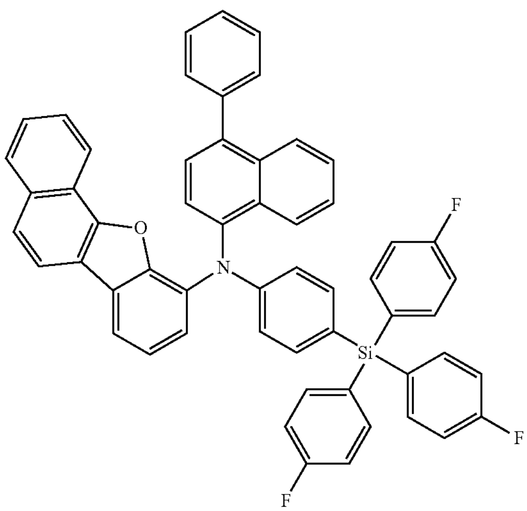
D129
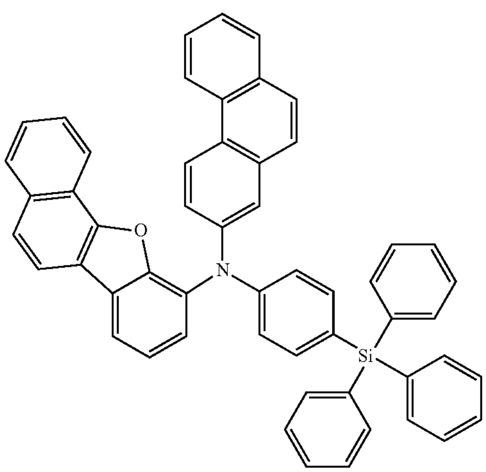
-continued
D130
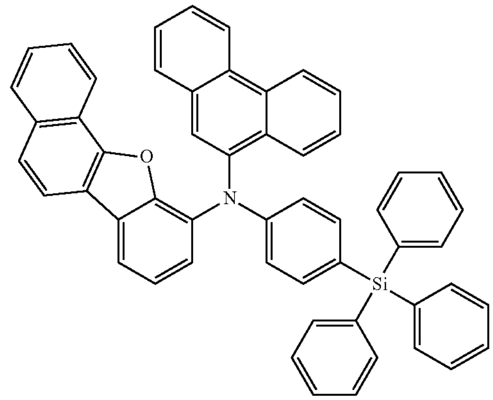
D131
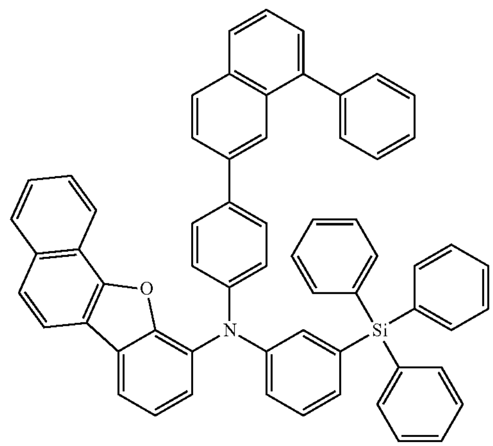
D132
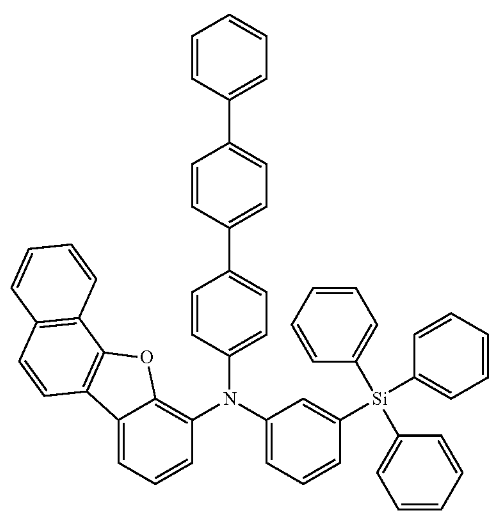

-continued
D133
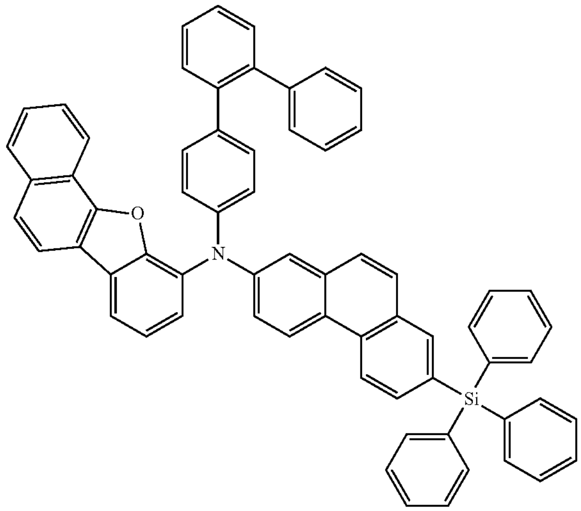
D134
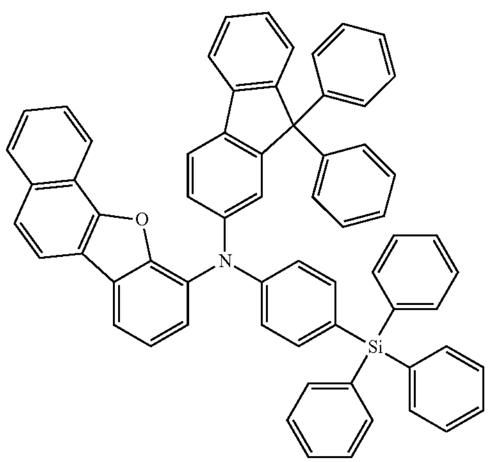
D135
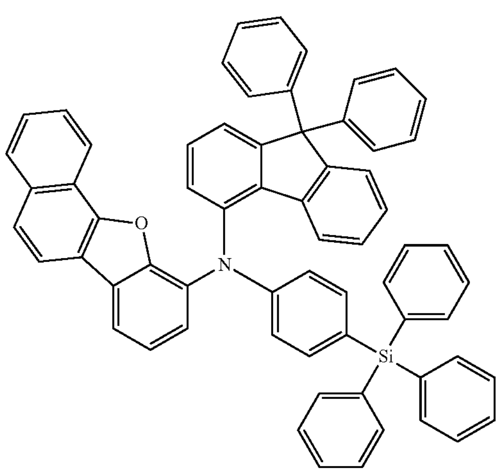
-continued
D136
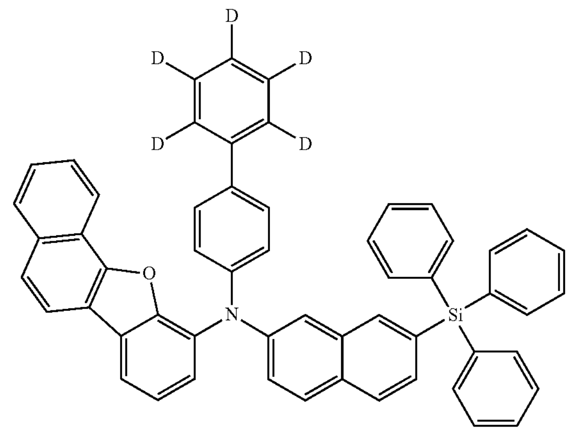
D138
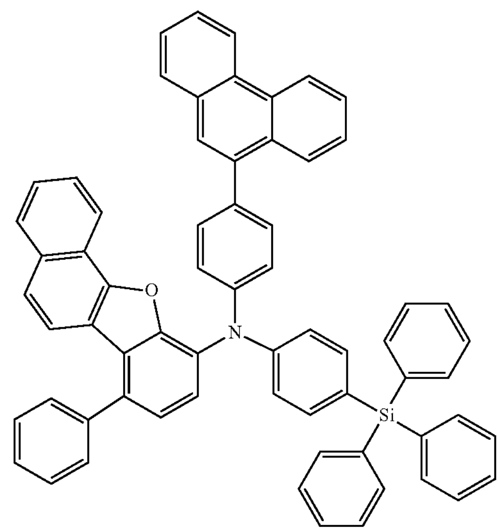
D139
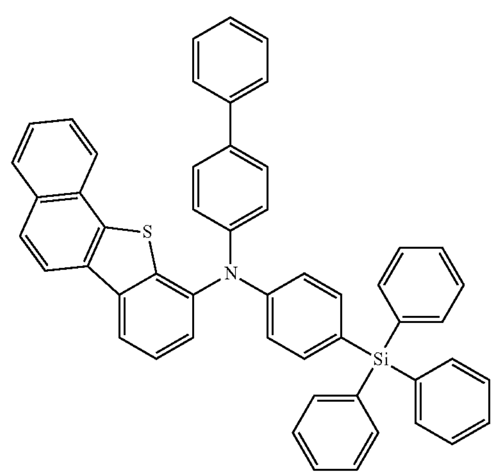

-continued
D140
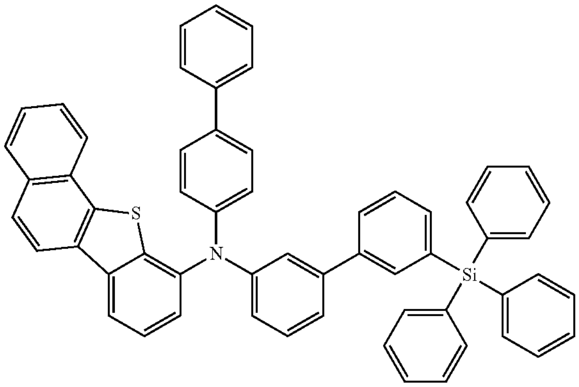
D141
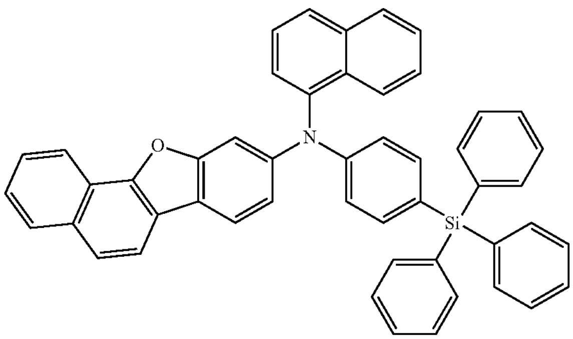
D142
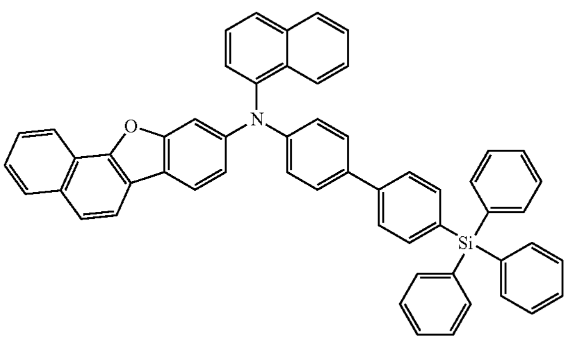
D143
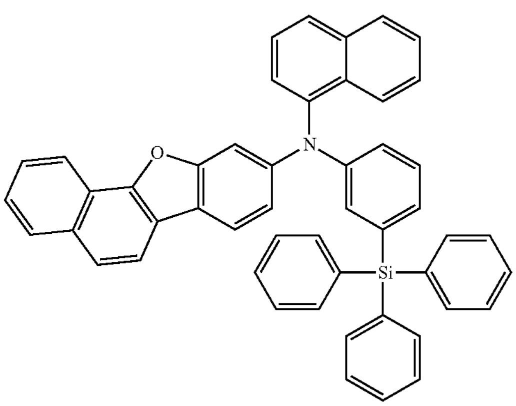
-continued
D144
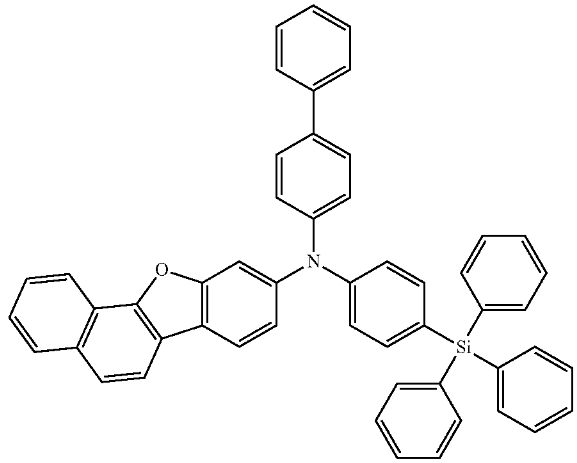
D145
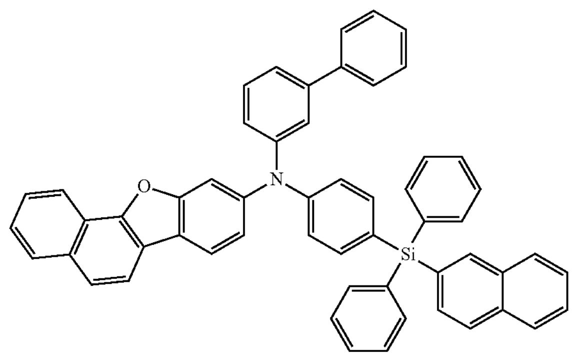
D146
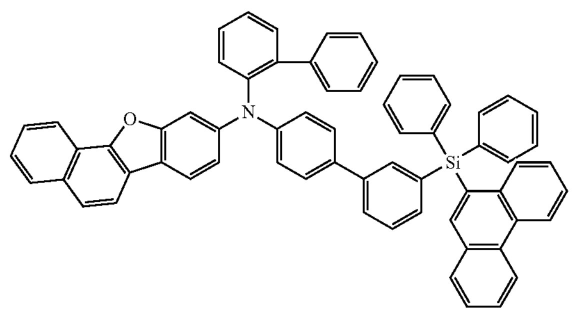
D147
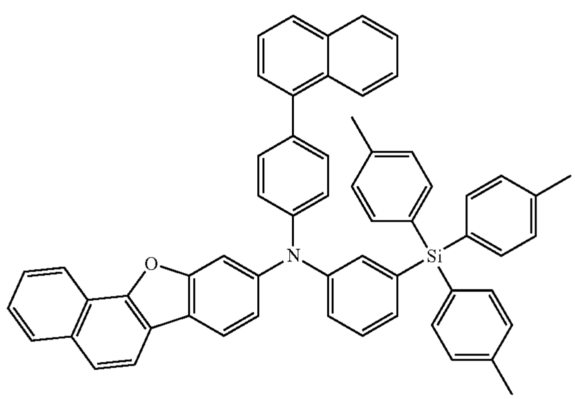

D148
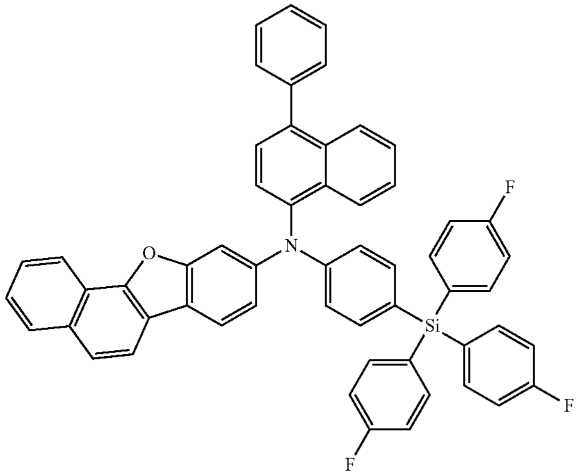
D149
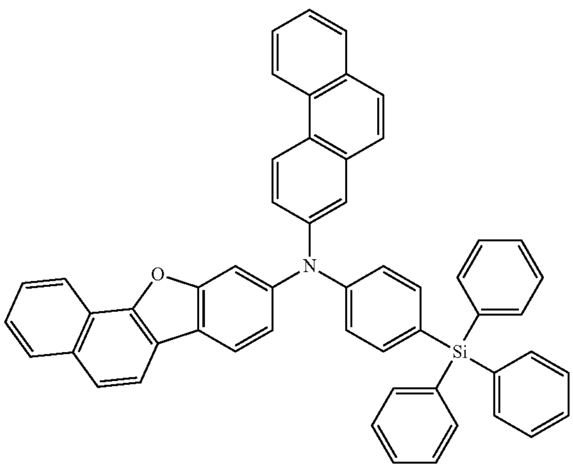
D150
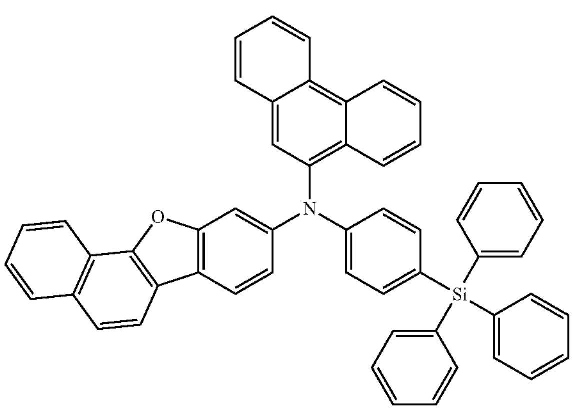
D151
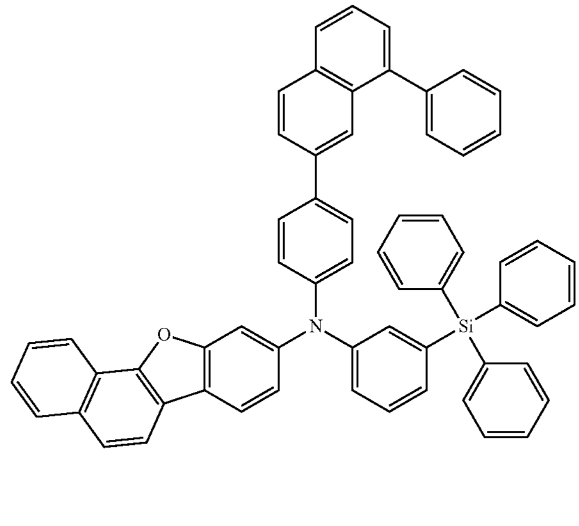
D152
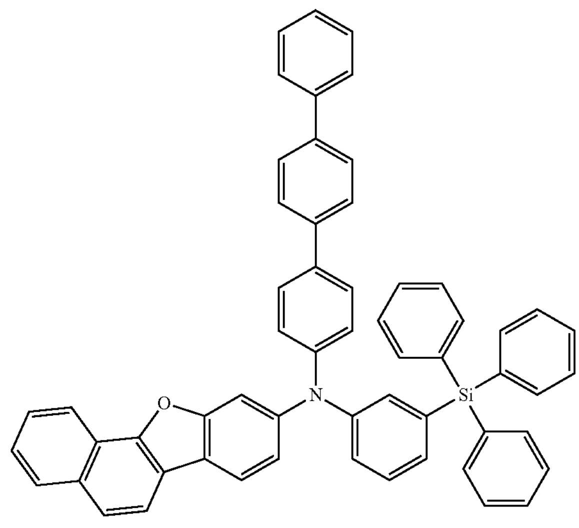
D153
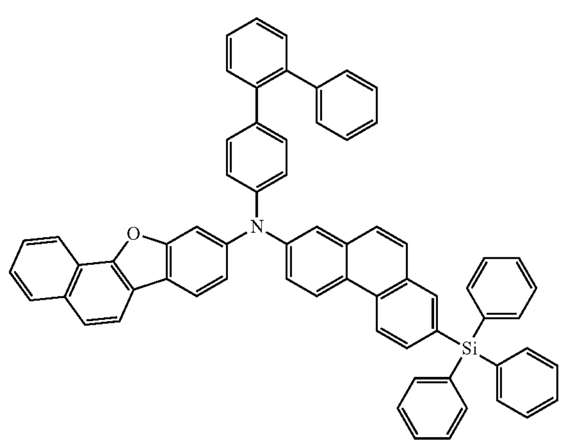

-continued
D154
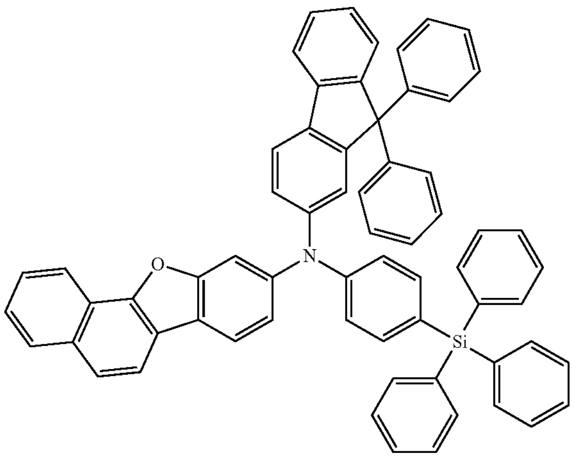
D155
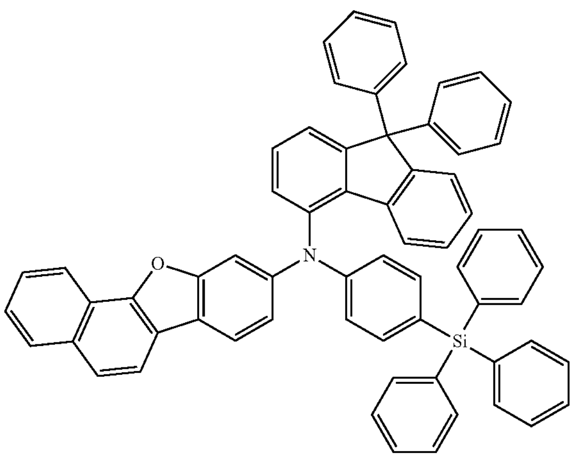
D156
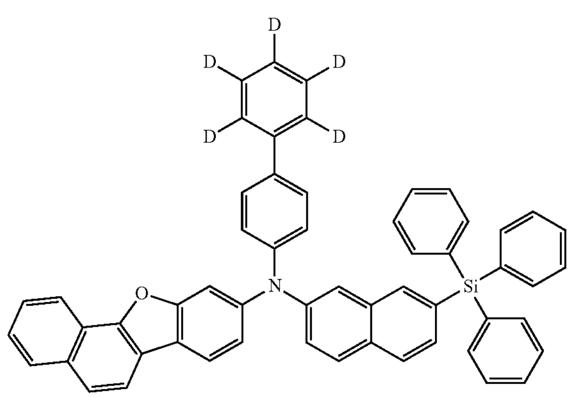
-continued
D158
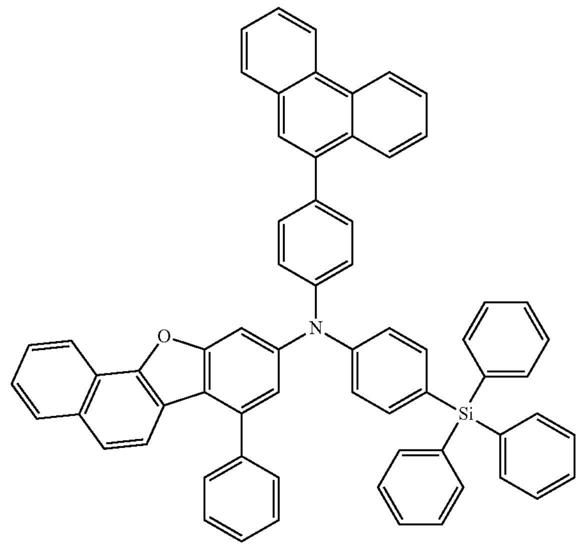
D159
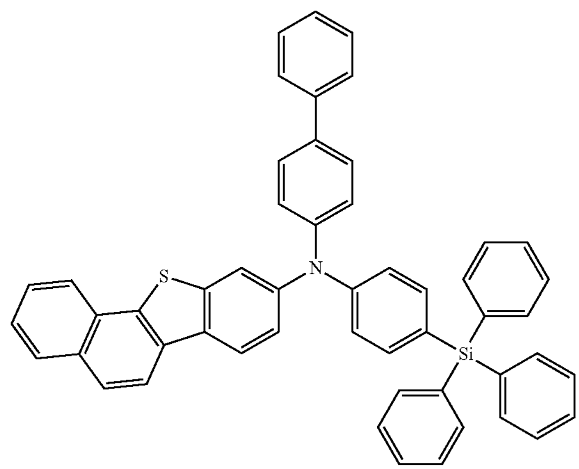
D160
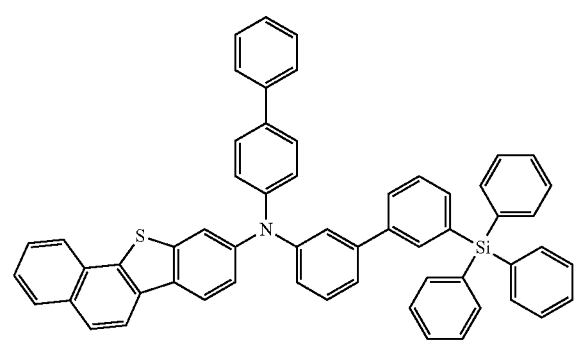

-continued
D161
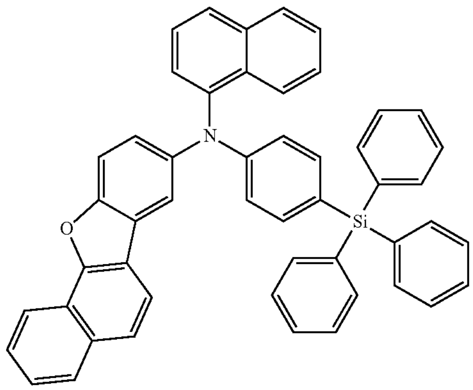
D162
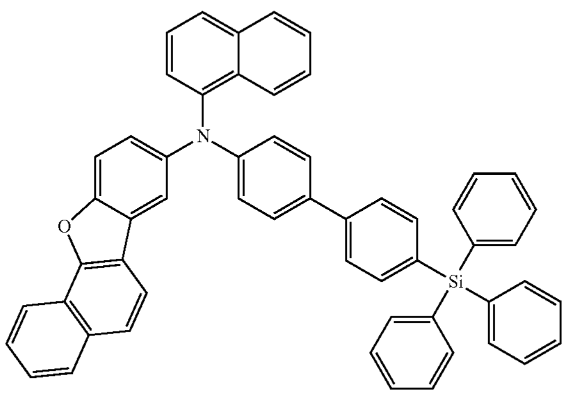
D163
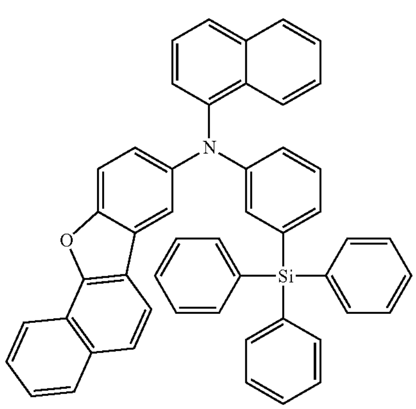
-continued
D164
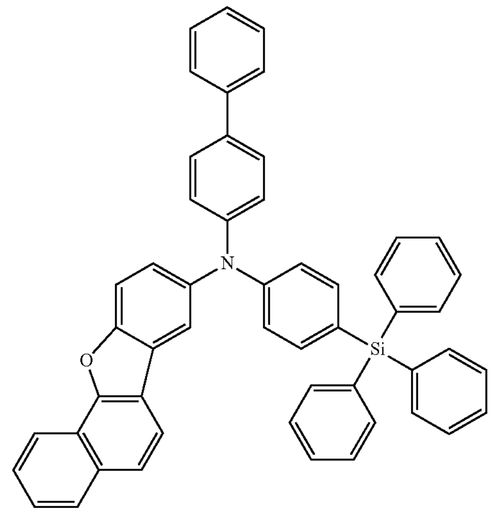
D165
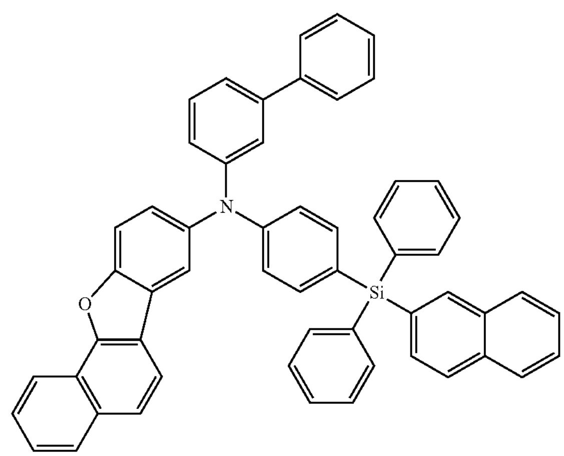
D166
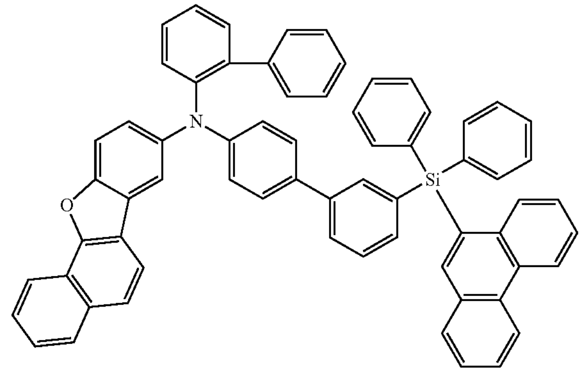

-continued
D167
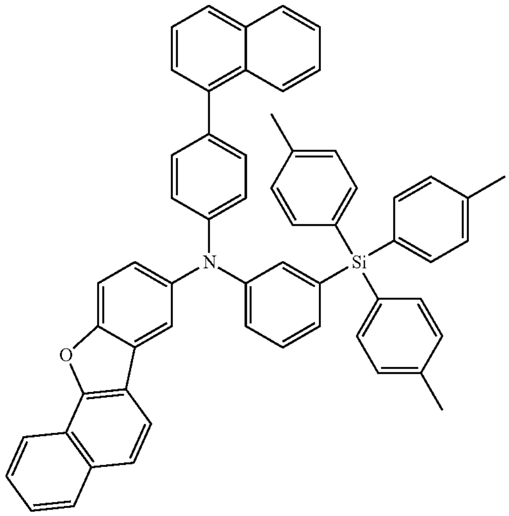
D168
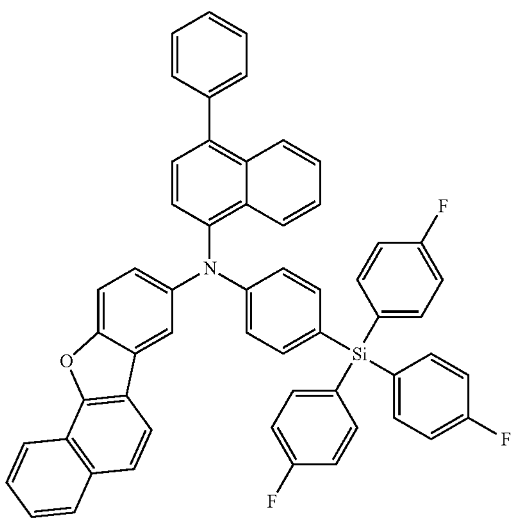
D169
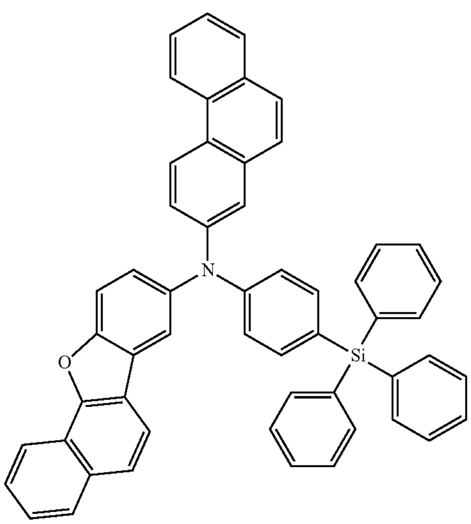
-continued
D170
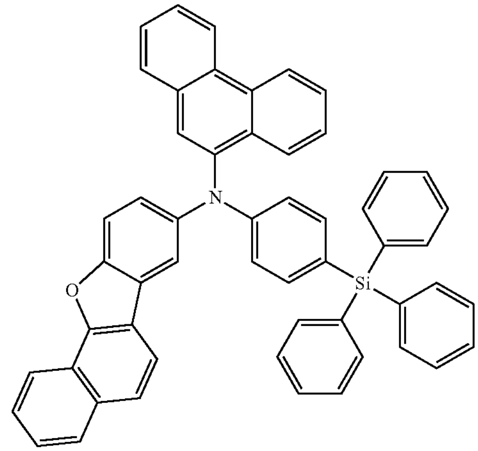
D171
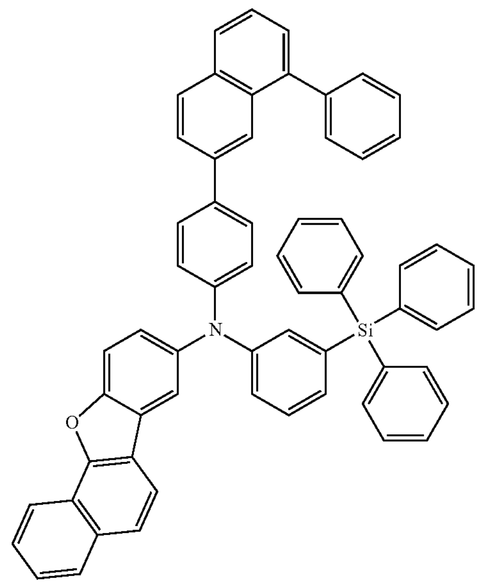
D172
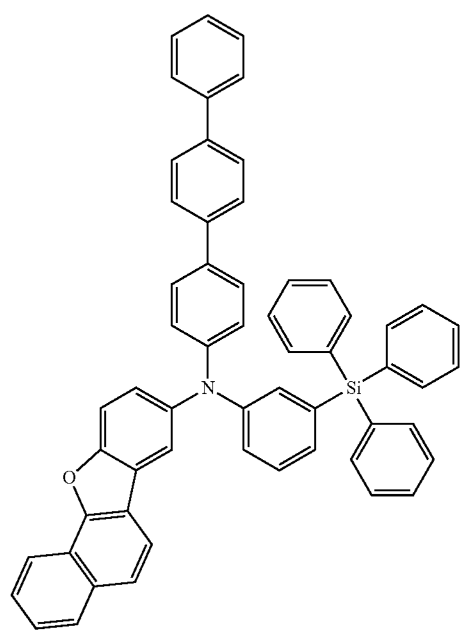

-continued
D173
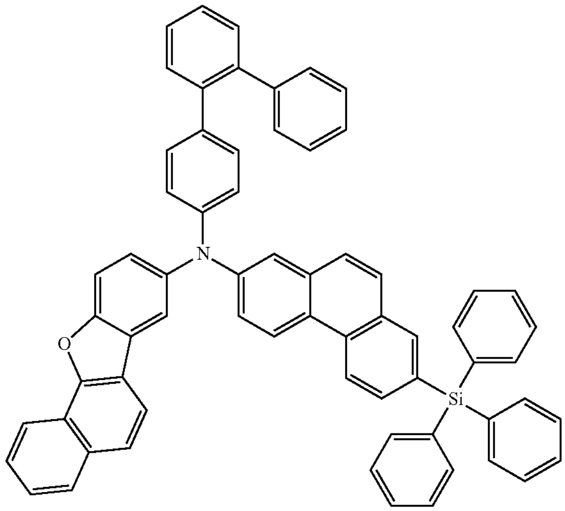
D174
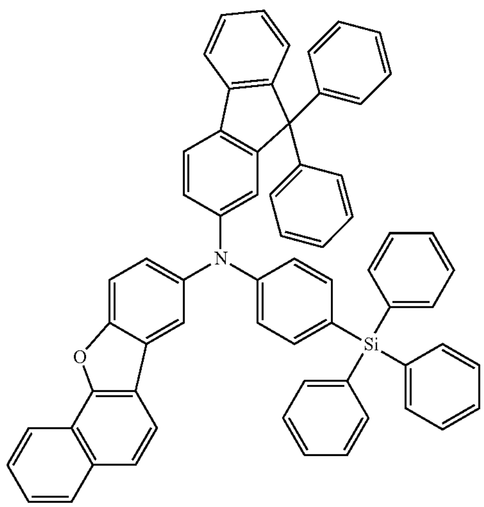
D175
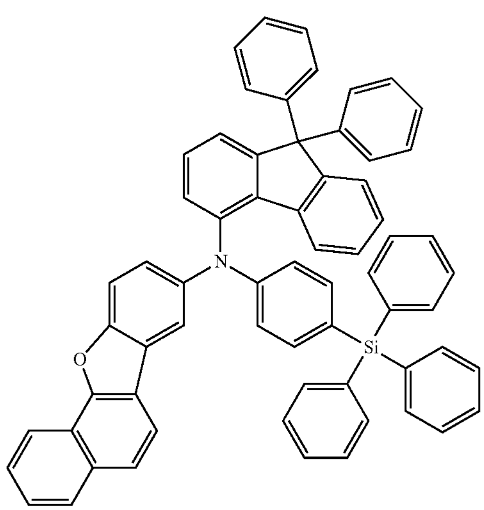
-continued
D176
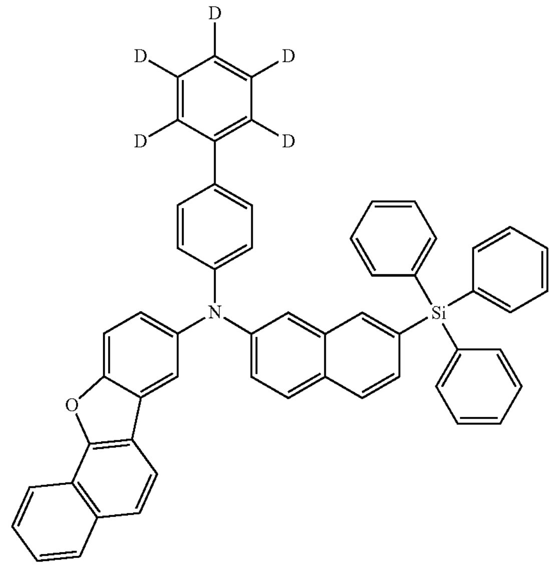
D178
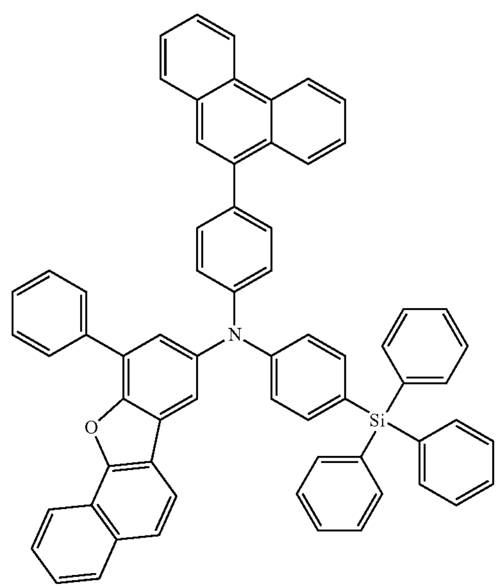

-continued
D179
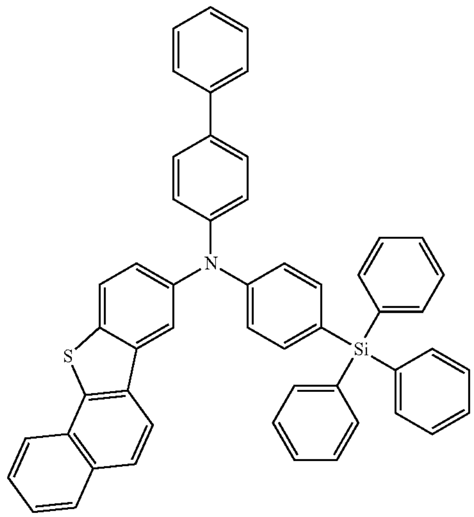
D180
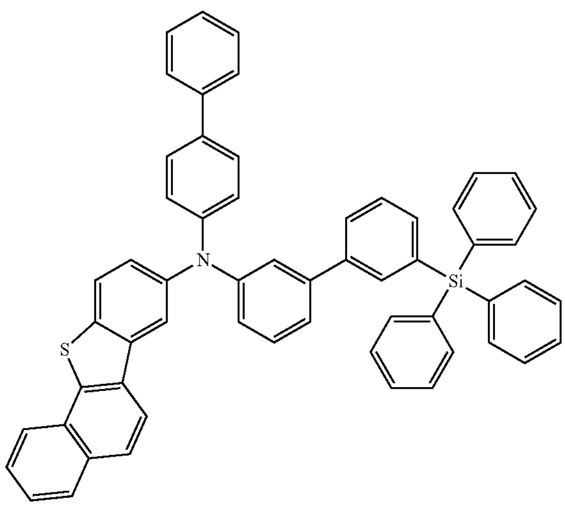
D181
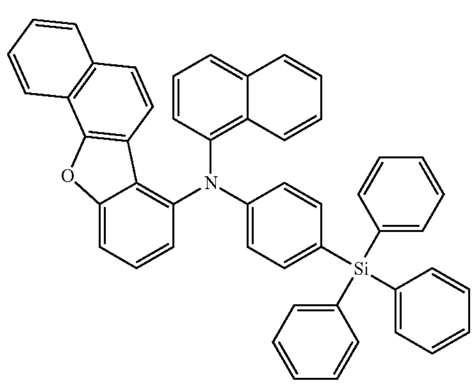
-continued
D182
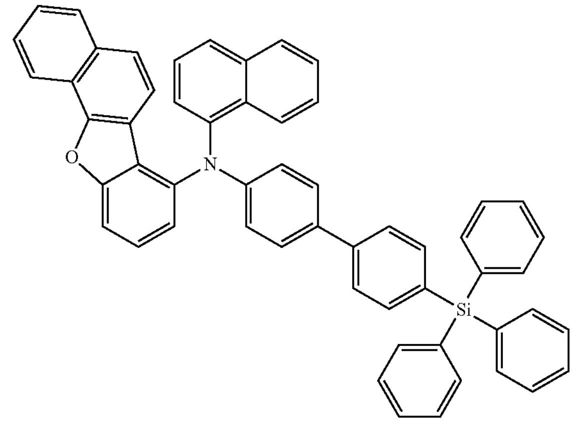
D183
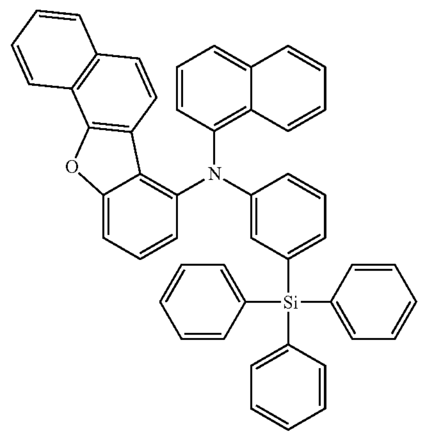
D184
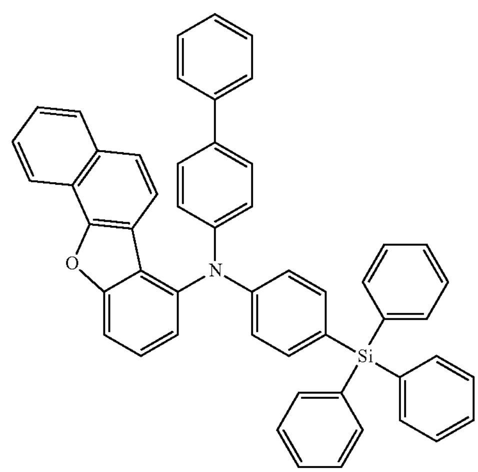

-continued
D185
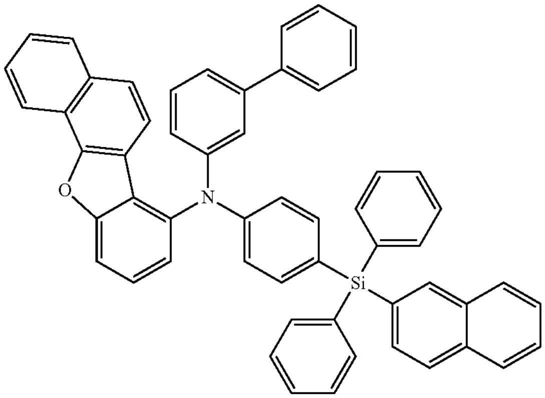
D186
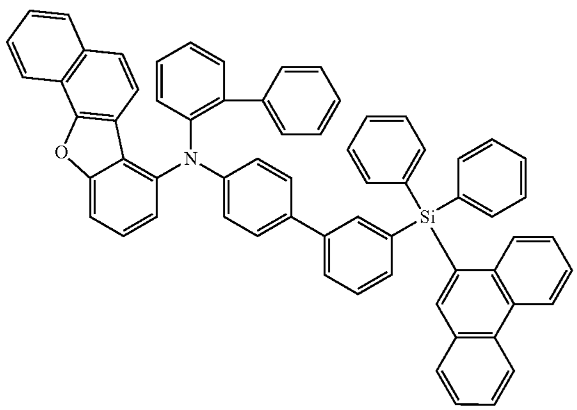
D187
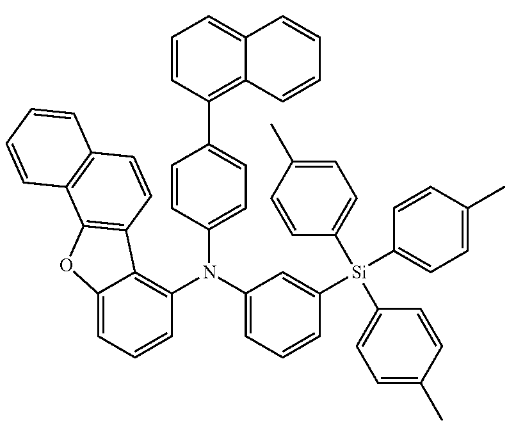
-continued
D188
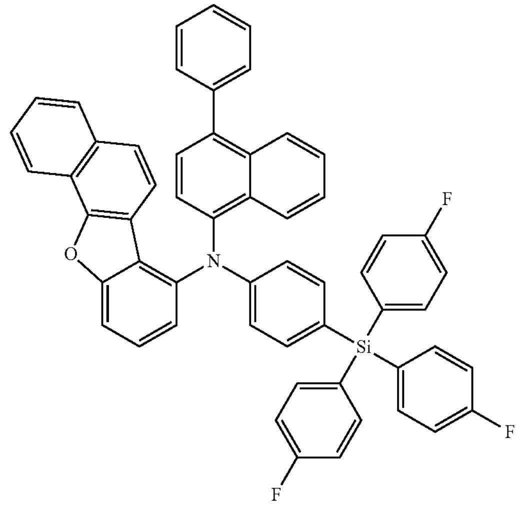
D189
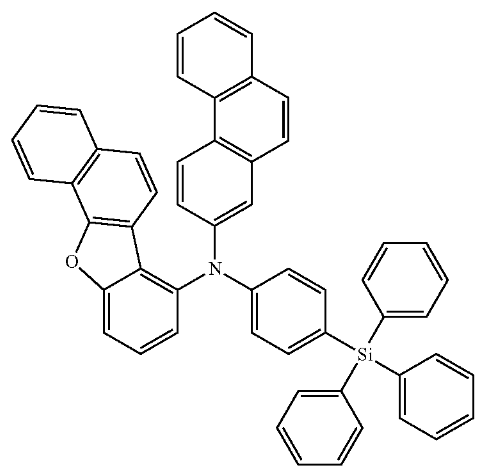
D190
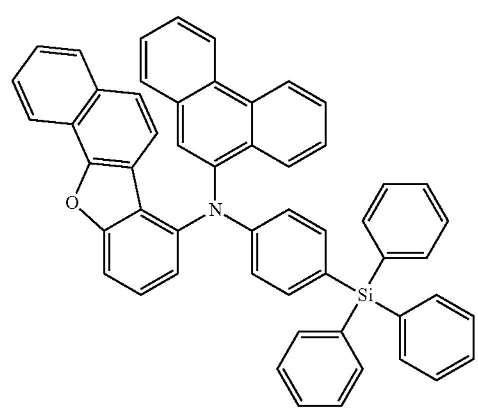

-continued
D191
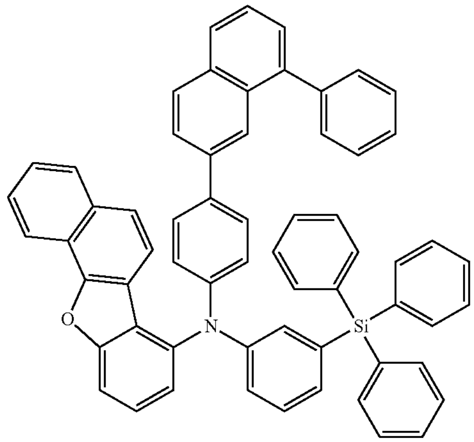
D192
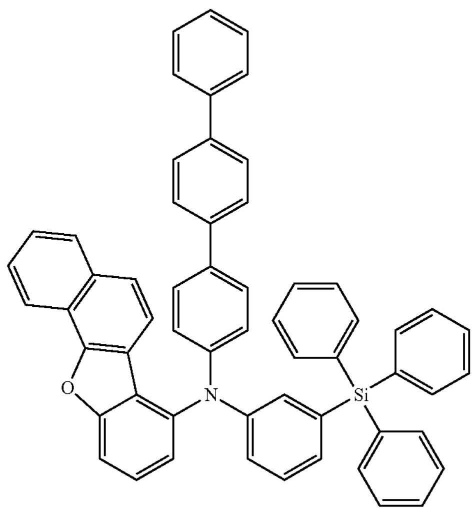
D193
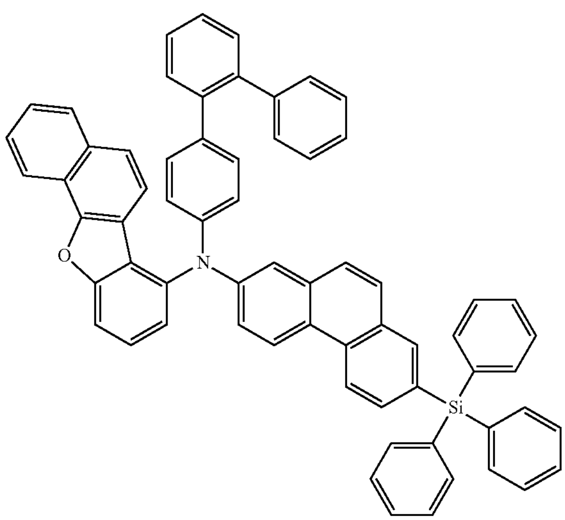
-continued
D194
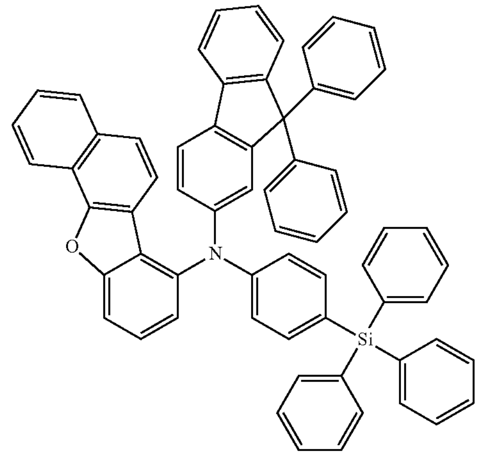
D195
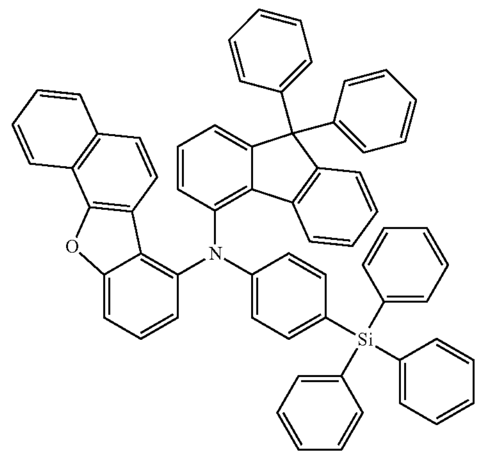
D196
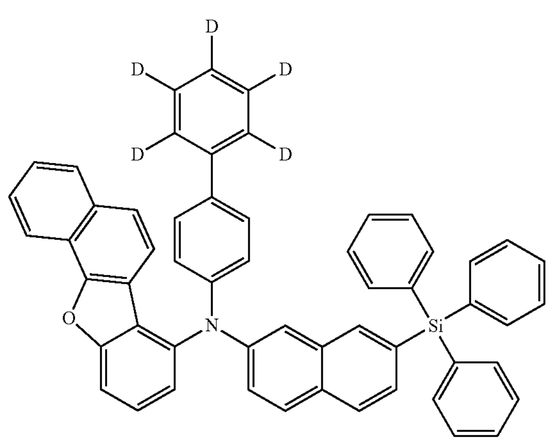

-continued
D198
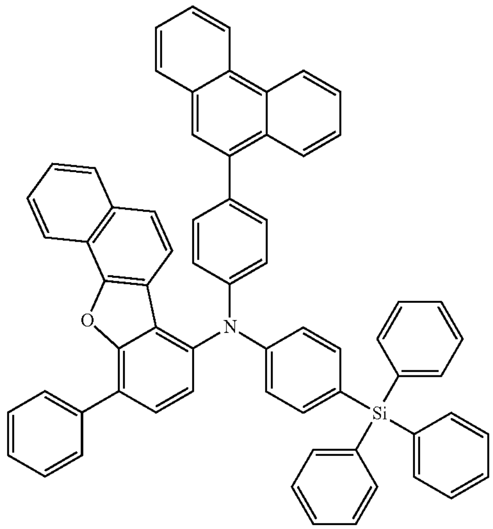
D199
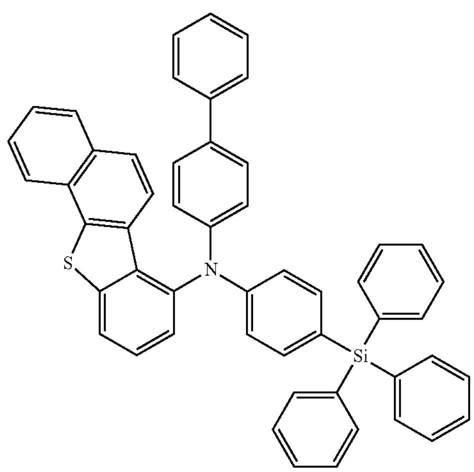
D200
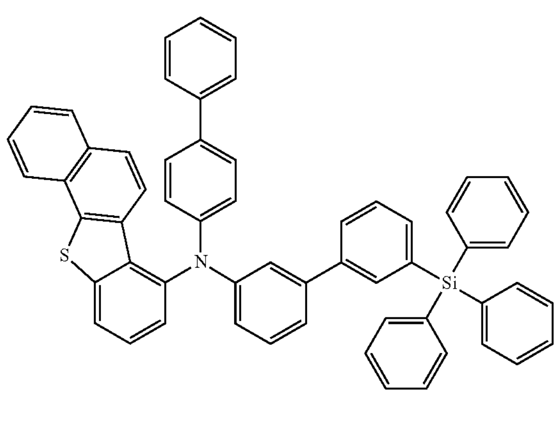
D17
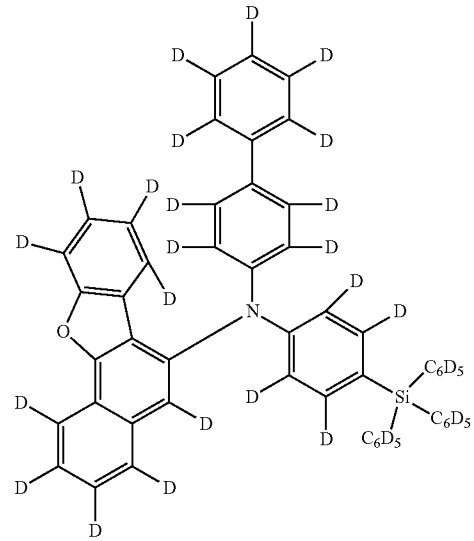
D37
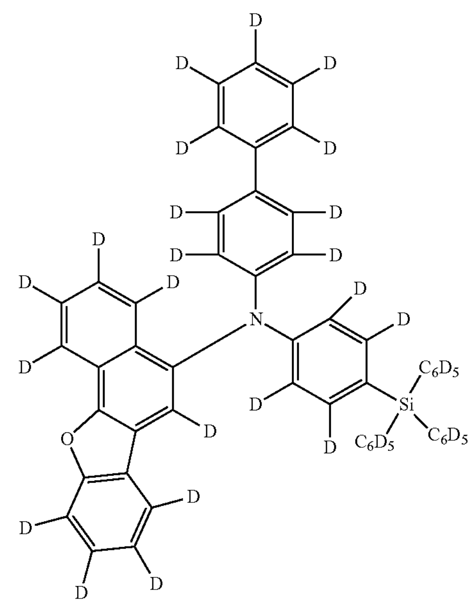
D117
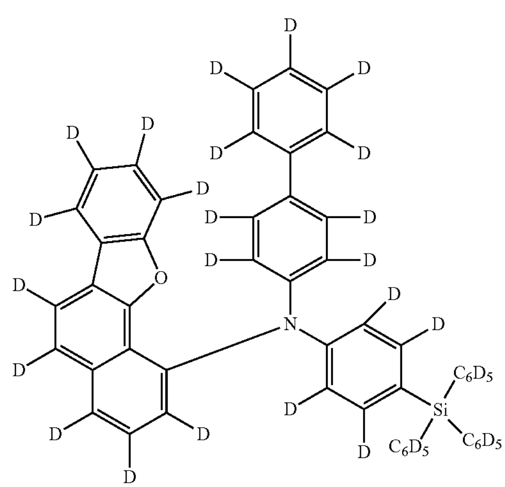

-continued
D137
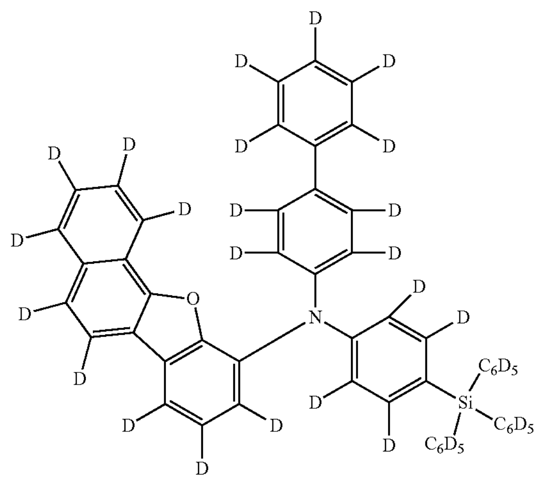
D177
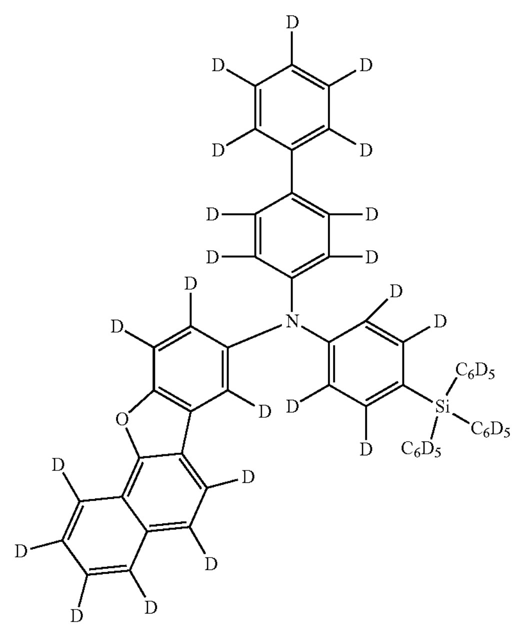
D197
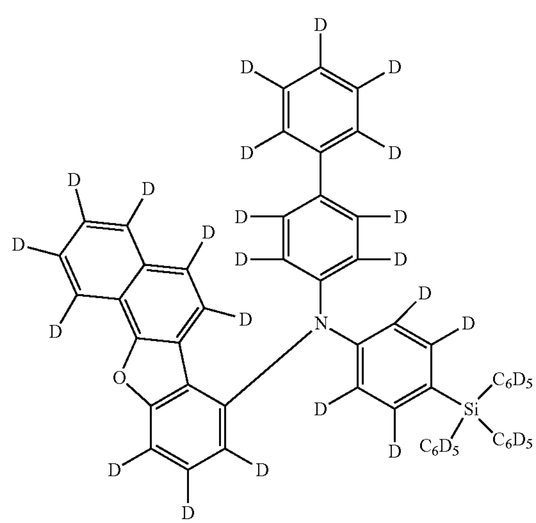
-continued
D57
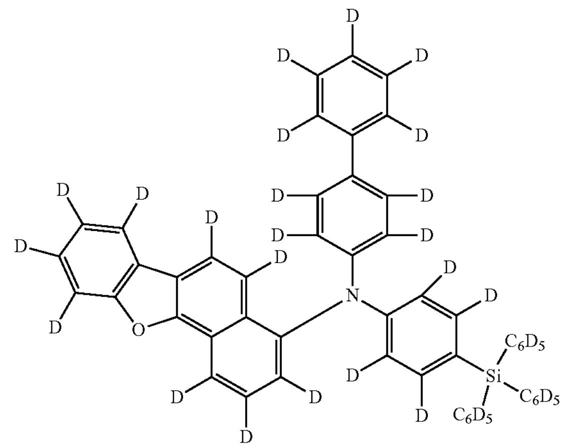
D77
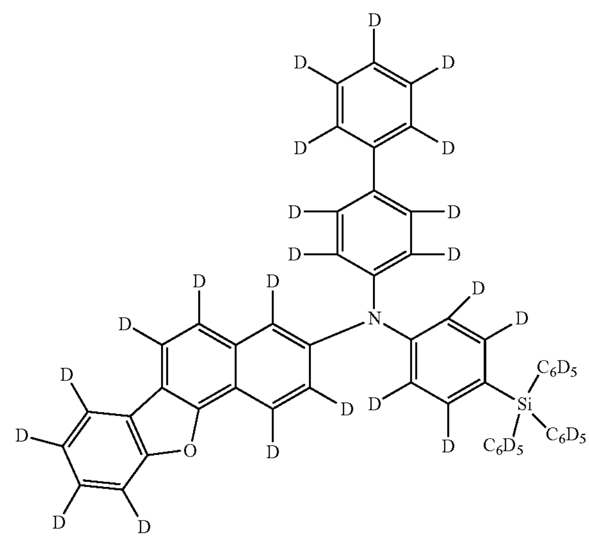
D97
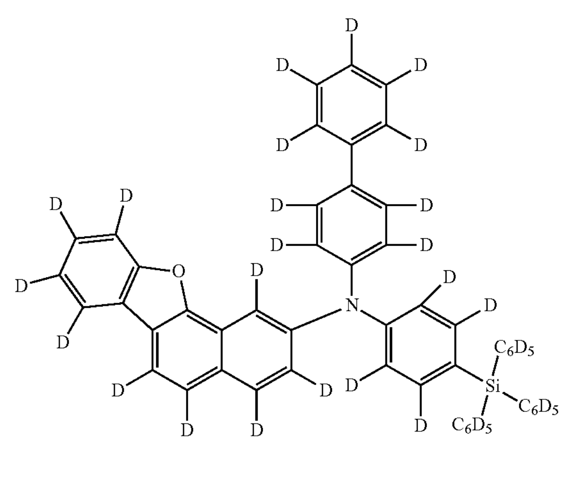

-continued
D157
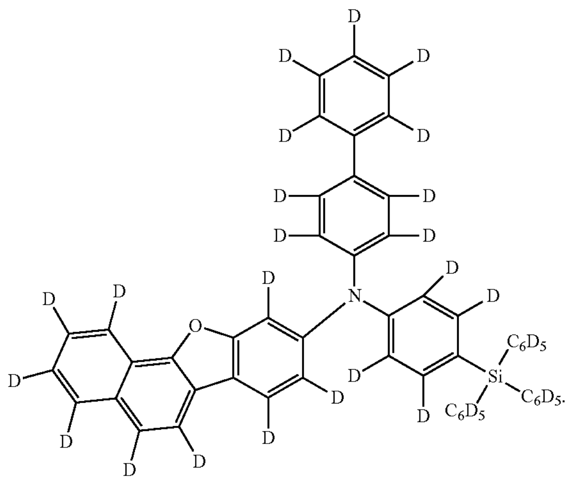
* * * * *